United States Patent
Dutheuil et al.

(10) Patent No.: US 12,091,400 B2
(45) Date of Patent: Sep. 17, 2024

(54) PIPERIDINE DERIVATIVES AS METTL3 INHIBITORS

(71) Applicant: EPICS THERAPEUTICS, Gosselies (BE)

(72) Inventors: Guillaume Dutheuil, Gosselies (BE);
Graeme Fraser, Gosselies (BE);
Catherine Sorlet, Gosselies (BE);
Killian Oukoloff, Gosselies (BE);
François Lenoir, Gosselies (BE);
Julien Korac, Gosselies (BE)

(73) Assignee: EPICS THERAPEUTICS, Gosselies (BE)

( * ) Notice: Subject to any disclaimer, the term of this patent is extended or adjusted under 35 U.S.C. 154(b) by 0 days.

(21) Appl. No.: 18/417,159

(22) Filed: Jan. 19, 2024

(65) Prior Publication Data

US 2024/0270716 A1 Aug. 15, 2024

Related U.S. Application Data

(60) Provisional application No. 63/511,959, filed on Jul. 5, 2023, provisional application No. 63/480,733, filed on Jan. 20, 2023.

(30) Foreign Application Priority Data

Jan. 20, 2023 (EP) .................................. 23152595

(51) Int. Cl.
| | |
|---|---|
| *C07D 401/14* | (2006.01) |
| *A61K 31/501* | (2006.01) |
| *A61P 35/00* | (2006.01) |
| *C07D 405/14* | (2006.01) |
| *C07D 413/14* | (2006.01) |
| *C07D 417/14* | (2006.01) |
| *C07D 471/04* | (2006.01) |
| *C07D 513/04* | (2006.01) |

(52) U.S. Cl.
CPC .......... *C07D 401/14* (2013.01); *A61K 31/501* (2013.01); *A61P 35/00* (2018.01); *C07D 405/14* (2013.01); *C07D 413/14* (2013.01); *C07D 417/14* (2013.01); *C07D 471/04* (2013.01); *C07D 513/04* (2013.01)

(58) Field of Classification Search
CPC .. C07D 401/14; C07D 405/14; C07D 413/14; A61P 35/00; A61K 31/501
USPC ........................................................ 514/317
See application file for complete search history.

(56) References Cited

U.S. PATENT DOCUMENTS

2022/0125768 A1 4/2022 Mohr et al.

FOREIGN PATENT DOCUMENTS

| WO | 2020142557 A1 | 7/2020 |
|---|---|---|
| WO | 2020201773 A1 | 10/2020 |
| WO | 2021079196 A2 | 4/2021 |
| WO | 2021081211 A1 | 4/2021 |
| WO | 2021111124 A1 | 6/2021 |
| WO | 2022074379 A1 | 4/2022 |
| WO | 2022074391 A1 | 4/2022 |
| WO | 2022081739 A1 | 4/2022 |
| WO | 2022243333 A1 | 11/2022 |
| WO | 2023129933 A2 | 7/2023 |
| WO | 2023222762 A1 | 11/2023 |

OTHER PUBLICATIONS

Roundtree et al., "Dynamic RNA Modifications in Gene Expression Regulation", Cell, Elsevier Inc., Jun. 15, 2017, vol. 169, pp. 1187-1200.
Liu et al., "A METTL3-METTL14 Complex Mediates Mammalian Nuclear RNA N6-Adenosine Methylation", Nature Chemical Biology, Aug. 1, 2014, vol. 10, No. 2, pp. 93-95.
Yang et al., "The Role of m6A Modification in Physiology and Disease", Cell Death & Disease, Springer Nature CDDpress, Nov. 8, 2020, vol. 11, No. 960, 16 pages.
Barbieri et al., "Role of RNA Modifications in Cancer", Nature Reviews | Cancer, Jun. 2020, vol. 20, pp. 303-322.
Barbieri et al., "Promoter-Bound METTL3 Maintains Myeloid Leukaemia by m6A-Dependent Translation Control", Nature, Macmillan Publishers Limited, Dec. 7, 2017, vol. 552, pp. 126-131.
Vu et al., "The N6-Methyladenosine (m6A)-Forming Enzyme METTL3 Controls Myeloid Differentiation of Normal Hematopoietic and Leukemia Cells", Nature Medicine, Nature America, Inc., Sep. 18, 2017, vol. 23, No. 11, pp. 1369-1376.

(Continued)

*Primary Examiner* — Kahsay Habte
(74) *Attorney, Agent, or Firm* — Maier & Maier, PLLC

(57) ABSTRACT

Compounds of formula (I), or the pharmaceutically acceptable salts and/or the solvates thereof, wherein m, n, $R^1$, $R^2$, $R^3$, $R^4$, $R^5$, L, $Ar^1$ and $Ar^2$ are as defined as disclosed, which are useful as inhibitors of METTL3 (N6-adenosine-methyltransferase subunit) activity, in particular for the treatment of proliferative diseases such as cancers.

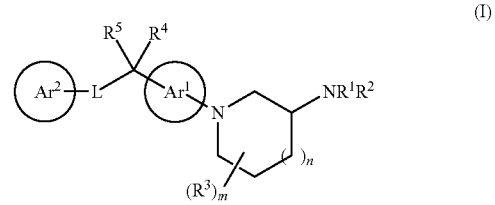

17 Claims, No Drawings
Specification includes a Sequence Listing.

(56) References Cited

OTHER PUBLICATIONS

Yankova et al., "Small-Molecule Inhibition of METTL3 As a Strategy Against Myeloid Leukaemia", Nature, Apr. 26, 2021, vol. 593, pp. 597-601.

Visvanathan et al., "Essential role of METTL3-mediated m6A Modification in Glioma Stem-Like Cells Maintenance and Radioresistance", Oncogene, Macmillan Publishers, Oct. 9, 2017, vol. 37, pp. 522-533.

Lin et al., "RNA m6A Methylation Regulates the Epithelial Mesenchymal Transition of Cancer Cells and Translation of Snail", Nature Communications, The Authors, 2019, vol. 10, No. 2065, 13 pages.

Wang et al., "N6-Methyladenosine METTL3 Promotes Cervical Cancer Tumorigenesis and Warburg Effect Through YTHDF1/HK2 Modification", Cell Death and Disease, The Authors, Springer Nature CDDpress, 2020, vol. 11, No. 911, 10 pages.

Wang et al., "N6-Methyladenosine METTL3 Promotes the Breast Cancer Progression via Targeting Bcl-2", Gene, Elsevier B.V., Aug. 24, 2019, vol. 722, 6 pages.

Cheng et al., "The m6A Methyltransferase METTL3 Promotes Bladder Cancer Progression via AFF4/NF-κB/MYC Signaling Network", Oncogene, Springer Nature Limited, Jan. 18, 2019, vol. 38, pp. 3667-3680.

Li et al., "METTL3 Facilitates Tumor Progression via an m6A-IGF2BP2-Dependent Mechanism in Colorectal Carcinoma", Molecular Cancer, BMC, 2019, vol. 18, 112, 15 pages.

Wang et al., "METTL3 Promotes Tumour Development by Decreasing APC Expression Mediated by APC mRNA N6-Methyladenosine-Dependent YTHDF Binding", Nature Communications, The Authors, 2021, vol. 12, No. 3803, 13 pages.

Winkler et al., "m6A Modification Controls the Innate Immune Response to Infection by Targeting Type I Interferons", Nature Immunology, Feb. 2019, vol. 20, pp. 173-182.

Kim et al., "N6-Methyladenosine Modification of Hepatitis B and C Viral RNAs Attenuates Host Innate Immunity via RIG-I Signaling", Journal Biological Chemistry, The American Society for Biochemistry and Molecular Biology, Inc., Jul. 27, 2020, vol. 295, No. 37, pp. 13123-131333.

Li et al., "METTL3 Regulates Viral m6A RNA Modification and Host Cell Innate Immune Responses During SARS-CoV-2 Infection", Cell Reports, The Authors, CellPress, May 11, 2021, vol. 35, 21 pages.

Lee et al., "Discovery of Substituted Indole Derivatives as Allosteric Inhibitors of m6A-RNA Methyltransferase, METTL3-14 Complex", Drug Development Research, Wiley Periodicals, Inc., Jan. 4, 2022, vol. 83, pp. 783-799.

SEQUENCE LISTING

```
Sequence total quantity: 1
SEQ ID NO: 1                moltype = RNA   length = 27
FEATURE                     Location/Qualifiers
source                      1..27
                            mol_type = other RNA
                            organism = synthetic construct
SEQUENCE: 1
tacactcgat ctggactaaa ggtgctc                                            27
```

PIPERIDINE DERIVATIVES AS METTL3 INHIBITORS

CROSS REFERENCE TO RELATED APPLICATIONS

This application claims the benefit of priority from U.S. Provisional Patent Application No. 63/480,733, filed Jan. 20, 2023, U.S. Provisional Patent Application No. 63/511,959, filed Jul. 5, 2023, and European Patent Application No. EP23152595.7, filed Jan. 20, 2023, the contents of which are incorporated herein by reference in its entirety.

REFERENCE TO A SEQUENCE LISTING

In accordance with 37 CFR § 1.831, the present specification makes reference to a Sequence Listing submitted electronically as a .xml file named "2297 US 3 Sequence listing.xml". The .xml file was generated on Jan. 10, 2024, and is 1,983 bytes in size. The entire contents of the Sequence Listing are hereby incorporated by reference.

FIELD

The present invention relates to piperidine derivatives, especially compounds of formula (I) as detailed hereafter, which are useful as inhibitors of METTL3 (N6-adenosine-methyltransferase subunit) activity, in particular for the treatment of proliferative conditions such as cancers.

BACKGROUND

The best characterized and most prevalent posttranscriptional internal mRNA modification in eukaryotes is the methylation of adenosine at position 6, which forms N6-methyladenosine (m6A). By means of high throughput sequencing technologies, this modification has been transcriptome-wide mapped firstly and ever since a significant progress has been made in attempt to decipher its prevalence, distribution, and biological function. Approximately 0.1-0.4% of all mRNA adenosines are m6A-methylated, accounting for nearly 3-5 modifications per mRNA molecule. Its distribution has been shown to be species and tissue-specific with the highest abundance in brain, liver, kidney and malignant tissues. m6A modification has been shown to play a key role in the regulation of gene expression by exerting a variety of biological functions, including RNA stability, maturation, export, decay and translation (Roundtree et al., Cell, 2017, 169, 1187-1200).

Multiple m6A regulatory enzymes have been identified and classified as m6A "writers", "erasers", and "readers". Evidences suggest that m6A modification is dynamic and its installation requires a multicomponent system with two methyltransferases METTL3-METTL14 playing a major role in the process (Liu et al., Nature Chemical Biology, 2014, 10, 93-95). METTL3 operates as the main catalytic subunit, while METTL14 acts as RNA-binding scaffold. m6A is also a reversible modification by the action of the two RNA demethylases FTO and ALKBH5. Alterations of m6A machinery is linked to several pathological conditions, including neurological disorders, diabetes, obesity, cardiovascular, immune and infectious diseases (Yang et al., Cell Death & Disease, 2020, 11, 960). The importance of m6A modification in cancer is emerging, with critical roles played by m6A enzymes in both solid tumors and haematological malignancies (Barbieri and Kouzarides, Nature Reviews Cancer, 2020, 20, 303-322).

The m6A methyltransferase METTL3 is the primary enzyme responsible for the catalysis of m6A deposition on nascent mRNAs in nuclear speckles. Together with METTL14, METTL3 forms the heterodimeric catalytic complex that mediates the transfer of a methyl group from S-adenosyl-methionine to the mRNA molecule. The m6A installation is mediated by additional cofactors including regulatory proteins such as Wilms' tumour 1-associating protein (WTAP), VIRMA and RNA-binding motif proteins (RBM15), playing a role in complex formation and substrate binding. In addition to its methyltransferase activity, METTL3 has been shown to promote translation of specific mRNA targets.

The physiological role of METTL3-mediated m6A modification has been reported, with this writer being involved in the regulation of neurogenesis and neuronal lineage reprogramming, immune response, stemness, cardiac homeostasis and reproduction. METTL3 is also implicated in several pathological conditions, notably neurodegenerative and metabolic disorders, inflammatory responses, and cancer (ibid. Yang et al., 2020).

METTL3 enzyme has been linked to all hallmarks of cancer and regulates major tumorigenic processes: cell cycle and proliferation, apoptosis, migration, stemness, metabolism and immune surveillance. An oncogenic activity has been attributed to this methyltransferase in most cancers (ibid. Barbieri and Kouzarides, 2020). METTL3 pro-tumoral activity primarily relies on its ability to regulate the stability and translation of key oncogene and tumor suppressor mRNA targets (MYC, SOX4, mTORC, PTEN, BCL2, SP1) in a m6A-dependent manner.

Several studies have shown the involvement of m6A-related enzymes in tumor proliferation, uncovering the m6A writer METTL3 as essential to the growth and maintenance of acute myeloid leukaemia (AML) (Barbieri et al., Nature, 2017, 552, 126-131; Vu et al., Nature Medicine, 2017, 23, 1369-1376). By using a CRISPR screen approach, in vitro and in vivo models, it has been revealed that METTL3 is a required gene for AML growth and myeloid undifferentiation. Among all identified RNA-modifying enzymes, METTL3 performed the highest score in the CRISPR screen, confirmed by in vitro growth assays on a panel of ten AML cell lines. Genetic ablation of METTL3 resulted in cell cycle arrest, differentiation of AML cells and failure to develop leukaemia in in vivo models. Mechanistically, METTL3 exerts its pro-leukaemic activity by promoting the translation of oncogenic targets (SP1/2) in a m6A-dependent manner.

METTL3 has also been found to be upregulated in AML when compared to healthy human hematopoietic stem/progenitor cells and other types of tumor cells (ibid. Vu et al., 2017). METTL3 depletion promotes leukaemia cell differentiation and impairs tumor growth, while the overexpression of its wildtype, but not catalytically mutant form, sustains AML maintenance and proliferation. The same study reported that downregulation of METTL3 in leukaemia in vivo models favours cell differentiation and apoptosis of AML. The pro-tumorigenic function of METTL3-mediated m6A modification in AML was attributed to the increased translation of key leukaemia mRNA targets c-MYC, BCL2 and PTEN and activation of AKT signalling pathway. Inhibition of METTL3 activity by small-inhibitors molecules has been proved to have a successful anti-cancer response in patient-derived leukaemia models (Yankova et al., Nature, 2021, 593, 597-601).

Altogether, these findings identify METTL3 catalytic activity as a promising therapeutic target in AML.

METTL3 has been also associated to the onset, progression, and metastasis of solid cancers. Aberrant expression of this writer has been reported in several solid tumors, including glioblastoma (Visvanathan et al., Oncogene, 2018, 37, 522-533), hepatocellular carcinoma (Lin et al., Nature Communications, 2019, 10, 2065), cervical (Wang et al., Cell Death & Disease, 2020, 11, 911), breast (Wang et al., Gene, 2020, 722, 144076), bladder (Cheng et al., Oncogene, 2019, 38, 3667-3680), colorectal (Li et al., Molecular Cancer, 2019, 18, 112), and oesophageal cancers (Wang et al., Nature Communications, 2021, 12, 3803). In these cancers, METTL3 promotes the translation of key oncogenic targets (SOX2, SNAIL, BCL2, MYC, IKBKB) and is associated to poor patient outcome. Genetic targeting of METTL3 in cellular and in vivo models has been shown to impair tumor growth, invasion, metabolic reprogramming, and immune escape (ibid. Barbieri and Kouzarides, 2020).

Overall, these findings suggest that pharmacological targeting of METTL3 provides a promising and powerful therapeutic opportunity to develop new anti-cancer epidrugs.

Recent studies have revealed that depletion of METTL3 leads to alterations in the propagation of diverse viruses (Winkler et al., Nature Immunology, 2019, 20, 173-182). Following viral infection or stimulation of cells with an inactivated virus, deletion of METTL3 led to an increase in the induction of interferon-stimulated genes. Consequently, propagation of different viruses was suppressed in an interferon-signalling-dependent manner. Significantly, the mRNA of IFNB, was m6A modified and was stabilized following repression of METTL3. m6A serves as a negative regulator of interferon response by dictating the fast turnover of interferon mRNAs and consequently facilitating viral propagation.

METTL3-dependent m6A on HBV and HCV viral genome regulates recognition of the viral genome by RIG-I RNA sensor. Depletion of METTL3 enhances viral dsRNA recognition and induces an anti-viral immune response (Kim et al., J. Biol. Chem., 2020, 295, 13123-131333).

Recent studies have shown that (i) METTL3 depletion enhances innate immune effector gene expression, suggesting that reduced m6A levels in SARS-COV-2 RNA may increase host cell immunity to viral infection and (ii) METTL3 depletion reduces mRNA expression and m6A levels of several proviral host genes during SARS-COV-2 infection (Li et al., Cell Reports, 2021, 35, 109091). The combined effects of directly regulating m6A levels in the virus to enhance a timely innate immune response and indirectly perturbing the viral life cycle by METTL3 depletion/inhibition may benefit the treatment of COVID-19 patients, especially for patients with mild or moderate disease who have not developed a cytokine storm (ibid. Li et al., 2021). The capacity of METTL3 small inhibitors molecules to restrict coronavirus replication has been recently shown in cell line models (US2022/125768).

Therefore, METTL3 inhibitors may also provide a novel therapeutic approach to treat a range of infectious and inflammatory diseases. In particular, they provide a potential treatment for viral diseases.

The present invention thus provides new METTL3 (N6 adenosine-methyltransferase subunit) inhibitors, which can be useful in the treatment of METTL3/14 complex-related diseases, especially cancers, infectious and inflammatory diseases.

SUMMARY

This invention thus relates to compounds of Formula (I):

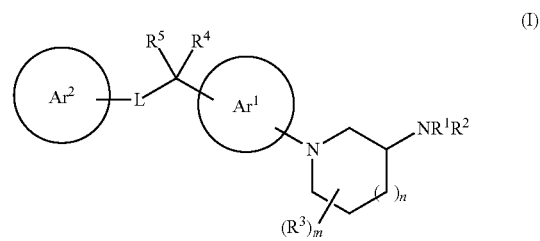

or pharmaceutically acceptable salts and/or solvates thereof, wherein m, n, $R^1$, $R^2$, $R^3$, $R^4$, $R^5$, L, $Ar^1$ and $Ar^2$ are as defined in the claims and hereafter.

The invention also relates to a pharmaceutical composition comprising a compound according to the invention or a pharmaceutically acceptable salt and/or solvate thereof, and at least one pharmaceutically acceptable carrier.

Another aspect of the invention is directed to a compound according to the invention, or a pharmaceutically acceptable salt and/or solvate thereof, for use as a medicament.

The invention is also directed to a compound according to the invention, or a pharmaceutically acceptable salt and/or solvate thereof, for use in the treatment of a proliferative condition, preferably cancer. In one embodiment, the cancer is selected from acute lymphocytic leukaemia, acute myeloid leukaemia (AML), chronic myeloid leukaemia, leukaemia, lymphoma, multiple myeloma, non-Hodgkin's lymphoma (NHL), bladder cancer, bone cancer, breast cancer, cervical cancer, colorectal cancer, endometrial cancer, esophageal/upper aerodigestive cancer, glioblastoma, hepatocellular carcinoma, kidney cancer, liver cancer, lung cancer, non-small cell lung cancer (NSCLC), head and neck cancer, oral squamous cell carcinoma, melanoma, mesothelioma, ovarian cancer, pancreatic cancer, prostate cancer, sarcoma, skin cancer, stomach cancer, and thyroid cancer.

The invention is further directed to a compound according to the invention, or a pharmaceutically acceptable salt and/or solvate thereof, for use in the treatment of an autoimmune disease, a neurological disease, an inflammatory disease, or an infectious disease.

The invention is further directed to a compound according to the invention, or a pharmaceutically acceptable salt and/or solvate thereof, for use in the inhibition of METTL3 activity.

Definitions

The definitions and explanations below are for the terms as used throughout the entire application, including both the specification and the claims. When describing the compounds of the invention, the terms used are to be construed in accordance with the following definitions, unless indicated otherwise.

Where chemical substituents are combinations of chemical groups, the point of attachment of the substituent to the molecule is by the last chemical group recited. For example, an arylalkyl substituent is linked to the rest of the molecule through the alkyl moiety and it may by represented as follows: "-alkyl-aryl".

In the present invention, the following terms have the following meanings:

"Alkyl", by itself or as part of another substituent, refers to a hydrocarbyl radical of formula $C_nH_{2n+1}$ wherein n is a number greater than or equal to 1. Generally, alkyl groups of this invention comprise from 1 to 12 carbon atoms, from 1 to 6 carbon atoms, preferably from 1 to 4 carbon atoms. Alkyl groups may be linear or branched and may be substituted as indicated herein. Suitable alkyl groups include methyl, ethyl, n-propyl, i-propyl, n-butyl, i-butyl, s-butyl, t-butyl, pentyl and its isomers (e.g. n-pentyl, iso-pentyl), and hexyl and its isomers (e.g. n-hexyl, iso-hexyl). Preferred alkyl groups include methyl, ethyl, n-propyl, i-propyl, n-butyl, i-butyl, s-butyl, and 1-butyl.

"Alkylamino" as used herein means an amino group (i.e. —NH$_2$) substituted with one alkyl group as herein defined. "Dialkylamino" as used herein means an amino group substituted with two alkyl groups as herein defined.

"Alkylaminocarbonyl" and "dialkylaminocarbonyl", refer to any group —(C=O)-alkylamino and —(C=O)-dialkylamino respectively, wherein alkylamino and dialkylamino are as defined above.

"Alkoxy" as used herein refers to any group —O-alkyl, wherein alkyl is as defined above. Suitable alkoxy groups include for example methoxy, ethoxy, n-propoxy, iso-propoxy, n-butoxy, t-butoxy, s-butoxy, and n-pentoxy.

"Alkynyl" as used herein refers to a monovalent unsaturated hydrocarbyl group, wherein the unsaturation arises from the presence of one or more carbon-carbon triple bonds. Generally, alkynyl groups comprise from 2 to 6 carbon atoms, preferably from 2 to 4 carbon atoms. Suitable alkynyl groups include ethynyl, 1-propynyl, 2-propynyl, 2-butynyl, 3-butynyl, and the like.

"Aryl", by itself or as part of another substituent, refers to a polyunsaturated, aromatic hydrocarbyl group having a single ring (i.e. phenyl) or multiple aromatic rings fused together (e.g. naphthyl) or linked covalently, typically containing 5 to 12 atoms; preferably 6 to 10, wherein at least one ring is aromatic. The aromatic ring may optionally include one to two additional rings (either cycloalkyl, heterocyclyl or heteroaryl) fused thereto. Aryl is also intended to include the partially hydrogenated derivatives of the carbocyclic systems enumerated herein. Non-limiting examples of aryl comprise phenyl, biphenylyl, biphenylenyl, 5- or 6-tetralinyl, naphthalen-1- or -2-yl, 4-, 5-, 6 or 7-indenyl, 1- 2-, 3-, 4- or 5-acenaphtylenyl, 3-, 4- or 5-acenaphtenyl, 1- or 2-pentalenyl, 4- or 5-indanyl, 5-, 6-, 7- or 8-tetrahydronaphthyl, 1,2,3,4-tetrahydronaphthyl, 1,4-dihydronaphthyl, 1-, 2-, 3-, 4- or 5-pyrenyl.

"Cycloalkyl", by itself or as part of another substituent, refers to a cyclic alkyl group, that is to say, a monovalent, saturated, or unsaturated hydrocarbyl group having 1 or 2 cyclic structures. Cycloalkyl includes monocyclic or bicyclic hydrocarbyl groups. Cycloalkyl groups may comprise 3 or more carbon atoms in the ring and generally, according to this invention comprise from 3 to 10, more preferably from 3 to 8 carbon atoms still more preferably from 3 to 6 carbon atoms. Examples of cycloalkyl groups include but are not limited to cyclopropyl, cyclobutyl, cyclopentyl, cyclohexyl.

"Cycloalkyl-alkyl", refers to any group -alkyl-cycloalkyl, wherein alkyl and cycloalkyl are as defined above.

"Cycloalkyloxy", refers to any group —O-cycloalkyl, wherein cycloalkyl is as defined above.

"Haloalkyl", by itself or as part of another substituent, refers to an alkyl radical having the meaning as defined above wherein one or more hydrogens are replaced with a halogen as defined above. Non-limiting examples of such haloalkyl radicals include chloromethyl, 1-bromoethyl, fluoromethyl, difluoromethyl, trifluoromethyl, 1,1,1-trifluoroethyl and the like.

"Haloalkoxy", by itself or as part of another substituent, refers to an alkoxy radical having the meaning as defined above wherein one or more hydrogens are replaced with a halogen as defined above. Suitable haloalkoxy groups include for example trifluoromethoxy.

"Heteroaryl", by itself or as part of another substituent, refers to 5 to 12 carbon-atom aromatic rings or ring systems containing 1 to 2 rings which are fused together or linked covalently, typically containing 5 to 6 atoms; at least one of which is aromatic, in which one or more carbon atoms in one or more of these rings is replaced by oxygen, nitrogen and/or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxopyridazin-1 (6H)-yl, 2-oxopyridin-1 (2H)-yl, 6-oxopyridazin-1 (6H)-yl, 2-oxopyridin-1 (2H)-yl, 1,3-benzodioxolyl, quinolinyl, isoquinolinyl, cinnolinyl, quinazolinyl, quinoxalinyl.

"Heterocyclyl", by itself or as part of another substituent, refers to non-aromatic, fully saturated or partially unsaturated cyclic groups (for example, 3- to 7-member monocyclic, 7- to 11-member bicyclic, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen, oxygen and/or sulfur atoms, where the nitrogen and sulfur heteroatoms may optionally be oxidized and the nitrogen heteroatoms may optionally be quaternized. Any of the carbon atoms of the heterocyclic group may be substituted by oxo (for example piperidone, pyrrolidinone). The heterocyclic group may be attached at any heteroatom or carbon atom of the ring or ring system, where valence allows. The rings of multi-ring heterocycles may be fused, bridged and/or joined through one or more spiro atoms. Non limiting exemplary heterocyclic groups include oxetanyl, piperidinyl, azetidinyl, 2-imidazolinyl, pyrazolidinyl imidazolidinyl, isoxazolinyl, oxazolidinyl, isoxazolidinyl, thiazolidinyl, isothiazolidinyl, piperidinyl, 3H-indolyl, indolinyl, isoindolinyl, 2-oxopiperazinyl, piperazinyl, homopiperazinyl, 2-pyrazolinyl, 3-pyrazolinyl, tetrahydro-2H-pyranyl, 2H-pyranyl, 4H-pyranyl, 3,4-dihydro-2H-pyranyl, 3-dioxolanyl, 1,4-dioxanyl, 2,5-dioximidazolidinyl, 2-oxopiperidinyl, 2-oxopyrrolodinyl, indolinyl, tetrahydropyranyl, tetrahydrofuranyl, tetrahydroquinolinyl, tetrahydroisoquinolin-1-yl, tetrahydroisoquinolin-2-yl, tetrahydroisoquinolin-3-yl, tetrahydroisoquinolin-4-yl, thiomorpholin-4-yl, thiomorpholin-4-ylsulf oxide, thiomorpholin-4-ylsulfone, 1,3-dioxolanyl, 1,4-oxathianyl, 1H-pyrrolizinyl, tetrahydro-1,1-dioxothiophenyl, N-formylpiperazinyl, and morpholin-4-yl.

"Heterocyclyl-alkyl", refers to any group -alkyl-heterocyclyl, wherein alkyl and heterocyclyl are as defined above.

"Oxo", refers to the substituent =O. "Thioxo", refers to the substituent =S.

"Pharmaceutically acceptable" means that the component not deleterious to the subject to which it is administered and is compatible with each other component administered together.

"Pharmaceutically acceptable carrier" refers to an excipient that does not produce an adverse, allergic, or other untoward reaction when administered to an animal, preferably a human. It includes any and all solvents, dispersion media, coatings, antibacterial and antifungal agents, isotonic and absorption delaying agents and the like. For human administration, preparations should meet sterility, pyrogenicity, general safety and purity standards as required by regulatory offices, such as, e.g., FDA Office or EMA.

"Prodrug" as used herein means the pharmacologically acceptable derivatives of the compounds of the invention, whose in vivo biotransformation product is the active drug. Prodrugs are characterized by increased bio-availability and are readily metabolized into the active compounds in vivo. Suitable prodrugs for the purpose of the invention include carboxylic esters, in particular alkyl esters, aryl esters, acyloxyalkyl esters, and dioxolene carboxylic esters; ascorbic acid esters.

"Solvate" is used herein to describe a molecular complex comprising a compound of the invention and contains stoichiometric or sub-stoichiometric amounts of one or more pharmaceutically acceptable solvent molecule such as ethanol. The term "hydrate" refers to when said solvent is water.

"Administration", or a variant thereof (e.g., "administering"), means providing the active agent or active ingredient, alone or as part of a pharmaceutically acceptable composition, to the subject in need thereof.

"Subject" refers to a mammal, preferably a human. According to the present invention, a subject is a mammal, preferably a human, suffering from the targeted disease and/or prone to develop the targeted disease. In one embodiment, the subject is a "patient", i.e., a mammal, preferably a human, who/which is awaiting the receipt of, or is receiving medical care or was/is/will be the object of a medical procedure or is monitored for the development of the targeted disease.

"Therapeutically effective amount" (or more simply an "effective amount") as used herein refers to the amount of active agent or active ingredient that is aimed at, without causing significant negative or adverse side effects to the subject in need of treatment, preventing, reducing, alleviating, or slowing down (lessening) one or more of the symptoms of the targeted disease "Treating" or "treatment" refers to a therapeutic treatment, to a prophylactic (or preventative) treatment, or to both a therapeutic treatment and a prophylactic (or preventative) treatment, wherein the object is to prevent, reduce, alleviate, and/or slow down (lessen) one or more of the symptoms the targeted disease, in a subject in need thereof. Those in need of treatment include those already with the disorder as well as those prone to have the disorder or those in whom the disorder is to be prevented.

DETAILED DESCRIPTION

Compounds

This invention relates to a compound of formula (I)

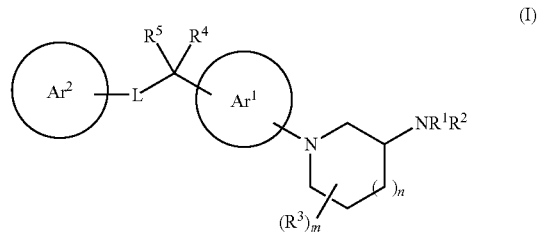

or a pharmaceutically acceptable salt and/or solvate thereof, wherein:

$R^1$ is $C_{2-12}$-alkyl, $C_{2-12}$-haloalkyl, $C_{3-8}$-cycloalkyl-$C_{1-3}$-alkyl, heterocyclyl-$C_{1-3}$-alkyl, $C_{3-8}$-cycloalkyl, or heterocyclyl;
  in which the cycloalkyl and heterocyclyl moieties are optionally substituted by one of more substituents selected from $C_{1-4}$-alkyl, $C_{3-6}$-cycloalkyl, $C_{1-4}$-haloalkyl, halo, cyano, hydroxy, $C_{1-4}$-alkoxy, and $C_{1-4}$-haloalkoxy;
  and/or the cycloalkyl and heterocyclyl moieties are optionally spiro-fused to a $C_{3-6}$-cycloalkyl or heterocyclyl ring, which spiro-ring can optionally be substituted by one or more substituent selected from $C_{1-4}$-alkyl, $C_{3-6}$-cycloalkyl, $C_{1-4}$-haloalkyl, halo, cyano, hydroxy, $C_{1-4}$-alkoxy, and $C_{1-4}$-haloalkoxy;
  and/or the cycloalkyl and heterocyclyl moieties are optionally bridged ring systems;

$R^2$ is H, a $C_{1-4}$-alkyl optionally substituted by one or more substituent selected from halo, cyano, hydroxy, $C_{1-4}$-alkoxy, and $C_{1-4}$-haloalkoxy; or a $C_{3-6}$-cycloalkyl;

or $R^1$ and $R^2$ form together with the nitrogen atom to which they are attached a heterocyclic ring,
  wherein the heterocyclic ring is optionally substituted by one or more substituent selected from $C_{1-4}$-alkyl, $C_{3-6}$-cycloalkyl, $C_{1-4}$-haloalkyl, halo, cyano, hydroxy, $C_{1-4}$-alkoxy, and $C_{1-4}$-haloalkoxy;
  and/or the heterocyclic ring is optionally spiro-fused to a $C_{3-6}$-cycloalkyl or heterocyclyl ring, which spiro-ring can optionally be substituted by one or more substituent selected from $C_{1-4}$-alkyl, $C_{3-6}$-cycloalkyl, $C_{1-4}$-haloalkyl, halo, cyano, hydroxy, $C_{1-4}$-alkoxy, and $C_{1-4}$-haloalkoxy;
  and/or the heterocyclyl ring is optionally a bridged ring system;

each $R^3$ is independently $C_{1-4}$-alkyl, $C_{3-6}$-cycloalkyl, $C_{1-4}$-haloalkyl, halo, cyano, hydroxy, $C_{1-4}$-alkoxy, $C_{1-4}$-haloalkoxy, oxo, or thioxo; or two $R^3$ groups present on the same carbon atom form together with the carbon atom to which they are attached a spiro-fused $C_{3-6}$-cycloalkyl; or two $R^3$ groups present on two adjacent carbon atoms form together with the carbon atoms to which they are attached a fused $C_{3-6}$-cycloalkyl; or two $R^3$ groups present on two non-adjacent carbon atoms are linked and form a $C_{1-4}$-alkyl bridge;

m is 0, 1, 2, 3 or 4;

n is 1 or 2;

$R^4$ and $R^5$ are each independently H, $C_{1-4}$-alkyl, $C_{1-4}$-haloalkyl, $C_{3-6}$-cycloalkyl, halo, cyano or hydroxy; or $R^4$ and $R^5$ form together with the carbon atom to which they are attached a heterocyclyl ring or a $C_{3-4}$-cycloalkyl ring, in which the heterocyclyl and cycloalkyl moieties are optionally substituted by one or more substituent selected from $C_{1-4}$-alkyl, $C_{3-6}$-cycloalkyl, $C_{1-4}$-haloalkyl, halo, or cyano; or $R^4$ and $R^5$ form together with the carbon atom to which they are attached an ethylenyl;

$Ar^1$ is an aryl or heteroaryl group selected from $(Ar^{1a})$, $(Ar^{1b})$ and $(Ar^{1c})$:

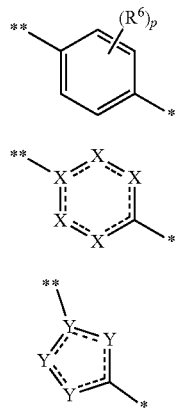

wherein:

p is 0, 1, 2, 3 or 4;

$R^6$ is $C_{1-4}$-alkyl, $C_{3-6}$-cycloalkyl, $C_{1-4}$-haloalkyl, halo, or cyano;

each X is independently selected from N, $NR^7$, C, $CR^8$, C(O), and C(S), wherein at least one of X is N or $NR^7$;

$R^7$ is H, $C_{1-4}$-alkyl, $C_{3-6}$-cycloalkyl, or $C_{1-4}$-haloalkyl;

$R^8$ is H, $C_{1-4}$-alkyl, $C_{3-6}$-cycloalkyl, $C_{1-4}$-haloalkyl, halo, cyano, hydroxy, $C_{1-4}$-alkoxy, or $C_{1-4}$-haloalkoxy;

each Y is independently selected from N, $NR^9$, S, O, C, $CR^{10}$, C(O), and C(S), wherein at least one of Y is N, $NR^9$, S, or O;

$R^9$ is H, $C_{1-4}$-alkyl, $C_{3-6}$-cycloalkyl, or $C_{1-4}$-haloalkyl;

$R^{10}$ is H, $C_{1-4}$-alkyl, $C_{3-6}$-cycloalkyl, $C_{1-4}$-haloalkyl, halo, cyano, hydroxy, $C_{1-4}$-alkoxy, or $C_{1-4}$-haloalkoxy;

- - - represents a single or double bond, depending on X or Y;

*represents the point of attachment to the piperidine ring; and

** represents the point of attachment to the —$CR^4R^5$— moiety;

L is selected from $(L^1)$, $(L^2)$ and 5-membered heteroaryl $(L^3)$:

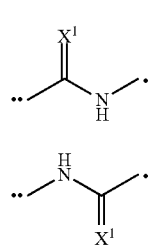

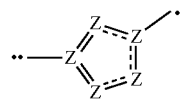

wherein:

$X^1$ is O or S; preferably $X^1$ is O;

each Z is independently selected from N, $NR^{11}$, S, O, C, $CR^{12}$, C(O), and C(S), wherein at least one of Z is N, $NR^{11}$, S, or O;

$R^{11}$ is H, $C_{1-4}$-alkyl, $C_{3-6}$-cycloalkyl, or $C_{1-4}$-haloalkyl;

$R^{12}$ is H, $C_{1-4}$-alkyl, $C_{3-6}$-cycloalkyl, $C_{1-4}$-haloalkyl, halo, cyano, hydroxy, $C_{1-4}$-alkoxy, or $C_{1-4}$-haloalkoxy;

- - - represents a single or double bond, depending on Z;

• represents the point of attachment to the —$CR^4R^5$— moiety; and

•• represents the point of attachment to $Ar^2$;

$Ar^2$ is a 5- to 10-membered, mono- or bicyclo-, aryl or heteroaryl group, optionally substituted by one or more substituent selected preferably from halo, cyano, oxo, hydroxy, amino, $C_{1-4}$-alkylamino, $C_{1-4}$-haloalkylamino, di($C_{1-4}$-alkyl)amino, di($C_{1-4}$-haloalkyl)amino, N—($C_{1-4}$-alkyl)-N—($C_{1-4}$-haloalkyl)amino, $C_{1-4}$-alkoxy, $C_{1-4}$-haloalkoxy, $C_{3-6}$-cycloalkyloxy, ($C_{1-4}$-alkyl)aminocarbonyl, ($C_{1-4}$-haloalkyl)aminocarbonyl, di($C_{1-4}$-alkyl)aminocarbonyl, di($C_{1-4}$-haloalkyl)aminocarbonyl, N—($C_{1-4}$-alkyl)-N—($C_{1-4}$-haloalkyl)aminocarbonyl, $C_{1-4}$-alkyl, $C_{1-4}$-haloalkyl, $C_{3-6}$-cycloalkyl, $C_{2-4}$-alkynyl, $C_{6-10}$-aryl, heteroaryl, and heterocyclyl; wherein the substituents are optionally substituted by one or more group selected preferably from halo, cyano, oxo, hydroxy, $C_{1-4}$-alkyl, $C_{1-4}$-haloalkyl, $C_{3-6}$-cycloalkyl, $C_{1-4}$-alkoxy, $C_{1-4}$-haloalkoxy, amino, $C_{1-4}$-alkylamino, $C_{1-4}$-haloalkylamino, di($C_{1-4}$-alkyl)amino, di($C_{1-4}$-haloalkyl)amino, N—($C_{1-4}$-alkyl)-N—($C_{1-4}$-haloalkyl)amino; or fused to the heterocyclyl substituent may be one or more $C_{3-6}$-cycloalkyl or heterocyclyl group; or spiro-fused to the heterocyclyl substituent may be one or more $C_{3-6}$-cycloalkyl or heterocyclyl group optionally substituted by one or more halo.

n, m, $R^3$

According to one embodiment, the compounds of formula (I) comprise a piperidine group, i.e. n is 1. According to another embodiment, the compounds of formula (I) comprise an azepane group, i.e. n is 2. According to a preferred embodiment, n is 1.

According to one embodiment, m is preferably 0, 1 or 2. In one preferred embodiment, m is 0.

According to one embodiment, when present, $R^3$ is selected from $C_{1-4}$-alkyl, $C_{3-6}$-cycloalkyl, $C_{1-4}$-haloalkyl, halo, cyano, hydroxy, $C_{1-4}$-alkoxy, and oxo; preferably $R^3$ is $C_{1-2}$-alkyl or halo; more preferably $R^3$ is methyl or F.

According to another embodiment, m is at least equal to 2 and two $R^3$ groups are linked together. When the two $R^3$ groups are present on the same carbon atom, they can form a spiro-fused cycloalkyl with the carbon atom to which they are attached. When the two $R^3$ groups are present on two adjacent carbon atoms, they can form a fused cycloalkyl with the carbon atoms to which they are attached. When the two $R^3$ groups are present on two non-adjacent carbon atoms, they can form an alkyl bridge on the piperidine or azepane group to which they are attached.
NR¹R²

According to one embodiment, $R^1$ is $C_{2-12}$-alkyl, $C_{2-12}$-haloalkyl, $C_{3-8}$-cycloalkyl-$C_{1-3}$-alkyl, heterocyclyl-$C_{1-3}$-alkyl, $C_{3-8}$-cycloalkyl, or heterocyclyl;
  in which the cycloalkyl and heterocyclyl moieties are optionally substituted by one of more substituents selected from $C_{1-4}$-alkyl, $C_{3-6}$-cycloalkyl, $C_{1-4}$-haloalkyl, halo, cyano, hydroxy, $C_{1-4}$-alkoxy, and $C_{1-4}$-haloalkoxy;
  and/or the cycloalkyl and heterocyclyl moieties are optionally spiro-fused to a
    $C_{3-6}$-cycloalkyl or heterocyclyl ring, which spiro-ring can optionally be substituted by one or more substituent selected from $C_{1-4}$-alkyl,
    $C_{3-6}$-cycloalkyl, $C_{1-4}$-haloalkyl, halo, cyano, hydroxy, $C_{1-4}$-alkoxy, and
    $C_{1-4}$-haloalkoxy;
  and/or the cycloalkyl and heterocyclyl moieties are optionally bridged ring systems.

In above definition of $R^1$, the expressions "in which the cycloalkyl and heterocyclyl moieties are optionally . . . " refer both to the groups as such, i.e. $C_{3-8}$-cycloalkyl and heterocyclyl, and also to the moieties being part of a composed group, i.e. the cycloalkyl or heterocyclyl groups in the $C_{3-8}$-cycloalkyl-$C_{1-3}$-alkyl or heterocyclyl-$C_{1-3}$-alkyl groups.

According to one embodiment, $R^2$ is H, or a $C_{1-4}$-alkyl, optionally substituted by one or more substituent selected from halo, cyano, hydroxy, $C_{1-4}$-alkoxy, and
$C_{1-4}$-haloalkoxy, or a $C_{3-6}$-cycloalkyl; preferably $R^2$ is H or methyl; more preferably $R^2$ is H;

According to another embodiment, $R^1$ and $R^2$ form together with the nitrogen atom to which they are attached a heterocyclic ring,
  wherein the heterocyclic ring is optionally substituted by one or more substituent selected from $C_{1-4}$-alkyl, $C_{3-6}$-cycloalkyl, $C_{1-4}$-haloalkyl, halo, cyano, hydroxy, $C_{1-4}$-alkoxy, and $C_{1-4}$-haloalkoxy;
  and/or the heterocyclic ring is optionally spiro-fused to a $C_{3-6}$-cycloalkyl or heterocyclyl ring, which spiro-ring can optionally be substituted by one or more substituent selected from $C_{1-4}$-alkyl, $C_{3-6}$-cycloalkyl, $C_{1-4}$-haloalkyl, halo, cyano, hydroxy, $C_{1-4}$-alkoxy, and $C_{1-4}$-haloalkoxy;
  and/or the heterocyclyl ring is optionally a bridged ring system.

When $R^1$ and $R^2$ form together with the nitrogen atom to which they are attached a heterocyclic ring, this heterocyclic ring may comprise one or more supplementary heteroatom selected from nitrogen, oxygen and/or sulfur atoms, where the nitrogen and sulfur heteroatoms may optionally be oxidized and the nitrogen heteroatoms may optionally be quaternized.

According to one embodiment, NR¹R² is selected from:

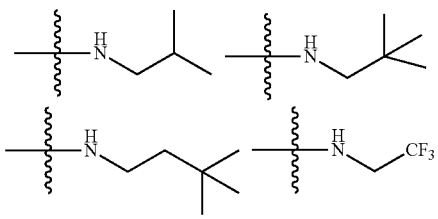

-continued

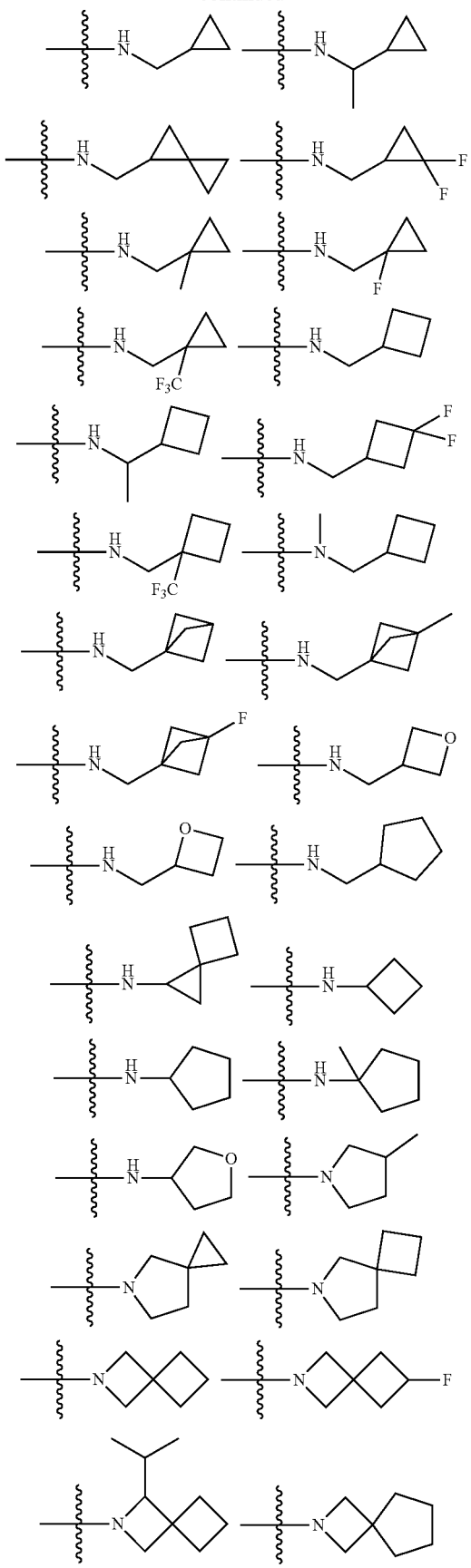

-continued
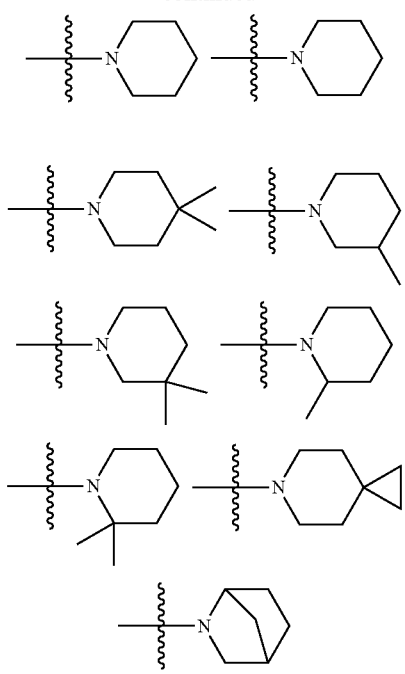
wherein -ξ- represents the point of attachment to the rest of the compound.
According to one embodiment, NR¹R² is selected from:
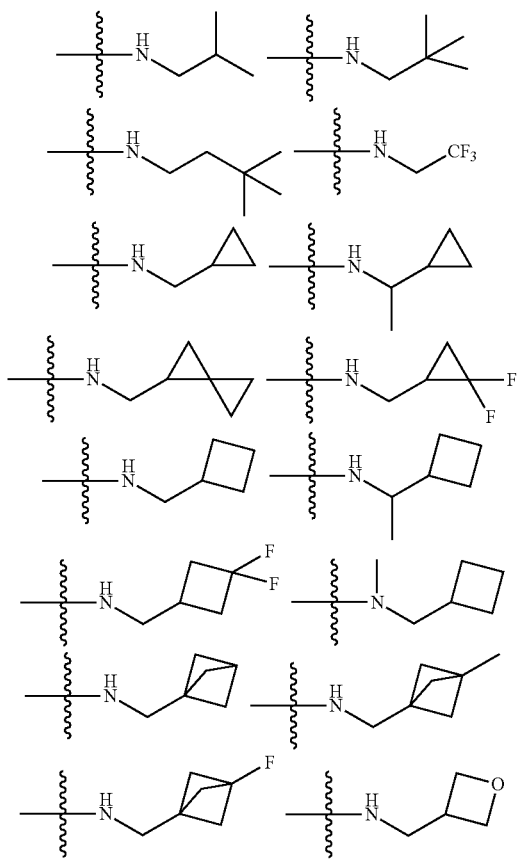
-continued
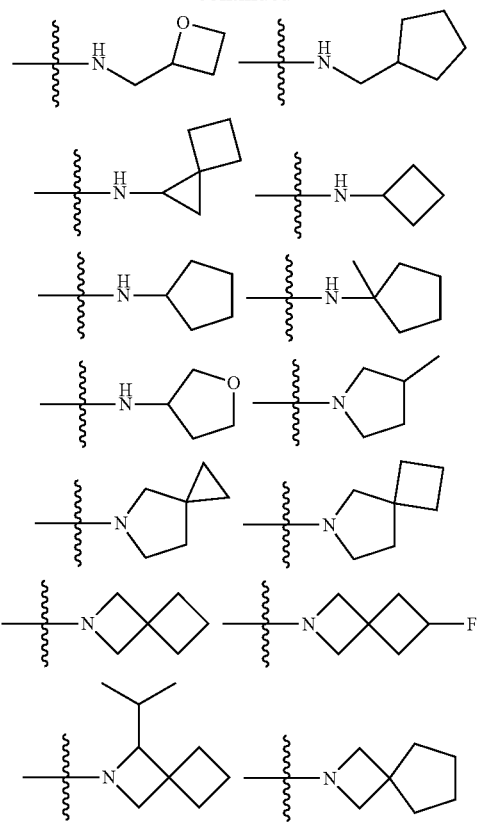
wherein -ξ- represents the point of attachment to the rest of the compound.
According to one embodiment, NR¹R² is selected from:
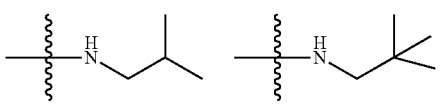

-continued

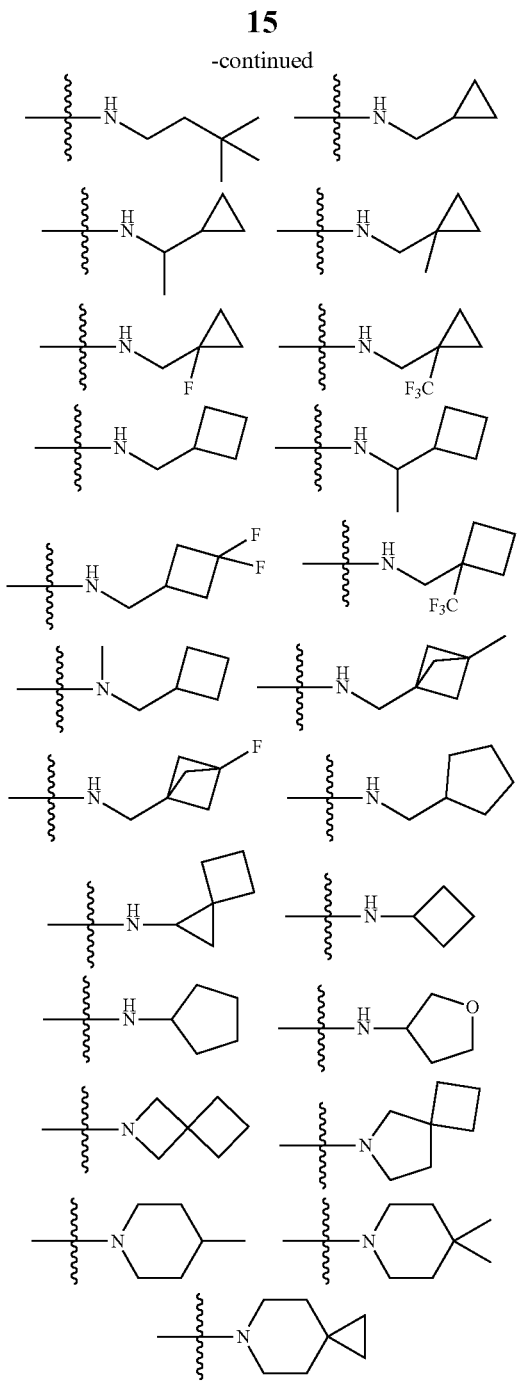

wherein -ξ- represents the point of attachment to the rest of the compound.

According to one embodiment, NR¹R² is selected from:

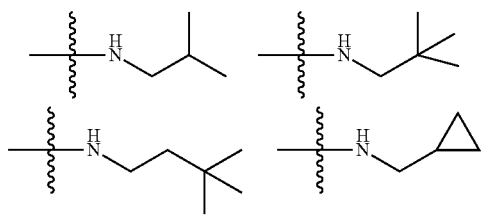

-continued

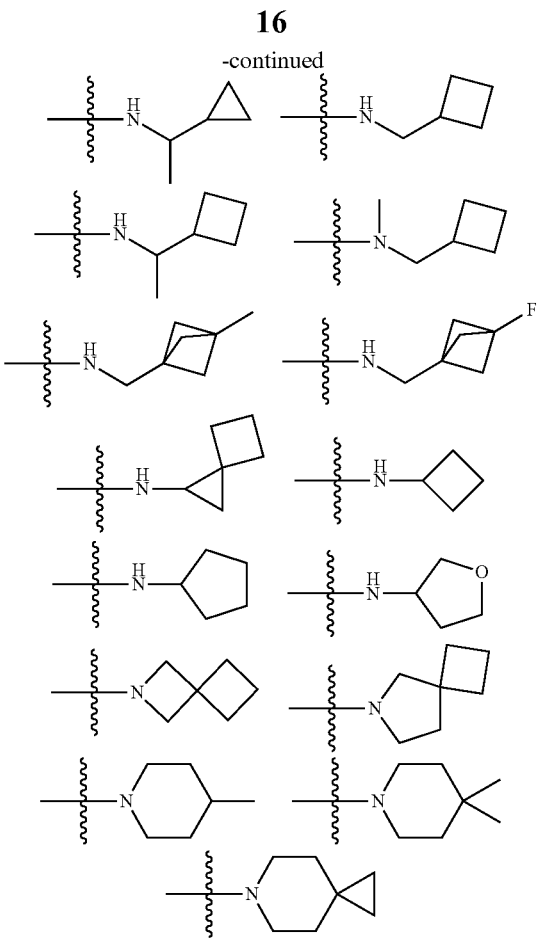

wherein -ξ- represents the point of attachment to the rest of the compound.

Ar¹

In the compounds of the invention, Ar¹ is a 6-membered aryl or 5- or 6-membered heteroaryl group, selected from (Ar^{1a}), (Ar^{1b}) and (Ar^{1c}) as defined hereinabove.

According to one embodiment, Ar¹ is a 6-membered aryl group (Ar^{1a}):

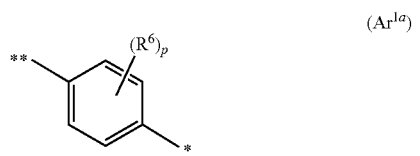

wherein:
p is 0, 1, 2, 3 or 4; preferably p is 0 or 1; more preferably p is 0;
R⁶ is $C_{1-4}$-alkyl, $C_{3-6}$-cycloalkyl, $C_{1-4}$-haloalkyl, halo, or cyano; preferably R⁶ is methyl, F, Cl, or cyano;
* represents the point of attachment to the piperidine ring; and
** represents the point of attachment to the —CR⁴R⁵— moiety.

According to one embodiment, Ar¹ is a 6-membered heteroaryl group (Ar^{1b}):

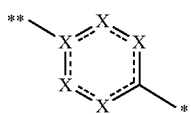

(Ar$^{1b}$)

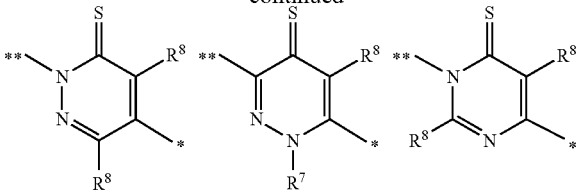

-continued wherein:
each X is independently selected from N, NR$^7$, C, CR$^8$, C(O), and C(S), wherein at least one of X is N or NR$^7$;

R$^7$ is H, C$_{1-4}$-alkyl, C$_{3-6}$-cycloalkyl, or C$_{1-4}$-haloalkyl; preferably R$^7$ is H;

R$^8$ is H, C$_{1-4}$-alkyl, C$_{3-6}$-cycloalkyl, C$_{1-4}$-haloalkyl, halo, cyano, hydroxy, C$_{1-4}$-alkoxy, or C$_{1-4}$-haloalkoxy; preferably R$^8$ is H, methyl, halo; more preferably R$^8$ is H;

- - - represents a single or double bond, depending on X;

\* represents the point of attachment to the piperidine ring; and

\*\* represents the point of attachment to the —CR$^4$R$^5$— moiety.

In one embodiment, Ar$^{1b}$ is preferably selected from:

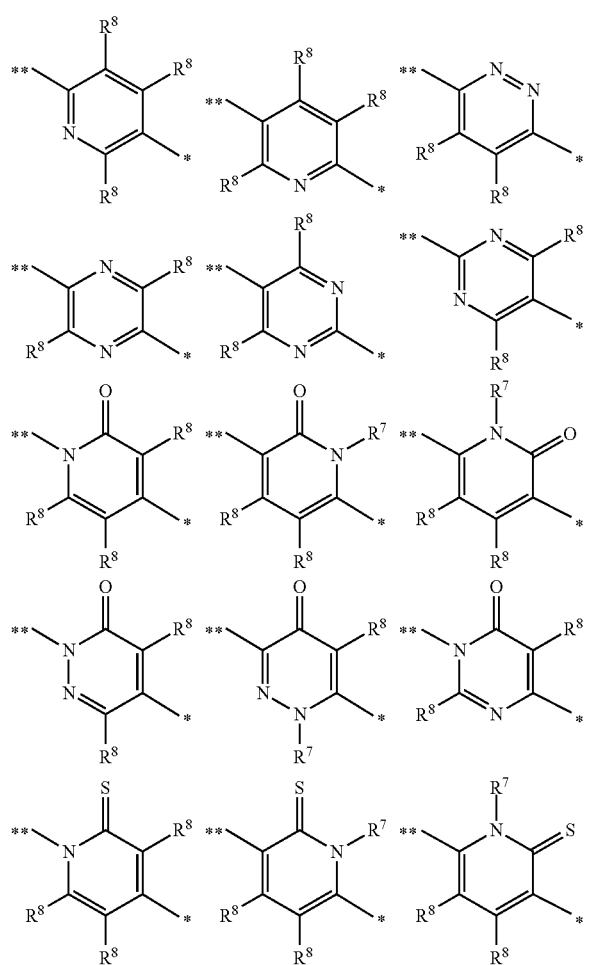

wherein:
R$^7$ is H, C$_{1-4}$-alkyl, C$_{3-6}$-cycloalkyl, or C$_{1-4}$-haloalkyl; preferably R$^7$ is H;

R$^8$ is H, C$_{1-4}$-alkyl, C$_{3-6}$-cycloalkyl, C$_{1-4}$-haloalkyl, halo, cyano, hydroxy, C$_{1-4}$-alkoxy, or C$_{1-4}$-haloalkoxy; preferably R$^8$ is H, methyl, halo; more preferably R$^8$ is H;

\* represents the point of attachment to the piperidine ring; and

\*\* represents the point of attachment to the —CR$^4$R$^5$— moiety.

According to one embodiment, Ar$^1$ is a 5-membered heteroaryl group (Ar$^{1c}$):

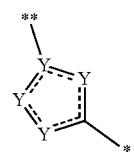

(AR$^{1c}$)

wherein:
each Y is independently selected from N, NR$^9$, S, O, C, CR$^{10}$, C(O), and C(S), wherein at least one of Y is N, NR$^9$, S, or O;

R$^9$ is H, C$_{1-4}$-alkyl, C$_{3-6}$-cycloalkyl, or C$_{1-4}$-haloalkyl; preferably R$^9$ is H;

R$^{10}$ is H, C$_{1-4}$-alkyl, C$_{3-6}$-cycloalkyl, C$_{1-4}$-haloalkyl, halo, cyano, hydroxy, C$_{1-4}$-alkoxy, or C$_{1-4}$-haloalkoxy; preferably R$^{10}$ is H;

- - - represents a single or double bond, depending on Y;

\* represents the point of attachment to the piperidine ring; and

\*\* represents the point of attachment to the —CR$^4$R$^5$— moiety.

According to another one embodiment, Ar$^{1c}$ is selected from:

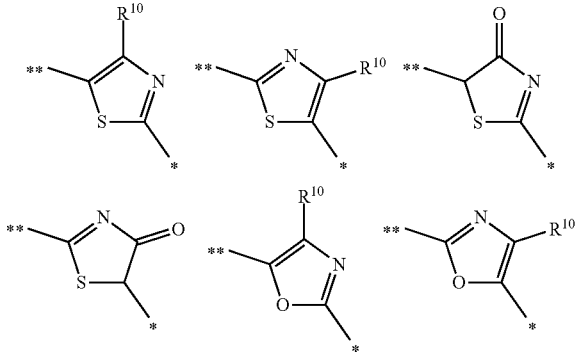

-continued

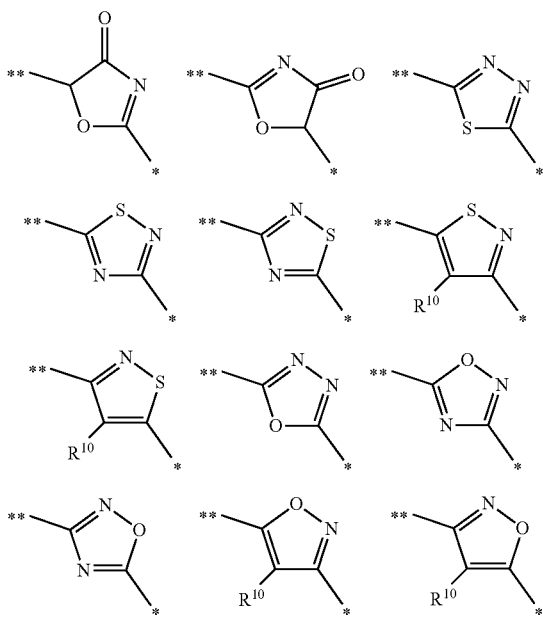

wherein:

R⁹ is H, $C_{1-4}$-alkyl, $C_{3-6}$-cycloalkyl, or $C_{1-4}$-haloalkyl; preferably R⁹ is H;

R¹⁰ is H, $C_{1-4}$-alkyl, $C_{3-6}$-cycloalkyl, $C_{1-4}$-haloalkyl, halo, cyano, hydroxy, $C_{1-4}$-alkoxy, or $C_{1-4}$-haloalkoxy; preferably R¹⁰ is H;

\* represents the point of attachment to the piperidine ring; and

\*\* represents the point of attachment to the —CR⁴R⁵— moiety.

According to one embodiment, Ar¹ is selected from:

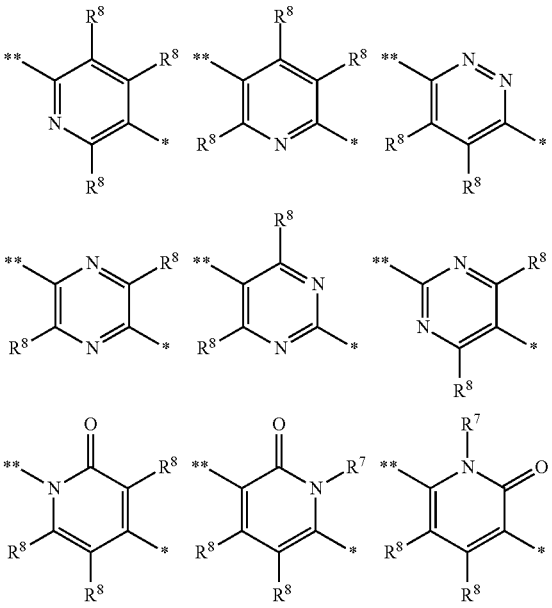

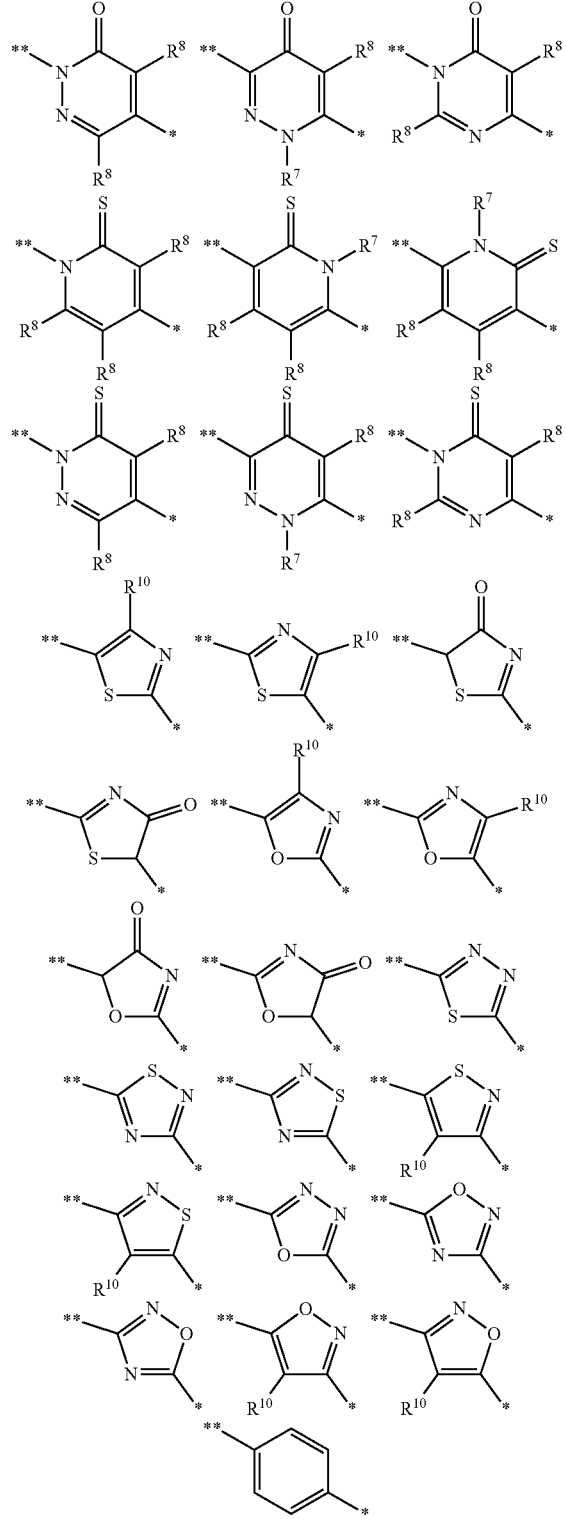

wherein:

R⁷ is H, $C_{1-4}$-alkyl, $C_{3-6}$-cycloalkyl, or $C_{1-4}$-haloalkyl; preferably R⁷ is H;

R⁸ is H, $C_{1-4}$-alkyl, $C_{3-6}$-cycloalkyl, $C_{1-4}$-haloalkyl, halo, cyano, hydroxy, $C_{1-4}$-alkoxy, or $C_{1-4}$-haloalkoxy; preferably R⁸ is H, methyl, halo; more preferably R⁸ is H;

$R^9$ is H, $C_{1-4}$-alkyl, $C_{3-6}$-cycloalkyl, or $C_{1-4}$-haloalkyl; preferably $R^9$ is H;

$R^{10}$ is H, $C_{1-4}$-alkyl, $C_{3-6}$-cycloalkyl, $C_{1-4}$-haloalkyl, halo, cyano, hydroxy, $C_{1-4}$-alkoxy, or $C_{1-4}$-haloalkoxy; preferably $R^{10}$ is H;

* represents the point of attachment to the piperidine ring; and
** represents the point of attachment to the —$CR^4R^5$— moiety.

$R^4$, $R^5$

According to one embodiment, $R^4$ and $R^5$ are each independently H, $C_{1-4}$-alkyl, $C_{1-4}$-haloalkyl, $C_{3-6}$-cycloalkyl, halo, cyano or hydroxy; preferably $R^4$ and $R^5$ are each independently H, $C_{1-4}$-alkyl, $C_{1-4}$-haloalkyl, $C_{3-6}$-cycloalkyl; more preferably $R^4$ and $R^5$ are each independently H, methyl, ethyl, $CF_3$, cyclopropyl. In one preferred embodiment, $R^4$ and $R^5$ are both H, or one is H and the other is methyl.

According to another embodiment, $R^4$ and $R^5$ form together with the carbon atom to which they are attached:
- a heterocyclyl ring or a $C_{3-4}$-cycloalkyl ring, in which the heterocyclyl and cycloalkyl moieties are optionally substituted by one or more substituent selected from $C_{1-4}$-alkyl, $C_{3-6}$-cycloalkyl, $C_{1-4}$-haloalkyl, halo, or cyano; or
- an ethylenyl group.

In one embodiment, $R^4$ and $R^5$ form together with the carbon atom to which they are attached a group selected from oxetane, cyclopropyl, cyclobutyl optionally substituted by one or two halo substituents (preferably fluoro), azetidine optionally substituted by $C_{1-4}$-alkyl (preferably methyl), and ethylenyl. In one preferred embodiment, $R^4$ and $R^5$ form together with the carbon atom to which they are attached a group selected from oxetane, cyclopropyl, and ethylenyl. In one more preferred embodiment, $R^4$ and $R^5$ form together with the carbon atom to which they are attached an oxetane group.

In another preferred embodiment, $R^4$ and $R^5$ are both H; or one is H and the other is methyl; or $R^4$ and $R^5$ form together with the carbon atom to which they are attached an oxetane group.

Linker L

According to one embodiment, L is selected from amide or thioamide ($L^1$), retro-amide or retro-thioamide ($L^2$) and 5-membered heteroaryl ($L^3$) as defined hereinabove.

According to one embodiment, L is an amide link ($L^{1a}$), corresponding to $L^1$ wherein $X^1$ is O:

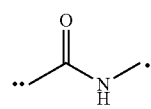

(L$^{1a}$)

wherein:
• represents the point of attachment to the —$CR^4R^5$— moiety; and
** represents the point of attachment to $Ar^2$.

According to one embodiment, L is a retro-amide link ($L^{2a}$), corresponding to $L^2$ wherein $X^1$ is O:

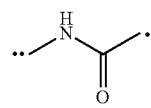

(L$^{2a}$)

wherein:
• represents the point of attachment to the —$CR^4R^5$— moiety; and
** represents the point of attachment to $Ar^2$.

According to one embodiment, L is a 5-membered heteroaryl link ($L^3$):

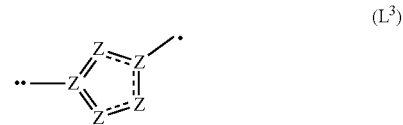

(L$^3$)

wherein:
each Z is independently selected from N, $NR^{11}$, S, O, C, $CR^{12}$, C(O), and C(S), wherein at least one of Z is N, $NR^{11}$, S, or O;

$R^{11}$ is H, $C_{1-4}$-alkyl, $C_{3-6}$-cycloalkyl, or $C_{1-4}$-haloalkyl;

$R^{12}$ is H, $C_{1-4}$-alkyl, $C_{3-6}$-cycloalkyl, $C_{1-4}$-haloalkyl, halo, cyano, hydroxy, $C_{1-4}$-alkoxy, or $C_{1-4}$-haloalkoxy;

- - - represents a single or double bond, depending on Z;

• represents the point of attachment to the —$CR^4R^5$— moiety; and
** represents the point of attachment to $Ar^2$.

According to one embodiment, $L^3$ is selected from:

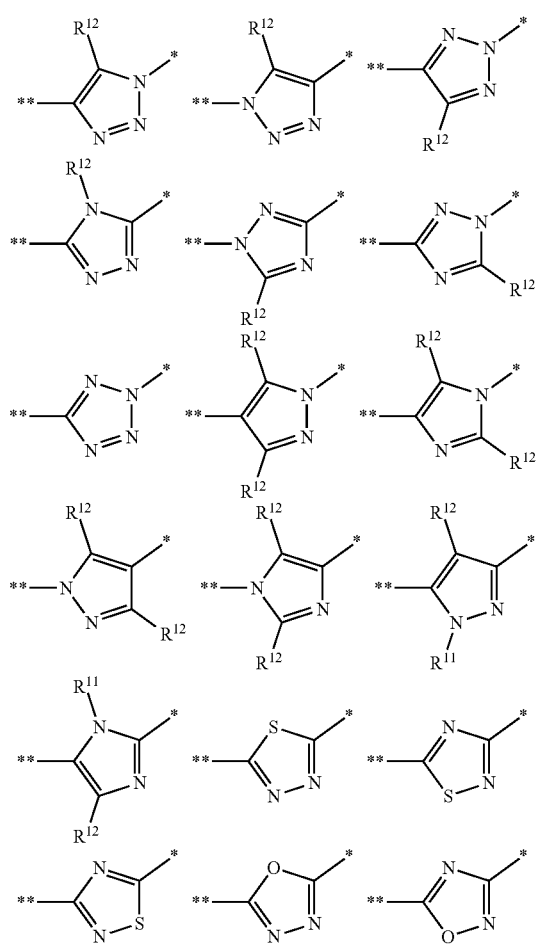

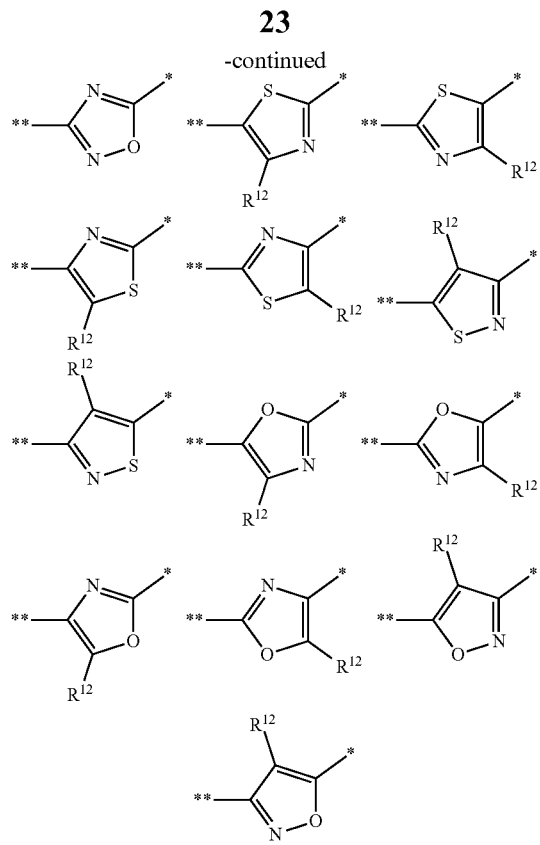

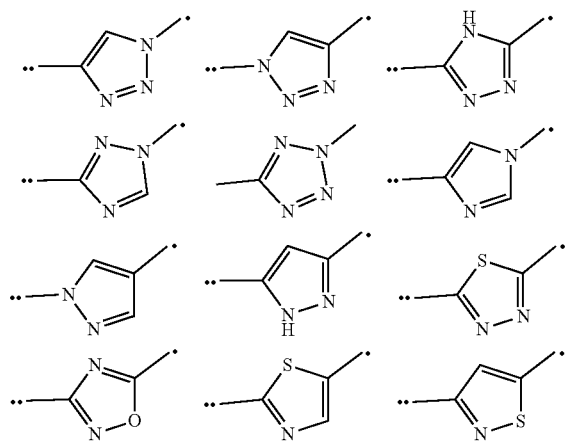

wherein:
- each $R^{11}$ is independently H, $C_{1-4}$-alkyl, $C_{3-6}$-cycloalkyl, or $C_{1-4}$-haloalkyl;
- preferably $R^{11}$ is H or methyl; more preferably $R^{11}$ is H;
- each $R^{12}$ is independently H, $C_{1-4}$-alkyl, $C_{3-6}$-cycloalkyl, $C_{1-4}$-haloalkyl, halo, cyano, hydroxy, $C_{1-4}$-alkoxy, or $C_{1-4}$-haloalkoxy; preferably $R^{12}$ is H, methyl, halo, cyano or methoxy; more preferably $R^{12}$ is H;
- * represents the point of attachment to the —$CR^4R^5$— moiety; and
- ** represents the point of attachment to $Ar^2$.

According to one preferred embodiment, $L^3$ is selected from:

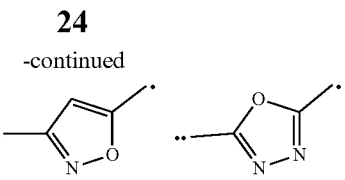

wherein:
- * represents the point of attachment to the —$CR^4R^5$— moiety; and
- ** represents the point of attachment to $Ar^2$.

According to one preferred embodiment, $L^3$ is selected from:

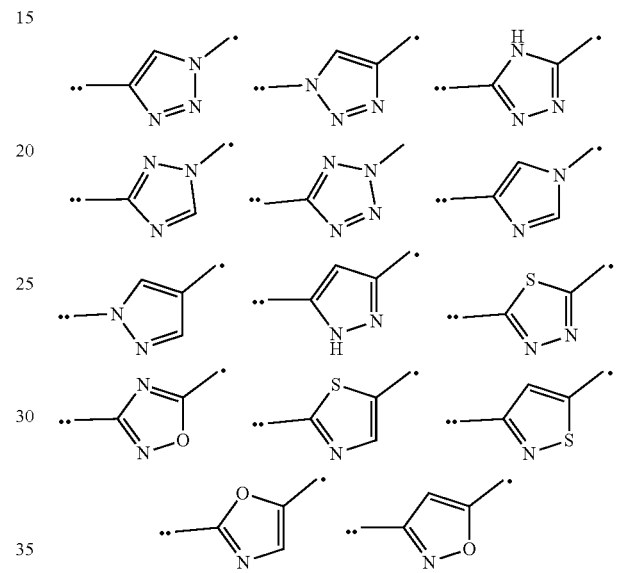

wherein:
- * represents the point of attachment to the —$CR^4R^5$— moiety; and
- ** represents the point of attachment to $Ar^2$.

According to one embodiment, L is selected from:

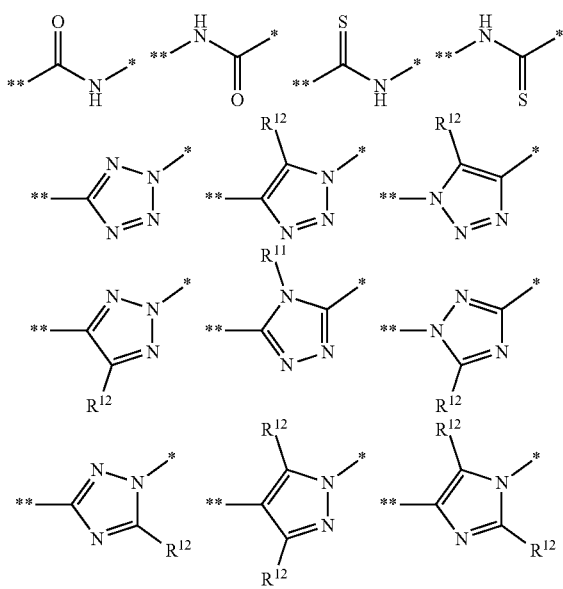

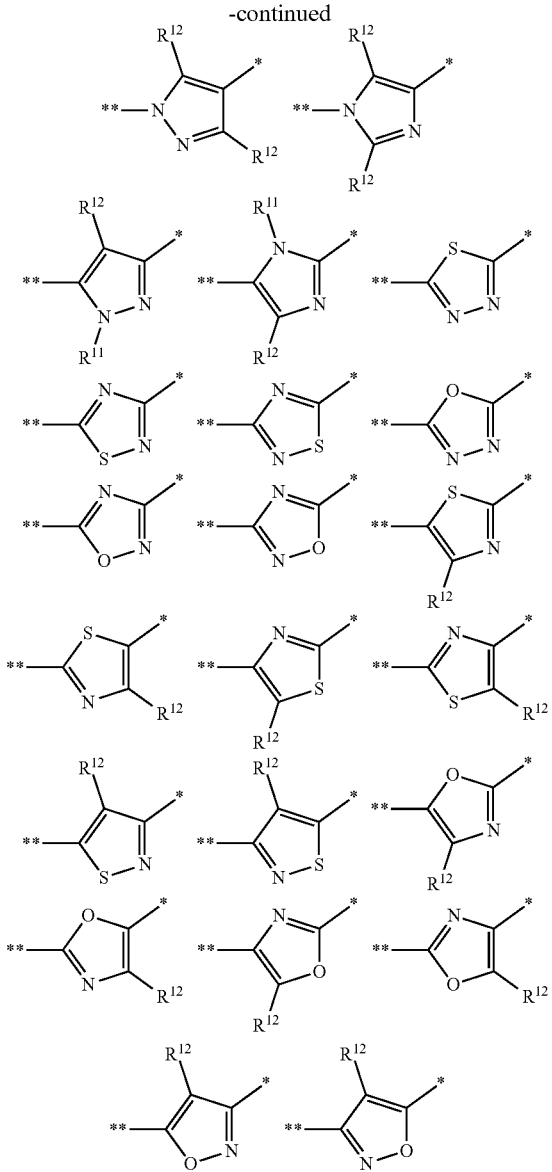

wherein:
each $R^{11}$ is independently H, $C_{1-4}$-alkyl, $C_{3-6}$-cycloalkyl, or $C_{1-4}$-haloalkyl;
preferably $R^{11}$ is H or methyl; more preferably $R^{11}$ is H;
each $R^{12}$ is independently H, $C_{1-4}$-alkyl, $C_{3-6}$-cycloalkyl, $C_{1-4}$-haloalkyl, halo, cyano, hydroxy, $C_{1-4}$-alkoxy, or $C_{1-4}$-haloalkoxy; preferably $R^{12}$ is H, methyl, halo, cyano or methoxy; more preferably $R^{12}$ is H;
• represents the point of attachment to the —$CR^4R^5$— moiety; and
•• represents the point of attachment to $Ar^2$.

According to one embodiment, L is preferably selected from:

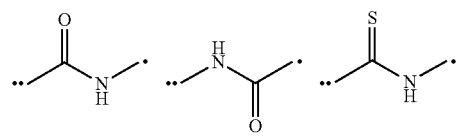

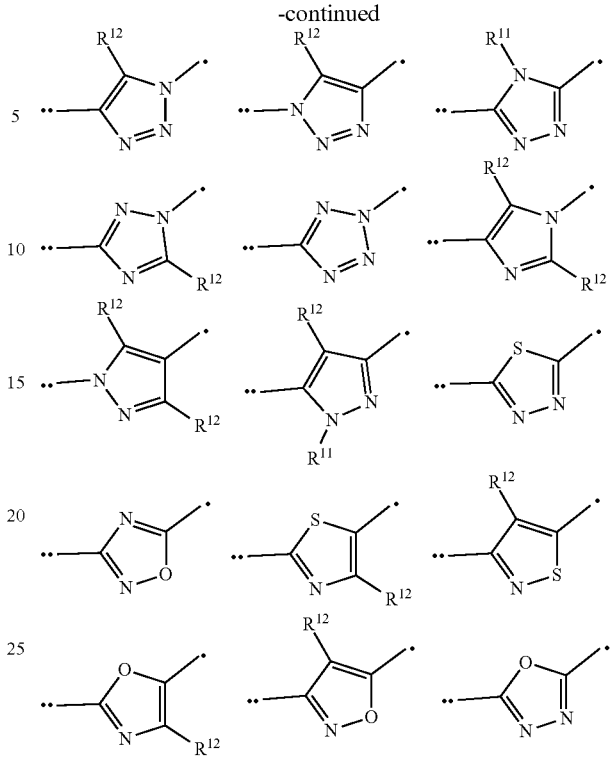

each $R^{11}$ is independently H, $C_{1-4}$-alkyl, $C_{3-6}$-cycloalkyl, or $C_{1-4}$-haloalkyl;
preferably $R^{11}$ is H or methyl; more preferably $R^{11}$ is H;
each $R^{12}$ is independently H, $C_{1-4}$-alkyl, $C_{3-6}$-cycloalkyl, $C_{1-4}$-haloalkyl, halo, cyano, hydroxy, $C_{1-4}$-alkoxy, or $C_{1-4}$-haloalkoxy; preferably $R^{12}$ is H, methyl, halo, cyano or methoxy; more preferably $R^{12}$ is H;
• represents the point of attachment to the —$CR^4R^5$— moiety; and
•• represents the point of attachment to $Ar^2$.

According to one embodiment, L is preferably selected from:

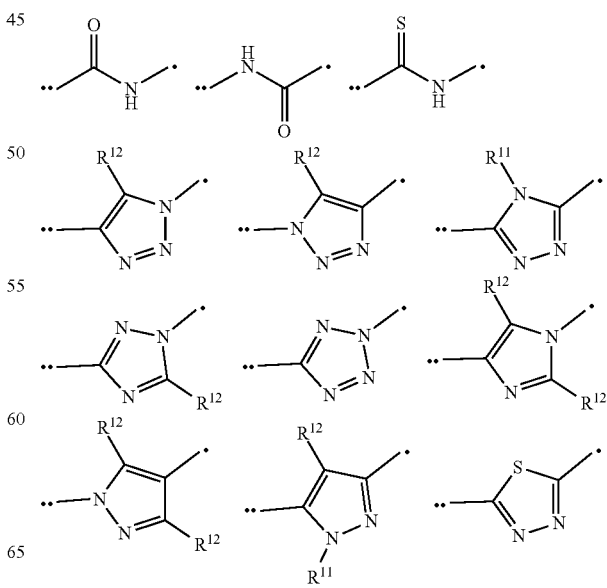

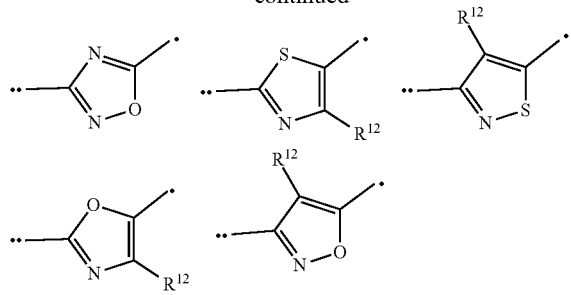

each $R^{11}$ is independently H, $C_{1-4}$-alkyl, $C_{3-6}$-cycloalkyl, or $C_{1-4}$-haloalkyl;
preferably $R^{11}$ is H or methyl; more preferably $R^{11}$ is H;
each $R^{12}$ is independently H, $C_{1-4}$-alkyl, $C_{3-6}$-cycloalkyl, $C_{1-4}$-haloalkyl, halo, cyano, hydroxy, $C_{1-4}$-alkoxy, or $C_{1-4}$-haloalkoxy; preferably $R^{12}$ is H, methyl, halo, cyano or methoxy; more preferably $R^{12}$ is H;
• represents the point of attachment to the —$CR^4R^5$— moiety; and
•• represents the point of attachment to $Ar^2$.

$Ar^2$

In the compounds of the invention, $Ar^2$ is a 5- to 10-membered, mono- or bicyclo-, aryl or heteroaryl group, optionally substituted by one or more substituent selected preferably from halo, cyano, oxo, hydroxy, amino, $C_{1-4}$-alkylamino, $C_{1-4}$-haloalkylamino, di($C_{1-4}$-alkyl)amino, di($C_{1-4}$-haloalkyl)amino, N—($C_{1-4}$-alkyl)-N—($C_{1-4}$-haloalkyl)amino, $C_{1-4}$-alkoxy, $C_{1-4}$-haloalkoxy, $C_{3-6}$-cycloalkyloxy, ($C_{1-4}$-alkyl)aminocarbonyl, ($C_{1-4}$-haloalkyl)aminocarbonyl, di($C_{1-4}$-alkyl)aminocarbonyl, di($C_{1-4}$-haloalkyl)aminocarbonyl, N—($C_{1-4}$-alkyl)-N—($C_{1-4}$-haloalkyl)aminocarbonyl, $C_{1-4}$-alkyl, $C_{1-4}$-haloalkyl, $C_{3-6}$-cycloalkyl, $C_{2-4}$-alkynyl, $C_{6-10}$-aryl, heteroaryl, and heterocyclyl; wherein the substituents are optionally substituted by one or more group selected preferably from halo, cyano, oxo, hydroxy, $C_{1-4}$-alkyl, $C_{1-4}$-haloalkyl, $C_{3-6}$-cycloalkyl, $C_{1-4}$-alkoxy, $C_{1-4}$-haloalkoxy, amino, $C_{1-4}$-alkylamino, $C_{1-4}$-haloalkylamino, di($C_{1-4}$-alkyl)amino, di($C_{1-4}$-haloalkyl)amino, N—($C_{1-4}$-alkyl)-N—($C_{1-4}$-haloalkyl)amino; or fused to the heterocyclyl substituent may be one or more $C_{3-6}$-cycloalkyl or heterocyclyl group; or spiro-fused to the heterocyclyl substituent may be one or more $C_{3-6}$-cycloalkyl or heterocyclyl group optionally substituted by one or more halo.

In the compounds of the invention, $Ar^2$ is a 5- to 10-membered, mono- or bicyclo-, aryl or heteroaryl group, optionally substituted by one or more substituent selected preferably from halo, cyano, oxo, hydroxy, amino, $C_{1-4}$-alkylamino, $C_{1-4}$-haloalkylamino, di($C_{1-4}$-alkyl)amino, di($C_{1-4}$-haloalkyl)amino, N—($C_{1-4}$-alkyl)-N—($C_{1-4}$-haloalkyl)amino, $C_{1-4}$-alkoxy, $C_{1-4}$-haloalkoxy, ($C_{1-4}$-alkyl)aminocarbonyl, ($C_{1-4}$-haloalkyl)aminocarbonyl, di($C_{1-4}$-alkyl)aminocarbonyl, di($C_{1-4}$-haloalkyl)aminocarbonyl, N—($C_{1-4}$-alkyl)-N—($C_{1-4}$-haloalkyl)aminocarbonyl, $C_{1-4}$-alkyl, $C_{1-4}$-haloalkyl, $C_{3-6}$-cycloalkyl, $C_{6-10}$-aryl, heteroaryl, and heterocyclyl; wherein the substituents are optionally substituted by one or more group selected preferably from halo, cyano, oxo, hydroxy, $C_{1-4}$-alkyl, $C_{1-4}$-haloalkyl, $C_{1-4}$-alkoxy, $C_{1-4}$-haloalkoxy, amino, $C_{1-4}$-alkylamino, $C_{1-4}$-haloalkylamino, di($C_{1-4}$-alkyl)amino, di($C_{1-4}$-haloalkyl)amino, N—($C_{1-4}$-alkyl)-N—($C_{1-4}$-haloalkyl)amino; or fused to the heterocyclyl substituent may be one or more $C_{3-6}$-cycloalkyl or heterocyclyl group; or spiro-fused to the heterocyclyl substituent may be one or more $C_{3-6}$-cycloalkyl or heterocyclyl group optionally substituted by one or more halo.

According to one embodiment, $Ar^2$ is selected from:

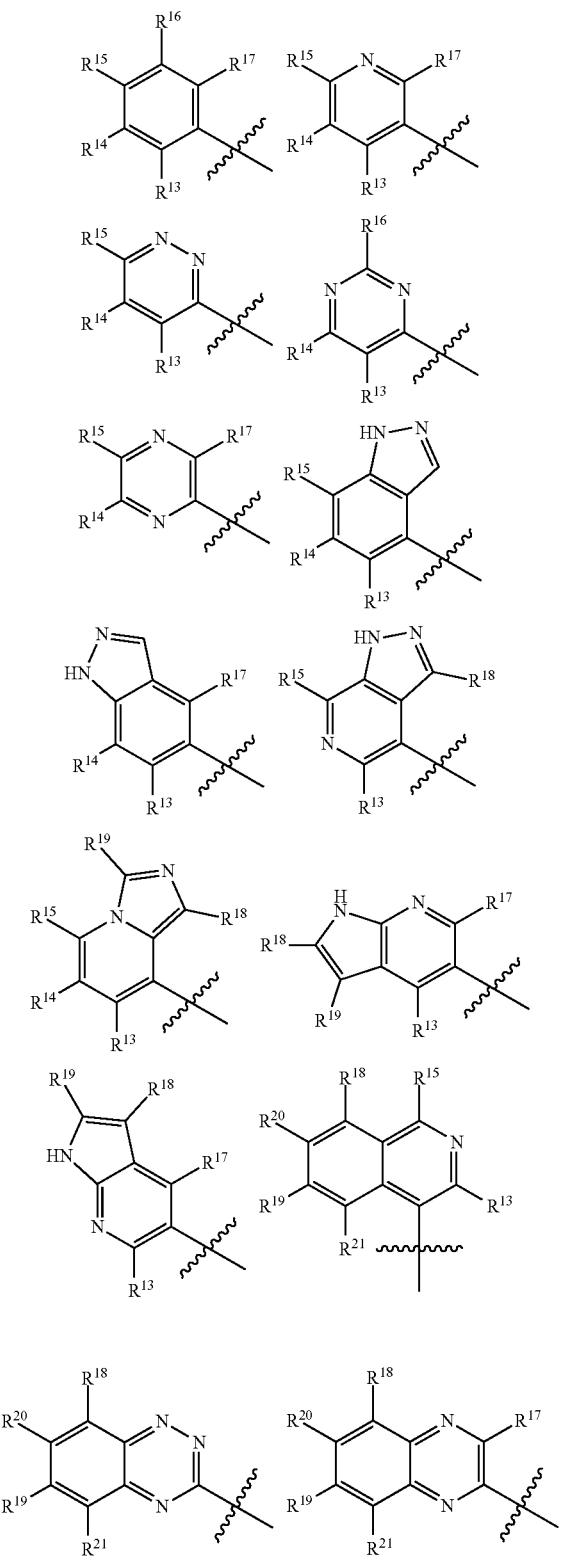

-continued

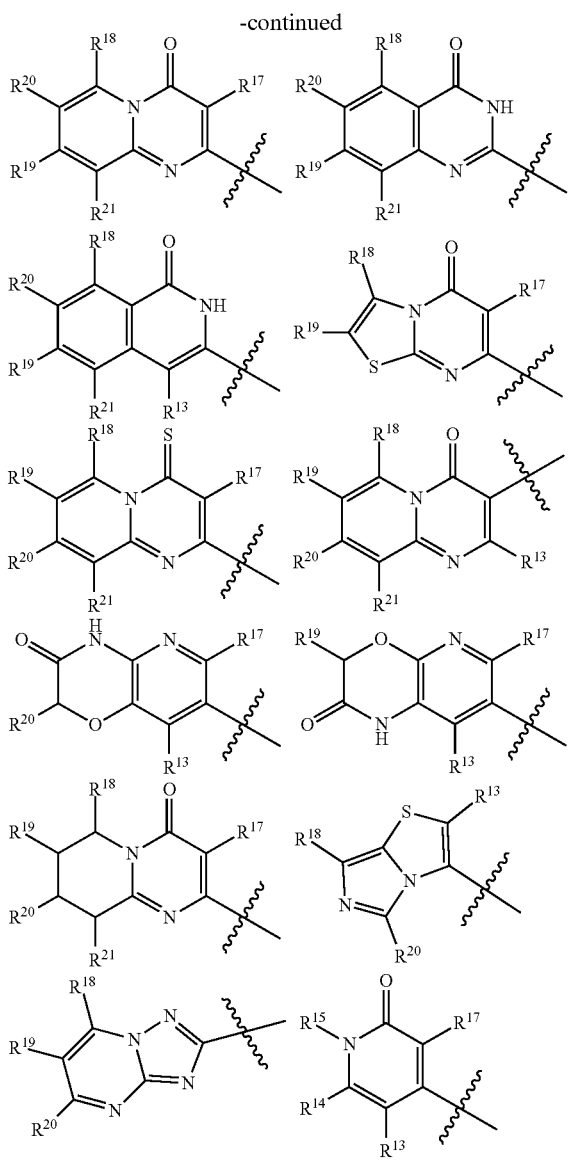

wherein $R^{13}$, $R^{14}$, $R^{15}$, $R^{16}$, $R^{17}$, $R^{18}$, $R^{19}$, $R^{20}$, and $R^{21}$, are each independently selected from H, halo, cyano, oxo, hydroxy, amino, $C_{1-4}$-alkylamino, $C_{1-4}$-haloalkylamino, di($C_{1-4}$-alkyl)amino, di($C_{1-4}$-haloalkyl)amino,
N—($C_{1-4}$-alkyl)-N—($C_{1-4}$-haloalkyl)amino, $C_{1-4}$-alkoxy, $C_{1-4}$-haloalkoxy,
$C_{3-6}$-cycloalkyloxy, ($C_{1-4}$-alkyl)aminocarbonyl, ($C_{1-4}$-haloalkyl)aminocarbonyl,
di($C_{1-4}$-alkyl)aminocarbonyl, di($C_{1-4}$-haloalkyl)aminocarbonyl,
N—($C_{1-4}$-alkyl)-N—($C_{1-4}$-haloalkyl)aminocarbonyl, $C_{1-4}$-alkyl, $C_{1-4}$-haloalkyl,
$C_{3-6}$-cycloalkyl, $C_{2-4}$-alkynyl, $C_{6-10}$-aryl, heteroaryl, and heterocyclyl; wherein these substituents are optionally substituted by one or more group selected preferably from halo, cyano, oxo, hydroxy, $C_{1-4}$-alkyl, $C_{1-4}$-haloalkyl, $C_{3-6}$-cycloalkyl,
$C_{1-4}$-alkoxy, $C_{1-4}$-haloalkoxy, amino, $C_{1-4}$-alkylamino, $C_{1-4}$-haloalkylamino,
di($C_{1-4}$-alkyl)amino, di($C_{1-4}$-haloalkyl)amino,
N—($C_{1-4}$-alkyl)-N—($C_{1-4}$-haloalkyl)amino; or fused to the heterocyclyl substituent may be one or more $C_{3-6}$-cycloalkyl or heterocyclyl group; or spiro-fused to the heterocyclyl substituent may be one or more $C_{3-6}$-cycloalkyl or heterocyclyl group optionally substituted by one or more halo; and ⸺ represents the point of attachment to the rest of the compound.

According to one embodiment, $Ar^2$ is selected from:

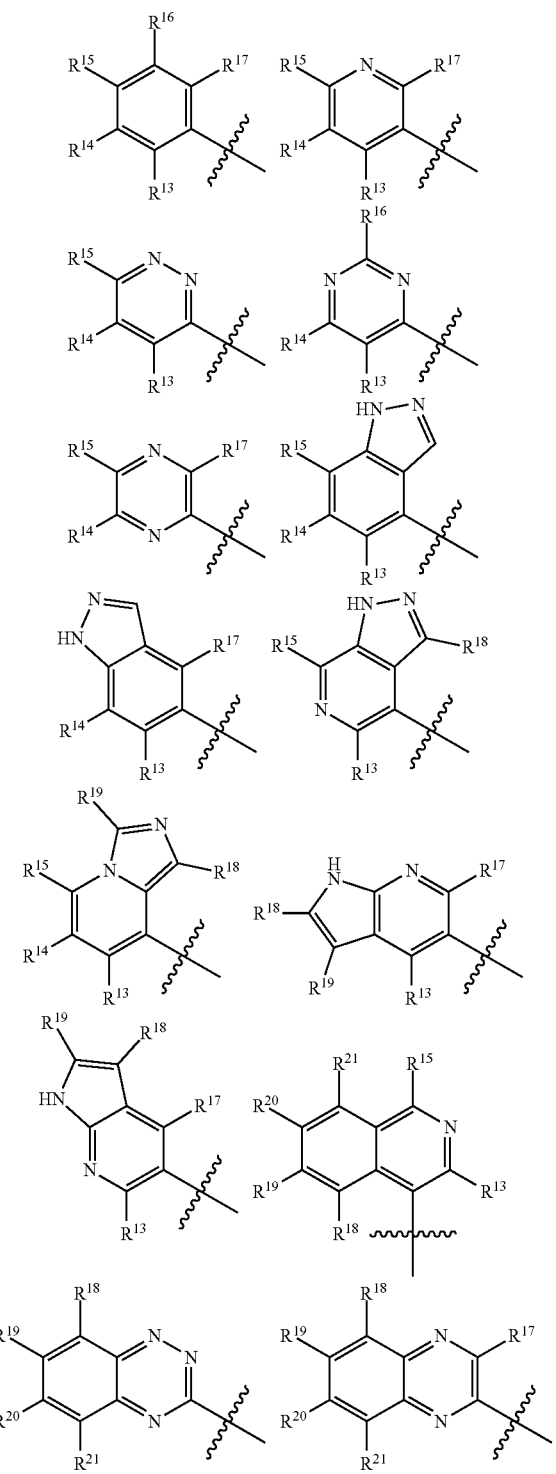

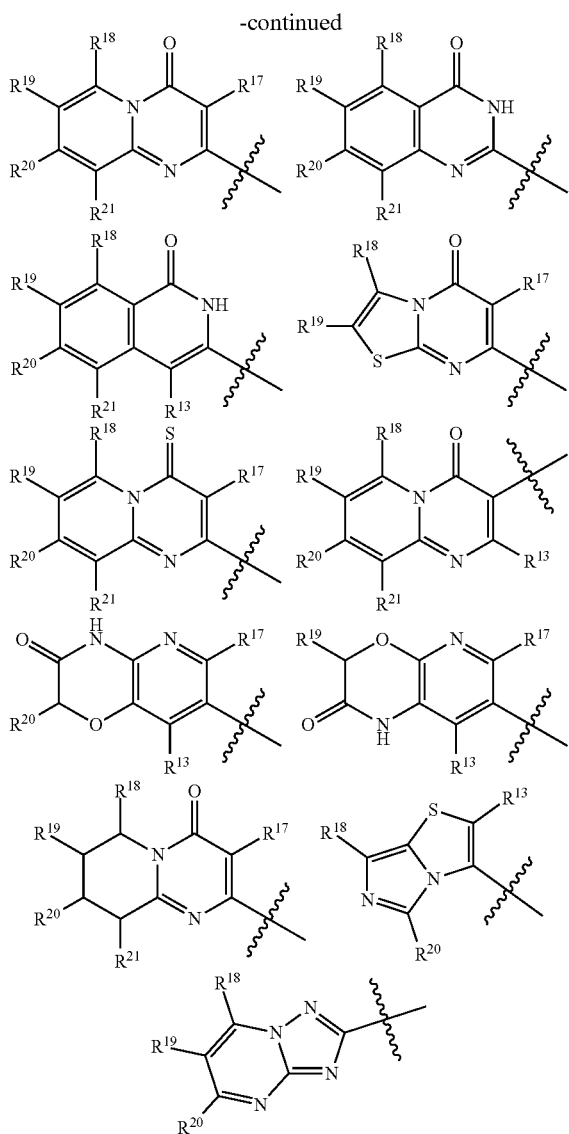

wherein $R^{13}$, $R^{14}$, $R^{15}$, $R^{16}$, $R^{17}$, $R^{18}$, $R^{19}$, $R^{20}$, and $R^{21}$, are each independently selected from H, halo, cyano, oxo, hydroxy, amino, $C_{1-4}$-alkylamino, $C_{1-4}$-haloalkylamino, di($C_{1-4}$-alkyl)amino, di($C_{1-4}$-haloalkyl)amino, N—($C_{1-4}$-alkyl)-N—($C_{1-4}$-haloalkyl)amino, $C_{1-4}$-alkoxy, $C_{1-4}$-haloalkoxy, ($C_{1-4}$-alkyl)aminocarbonyl, ($C_{1-4}$-haloalkyl)aminocarbonyl, di($C_{1-4}$-alkyl)aminocarbonyl, di($C_{1-4}$-haloalkyl)aminocarbonyl, N—($C_{1-4}$-alkyl)-N—($C_{1-4}$-haloalkyl)aminocarbonyl, $C_{1-4}$-alkyl, $C_{1-4}$-haloalkyl, $C_{3-6}$-cycloalkyl, $C_{6-10}$-aryl, heteroaryl, and heterocyclyl; wherein these substituents are optionally substituted by one or more group selected preferably from halo, cyano, oxo, hydroxy, $C_{1-4}$-alkyl, $C_{1-4}$-haloalkyl, $C_{1-4}$-alkoxy, $C_{1-4}$-haloalkoxy, amino, $C_{1-4}$-alkylamino, $C_{1-4}$-haloalkylamino, di($C_{1-4}$-alkyl)amino, di($C_{1-4}$-haloalkyl)amino, N—($C_{1-4}$-alkyl)-N—($C_{1-4}$-haloalkyl)amino; or fused to the heterocyclyl substituent may be one or more $C_{3-6}$-cycloalkyl or heterocyclyl group; or spiro-fused to the heterocyclyl substituent may be one or more $C_{3-6}$-cycloalkyl or heterocyclyl group optionally substituted by one or more halo; and ⁓ represents the point of attachment to the rest of the compound.

In one embodiment, $R^{13}$, $R^{14}$, $R^{15}$, $R^{16}$, $R^{17}$, $R^{18}$, $R^{19}$, $R^{20}$, and $R^{21}$, are preferably each independently selected from H, F, Cl, Br, cyano, hydroxy, methylamino, isopropylamino, 2-hydroxyethylamino, dimethylamino, N-methyl-N-ethylamino, N-methyl-N-(2,2,2-trifluoroethyl)amino, N-methyl-N-(trifluoromethyl)amino, methoxy, ethoxy, difluoromethoxy, trifluoromethoxy, cyclobutoxy, methyl, cyclopropylmethyl, cyclopropyl, cyclopentyl, 1-propynyl, pyrazolyl, imidazolyl, morpholinyl, azetidinyl, pyrrolidinyl, piperidinyl, 3-methyl-2-oxoimidazolidin-1-yl, 2-oxopyrrolidin-1-yl, 4 methylpiperazin-1-yl, 2-methylpyrrolidin-1-yl, 3-methylazetidin-1-yl, 3,3-difluoroazetidin-1-yl, 3-methoxyazetidin-1-yl, 3-(difluoromethyl)azetidin-1-yl, 3,3-dimethylpyrrolidin-1-yl, 3,3-difluoropyrrolidin-1-yl, 3-methylpyrrolidin-1-yl, 3-fluoropyrrolidin-1-yl, azabicyclo[3.1.0]hexan-3-yl, 2-oxa-6-azaspiro[3.3]heptan-2-yl, 2-azaspiro[3.3]heptan-2-yl, 5-azaspiro[2.3]hexan-5-yl, 1,1-difluoro-5-azaspiro[2.3]hexan-5-yl, and 5-azaspiro[2.4]heptan-5-yl.

In one embodiment, $R^{13}$, $R^{14}$, $R^{15}$, $R^{16}$, $R^{17}$, $R^{18}$, $R^{19}$, $R^{20}$, and $R^{21}$, are preferably each independently selected from H, F, Cl, Br, cyano, hydroxy, methylamino, isopropylamino, 2-hydroxyethylamino, dimethylamino, N-methyl-N-ethylamino, N-methyl-N-(2,2,2-trifluoroethyl)amino, N-methyl-N-(trifluoromethyl)amino, methoxy, ethoxy, difluoromethoxy, trifluoromethoxy, methyl, cyclopropyl, cyclopentyl, pyrazolyl, imidazolyl, morpholinyl, azetidinyl, pyrrolidinyl, piperidinyl, 3-methyl-2-oxoimidazolidin-1-yl, 2-oxopyrrolidin-1-yl, 4-methylpiperazin-1-yl, 2-methylpyrrolidin-1-yl, 3-methylazetidin-1-yl, 3,3-difluoroazetidin-1-yl, 3-methoxyazetidin-1-yl, 3-(difluoromethyl)azetidin-1-yl, 3,3-dimethylpyrrolidin-1-yl, 3,3-difluoropyrrolidin-1-yl, 3-methylpyrrolidin-1-yl, 3-fluoropyrrolidin-1-yl, azabicyclo[3.1.0]hexan-3-yl, 2-oxa-6-azaspiro[3.3]heptan-2-yl, 2-azaspiro[3.3]heptan-2-yl, 5-azaspiro[2.3]hexan-5-yl, 1,1-difluoro-5-azaspiro[2.3]hexan-5-yl, and 5-azaspiro[2.4]heptan-5-yl.

According to one embodiment, $Ar^2$ is selected from:

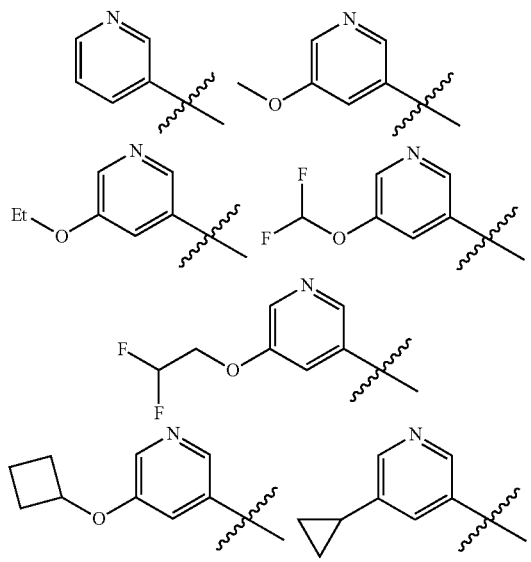

-continued
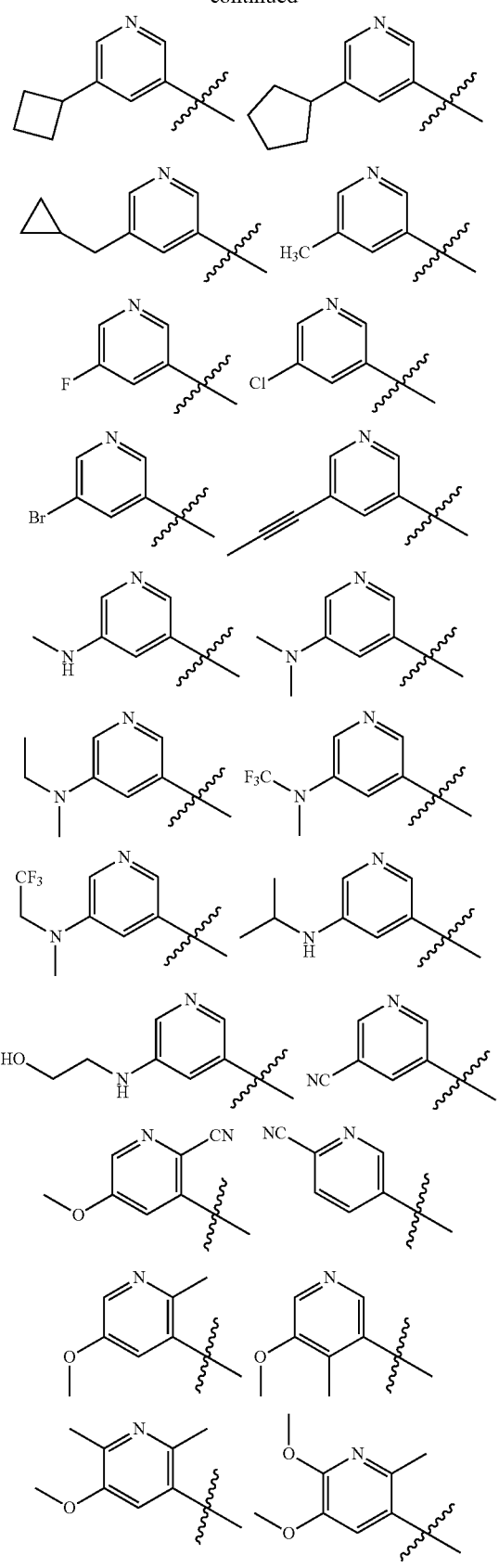
-continued
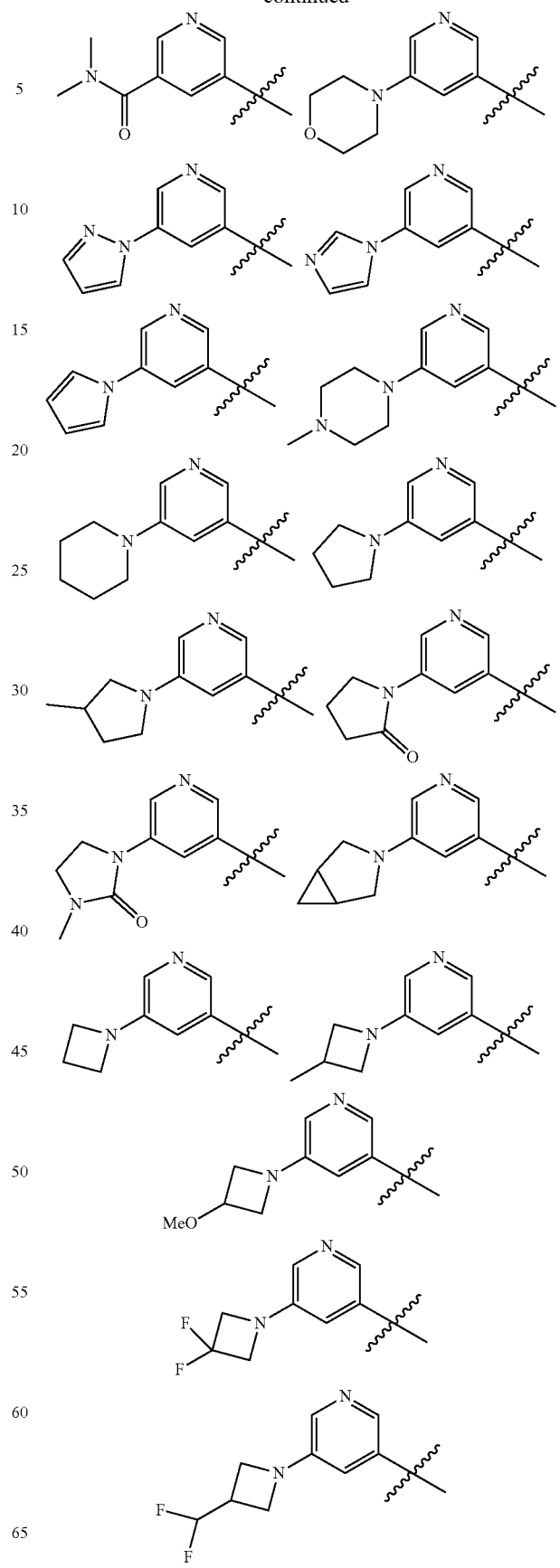

-continued
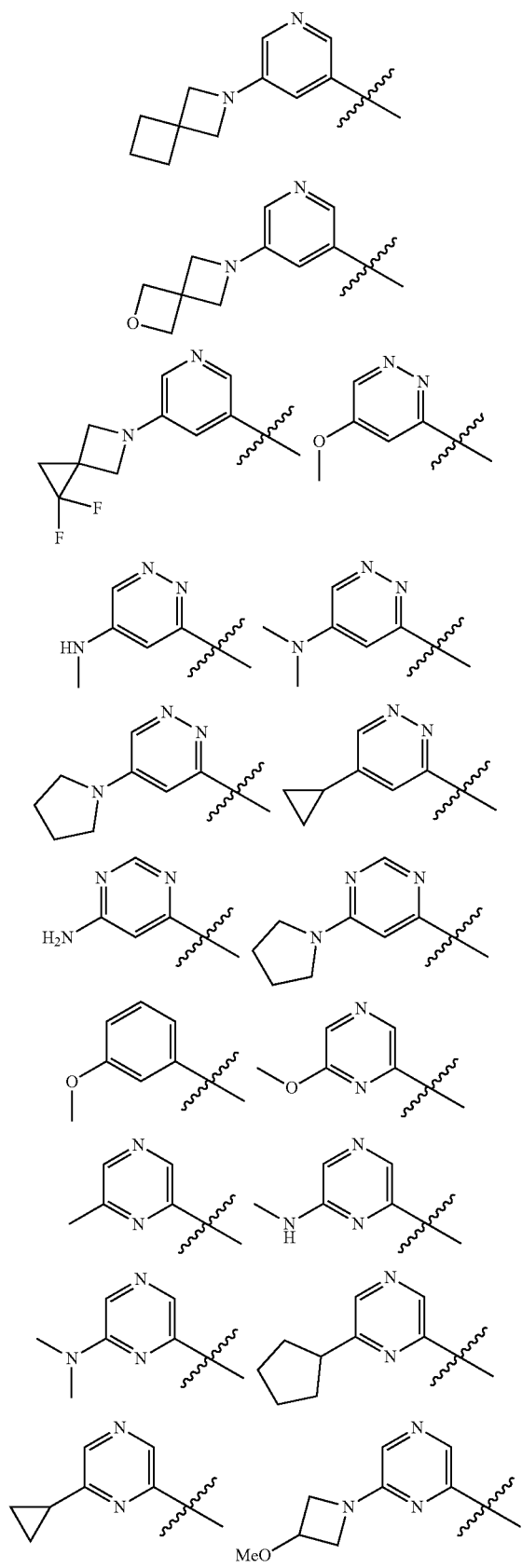
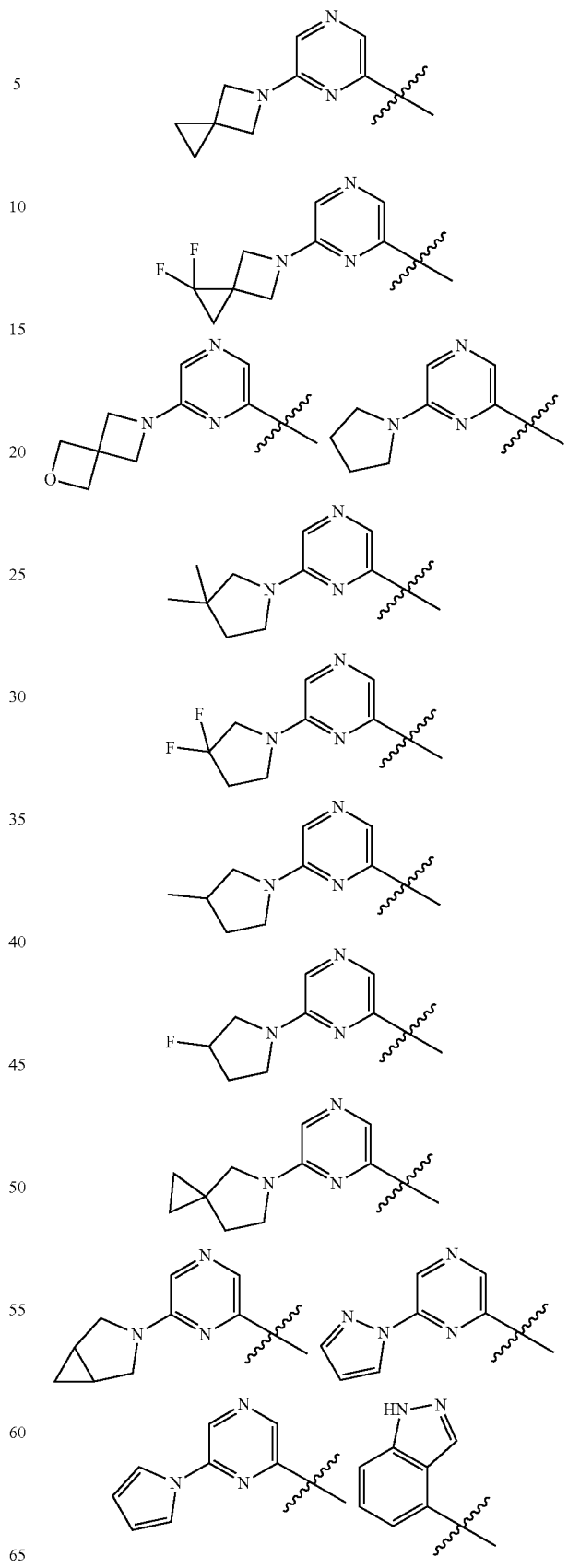

-continued
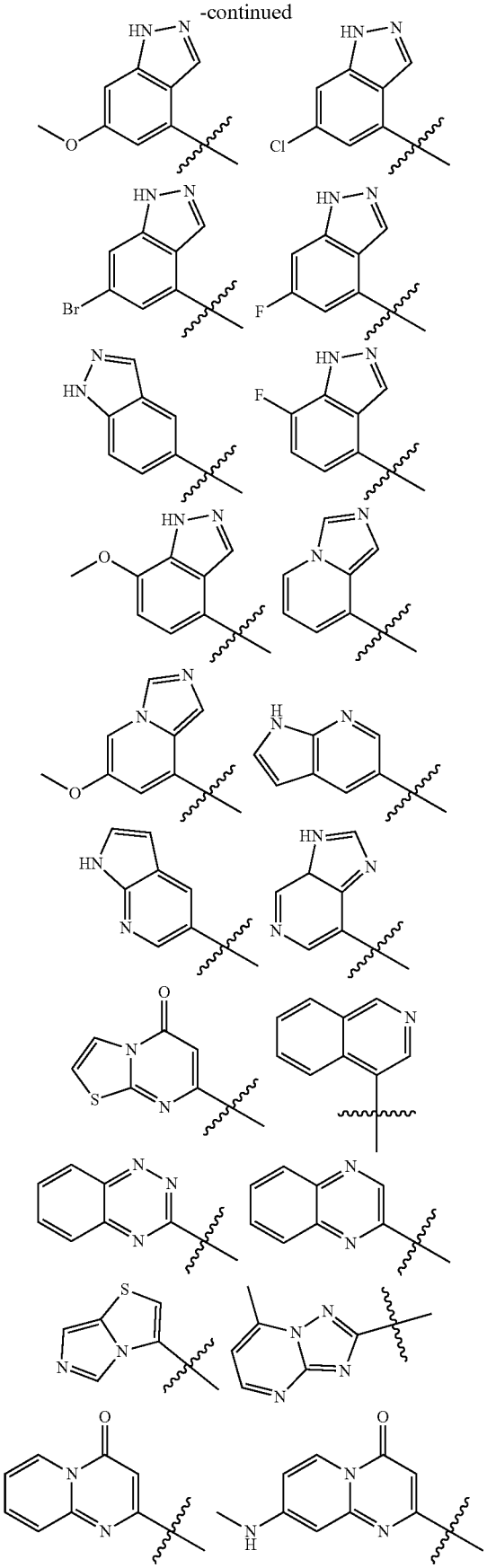
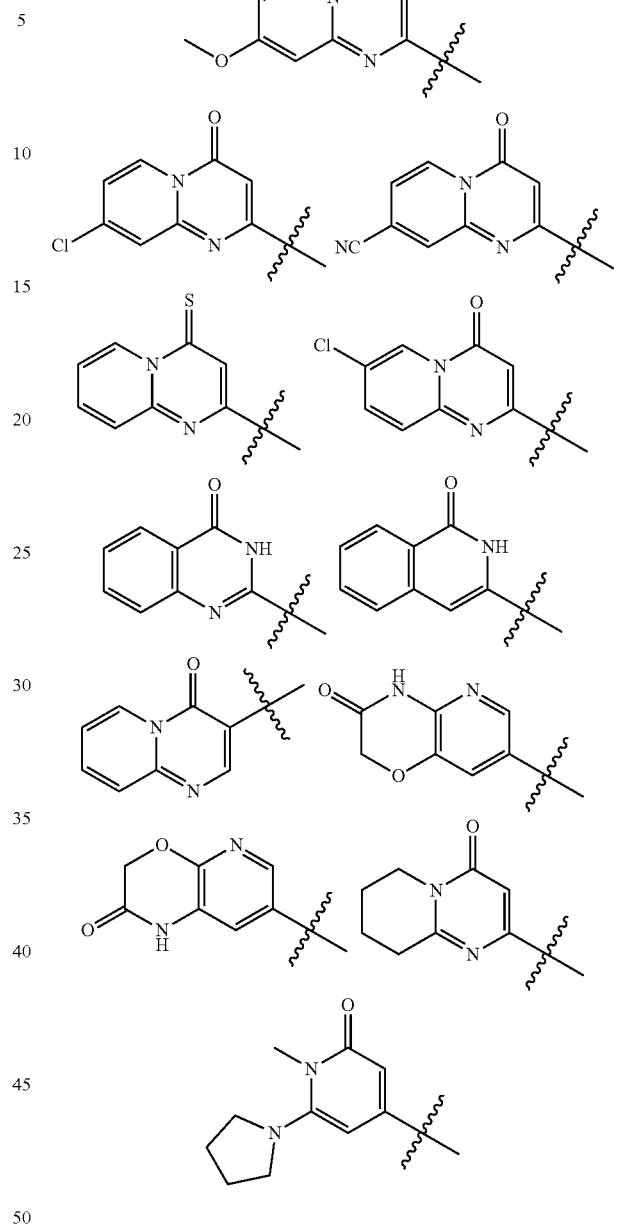
In one embodiment, the compounds of the invention are of formula (Ia):
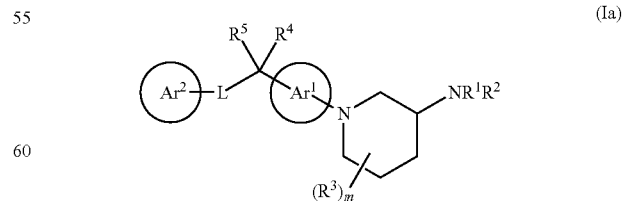
wherein m, $R^1$, $R^2$, $R^3$, $R^4$, $R^5$, L, $Ar^1$ and $Ar^2$ are as defined above.
In one embodiment, the compounds of the invention are of formula (Ia'):

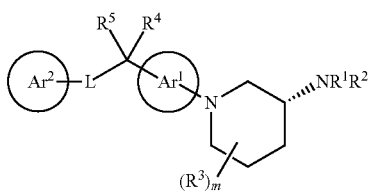
(Ia')

wherein m, $R^1$, $R^2$, $R^3$, $R^4$, $R^5$, L, $Ar^1$ and $Ar^2$ are as defined above.

In one embodiment, the compounds of the invention of formula (Ib):

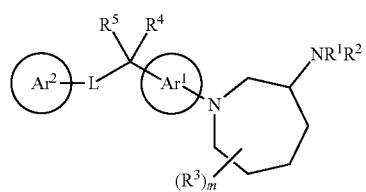
(Ib)

wherein m, $R^1$, $R^2$, $R^3$, $R^4$, $R^5$, L, $Ar^1$ and $Ar^2$ are as defined above.

In one embodiment, the compounds of the invention are of formula (I-1):

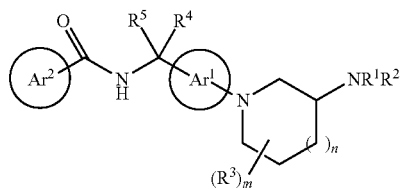
(I-1)

wherein m, n, $R^1$, $R^2$, $R^3$, $R^4$, $R^5$, $Ar^1$ and $Ar^2$ are as defined above.

In one embodiment, the compounds of the invention are of formula (I-2):

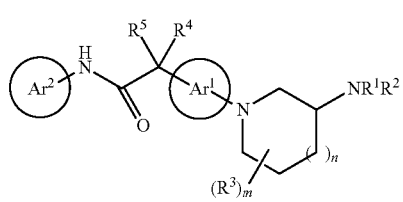
(I-2)

wherein m, n, $R^1$, $R^2$, $R^3$, $R^4$, $R^5$, $Ar^1$ and $Ar^2$ are as defined above.

In one embodiment, the compounds of the invention are of formula (I-3):

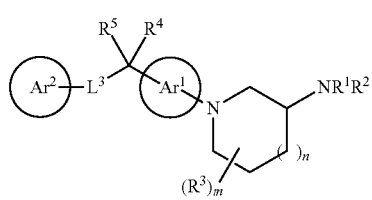
(I-3)

wherein m, n, $R^1$, $R^2$, $R^3$, $R^4$, $R^5$, $L^3$, $Ar^1$ and $Ar^2$ are as defined above.

In one embodiment, in formula (I-3), $L^3$ is preferably selected from:

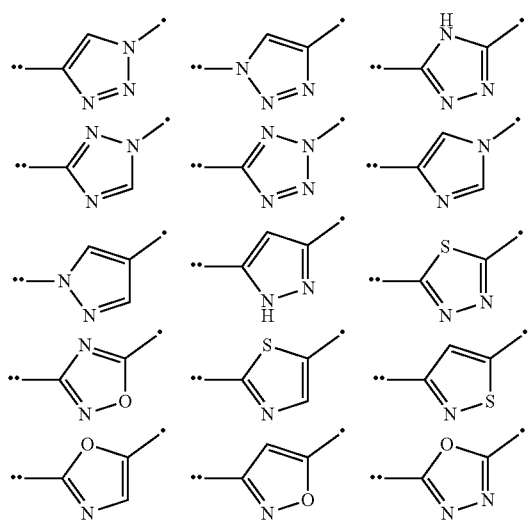

wherein • represents the point of attachment to the —$CR^4R^5$— moiety; and •• represents the point of attachment to $Ar^2$.

In one embodiment, in formula (I-3), $L^3$ is preferably selected from:

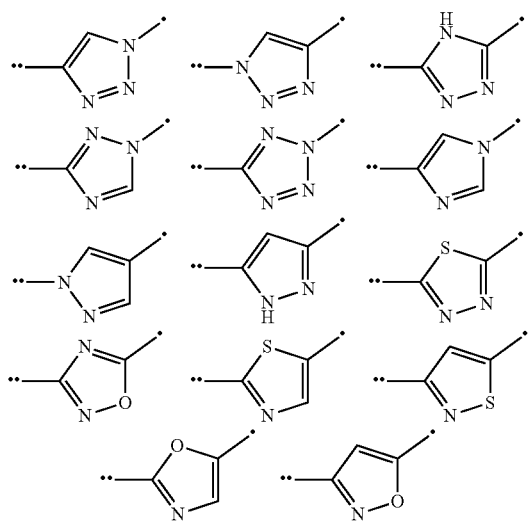

wherein • represents the point of attachment to the —$CR^4R^5$— moiety; and •• represents the point of attachment to $Ar^2$.

Unless otherwise specified, when it is referred to formula (I), it also encompasses any of above subformulae thereof.

According to one embodiment, the compound according to the invention is selected from those listed in Table 1:

TABLE 1

| | | |
|---|---|---|
| 001 | | (R)-N-(cyclobutylmethyl)-1-(6-((4-(6-methoxy-1H-indazol-4-yl)-1H-1,2,3-triazol-1-yl)methyl)pyridazin-3-yl)piperidin-3-amine |
| 002 | | (R)-N-((6-(3-((cyclobutylmethyl)amino)piperidin-1-yl)pyridazin-3-yl)methyl)-4-oxo-4H-pyrido[1,2-a]pyrimidine-2-carboxamide |
| 003 | | (R)-N-(cyclobutylmethyl)-1-(6-((4-(imidazo[1,5-a]pyridin-8-yl)-1H-1,2,3-triazol-1-yl)methyl)pyridazin-3-yl)piperidin-3-amine |
| 004 | | (R)-N-((6-(3-((cyclobutylmethyl)amino)piperidin-1-yl)pyridazin-3-yl)methyl)-5-methoxynicotinamide |
| 005 | | (R)-N-((6-(3-((cyclobutylmethyl)amino)piperidin-1-yl)pyridazin-3-yl)methyl)-6-methoxy-1H-indazole-4-carboxamide |

TABLE 1-continued

| 006 | 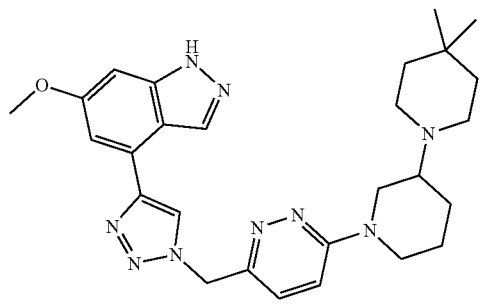 [SMILES: COc1cc(-c2cn(Cc3ccc(N4CCCC(N5CCC(C)(C)CC5)C4)nn3)nn2)c2cn[nH]c2c1] | 4-(1-((6-(4,4-dimethyl-[1,3'-bipiperidin]-1'-yl)pyridazin-3-yl)methyl)-1H-1,2,3-triazol-4-yl)-6-methoxy-1H-indazole |
| --- | --- | --- |
| 007 | 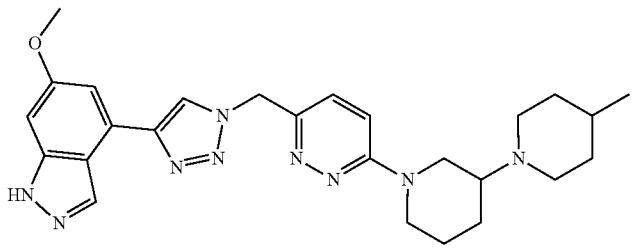 [SMILES: COc1cc(-c2cn(Cc3ccc(N4CCCC(N5CCC(C)CC5)C4)nn3)nn2)c2cn[nH]c2c1] | 6-methoxy-4-(1-((6-(4-methyl-[1,3'-bipiperidin]-1'-yl)pyridazin-3-yl)methyl)-1H-1,2,3-triazol-4-yl)-1H-indazole |
| 008 | 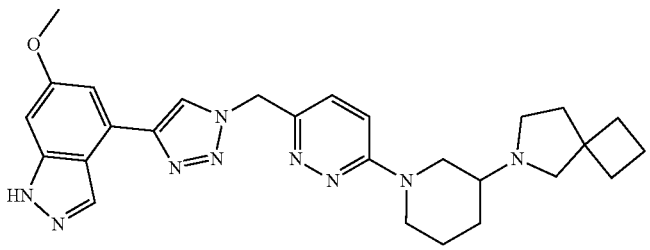 [SMILES: COc1cc(-c2cn(Cc3ccc(N4CCCC(N5CCC6(CCC6)C5)C4)nn3)nn2)c2cn[nH]c2c1] | 4-(1-((6-(3-(6-azaspiro[3.4]octan-6-yl)piperidin-1-yl)pyridazin-3-yl)methyl)-1H-1,2,3-triazol-4-yl)-6-methoxy-1H-indazole |
| 009 | 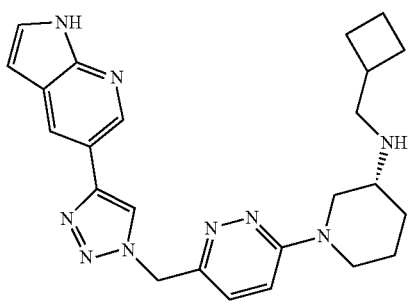 [SMILES: c1cc2cc(-c3cn(Cc4ccc(N5CCC[C@@H](NCC6CCC6)C5)nn4)nn3)cnc2[nH]1] | (R)-1-(6-((4-(1H-pyrrolo[2,3-b]pyridin-5-yl)-1H-1,2,3-triazol-1-yl)methyl)pyridazin-3-yl)-N-(cyclobutylmethyl)piperidin-3-amine |
| 010 | 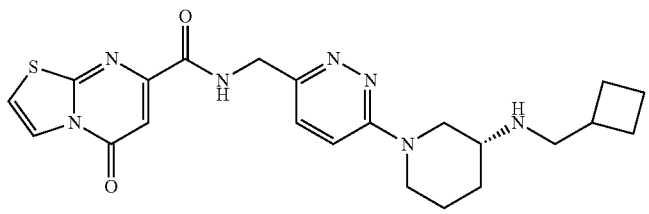 [SMILES: O=C(NCc1ccc(N2CCC[C@@H](NCC3CCC3)C2)nn1)c1cc(=O)n2ccsc2n1] | (R)-N-((6-(3-((cyclobutylmethyl)amino)piperidin-1-yl)pyridazin-3-yl)methyl)-5-oxo-5H-thiazolo[3,2-a]pyrimidine-7-carboxamide |
| 011 | 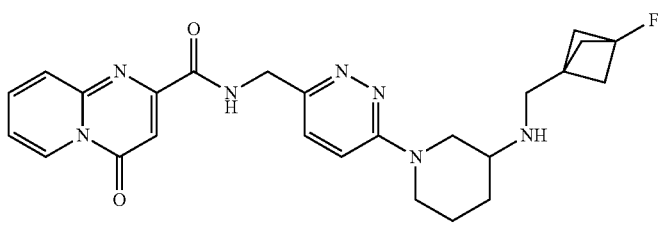 [SMILES: O=C(NCc1ccc(N2CCCC(NCC34CC(F)(C3)C4)C2)nn1)c1cc(=O)n2ccccc2n1] | N-((6-(3-(((3-fluorobicyclo[1.1.1]pentan-1-yl)methyl)amino)piperidin-1-yl)pyridazin-3-yl)methyl)-4-oxo-4H-pyrido[1,2-a]pyrimidine-2-carboxamide |

TABLE 1-continued

| 012 | 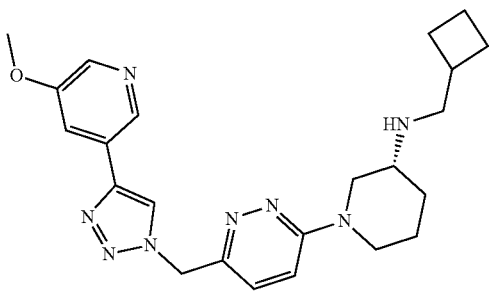 [SMILES: COc1cncc(-c2cn(Cc3ccc(N4CCC[C@@H](NCC5CCC5)C4)nn3)nn2)c1] | (R)-N-(cyclobutylmethyl)-1-(6-((4-(5-methoxypyridin-3-yl)-1H-1,2,3-triazol-1-yl)methyl)pyridazin-3-yl)piperidin-3-amine |
| 013 | 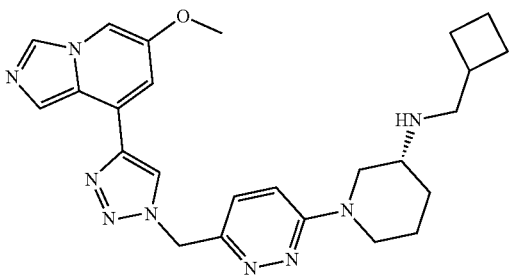 [SMILES: COc1cc(-c2cn(Cc3ccc(N4CCC[C@@H](NCC5CCC5)C4)nn3)nn2)c2cncn2c1] | (R)-N-(cyclobutylmethyl)-1-(6-((4-(6-methoxyimidazo[1,5-a]pyridin-8-yl)-1H-1,2,3-triazol-1-yl)methyl)pyridazin-3-yl)piperidin-3-amine |
| 014 | 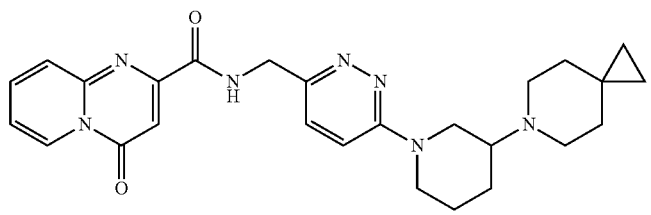 [SMILES: O=C(NCc1ccc(N2CCCC(N3CCC4(CC3)CC4)C2)nn1)c1cc(=O)n2ccccc2n1] | N-((6-(3-(6-azaspiro[2.5]octan-6-yl)piperidin-1-yl)pyridazin-3-yl)methyl)-4-oxo-4H-pyrido[1,2-a]pyrimidine-2-carboxamide |
| 015 | 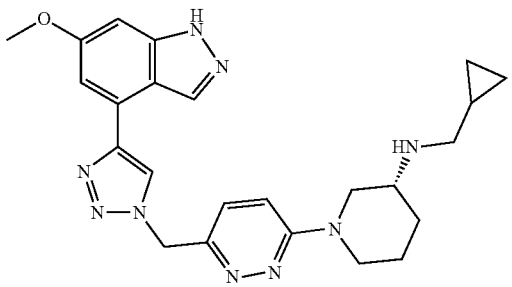 | (R)-N-(cyclopropylmethyl)-1-(6-((4-(6-methoxy-1H-indazol-4-yl)-1H-1,2,3-triazol-1-yl)methyl)pyridazin-3-yl)piperidin-3-amine |
| 016 | 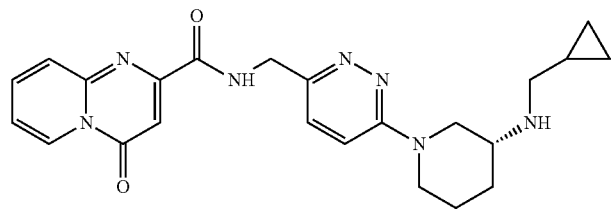 [SMILES: O=C(NCc1ccc(N2CCC[C@@H](NCC3CC3)C2)nn1)c1cc(=O)n2ccccc2n1] | (R)-N-((6-(3-((cyclopropylmethyl)amino)piperidin-1-yl)pyridazin-3-yl)methyl)-4-oxo-4H-pyrido[1,2-a]pyrimidine-2-carboxamide |
| 017 | 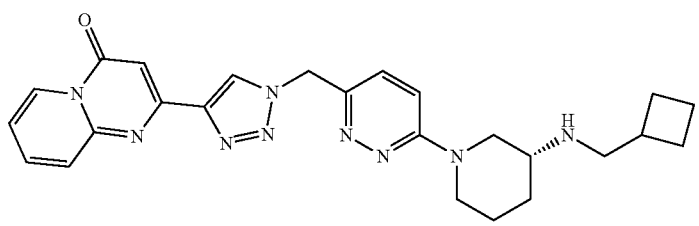 [SMILES: O=c1cc(-c2cn(Cc3ccc(N4CCC[C@@H](NCC5CCC5)C4)nn3)nn2)nc2ccccn12] | (R)-2-(1-((6-(3-((cyclobutylmethyl)amino)piperidin-1-yl)pyridazin-3-yl)methyl)-1H-1,2,3-triazol-4-yl)-4H-pyrido[1,2-a]pyrimidin-4-one |

TABLE 1-continued

| | | |
|---|---|---|
| 018 | 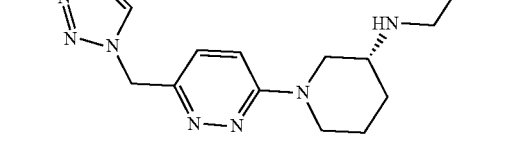 | (R)-N-((3-fluorobicyclo[1.1.1]pentan-1-yl)methyl)-1-(6-((4-(6-methoxy-1H-indazol-4-yl)-1H-1,2,3-triazol-1-yl)methyl)pyridazin-3-yl)piperidin-3-amine |
| 019 | 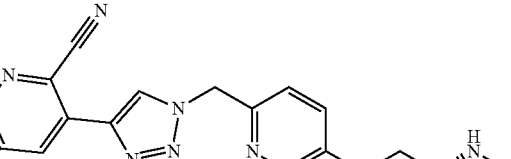 | (R)-3-(1-((6-(3-((cyclobutylmethyl)amino)piperidin-1-yl)pyridazin-3-yl)methyl)-1H-1,2,3-triazol-4-yl)-5-methoxypicolinonitrile |
| 020 |  | 1-(6-((4-(6-methoxy-1H-indazol-4-yl)-1H-1,2,3-triazol-1-yl)methyl)pyridazin-3-yl)-N-((3-methylbicyclo[1.1.1]pentan-1-yl)methyl)piperidin-3-amine |
| 021 | 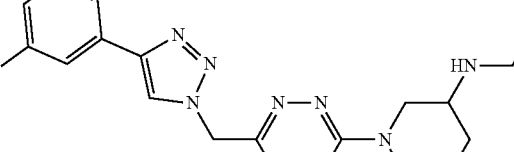 | (R)-5-(1-((6-(3-((cyclobutylmethyl)amino)piperidin-1-yl)pyridazin-3-yl)methyl)-1H-1,2,3-triazol-4-yl)nicotinonitrile |
| 022 | 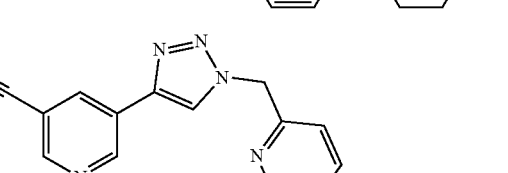 | (R)-N-(cyclobutylmethyl)-1-(6-((4-(6-methoxy-1H-indazol-4-yl)-1H-1,2,3-triazol-1-yl)methyl)pyridazin-3-yl)-N-methylpiperidin-3-amine |
| 023 | 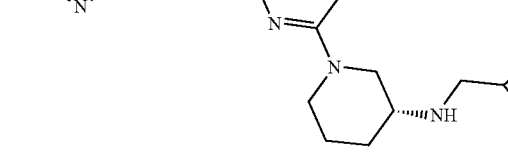 | (R)-N-cyclopentyl-1-(6-((4-(6-methoxy-1H-indazol-4-yl)-1H-1,2,3-triazol-1-yl)methyl)pyridazin-3-yl)piperidin-3-amine |

TABLE 1-continued

| | | |
|---|---|---|
| 024 | 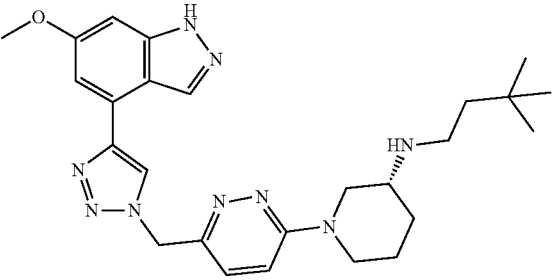 | (R)-N-(3,3-dimethylbutyl)-1-(6-((4-(6-methoxy-1H-indazol-4-yl)-1H-1,2,3-triazol-1-yl)methyl)pyridazin-3-yl)piperidin-3-amine |
| 025 | 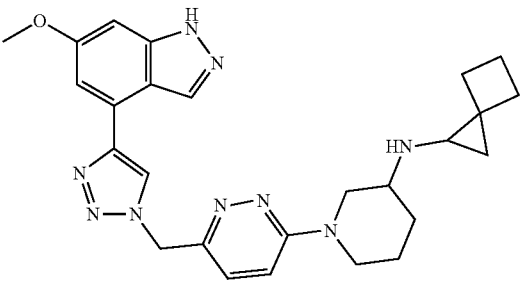 [SMILES: COc1cc(-c2cn(Cc3ccc(N4CCCC(NC5CC56CCC6)C4)nn3)nn2)c2cn[nH]c2c1] | 1-(6-((4-(6-methoxy-1H-indazol-4-yl)-1H-1,2,3-triazol-1-yl)methyl)pyridazin-3-yl)-N-(spiro[2.3]hexan-1-yl)piperidin-3-amine |
| 026 | 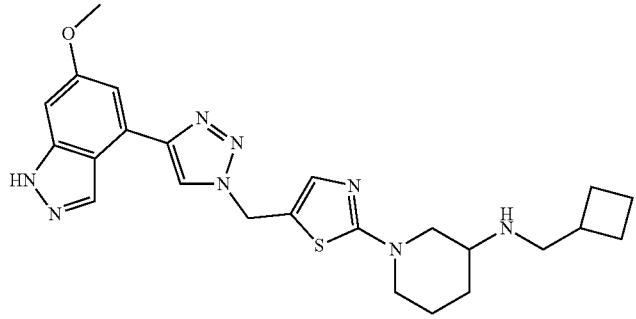 [SMILES: COc1cc(-c2cn(Cc3cnc(N4CCCC(NCC5CCC5)C4)s3)nn2)c2cn[nH]c2c1] | N-(cyclobutylmethyl)-1-(5-((4-(6-methoxy-1H-indazol-4-yl)-1H-1,2,3-triazol-1-yl)methyl)thiazol-2-yl)piperidin-3-amine |
| 027 | 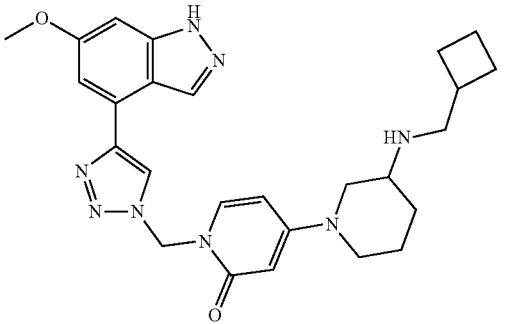 [SMILES: COc1cc(-c2cn(Cn3ccc(N4CCCC(NCC5CCC5)C4)cc3=O)nn2)c2cn[nH]c2c1] | 4-(3-((cyclobutylmethyl)amino)piperidin-1-yl)-1-((4-(6-methoxy-1H-indazol-4-yl)-1H-1,2,3-triazol-1-yl)methyl)pyridin-2(1H)-one |
| 028 | 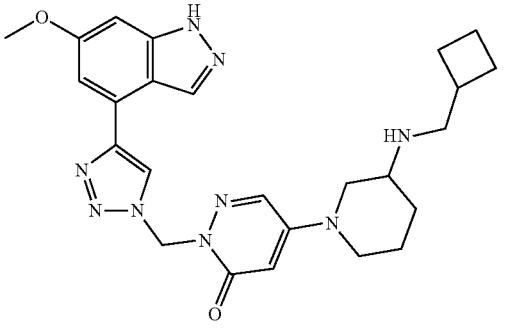 [SMILES: COc1cc(-c2cn(Cn3ncc(N4CCCC(NCC5CCC5)C4)cc3=O)nn2)c2cn[nH]c2c1] | 5-(3-((cyclobutylmethyl)amino)piperidin-1-yl)-2-((4-(6-methoxy-1H-indazol-4-yl)-1H-1,2,3-triazol-1-yl)methyl)pyridazin-3(2H)-one |

TABLE 1-continued

| | | |
|---|---|---|
| 029 | 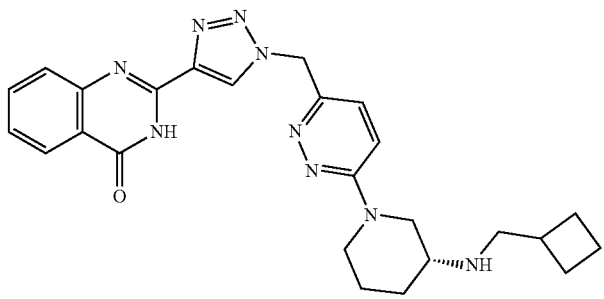 [SMILES: O=c1[nH]c(-c2cn(Cc3ccc(N4CCC[C@@H](NCC5CCC5)C4)nn3)nn2)nc2ccccc12] | (R)-2-(1-((6-(3-((cyclobutylmethyl)amino)piperidin-1-yl)pyridazin-3-yl)methyl)-1H-1,2,3-triazol-4-yl)quinazolin-4(3H)-one |
| 030 | 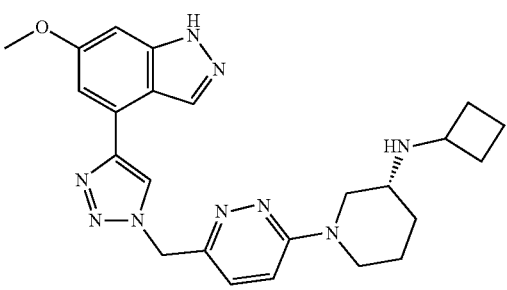 [SMILES: COc1cc(-c2cn(Cc3ccc(N4CCC[C@@H](NC5CCC5)C4)nn3)nn2)c2cn[nH]c2c1] | (R)-N-cyclobutyl-1-(6-((4-(6-methoxy-1H-indazol-4-yl)-1H-1,2,3-triazol-1-yl)methyl)pyridazin-3-yl)piperidin-3-amine |
| 031 | 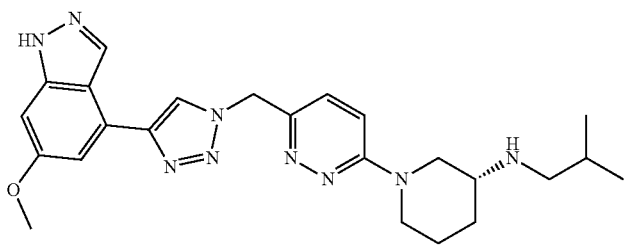 [SMILES: COc1cc(-c2cn(Cc3ccc(N4CCC[C@@H](NCC(C)C)C4)nn3)nn2)c2cn[nH]c2c1] | (R)-N-isobutyl-1-(6-((4-(6-methoxy-1H-indazol-4-yl)-1H-1,2,3-triazol-1-yl)methyl)pyridazin-3-yl)piperidin-3-amine |
| 032 | 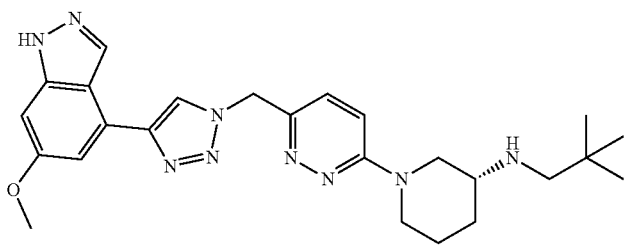 [SMILES: COc1cc(-c2cn(Cc3ccc(N4CCC[C@@H](NCC(C)(C)C)C4)nn3)nn2)c2cn[nH]c2c1] | (R)-1-(6-((4-(6-methoxy-1H-indazol-4-yl)-1H-1,2,3-triazol-1-yl)methyl)pyridazin-3-yl)-N-neopentylpiperidin-3-amine |
| 033 | 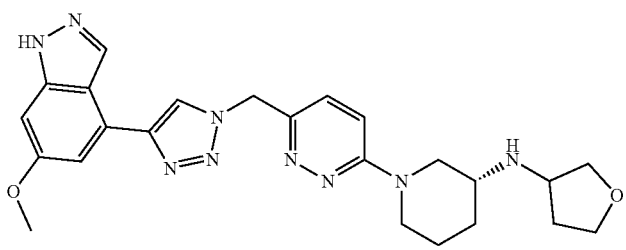 [SMILES: COc1cc(-c2cn(Cc3ccc(N4CCC[C@@H](NC5CCOC5)C4)nn3)nn2)c2cn[nH]c2c1] | (3R)-1-(6-((4-(6-methoxy-1H-indazol-4-yl)-1H-1,2,3-triazol-1-yl)methyl)pyridazin-3-yl)-N-(tetrahydrofuran-3-yl)piperidin-3-amine |
| 034 | 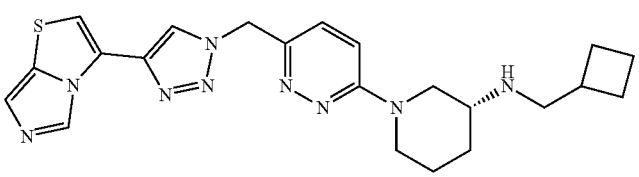 [SMILES: c1cc(N2CCC[C@@H](NCC3CCC3)C2)nnc1Cn1cc(-c2csc3cncn23)nn1] | (R)-N-(cyclobutylmethyl)-1-(6-((4-(imidazo[5,1-b]thiazol-3-yl)-1H-1,2,3-triazol-1-yl)methyl)pyridazin-3-yl)piperidin-3-amine |

TABLE 1-continued

| 035 | 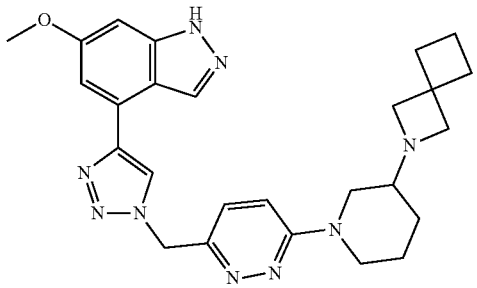 [SMILES: COc1cc(-c2cn(Cc3ccc(N4CCCC(N5CC6(CCC6)C5)C4)nn3)nn2)c2cn[nH]c2c1] | 4-(1-((6-(3-(2-azaspiro[3.3]heptan-2-yl)piperidin-1-yl)pyridazin-3-yl)methyl)-1H-1,2,3-triazol-4-yl)-6-methoxy-1H-indazole |
| 036 | 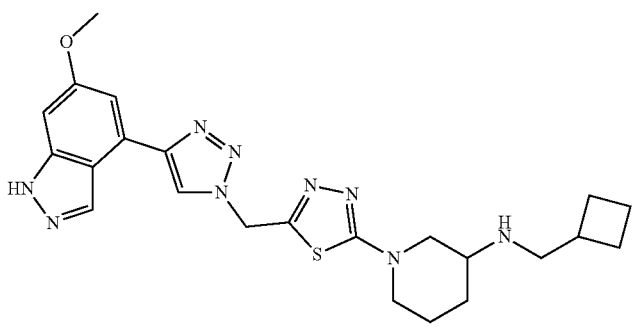 [SMILES: COc1cc(-c2cn(Cc3nnc(N4CCCC(NCC5CCC5)C4)s3)nn2)c2cn[nH]c2c1] | N-(cyclobutylmethyl)-1-(5-((4-(6-methoxy-1H-indazol-4-yl)-1H-1,2,3-triazol-1-yl)methyl)-1,3,4-thiadiazol-2-yl)piperidin-3-amine |
| 037 | 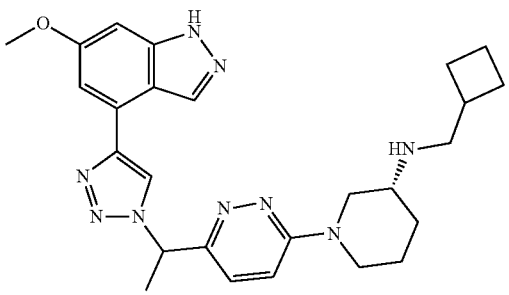 [SMILES: COc1cc(-c2cn(C(C)c3ccc(N4CCC[C@@H](NCC5CCC5)C4)nn3)nn2)c2cn[nH]c2c1] | (3R)-N-(cyclobutylmethyl)-1-(6-(1-(4-(6-methoxy-1H-indazol-4-yl)-1H-1,2,3-triazol-1-yl)ethyl)pyridazin-3-yl)piperidin-3-amine |
| 038 | 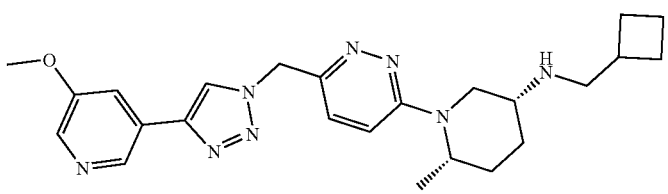 [SMILES: COc1cncc(-c2cn(Cc3ccc(N4C[C@H](NCC5CCC5)CC[C@@H]4C)nn3)nn2)c1] | (3R,6S)-N-(cyclobutylmethyl)-1-(6-((4-(5-methoxypyridin-3-yl)-1H-1,2,3-triazol-1-yl)methyl)pyridazin-3-yl)-6-methylpiperidin-3-amine |
| 039 | 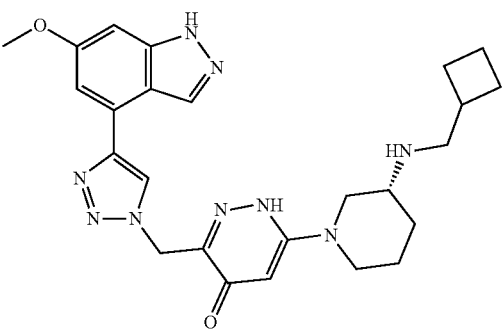 [SMILES: COc1cc(-c2cn(Cc3n[nH]c(N4CCC[C@@H](NCC5CCC5)C4)cc3=O)nn2)c2cn[nH]c2c1] | (R)-6-(3-((cyclobutylmethyl)amino)piperidin-1-yl)-3-((4-(6-methoxy-1H-indazol-4-yl)-1H-1,2,3-triazol-1-yl)methyl)pyridazin-4(1H)-one |

TABLE 1-continued

| | | |
|---|---|---|
| 040 | | (R)-N-(cyclobutylmethyl)-1-(5-((4-(6-methoxy-1H-indazol-4-yl)-1H-1,2,3-triazol-1-yl)methyl)pyridin-2-yl)piperidin-3-amine |
| 041 | | (R)-6-(3-((cyclobutylmethyl)amino)piperidin-1-yl)-3-((4-(6-methoxy-1H-indazol-4-yl)-1H-1,2,3-triazol-1-yl)methyl)pyrimidin-4(3H)-one |
| 042 | | (R)-N-(cyclobutylmethyl)-1-(6-((4-(6-methoxy-1H-indazol-4-yl)-1H-1,2,3-triazol-1-yl)methyl)pyridin-3-yl)piperidin-3-amine |
| 043 | | N-(cyclobutylmethyl)-1-(2-((4-(6-methoxy-1H-indazol-4-yl)-1H-1,2,3-triazol-1-yl)methyl)pyrimidin-5-yl)piperidin-3-amine |
| 044 | | (3R)-N-(1-cyclobutylethyl)-1-(6-((4-(6-methoxy-1H-indazol-4-yl)-1H-1,2,3-triazol-1-yl)methyl)pyridazin-3-yl)piperidin-3-amine |

TABLE 1-continued

| | | |
|---|---|---|
| 045 | 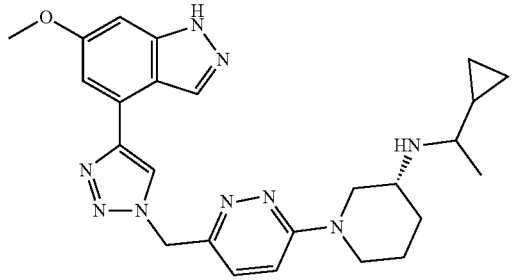 [SMILES: COc1cc(-c2cn(Cc3ccc(N4CCC[C@@H](NC(C)C5CC5)C4)nn3)nn2)c2cn[nH]c2c1] | (3R)-N-(1-cyclopropylethyl)-1-(6-((4-(6-methoxy-1H-indazol-4-yl)-1H-1,2,3-triazol-1-yl)methyl)pyridazin-3-yl)piperidin-3-amine |
| 046 | 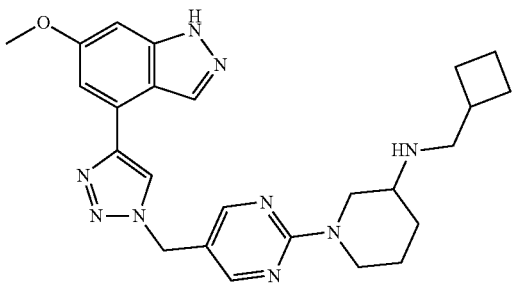 [SMILES: COc1cc(-c2cn(Cc3cnc(N4CCCC(NCC5CCC5)C4)nc3)nn2)c2cn[nH]c2c1] | N-(cyclobutylmethyl)-1-(5-((4-(6-methoxy-1H-indazol-4-yl)-1H-1,2,3-triazol-1-yl)methyl)pyrimidin-2-yl)piperidin-3-amine |
| 047 | 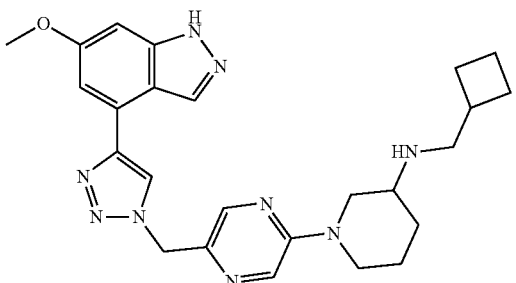 | N-(cyclobutylmethyl)-1-(5-((4-(6-methoxy-1H-indazol-4-yl)-1H-1,2,3-triazol-1-yl)methyl)pyrazin-2-yl)piperidin-3-amine |
| 048 | 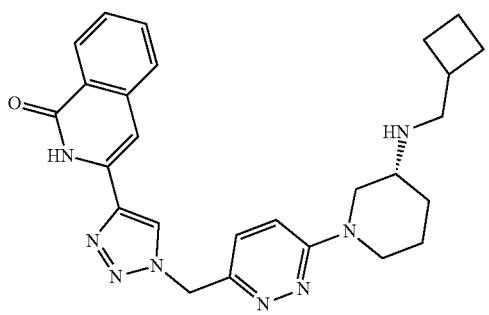 [SMILES: O=c1[nH]c(-c2cn(Cc3ccc(N4CCC[C@@H](NCC5CCC5)C4)nn3)nn2)cc2ccccc12] | (R)-3-(1-((6-(3-((cyclobutylmethyl)amino)piperidin-1-yl)pyridazin-3-yl)methyl)-1H-1,2,3-triazol-4-yl)isoquinolin-1(2H)-one |
| 049 | 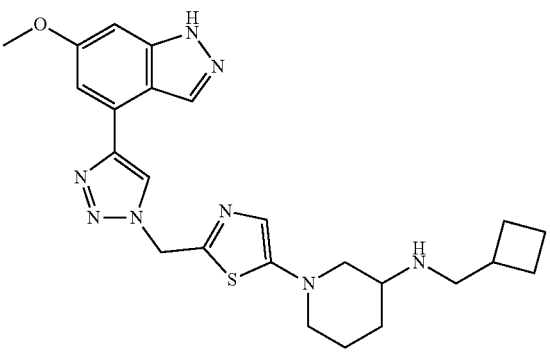 [SMILES: COc1cc(-c2cn(Cc3ncc(N4CCCC(NCC5CCC5)C4)s3)nn2)c2cn[nH]c2c1] | N-(cyclobutylmethyl)-1-(2-((4-(6-methoxy-1H-indazol-4-yl)-1H-1,2,3-triazol-1-yl)methyl)thiazol-5-yl)piperidin-3-amine |

TABLE 1-continued

| | | |
|---|---|---|
| 050 | | 4-((R)-3-((cyclobutylmethyl)amino)piperidin-1-yl)-1-(1-(4-(6-methoxy-1H-indazol-4-yl)-1H-1,2,3-triazol-1-yl)ethyl)pyridin-2(1H)-one |
| 051 | | N-(1-(6-((R)-3-((cyclobutylmethyl)amino)piperidin-1-yl)pyridazin-3-yl)ethyl)-4-oxo-4H-pyrido[1,2-a]pyrimidine-2-carboxamide |
| 052 | | 3-(3-((cyclobutylmethyl)amino)piperidin-1-yl)-6-((4-(6-methoxy-1H-indazol-4-yl)-1H-1,2,3-triazol-1-yl)methyl)pyridin-2(1H)-one |
| 053 | | N-(cyclobutylmethyl)-1-(6-((4-(5-methoxypyridin-3-yl)-1H-1,2,3-triazol-1-yl)methyl)pyridazin-3-yl)-3-methylpiperidin-3-amine |
| 054 | | 4-(3-((cyclobutylmethyl)amino)piperidin-1-yl)-5-fluoro-1-((4-(6-methoxy-1H-indazol-4-yl)-1H-1,2,3-triazol-1-yl)methyl)pyridin-2(1H)-one |
| 055 | | 4-((R)-3-((cyclobutylmethyl)amino)piperidin-1-yl)-1-(1-(4-(5-methoxypyridin-3-yl)-1H-1,2,3-triazol-1-yl)ethyl)pyridin-2(1H)-one |

TABLE 1-continued

| | | |
|---|---|---|
| 056 | | (3R,5S)-N-(cyclobutylmethyl)-5-fluoro-1-(6-((4-(5-methoxypyridin-3-yl)-1H-1,2,3-triazol-1-yl)methyl)pyridazin-3-yl)piperidin-3-amine |
| 057 | | (R)-1-(6-((4-(6-chloro-1H-indazol-4-yl)-1H-1,2,3-triazol-1-yl)methyl)pyridazin-3-yl)-N-(cyclobutylmethyl)piperidin-3-amine |
| 058 | | N-(1-(5-((R)-3-((cyclobutylmethyl)amino)piperidin-1-yl)pyridin-2-yl)ethyl)-4-oxo-4H-pyrido[1,2-a]pyrimidine-2-carboxamide |
| 059 | | N-(cyclobutylmethyl)-4,4-difluoro-1-(6-((4-(5-methoxypyridin-3-yl)-1H-1,2,3-triazol-1-yl)methyl)pyridazin-3-yl)piperidin-3-amine |
| 060 | | (R)-N-((5-(3-((cyclobutylmethyl)amino)piperidin-1-yl)pyridin-2-yl)methyl)-4-oxo-4H-pyrido[1,2-a]pyrimidine-2-carboxamide |
| 061 | | (R)-N-((6-(3-((cyclobutylmethyl)amino)piperidin-1-yl)pyridin-3-yl)methyl)-4-oxo-4H-pyrido[1,2-a]pyrimidine-2-carboxamide |
| 062 | | (R)-5-(3-((cyclobutylmethyl)amino)piperidin-1-yl)-2-((4-(5-methoxypyridin-3-yl)-1H-1,2,3-triazol-1-yl)methyl)pyridazin-3(2H)-one |

TABLE 1-continued

| | | |
|---|---|---|
| 063 | | (R)-4-(3-((cyclobutylmethyl)amino)piperidin-1-yl)-1-((4-(5-methoxypyridin-3-yl)-1H-1,2,3-triazol-1-yl)methyl)pyridin-2(1H)-one |
| 064 | | (3R)-N-(cyclobutylmethyl)-1-(6-(2,2,2-trifluoro-1-(4-(5-methoxypyridin-3-yl)-1H-1,2,3-triazol-1-yl)ethyl)pyridazin-3-yl)piperidin-3-amine |
| 065 | | N-(1-(6-((R)-3-((cyclobutylmethyl)amino)piperidin-1-yl)pyridazin-3-yl)-2,2,2-trifluoroethyl)-4-oxo-4H-pyrido[1,2-a]pyrimidine-2-carboxamide |
| 066 | | (3R)-N-(cyclobutylmethyl)-1-(6-(1-(4-(5-methoxypyridin-3-yl)-1H-1,2,3-triazol-1-yl)ethyl)pyridazin-3-yl)piperidin-3-amine |
| 067 | | 5-((R)-3-((cyclobutylmethyl)amino)piperidin-1-yl)-2-(1-(4-(5-methoxypyridin-3-yl)-1H-1,2,3-triazol-1-yl)ethyl)pyridazin-3(2H)-one |
| 068 | | (R)-N-(cyclobutylmethyl)-1-(4-((4-(5-methoxypyridin-3-yl)-1H-1,2,3-triazol-1-yl)methyl)phenyl)piperidin-3-amine |

TABLE 1-continued

| | | |
|---|---|---|
| 069 | 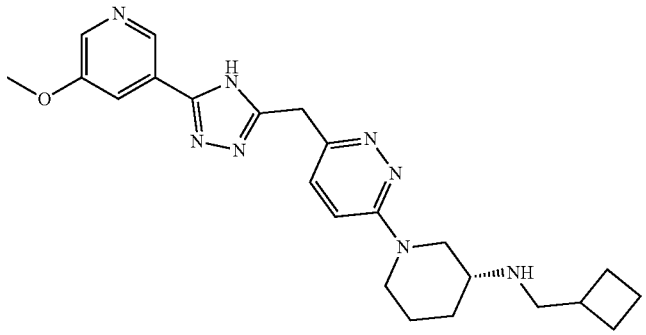 [SMILES: COc1cncc(-c2nnc(Cc3ccc(N4CCC[C@@H](NCC5CCC5)C4)nn3)[nH]2)c1] | (R)-N-(cyclobutylmethyl)-1-(6-((5-(5-methoxypyridin-3-yl)-4H-1,2,4-triazol-3-yl)methyl)pyridazin-3-yl)piperidin-3-amine |
| 070 | 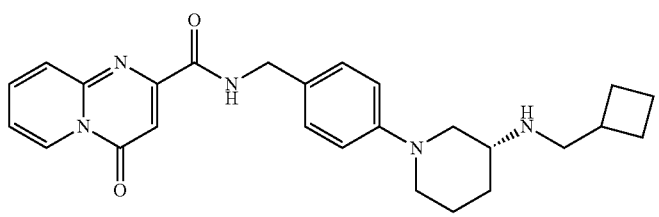 [SMILES: O=C(NCc1ccc(N2CCC[C@@H](NCC3CCC3)C2)cc1)c1cc(=O)n2ccccc2n1] | (R)-N-(4-(3-((cyclobutylmethyl)amino)piperidin-1-yl)benzyl)-4-oxo-4H-pyrido[1,2-a]pyrimidine-2-carboxamide |
| 071 | 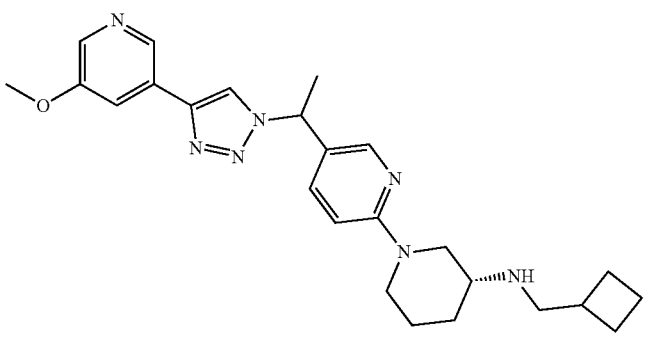 [SMILES: COc1cncc(-c2cn(C(C)c3ccc(N4CCC[C@@H](NCC5CCC5)C4)nc3)nn2)c1] | (3R)-N-(cyclobutylmethyl)-1-(5-(1-(4-(5-methoxypyridin-3-yl)-1H-1,2,3-triazol-1-yl)ethyl)pyridin-2-yl)piperidin-3-amine |
| 072 | 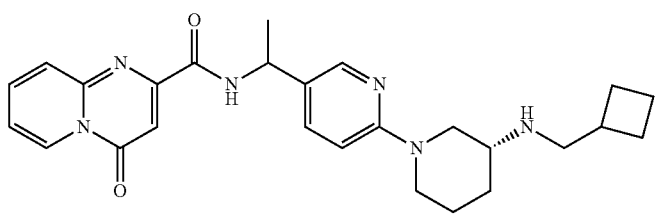 [SMILES: CC(NC(=O)c1cc(=O)n2ccccc2n1)c1ccc(N2CCC[C@@H](NCC3CCC3)C2)nc1] | N-(1-(6-((R)-3-((cyclobutylmethyl)amino)piperidin-1-yl)pyridin-3-yl)ethyl)-4-oxo-4H-pyrido[1,2-a]pyrimidine-2-carboxamide |
| 073 | 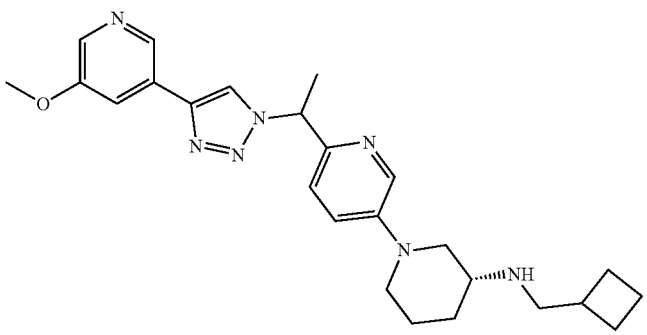 [SMILES: COc1cncc(-c2cn(C(C)c3ccc(N4CCC[C@@H](NCC5CCC5)C4)cn3)nn2)c1] | (3R)-N-(cyclobutylmethyl)-1-(6-(1-(4-(5-methoxypyridin-3-yl)-1H-1,2,3-triazol-1-yl)ethyl)pyridin-3-yl)piperidin-3-amine |

TABLE 1-continued

| | | |
|---|---|---|
| 074 | | N-((S)-1-(4-((R)-3-((cyclobutylmethyl)amino)piperidin-1-yl)phenyl)ethyl)-4-oxo-4H-pyrido[1,2-a]pyrimidine-2-carboxamide |
| 075 | | (R)-4-(3-((cyclobutylmethyl)amino)piperidin-1-yl)-1-((1-(5-methoxypyridin-3-yl)-1H-1,2,3-triazol-4-yl)methyl)pyridin-2(1H)-one |
| 076 | | (3R)-N-(cyclobutylmethyl)-1-(4-(1-(4-(5-methoxypyridin-3-yl)-1H-1,2,3-triazol-1-yl)ethyl)phenyl)piperidin-3-amine |
| 077 | | (R)-4-(3-((cyclobutylmethyl)amino)piperidin-1-yl)-1-((5-(5-methoxypyridin-3-yl)-1,3,4-thiadiazol-2-yl)methyl)pyridin-2(1H)-one |
| 078 | | 1-(1-(4-(5-chloropyridin-3-yl)-1H-1,2,3-triazol-1-yl)ethyl)-4-((R)-3-((cyclobutylmethyl)amino)piperidin-1-yl)pyridin-2(1H)-one |
| 079 | | 4-((R)-3-((cyclobutylmethyl)amino)piperidin-1-yl)-1-(1-(4-(pyridin-3-yl)-1H-1,2,3-triazol-1-yl)ethyl)pyridin-2(1H)-one |
| 080 | | 4-((R)-3-((cyclobutylmethyl)amino)piperidin-1-yl)-1-(1-(4-(5-methylpyridin-3-yl)-1H-1,2,3-triazol-1-yl)ethyl)pyridin-2(1H)-one |

TABLE 1-continued

| 081 | 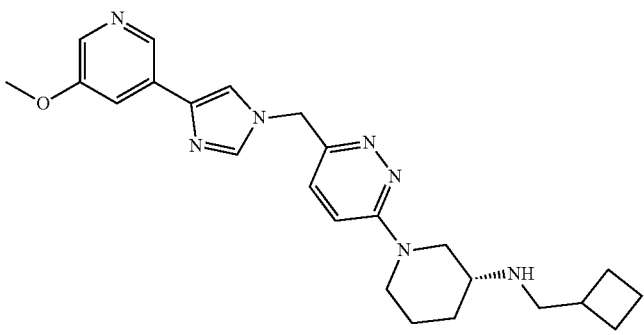 [SMILES: COc1cncc(-c2cn(Cc3ccc(N4CCC[C@@H](NCC5CCC5)C4)nn3)cn2)c1] | (R)-N-(cyclobutylmethyl)-1-(6-((4-(5-methoxypyridin-3-yl)-1H-imidazol-1-yl)methyl)pyridazin-3-yl)piperidin-3-amine |
| 082 | 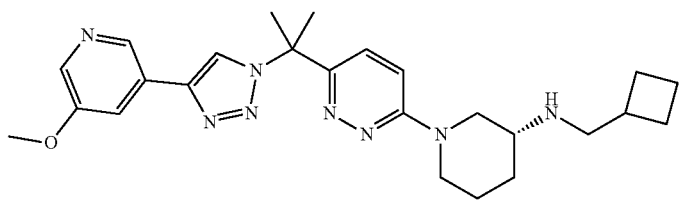 [SMILES: COc1cncc(-c2cn(C(C)(C)c3ccc(N4CCC[C@@H](NCC5CCC5)C4)nn3)nn2)c1] | (R)-N-(cyclobutylmethyl)-1-(6-(2-(4-(5-methoxypyridin-3-yl)-1H-1,2,3-triazol-1-yl)propan-2-yl)pyridazin-3-yl)piperidin-3-amine |
| 083 | 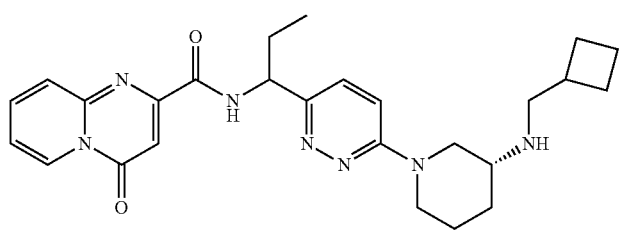 [SMILES: CCC(NC(=O)c1cc(=O)n2ccccc2n1)c1ccc(N2CCC[C@@H](NCC3CCC3)C2)nn1] | N-(1-(6-((R)-3-((cyclobutylmethyl)amino)piperidin-1-yl)pyridazin-3-yl)propyl)-4-oxo-4H-pyrido[1,2-a]pyrimidine-2-carboxamide |
| 084 | 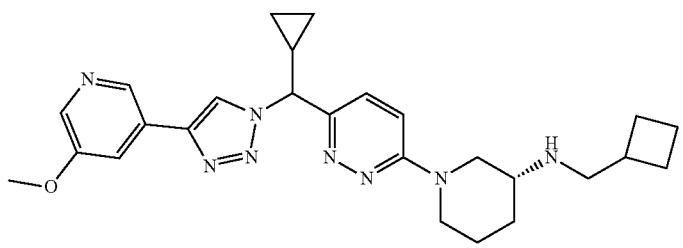 [SMILES: COc1cncc(-c2cn(C(c3ccc(N4CCC[C@@H](NCC5CCC5)C4)nn3)C3CC3)nn2)c1] | (3R)-N-(cyclobutylmethyl)-1-(6-(cyclopropyl(4-(5-methoxypyridin-3-yl)-1H-1,2,3-triazol-1-yl)methyl)pyridazin-3-yl)piperidin-3-amine |
| 085 | 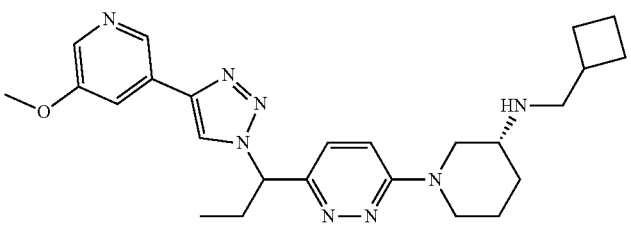 [SMILES: CCC(c1ccc(N2CCC[C@@H](NCC3CCC3)C2)nn1)n1cc(-c2cncc(OC)c2)nn1] | (3R)-N-(cyclobutylmethyl)-1-(6-(1-(4-(5-methoxypyridin-3-yl)-1H-1,2,3-triazol-1-yl)propyl)pyridazin-3-yl)piperidin-3-amine |
| 086 | 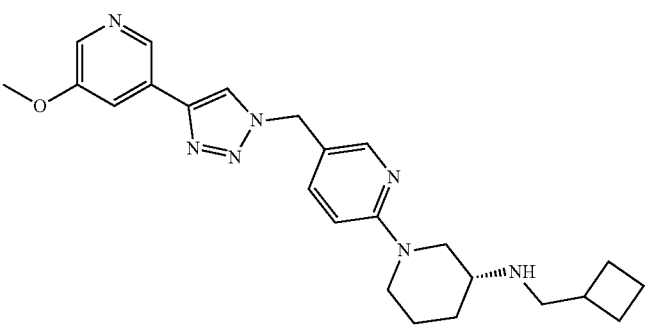 [SMILES: COc1cncc(-c2cn(Cc3ccc(N4CCC[C@@H](NCC5CCC5)C4)nc3)nn2)c1] | (R)-N-(cyclobutylmethyl)-1-(5-((4-(5-methoxypyridin-3-yl)-1H-1,2,3-triazol-1-yl)methyl)pyridin-2-yl)piperidin-3-amine |

TABLE 1-continued

| 087 | 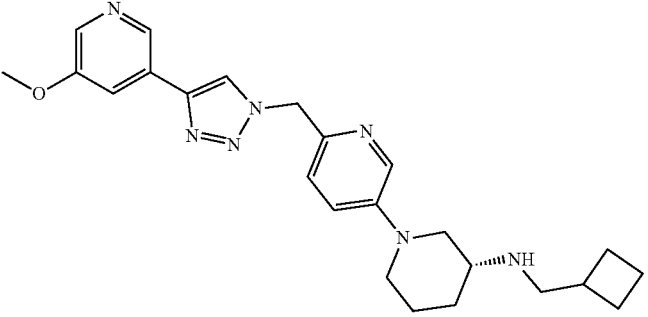 [SMILES: COc1cncc(-c2cn(Cc3ccc(N4CCC[C@@H](NCC5CCC5)C4)cn3)nn2)c1] | (R)-N-(cyclobutylmethyl)-1-(6-((4-(5-methoxypyridin-3-yl)-1H-1,2,3-triazol-1-yl)methyl)pyridin-3-yl)piperidin-3-amine |
| 088 | 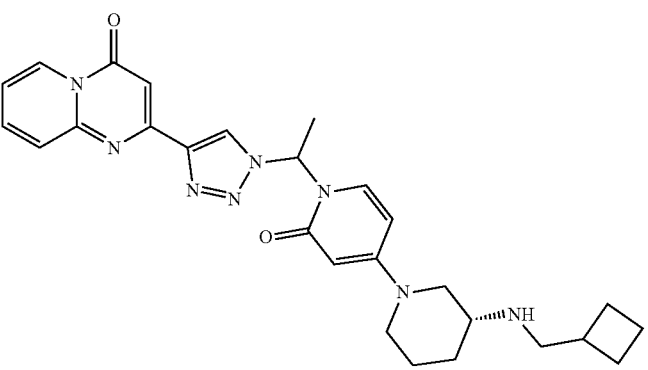 [SMILES: CC(n1cc(-c2cc(=O)n3ccccc3n2)nn1)n1ccc(N2CCC[C@@H](NCC3CCC3)C2)cc1=O] | 2-(1-(1-(4-((R)-3-((cyclobutylmethyl)amino)piperidin-1-yl)-2-oxopyridin-1(2H)-yl)ethyl)-1H-1,2,3-triazol-4-yl)-4H-pyrido[1,2-a]pyrimidin-4-one |
| 089 | 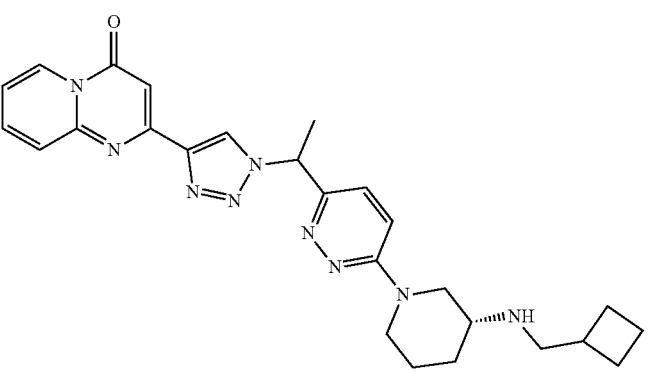 [SMILES: CC(c1ccc(N2CCC[C@@H](NCC3CCC3)C2)nn1)n1cc(-c2cc(=O)n3ccccc3n2)nn1] | 2-(1-(1-(6-((R)-3-((cyclobutylmethyl)amino)piperidin-1-yl)pyridazin-3-yl)ethyl)-1H-1,2,3-triazol-4-yl)-4H-pyrido[1,2-a]pyrimidin-4-one |
| 090 | 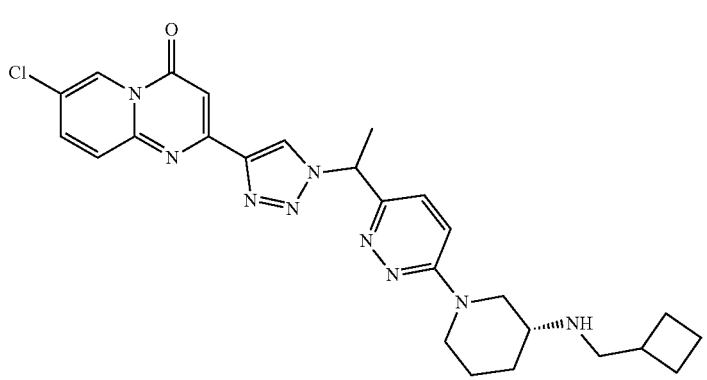 [SMILES: CC(c1ccc(N2CCC[C@@H](NCC3CCC3)C2)nn1)n1cc(-c2cc(=O)n3cc(Cl)ccc3n2)nn1] | 7-chloro-2-(1-(1-(6-((R)-3-((cyclobutylmethyl)amino)piperidin-1-yl)pyridazin-3-yl)ethyl)-1H-1,2,3-triazol-4-yl)-4H-pyrido[1,2-a]pyrimidin-4-one |
| 091 | 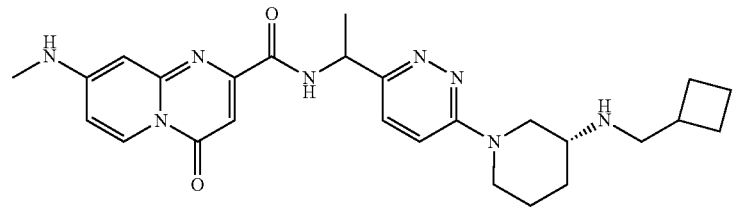 [SMILES: CNc1ccn2c(=O)cc(C(=O)NC(C)c3ccc(N4CCC[C@@H](NCC5CCC5)C4)nn3)nc2c1] | N-(1-(6-((R)-3-((cyclobutylmethyl)amino)piperidin-1-yl)pyridazin-3-yl)ethyl)-8-(methylamino)-4-oxo-4H-pyrido[1,2-a]pyrimidine-2-carboxamide |

TABLE 1-continued

| | | |
|---|---|---|
| 092 | 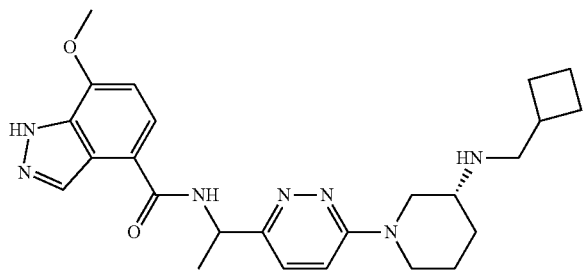 [SMILES: COc1ccc(C(=O)NC(C)c2ccc(N3CCC[C@@H](NCC4CCC4)C3)nn2)c2cn[nH]c12] | N-(1-(6-((R)-3-((cyclobutylmethyl)amino)piperidin-1-yl)pyridazin-3-yl)ethyl)-7-methoxy-1H-indazole-4-carboxamide |
| 093 | 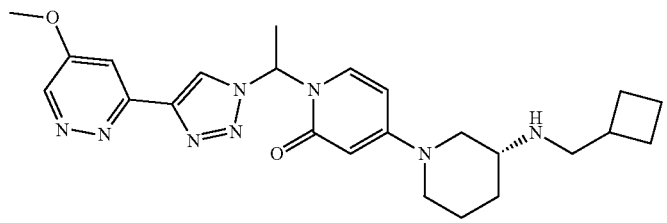 [SMILES: COc1cnnc(-c2cn(C(C)n3ccc(N4CCC[C@@H](NCC5CCC5)C4)cc3=O)nn2)c1] | 4-((R)-3-((cyclobutylmethyl)amino)piperidin-1-yl)-1-(1-(4-(5-methoxypyridazin-3-yl)-1H-1,2,3-triazol-1-yl)ethyl)pyridin-2(1H)-one |
| 094 | 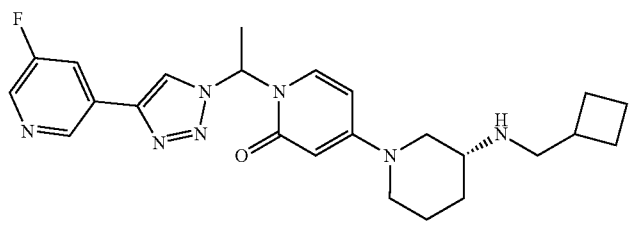 [SMILES: CC(n1cc(-c2cncc(F)c2)nn1)n1ccc(N2CCC[C@@H](NCC3CCC3)C2)cc1=O] | 4-((R)-3-((cyclobutylmethyl)amino)piperidin-1-yl)-1-(1-(4-(5-fluoropyridin-3-yl)-1H-1,2,3-triazol-1-yl)ethyl)pyridin-2(1H)-one |
| 095 | 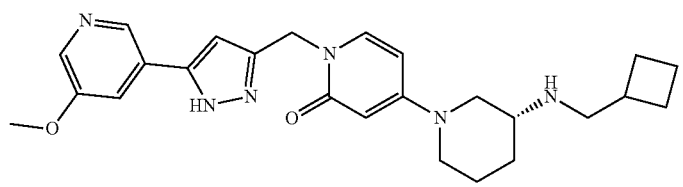 [SMILES: COc1cncc(-c2cc(Cn3ccc(N4CCC[C@@H](NCC5CCC5)C4)cc3=O)n[nH]2)c1] | (R)-4-(3-((cyclobutylmethyl)amino)piperidin-1-yl)-1-((5-(5-methoxypyridin-3-yl)-1H-pyrazol-3-yl)methyl)pyridin-2(1H)-one |
| 096 | 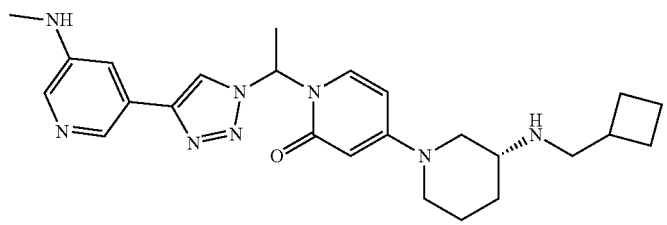 [SMILES: CNc1cncc(-c2cn(C(C)n3ccc(N4CCC[C@@H](NCC5CCC5)C4)cc3=O)nn2)c1] | 4-((R)-3-((cyclobutylmethyl)amino)piperidin-1-yl)-1-(1-(4-(5-(methylamino)pyridin-3-yl)-1H-1,2,3-triazol-1-yl)ethyl)pyridin-2(1H)-one |
| 097 | 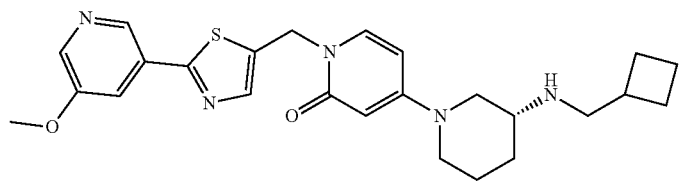 [SMILES: COc1cncc(-c2ncc(Cn3ccc(N4CCC[C@@H](NCC5CCC5)C4)cc3=O)s2)c1] | (R)-4-(3-((cyclobutylmethyl)amino)piperidin-1-yl)-1-((2-(5-methoxypyridin-3-yl)thiazol-5-yl)methyl)pyridin-2(1H)-one |
| 098 | 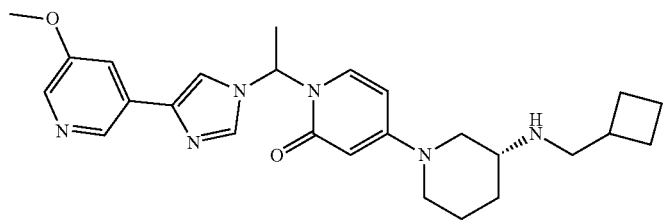 | 4-((R)-3-((cyclobutylmethyl)amino)piperidin-1-yl)-1-(1-(4-(5-methoxypyridin-3-yl)-1H-imidazol-1-yl)ethyl)pyridin-2(1H)-one |

TABLE 1-continued

| | | |
|---|---|---|
| 099 | 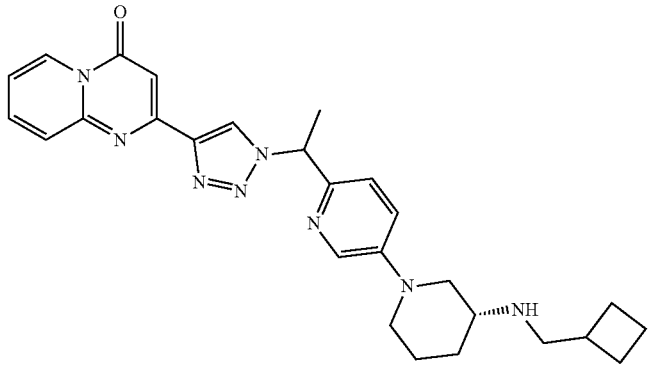 [SMILES: CC(c1ccc(N2CCC[C@@H](NCC3CCC3)C2)cn1)n1cc(-c2cc(=O)n3ccccc3n2)nn1] | 2-(1-(1-(5-((R)-3-((cyclobutylmethyl)amino)piperidin-1-yl)pyridin-2-yl)ethyl)-1H-1,2,3-triazol-4-yl)-4H-pyrido[1,2-a]pyrimidin-4-one |
| 100 | 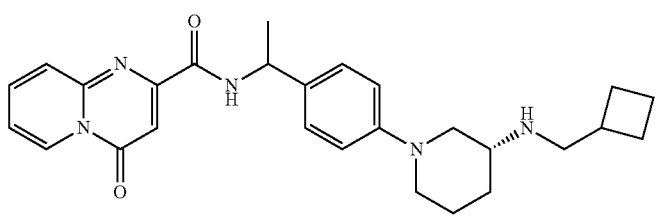 [SMILES: CC(NC(=O)c1cc(=O)n2ccccc2n1)c1ccc(N2CCC[C@@H](NCC3CCC3)C2)cc1] | N-(1-(4-((R)-3-((cyclobutylmethyl)amino)piperidin-1-yl)phenyl)ethyl)-4-oxo-4H-pyrido[1,2-a]pyrimidine-2-carboxamide |
| 101 | 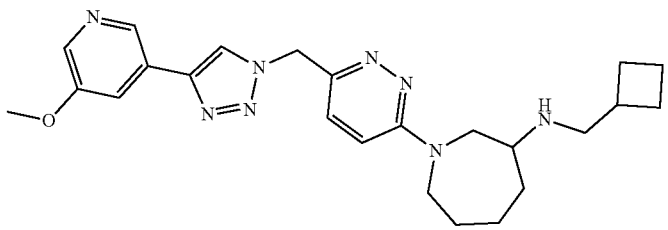 [SMILES: COc1cncc(-c2cn(Cc3ccc(N4CCCCC(NCC5CCC5)C4)nn3)nn2)c1] | N-(cyclobutylmethyl)-1-(6-((4-(5-methoxypyridin-3-yl)-1H-1,2,3-triazol-1-yl)methyl)pyridazin-3-yl)azepan-3-amine |
| 102 | 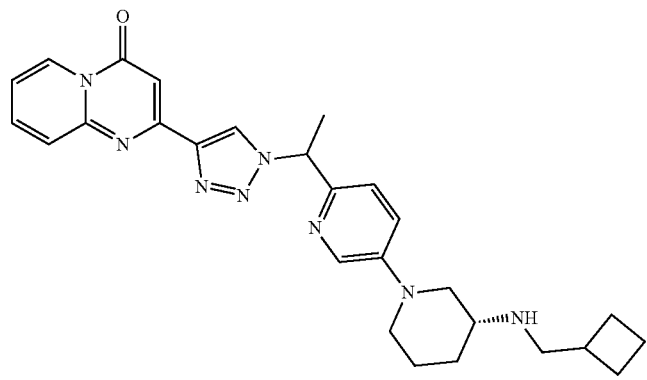 [SMILES: CC(c1ccc(N2CCC[C@@H](NCC3CCC3)C2)cn1)n1cc(-c2cc(=O)n3ccccc3n2)nn1] | 2-(1-(1-(4-((R)-3-((cyclobutylmethyl)amino)piperidin-1-yl)phenyl)ethyl)-1H-1,2,3-triazol-4-yl)-4H-pyrido[1,2-a]pyrimidin-4-one |
| 103 | 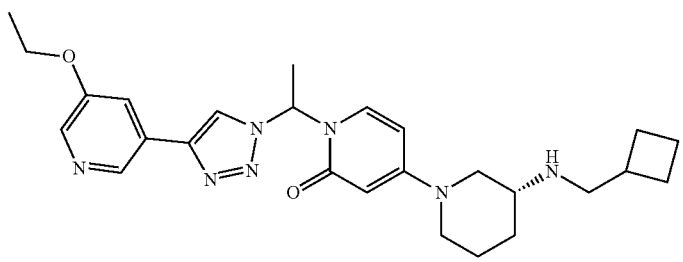 [SMILES: CCOc1cncc(-c2cn(C(C)n3ccc(N4CCC[C@@H](NCC5CCC5)C4)cc3=O)nn2)c1] | 4-((R)-3-((cyclobutylmethyl)amino)piperidin-1-yl)-1-(1-(4-(5-ethoxypyridin-3-yl)-1H-1,2,3-triazol-1-yl)ethyl)pyridin-2(1H)-one |

TABLE 1-continued

| 104 | 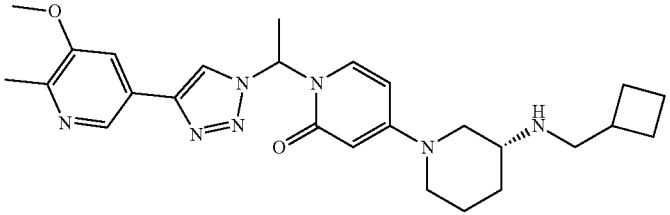 [SMILES: COc1cc(-c2cn(C(C)n3ccc(N4CCC[C@@H](NCC5CCC5)C4)cc3=O)nn2)cnc1C] | 4-((R)-3-((cyclobutylmethyl)amino)piperidin-1-yl)-1-(1-(4-(5-methoxy-6-methylpyridin-3-yl)-1H-1,2,3-triazol-1-yl)ethyl)pyridin-2(1H)-one |
| --- | --- | --- |
| 105 | 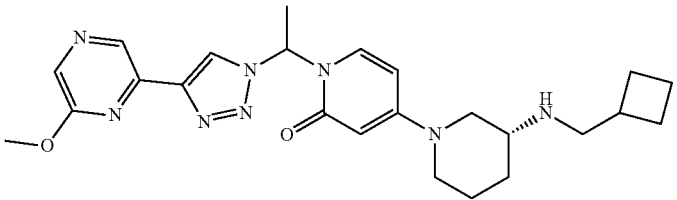 [SMILES: COc1cncc(-c2cn(C(C)n3ccc(N4CCC[C@@H](NCC5CCC5)C4)cc3=O)nn2)n1] | 4-((R)-3-((cyclobutylmethyl)amino)piperidin-1-yl)-1-(1-(4-(6-methoxypyrazin-2-yl)-1H-1,2,3-triazol-1-yl)ethyl)pyridin-2(1H)-one |
| 106 | 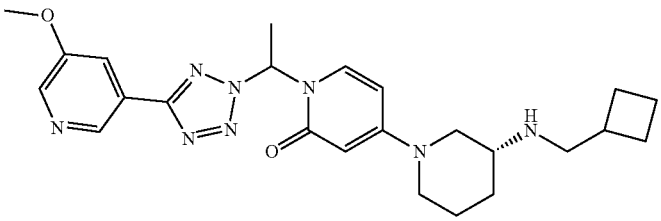 [SMILES: COc1cncc(-c2nnn(C(C)n3ccc(N4CCC[C@@H](NCC5CCC5)C4)cc3=O)n2)c1] | 4-((R)-3-((cyclobutylmethyl)amino)piperidin-1-yl)-1-(1-(5-(5-methoxypyridin-3-yl)-2H-tetrazol-2-yl)ethyl)pyridin-2(1H)-one |
| 107 | 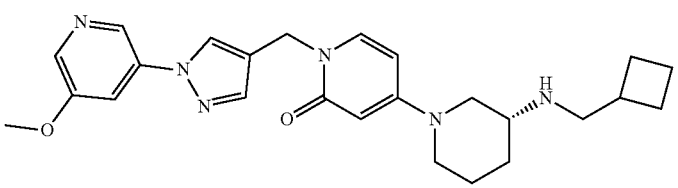 [SMILES: COc1cncc(-n2cc(Cn3ccc(N4CCC[C@@H](NCC5CCC5)C4)cc3=O)cn2)c1] | (R)-4-(3-((cyclobutylmethyl)amino)piperidin-1-yl)-1-((1-(5-methoxypyridin-3-yl)-1H-pyrazol-4-yl)methyl)pyridin-2(1H)-one |
| 108 | 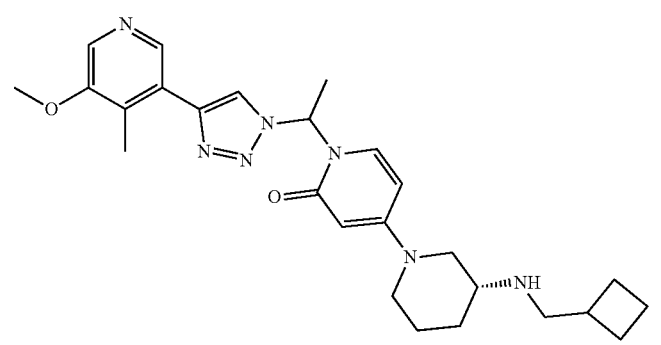 [SMILES: COc1cncc(-c2cn(C(C)n3ccc(N4CCC[C@@H](NCC5CCC5)C4)cc3=O)nn2)c1C] | 4-((R)-3-((cyclobutylmethyl)amino)piperidin-1-yl)-1-(1-(4-(5-methoxy-4-methylpyridin-3-yl)-1H-1,2,3-triazol-1-yl)ethyl)pyridin-2(1H)-one |
| 109 | 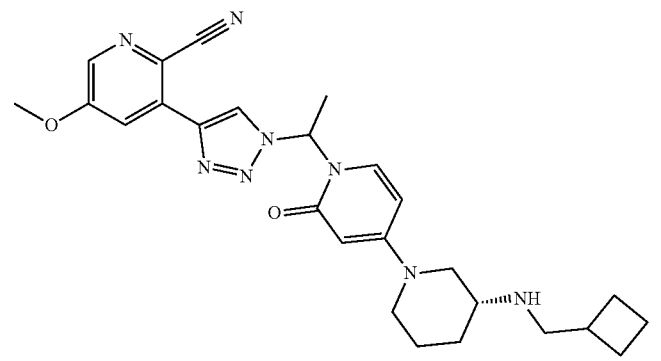 [SMILES: COc1cnc(C#N)c(-c2cn(C(C)n3ccc(N4CCC[C@@H](NCC5CCC5)C4)cc3=O)nn2)c1] | 3-(1-(1-(4-((R)-3-((cyclobutylmethyl)amino)piperidin-1-yl)-2-oxopyridin-1(2H)-yl)ethyl)-1H-1,2,3-triazol-4-yl)-5-methoxypicolinonitrile |

TABLE 1-continued

| | | |
|---|---|---|
| 110 | 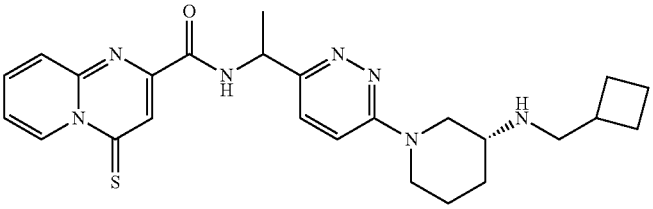 | N-(1-(6-((R)-3-((cyclobutylmethyl)amino)piperidin-1-yl)pyridazin-3-yl)ethyl)-4-thioxo-4H-pyrido[1,2-a]pyrimidine-2-carboxamide |
| 111 | 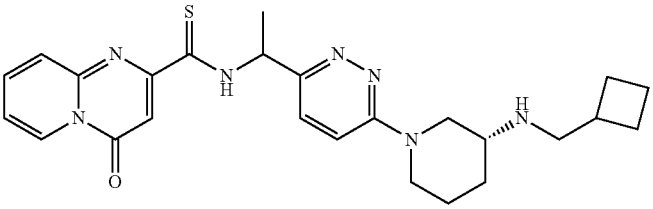 [SMILES: CC(NC(=S)c1cc(=O)n2ccccc2n1)c1ccc(N2CCC[C@@H](NCC3CCC3)C2)nn1] | N-(1-(6-((R)-3-((cyclobutylmethyl)amino)piperidin-1-yl)pyridazin-3-yl)ethyl)-4-oxo-4H-pyrido[1,2-a]pyrimidine-2-carbothioamide |
| 112 | 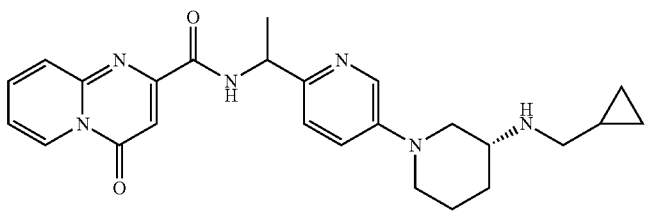 [SMILES: CC(NC(=O)c1cc(=O)n2ccccc2n1)c1ccc(N2CCC[C@@H](NCC3CC3)C2)cn1] | N-(1-(5-((R)-3-((cyclopropylmethyl)amino)piperidin-1-yl)pyridin-2-yl)ethyl)-4-oxo-4H-pyrido[1,2-a]pyrimidine-2-carboxamide |
| 113 | 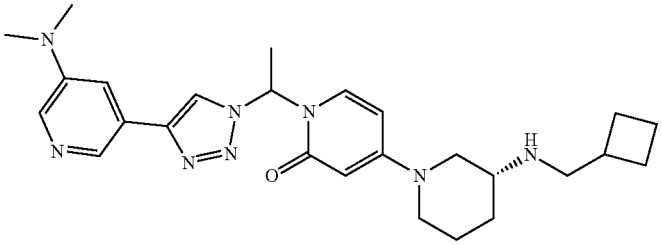 | 4-((R)-3-((cyclobutylmethyl)amino)piperidin-1-yl)-1-(1-(4-(5-(dimethylamino)pyridin-3-yl)-1H-1,2,3-triazol-1-yl)ethyl)pyridin-2(1H)-one |
| 114 | 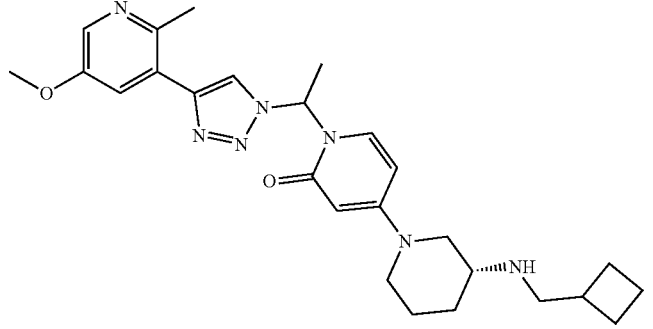 [SMILES: COc1cnc(C)c(-c2cn(C(C)n3ccc(N4CCC[C@@H](NCC5CCC5)C4)cc3=O)nn2)c1] | 4-((R)-3-((cyclobutylmethyl)amino)piperidin-1-yl)-1-(1-(4-(5-methoxy-2-methylpyridin-3-yl)-1H-1,2,3-triazol-1-yl)ethyl)pyridin-2(1H)-one |
| 115 | 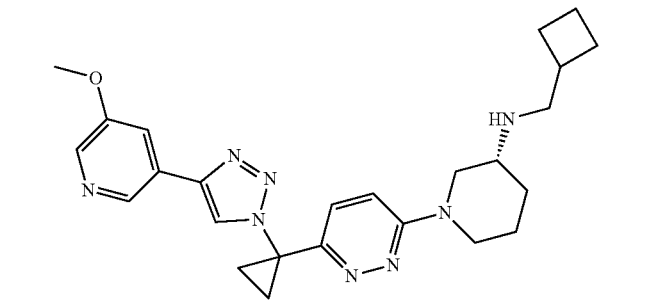 [SMILES: COc1cncc(-c2cn(C3(c4ccc(N5CCC[C@@H](NCC6CCC6)C5)nn4)CC3)nn2)c1] | (R)-N-(cyclobutylmethyl)-1-(6-(1-(4-(5-methoxypyridin-3-yl)-1H-1,2,3-triazol-1-yl)cyclopropyl)pyridazin-3-yl)piperidin-3-amine |

TABLE 1-continued

| | | |
|---|---|---|
| 116 | 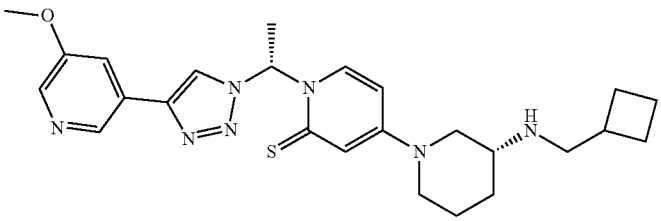 | 4-((R)-3-((cyclobutylmethyl) amino)piperidin-1-yl)-1-((R)-1-(4-(5-methoxypyridin-3-yl)-1H-1,2,3-triazol-1-yl)ethyl)pyridine-2(1H)-thione |
| 117 | 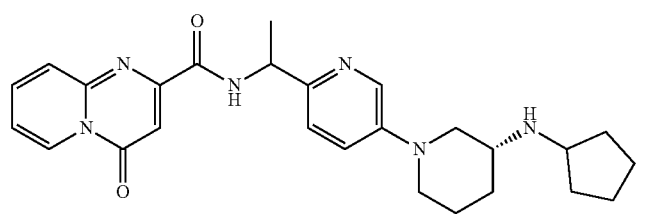 [SMILES: CC(NC(=O)c1cc(=O)n2ccccc2n1)c1ccc(N2CCC[C@@H](NC3CCCC3)C2)cn1] | N-(1-(5-((R)-3-(cyclopentylamino)piperidin-1-yl)pyridin-2-yl)ethyl)-4-oxo-4H-pyrido[1,2-a]pyrimidine-2-carboxamide |
| 118 | 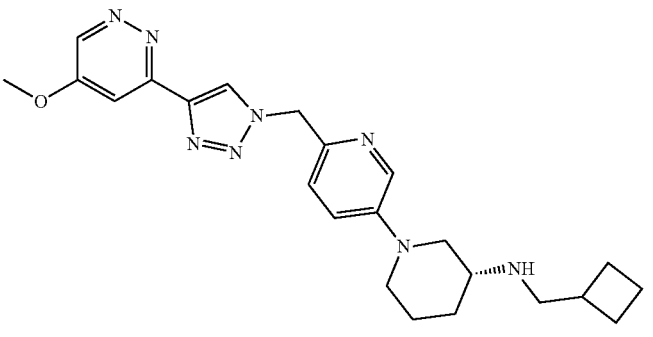 [SMILES: COc1cnnc(-c2cn(Cc3ccc(N4CCC[C@@H](NCC5CCC5)C4)cn3)nn2)c1] | (R)-N-(cyclobutylmethyl)-1-(6-((4-(5-methoxypyridazin-3-yl)-1H-1,2,3-triazol-1-yl)methyl)pyridin-3-yl)piperidin-3-amine |
| 119 | 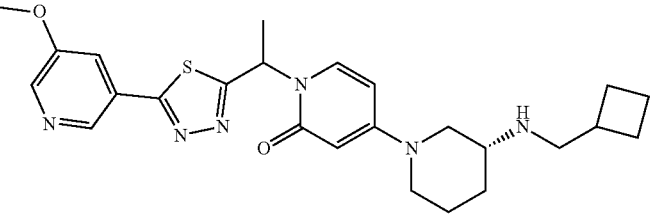 [SMILES: COc1cncc(-c2nnc(C(C)n3ccc(N4CCC[C@@H](NCC5CCC5)C4)cc3=O)s2)c1] | 4-((R)-3-((cyclobutylmethyl)amino)piperidin-1-yl)-1-(1-(5-(5-methoxy pyridin-3-yl)-1,3,4-thiadiazol-2-yl)ethyl)pyridin-2(1H)-one |
| 120 | 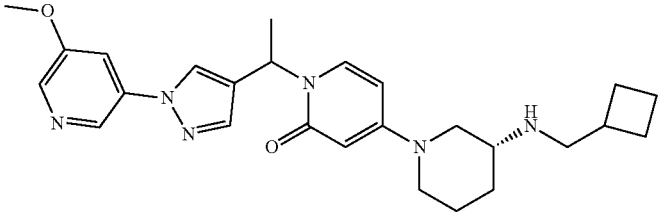 [SMILES: COc1cncc(-n2cc(C(C)n3ccc(N4CCC[C@@H](NCC5CCC5)C4)cc3=O)cn2)c1] | 4-((R)-3-((cyclobutylmethyl)amino)piperidin-1-yl)-1-(1-(1-(5-methoxy pyridin-3-yl)-1H-pyrazol-4-yl)ethyl)pyridin-2(1H)-one |
| 121 | 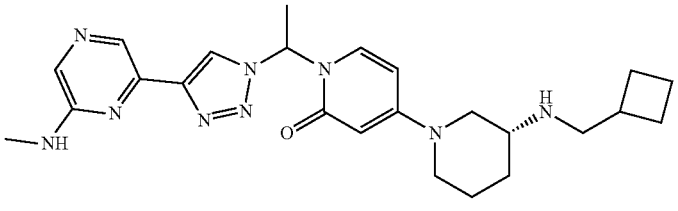 [SMILES: CNc1cncc(-c2cn(C(C)n3ccc(N4CCC[C@@H](NCC5CCC5)C4)cc3=O)nn2)n1] | 4-((R)-3-((cyclobutylmethyl) amino)piperidin-1-yl)-1-(1-(4-(6-(methyl amino)pyrazin-2-yl)-1H-1,2,3-triazol-1-yl)ethyl)pyridin-2(1H)-one |

TABLE 1-continued

| | | |
|---|---|---|
| 122 | | 4-((R)-3-((cyclobutylmethyl)amino)piperidin-1-yl)-1-(1-(4-(5-(methyl amino)pyridazin-3-yl)-1H-1,2,3-triazol-1-yl)ethyl)pyridin-2(1H)-one |
| 123 | | (R)-N-(cyclobutylmethyl)-1-(4-((4-(6-methoxy-1H-indazol-4-yl)-1-1,2,3-triazol-1-yl)methyl)phenyl)piperidin-3-amine |
| 124 | | 4-((R)-3-((cyclobutylmethyl)amino)piperidin-1-yl)-1-(1-(4-(imidazo[1,5-a]pyridin-8-yl)-1H-1,2,3-triazol-1-yl)ethyl)pyridin-2(1H)-one |
| 125 | | 4-((R)-3-((cyclobutylmethyl)amino)piperidin-1-yl)-1-(1-(3-(5-methoxypyridin-3-yl)-1,2,4-oxadiazol-5-yl)ethyl)pyridin-2(1H)-one |
| 126 | | 4-((R)-3-((cyclobutylmethyl)amino)piperidin-1-yl)-3-fluoro-1-(1-(4-(5-methoxypyridin-3-yl)-1H-1,2,3-triazol-1-yl)ethyl)pyridin-2(1H)-one |
| 127 | | (R)-2-(1-((5-(3-((cyclobutylmethyl)amino)piperidin-1-yl)pyridin-2-yl)methyl)-1H-1,2,3-triazol-4-yl)-4H-pyrido[1,2-a]pyrimidin-4-one |

TABLE 1-continued

| 128 | 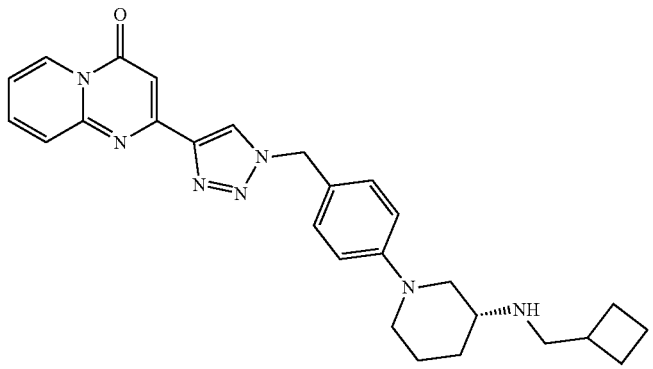 [SMILES: O=c1cc(-c2cn(Cc3ccc(N4CCC[C@@H](NCC5CCC5)C4)cc3)nn2)nc2ccccn12] | (R)-2-(1-(4-(3-((cyclobutylmethyl)amino)piperidin-1-yl)benzyl)-1H-1,2,3-triazol-4-yl)-4H-pyrido[1,2-a]pyrimidin-4-one |
| 129 | 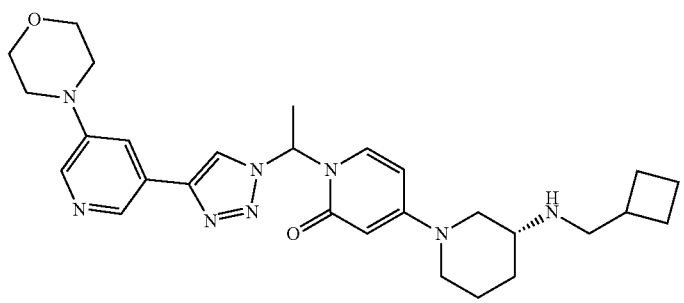 [SMILES: CC(n1cc(-c2cncc(N3CCOCC3)c2)nn1)n1ccc(N2CCC[C@@H](NCC3CCC3)C2)cc1=O] | 4-((R)-3-((cyclobutylmethyl)amino)piperidin-1-yl)-1-(1-(4-(5-morpholinopyridin-3-yl)-1H-1,2,3-triazol-1-yl)ethyl)pyridin-2(1H)-one |
| 130 | 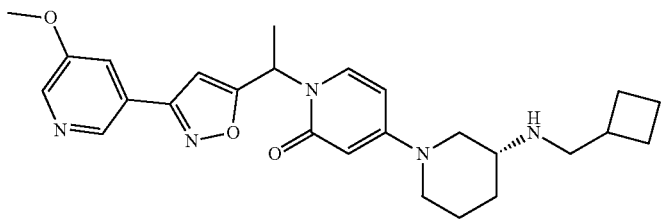 [SMILES: COc1cncc(-c2cc(C(C)n3ccc(N4CCC[C@@H](NCC5CCC5)C4)cc3=O)on2)c1] | 4-((R)-3-((cyclobutylmethyl)amino)piperidin-1-yl)-1-(1-(3-(5-methoxypyridin-3-yl)isoxazol-5-yl)ethyl)pyridin-2(1H)-one |
| 131 | 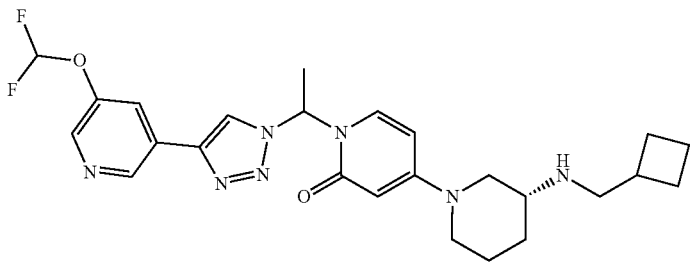 [SMILES: CC(n1cc(-c2cncc(OC(F)F)c2)nn1)n1ccc(N2CCC[C@@H](NCC3CCC3)C2)cc1=O] | 4-((R)-3-((cyclobutylmethyl)amino)piperidin-1-yl)-1-(1-(4-(5-(difluoromethoxy)pyridin-3-yl)-1H-1,2,3-triazol-1-yl)ethyl)pyridin-2(1H)-one |
| 132 | 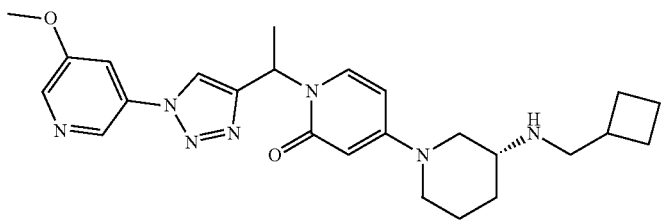 | 4-((R)-3-((cyclobutylmethyl)amino)piperidin-1-yl)-1-(1-(1-(5-methoxypyridin-3-yl)-1H-1,2,3-triazol-4-yl)ethyl)pyridin-2(1H)-one |

TABLE 1-continued

| | | |
|---|---|---|
| 133 | | 5-(1-(1-(6-((R)-3-((cyclobutylmethyl)amino)piperidin-1-yl)pyridazin-3-yl)ethyl)-1H-1,2,3-triazol-4-yl)-N,N-dimethylpyridin-3-amine |
| 134 | | (R)-N-(cyclobutylmethyl)-1-(4-(3-(4-(5-methoxypyridin-3-yl)-1H-1,2,3-triazol-1-yl)oxetan-3-yl)phenyl)piperidin-3-amine |
| 135 | | 4-((R)-3-((cyclobutylmethyl)amino)piperidin-1-yl)-1-(1-(3-(5-methoxypyridin-3-yl)-1H-1,2,4-triazol-1-yl)ethyl)pyridin-2(1H)-one |
| 136 | | (R)-N-(cyclobutylmethyl)-1-(4-((4-(5-methoxypyridazin-3-yl)-1H-1,2,3-triazol-1-yl)methyl)phenyl)piperidin-3-amine |
| 137 | | (3R)-N-(cyclobutylmethyl)-1-(6-(1-(4-(5-methoxypyridazin-3-yl)-1H-1,2,3-triazol-1-yl)ethyl)pyridazin-3-yl)piperidin-3-amine |
| 138 | | (3R)-N-(cyclobutylmethyl)-1-(6-fluoro-5-(1-(4-(5-methoxypyridin-3-yl)-1H-1,2,3-triazol-1-yl)ethyl)pyridin-2-yl)piperidin-3-amine |

TABLE 1-continued

| | | |
|---|---|---|
| 139 | 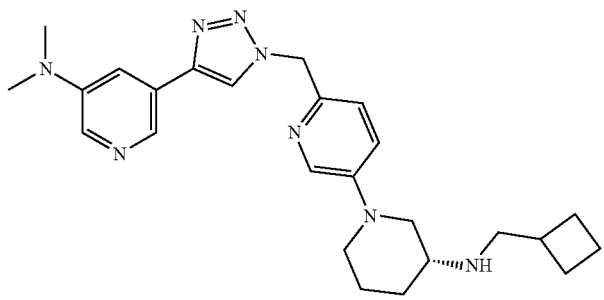 [SMILES: CN(C)c1cncc(-c2cn(Cc3ccc(N4CCC[C@@H](NCC5CCC5)C4)cn3)nn2)c1] | (R)-5-(1-((5-(3-((cyclobutylmethyl)amino)piperidin-1-yl)pyridin-2-yl)methyl)-1H-1,2,3-triazol-4-yl)-N,N-dimethylpyridin-3-amine |
| 140 | 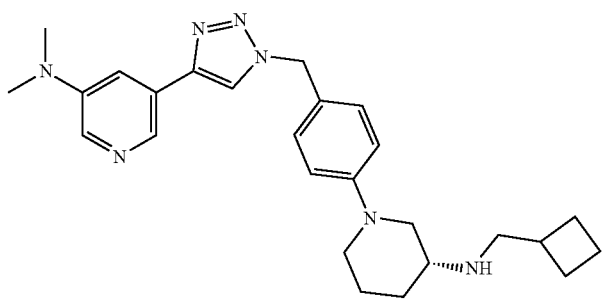 [SMILES: CN(C)c1cncc(-c2cn(Cc3ccc(N4CCC[C@@H](NCC5CCC5)C4)cc3)nn2)c1] | (R)-5-(1-(4-(3-((cyclobutylmethyl)amino)piperidin-1-yl)benzyl)-1H-1,2,3-triazol-4-yl)-N,N-dimethylpyridin-3-amine |
| 141 | 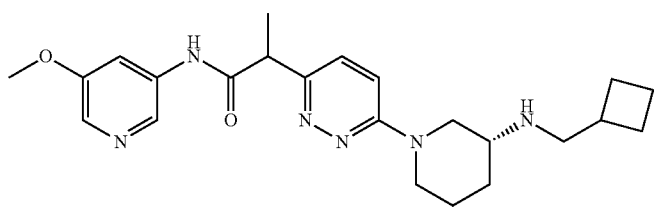 [SMILES: COc1cncc(NC(=O)C(C)c2ccc(N3CCC[C@@H](NCC4CCC4)C3)nn2)c1] | 2-(6-((R)-3-((cyclobutylmethyl)amino)piperidin-1-yl)pyridazin-3-yl)-N-(5-methoxypyridin-3-yl)propanamide |
| 142 | 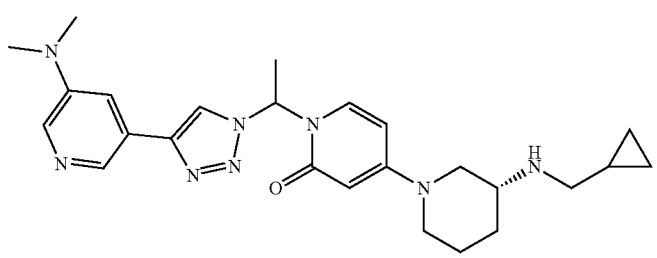 [SMILES: CC(n1cc(-c2cncc(N(C)C)c2)nn1)n1ccc(N2CCC[C@@H](NCC3CC3)C2)cc1=O] | 4-((R)-3-((cyclopropylmethyl)amino)piperidin-1-yl)-1-(1-(4-(5-(dimethylamino)pyridin-3-yl)-1H-1,2,3-triazol-1-yl)ethyl)pyridin-2(1H)-one |
| 143 | 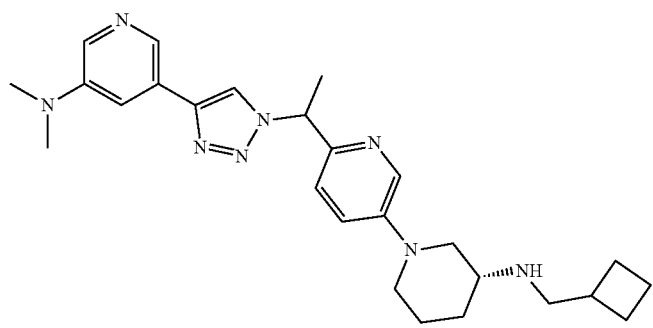 [SMILES: CC(c1ccc(N2CCC[C@@H](NCC3CCC3)C2)cn1)n1cc(-c2cncc(N(C)C)c2)nn1] | 5-(1-(1-(5-((R)-3-((cyclobutylmethyl)amino)piperidin-1-yl)pyridin-2-yl)ethyl)-1H-1,2,3-triazol-4-yl)-N,N-dimethylpyridin-3-amine |

TABLE 1-continued

| 144 | 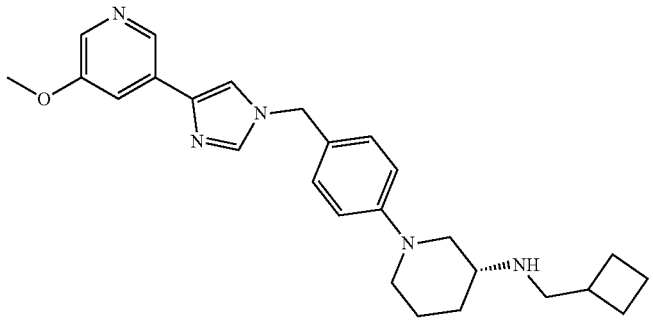 [SMILES: COc1cncc(-c2cn(Cc3ccc(N4CCC[C@@H](NCC5CCC5)C4)cc3)cn2)c1] | (R)-N-(cyclobutylmethyl)-1-(4-((4-(5-methoxypyridin-3-yl)-1H-imidazol-1-yl)methyl)phenyl)piperidin-3-amine |
| 145 | 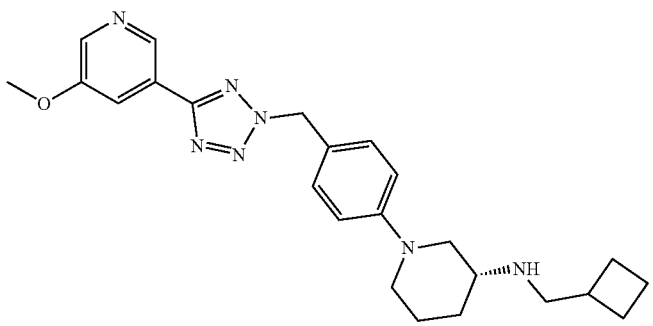 [SMILES: COc1cncc(-c2nnn(Cc3ccc(N4CCC[C@@H](NCC5CCC5)C4)cc3)n2)c1] | (R)-N-(cyclobutylmethyl)-1-(4-((5-(5-methoxypyridin-3-yl)-2H-tetrazol-2-yl)methyl)phenyl)piperidin-3-amine |
| 146 | 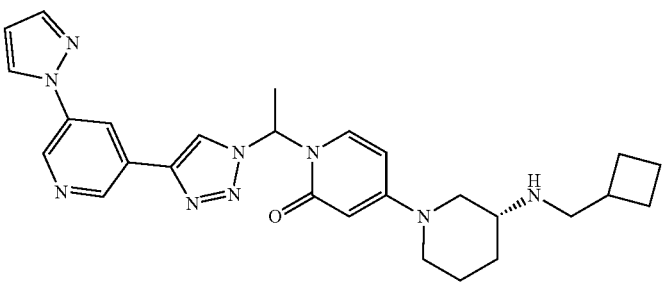 [SMILES: CC(n1cc(-c2cncc(-n3cccn3)c2)nn1)n1ccc(N2CCC[C@@H](NCC3CCC3)C2)cc1=O] | 1-(1-(4-(5-(1H-pyrazol-1-yl)pyridin-3-yl)-1H-1,2,3-triazol-1-yl)ethyl)-4-((R)-3-((cyclobutylmethyl)amino)piperidin-1-yl)pyridin-2(1H)-one |
| 147 | 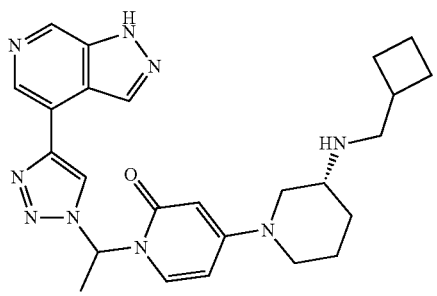 [SMILES: CC(n1cc(-c2cncc3[nH]ncc23)nn1)n1ccc(N2CCC[C@@H](NCC3CCC3)C2)cc1=O] | 1-(1-(4-(1H-pyrazolo[3,4-c]pyridin-4-yl)-1H-1,2,3-triazol-1-yl)ethyl)-4-((R)-3-((cyclobutylmethyl)amino)piperidin-1-yl)pyridin-2(1H)-one |
| 148 | 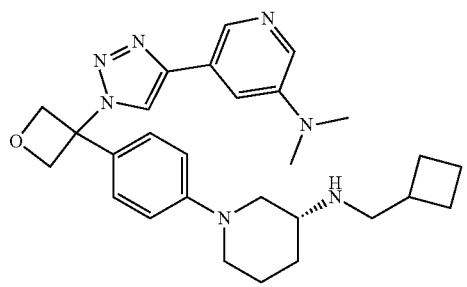 [SMILES: CN(C)c1cncc(-c2cn(C3(c4ccc(N5CCC[C@@H](NCC6CCC6)C5)cc4)COC3)nn2)c1] | (R)-5-(1-(3-(4-(3-((cyclobutylmethyl)amino)piperidin-1-yl)phenyl)oxetan-3-yl)-1H-1,2,3-triazol-4-yl)-N,N-dimethylpyridin-3-amine |

TABLE 1-continued

| | | |
|---|---|---|
| 149 | 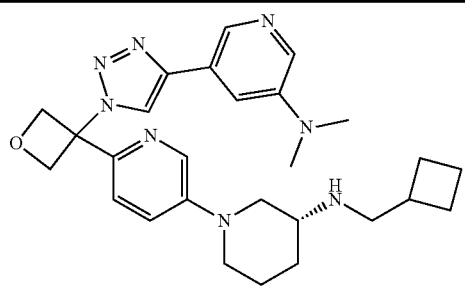 | (R)-5-(1-(3-(5-(3-((cyclobutylmethyl)amino)piperidin-1-yl)pyridin-2-yl)oxetan-3-yl)-1H-1,2,3-triazol-4-yl)-N,N-dimethylpyridin-3-amine |
| 150 | 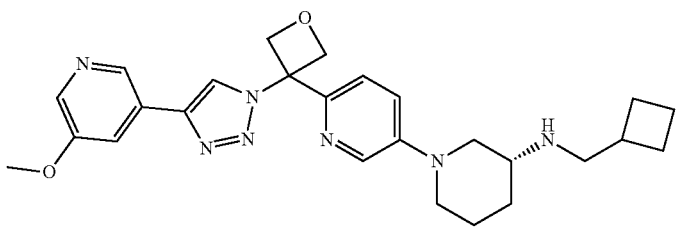 [SMILES: COc1cncc(-c2cn(C3(c4ccc(N5CCC[C@@H](NCC6CCC6)C5)cn4)COC3)nn2)c1] | (R)-N-(cyclobutylmethyl)-1-(6-(3-(4-(5-methoxypyridin-3-yl)-1H-1,2,3-triazol-1-yl)oxetan-3-yl)pyridin-3-yl)piperidin-3-amine |
| 151 | 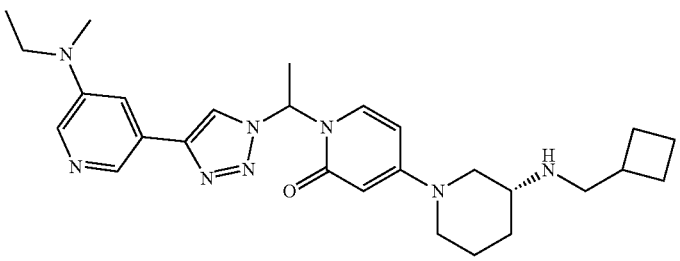 [SMILES: CCN(C)c1cncc(-c2cn(C(C)n3ccc(N4CCC[C@@H](NCC5CCC5)C4)cc3=O)nn2)c1] | 4-((R)-3-((cyclobutylmethyl)amino)piperidin-1-yl)-1-(1-(4-(5-(ethyl(methyl)amino)pyridin-3-yl)-1H-1,2,3-triazol-1-yl)ethyl)pyridin-2(1H)-one |
| 152 | 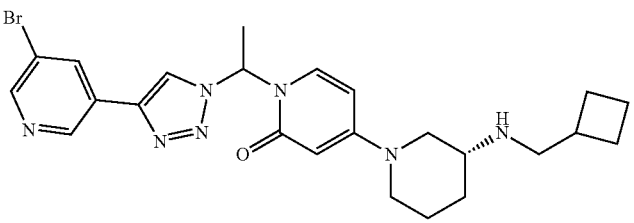 [SMILES: CC(n1cc(-c2cncc(Br)c2)nn1)n1ccc(N2CCC[C@@H](NCC3CCC3)C2)cc1=O] | 1-(1-(4-(5-bromopyridin-3-yl)-1H-1,2,3-triazol-1-yl)ethyl)-4-((R)-3-((cyclobutylmethyl)amino)piperidin-1-yl)pyridin-2(1H)-one |
| 153 | 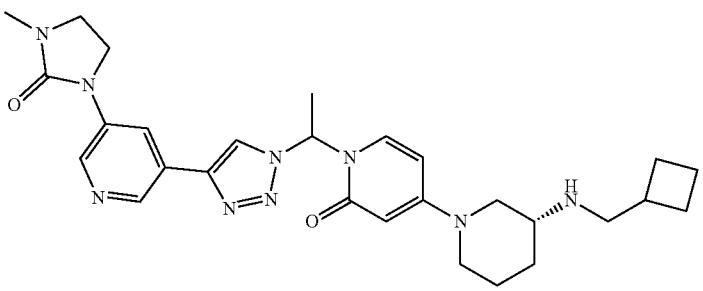 [SMILES: CC(n1cc(-c2cncc(N3CCN(C)C3=O)c2)nn1)n1ccc(N2CCC[C@@H](NCC3CCC3)C2)cc1=O] | 4-((R)-3-((cyclobutylmethyl)amino)piperidin-1-yl)-1-(1-(4-(5-(3-methyl-2-oxoimidazolidin-1-yl)pyridin-3-yl)-1H-1,2,3-triazol-1-yl)ethyl)pyridin-2(1H)-one |
| 154 | 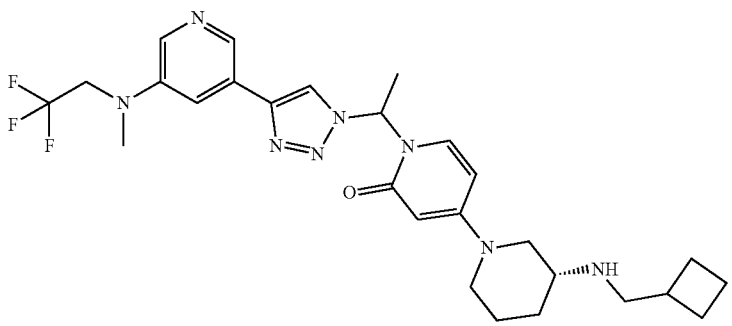 [SMILES: CC(n1cc(-c2cncc(N(C)CC(F)(F)F)c2)nn1)n1ccc(N2CCC[C@@H](NCC3CCC3)C2)cc1=O] | 4-((R)-3-((cyclobutylmethyl)amino)piperidin-1-yl)-1-(1-(4-(5-(methyl(2,2,2-trifluoroethyl)amino)pyridin-3-yl)-1H-1,2,3-triazol-1-yl)ethyl)pyridin-2(1H)-one |

TABLE 1-continued

| 155 | | (R)-5-(1-(1-(4-(3-((cyclobutylmethyl)amino)piperidin-1-yl)phenyl)vinyl)-1H-1,2,3-triazol-4-yl)-N,N-dimethylpyridin-3-amine |
|---|---|---|
| 156 | | 4-((R)-3-((cyclobutylmethyl)amino)piperidin-1-yl)-1-(1-(1-(5-(dimethylamino)pyridin-3-yl)-1H-pyrazol-4-yl)ethyl)pyridin-2(1H)-one |
| 157 | | 2-(6-((R)-3-((cyclobutylmethyl)amino)piperidin-1-yl)pyridazin-3-yl)-N-(5-(dimethylamino)pyridin-3-yl)propanamide |
| 158 | | 4-((R)-3-((cyclobutylmethyl)amino)piperidin-1-yl)-1-(1-(4-(5-(isopropylamino)pyridin-3-yl)-1H-1,2,3-triazol-1-yl)ethyl)pyridin-2(1H)-one |
| 159 | | 4-((R)-3-((cyclobutylmethyl)amino)piperidin-1-yl)-1-(1-(4-(5-(2-oxopyrrolidin-1-yl)pyridin-3-yl)-1H-1,2,3-triazol-1-yl)ethyl)pyridin-2(1H)-one |
| 160 | | 4-((R)-3-((cyclobutylmethyl)amino)piperidin-1-yl)-1-(1-(4-(5-(pyrrolidin-1-yl)pyridin-3-yl)-1H-1,2,3-triazol-1-yl)ethyl)pyridin-2(1H)-one |

TABLE 1-continued

| 161 | 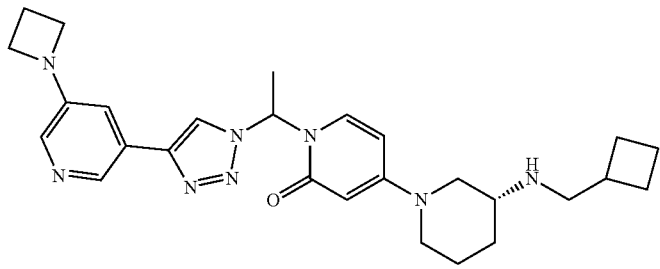 [SMILES: CC(n1cc(-c2cncc(N3CCC3)c2)nn1)n1ccc(N2CCC[C@@H](NCC3CCC3)C2)cc1=O] | 1-(1-(4-(5-(azetidin-1-yl)pyridin-3-yl)-1H-1,2,3-triazol-1-yl)ethyl)-4-((R)-3-((cyclobutylmethyl)amino)piperidin-1-yl)pyridin-2(1H)-one |
| --- | --- | --- |
| 162 | 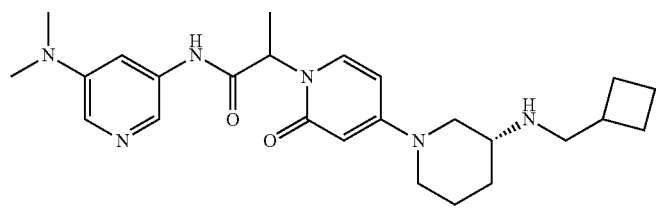 [SMILES: CC(C(=O)Nc1cncc(N(C)C)c1)n1ccc(N2CCC[C@@H](NCC3CCC3)C2)cc1=O] | 2-(4-((R)-3-((cyclobutylmethyl)amino)piperidin-1-yl)-2-oxopyridin-1(2H)-yl)-N-(5-(dimethylamino)pyridin-3-yl)propanamide |
| 163 | 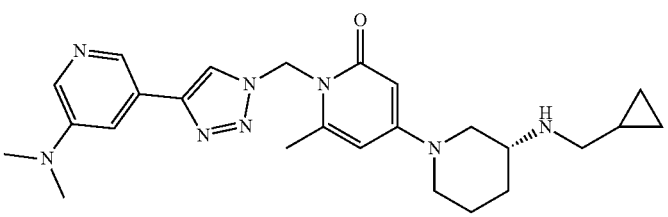 [SMILES: Cc1cc(N2CCC[C@@H](NCC3CC3)C2)cc(=O)n1Cn1cc(-c2cncc(N(C)C)c2)nn1] | (R)-4-(3-((cyclopropylmethyl)amino)piperidin-1-yl)-1-((4-(5-(dimethylamino)pyridin-3-yl)-1H-1,2,3-triazol-1-yl)methyl)-6-methylpyridin-2(1H)-one |
| 164 | 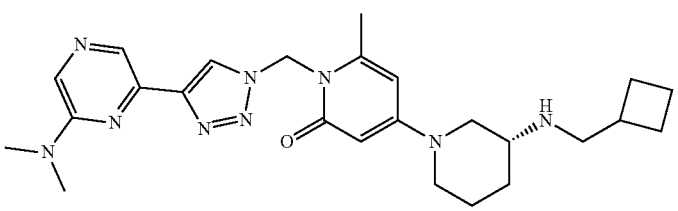 [SMILES: Cc1cc(N2CCC[C@@H](NCC3CCC3)C2)cc(=O)n1Cn1cc(-c2cncc(N(C)C)n2)nn1] | 4-((R)-3-((cyclobutylmethyl)amino)piperidin-1-yl)-1-(1-(4-(6-(dimethylamino)pyrazin-2-yl)-1H-1,2,3-triazol-1-yl)ethyl)pyridin-2(1H)-one |
| 165 | 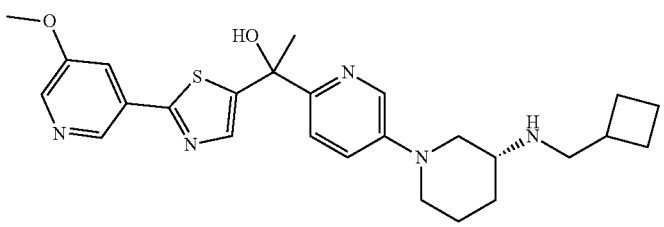 [SMILES: COc1cncc(-c2ncc(C(C)(O)c3ccc(N4CCC[C@@H](NCC5CCC5)C4)cn3)s2)c1] | 1-(5-((R)-3-((cyclobutylmethyl)amino)piperidin-1-yl)pyridin-2-yl)-1-(2-(5-methoxypyridin-3-yl)thiazol-5-yl)ethan-1-ol |
| 166 | 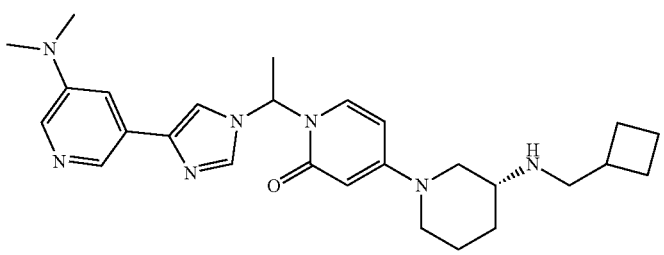 [SMILES: CC(n1cnc(-c2cncc(N(C)C)c2)c1)n1ccc(N2CCC[C@@H](NCC3CCC3)C2)cc1=O] | 4-((R)-3-((cyclobutylmethyl)amino)piperidin-1-yl)-1-(1-(4-(5-(dimethylamino)pyridin-3-yl)-1H-imidazol-1-yl)ethyl)pyridin-2(1H)-one |

TABLE 1-continued

| 167 | 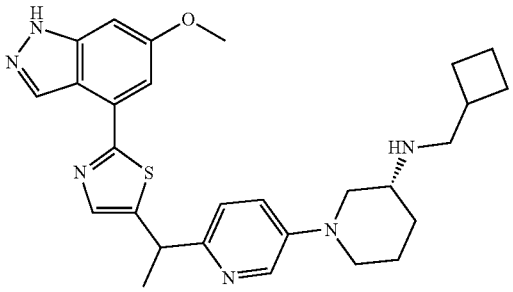 [SMILES: COc1cc(-c2ncc(C(C)c3ccc(N4CCC[C@@H](NCC5CCC5)C4)cn3)s2)c2cn[nH]c2c1] | (3R)-N-(cyclobutylmethyl)-1-(6-(1-(2-(6-methoxy-1H-indazol-4-yl)thiazol-5-yl)ethyl)pyridin-3-yl)piperidin-3-amine |
| 168 | 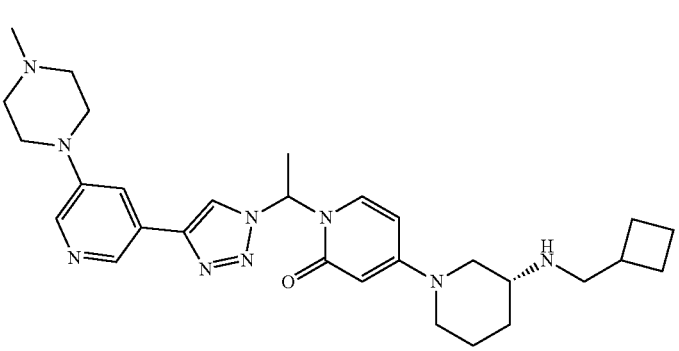 [SMILES: CC(n1cc(-c2cncc(N3CCN(C)CC3)c2)nn1)n1ccc(N2CCC[C@@H](NCC3CCC3)C2)cc1=O] | 4-((R)-3-((cyclobutylmethyl)amino)piperidin-1-yl)-1-(1-(4-(5-(4-methylpiperazin-1-yl)pyridin-3-yl)-1H-1,2,3-triazol-1-yl)ethyl)pyridin-2(1H)-one |
| 169 | 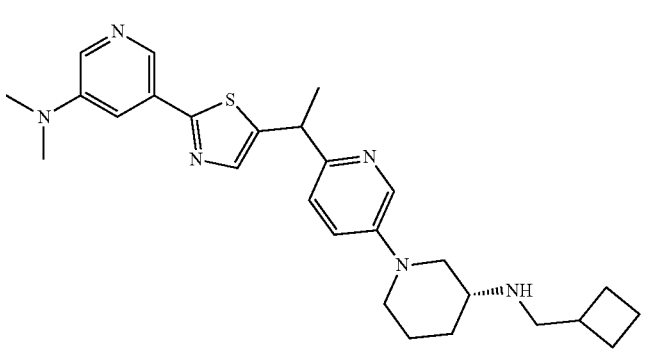 [SMILES: CC(c1ccc(N2CCC[C@@H](NCC3CCC3)C2)cn1)c1cnc(-c2cncc(N(C)C)c2)s1] | 5-(5-(1-(5-((R)-3-((cyclobutylmethyl)amino)piperidin-1-yl)pyridin-2-yl)ethyl)thiazol-2-yl)-N,N-dimethylpyridin-3-amine |
| 170 | 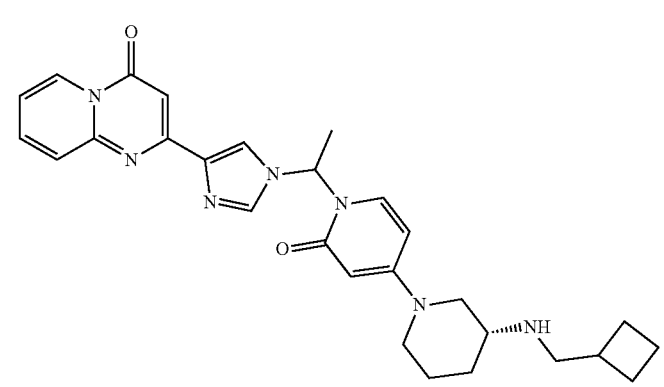 [SMILES: CC(n1cnc(-c2cc(=O)n3ccccc3n2)c1)n1ccc(N2CCC[C@@H](NCC3CCC3)C2)cc1=O] | 2-(1-(1-(4-((R)-3-((cyclobutylmethyl)amino)piperidin-1-yl)-2-oxopyridin-1(2H)-yl)ethyl)-1H-imidazol-4-yl)-4H-pyrido[1,2-a]pyrimidin-4-one |
| 171 | 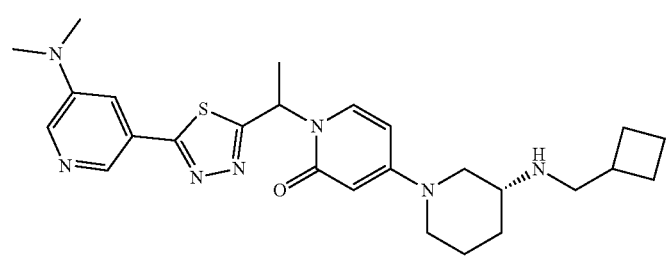 [SMILES: CC(c1nnc(-c2cncc(N(C)C)c2)s1)n1ccc(N2CCC[C@@H](NCC3CCC3)C2)cc1=O] | 4-((R)-3-((cyclobutylmethyl)amino)piperidin-1-yl)-1-(1-(5-(5-(dimethylamino)pyridin-3-yl)-1,3,4-thiadiazol-2-yl)ethyl)pyridin-2(1H)-one |

TABLE 1-continued

| | | |
|---|---|---|
| 172 | 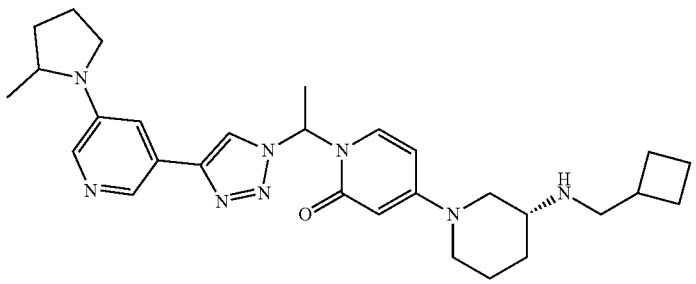 [SMILES: CC1CCCN1c1cncc(-c2cn(C(C)n3ccc(N4CCC[C@@H](NCC5CCC5)C4)cc3=O)nn2)c1] | 4-((R)-3-((cyclobutylmethyl)amino)piperidin-1-yl)-1-(1-(4-(5-(2-methylpyrrolidin-1-yl)pyridin-3-yl)-1H-1,2,3-triazol-1-yl)ethyl)pyridin-2(1H)-one |
| 173 | 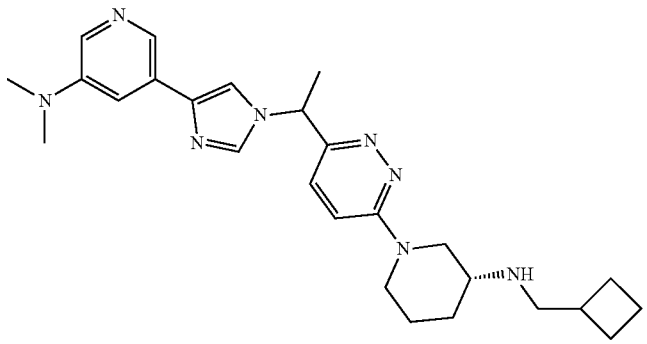 [SMILES: CC(c1ccc(N2CCC[C@@H](NCC3CCC3)C2)nn1)n1cnc(-c2cncc(N(C)C)c2)c1] | 5-(1-(1-(6-((R)-3-((cyclobutylmethyl)amino)piperidin-1-yl)pyridazin-3-yl)ethyl)-1H-imidazol-4-yl)-N,N-dimethylpyridin-3-amine |
| 174 | 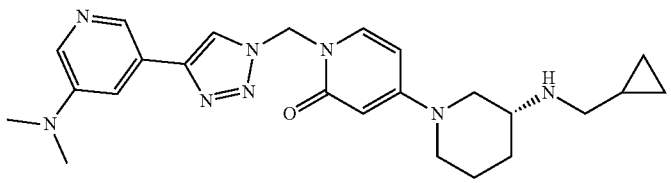 [SMILES: CN(C)c1cncc(-c2cn(Cn3ccc(N4CCC[C@@H](NCC5CC5)C4)cc3=O)nn2)c1] | (R)-4-(3-((cyclopropylmethyl)amino)piperidin-1-yl)-1-((4-(5-(dimethylamino)pyridin-3-yl)-1H-1,2,3-triazol-1-yl)methyl)pyridin-2(1H)-one |
| 175 | 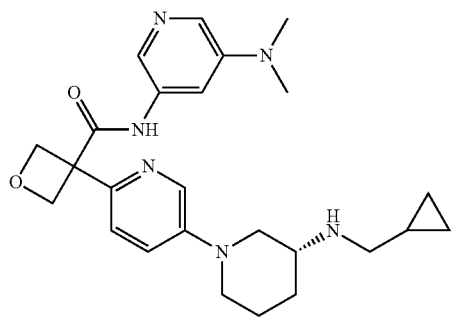 [SMILES: CN(C)c1cncc(NC(=O)C2(c3ccc(N4CCC[C@@H](NCC5CC5)C4)cn3)COC2)c1] | (R)-3-(5-(3-((cyclopropylmethyl)amino)piperidin-1-yl)pyridin-2-yl)-N-(5-(dimethylamino)pyridin-3-yl)oxetane-3-carboxamide |
| 176 | 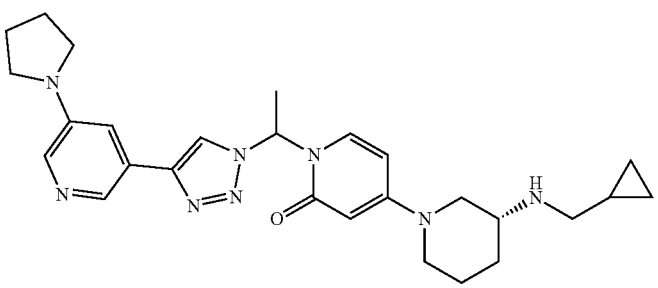 [SMILES: CC(n1cc(-c2cncc(N3CCCC3)c2)nn1)n1ccc(N2CCC[C@@H](NCC3CC3)C2)cc1=O] | 4-((R)-3-((cyclopropylmethyl)amino)piperidin-1-yl)-1-(1-(4-(5-(pyrrolidin-1-yl)pyridin-3-yl)-1H-1,2,3-triazol-1-yl)ethyl)pyridin-2(1H)-one |

TABLE 1-continued

| | | |
|---|---|---|
| 177 | | 4-((R)-3-((cyclobutylmethyl)amino)piperidin-1-yl)-1-(1-(4-(5-(3-methylazetidin-1-yl)pyridin-3-yl)-1H-1,2,3-triazol-1-yl)ethyl)pyridin-2(1H)-one |
| 178 | | 4-((R)-3-((cyclobutylmethyl)amino)piperidin-1-yl)-1-(1-(4-(5-(piperidin-1-yl)pyridin-3-yl)-1H-1,2,3-triazol-1-yl)ethyl)pyridin-2(1H)-one |
| 179 | | 4-((R)-3-((cyclobutylmethyl)amino)piperidin-1-yl)-1-(1-(5-(5-(dimethylamino)pyridin-3-yl)-2H-tetrazol-2-yl)ethyl)pyridin-2(1H)-one |
| 180 | | 4-((R)-3-((cyclopropylmethyl)amino)piperidin-1-yl)-1-(1-(4-(6-(pyrrolidin-1-yl)pyrazin-2-yl)-1H-1,2,3-triazol-1-yl)ethyl)pyridin-2(1H)-one |
| 181 | | (3R)-N-(cyclobutylmethyl)-1-(6-(1-(2-(5-methoxypyridin-3-yl)thiazol-5-yl)ethyl)pyridin-3-yl)piperidin-3-amine |

TABLE 1-continued

| 182 | 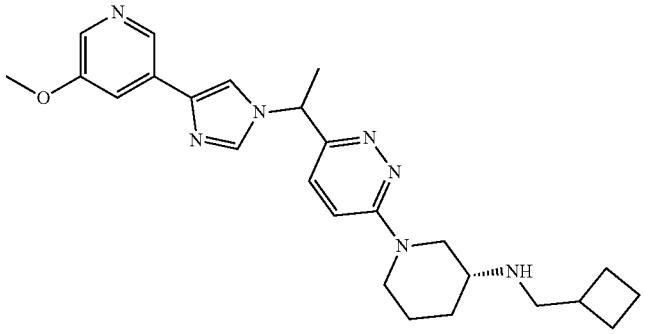 [SMILES: COc1cncc(-c2cn(C(C)c3ccc(N4CCC[C@@H](NCC5CCC5)C4)nn3)cn2)c1] | (3R)-N-(cyclobutylmethyl)-1-(6-(1-(4-(5-methoxypyridin-3-yl)-1H-imidazol-1-yl)ethyl)pyridazin-3-yl)piperidin-3-amine |
| 183 | 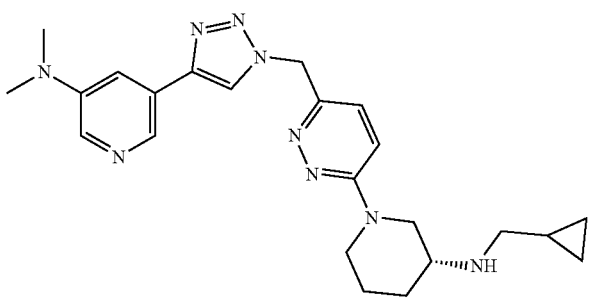 [SMILES: CN(C)c1cncc(-c2cn(Cc3ccc(N4CCC[C@@H](NCC5CC5)C4)nn3)nn2)c1] | (R)-5-(1-((6-(3-((cyclopropylmethyl)amino)piperidin-1-yl)pyridazin-3-yl)methyl)-1H-1,2,3-triazol-4-yl)-N,N-dimethylpyridin-3-amine |
| 184 | 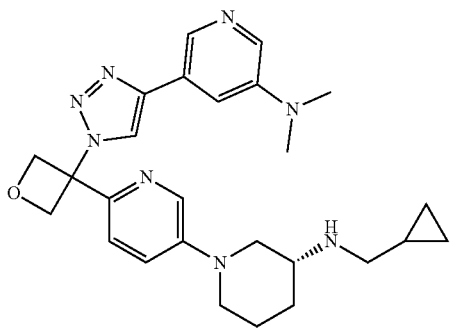 [SMILES: CN(C)c1cncc(-c2cn(C3(c4ccc(N5CCC[C@@H](NCC6CC6)C5)cn4)COC3)nn2)c1] | (R)-5-(1-(3-(5-(3-((cyclopropylmethyl)amino)piperidin-1-yl)pyridin-2-yl)oxetan-3-yl)-1H-1,2,3-triazol-4-yl)-N,N-dimethylpyridin-3-amine |
| 185 | 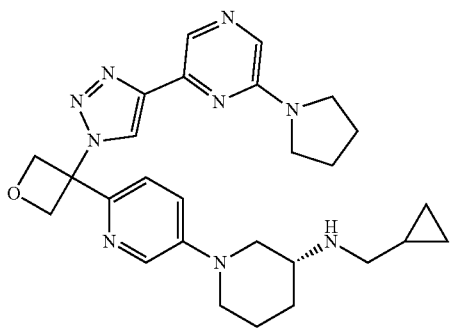 [SMILES: c1cc(C2(n3cc(-c4cncc(N5CCCC5)n4)nn3)COC2)ncc1N1CCC[C@@H](NCC2CC2)C1] | (R)-N-(cyclopropylmethyl)-1-(6-(3-(4-(6-(pyrrolidin-1-yl)pyrazin-2-yl)-1H-1,2,3-triazol-1-yl)oxetan-3-yl)pyridin-3-yl)piperidin-3-amine |
| 186 | 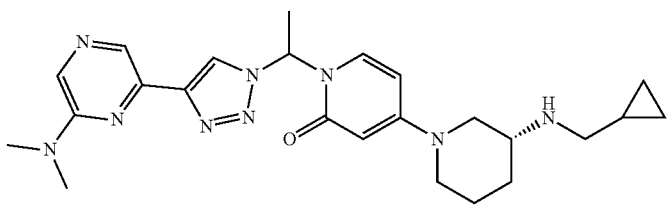 [SMILES: CC(n1cc(-c2cncc(N(C)C)n2)nn1)n1ccc(N2CCC[C@@H](NCC3CC3)C2)cc1=O] | 4-((R)-3-((cyclopropylmethyl)amino)piperidin-1-yl)-1-(1-(4-(6-(dimethylamino)pyrazin-2-yl)-1H-1,2,3-triazol-1-yl)ethyl)pyridin-2(1H)-one |

TABLE 1-continued

| 187 | 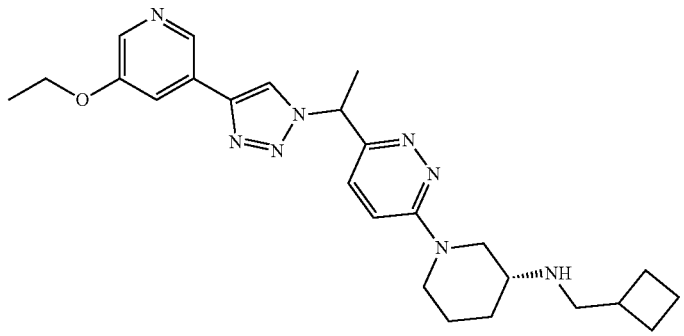 [SMILES: CCOc1cncc(-c2cn(C(C)c3ccc(N4CCC[C@@H](NCC5CCC5)C4)nn3)nn2)c1] | (3R)-N-(cyclobutylmethyl)-1-(6-(1-(4-(5-ethoxypyridin-3-yl)-1H-1,2,3-triazol-1-yl)ethyl)pyridazin-3-yl)piperidin-3-amine |
| --- | --- | --- |
| 188 | 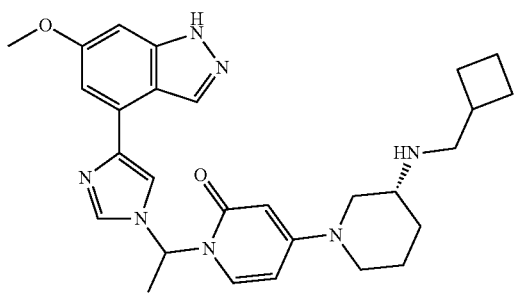 [SMILES: COc1cc(-c2cn(C(C)n3ccc(N4CCC[C@@H](NCC5CCC5)C4)cc3=O)cn2)c2cn[nH]c2c1] | 4-((R)-3-((cyclobutylmethyl)amino)piperidin-1-yl)-1-(1-(4-(6-methoxy-1H-indazol-4-yl)-1H-imidazol-1-yl)ethyl)pyridin-2(1H)-one |
| 189 | 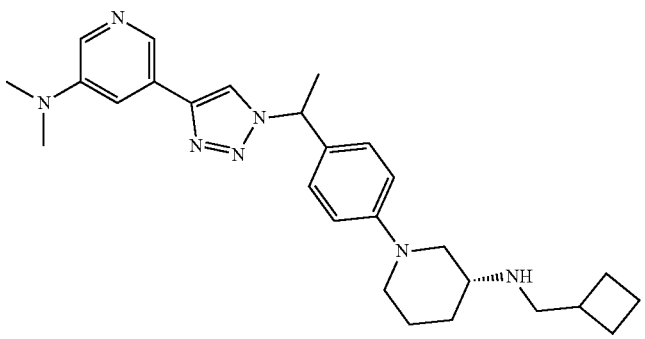 [SMILES: CC(c1ccc(N2CCC[C@@H](NCC3CCC3)C2)cc1)n1cc(-c2cncc(N(C)C)c2)nn1] | 5-(1-(1-(4-((R)-3-((cyclobutylmethyl)amino)piperidin-1-yl)phenyl)ethyl)-1H-1,2,3-triazol-4-yl)-N,N-dimethylpyridin-3-amine |
| 190 | 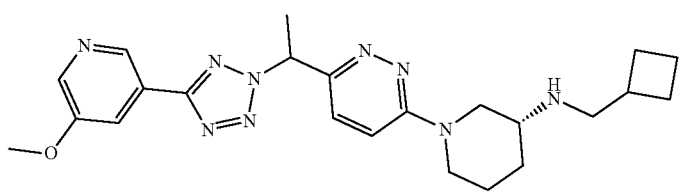 [SMILES: COc1cncc(-c2nnn(C(C)c3ccc(N4CCC[C@@H](NCC5CCC5)C4)nn3)n2)c1] | (3R)-N-(cyclobutylmethyl)-1-(6-(1-(5-(5-methoxypyridin-3-yl)-2H-tetrazol-2-yl)ethyl)pyridazin-3-yl)piperidin-3-amine |
| 191 | 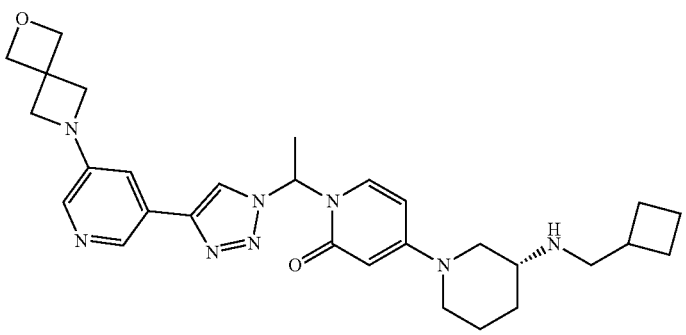 [SMILES: CC(n1cc(-c2cncc(N3CC4(COC4)C3)c2)nn1)n1ccc(N2CCC[C@@H](NCC3CCC3)C2)cc1=O] | 1-(1-(4-(5-(2-oxa-6-azaspiro[3.3]heptan-6-yl)pyridin-3-yl)-1H-1,2,3-triazol-1-yl)ethyl)-4-((R)-3-((cyclobutylmethyl)amino)piperidin-1-yl)pyridin-2(1H)-one |

| | | |
|---|---|---|
| 192 | 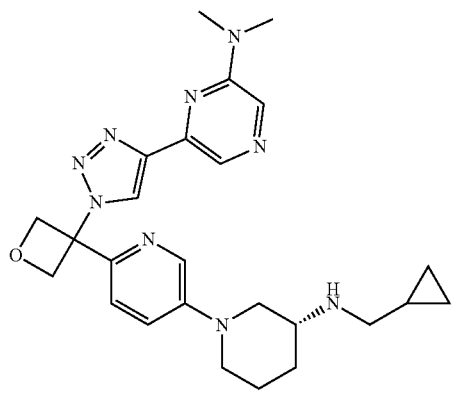 [SMILES: CN(C)c1cncc(-c2cn(C3(c4ccc(N5CCC[C@@H](NCC6CC6)C5)cn4)COC3)nn2)n1] | (R)-6-(1-(3-(5-(3-((cyclopropylmethyl)amino)piperidin-1-yl)pyridin-2-yl)oxetan-3-yl)-1H-1,2,3-triazol-4-yl)-N,N-dimethylpyrazin-2-amine |
| 193 | 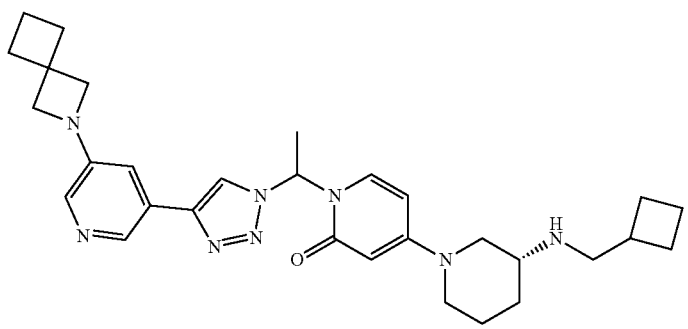 [SMILES: CC(n1cc(-c2cncc(N3CC4(CCC4)C3)c2)nn1)n1ccc(N2CCC[C@@H](NCC3CCC3)C2)cc1=O] | 1-(1-(4-(5-(2-azaspiro[3.3]heptan-2-yl)pyridin-3-yl)-1H-1,2,3-triazol-1-yl)ethyl)-4-((R)-3-((cyclobutylmethyl)amino)piperidin-1-yl)pyridin-2(1H)-one |
| 194 | 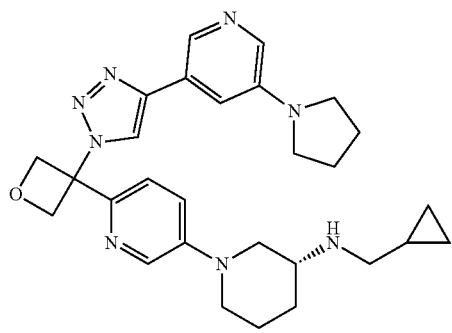 [SMILES: c1ncc(N2CCCC2)cc1-c1cn(C2(c3ccc(N4CCC[C@@H](NCC5CC5)C4)cn3)COC2)nn1] | (R)-N-(cyclopropylmethyl)-1-(6-(3-(4-(5-(pyrrolidin-1-yl)pyridin-3-yl)-1H-1,2,3-triazol-1-yl)oxetan-3-yl)pyridin-3-yl)piperidin-3-amine |
| 195 | 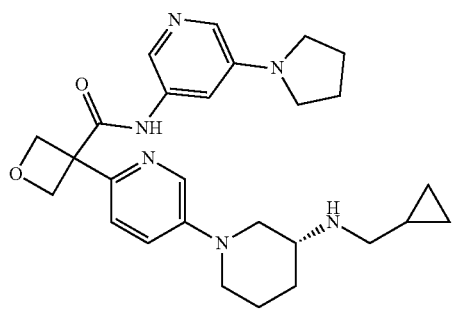 [SMILES: O=C(Nc1cncc(N2CCCC2)c1)C1(c2ccc(N3CCC[C@@H](NCC4CC4)C3)cn2)COC1] | (R)-3-(5-(3-((cyclopropylmethyl)amino)piperidin-1-yl)pyridin-2-yl)-N-(5-(pyrrolidin-1-yl)pyridin-3-yl)oxetane-3-carboxamide |
| 196 | 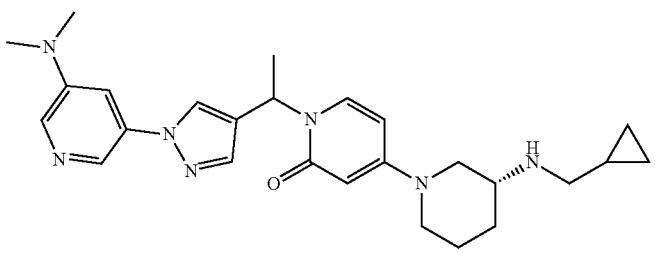 [SMILES: CC(c1cnn(-c2cncc(N(C)C)c2)c1)n1ccc(N2CCC[C@@H](NCC3CC3)C2)cc1=O] | 4-((R)-3-((cyclopropylmethyl)amino)piperidin-1-yl)-1-(1-(1-(5-(dimethylamino)pyridin-3-yl)-1H-pyrazol-4-yl)ethyl)pyridin-2(1H)-one |

TABLE 1-continued

| | | |
|---|---|---|
| 197 | | 4-((R)-3-((cyclopropylmethyl)amino)piperidin-1-yl)-1-(1-(4-(5-(3,3-difluoroazetidin-1-yl)pyridin-3-yl)-1H-1,2,3-triazol-1-yl)ethyl)pyridin-2(1H)-one |
| 198 | | 4-((R)-3-((cyclobutylmethyl)amino)piperidin-1-yl)-1-(1-(4-(5-(dimethylamino)pyridazin-3-yl)-1H-1,2,3-triazol-1-yl)ethyl)pyridin-2(1H)-one |
| 199 | | 4-((R)-3-((cyclobutylmethyl)amino)piperidin-1-yl)-1-(1-(4-(5-(3-methoxyazetidin-1-yl)pyridin-3-yl)-1H-1,2,3-triazol-1-yl)ethyl)pyridin-2(1H)-one |
| 200 | | 4-((R)-3-((cyclobutylmethyl)amino)piperidin-1-yl)-1-(1-(4-(5-(2,2,2-trifluoroethoxy)pyridin-3-yl)-1H-1,2,3-triazol-1-yl)ethyl)pyridin-2(1H)-one |
| 201 | | (R)-4-(3-((cyclopropylmethyl)amino)piperidin-1-yl)-1-((4-(6-(pyrrolidin-1-yl)pyrazin-2-yl)-1H-1,2,3-triazol-1-yl)methyl)pyridin-2(1H)-one |

TABLE 1-continued

| 202 | 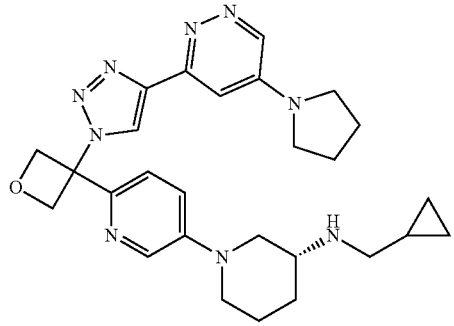 [SMILES: c1nnc(-c2cn(C3(c4ccc(N5CCC[C@@H](NCC6CC6)C5)cn4)COC3)nn2)cc1N1CCCC1] | (R)-N-(cyclopropylmethyl)-1-(6-(3-(4-(5-(pyrrolidin-1-yl)pyridazin-3-yl)-1H-1,2,3-triazol-1-yl)oxetan-3-yl)pyridin-3-yl)piperidin-3-amine |
| 203 | 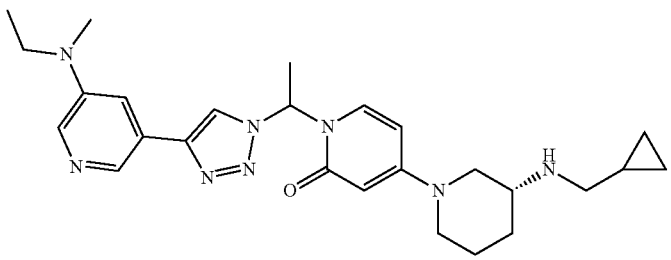 [SMILES: CCN(C)c1cncc(-c2cn(C(C)n3ccc(N4CCC[C@@H](NCC5CC5)C4)cc3=O)nn2)c1] | 4-((R)-3-((cyclopropylmethyl)amino)piperidin-1-yl)-1-(1-(4-(5-(ethyl(methyl)amino)pyridin-3-yl)-1H-1,2,3-triazol-1-yl)ethyl)pyridin-2(1H)-one |
| 204 | 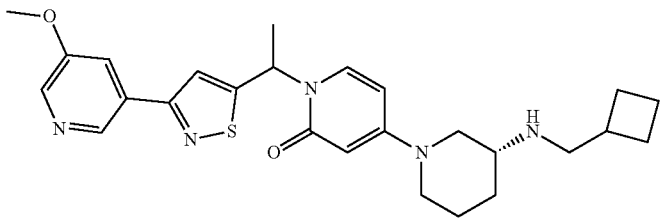 [SMILES: COc1cncc(-c2cc(C(C)n3ccc(N4CCC[C@@H](NCC5CCC5)C4)cc3=O)sn2)c1] | 4-((R)-3-((cyclobutylmethyl)amino)piperidin-1-yl)-1-(1-(3-(5-methoxypyridin-3-yl)isothiazol-5-yl)ethyl)pyridin-2(1H)-one |
| 205 | 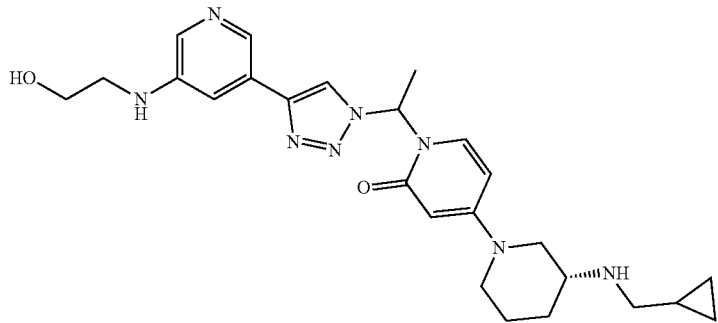 [SMILES: CC(n1cc(-c2cncc(NCCO)c2)nn1)n1ccc(N2CCC[C@@H](NCC3CC3)C2)cc1=O] | 4-((R)-3-((cyclopropylmethyl)amino)piperidin-1-yl)-1-(1-(4-(5-((2-hydroxyethyl)amino)pyridin-3-yl)-1H-1,2,3-triazol-1-yl)ethyl)pyridin-2(1H)-one |
| 206 | 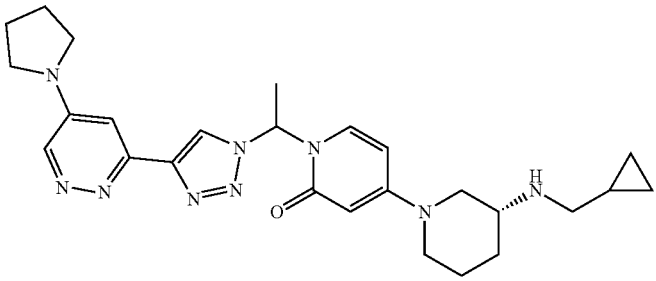 [SMILES: CC(n1cc(-c2cc(N3CCCC3)cnn2)nn1)n1ccc(N2CCC[C@@H](NCC3CC3)C2)cc1=O] | 4-((R)-3-((cyclopropylmethyl)amino)piperidin-1-yl)-1-(1-(4-(5-(pyrrolidin-1-yl)pyridazin-3-yl)-1H-1,2,3-triazol-1-yl)ethyl)pyridin-2(1H)-one |

TABLE 1-continued

| 207 | 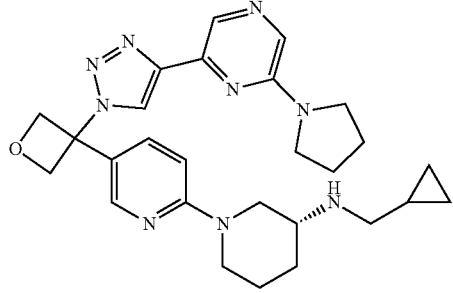 [SMILES: c1cc(N2CCC[C@@H](NCC3CC3)C2)ncc1C1(n2cc(-c3cncc(N4CCCC4)n3)nn2)COC1] | (R)-N-(cyclopropylmethyl)-1-(5-(3-(4-(6-(pyrrolidin-1-yl)pyrazin-2-yl)-1H-1,2,3-triazol-1-yl)oxetan-3-yl)pyridin-2-yl)piperidin-3-amine |
| 208 | 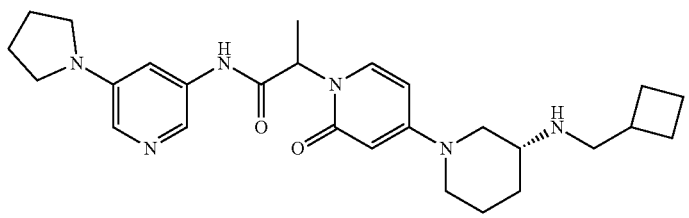 [SMILES: CC(C(=O)Nc1cncc(N2CCCC2)c1)n1ccc(N2CCC[C@@H](NCC3CCC3)C2)cc1=O] | 2-(4-((R)-3-((cyclobutylmethyl)amino)piperidin-1-yl)-2-oxopyridin-1(2H)-yl)-N-(5-(pyrrolidin-1-yl)pyridin-3-yl)propanamide |
| 209 | 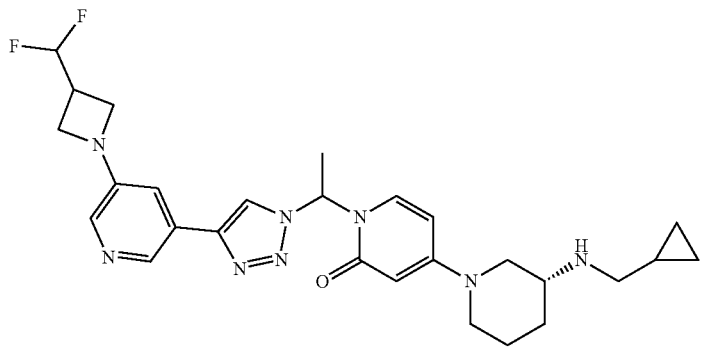 [SMILES: CC(n1cc(-c2cncc(N3CC(C(F)F)C3)c2)nn1)n1ccc(N2CCC[C@@H](NCC3CC3)C2)cc1=O] | 4-((R)-3-((cyclopropylmethyl)amino)piperidin-1-yl)-1-(1-(4-(5-(3-(difluoromethyl)azetidin-1-yl)pyridin-3-yl)-1H-1,2,3-triazol-1-yl)ethyl)pyridin-2(1H)-one |
| 210 | 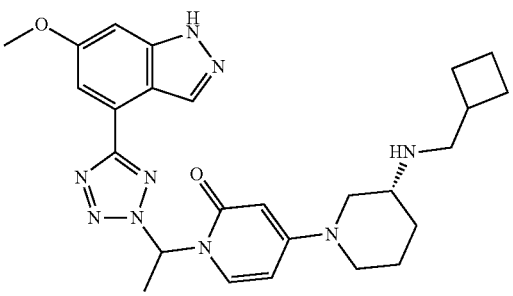 [SMILES: COc1cc(-c2nnn(C(C)n3ccc(N4CCC[C@@H](NCC5CCC5)C4)cc3=O)n2)c2cn[nH]c2c1] | 4-((R)-3-((cyclobutylmethyl)amino)piperidin-1-yl)-1-(1-(5-(6-methoxy-1H-indazol-4-yl)-2H-tetrazol-2-yl)ethyl)pyridin-2(1H)-one |
| 211 | 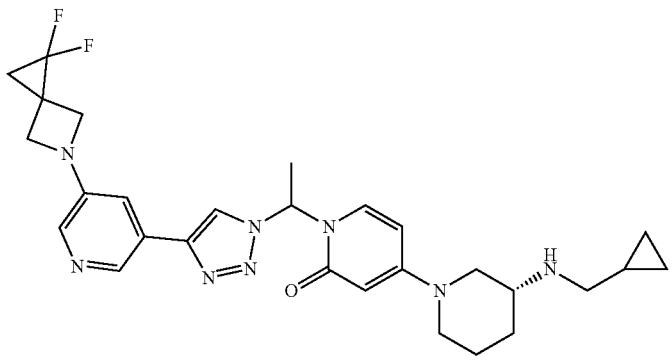 [SMILES: CC(n1cc(-c2cncc(N3CC4(C3)CC4(F)F)c2)nn1)n1ccc(N2CCC[C@@H](NCC3CC3)C2)cc1=O] | 4-((R)-3-((cyclopropylmethyl)amino)piperidin-1-yl)-1-(1-(4-(5-(1,1-difluoro-5-azaspiro[2.3]hexan-5-yl)pyridin-3-yl)-1H-1,2,3-triazol-1-yl)ethyl)pyridin-2(1H)-one |

TABLE 1-continued

| | | |
|---|---|---|
| 212 | 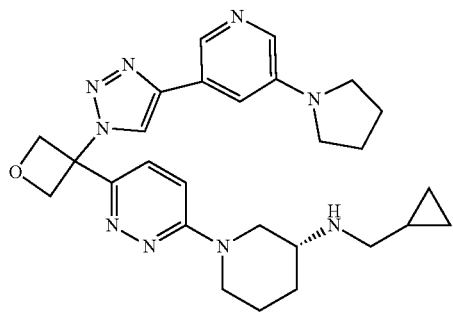 [SMILES: c1ncc(N2CCCC2)cc1-c1cn(C2(c3ccc(N4CCC[C@@H](NCC5CC5)C4)nn3)COC2)nn1] | (R)-N-(cyclopropylmethyl)-1-(6-(3-(4-(5-(pyrrolidin-1-yl)pyridin-3-yl)-1H-1,2,3-triazol-1-yl)oxetan-3-yl)pyridazin-3-yl)piperidin-3-amine |
| 213 | 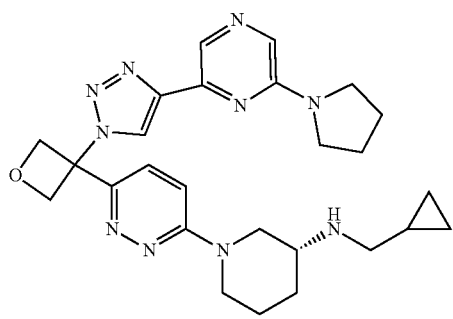 [SMILES: c1ncc(N2CCCC2)nc1-c1cn(C2(c3ccc(N4CCC[C@@H](NCC5CC5)C4)nn3)COC2)nn1] | (R)-N-(cyclopropylmethyl)-1-(6-(3-(4-(6-(pyrrolidin-1-yl)pyrazin-2-yl)-1H-1,2,3-triazol-1-yl)oxetan-3-yl)pyridazin-3-yl)piperidin-3-amine |
| 214 | 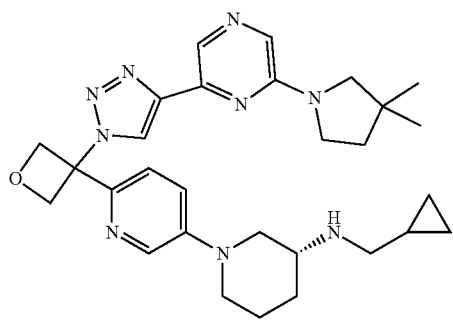 [SMILES: CC1(C)CCN(c2cncc(-c3cn(C4(c5ccc(N6CCC[C@@H](NCC7CC7)C6)cn5)COC4)nn3)n2)C1] | (R)-N-(cyclopropylmethyl)-1-(6-(3-(4-(6-(3,3-dimethylpyrrolidin-1-yl)pyrazin-2-yl)-1H-1,2,3-triazol-1-yl)oxetan-3-yl)pyridin-3-yl)piperidin-3-amine |
| 215 | 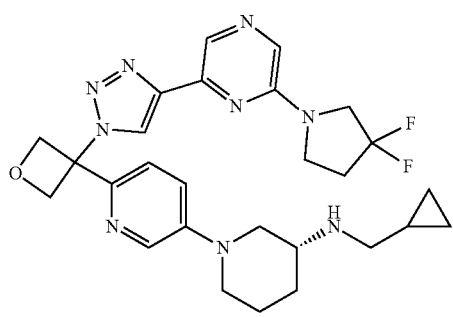 [SMILES: FC1(F)CCN(c2cncc(-c3cn(C4(c5ccc(N6CCC[C@@H](NCC7CC7)C6)cn5)COC4)nn3)n2)C1] | (R)-N-(cyclopropylmethyl)-1-(6-(3-(4-(6-(3,3-difluoropyrrolidin-1-yl)pyrazin-2-yl)-1H-1,2,3-triazol-1-yl)oxetan-3-yl)pyridin-3-yl)piperidin-3-amine |
| 216 | 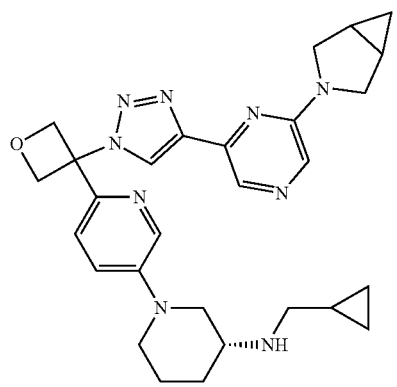 [SMILES: c1cc(C2(n3cc(-c4cncc(N5CC6CC6C5)n4)nn3)COC2)ncc1N1CCC[C@@H](NCC2CC2)C1] | (3R)-1-(6-(3-(4-(6-(3-azabicyclo[3.1.0]hexan-3-yl)pyrazin-2-yl)-1H-1,2,3-triazol-1-yl)oxetan-3-yl)pyridin-3-yl)-N-(cyclopropylmethyl)piperidin-3-amine |

TABLE 1-continued

| 217 | 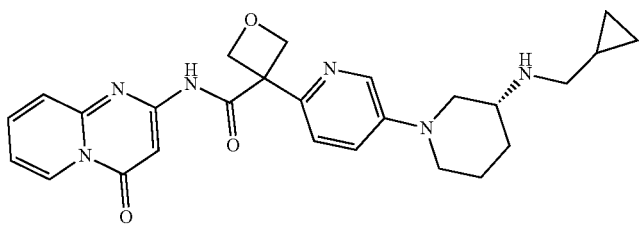 [SMILES: O=C(Nc1cc(=O)n2ccccc2n1)C1(c2ccc(N3CCC[C@@H](NCC4CC4)C3)cn2)COC1] | (R)-3-(5-(3-((cyclopropylmethyl)amino)piperidin-1-yl)pyridin-2-yl)-N-(4-oxo-4H-pyrido[1,2-a]pyrimidin-2-yl)oxetane-3-carboxamide |
| 218 | 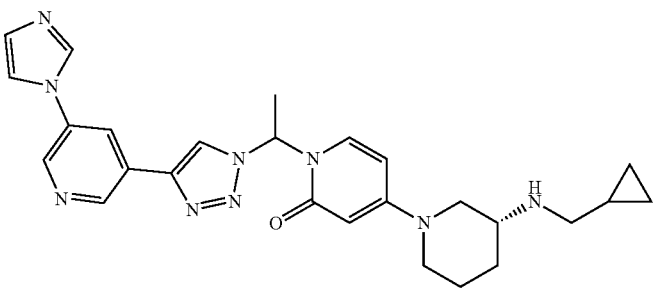 [SMILES: CC(n1cc(-c2cncc(-n3ccnc3)c2)nn1)n1ccc(N2CCC[C@@H](NCC3CC3)C2)cc1=O] | 1-(1-(4-(5-(1H-imidazol-1-yl)pyridin-3-yl)-1H-1,2,3-triazol-1-yl)ethyl)-4-((R)-3-((cyclopropylmethyl)amino)piperidin-1-yl)pyridin-2(1H)-one |
| 219 | 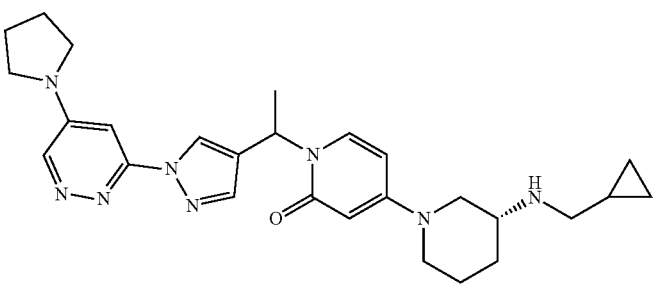 [SMILES: CC(c1cnn(-c2cc(N3CCCC3)cnn2)c1)n1ccc(N2CCC[C@@H](NCC3CC3)C2)cc1=O] | 4-((R)-3-((cyclopropylmethyl)amino)piperidin-1-yl)-1-(1-(1-(5-(pyrrolidin-1-yl)pyridazin-3-yl)-1H-pyrazol-4-yl)ethyl)pyridin-2(1H)-one |
| 220 | 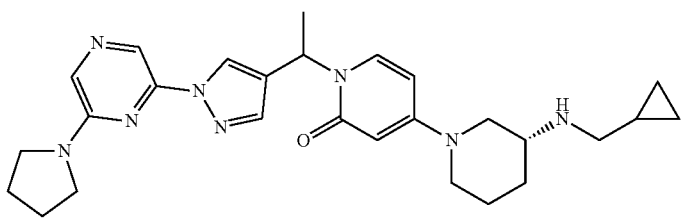 [SMILES: CC(c1cnn(-c2cncc(N3CCCC3)n2)c1)n1ccc(N2CCC[C@@H](NCC3CC3)C2)cc1=O] | 4-((R)-3-((cyclopropylmethyl)amino)piperidin-1-yl)-1-(1-(1-(6-(pyrrolidin-1-yl)pyrazin-2-yl)-1H-pyrazol-4-yl)ethyl)pyridin-2(1H)-one |
| 221 | 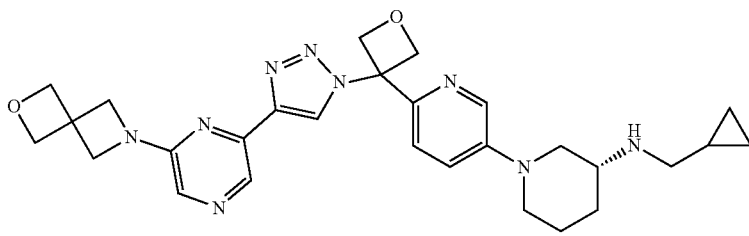 [SMILES: c1cc(C2(n3cc(-c4cncc(N5CC6(COC6)C5)n4)nn3)COC2)ncc1N1CCC[C@@H](NCC2CC2)C1] | (R)-1-(6-(3-(4-(6-(2-oxa-6-azaspiro[3.3]heptan-6-yl)pyrazin-2-yl)-1H-1,2,3-triazol-1-yl)oxetan-3-yl)pyridin-3-yl)-N-(cyclopropylmethyl)piperidin-3-amine |
| 222 | 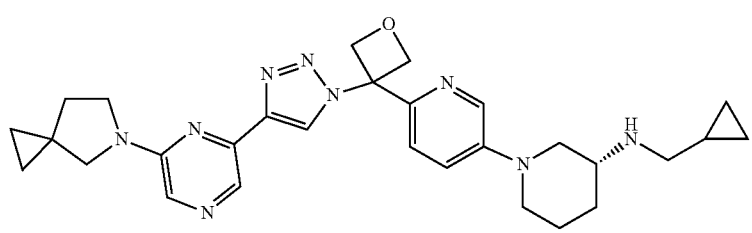 [SMILES: c1cc(C2(n3cc(-c4cncc(N5CCC6(CC6)C5)n4)nn3)COC2)ncc1N1CCC[C@@H](NCC2CC2)C1] | (R)-1-(6-(3-(4-(6-(5-azaspiro[2.4]heptan-5-yl)pyrazin-2-yl)-1H-1,2,3-triazol-1-yl)oxetan-3-yl)pyridin-3-yl)-N-(cyclopropyl-methyl)piperidin-3-amine |

TABLE 1-continued

| | | |
|---|---|---|
| 223 | 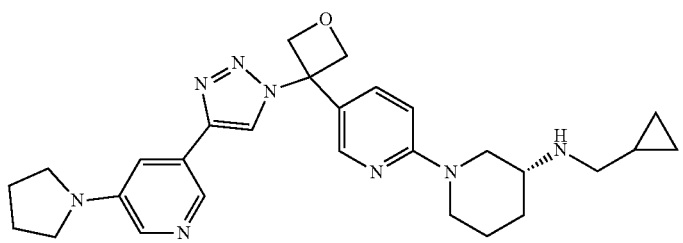 [SMILES: c1ncc(N2CCCC2)cc1-c1cn(C2(c3ccc(N4CCC[C@@H](NCC5CC5)C4)nc3)COC2)nn1] | (R)-N-(cyclopropylmethyl)-1-(5-(3-(4-(5-(pyrrolidin-1-yl)pyridin-3-yl)-1H-1,2,3-triazol-1-yl)oxetan-3-yl)pyridin-2-yl)piperidin-3-amine |
| 224 | 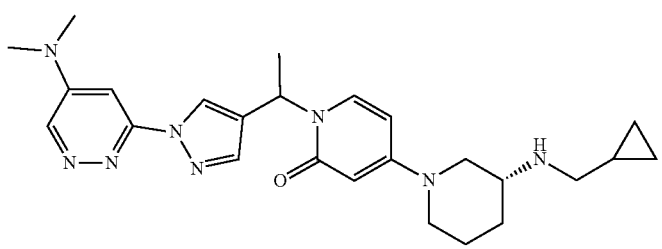 [SMILES: CC(c1cnn(-c2cc(N(C)C)cnn2)c1)n1ccc(N2CCC[C@@H](NCC3CC3)C2)cc1=O] | 4-((R)-3-((cyclopropylmethyl)amino)piperidin-1-yl)-1-(1-(1-(5-(dimethylamino)pyridazin-3-yl)-1H-pyrazol-4-yl)ethyl)pyridin-2(1H)-one |
| 225 | 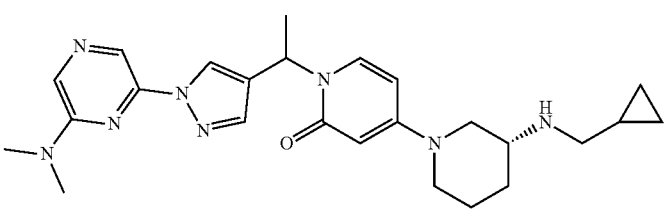 [SMILES: CC(c1cnn(-c2cncc(N(C)C)n2)c1)n1ccc(N2CCC[C@@H](NCC3CC3)C2)cc1=O] | 4-((R)-3-((cyclopropylmethyl)amino)piperidin-1-yl)-1-(1-(1-(6-(dimethylamino)pyrazin-2-yl)-1H-pyrazol-4-yl)ethyl)pyridin-2(1H)-one |
| 226 | 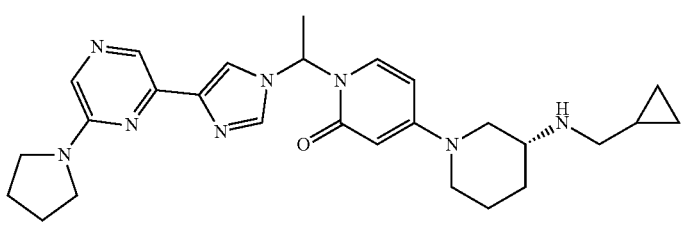 [SMILES: CC(n1cnc(-c2cncc(N3CCCC3)n2)c1)n1ccc(N2CCC[C@@H](NCC3CC3)C2)cc1=O] | 4-((R)-3-((cyclopropylmethyl)amino)piperidin-1-yl)-1-(1-(4-(6-(pyrrolidin-1-yl)pyrazin-2-yl)-1H-imidazol-1-yl)ethyl)pyridin-2(1H)-one |
| 227 | 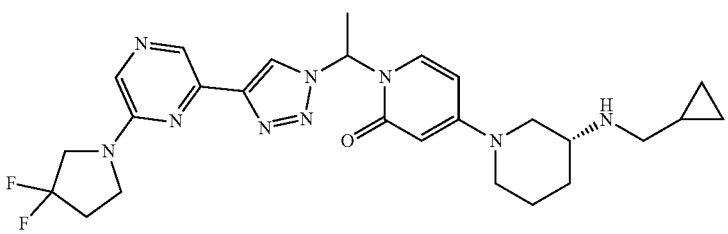 [SMILES: CC(n1cc(-c2cncc(N3CCC(F)(F)C3)n2)nn1)n1ccc(N2CCC[C@@H](NCC3CC3)C2)cc1=O] | 4-((R)-3-((cyclopropylmethyl)amino)piperidin-1-yl)-1-(1-(4-(6-(3,3-difluoropyrrolidin-1-yl)pyrazin-2-yl)-1H-1,2,3-triazol-1-yl)ethyl)pyridin-2(1H)-one |
| 228 | 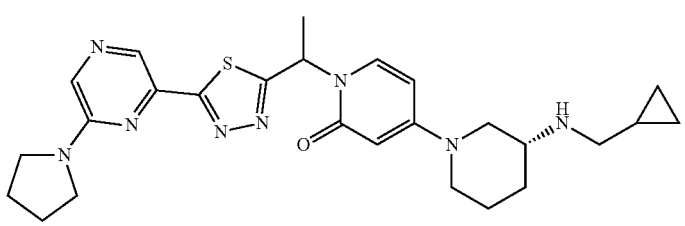 | 4-((R)-3-((cyclopropylmethyl)amino)piperidin-1-yl)-1-(1-(5-(6-(pyrrolidin-1-yl)pyrazin-2-yl)-1,3,4-thiadiazol-2-yl)ethyl)pyridin-2(1H)-one |
| 229 | 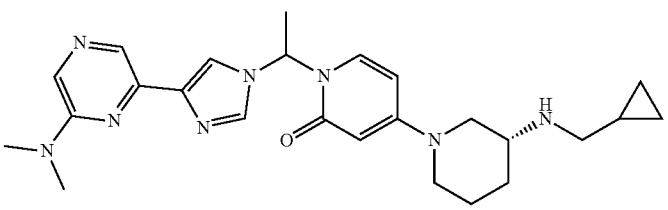 [SMILES: CC(n1cnc(-c2cncc(N(C)C)n2)c1)n1ccc(N2CCC[C@@H](NCC3CC3)C2)cc1=O] | 4-((R)-3-((cyclopropylmethyl)amino)piperidin-1-yl)-1-(1-(4-(6-(dimethylamino)pyrazin-2-yl)-1H-imidazol-1-yl)ethyl)pyridin-2(1H)-one |

TABLE 1-continued

| | | |
|---|---|---|
| 230 | | 4-((R)-3-((cyclopropylmethyl)amino)piperidin-1-yl)-1-(1-(4-(6-(3,3-dimethylpyrrolidin-1-yl)pyrazin-2-yl)-1H-1,2,3-triazol-1-yl)ethyl)pyridin-2(1H)-one |
| 231 | | 4-((R)-3-((cyclopropylmethyl)amino)piperidin-1-yl)-1-(1-(5-(6-(dimethylamino)pyrazin-2-yl)-1,3,4-thiadiazol-2-yl)ethyl)pyridin-2(1H)-one |
| 232 | | 4-((R)-3-((cyclopropylmethyl)amino)piperidin-1-yl)-1-(1-(4-(5-methoxypyridin-3-yl)-1H-1,2,3-triazol-1-yl)ethyl)pyridin-2(1H)-one |
| 233 | | 4-((R)-3-((cyclopropylmethyl)amino)piperidin-1-yl)-1-(1-(2-(6-(pyrrolidin-1-yl)pyrazin-2-yl)thiazol-5-yl)ethyl)pyridin-2(1H)-one |
| 234 | | 1-(1-(4-(6-(3-azabicyclo[3.1.0]hexan-3-yl)pyrazin-2-yl)-1H-1,2,3-triazol-1-yl)ethyl)-4-((R)-3-((cyclopropylmethyl)amino)piperidin-1-yl)pyridin-2(1H)-one |
| 235 | | 1-(1-(4-(6-(5-azaspiro[2.4]heptan-5-yl)pyrazin-2-yl)-1H-1,2,3-triazol-1-yl)ethyl)-4-((R)-3-((cyclopropylmethyl)amino)piperidin-1-yl)pyridin-2(1H)-one |
| 236 | | 4-((R)-3-((cyclopropylmethyl)amino)piperidin-1-yl)-1-(1-(4-(5-(methyl(trifluoromethyl)amino)pyridin-3-yl)-1H-1,2,3-triazol-1-yl)ethyl)pyridin-2(1H)-one |

TABLE 1-continued

| | | |
|---|---|---|
| 237 | 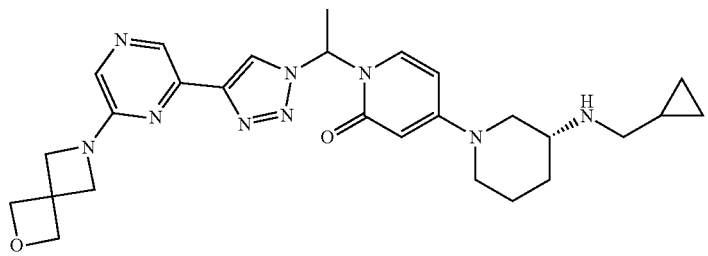 [SMILES: CC(n1cc(-c2cncc(N3CC4(COC4)C3)n2)nn1)n1ccc(N2CCC[C@@H](NCC3CC3)C2)cc1=O] | 1-(1-(4-(6-(2-oxa-6-azaspiro[3.3]heptan-6-yl)pyrazin-2-yl)-1H-1,2,3-triazol-1-yl)ethyl)-4-((R)-3-((cyclopropylmethyl)amino)piperidin-1-yl)pyridin-2(1H)-one |
| 238 | 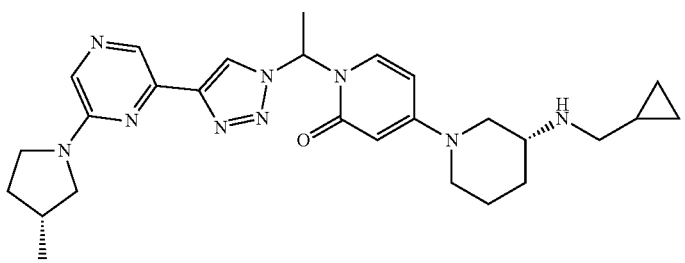 [SMILES: CC(n1cc(-c2cncc(N3CC[C@@H](C)C3)n2)nn1)n1ccc(N2CCC[C@@H](NCC3CC3)C2)cc1=O] | 4-((R)-3-((cyclopropylmethyl)amino)piperidin-1-yl)-1-(1-(4-(6-((R)-3-methylpyrrolidin-1-yl)pyrazin-2-yl)-1H-1,2,3-triazol-1-yl)ethyl)pyridin-2(1H)-one |
| 239 | 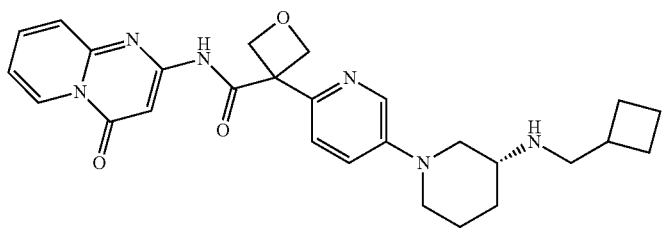 [SMILES: O=C(Nc1cc(=O)n2ccccc2n1)C1(c2ccc(N3CCC[C@@H](NCC4CCC4)C3)cn2)COC1] | (R)-3-(5-(3-((cyclobutylmethyl)amino)piperidin-1-yl)pyridin-2-yl)-N-(4-oxo-4H-pyrido[1,2-a]pyrimidin-2-yl)oxetane-3-carboxamide |
| 240 | 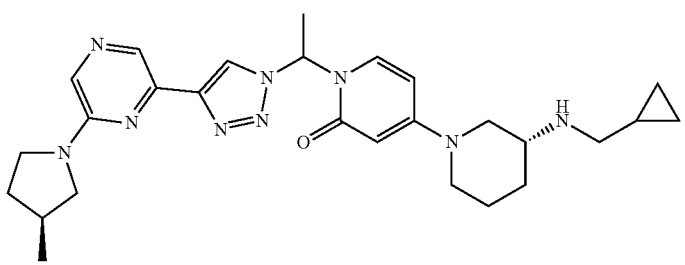 [SMILES: CC(n1cc(-c2cncc(N3CC[C@H](C)C3)n2)nn1)n1ccc(N2CCC[C@@H](NCC3CC3)C2)cc1=O] | 4-((R)-3-((cyclopropylmethyl)amino)piperidin-1-yl)-1-(1-(4-(6-((S)-3-methylpyrrolidin-1-yl)pyrazin-2-yl)-1H-1,2,3-triazol-1-yl)ethyl)pyridin-2(1H)-one |
| 241 | 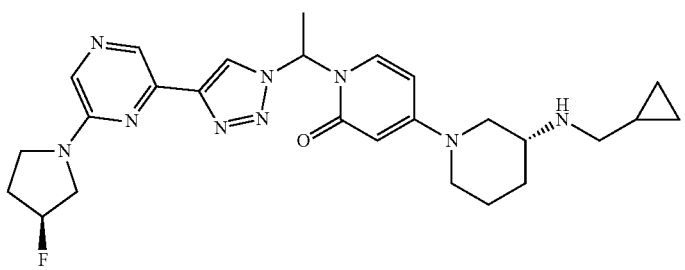 [SMILES: CC(n1cc(-c2cncc(N3CC[C@H](F)C3)n2)nn1)n1ccc(N2CCC[C@@H](NCC3CC3)C2)cc1=O] | 4-((R)-3-((cyclopropylmethyl)amino)piperidin-1-yl)-1-(1-(4-(6-((S)-3-fluoropyrrolidin-1-yl)pyrazin-2-yl)-1H-1,2,3-triazol-1-yl)ethyl)pyridin-2(1H)-one |
| 242 | 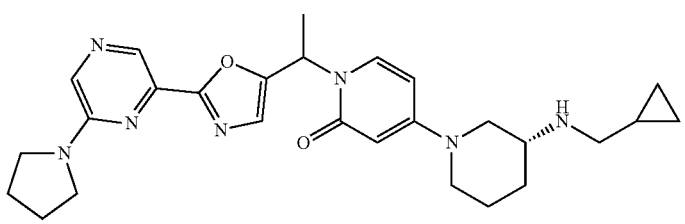 | 4-((R)-3-((cyclopropylmethyl)amino)piperidin-1-yl)-1-(1-(2-(6-(pyrrolidin-1-yl)pyrazin-2-yl)oxazol-5-yl)ethyl)pyridin-2(1H)-one |

TABLE 1-continued

| | | |
|---|---|---|
| 243 | 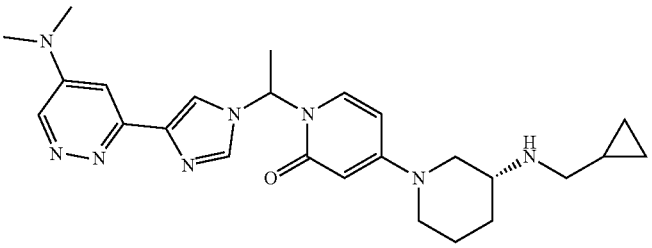 [SMILES: CC(n1cnc(-c2cc(N(C)C)cnn2)c1)n1ccc(N2CCC[C@@H](NCC3CC3)C2)cc1=O] | 4-((R)-3-((cyclopropylmethyl)amino)piperidin-1-yl)-1-(1-(4-(5-(dimethylamino)pyridazin-3-yl)-1H-imidazol-1-yl)ethyl)pyridin-2(1H)-one |
| 244 | 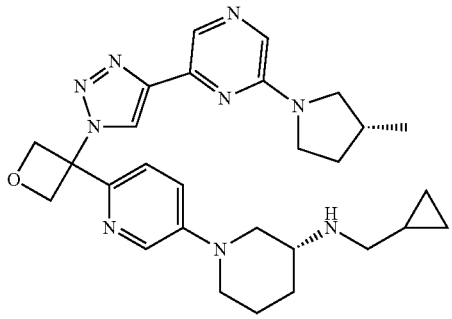 [SMILES: C[C@@H]1CCN(c2cncc(-c3cn(C4(c5ccc(N6CCC[C@@H](NCC7CC7)C6)cn5)COC4)nn3)n2)C1] | (R)-N-(cyclopropylmethyl)-1-(6-(3-(4-(6-((R)-3-methylpyrrolidin-1-yl)pyrazin-2-yl)-1H-1,2,3-triazol-1-yl)oxetan-3-yl)pyridin-3-yl)piperidin-3-amine |
| 245 | 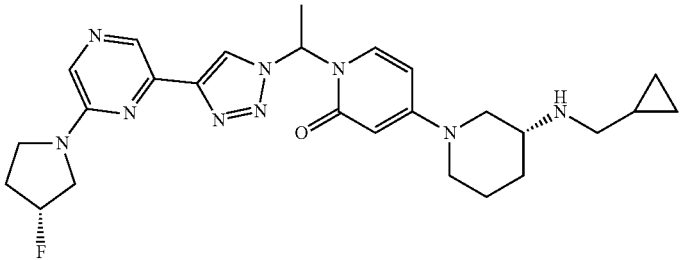 [SMILES: CC(n1cc(-c2cncc(N3CC[C@@H](F)C3)n2)nn1)n1ccc(N2CCC[C@@H](NCC3CC3)C2)cc1=O] | 4-((R)-3-((cyclopropylmethyl)amino)piperidin-1-yl)-1-(1-(4-(6-((R)-3-fluoropyrrolidin-1-yl)pyrazin-2-yl)-1H-1,2,3-triazol-1-yl)ethyl)pyridin-2(1H)-one |
| 246 | 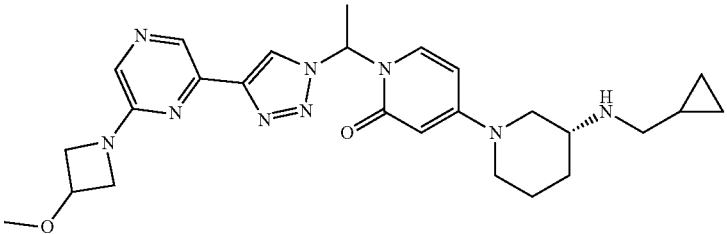 [SMILES: COC1CN(c2cncc(-c3cn(C(C)n4ccc(N5CCC[C@@H](NCC6CC6)C5)cc4=O)nn3)n2)C1] | 4-((R)-3-((cyclopropylmethyl)amino)piperidin-1-yl)-1-(1-(4-(6-(3-methoxyazetidin-1-yl)pyrazin-2-yl)-1H-1,2,3-triazol-1-yl)ethyl)pyridin-2(1H)-one |
| 247 | 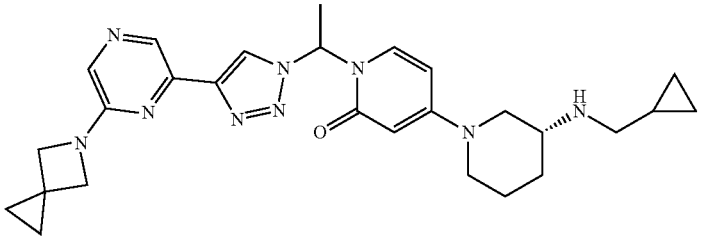 [SMILES: CC(n1cc(-c2cncc(N3CC4(CC4)C3)n2)nn1)n1ccc(N2CCC[C@@H](NCC3CC3)C2)cc1=O] | 1-(1-(4-(6-(5-azaspiro[2.3]hexan-5-yl)pyrazin-2-yl)-1H-1,2,3-triazol-1-yl)ethyl)-4-((R)-3-((cyclopropylmethyl)amino)piperidin-1-yl)pyridin-2(1H)-one |
| 248 | 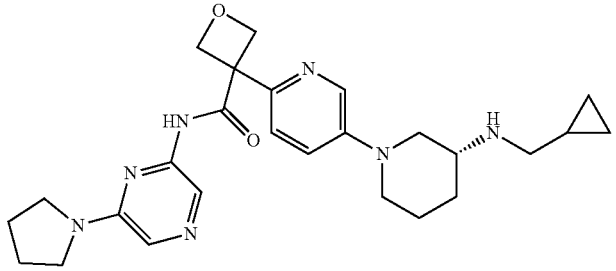 [SMILES: O=C(Nc1cncc(N2CCCC2)n1)C1(c2ccc(N3CCC[C@@H](NCC4CC4)C3)cn2)COC1] | (R)-3-(5-(3-((cyclopropylmethyl)amino)piperidin-1-yl)pyridin-2-yl)-N-(6-(pyrrolidin-1-yl)pyrazin-2-yl)oxetane-3-carboxamide |

TABLE 1-continued

| | | |
|---|---|---|
| 249 | 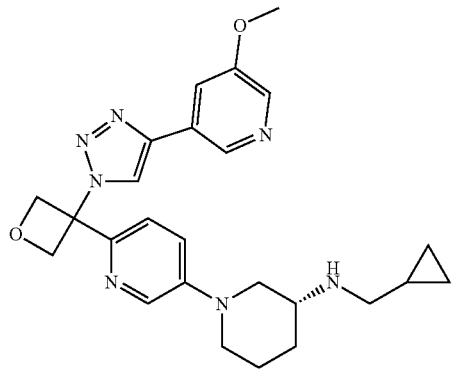 [SMILES: COc1cncc(-c2cn(C3(c4ccc(N5CCC[C@@H](NCC6CC6)C5)cn4)COC3)nn2)c1] | (R)-N-(cyclopropylmethyl)-1-(6-(3-(4-(5-methoxypyridin-3-yl)-1H-1,2,3-triazol-1-yl)oxetan-3-yl)pyridin-3-yl)piperidin-3-amine |
| 250 | 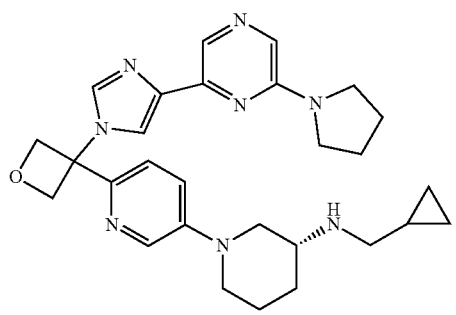 [SMILES: c1cc(C2(n3cnc(-c4cncc(N5CCCC5)n4)c3)COC2)ncc1N1CCC[C@@H](NCC2CC2)C1] | (R)-N-(cyclopropylmethyl)-1-(6-(3-(4-(6-(pyrrolidin-1-yl)pyrazin-2-yl)-1H-imidazol-1-yl)oxetan-3-yl)pyridin-3-yl)piperidin-3-amine |
| 251 | 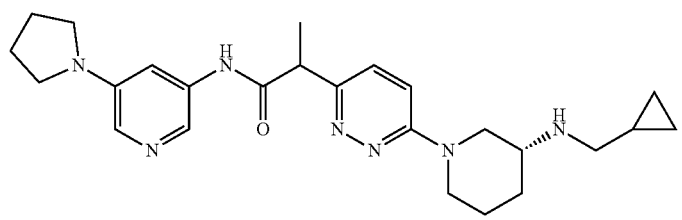 [SMILES: CC(C(=O)Nc1cncc(N2CCCC2)c1)c1ccc(N2CCC[C@@H](NCC3CC3)C2)nn1] | 2-(6-((R)-3-((cyclopropylmethyl)amino)piperidin-1-yl)pyridazin-3-yl)-N-(5-(pyrrolidin-1-yl)pyridin-3-yl)propanamide |
| 252 | 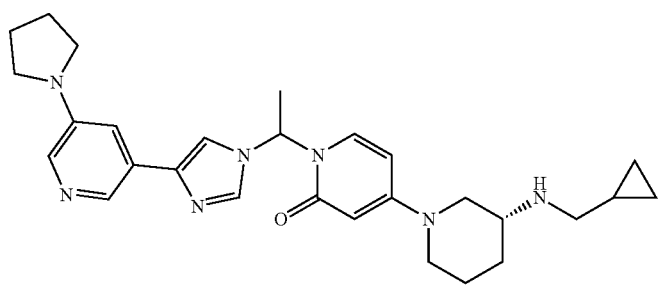 [SMILES: CC(n1cnc(-c2cncc(N3CCCC3)c2)c1)n1ccc(N2CCC[C@@H](NCC3CC3)C2)cc1=O] | 4-((R)-3-((cyclopropylmethyl)amino)piperidin-1-yl)-1-(1-(4-(5-(pyrrolidin-1-yl)pyridin-3-yl)-1H-imidazol-1-yl)ethyl)pyridin-2(1H)-one |
| 253 | 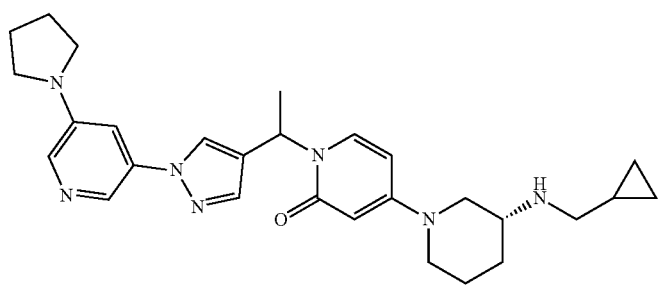 [SMILES: CC(c1cnn(-c2cncc(N3CCCC3)c2)c1)n1ccc(N2CCC[C@@H](NCC3CC3)C2)cc1=O] | 4-((R)-3-((cyclopropylmethyl)amino)piperidin-1-yl)-1-(1-(1-(5-(pyrrolidin-1-yl)pyridin-3-yl)-1H-pyrazol-4-yl)ethyl)pyridin-2(1H)-one |

TABLE 1-continued

| 254 | 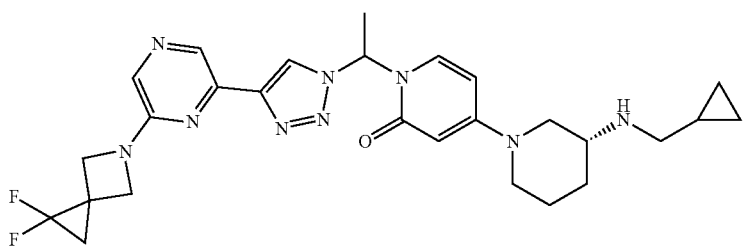 [SMILES: CC(n1cc(-c2cncc(N3CC4(C3)CC4(F)F)n2)nn1)n1ccc(N2CCC[C@@H](NCC3CC3)C2)cc1=O] | 4-((R)-3-((cyclopropylmethyl)amino)piperidin-1-yl)-1-(1-(4-(6-(1,1-difluoro-5-azaspiro[2.3]hexan-5-yl)pyrazin-2-yl)-1H-1,2,3-triazol-1-yl)ethyl)pyridin-2(1H)-one |
| --- | --- | --- |
| 255 | 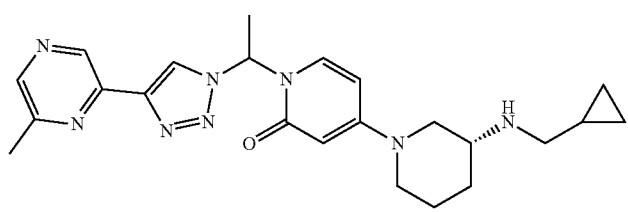 [SMILES: Cc1cncc(-c2cn(C(C)n3ccc(N4CCC[C@@H](NCC5CC5)C4)cc3=O)nn2)n1] | 4-((R)-3-((cyclopropylmethyl)amino)piperidin-1-yl)-1-(1-(4-(6-methylpyrazin-2-yl)-1H-1,2,3-triazol-1-yl)ethyl)pyridin-2(1H)-one |
| 256 | 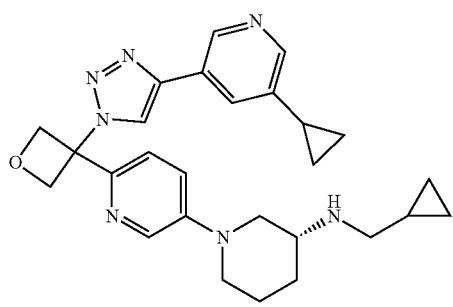 [SMILES: c1ncc(C2CC2)cc1-c1cn(C2(c3ccc(N4CCC[C@@H](NCC5CC5)C4)cn3)COC2)nn1] | (R)-N-(cyclopropylmethyl)-1-(6-(3-(4-(5-cyclopropylpyridin-3-yl)-1H-1,2,3-triazol-1-yl)oxetan-3-yl)pyridin-3-yl)piperidin-3-amine |
| 257 | 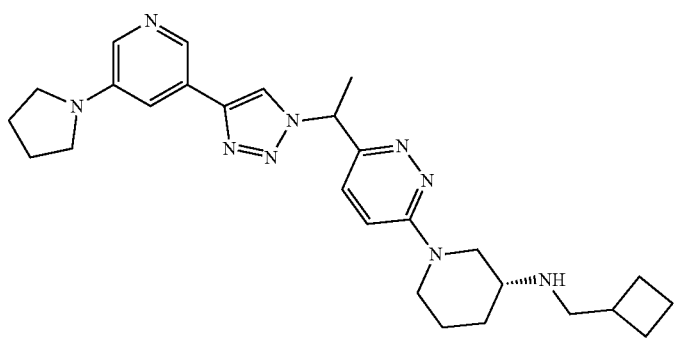 [SMILES: CC(c1ccc(N2CCC[C@@H](NCC3CCC3)C2)nn1)n1cc(-c2cncc(N3CCCC3)c2)nn1] | (3R)-N-(cyclobutylmethyl)-1-(6-(1-(4-(5-(pyrrolidin-1-yl)pyridin-3-yl)-1H-1,2,3-triazol-1-yl)ethyl)pyridazin-3-yl)piperidin-3-amine |
| 258 | 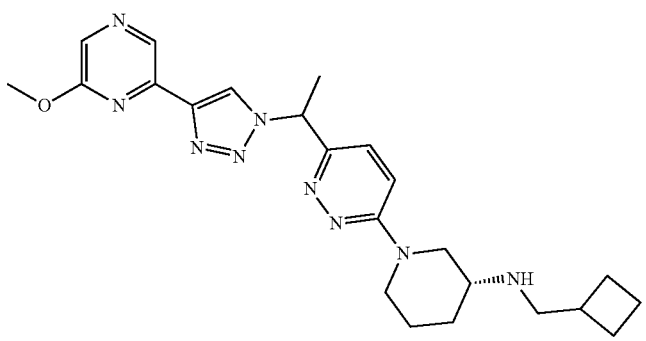 [SMILES: COc1cncc(-c2cn(C(C)c3ccc(N4CCC[C@@H](NCC5CCC5)C4)nn3)nn2)n1] | (3R)-N-(cyclobutylmethyl)-1-(6-(1-(4-(6-methoxypyrazin-2-yl)-1H-1,2,3-triazol-1-yl)ethyl)pyridazin-3-yl)piperidin-3-amine |

TABLE 1-continued

| 259 | 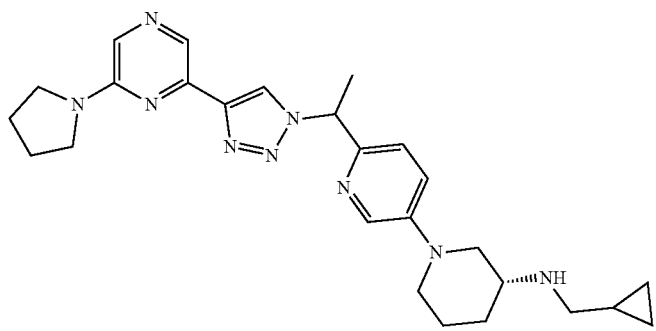 [SMILES: CC(c1ccc(N2CCC[C@@H](NCC3CC3)C2)cn1)n1cc(-c2cncc(N3CCCC3)n2)nn1] | (3R)-N-(cyclopropylmethyl)-1-(6-(1-(4-(6-(pyrrolidin-1-yl)pyrazin-2-yl)-1H-1,2,3-triazol-1-yl)ethyl)pyridin-3-yl)piperidin-3-amine |
| --- | --- | --- |
| 260 | 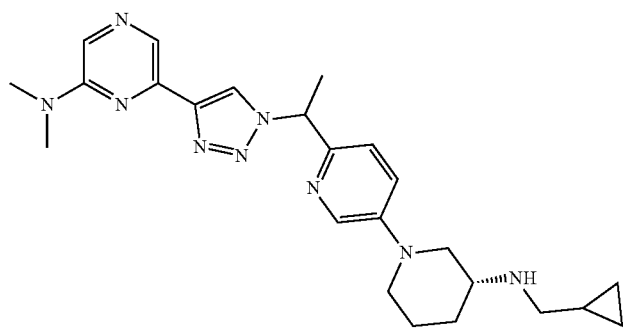 [SMILES: CC(c1ccc(N2CCC[C@@H](NCC3CC3)C2)cn1)n1cc(-c2cncc(N(C)C)n2)nn1] | 6-(1-(1-(5-((R)-3-((cyclopropylmethyl)amino)piperidin-1-yl)pyridin-2-yl)ethyl)-1H-1,2,3-triazol-4-yl)-N,N-dimethylpyrazin-2-amine |
| 261 | 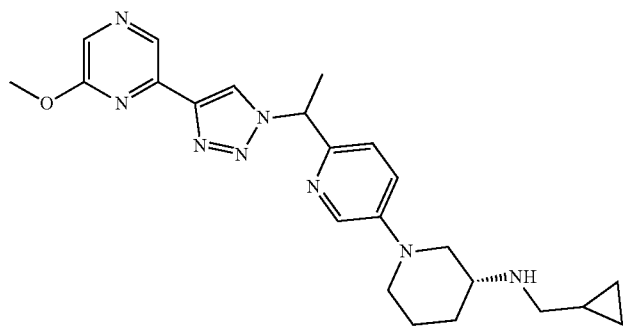 [SMILES: COc1cncc(-c2cn(C(C)c3ccc(N4CCC[C@@H](NCC5CC5)C4)cn3)nn2)n1] | (3R)-N-(cyclopropylmethyl)-1-(6-(1-(4-(6-methoxypyrazin-2-yl)-1H-1,2,3-triazol-1-yl)ethyl)pyridin-3-yl)piperidin-3-amine |
| 262 | 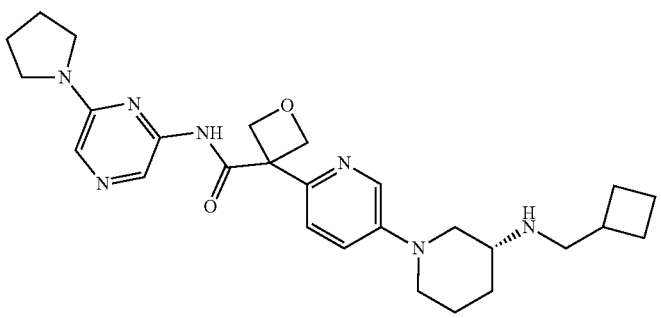 [SMILES: O=C(Nc1cncc(N2CCCC2)n1)C1(c2ccc(N3CCC[C@@H](NCC4CCC4)C3)cn2)COC1] | (R)-3-(5-(3-((cyclobutylmethyl)amino)piperidin-1-yl)pyridin-2-yl)-N-(6-(pyrrolidin-1-yl)pyrazin-2-yl)oxetane-3-carboxamide |
| 263 | 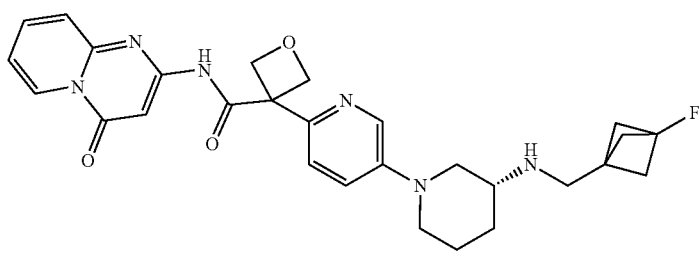 [SMILES: O=C(Nc1cc(=O)n2ccccc2n1)C1(c2ccc(N3CCC[C@@H](NCC45CC(F)(C4)C5)C3)cn2)COC1] | (R)-3-(5-(3-(((3-fluorobicyclo[1.1.1]pentan-1-yl)methyl)amino)piperidin-1-yl)pyridin-2-yl)-N-(4-oxo-4H-pyrido[1,2-a]pyrimidin-2-yl)oxetane-3-carboxamide |

TABLE 1-continued

| | | |
|---|---|---|
| 264 | 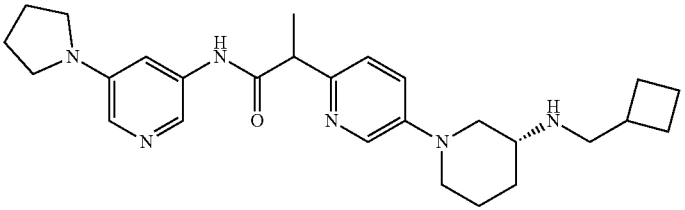 [SMILES: CC(C(=O)Nc1cncc(N2CCCC2)c1)c1ccc(N2CCC[C@@H](NCC3CCC3)C2)cn1] | 2-(5-((R)-3-((cyclobutylmethyl)amino)piperidin-1-yl)pyridin-2-yl)-N-(5-(pyrrolidin-1-yl)pyridin-3-yl)propanamide |
| 265 | 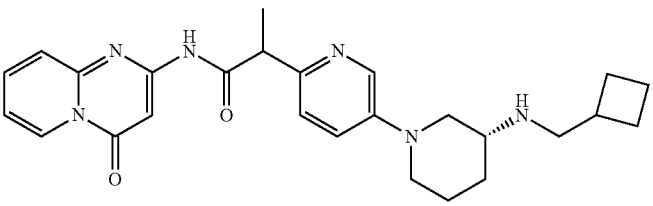 [SMILES: CC(C(=O)Nc1cc(=O)n2ccccc2n1)c1ccc(N2CCC[C@@H](NCC3CCC3)C2)cn1] | 2-(5-((R)-3-((cyclobutylmethyl)amino)piperidin-1-yl)pyridin-2-yl)-N-(4-oxo-4H-pyrido[1,2-a]pyrimidin-2-yl)propanamide |
| 266 | 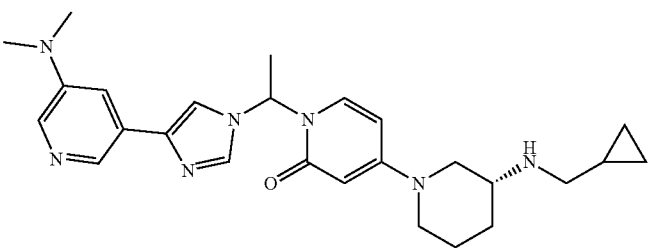 | 4-((R)-3-((cyclopropylmethyl)amino)piperidin-1-yl)-1-(1-(4-(5-(dimethylamino)pyridin-3-yl)-1H-imidazol-1-yl)ethyl)pyridin-2(1H)-one |
| 267 | 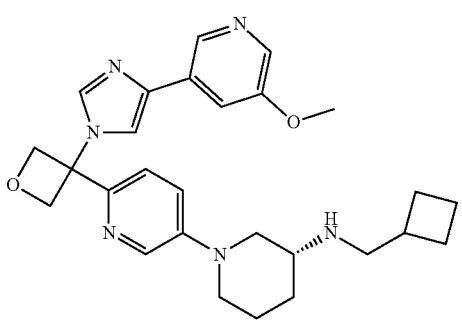 [SMILES: COc1cncc(-c2cn(C3(c4ccc(N5CCC[C@@H](NCC6CCC6)C5)cn4)COC3)cn2)c1] | (R)-N-(cyclobutylmethyl)-1-(6-(3-(4-(5-methoxypyridin-3-yl)-1H-imidazol-1-yl)oxetan-3-yl)pyridin-3-yl)piperidin-3-amine |
| 268 | 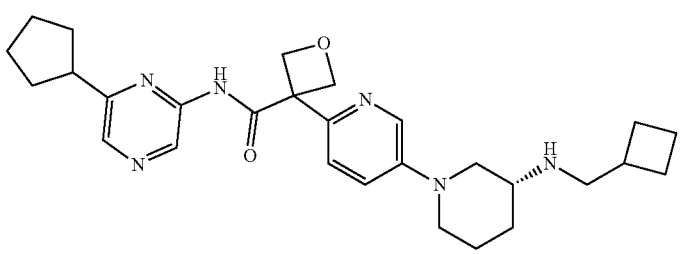 [SMILES: O=C(Nc1cncc(C2CCCC2)n1)C1(c2ccc(N3CCC[C@@H](NCC4CCC4)C3)cn2)COC1] | (R)-3-(5-(3-((cyclobutylmethyl)amino)piperidin-1-yl)pyridin-2-yl)-N-(6-cyclopentylpyrazin-2-yl)oxetane-3-carboxamide |
| 269 | 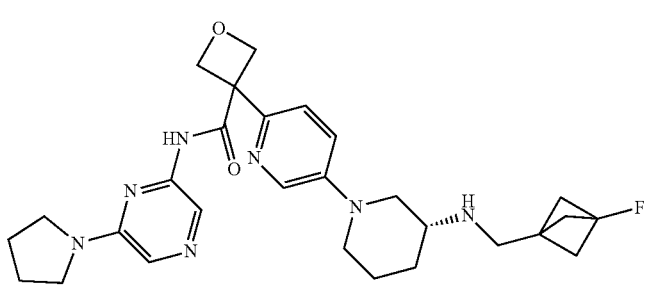 [SMILES: O=C(Nc1cncc(N2CCCC2)n1)C1(c2ccc(N3CCC[C@@H](NCC45CC(F)(C4)C5)C3)cn2)COC1] | (R)-3-(5-(3-(((3-fluorobicyclo[1.1.1]pentan-1-yl)methyl)amino)piperidin-1-yl)pyridin-2-yl)-N-(6-(pyrrolidin-1-yl)pyrazin-2-yl)oxetane-3-carboxamide |

TABLE 1-continued

| 270 | 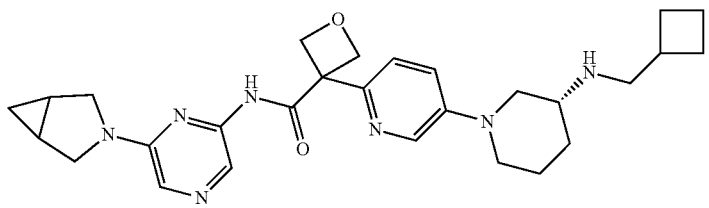 [SMILES: O=C(Nc1cncc(N2CC3CC3C2)n1)C1(c2ccc(N3CCC[C@@H](NCC4CCC4)C3)cn2)COC1] | N-(6-(3-azabicyclo[3.1.0]hexan-3-yl)pyrazin-2-yl)-3-(5-((R)-3-((cyclobutylmethyl)amino)piperidin-1-yl)pyridin-2-yl)oxetane-3-carboxamide |
| 271 | 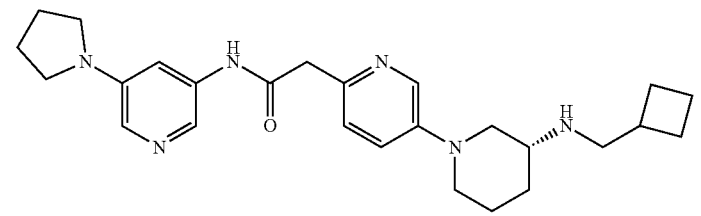 [SMILES: O=C(Cc1ccc(N2CCC[C@@H](NCC3CCC3)C2)cn1)Nc1cncc(N2CCCC2)c1] | (R)-2-(5-(3-((cyclobutylmethyl)amino)piperidin-1-yl)pyridin-2-yl)-N-(5-(pyrrolidin-1-yl)pyridin-3-yl)acetamide |
| 272 | 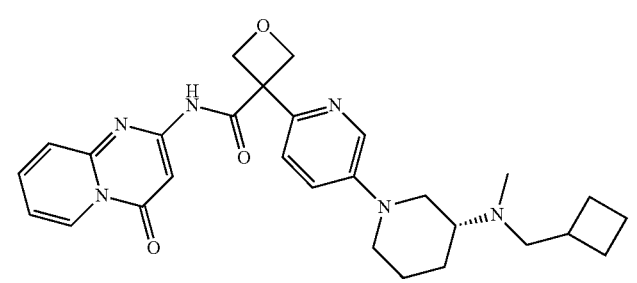 [SMILES: CN(CC1CCC1)[C@@H]1CCCN(c2ccc(C3(C(=O)Nc4cc(=O)n5ccccc5n4)COC3)nc2)C1] | (R)-3-(5-(3-((cyclobutylmethyl)(methyl)amino)piperidin-1-yl)pyridin-2-yl)-N-(4-oxo-4H-pyrido[1,2-a]pyrimidin-2-yl)oxetane-3-carboxamide |
| 273 | 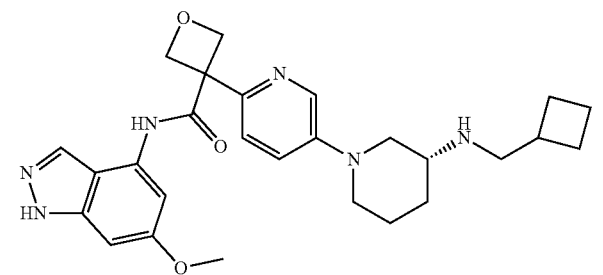 [SMILES: COc1cc(NC(=O)C2(c3ccc(N4CCC[C@@H](NCC5CCC5)C4)cn3)COC2)c2cn[nH]c2c1] | (R)-3-(5-(3-((cyclobutylmethyl)amino)piperidin-1-yl)pyridin-2-yl)-N-(6-methoxy-1H-indazol-4-yl)oxetane-3-carboxamide |
| 274 | 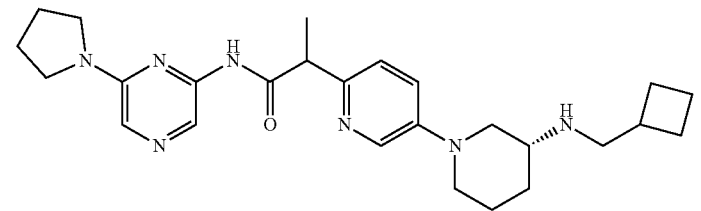 | 2-(5-((R)-3-((cyclobutylmethyl)amino)piperidin-1-yl)pyridin-2-yl)-N-(6-(pyrrolidin-1-yl)pyrazin-2-yl)propanamide |
| 275 | 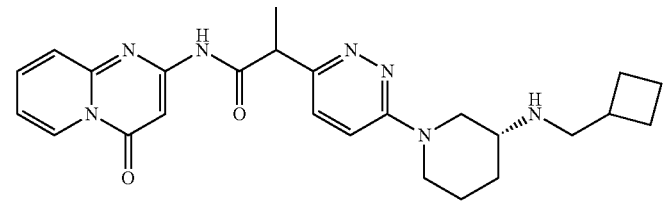 | 2-(6-((R)-3-((cyclobutylmethyl)amino)piperidin-1-yl)pyridazin-3-yl)-N-(4-oxo-4H-pyrido[1,2-a]pyrimidin-2-yl)propanamide |

TABLE 1-continued

| # | Name |
|---|------|
| 276 | (3R)-N-(cyclobutylmethyl)-1-(6-(1-(4-(5-methoxypyridin-3-yl)-1H-imidazol-1-yl)ethyl)pyridin-3-yl)piperidin-3-amine |
| 277 | (R)-2-(5-(3-((cyclobutylmethyl)amino)piperidin-1-yl)pyridin-2-yl)-N-(6-(pyrrolidin-1-yl)pyrazin-2-yl)acetamide |
| 278 | (R)-3-(4-(3-((cyclobutylmethyl)amino)piperidin-1-yl)phenyl)-N-(4-oxo-4H-pyrido[1,2-a]pyrimidin-2-yl)oxetane-3-carboxamide |
| 279 | 2-(6-((R)-3-((cyclobutylmethyl)amino)piperidin-1-yl)pyridazin-3-yl)-N-(6-(pyrrolidin-1-yl)pyrazin-2-yl)propanamide |
| 280 | (3R)-N-(cyclobutylmethyl)-1-(6-(1-(4-(6-(pyrrolidin-1-yl)pyrazin-2-yl)-1H-1,2,3-triazol-1-yl)ethyl)pyridin-3-yl)piperidin-3-amine |
| 281 | (R)-3-(4-(3-((cyclobutylmethyl)amino)piperidin-1-yl)phenyl)-N-(6-(pyrrolidin-1-yl)pyrazin-2-yl)oxetane-3-carboxamide |

TABLE 1-continued

| 282 | 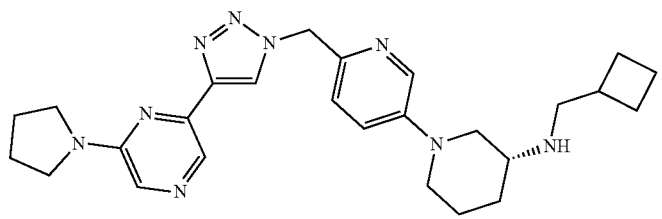 [SMILES: c1cc(Cn2cc(-c3cncc(N4CCCC4)n3)nn2)ncc1N1CCC[C@@H](NCC2CCC2)C1] | (R)-N-(cyclobutylmethyl)-1-(6-((4-(6-(pyrrolidin-1-yl)pyrazin-2-yl)-1H-1,2,3-triazol-1-yl)methyl)pyridin-3-yl)piperidin-3-amine |
| --- | --- | --- |
| 283 | 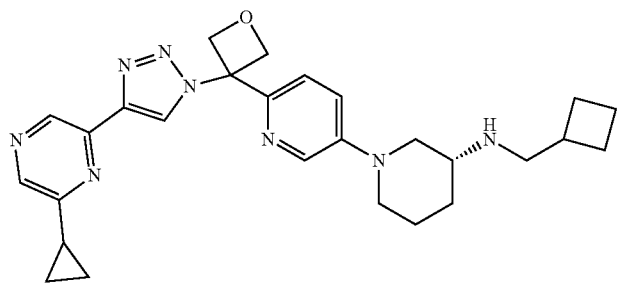 [SMILES: c1cc(C2(n3cc(-c4cncc(C5CC5)n4)nn3)COC2)ncc1N1CCC[C@@H](NCC2CCC2)C1] | (R)-N-(cyclobutylmethyl)-1-(6-(3-(4-(6-cyclopropylpyrazin-2-yl)-1H-1,2,3-triazol-1-yl)oxetan-3-yl)pyridin-3-yl)piperidin-3-amine |
| 284 | 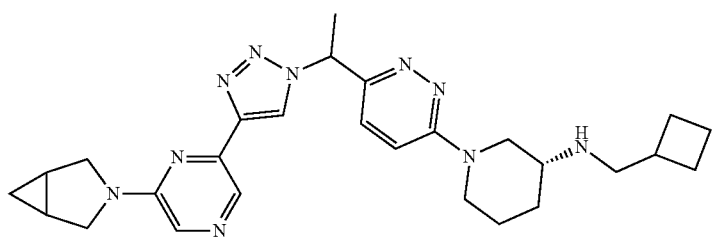 [SMILES: CC(c1ccc(N2CCC[C@@H](NCC3CCC3)C2)nn1)n1cc(-c2cncc(N3CC4CC4C3)n2)nn1] | (3R)-1-(6-(1-(4-(6-(3-azabicyclo[3.1.0]hexan-3-yl)pyrazin-2-yl)-1H-1,2,3-triazol-1-yl)ethyl)pyridazin-3-yl)-N-(cyclobutylmethyl)piperidin-3-amine |
| 285 | 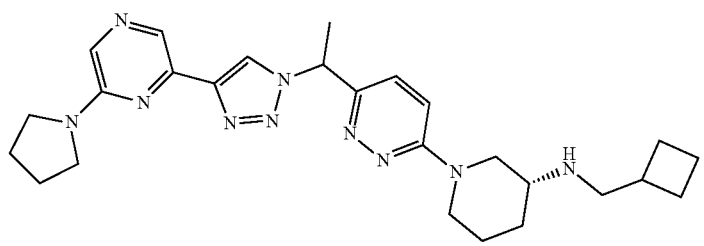 [SMILES: CC(c1ccc(N2CCC[C@@H](NCC3CCC3)C2)nn1)n1cc(-c2cncc(N3CCCC3)n2)nn1] | (3R)-N-(cyclobutylmethyl)-1-(6-(1-(4-(6-(pyrrolidin-1-yl)pyrazin-2-yl)-1H-1,2,3-triazol-1-yl)ethyl)pyridazin-3-yl)piperidin-3-amine |
| 286 | 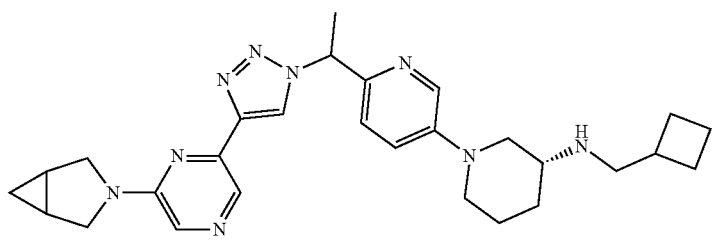 [SMILES: CC(c1ccc(N2CCC[C@@H](NCC3CCC3)C2)cn1)n1cc(-c2cncc(N3CC4CC4C3)n2)nn1] | (3R)-1-(6-(1-(4-(6-(3-azabicyclo[3.1.0]hexan-3-yl)pyrazin-2-yl)-1H-1,2,3-triazol-1-yl)ethyl)pyridin-3-yl)-N-(cyclobutylmethyl)piperidin-3-amine |
| 287 | 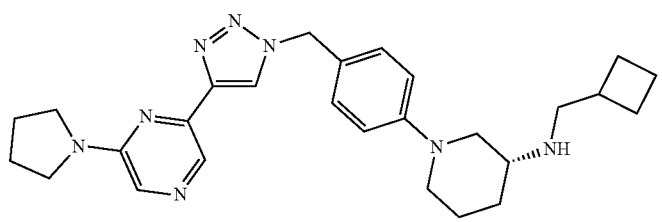 [SMILES: c1cc(N2CCC[C@@H](NCC3CCC3)C2)ccc1Cn1cc(-c2cncc(N3CCCC3)n2)nn1] | (R)-N-(cyclobutylmethyl)-1-(4-((4-(6-(pyrrolidin-1-yl)pyrazin-2-yl)-1H-1,2,3-triazol-1-yl)methyl)phenyl)piperidin-3-amine |

TABLE 1-continued

| | | |
|---|---|---|
| 288 | 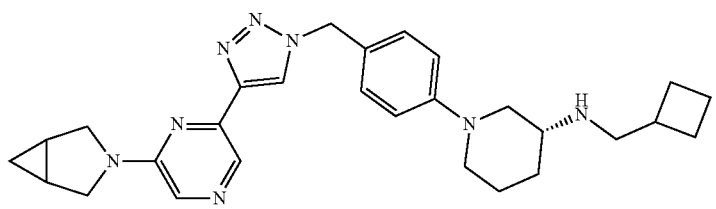 [SMILES: c1cc(N2CCC[C@@H](NCC3CCC3)C2)ccc1Cn1cc(-c2cncc(N3CC4CC4C3)n2)nn1] | (3R)-1-(4-((4-(6-(3-azabicyclo[3.1.0]hexan-3-yl)pyrazin-2-yl)-1H-1,2,3-triazol-1-yl)methyl)phenyl)-N-(cyclobutylmethyl)piperidin-3-amine |
| 289 | 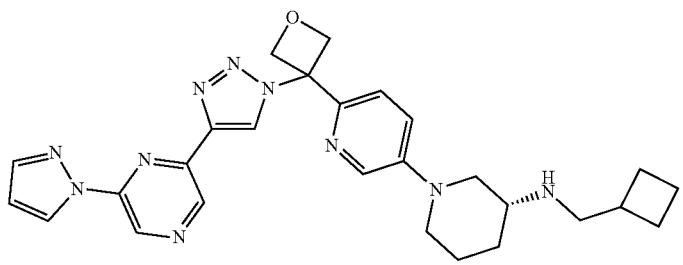 [SMILES: c1cnn(-c2cncc(-c3cn(C4(c5ccc(N6CCC[C@@H](NCC7CCC7)C6)cn5)COC4)nn3)n2)c1] | (R)-1-(6-(3-(4-(6-(1H-pyrazol-1-yl)pyrazin-2-yl)-1H-1,2,3-triazol-1-yl)oxetan-3-yl)pyridin-3-yl)-N-(cyclobutylmethyl)piperidin-3-amine |
| 290 | 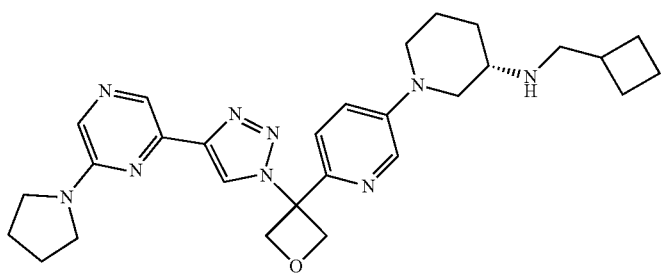 [SMILES: c1cc(C2(n3cc(-c4cncc(N5CCCC5)n4)nn3)COC2)ncc1N1CCC[C@H](NCC2CCC2)C1] | (R)-N-(cyclobutylmethyl)-1-(6-(3-(4-(6-(pyrrolidin-1-yl)pyrazin-2-yl)-1H-1,2,3-triazol-1-yl)oxetan-3-yl)pyridin-3-yl)piperidin-3-amine |
| 291 | 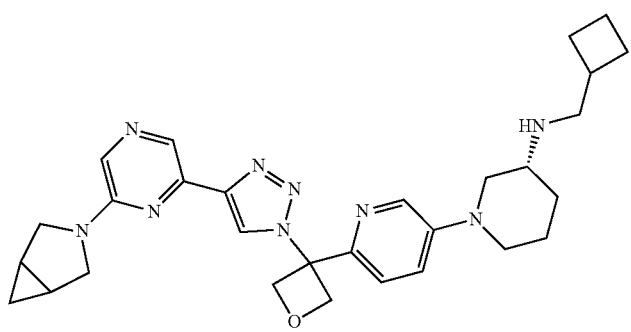 [SMILES: c1cc(C2(n3cc(-c4cncc(N5CC6CC6C5)n4)nn3)COC2)ncc1N1CCC[C@@H](NCC2CCC2)C1] | (3R)-1-(6-(3-(4-(6-(3-azabicyclo[3.1.0]hexan-3-yl)pyrazin-2-yl)-1H-1,2,3-triazol-1-yl)oxetan-3-yl)pyridin-3-yl)-N-(cyclobutylmethyl)piperidin-3-amine |
| 292 | 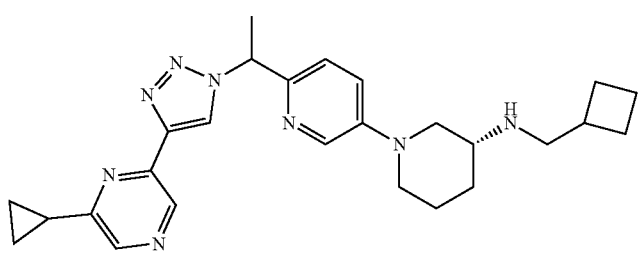 [SMILES: CC(c1ccc(N2CCC[C@@H](NCC3CCC3)C2)cn1)n1cc(-c2cncc(C3CC3)n2)nn1] | (3R)-N-(cyclobutylmethyl)-1-(6-(1-(4-(6-cyclopropylpyrazin-2-yl)-1H-1,2,3-triazol-1-yl)ethyl)pyridin-3-yl)piperidin-3-amine |
| 293 | 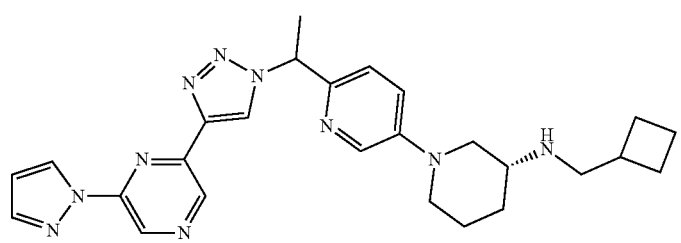 [SMILES: CC(c1ccc(N2CCC[C@@H](NCC3CCC3)C2)cn1)n1cc(-c2cncc(-n3cccn3)n2)nn1] | (3R)-1-(6-(1-(4-(6-(1H-pyrazol-1-yl)pyrazin-2-yl)-1H-1,2,3-triazol-1-yl)ethyl)pyridin-3-yl)-N-(cyclobutylmethyl)piperidin-3-amine |

TABLE 1-continued

| | | |
|---|---|---|
| 294 | 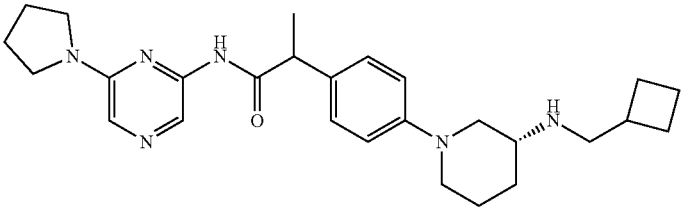 [SMILES: CC(C(=O)Nc1cncc(N2CCCC2)n1)c1ccc(N2CCC[C@@H](NCC3CCC3)C2)cc1] | 2-(4-((R)-3-((cyclobutylmethyl)amino)piperidin-1-yl)phenyl)-N-(6-(pyrrolidin-1-yl)pyrazin-2-yl)propanamide |
| 295 | 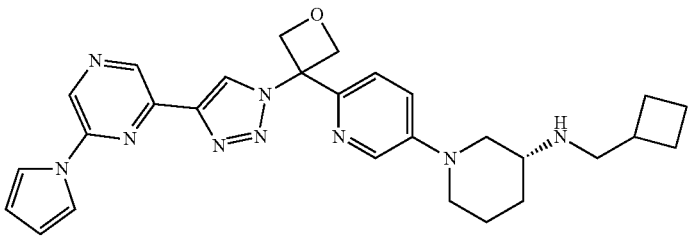 [SMILES: c1ccn(-c2cncc(-c3cn(C4(c5ccc(N6CCC[C@@H](NCC7CCC7)C6)cn5)COC4)nn3)n2)c1] | (R)-1-(6-(3-(4-(6-(1H-pyrrol-1-yl)pyrazin-2-yl)-1H-1,2,3-triazol-1-yl)oxetan-3-yl)pyridin-3-yl)-N-(cyclobutylmethyl)piperidin-3-amine |
| 296 | 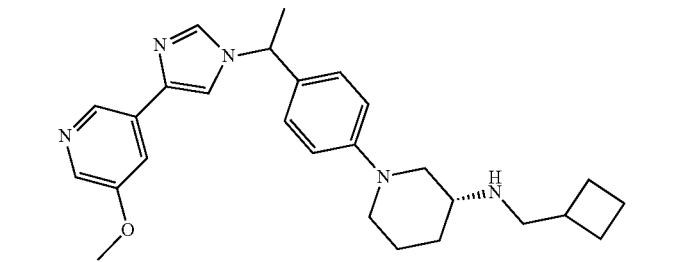 [SMILES: COc1cncc(-c2cn(C(C)c3ccc(N4CCC[C@@H](NCC5CCC5)C4)cc3)cn2)c1] | (3R)-N-(cyclobutylmethyl)-1-(4-(1-(4-(5-methoxypyridin-3-yl)-1H-imidazol-1-yl)ethyl)phenyl)piperidin-3-amine |
| 297 | 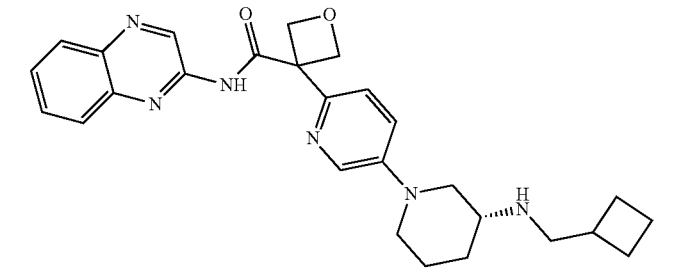 [SMILES: O=C(Nc1cnc2ccccc2n1)C1(c2ccc(N3CCC[C@@H](NCC4CCC4)C3)cn2)COC1] | (R)-3-(5-(3-((cyclobutylmethyl)amino)piperidin-1-yl)pyridin-2-yl)-N-(quinoxalin-2-yl)oxetane-3-carboxamide |
| 298 | 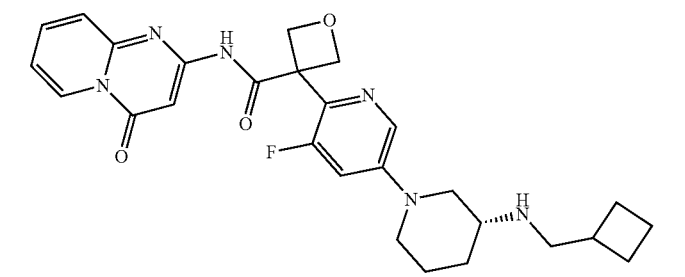 [SMILES: O=C(Nc1cc(=O)n2ccccc2n1)C1(c2ncc(N3CCC[C@@H](NCC4CCC4)C3)cc2F)COC1] | (R)-3-(5-(3-((cyclobutylmethyl)amino)piperidin-1-yl)-3-fluoropyridin-2-yl)-N-(4-oxo-4H-pyrido[1,2-a]pyrimidin-2-yl)oxetane-3-carboxamide |
| 299 | 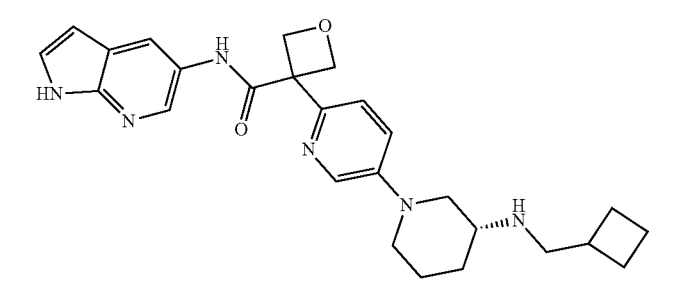 [SMILES: O=C(Nc1cnc2[nH]ccc2c1)C1(c2ccc(N3CCC[C@@H](NCC4CCC4)C3)cn2)COC1] | (R)-3-(5-(3-((cyclobutylmethyl)amino)piperidin-1-yl)pyridin-2-yl)-N-(1H-pyrrolo[2,3-b]pyridin-5-yl)oxetane-3-carboxamide |

TABLE 1-continued

| | | |
|---|---|---|
| 300 | | (3R)-N-(cyclobutylmethyl)-1-(6-(1-(1-(5-methoxypyridin-3-yl)-1H-pyrazol-4-yl)ethyl)pyridin-3-yl)piperidin-3-amine |
| 301 | | (R)-N-(cyclobutylmethyl)-1-(4-(3-(4-(6-(pyrrolidin-1-yl)pyrazin-2-yl)-1H-1,2,3-triazol-1-yl)oxetan-3-yl)phenyl)piperidin-3-amine |
| 302 | | (R)-3-(5-(3-((cyclobutylmethyl)amino)piperidin-1-yl)pyridin-2-yl)-N-(1-oxo-1,2-dihydroisoquinolin-3-yl)oxetane-3-carboxamide |
| 303 | | (3R)-N-(cyclobutylmethyl)-1-(5-fluoro-6-(1-(4-(6-(pyrrolidin-1-yl)pyrazin-2-yl)-1H-1,2,3-triazol-1-yl)ethyl)pyridin-3-yl)piperidin-3-amine |
| 304 | | (3R)-N-((3-fluorobicyclo[1.1.1]pentan-1-yl)methyl)-1-(6-(1-(4-(6-(pyrrolidin-1-yl)pyrazin-2-yl)-1H-1,2,3-triazol-1-yl)ethyl)pyridin-3-yl)piperidin-3-amine |

TABLE 1-continued

| 305 | 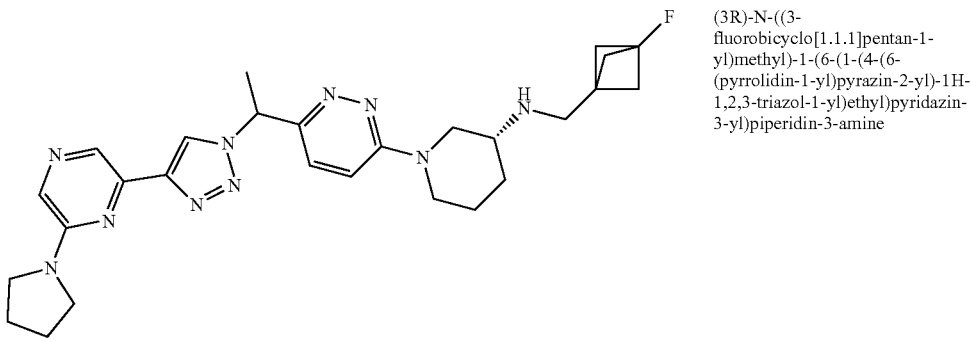 | (3R)-N-((3-fluorobicyclo[1.1.1]pentan-1-yl)methyl)-1-(6-(1-(4-(6-(pyrrolidin-1-yl)pyrazin-2-yl)-1H-1,2,3-triazol-1-yl)ethyl)pyridazin-3-yl)piperidin-3-amine |
| 306 | 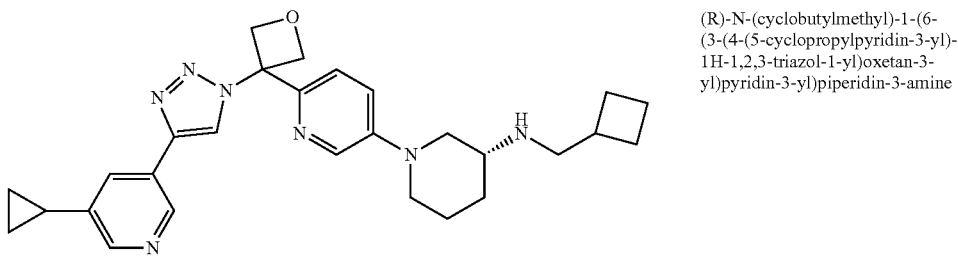 | (R)-N-(cyclobutylmethyl)-1-(6-(3-(4-(5-cyclopropylpyridin-3-yl)-1H-1,2,3-triazol-1-yl)oxetan-3-yl)pyridin-3-yl)piperidin-3-amine |
| 307 | 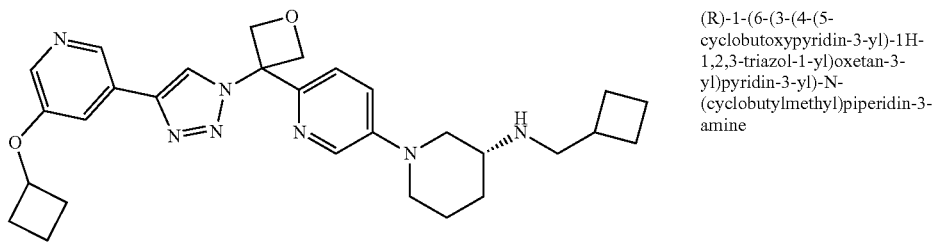 | (R)-1-(6-(3-(4-(5-cyclobutoxypyridin-3-yl)-1H-1,2,3-triazol-1-yl)oxetan-3-yl)pyridin-3-yl)-N-(cyclobutylmethyl)piperidin-3-amine |
| 308 | 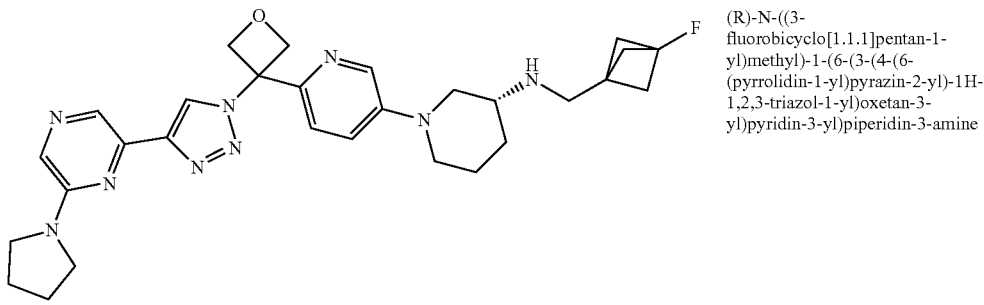 | (R)-N-((3-fluorobicyclo[1.1.1]pentan-1-yl)methyl)-1-(6-(3-(4-(6-(pyrrolidin-1-yl)pyrazin-2-yl)-1H-1,2,3-triazol-1-yl)oxetan-3-yl)pyridin-3-yl)piperidin-3-amine |
| 309 | 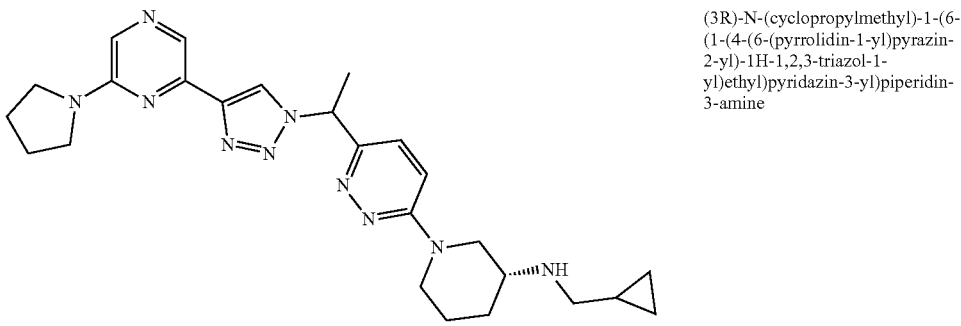 | (3R)-N-(cyclopropylmethyl)-1-(6-(1-(4-(6-(pyrrolidin-1-yl)pyrazin-2-yl)-1H-1,2,3-triazol-1-yl)ethyl)pyridazin-3-yl)piperidin-3-amine |

TABLE 1-continued

| | | |
|---|---|---|
| 310 | 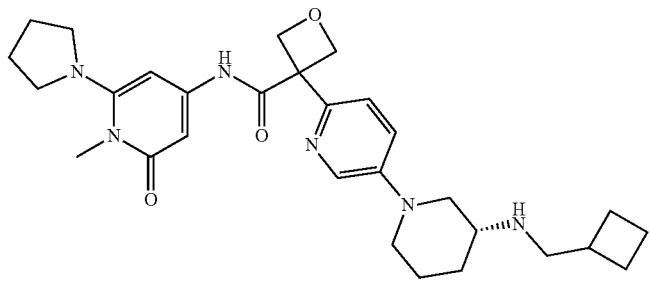 [SMILES: Cn1c(N2CCCC2)cc(NC(=O)C2(c3ccc(N4CCC[C@@H](NCC5CCC5)C4)cn3)COC2)cc1=O] | (R)-3-(5-(3-((cyclobutylmethyl)amino)piperidin-1-yl)pyridin-2-yl)-N-(1-methyl-2-oxo-6-(pyrrolidin-1-yl)-1,2-dihydropyridin-4-yl)oxetane-3-carboxamide |
| 311 | 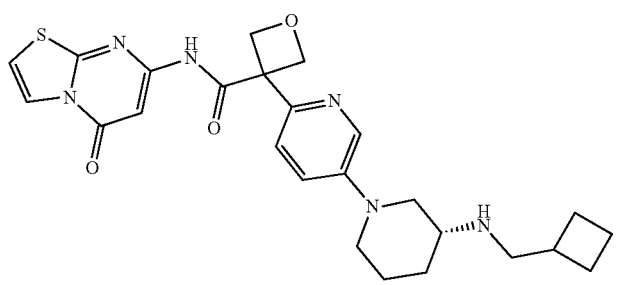 [SMILES: O=C(Nc1cc(=O)n2ccsc2n1)C1(c2ccc(N3CCC[C@@H](NCC4CCC4)C3)cn2)COC1] | (R)-3-(5-(3-((cyclobutylmethyl)amino)piperidin-1-yl)pyridin-2-yl)-N-(5-oxo-5H-thiazolo[3,2-a]pyrimidin-7-yl)oxetane-3-carboxamide |
| 312 | 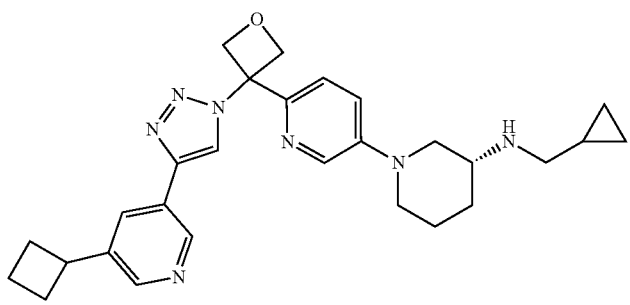 [SMILES: c1ncc(C2CCC2)cc1-c1cn(C2(c3ccc(N4CCC[C@@H](NCC5CC5)C4)cn3)COC2)nn1] | (R)-1-(6-(3-(4-(5-cyclobutylpyridin-3-yl)-1H-1,2,3-triazol-1-yl)oxetan-3-yl)pyridin-3-yl)-N-(cyclopropylmethyl)piperidin-3-amine |
| 313 | 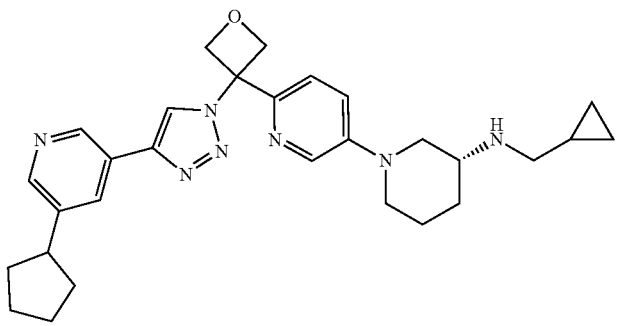 [SMILES: c1ncc(C2CCCC2)cc1-c1cn(C2(c3ccc(N4CCC[C@@H](NCC5CC5)C4)cn3)COC2)nn1] | (R)-1-(6-(3-(4-(5-cyclopentylpyridin-3-yl)-1H-1,2,3-triazol-1-yl)oxetan-3-yl)pyridin-3-yl)-N-(cyclopropylmethyl)piperidin-3-amine |
| 314 | 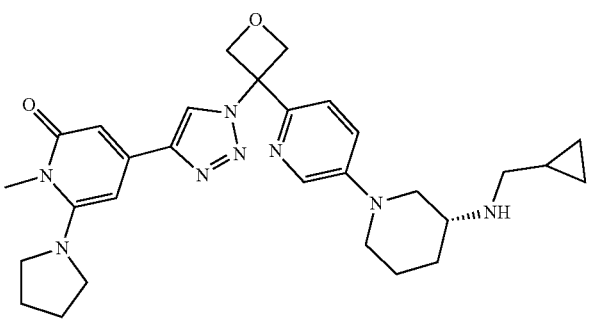 [SMILES: Cn1c(N2CCCC2)cc(-c2cn(C3(c4ccc(N5CCC[C@@H](NCC6CC6)C5)cn4)COC3)nn2)cc1=O] | (R)-4-(1-(3-(5-(3-((cyclopropylmethyl)amino)piperidin-1-yl)pyridin-2-yl)oxetan-3-yl)-1H-1,2,3-triazol-4-yl)-1-methyl-6-(pyrrolidin-1-yl)pyridin-2(1H)-one |

TABLE 1-continued

| | | |
|---|---|---|
| 315 | 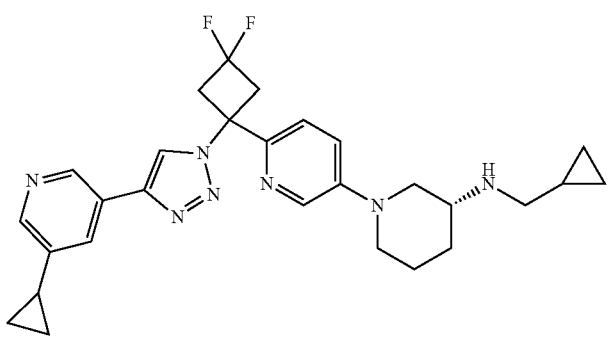 [SMILES: FC1(F)CC(c2ccc(N3CCC[C@@H](NCC4CC4)C3)cn2)(n2cc(-c3cncc(C4CC4)c3)nn2)C1] | (R)-N-(cyclopropylmethyl)-1-(6-(1-(4-(5-cyclopropylpyridin-3-yl)-1H-1,2,3-triazol-1-yl)-3,3-difluorocyclobutyl)pyridin-3-yl)piperidin-3-amine |
| 316 | 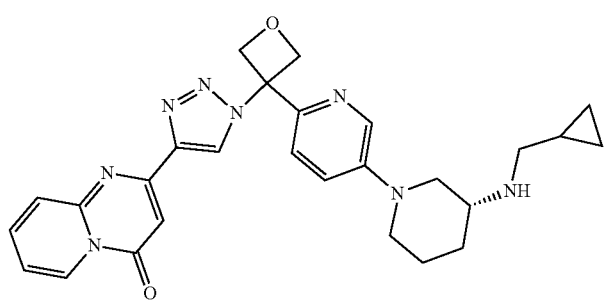 [SMILES: O=c1cc(-c2cn(C3(c4ccc(N5CCC[C@@H](NCC6CC6)C5)cn4)COC3)nn2)nc2ccccn12] | (R)-2-(1-(3-(5-(3-((cyclopropylmethyl)amino)piperidin-1-yl)pyridin-2-yl)oxetan-3-yl)-1H-1,2,3-triazol-4-yl)-4H-pyrido[1,2-a]pyrimidin-4-one |
| 317 | 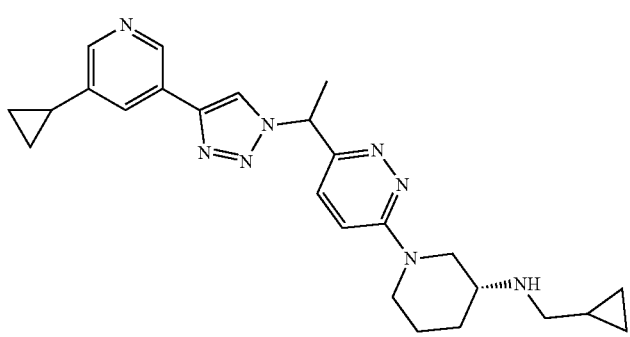 [SMILES: CC(c1ccc(N2CCC[C@@H](NCC3CC3)C2)nn1)n1cc(-c2cncc(C3CC3)c2)nn1] | (3R)-N-(cyclopropylmethyl)-1-(6-(1-(4-(5-cyclopropylpyridin-3-yl)-1H-1,2,3-triazol-1-yl)ethyl)pyridazin-3-yl)piperidin-3-amine |
| 318 | 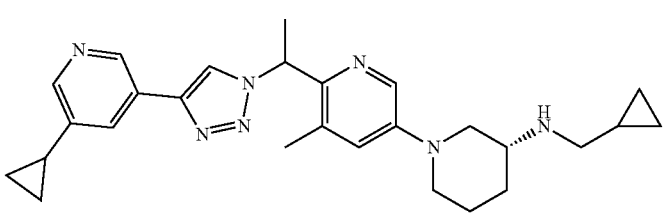 [SMILES: Cc1cc(N2CCC[C@@H](NCC3CC3)C2)cnc1C(C)n1cc(-c2cncc(C3CC3)c2)nn1] | (3R)-N-(cyclopropylmethyl)-1-(6-(1-(4-(5-cyclopropylpyridin-3-yl)-1H-1,2,3-triazol-1-yl)ethyl)-5-methylpyridin-3-yl)piperidin-3-amine |
| 319 | 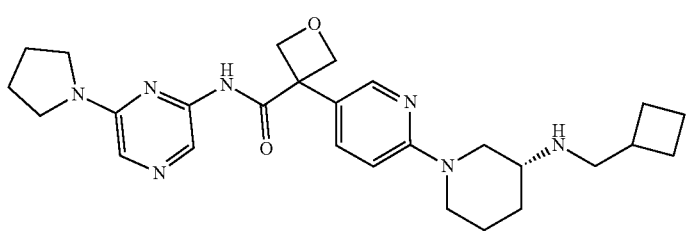 [SMILES: O=C(Nc1cncc(N2CCCC2)n1)C1(c2ccc(N3CCC[C@@H](NCC4CCC4)C3)nc2)COC1] | (R)-3-(6-(3-((cyclobutylmethyl)amino)piperidin-1-yl)pyridin-3-yl)-N-(6-(pyrrolidin-1-yl)pyrazin-2-yl)oxetane-3-carboxamide |

TABLE 1-continued

| | | |
|---|---|---|
| 320 | 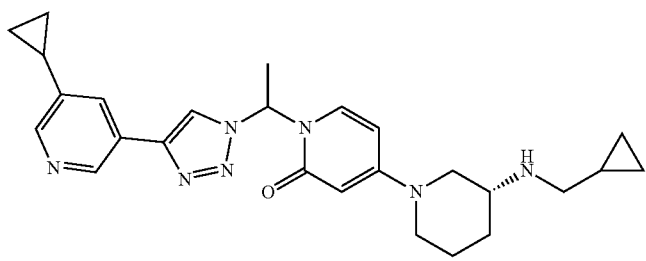 [SMILES: CC(n1cc(-c2cncc(C3CC3)c2)nn1)n1ccc(N2CCC[C@@H](NCC3CC3)C2)cc1=O] | 4-((R)-3-((cyclopropylmethyl)amino)piperidin-1-yl)-1-(1-(4-(5-cyclopropylpyridin-3-yl)-1H-1,2,3-triazol-1-yl)ethyl)pyridin-2(1H)-one |
| 321 | 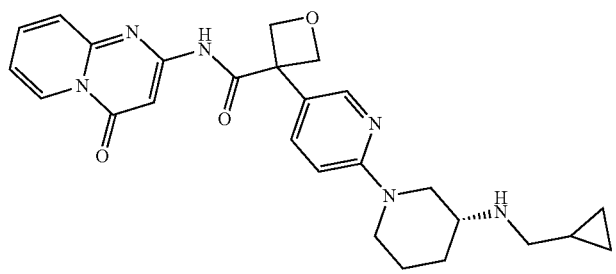 [SMILES: O=C(Nc1cc(=O)n2ccccc2n1)C1(c2ccc(N3CCC[C@@H](NCC4CC4)C3)nc2)COC1] | (R)-3-(6-(3-((cyclopropylmethyl)amino)piperidin-1-yl)pyridin-3-yl)-N-(4-oxo-4H-pyrido[1,2-a]pyrimidin-2-yl)oxetane-3-carboxamide |
| 322 | 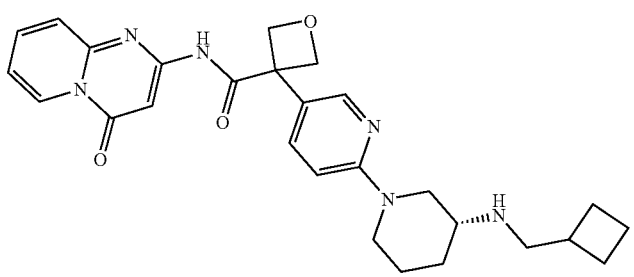 [SMILES: O=C(Nc1cc(=O)n2ccccc2n1)C1(c2ccc(N3CCC[C@@H](NCC4CCC4)C3)nc2)COC1] | (R)-3-(6-(3-((cyclobutylmethyl)amino)piperidin-1-yl)pyridin-3-yl)-N-(4-oxo-4H-pyrido[1,2-a]pyrimidin-2-yl)oxetane-3-carboxamide |
| 323 | 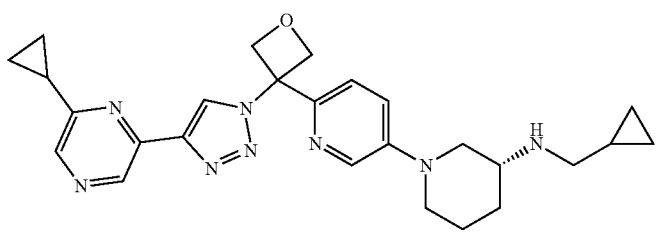 [SMILES: c1cc(C2(n3cc(-c4cncc(C5CC5)n4)nn3)COC2)ncc1N1CCC[C@@H](NCC2CC2)C1] | (R)-N-(cyclopropylmethyl)-1-(6-(3-(4-(6-cyclopropylpyrazin-2-yl)-1H-1,2,3-triazol-1-yl)oxetan-3-yl)pyridin-3-yl)piperidin-3-amine |
| 324 | 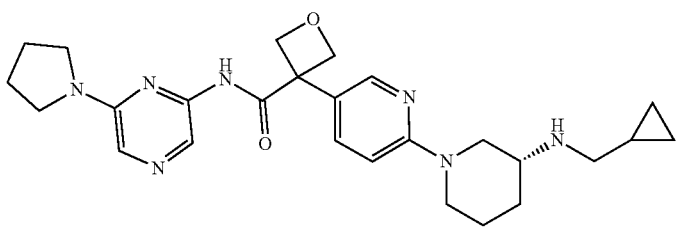 [SMILES: O=C(Nc1cncc(N2CCCC2)n1)C1(c2ccc(N3CCC[C@@H](NCC4CC4)C3)nc2)COC1] | (R)-3-(6-(3-((cyclopropylmethyl)amino)piperidin-1-yl)pyridin-3-yl)-N-(6-(pyrrolidin-1-yl)pyrazin-2-yl)oxetane-3-carboxamide |
| 325 | 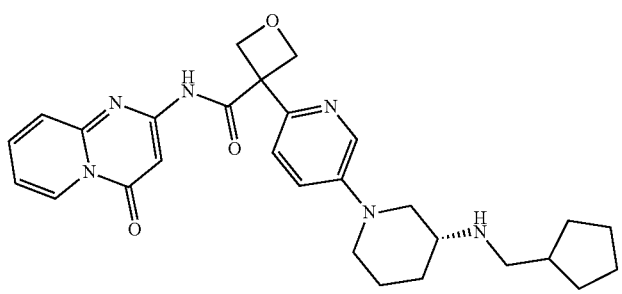 [SMILES: O=C(Nc1cc(=O)n2ccccc2n1)C1(c2ccc(N3CCC[C@@H](NCC4CCCC4)C3)cn2)COC1] | (R)-3-(5-(3-((cyclopentylmethyl)amino)piperidin-1-yl)pyridin-2-yl)-N-(4-oxo-4H-pyrido[1,2-a]pyrimidin-2-yl)oxetane-3-carboxamide |

TABLE 1-continued

| | | |
|---|---|---|
| 326 | 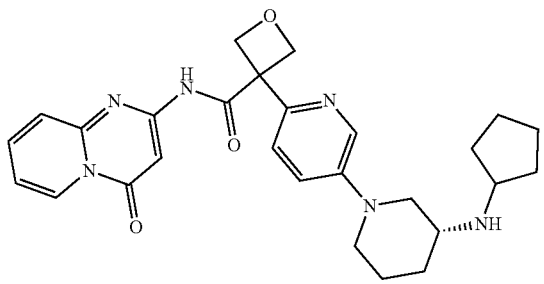 [SMILES: O=C(Nc1cc(=O)n2ccccc2n1)C1(c2ccc(N3CCC[C@@H](NC4CCCC4)C3)cn2)COC1] | (R)-3-(5-(3-(cyclopentylamino)piperidin-1-yl)pyridin-2-yl)-N-(4-oxo-4H-pyrido[1,2-a]pyrimidin-2-yl)oxetane-3-carboxamide |
| 327 | 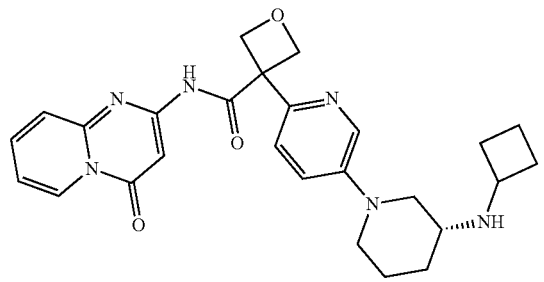 [SMILES: O=C(Nc1cc(=O)n2ccccc2n1)C1(c2ccc(N3CCC[C@@H](NC4CCC4)C3)cn2)COC1] | (R)-3-(5-(3-(cyclobutylamino)piperidin-1-yl)pyridin-2-yl)-N-(4-oxo-4H-pyrido[1,2-a]pyrimidin-2-yl)oxetane-3-carboxamide |
| 328 | 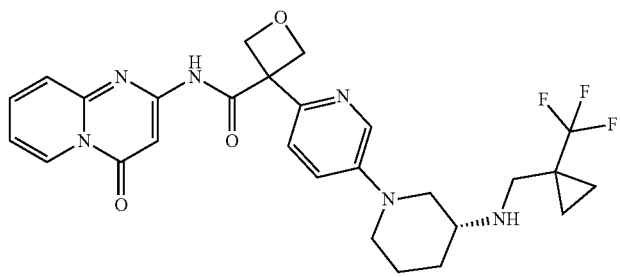 [SMILES: O=C(Nc1cc(=O)n2ccccc2n1)C1(c2ccc(N3CCC[C@@H](NCC4(C(F)(F)F)CC4)C3)cn2)COC1] | (R)-N-(4-oxo-4H-pyrido[1,2-a]pyrimidin-2-yl)-3-(5-(3-(((1-(trifluoromethyl)cyclopropyl)methyl)amino)piperidin-1-yl)pyridin-2-yl)oxetane-3-carboxamide |
| 329 | 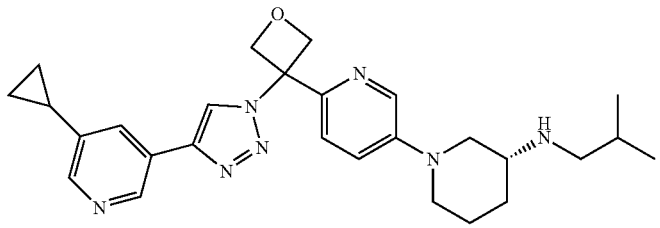 [SMILES: CC(C)CN[C@@H]1CCCN(c2ccc(C3(n4cc(-c5cncc(C6CC6)c5)nn4)COC3)nc2)C1] | (R)-1-(6-(3-(4-(5-cyclopropylpyridin-3-yl)-1H-1,2,3-triazol-1-yl)oxetan-3-yl)pyridin-3-yl)-N-isobutylpiperidin-3-amine |
| 330 | 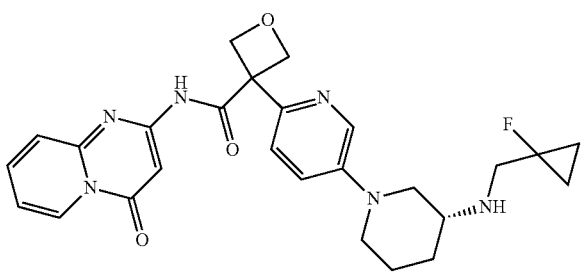 [SMILES: O=C(Nc1cc(=O)n2ccccc2n1)C1(c2ccc(N3CCC[C@@H](NCC4(F)CC4)C3)cn2)COC1] | (R)-3-(5-(3-(((1-fluorocyclopropyl)methyl)amino)piperidin-1-yl)pyridin-2-yl)-N-(4-oxo-4H-pyrido[1,2-a]pyrimidin-2-yl)oxetane-3-carboxamide |
| 331 | 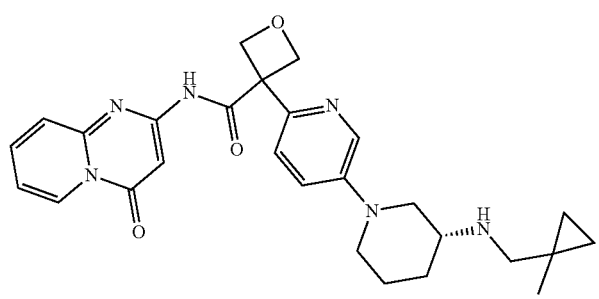 [SMILES: CC1(CN[C@@H]2CCCN(c3ccc(C4(C(=O)Nc5cc(=O)n6ccccc6n5)COC4)nc3)C2)CC1] | (R)-3-(5-(3-(((1-methylcyclopropyl)methyl)amino)piperidin-1-yl)pyridin-2-yl)-N-(4-oxo-4H-pyrido[1,2-a]pyrimidin-2-yl)oxetane-3-carboxamide |

TABLE 1-continued

| 332 | 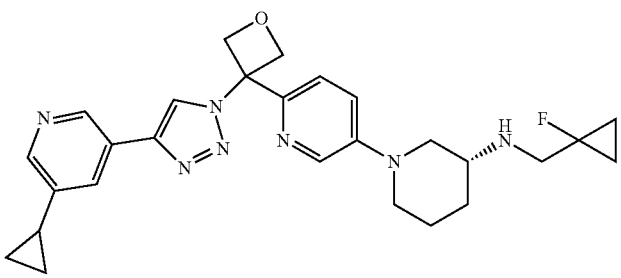 [SMILES: FC1(CN[C@@H]2CCCN(c3ccc(C4(n5cc(-c6cncc(C7CC7)c6)nn5)COC4)nc3)C2)CC1] | (R)-1-(6-(3-(4-(5-cyclopropylpyridin-3-yl)-1H-1,2,3-triazol-1-yl)oxetan-3-yl)pyridin-3-yl)-N-((1-fluorocyclopropyl)methyl)piperidin-3-amine |
| --- | --- | --- |
| 333 | 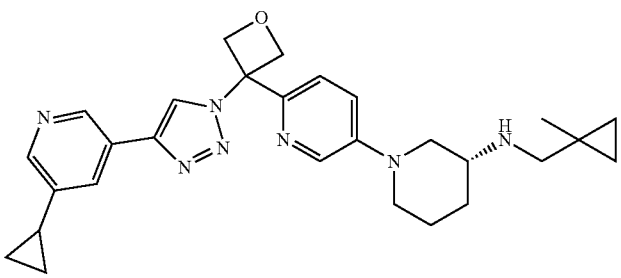 [SMILES: CC1(CN[C@@H]2CCCN(c3ccc(C4(n5cc(-c6cncc(C7CC7)c6)nn5)COC4)nc3)C2)CC1] | (R)-1-(6-(3-(4-(5-cyclopropylpyridin-3-yl)-1H-1,2,3-triazol-1-yl)oxetan-3-yl)pyridin-3-yl)-N-((1-methylcyclopropyl)methyl)piperidin-3-amine |
| 334 | 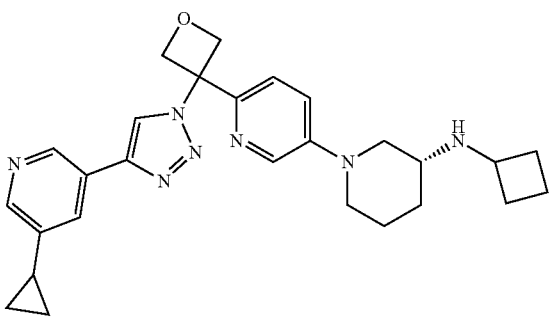 [SMILES: c1ncc(C2CC2)cc1-c1cn(C2(c3ccc(N4CCC[C@@H](NC5CCC5)C4)cn3)COC2)nn1] | (R)-N-cyclobutyl-1-(6-(3-(4-(5-cyclopropylpyridin-3-yl)-1H-1,2,3-triazol-1-yl)oxetan-3-yl)pyridin-3-yl)piperidin-3-amine |
| 335 | 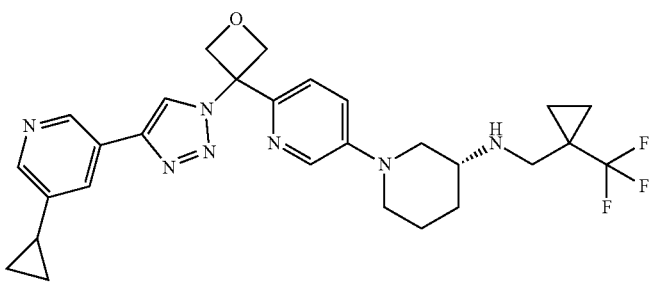 [SMILES: FC(F)(F)C1(CN[C@@H]2CCCN(c3ccc(C4(n5cc(-c6cncc(C7CC7)c6)nn5)COC4)nc3)C2)CC1] | (R)-1-(6-(3-(4-(5-cyclopropylpyridin-3-yl)-1H-1,2,3-triazol-1-yl)oxetan-3-yl)pyridin-3-yl)-N-((1-(trifluoromethyl)cyclopropyl)methyl)piperidin-3-amine |
| 336 | 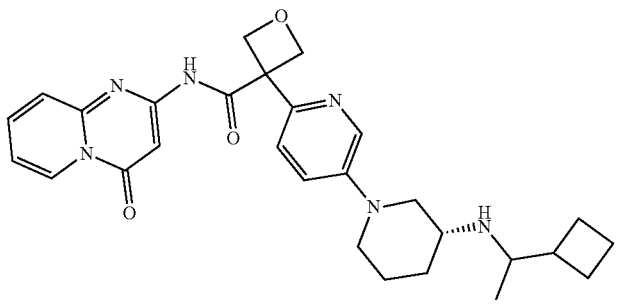 [SMILES: CC(N[C@@H]1CCCN(c2ccc(C3(C(=O)Nc4cc(=O)n5ccccc5n4)COC3)nc2)C1)C1CCC1] | 3-(5-((3R)-3-((1-cyclobutylethyl)amino)piperidin-1-yl)pyridin-2-yl)-N-(4-oxo-4H-pyrido[1,2-a]pyrimidin-2-yl)oxetane-3-carboxamide |

TABLE 1-continued

| | | |
|---|---|---|
| 337 | 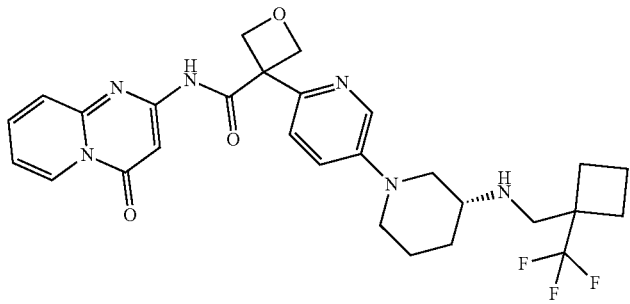 [SMILES: O=C(Nc1cc(=O)n2ccccc2n1)C1(c2ccc(N3CCC[C@@H](NCC4(C(F)(F)F)CCC4)C3)cn2)COC1] | (R)-N-(4-oxo-4H-pyrido[1,2-a]pyrimidin-2-yl)-3-(5-(3-(((1-(trifluoromethyl)cyclobutyl)methyl)amino)piperidin-1-yl)pyridin-2-yl)oxetane-3-carboxamide |
| 338 | 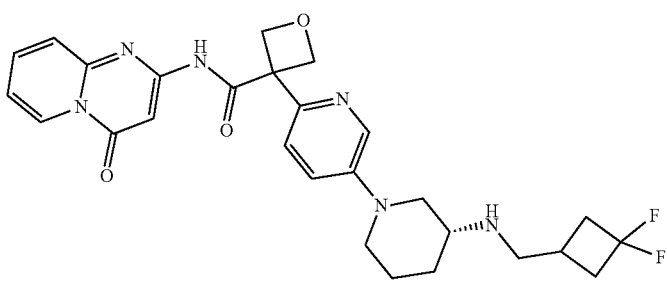 [SMILES: O=C(Nc1cc(=O)n2ccccc2n1)C1(c2ccc(N3CCC[C@@H](NCC4CC(F)(F)C4)C3)cn2)COC1] | (R)-3-(5-(3-(((3,3-difluorocyclobutyl)methyl)amino)piperidin-1-yl)pyridin-2-yl)-N-(4-oxo-4H-pyrido[1,2-a]pyrimidin-2-yl)oxetane-3-carboxamide |
| 339 | 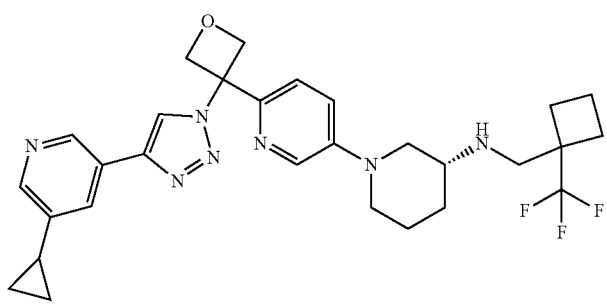 [SMILES: FC(F)(F)C1(CN[C@@H]2CCCN(c3ccc(C4(n5cc(-c6cncc(C7CC7)c6)nn5)COC4)nc3)C2)CCC1] | (R)-1-(6-(3-(4-(5-cyclopropylpyridin-3-yl)-1H-1,2,3-triazol-1-yl)oxetan-3-yl)pyridin-3-yl)-N-((1-(trifluoromethyl)cyclobutyl)methyl)piperidin-3-amine |
| 340 | 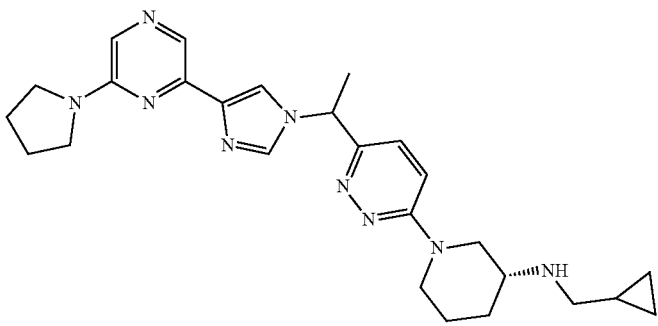 | (3R)-N-(cyclopropylmethyl)-1-(6-(1-(4-(6-(pyrrolidin-1-yl)pyrazin-2-yl)-1H-imidazol-1-yl)ethyl)pyridazin-3-yl)piperidin-3-amine |
| 341 | 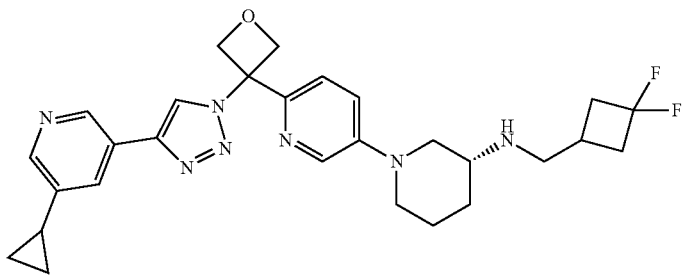 [SMILES: FC1(F)CC(CN[C@@H]2CCCN(c3ccc(C4(n5cc(-c6cncc(C7CC7)c6)nn5)COC4)nc3)C2)C1] | (R)-1-(6-(3-(4-(5-cyclopropylpyridin-3-yl)-1H-1,2,3-triazol-1-yl)oxetan-3-yl)pyridin-3-yl)-N-((3,3-difluorocyclobutyl)methyl)piperidin-3-amine |

TABLE 1-continued

| | | |
|---|---|---|
| 342 | 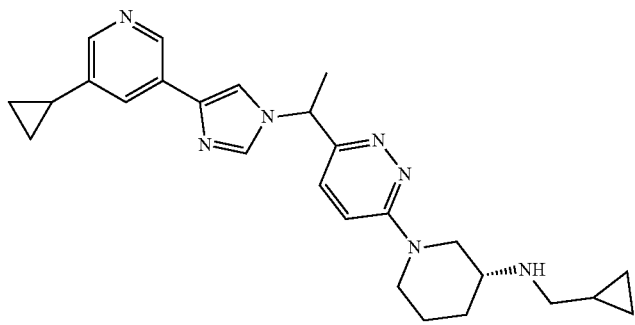 [SMILES: CC(c1ccc(N2CCC[C@@H](NCC3CC3)C2)nn1)n1cnc(-c2cncc(C3CC3)c2)c1] | (3R)-N-(cyclopropylmethyl)-1-(6-(1-(4-(5-cyclopropylpyridin-3-yl)-1H-imidazol-1-yl)ethyl)pyridazin-3-yl)piperidin-3-amine |
| 343 | 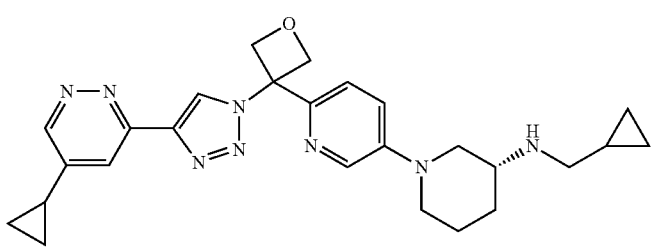 [SMILES: c1nnc(-c2cn(C3(c4ccc(N5CCC[C@@H](NCC6CC6)C5)cn4)COC3)nn2)cc1C1CC1] | (R)-N-(cyclopropylmethyl)-1-(6-(3-(4-(5-cyclopropylpyridazin-3-yl)-1H-1,2,3-triazol-1-yl)oxetan-3-yl)pyridin-3-yl)piperidin-3-amine |
| 344 | 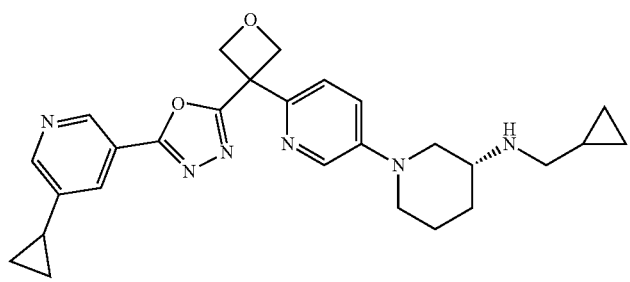 | (R)-N-(cyclopropylmethyl)-1-(6-(3-(5-(5-cyclopropylpyridin-3-yl)-1,3,4-oxadiazol-2-yl)oxetan-3-yl)pyridin-3-yl)piperidin-3-amine |
| 345 | 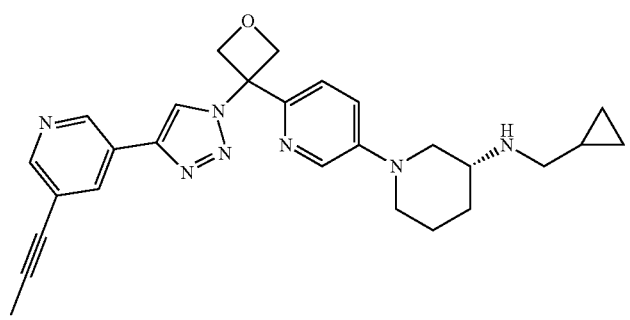 [SMILES: CC#Cc1cncc(-c2cn(C3(c4ccc(N5CCC[C@@H](NCC6CC6)C5)cn4)COC3)nn2)c1] | (R)-N-(cyclopropylmethyl)-1-(6-(3-(4-(5-(prop-1-yn-1-yl)pyridin-3-yl)-1H-1,2,3-triazol-1-yl)oxetan-3-yl)pyridin-3-yl)piperidin-3-amine |
| 346 | 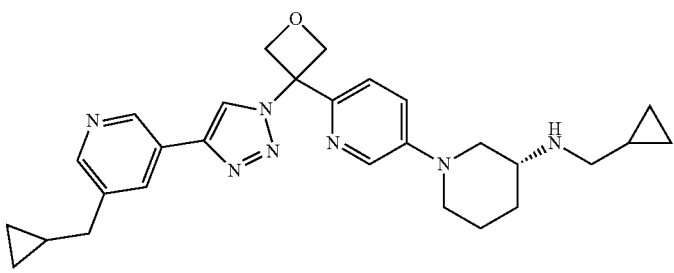 [SMILES: c1ncc(-c2cn(C3(c4ccc(N5CCC[C@@H](NCC6CC6)C5)cn4)COC3)nn2)cc1CC1CC1] | (R)-N-(cyclopropylmethyl)-1-(6-(3-(4-(5-(cyclopropylmethyl)pyridin-3-yl)-1H-1,2,3-triazol-1-yl)oxetan-3-yl)pyridin-3-yl)piperidin-3-amine |

TABLE 1-continued

| | | |
|---|---|---|
| 347 | 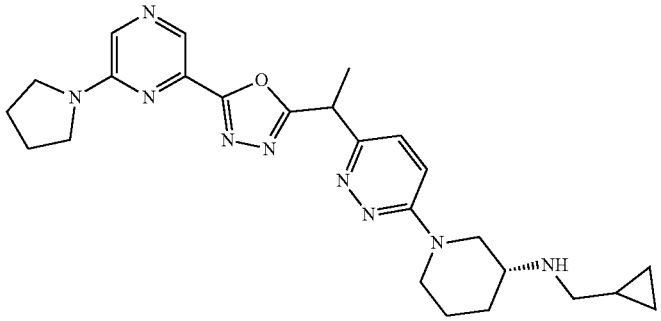 [SMILES: CC(c1ccc(N2CCC[C@@H](NCC3CC3)C2)nn1)c1nnc(-c2cncc(N3CCCC3)n2)o1] | (3R)-N-(cyclopropylmethyl)-1-(6-(1-(5-(6-(pyrrolidin-1-yl)pyrazin-2-yl)-1,3,4-oxadiazol-2-yl)ethyl)pyridazin-3-yl)piperidin-3-amine |
| 348 | 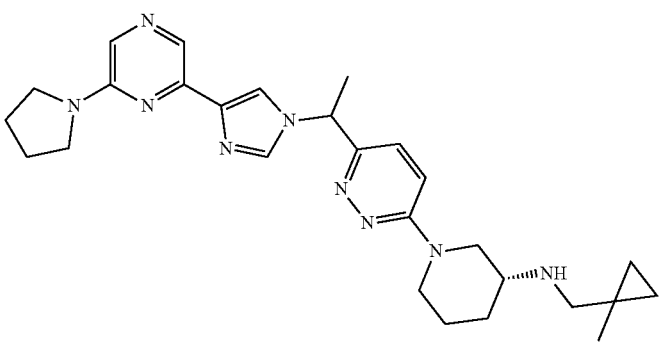 [SMILES: CC(c1ccc(N2CCC[C@@H](NCC3(C)CC3)C2)nn1)n1cnc(-c2cncc(N3CCCC3)n2)c1] | (3R)-N-((1-methylcyclopropyl)methyl)-1-(6-(1-(4-(6-(pyrrolidin-1-yl)pyrazin-2-yl)-1H-imidazol-1-yl)ethyl)pyridazin-3-yl)piperidin-3-amine |
| 349 | 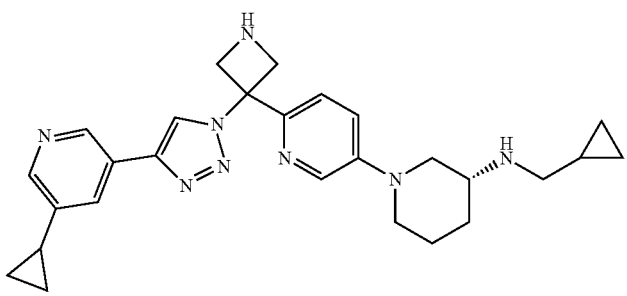 [SMILES: c1ncc(C2CC2)cc1-c1cn(C2(c3ccc(N4CCC[C@@H](NCC5CC5)C4)cn3)CNC2)nn1] | (R)-N-(cyclopropylmethyl)-1-(6-(3-(4-(5-cyclopropylpyridin-3-yl)-1H-1,2,3-triazol-1-yl)azetidin-3-yl)pyridin-3-yl)piperidin-3-amine |
| 350 | 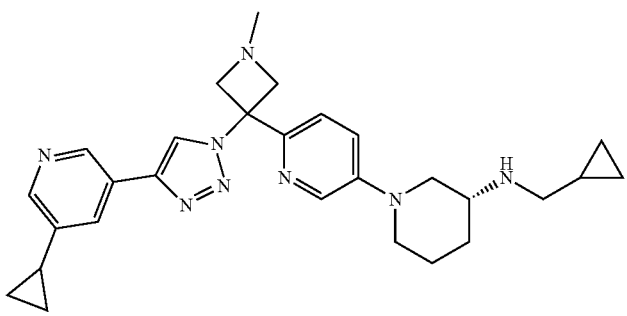 [SMILES: CN1CC(c2ccc(N3CCC[C@@H](NCC4CC4)C3)cn2)(n2cc(-c3cncc(C4CC4)c3)nn2)C1] | (R)-N-(cyclopropylmethyl)-1-(6-(3-(4-(5-cyclopropylpyridin-3-yl)-1H-1,2,3-triazol-1-yl)-1-methylazetidin-3-yl)pyridin-3-yl)piperidin-3-amine |
| 351 | 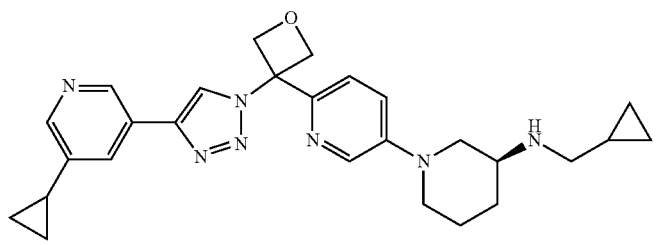 [SMILES: c1ncc(C2CC2)cc1-c1cn(C2(c3ccc(N4CCC[C@H](NCC5CC5)C4)cn3)COC2)nn1] | (S)-N-(cyclopropylmethyl)-1-(6-(3-(4-(5-cyclopropylpyridin-3-yl)-1H-1,2,3-triazol-1-yl)oxetan-3-yl)pyridin-3-yl)piperidin-3-amine |

TABLE 1-continued

| | | |
|---|---|---|
| 352 | 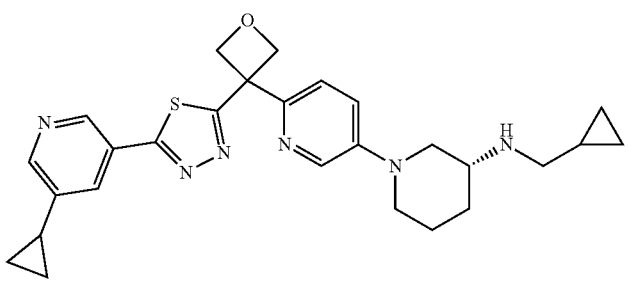 [SMILES: c1ncc(C2CC2)cc1-c1nnc(C2(c3ccc(N4CCC[C@@H](NCC5CC5)C4)cn3)COC2)s1] | (R)-N-(cyclopropylmethyl)-1-(6-(3-(5-(5-cyclopropylpyridin-3-yl)-1,3,4-thiadiazol-2-yl)oxetan-3-yl)pyridin-3-yl)piperidin-3-amine |
| 353 | 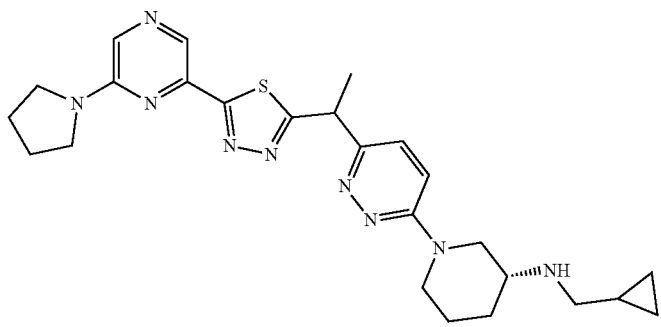 | (3R)-N-(cyclopropylmethyl)-1-(6-(1-(5-(6-(pyrrolidin-1-yl)pyrazin-2-yl)-1,3,4-thiadiazol-2-yl)ethyl)pyridazin-3-yl)piperidin-3-amine |
| 354 | 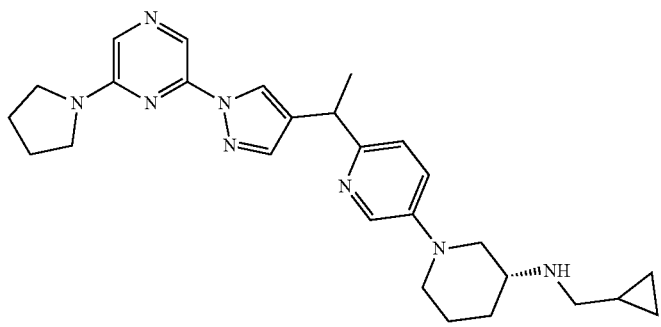 [SMILES: CC(c1cnn(-c2cncc(N3CCCC3)n2)c1)c1ccc(N2CCC[C@@H](NCC3CC3)C2)cn1] | (3R)-N-(cyclopropylmethyl)-1-(6-(1-(6-(pyrrolidin-1-yl)pyrazin-2-yl)-1H-pyrazol-4-yl)ethyl)pyridin-3-yl)piperidin-3-amine |
| 355 | 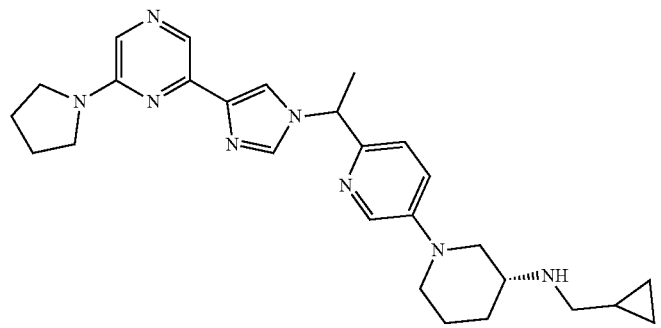 [SMILES: CC(c1ccc(N2CCC[C@@H](NCC3CC3)C2)cn1)n1cnc(-c2cncc(N3CCCC3)n2)c1] | (3R)-N-(cyclopropylmethyl)-1-(6-(1-(4-(6-(pyrrolidin-1-yl)pyrazin-2-yl)-1H-imidazol-1-yl)ethyl)pyridin-3-yl)piperidin-3-amine |
| 356 | 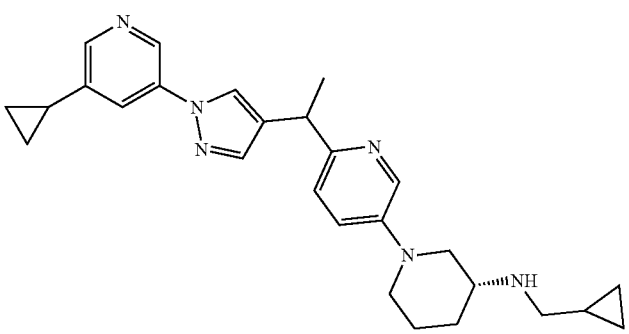 [SMILES: CC(c1cnn(-c2cncc(C3CC3)c2)c1)c1ccc(N2CCC[C@@H](NCC3CC3)C2)cn1] | (3R)-N-(cyclopropylmethyl)-1-(6-(1-(1-(5-cyclopropylpyridin-3-yl)-1H-pyrazol-4-yl)ethyl)pyridin-3-yl)piperidin-3-amine |

TABLE 1-continued

| | | |
|---|---|---|
| 357 | 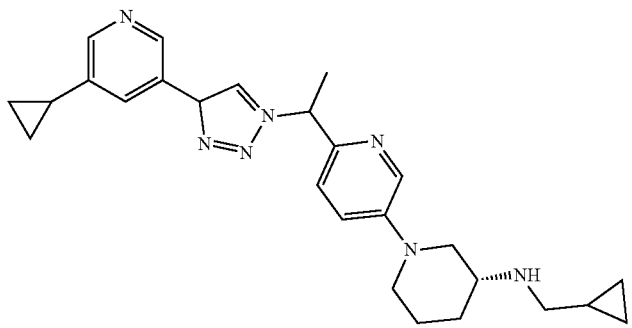 | (3R)-N-(cyclopropylmethyl)-1-(6-(1-(4-(5-cyclopropylpyridin-3-yl)-1H-1,2,3-triazol-1-yl)ethyl)pyridin-3-yl)piperidin-3-amine |
| 358 | 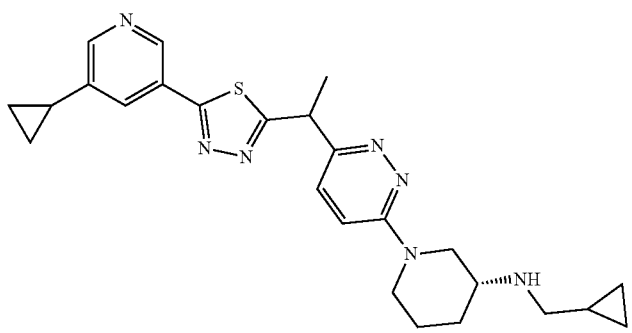 [SMILES: CC(c1ccc(N2CCC[C@@H](NCC3CC3)C2)nn1)c1nnc(-c2cncc(C3CC3)c2)s1] | (3R)-N-(cyclopropylmethyl)-1-(6-(1-(5-(5-cyclopropylpyridin-3-yl)-1,3,4-thiadiazol-2-yl)ethyl)pyridazin-3-yl)piperidin-3-amine |
| 359 | 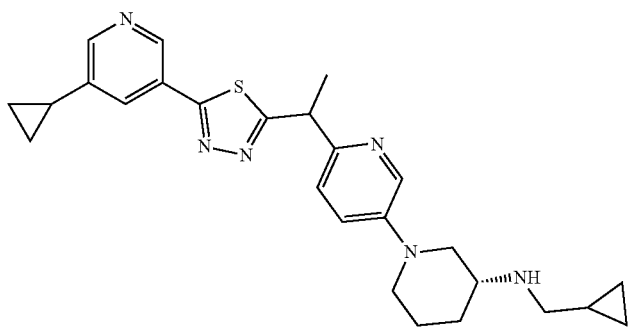 [SMILES: CC(c1ccc(N2CCC[C@@H](NCC3CC3)C2)cn1)c1nnc(-c2cncc(C3CC3)c2)s1] | (3R)-N-(cyclopropylmethyl)-1-(6-(1-(5-(5-cyclopropylpyridin-3-yl)-1,3,4-thiadiazol-2-yl)ethyl)pyridin-3-yl)piperidin-3-amine |
| 360 | 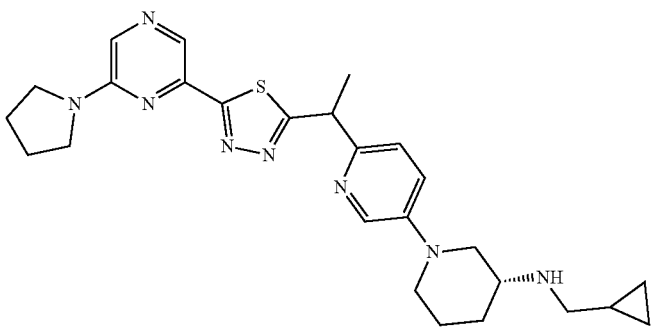 [SMILES: CC(c1ccc(N2CCC[C@@H](NCC3CC3)C2)cn1)c1nnc(-c2cncc(N3CCCC3)n2)s1] | (3R)-N-(cyclopropylmethyl)-1-(6-(1-(5-(6-(pyrrolidin-1-yl)pyrazin-2-yl)-1,3,4-thiadiazol-2-yl)ethyl)pyridin-3-yl)piperidin-3-amine |
| 361 | 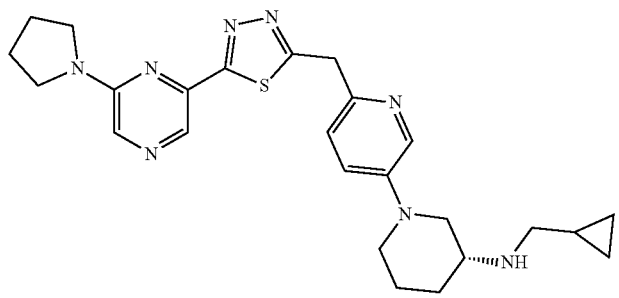 [SMILES: c1cc(Cc2nnc(-c3cncc(N4CCCC4)n3)s2)ncc1N1CCC[C@@H](NCC2CC2)C1] | (R)-N-(cyclopropylmethyl)-1-(6-((5-(6-(pyrrolidin-1-yl)pyrazin-2-yl)-1,3,4-thiadiazol-2-yl)methyl)pyridin-3-yl)piperidin-3-amine |

TABLE 1-continued

| | | |
|---|---|---|
| 362 | 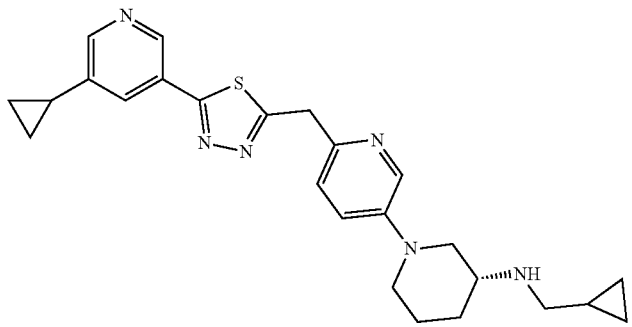 [SMILES: c1ncc(C2CC2)cc1-c1nnc(Cc2ccc(N3CCC[C@@H](NCC4CC4)C3)cn2)s1] | (R)-N-(cyclopropylmethyl)-1-(6-((5-(5-cyclopropylpyridin-3-yl)-1,3,4-thiadiazol-2-yl)methyl)pyridin-3-yl)piperidin-3-amine |
| 363 | 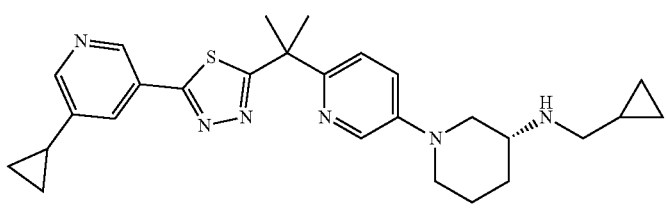 [SMILES: CC(C)(c1ccc(N2CCC[C@@H](NCC3CC3)C2)cn1)c1nnc(-c2cncc(C3CC3)c2)s1] | (R)-N-(cyclopropylmethyl)-1-(6-(2-(5-(5-cyclopropylpyridin-3-yl)-1,3,4-thiadiazol-2-yl)propan-2-yl)pyridin-3-yl)piperidin-3-amine |
| 364 | 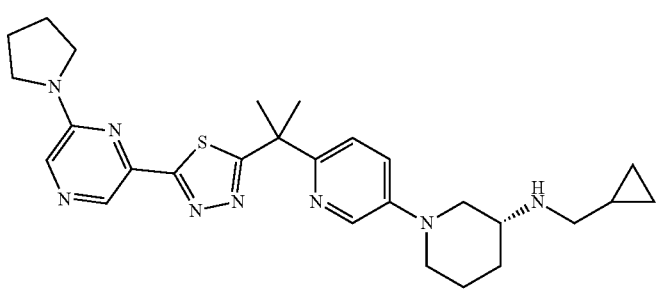 [SMILES: CC(C)(c1ccc(N2CCC[C@@H](NCC3CC3)C2)cn1)c1nnc(-c2cncc(N3CCCC3)n2)s1] | (R)-N-(cyclopropylmethyl)-1-(6-(2-(5-(6-(pyrrolidin-1-yl)pyrazin-2-yl)-1,3,4-thiadiazol-2-yl)propan-2-yl)pyridin-3-yl)piperidin-3-amine |
| 365 | 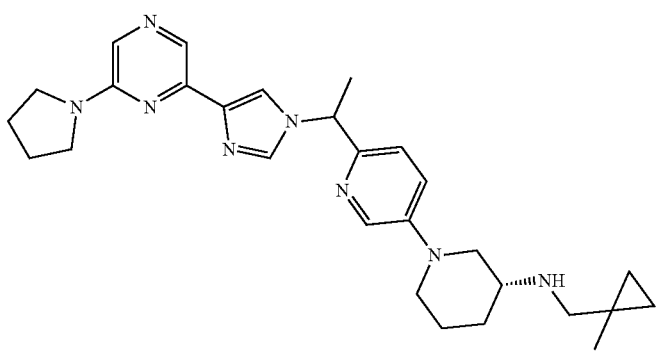 [SMILES: CC(c1ccc(N2CCC[C@@H](NCC3(C)CC3)C2)cn1)n1cnc(-c2cncc(N3CCCC3)n2)c1] | (3R)-N-((1-methylcyclopropyl)methyl)-1-(6-(1-(4-(6-(pyrrolidin-1-yl)pyrazin-2-yl)-1H-imidazol-1-yl)ethyl)pyridin-3-yl)piperidin-3-amine |
| 366 | 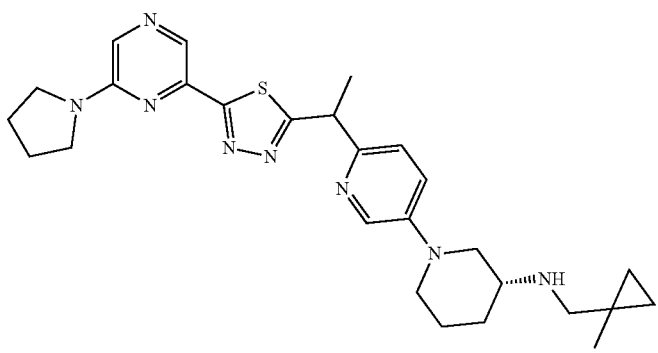 [SMILES: CC(c1ccc(N2CCC[C@@H](NCC3(C)CC3)C2)cn1)c1nnc(-c2cncc(N3CCCC3)n2)s1] | (3R)-N-((1-methylcyclopropyl)methyl)-1-(6-(1-(5-(6-(pyrrolidin-1-yl)pyrazin-2-yl)-1,3,4-thiadiazol-2-yl)ethyl)pyridin-3-yl)piperidin-3-amine |

TABLE 1-continued

| 367 | [structure] | (R)-N-((1-methylcyclopropyl)methyl)-1-(6-(3-(5-(6-(pyrrolidin-1-yl)pyrazin-2-yl)-1,3,4-thiadiazol-2-yl)oxetan-3-yl)pyridin-3-yl)piperidin-3-amine |
| --- | --- | --- |
| 368 | [structure] | (R)-1-(6-(3-(5-(5-cyclopropylpyridin-3-yl)-1,3,4-thiadiazol-2-yl)oxetan-3-yl)pyridin-3-yl)-N-((1-methylcyclopropyl)methyl)piperidin-3-amine |
| 369 | [structure] | (R)-N-(cyclopropylmethyl)-1-(6-(3-(5-(6-(pyrrolidin-1-yl)pyrazin-2-yl)-1,3,4-thiadiazol-2-yl)oxetan-3-yl)pyridin-3-yl)piperidin-3-amine | and pharmaceutically acceptable salts and/or solvates thereof.

The compounds of Table 1 were named using ChemDraw 21® purchased from CambridgeSoft (Cambridge, MA, USA).

All references to compounds of formula (I) include references to salts, solvates, multi-component complexes and/or liquid crystals thereof. All references to compounds of formula (I) include references to polymorphs and/or crystal habits thereof. All references to compounds of formula (I) include references to pharmaceutically acceptable prodrugs thereof.

The compounds of formula (I) and subformulae thereof contain at least one asymmetric centre(s) and thus may exist as different stereoisomeric forms. Accordingly, all references to compounds of formula (I) include references to all possible stereoisomers and includes not only the racemic compounds but the individual enantiomers and their non-racemic mixtures as well. When a compound is desired as a single enantiomer, such single enantiomer may be obtained by stereospecific synthesis, by resolution of the final product or any convenient intermediate, or by chiral chromatographic methods as each are known in the art. Resolution of the final product, an intermediate, or a starting material may be carried out by any suitable method known in the art.

Bonds from an asymmetric carbon in compounds are generally depicted using a solid line (_____), a solid wedge (▬▬), or a dotted wedge (······). The use of either a solid or dotted wedge to depict bonds from an asymmetric carbon atom is meant to indicate that only the stereoisomer shown is meant to be included. The use of a solid line to depict bonds from an asymmetric carbon atom is meant to indicate that all possible stereoisomers are meant to be included, unless it is clear from the context that a specific stereoisomer is intended.

All references to compounds of formula (I) include references to isotopically-labelled compounds of formula (I), including deuterated compounds of formula (I).

The compounds of the invention may be in the form of pharmaceutically acceptable salts. Pharmaceutically acceptable salts of the compounds of formula (I) include the acid addition and base salts thereof.

Suitable acid addition salts are formed from acids which form non-toxic salts. Examples include the acetate, adipate, ammonium, aspartate, benzenesulfonate, benzoate, besylate, bicarbonate/carbonate, bisulphate/sulphate, bitartrate/tartrate, borate, bromide, calcium edetate, camsylate, chloride, citrate, clavulanate, cyclamate, dihydrochloride, edetate, edisylate, estolate, esylate, formate, fumarate, gluceptate, gluconate, glucuronate, glutamate, glycollylarsanilate, hexafluorophosphate, hexylresorcinate, hibenzate, hydrochloride/chloride, hydrabamine, hydrobromide/bromide, hydroiodide/iodide, hydroxynaphthoate, isethionate, lactate, lactobionate, laurate, malate, maleate, malonate, mandelate, mesylate, methylbromide, N-methylglucamine, methylnitrate, methylsulphate, mucate, naphthylate, napsylate, nicotinate, nitrate, oleate, orotate, oxalate, palmitate, pamoate, pantothenate, phosphate/hydrogen phosphate/dihydrogen phosphate, polygalacturonate, pyroglutamate, saccharate, salicylate, stearate, succinate, sulfate, subacetate, tannate, teoclate, tosylate, triethiodide, trifluoroacetate, valerate, and xinofoate salts.

Suitable base salts are formed from bases which form non-toxic salts. Examples include the aluminium, ammonia, arginine, benzathine, N-benzylphenethylamine, calcium, choline, chloroprocaine, N,N'-dibenzylethylenediamine, diethanolamine, diethylamine, 2-(diethylamino)ethanol, diolamine, ethylenediamine, ethanolamine, glycine, 4-(2-hydroxyethyl)morpholine, lithium, lysine, magnesium, meglumine, N-methyl-glutamine, morpholine, olamine, ornithine, potassium, piperazine, procaine, sodium, tetramethylammonium hydroxide, tris(hydroxymethyl)aminomethane, tromethamine and zinc salts.

Hemisalts of acids and bases may also be formed, for example, hemisulphate and hemicalcium salts.

When the compounds of formula (I) contain an acidic group as well as a basic group the compounds of the invention may also form internal salts, and such compounds are within the scope of the invention. When the compounds of the invention contain a hydrogen-donating heteroatom (e.g., NH), the invention also covers salts and/or isomers formed by transfer of said hydrogen atom to a basic group or atom within the molecule.

Pharmaceutically acceptable salts of compounds of formula (I) may be prepared by one or more of these methods:
  (i) by reacting the compound of formula (I) with the desired acid;
  (ii) by reacting the compound of formula (I) with the desired base;
  (iii) by removing an acid- or base-labile protecting group from a suitable precursor of the compound of formula (I) or by ring-opening a suitable cyclic precursor, e.g., a lactone or lactam, using the desired acid; and/or
  (iv) by converting one salt of the compound of formula (I) to another by reaction with an appropriate acid or by means of a suitable ion exchange column.

All these reactions are typically carried out in solution. The salt may precipitate from solution and be collected by filtration or may be recovered by evaporation of the solvent. The degree of ionization in the salt may vary from completely ionized to almost non-ionized.

Although generally, with respect to the salts of the compounds of the invention, pharmaceutically acceptable salts are preferred, it should be noted that the invention in its broadest sense also included non-pharmaceutically acceptable salts, which may for example be used in the isolation and/or purification of the compounds of the invention. For example, salts formed with optically active acids or bases may be used to form diastereoisomeric salts that can facilitate the separation of optically active isomers of the compounds of formula (I) above.

Process of Manufacturing

The compound of invention can be synthesized by methods known in the art. Especially, the compound of invention can be synthesized by the methods detailed in the experimental part below.

Pharmaceutical Composition

This invention also relates to a pharmaceutical composition comprising a compound according to the invention, as described hereinabove, and at least one pharmaceutically acceptable carrier.

According to a first embodiment, the pharmaceutical composition comprises the compound according to the invention as sole therapeutic agent.

According to a second embodiment, the pharmaceutical composition further comprises at least another therapeutic agent. In one embodiment, the other therapeutic agent is selected from therapeutic agents detailed hereafter with regard to combination therapy.

The pharmaceutical composition of the invention may further comprise therapeutically active compounds other than those listed herein, which are usually applied in the treatment of the targeted pathological conditions.

Medical Use and Methods of Treatment

This invention also relates to a compound according to the invention, as described hereinabove, for use as a medicament.

This invention also relates to a compound according to the invention, as described hereinabove, for use as inhibitor of METTL3 activity.

This invention also relates to a compound according to the invention, as described hereinabove, for use in the treatment of a disease or disorder in which METTL3 activity is implicated. Examples of diseases or disorders in which METTL3 activity is implicated include proliferative conditions such as cancers, autoimmune diseases, inflammatory diseases, neurological diseases, and infectious disease such as viral infections.

This invention also relates to a compound according to the invention, as described hereinabove, for use in the treatment of a disease or disorder in which METTL3/14 complex activity is implicated. Examples of diseases or disorders in which METTL3/14 complex activity is implicated include proliferative conditions such as cancers, autoimmune diseases, inflammatory diseases, neurological diseases, and infectious disease such as viral infections.

In one embodiment, the invention provides a compound according to the invention, as described hereinabove, for use in the treatment of a proliferative condition.

The terms "proliferative condition" and "proliferative disorder" are used interchangeably herein and pertain to an unwanted or uncontrolled cellular proliferation of excessive or abnormal cells which is undesired, such as, neoplastic, or hyperplastic growth, whether in vitro or in vivo. Examples of proliferative conditions include pre-malignant and malignant cellular proliferation, including but not limited to, malignant neoplasms and tumours, cancers, leukaemias, psoriasis, bone diseases, fibroproliferative disorders (e.g., of connective tissues), and atherosclerosis. Any type of cell may be treated, including but not limited to, lung, colon, breast, ovarian, prostate, liver, pancreas, brain, and skin. The effects on cellular viability of cancer cells of the compounds of the present invention have particular application in the treatment of human cancers (by virtue of their inhibition of METTL3 activity). The anti-cancer effect may arise through one or more mechanisms, including but not limited to, the regulation of cell proliferation, the regulation of cell viability, the inhibition of angiogenesis (the formation of new blood vessels), the inhibition of metastasis (the spread of a tumor from its origin), the inhibition of invasion (the spread of tumor cells into neighboring normal structures), or the promotion of apoptosis (programmed cell death).

In one embodiment, the proliferative condition is cancer. The invention thus provides a compound according to the invention, as described hereinabove, for use in the treatment of cancer. In a particular embodiment, the cancer is human cancer. In an embodiment the cancer is a solid cancer. In another embodiment, the cancer is a non-solid cancer.

Examples of cancers include, without being limited to, acute lymphocytic leukaemia (ALL), acute myeloid leukaemia (AML), chronic myeloid leukaemia, leukaemia, lymphoma, multiple myeloma, non-Hodgkin's lymphoma (NHL), bladder cancer, bone cancer, breast cancer, cervical cancer, colorectal cancer, endometrial cancer, esophageal/upper aerodigestive cancer, glioblastoma, hepatocellular carcinoma, kidney cancer, liver cancer, lung cancer, non small cell lung cancer (NSCLC), head and neck cancer, oral squamous cell carcinoma, melanoma, mesothelioma, ovarian cancer, pancreatic cancer, prostate cancer, sarcoma, skin cancer, stomach cancer, and thyroid cancer.

The invention also provides a compound according to the invention, as described hereinabove, for use in the treatment of an autoimmune disease. Examples of autoimmune diseases include, without being limited to, colitis, multiple sclerosis, rheumatoid arthritis, lupus, cirrhosis, and dermatitis.

The present invention also provides a compound according to the invention, as described hereinabove, for use in the treatment of an inflammatory disease.

The present invention also provides a compound according to the invention, as described hereinabove, for use in the treatment of a neurological disease.

The present invention also provides a compound according to the invention, as described hereinabove, for use in the treatment of an infectious disease. Infectious diseases include viral infections. Viral infections include RNA viral infections. Examples of viral infections include infections by human papillomavirus (HPV), hepatitis viruses such as Hepatitis B virus (HBV) or Hepatitis C virus (HCV), and SARS-COV-2.

This invention also relates to the use of a compound according to the invention, as described hereinabove, in the manufacture of a medicament for inhibiting METTL3 activity.

This invention also relates to the use of a compound according to the invention, as described hereinabove, in the manufacture of a medicament for the treatment of a disease or disorder in which METTL3 activity is implicated, as defined above.

In one embodiment, the invention provides the use of a compound according to the invention, as described hereinabove, in the manufacture of a medicament for the treatment of a proliferative condition, as defined above.

The invention thus provides the use of a compound according to the invention, as described hereinabove, in the manufacture of a medicament for the treatment of cancer, as defined above.

The invention also provides the use of a compound according to the invention, as described hereinabove, in the manufacture of a medicament for the treatment of an autoimmune disease, as defined above.

The present invention also provides the use of a compound according to the invention, as described hereinabove, in the manufacture of a medicament for the treatment of an inflammatory disease.

The present invention also provides the use of a compound according to the invention, as described hereinabove, in the manufacture of a medicament for the treatment of a neurological disease.

The present invention also provides the use of a compound according to the invention, as described hereinabove, in the manufacture of a medicament for the treatment of an infectious disease as defined above.

This invention also relates to a method of inhibiting METTL3 activity in a subject in need thereof, comprising a step of administrating to said subject a therapeutically effective amount of a compound according to the invention, as described hereinabove.

This invention also relates to a method for the treatment of a disease or disorder in which METTL3 activity is implicated, in a subject in need thereof, comprising a step of administrating to said subject a therapeutically effective amount of a compound according to the invention, as described hereinabove.

This invention also relates to a method for the treatment of a proliferative condition, in a subject in need thereof, comprising a step of administrating to said subject a therapeutically effective amount of a compound according to the invention, as described hereinabove.

This invention also relates to a method for the treatment of a cancer, in a subject in need thereof, comprising a step of administrating to said subject a therapeutically effective amount of a compound according to the invention, as described hereinabove.

This invention also relates to a method for the treatment of an autoimmune disease, in a subject in need thereof, comprising a step of administrating to said subject a therapeutically effective amount of a compound according to the invention, as described hereinabove.

This invention also relates to a method for the treatment of an inflammatory disease, in a subject in need thereof, comprising a step of administrating to said subject a therapeutically effective amount of a compound according to the invention.

This invention also relates to a method for the treatment of a neurological disease, in a subject in need thereof, comprising a step of administrating to said subject a therapeutically effective amount of a compound according to the invention.

This invention also relates to a method for the treatment of an infectious disease, in a subject in need thereof, comprising a step of administrating to said subject a therapeutically effective amount of a compound according to the invention, as described hereinabove.

Combination Therapies

According to one embodiment, the compound according to the invention is administrated to the subject as sole therapeutic agent.

According to another embodiment, the compound according to the invention is administrated to the subject in combination with at least another therapeutic agent.

In one embodiment, the other therapeutic agent may be selected from a second anti-cancer therapy, such as chemotherapy, immunotherapy, cell therapy and/or any anti-cancer agent currently in clinical use or in clinical trials According to one embodiment, the compound according to the invention may be administered in combination with conventional surgery, radiotherapy, or transplantation, and/or with at least another therapeutic agent as mentioned above.

Such conjoint treatments may be achieved by way of the simultaneous, sequential, or separate dosing of the individual components of the treatment. Such combination products employ the compounds of the invention within the dosage range described herein and the other therapeutic agent within its approved dosage range.

In the context of the present invention the term "combination" preferably means a combined occurrence of the compound according to the invention and an additional therapeutic agent. Therefore, the combination may occur either as one composition, comprising all the components in one and the same mixture (e.g. a pharmaceutical composition), or may occur as a kit of parts, wherein the different components form different parts of such a kit of parts. The administration of the compound according to the invention and of the additional therapeutic agent may occur either simultaneously or timely staggered, with similar or different timing of administration (i.e. similar or different numbers of administration of each component), either at the same site of administration or at different sites of administration, under similar of different dosage forms.

Methods of Administration

The compounds of the invention may be administered by oral, parenteral (e.g., intramuscular, intraperitoneal, intravenous, intracerebroventricular, intracisternal injection or infusion, subcutaneous injection, or implant), by inhalation spray, nasal, vaginal, rectal, sublingual, or topical routes of administration and may be formulated in suitable dosage unit formulations containing conventional non-toxic pharmaceutically acceptable carriers, adjuvants and vehicles appropriate for each route of administration.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active ingredient is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents, and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions, or suspensions, etc., containing the compounds of the present invention are employed.

In the treatment or prevention of METTL3-related diseases, an appropriate dosage level will generally be about 0.01 to 250 mg per kg patient body weight per day (mg/kg per day) which can be administered in single or multiple doses. Preferably, the dosage level will be about 0.1 to about 100 mg/kg per day, such as between 0.1 and 50 mg/kg per day. For oral administration, the compositions are preferably provided in the form of tablets containing 1.0 to 1000 mg of the active ingredient for the symptomatic adjustment of the dosage to the patient to be treated. The compounds may be administered as a single daily dose, divided over one or more daily doses, for example on a regimen of 1 to 4 times per day. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

EXAMPLES

The present invention is further illustrated by the following examples.

CHEMISTRY EXAMPLES

Material and Methods

All reported temperatures are expressed in degrees Celsius (C); all reactions were carried out at room temperature (rt) unless otherwise stated.
Analytical Methods:
Analytical thin layer chromatography (TLC) was used to monitor reactions, establish flash chromatography conditions and verify purity of intermediates or final products. TLC plates used were Merck TLC aluminum sheet silica gel 60 F254. TLC plates were revealed using ultraviolet irradiation (wavelength=254 nm) at room temperature or $KMnO_4$ revelator upon heating at 160° C. The $KMnO_4$ TLC stain was prepared by dissolving 1.5 g of $KMnO_4$, 10 g $K_2CO_3$, and 1.25 mL 10% NaOH in 200 mL of water. The vanillin TLC stain was prepared by dissolving, 15 g vanillin, 2.5 mL concentrated sulfuric acid in 250 mL of 96% ethanol.

The phosphomolybdic acid stain was prepared by dissolving 10 g of phosphomolybdic acid in 100 mL of 96% ethanol.

$^1$H and $^{13}$C NMR spectra were recorded on a Bruker ARX 300 MHz. Chemical shifts are expressed in parts per million (ppm, δ units). Coupling constants are expressed in Hertz (Hz). Splitting patterns describe apparent multiplicities and are described as s (singlet), d (doublet), t (triplet), q (quartet), p (pentet), sex (sextet), sept (septet), m (multiplet), or br (broad).

HPLC-MS spectra were obtained:

Gradient A: on Agilent LCMS using Electrospray ionization (ESI). The instrument includes an autosampler 1200, a binary pump 1100, a multiwavelength detector 1100 and a 6100 single quadrupole mass spectrometric detector. The column used was an Sunfire C18 3.5 μm 3.0×50 mm. Eluent was a mixture of solution "A" (0.1% TFA in H$_2$O) and solution "B" (0.1% TFA in MeCN). Gradient used is as follows: held the initial conditions of 5% solution "B" for 0.2 min, increased linearly to 95% solution "B" over 1.8 min, held at 95% for 1.75 min, returned to initial conditions over 0.25 min. Flow: 1.0 mL/min.

Gradient B: on Agilent LCMS using Electrospray ionization (ESI). The instrument includes an autosampler 1200, a binary pump 1100, a multiwavelength detector 1100 and a 6100 single quadrupole mass spectrometric detector. The column used was an Sunfire C18 3.5 μm 3.0×50 mm. Eluent was a mixture of solution "A" (0.1% TFA in H$_2$O) and solution "B" (0.1% TFA in MeCN). Gradient used is as follows: held the initial conditions of 5% solution B for 0.2 min, increased linearly to 95% over 5.3 min, held at 95% for 2.25 min, returned to initial conditions over 0.25 min. Flow: 1.0 mL/min.

Gradient C: on Waters Acquity UPLC. UV Detection: Waters Acquity PDA (198-360 nm). MS Detection: Waters SQD, ESI (ES+/ES−, 120-1200 amu). The column used was Waters Acquity UPLC CSH C18, 1.8 μm, 2.1×30 mm at 40° C. Eluent was a mixture of solution "A" (Milli-Q H$_2$O+10 mM ammonium bicarbonate pH: 10) and solution "B" (ACN). Gradient used is as follows: increased linearly from 5 to 100% "B" over 2.0 min, held at 100% for 0.7 min. Flow: 0.9 mL/min.

Gradient D: on Waters Alliance 2695. UV Detection: Waters Acquity PDA (198-360 nm). MS Detection: Waters ZD 2000, ESI (ES+, 100-1200 amu). The column used was Waters Acquity UPLC CSH C18, 3.5 μm, 4.6×30 mm. Eluent was a mixture of solution "A" (Milli-Q H$_2$O+10 mM ammonium bicarbonate pH: 10) and solution "B" (ACN). Gradient used is as follows: held at 5% "B" for 0.2 min, increased linearly to 100% "B" in 1.8 min, held at 100% for 1.0 min. Flow: 3.0 mL/min.

Gradient E: on Waters Acquity UPLC. UV Detection: Waters Acquity PDA (198-360 nm). MS Detection: Waters SQD, ESI (ES+/ES−, 120-1200 amu). The column used was Waters Acquity UPLC CSH C18, 1.8 μm, 2.1×30 mm at 40° C. Eluent was a mixture of solution "A" (Milli-Q H$_2$O+10 mM ammonium bicarbonate pH: 10) and solution "B" (ACN). Gradient used is as follows: increased linearly from 5 to 100% "B" over 5.2 min, held at 100% for 1.8 min. Flow: 0.9 mL/min.

Gradient F: on Waters Acquity UPLC. UV Detection: Waters Acquity PDA (198-360 nm). MS Detection: Waters 3100, ESI (ES+/ES−, 120-1200 amu). The column used was Waters Acquity UPLC CSH C18, 1.8 μm, 2.1×30 mm at 40° C. Eluent was a mixture of solution "A" (Milli-Q H$_2$O+10 mM ammonium formate pH: 3.8) and solution "B" (ACN). Gradient used is as follows: increased linearly from 5 to 100% "B" over 2.0 min, held at 100% for 0.7 min. Flow: 0.9 mL/min.

Determination of chiral purity was performed on an Agilent 1100 HPLC instrument. The instrument includes an autosampler 1100, a binary pump 1100 and a multiwavelength detector 1100. The columns used were Chiralpak IA, Chiralpak IB, Chiralpak IC, Chiralpak ID and Chiralpak IE, each of said columns were filled with 5 μm particles, 4.6×250 mm in dimensions. Mixtures of eluents were selected individually depending on the separation obtained of enantiomers or diastereoisiomers.

Preparative HPLC purifications were carried out on Agilent 1200 preparative HPLC instrument. This instrument consists of gradient pump 1200, a multiwavelength detector 1200 and Rheodyne manual injector.

For reverse phase preparative HPLC purifications the columns used were a Waters XBridge C18 5 μm 19×100 mm or Phenomenex Luna C18 (2) 5 μm 21.2×100 mm. The gradient was adapted depending on nature of the purified compound and impurities, to allow sufficient separation between impurities and target compound. Unless noted otherwise, eluent was a mixture of solution "A" (ammonium bicarbonate 0.02 M) and solution "B" (MeCN).

For chiral preparative HPLC purifications the columns used were Chiralpak IA, Chiralpak IB, Chiralpak ID and Chiralpak IE, each of said columns were filled with 5 μm particles, 10 or 20×250 mm in dimensions. Mixtures of eluents were selected depending on the separation of enantiomers or diastereoisomers obtained with the analytical method. Usually, eluent mixtures were the same as those used for the determination of ee or de. Unless otherwise specified, wavelength used was 280 nm.

Solvents, reagents and starting materials were purchased and used as received from commercial vendors unless otherwise specified.

Abbreviations

The following abbreviations are used:
ACN or MeCN: Acetonitrile,
Ar: Argon,
BINAP: 2,2'-Bis(diphenylphosphino)-1,1'-binaphthyl
dba: Dibenzylideneacetone,
Boc: tert-Butoxycarbonyle,
DCE: 1,2-Dichloroethane,
DCM: Dichloromethane,
DIEA or DIPEA: N,N-diisopropylethylamine,
DMF: N,N-dimethylformamide,
DMSO: Dimethylsulfoxide,
DPPA: Diphenylphosphorylazide,
ee: Enantiomeric excess,
eq: Equivalent,
EtOAc or AcOEt: Ethyl acetate,
EtOH: Ethanol,
g: Grams,
h: Hours,
HATU: 1-[Bis(dimethylamino)methylene]-1H-1,2,3-triazolo[4,5-b]pyridinium 3-oxid hexa fluorophosphates,
HPLC: High performance liquid chromatography,
IM: Intermediate
L: Liters,
LDA: Lithium diisopropylamide,
LiHMDS: Lithium hexamethyldisilazane,
MeOH: Methanol, min: Minutes,
mg: Milligrams,
mL: Milliliters,
mmol: Millimoles,
mol: Moles,
MS: Mass spectrometry,
MW: Molecular weight,
NMP: N-methylpyrrolidinone,
NMR: Nuclear Magnetic Resonance,
P: UV purity at 254 nm determined by HPLC-MS,
PMB: para-Methoxybenzyl,
rt: room temperature,
RuPhos: 2-Dicyclohexylphosphino-2',6'-diisopropoxybiphenyl,
T3P: Tripropylphosphonic anhydride,
TBAF: Tetrabutylammonium fluoride,
TBME: Tert-butylmethylether
TFA: Trifluoroacetic acid,
THF: Tetrahydrofuran,
THP: Tetrahydropyran,
TLC: Thin layer chromatography,
TMS: Trimethylsilyl,
Vol: Volume (L of solvent by g of starting material),
Xantphos: 4,5-Bis(diphenylphosphino)-9,9-dimethylxanthene,
Y: Yield,
μL: Microliters.

All compounds disclosed in the present application were named using ChemDraw 21® purchased from CambridgeSoft (Cambridge, MA, USA).

General Synthetic Schemes

Compounds of the invention may be synthesized using the general pathways described in Schemes 1 to 6 below which represent either a product synthesis as a racemic mixture, or a mixture of diastereoisomers where chiral starting materials were used in conjunction with an uncontrolled second stereocenter, or a chiral synthesis where enantiopure starting materials were used. The non-enantiopure products may then be subjected to chiral HPLC for chiral separation.

Scheme 1: General scheme to access compounds of the invention wherein L is a triazole.

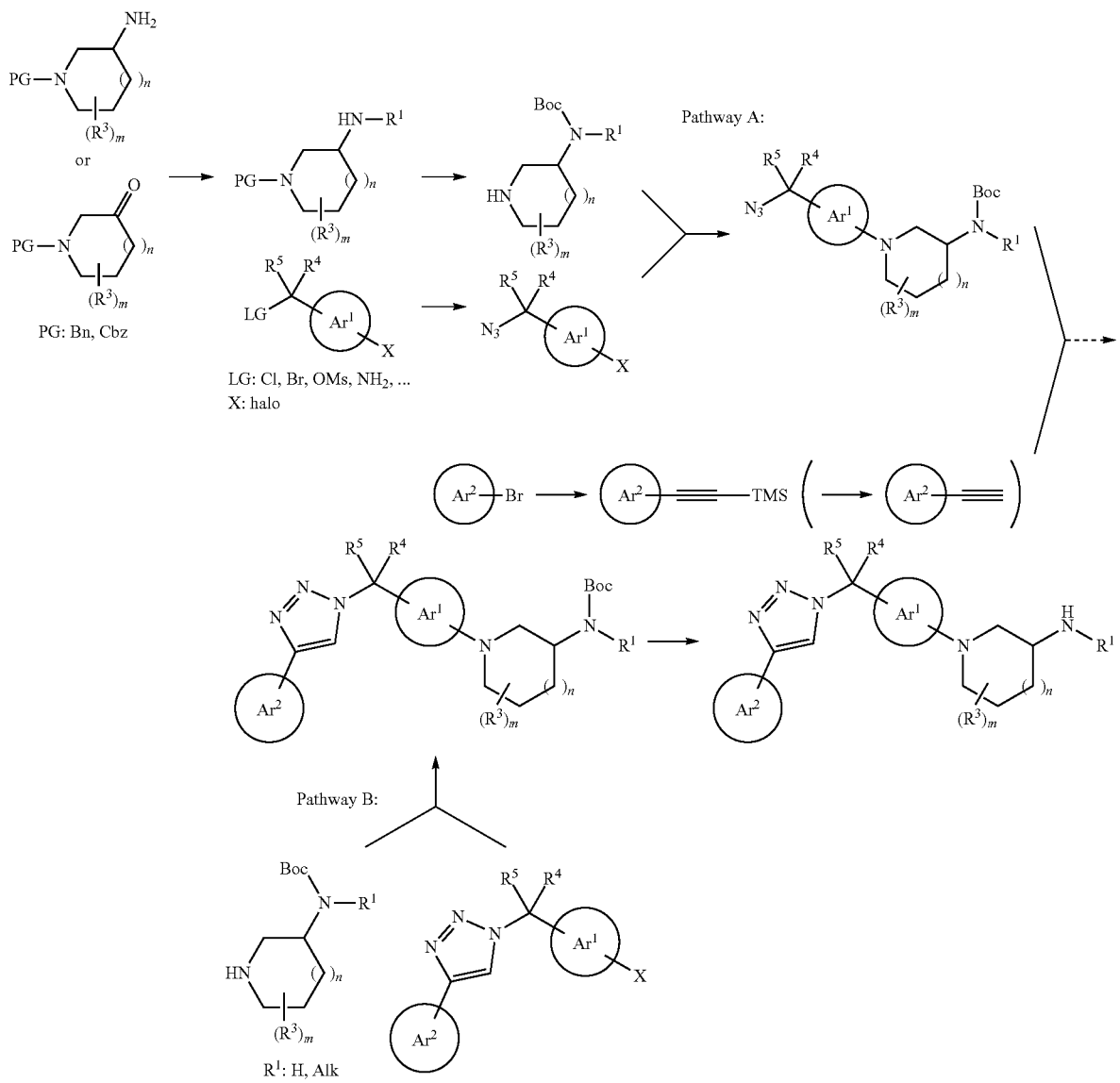

-continued
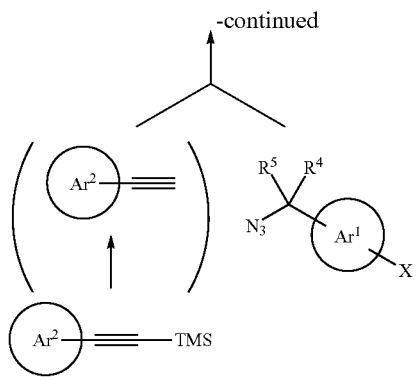
Scheme 2: General scheme to access compounds of the invention wherein L is the amide or thioamide link.
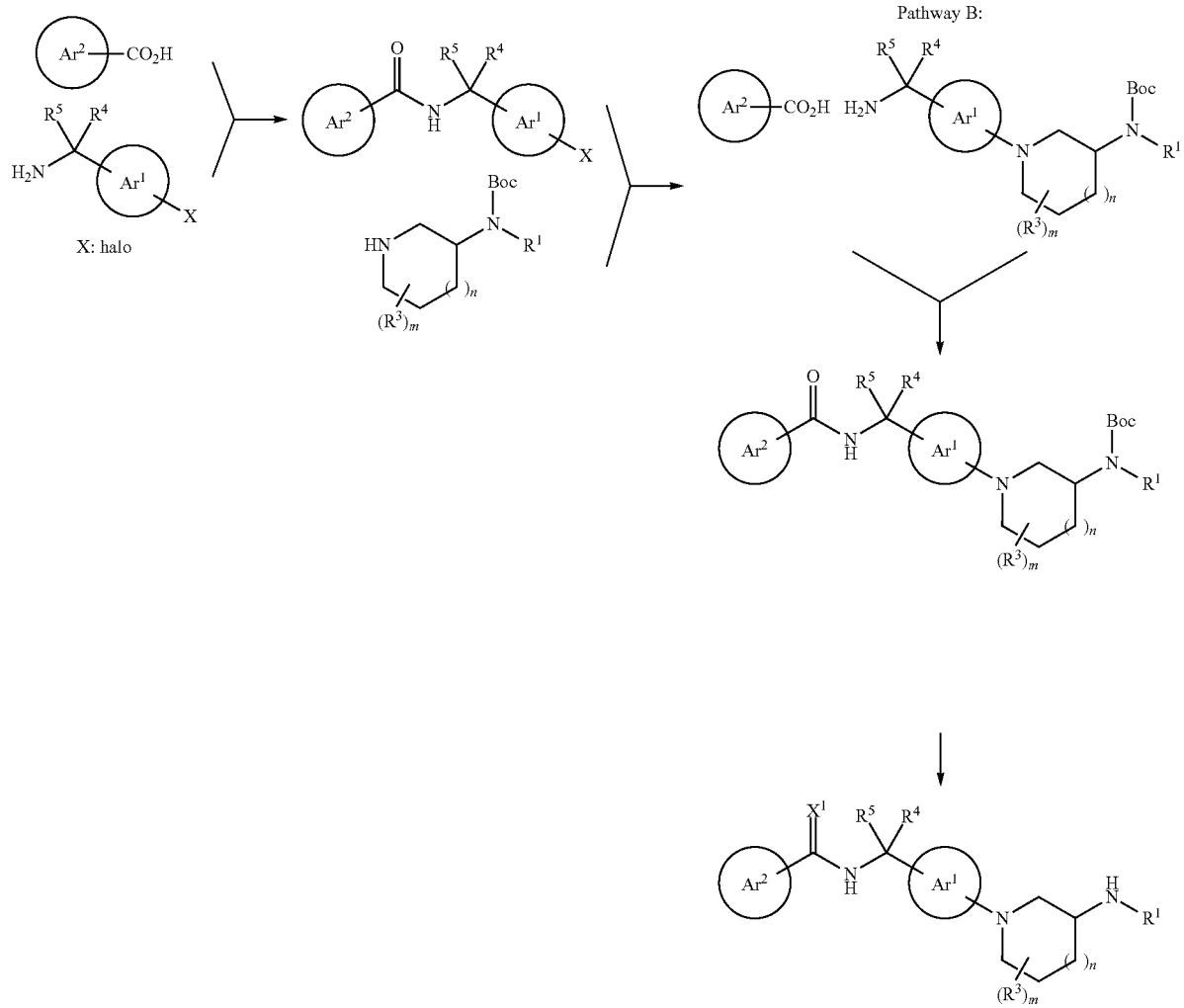

Scheme 3: General scheme to access compounds of the invention wherein L is a 1,3,4-thiadiazole or thiazole
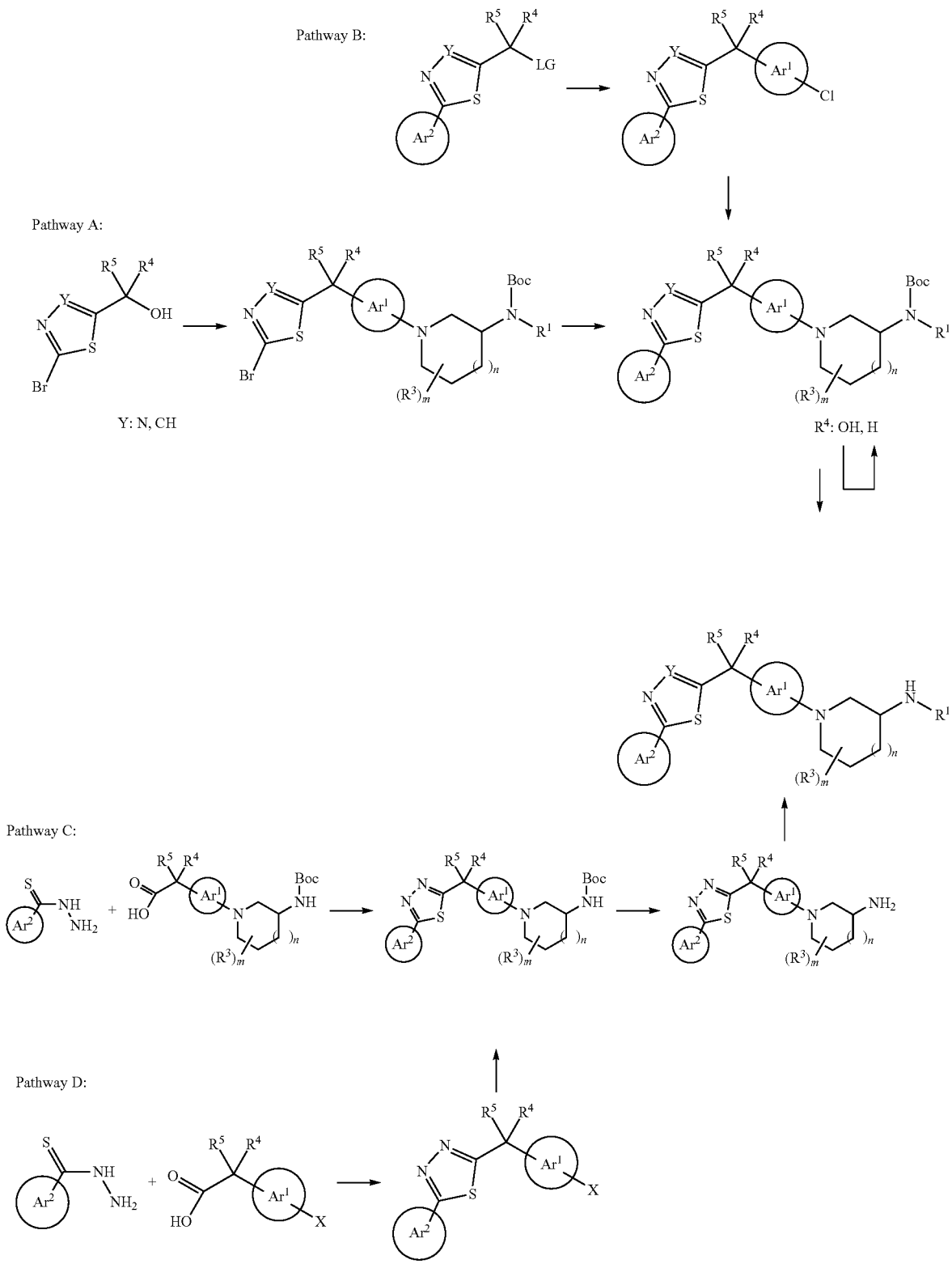

Scheme 4: General scheme to access compounds of the invention wherein L is an imidazole.
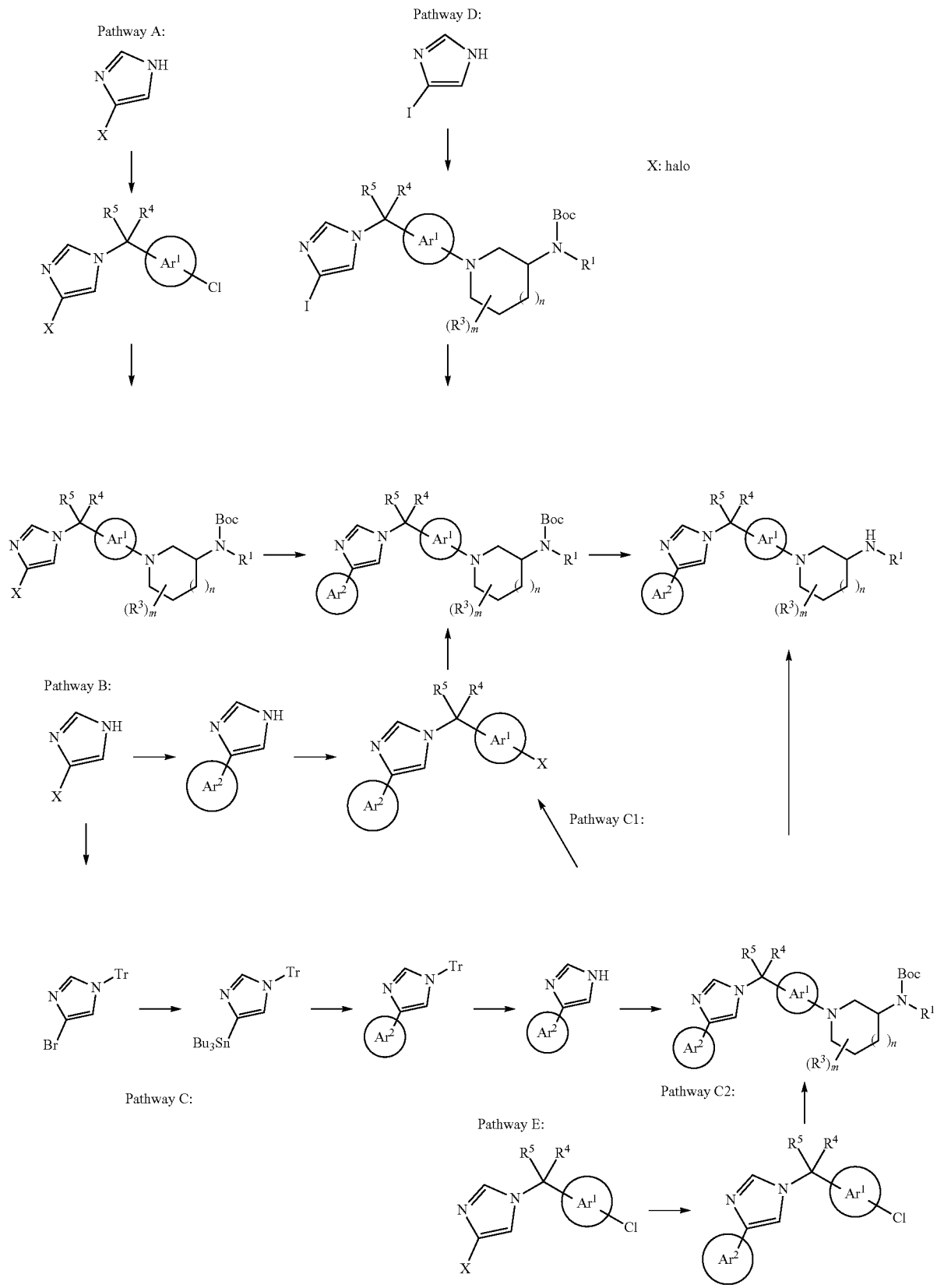

Scheme 5: General scheme to access compounds of the invention wherein L is a pyrazole.
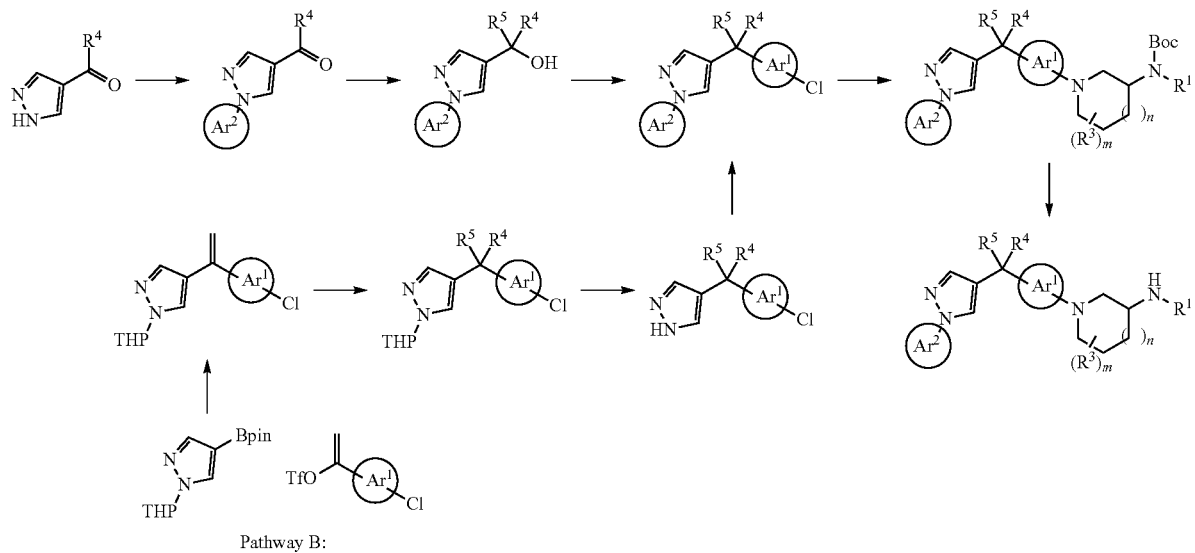

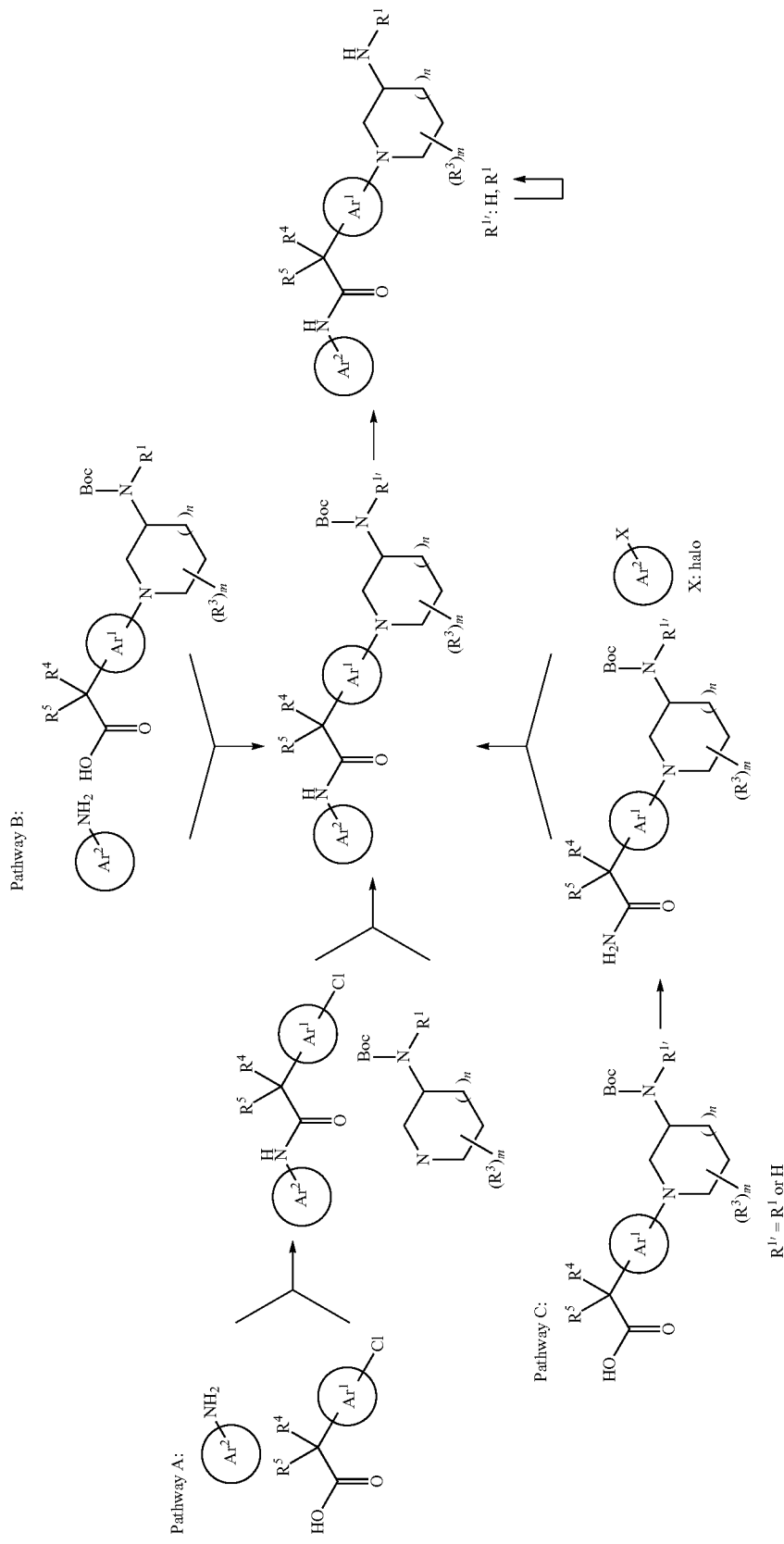
Scheme 6: General scheme to access compounds of the invention wherein L is the retroamide link.

General Procedures:
General Procedure A1: HCl Deprotection

To a solution of protected substrate (THP, Boc) (1.0 eq) in methanol (between 0.05 and 1.2 mol/L, typically between 0.10 and 0.20 mol/L) under argon atmosphere at 0° C. (ice bath) was added a solution of hydrogen chloride (4 N in 1,4-dioxane, between 10 and ~110 eq, typically 30 eq). The resulting solution was allowed to stir at rt. The reaction progress was monitored by HPLC-MS. After completion (between 0.25 to 20 h, typically 1-4 h), the reaction mixture was concentrated under reduced pressure. Residue was taken up in DCM and aqueous saturated $K_2CO_3$ solution. The layers were separated and the aqueous layer was extracted with DCM (2×). Organic layer was dried over $MgSO_4$, filtered, concentrated under reduced pressure to dryness, and crude residue may be purified using SCX-2 cartridge (eluent: MeOH, released with $MeOH/NH_3$ 7 N in MeOH (2/1)) or by reverse phase preparative HPLC.

General Procedure A2: TFA Deprotection

To a solution of protected substrate (THP, Boc, PMB) (1.0 eq) in anhydrous DCM (between 0.05 and 0.20 mol/L) under argon atmosphere at rt was added TFA (between 10 and 140 eq, typically between 25 and 40 eq) and resulting solution was stirred at rt. The reaction progress was monitored by HPLC-MS (when kinetic was slow, reaction was heated to 50° C.). After completion (typically <2 h), the reaction mixture was concentrated under reduced pressure to dryness and residue may be purified with SCX-2 cartridge (eluent: MeOH, released with $MeOH/NH_3$ 7 N in MeOH (2/1)) or by reverse phase flash chromatography (Biotage, C18 cartridge) using a gradient of MeCN in 10 mM ammonium bicarbonate buffer, or by reverse phase preparative HPLC.

General Procedure B: Click Chemistry

A solution of azide substrate (1.0 eq) and alkyne substrate (between 1.00 and 1.25 eq, typically 1.05 eq) in anhydrous DMF (between 0.1 to 0.3 mol/L, typically 0.25 mol/L) was degassed under stirring by bubbling argon for 15 min. Copper iodide (between 0.05 and 0.2 eq) was added and the resulting suspension was stirred at rt in the dark (flask was covered with an aluminum foil). The reaction progress was monitored by HPLC-MS. After completion (typically <4 h), the reaction mixture was diluted with EtOAc (10 to 100× DMF vol). The resulting solution was washed with water (5×5 to 50×DMF vol) then brine (5×5 to 50×DMF vol), dried over $MgSO_4$, then filtered. The solvent mixture was concentrated under reduced pressure to dryness to afford the product typically as a solid with high purity used as crude in the following step or purified by flash chromatography on silica gel.

General Procedure C: $S_NAr$

To a solution of electrophile (1.0 eq) in anhydrous NMP (between 0.1 and 1.3 mol/L, typically 0.3 to 0.9 mol/L) under an argon atmosphere at rt were added either triethylamine (between 2.0 to 4.3 eq, typically 3.0 eq) or diisopropylethylamine (between 2.0 to 3.6 eq, typically 3.0 eq) and the nucleophile (between 1.05 and 2.00 eq, typically 1.1 eq). The resulting mixture was stirred at 120° C. and monitored by HPLC-MS. When conversion did not increase anymore (typically 20 h), the reaction was allowed to cool to rt. The mixture was diluted in EtOAc (20 NMP vol), washed with brine (5×50 NMP vol), dried over $MgSO_4$, filtered and concentrated to give the crude product. The crude product was purified by flash chromatography on silica gel.

General Procedure D1: Alkyne-TMS Deprotection with $K_2CO_3$

To a solution of potassium bicarbonate (between 0.30 and 2.00 eq, typically 0.37 eq) in anhydrous methanol (between 0.1 and 0.5 mol/L, typically 0.3 mol/L) was added the intermediate to deprotect (1 eq). The mixture was stirred at rt and the reaction progress was monitored by HPLC-MS. After complete conversion (typically 30 min), the reaction mixture was concentrated under reduced pressure, and the crude product was purified by flash chromatography on silica gel.

General Procedure D2: Alkyne-TMS Deprotection with TBAF

To a suspension of crude ethynyl-trimethyl-silane substrate (1.0 eq) in anhydrous THF (0.1 mol/L) under an argon atmosphere was added TBAF (1.5 eq) at once at rt. The resulting solution was stirred at rt and reaction progress was monitored by HPLC-MS. After complete conversion (typically 30 min), the reaction mixture was diluted with water (6 THF vol) and EtOAc (25 THF vol) and layers were separated. The organic layer was washed with water (3×6 THF vol), dried over $MgSO_4$, filtered and the filtrate was concentrated under reduced pressure to dryness. The crude product may be purified by flash chromatography on silica gel.

General Procedure E1: Sonogashira Coupling

To a Schlenk tube under argon were added ethynyltrimethylsilane (between 1.1 and 1.4 eq, typically 1.2 eq), triethylamine (between 2.5 and 11.0 eq, typically between 2.5 and 3.0 eq) and halo-aromatic substrate (1.0 eq) in anhydrous DMF (between 0.15 and 0.40 mol/L, typically 0.15 mol/L). The mixture was degassed with argon (bubbling over 5 min). Then, dichlorobis(triphenylphosphine) palladium(II) (0.05 eq) and copper(I) iodide (0.05 eq) were added and the mixture was degassed with argon (3× vacuum/argon cycles). The reaction mixture was stirred at a temperature between rt and 70° C. and reaction progress was monitored by HPLC-MS. After complete conversion (typically 16-21 h), the reaction was cooled to rt. EtOAc was added (60 Vol based on halo-aromatic substrate) and washed with water (3×30 Vol), then brine (2×12 Vol). The organic layer was dried over $MgSO_4$, filtered and concentrated under reduced pressure. The crude product was purified by flash chromatography on silica gel.

Variant General Procedure E2:

To a Schlenk tube under argon were added ethynyltrimethylsilane (between 1.4 and 3.0 eq, typically 1.5 eq.), triethylamine (between 4.4 and 5.0 eq) and halo-aromatic substrate (1.0 eq) in anhydrous DMF (between 0.2 and 1.0 mol/L). The mixture was degassed with argon (bubbling over 5 min). Then, [1,1'-bis(diphenylphosphino)ferrocene] dichloropalladium(II) (between 0.04 and 0.10 eq) and copper(I) iodide (between 0.05 and 0.10 eq) were added and the mixture was degassed with argon (3× vacuum/argon cycles). The reaction mixture was stirred at a temperature between rt and 120° C. (typically 100° C.) and reaction progress was monitored by HPLC-MS. After complete conversion (typically 2 h), the reaction was cooled to rt, diluted with EtOAc (5×DMF Vol) and filtered through Celite. The filtrate was concentrated under reduced pressure and the crude product was purified by flash chromatography on silica gel.

Variant General Procedure E3:

To a Schlenk tube under argon were added halo-aromatic substrate (1.0 eq), tetrakis(triphenylphosphine)palladium (0.05 eq), copper(I) iodide (0.1 eq), DIEA (1.5 eq) in anhydrous DMF (0.25 mol/L). The mixture was degassed with argon (bubbling over 5 min). Ethynyltrimethylsilane (1.2 eq) was slowly added the reaction mixture was stirred at 60° C. Reaction progress was monitored by HPLC-MS. After complete conversion (typically 16 h), the reaction was cooled to rt, water was added (10 DMF vol). The mixture was extracted with EtOAc (2×7 DMF vol). The combined organic layers were washed with water (5×3 DMF vol), brine (2×DMF vol), dried over $MgSO_4$, filtered and concentrated under vacuum. The crude product may be purified by flash chromatography on silica gel.

General Procedure F: T3P Coupling Reaction

Acid (between 1.0 and 1.5 eq, typically 1.2 eq) was dissolved in anhydrous DMF (0.15 mol/L) under argon at rt and DIEA (between 1.75 and 4.6 eq, typically 2.4 eq) was added, followed by T3P (50% w/w solution in AcOEt) (1.3 eq). After 15 min stirring at rt, a solution of amine (between 1.0-1.5 eq, typically 1.0 eq) in anhydrous DMF (0.15 mol/L) was added dropwise to the suspension. Reaction progress was monitored by HPLC-MS. After complete conversion (typically <1 h), the reaction mixture was diluted with water (8 DMF vol) and extracted with EtOAc (3×12 DMF vol). The organic layers were merged, washed with brine (8 DMF vol), dried over $MgSO_4$, filtered and concentrated under reduced pressure. The crude product may be purified by flash chromatography on silica gel.

General Procedure G: One-Pot Debenzylation-Boc Protection

A solution of benzyl-amine (1.0 eq) in anhydrous ethanol (0.18 mol/L) under an argon atmosphere was degassed by bubbling argon under stirring for 15 min, then palladium on carbon dry (10 wt %) (0.2 eq) was added at rt, followed by di-tert-butyldicarbonate (1.5 eq) and the resulting solution was placed into pressure vessel and charged with 10 bars of hydrogen. The suspension was vigorously stirred at rt and reaction progress was monitored by HPLC-MS. After complete conversion (up to 3.5 days), the pressure was released and reaction mixture was degassed with argon. The solvent was then removed under reduced pressure and the obtained black mixture was purified by flash chromatography on silica gel.

General Procedure H1: Reductive Amination

To a mixture of aldehyde (or ketone) (between 1.0 and 6.5 eq, typically 1.1 eq) in anhydrous methanol (between 0.07 and 0.7 mol/L) under argon at 0° C. (ice bath) was added titanium(IV) isopropoxide (2.0 eq) dropwise. After 45 min at 0° C., an ice-cooled solution of amine (between 1.0 and 15.0 eq, typically 1.0 eq) in anhydrous methanol (between 0.02 and 0.25 mol/L) at 0° C. was added to the reaction mixture to afford a pale brown suspension. This suspension was allowed to stir at rt (ice bath removed) for 0.5 to 2.5 h and was cooled to 0° C. (ice bath) and sodium borohydride (between 1.2 and 2.2 eq, typically 2.0 eq) was added carefully and portionwise over 30 min (intensive bubbling observed with foam). The resulting foamy suspension was stirred at 0° C. for 25 min and then at rt to afford a yellow solution. After about 1 h, the reaction was quenched with an aqueous solution of $NH_4OH$ (2.5% in water) under vigorous stirring to afford a white suspension which was further stirred for 10 min. The suspension was then filtered and rinsed with methanol. The filtrate was concentrated under reduced pressure. The residue was taken up with DCM (10 MeOH vol) and water (3 MeOH vol). The layers were separated. The organic layer was washed with brine (3 MeOH vol), dried over $MgSO_4$, filtered and concentrated under reduced pressure to dryness to afford the desired product.

Variant General Procedure H2: Reductive Amination from Amine Salt

To a mixture of aldehyde or ketone (between 1.0 and 3.0 eq, typically 1.0 eq) in anhydrous methanol (between 0.1 and 1.0 mol/L, typically 0.7 mol/L) under argon at rt was added titanium(IV) isopropoxide (2.6 eq) dropwise. After 30-55 min at rt, amine (1.05 eq) was added (followed by DIEA (between 1.5 to 3.6 eq, typically 2.5 eq) if amine hydrochloride salt used). The suspension was stirred at rt for 0.5-2 h, and then cooled to 0° C. (ice bath). Sodium borohydride (between 1.2 and 2.7 eq, typically 2.0 eq) was added carefully and portionwise over 30 min (intensive bubbling observed with foam). The resulting foamy suspension was stirred at 0° C. for 15 min (complete conversion checked by HPLC-MS). The reaction mixture was poured into solution of $NH_4OH$ (1.5 N, 2-3 MeOH vol) under vigorous stirring at rt. Mixture was stirred at rt for 10 min, filtered and residue on the filter was rinsed with DCM (3×15-20 MeOH vol). Layers of the filtrate were separated and organic layer was dried over $MgSO_4$, filtered and concentrated under reduced pressure to dryness to afford the crude desired product.

General Procedure I: N-Debenzylation

To a solution of N-benzylated substrate (1.0 eq) in anhydrous ethanol (between 0.12 and 0.25 mol/L, typically 0.15 mol/L) under argon was added hydrazine monohydrate (between 2.0 and 4.0 eq, typically 2.2 eq). The mixture was degassed by bubbling argon (for 5 min). Then, palladium on activated carbon (10 wt. %) (between 0.08 and 0.20 eq) was added and reaction mixture was stirred at reflux. After full N-debenzylation monitored by HPLC-MS, the reaction was cooled to rt, filtered through Celite, rinsed with EtOH and DCM. The filtrate was concentrated under reduced pressure to dryness to give the desired product.

General Procedure J: Amine Protection

To a solution of amine (1.0 eq) in anhydrous DCM (between 0.15 and 0.40 mol/L, typically 0.15 mol/L) under argon at 0° C. (ice bath) was added triethylamine (between 2.0 and 6.0 eq, typically 2.0 eq). A solution of di-tert-butyl dicarbonate (between 1.1 and 6.0 eq, typically 1.2 eq) in anhydrous DCM (between 0.1 and 0.2 mol/L, typically 0.15 mol/L) was added over 15 min at 0° C. 5 min after the end of the addition, the ice bath was removed and the reaction was stirred at rt. After 16 h, water was added and the layers were separated. The organic layer was washed with NaOH 1 M, water, dried over $MgSO_4$, filtered and concentrated under reduced pressure to dryness to afford the crude product. The crude product was purified by flash chromatography on silica gel.

General Procedure K: Phthalimide Removal

To a solution of protected amine (1.0 eq) in ethanol (0.09 mol/L) was added hydrazine monohydrate (6.5 eq). The reaction mixture was stirred at 80° C. where a white suspension usually appeared within a few minutes at 80° C. After full conversion monitored by HPLC-MS (typically <1 h), the reaction was concentrated in vacuum. To the residue was added $Et_2O$ (2 EtOH vol) to the reaction mixture which was sonicated (2 min) and filtered. The solid was rinsed with $Et_2O$ (1.5 EtOH vol) and the filtrate was recovered and concentrated in vacuum to afford the crude product.

General Procedure L: Hydrogen Debenzylation or Azide Reduction

A solution of benzyl protected amine (1.0 eq) in anhydrous ethanol (0.05-0.02 mol/L) under Ar atmosphere was degassed by Ar bubbling under stirring for 15 min. Then palladium on activated carbon (10 wt % on dry carbon, 0.1-0.2 eq) was added and $H_2$ was bubbled in the resulting solution under stirring for 5 min then a balloon (about 3 bars) of hydrogen was placed and mixture was vigorously stirred at rt. After complete disappearance of starting material (monitored by HPLC-MS, typically 14 h), $H_2$ balloon was removed and Ar was bubbled in the reaction mixture during 5 min, then the mixture was filtered through a short pad of Celite, which was then rinsed with MeOH (3×EtOH vol/6). Filtrate was concentrated under reduced pressure to dryness to afford the desired amine to be used crude in next step.

General Procedure M: DPPA

To a sealed tube with a magnetic stir bar under argon were added alcohol substrate (1.0 eq) and a solution of diphenylphosphorylazide (between 1.3 and 3.3 eq, typically 1.3 eq) in anhydrous Toluene (0.2 mol/L). The solution was cooled to 0° C., in which 1,8-diazabicyclo[5.4.0]undec-7-ene (between 1.3 and 3.3 eq, typically 1.3 eq) was added dropwise. The reaction was allowed to warm to rt overnight. Water was added (10 Toluene vol) and the mixture was vigorously stirred. EtOAc was added (30 toluene vol) and the layers were separated. The organic layer was washed with water (20 toluene vol), HCl aq. (0.1 N, 10 toluene vol), brine (10 toluene vol), dried over $MgSO_4$, filtered and concentrated under reduced pressure. The crude product was purified by flash chromatography on silica gel.

General Procedure N: Azide Introduction

To a stirred solution of electrophile (1.0 eq) in anhydrous DMF (between 0.1 and 0.9 mol/L, typically 0.5 mol/L) under Ar atmosphere was added $NaN_3$ (between 1.0 and 3.0 eq, typically 1.4 eq) at rt and the reaction mixture was stirred at rt or heated at 70° C. The reaction progress was monitored by HPLC-MS. After completion (HPLC-MS monitoring), reaction mixture was diluted with EtOAc (50 Vol) and washed with water (5×3.7 Vol), and with brine (2×0.5 Vol), dried over $MgSO_4$, filtered and concentrated under reduced pressure to dryness to give the crude product.

General Procedure O1: N-alkylation with CMCF

N-nucleophile (1.0 eq) was suspended in anhydrous DCM (0.2 mol/L). Chloromethyl chloroformate (1.2 eq) was added followed by DMF (0.2 mol/L). The mixture was stirred at rt and the reaction progress was monitored by HPLC-MS. When conversion did not progress anymore (typically 10-16 h), ethyl acetate (10 DCM vol) was added and the organic layer was washed with saturated aqueous sodium bicarbonate solution (10 DCM vol) and brine (8 DCM vol), dried with $MgSO_4$, filtered and evaporated under vacuum to afford the crude product, which was used as such in the next step.

Variant General Procedure O2: N-alkylation with CECF

To a slurry of N-nucleophile (1.0 eq) in anhydrous DCE (0.3 mol/L) and DMF (0.3 mol/L) was added 1,4-diazabicyclo[2.2.2]octane (0.5 eq) at rt. To the slurry was added 1-chloroethyl chloroformate (1.5 eq) dropwise at rt. The resulting mixture was stirred at 60° C. under argon (typically overnight) and reaction progress was monitored by HPLC-MS. The reaction mixture was cooled to rt, and the suspension was filtered and rinsed with DCM (2 DCE vol). The filtrate was washed with water (2 DCE vol), aqueous saturated $NaHCO_3$ solution (2 DCE vol), brine (DMF vol), dried over $MgSO_4$, filtered and concentrated under vacuum to dryness to afford the crude product.

General Procedure P: Mesylate Formation

Alcohol substrate (1.0 eq) was treated with triethylamine (between 1.3 and 2.0 eq, typically, 1.3 eq) and methanesulfonyl chloride (between 1.1 and 1.6 eq, typically 1.2 eq) at 0° C. in DCM (between 0.2 and 0.5 mol/L, typically 0.25 mol/L), and then allowed to stir at rt for 1 h (reaction progress was monitored by TLC). The resulting reaction was quenched with aqueous saturated $NH_4Cl$ (25 DCM vol) and extracted with DCM (3×$NH_4Cl$ vol), then dried over $MgSO_4$ and concentrated under reduced pressure to afford the crude product, which was used as such in the next step.

General Procedure Q: Aldehyde Methylation

To a solution of aldehyde substrate (1.0 eq) in anhydrous THF (0.25 mol/L) at −78° C. was added dropwise methylmagnesium bromide solution (3 N in $Et_2O$, 1.2 eq). The reaction was stirred at −78° C. and reaction progress was monitored by HPLC-MS. After 1.5 h, the reaction was quenched with HCl 0.1 N (THF vol) and was stirred at rt for 5 min. Water (4 THF vol) was added and the reaction mixture was then extracted with EtOAc (2×8 THF vol). The combined organic layers were washed with water (6 THF vol), brine (4 THF vol), dried over $MgSO_4$, filtered and concentrated under reduced pressure. The crude product may be purified by flash chromatography on silica gel.

General Procedure R: Azide Reduction with TPP

A mixture of azide substrate (1.0 eq) and triphenylphosphine supported on resin (1.6 eq, 3 mmol/g) in anhydrous Methanol (0.06 mol/L) under Ar atmosphere was stirred under reflux and reaction progress was monitored by HPLC-MS. After typically 5 h, the mixture was allowed to reach rt and then filtered. The solid was rinsed with MeOH (4× half reaction vol) and the filtrate was concentrated under reduced pressure to dryness to afford crude product, which was used as such in the next step.

General Procedure S: N—C Coupling Reaction

Amino substrate (1.0 eq), Halo-aromatic substrate (1.0 eq), and cesium carbonate (1.5 eq) were added to anhydrous toluene (0.15 mol/L) under argon at rt. The reaction mixture was degassed with argon for 5 min, and rac-BINAP (0.1 eq) and palladium(II) acetate (0.1 eq) were added. The reaction mixture was stirred at 95-110° C. for 5-16 h (reaction progress monitored by HPLC-MS). The reaction mixture was then cooled to rt, filtered through Celite, rinsed with toluene (6 reaction vol) and concentrated under reduced pressure to dryness. The crude product was purified by silica gel flash chromatography.

General Procedure T: Mitsunobu Reaction

To a solution of alcohol substrate (1.15 eq) and pyridone substrate (1.00 eq) in anhydrous THF (0.1 mol/L), cooled to 0° C., were added triphenylphosphine (1.20 eq) and diisopropyl-azodicarboxylate (1.20 eq). Ice bath was removed and the reaction mixture was stirred at rt for 16 h. Reaction mixture was concentrated under reduced pressure and the crude residue was purified by reverse phase flash chromatography (Biotage, C18 cartridge) using a gradient of MeCN (0-100%) in 10 mM ammonium bicarbonate buffer.

General Procedure U: Suzuki Reaction

To a microwave vial, under nitrogen, halo-aromatic substrate (1.0 eq), 5-Methoxy-3-pyridineboronic acid pinacol ester (between 1.1 to 1.6 eq, typically 1.1 eq), potassium carbonate (2.5 eq), tetrakis(triphenylphosphine)palladium (0) (0.06 to 0.10 eq), dioxane/water (0.13 mol/L, 5/1) were successively added. The mixture was degassed with nitrogen for 15 min then was heated to 100° C. for 1 to 48 h. After cooling to rt, the mixture was purified by reverse phase flash chromatography (Biotage C18 cartridge, loaded in dioxane) using a gradient of MeCN (0-100%) in 10 mM ammonium bicarbonate buffer.

General Procedure V: Azide Formation

To a mixture of amino substrate (1.0 eq) and diethyl amine (5.0 eq) in anhydrous MeCN (0.15 mol/L) under Ar atmosphere was added dropwise (over 5 min) at rt a solution of 2-azido-1,3-dimethylimidazolinium hexafluorophosphate (between 1.2 to 1.5 eq, typically 1.5 eq) in anhydrous MeCN (0.35 mol/L). The reaction mixture was stirred at 30° C. and reaction progression was monitored by HPLC-MS. After 1 h, a solution of 2-azido-1,3-dimethylimidazolinium hexafluorophosphate (between 0.5 to 0.8 eq, typically 0.7 eq) in anhydrous MeCN (0.35 mol/L) was added and complete conversion was reached 15 min later. Reaction mixture was allowed to cool to rt (oil bath removed) and was diluted with EtOAc (12 MeCN vol), then washed with NaHCO$_3$ saturated solution (2×12 MeCN vol), dried over MgSO$_4$, filtered and filtrate was concentrated under reduced pressure to dryness.

General Procedure W: Reductive Amination with Ammonia

To a solution of ketone (1.0 eq) in anhydrous methanol (between 0.1 to 0.3 mol/L, typically 0.3 mol/L) were added ammonium acetic acid salt (between 5.0 to 10.0 eq, typically 10 eq) and sodium cyanoborohydride (5.0 eq). The mixture was stirred at 90° C. and reaction progress was monitored by HPLC-MS. After 1 h, reaction mixture was quenched with water (5 mL) and extracted with DCM (3×20 mL). Organic layers were merged, dried over MgSO$_4$, filtered and concentrated under reduced pressure to dryness.

General Procedure X: One-Pot Alkyne Deprotection/Click Reaction

To trimethylsilyl alkyne substrate −181-02 (between 1.0 to 1.7 eq, typically 1.1 eq) in solution in DMF (between 0.15 to 0.19 mol/L, typically 0.15 mol/L) were added azide substrate (1.0 eq) and CuF$_2$ (between 1.8 to 2.0 eq, typically 2.0 eq). The reaction mixture was purged with N$_2$ during 5 min then stirred at 60° C. for 18 h. The mixture diluted in water (15 DMF vol) and extracted with DCM (3×5 DMF vol). The organic phase was dried over MgSO$_4$, filtered and concentrated under reduce pressure. Residue was purified by reverse phase flash chromatography on a C18 cartridge.

General Procedure Y: RuPhos C—N Cross Coupling

To a mixture of amino substrate (1.05 eq), halo-(hetero)aromatic substrate (1.00 eq), RuPhos Pd G4 (0.06 to 0.20 eq, typically 0.06 eq), RuPhos (0.08 to 0.15 eq, typically 0.08 eq) and cesium carbonate (3.00 eq) under Ar atmosphere was added anhydrous, degassed tert-amyl alcohol (0.3 mol/L). The reaction mixture was stirred at 80° C. for 19 h. The reaction was cooled to rt, diluted with DCM (10 Vol) and filtered over Celite. The Celite was rinsed with DCM (30 Vol) and the filtrate was concentrated under reduced pressure and purified to afford the desired product.

General Procedure Z: Hydrogen Deshydroxylation

A solution of hydroxyl (hetero)benzyl substrate (1.0 eq) in anhydrous methanol (0.05 mol/L) was evacuated and backfilled with Ar (3×). 4-methylbenzenesulfonic acid hydrate (1.5 to 2.5 eq, preferably 1.6 eq) and palladium on activated carbon (10 wt % on dry carbon, 0.3 eq) was added and the reaction mixture was evacuated and backfilled with hydrogen and vigorously stirred at rt for 22-40 h. The reaction mixture was evacuated and backfilled with ar, then filtered through Celite, rinsed with MeOH (6 reaction volumes) and concentrated under reduced pressure. The residue was treated with saturated aqueous NaHCO$_3$ solution (4 reaction volumes) and extracted with DCM (3×4 reaction volumes). The organic layers were merged, dried over MgSO$_4$, filtered and concentrated under reduced pressure. Crude product was typically purified using by an automated flash chromatography system (dryload in Celite, 0 to 100% EtOAc in Heptane) to afford the desired deshydroxylated product.

General Procedure AA: Ullmann Cross-Coupling

In a sealed tube, a mixture of bromo-aryl (1 eq), L(−)-proline (0.2 eq), amino substrate (1.3 to 6.0 eq, typically 1.5 eq. added up to 4$^{th}$ time when volatile), potassium carbonate (1.5 to 7.0 eq, typically 1.6 eq), copper(I) iodide (0.1 eq) in anhydrous and degassed DMSO (1 mol/L) was stirred and heated at 90° C. for typically 18 h. When reaction completion was not reached, amino substrate was added and reaction mixture was stirred for additional 16 h at 90° C. Additional reagent addition could be applied up to 4 times. The cooled mixture was then partitioned between water (10 DMSO vol) and ethyl acetate (10 DMSO vol). The organic layer was separated, and the aqueous layer was extracted with ethyl acetate (10 DMSO vol). The combined organic layers were washed with water (10 DMSO vol), brine (10 DMSO vol), dried over MgSO$_4$, filtered and concentrated under reduced pressure to give the crude product as a brown foam. The crude product was purified by flash automated chromatography to afford the desired product.

General Procedure AB: Buchwald Cross-Coupling Using Xantphos

To a mixture of Pd$_2$(dba)$_3$ (between 0.5 to 0.13 eq, typically 1.0 eq), Xantphos (between 0.15 to 0.25 eq, typically 0.2 eq), cesium carbonate (between 2.0 to 2.6 eq, typically 2.0 eq), and halo substrate (between 0.8 to 1.5 eq, typically 1.5 eq) was added at rt a solution of carboxamide substrate (1.0 eq) in anhydrous 1,4-dioxane (between 0.10 to 0.13 mol/L, typically 0.12 mol/L) (previously degassed with argon). The reaction mixture was sonicated 15 sec and stirred at 80-100° C. (typically 100° C., pre-heated oil bath) for 1.5-21.0 h. The reaction mixture was cooled to rt and diluted with EtOAc (5 Vol) and filtered over Celite. The Celite was rinsed with EtOAc (10 Vol). The filtrate was concentrated in vacuo to give the crude product, which was purified by an automated normal or reverse flash chromatography system to afford the desired product.

General Procedure AC: Carboxamide Formation

To a mixture of carboxylic acid substrate (potentially as hydrochloride salt) (1.0 eq), ammonium chloride (4.0 to 6.0 eq), HATU (1.0 to 1.4 eq) in anhydrous DMF (4 Vol) under Ar atmosphere at rt was added DIEA (1.0 to 2.5 eq) to afford a suspension which was stirred at rt for 0.33 to 2.25 h, then extra HATU (based on LC conversion) and extra DIEA (idem) could be added and the reaction mixture was stirred for up to an extra 3 h. The reaction mixture was diluted with EtOAc (15 to 100 Vol) and washed with NaHCO$_3$ saturated aqueous solution (2×40 Vol), brine (40 Vol) and dried over MgSO$_4$, filtered. The filtrate was concentrated under reduced pressure to dryness to afford a crude oil, which was purified by an automated normal or reverse phase flash chromatography system to afford the desired product.

General Procedure AD: Cyano Hydrolysis to Acid

To a solution of cyano intermediate (1 eq) in ethanol (9 Vol) was added a solution of sodium hydroxide (4.0 to 4.6 eq) in water (4 Vol) at rt and the rxn mixture was stirred at 80° C. for 1.0 to 3 h. The reaction mixture was cooled to rt, then concentrated under reduced pressure to dryness. The residue was solubilized in water (50 Vol), pH was acidified to pH ~2 by addition of HCl 1M (some precipitation observed) and the mixture was extracted with DCM (3×50 Vol). The combined organic layers were dried over MgSO4, filtered and the filtrate was concentrated under reduced pressure to dryness to afford crude acid, potentially as HCl salt.

General Procedure AE: Reductive Amination with Alkyl-Aldehyde

To a solution of aldehyde or ketone (1.04 to 4.80 eq, typically 1.30 eq) and amine substrate (1.00 eq) in anhydrous methanol (0.1 mol/L) under Ar was added acetic acid (1.00 eq). After 1.5 h stirring at rt, sodium cyanoborohydride (5.6 to 8.2 eq) was added in one portion and the mixture was stirred at rt for 1.5 h. Reaction mixture was then quenched with saturated aqueous NaHCO$_3$ solution (20 Vol) and extracted with DCM (3×20 Vol). Organic layers were merged, dried over MgSO4, filtered and concentrated under reduced pressure to dryness.

Syntheses of the Compound of the Invention:

Compound 1: (3R)—N-(cyclobutylmethyl)-1-[6-[[4-(6-methoxy-1H-indazol-4-yl)triazol-1-yl]methyl]pyridazin-3-yl]piperidin-3-amine was Obtained Using General Scheme 1 Pathway B Synthesis of tert-butyl (R)-(cyclobutylmethyl)(piperidin-3-yl)carbamate IM3: Stage 1: General Procedure H1 was used from cyclobutanecarboxaldehyde and (R)-1-benzylpiperidin-3-amine to afford (R)-1-benzyl-N-(cyclobutylmethyl)piperidin-3-amine IM1: 27.05 g, 72% yield, P=71% (gradient A), retention time=1.9 min, (M+H)$^+$: 259. Stage 2: General Procedure J was used from IM1 to afford tert-butyl (R)-(1-benzylpiperidin-3-yl)(cyclobutylmethyl)carbamate IM2 as colourless oil: 25.76 g, 96% yield, P=100%, retention time=2.5 min (gradient A), (M+H)$^+$: 359. Stage 3: General Procedure L was used from IM2 to afford tert-butyl (R)-(cyclobutylmethyl)(piperidin-3-yl)carbamate IM3 as colourless oil: 3.5 g, 99% yield.

Synthesis of 3-(azidomethyl)-6-chloropyridazine IM5: Stage 1: To a stirred solution (dark brown) of 3-chloro-6-methylpyridazine (25 g, 190.57 mmol) in chloroform (953 mL) under argon atmosphere at 60° C. was added trichloroisocyanuric acid (22.17 g, 95.39 mmol) at 60° C. The resulting mixture was stirred at this temperature and the reaction was monitored by HPLC-MS. After completion (18 h), reaction mixture was allowed to reach rt, then stirred at 0° C. (ice bath) for 10 min, then suspension was filtered through a short pad of Celite which was rinsed with DCM (800 mL). Resulting yellow filtrate was concentrated under reduced pressure to dryness to give 21.7 g of a dark brown crude solid, which was purified by silica gel flash chromatography (n-heptane/EtOAc: 8/2) to afford 3-chloro-6-(chloromethyl)pyridazine IM4 (R$_f$=0.3, n-heptane/EtOAC: 1/1) as pinky crystalline solid: 14.58 g, 47% yield, P>95%, retention time=2.5 min (gradient A), (M+H)$^+$: 163. Stage 2: General Procedure N was used from IM4 to afford 3-(azidomethyl)-6-chloropyridazine IM5 as an off-white solid: 9.19 g, 99% yield, P=97%, retention time=2.2 min (gradient A), (M+H)$^+$: 170.

Synthesis of 4-ethynyl-6-methoxy-1-(tetrahydro-2H-pyran-2-yl)-1H-indazole IM8: Stage 1: To a stirred solution of 4-bromo-6-methoxy-1H-indazole (2.60 g, 10.53 mmol) in anhydrous THF (105 mL) was added 4-methylbenzenesulfonic acid hydrate (102 mg, 0.53 mmol) and 3,4-dihydro-2H-pyran (3.66 g, 42.2 mmol) at rt. The reaction mixture was degassed by bubbling with argon and refluxed. Reaction progress was monitored by HPLC-MS for 18 h, and the solvent was then removed under reduced pressure. The residue (6.2 g) was purified by flash chromatography on silica gel (n-Heptane/EtOAc: 1/0 to 1/1) to afford 4-bromo-6-methoxy-1-tetrahydropyran-2-yl-indazole IM6 (R$_f$=0.7, n-Heptane/EtOAc: 1/1) as white solid: 1.6 g, 46% yield, P=95%, retention time=3.3 min (gradient A), (M+H)$^+$: 311/313. Stage 2: General Procedure E1 was used from IM6 to afford 6-methoxy-1-(tetrahydro-2H-pyran-2-yl)-4-((trimethylsilyl)ethynyl)-1H-indazole IM7 as orange oil: 1.60 g, 91% yield, P=92%, retention time=3.4 min (gradient A), (M+H)$^+$: 329. Stage 3: General Procedure D1 was used IM7 to afford 4-ethynyl-6-methoxy-1-(tetrahydro-2H-pyran-2-yl)-1H-indazole IM8 as yellow oil: 0.79 g, 63% yield, P=90%, retention time=3.1 min (gradient A), (M+H)$^+$: 257.

Synthesis of 4-(1-(((6-chloropyridazin-3-yl)methyl)-1H-1,2,3-triazol-4-yl)-6-methoxy-1-(tetrahydro-2H-pyran-2-yl)-1H-indazole IM9: General Procedure B was used between IM5 and IM8 to afford 4-(1-(((6-chloropyridazin-3-yl)methyl)-1H-1,2,3-triazol-4-yl)-6-methoxy-1-(tetrahydro-2H-pyran-2-yl)-1H-indazole IM9 as an off-white solid: 9.64 g, 92% yield, P=96%, retention time=4.2 min (gradient A), (M+H)$^+$: 426.

Synthesis of (3R)—N-(cyclobutylmethyl)-1-[6-[[4-(6-methoxy-1H-indazol-4-yl)triazol-1-yl]methyl]pyridazin-3-yl]piperidin-3-amine (compound 1): Stage 1: General Procedure C was used between IM3 and IM9 to afford tert-butyl (cyclobutylmethyl)((3R)-1-(6-((4-(6-methoxy-1-(tetrahydro-2H-pyran-2-yl)-1H-indazol-4-yl)-1H-1,2,3-triazol-1-yl)methyl)pyridazin-3-yl)piperidin-3-yl)carbamate IM10 as a beige solid: 10.01 g, 68% yield, P=97%, retention time=4.6 min (gradient B), (M+H)$^+$: 658. Stage 2: General Procedure A1 was used from IM10 to afford compound 1 as a white powder: 5.17 g, 73% yield, P=100%, retention time=2.8 min (gradient B), (M+H)$^+$: 474. Chiral HPLC (IB, TBME/MEOH/DEA: 85/15/0.1%, flow rate: 1 mL/min): P=100%. $^1$H NMR (300 MHz, CD$_3$OD) δ 8.58 (s, 1H), 8.40 (s, 1H), 7.43 (d, J=9.4 Hz, 1H), 7.32-7.18 (m, 2H), 6.95 (s, 1H), 5.80 (s, 2H), 4.38 (dd, J=13.0, 3.7 Hz, 1H), 4.08 (d, J=13.6 Hz, 1H), 3.89 (s, 3H), 3.17-3.02 (m, 1H), 3.02-2.87 (m, 1H), 2.75-2.59 (m, 3H), 2.52-2.37 (m, 1H), 2.14-1.97 (m, 4H), 1.97-1.38 (m, 6H), 2H exchanged with CD$_3$OD. $^{13}$C-NMR (CD$_3$OD): δ 161.0, 160.7, 149.1, 147.5, 143.6, 134.8, 129.1, 125.0, 124.0, 116.0, 115.4, 111.5, 92.0, 56.1, 54.6, 54.2, 53.4, 50.3, 49.9, 49.6, 19.3, 48.7, 48.4, 48.2, 46.5, 36.1, 31.2, 23.3, 24.2, 19.5.

Compound 2: (R)—N-((6-(3-((cyclobutylmethyl)amino)piperidin-1-yl)pyridazin-3-yl)methyl)-4-oxo-4H-pyrido[1,2-a]pyrimidine-2-carboxamide was Obtained Using General Scheme 2 Pathway A Stage 1: 4-oxopyrido[1,2-a]pyrimidine-2-carboxylic acid hydrochloride (130 mg, 0.57 mmol) was dissolved in anhydrous DMF (4 mL) under argon at rt. DIEA (250 µL, 1.43 mmol) was then added followed by HATU (220 mg, 0.58 mmol). After 30 min at rt, a solution of (6-chloropyridazin-3-yl)methanamine (102 mg, 0.71 mmol) in anhydrous DMF (2 mL) was added dropwise to the solution. Reaction progress was monitored by HPLC-MS and conversion was stopped after 1 h. HATU (115 mg, 0.30 mmol) was added to the reaction mixture and complete conversion was reached 30 min later. Reaction mixture was diluted with water (20 mL) and extracted with EtOAc (3×20 mL). Organics layer were merged, washed with water (2×20 mL) and brine (2×10 mL). Resulting organic layer was dried over MgSO$_4$, filtered and concentrated under reduced pressure to dryness to afford 352 mg of crude yellow solid. The residue was purified by flash chromatography on silica gel (DCM/MeOH: I/O to 98/2) to afford N-((6-chloropyridazin-3-yl)methyl)-4-oxo-4H-pyrido[1,2-a]pyrimidine-2-carboxamide IM11 (R$_f$=0.25, DCM/MeOH: 98/2) as an off-white solid: 71 mg, 37% yield, P=98%, retention time=2.9 min (gradient B), (M+H)+: 316/318.

Stage 2: General Procedure C was used between IM3 and IM11 to afford tert-butyl (R)-(cyclobutylmethyl)(1-(6-((4-oxo-4H-pyrido[1,2-a]pyrimidine-2-carboxamido)methyl)pyridazin-3-yl)piperidin-3-yl)carbamate IM12 as a light yellow solid: 78 mg, 66% yield, P=98%, retention time=3.9 min (gradient B), (M+H)$^+$: 548.

Stage 3: General Procedure A1 was used from IM12 to afford compound 2 dihydrochloride salt as a greenish powder: 80 mg, 100% yield, P=98%, retention time=2.5 min (gradient B), (M+H)$^+$: 448.

The product was further purified by reverse phase preparative HPLC purification (Waters XBridge C18 5 µm 19×100 mm). Solution "A" was adjusted to pH=9 with NH₄OH. Gradient used: increased linearly from 15 to 50% solution "B" over 5.0 min, then increased linearly from 50 to 85% solution "B" over 1.5 min, returned to initial conditions over 1.0 min. Flow Rate: 15 ml/min. P=100%. Chiral HPLC (IA, TBME/MEOH/DEA: 85/15/0.1%, flow rate: 1 mL/min): 99.7% purity at 254 nm. $^1$H NMR (300 MHz, CDCl₃) δ 9.05 (d, J=8.1 Hz, 1H), 8.81 (bs, 1H), 7.82-7.74 (m, 1H), 7.69 (d, J=8.1 Hz, 1H), 7.27 (d, J=10.8 Hz, 1H), 7.26 (s, 1H), 7.18 (td, J=6.8, 1.5 Hz, 1H), 6.90 (d, J=10.8 Hz, 1H), 4.77 (d, J=5.9 Hz, 2H), 4.34 (dd, J=12.8, 3.9 Hz, 1H), 4.05 (d, J=13.2 Hz, 1H), 3.13-3.01 (m, 1H), 2.86 (dd, J=12.7, 9.2 Hz, 1H), 2.77-2.60 (m, 3H), 2.49-2.33 (m, 1H), 2.11-1.94 (m, 2H), 1.93-1.74 (m, 2H), 1.60 (q, J=9.4 Hz, 5H), 1.48-1.30 (m, 1H), 1H exchanged with solvent.

Compound 3: (R)—N-(cyclobutylmethyl)-1-(6-((4-(imidazo[1,5-a]pyridin-8-yl)-1H-1,2,3-triazol-1-yl)methyl)pyridazin-3-yl)piperidin-3-amine was obtained Using General Scheme 1 Pathway B Stage 1: General Procedure E2 was used from 8-bromo-imidazo[1,5-a]pyridine to afford 8-((trimethylsilyl)ethynyl)imidazo[1,5-a]pyridine IM13 as yellow oil: 105 mg, 66% yield, P=95%, retention time=1.4 min (gradient A), (M+H)⁺: 215.

Stage 2: General Procedure D1 was used from IM13 to afford 8-ethynylimidazo[1,5-a]pyridine IM14 as a brown solid: 70 mg, 95% yield, P=90%, retention time=1.6 min (gradient A), (M+H)⁺: 143.

Stage 3: General Procedure B was used between IM5 and IM14 to afford 8-(1-((6-chloropyridazin-3-yl)methyl)-1H-1,2,3-triazol-4-yl)imidazo[1,5-a]pyridine IM15 as a brown solid: 208 mg, 99% yield, P=68%, retention time=2.0 min (gradient A), (M+H)⁺: 311/313.

Stage 4: General Procedure C was used between IM3 and IM15 to afford tert-butyl (R)-(cyclobutylmethyl)(1-(6-((4-(imidazo[1,5-a]pyridin-8-yl)-1H-1,2,3-triazol-1-yl)methyl)pyridazin-3-yl)piperidin-3-yl) carbamate IM16 as a yellow solid: 124 mg, 40% yield, P=90%, retention time=2.4 min (gradient A), (M+H)⁺: 544.

Stage 5: General Procedure A1 was used from IM16 to afford crude compound 3 as brown oil: 109 mg, 99% yield, P=87%, retention time=2.4 min (gradient B), (M+H)⁺: 444.

The product was further purified by reverse phase preparative HPLC purification (Waters XBridge C18 5 μm 19×100 mm). Solution "A" was ammonium bicarbonate 0.04 M. Gradient used: increased linearly from 10 to 45% solution "B" over 5.5 min, then increased linearly to 90% solution "B" over 0.5 min, held at 90% during 0.2 min, returned to initial conditions over 0.3 min. Flow Rate: 20 mL/min. P=100%. Chiral HPLC (IA, TBME/MeOH/DEA: 85/15/0.1%, flow rate: 1 mL/min): 99.7% purity at 254 nm. $^1$H NMR (300 MHz, DMSO-d6) δ 8.88 (s, 1H), 8.46 (s, 1H), 8.36 (d, J=6.9 Hz, 1H), 7.89 (s, 1H), 7.42 (d, J=9.5 Hz, 1H), 7.38 (d, J=6.9 Hz, 1H), 7.27 (d, J=9.5 Hz, 1H), 6.77 (t, J=6.9 Hz, 1H), 5.80 (s, 2H), 4.29 (d, J=13.0 Hz, 1H), 4.09 (d, J=13.5 Hz, 1H), 3.11-2.94 (m, 1H), 2.77 (dd, J=12.9, 9.3 Hz, 1H), 2.64-2.44 (m, 3H), 2.39-2.23 (m, 1H), 2.03-1.86 (m, 4H), 1.87-1.53 (m, 4H), 1.49-1.20 (m, 2H), 1H exchanged with CD₃OD.

Compound 4: (R)—N-((6-(3-((cyclobutylmethyl)amino)piperidin-1-yl)pyridazin-3-yl)methyl)-5-methoxynicotinamide was Obtained Using General Scheme 2 Pathway A Stage 1: General Procedure F was used between 5-methoxy-nicotinic acid and 6-chloropyridazin-3-yl)methanamine to afford N-[(6-chloropyridazin-3-yl)methyl]-5-methoxy-pyridine-3-carboxamide IM17 as a yellow solid: 56 mg, 59% yield, P=96%, retention time=2.0 min (gradient A), (M+H)⁺: 279/281.

Stage 2: General Procedure C was used between IM3 and IM17 to afford tert-butyl (R)-(cyclobutylmethyl)(1-(6-((5-methoxynicotinamido)methyl)pyridazin-3-yl)piperidin-3-yl) carbamate IM18 as a light yellow solid: 65 mg, 59% yield, P=89%, retention time=2.4 min (gradient A), (M+H)⁺: 511.

Stage 3: General Procedure A1 was used from IM18 to afford crude compound 4 as brown oil: 60 mg, 84% yield, P=82%, retention time=2.3 min (gradient B), (M+H)⁺: 411.

The product was further purified by reverse phase preparative HPLC purification (Waters XBridge C18 5 μm 19×100 mm). Solution "A" was adjusted to pH=9 with NH₄OH. Gradient used: increased linearly from 15 to 50% solution "B" over 5.0 min, then increased linearly from 50 to 85% solution "B" over 1.5 min, returned to initial conditions over 1.0 min. Flow Rate: 15 mL/min. P=100%, $^1$H NMR (300 MHz, CD₃OD) δ 8.61 (s, 1H), 8.38 (s, 1H), 7.83 (s, 1H), 7.44 (d, J=9.5 Hz, 1H), 7.24 (d, J=9.5 Hz, 1H), 4.71 (s, 2H), 4.38 (d, J=12.0 Hz, 1H), 4.09 (d, J=13.3 Hz, 1H), 3.93 (s, 3H), 3.07 (t, J=11.9 Hz, 1H), 2.89 (dd, J=12.7, 9.6 Hz, 1H), 2.80-2.58 (m, 3H), 2.56-2.37 (m, 1H), 2.17-1.99 (m, 3H), 2.00-1.76 (m, 3H), 1.75-1.37 (m, 4H), 2H exchanged with CD₃OD.

Compound 5: (R)—N-((6-(3-((cyclobutylmethyl)amino)piperidin-1-yl)pyridazin-3-yl)methyl)-6-methoxy-1H-indazole-4-carboxamide was Obtained Using General Scheme 2 Pathway A Stage 1: To a mixture of IM8 (100 mg, 0.38 mmol) and FeCl₃ (3.2 mg, 0.02 mmol) were added tert-butyl hydroperoxide (70% solution in water, 0.32 mL, 2.31 mmol) and Water (0.2 mL). After 1 h, sodium hydroxide (62 mg, 1.55 mmol) was added. The reaction mixture was then heated at 80° C. and reaction progress was monitored by HPLC-MS. After 5 h, conversion did not evolve anymore (~ 50%) and reaction mixture was cooled to rt, diluted with water (5 mL) and acidified with HCl 1N to pH ~3-4. EtOAc (20 mL) was added and layers were separated. Aqueous layer was extracted with EtOAc (2×10 mL). Organics layer were merged, washed with brine (10 mL), dried over MgSO₄, filtered and concentrated under reduced pressure to dryness to afford 130 mg of yellow oil. The residue was purified by flash chromatography on silica gel (EtOAc/MeOH: 1/0 to 95/5) to afford 6-methoxy-1-(tetrahydro-2H-pyran-2-yl)-1H-indazole-4-carboxylic acid IM19 (R$_f$~0.7, EtOAc/MeOH: 9/1) as yellow oil: 70 mg, 31% yield, P=47%, retention time=2.5 min (gradient A), (M+H)⁺: 277.

Stage 2: General Procedure F was used between IM19 and IM5 to afford N-((6-chloropyridazin-3-yl)methyl)-6-methoxy-1-(tetrahydro-2H-pyran-2-yl)-1H-indazole-4-carboxamide IM20 as yellow oil: 34 mg, 60% yield, P=80%, retention time=3.8 min (gradient A), (M+H)⁺: 402/404.

Stage 3: General Procedure C was used between IM3 and IM20 to afford tert-butyl (cyclobutylmethyl)((3R)-1-(6-((6-methoxy-1-(tetrahydro-2H-pyran-2-yl)-1H-indazole-4-carboxamido)methyl)pyridazin-3-yl)piperidin-3-yl)carbamate IM21 as a light brown foam: 26 mg, 41% yield, P=85%, retention time=2.6 min (gradient A), (M+H)⁺: 634.

Stage 4: General Procedure A2 was used from IM21 to afford crude compound 5 as brown oil: 25 mg, 65% yield, P=72%, retention time=2.5 min (gradient B), (M+H)⁺: 450.

The product was purified by reverse phase preparative HPLC purification (Waters XBridge C18 5 μm 19×100 mm). Gradient used: increased linearly from 25 to 35% solution "B" over 4.0 min, then increased linearly to 40% solution "B" over 1.0 min, then increased linearly to 85% solution "B" over 1.5 min and returned to initial conditions over 1.0 min. Flow Rate: 15 mL/min. P=98%. $^1$H NMR (300 MHz, CDCl$_3$): δ 8.37 (s, 1H), 7.69 (bs, 1H), 7.34-7.20 (m, 2H), 7.00-6.91 (m, 2H), 4.82 (d, J=5.0 Hz, 2H), 4.33 (d, J=12.9 Hz, 1H), 4.05 (d, J=13.3 Hz, 1H), 3.86 (s, 3H), 3.19-3.06 (m, 1H), 3.03-2.92 (m, 1H), 2.79-2.65 (m, 2H), 2.54-2.38 (m, 1H), 2.13-1.96 (m, 2H), 1.95-1.75 (m, 3H), 1.73-1.41 (m, 5H).

Compound 6: 4-(1-((6-(4,4-dimethyl-[1,3'-bipiperidin]-1'-yl)pyridazin-3-yl)methyl)-1H-1,2,3-triazol-4-yl)-6-methoxy-1H-indazole was Obtained Using General Scheme 1 Pathway B Stage 1: General Procedure H$_2$ was used between 1-benzylpiperidin-3-one and 4,4-dimethylpiperidine hydrochloride to afford 1-(1-benzyl-3-piperidyl)-4,4-dimethylpiperidine IM22 as orange oil: 128 mg, 47% yield, P=80%, retention time=2.0 min (gradient A), (M+H)$^+$: 287.

Stage 2: General Procedure G was used from IM22 to afford tert-butyl 4,4-dimethyl-[1,3'-bipiperidine]-1'-carboxylate IM23 as yellow oil: 68 mg, 73% yield, retention time=2.3 min (gradient A), (M+H)$^+$: 297.

Stage 3: General Procedure A1 was used from IM23 to afford crude 4,4-dimethyl-1,3'-bipiperidine dihydrochloride IM24 (no work up applied) as yellow oil: 62 mg, 100% yield.

Stage 4: General Procedure C was used between IM24 and IM9 to afford 4-(1-((6-(4,4-dimethyl-[1,3'-bipiperidin]-1'-yl)pyridazin-3-yl)methyl)-1H-1,2,3-triazol-4-yl)-6-methoxy-1-(tetrahydro-2H-pyran-2-yl)-1H-indazole IM25 as brown oil: 89 mg, 58% yield, P=63%, retention time=2.4 min (gradient A), (M+H)$^+$: 586.

Stage 5: General Procedure A2 was used from IM25 to afford crude compound 6 as brown oil: 25 mg, 100% yield, P=75%, retention time=2.2 min (gradient A), (M+H)$^+$: 502.

The product was purified by reverse phase preparative HPLC purification (Waters XBridge C18 5 μm 19×100 mm). Gradient used: increased linearly from 25 to 35% solution "B" over 4.0 min, then increased linearly to 85% solution "B" over 2.2 min, held at 85% during 0.3 min and returned to initial conditions over 1.0 min. Flow Rate: 15 ml/min. P=98%. $^1$H NMR (300 MHz, CD$_3$OD) δ 8.58 (s, 1H), 8.40 (s, 1H), 7.44 (d, J=9.6 Hz, 1H), 7.27 (d, J=1.9 Hz, 1H), 7.23 (d, J=9.6 Hz, 1H), 6.96 (s, 1H), 5.81 (s, 2H), 4.63 (d, J=13.0 Hz, 1H), 4.25 (d, J=13.0 Hz, 1H), 3.89 (s, 3H), 3.03-2.84 (m, 2H), 2.74-2.56 (m, 4H), 2.49-2.37 (m, 1H), 2.14-2.03 (m, 1H), 1.90-1.79 (m, 1H), 1.67-1.50 (m, 2H), 1.42 (t, J=5.6 Hz, 4H), 0.93 (s, 6H), 1H exchanged with CD$_3$OD.

The racemic mixture was further purified by chiral preparative HPLC purifications using Chiralpak IB column (5 μm, 10×250 mm). Eluent used: MTBE/MeOH/DEA 85/15/0.1% at flow rate of 7 mL/min. First eluted enantiomer: P=95%, retention time=5.1 min, chiral HPLC: P=100%. Second eluted enantiomer: P=98%, retention time=8.1 min, chiral HPLC: P=100%.

Compound 7: 6-methoxy-4-(1-((6-(4-methyl-[1,3'-bipiperidin]-1'-yl)pyridazin-3-yl)methyl)-1H-1,2,3-triazol-4-yl)-1H-indazole was Obtained Using General Scheme 1 Pathway B Stage 1: General Procedure H1 was used between 1-benzylpiperidin-3-one and 4-methylpiperidine to afford 1-benzyl-3-(4-methyl-1-piperidyl)piperidine IM26 as orange oil: 55 mg, 13% yield, P=50%, retention time=1.9 min (gradient A), (M+H)$^+$: 273.

Stage 2: General Procedure G was used from IM26 to afford tert-butyl 3-(4-methyl-1-piperidyl)piperidine-1-carboxylate IM27 as yellow oil: 14 mg, 49% yield, retention time=2.2 min (gradient A), (M+H)$^+$: 285.

Stage 3: General Procedure A1 was used from IM27 to afford crude 4-methyl-1,3'-bipiperidine dihydrochloride IM28 (no work up applied) as yellow oil: 12 mg, 95% yield.

Stage 4: General Procedure C was used between IM27 and IM9 to afford 4 6-methoxy-4-(1-((6-(4-methyl-[1,3'-bipiperidin]-1'-yl)pyridazin-3-yl)methyl)-1H-1,2,3-triazol-4-yl)-1-(tetrahydro-2H-pyran-2-yl)-1H-indazole IM28 as orange oil: 42 mg, 65% yield, P=40%, retention time=2.3 min (gradient A), (M+H)$^+$: 572.

Stage 5: General Procedure A2 was used from IM28 to afford crude compound 7 as orange oil: 30 mg, 68% yield, P=40%, retention time=2.1 min (gradient A), (M+H)$^+$: 488.

The product was purified by reverse phase preparative HPLC purification (Waters XBridge C18 5 μm 19×100 mm). Gradient used: increased linearly from 30 to 35% solution "B" over 3.5 min, then increased linearly to 60% solution "B" over 1.5 min, then increased linearly to 85% solution "B" over 1.2 min and returned to initial conditions over 1.0 min. Flow Rate: 15 mL/min. P=97%. $^1$H NMR (300 MHz, CD$_3$OD) δ 8.59 (s, 1H), 8.41 (s, 1H), 7.44 (d, J=9.6 Hz, 1H), 7.28 (d, J=1.7 Hz, 1H), 7.24 (d, J=9.6 Hz, 1H), 6.97 (s, 1H), 5.81 (s, 2H), 4.62 (d, J=12.2 Hz, 2H), 4.26 (d, J=12.2 Hz, 1H), 3.90 (s, 3H), 3.10-2.85 (m, 4H), 2.51-2.24 (m, 3H), 2.12-2.03 (m, 1H), 1.92-1.79 (m, 1H), 1.77-1.50 (m, 4H), 1.44-1.16 (m, 3H), 0.93 (d, J=6.3 Hz, 3H), 1H exchanged with CD$_3$OD.

The racemic mixture was further purified by chiral preparative HPLC purifications using Chiralpak IB column (5 μm, 10×250 mm). Eluent used: MTBE/MeOH/DEA 85/15/0.1% at flow rate of 7 mL/min. First eluted enantiomer: P=97%, retention time=5.5 min, chiral HPLC: P=100%. Second eluted enantiomer: P=98%, retention time=9.6 min, chiral HPLC: P=100%.

Compound 8: 4-(1-((6-(3-(6-azaspiro[3.4]octan-6-yl)piperidin-1-yl)pyridazin-3-yl)methyl)-1H-1,2,3-triazol-4-yl)-6-methoxy-1H-indazole was Obtained Using General Scheme 1 Pathway B Stage 1: General Procedure H1 was used between 1-benzylpiperidin-3-one and 6-Aza-spiro[3.4]octane to afford 6-(1-benzylpiperidin-3-yl)-6-azaspiro[3.4]octane IM29 as green oil: 158 mg, 41% yield, P=56%, retention time=2.0 min (gradient A), (M+H)$^+$: 285.

Stage 2: General Procedure G was used from IM29 to afford tert-butyl 3-(6-azaspiro[3.4]octan-6-yl)piperidine-1-carboxylate IM30 as yellow oil: 38 mg, 47% yield, retention time=2.2 min (gradient A), (M+H)$^+$: 295.

Stage 3: General Procedure A1 was used from IM30 to afford crude 6-(3-piperidyl)-6-azaspiro[3.4]octane dihydrochloride IM31 (no work up applied) as light brown solid: 29 mg, 67% yield.

Stage 4: General Procedure C was used between IM31 and IM9 to afford crude 4-(1-((6-(3-(6-azaspiro[3.4]octan-6-yl)piperidin-1-yl)pyridazin-3-yl)methyl)-1H-1,2,3-triazol-4-yl)-6-methoxy-1-(tetrahydro-2H-pyran-2-yl)-1H-indazole IM32 as brown oil: 50 mg, 44% yield, P=46%, retention time=2.4 min (gradient A), (M+H)$^+$: 585.

Stage 5: General Procedure A2 was used from IM32 to afford crude compound 8 as brown oil: 60 mg, 85% yield, P=35%, retention time=2.2 min (gradient A), (M+H)⁺: 500.

The product was purified by reverse phase preparative HPLC purification (Waters XBridge C18 5 μm 19×100 mm). Gradient used: increased linearly from 15 to 40% solution "B" over 5.0 min, then increased linearly to 85% solution "B" over 1.5 min and returned to initial conditions over 1.0 min. Flow Rate: 15 mL/min. P=98%. $^1$H NMR (300 MHz, CD$_3$OD) δ 8.59 (s, 1H), 8.41 (s, 1H), 7.46 (d, J=9.4 Hz, 1H), 7.31-7.22 (m, 2H), 6.97 (s, 1H), 5.82 (s, 2H), 4.58 (d, J=14.1 Hz, 1H), 4.12 (d, J=11.4 Hz, 1H), 3.90 (s, 3H), 3.12-2.97 (m, 2H), 2.93-2.76 (m, 4H), 2.45-2.32 (m, 1H), 2.18-1.74 (m, 10H), 1.68-1.52 (m, 1H), 1.39-1.25 (m, 1H).

The racemic mixture was further purified by chiral preparative HPLC purifications using Chiralpak IB column (5 μm, 10×250 mm). Eluent used: MTBE/MeOH/DEA 85/15/0.1% at flow rate of 7 mL/min. First eluted enantiomer: P=98%, retention time=6.1 min, chiral HPLC: P=100%. Second eluted enantiomer: P=98%, retention time=9.6 min, chiral HPLC: P=99%.

Compound 9: (3R)—N-(cyclobutylmethyl)-1-(6-((4-(2,3-dihydro-1H-pyrrolo[2,3-b]pyridin-5-yl)-1H-1,2,3-triazol-1-yl)methyl)pyridazin-3-yl)piperidin-3-amine was Obtained Using General Scheme 1 Pathway B Stage 1: General Procedure E3 was used from 5-bromo-7-azaindole to afford trimethyl-[2-(1H-pyrrolo[2,3-b]pyridin-5-yl)ethynyl]silane IM33 as a yellow solid: 920 mg, 76% yield, P=60% ($^1$H-NMR), retention time=2.9 min (gradient A), (M+H)⁺: 215.

Stage 2: General Procedure D1 was used from IM33 to afford 5-ethynyl-2,3-dihydro-1H-pyrrolo[2,3-b]pyridine IM34 as a brown solid: 73 mg, 18% yield, P=90% ($^1$H-NMR), retention time=2.3 min (gradient A), (M+H)⁺: 143.

Stage 3: General Procedure B was used between IM5 and IM34 to afford 5-(1-((6-chloropyridazin-3-yl)methyl)-1H-1,2,3-triazol-4-yl)-1H-pyrrolo[2,3-b]pyridine IM35 as a beige solid: 88 mg, 43% yield, P=71%, retention time=2.1 min (gradient A), (M+H)⁺: 311/313.

Stage 4: General Procedure C was used between IM3 and IM35 to afford tert-butyl (cyclobutylmethyl)((3R)-1-(6-((4-(1H-pyrrolo[2,3-b]pyridin-5-yl)-1H-1,2,3-triazol-1-yl)methyl) pyridazin-3-yl)piperidin-3-yl)carbamate IM36 as a brown foam: 103 mg, 76% yield, P=80%, retention time=2.5 min (gradient A), (M+H)⁺: 544.

Stage 5: General Procedure A1 was used from IM36 to afford crude compound 9 as a brown foam: 78 mg, 100% yield, P=87%, retention time=2.1 min (gradient A), (M+H)⁺: 444.

The product was further purified by reverse phase preparative HPLC purification (Waters XBridge C18 5 μm 19×100 mm). Gradient used: increased linearly from 25 to 50% solution "B" over 4.5 min, then increased linearly to 85% solution "B" over 2.0 min, held at 90% during 0.4 min, returned to initial conditions over 1.1 min. Flow Rate: 15 mL/min. P=100%. $^1$H NMR (300 MHz, CD$_3$OD) δ 8.65 (s, 1H), 8.44-8.36 (m, 2H), 7.48-7.38 (m, 2H), 7.25 (d, J=9.7 Hz, 1H), 6.54 (d, J=3.4 Hz, 1H), 5.78 (s, 2H), 4.40 (d, J=12.3 Hz, 1H), 4.11 (d, J=14.1 Hz, 1H), 3.17-3.03 (m, 1H), 2.93 (dd, J=12.6, 9.6 Hz, 1H), 2.74-2.59 (m, 3H), 2.54-2.38 (m, 1H), 2.14-1.99 (m, 3H), 1.95-1.56 (m, 5H), 1.56-1.38 (m, 2H), 2H exchanged with CD$_3$OD.

Compound 10: (R)—N-((6-(3-((cyclobutylmethyl)amino)piperidin-1-yl)pyridazin-3-yl)methyl)-5-oxo-5H-thiazolo[3,2-a]pyrimidine-7-carboxamide was Obtained Using General Scheme 2 Pathway B Stage 1: To a solution 3-chloro-6-(chloromethyl)pyridazine (250 mg, 1.53 mmol) in anhydrous DMF (6.2 mL) was added potassium phthalimide (305 mg, 1.61 mmol) in a small portions. The mixture was stirred at rt and reaction progress was monitored by HPLC-MS. After complete conversion (2 h), water was added (20 mL). The mixture was cooled to 0° C. and filtered. The solid was rinsed with water (10 mL) and then was triturated in EtOH (6 mL) to give desired 2-((6-chloropyridazin-3-yl)methyl)isoindoline-1,3-dione IM37 after drying as a grey solid: 300 mg, 71% yield, P=100%, retention time=2.5 min (gradient A), (M+H)⁺: 274/276.

Stage 2: General Procedure C was used between IM3 and IM37 to afford (tert-butyl (R)-(cyclobutylmethyl)(1-(6-((1,3-dioxoisoindolin-2-yl)methyl)pyridazin-3-yl)piperidin-3-yl)carbamate IM38 as a white foam: 335 mg, 73% yield, P=100%, retention time=2.6 min (gradient A), (M+H)⁺: 506.

Stage 3: General Procedure K was used from IM38 to afford tert-butyl (R)-(1-(6-(aminomethyl)pyridazin-3-yl)piperidin-3-yl)(cyclobutylmethyl)carbamate IM39 as a yellow gum: 186 mg, 85% yield, P=100%, retention time=2.3 min (gradient A), (M+H)⁺: 376.

Stage 4: General Procedure F was used between IM39 and 5-oxo-5H-thiazolo[3,2-a]pyrimidine-7-carboxylic acid to afford crude tert-butyl (R)-(cyclobutylmethyl)(1-(6-((5-oxo-5H-thiazolo[3,2-a]pyrimidine-7-carboxamido)methyl)pyridazin-3-yl)piperidin-3-yl)carbamate IM40 as a yellow foam: 38 mg, 78% yield, P=100%, retention time=2.5 min (gradient A), (M+H)⁺: 554.

Stage 5: General Procedure A1 was used from IM40 to afford compound 10 as an off-white powder: 18 mg, 62 yield, P=98%, retention time=2.4 min (gradient B), (M+H)⁺: 454. $^1$H NMR (300 MHZ, CD$_3$OD) δ 8.10 (d, J=4.9 Hz, 1H), 7.54 (d, J=4.9 Hz, 1H), 7.42 (d, J=9.5 Hz, 1H), 7.24 (d, J=9.5 Hz, 1H), 6.98 (s, 1H), 4.70 (s, 2H), 4.37 (d, J=12.9 Hz, 1H), 4.08 (d, J=13.3 Hz, 1H), 3.14-3.00 (m, 1H), 2.91 (dd, J=12.9, 9.4 Hz, 1H), 2.78-2.59 (m, 3H), 2.57-2.40 (m, 1H), 2.09 (d, J=9.3 Hz, 3H), 1.94-1.65 (m, 5H), 1.55-1.37 (m, 2H), 2H exchanged with CD$_3$OD.

Compound 11: (R)—N-((6-(3-(((3-fluorobicyclo[1.1.1]pentan-1-yl)methyl)amino)piperidin-1-yl)pyridazin-3-yl)methyl)-4-oxo-4H-pyrido[1,2-a]pyrimidine-2-carboxamide was Obtained Using General Scheme 2 Pathway A Stage 1: General Procedure H2 was used between 1-benzylpiperidin-3-one hydrochloride and 1-{3-fluorobicyclo[1.1.1]pentan-1-ylmethanamine hydrochloride to afford 1-benzyl-N-((3-fluorobicyclo[1.1.1]pentan-1-yl)methyl)piperidin-3-amine IM41 as yellow oil: 264 mg, 79% yield, P=73%, retention time=2.0 min (gradient A), (M+H)⁺: 289.

Stage 2: General Procedure J was used from IM41 to afford tert-butyl (1-benzylpiperidin-3-yl)((3-fluorobicyclo[1.1.1]pentan-1-yl)methyl)carbamate IM42 as colourless oil: 309 mg, 85% yield.

Stage 3: A solution of IM41 (309 mg, 0.76 mmol) in anhydrous Ethanol (15.1 mL) under Ar atmosphere was degassed by Ar bubbling under stirring for 15 min. Then palladium on activated carbon (10 wt % on dry carbon, 157 mg, 0.15 mmol) was added and hydrogen was bubbled into the resulting solution under stirring for 5 min then a balloon (~3 bars) of hydrogen was placed and mixture was vigorously stirred at rt and reaction progress was monitored by HPLC-MS. After 16 h, Ar was bubbled into the rxn mixture during 5 min and the mixture was then filtered through a short pad of Celite, which was then rinsed with MeOH (5 mL then 4×10 mL). Filtrate was concentrated under reduced pressure to dryness to afford tert-butyl ((3-fluorobicyclo [1.1.1]pentan-1-yl)methyl)(piperidin-3-yl)carbamate IM43 as a colourless oil: 275 mg, 98% yield.

Stage 4: General Procedure C was used between IM11 and IM43 to afford crude Compound 11 (in situ partial Boc deprotection) as orange oil: 30 mg, 11% yield, P=50%, retention time=1.8 min (gradient A), $(M+H)^+$: 478.

The product was further purified by reverse phase preparative HPLC purification (Waters XBridge C18 5 μm 19×100 mm). Solution "A" was water+0.1% TFA. Gradient used: increased linearly from 23 to 35% solution "B" over 5.0 min, then increased linearly to 85% solution "B" over 1.0 min, and returned to initial conditions over 1.0 min. Flow Rate: 15 ml/min. P=100%. $^1$H NMR (300 MHz, CD$_3$OD) δ 9.08 (d, J=7.1 Hz, 1H), 8.07-7.95 (m, 1H), 7.84 (d, J=8.9 Hz, 1H), 7.49-7.36 (m, 2H), 7.24 (d, J=9.5 Hz, 1H), 7.10 (s, 1H), 4.37 (d, J=12.8 Hz, 1H), 4.09 (d, J=13.3 Hz, 1H), 3.17-3.01 (m, 1H), 3.00-2.85 (m, 3H), 2.75-2.61 (m, 1H), 2.11-2.00 (m, 1H), 1.95 (d, J=2.6 Hz, 6H), 1.87-1.76 (m, 1H), 1.64-1.36 (m, 2H), benzylic CH$_2$ masked by water signal & 1H exchanged with CD$_3$OD. $^{19}$F NMR (H decoupled) (282 MHZ, CD$_3$OD) δ −144.08.

The racemic mixture was further purified by chiral preparative HPLC purifications using Chiralpak IA column (5 μm, 10×250 mm). Eluent used: EtOAc/EtOH/TFA 75/25/0.1% at flow rate of 7 mL/min. First eluted enantiomer: retention time=3.7 min. Second eluted enantiomer: retention time=4.4 min.

Residual TFA was removed by reverse phase preparative HPLC purification (Waters XBridge C18 5 μm 19×100 mm). Gradient used: increased linearly from 5 to 40% solution "B" over 6.0 min, and returned to initial conditions over 1.0 min. Flow Rate: 15 mL/min. First eluted enantiomer: P=100%, chiral HPLC: P=100%. Second eluted enantiomer: P=100%, chiral HPLC: P=99.3%.

Compound 12: (3R)—N-(cyclobutylmethyl)-1-(6-((4-(5-methoxypyridin-3-yl)-1H-1,2,3-triazol-1-yl) methyl)pyridazin-3-yl)piperidin-3-amine was Obtained Using General Scheme 1 Pathway A Synthesis of 3-ethynyl-5-methoxypyridine IM44: To a mixture of 3-bromo-5-methoxypyridine (379 mg, 2.02 mmol), Tetrakis(triphenylphosphine)palladium (76 mg, 0.06 mmol) and copper(I) Iodide (15 mg, 0.08 mmol) under Ar atmosphere was degassed by Ar bubbling at rt for 15 min. Triethylamine (1.2 mL, 8.8 mmol) was added, followed by ethynyltrimethylsilane (450 μL, 3.09 mmol) one shot at rt and the reaction mixture (yellow suspension) was stirred at 55° C. Reaction progress was monitored by HPLC-MS. After 3 h (complete conversion), reaction mixture was allowed to cool to rt, was diluted with Et$_2$O (15 mL) and washed with water (4×30 mL). The organic layer was dried over MgSO$_4$, filtered through a short pad of Celite, which was rinsed with Et$_2$O (2×10 mL). TBAF (3.0 mL, 3.0 mmol) was added one shot to the brown filtrate under stirring at rt for 30 min. The reaction mixture was then washed with water (3×30 mL) and organic phase was dried over MgSO$_4$, filtered and filtrate was concentrated under reduced pressure to dryness to give 294 mg of crude brown oil containing some white needles. The residue was purified by flash chromatography on silica gel (n-Heptane/EtOAc: 9/1) to afford 3-ethynyl-5-methoxypyridine IM44 ($R_f$=0.2, n-Heptane/EtOAc: 4/1) as a white solid: 154 mg, 56% yield, P=98%, retention time=1.7 min (gradient A), $(M+H)^+$: 134.

Synthesis of tert-butyl (R)-(1-(6-(azidomethyl)pyridazin-3-yl)piperidin-3-yl)(cyclobutyl methyl) carbamate IM45: General Procedure V was used from IM39 to afford crude tert-butyl (R)-(1-(6-(azidomethyl)pyridazin-3-yl)piperidin-3-yl)(cyclobutylmethyl)carbamate IM45 as yellow oil: 66 mg, 96% yield, P=78% (215 nm), retention time=2.6 min (gradient A), $(M+H)^+$: 402.

Synthesis of (3R)—N-(cyclobutylmethyl)-1-(6-((4-(5-methoxypyridin-3-yl)-1H-1,2,3-triazol-1-yl)methyl) pyridazin-3-yl)piperidin-3-amine (compound 12): Stage 1: General Procedure B was used between IM44 and IM45 to afford tert-butyl (cyclobutylmethyl)((3R)-1-(6-((4-(5-methoxypyridin-3-yl)-1,2l2,3l2-triazolidin-1-yl)methyl) pyridazin-3-yl)piperidin-3-yl)carbamate IM46 as yellow oil: 24 mg, 32% yield, P=90%, retention time=2.4 min (gradient A), $(M+H)^+$: 535. Stage 2: General Procedure A1 was used from IM46 to afford compound 12 as a light yellow solid: 18 mg, 94% yield, P=92%, retention time=2.4 min (gradient B), $(M+H)^+$: 435. $^1$H NMR (300 MHz, CD$_3$OD) δ 8.58 (s, 1H), 8.54 (s, 1H), 8.19 (s, 1H), 7.86-7.79 (m, 1H), 7.43 (d, J=9.5 Hz, 1H), 7.24 (d, J=9.5 Hz, 1H), 5.78 (s, 2H), 4.39 (d, J=13.6 Hz, 1H), 4.17-4.04 (m, 1H), 3.93 (d, J=0.9 Hz, 3H), 3.16-3.01 (m, 1H), 2.99-2.85 (m, 1H), 2.78-2.55 (m, 3H), 2.54-2.37 (m, 1H), 2.13-1.99 (m, 3H), 1.96-1.35 (m, 7H), 1H exchanged with CD$_3$OD.

Compound 13: (R)—N-(cyclobutylmethyl)-1-(6-((4-(6-methoxyimidazo[1,5-a]pyridin-8-yl)-1H-1,2,3-triazol-1-yl)methyl)pyridazin-3-yl)piperidin-3-amine was Obtained Using General Scheme 1 Pathway A Stage 1: General Procedure E3 was used from 8-bromo-6-methoxyimidazo[1,5-a]pyridine to afford crude 6-methoxy-8-((trimethylsilyl)ethynyl)imidazo[1,5-a]pyridine IM47 as a brown solid: 112 mg, 99% yield, P=30%, retention time=2.4 min (gradient A), $(M+H)^+$: 245.

Stage 2: General Procedure D was used from IM47 to afford 8-ethynyl-6-methoxy-imidazo[1,5-a]pyridine IM48 as an orange solid: 8 mg, 30% yield, P=89%, retention time=2.0 min (gradient A), $(M+H)^+$: 173.

Stage 3: General Procedure B was used between IM45 and IM48 to afford tert-butyl (R)-(cyclobutylmethyl)(1-(6-((4-(6-methoxyimidazo[1,5-a]pyridin-8-yl)-1H-1,2,3-triazol-1-yl)methyl)pyridazin-3-yl)piperidin-3-yl)carbamate IM49 as a yellow film: 8 mg, 39% yield, P=98%, retention time=2.4 min (gradient A), $(M+H)^+$: 574.

Stage 4: General Procedure A1 was used from IM49 to afford crude compound 13 as a yellow solid: 7 mg, 100% yield, P=97%, retention time=2.5 min (gradient B), $(M+H)^+$: 474. $^1$H NMR (300 MHz, CD$_3$OD) δ 8.63 (s, 1H), 8.27 (s, 1H), 7.91 (s, 1H), 7.80 (s, 1H), 7.45 (d, J=9.5 Hz, 1H), 7.25 (d, J=9.5 Hz, 1H), 7.17 (d, J=1.9 Hz, 1H), 5.81 (s, 2H), 4.40 (d, J=13.0 Hz, 1H), 4.14-4.03 (m, 1H), 3.85 (s, 3H), 3.19-3.04 (m, 1H), 2.98 (dd, J=12.9, 9.4 Hz, 1H), 2.81-2.62 (m, 3H), 2.55-2.37 (m, 1H), 2.16-2.00 (m, 3H), 2.00-1.77 (m, 3H), 1.77-1.39 (m, 4H), 1H exchanged with CD$_3$OD.

Compound 14: N-((6-(3-(6-azaspiro[2.5]octan-6-yl) piperidin-1-yl)pyridazin-3-yl)methyl)-4-oxo-4H-pyrido[1,2-a]pyrimidine-2-carboxamide was Obtained Using General Scheme 2 Pathway A Stage 1: General Procedure H2 was used between 1-benzylpiperidin-3-one hydrochloride and 6-azaspiro[2.5]octane hydrochloride to afford crude 6-(1-benzyl-3-piperidyl)-6-azaspiro[2.5]octane IM50 as yellow oil: 198 mg, 82% yield, P=82%, retention time=1.9 min (gradient A), (M+H)$^+$: 285.

Stage 2: General Procedure I was used from IM50 to afford crude 6-(piperidin-3-yl)-6-azaspiro[2.5]octane IM51 as colourless oil: 105 mg, 78% yield.

Stage 3: General Procedure C was used between IM51 and IM11 to afford Compound 14 as pale yellow oil: 20 mg, 27% yield, P=96%, retention time=2.5 min (gradient B), (M+H)$^+$: 474. $^1$H NMR (300 MHz, CD$_3$OD) δ 9.08 (d, J=7.0 Hz, 1H), 8.07-7.95 (m, 1H), 7.84 (d, J=8.8 Hz, 1H), 7.49-7.36 (m, 2H), 7.24 (d, J=9.5 Hz, 1H), 7.09 (s, 1H), 4.63 (d, J=12.8 Hz, 1H), 4.25 (d, J=13.4 Hz, 1H), 3.05-2.85 (m, 2H), 2.87-2.65 (m, 4H), 2.65-2.48 (m, 1H), 2.17-2.06 (m, 1H), 1.93-1.82 (m, 1H), 1.71-1.53 (m, 2H), 1.52-1.42 (m, 4H), 0.31 (s, 4H), benzylic CH$_2$ masked by water signal & 1H exchanged with CD$_3$OD.

The racemic mixture was further purified by chiral preparative HPLC purifications using Chiralpak IA column (5 μm, 10×250 mm). Eluent used: TBME/EtOH/DCM/DEA: 80/20/10/0.1% at flow rate of 7 mL/min. First eluted enantiomer: P=100%, retention time=15.1 min, chiral HPLC: P=100%. Second eluted enantiomer: P=100%, retention time=17.2 min, chiral HPLC: P=98%.

Compound 15: (3R)—N-(cyclopropylmethyl)-1-(6-((4-(6-methoxy-1H-indazol-4-yl)-1H-1,2,3-triazol-1-yl)methyl)pyridazin-3-yl)piperidin-3-amine was Obtained Using General Scheme 1 Pathway B Stage 1: General Procedure H1 was used from cyclopropanecarboxaldehyde and (R)-1-benzylpiperidin-3-amine to afford (R)-1-benzyl-N-(cyclopropylmethyl)piperidin-3-amine IM52: 333 mg, 92% yield, P=90% (215 nm), retention time=1.8 min (gradient A), (M+H)$^+$: 245.

Stage 2: General Procedure J was used from IM52 to afford tert-butyl (R)-(1-benzylpiperidin-3-yl)(cyclopropylmethyl)carbamate IM53 as colourless oil: 406 mg, 94% yield, P=98% (215 nm), retention time=2.4 min (gradient A), (M+H)$^+$: 345.

Stage 3: General Procedure I was used from IM53 to afford tert-butyl (R)-(cyclopropylmethyl)(piperidin-3-yl)carbamate IM54 as colourless oil: 287 mg, 98% yield.

Stage 4: General Procedure C was used between IM9 and IM54 to afford tert-butyl (cyclopropylmethyl)((3R)-1-(6-((4-(6-methoxy-1-(tetrahydro-2H-pyran-2-yl)-1H-indazol-4-yl)-1H-1,2,3-triazol-1-yl)methyl)pyridazin-3-yl)piperidin-3-yl)carbamate IM55 as yellow film: 84 mg, 70% yield, P=98%, retention time=2.7 min (gradient A), (M+H)$^+$: 644.

Stage 5: General Procedure A1 was used from IM55 to afford compound 15 as an off-white solid: 54 mg, 90% yield, P=98%, retention time=2.7 min (gradient B), (M+H)$^+$: 460. $^1$H NMR (300 MHZ, CD$_3$OD) δ 8.55 (s, 1H), 8.39 (d, J=1.1 Hz, 1H), 7.38 (d, J=9.5 Hz, 1H), 7.21 (d, J=2.0 Hz, 1H), 7.15 (d, J=9.5 Hz, 1H), 6.91 (dd, J=2.0, 1.0 Hz, 1H), 5.77 (s, 2H), 4.41-4.28 (m, 1H), 4.03 (d, J=13.4 Hz, 1H), 3.85 (s, 3H), 3.12-2.94 (m, 1H), 2.87 (dd, J=12.9, 9.4 Hz, 1H), 2.71-2.55 (m, 1H), 2.46 (d, J=6.9 Hz, 2H), 2.04-1.91 (m, 1H), 1.82-1.68 (m, 1H), 1.62-1.22 (m, 2H), 0.97-0.77 (m, 1H), 0.52-0.37 (m, 2H), 0.18-0.04 (m, 2H), 1H exchanged with CD$_3$OD. Chiral HPLC (ID, TBME/EtOH/DEA: 80/20/0.1%, flow rate: 1 mL/min): 98.3% purity at 280 nm.

Compound 16: (R)—N-((6-(3-((cyclopropylmethyl)amino)piperidin-1-yl)pyridazin-3-yl)methyl)-4-oxo-4H-pyrido[1,2-a]pyrimidine-2-carboxamide was Obtained Using General Scheme 2 Pathway A Stage 1: General Procedure C was used between IM3 and IM11 to afford tert-butyl (R)-(cyclopropylmethyl)(1-(6-((4-oxo-4H-pyrido[1,2-a]pyrimidine-2-carboxamido)methyl)pyridazin-3-yl)piperidin-3-yl)carbamate IM56 as yellow film: 23 mg, 47% yield, P=98%, retention time=2.4 min (gradient A), (M+H)$^+$: 534.

Stage 2: General Procedure A1 was used from IM56 to afford compound 16 as a pale yellow solid: 17 mg, 90% yield, P=97%, retention time=2.3 min (gradient B), (M+H)$^+$: 434. $^1$H NMR (300 MHZ, CD$_3$OD) δ 9.06 (s, 1H), 7.98 (dd, J=6.7, 1.6 Hz, 1H), 7.81 (d, J=8.9 Hz, 1H), 7.47-7.33 (m, 2H), 7.22 (d, J=9.5 Hz, 1H), 7.06 (s, 1H), 4.45-4.31 (m, 1H), 4.14-4.03 (m, 1H), 3.14-2.98 (m, 1H), 2.89 (dd, J=12.8, 9.4 Hz, 1H), 2.79-2.62 (m, 1H), 2.53 (d, J=6.9 Hz, 2H), 2.11-1.97 (m, 1H), 1.87-1.75 (m, 1H), 1.67-1.35 (m, 2H), 1.01-0.80 (m, 1H), 0.55-0.45 (m, 2H), 0.22-0.12 (m, 2H), benzylic CH$_2$ masked by water signal & 1H exchanged with CD$_3$OD.

Compound 17: 2-(1-((6-((R)-3-((cyclobutylmethyl)amino)piperidin-1-yl)pyridazin-3-yl)methyl)-1H-1,2,3-triazol-4-yl)-4H-pyrido[1,2-a]pyrimidin-4-one was Obtained Using General Scheme 1 Pathway A Stage 1: General Procedure E2 was used from 2-chloro-4H-pyrido[1,2-a]pyrimidin-4-one to afford crude 2-((trimethylsilyl)ethynyl)-4H-pyrido[1,2-a]pyrimidin-4-one IM57 as a black solid: 468 mg, 99% yield, P=78%, retention time=2.8 min (gradient A), (M+H)$^+$: 243.

Stage 2: General Procedure D1 was used from IM57 to afford 2-ethynylpyrido[1,2-a]pyrimidin-4-one IM58 as off-white solid: 156 mg, 51% yield, P=96%, retention time=2.1 min (gradient A), (M+H)$^+$: 171.

Stage 3: General Procedure B was used between IM45 and IM58 to afford crude tert-butyl (cyclobutylmethyl)((3R)-1-(6-((4-(4-oxo-4H-pyrido[1,2-a]pyrimidin-2-yl)-1H-1,2,3-triazol-1-yl) methyl)pyridazin-3-yl)piperidin-3-yl)carbamate IM59 as a brown solid: 28 mg, 42% yield, P=44%, retention time=2.5 min (gradient A), (M+H)$^+$: 572.

Stage 4: General Procedure A1 was used from IM59 to afford crude compound 17 as a brown solid: 7 mg, 100% yield, P=35%, retention time=2.0 min (gradient A), (M+H)$^+$: 472.

The product was further purified by reverse phase preparative HPLC purification (Waters XBridge C18 5 μm 19×100 mm). Gradient used: increased linearly from 10 to 30% solution "B" over 3.0 min, then increased linearly to 50% solution "B" over 2.5 min, then increased linearly to 55% solution "B" over 1.0 min, then increased linearly to 85% solution "B" over 1.0 min, held at 85% during 0.3 min, and returned to initial conditions over 0.2 min. Flow Rate: 15 mL/min. P=99%. $^1$H NMR (300 MHz, CDCl$_3$) δ 9.07 (d, J=6.8 Hz, 1H), 8.36 (s, 1H), 7.72 (t, J=8.0 Hz, 1H), 7.61 (d, J=8.9 Hz, 1H), 7.35-7.22 (m, 2H), 7.10 (t, J=7.0 Hz, 1H), 6.89 (d, J=9.4 Hz, 1H), 5.76 (s, 2H), 4.38 (d, J=13.2 Hz, 1H), 4.09 (d, J=13.6 Hz, 1H), 3.12 (t, J=12.0 Hz, 1H), 2.93 (t, J=11.1 Hz, 1H), 2.71 (t, J=10.3 Hz, 3H), 2.49-2.37 (m, 1H), 2.05 (s, 3H), 1.87 (d, J=8.4 Hz, 3H), 1.73-1.35 (m, 4H), 1H exchanged with solvent.

Compound 18: (3R)—N-((3-fluorobicyclo[1.1.1]pentan-1-yl)methyl)-1-(6-((4-(6-methoxy-1H-indazol-4-yl)-1H-1,2,3-triazol-1-yl)methyl)pyridazin-3-yl)piperidin-3-amine was Obtained Using General Scheme 1 Pathway B Stage 1: General Procedure H1 was used from 3-fluorobicyclo[1.1.1]pentane-1-carbaldehyde and (R)-1-benzylpiperidin-3-amine to afford (3R)-1-benzyl-N-[(3-fluoro-1-bicyclo[1.1.1] pentanyl)methyl]piperidin-3-amine IM60: 553 mg, 64% yield, P=63% (215 nm), retention time=2.0 min (gradient A), (M+H)⁺: 289.

Stage 2: General Procedure J was used from IM60 to afford tert-butyl (R)-(1-benzylpiperidin-3-yl)((3-fluorobicyclo[1.1.1]pentan-1-yl)methyl)carbamate IM61 as colourless oil: 510 mg, 74% yield, P=68%, retention time=2.5 min (gradient A), (M+H)⁺: 389.

Stage 3: General Procedure L was used from IM61 to afford tert-butyl (R)-((3-fluorobicyclo[1.1.1]pentan-1-yl)methyl)(piperidin-3-yl)carbamate IM62 as colourless oil: 350 mg, 89% yield.

Stage 4: General Procedure C was used between IM9 and IM62 to afford tert-butyl ((3-fluorobicyclo[1.1.1]pentan-1-yl)methyl)((3R)-1-(6-((4-(6-methoxy-1-(tetrahydro-2H-pyran-2-yl)-1H-indazol-4-yl)-1H-1,2,3-triazol-1-yl)methyl)pyridazin-3-yl)piperidin-3-yl)carbamate IM63 as an off-white solid: 201 mg, 56% yield, P=100%, retention time=2.7 min (gradient A), (M+H)⁺: 688.

Stage 5: General Procedure A1 was used from IM63 to afford compound 18 as a white solid: 140 mg, 96% yield, P=100%, retention time=2.9 min (gradient B), (M+H)⁺: 504. ¹H NMR (300 MHz, CD₃OD) δ 8.59 (s, 1H), 8.40 (d, J=1.0 Hz, 1H), 7.45 (d, J=9.5 Hz, 1H), 7.30-7.20 (m, 2H), 6.96 (s, 1H), 5.81 (s, 2H), 4.42 (dd, J=12.6, 3.8 Hz, 1H), 4.16-4.02 (m, 1H), 3.89 (s, 3H), 3.17-3.02 (m, 1H), 3.00 (s, 3H), 3.00-2.89 (m, 1H), 2.79-2.66 (m, 1H), 2.12-2.00 (m, 1H), 1.96 (d, J=2.6 Hz, 6H), 1.88-1.76 (m, 1H), 1.65-1.39 (m, 2H), 2H exchanged with CD₃OD. ¹⁹F NMR (282 MHZ, CD₃OD) δ −144.17. Chiral HPLC (IB, MeCN/MeOH/DEA: 95/5/0.1%, flow rate: 1 mL/min): 97.8% purity at 280 nm.

Compound 19: 3-(1-((6-((R)-3-((cyclobutylmethyl)amino)piperidin-1-yl)pyridazin-3-yl)methyl)-1H-1,2,3-triazol-4-yl)-5-methoxypicolinonitrile was Obtained Using General Scheme 1 Pathway A Stage 1: General Procedure E2 was used from 3-bromo-5-methoxypicolinonitrile to afford 5-methoxy-3-((trimethylsilyl)ethynyl)picolinonitrile IM64 as yellow oil: 9 mg, 15% yield, P=90%, retention time=2.6 min (gradient A), (M+H)⁺: 281.

Stage 2: A solution of TBAF (60 μL, 0.06 mmol) was added to a solution of IM45 (14 mg, 0.03 mmol), IM64 (9 mg, 0.04 mmol), copper(I) iodide (1.1 mg, 0.01 mmol) and DIEA (4 μL, 0.02 mmol) in anhydrous tert-butanol (360 μL) under Ar atmosphere. Reaction mixture was heated to 130° C. and reaction progress was monitored by HPLC-MS. After 15 min, the reaction mixture was allowed to cool to rt, diluted with EtOAc (20 mL) and washed with water (5 mL). Layers were separated and organic layer was dried over MgSO₄, filtered and concentrated under reduced pressure to afford 30 mg of brown oil. The residue was purified by flash chromatography on silica gel (EtOAc/n-Heptane: 7/3 to 9/1) to afford tert-butyl ((3R)-1-(6-((4-(2-cyano-5-methoxypyridine-3-yl)-1H-1,2,3-triazol-1-yl)methyl)pyridazin-3-yl)piperidin-3-yl)(cyclobutylmethyl)carbamate IM65 (Rf~0.7, EtOAc/MeOH: 9/1) as a brown solid: 7 mg, 34% yield, P=96%, retention time=2.7 min (gradient A), (M+H)⁺: 560.

Stage 3: General Procedure A2 was used from IM65 to afford crude compound 19 as pale brown oil: 25 mg, 96% yield (+TFA), P=98%, retention time=2.2 min (gradient A), (M+H)⁺: 460.

The product was further purified by reverse phase preparative HPLC purification (Waters XBridge C18 5 μm 19×100 mm). Gradient used: increased linearly from 10 to 40% solution "B" over 4.5 min, then increased linearly to 85% solution "B" over 1.5 min, and returned to initial conditions over 1.0 min. Flow Rate: 15 mL/min. P=100%. ¹H NMR (300 MHz, CDCl₃) δ 8.58 (s, 1H), 8.31 (d, J=2.8 Hz, 1H), 8.08 (d, J=2.8 Hz, 1H), 7.23 (d, J=9.5 Hz, 1H), 6.90 (d, J=9.5 Hz, 1H), 5.80 (s, 2H), 4.38 (d, J=13.0 Hz, 1H), 4.09 (d, J=13.3 Hz, 1H), 3.99 (s, 3H), 3.19-3.04 (m, 1H), 2.91 (dd, J=12.8, 9.2 Hz, 1H), 2.77-2.60 (m, 3H), 2.51-2.35 (m, 1H), 2.12-1.96 (m, 3H), 1.94-1.73 (m, 3H), 1.73-1.51 (m, 4H). 1 NH exchanged with solvent Compound 20: ((3R)-1-(6-((4-(6-methoxy-1H-indazol-4-yl)-1H-1,2,3-triazol-1-yl)methyl)pyridazin-3-yl)-N-((3-methylbicyclo[1.1.1]pentan-1-yl)methyl)piperidin-3-amine was Obtained Using General Scheme 1 Pathway B Stage 1: To a solution of 3-methylbicyclo[1.1.1]pentane-1-carboxylic acid (143 mg, 1.1 mmol) in anhydrous DMF (6.8 mL) was added DIEA (390 μL, 2.23 mmol), 1-Benzylpiperidin-3-amine (200 mg, 1.05 mmol) and then T3P (tripropylphosphonic anhydride in AcOEt, 50% w/w solution) (800 μL, 1.34 mmol). The reaction is stirred at rt for 30 min and NaHCO₃ saturated solution (20 mL) was added. The mixture was extracted with EtOAc (50 mL). and the organic layer was further washed with NaHCO₃ saturated solution (3×20 mL), dried over MgSO₄, filtered and concentrated in vacuum to dryness to afford N-(1-benzylpiperidin-3-yl)-3-methylbicyclo[1.1.1]pentane-1-carboxamide IM66 as an off-white solid: 276 mg, 88% yield, P=100% (215 nm), retention time=2.2 min (gradient A), (M+H)⁺: 299.

Stage 2: A solution of IM66 (276 mg, 0.92 mmol) in anhydrous THF (2 mL), under Ar atmosphere was cooled to 0° C. and borane (THF complex, 1M in THF, 10 mL, 10 mmol) was added. Reaction mixture was then stirred at 80° C. Reaction progress was monitored by HPLC-MS and more borane (THF complex, 1M in THF) was added after 3 h (2 mL, 2 mmol). After 5 h, the reaction mixture was quenched with addition of water/MeOH (1/1, 20 mL) and concentrated under reduced pressure to afford a white paste. The latter was solubilized with MeOH (30 mL) and hydrogen chloride in water (1 N, 30 mL, 30 mmol) was added. This solution was heated to 70° C. for 1 h and then cooled to rt. Reaction mixture was concentrated under reduced pressure to afford a white paste. NaOH 1N (10 mL) was added to the paste (pH ~9-10), and EtOAc (30 mL). Layers were separated, and basic aqueous layer was further extracted with EtOAc (3×30 mL). Organic layers were merged and dried over MgSO₄, filtered and concentrated under reduced pressure to dryness to afford 1-benzyl-N-((3-methylbicyclo[1.1.1]pentan-1-yl)methyl)piperidin-3-amine IM67 as colourless oil: 250 mg, 94% yield, P=99% (215 nm), retention time=2.1 min (gradient A), (M+H)⁺: 285.

Stage 3: General Procedure J was used from IM67 to afford tert-butyl (1-benzylpiperidin-3-yl)((3-methylbicyclo[1.1.1]pentan-1-yl)methyl)carbamate IM68 as colourless oil: 266 mg, 79% yield, P=100%, retention time=2.6 min (gradient A), (M+H)⁺: 385.

Stage 4: General Procedure I was used from IM68 to afford tert-butyl ((3-methylbicyclo[1.1.1]pentan-1-yl)methyl)(piperidin-3-yl)carbamate IM69 as colourless oil: 170 mg, 83% yield.

Stage 5: General Procedure C was used between IM9 and IM69 to afford tert-butyl (1-(6-((4-(6-methoxy-1-(tetrahydro-2H-pyran-2-yl)-1H-indazol-4-yl)-1H-1,2,3-triazol-1-yl)methyl) pyridazin-3-yl)piperidin-3-yl)((3-methylbicyclo

[1.1.1]pentan-1-yl)methyl)carbamate IM70 as a yellow solid: 47 mg, 71% yield, P=94%, retention time=2.8 min (gradient A), (M+H)⁺: 684.

Stage 6: General Procedure A1 was used from IM70 to afford compound 20 as a white solid: 27 mg, 76% yield, P=97%, retention time=3.1 min (gradient B), (M+H)⁺: 500. ¹H NMR (300 MHz, CD₃OD) δ 8.58 (s, 1H), 8.40 (s, 1H), 7.44 (d, J=9.8 Hz, 1H), 7.27 (s, 1H), 7.24 (d, J=9.8 Hz, 1H), 6.96 (s, 1H), 5.81 (s, 2H), 4.37 (d, J=12.7 Hz, 1H), 4.11 (d, J=14.2 Hz, 1H), 3.90 (s, 3H), 3.17-3.04 (m, 1H), 3.01-2.88 (m, 1H), 2.78-2.61 (m, 2H), 2.12-1.97 (m, 1H), 1.78 (s, 2H), 1.55 (s, 6H), 1.52-1.39 (m, 1H), 1.11 (s, 3H). 2H exchanged with CD₃OD.

The racemic mixture was further purified by chiral preparative HPLC purifications using Chiralpak IB column (5 μm, 10×250 mm). Eluent used: TBME/MeOH/DEA: 88/12/0.1% at flow rate of 6 mL/min. First eluted enantiomer: P=100%, retention time=7.1 min, chiral HPLC: P=98.0%. Second eluted enantiomer: P=98%, retention time=8.0 min, chiral HPLC: P=98.7%.

Compound 21: 5-(1-((6-((R)-3-((cyclobutylmethyl) amino)piperidin-1-yl)pyridazin-3-yl)methyl)-1H-1,2, 3-triazol-4-yl)nicotinonitrile was Obtained Using General Scheme 1 Pathway A Stage 1: General Procedure E2 (in THF instead of DMF) was used from 5-bromonicotinonitrile to afford 5-((trimethylsilyl)ethynyl)nicotinonitrile IM71 as a yellow solid: 187 mg, 84% yield, P=98%, retention time=3.0 min (gradient A), (M+H)⁺: 201.

Stage 2: General Procedure D2 was used from IM71 to afford 5-ethynylnicotinonitrile IM72 as a yellow solid: 61 mg, 52% yield, P=100%, retention time=2.3 min (gradient A), (M+H)⁺: 129.

Stage 3: General Procedure B was used between IM45 and IM72 to afford tert-butyl ((3R)-1-(6-((4-(5-cyanopyridin-3-yl)-1H-1,2,3-triazol-1-yl)methyl)pyridazin-3-yl)piperidin-3-yl) (cyclobutylmethyl)carbamate IM73 as yellow oil: 30 mg, 45% yield, P=50%, retention time=2.6 min (gradient A), (M+H)⁺: 530.

Stage 4: General Procedure A2 was used from IM73 to afford crude compound 21 as yellow oil: 30 mg, 99% yield, P=57%, retention time=2.1 min (gradient A), (M+H)⁺: 430.

The product was further purified by reverse phase preparative HPLC purification (Waters XBridge C18 5 μm 19×100 mm). Gradient used: increased linearly from 20 to 40% solution "B" over 3.5 min, then increased linearly to 85% solution "B" over 2.5 min, and returned to initial conditions over 1.0 min. Flow Rate: 15 mL/min. P=99%. ¹H NMR (300 MHz, CDCl₃) δ 9.16 (d, J=2.0 Hz, 1H), 8.81 (d, J=1.8 Hz, 1H), 8.43 (dd, J=2.0, 1.8 Hz, 1H), 8.13 (s, 1H), 7.29 (d, J=9.5 Hz, 1H), 6.90 (d, J=9.5 Hz, 1H), 5.75 (s, 2H), 4.36 (d, J=9.7 Hz, 1H), 4.09 (d, J=13.1 Hz, 1H), 3.21-3.06 (m, 1H), 2.93 (dd, J=12.8, 9.4 Hz, 1H), 2.76-2.59 (m, 3H), 2.50-2.34 (m, 1H), 2.10-2.02 (m, 2H), 1.95-1.80 (m, 3H), 1.71-1.48 (m, 5H). (1 NH exchanged with solvent).

Compound 22: (3R)—N-(cyclobutylmethyl)-1-(6-((4-(6-methoxy-1H-indazol-4-yl)-1H-1,2,3-triazol-1-yl)methyl) pyridazin-3-yl)-N-methylpiperidin-3-amine was obtained via reductive amination: To a solution of compound 1 (23 mg, 0.05 mmol) and formaldehyde (6 μL, 0.08 mmol) in MeCN (0.5 mL) were added acetic acid (3 μL, 0.05 mmol) and sodium cyanoborohydride (6 mg, 0.10 mmol) one shot. The suspension was stirred at rt and reaction progress was monitored by HPLC-MS. After 3 h (complete conversion), the reaction mixture was diluted with water (5 mL), extracted with EtOAc (2×5 mL). Aqueous layer was basified to pH=9 with NaOH 1N and extracted with EtOAc (3×5 mL). Combined organic layer was dried over MgSO₄, filtered and concentrated under reduced pressure to dryness to afford crude compound 22 as a colorless oil: 16 mg, 23% yield, P=32%, retention time=2.9 min (gradient B), (M+H)⁺: 488.

The product was further purified by reverse phase preparative HPLC purification (Waters XBridge C18 5 μm 19×100 mm). Gradient used: increased linearly from 10 to 70% solution "B" over 6.0 min, and returned to initial conditions over 1.0 min. Flow Rate: 15 mL/min. P=100%. ¹H NMR (300 MHz, CD₃OD) δ 8.59 (s, 1H), 8.41 (s, 1H), 7.44 (d, J=9.5 Hz, 1H), 7.27 (s, 1H), 7.23 (d, J=9.5 Hz, 1H), 6.96 (s, 1H), 5.81 (s, 2H), 4.57 (d, J=12.1 Hz, 1H), 4.24 (d, J=12.4 Hz, 1H), 3.90 (s, 3H), 2.99-2.84 (m, 2H), 2.68-2.43 (m, 4H), 2.30 (s, 3H), 2.14-1.95 (m, 3H), 1.95-1.65 (m, 5H), 1.65-1.49 (m, 2H). 1 NH exchanged with CD₃OD.

Compound 23: (3R)—N-cyclopentyl-1-(6-((4-(6-methoxy-1H-indazol-4-yl)-1H-1,2,3-triazol-1-yl) methyl)pyridazin-3-yl)piperidin-3-amine was Obtained Using General Scheme 1 Pathway B Stage 1: General Procedure C was used between IM9 and tert-butyl (R)-piperidin-3-ylcarbamate to afford tert-butyl ((3R)-1-(6-((4-(6-methoxy-1-(tetrahydro-2H-pyran-2-yl)-1H-indazol-4-yl)-1H-1,2,3-triazol-1-yl)methyl)pyridazin-3-yl)piperidin-3-yl)carbamate IM74 as a white solid: 670 mg, 100% yield, P=100%, retention time=2.5 min (gradient A), (M+H)⁺: 590.

Stage 2: General Procedure A1 was used from IM74 to afford crude (3R)-1-(6-((4-(6-methoxy-1H-indazol-4-yl)-1H-1,2,3-triazol-1-yl)methyl)pyridazin-3-yl)piperidin-3-amine as a white solid: 450 mg, 96% yield, P=100%, retention time=1.9 min (gradient A), (M+H)⁺: 406.

Stage 3: General Procedure H1 was used between cyclopentanone and IM74 to afford compound 23 as a white solid: 30 mg, 48% yield, P=94%, retention time=2.9 min (gradient B), (M+H)⁺: 474. ¹H NMR (300 MHz, CD₃OD) δ 8.59 (s, 1H), 8.40 (s, 1H), 7.43 (d, J=9.6 Hz, 1H), 7.24 (d, J=12.9 Hz, 2H), 6.96 (s, 1H), 5.81 (s, 2H), 4.46 (d, J=12.8 Hz, 1H), 4.12 (d, J=13.3 Hz, 1H), 3.89 (s, 3H), 3.29-3.20 (m, 1H), 3.15-2.98 (m, 1H), 2.94-2.79 (m, 1H), 2.77-2.64 (m, 1H), 2.14-1.21 (m, 12H). 2 NH exchanged with CD₃OD. Chiral HPLC (ID, TBME/EtOH/DEA: 80/20/0.1%, flow rate: 1 mL/min): 97.5% purity at 280 nm.

Compound 24: (3R)—N-(3,3-dimethylbutyl)-1-(6-((4-(6-methoxy-1H-indazol-4-yl)-1H-1,2,3-triazol-1-yl)methyl)pyridazin-3-yl)piperidin-3-amine was Obtained Using General Scheme 1 Pathway B General Procedure H1 was used between 3,3-Dimethylbutyraldehyde and IM74 to afford compound 24 as a white solid: 17 mg, 45% yield, P=97%, retention time=3.1 min (gradient B), (M+H)⁺: 490. ¹H NMR (300 MHz, CD₃OD) δ 8.57 (s, 1H), 8.40 (s, 1H), 7.48-7.38 (m, 1H), 7.30-7.17 (m, 2H), 6.95 (s, 1H), 5.80 (s, 2H), 4.41 (d, J=13.0 Hz, 1H), 4.07 (d, J=13.2 Hz, 1H), 3.88 (s, 3H), 3.16-3.01 (m, 1H), 3.00-2.85 (m, 1H), 2.76-2.55 (m, 3H), 2.09-1.99 (m, 1H), 1.86-1.73 (m, 1H), 1.65-1.33 (m, 4H), 0.90 (s, 9H). 2 NH exchanged with CD₃OD. Chiral HPLC (ID, TBME/EtOH/DEA: 80/20/0.1%, flow rate: 1 mL/min): 98.5% purity at 280 nm.

Compound 25: 1-(6-((4-(6-methoxy-1H-indazol-4-yl)-1H-1,2,3-triazol-1-yl)methyl)pyridazin-3-yl)-N-(spiro[2.3]hexan-1-yl)piperidin-3-amine was Obtained Using General Scheme 1 Pathway B Stage 1: General Procedure $H_2$ was used from spiro[2.3]hexan-1-amine hydrochloride and 1-Benzylpiperidin-3-one, HCl to afford 1-benzyl-N-(spiro[2.3]hexan-1-yl)piperidin-3-amine IM75: 230 mg, 25% yield, P=38% (215 nm), retention time=2.0 min (gradient A), (M+H)$^+$: 271.

Stage 2: General Procedure J was used from IM75 to afford tert-butyl (1-benzylpiperidin-3-yl)(spiro[2.3]hexan-1-yl)carbamate IM76 as yellow oil: 115 mg, 29% yield, P=95% (215 nm), retention time=2.6 min (gradient A), (M+H)$^+$: 371.

Stage 3: General Procedure L was used from IM76 to afford tert-butyl piperidin-3-yl(spiro[2.3]hexan-1-yl)carbamate IM77 as a white solid: 86 mg, 100% yield.

Stage 4: General Procedure C was used between IM9 and IM77 to afford tert-butyl (1-(6-((4-(6-methoxy-1-(tetrahydro-2H-pyran-2-yl)-1H-indazol-4-yl)-1H-1,2,3-triazol-1-yl)methyl) pyridazin-3-yl)piperidin-3-yl)(spiro[2.3]hexan-1-yl)carbamate IM78 as colourless oil: 44 mg, 35% yield, P=98%, retention time=2.8 min (gradient A), (M+H)$^+$: 670.

Stage 5: General Procedure A1 was used from IM78 to afford compound 25 as a white solid: 21 mg, 61% yield, P=93%, retention time=2.9 min (gradient B), (M+H)$^+$: 486.

The racemic mixture was further purified by chiral preparative HPLC purifications using Chiralpak IB column (5 μm, 10×250 mm). Eluent used: ACN/MeOH/DEA: 95/5/0.1% at flow rate of 7 mL/min. First eluted fraction was a mixture of 2 stereoisomers: P=100%, retention time=6.4 min. Second eluted fraction: P=97%, retention time=7.0 min, chiral HPLC: P=97.1%. $^1$H NMR (300 MHZ, CD$_3$OD) δ 8.59 (s, 1H), 8.41 (s, 1H), 7.45 (d, J=9.5 Hz, 1H), 7.28 (d, J=2.0 Hz, 1H), 7.25 (d, J=9.6 Hz, 1H), 6.96 (s, 1H), 5.81 (s, 2H), 4.52-4.42 (m, 1H), 4.19-4.09 (m, 1H), 3.90 (s, 3H), 3.16-3.02 (m, 1H), 2.97 (dd, J=12.8, 9.6 Hz, 1H), 2.83-2.69 (m, 1H), 2.26-2.12 (m, 1H), 2.15-1.96 (m, 7H), 1.91-1.76 (m, 1H), 1.70-1.37 (m, 2H), 0.63 (dd, J=7.4, 5.3 Hz, 1H), 0.30 (t, J=4.8 Hz, 1H). 2 NH exchanged with CD$_3$OD.

Third eluted fraction: P=95%, retention time=8.1 min, chiral HPLC: P=98.1%. $^1$H NMR (300 MHz, CD$_3$OD) δ 8.59 (s, 1H), 8.41 (s, 1H), 7.45 (d, J=9.5 Hz, 1H), 7.28 (d, J=2.0 Hz, 1H), 7.25 (d, J=9.6 Hz, 1H), 6.96 (s, 1H), 5.81 (s, 2H), 4.52-4.42 (m, 1H), 4.19-4.09 (m, 1H), 3.90 (s, 3H), 3.16-3.02 (m, 1H), 2.97 (dd, J=12.8, 9.6 Hz, 1H), 2.83-2.69 (m, 1H), 2.26-2.12 (m, 1H), 2.15-1.96 (m, 7H), 1.91-1.76 (m, 1H), 1.70-1.37 (m, 2H), 0.63 (dd, J=7.4, 5.3 Hz, 1H), 0.30 (t, J=4.8 Hz, 1H). 2 NH exchanged with CD$_3$OD.

The first fraction was further purified by chiral preparative HPLC purification using Chiralpak ID column (5 μm, 10×250 mm). Eluent used: EtOAc/EtOH/DEA: 93/7/0.1% at flow rate of 6 mL/min. First eluted stereoisomer: P=92%, retention time=25.7 min, chiral HPLC: P=98.1%, $^1$H NMR (300 MHz, CD$_3$OD) δ 8.59 (s, 1H), 8.41 (s, 1H), 7.46 (d, J=9.4 Hz, 1H), 7.31-7.21 (m, 2H), 6.97 (s, 1H), 5.82 (s, 2H), 4.48 (d, J=10.7 Hz, 1H), 4.13 (d, J=13.3 Hz, 1H), 3.90 (s, 3H), 3.17-2.93 (m, 2H), 2.88-2.72 (m, 1H), 2.26-2.17 (m, 1H), 2.16-2.00 (m, 7H), 1.89-1.70 (m, 1H), 1.64-1.45 (m, 2H), 0.70-0.62 (m, 1H), 0.35-0.27 (m, 1H). 2 NH exchanged with CD$_3$OD.

First eluted stereoisomer: P=92%, retention time=26.1 min, chiral HPLC: P=96.9%, $^1$H NMR (300 MHz, CD$_3$OD) δ 8.59 (s, 1H), 8.41 (s, 1H), 7.46 (d, J=9.4 Hz, 1H), 7.31-7.21 (m, 2H), 6.97 (s, 1H), 5.82 (s, 2H), 4.48 (d, J=10.7 Hz, 1H), 4.13 (d, J=13.3 Hz, 1H), 3.90 (s, 3H), 3.17-2.93 (m, 2H), 2.88-2.72 (m, 1H), 2.26-2.17 (m, 1H), 2.16-2.00 (m, 7H), 1.89-1.70 (m, 1H), 1.64-1.45 (m, 2H), 0.70-0.62 (m, 1H), 0.35-0.27 (m, 1H), 2 NH exchanged with CD$_3$OD.

Compound 26: N-(cyclobutylmethyl)-1-(5-((4-(6-methoxy-1H-indazol-4-yl)-1H-1,2,3-triazol-1-yl)methyl)thiazol-2-yl)piperidin-3-amine was Obtained Using General Scheme 1 Pathway A Stage 1: A mixture of -butyl (cyclobutylmethyl)(piperidin-3-yl)carbamate IM79 (68 mg, 0.25 mmol), 2-Bromothiazole-5-methanol (50 mg, 0.25 mmol), dipotassium carbonate (70 mg, 0.51 mmol) in anhydrous DMF (250 μL) was stirred at 110° C. and reaction progress was monitored by HPLC-MS. When conversion did not increase anymore, the reaction was allowed to reach rt. Water was added (10 mL) and the mixture was extracted with EtOAc (3×20 mL). The combined organic layers were washed with water (3×20 mL), brine (20 mL), dried over MgSO$_4$, filtered and concentrated under reduced pressure. The crude product was purified over silica gel flash chromatography (n-Heptane/EtOAc: 100/0 to 50/50) to afford tert-butyl (cyclobutylmethyl)(1-(5-(hydroxymethyl)thiazol-2-yl)piperidin-3-yl)carbamate IM80 (R$_f$=0.2, nHept/EtOAc: 1/1) as yellow oil: 68 mg, 67% yield, P=95%, retention time=2.4 min (gradient A), (M+H)$^+$: 382.

Stage 2: General Procedure M was used from IM80 to afford tert-butyl (1-(5-(azidomethyl)thiazol-2-yl)piperidin-3-yl)(cyclobutylmethyl)carbamate IM81 as colourless oil: 27 mg, 37% yield, P=74%, retention time=2.8 min (gradient A), (M+H)$^+$: 407.

Stage 3: General Procedure B was used between IM8 and IM81 to afford tert-butyl (cyclobutylmethyl)(1-(5-((4-(6-methoxy-1-(tetrahydro-2H-pyran-2-yl)-1H-indazol-4-yl)-1H-1,2,3-triazol-1-yl)methyl)thiazol-2-yl)piperidin-3-yl)carbamate IM82 as a white solid: 32 mg, 69% yield, P=95% (215 nm), retention time=2.9 min (gradient A), (M+H–THP)$^+$: 579.

Stage 4: General Procedure A1 was used from IM82 to afford compound 26 as a white solid: 21 mg, 88% yield, P=92%, retention time=2.2 min (gradient A), (M+H)$^+$: 479. $^1$H NMR (300 MHz, CD$_3$OD) δ 8.51 (s, 1H), 8.39 (s, 1H), 7.28 (s, 1H), 7.26 (d, J=2.0 Hz, 1H), 6.96 (s, 1H), 5.74 (s, 2H), 3.99-3.93 (m, 1H), 3.90 (s, 3H), 3.78-3.67 (m, 1H), 3.17-3.07 (m, 1H), 2.92 (dd, J=12.6, 9.4 Hz, 1H), 2.72-2.58 (m, 3H), 2.51-2.39 (m, 1H), 2.11-2.01 (m, 2H), 1.94-1.73 (m, 4H), 1.67 (s, 3H), 1.43-1.35 (m, 1H). 2 NH exchanged with CD$_3$OD.

The racemic mixture was further purified by chiral preparative HPLC purification using Chiralpak IA column (5 μm, 10×250 mm). Eluent used: TBME/MeOH/DEA: 93/7/0.1% at flow rate of 6 mL/min. First eluted enantiomer: P=98%, retention time=12.2 min, chiral HPLC: P=98.0%. Second eluted enantiomer: P=93%, retention time=13.1 min, chiral HPLC: P=91.0%.

Compound 27: 4-(3-((cyclobutylmethyl)amino)piperidin-1-yl)-1-((4-(6-methoxy-1H-indazol-4-yl)-1H-1,2,3-triazol-1-yl)methyl)pyridin-2 (1H)-one was Obtained Using General Scheme 1 Pathway B Stage 1: General Procedure O1 was used from 4-chloro-2-hydroxypyridine to afford 4-chloro-1-(chloromethyl)pyridin-2-one IM83 as a white solid: 113 mg, 78% yield, P=92%, retention time=2.3 min (gradient A), (M+H)$^+$: 178/180.

Stage 2: General Procedure N was used from IM83 to afford 1-(azidomethyl)-4-chloropyridin-2 (1H)-one IM84 as a white solid: 80 mg, 68% yield, P=100% ($^1$H-NMR), retention time=2.3 min (gradient A), (M+H)$^+$: 185.

Stage 3: General Procedure B was used between IM8 and IM84 to afford 5-chloro-2-((4-(6-methoxy-1-(tetrahydro-2H-pyran-2-yl)-1H-indazol-4-yl)-1H-1,2,3-triazol-1-yl) methyl) pyridazin-3 (2H)-one IM85 as a white foam: 207 mg, 100% yield, P=98% (215 nm), retention time=2.7 min (gradient A), (M+H)$^+$: 441/443.

Stage 4: General Procedure C was used between IM79 and IM85 to afford tert-butyl (cyclobutylmethyl)(1-(1-((4-(6-methoxy-1-(tetrahydro-2H-pyran-2-yl)-1H-indazol-4-yl)-1H-1,2,3-triazol-1-yl)methyl)-2-oxo-1,2-dihydropyridin-4-yl)piperidin-3-yl)carbamate IM86 as an orange foam: 260 mg, 95% yield, P=98%, retention time=3.1 min (gradient A), (M+H)$^+$: 673.

Stage 5: General Procedure A1 was used from IM86 to afford crude compound 27 as brown oil: 203 mg, 100% yield, P=96%, retention time=2.2 min (gradient A), (M+H)$^+$: 489. $^1$H NMR (300 MHz, CD$_3$OD) δ 8.64 (s, 1H), 8.40 (s, 1H), 7.70 (d, J=8.0 Hz, 1H), 7.27 (d, J=2.0 Hz, 1H), 6.97 (s, 1H), 6.46 (s, 2H), 6.32 (dd, J=8.0, 2.7 Hz, 1H), 5.69 (d, J=2.7 Hz, 1H), 3.90 (s, 3H), 3.92-3.84 (m, 1H), 3.75 (d, J=13.6 Hz, 1H), 3.06-2.93 (m, 1H), 2.82 (dd, J=13.1, 9.6 Hz, 1H), 2.66 (d, J=7.3 Hz, 2H), 2.62-2.53 (m, 1H), 2.51-2.37 (m, 1H), 2.11-1.98 (m, 3H), 1.94-1.64 (m, 6H), 1.44-1.30 (m, 1H), 2 NH exchanged with CD$_3$OD.

The racemic mixture was further purified by chiral preparative HPLC purification using Chiralpak ID column (5 μm, 10×250 mm). Eluent used: TBME/MeOH/DEA: 60/40/0.1% at flow rate of 6 mL/min. First eluted enantiomer: P=98%, retention time=7.8 min, chiral HPLC: P=100%. Second eluted enantiomer: P=98%, retention time=9.8 min, chiral HPLC: P=100%.

Compound 28: 5-(3-((cyclobutylmethyl)amino)piperidin-1-yl)-2-((4-(6-methoxy-1H-indazol-4-yl)-1H-1,2,3-triazol-1-yl)methyl)pyridazin-3 (2H)-one was Obtained Using General Scheme 1 Pathway B Stage 1: General Procedure O1 was used from 5-chloropyridazin-3 (2H)-one to afford 5-chloro-2-(chloromethyl) pyridazin-3-one IM87 as yellow liquid: 263 mg, 93% yield, P=95% ($^1$H-NMR), retention time=2.3 min (gradient A), (M+H)$^+$: 179/181.

Stage 2: General Procedure N was used from IM87 to afford 2-(azidomethyl)-5-chloro-pyridazin-3-one IM88 as yellow liquid: 118 mg, 46% yield, P=100%, retention time=2.4 min (gradient A), (M+H)$^+$: 186.

Stage 3: General Procedure B was used between IM8 and IM88 to afford 5-chloro-2-[[4-(6-methoxy-1-tetrahydropyran-2-yl-indazol-4-yl)triazol-1-yl]methyl]pyridazin-3-one IM89 as a white foam: 218 mg, 72% yield, P=93%, retention time=2.7 min (gradient A), (M+H)$^+$: 441/443.

Stage 4: General Procedure C was used between IM79 and IM89 to afford tert-butyl N-(cyclobutylmethyl)-N-[1-[1-[[4-(6-methoxy-1-tetrahydropyran-2-yl-indazol-4-yl)triazol-1-yl]methyl]-6-oxo-pyridazin-4-yl]-3-piperidyl]carbamate IM90 as a yellow foam: 215 mg, 92% yield, P=79% ($^1$H-NMR), retention time=3.2 min (gradient A), (M+H)$^+$: 674.

Stage 5: General Procedure A1 was used from IM90 to afford compound 28 as a beige foam: 109 mg, 82% yield, P=90%, retention time=2.2 min (gradient A), (M+H)$^+$: 490. $^1$H NMR (300 MHZ, CD$_3$OD) δ 8.61 (s, 1H), 8.40 (s, 1H), 8.03 (d, J=2.8 Hz, 1H), 7.26 (d, J=2.0 Hz, 1H), 6.97 (s, 1H), 6.60 (s, 2H), 5.89 (d, J=2.8 Hz, 1H), 3.94-3.87 (m, 1H), 3.85 (s, 3H), 3.81-3.70 (m, 1H), 3.13-2.99 (m, 1H), 2.90 (dd, J=13.1, 9.3 Hz, 1H), 2.70-2.57 (m, 3H), 2.51-2.34 (m, 1H), 2.10-1.97 (m, 3H), 1.96-1.62 (m, 6H), 1.47-1.25 (m, 1H), 2 NH exchanged with CD$_3$OD.

The racemic mixture was further purified by chiral preparative HPLC purification using Chiralpak ID column (5 μm, 10×250 mm). Eluent used: TBME/MeOH/DEA: 70/30/0.1% at flow rate of 6 mL/min. First eluted enantiomer: P=100%, retention time=6.5 min, chiral HPLC: P=97.1%. Second eluted enantiomer: P=97%, retention time=7.0 min, chiral HPLC: P=96.6%.

Compound 29: 2-(1-(((6-((R)-3-((cyclobutylmethyl) amino)piperidin-1-yl)pyridazin-3-yl)methyl)-1H-1,2,3-triazol-4-yl)quinazolin-4 (3H)-one was Obtained Using General Scheme 1 Pathway A Stage 1: 2-Chloroquinazolin-4 (3H)-one (300 mg, 1.58 mmol) was dissolved into anhydrous DMF (3.2 mL) and potassium carbonate (480 mg, 3.47 mmol) was added, followed by 4-methoxybenzylbromide (441 mg, 2.19 mmol). Reaction mixture was heated to 80° C. for 1 h and then cooled to rt. The reaction mixture was diluted with EtOAc (30 mL) and washed with water (3×10 mL), followed by brine (10 mL). Resulting organic layer was dried over MgSO$_4$, filtered, and concentrated under reduced pressure to dryness. The crude product was purified over silica gel flash chromatography (n-Heptane/EtOAc: 1/0 to 9/1) to afford 2-chloro-3-[(4-methoxyphenyl)methyl]quinazolin-4-one IM91 (R$_f$~0.6, nHept/EtOAc: 1/1) as a white solid: 295 mg, 62% yield, P=95%, retention time=3.0 min (gradient A), (M+H)$^+$: 301/303.

Stage 2: General Procedure E2 (in THF instead of DMF) was used from IM91 to afford 3-(4-methoxybenzyl)-2-((trimethylsilyl)ethynyl)quinazolin-4 (3H)-one IM92 as colourless oil: 120 mg, 33% yield, P=90%, retention time=3.2 min (gradient A), (M+H)$^+$: 363.

Stage 3: IM92 (84 mg, 0.21 mmol) was suspended in anhydrous methanol (1.6 mL) and the reaction mixture was stirred at rt for 1 h and concentrated under reduced pressure to afford 2-ethynyl-3-[(4-methoxyphenyl)methyl]quinazolin-4-one IM93 as a brown solid: 60 mg, 90% yield, P=92%, retention time=2.8 min (gradient A), (M+H)$^+$: 291.

Stage 4: General Procedure B was used between IM45 and IM93 to afford tert-butyl N-(cyclobutylmethyl)-N-[(3R)-1-[6-[4-[3-[(4-methoxyphenyl)methyl]-4-oxo-quinazolin-2-yl]triazol-1-yl]methyl]pyridazin-3-yl]-3-piperidyl]carbamate IM94 as a light brown solid: 80 mg, 95% yield, P=100%, retention time=2.8 min (gradient A), (M+H)$^+$: 692.

Stage 5: General Procedure A2 was used from IM94 to afford crude compound 29 as n off-white powder: 33 mg, 59% yield, P=99%, retention time=2.9 min (gradient B), (M+H)$^+$: 472. $^1$H NMR (300 MHz, CD$_3$OD) δ 8.73 (s, 1H), 8.23 (d, J=8.3 Hz, 1H), 7.81 (dd, J=7.6, 7.6 Hz, 1H), 7.72 (d, J=8.1 Hz, 1H), 7.51 (t, J=7.7 Hz, 1H), 7.46 (d, J=9.5 Hz, 1H), 7.26 (d, J=9.5 Hz, 1H), 5.84 (s, 2H), 4.41 (d, J=13.0 Hz, 1H), 4.11 (d, J=13.2 Hz, 1H), 3.17-3.05 (m, 1H), 2.95 (dd, J=12.9, 9.5 Hz, 1H), 2.77-2.59 (m, 3H), 2.53-2.41 (m, 1H), 2.15-2.00 (m, 3H), 1.99-1.76 (m, 4H), 1.75-1.62 (m, 2H), 1.52-1.37 (m, 1H), 2 NH exchanged with CD$_3$OD.

Compound 30: (3R)—N-cyclobutyl-1-[6-[[4-(6-methoxy-1H-indazol-4-yl)triazol-1-yl]methyl] pyridazin-3-yl]piperidin-3-amine was Obtained Using General Scheme 1 Pathway B General Procedure H1 was used between cyclobutanone and IM74 to afford compound 30 as a white solid: 22 mg, 63% yield, P=97%, retention time=2.1 min (gradient A), (M+H)+: 460. $^1$H NMR (300 MHZ, CD$_3$OD) δ 8.59 (s, 1H), 8.41 (s, 1H), 7.44 (d, J=9.5 Hz, 1H), 7.27 (d, J=2.0 Hz, 1H), 7.23 (d, J=9.5 Hz, 1H), 6.96 (s, 1H), 5.81 (s, 2H), 4.37 (d, J=12.7 Hz, 1H), 4.12 (d, J=13.5 Hz, 1H), 3.90 (s, 3H), 3.49-3.34 (m, 1H), 3.11-2.98 (m, 1H), 2.84 (dd, J=12.8, 9.7 Hz, 1H), 2.71-2.58 (m, 1H), 2.29-2.15 (m, 2H), 2.07-1.93 (m, 1H), 1.87-1.62 (m, 6H), 1.59-1.33 (m, 1H), 2 NH exchanged with CD$_3$OD.

Compound 31: (3R)—N-isobutyl-1-[6-[[4-(6-methoxy-1H-indazol-4-yl)triazol-1-yl]methyl] pyridazin-3-yl]piperidin-3-amine was Obtained Using General Scheme 1 Pathway B General Procedure H1 was used between isobutyraldehyde and IM74 to afford compound 31 as a white solid: 8 mg, 24% yield, P=90%, retention time=2.1 min (gradient A), (M+H)+: 462. $^1$H NMR (300 MHz, CD$_3$OD) δ 8.59 (s, 1H), 8.40 (s, 1H), 7.44 (d, J=9.5 Hz, 1H), 7.27 (s, 1H), 7.25 (d, J=9.5 Hz, 1H), 6.97 (s, 1H), 5.81 (s, 2H), 4.41 (d, J=13.2 Hz, 1H), 4.11 (d, J=13.7 Hz, 1H), 3.90 (s, 3H), 3.19-3.03 (m, 1H), 2.96 (dd, J=12.9, 9.4 Hz, 1H), 2.74-2.58 (m, 1H), 2.50 (d, J=7.4 Hz, 2H), 2.13-1.99 (m, 1H), 1.89-1.66 (m, 2H), 1.68-1.39 (m, 2H), 0.91 (dd, J=6.7, 3.9 Hz, 6H), 2 NH exchanged with CD$_3$OD.

Compound 32: (3R)—N-(2,2-dimethylpropyl)-1-[6-[[4-(6-methoxy-1H-indazol-4-yl)triazol-1-yl]methyl] pyridazin-3-yl]piperidin-3-amine was Obtained Using General Scheme 1 Pathway B General Procedure H1 was used between trimethylacetaldehyde and IM74 to afford compound 32 as a white solid: 20 mg, 60% yield, P=91%, retention time=2.1 min (gradient A), (M+H)+: 476. $^1$H NMR (300 MHZ, CD$_3$OD) δ 8.58 (s, 1H), 8.40 (s, 1H), 7.43 (d, J=9.5 Hz, 1H), 7.27 (d, J=2.0 Hz, 1H), 7.24 (d, J=9.5 Hz, 1H), 6.96 (d, J=2.0 Hz, 1H), 5.80 (s, 2H), 4.43-4.30 (m, 1H), 4.17-4.00 (m, 1H), 3.90 (s, 3H), 3.19-3.04 (m, 1H), 2.97 (dd, J=13.0, 9.2 Hz, 1H), 2.64-2.51 (m, 1H), 2.43 (d, J=3.4 Hz, 2H), 2.10-1.93 (m, 1H), 1.86-1.76 (m, 1H), 1.66-1.38 (m, 2H), 0.89 (s, 9H), 2 NH exchanged with CD$_3$OD.
Chiral HPLC (ID, TBME/EtOH/DEA: 80/20/0.1%, flow rate: 1 mL/min): 100% purity at 280 nm.

Compound 33: (3R)-1-[6-[[4-(6-methoxy-1H-indazol-4-yl)triazol-1-yl]methyl]pyridazin-3-yl]-N-tetrahydrofuran-3-yl-piperidin-3-amine was Obtained Using General Scheme 1 Pathway B General Procedure H1 was used between 3-oxotetrahydrofuran and IM74 to afford crude compound 33 as a white solid: 30 mg, 79% yield, P=93%, retention time=2.0 min (gradient A), (M+H)+: 476.
The mixture of diastereomers was further purified by chiral preparative HPLC purification using Chiralpak ID column (5 μm, 10×250 mm). Eluent used: DCM/EtOH/DEA: 85/15/0.1% at flow rate of 5 mL/min. First eluted diastereomer: P=100%, retention time=16.1 min, chiral HPLC: P=100%, $^1$H NMR (300 MHz, CD$_3$OD) δ 8.61 (s, 1H), 8.40 (s, 1H), 7.52 (d, J=9.5 Hz, 1H), 7.33 (d, J=9.5 Hz, 1H), 7.26 (d, J=2.1 Hz, 1H), 6.97 (s, 1H), 5.84 (s, 2H), 4.54 (d, J=12.6 Hz, 1H), 4.08-3.94 (m, 4H), 3.89 (s, 3H), 3.86 (d, J=5.5 Hz, 1H), 3.43-3.33 (m, 1H), 3.31-3.18 (m, 3H), 2.46-2.29 (m, 1H), 2.27-2.15 (m, 1H), 2.07-1.91 (m, 1H), 1.95-1.83 (m, 1H), 1.83-1.60 (m, 2H), 2 NH exchanged with CD$_3$OD.
Second eluted diastereomer: P=100%, retention time=28.7 min, chiral HPLC: P=99.3%, $^1$H NMR (300 MHz, MeOH) δ 8.60 (s, 1H), 8.40 (s, 1H), 7.49 (d, J=9.5 Hz, 1H), 7.35-7.24 (m, 2H), 6.97 (s, 1H), 5.83 (s, 2H), 4.49 (d, J=13.1 Hz, 1 Hz), 4.06-3.93 (m, 2H), 3.90 (s, 3H), 3.89-3.80 (m, 2H), 3.80-3.60 (m, 2H), 3.21-3.12 (m, 2H), 3.01-2.96 (m, 1H), 2.31-2.16 (m, 1H), 2.16-2.08 (m, 1H), 1.91-1.80 (m, 2H), 1.68-1.53 (m, 2H), 2 NH exchanged with CD$_3$OD Compound 34: (3R)—N-(cyclobutylmethyl)-1-[6-[(4-imidazo[5,1-b]thiazol-3-yltriazol-1-yl)methyl] pyridazin-3-yl]piperidin-3-amine was Obtained Using General Scheme 1 Pathway A Stage 1: General Procedure E2 was used from 3-bromo-imidazo[5,1-b]thiazole to afford 2-imidazo[5,1-b]thiazol-3-ylethynyl(trimethyl)silane IM95 as pink oil: 35 mg, 31% yield, P=95%, retention time=2.3 min (gradient A), (M+H)+: 221.
Stage 2: General Procedure D1 was used from IM95 to afford 3-ethynylimidazo[5,1-b]thiazole IM96 as a yellow solid: 22 mg, 92% yield, P=93%, retention time=0.8 min (gradient A), (M+H)+: 149.
Stage 3: General Procedure B was used between IM45 and IM96 to afford tert-butyl N-(cyclobutylmethyl)-N-[(3R)-1-[6-[(4-imidazo[5,1-b]thiazol-3-yltriazol-1-yl) methyl]pyridazin-3-yl]-3-piperidyl]carbamate IM97 as yellow oil: 26 mg, 35% yield, P=92%, retention time=2.4 min (gradient A), (M+H)+: 550.
Stage 4: General Procedure A1 was used from IM97 to afford crude compound 34 as a yellow solid: 18 mg, 100% yield, P=94%, retention time=1.9 min (gradient A), (M+H)+: 450.
The product was further purified by reverse phase preparative HPLC purification (Waters XBridge C18 5 μm 19×100 mm). Gradient used: increased linearly from 5 to 40% solution "B" over 5.0 min, then increased linearly to 85% solution "B" over 1.5 min, and returned to initial conditions over 1.0 min. Flow Rate: 15 mL/min. P=100%. $^1$H NMR (300 MHz, CD$_3$OD) δ 8.77 (s, 1H), 8.62 (s, 1H), 7.44 (d, J=10.0 Hz, 2H), 7.24 (d, J=9.5 Hz, 1H), 7.13 (s, 1H), 5.81 (s, 2H), 4.45-4.35 (m, 1H), 4.16-4.05 (m, 1H), 3.31 (s, 2H), 3.10 (s, 1H), 2.91 (dd, J=12.8, 9.5 Hz, 1H), 2.78-2.55 (m, 3H), 2.45 (hept, J=7.6 Hz, 1H), 2.06 (dt, J=10.9, 5.5 Hz, 2H), 1.95-1.39 (m, 8H), 1H exchanged with CD$_3$OD.

Compound 35: 4-[1-[[6-[3-(2-azaspiro[3.3]heptan-2-yl)-1-piperidyl]pyridazin-3-yl]methyl] triazol-4-yl]-6-methoxy-1H-indazole was Obtained Using General Scheme 1 Pathway B Stage 1: General Procedure H$_2$ was used between 1-benzylpiperidin-3-one hydrochloride and 2-Azaspiro[3.3]heptane hemioxalate to afford 2-(1-benzyl-3-piperidyl)-2-azaspiro[3.3]heptane IM98 as yellow oil: 214 mg, 93% yield, P=95%, retention time=1.9 min (gradient A), (M+H)+: 271.
Stage 2: General Procedure L was used from IM98 to afford crude 2-(3-piperidyl)-2-azaspiro[3.3]heptane IM99 as pale yellow oil: 103 mg, 92% yield, P=95% ($^1$H-NMR).
Stage 3: General Procedure C was used between IM9 and IM99 to afford 4-[1-[[6-[3-(2-azaspiro[3.3]heptan-2-yl)-1-piperidyl]pyridazin-3-yl]methyl]triazol-4-yl]-6-methoxy-1- tetrahydropyran-2-yl-indazole IM100 as a yellow solid: 19 mg, 28% yield, P=95%, retention time=2.8 min (gradient A), (M+H)+: 684.

Stage 4: General Procedure A1 was used from IM100 to afford crude compound 35 as an off-white solid: 14 mg, 86% yield, P=96%, retention time=2.9 min (gradient B), (M+H)+: 486. $^1$H NMR (300 MHz, CD$_3$OD) δ 8.60 (s, 1H), 8.40 (s, 1H), 7.49 (d, J=9.5 Hz, 1H), 7.33-7.24 (m, 2H), 6.97 (s, 1H), 5.83 (s, 2H), 4.25-4.13 (m, 1H), 3.90 (s, 4H), 3.70 (s, 4H), 3.31-3.21 (m, 2H), 2.77 (s, 1H), 2.18 (t, J=7.7 Hz, 4H), 1.99-1.36 (m, 6H), 1H exchanged with CD$_3$OD.

The racemic mixture was further purified by chiral preparative HPLC purification using Chiralpak IA column (5 μm, 10×250 mm). Eluent used: ACN/MeOH/DEA: 95/5/0.1% at flow rate of 7 mL/min. First eluted enantiomer: P=100%, retention time=6.8 min, chiral HPLC: P=99.8%. Second eluted enantiomer: P=93%, retention time=8.9 min, chiral HPLC: P=97.6%.

Compound 36: N-(cyclobutylmethyl)-1-[5-[[4-(6-methoxy-1H-indazol-4-yl)triazol-1-yl]methyl]-1,3,4-thiadiazol-2-yl]piperidin-3-amine was Obtained Using General Scheme 1 Pathway A Stage 1: Ethyl 5-bromo-1,3,4-thiadiazole-2-carboxylate (50 mg, 0.20 mmol) was diluted in anhydrous DMSO (0.25 mL), and tert-butyl N-(cyclobutylmethyl)-N-[3-piperidyl] carbamate (80 mg, 0.30 mmol) was added, followed by triethylamine (83 μL, 0.60 mmol). The vial was sealed and mixture was heated to 90° C. for 15 min. Reaction mixture was cooled to rt, diluted in EtOAc (20 mL) and washed with NH$_4$Cl (20 mL). The resulting organic layer was dried over MgSO$_4$, filtered and concentrated under reduced pressure to afford colourless oil. The latter was purified by flash chromatography on silica gel (30% ethyl acetate in heptane) to afford ethyl 5-[3-[tert-butoxycarbonyl(cyclobutylmethyl) amino]-1-piperidyl]-1,3,4-thiadiazole-2-carboxylate IM101 as colourless oil: 66 mg, 78% yield, P=100% ($^1$H-NMR), retention time=3.2 min (gradient A), (M+H)+: 425.

Stage 2: IM101 (62 mg, 0.15 mmol) in Methanol (2 mL) was cooled to 0° C. and sodium borohydride (16 mg, 0.42 mmol) was added slowly. The reaction mixture was allowed to stir for 16 hours at room temperature. Reaction not complete according to HPLC-MS monitoring, so extra amount of sodium borohydride was added at rt every 3 h (4×16 mg, 0.42 mmol). The reaction mixture was then quenched with acetic acid (1 mL), and treated with sodium bicarbonate saturated solution (20 mL), extracted with ethyl acetate (2×50 mL), and washed with brine (10 mL). The organic layer was separated, dried over MgSO$_4$, filtered and evaporated under reduced pressure to afford crude tert-butyl N-(cyclobutylmethyl)-N-[1-[5-(hydroxymethyl)-1,3,4-thiadiazol-2-yl]-3-piperidyl]carbamate IM102 as colourless oil: 64 mg, 97% yield, P=96%, retention time=3.2 min (gradient A), (M+H)+: 425.

Stages 3 and 4: General Procedure P was used from IM102 to afford the desired crude mesylate, which was directly used (assuming 100% yield) in General Procedure N to afford crude tert-butyl N-[1-[5-(azidomethyl)-1,3,4-thiadiazol-2-yl]-3-piperidyl]-N-(cyclobutylmethyl) carbamate IM103 as brown oil: 70 mg, 99% yield, P=86%, retention time=3.2 min (gradient A), (M+H)+: 408.

Stage 5: General Procedure B was used between IM8 and IM103 to afford tert-butyl N-(cyclobutylmethyl)-N-[1-[5-[[4-(6-methoxy-1-tetrahydropyran-2-yl-indazol-4-yl)triazol-1-yl]methyl]-1,3,4-thiadiazol-2-yl]-3-piperidyl]carbamate IM104 as yellowish oil: 84 mg, 62% yield, P=84%, retention time=3.2 min (gradient A), (M+H)+: 664.

Stage 6: General Procedure A1 was used from IM104 to afford compound 36 as an off-white powder: 45 mg, 80% yield, P=91%, retention time=3.0 min (gradient B), (M+H)+: 480. $^1$H NMR (300 MHz, CD$_3$OD) δ 8.62 (s, 1H), 8.41 (d, J=1.0 Hz, 1H), 7.28 (d, J=2.1 Hz, 1H), 7.01-6.93 (m, 1H), 5.97 (s, 2H), 4.02-3.91 (m, 1H), 3.90 (s, 3H), 3.74-3.62 (m, 1H), 3.28-3.15 (m, 1H), 3.07 (dd, J=12.7, 9.2 Hz, 1H), 2.84-2.67 (m, 3H), 2.46 (hept, J=7.6 Hz, 1H), 2.07 (qt, J=7.8, 4.0 Hz, 2H), 1.94-1.39 (m, 8H), 2H exchanged with CD$_3$OD.

The racemic mixture was further purified by chiral preparative HPLC purification using Chiralpak ID column (5 μm, 10×250 mm). Eluent used: EtOAc/EtOH/DEA: 95/5/0.1% at flow rate of 6 mL/min. First eluted enantiomer: P=100%, retention time=10.3 min, chiral HPLC: P=99.4%. Second eluted enantiomer: P=95%, retention time=11.8 min, chiral HPLC: P=98.4%.

Compound 37: (3R)—N-(cyclobutylmethyl)-1-[6-[1-[4-(6-methoxy-1H-indazol-4-yl)triazol-1-yl]ethyl] pyridazin-3-yl]piperidin-3-amine was Obtained Using General Scheme 1 Pathway B Stage 1: General Procedure Q was used from 6-chloropyridazine-3-carbaldehyde to afford 1-(6-chloropyridazin-3-yl)ethanol IM105 as brownish oil: 60 mg, 54% yield, P=95% (215 nm), retention time=1.4 min (gradient A), (M+H)+: 159/161.

Stage 2: General Procedure M was used from IM105 to afford 3-(1-azidoethyl)-6-chloro-pyridazine IM106 as yellowish liquid: 42 mg, 59% yield, P=93% (215 nm), retention time=2.5 min (gradient A), (M+H)+: 184/186.

Stage 3: General Procedure B was used between IM8 and IM106 to afford 4-[1-[1-(6-chloropyridazin-3-yl)ethyl]triazol-4-yl]-6-methoxy-1-tetrahydropyran-2-yl-indazole IM107 as a white gum: 73 mg, 68% yield, P=87%, retention time=2.8 min (gradient A), (M+H)+: 440/442.

Stage 4: General Procedure C was used between IM3 and IM107 to afford tert-butyl N-(cyclobutylmethyl)-N-[(3R)-1-[6-[1-[4-(6-methoxy-1-tetrahydropyran-2-yl-indazol-4-yl) triazol-1-yl]ethyl]pyridazin-3-yl]-3-piperidyl]carbamate IM108 as a brownish gum: 80 mg, 66% yield, P=93%, retention time=4.7 min (gradient B), (M+H)+: 672.

Stage 5: General Procedure A1 was used from IM108 to afford crude compound 37 as a brownish foam: 48 mg, 94% yield, P=93%, retention time=2.2 min (gradient A), (M+H)+: 488.

The mixture of diastereomers was further purified by chiral preparative HPLC purification using Chiralpak IA column (5 μm, 10×250 mm). Eluent used: TBME/MeOH/DEA: 85/15/0.1% at flow rate of 6 mL/min. First eluted diastereoisomer: P=99%, retention time=7.3 min, chiral HPLC: P=98.3%, $^1$H NMR (300 MHZ, CD$_3$OD) δ 8.61 (s, 1H), 8.42 (d, J=1.0 Hz, 1H), 7.42 (d, J=9.6 Hz, 1H), 7.26 (d, J=2.0 Hz, 1H), 7.23 (d, J=9.6 Hz, 1H), 6.95 (d, J=1.9 Hz, 1H), 6.13 (q, J=7.1 Hz, 1H), 4.43-4.32 (m, 1H), 4.14-4.03 (m, 1H), 3.89 (s, 3H), 3.16-3.01 (m, 1H), 2.93 (dd, J=12.9, 9.3 Hz, 1H), 2.77-2.55 (m, 3H), 2.45 (hept, J=7.6 Hz, 1H), 2.14-1.24 (m, 13H), 1H exchanged with CD$_3$OD. Second eluted enantiomer: P=100%, retention time=10.8 min, chiral HPLC: P=99.3%, $^1$H NMR (300 MHz, CD$_3$OD) δ 8.61 (s, 1H), 8.42 (d, J=1.0 Hz, 1H), 7.43 (d, J=9.6 Hz, 1H), 7.27 (d, J=2.1 Hz, 1H), 7.24 (d, J=9.6 Hz, 1H), 7.00-6.92 (m, 1H), 6.13 (q, J=7.1 Hz, 1H), 4.44-4.33 (m, 1H), 4.13-4.02 (m, 1H), 3.89 (s, 3H), 3.17-3.04 (m, 1H), 2.95 (dd, J=12.9, 9.4

Hz, 1H), 2.80-2.58 (m, 3H), 2.46 (dt, J=15.3, 7.6 Hz, 1H), 2.14-1.24 (m, 13H), 2H exchanged with CD$_3$OD.

Compound 38: (3R,6S)—N-(cyclobutylmethyl)-1-[6-[[4-(5-methoxy-3-pyridyl)triazol-1-yl]methyl]pyridazin-3-yl]-6-methyl-piperidin-3-amine was Obtained Using General Scheme 1 Pathway B Synthesis of tert-butyl N-(cyclobutylmethyl)-N-[(3R,6S)-6-methyl-3-piperidyl]carbamate IM111: Stage 1: General Procedure H1 was used between cyclobutanecarboxaldehyde and (2S,5R)-5-amino-2-methyl-piperidine-1-carboxylic acid benzyl ester to afford crude benzyl (2S,5R)-5-(cyclobutylmethylamino)-2-methyl-piperidine-1-carboxylate IM109 as yellow oil: 349 mg, 34% yield, P=37% (215 nm), retention time=2.4 min (gradient A), (M+H)$^+$: 317. Stage 2: General Procedure J was used from IM109 to afford benzyl (2S,5R)-5-[tert-butoxycarbonyl(cyclobutylmethyl)amino]-2-methyl-piperidine-1-carboxylate IM110 as colourless oil: 160 mg, 85% yield, P=90% (215 nm), retention time=3.6 min (gradient A), (M+H)$^+$: 417. Stage 3: General Procedure L was used from IM110 to afford tert-butyl N-(cyclobutylmethyl)-N-[(3R,6S)-6-methyl-3-piperidyl]carbamate IM111 as colourless oil: 106 mg, 98% yield.

Synthesis of 3-chloro-6-[[4-(5-methoxy-3-pyridyl)triazol-1-yl]methyl]pyridazine IM112: Stage 4: General Procedure B was used between IM5 and IM44 to afford crude 3-chloro-6-[[4-(5-methoxy-3-pyridyl)triazol-1-yl]methyl]pyridazine IM112 as a yellow solid: 1.53 g, 80% yield, P=92%, retention time=2.4 min (gradient B), (M+H)$^+$: 303.

Stage 5: General Procedure C was used between IM111 and IM112 to afford tert-butyl N-(cyclobutylmethyl)-N-[(3R,6S)-1-[6-[[4-(5-methoxy-3-pyridyl)triazol-1-yl]methyl]pyridazin-3-yl]-6-methyl-3-piperidyl]carbamate IM113 as dark yellow oil: 36 mg, 37% yield, P=81%, retention time=2.5 min (gradient A), (M+H)$^+$: 549.

Stage 6: General Procedure A1 was used from IM113 to afford crude compound 38 dihydrochloride as dark yellow oil: 42 mg, 99% yield, P=83%, retention time=2.0 min (gradient B), (M+H)$^+$: 449.

The product was further purified by reverse phase preparative HPLC purification (Waters XBridge C18 5 μm 19×100 mm). Gradient used: increased linearly from 10 to 40% solution "B" over 5.5 min, increased linearly to 85% solution "B" over 1.0 min, and returned to initial conditions over 1.0 min. Flow Rate: 15 mL/min. P=98%. $^1$H NMR (300 MHz, CD$_3$OD) δ 8.62-8.50 (m, 2H), 8.20 (d, J=2.8 Hz, 1H), 7.83 (dd, J=2.8, 1.7 Hz, 1H), 7.43 (d, J=9.5 Hz, 1H), 7.23 (d, J=9.6 Hz, 1H), 5.79 (s, 2H), 4.68-4.57 (m, 1H), 4.56-4.44 (m, 1H), 3.93 (s, 3H), 2.82-2.67 (m, 3H), 2.67-2.39 (m, 2H), 2.11 (tt, J=7.8, 5.8 Hz, 2H), 1.99-1.42 (m, 8H), 1.20 (d, J=6.8 Hz, 3H), 1H exchanged with CD$_3$OD.

Compound 39: (R)-6-(3-((cyclobutylmethyl)amino) piperidin-1-yl)-3-((4-(6-methoxy-1H-indazol-4-yl)-1H-1,2,3-triazol-1-yl)methyl)pyridazin-4 (1H)-one was Obtained Using General Scheme 1 Pathway B Stage 1: To a solution of methyl 4,6-dichloropyridazine-3-carboxylate (207 mg, 980 μmol) and 4-methoxybenzyl alcohol (167 mg, 1.19 mmol) in MeCN (25 mL) was added cesiumcarbonate (387 mg, 1.18 mmol) and reaction mixture was stirred at rt for 18 h. The mixture was concentrated down and directly purified by C18 column (40 g column, 0-100% MeCN in AmB) to afford methyl 6-chloro-4-((4-methoxybenzyl)oxy)pyridazine-3-carboxylate IM114 as tan solid: 136 mg, 38% yield, P=84%, retention time=2.1 min (gradient C), (M+Na)$^+$: 331.

Stage 2: To a solution of IM114 (130 mg, 421 μmol) in THF (1.1 mL)/MeOH (217 μL) at 0° C. was added lithiumborohydride (2 N in THF, 526 μL, 1.05 mmol) and the mixture was stirred at rt for 1 h. The mixture was directly purified by C18 column (30 g, 0-100% MeCN in AmB, the product was eluted with 35% MeCN) to afford (6-chloro-4-((4-methoxybenzyl)oxy)pyridazin-3-yl)methanol as a white solid: 58 mg, 47% yield, P=95%, retention time=0.8 min (gradient C), (M+H)$^+$: 281.

Stage 3: General Procedure M was used from IM114 to afford 3-(azidomethyl)-6-chloro-4-((4-methoxybenzyl)oxy) pyridazine IM115 as a white solid: 30 mg, 50% yield, P=100%, retention time=1.6 min (gradient D), (M+H)$^+$: 306.

Stage 4: General Procedure B was used between IM8 and IM115 to afford 3 4-(1-((6-chloro-4-((4-methoxybenzyl)oxy)pyridazin-3-yl)methyl)-1H-1,2,3-triazol-4-yl)-6-methoxy-1-(tetrahydro-2H-pyran-2-yl)-1H-indazole IM116 as a tan solid: 43 mg, 89% yield, P=100%, retention time=1.3 min (gradient C), (M+H)$^+$: 562/564.

Stage 5: General Procedure C was used between IM116 and IM3 to afford tert-butyl (cyclobutylmethyl)((3R)-1-(6-((4-(6-methoxy-1-(tetrahydro-2H-pyran-2-yl)-1H-indazol-4-yl)-1H-1,2,3-triazol-1-yl)methyl)-5-((4-methoxybenzyl) oxy)pyridazin-3-yl)piperidin-3-yl)carbamate IM117 as a light brown film: 18 mg, 38% yield, P=98% (gradient C), (M+H)$^+$: 674.

Stage 6: General Procedure A2 was used from IM117 to afford compound 39 as a white powder: 7 mg, 52% yield, P=100%, retention time=2.0 min (gradient D), (M+H)$^+$: 490. $^1$H NMR (400 MHZ, CD$_3$OD) δ 8.59 (s, 1H), 8.39 (d, J=0.8 Hz, 1H), 7.27 (d, J=2.0 Hz, 1H), 6.96 (dd, J=1.8, 0.8 Hz, 1H), 6.06 (s, 1H), 5.69 (s, 2H), 3.91 (s, 3H), 3.90-3.85 (m, 1H), 3.74-3.62 (m, 1H), 3.11-3.00 (m, 1H), 2.95 (dd, J=12.9, 9.2 Hz, 1H), 2.83-2.69 (m, 3H), 2.56-2.41 (m, 1H), 2.15-1.98 (m, 3H), 1.96-1.58 (m, 6H), 1.50-1.41 (m, 1H), 3H exchanged with CD$_3$OD.

Compound 40: (3R)—N-(cyclobutylmethyl)-1-[5-[[4-(6-methoxy-1H-indazol-4-yl)triazol-1-yl] methyl]-2-pyridyl]piperidin-3-amine was Obtained Using General Scheme 1 Pathway A Stage 1: General Procedure C (in ACN) was used between 6-Fluoronicotinic acid methyl ester and IM3 to afford methyl 6-[(3R)-3-[tert-butoxycarbonyl(cyclobutylmethyl) amino]-1-piperidyl]pyridine-3-carboxylate IM118 as colourless oil: 261 mg, 74% yield, P=100%, retention time=2.8 min (gradient Z), (M+H)$^+$: 404.

Stage 2: IM118 (261 mg, 0.55 mmol) in anhydrous THF (3.2 mL) was cooled to 0° C. under argon atmosphere and then lithium borohydride (40 mg, 1.65 mmol) was added one shot. The reaction mixture was allowed to stir at rt and reaction progress was monitored by HPLC-MS. After 16 h, lithium borohydride (40 mg, 1.65 mmol) was added at 0° C. and reaction mixture was allowed to stir at rt for 21 h more. Reaction was quenched with water (5 mL) and concentrated under reduced pressure to afford a yellow paste. EtOAc (50 mL) was added, followed by water (10 mL). Layers were separated and organic layer was washed with water (2×10 mL), dried over MgSO$_4$, filtered and concentrated under reduced pressure to give 250 mg as pink oil. The latter was purified by flash chromatography on silica gel (n-heptane/ EtOAc: 1/0 to 4/1) to afford tert-butyl (R)-(cyclobutylmethyl)(1-(5-(hydroxymethyl)pyridin-2-yl)piperidin-3-yl)

carbamate IM119 as colourless oil: 206 mg, 100% yield, P=100%, retention time=2.4 min (gradient A), (M+H)⁺: 376.

Stage 3: General Procedure M was used from IM119 to afford tert-butyl N-[(3R)-1-[5-(azidomethyl)-2-pyridyl]-3-piperidyl]-N-(cyclobutylmethyl)carbamate IM120 as colourless oil: 142 mg, 56% yield, P=99%, retention time=2.6 min (gradient D), (M+H)⁺: 401.

Stage 4: General Procedure B was used between IM8 and IM120 to afford tert-butyl N-(cyclobutylmethyl)-N-[(3R)-1-[5-[[4-(6-methoxy-1-tetrahydropyran-2-yl-indazol-4-yl)triazol-1-yl]methyl]-2-pyridyl]-3-piperidyl]carbamate IM121 as a white solid: 107 mg, 80% yield, P=98%, retention time=2.7 min (gradient A), (M+H)⁺: 657.

Stage 6: General Procedure A1 was used from IM121 to afford compound 40 as a white powder: 50 mg, 70% yield, P=97%, retention time=2.8 min (gradient B), (M+H)⁺: 473. $^1$H NMR (300 MHz, CD$_3$OD) δ 8.65 (s, 1H), 8.51 (s, 1H), 8.40 (s, 1H), 7.27 (d, J=2.0 Hz, 1H), 6.97 (d, J=1.9 Hz, 1H), 6.51 (s, 2H), 5.49 (s, 1H), 4.32 (d, J=13.2 Hz, 1H), 3.90 (s, 4H), 3.12 (q, J=9.6 Hz, 2H), 2.92-2.78 (m, 3H), 2.57-2.43 (m, 1H), 2.17-2.05 (m, 2H), 2.02-1.42 (m, 8H), 2H exchanged with CD$_3$OD.

Compound 41: 6-[(3R)-3-(cyclobutylmethylamino)-1-piperidyl]-3-[[4-(6-methoxy-1H-indazol-4-yl)triazol-1-yl]methyl]pyrimidin-4-one was Obtained Using General Scheme 1 Pathway B Stage 1: General Procedure O1 was used from 6-Chloro-4-hydroxypyrimidine to afford 6-chloro-3-(chloromethyl)pyrimidin-4-one IM122 as pink oil: 152 mg, 78% yield, P=85%, retention time=2.2 min (gradient A), (M+H)⁺: 178/180.

Stage 2: General Procedure N was used from IM122 to afford 3-(azidomethyl)-6-chloro-pyrimidin-4-one IM123 as pink oil: 137 mg, 98% yield, P=80%, retention time=2.2 min (gradient A), (M+H)⁺: 186/188.

Stage 3: General Procedure B was used between IM8 and IM123 to afford 6-chloro-3-[[4-(6-methoxy-1-tetrahydropyran-2-yl-indazol-4-yl)triazol-1-yl]methyl]pyrimidin-4-one IM124 as a white solid: 77 mg, 83% yield, P=93%, retention time=2.7 min (gradient A), (M+H)⁺: 442/444.

Stage 4: General Procedure C was used between IM3 and IM124 to afford tert-butyl N-(cyclobutylmethyl)-N-[(3R)-1-[1-[[4-(6-methoxy-1-tetrahydropyran-2-yl-indazol-4-yl)triazol-1-yl]methyl]-6-oxo-pyrimidin-4-yl]-3-piperidyl]carbamate IM125 as yellow oil: 48 mg, 36% yield, P=97%, retention time=3.2 min (gradient A), (M+H)⁺: 674.

Stage 5: General Procedure A1 was used from IM125 to afford compound 41 as an off-white solid: 24 mg, 89% yield, P=96%, retention time=3.0 min (gradient B), (M+H)⁺: 490. $^1$H NMR (300 MHz, CD$_3$OD): δ 8.65 (s, 1H), 8.51 (s, 1H), 8.40 (s, 1H), 7.27 (d, J=2.0 Hz, 1H), 6.97 (d, J=1.9 Hz, 1H), 6.51 (s, 2H), 5.49 (s, 1H), 4.32 (d, J=13.2 Hz, 1H), 4.00-3.83 (m, 4H), 3.19-3.02 (m, 2H), 2.92-2.78 (m, 3H), 2.57-2.43 (m, 1H), 2.17-2.05 (m, 3H), 2.01-1.85 (m, 1H), 1.83-1.68 (m, 4H), 1.61-1.47 (s, 2H), 1H exchanged with CD$_3$OD.

Compound 42: (3R)—N-(cyclobutylmethyl)-1-[6-[[4-(6-methoxy-1H-indazol-4-yl)triazol-1-yl]_methyl]-3-pyridyl]piperidin-3-amine was Obtained Using General Scheme 1 Pathway A Stage 1: General Procedure S was used between IM3 and methyl 5-bromopicolinate to afford methyl 5-[(3R)-3-[tert-butoxycarbonyl(cyclobutylmethyl) amino]-1-piperidyl]pyridine-2-carboxylate IM126 as light yellow oil: 10.1 g, 82% yield, P=93% ($^1$H-NMR), retention time=2.7 min (gradient A), (M+H)⁺: 404.

Stage 2: To a solution of IM126 (1.21 g, 2.79 mmol) in anhydrous DCM (25 mL) under Ar atmosphere at −78° C. was added diisobutylaluminium hydride in DCM solution (1 N, 14 mL, 14 mmol) dropwise over 2 min to afford a yellow solution which was stirred at −78° C. for 5 min then allowed to stir at rt (cooling bath removed). After 1 h, the reaction mixture was cooled down to 0° C. (ice bath) and quenched by adding MeOH (3 mL), then stirred at rt for 10 min, then Rochelle's salt saturated solution (20 mL) was carefully added at rt to afford a jelly, which was vigorously stirred at rt and diluted with water (10 mL) and DCM (20 mL) to improve stirring. The mixture was stirred at rt for 30 min, then diluted again with water (20 mL), DCM (20 mL) and Rochelle's salt saturated solution (10 mL) and the mixture was vigorously stirred at rt for 16 h to afford 2 clear phases which were separated. The organic phase was extracted with DCM (2×40 mL), then combined organic phases were washed with water (20 mL), dried over MgSO$_4$, filtered and the filtrate was concentrated under reduced pressure to dryness to afford 1.164 g of crude brown oil. This material was purified by an automated flash system (liquid injection in DCM, 0 to 20% MeOH in DCM over 30 min, 30SIHP-24G, 20 mL/min) to afford tert-butyl N-(cyclobutylmethyl)-N-[(3R)-1-[6-(hydroxymethyl)-3-pyridyl]-3-piperidyl] carbamate IM127 as yellow oil: 504 mg, 47% yield, P=99%, retention time=2.5 min (gradient A), (M+H)⁺: 376.

Stage 3: General Procedure M was used from IM127 to afford tert-butyl N-[(3R)-1-[6-(azidomethyl)-3-pyridyl]-3-piperidyl]-N-(cyclobutylmethyl)carbamate IM128 as light yellow oil: 57 mg, 75% yield, P=97% ($^1$H-NMR), retention time=2.6 min (gradient A), (M+H)⁺: 401.

Stage 4: General Procedure B was used between IM8 and IM128 to afford tert-butyl N-(cyclobutylmethyl)-N-[(3R)-1-[6-[[4-(6-methoxy-1-tetrahydropyran-2-yl-indazol-4-yl)triazol-1-yl]methyl]-3-pyridyl]-3-piperidyl]carbamate IM129 as an off-white solid: 821 mg, 78% yield, P=95% ($^1$H-NMR), retention time=2.9 min (gradient A), (M+H)⁺: 657.

Stage 5: General Procedure A1 was used from IM129 to afford compound 42 as an off-white solid: 490 mg, 84% yield, P=94%, retention time=2.9 min (gradient B), (M+H)⁺: 473. $^1$H NMR (300 MHz, CD$_3$OD): δ 8.51 (s, 1H), 8.40 (s, 1H), 8.22 (d, J=2.3 Hz, 1H), 7.34 (dd, J=8.6, 2.7 Hz, 1H), 7.29 (d, J=8.6 Hz, 1H), 7.25 (d, J=2.3 Hz, 1H), 6.94 (s, 1H), 5.65 (s, 2H), 3.88 (s, 3H), 3.71 (q, J=9.0 Hz, 1H), 3.59-3.45 (m, 1H), 2.83 (td, J=11.5, 3.2 Hz, 1H), 2.74-2.59 (m, 4H), 2.45 (hept, J=7.3 Hz, 1H), 2.16-1.54 (m, 10H), 1H exchanged with CD$_3$OD.

Compound 43: N-(cyclobutylmethyl)-1-[2-[[4-(6-methoxy-1H-indazol-4-yl)triazol-1-yl]methyl]pyrimidin-5-yl]piperidin-3-amine was Obtained Using General Scheme 1 Pathway A Stage 1: General Procedure S was used between methyl 5-bromopyrimidine-2-carboxylate and IM79 to afford methyl 5-[3-[tert-butoxycarbonyl(cyclobutylmethyl) amino]-1-piperidyl]pyrimidine-2-carboxylate IM130 as an off-white solid: 150 mg, 42% yield, P=100% ($^1$H-NMR), retention time=3.0 min (gradient A), (M+H)⁺: 405.

Stage 2: IM130 (120 mg, 0.17 mmol) in anhydrous THF (1 mL) under argon atmosphere was cooled to 0° C. and then lithium borohydride (13 mg, 0.54 mmol) was added one shot. The reaction mixture was allowed to stir at rt for 1 h. Reaction mixture was then quenched with water (5 mL) and concentrated under reduced pressure to give a yellow paste. EtOAc (50 mL) was added to the paste followed by water (10 mL). Layers were separated and organic layer was washed with water (2×10 mL), dried over MgSO$_4$, filtered and concentrated under reduced pressure to afford 128 mg of yellow oil. The crude product was purified by flash chromatography on silica gel (n-heptane/EtOAc: 1/1 to 0/1+ MeOH) to afford tert-butyl N-(cyclobutylmethyl)-N-[1-[2-(hydroxymethyl)pyrimidin-5-yl]-3-piperidyl]carbamate IM131 as colourless oil: 27 mg, 24% yield, P=80%, retention time=2.6 min (gradient A), (M+H)$^+$: 377.

Stage 3: General Procedure M was used from IM131 to afford tert-butyl N-[1-[2-(azidomethyl)pyrimidin-5-yl]-3-piperidyl]-N-(cyclobutylmethyl)carbamate IM132 as colourless oil: 15 mg, 90% yield, P=100%, retention time=2.6 min (gradient A), (M+H)$^+$: 402.

Stage 4: General Procedure B was used between IM8 and IM132 to afford tert-butyl N-(cyclobutylmethyl)-N-[1-[2-[[4-(6-methoxy-1-tetrahydropyran-2-yl-indazol-4-yl)triazol-1-yl]methyl]pyrimidin-5-yl]-3-piperidyl]carbamate IM133 as a colourless film: 14 mg, 38% yield, P=94%, retention time=3.4 min (gradient A), (M+H)$^+$: 658.

Stage 5: General Procedure A1 was used from IM133 to afford compound 43 as a colourless film: 7 mg, 100% yield, P=93%, retention time=2.4 min (gradient A), (M+H)$^+$: 474.

The racemic mixture was further purified by chiral preparative HPLC purification using Chiralpak ID column (5 µm, 10×250 mm). Eluent used: DCM/MeOH/DEA: 95/5/0.1% at flow rate of 7 mL/min. First eluted enantiomer: P=96%, retention time=6.4 min, chiral HPLC: P=99.7%. Second eluted enantiomer: P=100%, retention time=7.5 min, chiral HPLC: P=99.9%. $^1$H NMR (300 MHz, CD$_3$OD): δ 8.59 (s, 1H), 8.47 (s, 2H), 8.40 (s, 1H), 7.28 (s, 1H), 6.97 (s, 1H), 5.81 (s, 2H), 3.91 (s, 3H), 3.81 (d, J=13.0 Hz, 1H), 3.58 (d, J=11.5 Hz, 1H), 3.19-2.88 (m, 5H), 2.66-2.52 (m, 1H), 2.22-1.51 (m, 10H), 1H exchanged with CD$_3$OD.

Compound 44: (3R)—N-(1-cyclobutylethyl)-1-[6-[[4-(6-methoxy-1H-indazol-4-yl)triazol-1-yl]methyl]pyridazin-3-yl]piperidin-3-amine was Obtained Using General Scheme 1 Pathway B General Procedure H1 was used between 1-cyclobutylethanone and IM74 to afford compound 44 as a white solid: 31 mg, 48% yield, P=94%, retention time=3.0 min (gradient B), (M+H)$^+$: 488. $^1$H NMR (300 MHZ, CDCl$_3$): δ 8.51 (s, 1H), 8.07 (s, 1H), 7.32 (d, J=9.5 Hz, 1H), 7.16 (d, J=1.9 Hz, 1H), 6.91 (d, J=9.5 Hz, 1H), 6.86 (s, 1H), 5.78 (s, 2H), 4.40 (d, J=10.4 Hz, 1H), 4.01 (d, J=13.2 Hz, 1H), 3.88 (s, 3H), 3.13 (t, J=11.8 Hz, 1H), 2.99 (br s, 1H), 2.80 (br s, 2H), 2.28-2.11 (m, 1H), 2.01-1.40 (m, 11H), 1.00 (d, J=6.1 Hz, 3H), NH exchanged.

Compound 45: (3R)—N-(1-cyclopropylethyl)-1-[6-[[4-(6-methoxy-1H-indazol-4-yl)triazol-1-yl]methyl]pyridazin-3-yl]piperidin-3-amine was Obtained Using General Scheme 1 Pathway B General Procedure H1 was used between 1-cyclopropylethanone and IM74 to afford crude compound 45 as colourless oil: 60 mg, 45% yield, P=44%, retention time=2.1 min (gradient A), (M+H)$^+$: 474.

The product was further purified by reverse phase preparative HPLC purification (Waters XBridge C18 5 µm 19×100 mm). Gradient used: increased linearly from 5 to 40% solution "B" over 6.0 min, increased linearly to 90% solution "B" over 1.0 min, and returned to initial conditions over 1.0 min. Flow Rate: 15 mL/min. P=100%.

The mixture of diastereomers was further purified by chiral preparative HPLC purification using Chiralpak ID column (5 µm, 10×250 mm). Eluent used: EtOAc/EtOH/DEA: 85/15/0.1% at flow rate of 7 mL/min. First eluted diastereomer: P=100%, retention time=9.8 min, chiral HPLC: P=98.9%, $^1$H NMR (300 MHz, CD$_3$OD): δ 8.59 (s, 1H), 8.40 (s, 1H), 7.48 (d, J=9.5 Hz, 1H), 7.28 (d, J=9.5 Hz, 1H), 7.27 (s, 1H), 6.97 (s, 1H), 5.83 (s, 2H), 4.51-4.35 (m, 1H), 3.98 (d, J=13.6 Hz, 1H), 3.90 (s, 3H), 3.24-3.08 (m, 3H), 2.49-2.37 (m, 1H), 2.14-2.00 (m, 1H), 1.85 (s, 1H), 1.62 (s, 2H), 1.27 (d, J=6.3 Hz, 3H), 0.88-0.16 (m, 5H), 1H exchanged with CD$_3$OD. Second eluted diastereomer: P=97%, retention time=10.8 min, chiral HPLC: P=99.1, $^1$H NMR (300 MHz, CD$_3$OD): δ 8.59 (s, 1H), 8.40 (s, 1H), 7.48 (d, J=9.4 Hz, 1H), 7.28 (d, J=9.4 Hz, 2H), 7.27 (s, 1H), 6.97 (s, 1H), 5.83 (s, 2H), 4.56 (d, J=12.4 Hz, 1H), 4.02 (d, J=13.3 Hz, 1H), 3.90 (s, 3H), 3.22-3.09 (m, 3H), 2.52-2.41 (m, 1H), 2.19-2.03 (m, 1H), 1.82 (s, 1H), 1.72-1.48 (m, 2H), 1.25 (d, J=6.9 Hz, 3H), 1.22-0.41 (m, 8H), 1H exchanged with CD$_3$OD.

Compound 46: N-(cyclobutylmethyl)-1-[5-[[4-(6-methoxy-1H-indazol-4-yl)triazol-1-yl]methyl]pyrimidin-2-yl]piperidin-3-amine was Obtained Using General Scheme 1 Pathway A Stage 1: A solution of methyl 2-chloropyrimidine-5-carboxylate (100 mg, 0.56 mmol) in DCM (1.4 mL) was added at rt to a solution of IM79 (157 mg, 0.58 mmol) and DIEA (240 µL, 1.37 mmol) under Argon flow. The mixture was stirred at room temperature for 2 hours. The reaction mixture was poured into water (25 mL) and extracted with DCM (2×25 mL). The organic layer was dried over MgSO$_4$, filtered and the solvent was evaporated under reduced pressure to afford 283 mg of crude yellowish oil. The crude product was purified by flash chromatography on silica gel (n-heptane/EtOAc: 4/1) to afford methyl 2-[3-[tert-butoxycarbonyl(cyclobutylmethyl)amino]-1-piperidyl]pyrimidine-5-carboxylate IM134 as colourless oil: 239 mg, 100% yield, P=99%, retention time=3.5 min (gradient A), (M+H)$^+$: 405.

Stage 2: Diisobutylaluminium hydride (1 N, 2.5 mL, 2.5 mmol) was added to a solution of IM134 (218 mg, 0.51 mmol) in anhydrous THF (5 mL) at −78° C. and reaction mixture was allowed to stir at rt and reaction progress was monitored by HPLC-MS. After 20 h, same amount of diisobutylaluminium hydride was added at −78° C. (reaction mixture then stirred at rt) and a 3rd portion 25 h later. The reaction mixture then stirred at rt for 72 h more. The reaction mixture was then diluted with diethyl ether (50 mL) and cooled to 0° C., water (0.3 mL) was added, followed by 1M aqueous sodium hydroxide (0.3 mL) and water (0.76 mL). The mixture was stirred at rt for 15 min, and MgSO$_4$ was added and stirred for 15 min, then filtered to remove salts, and concentrated under reduced pressure. The crude product was purified by flash chromatography on silica gel (n-heptane/EtOAc: 1/1) to afford tert-butyl N-(cyclobutylmethyl)-N-[1-[5-(hydroxymethyl)pyrimidin-2-yl]-3-piperidyl]carbamate IM135 as colourless crystals: 79 mg, 41% yield, P=99%, retention time=2.7 min (gradient A), (M+H)$^+$: 377.

Stages 3 and 4: General Procedure P was used from IM135 to afford the desired crude mesylate, which was directly used (assuming 100% yield) in General Procedure N to afford tert-butyl N-[1-[5-(azidomethyl)pyrimidin-2-yl]-3- piperidyl]-N-(cyclobutylmethyl)carbamate IM136 as orange oil: 68 mg, 82% yield, P=99%, retention time=3.3 min (gradient A), (M+H)$^+$: 402.

Stage 5: General Procedure B was used between IM8 and IM136 to afford tert-butyl N-(cyclobutylmethyl)-N-[1-[5-[[4-(6-methoxy-1-tetrahydropyran-2-yl-indazol-4-yl) triazol-1-yl]methyl]pyrazin-2-yl]-3-piperidyl]carbamate IM137 as a white solid: 108 mg, 87% yield, P=96%, retention time=3.4 min (gradient A), (M+H)$^+$: 658.

Stage 6: General Procedure A1 was used from IM137 to afford compound 46 as a yellow solid: 76 mg, 96% yield, P=92% (215 nm), retention time=3.2 min (gradient B), (M+H)$^+$: 474. $^1$H NMR (300 MHz, CD$_3$OD): δ 8.54 (s, 1H), 8.46 (s, 2H), 8.40 (s, 1H), 7.25 (d, J=1.9 Hz, 1H), 6.96 (s, 1H), 5.53 (s, 2H), 4.66-4.54 (m, 1H), 4.42-4.29 (m, 1H), 3.89 (s, 3H), 3.22-3.10 (m, 1H), 3.03 (dd, J=12.8, 9.2 Hz, 1H), 2.84-2.58 (m, 3H), 2.47 (hept, J=7.6 Hz, 1H), 2.14-1.37 (m, 10H), 1H exchanged with CD$_3$OD.

The racemic mixture was further purified by chiral preparative HPLC purification using Chiralpak ID column (5 μm, 10×250 mm). Eluent used: EtOAc/EtOH/DEA: 90/10/0.1% at flow rate of 7 mL/min. First eluted enantiomer: P=100%, retention time=9.8 min, chiral HPLC: P=100%. Second eluted enantiomer: P=96%, retention time=10.8 min, chiral HPLC: P=100%.

Compound 47: (3R)—N-(cyclobutylmethyl)-1-[5-[[4-(6-methoxy-1H-indazol-4-yl)triazol-1-yl]methyl] pyrazin-2-yl]piperidin-3-amine was Obtained Using General Scheme 1 Pathway A Stage 1: To a solution of IM79 (280 mg, 1.04 mmol) and Methyl 5-chloropyrazine-2-carboxylate (150 mg, 0.87 mmol) in anhydrous DMF (1 mL) under argon atmosphere at rt was added DIEA (310 μL, 1.74 mmol). The resulting mixture was stirred at rt for 1 h and the reaction was diluted with EtOAc (20 mL) and washed with NaHCO$_3$ saturated solution (2×10 mL), then dried over MgSO$_4$, filtered and concentrated under reduced pressure to dryness to afford a yellow oil. The crude product was purified by flash chromatography on silica gel (n-heptane/EtOAc: 1/1) to afford methyl 5-[3-[tert-butoxycarbonyl(cyclobutylmethyl) amino]-1-piperidyl]pyrazine-2-carboxylate IM138 as colourless oil: 295 mg, 84% yield, P=100%, retention time=3.2 min (gradient A), (M+H)$^+$: 405.

Stage 2: A solution of IM138 (253 mg, 0.6300 mmol) in anhydrous THF (2.2 mL) under argon atmosphere was cooled to 0° C. and then lithium borohydride (23 mg, 0.95 mmol) was added one shot. The reaction mixture was allowed to stir at rt for 4 h. Reaction was quenched with water (5 mL) and concentrated under reduced pressure to give a yellow paste. EtOAc (50 mL) was added to the paste followed by water (10 mL). Layers were separated and organic layer was washed with water (2×10 mL), dried over MgSO$_4$, filtered and concentrated under reduced pressure to afford 258 mg as yellow oil. The crude product was purified by flash chromatography on silica gel (n-heptane/EtOAc: 1/1 to 1/4) to afford tert-butyl N-(cyclobutylmethyl)-N-[1-[5-(hydroxymethyl)pyrazin-2-yl]-3-piperidyl]carbamate IM139 as colourless oil: 116 mg, 42% yield, P=100%, retention time=2.8 min (gradient A), (M+H)$^+$: 377.

Stage 3: General Procedure M was used from IM139 to afford tert-butyl N-[1-[5-(azidomethyl)pyrazin-2-yl]-3-piperidyl]-N-(cyclobutylmethyl)carbamate IM140 as yellow oil: 100 mg, 73% yield, P=97%, retention time=3.4 min (gradient A), (M+H)$^+$: 402.

Stage 4: General Procedure B was used between IM8 and IM140 to afford tert-butyl N-(cyclobutylmethyl)-N-[1-[5-[[4-(6-methoxy-1-tetrahydropyran-2-yl-indazol-4-yl)triazol-1-yl]methyl]pyrazin-2-yl]-3-piperidyl]carbamate IM141 as a white solid: 60 mg, 88% yield, P=96%, retention time=3.4 min (gradient A), (M+H)$^+$: 658.

Stage 5: General Procedure A1 was used from IM141 to afford compound 47 as a white powder: 40 mg, 95% yield, P=97%, retention time=3.1 min (gradient B), (M+H)$^+$: 474. $^1$H NMR (300 MHz, CD$_3$OD): δ 8.51 (s, 1H), 8.39 (s, 1H), 8.19 (s, 1H), 8.15 (s, 1H), 7.22 (d, J=1.9 Hz, 1H), 6.93 (s, 1H), 5.62 (s, 2H), 4.37-4.25 (m, 1H), 4.10-3.99 (m, 1H), 3.87 (s, 3H), 3.09-2.79 (m, 3H), 2.75-2.53 (m, 3H), 2.43 (hept, J=7.5 Hz, 1H), 2.07-1.37 (m, 10H), 1H exchanged with CD$_3$OD.

The racemic mixture was further purified by chiral preparative HPLC purification using Chiralpak ID column (5 μm, 10×250 mm). Eluent used: DCM/MeOH/DEA: 94/6/0.1% at flow rate of 7 mL/min. First eluted enantiomer: P=97%, retention time=6.3 min, chiral HPLC: P=96.4%. Second eluted enantiomer: P=98%, retention time=7.6 min, chiral HPLC: P=97.1%.

Compound 48: 3-[1-[[6-[(3R)-3-(cyclobutylmethylamino)-1-piperidyl]pyridazin-3-yl]methyl]triazol-4-yl]-2H-isoquinolin-1-one was Obtained Using General Scheme 1 Pathway A Stage 1: 3-chloroisoquinolin-1-ol (250 mg, 1.32 mmol) was dissolved into anhydrous DMF (2.6 mL) at rt and potassium carbonate (400 mg, 2.89 mmol) was added, followed by 4-methoxybenzyl bromide (370 mg, 1.84 mmol). Reaction mixture was heated to 80° C. for 2 h and then diluted with EtOAc (30 mL) and washed with water (3×10 mL), followed by brine (10 mL). Resulting organic layer was dried over MgSO$_4$, filtered, and concentrated under reduced pressure to dryness to give 386 mg as light brown oil. The crude product was purified by flash chromatography on silica gel (n-heptane/EtOAc: 1/0 to 4/1) to afford 3-chloro-2-[(4-methoxyphenyl)methyl]isoquinolin-1-one IM142 as colourless oil: 260 mg, 58% yield, P=95%, retention time=3.1 min (gradient A), (M+Na)$^+$: 322/324.

Stage 2: To a solution of IM42 (123 mg, 0.36 mmol) in anhydrous toluene (3.6 mL, previously degassed) were added 1-tributylstannyl-2-trimethylsilylacetylene (450 μL, 1.08 mmol) and dichlorobis(triphenylphosphine)palladium (13 mg, 0.02 mmol). The resulting mixture was heated to reflux for 5 days. Reaction was then cooled to rt and concentrated under reduced pressure to dryness to afford black oil. The crude product was purified by flash chromatography on silica gel (n-heptane/EtOAc: 1/0 to 9/1) to afford 2-[(4-methoxyphenyl)methyl]-3-(2-trimethylsilylethynyl)isoquinolin-1-one IM143 as brown oil: 68 mg, 33% yield, P=71%, retention time=3.4 min (gradient A), (M+H)$^+$: 362.

Stage 3: General Procedure D1 was used from IM143 to afford 3-ethynyl-2-[(4-methoxyphenyl)methyl]isoquinolin-1-one IM144 as a yellow solid: 27 mg, 71% yield, P=95%, retention time=2.8 min (gradient A), (M+H)$^+$: 290.

Stage 4: General Procedure B was used between IM39 and IM144 to afford tert-butyl N-(cyclobutylmethyl)-N-[(3R)-1-[6-[[4-[2-[(4-methoxyphenyl)methyl]-1-oxo-3-isoquinolyl] triazol-1-yl]methyl]pyridazin-3-yl]-3-piperidyl] carbamate IM145 as a yellow foam: 40 mg, 32% yield, P=98%, retention time=2.8 min (gradient A), (M+H)$^+$: 691.

Stage 5: General Procedure A2 was used from IM145 to afford compound 48 as an off-white powder: 15 mg, 97% yield, P=89%, retention time=2.2 min (gradient A), (M+H)⁺: 471.

The product was further purified by reverse phase preparative HPLC purification (Waters XBridge C18 5 μm 19×100 mm). Gradient used: increased linearly from 25 to 50% solution "B" over 6.5 min, increased linearly to 85% solution "B" over 1.5 min, and returned to initial conditions over 1.0 min. Flow Rate: 15 mL/min. P=100%. $^1$H NMR (300 MHz, CDCl$_3$): δ 8.40 (d, J=8.0 Hz, 1H), 8.35 (s, 1H), 7.66 (ddd, J=8.0, 6.9, 1.3 Hz, 1H), 7.58-7.46 (2H), 7.28 (d, J=9.4 Hz, 1H), 6.90 (d, J=9.4 Hz, 1H), 6.89 (s, 1H), 5.76 (s, 2H), 4.42-4.31 (m, 1H), 4.16-4.03 (m, 1H), 3.20-3.04 (m, 1H), 2.90 (dd, J=12.8, 9.3 Hz, 1H), 2.78-2.58 (m, 3H), 2.41 (hept, J=7.5 Hz, 1H), 2.10-1.77 (m, 6H), 1.71-1.36 (m, 4H), NH exchanged.

Compound 49: N-(cyclobutylmethyl)-1-[2-[[4-(6-methoxy-1H-indazol-4-yl)triazol-1-yl]methyl]thiazol-5-yl]piperidin-3-amine was Obtained Using General Scheme 1 Pathway A Stage 1: General Procedure S was used between IM79 and methyl 5-bromo-1,3-thiazole-2-carboxylate to afford 2 methyl 5-[3-[tert-butoxycarbonyl(cyclobutylmethyl) amino]-1-piperidyl]thiazole-2-carboxylate IM146 as orange oil: 443 mg, 89% yield, P=88% ($^1$H-NMR), retention time=3.3 min (gradient A), (M+H)⁺: 410.

Stage 2: Diisobutylaluminium hydride (1 N in THF, 2.39 mL, 2.39 mmol) was added to a solution of IM146 (97 mg, 0.24 mmol) in anhydrous THF (2.5 mL) at −78° C. and reaction mixture was allowed to stir at rt for 14 h. The reaction mixture was then diluted with diethyl ether (20 mL) and cooled to 0° C., water (0.1 mL) was added, followed by 1 N aqueous sodium hydroxide solution (0.1 mL) and water (0.25 mL). The mixture was stirred at rt for 15 min, and MgSO$_4$ was added and stirred for 15 min, then filtered to remove salts, rinsed thoroughly with AcOEt (150 mL) and concentrated under reduced pressure. The crude product was purified by flash chromatography on silica gel (2.5% MeOH in DCM) to afford tert-butyl N-(cyclobutylmethyl)-N-[1-[2-(hydroxymethyl)thiazol-5-yl]-3-piperidyl]carbamate IM147 as yellow oil: 69 mg, 73% yield, P=95%, retention time=2.7 min (gradient A), (M+H)⁺: 382.

Stages 3 and 4: General Procedure P was used from IM147 to afford the desired crude mesylate, which was directly used (assuming 100% yield) in General Procedure N to afford tert-butyl N-[1-[2-(azidomethyl)thiazol-5-yl]-3-piperidyl]-N-(cyclobutylmethyl)carbamate IM148 as brown oil: 50 mg, 61% yield, P=90% ($^1$H-NMR), retention time=3.3 min (gradient A), (M+H)⁺: 407.

Stage 5: General Procedure B was used between IM8 and IM148 to afford tert-butyl N-(cyclobutylmethyl)-N-[1-[2-[[4-(6-methoxy-1-tetrahydropyran-2-yl-indazol-4-yl)triazol-1-yl]methyl]thiazol-5-yl]-3-piperidyl]carbamate IM149 as brown oil: 63 mg, 81% yield, P=87% ($^1$H-NMR), retention time=3.4 min (gradient A), (M+Na+MeCN+2H)⁺: 364.

Stage 6: General Procedure A1 was used from IM149 to afford compound 49 as a brown solid: 39 mg, 56% yield, P=63%, retention time=3.1 min (gradient B), (M+2H)⁺: 240.

The product was further purified by reverse phase preparative HPLC purification (Waters XBridge C18 5 μm 19×100 mm). Gradient used: increased linearly from 30 to 50% solution "B" over 5.0 min, increased linearly to 51% solution "B" over 0.3 min, increased linearly to 85% solution "B" over 1.2 min, held at 85% for 0.2 min, and returned to initial conditions over 0.8 min. Flow Rate: 15 mL/min. P=98%. $^1$H NMR (300 MHZ, CD$_3$OD): δ 8.57 (s, 1H), 8.41 (s, 1H), 7.28 (d, J=2.0 Hz, 1H), 6.97 (br s, 1H), 6.95 (s, 1H), 5.84 (s, 2H), 3.90 (s, 3H), 3.47 (d, J=8.0 Hz, 1H), 2.95-2.80 (m, 1H), 2.77-2.61 (m, 4H), 2.45 (hept, J=7.6 Hz, 1H), 2.14-1.64 (m, 10H), 1H exchanged with CD$_3$OD.

Compound 50: 4-[(3R)-3-(cyclobutylmethylamino)-1-piperidyl]-1-[1-[4-(6-methoxy-1H-indazol-4-yl)triazol-1-yl]ethyl]pyridin-2-one was Obtained Using General Scheme 1 Pathway B Stage 1: General Procedure O2 was used from 4-chloro-2-hydroxypyridine to afford 4-chloro-1-(1-chloroethyl)pyridin-2-one IM150 as orange oil: 15.4 g, 91% yield, P=85% ($^1$H-NMR), retention time=2.5 min (gradient A), (M+H)⁺: 192/194.

Stage 2: General Procedure N was used from IM150 to afford 1-(1-azidoethyl)-4-chloro-pyridin-2-one IM151 as yellowish liquid: 300 mg, 92% yield, P=100% (215 nm), retention time=2.5 min (gradient A), (M+H)⁺: 199/201.

Stage 3: General Procedure B was used between IM8 and IM151 to afford 4-chloro-1-[1-[4-(6-methoxy-1-tetrahydropyran-2-yl-indazol-4-yl)triazol-1-yl]ethyl]pyridin-2-one IM152 as a pale beige foam: 193 mg, 96% yield, P=91% (215 nm), retention time=4.6 min (gradient B), (M+H)⁺: 455/457.

Stage 4: General Procedure C was used between IM3 and IM152 to afford crude tert-butyl N-(cyclobutylmethyl)-N-[(3R)-1-[1-[1-[4-(6-methoxy-1-tetrahydropyran-2-yl-indazol-4-yl)triazol-1-yl]ethyl]-2-oxo-4-pyridyl]-3-piperidyl] carbamate IM153 as a brownish gum: 177 mg, 100% yield, P=92%, retention time=3.2 min (gradient A), (M+H)⁺: 687.

Stage 5: General Procedure A1 was used from IM153 to afford crude compound 50 as a beige foam: 80 mg, 76% yield, P=96%, retention time=2.2 min (gradient A), (M+H)⁺: 503.

The mixture of diastereomers was further purified by chiral preparative HPLC purification using Chiralpak IE column (5 μm, 10×250 mm). Eluent used: TBME/MeOH/DEA: 60/40/0.1% at flow rate of 7 mL/min. First eluted diastereomer: P=100%, retention time=8.1 min, chiral HPLC: P=94.7%, $^1$H NMR (300 MHz, CDCl$_3$): δ 8.51 (s, 1H), 8.38 (s, 1H), 7.67 (q, J=6.9 Hz, 1H), 7.48 (d, J=8.1 Hz, 1H), 7.21 (d, J=1.6 Hz, 1H), 6.83 (s, 1H), 5.99 (dd, J=8.1, 2.4 Hz, 1H), 5.71 (d, J=2.3 Hz, 1H), 3.81 (s, 3H), 3.74 (d, J=11.7 Hz, 1H), 3.58 (d, J=13.2 Hz, 1H), 2.96-2.81 (m, 1H), 2.76-2.51 (m, 4H), 2.36 (hept, J=7.6 Hz, 1H), 2.18 (d, J=7.0 Hz, 3H), 2.11-1.50 (m, 9H), 1.41-1.22 (m, 1H), NH exchanged. Second eluted diastereomer: P=100%, retention time=11.8 min, chiral HPLC: P=100%, $^1$H NMR (300 MHz, CDCl$_3$): δ 8.51 (s, 1H), 8.38 (s, 1H), 7.67 (q, J=6.8 Hz, 1H), 7.48 (d, J=8.1 Hz, 1H), 7.20 (s, 1H), 6.83 (s, 1H), 5.98 (dd, J=8.2, 3.0 Hz, 1H), 5.71 (d, J=2.9 Hz, 1H), 3.80 (s, 3H), 3.74 (d, J=12.9 Hz, 1H), 3.58 (d, J=13.0 Hz, 1H), 2.89 (t, J=11.1 Hz, 1H), 2.77-2.53 (m, 4H), 2.38 (hept, J=7.6 Hz, 1H), 2.18 (d, J=6.9 Hz, 3H), 2.08-1.40 (m, 9H), 1.41-1.22 (m, 1H), NH exchanged.

Compound 51: N-[1-[6-[(3R)-3-(cyclobutylmethyl-amino)-1-piperidyl]pyridazin-3-yl]ethyl]-4-oxo-pyrido[1,2-a]pyrimidine-2-carboxamide was Obtained Using General Scheme 2 Pathway A Stage 1: General Procedure R was used from IM106 to afford crude 1-(6-chloropyridazin-3-yl)ethanamine IM154 as orange oil: 51 mg, 66% yield, P=98% (¹H-NMR), retention time=0.3 and 0.6 min (gradient A), (M+H)⁺: 158.

Stage 2: General Procedure F was used between 4-oxopyrido[1,2-a]pyrimidine-2-carboxylic acid hydrochloride and IM154 to afford crude N-[1-(6-chloropyridazin-3-yl)ethyl]-4-oxo-pyrido[1,2-a]pyrimidine-2-carboxamide IM155 as yellow oil: 61 mg, 52% yield, P=90%, retention time=2.4 min (gradient A), (M+H)⁺: 330.

Stage 3: General Procedure C was used between IM3 and IM155 to afford tert-butyl N-(cyclobutylmethyl)-N-[(3R)-1-[6-[1-[(4-oxopyrido[1,2-a]pyrimidine-2-carbonyl)amino]ethyl] pyridazin-3-yl]-3-piperidyl]carbamate IM156 as brown oil: 159 mg, 96% yield, P=57% (¹H-NMR), retention time=2.5 min (gradient A), (M+H)⁺: 562.

Stage 4: General Procedure A1 was used from IM156 to afford compound 51 as a brown solid: 74 mg, 75% yield, P=80%, retention time=2.0 min (gradient A), (M+H)⁺: 462.

The product was further purified by reverse phase preparative HPLC purification (Waters XBridge C18 5 μm 19×100 mm). Gradient used: increased linearly from 15 to 50% solution "B" over 5.0 min, increased linearly to 85% solution "B" over 1.5 min, and returned to initial conditions over 1.0 min. Flow Rate: 15 mL/min. P=100%.

The mixture of diastereomers was further purified by chiral preparative HPLC purification using Chiralpak IA column (5 μm, 10×250 mm). Eluent used: TBME/MeOH/DEA: 75/25/0.1% at flow rate of 7 mL/min. First eluted diastereomer: P=100%, retention time=6.6 min, chiral HPLC: P=99.1%, ¹H NMR (300 MHz, CD₃OD): δ 9.08 (d, J=7.2 Hz, 1H), 8.01 (dd, J=9.0, 7.2 Hz, 1H), 7.87 (d, J=9.0 Hz, 1H), 7.46 (d, J=9.5 Hz, 1H), 7.41 (t, J=7.2 Hz, 1H), 7.25 (d, J=9.5 Hz, 1H), 7.07 (s, 1H), 5.30 (q, J=7.0 Hz, 1H), 4.44-4.32 (m, 1H), 4.15-4.04 (m, 1H), 3.08 (t, J=12.0 Hz, 1H), 2.91 (dd, J=12.8, 9.4 Hz, 1H), 2.81-2.59 (m, 3H), 2.48 (hept, J=7.6 Hz, 1H), 2.18-2.00 (m, 3H), 2.00-1.35 (m, 10H), 2H exchanged with CD₃OD. Second eluted diastereomer: P=100%, retention time=7.2 min, chiral HPLC: P=97.3%, ¹H NMR (300 MHz, CD₃OD): δ 9.07 (d, J=7.1 Hz, 1H), 8.01 (dd, J=8.9, 7.1 Hz, 1H), 7.86 (d, J=8.9 Hz, 1H), 7.46 (d, J=9.5 Hz, 1H), 7.40 (t, J=7.1 Hz, 1H), 7.24 (d, J=9.5 Hz, 1H), 7.06 (s, 1H), 5.30 (q, J=7.0 Hz, 1H), 4.41-4.30 (m, 1H), 4.15-4.03 (m, 1H), 3.13-3.00 (m, 1H), 2.91 (dd, J=12.7, 9.5 Hz, 1H), 2.81-2.58 (m, 3H), 2.48 (hept, J=7.5 Hz, 1H), 2.18-1.34 (m, 13H), 2H exchanged with CD₃OD.

Compound 52: 6-[[4-(6-methoxy-1H-indazol-4-yl)triazol-1-yl]methyl]-3-[3-(cyclobutyl methylamino)-1-piperidyl]-1H-pyridin-2-one was Obtained Using General Scheme 1 Pathway A Stage 1: Silver carbonate (1.9 g, 6.89 mmol) and benzylbromide (1 mL, 8.32 mmol) were added to a solution of methyl 5-bromo-6-oxo-1,6-dihydropyridine-2-carboxylate (994 mg, 4.2 mmol) in anhydrous toluene (23 mL) and stirred at 40° C. for 6 h under argon. The reaction mixture was filtered through Celite, rinsed with toluene (5 mL) and the filtrate concentrated under reduced pressure to dryness. The crude product was purified by flash chromatography on silica gel (n-heptane/EtOAc: 9/1) to afford methyl 6-benzyloxy-5-bromo-pyridine-2-carboxylate IM157 as colourless oil: 1.32 g, 98% yield, P=99%, retention time=3.1 min (gradient A), (M+H)⁺: 321/323.

Stage 2: General Procedure S was used between IM157 and IM79 (209 mg, 0.78 mmol) to afford methyl 6-benzyloxy-5-[3-[tert-butoxycarbonyl(cyclobutylmethyl)amino]-1-piperidyl] pyridine-2-carboxylate IM158 as a white gum: 333 mg, 85% yield, P=97% (¹H-NMR), retention time=3.7 min (gradient A), (M+H)⁺: 510.

Stage 3: Diisobutylaluminium hydride (1 N in THF, 5.2 mL, 5.2 mmol) was added to a solution of IM158 (282 mg, 0.53 mmol) in anhydrous THF (5 mL) at −78° C. and reaction mixture was allowed to stir at rt. After 14 h, diisobutylaluminium hydride (1 N in THF, 2.6 mL, 2.6 mmol) was further added at −78° C. and reaction mixture was allowed to stir at rt for 6 h (complete conversion by HPLC-MS). The reaction mixture was then diluted with diethyl ether (50 mL) and cooled to 0° C., water (0.3 mL) was added, followed by 1 N aqueous sodium hydroxide solution (0.3 mL) and water (0.8 mL). The mixture was stirred at rt for 15 min, and MgSO₄ was added and stirred for 15 min, then filtered to remove salts, rinsed thoroughly with AcOEt (150 mL) and concentrated under reduced pressure. The crude product was purified by flash chromatography on silica gel (n-heptane/EtOAc: 7/3) to afford tert-butyl N-[1-[2-benzyloxy-6-(hydroxymethyl)-3-pyridyl]-3-piperidyl]-N-(cyclobutylmethyl)carbamate IM159 as a white gum: 254 mg, 97% yield, P=97% (¹H-NMR), retention time=3.0 min (gradient A), (M+H)⁺: 482.

Stage 4: General Procedure M was used from IM159 to afford crude tert-butyl N-[1-[6-(azidomethyl)-2-benzyloxy-3-pyridyl]-3-piperidyl]-N-(cyclobutylmethyl)carbamate IM160 as a white gum: 271 mg, 100% yield, P=84% (215 nm), retention time=3.6 min (gradient A), (M+H)⁺: 507.

Stage 5: General Procedure B was used between IM8 and IM160 to afford tert-butyl N-[1-[2-benzyloxy-6-[[4-(6-methoxy-1-tetrahydropyran-2-yl-indazol-4-yl)triazol-1-yl]methyl]-3-pyridyl]-3-piperidyl]-N-(cyclobutylmethyl)carbamate IM161 as a white foam: 305 mg, 83% yield, P=95% (¹H-NMR), retention time=3.5 min (gradient A), (M+H)⁺: 763.

Stage 6: General Procedure L was used from IM161 to afford tert-butyl N-(cyclobutylmethyl)-N-[1-[2-hydroxy-6-[[4-(6-methoxy-1-tetrahydropyran-2-yl-indazol-4-yl)triazol-1-yl]methyl]-3-pyridyl]-3-piperidyl]carbamate IM162 as an off-white foam: 258 mg, 99% yield, P=100% (215 nm), retention time=2.9 min (gradient A), (M+H)⁺: 673.

Stage 7: General Procedure A1 was used from IM162 to afford compound 52 as a white solid: 175 mg, 91% yield, P=95%, retention time=3.1 min (gradient B), (M+H)⁺: 489. ¹H NMR (300 MHz, CD₃OD): δ 8.53 (s, 1H), 8.39 (s, 1H), 7.27 (s, 1H), 6.97 (s, 1H), 6.88 (d, J=7.5 Hz, 1H), 6.32 (d, J=7.5 Hz, 1H), 5.53 (s, 2H), 3.90 (s, 3H), 3.62-3.51 (m, 1H), 3.29-3.21 (m, 1H), 2.88-2.78 (m, 1H), 2.78-2.65 (m, 3H), 2.61-2.43 (m, 2H), 2.09 (d, J=8.3 Hz, 2H), 2.00-1.61 (m, 8H), 1H exchanged with CD₃OD.

The racemic mixture was further purified by chiral preparative HPLC purification using Chiralpak IA column (5 μm, 20×250 mm). Eluent used: EtOAc/EtOH/DEA: 90/10/0.1% at flow rate of 20 mL/min. First eluted enantiomer: P=95%, retention time=7.4 min, chiral HPLC: P=99.4%. Second eluted enantiomer: P=96%, retention time=11.2 min, chiral HPLC: P=99.2%.

Compound 53: N-(cyclobutylmethyl)-1-[6-[[4-(5-methoxy-3-pyridyl)triazol-1-yl]methyl] pyridazin-3-yl]-3-methyl-piperidin-3-amine was Obtained Using General Scheme 1 Pathway B Stage 1: General Procedure C was used between IM112 and tert-butyl n-(3-methylpiperidin-3-yl)carbamate to afford crude tert-butyl N-[1-[6-[[4-(5-methoxy-3-pyridyl)triazol-1-yl]methyl]pyridazin-3-yl]-3-methyl-3-piperidyl]carbamate IM163 as a brown solid: 58 mg, 91% yield, P=95%, retention time=2.2 min (gradient A), (M+H)+: 481.

Stage 2: General Procedure A1 was used from IM163 to afford crude 1-[6-[[4-(5-methoxy-3-pyridyl)triazol-1-yl]methyl]pyridazin-3-yl]-3-methyl-piperidin-3-amine dihydrochloride IM164 as a brown solid: 76 mg, 99% yield, retention time=1.8 min (gradient A), (M+H)+: 381.

Stage 3: General Procedure $H_2$ was used between Cyclobutanecarboxaldehyde and IM164 to afford crude compound 53 as a brown solid: 42 mg, 40% yield, P=52%, retention time=1.9 min (gradient A), (M+H)+: 449.

The product was further purified by reverse phase preparative HPLC purification (Waters XBridge C18 5 μm 19×100 mm). Gradient used: increased linearly from 25 to 40% solution "B" over 5.5 min, increased linearly to 85% solution "B" over 1.0 min, and returned to initial conditions over 1.0 min. Flow Rate: 15 mL/min. P=100%. $^1$H NMR (300 MHz, CD$_3$OD): δ 8.58 (s, 1H), 8.53 (s, 1H), 8.20 (d, J=2.7 Hz, 1H), 7.83 (s, 1H), 7.44 (d, J=9.5 Hz, 1H), 7.27 (d, J=9.5 Hz, 1H), 5.78 (s, 2H), 3.93 (s, 3H), 3.84 (s, 1H), 3.80 (s, 1H), 3.48-3.33 (m, 1H), 3.30-3.24 (m, 1H), 2.57 (d, J=7.2 Hz, 2H), 2.31 (hept, J=7.6 Hz, 1H), 2.04-1.91 (m, 2H), 1.83-1.39 (m, 8H), 1.09 (s, 3H), 1H exchanged with CD$_3$OD.

The mixture of enantiomers was further purified by chiral preparative HPLC purification using Chiralpak IA column (5 μm, 10×250 mm). Eluent used: TBME/MeOH/DEA: 65/35/0.1% at flow rate of 6 mL/min. First eluted enantiomer: P=100%, retention time=7.6 min, chiral HPLC: P=97.9%. Second eluted enantiomer: P=100%, retention time=10.6 min, chiral HPLC: P=98.7%.

Compound 54: 5-fluoro-1-[[4-(6-methoxy-1H-indazol-4-yl)triazol-1-yl]methyl]-4-[3-(cyclobutylmethylamino)-1-piperidyl]pyridin-2-one was Obtained Using General Scheme 1 Pathway A Stage 1: General Procedure C (in DMSO instead of NMP, at 100° C.) was used between IM79 and 5-fluoro-4-iodo-1H-pyridin-2-one to afford tert-butyl N-(cyclobutylmethyl)-N-[1-(5-fluoro-2-oxo-1H-pyridin-4-yl)-3-piperidyl]carbamate IM165 as an off-white solid: 207 mg, 64% yield, P=98% (215 nm), retention time=2.7 min (gradient A), (M+H)+: 380.

Stage 2: To a solution of formaldehyde (37% in water, 1.0 mL, 13.43 mmol) in DMF (1.3 mL) were added triethylamine (0.37 mL, 2.63 mmol) and IM165 (100 mg, 0.26 mmol). The mixture was heated at 80° C. and reaction progress monitored by HPLC-MS. After 16 h, extra formaldehyde (37% in water, 1.0 mL, 13.43 mmol) and triethylamine (0.37 mL, 2.63 mmol) were added and the mixture was further stirred at 110° C. for 2 days, at which point both reagents were added again. After further 3 days at 110° C., the reaction mixture was allowed to cool to rt, diluted with AcOEt (50 mL), and rinsed with water (50 mL). The aqueous layer was extracted with AcOEt (50 mL). The combined organic layers were dried over MgSO$_4$, filtered and concentrated under reduced pressure to afford a colorless oil. The crude product was purified by an automated flash system (liquid injection in DCM, DCM over 1 min, 0 to 10% MeOH in DCM over 25 min, 30SIHP-12G, 20 mL/min) to afford tert-butyl N-(cyclobutylmethyl)-N-[1-[5-fluoro-1-(hydroxymethyl)-2-oxo-4-pyridyl]-3-piperidyl]carbamate IM166 as colourless oil: 98 mg, 45% yield, P=49% (215 nm), retention time=2.8 min (gradient A), (M+H)+: 380.

Stage 3: General Procedure M was used from IM166 to afford tert-butyl N-[1-[1-(azidomethyl)-5-fluoro-2-oxo-4-pyridyl]-3-piperidyl]-N-(cyclobutylmethyl)carbamate IM167 as colourless oil: 20 mg, 39% yield, P=100% (215 nm), retention time=3.1 min (gradient A), (M+H)+: 435.

Stage 5: General Procedure B was used between IM8 and IM167 to afford tert-butyl N-(cyclobutylmethyl)-N-[1-[5-fluoro-1-[[4-(6-methoxy-1-tetrahydropyran-2-yl-indazol-4-yl) triazol-1-yl]methyl]-2-oxo-4-pyridyl]-3-piperidyl]carbamate IM168 as a colourless glass: 25 mg, 79% yield, P=100% (215 nm), retention time=3.2 min (gradient A), (M+H)+: 691.

Stage 6: General Procedure A1 was used from IM168 to afford compound 54 as a yellowish glass: 17 mg, 83% yield, P=80%, retention time=2.2 min (gradient B), (M+H)+: 507. $^1$H NMR (300 MHz, CDCl$_3$): δ 8.52 (s, 1H), 8.36 (s, 1H), 7.21 (s, 2H), 6.79 (s, 1H), 5.59 (s, 2H), 3.83 (s, 4H), 3.49-2.30 (m, 8H), 2.09-1.91 (m, 2H), 1.91-1.40 (m, 8H), NH exchanged.

The racemic mixture was further purified by chiral preparative HPLC purification using Chiralpak IE column (5 μm, 10×250 mm). Eluent used: TBME/MeOH/DCM/DEA: 73/20/7/0.1% at flow rate of 7 mL/min. First eluted enantiomer: P=93%, retention time=6.6 min, chiral HPLC: P=97.2%. Second eluted enantiomer: P=97%, retention time=7.7 min, chiral HPLC: P=97.2%.

Compound 55: 4-[(3R)-3-(cyclobutylmethylamino)-1-piperidyl]-1-[1-[4-(5-methoxy-3-pyridyl)triazol-1-yl]ethyl]pyridin-2-one was Obtained Using General Scheme 1 Pathway B Stage 1: General Procedure B was used between IM44 and IM151 to afford 4-chloro-1-[1-[4-(5-methoxy-3-pyridyl)triazol-1-yl]ethyl]pyridin-2-one IM169 as a yellow solid: 151 mg, 83% yield, P=92%, retention time=2.1 min (gradient A), (M+H)+: 332/334.

Stage 2: General Procedure C was used between IM3 and IM169 to afford crude tert-butyl N-(cyclobutylmethyl)-N-[(3R)-1-[1-[1-[4-(5-methoxy-3-pyridyl)triazol-1-yl]ethyl]-2-oxo-4-pyridyl]-3-piperidyl]carbamate IM170 as an off-white solid: 335 mg, 99% yield, P=70%, retention time=3.6 min (gradient A), (M+H)+: 564.

Stage 3: General Procedure A1 was used from IM170 to afford crude compound 55 as an off-white solid: 173 mg, 89% yield, P=100%, retention time=2.0 min (gradient A), (M+H)+: 464.

The mixture of diastereomers was further purified by chiral preparative HPLC purification using Chiralpak IA column (5 μm, 20×250 mm). Eluent used: TBME/MeOH/DCM/DEA: 50/30/30/0.1% at flow rate of 20 mL/min. First eluted diastereomer: P=100%, retention time=8.3 min, chiral HPLC: P=100%, $^1$H NMR (300 MHz, CDCl$_3$): δ 8.53 (s, 1H), 8.20 (d, J=2.6 Hz, 1H), 8.12 (s, 1H), 7.63 (s, 1H), 7.50 (q, J=7.0 Hz, 1H), 7.37 (d, J=8.1 Hz, 1H), 5.94 (dd, J=8.1, 2.5 Hz, 1H), 5.59 (d, J=2.4 Hz, 1H), 3.83 (s, 3H), 3.69 (d, J=12.5 Hz, 1H), 3.54 (d, J=13.3 Hz, 1H), 2.90-2.78 (m, 2H), 2.72-2.44 (m, 4H), 2.33 (hept, J=7.6 Hz, 1H), 2.11 (d, J=7.0 Hz, 3H), 2.05-1.41 (m, 9H), 1.36-1.17 (m, 1H), NH exchanged. Second eluted diastereomer: P=100%, retention time=11.8 min, chiral HPLC: P=99.4%, $^1$H NMR (300 MHz, CDCl$_3$): δ 8.54 (s, 1H), 8.22 (d, J=2.6 Hz, 1H), 8.13 (s, 1H), 7.65 (s, 1H), 7.51 (q, J=7.0 Hz, 1H), 7.39 (d, J=8.1 Hz, 1H), 5.95 (dd, J=8.1, 2.5 Hz, 1H), 5.61 (d, J=2.4 Hz, 1H), 3.85 (s, 3H), 3.71 (d, J=11.9 Hz, 1H), 3.56 (d, J=13.3 Hz, 1H), 2.97-2.78 (m, 2H), 2.74-2.47 (m, 4H), 2.34 (hept, J=7.3 Hz, 1H), 2.13 (d, J=7.0 Hz, 3H), 2.08-1.42 (m, 9H), 1.39-1.20 (m, 1H), NH exchanged.

Compound 56: (3R,5S)—N-(cyclobutylmethyl)-5-fluoro-1-[6-[[4-(5-methoxy-3-pyridyl)triazol-1-yl]methyl]pyridazin-3-yl]piperidin-3-amine was Obtained Using General Scheme 1 Pathway B Stage 1: General Procedure C was used between IM112 and tert-butyl N-[(3R,5S)-5-fluoropiperidin-3-yl]carbamate to afford tert-butyl N-[(3R,5S)-5-fluoro-1-[6-[[4-(5-methoxy-3-pyridyl)triazol-1-yl]methyl]pyridazin-3-yl]-3-piperidyl]carbamate IM171 as yellow oil: 21 mg, 34% yield, P=95%, retention time=2.2 min (gradient A), (M+H)$^+$: 485.

Stage 2: General Procedure A1 was used from IM171 to afford crude (3R,5S)-5-fluoro-1-[6-[[4-(5-methoxy-3-pyridyl)triazol-1-yl]methyl]pyridazin-3-yl]piperidin-3-amine dihydrochloride IM172 as a yellow solid: 31 mg, 100% yield, retention time=1.7 min (gradient A), (M+H)$^+$: 385.

Stage 3: General Procedure H$_2$ was used between cyclobutanecarboxaldehyde and IM172 dihydrochloride to afford compound 56 as a pale yellow powder: 23 mg, 100% yield, P=96%, retention time=2.5 min (gradient B), (M+H)$^+$: 453. $^1$H NMR (300 MHz, CDCl$_3$): δ 8.53 (d, J=1.7 Hz, 1H), 8.26 (d, J=2.8 Hz, 1H), 8.02 (s, 1H), 7.73 (dd, J=2.8, 1.7 Hz, 1H), 7.32 (d, J=9.5 Hz, 1H), 7.00 (d, J=9.5 Hz, 1H), 5.75 (s, 2H), 4.90-4.54 (m, 1H), 4.25-4.02 (m, 2H), 3.90 (s, 3H), 3.59-3.46 (m, 1H), 3.29 (dd, J=13.2, 8.2 Hz, 1H), 2.92-2.78 (m, 1H), 2.78-2.67 (m, 2H), 2.53-2.23 (m, 2H), 2.11-1.98 (m, 2H), 1.95-1.75 (m, 3H), 1.72-1.55 (m, 2H), NH exchanged. $^{19}$F NMR (282 MHZ, CDCl$_3$): δ −177.78 (d, J=45.9 Hz).

Compound 57: (3R)-1-[6-[[4-(6-chloro-1H-indazol-4-yl)triazol-1-yl]methyl]pyridazin-3-yl]-N-(cyclobutylmethyl)piperidin-3-amine was Obtained Using General Scheme 1 Pathway B Stage 1: A round-bottom flask equipped with a reflux condenser and nitrogen balloon was charged with 4-Bromo-6-chloro-1h-indazole (500 mg, 2.07 mmol), anhydrous EtOAc (6 mL) and 3,4-dihydro-2H-pyran (663 μL, 7.05 mmol). The reaction mixture was stirred for 2 min at rt before adding trifluoroacetic acid (162 μL, 2.08 mmol).

The resulting mixture was stirred at for 1.15 h, cooled to rt and concentrated under reduced pressure. The residue was taken-up in EtOAc (30 mL) and washed with and saturated aqueous solution of NaHCO$_3$ (2×20 mL), followed by brine (30 mL). Resulting organic layer was dried over MgSO$_4$, filtered and concentrated under reduced pressure to give the crude product as red/orange oil (1.2 g). The crude product was purified by an automated flash system (liquid injection in n-Heptane, n-heptane for 0.9 min, 0 to 10% EtOAc in n-heptane over 9.1 min, 30SIHP-12G, 15 mL/min) to afford 4-bromo-6-chloro-1-tetrahydropyran-2-yl-indazole IM173 as an orange solid: 534 mg, 80% yield, P=98%, retention time=3.3 min (gradient A), (M+H)$^+$: 315/317.

Stage 2: General Procedure E1 was used from IM173 to afford 2-(6-chloro-1-tetrahydropyran-2-yl-indazol-4-yl) ethynyl-trimethyl-silane IM174 as yellow oil: 438 mg, 75% yield, P=95%, retention time=3.7 min (gradient A), (M+H)$^+$: 333/335.

Stage 3: General Procedure D1 was used from IM174 to afford 4 6-chloro-4-ethynyl-1-tetrahydropyran-2-yl-indazole IM175 as a yellow solid: 307 mg, 88% yield, P=95%, retention time=3.1 min (gradient A), (M+H)$^+$: 261.

Stage 4: General Procedure B was used between IM175 and IM5 to afford 6-chloro-4-[1-[(6-chloropyridazin-3-yl)methyl]triazol-4-yl]-1-tetrahydropyran-2-yl-indazole IM176 as a white solid: 125 mg, 79% yield, P=100%, retention time=2.8 min (gradient A), (M+H)$^+$: 430/432.

Stage 5: General Procedure C was used between IM3 and IM176 to afford tert-butyl N-[(3R)-1-[6-[[4-(6-chloro-1-tetrahydropyran-2-yl-indazol-4-yl)triazol-1-yl]methyl]pyridazin-3-yl]-3-piperidyl]-N-(cyclobutylmethyl)carbamate IM177 as yellow oil: 100 mg, 87% yield, P=90%, retention time=2.7 min (gradient A), (M+H)$^+$: 662/664.

Stage 6: General Procedure A1 was used from IM177 to afford crude compound 57 as a white solid: 55 mg, 78% yield, P=94%, retention time=3.1 min (gradient B), (M+H)$^+$: 478. $^1$H NMR (300 MHz, CD$_3$OD): δ 8.66 (s, 1H), 8.56 (s, 1H), 7.61 (d, J=1.6 Hz, 1H), 7.55 (d, J=1.6 Hz, 1H), 7.46 (d, J=9.5 Hz, 1H), 7.26 (d, J=9.5 Hz, 1H), 5.82 (s, 2H), 4.39 (d, J=14.0 Hz, 1H), 4.10 (d, J=13.6 Hz, 1H), 3.18-3.02 (m, 1H), 2.95 (dd, J=12.9, 9.4 Hz, 1H), 2.77-2.55 (m, 3H), 2.54-2.40 (m, 1H), 2.14-1.98 (m, 3H), 1.92-1.37 (m, 8H), 1H exchanged with CD$_3$OD.

Compound 58: N-[1-[5-[(3R)-3-(cyclobutylmethyl-amino)-1-piperidyl]-2-pyridyl]ethyl]-4-oxo-pyrido[1,2-a]pyrimidine-2-carboxamide was Obtained Using General Scheme 2 Pathway B Stage 1: To a suspension of lithium aluminium hydride (146 mg, 3.65 mmol) in anhydrous THF (13 mL) under Ar atmosphere at −78° C. was added dropwise over 5 min a solution of IM127 (1.12 g, 2.57 mmol) in anhydrous THF (10 mL). The reaction mixture was stirred at −78° C. for 2 h and then further lithium aluminium hydride (55 mg, 1.38 mmol) was added and a third portion (75 mg, 1.88 mmol) after another hour. After 30 min, reaction mixture was warmed to 0° C. and quenched by slowly adding EtOAc (40 mL). The resulting mixture was stirred at 0° C. for 5 min, then a saturated solution of Rochelle's salt (30 mL) was added very slowly (violent reaction upon addition of the first drops) at 0° C. and the mixture was vigorously stirred at rt for 17 h. Phases were then separated and the aqueous phase was extracted with EtOAc (3×30 mL). Combined organic phases were dried over MgSO$_4$, filtered and concentrated under reduced pressure to dryness to afford 1.11 g as yellow oil. The crude material was purified by an automated flash system (liquid injection in DCM, 0-15% MeOH in DCM over 30 min, 30SIHP-40G, 20 mL/min) to afford tert-butyl N-(cyclobutylmethyl)-N-[(3R)-1-[6-(hydroxymethyl)-3-pyridyl]-3-piperidyl]carbamate IM178 as yellow oil: 658 mg, 67% yield, P=100%, retention time=2.5 min (gradient A), (M+H)$^+$: 376; and tert-butyl N-(cyclobutylmethyl)-N-[(3R)-1-[6-formyl-3-pyridyl]-3-piperidyl]carbamate IM179 as green oil: 152 mg, 14% yield, P=90%, retention time=2.9 min (gradient A), (M+H)$^+$: 374.

Stage 2: General Procedure Q was used from IM179 to afford tert-butyl N-(cyclobutylmethyl)-N-[(3R)-1-[6-(1-hydroxyethyl)-3-pyridyl]-3-piperidyl]carbamate IM180 as yellow oil: 155 mg, 96% yield, P=88%, retention time=2.5 min (gradient A), (M+H)$^+$: 390.

Stage 3: General Procedure M was used from IM180 to afford tert-butyl N-[(3R)-1-[6-(1-azidoethyl)-3-pyridyl]-3-piperidyl]-N-(cyclobutylmethyl)carbamate IM181 as colourless oil: 85 mg, 44% yield, P=75%, retention time=2.7 min (gradient A), (M+H)$^+$: 415.

Stage 4: General Procedure R was used from IM181 to afford crude tert-butyl N-[(3R)-1-[6-(1-aminoethyl)-3-pyridyl]-3-piperidyl]-N-(cyclobutylmethyl)carbamate IM182 as yellow oil: 60 mg, 76% yield, P=58%, retention time=2.4 min (gradient A), (M+H)+: 389.

Stage 5: General Procedure F was used between 4-oxopyrido[1,2-a]pyrimidine-2-carboxylic acid hydrochloride and IM182 to afford crude tert-butyl N-(cyclobutylmethyl)-N-[(3R)-1-[6-[1-[(4-oxopyrido[1,2-a]pyrimidine-2-carbonyl)amino]ethyl]-3-pyridyl]-3-piperidyl]carbamate IM183 as brown oil: 90 mg, 94% yield, P=70%, retention time=2.6 min (gradient A), (M+H)+: 561.

Stage 6: General Procedure A1 was used from IM183 to afford crude compound 58 as orange oil: 60 mg, 93% yield, P=80%, retention time=2.0 min (gradient A), (M+H)+: 461.

The product was further purified by reverse phase preparative HPLC purification (Waters XBridge C18 5 μm 19×100 mm). Gradient used: held at 35% solution "B" for 1.5 min, increased linearly from 35 to 40% solution "B" over 3.5 min, increased linearly to 85% solution "B" over 1.2 min, held at 85% solution "B" for 0.3 min and returned to initial conditions over 1.0 min. Flow Rate: 15 mL/min. P=100%.

The mixture of diastereomers was further purified by chiral preparative HPLC purification using Chiralpak IA column (5 μm, 10×250 mm). Eluent used: TBME/MeOH/DEA: 75/25/0.1% at flow rate of 7 mL/min. First eluted diastereomer: P=100%, retention time=3.0 min, chiral HPLC: P=99.6%, $^1$H NMR (300 MHz, CDCl$_3$): δ 9.07 (d, J=6.8 Hz, 1H), 8.90 (d, J=7.2 Hz, 1H), 8.30 (s, 1H), 7.77 (br s, 2H), 7.26-7.11 (m, 4H), 5.31-5.19 (m, 1H), 4.08-3.90 (m, 1H), 3.45-3.32 (m, 1H), 3.23-3.09 (m, 2H), 3.06-2.74 (m, 5H), 2.29-2.09 (m, 3H), 1.98-1.71 (m, 6H), 1.57 (d, J=6.5 Hz, 3H), 1.43 (t, J=7.1 Hz, 1H), NH exchanged. Second eluted diastereomer: P=99%, retention time=8.7 min, chiral HPLC: P=100%, $^1$H NMR (300 MHz, CDCl$_3$): δ 9.00 (d, J=7.0 Hz, 1H), 8.83 (d, J=7.5 Hz, 1H), 8.21 (s, 1H), 7.72 (d, J=3.7 Hz, 2H), 7.21 (s, 1H), 7.16-7.10 (m, 1H), 7.07 (d, J=8.4 Hz, 1H), 5.23-5.11 (m, 1H), 4.03-3.89 (m, 1H), 3.36-3.24 (m, 1H), 3.18-2.72 (m, 6H), 2.20-2.02 (m, 3H), 1.89-1.68 (m, 6H), 1.48 (d, J=6.7 Hz, 3H), 1.36 (t, J=7.2 Hz, 1H), NH exchanged.

Compound 59: N-(cyclobutylmethyl)-4,4-difluoro-1-[6-[[4-(5-methoxy-3-pyridyl)triazol-1-yl]methyl]pyridazin-3-yl]piperidin-3-amine was Obtained Using General Scheme 1 Pathway B Stage 1: General Procedure C was used between IM112 and tert-butyl tert-butyl N-(4,4-difluoropiperidin-3-yl)carbamate to afford tert-butyl N-[4,4-difluoro-1-[6-[[4-(5-methoxy-3-pyridyl)triazol-1-yl]methyl]pyridazin-3-yl]-3-piperidyl]carbamate IM184 as dark yellow oil: 37 mg, 56% yield, P=95%, retention time=2.3 min (gradient A), (M+H)+: 503.

Stage 2: General Procedure A1 was used from IM184 to afford crude 4,4-difluoro-1-[6-[[4-(5-methoxy-3-pyridyl)triazol-1-yl]methyl]pyridazin-3-yl]piperidin-3-amine dihydrochloride IM185 as a pale brown solid: 42 mg, 100% yield, retention time=1.8 min (gradient A), (M+H)+: 403.

Stage 3: General Procedure H$_2$ was used between cyclobutanecarboxaldehyde and IM185 to afford crude compound 59 as a yellow solid: 23 mg, 100% yield, P=94%, retention time=2.0 min (gradient A), (M+H)+: 471. $^1$H NMR (300 MHz, CDCl$_3$): δ 8.54 (s, 1H), 8.27 (s, 1H), 8.01 (s, 1H), 7.73 (s, 1H), 7.33 (d, J=9.4 Hz, 1H), 6.96 (d, J=9.4 Hz, 1H), 5.76 (s, 2H), 4.07-3.94 (m, J=13.2 Hz, 2H), 3.91 (s, 3H), 3.66-3.45 (m, 2H), 2.90 (br s, 1H), 2.84-2.68 (m, 2H), 2.37 (hept, 1H), 2.30 (s, 1H), 2.00 (br s, 2H), 1.92-1.77 (m, 2H), 1.69-1.46 (m, 4H), NH exchanged. $^{19}$F NMR (282 MHz, CDCl$_3$): δ −99.42 (dd, J=239.1, 16.0 Hz), −111.04 (d, J=240.0 Hz).

The racemic mixture was further purified by chiral preparative HPLC purification using Chiralpak IA column (5 μm, 10×250 mm). Eluent used: TBME/MeOH/DCM/DEA: 60/20/20/0.1% at flow rate of 7 mL/min. First eluted enantiomer: P=100%, retention time=8.2 min, chiral HPLC: P=94.7%. Second eluted enantiomer: P=100%, retention time=9.4 min, chiral HPLC: P=100%.

Compound 60: N-[[5-[(3R)-3-(cyclobutylmethyl-amino)-1-piperidyl]-2-pyridyl]methyl]-4-oxo-pyrido[1,2-a]pyrimidine-2-carboxamide was Obtained Using General Scheme 2 Pathway B Stage 1: General Procedure R was used from IM128 to afford crude tert-butyl N-[(3R)-1-[6-(aminomethyl)-3-pyridyl]-3-piperidyl]-N-(cyclobutylmethyl)carbamate IM186 as orange oil: 44 mg, 81% yield, P=60%, retention time=2.4 min (gradient A), (M+H)+: 375.

Stage 2: General Procedure F was used between 4-oxopyrido[1,2-a]pyrimidine-2-carboxylic acid hydrochloride and IM186 to afford tert-butyl N-(cyclobutylmethyl)-N-[(3R)-1-[6-[[(4-oxo pyrido[1,2-a]pyrimidine-2-carbonyl)amino]methyl]-3-pyridyl]-3-piperidyl]carbamate IM187 as colourless oil: 25 mg, 65% yield, P=100%, retention time=2.6 min (gradient A), (M+H)+: 547.

Stage 3: General Procedure A1 was used from IM187 to afford compound 60 as a white solid: 19 mg, 89% yield, P=96%, retention time=2.5 min (gradient B), (M+H)+: 447. $^1$H NMR (300 MHz, CDCl$_3$): δ 9.06 (d, J=7.2 Hz, 1H), 8.18 (d, J=2.8 Hz, 1H), 7.99 (ddd, J=8.5, 6.7, 1.6 Hz, 1H), 7.82 (d, J=8.8 Hz, 1H), 7.43-7.32 (m, 2H), 7.28 (d, J=8.8 Hz, 1H), 7.08 (br s, 1H), 4.62 (s, 2H), 3.72-3.64 (m, 1H), 3.55-4.46 (m, 1H), 2.95-2.77 (m, 1H), 2.77-2.64 (m, 4H), 2.48 (hept, J=7.5 Hz, 1H), 2.18-1.59 (m, 9H), 1.43-1.27 (m, 1H), NH exchanged.

Compound 61: N-[[6-[(3R)-3-(cyclobutylmethyl-amino)-1-piperidyl]-3-pyridyl]methyl]-4-oxo-pyrido[1,2-a]pyrimidine-2-carboxamide was Obtained Using General Scheme 2 Pathway B Stage 1: General Procedure L was used from IM120 to afford crude tert-butyl N-[(3R)-1-[5-(aminomethyl)-2-pyridyl]-3-piperidyl]-N-(cyclobutylmethyl)carbamate IM188 as yellow oil: 87 mg, 81% yield, P=75%, retention time=2.3 min (gradient A), (M+H)+: 375.

Stage 2: General Procedure F was used between 4-oxopyrido[1,2-a]pyrimidine-2-carboxylic acid hydrochloride and IM188 to afford tert-butyl N-(cyclobutylmethyl)-N-[(3R)-1-[5-[[(4-oxo pyrido[1,2-a]pyrimidine-2-carbonyl)amino]methyl]-2-pyridyl]-3-piperidyl]carbamate IM189 as colourless oil: 71 mg, 69% yield, P=92%, retention time=2.5 min (gradient A), (M+H)+: 547.

Stage 3: General Procedure A1 was used from IM189 to afford compound 61 as an off-white solid: 35 mg, 64% yield, P=97%, retention time=2.5 min (gradient B), (M+H)+: 447. $^1$H NMR (300 MHz, CD$_3$OD) δ 9.06 (d, J=7.0 Hz, 1H), 8.11 (d, J=2.5 Hz, 1H), 7.98 (ddd, J=9.0, 7.0, 1.5 Hz, 1H), 7.81 (d, J=9.0 Hz, 1H), 7.58 (dd, J=8.9, 2.5 Hz, 1H), 7.39 (td, J=7.0, 1.3 Hz, 1H), 7.08 (s, 1H), 6.78 (d, J=8.9 Hz, 1H), 4.47 (s, 2H), 4.24 (d, J=12.1 Hz, 1H), 3.98 (d, J=13.2 Hz, 1H), 3.02-2.86 (m, 1H), 2.82-2.66 (m, 3H), 2.67-2.52 (m, 1H), 2.47 (hept, J=7.6 Hz, 1H), 2.15-1.49 (m, 9H), 1.46-1.26 (m, 1H), 2H exchanged with CD₃OD.

Compound 62: 5-[(3R)-3-(cyclobutylmethylamino)-1-piperidyl]-2-[[4-(5-methoxy-3-pyridyl) triazol-1-yl]methyl]pyridazin-3-one was Obtained Using General Scheme 1 Pathway B Stage 1: General Procedure B was used between IM44 and IM88 to afford 5-chloro-2-[[4-(5-methoxy-3-pyridyl)triazol-1-yl]methyl]pyridazin-3-one IM190 as a white solid: 52 mg, 56% yield, P=93%, retention time=2.0 min (gradient A), (M+H)⁺: 319/321.

Stage 2: General Procedure C was used between IM3 and IM190 to afford tert-butyl N-(cyclobutylmethyl)-N-[(3R)-1-[1-[[4-(5-methoxy-3-pyridyl)triazol-1-yl]methyl]-6-oxo-pyridazin-4-yl]-3-piperidyl]carbamate IM191 as a light brown solid: 60 mg, 69% yield, P=99%, retention time=2.6 min (gradient A), (M+H)⁺: 551.

Stage 3: General Procedure A1 was used from IM191 to afford compound 62 as a beige solid: 45 mg, 90% yield, P=96%, retention time=2.0 min (gradient A), (M+H)⁺: 451. ¹H NMR (300 MHz, CD₃OD) δ 8.59 (d, J=1.6 Hz, 1H), 8.59 (s, 1H), 8.21 (d, J=2.9 Hz, 1H), 8.02 (d, J=2.9 Hz, 1H), 7.84 (dd, J=2.9, 1.6 Hz, 1H), 6.57 (s, 2H), 5.89 (d, J=2.9 Hz, 1H), 3.94 (s, 3H), 3.92-3.82 (m, 1H), 3.82-3.71 (m, 1H), 3.13-2.98 (m, 1H), 2.91 (dd, J=13.2, 9.3 Hz, 1H), 2.70-2.57 (m, 2H), 2.44 (hept, J=7.1 Hz, 1H), 2.11-1.97 (m, 3H), 1.95-1.37 (m, 7H), 1H exchanged with CD₃OD.

Compound 63: 4-[(3R)-3-(cyclobutylmethylamino)-1-piperidyl]-1-[[4-(5-methoxy-3-pyridyl) triazol-1-yl]methyl]pyridin-2-one was Obtained Using General Scheme 1 Pathway B Stage 1: General Procedure B was used between IM44 and IM84 to afford 4-chloro-1-[[4-(5-methoxy-3-pyridyl)triazol-1-yl]methyl]pyridin-2-one IM192 as a white solid: 300 mg, 97% yield, P=95%, retention time=2.1 min (gradient A), (M+H)⁺: 318/320.

Stage 2: General Procedure C was used between IM3 and IM192 to afford tert-butyl N-(cyclobutylmethyl)-N-[(3R)-1-[1-[[4-(5-methoxy-3-pyridyl)triazol-1-yl]methyl]-2-oxo-4-pyridyl]-3-piperidyl]carbamate IM193 as yellow oil: 105 mg, 81% yield, P=100%, retention time=2.6 min (gradient A), (M+H)⁺: 550.

Stage 3: General Procedure A1 was used from IM193 to afford compound 63 as a white solid: 79 mg, 88% yield, P=96%, retention time=2.5 min (gradient B), (M+H)⁺: 450. ¹H NMR (300 MHz, CD₃OD) δ 8.61 (s, 1H), 8.60 (d, J=1.7 Hz, 1H), 8.21 (d, J=2.7 Hz, 1H), 7.87-7.81 (m, 1H), 7.68 (d, J=7.9 Hz, 1H), 6.43 (s, 2H), 6.31 (dd, J=7.9, 2.8 Hz, 1H), 5.67 (d, J=2.8 Hz, 1H), 3.94 (s, 3H), 3.92-3.84 (m, 1H), 3.81-3.71 (m, 1H), 3.05-2.93 (m, 1H), 2.82 (dd, J=13.1, 9.6 Hz, 1H), 2.67 (d, J=7.3 Hz, 2H), 2.64-2.51 (m, 1H), 2.45 (hept, J=7.6 Hz, 1H), 2.17-1.26 (m, 10H). 1H exchanged with CD₃OD.

Compound d 64: (3R)—N-(cyclobutylmethyl)-1-[6-[2,2,2-trifluoro-1-[4-(5-methoxy-3-pyridyl) triazol-1-yl]ethyl]pyridazin-3-yl]piperidin-3-amine was Obtained Using General Scheme 1 Pathway A Stage 1: To a solution of 6-chloropyridazine-3-carbaldehyde (897 mg, 6.10 mmol) in anhydrous THF (17 mL) was added dropwise Trifluoromethyl)trimethylsilane (1.35 mL, 9.04 mmol) at 0° C. The reaction mixture was stirred at 0° C. for 10 min and then TBAF (1 N in THF, 17 mL, 17 mmol) was added dropwise. The resulting mixture was stirred at rt for 1 h. The reaction was diluted with water (40 mL) and extracted with DCM (3×35 mL). The combined organic layers were washed with brine (20 mL), dried over MgSO₄, and concentrated under reduced pressure to give a black oil. The crude residue was purified by silica gel flash chromatography (nHeptane/EtOAc: 1/0 to 6/4) to afford 1-(6-chloropyridazin-3-yl)-2,2,2-trifluoro-ethanol IM194 as an orange solid: 651 mg, 48% yield, P=95%, retention time=2.3 min (gradient A), (M+H)⁺: 213/215.

Stage 2: General Procedure C was used between IM3 and IM194 to afford tert-butyl N-(cyclobutylmethyl)-N-[(3R)-1-[6-(2,2,2-trifluoro-1-hydroxy-ethyl)pyridazin-3-yl]-3-piperidyl] carbamate IM195 as a beige foam: 397 mg, 98% yield, P=98%, retention time=2.6 min (gradient A), (M+H)⁺: 445.

Stage 3: General Procedure P was used from IM195 to afford crude [1-[6-[(3R)-3-[tert-butoxycarbonyl(cyclobutylmethyl)amino]-1-piperidyl]pyridazin-3-yl]-2,2,2-trifluoro-ethyl] methanesulfonate IM196 as an orange solid: 489 mg, 98% yield, P=92% (215 nm), retention time=2.9 min (gradient A).

Stage 4: General Procedure N was used from crude IM196 to afford tert-butyl N-(3R)-1-[6-(1-azido-2,2,2-trifluoro-ethyl)pyridazin-3-yl]-3-piperidyl]-N-(cyclobutylmethyl) carbamate IM197 as orange sticky oil: 186 mg, 42% yield, P=95%, retention time=3.0 min (gradient A), (M+H)⁺: 470.

Stage 5: General Procedure B was used between IM44 and IM197 to afford tert-butyl N-(cyclobutylmethyl)-N-[(3R)-1-[6-[2,2,2-trifluoro-1-[4-(5-methoxy-3-pyridyl)triazol-1-yl]ethyl] pyridazin-3-yl]-3-piperidyl]carbamate IM198 as yellowish sticky oil: 78 mg, 70% yield, P=95%, retention time=2.8 min (gradient A), (M+H)⁺: 603.

Stage 6: General Procedure A1 was used from IM198 to afford crude compound 64 as a yellow foam: 62 mg, 88% yield, P=88%, retention time=2.2 min (gradient A), (M+H)⁺: 503.

The product was further purified by reverse phase preparative HPLC purification (Waters XBridge C18 5 μm 19×100 mm). Gradient used: increased linearly from 35 to 50% solution "B" over 4.5 min, increased linearly to 85% solution "B" over 1.7 min, held at 85% solution "B" for 0.3 min and returned to initial conditions over 0.8 min. Flow Rate: 15 mL/min. P=100%.

The mixture of diastereomers was further purified by chiral preparative HPLC purification using Chiralpak IA column (5 μm, 10×250 mm). Eluent used: EtOAc/MeOH/DCM/DEA: 90/5/5/0.1% at flow rate of 7 mL/min. First eluted diastereomer: P=100%, retention time=4.1 min, chiral HPLC: P=95.3%, ¹H NMR (300 MHz, CDCl₃) δ 8.65 (d, J=1.7 Hz, 1H), 8.55 (s, 1H), 8.30 (d, J=2.6 Hz, 1H), 7.76 (dd, J=2.6, 1.7 Hz, 1H), 7.49 (d, J=9.6 Hz, 1H), 6.96 (d, J=9.6 Hz, 1H), 6.48 (q, J=7.3 Hz, 1H), 4.43-4.35 (m, 1H), 4.20-4.07 (m, 1H), 3.93 (s, 3H), 3.21-3.11 (m, 1H), 2.99 (dd, J=12.6, 9.2 Hz, 1H), 2.76-2.62 (m, 3H), 2.57-2.35 (m, 1H), 2.06 (s, 2H), 1.95-1.80 (m, 3H), 2.12-1.45 (m, 10H), ¹⁹F NMR (282 MHZ, CDCl₃) δ −68.79 (d, J=7.5 Hz). Second eluted diastereomer: P=100%, retention time=10.3 min, chiral HPLC: P=95.6%, ¹H NMR (300 MHz, CDCl₃) δ 8.65 (d, J=1.7 Hz, 1H), 8.54 (s, 1H), 8.30 (d, J=2.6 Hz, 1H), 7.76 (dd, J=2.6, 1.7 Hz, 1H), 7.50 (d, J=9.6 Hz, 1H), 6.96 (d, J=9.6 Hz, 1H), 6.48 (q, J=7.3 Hz, 1H), 4.44-4.32 (m, 1H), 4.19-4.09 (m, 1H), 3.93 (s, 3H), 3.24-3.13 (m, 1H), 3.09-2.95 (m, 1H), 2.78-2.62 (m, 3H), 2.44 (hept, J=7.6 Hz, 1H), 2.11-1.99 (m, 2H), 1.95-1.81 (m, 2H), 1.69-1.40 (m, 6H), NH exchanged, $^{19}$F NMR (282 MHZ, CDCl$_3$) δ −68.75 (d, J=6.8 Hz).

Compound 65: N-[1-[6-[(3R)-3-(cyclobutylmethylamino)-1-piperidyl]pyridazin-3-yl]-2,2,2-trifluoroethyl]-4-oxo-pyrido[1,2-a]pyrimidine-2-carboxamide was Obtained Using General Scheme 2 Pathway B Stage 1: General Procedure L was used from IM197 to afford crude tert-butyl N-[(3R)-1-[6-(1-amino-2,2,2-trifluoro-ethyl)pyridazin-3-yl]-3-piperidyl]-N-(cyclobutylmethyl)carbamate IM199 as yellow sticky oil: 77 mg, 83% yield, P=92%, retention time=2.5 min (gradient A), (M+H)$^+$: 444.

Stage 2: General Procedure F was used between 4-oxopyrido[1,2-a]pyrimidine-2-carboxylic acid hydrochloride and IM199 to afford tert-butyl N-((cyclobutylmethyl)-N-[(3R)-1-[6-[2,2,2-trifluoro-1-[(4-oxopyrido[1,2-a]pyrimidine-2-carbonyl)amino]ethyl]pyridazin-3-yl]-3-piperidyl]carbamate IM200 as a yellow gum: 67 mg, 77% yield, P=82%, retention time=2.9 min (gradient A), (M+H)$^+$: 616.

Stage 3: General Procedure A1 was used from IM200 to afford crude compound 65 as yellow sticky oil: 64 mg, 100% yield, P=83%, retention time=2.3 min (gradient A), (M+H)$^+$: 516.

The mixture of diastereomers was further purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=100%, retention time=4.4 min, chiral HPLC: P=99.5%, $^1$H NMR (300 MHz, CDCl$_3$) δ 9.46 (d, J=9.4 Hz, 1H), 9.09 (d, J=7.1 Hz, 1H), 7.89-7.78 (m, 2H), 7.33-7.18 (m, 2H), 6.94 (d, J=9.5 Hz, 1H), 5.92 (q, J=7.4 Hz, 1H), 4.45-4.37 (m, 1H), 4.18-4.04 (m, 1H), 3.20-3.06 (m, 1H), 3.01-2.87 (m, 1H), 2.78-2.66 (m, 3H), 2.62-2.36 (m, 2H), 2.13-1.97 (m, 2H), 1.96-1.36 (m, 8H), $^{19}$F NMR (282 MHZ, CDCl$_3$) δ −71.13 (d, J=7.0 Hz). Second eluted diastereomer: P=100%, retention time=5.3 min, chiral HPLC: P=100%, $^1$H NMR (300 MHz, CDCl$_3$) δ 9.47 (d, J=9.3 Hz, 1H), 9.10 (d, J=7.1 Hz, 1H), 7.90-7.78 (m, 2H), 7.33-7.18 (m, 2H), 6.95 (d, J=9.4 Hz, 1H), 5.92 (q, J=7.4 Hz, 1H), 4.46-4.47 (m, 1H), 4.18-4.08 (m, 1H), 3.22-3.80 (m, 1H), 3.02-2.88 (m, 1H), 2.79-2.68 (m, 3H), 2.58-2.36 (m, 2H), 2.11-1.96 (m, 2H), 1.95-1.39 (m, 8H), $^{19}$F NMR (282 MHZ, CDCl$_3$) δ −71.15 (d, J=6.8 Hz).

Compound 66: (3R)—N-(cyclobutylmethyl)-1-[6-[1-[4-(5-methoxy-3-pyridyl)triazol-1-yl]ethyl]pyridazin-3-yl]piperidin-3-amine was Obtained Using General Scheme 1 Pathway A Stage 1: General Procedure B was used between IM106 and IM44 to afford 3-chloro-6-[1-[4-(5-methoxy-3-pyridyl)triazol-1-yl]ethyl]pyridazine IM201 as yellow oil: 123 mg, 81% yield, P=100%, retention time=2.1 min (gradient A), (M+H)$^+$: 317/319.

Stage 2: General Procedure C was used between IM3 and IM201 to afford tert-butyl N-(cyclobutylmethyl)-N-[(3R)-1-[6-[1-[4-(5-methoxy-3-pyridyl)triazol-1-yl]ethyl]pyridazin-3-yl]-3-piperidyl]carbamate IM202 as a yellowish solid: 115 mg, 52% yield, P=95%, retention time=3.5 min (gradient B), (M+H)$^+$: 549.

Stage 3: General Procedure A1 was used from IM202 to afford crude compound 66 as a yellow sticky foam: 100 mg, 100% yield, P=96%, retention time=3.5 min (gradient B), (M+H)$^+$: 449.

The mixture of diastereomers was further purified by chiral preparative HPLC purification using Chiralpak IA column (5 μm, 20×250 mm). Eluent used: TBME/MeOH/DCM/DEA: 40/40/25/0.1% at flow rate of 20 mL/min. First eluted diastereomer: P=99%, retention time=4.5 min, chiral HPLC: P=99.2%, $^1$H NMR (300 MHz, CDCl$_3$) δ 8.55 (d, J=1.7 Hz, 1H), 8.26 (d, J=2.9 Hz, 1H), 8.04 (s, 1H), 7.73 (br s, 1H), 7.23 (d, J=9.6 Hz, 1H), 6.89 (d, J=9.6 Hz, 1H), 6.04 (q, J=7.1 Hz, 1H), 4.43-4.31 (m, 1H), 4.12-4.02 (m, 1H), 3.91 (s, 3H), 3.19-3.04 (m, 1H), 2.90 (dd, J=12.8, 9.2 Hz, 1H), 2.80-2.59 (m, 3H), 2.59-2.34 (m, 2H), 2.11 (d, J=7.2 Hz, 3H), 2.10-1.97 (m, 2H), 1.93-1.77 (m, 2H), 1.73-1.36 (m, 6H), NH exchanged. Second eluted diastereomer: P=99%, retention time=14.7 min, chiral HPLC: P=99.4%, $^1$H NMR (300 MHz, CDCl$_3$) δ 8.55 (s, 1H), 8.27 (s, 1H), 8.04 (s, 1H), 7.73 (s, 1H), 7.23 (d, J=9.4 Hz, 1H), 6.90 (d, J=9.4 Hz, 1H), 6.04 (q, J=7.1 Hz, 1H), 4.42-4.04 (m, 2H), 4.13-4.03 (m, 1H), 3.91 (s, 3H), 3.19-3.04 (m, 1H), 3.02-2.86 (m, 1h), 2.80-2.62 (m, 3H), 2.56-2.38 (m, 2H), 2.11 (d, J=7.1 Hz, 3H), 2.06-1.96 (m, 2H), 1.88-1.74 (m, 2H), 1.71-1.52 (m, 6H), NH exchanged.

Compound 67: 2-[1-[4-(5-methoxy-3-pyridyl)triazol-1-yl]ethyl]-5-[(3R)-3-(cyclobutylmethyl amino)-1-piperidyl]pyridazin-3-one was Obtained Using General Scheme 1 Pathway B Stage 1: General Procedure O2 was used from 5-chloro-pyridazin-3 (2H)-one to afford 5-chloro-2-(1-chloroethyl)pyridazin-3-one IM203 as yellow oil: 0.96 g, 66% yield, P=100% ($^1$H-NMR), retention time=2.6 min (gradient A), (M+H)$^+$: 193/195.

Stage 2: General Procedure N was used from IM203 to afford 2-(1-azidoethyl)-5-chloro-pyridazin-3-one IM204 as yellow oil: 550 mg, 50% yield, P=97%, retention time=3.7 min (gradient B), (M+H)$^+$: 200/202.

Stage 3: General Procedure B was used between IM44 and IM204 to afford 5-chloro-2-[1-[4-(5-methoxy-3-pyridyl)triazol-1-yl]ethyl]pyridazin-3-one IM205 as an off-white solid: 150 mg, 66% yield, P=99%, retention time=2.1 min (gradient A), (M+H)$^+$: 333/335.

Stage 4: General Procedure C was used between IM3 and IM205 to afford crude tert-butyl N-(cyclobutylmethyl)-N-[(3R)-1-[1-[1-[4-(5-methoxy-3-pyridyl)triazol-1-yl]ethyl]-6-oxo-pyridazin-4-yl]-3-piperidyl]carbamate IM206 as a yellowish solid: 201 mg, 81% yield, P=100%, retention time=3.5 min (gradient B), (M+H)$^+$: 565.

Stage 5: General Procedure A1 was used from IM206 to afford crude compound 57 as a yellow foam: 136 mg, 82% yield, P=99%, retention time=2.6 min (gradient B), (M+H)$^+$: 465.

The mixture of diastereomers was further purified by chiral preparative HPLC purification using Chiralpak IA column (5 μm, 20×250 mm). Eluent used: TBME/MeOH/DCM/DEA: 40/40/25/0.1% at flow rate of 20 mL/min. First eluted diastereomer: P=100%, retention time=4.6 min, chiral HPLC: P=100%, $^1$H NMR (300 MHz, CDCl$_3$) δ 8.56 (d, J=1.3 Hz, 1H), 8.26 (d, J=2.8 Hz, 1H), 8.15 (s, 1H), 7.75 (s, 2H), 7.58 (q, J=6.9 Hz, 1H), 5.82 (d, J=2.9 Hz, 1H), 3.90 (s, 3H), 3.76-3.67 (m, 1H), 3.63-3.48 (m, 1H), 3.06-2.91 (m, 1H), 2.80 (dd, J=12.9, 9.1 Hz, 1H), 2.65 (d, J=7.2 Hz, 2H), 2.63-2.55 (m, 1H), 2.38 (hept, J=7.3 Hz, 1H), 2.15 (d, J=6.9 Hz, 3H), 2.13-1.95 (m, 3H), 1.93-1.74 (m, 3H), 1.69-1.48

(m, 3H), 1.47-1.28 (m, 1H), NH exchanged. Second eluted diastereomer: P=100%, retention time=5.6 min, chiral HPLC: P=100%, $^1$H NMR (300 MHz, CDCl$_3$) δ 8.56 (s, 1H), 8.25 (d, J=2.7 Hz, 1H), 8.15 (s, 1H), 7.75 (s, 2H), 7.58 (q, J=6.8 Hz, 1H), 5.82 (d, J=2.8 Hz, 1H), 3.90 (s, 3H), 3.76-3.64 (m, 1H), 3.63-3.52 (m, 1H), 3.05-2.92 (m, 1H), 2.79 (dd, J=12.9, 9.1 Hz, 1H), 2.64 (d, J=7.1 Hz, 2H), 2.62-2.56 (m, 1H), 2.37 (hept, J=7.5 Hz, 1H), 2.15 (d, J=6.9 Hz, 3H), 2.08-1.74 (m, 6H), 1.70-1.54 (m, 3H), 1.53-1.29 (m, 1H), NH exchanged.

Compound 68: (3R)—N-(cyclobutylmethyl)-1-[4-[[4-(5-methoxy-3-pyridyl)triazol-1-yl]methyl]phenyl]piperidin-3-amine was Obtained Using General Scheme 1 Pathway A Stage 1: General Procedure S was used (1,4-dioxane was used instead of toluene) between IM3 and methyl 4-bromobenzoate to afford methyl 4-[(3R)-3-[tert-butoxycarbonyl(cyclobutylmethyl)amino]-1-piperidyl]benzoate IM207 as colourless oil: 776 mg, 39% yield, P=93% ($^1$H-NMR), retention time=3.5 min (gradient A), (M+H)$^+$: 403.

Stage 2: Diisobutylaluminium hydride (1 N in THF, 2.3 mL, 2.3 mmol) was added to a solution of IM207 (104 mg, 0.24 mmol) in anhydrous THF (2.3 mL) at −78° C. and reaction mixture was allowed to stir at rt. After 14 h, diisobutylaluminium hydride (1 N in THF, 2.3 mL, 2.3 mmol) was further added at −78° C. and reaction mixture was allowed to stir at rt for 4 h (complete conversion by HPLC-MS). The reaction mixture was then diluted with diethyl ether (10 mL) and cooled to 0° C., water (0.2 mL) was added, followed by 1 N aqueous sodium hydroxide solution (0.2 mL) and water (0.5 mL). The mixture was stirred at rt for 15 min, and MgSO$_4$ was added and stirred for 15 min, then filtered to remove salts, rinsed thoroughly with AcOEt (100 mL) and concentrated under reduced pressure. The crude product was purified by an automated flash system (liquid injection in DCM, 0 to 4% MeOH in DCM over 19 min, 30SIHP-4G, 10 mL/min) to afford tert-butyl N-(cyclobutylmethyl)-N-[(3R)-1-[4-(hydroxymethyl) phenyl]-3-piperidyl]carbamate IM208 as colourless oil: 72 mg, 70% yield, P=88% (215 nm), retention time=2.5 min (gradient A), (M+H)$^+$: 375.

Stage 3: General Procedure M was used from IM208 to afford tert-butyl N-[(3R)-1-[4-(azidomethyl)phenyl]-3-piperidyl]-N-(cyclobutylmethyl)carbamate IM209 as a white gum: 48 mg, 70% yield, P=99% (215 nm), retention time=2.9 min (gradient A), (M+H)$^+$: 400.

Stage 5: General Procedure B was used between IM44 and IM209 to afford tert-butyl N-[(3R)-1-[4-(azidomethyl) phenyl]-3-piperidyl]-N-(cyclobutylmethyl)carbamate IM210 as colourless oil: 61 mg, 88% yield, P=91% ($^1$H-NMR), retention time=2.6 min (gradient A), (M+H)$^+$: 533.

Stage 6: General Procedure A1 was used from IM210 to afford compound 68 as colourless oil: 44 mg, 96% yield, P=99%, retention time=2.9 min (gradient B), (M+H)$^+$: 433. $^1$H NMR (300 MHz, CD$_3$OD) δ 8.53 (d, J=1.7 Hz, 1H), 8.35 (s, 1H), 8.15 (d, J=2.8 Hz, 1H), 7.76 (d, J=1.1 Hz, 1H), 7.25 (d, J=8.7 Hz, 2H), 6.92 (d, J=8.7 Hz, 2H), 5.49 (s, 2H), 3.88 (s, 3H), 3.70-3.56 (m, 1H), 3.43 (d, J=12.4 Hz, 1H), 2.84-2.53 (m, 5H), 2.45 (hept, J=7.4 Hz, 1H), 2.15-2.00 (m, 2H), 2.00-1.52 (m, 7H), 1.39-1.16 (m, 1H), 1H exchanged with CD$_3$OD.

Compound 69: (3R)—N-(cyclobutylmethyl)-1-[6-[[5-(5-methoxy-3-pyridyl)-4H-1,2,4-triazol-3-yl]methyl]pyridazin-3-yl]piperidin-3-amine was Obtained Using the Following Procedures Stage 1: Cesium carbonate (21.6 g, 65.8 mmol) was added to a solution of 3,6-dichloropyridazine (5.00 g, 32.9 mmol) and diethyl malonate (7.57 mL, 49.3 mmol) in DMSO (11 mL) at rt. Flask was equipped with a condenser and the reaction mixture was stirred at 110° C. for 2.25 h. The reaction was then cooled down to rt, poured into water (120 mL) and extracted with EtOAc (3×30 mL). The organic phase was dried over Na$_2$SO$_4$, filtered and concentrated under reduced pressure. Residue was purified by silica gel chromatography on a 100 g cartridge, eluting with a gradient of EtOAc in hexanes (0 to 30%) to afford IM211 as orange oil: 7.09 g, 73% yield, P=92%, retention time=0.9 min (gradient C), (M+H)$^+$: 273.

Stage 2: IM211 (1.59 g, 5.36 mmol), NaCl (1.25 g, 21.5 mmol) were solubilized in DMSO (8.44 mL) and water (141 µL). The reaction mixture was heated at 150° C. for 2.75 h. Reaction was cooled down to rt, poured into water (100 mL) and extracted with EtOAc (4×30 mL). The organic phase was dried over Na$_2$SO$_4$, filtered and concentrated under reduced pressure. Residue was purified by silica gel chromatography on a 35 g cartridge, eluting with a gradient of EtOAc in hexanes (0 to 50%) to afford ethyl 2-(6-chloropyridazin-3-yl)acetate IM212 as a beige solid: 953 mg, 81% yield, P=92%, retention time=0.8 min (gradient C), (M+H)$^+$: 201.

Stage 3: General Procedure C was used between IM3 and IM212 to afford ethyl (R)-2-(6-(3-((tert-butoxycarbonyl)(cyclobutylmethyl)amino)piperidin-1-yl)pyridazin-3-yl)acetate IM213 as a white solid: 153 mg, 46% yield, P=99%, retention time=1.7 min (gradient C), (M+H)$^+$: 433.

Stage 4: Hydrazine hydrate solution (201 µL, 3.48 mmol) was added to IM213 (152 mg, 348 µmol) in solution in EtOH (6.96 mL). The solution was stirred at rt during 2.25 h, then heated at reflux for 17 h. The reaction mixture was stirred at rt for 2 days then heated again at reflux for 8 h. More Hydrazine hydrate solution (401 µL, 6.96 mmol) was added and stirring at reflux was continued for 16 h. The reaction mixture was cooled down to rt, concentrated under reduced pressure, diluted in DCM (25 mL), washed with water (10 mL) and concentrated under reduced pressure to afford crude tert-butyl (R)-(cyclobutylmethyl)(1-(6-(2-hydrazineyl-2-oxoethyl)pyridazin-3-yl)piperidin-3-yl)carbamate IM214 as an off-white solid: 148 mg, 99% yield, P=98%, retention time=1.3 min (gradient C), (M+H)$^+$: 419.

Stage 5: IM214 (88 mg, 206 µmol) was dissolved in butan-1-ol (412 µL). 5-methoxy nicotinonitrile (83 mg, 618 µmol) and potassium carbonate (29 mg, 206 µmol) were added and the reaction mixture was stirred at 125° C. for 3 h. The reaction was cooled down to rt overnight, concentrated under reduced pressure. Residue was directly purified by reverse phase chromatography on a 40 g C18 cartridge, eluting with a gradient of MeCN in basic water (10 mM NH$_4$HCO$_3$/NH$_4$OH buffer pH=10), to afford tert-butyl (R)-(cyclobutylmethyl)(1-(6-((5-(5-methoxypyridin-3-yl)-4H-1,2,4-triazol-3-yl)methyl)pyridazin-3-yl)piperidin-3-yl)carbamate IM215 as a beige solid: 95 mg, 78% yield, P=90%, retention time=1.4 min (gradient C), (M+H)$^+$: 535.

Stage 6: General Procedure A2 was used from IM215 to afford compound 69 as a white solid: 27 mg, 37% yield, P=96%, retention time=1.8 min (gradient C), (M+H)$^+$: 435. $^1$H-NMR (400 MHZ, CD$_3$OD): δ 8.75 (d, J=1.5 Hz, 1H), 8.27 (d, J=2.8 Hz, 1H), 7.98-7.94 (m, 1H), 7.43 (d, J=9.5 Hz, 1H), 7.27 (d, J=9.5 Hz, 1H), 4.45-4.38 (m, 1H), 4.37 (s, 2H), 4.12-4.04 (m, 1H), 3.94 (s, 3H), 3.12-3.04 (m, 1H), 2.94 (dd, J=12.8, 9.5 Hz, 1H), 2.79-2.68 (m, 3H), 2.50 (sept, J=7.6 Hz, 1H), 2.15-2.05 (m, 3H), 1.98-1.79 (m, 3H), 1.77-1.68 (m, 2H), 1.65-1.54 (m, 1H), 1.52-1.41 (m, 1H), 2H exchanged with CD$_3$OD.

Compound 70: N-[[4-[(3R)-3-(cyclobutylmethylamino)-1-piperidyl]phenyl]methyl]-4-oxo-pyrido[1,2-a]pyrimidine-2-carboxamide was Obtained Using General Scheme 2 Pathway B Stage 1: General Procedure R was used from IM209 to afford tert-butyl N-[(3R)-1-[4-(aminomethyl)phenyl]-3-piperidyl]-N-(cyclobutylmethyl)carbamate IM216 as colourless oil: 56 mg, 36% yield, P=87%, retention time=2.4 min (gradient A), (M+H)$^+$: 374.

Stage 2: General Procedure F was used between 4-oxopyrido[1,2-a]pyrimidine-2-carboxylic acid hydrochloride and IM216 to afford tert-butyl N-((cyclobutylmethyl)-N-[(3R)-1-[4-[[(4-oxopyrido[1,2-a]pyrimidine-2-carbonyl)amino]methyl]phenyl]-3-piperidyl]carbamate IM217 as a yellowish gum: 51 mg, 64% yield, P=94%, retention time=2.6 min (gradient A), (M+H)$^+$: 546.

Stage 3: General Procedure A1 was used from IM217 to afford crude compound 70 as yellow oil: 48 mg, 100% yield, P=97%, retention time=2.9 min (gradient B), (M+H)$^+$: 446.

The product was further purified by reverse phase preparative HPLC purification (Waters XBridge C18 5 µm 19×100 mm). Gradient used: increased linearly from 25 to 40% solution "B" over 5.0 min, increased linearly to 85% solution "B" over 1.0 min, held at 85% solution "B" for 0.4 min and returned to initial conditions over 0.8 min. Flow Rate: 15 mL/min. P=100%. $^1$H NMR (300 MHz, CDCl$_3$) δ 9.08 (d, J=7.3 Hz, 1H), 8.18 (s, 1H), 7.77 (t, J=7.9 Hz, 1H), 7.62 (d, J=9.0 Hz, 1H), 7.35-7.11 (m, 4H), 6.93 (d, J=8.4 Hz, 2H), 4.58 (d, J=6.0 Hz, 2H), 3.67-3.55 (m, 1H), 3.49-3.35 (m, 1H), 2.89-2.56 (m, 5H), 2.48 (hept, J=7.6 Hz, 1H), 2.13-1.18 (m, 10H), NH exchanged.

Compound 71: (3R)—N-(cyclobutylmethyl)-1-[5-[1-[4-(5-methoxy-3-pyridyl)triazol-1-yl]ethyl]-2-pyridyl]piperidin-3-amine was Obtained Using General Scheme 1 Pathway B Stage 1: 1-(6-chloro-3-pyridyl)ethanone (1 g, 6.3 mmol) was dissolved in anhydrous methanol (60 mL) at 0° C. Then, sodium borohydride (240 mg, 6.34 mmol) was added one shot. The reaction was stirred at 0° C. for 20 min. Acetone (3 mL) was added at 0° C. and the reaction mixture was stirred for 2 min at 0° C. and then 2 min a rt.

The mixture was concentrated under reduced pressure to dryness. EtOAc (50 mL) was added to the residue, and obtained solution was washed with brine (3×20 mL). Organic layer was dried over MgSO$_4$, filtered and concentrated under reduced pressure to afford crude 1-(6-chloro-3-pyridyl)ethanol IM218 as orange oil: 1.0 g, 93% yield, P=95%, retention time=2.1 min (gradient A), (M+H)$^+$: 158/160.

Stage 2: General Procedure P was used from IM218 to afford crude 1-(6-chloro-3-pyridyl)ethyl methanesulfonate IM219 as yellow oil: 650 mg, 87% yield, P=87% ($^1$H-NMR), retention time=2.5 min (gradient A), (M+H)$^+$: 236/238.

Stage 3: General Procedure N was used from IM219 to afford 2 5-(1-azidoethyl)-2-chloro-pyridine IM220 as yellow oil: 380 mg, 96% yield, P=86%, retention time=2.7 min (gradient A), (M+H)$^+$: 182/184.

Stage 4: General Procedure B was used between IM44 and IM220 to afford 2-chloro-5-[1-[4-(5-methoxy-3-pyridyl)triazol-1-yl]ethyl]pyridine IM221 as yellow oil: 103 mg, 60% yield, P=100%, retention time=2.2 min (gradient A), (M+H)$^+$: 316/318.

Stage 5: General Procedure C was used between IM3 and IM221 to afford tert-butyl N-(cyclobutylmethyl)-N-[(3R)-1-[5-[1-[4-(5-methoxy-3-pyridyl)triazol-1-yl]ethyl]-2-pyridyl]-3-piperidyl]carbamate IM222 as colourless oil: 30 mg, 15% yield, P=90%, retention time=2.4 min (gradient A), (M+H)$^+$: 548.

Stage 6: General Procedure A1 was used from IM222 to afford crude compound 71 as a light brown film: 21 mg, 71% yield, P=93%, retention time=2.5 min (gradient B), (M+H)$^+$: 448.

The mixture of diastereomers was further purified by chiral preparative HPLC purification using Chiralpak IA column (5 µm, 20×250 mm). Eluent used: TBME/MeOH/DEA: 70/30/0.1% at flow rate of 20 mL/min. First eluted diastereomer: P=100%, retention time=6.7 min, chiral HPLC: P=100%, $^1$H NMR (300 MHZ, CDCl$_3$) δ 8.48 (s, 1H), 8.23 (dd, J=15.5, 2.6 Hz, 2H), 7.75 (s, 1H), 7.68 (s, 1H), 7.42 (dd, J=8.9, 2.6 Hz, 1H), 6.65 (d, J=8.9 Hz, 1H), 5.76 (q, J=7.1 Hz, 1H), 4.29-4.19 (m, 1H), 4.07-3.97 (m, 1H), 3.90 (s, 3H), 2.99 (td, J=12.1, 3.1 Hz, 1H), 2.86-2.56 (m, 4H), 2.43 (hept, J=7.6 Hz, 1H), 2.14-1.75 (m, 9H), 1.75-1.47 (m, 3H), 1.44-1.32 (m, 1H), NH exchanged. Second eluted diastereomer: P=100%, retention time=8.4 min, chiral HPLC: P=99.5%, $^1$H NMR (300 MHz, CDCl$_3$) δ 8.48 (d, J=1.6 Hz, 1H), 8.22 (dd, J=15.6, 2.7 Hz, 2H), 7.75 (t, J=2.2 Hz, 1H), 7.68 (s, 1H), 7.42 (dd, J=8.8, 2.6 Hz, 1H), 6.65 (d, J=8.9 Hz, 1H), 5.76 (q, J=7.0 Hz, 1H), 4.31-4.18 (m, 1H), 4.07-3.96 (m, 1H), 3.90 (s, 3H), 3.07-2.92 (m, 1H), 2.87-2.56 (m, 4H), 2.44 (hept, J=7.6 Hz, 1H), 2.13-1.72 (m, 7H), 1.71-1.44 (m, 5H), 1.46-1.23 (m, 1H), NH exchanged.

Compound 72: N-[1-[6-[(3R)-3-(cyclobutylmethylamino)-1-piperidyl]-3-pyridyl]ethyl]-4-oxo-pyrido[1,2-a]pyrimidine-2-carboxamide was Obtained Using General Scheme 2 Pathway B Stage 1: General Procedure C was used between IM3 and 1-(6-chloro-3-pyridyl)ethanone to afford tert-butyl N-[(3R)-1-(5-acetyl-2-pyridyl)-3-piperidyl]-N-(cyclobutylmethyl)carbamate IM223 as colourless oil: 613 mg, 80% yield, P=95%, retention time=2.8 min (gradient A), (M+H)$^+$: 388.

Stage 2: General Procedure H1 was used between ammonia (7 N in methanol) and IM224 to afford crude tert-butyl N-[(3R)-1-[5-(1-aminoethyl)-2-pyridyl]-3-piperidyl]-N-(cyclobutyl methyl)carbamate as colourless oil: 250 mg, 67% yield, P=85%, retention time=2.3 min (gradient A), (M+H)$^+$: 389.

Stage 3: General Procedure F was used between 4-oxopyrido[1,2-a]pyrimidine-2-carboxylic acid hydrochloride and IM224 to afford tert-butyl N-((cyclobutylmethyl)-N-[(3R)-1-[5-[1-[(4-oxopyrido[1,2-a]pyrimidine-2-carbonyl)amino]ethyl]-2-pyridyl]-3-piperidyl]carbamate IM225 as a white foam: 113 mg, 66% yield, P=97%, retention time=2.5 min (gradient A), (M+H)$^+$: 561.

Stage 4: General Procedure A1 was used from IM225 to afford crude compound 72 as an off-white solid: 75 mg, 77% yield, P=95%, retention time=2.6 min (gradient B), (M+H)$^+$: 461.

The mixture of diastereomers was further purified by chiral preparative HPLC purification using Chiralpak IA column (5 µm, 20×250 mm). Eluent used: TBME/MeOH/DEA: 70/30/0.1% at flow rate of 20 mL/min. First eluted diastereomer: P=100%, retention time=6.8 min, chiral HPLC: P=98.9%, $^1$H NMR (300 MHZ, CDCl$_3$) δ 9.07 (d, J=7.2 Hz, 1H), 8.24 (d, J=2.5 Hz, 1H), 8.11 (d, J=8.2 Hz, 1H), 7.78 (ddd, J=8.2, 6.8, 1.6 Hz, 1H), 7.65 (d, J=9.0 Hz, 1H), 7.50 (dd, J=8.8, 2.5 Hz, 1H), 7.28 (s, 1H), 7.18 (td, J=6.8, 1.5 Hz, 1H), 6.65 (d, J=8.8 Hz, 1H), 5.22 (p, J=7.1 Hz, 1H), 4.30-4.18 (m, 1H), 4.06-3.93 (m, 1H), 2.96 (ddd, J=13.3, 10.8, 3.2 Hz, 1H), 2.83-2.66

(m, 3H), 2.67-2.56 (m, 1H), 2.45 (hept, J=7.6 Hz, 1H), 2.12-1.23 (m, 13H), NH exchanged. Second eluted diastereomer: P=100%, retention time=8.5 min, chiral HPLC: P=98.6%, ¹H NMR (300 MHz, CDCl₃) δ 9.07 (d, J=7.2 Hz, 1H), 8.24 (d, J=2.3 Hz, 1H), 8.11 (d, J=8.3 Hz, 1H), 7.83-7.72 (m, 1H), 7.65 (d, J=8.9 Hz, 1H), 7.50 (dd, J=8.8, 2.3 Hz, 1H), 7.31-7.23 (m, 1H), 7.18 (t, J=6.9 Hz, 1H), 6.65 (d, J=8.8 Hz, 1H), 5.22 (p, J=7.1 Hz, 1H), 4.28-4.17 (m, 1H), 4.00 (d, J=13.1 Hz, 1H), 3.04-2.89 (m, 1H), 2.84-2.58 (m, 4H), 2.45 (hept, J=7.5 Hz, 1H), 2.11-1.23 (m, 13H), NH exchanged.

Compound 73: (3R)—N-(cyclobutylmethyl)-1-[6-[1-[4-(5-methoxy-3-pyridyl)triazol-1-yl]ethyl]-3-pyridyl]piperidin-3-amine was Obtained Using General Scheme 1 Pathway B Stage 1: General Procedure Q was used from 5-bromopyridine-2-carboxaldehyde to afford 1 1-(5-bromo-2-pyridyl)ethanol IM226 as yellow oil: 208 mg, 86% yield, P=95%, retention time=2.0 min (gradient A), (M+H)⁺: 202/204.

Stage 2: General Procedure P was used from IM226 to afford crude 1-(5-bromo-2-pyridyl)ethyl methanesulfonate IM230 as yellow oil: 250 mg, 96% yield, P=100%, retention time=2.5 min (gradient A), (M+H)⁺: 280/282.

Stage 3: General Procedure N was used from IM230 to afford crude 2-(1-azidoethyl)-5-bromo-pyridine IM231 as yellow oil: 205 mg, 94% yield, P=95%, retention time=2.7 min (gradient A), (M+H)⁺: 227/229.

Stage 4: General Procedure B was used between IM44 and IM231 to afford 3-[1-[1-(5-bromo-2-pyridyl)ethyl]triazol-4-yl]-5-methoxy-pyridine IM232 as yellow oil: 150 mg, 47% yield, P=100%, retention time=2.3 min (gradient A), (M+H)⁺: 360/362.

Stage 5: General Procedure S was used between IM3 and IM232 to afford tert-butyl N-(cyclobutylmethyl)-N-[(3R)-1-[6-[1-[4-(5-methoxy-3-pyridyl)triazol-1-yl]ethyl]-3-pyridyl]-3-piperidyl]carbamate IM233 as colourless oil: 128 mg, 65% yield, P=88%, retention time=2.6 min (gradient A), (M+H)⁺: 548.

Stage 6: General Procedure A1 was used from IM233 to afford crude compound 73 as colourless oil: 100 mg, 98% yield, P=90%, retention time=2.0 min (gradient A), (M+H)⁺: 448.

The mixture of diastereomers was further purified by chiral preparative HPLC purification using Chiralpak IA column (5 μm, 20×250 mm). Eluent used: EtOAc/MeOH/DEA: 95/5/0.1% at flow rate of 20 mL/min. First eluted diastereomer: P=100%, retention time=5.6 min, chiral HPLC: P=99.8%, ¹H NMR (300 MHz, CDCl₃) δ 8.53 (s, 1H), 8.32-8.22 (m, 2H), 8.00 (s, 1H), 7.79-7.75 (m, 1H), 7.15 (s, 2H), 5.92 (q, J=7.0 Hz, 1H), 3.90 (d, J=1.5 Hz, 3H), 3.65 (d, J=9.2 Hz, 1H), 3.48 (d, J=12.2 Hz, 1H), 2.87 (t, J=10.4 Hz, 1H), 2.69 (t, J=6.5 Hz, 4H), 2.44 (p, J=7.6 Hz, 1H), 2.11-1.96 (m, 6H), 1.96-1.76 (m, 4H), 1.66 (d, J=9.5 Hz, 3H), 1.37-1.24 (m, 1H), NH exchanged. Second eluted diastereomer: P=100%, retention time=9.0 min, chiral HPLC: P=99.8%, ¹H NMR (300 MHz, CDCl₃) δ 8.53 (s, 1H), 8.31-8.15 (m, 2H), 8.00 (s, 1H), 7.76 (s, 1H), 7.14 (s, 2H), 5.95-5.82 (m, 1H), 3.89 (s, 3H), 3.69-3.60 (m, 1H), 3.53-3.43 (m, 1H), 2.93-2.79 (m, 1H), 2.74-2.60 (m, 4H), 2.43 (hept, J=7.6 Hz, 1H), 2.12-1.75 (m, 9H), 1.66-1.50 (m, 3H), 1.37-1.23 (m, 1H), NH exchanged.

Compound 74: N—((S)-1-(4-((R)-3-((cyclobutylmethyl)amino)piperidin-1-yl)phenyl)ethyl)-4-oxo-4H-pyrido[1,2-a]pyrimidine-2-carboxamide was Obtained Using General Scheme 2 Pathway A Stage 1: General Procedure F was used between 4-oxopyrido[1,2-a]pyrimidine-2-carboxylic acid hydrochloride and (S)-(−)-1-(4-Bromophenyl)ethylamine to afford crude N-[(1S)-1-(4-bromophenyl)ethyl]-4-oxo-pyrido[1,2-a]pyrimidine-2-carboxamide IM234 as yellow oil: 240 mg, 93% yield, P=100%, retention time=2.8 min (gradient A), (M+H)⁺: 372/374.

Stage 2: General Procedure S was used between IM3 and IM234 to afford tert-butyl N-(cyclobutylmethyl)-N-[(3R)-1-[4-[(1S)-1-[(4-oxopyrido[1,2-a]pyrimidine-2-carbonyl)amino]ethyl]phenyl]-3-piperidyl]carbamate IM235 as colourless oil: 150 mg, 42% yield, P=100%, retention time=2.6 min (gradient A), (M+H)⁺: 560.

Stage 3: General Procedure A1 was used from IM235 to afford crude compound 74 as an off-white solid: 120 mg, 92% yield, P=98%, retention time=3.3 min (gradient B), (M+H)⁺: 460. ¹H NMR (300 MHz, CDCl₃) δ 9.07 (d, J=7.0 Hz, 1H), 8.14 (d, J=8.4 Hz, 1H), 7.77 (ddd, J=8.4, 7.0, 1.6 Hz, 1H), 7.65 (d, J=8.9 Hz, 1H), 7.32-7.27 (m, 2H), 7.17 (t, J=7.0 Hz, 1H), 6.92 (d, J=8.4 Hz, 2H), 5.32-5.14 (m, 1H), 3.68-3.54 (m, 1H), 3.48-3.38 (m, 1H), 2.87-2.68 (m, 4H), 2.61 (dd, J=11.5, 8.8 Hz, 1H), 2.45 (hept, J=7.6 Hz, 1H), 2.14-1.98 (m, 2H), 1.96-1.75 (m, 5H), 1.71-1.56 (m, 5H), 1.36-1.21 (m, 1H), NH exchanged. Chiral HPLC (IA, TBME/MEOH/DEA: 70/30/0.1%, flow rate: 1 mL/min): P=99.0%.

Compound 75: 4-[(3R)-3-(cyclobutylmethylamino)-1-piperidyl]-1-[[1-(5-methoxy-3-pyridyl) triazol-4-yl]methyl]pyridin-2-one was Obtained Using the Following Procedures Stage 1: Sodium azide (100 mg, 1.52 mmol) and copper (II) sulfate pentahydrate (32 mg, 0.13 mmol) were placed in a round bottomed flask. Anhydrous methanol (2.5 mL) and (5-methoxypyridine-3-boronic acid (200 mg, 1.27 mmol) were added at rt. The mixture was stirred at rt for 40 h. The mixture was concentrated under reduced pressure. Diethyl ether (20 mL) was added to the resulting solid and the suspension was sonicated (2 min), filtered over Celite and rinsed with diethyl ether (30 mL). The filtrate was dried over MgSO₄, filtered and concentrated under reduced pressure to dryness to afford crude IM236 as yellow liquid: 28 mg, 12% yield, P=98%, retention time=1.4 min (gradient A), (M+H)⁺: 151.

Stage 2: A solution of propargyl bromide in toluene (375 μL, 3.37 mmol) was added to a solution of 4-chloro-2-hydroxypyridine (300 mg, 2.25 mmol) and potassium carbonate (630 mg, 4.51 mmol) in dry DME (4.5 mL). The mixture was stirred at 60° C. for 4 h and then allowed to cool to rt and stirred at rt overnight. The suspension was filtered and the solid was rinsed with DCM (20 mL). The filtrate was concentrated under reduced pressure to dryness. The resulting oil was solubilized with DCM (40 mL) and washed with water (30 mL), brine (10 mL), dried over MgSO₄, filtered and concentrated under reduced pressure to dryness to afford crude IM237 as brown oil: 356 mg, 95% yield, P=100%, retention time=2.2 min (gradient A), (M+H)⁺: 168/170.

Stage 3: General Procedure B was used between IM236 and IM237 to afford 4-chloro-1-[[1-(5-methoxy-3-pyridyl)

triazol-4-yl]methyl]pyridin-2-one IM238 as a white solid: 15 mg, 29% yield, P=94%, retention time=2.3 min (gradient A), (M+H)$^+$: 318/320.

Stage 4: General Procedure C was used between IM3 and IM238 to afford tert-butyl N-[(3R)-1-[1-[[1-(5-methoxy-3-pyridyl)triazol-4-yl]methyl]-2-oxo-4-pyridyl]-3-piperidyl] carbamate IM239 as yellow sticky oil: 22 mg, 83% yield, P=99%, retention time=2.8 min (gradient A), (M+H)$^+$: 550.

Stage 5: General Procedure A1 was used from IM239 to afford compound 75 as a beige solid: 15 mg, 91% yield, P=100%, retention time=2.8 min (gradient B), (M+H)$^+$: 450. $^1$H NMR (300 MHz, CDCl$_3$) δ 8.65 (d, J=2.1 Hz, 1H), 8.55 (s, 1H), 8.36 (d, J=2.6 Hz, 1H), 7.87 (t, J=2.3 Hz, 1H), 7.59 (d, J=7.8 Hz, 1H), 6.27 (dd, J=7.8, 2.8 Hz, 1H), 5.73 (d, J=2.8 Hz, 1H), 5.22 (s, 2H), 3.97 (s, 3H), 3.94-3.84 (m, 1H), 3.79-3.69 (m, 1H), 3.05-2.90 (m, 1H), 2.83 (dd, J=13.0, 9.6 Hz, 1H), 2.76-2.71 (m, 2H), 2.71-2.62 (m, 1H), 2.49 (hept, J=7.6 Hz, 1H), 2.18-2.00 (m, 4H), 1.98-1.84 (m, 2H), 1.81-1.66 (m, 3H), 1.62-1.42 (m, 1H), NH exchanged.

Compound 76: (3R)—N-(cyclobutylmethyl)-1-[4-[1-[4-(5-methoxy-3-pyridyl)triazol-1-yl]ethyl]phenyl]piperidin-3-amine was Obtained Using General Scheme 1 Pathway A Stage 1: General Procedure S was used between IM3 and 4-bromobenzaldehyde to afford tert-butyl N-(cyclobutylmethyl)-N-[(3R)-1-(4-formylphenyl)-3-piperidyl]carbamate IM240 as yellowish oil: 170 mg, 28% yield, P=98% (215 nm), retention time=3.3 min (gradient A), (M+H)$^+$: 373.

Stage 2: General Procedure Q (replacing MeMgBr with MeMgCl) was used from IM240 to afford tert-butyl N-(cyclobutylmethyl)-N-[(3R)-1-[4-(1-hydroxyethyl)phenyl]-3-piperidyl] carbamate IM241 as colourless oil: 177 mg, 96% yield, P=94% ($^1$H-NMR), retention time=2.5 min (gradient A), (M+H)$^+$: 389.

Stage 3: General Procedure M was used from IM241 to afford tert-butyl N-[(3R)-1-[4-(1-azidoethyl)phenyl]-3-piperidyl]-N-(cyclobutylmethyl)carbamate IM242 as colourless oil: 95 mg, 41% yield, P=77% (215 nm), retention time=3.0 min (gradient A), (M+H)$^+$: 414.

Stage 4: General Procedure B was used between IM44 and IM242 to afford tert-butyl N-(cyclobutylmethyl)-N-[(3R)-1-[4-[1-[4-(5-methoxy-3-pyridyl)triazol-1-yl]ethyl] phenyl]-3-piperidyl]carbamate IM243 as a white foam: 69 mg, 68% yield, P=95% ($^1$H-NMR), retention time=2.6 min (gradient A), (M+H)$^+$: 547.

Stage 6: General Procedure A1 was used from IM243 to afford compound 76 as colourless oil: 55 mg, 100% yield, P=96%, retention time=3.0 min (gradient B), (M+H)$^+$: 446.

The mixture of diastereomers was further purified by chiral preparative HPLC purification using Chiralpak IA column (5 μm, 20×250 mm). Eluent used: TBME/MeOH/DEA: 70/30/0.1% at flow rate of 20 mL/min. First eluted diastereomer: P=100%, retention time=5.7 min, chiral HPLC: P=100%, $^1$H NMR (300 MHz, CDCl$_3$) δ 8.47 (s, 1H), 8.24 (d, J=2.7 Hz, 1H), 7.75 (s, 1H), 7.63 (s, 1H), 7.22 (d, J=8.6 Hz, 2H), 6.91 (d, J=8.7 Hz, 2H), 5.79 (q, J=7.0 Hz, 1H), 3.89 (s, 3H), 3.70-3.59 (m, 1H), 3.53-3.42 (m, 1H), 2.86-2.75 (m, 1H), 2.75-2.56 (m, 4H), 2.44 (hept, J=7.3 Hz, 1H), 2.16-1.73 (m, 10H), 1.73-1.58 (m, 2H), 1.39-1.19 (m, 1H), NH exchanged. Second eluted diastereomer: P=100%, retention time=6.5 min, chiral HPLC: P=96.2%, $^1$H NMR (300 MHz, CDCl$_3$) δ 8.46 (s, 1H), 8.23 (d, J=2.7 Hz, 1H), 7.74 (s, 1H), 7.63 (s, 1H), 7.21 (d, J=8.6 Hz, 2H), 6.91 (d, J=8.7 Hz, 2H), 5.78 (q, J=7.0 Hz, 1H), 3.89 (s, 3H), 3.69-3.59 (m, 1H), 3.52-3.41 (m, 1H), 2.89-2.75 (m, 1H), 2.75-2.56 (m, 5H), 2.44 (hept, J=7.5 Hz, 1H), 2.15-1.57 (m, 12H), 1.41-1.19 (m, 1H).

Compound 77: (R)-4-(3-((cyclobutylmethyl)amino) piperidin-1-yl)-1-((5-(5-methoxypyridin-3-yl)-1,3,4-thiadiazol-2-yl)methyl)pyridin-2 (1H)-one was Obtained Using General Scheme 3 Pathway A Stage 1: General Procedure C was used between IM3 and 4-Chloro-2-hydroxypyridine to afford tert-butyl (R)-(cyclobutylmethyl)(1-(2-oxo-1,2-dihydropyridin-4-yl)piperidin-3-yl) carbamate IM244 as yellow solid: 1.47 g, 54% yield, P=100%, retention time=1.4 min (gradient C), (M+H)$^+$: 362.

Stage 2: General Procedure T was used between (5-bromo-1,3,4-thiadiazol-2-yl)methanol and IM244 to afford tert-butyl (R)-(1-(1-((5-bromo-1,3,4-thiadiazol-2-yl) methyl)-2-oxo-1,2-dihydropyridin-4-yl)piperidin-3-yl)(cyclobutylmethyl)carbamate IM245 as a white solid: 23 mg, 15% yield, P=93%, retention time=1.7 min (gradient C), (M+H)$^+$: 538/540.

Stage 3: General Procedure U was used from IM245 to afford tert-butyl (R)-(cyclobutylmethyl)(1-(1-((5-(5-methoxypyridin-3-yl)-1,3,4-thiadiazol-2-yl)methyl)-2-oxo-1,2-dihydropyridin-4-yl)piperidin-3-yl)carbamate IM246 as a white solid: 13 mg, 56% yield, P=100%, retention time=1.6 min (gradient C), (M+H)$^+$: 567.

Stage 4: General Procedure A2 was used from IM246 to afford compound 77 as a white powder: 6 mg, 56% yield, P=96%, retention time=2.2 min (gradient E), (M+H)$^+$: 471. $^1$H NMR (400 MHZ, CD$_3$OD) δ 8.67 (d, J=1.7 Hz, 1H), 8.40 (d, J=2.8 Hz, 1H), 7.93 (dd, J=2.8, 1.8 Hz, 1H), 7.59 (d, J=7.9 Hz, 1H), 6.33 (dd, J=7.9, 2.8 Hz, 1H), 5.74 (d, J=2.8 Hz, 1H), 5.49 (s, 2H), 3.97 (s, 3H), 3.96-3.89 (m, 1H), 3.84-3.74 (m, 1H), 3.05-2.93 (m, 1H), 2.81 (dd, J=13.1, 9.8 Hz, 1H), 2.69 (d, J=7.3 Hz, 2H), 2.65-2.56 (m, 1H), 2.53-2.43 (m, 1H), 2.15-2.01 (m, 3H), 1.98-1.83 (m, 2H), 1.83-1.67 (m, 3H), 1.61-1.50 (m, 1H), 1.46-1.35 (m, 1H), 1H exchanged with CD$_3$OD.

Compound 78: 1-[1-[4-(5-chloro-3-pyridyl)triazol-1-yl]ethyl]-4-[-(3R)-3-(cyclobutylmethyl amino)-1-piperidyl]pyridin-2-one was Obtained Using General Scheme 1 Pathway B Stage 1: General Procedure B was used between 3-Chloro-5-ethynylpyridine and IM151 to afford 4-chloro-1-(1-(4-(5-chloropyridin-3-yl)-1H-1,2,3-triazol-1-yl)ethyl) pyridin-2 (1H)-one IM247 as a yellow solid: 185 mg, 80% yield, P=97%, retention time=1.0 min (gradient C), (M+H)$^+$: 336.

Stage 2: General Procedure C was used between IM3 and IM247 to afford tert-butyl (3R)-1-(1-(1-(4-(5-chloropyridin-3-yl)-1H-1,2,3-triazol-1-yl)ethyl)-2-oxo-1,2-dihydropyridin-4-yl) piperidin-3-yl)(cyclobutylmethyl)carbamate IM248 as a tan solid: 95 mg, 92% yield, P=98%, retention time=1.5 min (gradient C), (M+H)$^+$: 568/570.

Stage 6: General Procedure A2 was used from IM248 to afford crude compound 78 as an off-white solid: 56 mg, 76% yield, P=99%, retention time=2.6 min (gradient E), (M+H)$^+$: 468. $^1$H-NMR (400 MHZ, CD$_3$OD): δ 8.96 (d, J=1.8 Hz, 1H), 8.68 (s, 1H), 8.53 (d, J=2.3 Hz, 1H), 8.37-8.29 (m, 1H), 7.66 (d, J=8.1 Hz, 1H), 7.51 (q, J=6.9 Hz, 1H), 6.33 (dd, J=8.2, 2.9 Hz, 1H), 5.67 (d, J=2.8 Hz, 1H), 3.97-3.87 (m, 1H), 3.83-3.72 (m, 1H), 3.04-2.93 (m, 1H), 2.85-2.75 (m, 1H), 2.67 (d, J=7.4 Hz, 2H), 2.63-2.52 (m, 1H), 2.52-2.38

(m, 1H), 2.15 (d, J=7.0 Hz, 3H), 2.13-2.00 (m, 3H), 1.98-1.63 (m, 5H), 1.61-1.45 (m, 1H), 1.45-1.32 (m, 1H). 1H exchanged with CD$_3$OD.

The mixture of diastereomers was further purified by chiral preparative HPLC purification using Chiralpak IA column (5 μm, 20×250 mm). Eluent used: TBME/MeOH/DCM/DEA: 40/40/25/0.1% at flow rate of 20 mL/min. First eluted diastereomer: P=100%, retention time=5.4 min, chiral HPLC: P=100%, $^1$H NMR (300 MHz, CDCl$_3$) δ 8.88 (s, 1H), 8.55-8.47 (m, 1H), 8.20 (d, J=1.7 Hz, 1H), 8.18-8.12 (m, 1H), 7.53 (q, J=7.0 Hz, 1H), 7.42 (d, J=8.4 Hz, 1H), 6.03-5.95 (m, 1H), 5.68-5.62 (m, 1H), 3.83-3.72 (m, 1H), 3.66-3.55 (m, 1H), 3.01-2.85 (m, 1H), 2.83-2.57 (m, 4H), 2.42 (hept, J=7.6 Hz, 1H), 2.18 (d, J=6.7 Hz, 3H), 2.12-1.22 (m, 10H), NH exchanged. Second eluted diastereomer: P=100%, retention time=9.9 min, chiral HPLC: P=100%, $^1$H NMR (300 MHz, CDCl$_3$) δ 8.89 (d, J=1.8 Hz, 1H), 8.52 (d, J=2.3 Hz, 1H), 8.28-8.13 (m, 2H), 7.61-7.40 (m, 2H), 6.01 (dd, J=8.1, 2.8 Hz, 1H), 5.67 (d, J=2.8 Hz, 1H), 3.90-3.79 (m, 1H), 3.66-3.55 (m, 1H), 3.00-2.76 (m, 2H), 2.74-2.62 (m, 3H), 2.52-2.40 (m, 1H), 2.18 (d, J=7.1 Hz, 3H), 2.10-1.38 (m, 10H), NH exchanged.

Compound 79: 1-[1-[4-(3-pyridyl)triazol-1-yl]ethyl]-4-[-(3R)-3-(cyclobutylmethyl amino)-1-piperidyl]pyridin-2-one was Obtained Using General Scheme 1 Pathway B Stage 1: General Procedure B was used between 3-ethynylpyridine and IM151 to afford 4-chloro-1-(1-(4-(pyridin-3-yl)-1H-1,2,3-triazol-1-yl)ethyl)pyridin-2 (1H)-one IM249 as a white solid: 140 mg, 92% yield, P=98%, retention time=0.8 min (gradient C), (M+H)$^+$: 302/304.

Stage 2: General Procedure C was used between IM3 and IM249 to afford tert-butyl (3R)-1-(1-(1-(4-(pyridin-3-yl)-1H-1,2,3-triazol-1-yl)ethyl)-2-oxo-1,2-dihydropyridin-4-yl)piperidin-3-yl)(cyclobutylmethyl)carbamate IM250 as a white gum: 249 mg, 100% yield, P=98%, retention time=1.4 min (gradient C), (M+H)$^+$: 534.

Stage 3: General Procedure A2 was used from IM250 to afford compound 79 as a white solid: 105 mg, 51% yield, P=97%, retention time=1.8 min (gradient C), (M+H)$^+$: 434. $^1$H-NMR (400 MHZ, DMSO-d$_6$): δ 9.07 (d, J=1.7 Hz, 1H), 8.88 (d, J=1.8 Hz, 1H), 8.54 (dd, J=4.7, 1.4 Hz, 1H), 8.23 (dt, J=8.0, 1.8 Hz, 1H), 7.57 (d, J=8.1 Hz, 1H), 7.48 (dd, J=7.9, 4.8 Hz, 1H), 7.42 (br. q, J=6.8 Hz, 1H), 6.20 (dd, J=8.1, 2.7 Hz, 1H), 5.46 (d, J=2.5 Hz, 1H), 3.82-3.71 (m, 1H), 3.71-3.62 (m, 1H), 2.92-2.79 (m, 1H), 2.70-2.58 (m, 1H), 2.58-2.52 (m, 2H), 2.45-2.35 (m, 1H), 2.35-2.24 (m, 1H), 2.01 (d, J=6.9 Hz, 3H), 1.98-1.83 (m, 3H), 1.83-1.71 (m, 2H), 1.69-1.54 (m, 3H), 1.49-1.29 (m, 2H), 1.27-1.15 (m, 1H).

Compound 80: 1-[1-[4-(5-methyl-3-pyridyl)triazol-1-yl]ethyl]-4-[(3R)-3-(cyclobutylmethyl amino)-1-piperidyl]pyridin-2-one was Obtained Using General Scheme 1 Pathway B Stage 1: General Procedure B was used between 3-ethynyl-5-methylpyridine and IM151 to afford crude 4-chloro-1-(1-(4-(5-methylpyridin-3-yl)-1H-1,2,3-triazol-1-yl)ethyl)pyridin-2 (1H)-one IM251. The product was purified by reverse phase preparative HPLC purification (0-100% MeCN in 10 mM ammonium formate) to afford IM251 as a pale green solid: 91 mg, 38% yield, P=99%, retention time=1.0 min (gradient F), (M+H)$^+$: 316/318.

Stage 2: General Procedure C was used between IM3 and IM251 to afford tert-butyl (3R)-1-(1-(1-(4-(5-methylpyridin-3-yl)-1H-1,2,3-triazol-1-yl)ethyl)-2-oxo-1,2-dihydropyridin-4-yl) piperidin-3-yl)(cyclobutylmethyl)carbamate IM252 as a beige solid: 101 mg, 63% yield, P=99%, retention time=1.6 min (gradient F), (M+H)$^+$: 548.

Stage 3: General Procedure A2 was used from IM252 to afford compound 80 as a white solid: 68 mg, 82% yield, P=98%, retention time=2.4 min (gradient F), (M+H)$^+$: 448. $^1$H-NMR (400 MHZ, CD$_3$OD): δ 8.80 (d, J=1.6 Hz, 1H), 8.60 (s, 1H), 8.35 (d, J=1.3 Hz, 1H), 8.12-8.08 (m, 1H), 7.66 (d, J=8.1 Hz, 1H), 7.53-7.46 (m, 1H), 6.32 (dd, J=8.2, 2.9 Hz, 1H), 5.67 (d, J=2.8 Hz, 1H), 4.00-3.87 (m, 1H), 3.83-3.71 (m, 1H), 3.06-2.92 (m, 1H), 2.92-2.80 (m, 1H), 2.80-2.66 (m, 3H), 2.41 (s, 3H), 2.17-2.01 (m, 6H), 2.01-1.63 (m, 6H), 1.63-1.35 (m, 2H). 1H exchanged with CD$_3$OD.

The mixture of diastereomers was further purified by chiral preparative HPLC purification using Chiralpak IA column (5 μm, 20×250 mm). Eluent used: TBME/MeOH/DCM/DEA: 40/40/25/0.1% at flow rate of 20 mL/min. First eluted diastereomer: P=100%, retention time=5.0 min, chiral HPLC: P=100%, $^1$H NMR (300 MHz, CDCl$_3$) δ 8.81 (d, J=2.0 Hz, 1H), 8.39 (d, J=2.1 Hz, 1H), 8.14 (s, 1H), 7.96 (d, J=2.2 Hz, 1H), 7.53 (q, J=7.0 Hz, 1H), 7.42 (d, J=8.1 Hz, 1H), 5.99 (dd, J=8.2, 2.8 Hz, 1H), 5.66 (d, J=2.8 Hz, 1H), 3.85-3.74 (m, 1H), 3.66-3.54 (m, 1H), 2.98-2.86 (m, 1H), 2.82-2.73 (m, 1H), 2.71-2.55 (m, 3H), 2.52-2.39 (m, 1H), 2.37 (s, 3H), 2.16 (d, J=7.1 Hz, 3H), 2.11-1.40 (m, 10H), NH exchanged. Second eluted diastereomer: P=100%, retention time=9.7 min, chiral HPLC: P=100%, $^1$H NMR (300 MHz, CDCl$_3$) δ 8.81 (d, J=2.0 Hz, 1H), 8.39 (d, J=2.1 Hz, 1H), 8.14 (s, 1H), 7.96 (d, J=2.2 Hz, 1H), 7.53 (q, J=7.0 Hz, 1H), 7.42 (d, J=8.1 Hz, 1H), 5.99 (dd, J=8.2, 2.8 Hz, 1H), 5.66 (d, J=2.8 Hz, 1H), 3.85-3.74 (m, 1H), 3.66-3.54 (m, 1H), 2.98-2.86 (m, 1H), 2.82-2.73 (m, 1H), 2.71-2.55 (m, 3H), 2.52-2.39 (m, 1H), 2.37 (s, 3H), 2.16 (d, J=7.1 Hz, 3H), 2.11-1.40 (m, 10H), NH exchanged.

Compound 81: (3R)—N-(cyclobutylmethyl)-1-[6-[[4-(5-methoxy-3-pyridyl)imidazol-1-yl]methyl]pyridazin-3-yl]piperidin-3-amine was Obtained Using General Scheme 4 Pathway A Stage 1: To a solution of 4-bromo-1H-imidazole (175 mg, 1.17 mmol) in dry DMF (5.83 mL), cooled at 0° C., was added NaH (70 mg, 1.75 mmol). The reaction mixture was stirred a t0° C. for 10 min then a solution of 3-chloro-6-(chloromethyl)pyridazine (254 mg, 1.40 mmol) in DMF (3.89 mL) was added dropwise. The mixture was allowed to reach rt and stirred for 15 h. The reaction was quenched with few drops of water and directly purified by reverse phase chromatography on a 60 g C18 cartridge, eluting with a gradient of MeCN in basic water (10 mM NH$_4$HCO$_3$/NH$_4$OH buffer pH=10, 5 to 40%), to afford 3-((4-bromo-1H-imidazol-1-yl)methyl)-6-chloropyridazine IM253 as a black gum: 179 mg, 48% yield, P=86%, retention time=0.8 min (gradient C), (M+H)$^+$: 273.

Stage 2: General Procedure C was used between IM3 and IM253 to afford tert-butyl (R)-(1-(6-((4-bromo-1H-imidazol-1-yl)methyl)pyridazin-3-yl)piperidin-3-yl)(cyclobutylmethyl) carbamate IM254 as a brown gum: 214 mg, 75% yield, P=99%, retention time=1.7 min (gradient C), (M+H)$^+$: 505/507.

Stage 3: General Procedure U was used from IM254 to afford tert-butyl (R)-(cyclobutylmethyl)(1-(6-((4-(5-methoxypyridin-3-yl)-1H-imidazol-1-yl)methyl)pyridazin- 3-yl) piperidin-3-yl)carbamate IM255 as a yellow gum: 41 mg, 19% yield, P=97%, retention time=1.6 min (gradient C), (M+H)+: 534.

Stage 4: General Procedure A2 was used from IM255 to afford compound 81 as a beige solid: 15 mg, 44% yield, P=94%, retention time=2.2 min (gradient C), (M+H)+: 434.

The product was further purified by reverse phase preparative HPLC purification (Waters XBridge C18 5 μm 19×100 mm). Gradient used: increased linearly from 10 to 30% solution "B" over 4.0 min, increased linearly to 85% solution "B" over 2.0 min, and returned to initial conditions over 1.0 min. Flow Rate: 15 mL/min. P=100%. $^1$H NMR (300 MHz, CDCl$_3$) δ 8.52 (s, 1H), 8.18 (d, J=2.8 Hz, 1H), 7.66 (s, 1H), 7.64 (s, 1H), 7.35 (s, 1H), 7.04 (d, J=9.4 Hz, 1H), 6.88 (d, J=9.5 Hz, 1H), 5.30 (s, 2H), 4.43-4.35 (m, 1H), 4.15-4.04 (m, 1H), 3.89 (s, 3H), 3.18-3.07 (m, 1H), 2.91 (dd, J=12.9, 9.3 Hz, 1H), 2.76-2.59 (m, 3H), 2.41 (hept, J=7.5 Hz, 1H), 2.11-2.01 (m, 2H), 1.95-1.79 (m, 3H), 1.70-1.57 (m, 4H), 1.42 (d, J=10.4 Hz, 1H), NH exchanged.

Compound 82: (3R)—N-(cyclobutylmethyl)-1-[6-[1-[4-(5-methoxy-3-pyridyl)triazol-1-yl]-1-methyl-ethyl]pyridazin-3-yl]piperidin-3-amine was Obtained Using General Scheme 1 Pathway A Stage 1: General Procedure C was used between IM3 and 4 1-(6-chloropyridazin-3-yl)ethanone to afford tert-butyl N-[(3R)-1-(6-acetylpyridazin-3-yl)-3-piperidyl]-N-(cyclobutyl methyl)carbamate IM256 as a yellow foam: 1.56 g, 92% yield, P=98%, retention time=2.9 min (gradient A), (M+H)+: 389.

Stage 2: To a solution of IM256 (300 mg, 0.76 mmol) in anhydrous THF (3.6 mL) was added 2-methyl-2-propanesulfinamide (103 mg, 0.82 mmol), followed by titanium(IV) isopropoxyde (450 μL, 1.47 mmol) added one shot. Reaction mixture was heated to 60° C. for 16 h and then cooled to rt, and water was added (10 mL), followed by MeOH (10 mL). A suspension was obtained after 1 h stirring at rt. It was filtered on Celite pad and solid was rinsed with MeOH (5×20 mL). Filtrate was concentrated under reduced pressure and the residue was purified by silica gel flash chromatography (nHeptane/EtOAc: 1/0 to 1/1) to afford tert-butyl N-[(3R)-1-[6-[(E)-N-tert-butylsulfinyl-C-methyl-carbonimidoyl]pyridazin-3-yl]-3-piperidyl]-N-(cyclo butylmethyl)carbamate IM257 as yellow oil: 115 mg, 28% yield, P=90%, retention time=2.8 min (gradient A), (M+H)+: 492.

Stage 3: General Procedure Q was used from IM257 to afford tert-butyl N-[(3R)-1-[6-[1-(tert-butylsulfinylamino)-1-methyl-ethyl]pyridazin-3-yl]-3-piperidyl]-N-(cyclobutylmethyl) carbamate IM258 as an off-white foam: 53 mg, 53% yield, P=95%, retention time=2.5 min (gradient A), (M+H)+: 508.

Stage 4: IM258 (0.27 g, 0.52 mmol) was dissolved in THF (1.5 mL) and water (0.3 mL). Iodine (41 mg, 0.16 mmol) was added and the mixture was stirred at 55° C. for 2 h. The reaction mixture was cooled to rt and partitioned between EtOAc (50 mL) and Na$_2$S$_2$O$_3$ (2.5 g) in saturated aqueous sodium bicarbonate (25 mL). The layers were separated and the aqueous layer was extracted with EtOAc (50 mL). The organics layers were combined and washed with saturated aqueous NaCl (20 mL), dried over MgSO$_4$, filtered and concentrated under reduced pressure to afford crude tert-butyl N-[(3R)-1-[6-(1-amino-1-methyl-ethyl)pyridazin-3-yl]-3-piperidyl]-N-(cyclobutylmethyl) IM259 as brown oil: 209 mg, 91% yield, P=93%, retention time=2.3 min (gradient A), (M+H)+: 404.

Stage 5: General Procedure V was used from IM259 to afford tert-butyl N-[(3R)-1-[6-(1-azido-1-methyl-ethyl)pyridazin-3-yl]-3-piperidyl]-N-(cyclobutylmethyl) carbamate IM260 as colourless oil: 150 mg, 70% yield, P=98%, retention time=2.7 min (gradient A), (M+H)+: 430.

Stage 6: General Procedure B was used between IM44 and IM260 to afford tert-butyl N-(cyclobutylmethyl)-N-[(3R)-1-[6-[1-[4-(5-methoxy-3-pyridyl)triazol-1-yl]-1-methyl-ethyl]pyridazin-3-yl]-3-piperidyl]carbamate IM261 as a colourless film: 15 mg, 23% yield, P=95%, retention time=2.4 min (gradient A), (M+H)+: 563.

Stage 7: General Procedure A1 was used from IM261 to afford compound 82 as a white solid: 10 mg, 83% yield, P=97%, retention time=2.6 min (gradient B), (M+H)+: 463. $^1$H NMR (300 MHz, CDCl$_3$) δ 8.46 (s, 1H), 8.19 (d, J=2.7 Hz, 1H), 7.82 (s, 1H), 7.68 (s, 1H), 6.95 (d, J=9.6 Hz, 1H), 6.78 (d, J=9.7 Hz, 1H), 4.31 (d, J=13.2 Hz, 1H), 4.02 (d, J=13.2 Hz, 1H), 3.84 (s, 3H), 3.03 (t, J=12.0 Hz, 1H), 2.87-2.75 (m, 1H), 2.69-2.51 (m, 3H), 2.34 (dt, J=14.9, 7.5 Hz, 1H), 2.15 (s, 6H), 2.02-1.69 (m, 6H), 1.66-1.22 (m, 4H), NH exchanged.

Compound 83: N-[1-[6-[(3R)-3-(cyclobutylmethyl-amino)-1-piperidyl]pyridazin-3-yl]propyl]-4-oxo-pyrido[1,2-a]pyrimidine-2-carboxamide was Obtained Using General Scheme 2 Pathway B Stage 1: To a stirred solution of 3-chloropyridazine-6-carboxylic acid (2.00 g, 12.62 mmol) in anhydrous DMF (62 mL) at rt, were added DIEA (4.00 mL, 22.47 mmol), N,O-dimethylhydroxylamine hydrochloride (1.38 g, 13.87 mmol) and HATU (6.20 g, 16.31 mmol). The reaction mixture was stirred at rt for 2.5 h. Reaction mixture was diluted with water (600 mL) and extracted with EtOAc (3×250 mL). Organic layers were combined and washed with NaHCO$_3$ saturated solution (2×100 mL) and brine (100 mL). Organic layer was dried over MgSO$_4$, filtered and concentrated under reduced pressure to afford 3.5 g as brown oil. The crude residue was purified by silica gel flash chromatography (nHeptane/EtOAc: 1/0 to 1/1) to afford 6-chloro-N-methoxy-N-methyl-pyridazine-3-carboxamide IM262 as colourless oil: 1.37 g, 53% yield, P=100%, retention time=2.0 min (gradient A), (M+H)+: 202/204.

Stage 2: General Procedure C was used between IM3 and IM262 to afford tert-butyl N-(cyclobutylmethyl)-N-[(3R)-1-[6-[methoxy(methyl)carbamoyl]pyridazin-3-yl]-3-piperidyl] carbamate IM263 as a pink foam: 1.35 g, 86% yield, P=95%, retention time=2.6 min (gradient A), (M+H)+: 434.

Stage 3: General Procedure Q (replacing MeMgBr with EtMgBr) was used from IM263 to afford tert-butyl N-(cyclobutylmethyl)-N-[(3R)-1-[6-(6-propanoylpyridazin-3-yl)-3-piperidyl] carbamate IM264 as colourless oil: 111 mg, 28% yield, P=100%, retention time=2.9 min (gradient A), (M+H)+: 403.

Stage 4: General Procedure W was used from IM264 to afford crude tert-butyl N-[(3R)-1-[6-(1-aminopropyl)pyridazin-3-yl]-3-piperidyl]-N-(cyclobutylmethyl)carbamate IM265 as colourless oil: 112 mg, 75% yield, P=86%, retention time=2.3 min (gradient A), (M+H)+: 404.

Stage 5: General Procedure F was used between 4-oxopyrido[1,2-a]pyrimidine-2-carboxylic acid hydrochloride and IM265 to afford tert-butyl N-(cyclobutylmethyl)-N-[(3R)-1-[6-[1-[(4-oxopyrido[1,2-a]pyrimidine-2-carbonyl)amino]propyl]pyridazin-3-yl]-3-piperidyl]carbamate IM266 as yellow oil: 40 mg, 58% yield, P=100%, retention time=2.6 min (gradient A), (M+H)+: 576.

Stage 6: General Procedure A1 was used from IM266 to afford crude compound 83 as yellow oil: 32 mg, 97% yield, P=100%, retention time=2.1 min (gradient A), (M+H)$^+$: 476.

The mixture of diastereomers was further purified by chiral preparative HPLC purification using Chiralpak IA column (5 μm, 20×250 mm). Eluent used: TBME/MeOH/DCM/DEA: 60/20/20/0.1% at flow rate of 20 mL/min. First eluted diastereomer: P=100%, retention time=5.1 min, chiral HPLC: P=99.3%, $^1$H NMR (300 MHz, CDCl$_3$) δ 9.06 (d, J=7.2 Hz, 1H), 8.87 (d, J=8.8 Hz, 1H), 7.85-7.70 (m, 2H), 7.25-7.13 (m, 2H), 6.96 (d, J=9.4 Hz, 1H), 5.17 (q, J=7.3 Hz, 1H), 4.59-4.49 (m, 1H), 4.14-4.03 (m, 1H), 3.16-2.96 (m, 2H), 2.90-2.81 (m, 3H), 2.60 (hept, J=7.6 Hz, 1H), 2.18-2.00 (m, 5H), 1.92-1.52 (m, 7H), 0.96 (t, J=7.4 Hz, 3H), 2NH exchanged. Second eluted diastereomer: P=100%, retention time=6.3 min, chiral HPLC: P=98.6%, $^1$H NMR (300 MHz, CDCl$_3$) δ 9.07 (d, J=7.2 Hz, 1H), 8.86 (d, J=8.8 Hz, 1H), 7.86-7.71 (m, 2H), 7.28 (s, 1H), 7.22-7.16 (m, 1H), 7.01 (d, J=9.4 Hz, 1H), 5.18 (q, J=7.3 Hz, 1H), 4.69 (d, J=12.7 Hz, 1H), 4.08 (d, J=13.2 Hz, 1H), 3.37-3.24 (m, 1H), 3.16-2.94 (m, 4H), 2.75 (hept, J=7.7 Hz, 1H), 2.28-2.03 (m, 5H), 1.93-1.76 (m, 6H), 1.61 (d, J=13.8 Hz, 1H), 0.96 (t, J=7.4 Hz, 3H), 2NH exchanged.

Compound 84: (3R)—N-(cyclobutylmethyl)-1-[6-[cyclopropyl-[4-(5-methoxy-3-pyridyl)triazol-1-yl]methyl]pyridazin-3-yl]piperidin-3-amine was Obtained Using General Scheme 1 Pathway A Stage 1: General Procedure Q (replacing MeMgBr with cPrMgBr) was used from IM263 to afford tert-butyl N-(cyclobutylmethyl)-N-[(3R)-1-[6-(cyclopropanecarbonyl)pyridazin-3-yl]-3-piperidyl]carbamate IM267 as colourless film: 190 mg, 44% yield, P=93%, retention time=3.0 min (gradient A), (M+H)$^+$: 415.

Stage 2: General Procedure W was used from IM267 to afford crude tert-butyl N-[(3R)-1-[6-[amino(cyclopropyl)methyl]pyridazin-3-yl]-3-piperidyl]-N-(cyclobutylmethyl)carbamate IM268 as pink oil: 190 mg, 86% yield, P=87%, retention time=2.3 min (gradient A), (M+H)$^+$: 416.

Stage 3: General Procedure V was used from IM268 to afford tert-butyl N-[(3R)-1-[6-[azido(cyclopropyl)methyl]pyridazin-3-yl]-3-piperidyl]-N-(cyclobutylmethyl)carbamate IM269 as colourless oil: 57 mg, 63% yield, P=94%, retention time=2.7 min (gradient A), (M+H)$^+$: 442.

Stage 4: General Procedure B was used between IM44 and IM269 to afford tert-butyl N-(cyclobutylmethyl)-N-[(3R)-1-[6-[cyclopropyl-[4-(5-methoxy-3-pyridyl)triazol-1-yl]methyl]pyridazin-3-yl]-3-piperidyl]carbamate IM270 as a colourless film: 49 mg, 63% yield, P=98%, retention time=2.5 min (gradient A), (M+H)$^+$: 575.

Stage 5: General Procedure A1 was used from IM270 to afford crude compound 83 as a white foam: 30 mg, 81% yield, P=98%, retention time=2.1 min (gradient A), (M+H)$^+$: 475.

The mixture of diastereomers was further purified by chiral preparative HPLC purification using Chiralpak IA column (5 μm, 20×250 mm). Eluent used: TBME/MeOH/DCM/DEA: 60/20/20/0.1% at flow rate of 20 mL/min. First eluted diastereomer: P=100%, retention time=5.8 min, chiral HPLC: P=100%, $^1$H NMR (300 MHz, CDCl$_3$) δ 8.58 (s, 1H), 8.25 (d, J=2.8 Hz, 1H), 8.23 (s, 1H), 7.74 (s, 1H), 7.29 (d, J=9.4 Hz, 1H), 6.90 (d, J=9.5 Hz, 1H), 5.05 (d, J=9.9 Hz, 1H), 4.42-4.31 (m, 1H), 4.07 (d, J=10.9, 6.6 Hz, 1H), 3.90 (s, 3H), 3.18-3.03 (m, 1H), 2.92 (dd, J=12.8, 9.2 Hz, 1H), 2.79-2.60 (m, 3H), 2.42 (hept, J=7.5 Hz, 1H), 2.11-1.97 (m, 4H), 1.91-1.77 (m, 3H), 1.62 (s, 3H), 1.49-1.37 (m, 1H), 0.88-0.71 (m, 2H), 0.58 (d, J=5.0 Hz, 2H), NH exchanged. Second eluted diastereomer: P=100%, retention time=8.4 min, chiral HPLC: P=100%, $^1$H NMR (300 MHz, CDCl$_3$) δ 8.58 (s, 1H), 8.25 (d, J=2.8 Hz, 1H), 8.23 (s, 1H), 7.74 (t, J=2.2 Hz, 1H), 7.29 (d, J=9.4 Hz, 1H), 6.90 (d, J=9.5 Hz, 1H), 5.05 (d, J=9.9 Hz, 1H), 4.44-4.32 (m, 1H), 4.14-4.02 (m, 1H), 3.90 (s, 3H), 3.19-3.03 (m, 1H), 2.94 (dd, J=12.8, 9.2 Hz, 1H), 2.77-2.63 (m, 3H), 2.44 (hept, J=7.6 Hz, 1H), 2.16-1.97 (m, 4H), 1.97-1.79 (m, 3H), 1.72-1.50 (m, 3H), 1.50-1.35 (m, 1H), 0.79 (q, J=8.7 Hz, 2H), 0.58 (d, J=5.0 Hz, 2H), NH exchanged.

Compound 85: (3R)—N-(cyclobutylmethyl)-1-[6-[1-[4-(5-methoxy-3-pyridyl)triazol-1-yl]propyl]pyridazin-3-yl]piperidin-3-amine was Obtained Using General Scheme 1 Pathway A Stage 1: General Procedure V was used from IM265 to afford tert-butyl N-[(3R)-1-[6-(1-azidopropyl)pyridazin-3-yl]-3-piperidyl]-N-(cyclobutylmethyl)carbamate IM271 as yellow oil: 37 mg, 63% yield, P=100%, retention time=2.7 min (gradient A), (M+H)$^+$: 430.

Stage 2: General Procedure B was used between IM44 and IM271 to afford tert-butyl N-(cyclobutylmethyl)-N-[(3R)-1-[6-[1-[4-(5-methoxy-3-pyridyl)triazol-1-yl]propyl]pyridazin-3-yl]-3-piperidyl]carbamate IM272 as yellow oil: 34 mg, 70% yield, P=100%, retention time=2.5 min (gradient A), (M+H)$^+$: 563.

Stage 3: General Procedure A1 was used from IM272 to afford crude compound 83 as colourless oil: 27 mg, 97% yield, P=100%, retention time=2.1 min (gradient A), (M+H)$^+$: 463.

The mixture of diastereomers was further purified by chiral preparative HPLC purification using Chiralpak IA column (5 μm, 20×250 mm). Eluent used: TBME/MeOH/DCM/DEA: 40/40/25/0.1% at flow rate of 20 mL/min. First eluted diastereomer: P=100%, retention time=4.8 min, chiral HPLC: P=100%, $^1$H NMR (300 MHz, CDCl$_3$) δ 8.56 (d, J=1.8 Hz, 1H), 8.25 (d, J=2.8 Hz, 1H), 8.12 (s, 1H), 7.73 (s, 1H), 7.28 (d, J=10.1 Hz, 1H), 6.88 (d, J=9.5 Hz, 1H), 5.72 (t, J=7.8 Hz, 1H), 4.40-4.31 (m, 1H), 4.13-4.02 (m, 1H), 3.90 (s, 3H), 3.18-3.03 (m, 1H), 2.90 (dd, J=12.8, 9.2 Hz, 1H), 2.79-2.47 (m, 5H), 2.40 (zhept, J=7.6 Hz, 1H), 2.13-1.96 (m, 3H), 1.86 (dqd, J=15.0, 7.8, 3.1 Hz, 3H), 1.72-1.55 (m, 3H), 1.50-1.36 (m, 1H), 1.04-0.93 (m, 3H), NH exchanged. Second eluted diastereomer: P=100%, retention time=19.4 min, chiral HPLC: P=100%, $^1$H NMR (300 MHz, CDCl$_3$) δ 8.56 (s, 1H), 8.25 (s, 1H), 8.12 (s, 1H), 7.76-7.68 (m, 1H), 7.28 (d, J=9.8 Hz, 1H), 6.89 (d, J=9.5 Hz, 1H), 5.72 (t, J=7.8 Hz, 1H), 4.42-4.31 (m, 1H), 4.08 (d, J=13.2 Hz, 1H), 3.90 (s, 3H), 3.18-3.03 (m, 1H), 2.93 (dd, J=12.9, 9.1 Hz, 1H), 2.76-2.60 (m, 3H), 2.61-2.48 (m, 2H), 2.43 (hept, J=7.3 Hz, 1H), 2.13-1.95 (m, 4H), 1.93-1.74 (m, 4H), 1.70-1.52 (m, 6H), 1.52-1.33 (m, 1H), 0.98 (t, J=7.3 Hz, 3H), NH exchanged.

Compound 86: (3R)—N-(cyclobutylmethyl)-1-[6-[1-[4-(5-methoxy-3-pyridyl)triazol-1-yl] propyl]pyridazin-3-yl]piperidin-3-amine was Obtained Using General Scheme 1 Pathway B Stage 1: General Procedure B was used between IM44 and IM120 to afford tert-butyl N-(cyclobutylmethyl)-N-[(3R)-1-[5-[[4-(5-methoxy-3-pyridyl)triazol-1-yl]methyl]-2-pyridyl]-3-piperidyl]carbamate IM273 as a white foam: 83 mg, 87% yield, P=100%, retention time=3.7 min (gradient B), (M+H)$^+$: 534.

Stage 2: General Procedure A1 was used from IM273 to afford compound 86 as a colourless gum: 65 mg, 98% yield, P=99%, retention time=2.4 min (gradient B), (M+H)$^+$: 434. $^1$H NMR (300 MHz, CD$_3$OD) δ 8.54 (d, J=1.7 Hz, 1H), 8.43 (s, 1H), 8.25-8.09 (m, 2H), 7.77 (dd, J=2.8, 1.6 Hz, 1H), 7.54 (dd, J=8.9, 2.5 Hz, 1H), 6.76 (d, J=8.9 Hz, 1H), 5.49 (s, 2H), 4.33-4.20 (m, 1H), 4.00 (dt, J=13.2, 4.1 Hz, 1H), 3.89 (s, 3H), 2.93 (ddd, J=13.5, 10.8, 3.1 Hz, 1H), 2.76 (dd, J=12.8, 9.5 Hz, 1H), 2.71-2.50 (m, 3H), 2.44 (p, J=7.7 Hz, 1H), 2.14-1.20 (m, 10H), 1H exchanged with CD$_3$OD.

Compound 87: (3R)—N-(cyclobutylmethyl)-1-[5-[[4-(5-methoxy-3-pyridyl)triazol-1-yl]methyl]-2-pyridyl]piperidin-3-amine was Obtained Using General Scheme 1 Pathway B Stage 1: General Procedure B was used between IM44 and IM128 to afford tert-butyl N-(cyclobutylmethyl)-N-[(3R)-1-[6-[[4-(5-methoxy-3-pyridyl)triazol-1-yl]methyl]-3-pyridyl]-3-piperidyl]carbamate IM274 as colourless oil: 37 mg, 58% yield, P=100%, retention time=2.5 min (gradient A), (M+H)$^+$: 534.

Stage 2: General Procedure A1 was used from IM274 to afford compound 87 as colourless oil: 30 mg, 100% yield, P=100%, retention time=2.5 min (gradient B), (M+H)$^+$: 434. $^1$H NMR (300 MHz, CDCl$_3$) δ 8.52 (d, J=1.7 Hz, 1H), 8.34-8.16 (m, 2H), 7.96 (s, 1H), 7.77 (dd, J=2.8, 1.7 Hz, 1H), 7.23-7.10 (m, 2H), 5.59 (s, 2H), 3.90 (s, 3H), 3.73-3.59 (m, 1H), 3.56-3.43 (m, 1H), 2.97-2.81 (m, 1H), 2.78-2.60 (m, 4H), 2.44 (hept, J=7.5 Hz, 1H), 2.14-2.01 (m, 2H), 2.01-1.75 (m, 4H), 1.72-1.56 (m, 3H), 1.43-1.23 (m, 1H), NH exchanged.

Compound 88: 2-[1-[1-[4-[(3R)-3-(cyclobutylmethylamino)-1-piperidyl]-2-oxo-1-pyridyl]_ethyl]triazol-4-yl]pyrido[1,2-a]pyrimidin-4-one was Obtained Using General Scheme 1 Pathway B Stage 1: General Procedure E2 was used from 2-Chloro-4H-pyrido[1,2-a]pyrimidin-4-one to afford 2-(2-trimethylsilylethynyl)pyrido[1,2-a]pyrimidin-4-one IM275 as light brown solid: 430 mg, 67% yield, P=96%, retention time=2.8 min (gradient A), (M+H)$^+$: 243.

Stage 2: General Procedure D1 was used from IM275 to afford 2-ethynylpyrido[1,2-a]pyrimidin-4-one IM276 as an off-white solid: 156 mg, 51% yield, P=97%, retention time=2.1 min (gradient A), (M+H)$^+$: 171.

Stage 3: General Procedure B was used between IM276 and IM151 to afford 2-1-[1-(4-chloro-2-oxo-1-pyridyl)ethyl]triazol-4-yl]pyrido[1,2-a]pyrimidin-4-one IM277 as a yellow solid: 101 mg, 78% yield, P=100%, retention time=2.4 min (gradient A), (M+H)$^+$: 369/371.

Stage 4: General Procedure C was used between IM3 and IM277 to afford tert-butyl N-(cyclobutylmethyl)-N-[(3R)-1-[2-oxo-1-[1-[4-(4-oxopyrido[1,2-a]pyrimidin-2-yl)triazol-1-yl]ethyl]-4-pyridyl]-3-piperidyl]carbamate IM278 as an off-white foam: 115 mg, 72% yield, P=100%, retention time=2.9 min (gradient A), (M+H)$^+$: 601.

Stage 5: General Procedure A1 was used from IM278 to afford compound 88 as a white foam: 93 mg, 97% yield, P=100%, retention time=2.1 min (gradient A), (M+H)$^+$: 501.

The mixture of diastereomers was further purified by chiral preparative HPLC purification using Chiralpak IA column (5 μm, 20×250 mm). Eluent used: TBME/MeOH/DCM/DEA: 40/40/25/0.1% at flow rate of 20 mL/min. First eluted diastereomer: P=100%, retention time=6.0 min, chiral HPLC: P=100%, $^1$H NMR (300 MHz, CDCl$_3$) δ 9.06 (d, J=7.1 Hz, 1H), 8.49 (s, 1H), 7.78-7.66 (m, 1H), 7.66-7.52 (m, 2H), 7.42 (d, J=8.1 Hz, 1H), 7.26 (s, 2H), 7.10 (t, J=6.9 Hz, 1H), 5.98 (dd, J=8.1, 2.8 Hz, 1H), 5.65 (d, J=2.8 Hz, 1H), 3.80-3.69 (m, 1H), 3.66-3.55 (m, 1H), 2.98-2.83 (m, 1H), 2.75-2.63 (m, 3H), 2.57 (dt, J=9.6, 5.5 Hz, 1H), 2.41 (dq, J=15.2, 7.6 Hz, 1H), 2.17 (d, J=7.1 Hz, 3H), 2.11-1.81 (m, 5H), 1.77-1.44 (m, 4H), 1.43-1.23 (m, 1H), NH exchanged. Second eluted diastereomer: P=100%, retention time=11.8 min, chiral HPLC: P=100%, $^1$H NMR (300 MHz, CDCl$_3$) δ 9.06 (d, J=7.1 Hz, 1H), 8.50 (s, 1H), 7.72 (ddd, J=8.5, 6.7, 1.6 Hz, 1H), 7.66-7.52 (m, 2H), 7.42 (d, J=8.1 Hz, 1H), 7.26 (s, 1H), 7.10 (td, J=6.9, 1.5 Hz, 1H), 5.98 (dd, J=8.1, 2.8 Hz, 1H), 5.65 (d, J=2.8 Hz, 1H), 3.81-3.69 (m, 1H), 3.66-3.55 (m, 1H), 2.92 (ddd, J=13.7, 10.9, 3.1 Hz, 1H), 2.78-2.51 (m, 4H), 2.39 (hept, J=7.4 Hz, 1H), 2.17 (d, J=7.0 Hz, 3H), 2.10-1.81 (m, 5H), 1.77-1.42 (m, 4H), 1.41-1.25 (m, 1H), NH exchanged.

Compound 89: 2-[1-[1-[6-[(3R)-3-(cyclobutylmethylamino)-1-piperidyl]pyridazin-3-yl]ethyl] triazol-4-yl]pyrido[1,2-a]pyrimidin-4-one was Obtained Using General Scheme 1 Pathway A Stage 1: General Procedure W was used from IM256 to afford crude tert-butyl N-[(3R)-1-[6-(1-aminoethyl)pyridazin-3-yl]-3-piperidyl]-N-(cyclobutylmethyl)carbamate IM279 as pink oil: 145 mg, 74% yield, P=74%, retention time=2.3 min (gradient A), (M+H)$^+$: 390.

Stage 2: General Procedure V was used from IM279 to afford tert-butyl N-[(3R)-1-[6-(1-azidoethyl)pyridazin-3-yl]-3-piperidyl]-N-(cyclobutylmethyl)carbamate IM280 as colourless oil: 85 mg, 75% yield, P=98%, retention time=2.6 min (gradient A), (M+H)$^+$: 416.

Stage 3: General Procedure B was used between IM276 and IM280 to afford tert-butyl N-[(3R)-1-[6-(1-azidoethyl)pyridazin-3-yl]-3-piperidyl]-N-(cyclobutylmethyl)carbamate IM281 as yellow oil: 85 mg, 65% yield, P=92%, retention time=2.6 min (gradient A), (M+H)$^+$: 586.

Stage 4: General Procedure A1 was used from IM281 to afford compound 89 as a white foam: 60 mg, 95% yield, P=100%, retention time=2.1 min (gradient A), (M+H)$^+$: 486.

The mixture of diastereomers was further purified by chiral preparative HPLC purification using Chiralpak IA column (5 μm, 20×250 mm). Eluent used: TBME/MeOH/DCM/DEA: 40/40/25/0.1% at flow rate of 20 mL/min. First eluted diastereomer: P=100%, retention time=5.5 min, chiral HPLC: P=100%, $^1$H NMR (300 MHz, CDCl$_3$) δ 9.06 (d, J=7.2 Hz, 1H), 8.39 (s, 1H), 7.71 (ddd, J=8.4, 6.6, 1.6 Hz, 1H), 7.60 (d, J=8.9 Hz, 1H), 7.26 (s, 1H), 7.21 (d, J=9.5 Hz, 1H), 7.09 (td, J=6.9, 1.5 Hz, 1H), 6.87 (d, J=9.5 Hz, 1H), 6.06 (q, J=7.1 Hz, 1H), 3.18-3.02 (m, 1H), 4.43-4.32 (m, 1H), 4.14-4.02 (m, 1H), 2.88 (dd, J=12.8, 9.2 Hz, 1H), 2.68 (ddq, J=13.8, 9.5, 4.5 Hz, 3H), 2.41 (p, J=7.6 Hz, 1H), 2.12 (d, J=7.2 Hz, 3H), 2.09-1.96 (m, 3H), 1.96-1.76 (m, 3H), 1.69-1.55 (m, 3H), 1.48-1.37 (m, 1H), NH exchanged. Second eluted diastereomer: P=100%, retention time=9.7 min, chiral HPLC: P=100%, $^1$H NMR (300 MHz, CDCl$_3$) δ 9.06 (d, J=7.0 Hz, 1H), 8.38 (s, 1H), 7.77-7.65 (m, 1H), 7.60 (d, J=8.9 Hz, 1H), 7.26 (s, 1H), 7.21 (d, J=9.5 Hz, 1H), 7.09 (t, J=7.0 Hz, 1H), 6.87 (d, J=9.5 Hz, 1H), 6.06 (q, J=7.0 Hz, 1H), 4.42-4.32 (m, 1H), 4.15-4.04 (m, 1H), 3.17-3.04 (m, 1H), 2.89 (dd, J=12.7, 9.3 Hz, 1H), 2.79-2.58 (m, 3H), 2.42 (hept, J=7.7 Hz, 1H), 2.12 (d, J=7.1 Hz, 3H), 2.08-1.96 (m, 3H), 1.95-1.78 (m, 3H), 1.71-1.56 (m, 3H), 1.48-1.37 (m, 1H), NH exchanged.

Compound 90: 8-chloro-4-oxo-N-[1-[6-[(3R)-3-(cyclobutylmethylamino)-1-piperidyl] pyridazin-3-yl]ethyl]pyrido[1,2-a]pyrimidine-2-carboxamide was Obtained Using General Scheme 2 Pathway B Stage 1: General Procedure F was used between 8-chloro-4-oxo-4H-pyrido[1,2-a]pyrimidine-2-carboxylic acid and IM279 to afford tert-butyl (3R)-1-(6-(1-(8-chloro-4-oxo-4H-pyrido[1,2-a]pyrimidine-2-carboxamido)ethyl)pyridazin-3-yl)piperidin-3-yl)(cyclobutylmethyl) carbamate IM282 as a beige solid: 90 mg, 44% yield, P=100%, retention time=1.9 min (gradient C), (M+H)+: 596.

Stage 2: General Procedure A2 was used from IM282 to afford compound 90 as a white solid: 17 mg, 60% yield, P=99%, retention time=2.7 min (gradient E), (M+H)+: 496. $^1$H NMR (400 MHZ, CD$_3$OD): δ 9.03 (d, J=7.6 Hz, 1H), 7.95 (d, J=2.2 Hz, 1H), 7.47 (d, J=9.5 Hz, 1H), 7.42 (dd, 1H, J=7.7, 2.3 Hz, 1H), 7.28 (d, J=9.6 Hz, 1H), 7.06 (s, 1H), 5.30 (q, J=6.9 Hz, 1H), 4.49-436 (m, 1H), 4.17-4.07 (m, 1H), 3.12-3.03 (m, 1H), 2.91 (dd, J=12.7, 9.7 Hz, 1H), 2.80-2.63 (m, 3H), 2.56-2.44 (m, 1H), 2.16-2.03 (m, 3H), 1.98-1.79 (m, 3H), 1.78-1.68 (m, 2H), 1.64 (d, J=6.9 Hz, 3H), 1.62-1.54 (m, 1H), 1.51-1.40 (m, 1H), 2H exchanged with CD$_3$OD.

Compound 91: 8-(methylamino)-4-oxo-N-[1-[6-[(3R)-3-(cyclobutylmethylamino)-1-piperidyl]pyridazin-3-yl]ethyl]pyrido[1,2-a]pyrimidine-2-carboxamide was Obtained by Nucleophilic Substitution of Above Intermediate Stage 1: In 10 mL RBF to IM282 (58 mg, 97.3 µmol) was added methylamine (2.43 mL, 4.86 mmol) (2M in THF) and the mixture was stirred at rt for 18 h (full conversion into the desired product by LC-MS). After solvent evaporation, tert-butyl (cyclobutylmethyl)((3R)-1-(6-(1-(8-(methylamino)-4-oxo-4H-pyrido[1,2-a]pyrimidine-2-carboxamido)ethyl)pyridazin-3-yl)piperidin-3-yl)carbamate IM283 was obtained as a tan film: 58 mg, 100% yield, P=100%, retention time=1.8 min (gradient D), (M+H)+: 591.

Stage 2: General Procedure A2 was used from IM283 to afford compound 91 as a light yellow powder: 35 mg, 72% yield, P=99%, retention time=2.7 min (gradient E), (M+H)+: 491. $^1$H NMR (400 MHZ, CD$_3$OD): δ 8.72 (d, J=7.8 Hz, 1H), 7.46 (d, J=9.5 Hz, 1H), 7.27 (d, J=9.6 Hz, 1H), 6.81 (d, J=6.4 Hz, 1H), 6.60 (s, 1H), 6.57 (d, J=0.8 Hz, 1H), 5.26 (q, J=6.9 Hz, 1H), 4.45-4.35 (m, 1H), 4.17-4.05 (m, 1H), 3.12-3.02 (m, 1H), 2.96 (s, 3H), 2.93-2.85 (m, 1H), 2.79-2.60 (m, 3H), 2.49 (hept, J=7.7 Hz, 1H), 2.16-2.01 (m, 3H), 1.99-1.78 (m, 3H), 1.77-1.65 (m, 2H), 1.62 (d, J=6.9 Hz, 3H), 1.61-1.52 (m, 1H), 1.50-1.38 (m, 1H), 3H exchanged with CD$_3$OD.

The mixture of diastereomers was further purified by chiral preparative HPLC purification using Chiralpak IE column (5 µm, 10×250 mm). Eluent used: TBME/MeOH/DCM/DEA: 55/35/10/0.1% at flow rate of 7 mL/min. First eluted diastereomer: P=99%, retention time=7.7 min, chiral HPLC: P=100%, $^1$H NMR (300 MHz, CDCl$_3$) δ 8.89-8.72 (m, 2H), 7.24 (s, 1H), 6.93 (d, J=9.4 Hz, 1H), 6.87 (s, 1H), 6.51 (d, J=6.3 Hz, 2H), 5.40-5.28 (m, 1H), 5.09 (s, 1H), 4.51-4.41 (m, 1H), 4.09-3.98 (m, 1H), 3.17-3.03 (m, 1H), 3.01 (d, J=5.0 Hz, 4H), 2.81 (d, J=7.2 Hz, 3H), 2.60-2.48 (m, 1H), 2.15-1.38 (m, 13H), NH exchanged. Second eluted diastereomer: P=99%, retention time=11.1 min, chiral HPLC: P=100%, $^1$H NMR (300 MHz, CDCl$_3$) δ 8.76 (dd, J=17.8, 8.1 Hz, 2H), 7.23 (d, J=9.4 Hz, 1H), 6.93 (d, J=9.3 Hz, 1H), 6.83 (s, 1H), 6.59 (d, J=6.1 Hz, 1H), 6.45 (s, 1H), 5.39-5.27 (m, 1H), 4.36-4.24 (m, 2H), 3.97-3.83 (m, 1H), 3.35-3.16 (m, 2H), 2.98 (d, J=4.9 Hz, 3H), 2.92-2.80 (m, 3H), 2.62-2.50 (m, 1H), 2.14-1.39 (m, 13H), NH exchanged.

Compound 92: 7-methoxy-N-[1-[6-[(3R)-3-(cyclobutylmethylamino)-1-piperidyl]pyridazin-3-yl]ethyl]-1H-indazole-4-carboxamide was Obtained Using General Scheme 2 Pathway B Stage 1: To a suspension of methyl 7-fluoro-1H-indazole-4-carboxylate (303 mg, 1.48 mmol)
In DCM (7.9 mL) under N$_2$ were added 3,4-dihydro-2H-pyran (418 µL, 4.45 mmol) and PTSA (26 mg, 148 µmol). The reaction was stirred at rt for 2 h. The reaction mixture was quenched with a saturated aqueous solution of NaHCO$_3$ (20 mL). Mixture was diluted with DCM (60 mL), phases were separated and organic layer was washed with a saturated aqueous solution of NaHCO$_3$ (2×15 mL) then brine (20 mL). Organic layer was dried over MgSO$_4$, filtered and concentrated under reduced pressure. Residue was purified by silica gel chromatography on a 70 g cartridge, eluting with a gradient of EtOAc in hexanes (0 to 20%) to afford methyl 7-fluoro-1-(tetrahydro-2H-pyran-2-yl)-1H-indazole-4-carboxylate IM284 as a white solid: 326 mg, 77% yield, P=98%, retention time=1.5 min (gradient C), (M−THP+H)+: 195.

Stage 2: LiOH (168 mg, 6.89 mmol) was added to IM284 (326 mg, 1.15 mmol) in solution in THF (4.35 mL) and water (4.35 mL). The reaction was stirred at rt for 16 h then concentrated under reduced pressure. The residue was dissolved in water (30 mL) and pH was adjusted to 2 using 1 N aqueous HCl solution. The resulting solution was extracted with EtOAc (3×20 mL). The organic phase was dried over Na$_2$SO$_4$, filtered and concentrated under reduced pressure to afford crude 7-fluoro-1-(tetrahydro-2H-pyran-2-yl)-1H-indazole-4-carboxylic acid IM285 as a white solid: 311 mg, 100% yield, P=100%, retention time=1.0 min (gradient C), (M+H)+: 265.

Stage 3: General Procedure F was used between IM285 and IM279 to afford tert-butyl (cyclobutylmethyl)((3R)-1-(6-(1-(7-fluoro-1-(tetrahydro-2H-pyran-2-yl)-1H-indazole-4-carboxamido)ethyl)pyridazin-3-yl)piperidin-3-yl)carbamate IM286 as a light yellow solid: 82 mg, 58% yield, P=98%, retention time=2.0 min (gradient C), (M+H)+: 576.

Stage 4: In a reaction tube were placed IM286 (41 mg, 63.2 µmol) and MeONa (25 wt. % in MeOH) (338 µL, 1.26 mmol). The vial was sealed and the reaction mixture was stirred at 75° C. for 66 h. The reaction was cooled down to rt and concentrated under reduced pressure. Residue was purified by reverse phase chromatography on a 25 g C18 cartridge, eluting with a gradient of MeCN in basic water (10 mM NH$_4$HCO$_3$/NH$_4$OH buffer pH=10) (5%, then 50 to 85%) to afford tert-butyl (cyclobutylmethyl)((3R)-1-(6-(1-(7-methoxy-1-(tetrahydro-2H-pyran-2-yl)-1H-indazole-4-carboxamido)ethyl)pyridazin-3-yl)piperidin-3-yl)carbamate IM287 as a white solid: 23 mg, 54% yield, P=97%, retention time=1.6 min (gradient C), (M+H)+: 649.

Stage 5: General Procedure A2 was used from IM287 to afford compound 92 as a white solid: 9 mg, 59% yield, P=99%, retention time=2.4 min (gradient E), (M+H)+: 464. $^1$H NMR (400 MHZ, CD$_3$OD): δ 8.36 (s, 1H), 7.67 (d, J=7.9 Hz, 1H), 7.49 (d, J=9.5 Hz, 1H), 7.27 (d, J=9.5 Hz, 1H), 6.89 (d, J=8.0 Hz, 1H), 5.37 (q, J=7.0 Hz, 1H), 4.46-4.37 (m, 1H), 4.16-4.08 (m, 1H), 4.07 (s, 3H), 3.11-3.02 (m, 1H), 2.91 (dd, J=12.5, 9.9 Hz, 1H), 2.77-2.64 (m, 3H), 2.49 (spt, J=7.6 Hz, 1H), 2.14-2.03 (m, 3H), 1.99-1.78 (m, 3H), 1.77-1.67 (m, 2H), 1.65 (d, J=7.0 Hz, 3H), 1.62-1.54 (m, 1H), 1.49-1.39 (m, 1H), 3H labile protons exchange with CD$_3$OD.

The mixture of diastereomers was further purified by chiral preparative HPLC purification using Chiralpak IE column (5 μm, 10×250 mm). Eluent used: TBME/MeOH/DCM/DEA: 55/35/10/0.1% at flow rate of 7 mL/min. First eluted diastereomer: P=100%, retention time=4.4 min, chiral HPLC: P=97.5%, $^1$H NMR (300 MHz, CDCl$_3$) δ 8.50 (s, 1H), 7.80 (d, J=7.3 Hz, 1H), 7.58 (d, J=8.0 Hz, 1H), 7.29 (d, J=9.4 Hz, 1H), 6.98 (d, J=9.4 Hz, 1H), 6.67 (d, J=7.9 Hz, 1H), 5.47-5.35 (m, 1H), 4.52-4.41 (m, 1H), 4.01 (s, 3H), 3.99-3.89 (m, 1H), 3.35-3.20 (m, 1H), 3.12 (t, J=10.6 Hz, 1H), 3.05-2.86 (m, 3H), 2.61 (hept, J=7.9 Hz, 1H), 2.12-2.01 (m, 2H), 1.91-1.04 (m, 11H), NH exchanged. Second eluted diastereomer: P=100%, retention time=7.0 min, chiral HPLC: P=100%, $^1$H NMR (300 MHz, CDCl$_3$) δ 8.57 (s, 1H), 7.82 (d, J=7.4 Hz, 1H), 7.62 (d, J=7.9 Hz, 1H), 7.30 (d, J=9.4 Hz, 1H), 6.97 (d, J=9.4 Hz, 1H), 6.69 (d, J=7.9 Hz, 1H), 5.46-5.35 (m, 1H), 4.48-4.38 (m, 1H), 4.04-3.92 (m, 4H), 3.26-3.02 (m, 2H), 2.95-2.76 (m, 3H), 2.64-2.53 (m, 1H), 2.08 (s, 2H), 1.94-1.82 (m, 2H), 1.79-1.49 (m, 9H), NH exchanged.

Compound 93: 1-[1-[4-(5-methoxypyridazin-3-yl)triazol-1-yl]ethyl]-4-[(3R)-3-(cyclobutyl methylamino)-1-piperidyl]pyridin-2-one was Obtained Using General Scheme 1 pathway B Stage 1: General Procedure E1 (in THF instead of DMF) was used from 3-chloro-5-methoxypyridazine to afford 3-ethynyl-5-methoxypyridazine IM288 (full desilylation upon concentration under reduced pressure of purified material) as a tan solid: 135 mg, 30% yield, P=100%, retention time=0.8 min (gradient D), (M+H)$^+$: 135.

Stage 2: General Procedure B was used between IM151 and IM288 to afford 4-chloro-1-(1-(4-(5-methoxypyridazin-3-yl)-1H-1,2,3-triazol-1-yl)ethyl)pyridin-2 (1H)-one IM289 as a light yellow solid: 230 mg, 81% yield, P=100%, retention time=1.2 min (gradient D), (M+H)$^+$: 333/335.

Stage 3: General Procedure C was used between IM3 and IM289 to afford tert-butyl (cyclobutylmethyl)((3R)-1-(1-(1-(4-(5-methoxypyridazin-3-yl)-1H-1,2,3-triazol-1-yl)ethyl)-2-oxo-1,2-dihydropyridin-4-yl)piperidin-3-yl)carbamate IM290 as light brown gummy oil: 375 mg, 91% yield, P=95%, retention time=1.8 min (gradient D), (M+H)$^+$: 565.

Stage 4: General Procedure A2 was used from IM290 to afford compound 93 as an off-white powder: 165 mg, 56% yield, P=100%, retention time=2.6 min (gradient E), (M+H)$^+$: 465. $^1$H NMR (400 MHZ, CD$_3$OD): δ 8.85 (d, J=2.9 Hz, 1H), 8.77 (s, 1H), 7.85 (d, J=2.9 Hz, 1H), 7.70 (d, J=8.1 Hz, 1H), 7.55 (q, J=7.0 Hz, 1H), 6.34 (dd, J=8.2, 2.9 Hz, 1H), 5.67 (d, J=2.8 Hz, 1H), 4.05 (s, 3H), 3.98-3.87 (m, 1H), 3.84-3.72 (m, 1H), 3.04-2.93 (m, 1H), 2.80 (ddd, J=12.9, 9.8, 2.7 Hz, 1H), 2.67 (d, J=7.3 Hz, 2H), 2.63-2.53 (m, 1H), 2.53-2.38 (m, 1H), 2.17 (d, J=7.0 Hz, 3H), 2.13-2.00 (m, 3H), 1.98-1.81 (m, 2H), 1.81-1.63 (m, 3H), 1.61-1.45 (m, 1H), 1.45-1.31 (m, 1H), 1H exchanged with CD$_3$OD.

The mixture of diastereomers was further purified by chiral preparative HPLC purification using Chiralpak IA column (5 μm, 20×250 mm). Eluent used: TBME/MeOH/DCM/DEA: 55/35/10/0.1% at flow rate of 20 mL/min. First eluted diastereomer: P=100%, retention time=9.6 min, chiral HPLC: P=100%, $^1$H NMR (300 MHz, CDCl$_3$) δ 8.80 (d, J=2.9 Hz, 1H), 8.57 (s, 1H), 7.72 (d, J=2.9 Hz, 1H), 7.61 (q, J=6.9 Hz, 1H), 7.33 (d, J=8.1 Hz, 1H), 5.97 (dd, J=8.1, 2.5 Hz, 1H), 5.66 (d, J=2.5 Hz, 1H), 3.97 (s, 3H), 3.81-3.70 (m, 1H), 3.65-3.54 (m, 1H), 2.91 (t, J=12.0 Hz, 1H), 2.65 (hept, J=9.4 Hz, 4H), 2.40 (hept, J=7.5 Hz, 1H), 2.15 (d, J=6.9 Hz, 3H), 2.09-1.47 (m, 9H), 1.43-1.32 (m, 1H), NH exchanged. Second eluted diastereomer: P=100%, retention time=12.6 min, chiral HPLC: P=100%, $^1$H NMR (300 MHz, CDCl$_3$) δ 8.80 (d, J=2.9 Hz, 1H), 8.57 (s, 1H), 7.71 (d, J=2.9 Hz, 1H), 7.60 (q, J=6.9 Hz, 1H), 7.33 (d, J=8.1 Hz, 1H), 5.97 (dd, J=8.1, 2.3 Hz, 1H), 5.65 (d, J=2.3 Hz, 1H), 3.96 (s, 3H), 3.81-3.71 (m, 1H), 3.65-3.54 (m, 1H), 2.97-2.83 (m, 1H), 2.79-2.54 (m, 4H), 2.40 (hept, J=7.4 Hz, 1H), 2.14 (d, J=6.9 Hz, 3H), 2.11-1.52 (m, 9H), 1.42-1.22 (m, 1H), NH exchanged.

Compound 94: 1-[1-[4-(5-fluoro-3-pyridyl)triazol-1-yl]ethyl]-4-[(3R)-3-(cyclobutylmethyl amino)-1-piperidyl]pyridin-2-one was Obtained Using General Scheme 1 Pathway B Stage 1: General Procedure E1 (using triethylamine as a solvent at 0.3 mol/L) was used from 3-bromo-5-fluoropyridine to afford 3-fluoro-5-((trimethylsilyl)ethynyl)pyridine IM291 as light yellow oil: 698 mg, 59% yield, P=93%, retention time=1.7 min (gradient C), (M+H)$^+$: 194.

Stage 2: General Procedure X was used between IM151 and IM291 to afford 4-chloro-1-(1-(4-(5-fluoropyridin-3-yl)-1H-1,2,3-triazol-1-yl)ethyl)pyridin-2 (1H)-one IM292 as a white solid: 131 mg, 77% yield, P=88%, retention time=1.2 min (gradient C), (M+H)$^+$: 320/322.

Stage 3: General Procedure C was used between IM3 and IM292 to afford tert-butyl (cyclobutylmethyl)((3R)-1-(1-(1-(4-(5-fluoropyridin-3-yl)-1H-1,2,3-triazol-1-yl)ethyl)-2-oxo-1,2-dihydropyridin-4-yl)piperidin-3-yl)carbamate IM293 as a brown gum: 161 mg, 84% yield, P=91%, retention time=1.8 min (gradient C), (M+H)$^+$: 552.

Stage 4: General Procedure A2 was used from IM293 to afford compound 94 as a white solid: 36 mg, 79% yield, P=98%, retention time=2.5 min (gradient E), (M+H)$^+$: 452. $^1$H NMR (400 MHZ, CD$_3$OD): δ 8.90 (s, 1H), 8.68 (s, 1H), 8.45 (d, J=2.6 Hz, 1H), 8.09 (ddd, J=9.6, 2.5, 1.8 Hz, 1H), 7.66 (d, J=8.1 Hz, 1H), 7.51 (q, J=6.9 Hz, 1H), 6.33 (dd, J=8.2, 2.8 Hz, 1H), 5.67 (d, J=2.8 Hz, 1H), 3.96-3.87 (m, 1H), 3.82-3.74 (m, 1H), 3.02-2.93 (m, 1H), 2.80 (ddd, J=13.3, 9.8, 3.9 Hz, 1H), 2.66 (d, J=7.4 Hz, 2H), 2.61-2.53 (m, 1H), 2.50-2.41 (m, 1H), 2.15 (d, J=7.0 Hz, 3H), 2.12-2.00 (m, 3H), 1.96-1.80 (m, 2H), 1.80-1.64 (m, 3H), 1.59-1.46 (m, 1H), 1.43-1.32 (m, 1H), 1H labile proton exchange with CD$_3$OD. $^{19}$F NMR (376 MHZ, CD$_3$OD): δ −127.78 (dd, J=9.6, 0.8 Hz, 1F).

Compound 95: (R)-4-(3-((cyclobutylmethyl)amino)piperidin-1-yl)-1-((5-(5-methoxypyridin-3-yl)-1H-pyrazol-3-yl)methyl)pyridin-2 (1H)-one was Obtained Using the Following Procedures Stage 1: To a solution of methyl 1H-pyrazole-3-carboxylate (1.00 g, 7.93 mmol) in THF (20.0 mL), cooled to 0° C., was added sodium hydride (406 mg, 10.1 mmol). The reaction mixture was slowly warmed to rt and stirred for 1 h. The mixture was then cooled back to 0° C. and (2-chloromethoxyethyl)trimethylsilane (1.72 mL, 9.52 mmol) was added dropwise. The mixture was then stirred at rt for 2 h (LCMS showed complete conversion of starting material). The reaction mixture was quenched with a saturated NH$_4$Cl solution. The organic layer was separated and the aqueous layer was extracted with EtOAc (3×50 mL). The combined organic extracts were washed with brine (20 mL), dried over MgSO$_4$, filtered and concentrated under reduced pressure to afford crude methyl 1-((2-(trimethylsilyl)ethoxy)methyl)-1H-pyrazole-3-carboxylate IM294 as yellow oil: 179 mg, 81% yield, P=95%, retention time=1.7 min (gradient F), (M+H)$^+$: 257.

Stage 2: To a vial, under nitrogen, were added IM294 (300 mg, 1.17 mmol), (1,5-cyclooctadiene)(methoxy)iridium(I) dimer (32 mg, 46.8 μmol), 4,4'-di-tert-butyl-2,2'-dipyridyl (32 mg, 117 μmol) and dry THF (2.34 mL). To the resulting mixture was then added dropwise 4,4,5,5-tetramethyl-1,3,2-dioxaborolane (445 μL, 3.07 mmol) and the reaction mixture was stirred at 55° C. for 1 h (LCMS showed complete conversion of starting material). After cooling to rt, the mixture was concentrated under reduced pressure. The crude residue was then purified by silica gel flash chromatography (dry load, 30 g cartridge) using a gradient of EtOAc (0-100%) in Heptanes to afford (3-(methoxycarbonyl)-1-((2-(trimethylsilyl)ethoxy)methyl)-1H-pyrazol-5-yl)boronic acid IM295 as pale yellow oil: 274 mg, 61% yield, P=95% ($^1$H-NMR), retention time=1.0 min (gradient C), m/z: no ionization.

Stage 3: General Procedure U was used from IM295 to afford methyl 5-(5-methoxypyridin-3-yl)-1-((2-(trimethylsilyl)ethoxy)methyl)-1H-pyrazole-3-carboxylate IM296 as a beige solid: 173 mg, 68% yield, P=93%, retention time=1.8 min (gradient C), (M+H)$^+$: 364.

Stage 4: To a solution of IM296 (173 mg, 476 μmol) in THF (4.8 mL), cooled to 0° C., was added dropwise under nitrogen lithium aluminum hydride (714 μL, 714 μmol) (1 N solution in THF) and the resulting mixture was stirred at 0° C. for 1 h (LCMS showed complete conversion of starting material into desired product). Then the mixture was filtered through a pad of Celite and washed with MTBE (4×10 mL). Filtrate was concentrated under reduced pressure to afford crude (5-(5-methoxypyridin-3-yl)-1-((2-(trimethylsilyl)ethoxy)methyl)-1H-pyrazol-3-yl) methanol IM297 as yellow oil: 137 mg, 86% yield, P=95%, retention time=1.4 min (gradient C), (M+H)$^+$: 336.

Stage 5: General Procedure T was used between IM297 and IM244 to afford tert-butyl (R)-(cyclobutylmethyl)(1-(1-((5-(5-methoxypyridin-3-yl)-1-((2-(trimethylsilyl)ethoxy)methyl)-1H-pyrazol-3-yl)methyl)-2-oxo-1,2-dihydropyridin-4-yl)piperidin-3-yl)carbamate IM298 as yellow oil: 15 mg, 23% yield, P=86%, retention time=2.1 min (gradient C), (M+H)$^+$: 680.

Stage 6: General Procedure A2 was used from IM298 to afford compound 95 as a white solid: 4 mg, 20% yield, P=95%, retention time=1.2 min (gradient C), (M+H)$^+$: 449. $^1$H NMR (400 MHZ, CD$_3$OD): δ 8.49 (s, 1H), 8.19 (s, 1H), 7.73 (s, 1H), 7.48 (d, J=7.8 Hz, 1H), 6.72 (s, 1H), 6.28 (dd, J=7.8, 2.8 Hz, 1H), 5.75 (d, J=2.7 Hz, 1H), 5.12 (s, 2H), 3.93 (s, 3H), 3.96-3.89 (m, 1H), 3.82-3.73 (m, 1H), 3.04-2.92 (m, 1H), 2.86-2.75 (m, 1H), 2.71 (d, J=7.3 Hz, 2H), 2.66-2.59 (m, 1H), 2.53-2.43 (m, 1H), 2.15-2.02 (m, 3H), 1.98-1.84 (m, 2H), 1.82-1.67 (m, 3H), 1.62-1.50 (m, 1H), 1.47-1.34 (m, 1H), 2H exchanged with CD$_3$OD.

Compound 96: 4-((R)-3-((cyclobutylmethyl)amino) piperidin-1-yl)-1-(1-(4-(5-(methylamino) pyridin-3-yl)-1H-1,2,3-triazol-1-yl)ethyl)pyridin-2 (1H)-one was Obtained Using General Scheme 1 Pathway B Stage 1: In a reaction tube, IM293 (70 mg, 119 μmol) was solubilized in dioxane (280 μL) and methylamine (40 wt. % in water) (1 mL, 11.6 mmol) was added. Tube was sealed and reaction was stirred at 140° C. during 22.5 h. The reaction mixture was concentrated under reduced pressure and directly purified by reverse phase chromatography on a 40 g C18 cartridge, eluting with a gradient of MeCN in basic water (10 mM NH$_4$HCO$_3$/NH$_4$OH buffer pH=10) to afford IM299 as a beige solid: 20 mg, 29% yield, P=98%, retention time=1.6 min (gradient C), (M+H)$^+$: 564.

Stage 2: General Procedure A2 was used from IM299 to afford compound 96 as a white solid: 20 mg, 100% yield, P=99%, retention time=2.3 min (gradient C), (M+H)$^+$: 463. $^1$H NMR (400 MHZ, CD$_3$OD): δ 8.56 (s, 1H), 8.21 (s, 1H), 7.88 (s, 1H), 7.65 (d, J=8.1 Hz, 1H), 7.51 (q, J=6.9 Hz, 1H), 7.40 (s, 1H), 6.33 (dd, J=8.1, 2.4 Hz, 1H), 5.68 (d, J=2.3 Hz, 1H), 3.96-3.87 (m, 1H), 3.83-3.74 (m, 1H), 3.03-2.93 (m, 1H), 2.85 (s, 3H), 2.84-2.76 (m, 1H), 2.67 (d, J=7.3 Hz, 2H), 2.62-2.54 (m, 1H), 2.50-2.41 (m, 1H), 2.14 (d, J=7.0 Hz, 3H), 2.11-2.00 (m, 3H), 1.96-1.81 (m, 2H), 1.80-1.65 (m, 3H), 1.59-1.46 (m, 1H), 1.44-1.33 (m, 1H), 2H exchanged with CD$_3$OD.

The mixture of diastereomers was further purified by chiral preparative HPLC purification using Chiralpak IA column (5 μm, 20×250 mm). Eluent used: TBME/MeOH/DEA: 70/30/0.1% at flow rate of 20 mL/min. First eluted diastereomer: P=100%, retention time=6.4 min, chiral HPLC: P=100%, $^1$H NMR (300 MHZ, CDCl$_3$) δ 8.32 (d, J=1.7 Hz, 1H), 8.10 (s, 1H), 7.98 (d, J=2.8 Hz, 1H), 7.56 (q, J=7.0 Hz, 1H), 7.42 (d, J=8.0 Hz, 1H), 7.39-7.33 (m, 1H), 5.98 (dd, J=8.1, 2.9 Hz, 1H), 5.66 (d, J=2.8 Hz, 1H), 3.89-3.82 (m, 1H), 3.80-3.70 (m, 1H), 3.66-3.56 (m, 1H), 2.99-2.85 (m, 4H), 2.77-2.51 (m, 4H), 2.40 (hept, J=7.5 Hz, 1H), 2.21-2.12 (m, 3H), 2.10-2.01 (m, 2H), 1.99-1.80 (m, 1H), 1.74-1.46 (m, 5H), 1.34-1.23 (m, 1H), NH exchanged. Second eluted diastereomer: P=100%, retention time=9.1 min, chiral HPLC: P=100%, $^1$H NMR (300 MHz, CDCl$_3$) δ 8.32 (d, J=1.7 Hz, 1H), 8.10 (s, 1H), 7.98 (d, J=2.8 Hz, 1H), 7.55 (q, J=7.0 Hz, 1H), 7.42 (d, J=8.1 Hz, 1H), 7.36 (t, J=2.3 Hz, 1H), 5.98 (dd, J=8.1, 2.8 Hz, 1H), 5.66 (d, J=2.9 Hz, 1H), 3.90-3.82 (m, 1H), 3.80-3.70 (m, 1H), 3.66-3.56 (m, 1H), 3.00-2.87 (m, 4H), 2.77-2.55 (m, 4H), 2.39 (hept, J=7.5 Hz, 1H), 2.16 (d, J=7.0 Hz, 3H), 2.03 (s, 2H), 2.01-1.45 (m, 7H), 1.42-1.23 (m, 1H), NH exchanged.

Compound 97: (R)-4-(3-((cyclobutylmethyl)amino) piperidin-1-yl)-1-((2-(5-methoxypyridin-3-yl)thiazol-5-yl)methyl)pyridin-2 (1H)-one was Obtained Using General Scheme 3 Pathway A Stage 1: General Procedure T was used between 2-Bromothiazole-5-methanol and IM244 to afford tert-butyl (R)-(1-(1-((2-bromothiazol-5-yl)methyl)-2-oxo-1,2-dihydropyridin-4-yl) piperidin-3-yl)(cyclobutylmethyl)carbamate IM300 as a white solid: 84 mg, 21% yield, P=100%, retention time=1.5 min (gradient C), (M+H)$^+$: 537/539.

Stage 3: General Procedure U was used from IM300 to afford tert-butyl (R)-(cyclobutylmethyl)(1-(1-((2-(5-methoxypyridin-3-yl)thiazol-5-yl)methyl)-2-oxo-1,2-dihydropyridin-4-yl)piperidin-3-yl)carbamate IM301 as a white solid: 42 mg, 57% yield, P=100%, retention time=1.4 min (gradient C), (M+H)$^+$: 566.

Stage 4: General Procedure A2 was used from IM301 to afford compound 97 as an off-white powder: 18 mg, 48% yield, P=96%, retention time=2.0 min (gradient E), (M+H)$^+$: 466. $^1$H NMR (400 MHZ, DMSO-d$_6$): δ 8.65 (d, J=1.7 Hz, 1H), 8.37 (d, J=2.8 Hz, 1H), 7.98 (s, 1H), 7.74 (dd, J=2.7, 1.9 Hz, 1H), 7.58 (d, J=7.9 Hz, 1H), 6.15 (dd, J=7.9, 2.7 Hz, 1H), 5.49 (d, J=2.7 Hz, 1H), 5.18 (s, 2H), 3.90 (s, 3H), 3.79-3.72 (m, 1H), 3.69-3.60 (m, 1H), 2.88-2.76 (m, 1H), 2.64-2.52 (m, 4H), 2.44-2.37 (m, 1H), 2.36-2.24 (m, 1H), 1.97-1.84 (m, 3H), 1.84-1.72 (m, 2H), 1.67-1.54 (m, 3H), 1.41-1.29 (m, 1H), 1.28-1.15 (m, 1H).

Compound 98: (4-((R)-3-((cyclobutylmethyl)amino)piperidin-1-yl)-1-(1-(4-(5-methoxy pyridin-3-yl)-1H-imidazol-1-yl)ethyl)pyridin-2 (1H)-one was Obtained Using General Scheme 4 Pathway A Stage 1: To a solution of 4-bromo-1H-imidazole (100 mg, 667 µmol) in dry DMF (3.33 mL), cooled to 0° C., was added NaH (40 mg, 1.00 mmol). The reaction mixture was stirred at 0° C. for 10 min then a solution of IM150 (154 mg, 800 µmol) in dry DMF (2.22 mL) was added dropwise. The mixture was allowed to reach rt and stirred for 1 h. The reaction was quenched with few drops of water and directly purified by reverse phase chromatography on a C18 60 g cartridge, eluting with a gradient of MeCN (0-100%) in basic water (10 mM NH$_4$HCO$_3$/NH$_4$OH buffer pH=10) to afford 1-(1-(4-bromo-1H-imidazol-1-yl)ethyl)-4-chloropyridin-2 (1H)-one IM302: 120 mg, 34% yield, P=58%, retention time=1.0 min (gradient C), (M+H)$^+$: 302/304/306.

Stage 2: General Procedure C was used between IM3 and IM3022 to afford tert-butyl ((3R)-1-(1-(1-(4-bromo-1H-imidazol-1-yl)ethyl)-2-oxo-1,2-dihydropyridin-4-yl)piperidin-3-yl) (cyclobutylmethyl)carbamate IM303 as yellow oil: 143 mg, 46% yield, P=68%, retention time=1.8 min (gradient F), (M+H)$^+$: 534/536.

Stage 3: General Procedure U was used from IM303 to afford tert-butyl (cyclobutylmethyl)((3R)-1-(1-(1-(4-(5-methoxypyridin-3-yl)-1H-imidazol-1-yl)ethyl)-2-oxo-1,2-dihydropyridin-4-yl)piperidin-3-yl)carbamate IM304 as a beige solid: 68 mg, 58% yield, P=87%, retention time=1.5 min (gradient C), (M+H)$^+$: 564.

Stage 4: General Procedure A2 was used from IM304 to afford compound 98 as a white powder: 21 mg, 36% yield, P=95%, retention time=2.1 min (gradient E), (M+H)$^+$: 464. $^1$H NMR (400 MHZ, CD$_3$OD): δ 8.50 (d, J=1.6 Hz, 1H), 8.10 (d, J=2.8 Hz, 1H), 8.06 (d, J=1.1 Hz, 1H), 7.94 (d, J=1.2 Hz, 1H), 7.75 (dd, J=2.7, 1.8 Hz, 1H), 7.59 (d, J=8.1 Hz, 1H), 7.20 (q, J=7.1 Hz, 1H), 6.32 (dd, J=8.1, 2.8 Hz, 1H), 5.69 (d, J=2.8 Hz, 1H), 3.92 (s, 3H), 3.96-3.87 (m, 1H), 3.82-3.73 (m, 1H), 3.06-2.92 (m, 1H), 2.87-2.77 (m, 1H), 2.68 (d, J=7.3 Hz, 2H), 2.64-2.54 (m, 1H), 2.52-2.41 (m, 1H), 2.14-2.00 (m, 6H), 1.98-1.83 (m, 2H), 1.81-1.65 (m, 3H), 1.59-1.49 (m, 1H), 1.45-1.36 (m, 1H), 1H exchanged with CD$_3$OD.

The mixture of diastereomers was further purified by chiral preparative HPLC purification using Chiralpak IA column (5 µm, 20×250 mm). Eluent used: TBME/MeOH/DEA: 50/50/0.1% at flow rate of 20 mL/min. First eluted diastereomer: P=100%, retention time=6.2 min, chiral HPLC: P=100%, $^1$H NMR (300 MHz, CDCl$_3$) δ 8.53 (d, J=1.7 Hz, 1H), 8.18 (d, J=2.9 Hz, 1H), 7.82 (d, J=1.3 Hz, 1H), 7.67-7.60 (m, 1H), 7.44 (d, J=1.3 Hz, 1H), 7.29 (d, J=7.0 Hz, 1H), 6.96 (d, J=8.0 Hz, 1H), 5.97 (dd, J=8.1, 2.8 Hz, 1H), 5.69 (d, J=2.8 Hz, 1H), 3.89 (s, 3H), 3.80-3.70 (m, 1H), 3.66-3.55 (m, 1H), 2.99-2.85 (m, 1H), 2.77-2.48 (m, 4H), 2.40 (hept, J=7.6 Hz, 1H), 2.14-1.21 (m, 13H), NH exchanged. Second eluted diastereomer: P=100%, retention time=32.4 min, chiral HPLC: P=100%, $^1$H NMR (300 MHz, CDCl$_3$) δ 8.53 (d, J=1.7 Hz, 1H), 8.18 (d, J=2.9 Hz, 1H), 7.82 (d, J=1.4 Hz, 1H), 7.63 (dd, J=2.9, 1.7 Hz, 1H), 7.43 (d, J=1.3 Hz, 1H), 7.29 (q, J=6.9 Hz, 1H), 6.97 (d, J=8.1 Hz, 1H), 5.97 (dd, J=8.1, 2.9 Hz, 1H), 5.69 (d, J=2.9 Hz, 1H), 3.89 (s, 3H), 3.80-3.70 (m, 1H), 3.65-3.55 (m, 1H), 3.00-2.85 (m, 1H), 2.78-2.53 (m, 4H), 2.39 (hept, J=7.5 Hz, 1H), 2.13-1.24 (m, 13H), NH exchanged.

Compound 99: 2-(1-(1-(5-((R)-3-((cyclobutylmethyl)amino)piperidin-1-yl)pyridin-2-yl)ethyl)-1H-1,2,3-triazol-4-yl)-4H-pyrido[1,2-a]pyrimidin-4-one was Obtained Using General Scheme 1 Pathway A Stage 1: General Procedure B was used between IM276 and IM181 to afford tert-butyl (cyclobutylmethyl)((3R)-1-(6-(1-(4-(4-oxo-4H-pyrido[1,2-a]pyrimidin-2-yl)-1H-1,2,3-triazol-1-yl)ethyl)pyridin-3-yl)piperidin-3-yl)carbamate IM305 as a yellow foam: 34 mg, 87% yield, P=94%, retention time=2.8 min (gradient A), (M+H)$^+$: 586.

Stage 2: General Procedure A1 was used from IM305 to afford compound 99 as a white powder: 11 mg, 43% yield, P=99%, retention time=2.3 min (gradient B), (M+H)$^+$: 486. $^1$H NMR (300 MHz, CDCl$_3$) δ 9.07 (d, J=7.2 Hz, 1H), 8.35 (s, 1H), 8.30 (s, 1H), 7.71 (dd, J=8.8, 6.9 Hz, 1H), 7.62 (d, J=9.0 Hz, 1H), 7.28 (s, 1H), 7.14 (d, J=13.8 Hz, 2H), 7.13-7.05 (m, 1H), 5.94 (q, J=7.0 Hz, 1H), 3.72-3.60 (m, 1H), 3.52-3.42 (m, 1H), 2.93-2.80 (m, 1H), 2.69 (2d, J=7.6 Hz, 4H), 2.44 (hept, J=7.6 Hz, 1H), 2.14-2.05 (m, 1H), 2.02 (d, J=7.1 Hz, 3H), 1.95-1.78 (m, 4H), 1.71-1.24 (m, 5H), NH exchanged.

The mixture of diastereomers was further purified by chiral preparative HPLC purification using Chiralpak IA column (5 µm, 20×250 mm). Eluent used: TBME/MeOH/DEA: 60/40/0.1% at flow rate of 20 mL/min. First eluted diastereomer: P=100%, retention time=6.1 min, chiral HPLC: P=99.9%, $^1$H NMR (300 MHZ, CDCl$_3$) δ 9.07 (d, J=7.2 Hz, 1H), 8.35 (s, 1H), 8.30 (s, 1H), 7.68 (dd, J=8.8, 6.9 Hz, 1H), 7.62 (m, 1H), 7.28 (s, 1H), 7.14-7.07 (m, 3H), 5.94 (q, J=7.0 Hz, 1H), 3.65 (d, J=9.8 Hz, 1H), 3.48 (m, 1H), 2.87 (m, 1H), 2.69 (d, J=7.2 Hz, 4H), 2.44 (hept, J=7.7 Hz, 1H), 2.09-2.01 (m, 1H), 2.02 (d, J=7.1 Hz, 3H), 1.93-1.79 (m, 4H), 1.68-1.26 (m, 5H), NH exchanged. Second eluted diastereomer: P=100%, retention time=6.9 min, chiral HPLC: P=100%, $^1$H NMR (300 MHz, CDCl$_3$) δ 9.07 (d, J=7.2 Hz, 1H), 8.35 (s, 1H), 8.29 (s, 1H), 7.71 (m, 1H), 7.62 (d, J=8.9 Hz, 1H), 7.28 (s, 1H), 7.12 (d, J=13.7 Hz, 2H), 7.14-7.07 (m, 1H), 5.95 (q, J=7.0 Hz, 1H), 3.65 (d, J=9.1 Hz, 1H), 3.47 (m, 1H), 2.90-2.82 (m, 1H), 2.71 (d, J=7.7 Hz, 4H), 2.45 (hept, J=7.6 Hz, 1H), 2.09-1.61 (m, 12H), 1.37-1.26 (m, 2H), NH exchanged.

Compound 100: N-(1-(4-((R)-3-((cyclobutylmethyl)amino)piperidin-1-yl)phenyl)ethyl)-4-oxo-4H-pyrido[1,2-a]pyrimidine-2-carboxamide was Obtained Using General Scheme 2 Pathway B Stage 1: General Procedure L was used from IM242 to afford tert-butyl ((3R)-1-(4-(1-aminoethyl)phenyl)piperidin-3-yl)(cyclobutylmethyl)carbamate IM306 as yellow oil: 100 mg, 57% yield, P=30%, retention time=2.5 min (gradient A), (M+H)$^+$: 388.

Stage 2: General Procedure F was used between 4-oxopyrido[1,2-a]pyrimidine-2-carboxylic acid hydrochloride and IM306 to afford tert-butyl (cyclobutylmethyl)((3R)-1-(4-(1-(4-oxo-4H-pyrido[1,2-a]pyrimidine-2-carboxamido)ethyl)phenyl)piperidin-3-yl)carbamate IM307 as yellow oil: 100 mg, 90% yield, P=52%, retention time=2.7 min (gradient A), (M+H)$^+$: 560.

Stage 3: General Procedure A1 was used from IM307 to afford crude compound 100 as an off-white solid: 27 mg, 71% yield, P=96%, retention time=2.3 min (gradient B), (M+H)$^+$: 460. $^1$H NMR (300 MHZ, CD$_3$OD) δ 9.05 (d, J=7.2 Hz, 1H), 7.97 (td, J=7.7, 1.6 Hz, 1H), 7.82 (d, J=8.9 Hz, 1H), 7.38 (t, J=7.0 Hz, 1H), 7.28 (d, J=8.3 Hz, 2H), 7.05 (s, 1H), 6.94 (d, J=8.3 Hz, 2H), 5.17 (t, J=7.0 Hz, 1H), 3.66-3.52 (m, 1H), 3.53-3.37 (m, 1H), 2.82-2.55 (m, 5H), 2.48 (hept, J=7.6 Hz, 1H), 2.09 (s, 2H), 2.05-1.64 (m, 8H), 1.58 (d, J=6.9 Hz, 3H), 1.33 (t, J=10.5 Hz, 1H), 2H exchanged with $CD_3OD$.

Compound 101: N-(cyclobutylmethyl)-1-(6-((4-(5-methoxypyridin-3-yl)-1H-1,2,3-triazol-1-yl)methyl)pyridazin-3-yl)azepan-3-amine was Obtained Using General Scheme 1 Pathway B Stage 1: General Procedure H1 was used between cyclobutylmethylamine and 1-benzyl-azepan-3-one to afford crude 1-benzyl-N-(cyclobutylmethyl)azepan-3-amine IM308 as orange oil: 318 mg, 65% yield, P=77% (215 nm), retention time=2.0 min (gradient A), $(M+H)^+$: 273.

Stage 2: General Procedure J was used from IM308 to afford tert-butyl N-(1-benzylazepan-3-yl)-N-(cyclobutylmethyl)carbamate IM309 as colourless oil: 274 mg, 76% yield, P=93% (215 nm), retention time=2.6 min (gradient A), $(M+H)^+$: 373.

Stage 3: General Procedure I was used from IM309 to afford crude tert-butyl N-(azepan-3-yl)-N-(cyclobutylmethyl)carbamate IM310 as colourless oil: 206 mg, 95% yield, P=89% ($^1$H NMR), retention time=2.5 min (gradient A), $(M+H)^+$: 283.

Stage 4: General Procedure C was used between IM310 and IM112 to afford crude tert-butyl N-(cyclobutylmethyl)-N-[1-[6-[[4-(5-methoxy-3-pyridyl)triazol-1-yl]methyl]pyridazin-3-yl] azepan-3-yl]carbamate IM311 as brown oil: 102 mg, 79% yield, P=66% ($^1$H NMR), retention time=2.4 min (gradient A), $(M+H)^+$: 549.

Stage 5: General Procedure A1 was used from IM311 to afford crude compound 101 dihydrochloride as brown oil: 150 mg, 98% yield, P=92%, retention time=2.1 min (gradient A), $(M+H)^+$: 449.

The product was further purified by reverse phase preparative HPLC purification (Waters XBridge C18 5 µm 19×100 mm). Gradient used: increased linearly from 15 to 40% solution "B" over 5.5 min, increased linearly to 85% solution "B" over 0.8 min, and returned to initial conditions over 1.0 min. Flow Rate: 15 mL/min. P=100%. $^1$H NMR (300 MHz, $CDCl_3$) δ 8.54 (s, 1H), 8.26 (d, J=2.7 Hz, 1H), 8.02 (s, 1H), 7.73 (s, 1H), 7.24 (d, J=9.5 Hz, 1H), 6.83 (d, J=9.5 Hz, 1H), 5.73 (s, 2H), 4.17-4.06 (m, 1H), 3.90 (s, 3H), 3.84-3.74 (m, 1H), 3.63-3.48 (m, 1H), 3.29 (dd, J=14.4, 8.4 Hz, 1H), 2.97-2.83 (m, 1H), 2.72 (d, J=7.2 Hz, 2H), 2.45 (hept, J=7.6 Hz, 1H), 2.07 (d, J=8.3 Hz, 1H), 1.94-1.59 (m, 9H), 1.47-1.31 (m, 1H), NH exchanged.

The racemic mixture was further purified by chiral preparative HPLC purification using Chiralpak IB column (5 µm, 10×250 mm). Eluent used: TBME/MeOH/DEA: 80/20/0.1% at flow rate of 7 mL/min. First eluted enantiomer: P=100%, retention time=4.7 min, chiral HPLC: P=100%. Second eluted enantiomer: P=100%, retention time=5.7 min, chiral HPLC: P=100%.

Compound 102: N-(1-(4-((R)-3-((cyclobutylmethyl)amino)piperidin-1-yl)phenyl)ethyl)-4-oxo-4H-pyrido[1,2-a]pyrimidine-2-carboxamide was Obtained Using General Scheme 1 Pathway A Stage 1: General Procedure B was used between IM276 and IM242 to afford tert-butyl N-(cyclobutylmethyl)-N-[(3R)-1-[4-[1-[4-(4-oxopyrido[1,2-a]pyrimidin-2-yl)triazol-1-yl]ethyl] phenyl]-3-piperidyl]carbamate IM312 as yellowish oil: 60 mg, 77% yield, P=99%, retention time=2.8 min (gradient A), $(M+H)^+$: 584.

Stage 2: General Procedure A1 was used from IM312 to afford compound 102 as a white powder: 44 mg, 99% yield, P=100%, retention time=3.3 min (gradient B), $(M+H)^+$: 484. $^1$H NMR (300 MHz, $CD_3OD$) δ 8.93 (d, J=7.2 Hz, 1H), 8.39 (s, 1H), 7.83 (ddd, J=8.6, 6.7, 1.6 Hz, 1H), 7.59 (d, J=8.9 Hz, 1H), 7.26 (d, J=8.6 Hz, 2H), 7.20 (td, J=6.9, 1.4 Hz, 1H), 7.01 (s, 1H), 6.93 (d, J=8.7 Hz, 2H), 5.84 (d, J=7.1 Hz, 1H), 3.77-3.52 (m, 1H), 3.51-3.37 (m, 1H), 2.82-2.53 (m, 5H), 2.45 (hept, J=7.6 Hz, 1H), 2.12-2.02 (m, 2H), 1.96 (d, J=7.0 Hz, 3H), 1.93-1.54 (m, 8H), 1H exchanged with $CD_3OD$.

The mixture of diastereomers was further purified by chiral preparative HPLC purification using Chiralpak IA column (5 µm, 20×250 mm). Eluent used: TBME/MeOH/DEA: 70/30/0.1% at flow rate of 20 mL/min. First eluted diastereomer: P=100%, retention time=7.8 min, chiral HPLC: P=100%, $^1$H NMR (300 MHz, $CDCl_3$) δ 9.06 (d, J=7.1 Hz, 1H), 8.02 (s, 1H), 7.76-7.63 (m, 1H), 7.58 (d, J=8.8 Hz, 1H), 7.28 (s, 1H), 7.24 (d, J=8.7 Hz, 2H), 7.14-7.02 (m, 1H), 6.91 (d, J=8.8 Hz, 2H), 5.82 (q, J=7.0 Hz, 1H), 3.65 (d, J=11.4 Hz, 1H), 3.53-3.42 (m, 1H), 2.89-2.56 (m, 5H), 2.45 (hept, J=7.5 Hz, 1H), 2.12-1.95 (m, 5H), 1.93-1.77 (m, 3H), 1.71-1.59 (m, 3H), 1.39-1.26 (m, 2H), NH exchanged. Second eluted diastereomer: P=100%, retention time=10.0 min, chiral HPLC: P=100%, $^1$H NMR (300 MHz, $CDCl_3$) δ 9.06 (d, J=7.2 Hz, 1H), 8.03 (s, 1H), 7.69 (ddd, J=8.2, 6.6, 1.5 Hz, 1H), 7.58 (d, J=8.8 Hz, 1H), 7.28 (s, 1H), 7.23 (d, J=8.7 Hz, 2H), 7.14-7.02 (m, 1H), 6.91 (d, J=8.7 Hz, 2H), 5.82 (q, J=7.0 Hz, 1H), 3.65 (d, J=11.3 Hz, 1H), 3.52-3.42 (m, 1H), 2.89-2.57 (m, 5H), 2.45 (hept, J=7.5 Hz, 1H), 2.19-1.95 (m, 5H), 1.95-1.74 (m, 3H), 1.74-1.56 (m, 3H), 1.48-1.23 (m, 2H), NH exchanged.

Compound 103: 4-((R)-3-((cyclobutylmethyl)amino)piperidin-1-yl)-1-(1-(4-(5-ethoxypyridin-3-yl)-1H-1,2,3-triazol-1-yl)ethyl)pyridin-2 (1H)-one was Obtained Using General Scheme 1 Pathway B Stage 1: In a reaction tube were placed IM293 (70 mg, 1229 µmol) and EtONa (21 wt. % in EtOH) (910 µL, 2.44 mmol). Tube was sealed and reaction was stirred at 80° C. during 7 h. The reaction was cooled down to rt and concentrated under reduced pressure and directly purified by reverse phase chromatography on a 25 g C18 cartridge, eluting with a gradient of MeCN in basic water (10 mM $NH_4HCO_3/NH_4OH$ buffer pH=10) to afford tert-butyl (cyclobutylmethyl)((3R)-1-(1-(1-(4-(5-ethoxypyridin-3-yl)-1H-1,2,3-triazol-1-yl)ethyl)-2-oxo-1,2-dihydropyridin-4-yl)piperidin-3-yl)carbamate IM313 as a yellow solid: 52 mg, 72% yield, P=97%, retention time=1.7 min (gradient C), $(M+H)^+$: 579.

Stage 2: General Procedure A2 was used from IM313 to afford compound 103 as a white solid: 36 mg, 86% yield, P=98%, retention time=2.4 min (gradient C), $(M+H)^+$: 479.

The mixture of diastereomers was further purified by chiral preparative HPLC purification using Chiralpak IA column (5 µm, 20×250 mm). Eluent used: TBME/MeOH/DEA: 60/40/0.1% at flow rate of 20 mL/min. First eluted diastereomer: P=100%, retention time=11.4 min, chiral HPLC: P=100%, $^1$H NMR (300 MHz, $CDCl_3$) δ 8.56 (d, J=1.7 Hz, 1H), 8.25 (d, J=2.8 Hz, 1H), 8.14 (s, 1H), 7.67 (dd, J=2.9, 1.7 Hz, 1H), 7.54 (q, J=7.0 Hz, 1H), 7.42 (d, J=8.1 Hz, 1H), 5.99 (dd, J=8.1, 2.9 Hz, 1H), 5.65 (d, J=2.8 Hz, 1H), 4.13 (q, J=7.0 Hz, 2H), 3.75 (d, J=12.7 Hz, 1H), 3.67-3.55 (m, 1H), 2.99-2.83 (m, 1H), 2.79-2.67 (m, 1H), 2.65 (d, J=7.5 Hz, 2H), 2.61-2.51 (m, 1H), 2.47-2.29 (m, 1H), 2.16 (d, J=7.0 Hz, 3H), 2.11-1.97 (m, 3H), 1.96-1.79 (m, 2H), 1.79-1.61 (m, 1H), 1.59-1.50 (m, 3H), 1.44 (t, J=7.0 Hz, 3H), 1.36-1.25 (m, 1H). 1H exchanged with solvent. Second eluted diastereomer: P=100%, retention time=18.4 min, chiral HPLC: P=100%, ¹H NMR (300 MHz, CDCl₃) δ 8.55 (d, J=1.7 Hz, 1H), 8.24 (d, J=2.8 Hz, 1H), 8.13 (s, 1H), 7.71-7.63 (m, 1H), 7.54 (q, J=7.0 Hz, 1H), 7.42 (d, J=8.1 Hz, 1H), 5.98 (dd, J=8.1, 2.8 Hz, 1H), 5.65 (d, J=2.8 Hz, 1H), 4.12 (q, J=7.0 Hz, 2H), 3.79-3.68 (m, 1H), 3.65-3.57 (m, 1H), 2.99-2.84 (m, 1H), 2.70 (dd, J=12.8, 9.3 Hz, 1H), 2.64 (d, J=7.2 Hz, 2H), 2.61-2.51 (m, 1H), 2.48-2.27 (m, 1H), 2.16 (d, J=7.1 Hz, 3H), 2.11-1.97 (m, 2H), 1.95-1.79 (m, 3H), 1.78-1.66 (m, 1H), 1.66-1.49 (m, 3H), 1.44 (t, J=7.0 Hz, 3H), 1.40-1.23 (m, 1H). 1H exchanged with solvent.

Compound 104: 4-((R)-3-((cyclobutylmethyl)amino)piperidin-1-yl)-1-(1-(4-(5-methoxy-6-methylpyridin-3-yl)-1H-1,2,3-triazol-1-yl)ethyl)pyridin-2 (1H)-one was Obtained Using General Scheme 1 Pathway B Stage 1: To a stirred solution of 5-Bromo-2-methylpyridin-3-ol (736 mg, 3.84 mmol) in MeCN (11.0 mL) was added cesium carbonate (2.55 g, 7.68 mmol). The mixture was stirred at rt for 10 min. Then iodomethane (490 μL, 7.79 mmol) was added. The reaction mixture was stirred at rt for 1 h and then partitioned between EtOAc and water. The organic layer was dried over MgSO₄ and concentrated under reduced pressure to afford crude 5-bromo-3-methoxy-2-methylpyridine IM314 as brown oil: 514 mg, 66% yield, P=95% (¹H NMR), retention time=1.2 min (gradient C), (M+H)⁺: 202/204.

Stage 2: General Procedure E1 (in THF instead of DMF) was used from IM314 to afford 3-methoxy-2-methyl-5-((trimethylsilyl)ethynyl)pyridine IM315 as yellow oil: 661 mg, 100% yield, P=93%, retention time=1.6 min (gradient C), (M+H)⁺: 220.

Stage 3: General Procedure X was used between IM151 and IM315 to afford 4-chloro-1-(1-(4-(5-methoxy-6-methylpyridin-3-yl)-1H-1,2,3-triazol-1-yl)ethyl)pyridin-2 (1H)-one IM316 as a white solid: 133 mg, 73% yield, P=97%, retention time=1.1 min (gradient C), (M+H)⁺: 346.

Stage 4: General Procedure C was used between IM3 and IM316 to afford crude tert-butyl (cyclobutylmethyl)((3R)-1-(1-(1-(4-(5-methoxy-6-methylpyridin-3-yl)-1H-1,2,3-triazol-1-yl) ethyl)-2-oxo-1,2-dihydropyridin-4-yl)piperidin-3-yl)carbamate IM317 as yellow oil, which was used as is in the next step: retention time=1.7 min (gradient C), (M+H)⁺: 578.

Stage 5: General Procedure A2 was used from IM317 to afford compound 104 as a beige solid: 158 mg, 86% yield, P=100%, retention time=2.4 min (gradient E), (M+H)⁺: 478. ¹H NMR (400 MHZ, CD₃OD) δ 8.62 (s, 1H), 8.44 (d, J=1.7 Hz, 1H), 7.78 (d, J=1.6 Hz, 1H), 7.66 (d, J=8.1 Hz, 1H), 7.51 (q, J=6.9 Hz, 1H), 6.34 (dd, J=8.1, 2.8 Hz, 1H), 5.68 (d, J=2.8 Hz, 1H), 3.95 (s, 3H), 3.95-3.89 (m, 1H), 3.83-3.74 (m, 1H), 3.06-2.94 (m, 1H), 2.87-2.77 (m, 1H), 2.70 (d, J=7.4 Hz, 2H), 2.66-2.58 (m, 1H), 2.53-2.45 (m, 1H), 2.44 (s, 3H), 2.15 (d, J=7.0 Hz, 3H), 2.13-2.02 (m, 3H), 1.94-1.82 (m, 2H), 1.80-1.66 (m, 3H), 1.60-1.47 (m, 1H), 1.46-1.34 (m, 1H), 1H exchanged with CD₃OD.

Compound 105: 4-((R)-3-((cyclobutylmethyl)amino)piperidin-1-yl)-1-(1-(4-(6-methoxy pyrazin-2-yl)-1H-1,2,3-triazol-1-yl)ethyl)pyridin-2 (1H)-one was Obtained Using General Scheme 1 Pathway B Stage 1: General Procedure E1 (in THF instead of DMF) was used from 2-bromo-6-methoxypyrazine to afford 2-methoxy-6-((trimethylsilyl)ethynyl)pyrazine IM318 as light brown oil: 182 mg, 33% yield, P=100% (¹H NMR), retention time=1.8 min (gradient C), (M+H)⁺: 207.

Stage 2: General Procedure X was used between IM151 and IM318 to afford 4-chloro-1-(1-(4-(6-methoxypyrazin-2-yl)-1H-1,2,3-triazol-1-yl)ethyl)pyridin-2 (1H)-one IM319 as an off-white solid: 239 mg, 79% yield, P=97%, retention time=1.3 min (gradient C), (M+H)⁺: 333/335.

Stage 3: General Procedure C was used between IM3 and IM319 to afford tert-butyl (cyclobutylmethyl)((3R)-1-(1-(1-(4-(6-methoxypyrazin-2-yl)-1H-1,2,3-triazol-1-yl)ethyl)-2-oxo-1,2-dihydropyridin-4-yl)piperidin-3-yl)carbamate IM320 as a beige solid: 360 mg, 93% yield, P=100%, retention time=1.9 min (gradient C), (M+H)⁺: 565.

Stage 4: General Procedure A2 was used from IM319 to afford compound 105 as an off-white solid: 185 mg, 60% yield, P=96%, retention time=2.8 min (gradient E), (M+H)⁺: 465.

The mixture of diastereomers was further purified by chiral preparative HPLC purification using Chiralpak IA column (5 μm, 20×250 mm). Eluent used: EtOAc/MeOH/DEA: 60/40/0.1% at flow rate of 20 ml/min. First eluted diastereomer: P=100%, retention time=6.6 min, chiral HPLC: P=100%. ¹H NMR (300 MHz, CDCl₃) δ 8.90 (s, 1H), 8.36 (s, 1H), 8.13 (s, 1H), 7.58 (q, J=7.0 Hz, 1H), 7.44 (d, J=8.1 Hz, 1H), 5.98 (dd, J=8.1, 2.8 Hz, 1H), 5.64 (d, J=2.8 Hz, 1H), 3.97 (s, 3H), 3.79-3.68 (m, 1H), 3.59 (d, J=13.4 Hz, 1H), 2.98-2.83 (m, 1H), 2.79-2.66 (m, 1H), 2.64 (d, J=7.5 Hz, 2H), 2.61-2.50 (m, 1H), 2.48-2.28 (m, 1H), 2.16 (d, J=7.1 Hz, 3H), 2.11-1.80 (m, 5H), 1.78-1.67 (m, 1H), 1.67-1.57 (m, 2H), 1.57-1.42 (m, 1H), 1.42-1.21 (m, 1H). 1H exchanged with solvent. Second eluted diastereomer: P=100%, retention time=13.9 min, chiral HPLC: P=100%, ¹H NMR (300 MHz, CDCl₃) δ 8.89 (s, 1H), 8.36 (s, 1H), 8.13 (s, 1H), 7.58 (q, J=7.0 Hz, 1H), 7.44 (d, J=8.0 Hz, 1H), 5.98 (dd, J=8.1, 2.9 Hz, 1H), 5.64 (d, J=2.8 Hz, 1H), 3.97 (s, 3H), 3.73 (d, J=12.5 Hz, 1H), 3.65-3.52 (m, 1H), 2.98-2.83 (m, 1H), 2.69 (dd, J=12.7, 9.2 Hz, 1H), 2.63 (d, J=7.2 Hz, 2H), 2.60-2.49 (m, 1H), 2.47-2.26 (m, 1H), 2.15 (d, J=7.0 Hz, 3H), 2.08-1.78 (m, 5H), 1.77-1.66 (m, 1H), 1.66-1.54 (m, 2H), 1.54-1.44 (m, 1H), 1.41-1.22 (m, 1H). 1H exchanged with solvent.

Compound 106: 4-((R)-3-((cyclobutylmethyl)amino)piperidin-1-yl)-1-(1-(5-(5-methoxy pyridin-3-yl)-2H-tetrazol-2-yl)ethyl)pyridin-2 (1H)-one was Obtained was Obtained Using the Following Procedures Stage 1: To 5-methoxynicotinonitrile (100 mg, 731 μmol) in solution in DMF (2.56 mL) were added NH₄Cl (66 mg, 1.24 mmol) and NaN₃ (81 mg, 1.24 mmol). The resulting mixture was stirred at 100° C. for 17 h. The reaction was cooled down to rt, poured into ice water (50 mL), IN HCl solution was added to adjust pH to 3-4 and extracted with EtOAc (3×15 mL), then 2-MeTHF (3×15 mL). As some product stayed in the aqueous phase, the latter was saturated with NaCl then extracted with EtOAc (2×15 mL). The organic layer was dried over Na₂SO₄, filtered and concentrated under reduce pressure to afford 3-methoxy-5-(2H-tetrazol-5-yl)pyridine IM320 as an off-white solid: 132 mg, 96% yield, P=94%, retention time=0.4 min (gradient C), (M+H)⁺: 178.

Stage 2: To IM320 (132 mg, 700 μmol) and K₂CO₃ (296 mg, 2.10 mmol) in solution in DMF (5.6 mL) was added IM150 (231 mg, 1.05 mmol). The reaction was stirred at rt for 25 h, then heated to 100° C. for 2.5 h. The reaction mixture was cooled down to rt and diluted with water (50 mL). Aqueous phase was extracted with EtOAc (3×15 mL). Organic layer was dried over Na$_2$SO$_4$, filtered and concentrated under reduced pressure. Residue was purified by reverse phase chromatography on a 40 g C18 cartridge, eluting with a gradient of MeCN in basic water (10 mM NH$_4$HCO$_3$/NH$_4$OH buffer, pH=10) to afford 4-chloro-1-(1-(5-(5-methoxypyridin-3-yl)-2H-tetrazol-2-yl)ethyl)pyridin-2 (1H)-one IM321 as a beige solid: 123 mg, 52% yield, P=98%, retention time=1.1 min (gradient C), (M+H)$^+$: 333/335.

Stage 3: General Procedure C was used between IM3 and IM321 to afford tert-butyl (cyclobutylmethyl)((3R)-1-(1-(1-(5-(5-methoxypyridin-3-yl)-2H-tetrazol-2-yl)ethyl)-2-oxo-1,2-dihydropyridin-4-yl)piperidin-3-yl)carbamate IM322 as a brown solid: 115 mg, 52% yield, P=85%, retention time=1.7 min (gradient C), (M+H)$^+$: 565.

Stage 4: General Procedure A2 was used from IM322 to afford compound 106 as a beige solid: 43 mg, 52% yield, P=99%, retention time=2.4 min (gradient E), (M+H)$^+$: 465.

The mixture of diastereomers was further purified by chiral preparative HPLC purification using Chiralpak IE column (5 μm, 10×250 mm). Eluent used: EtOAc/MeOH/DEA: 85/15/0.1% at flow rate of 7 mL/min. First eluted diastereomer: P=100%, retention time=7.4 min, chiral HPLC: P=100%, $^1$H NMR (300 MHz, CDCl$_3$) δ 8.96 (d, J=1.6 Hz, 1H), 8.40 (d, J=2.9 Hz, 1H), 8.03 (q, J=7.0 Hz, 1H), 7.91 (dd, J=2.9, 1.7 Hz, 1H), 7.36 (d, J=8.1 Hz, 1H), 6.01 (dd, J=8.2, 2.9 Hz, 1H), 5.69 (d, J=2.8 Hz, 1H), 3.93 (s, 3H), 3.79 (d, J=12.8 Hz, 1H), 3.61 (d, J=13.4 Hz, 1H), 2.99-2.85 (m, 1H), 2.83-2.69 (m, 1H), 2.67 (d, J=7.3 Hz, 2H), 2.63-2.55 (m, 1H), 2.40 (hept, J=7.4 Hz, 1H), 2.12 (d, J=7.0 Hz, 3H), 2.09-1.35 (m, 10H), NH exchanged. Second eluted diastereomer: P=100%, retention time=9.2 min, chiral HPLC: P=100%, $^1$H NMR (300 MHz, CDCl$_3$) δ 8.97 (d, J=1.7 Hz, 1H), 8.41 (d, J=2.9 Hz, 1H), 8.03 (q, J=6.9 Hz, 1H), 7.94-7.87 (m, 1H), 7.36 (d, J=8.1 Hz, 1H), 6.02 (dd, J=8.1, 2.9 Hz, 1H), 5.70 (d, J=2.8 Hz, 1H), 3.93 (d, J=3.3 Hz, 3H), 3.81 (d, J=13.1 Hz, 1H), 3.61 (d, J=13.5 Hz, 1H), 2.99-2.88 (m, 1H), 2.79 (dd, J=12.9, 9.4 Hz, 1H), 2.71-2.53 (m, 3H), 2.44 (p, J=7.6 Hz, 1H), 2.11 (d, J=7.0 Hz, 3H), 2.05-1.36 (m, 10H), NH exchanged.

Compound 107: (R)-4-(3-((cyclobutylmethyl) amino)piperidin-1-yl)-1-((1-(5-methoxy pyridin-3-yl)-1H-pyrazol-4-yl)methyl)pyridin-2 (1H)-one was Obtained Using General Scheme 5

Stage 1: To a microwave vial, under nitrogen, were added methyl 1H-pyrazole-4-carboxylate (298 mg, 2.29 mmol), 3-bromo-5-methoxypyridine (400 mg, 2.08 mmol), potassium carbonate (588 mg, 4.17 mmol) and Copper(I) iodide (40.5 mg, 208 μmol). Dry DMF (5.2 mL) was then added. The mixture was degassed with nitrogen for 10 min, then vial was sealed and the reaction mixture was heated to 100° C. for 72 h (3 days).

After cooling to rt, the reaction mixture was filtered to remove insoluble and then purified by reverse phase chromatography (Biotage, C18 30 g cartridge) using a gradient of MeCN (0-100%) in basic water (10 mM NH$_4$HCO$_3$/NH$_4$OH buffer pH=10) to afford methyl 1-(5-methoxypyridin-3-yl)-1H-pyrazole-4-carboxylate IM323 as a white solid: 180 mg, 32% yield, P=87%, retention time=1.0 min (gradient C), (M+H)$^+$: 234.

Stage 2: To a solution of IM323 (170 mg, 729 μmol) in THF (7.3 mL), cooled to 0° C., was added dropwise under nitrogen lithium aluminum hydride (1.09 mL, 1.09 mmol) (1M solution in THF) and the resulting mixture was stirred at 0° C. for 1 h. Then the mixture was filtered through a pad of Celite and washed with TBME (4×10 mL). Filtrate was concentrated under reduced pressure to afford crude (1-(5-methoxypyridin-3-yl)-1H-pyrazol-4-yl)methanol IM324 as a beige solid: 140 mg, 89% yield, P=95%, retention time=0.7 min (gradient C), (M+H)$^+$: 206.

Stage 3: To a solution of IM324 (120 mg, 585 μmol) in a mixture of DCM (2.2 mL) and THF (110 μL) was added drop-wise, at 0° C., phosphorus tribromide (23 μL, 246 μmol). The reaction mixture was warmed to rt and stirred at rt for 1.25 h. The mixture was concentrated under reduced pressure to afford crude 3-(4-(bromomethyl)-1H-pyrazol-1-yl)-5-methoxypyridine hydrobromide IM325 as a white solid: 225 mg, 100% yield, P=77%, retention time=1.2 min (gradient C), (M+H)$^+$: 268/270.

Stage 4: To a solution of IM244 (110 mg, 304 μmol) in DMF (1.5 mL), cooled to 0° C., was added sodium hydride 60% in dispersion in mineral oil (38 mg, 943 μmol) and the reaction mixture was stirred at 0° C. for 10 min. Then a solution of IM325 (212 mg, 609 μmol) in DMF (0.5 mL) was added dropwise. The mixture was warmed to 60° C. and stirred for 1 h. After cooling to rt, the mixture was purified by reverse phase chromatography (Biotage, C-18 30 g cartridge, directly loaded in DMF) using a gradient of MeCN (0-100%) in 10 mM ammonium bicarbonate buffer to afford tert-butyl (R)-(cyclobutylmethyl)(1-(1-((1-(5-methoxypyridin-3-yl)-1H-pyrazol-4-yl)methyl)-2-oxo-1,2-dihydropyridin-4-yl)piperidin-3-yl)carbamate IM326 as a pale yellow: 12 mg, 7% yield, P=91%, retention time=1.6 min (gradient C), (M+H)$^+$: 549.

Stage 5: General Procedure A2 was used from IM326 to afford compound 107 as a white solid: 5 mg, 47% yield, P=95%, retention time=1.9 min (gradient E), (M+H)$^+$: 449. $^1$H NMR (400 MHZ, CD$_3$OD) δ 8.58 (d, J=2.0 Hz, 1H), 8.38 (s, 1H), 8.19 (d, J=2.5 Hz, 1H), 7.82-7.77 (m, 2H), 7.53 (d, J=7.8 Hz, 1H), 6.27 (dd, J=7.8, 2.8 Hz, 1H), 5.75 (d, J=2.7 Hz, 1H), 5.01 (s, 2H), 3.95 (s, 3H), 3.94-3.87 (m, 1H), 3.81-3.73 (m, 1H), 3.01-2.91 (m, 1H), 2.78 (dd, J=12.9, 9.7 Hz, 1H), 2.69 (d, J=7.3 Hz, 2H), 2.64-2.56 (m, 1H), 2.53-2.42 (m, 1H), 2.15-2.01 (m, 3H), 1.97-1.83 (m, 2H), 1.81-1.66 (m, 3H), 1.61-1.49 (m, 1H), 1.43-1.33 (m, 1H), 1H exchanged with CD$_3$OD.

Compound 108: 4-((R)-3-((cyclobutylmethyl) amino)piperidin-1-yl)-1-(1-(4-(5-methoxy-4-methylpyridin-3-yl)-1H-1,2,3-triazol-1-yl)ethyl)pyridin-2 (1H)-one was Obtained Using General Scheme 1 Pathway B Stage 1: General Procedure E1 (in THF instead of DMF) was used from 3-bromo-5-methoxy-4-methylpyridine to afford 3-methoxy-4-methyl-5-((trimethylsilyl)ethynyl)pyridine IM327 as an orange solid: 258 mg, 26% yield, P=52%, retention time=1.7 min (gradient C), (M+H)$^+$: 220.

Stage 2: General Procedure X was used between IM151 and IM327 to afford 4-chloro-1-(1-(4-(5-methoxy-4-methylpyridin-3-yl)-1H-1,2,3-triazol-1-yl)ethyl)pyridin-2 (1H)-one IM328 as a white solid: 72 mg, 28% yield, P=99%, retention time=1.1 min (gradient C), (M+H)$^+$: 346/348.

Stage 3: General Procedure C was used between IM3 and IM328 to afford tert-butyl (cyclobutylmethyl)((3R)-1-(1-(1-(4-(5-methoxy-4-methylpyridin-3-yl)-1H-1,2,3-triazol-1-yl) ethyl)-2-oxo-1,2-dihydropyridin-4-yl)piperidin-3-yl)carbamate IM329 as a white powder: 75 mg, 58% yield, P=94%, retention time=1.6 min (gradient C), (M+H)$^+$: 578.

Stage 4: General Procedure A2 was used from IM329 to afford compound 108 as an off-white solid: 12 mg, 18% yield, P=96%, retention time=2.7 min (gradient E), (M+H)⁺: 478. ¹H NMR (400 MHZ, CD₃OD) δ 8.42 (s, 1H), 8.38 (s, 1H), 8.20 (s, 1H), 7.70 (d, J=8.1 Hz, 1H), 7.53 (q, J=7.1 Hz, 1H), 6.35 (dd, J=8.1, 2.8 Hz, 1H), 5.68 (d, J=2.6 Hz, 1H), 3.99 (s, 3H), 3.97-3.88 (m, 1H), 3.84-3.73 (m, 1H), 3.05-2.93 (m, 1H), 2.87-2.76 (m, 1H), 2.69 (d, J=7.4 Hz, 2H), 2.64-2.55 (m, 1H), 2.53-2.41 (m, 1H), 2.33 (s, 3H), 2.16 (d, J=7.0 Hz, 3H), 2.12-2.01 (m, 3H), 1.96-1.83 (m, 2H), 1.82-1.63 (m, 3H), 1.60-1.47 (m, 1H), 1.47-1.34 (m, 1H), 1H exchanged with CD₃OD.

Compound 109: 3-(1-(1-(4-((R)-3-((cyclobutylmethyl)amino)piperidin-1-yl)-2-oxopyridin-1 (2H)-yl)ethyl)-1H-1,2,3-triazol-4-yl)-5-methoxypicolinonitrile was Obtained Using General Scheme 1 Pathway B Stage 1: To a solution of 3-bromo-5-fluoropicolinonitrile (500 mg, 2.44 mmol) in THF (5.0 mL) at rt was added sodium methoxide (716 µL, 2.68 mmol) and the mixture was stirred at rt for 15 min (heat evolved). The mixture was quenched with saturated NH₄Cl solution (10 mL) and then diluted with EtOAc (20 mL). The layers were separated and the aqueous phase was extracted with additional EtOAc (15 mL). The combined extracts were dried over anhydrous MgSO₄, filtered and concentrated under reduced pressure to dryness to afford crude 3-bromo-5-methoxypicolinonitrile IM330 as a white solid: 497 mg, 96% yield, P=100%, retention time=1.4 min (gradient C), (M+H)⁺: 215.

Stage 2: General Procedure E1 (in THF instead of DMF) was used from IM330 to afford 5-methoxy-3-((trimethylsilyl)ethynyl)picolinonitrile IM331 as a white solid: 473 mg, 84% yield, P=96%, retention time=1.6 min (gradient C), (M+H)⁺: 231.

Stage 3: General Procedure X was used between IM151 and IM331 to afford 3-(1-(1-(4-chloro-2-oxopyridin-1 (2H)-yl)ethyl)-1H-1,2,3-triazol-4-yl)-5-methoxypicolinonitrile IM332 as a white solid: 243 mg, 76% yield, P=76%, retention time=1.2 min (gradient C), (M+H)⁺: 357/359.

Stage 4: General Procedure C was used between IM3 and IM332 to afford tert-butyl ((3R)-1-(1-(1-(4-(2-cyano-5-methoxypyridin-3-yl)-1H-1,2,3-triazol-1-yl)ethyl)-2-oxo-1,2-dihydro pyridin-4-yl)piperidin-3-yl)(cyclobutylmethyl) carbamate IM333 as a beige solid: 155 mg, 43% yield, P=92%, retention time=1.7 min (gradient C), (M+H)⁺: 589.

Stage 5: General Procedure A2 was used from IM333 to afford compound 109 as a beige solid: 48 mg, 36% yield, P=97%, retention time=2.2 min (gradient E), (M+H)⁺: 489. ¹H NMR (400 MHZ, CD₃OD) δ 8.79 (s, 1H), 8.37 (d, J=2.8 Hz, 1H), 8.00 (d, J=2.8 Hz, 1H), 7.72 (d, J=8.2 Hz, 1H), 7.55 (q, J=6.9 Hz, 1H), 6.35 (dd, J=8.2, 2.8 Hz, 1H), 5.67 (d, J=2.8 Hz, 1H), 4.02 (s, 3H), 3.97-3.88 (m, 1H), 3.84-3.74 (m, 1H), 3.03-2.94 (m, 1H), 2.86-2.77 (m, 1H), 2.69 (d, J=7.3 Hz, 2H), 2.65-2.55 (m, 1H), 2.53-2.40 (m, 1H), 2.18 (d, J=7.0 Hz, 3H), 2.14-2.01 (m, 3H), 1.99-1.82 (m, 2H), 1.80-1.64 (m, 3H), 1.60-1.47 (m, 1H), 1.46-1.33 (m, 1H), 1H exchanged with CD₃OD.

The mixture of diastereomers was further purified by chiral preparative HPLC purification using Chiralpak IA column (5 µm, 20×250 mm). Eluent used: TBME/MeOH/DEA: 60/40/0.1% at flow rate of 20 mL/min. First eluted diastereomer: P=100%, retention time=7.8 min, chiral HPLC: P=99.9%, ¹H NMR (300 MHZ, CDCl₃) δ 8.66 (s, 1H), 8.31 (d, J=2.8 Hz, 1H), 8.00 (d, J=2.8 Hz, 1H), 7.58 (q, J=7.0 Hz, 1H), 7.42 (d, J=8.1 Hz, 1H), 6.00 (dd, J=8.1, 2.9 Hz, 1H), 5.65 (d, J=2.8 Hz, 1H), 3.97 (s, 3H), 3.80-3.70 (m, 1H), 3.66-3.55 (m, 1H), 2.99-2.84 (m, 1H), 2.76-2.51 (m, 5H), 2.39 (hept, J=7.5 Hz, 1H), 2.16 (d, J=6.9 Hz, 3H), 2.13-1.46 (m, 8H), 1.42-1.23 (m, 1H), NH exchanged. Second eluted diastereomer: P=100%, retention time=9.4 min, chiral HPLC: P=99.8%, ¹H NMR (300 MHz, CDCl₃) δ 8.66 (s, 1H), 8.31 (d, J=2.6 Hz, 1H), 7.99 (d, J=2.8 Hz, 1H), 7.58 (q, J=6.9 Hz, 1H), 7.42 (d, J=8.1 Hz, 1H), 6.00 (dd, J=8.1, 2.8 Hz, 1H), 5.65 (d, J=2.8 Hz, 1H), 3.97 (s, 3H), 3.80-3.69 (m, 1H), 3.65-3.55 (m, 1H), 2.98-2.83 (m, 1H), 2.77-2.51 (m, 3H), 2.39 (hept, J=7.5 Hz, 1H), 2.16 (d, J=7.0 Hz, 3H), 2.10-1.14 (m, 11H), NH exchanged.

Compound 110: N-(1-(6-((R)-3-((cyclobutylmethyl)amino)piperidin-1-yl)pyridazin-3-yl)ethyl)-4-thioxo-4H-pyrido[1,2-a]pyrimidine-2-carboxamide was Obtained Using General Scheme 2 Pathway B Stage 1: Ammonia, solution in methanol (49.25 mL, 344.75 mmol) was added to methyl 4-oxopyrido[1,2-a]pyrimidine-2-carboxylate (985 mg, 4.82 mmol) at rt. The reaction was stirred at rt for 15 h. The reaction was concentrated under reduced pressure to dryness. EtOH (10 mL) was added and the mixture was cooled to 0° C. and rinsed with cold EtOH (5 mL). The resulting grey solid was rinsed with pentane (10 mL) and collected to afford 4-oxopyrido[1,2-a]pyrimidine-2-carboxamide IM334 as a brown solid: 643 mg, 63% yield, P=98%, retention time=1.8 min (gradient A), (M+H)⁺: 190.

Stage 2: IM334 (200 mg, 0.95 mmol) was suspended into anhydrous DMF (2 mL). Brown suspension was cooled to 0° C., and phosphorus(V) oxychloride (100 µL, 1.07 mmol) was added dropwise. Reaction was stirred at 0° C. for 1 h. Reaction mixture was diluted with EtOAc (30 mL) and quenched with NaHCO₃ saturated solution (10 mL). Aqueous layer was basified with NaHCO₃, and extracted with EtOAc (2×20 mL). Organics layer were merged, and washed with brine (10 mL), dried over MgSO₄, filtered and concentrated under reduced pressure to dryness to afford 4-oxopyrido[1,2-a]pyrimidine-2-carbonitrile IM335 as a brown solid: 140 mg, 82% yield, P=95%, retention time=2.2 min (gradient A), (M+H)⁺: 172.

Stage 3: Lawesson's reagent (405 mg, 0.99 mmol) was added to a suspension of IM335 (120 mg, 0.67 mmol) in anhydrous 1,4-Dioxane (3 mL) and reaction mixture was heated to reflux for 3 h. Reaction mixture was then cooled to rt and concentrated under reduced pressure to dryness. The residue was purified The crude product was purified by an automated flash system (dryload, n-heptane/EtOAc: 1/1) to afford 4-thioxopyrido[1,2-a]pyrimidine-2-carbothioamide IM336 as an orange solid: 84 mg, 53% yield, P=94%, retention time=2.5 min (gradient A), (M+H)⁺: 222.

Stage 4: Iodine (94 mg, 0.37 mmol) was added to a suspension of IM336 (84 mg, 0.35 mmol) in anhydrous DCM (2.2 mL) with triethylamine (155 µL, 1.11 mmol). Reaction mixture was stirred at rt for 1 h and then diluted with DCM (20 mL) and washed with NaHCO₃ saturated solution (2×10 mL). Organic layer was dried over MgSO₄, filtered, and concentrated under reduced pressure to dryness. The crude product was purified by an automated flash chromatography system (liquid loading, n-heptane/EtOAc: 1/1) to afford 4-thioxopyrido[1,2-a]pyrimidine-2-carbonitrile IM337 as light brown solid: 48 mg, 68% yield, P=94%, retention time=2.6 min (gradient A), (M+H)⁺: 188.

Stage 5: A mixture of IM337 (48 mg, 0.24 mmol) in concentrated hydrogen chloride (1.6 mL, 19.2 mmol) was stirred at 90° C. for 4 h. Reaction mixture was then cooled to rt and concentrated under reduced pressure to afford crude 4-thioxopyrido[1,2-a]pyrimidine-2-carboxylic acid hydrochloride as a dark orange solid: 68 mg, 100% yield, P=87%, retention time=2.2 min (gradient A), (M+H)+: 207.

Stage 6: General Procedure F was used between IM337 and IM279 to afford tert-butyl (cyclobutylmethyl)((3R)-1-(6-(1-(4-thioxo-4H-pyrido[1,2-a]pyrimidine-2-carboxamido)ethyl) pyridazin-3-yl)piperidin-3-yl)carbamate IM338 as an orange solid: 56 mg, 33% yield, P=72% ($^1$H NMR), retention time=2.5 min (gradient A), (M+H)+: 578.

Stage 7: General Procedure A1 was used from IM338 to afford crude compound 110 as an orange solid: 20 mg, 56% yield, P=95%, retention time=2.9 min (gradient B), (M+H)+: 478.

The mixture of diastereomers was further purified by chiral preparative HPLC purification using Chiralpak IA column (5 μm, 20×250 mm). Eluent used: EtOAc/MeOH/DEA: 80/20/0.1% at flow rate of 7 mL/min. First eluted diastereomer: P=100%, retention time=4.9 min, chiral HPLC: P=100%, $^1$H NMR (300 MHz, CDCl$_3$) § 10.24 (d, J=7.3 Hz, 1H), 8.93 (d, J=8.3 Hz, 1H), 8.42 (s, 1H), 8.05-7.83 (m, 2H), 7.43 (dd, J=6.7, 6.7 Hz, 1H), 7.22 (s, 1H), 6.94 (d, J=9.4 Hz, 1H), 5.45-5.29 (m, 1H), 4.41 (d, J=13.3 Hz, 1H), 4.08 (d, J=13.2 Hz, 1H), 3.17-3.01 (m, 1H), 2.97-2.85 (m, 1H), 2.84-2.62 (m, 3H), 2.53-2.37 (m, 1H), 2.23-1.97 (m, 3H), 1.97-1.76 (m, 4H), 1.76-1.56 (m, 4H), 1.55-1.39 (m, 2H). 1H exchanged with solvent. Second eluted diastereomer: P=93%, retention time=7.2 min, chiral HPLC: P=100%, $^1$H NMR (300 MHz, CDCl$_3$) δ 10.24 (d, J=7.3 Hz, 1H), 8.93 (d, J=8.4 Hz, 1H), 8.42 (s, 1H), 8.00-7.85 (m, 2H), 7.43 (dd, J=6.9, 2.0 Hz, 1H), 7.23 (d, J=9.3 Hz, 1H), 6.94 (d, J=9.4 Hz, 1H), 5.44-5.28 (m, 1H), 4.40 (d, J=12.8 Hz, 1H), 4.08 (d, J=13.1 Hz, 1H), 3.16-3.03 (m, 1H), 2.91 (dd, 1H), 2.83-2.67 (m, 3H), 2.53-2.37 (m, 1H), 2.12-1.98 (m, 3H), 1.97-1.76 (m, 4H), 1.71-1.66 (m, 4H), 1.53-1.34 (m, 2H). 1H exchanged with solvent.

Compound 111: N-(1-(6-((R)-3-((cyclobutylmethyl)amino)piperidin-1-yl)pyridazin-3-yl)ethyl)-4-oxo-4H-pyrido[1,2-a]pyrimidine-2-carbothioamide IM156 (169 mg, 0.24 mmol) was added to a suspension of Lawesson's reagent (55 mg, 0.13 mmol) in anhydrous DCE (3 mL) and reaction mixture was heated to reflux for 1 h. Additional Lawesson's reagent (55 mg, 0.13 mmol) was added to the reaction mixture, which was stirred for extra 4 h. A third portion of Lawesson's reagent (55 mg, 0.13 mmol) was then added and reaction was stirred under reflux for extra 16 h. The mixture was then cooled to rt and concentrated under reduced pressure to dryness to afford crude compound 111: 360 mg, 60% yield, P=21%, retention time=2.2 min (gradient B), (M+H)+: 478.

The product was further purified by reverse phase preparative HPLC purification (Waters XBridge C18 5 μm 19×100 mm). Gradient used: increased linearly from 30 to 40% solution "B" over 5.0 min, increased linearly to 85% solution "B" over 1.2 min, held at 85% for 0.3 min and returned to initial conditions over 1.0 min. Flow Rate: 15 mL/min. P=100%.

The mixture of diastereomers was further purified by chiral preparative HPLC purification using Chiralpak IE column (5 μm, 10×250 mm). Eluent used: EtOAc/MeOH/DEA: 85/15/0.1% at flow rate of 7 mL/min. First eluted diastereomer: P=100%, retention time=5.1 min, chiral HPLC: P=100%, $^1$H NMR (300 MHZ, CDCl$_3$) δ 10.92 (d, J=8.2 Hz, 1H), 9.05 (d, J=7.1 Hz, 1H), 7.79 (d, J=3.6 Hz, 2H), 7.74 (s, 1H), 7.29 (d, J=9.4 Hz, 1H), 7.23-7.13 (m, 1H), 6.92 (d, J=9.4 Hz, 1H), 5.99-5.83 (m, 1H), 4.40 (d, J=12.8 Hz, 1H), 4.09 (d, J=13.2 Hz, 1H), 3.17-3.02 (m, 1H), 2.95-2.82 (m, 1H), 2.80-2.62 (m, 3H), 2.52-2.36 (m, 1H), 2.15-1.97 (m, 2H), 1.95-1.80 (m, 4H), 1.77 (d, J=6.8 Hz, 3H), 1.72-1.54 (m, 3H), 1.51-1.33 (m, 1H). 1H exchanged with solvent. Second eluted diastereomer: P=100%, retention time=7.8 min, chiral HPLC: P=100%, $^1$H NMR (300 MHz, CDCl$_3$) δ 10.91 (d, J=8.2 Hz, 1H), 9.05 (d, J=7.1 Hz, 1H), 7.83-7.75 (m, 2H), 7.74 (s, 1H), 7.29 (d, J=9.4 Hz, 1H), 7.23-7.12 (m, 1H), 6.92 (d, J=9.4 Hz, 1H), 5.91 (dd, J=7.9, 6.5 Hz, 1H), 4.44-4.33 (m, 1H), 4.15-4.03 (m, 1H), 3.17-3.02 (m, 1H), 2.89 (dd, J=12.7, 9.2 Hz, 1H), 2.81-2.60 (m, 3H), 2.51-2.33 (m, 1H), 2.14-1.98 (m, 2H), 1.98-1.79 (m, 4H), 1.77 (d, J=6.7 Hz, 3H), 1.73-1.52 (m, 3H), 1.51-1.32 (m, 1H). 1H exchanged with solvent.

Compound 112: N-(1-(5-((R)-3-((cyclopropylmethyl)amino)piperidin-1-yl)pyridin-2-yl)ethyl)-4-oxo-4H-pyrido[1,2-a]pyrimidine-2-carboxamide was Obtained Using General Scheme 2 Pathway B Stage 1: To a solution of 1-(5-bromopyridin-2-yl)ethanone (3.0 g, 14.7 mmol) and ethylene glycol (3.6 mL, 64.38 mmol) in anhydrous toluene (110 mL) was added para-toluenesulfonic acid monohydrate (130 mg, 0.75 mmol). The reaction mixture was stirred under reflux using a Dean-Stark apparatus for 2.5 h. The reaction mixture was cooled to rt and then concentrated to dryness under reduced pressure. The colorless oil obtained was solubilized in EtOAc (100 mL) and washed with aqueous saturated NaHCO$_3$ solution (50 mL). Organic phase was dried over MgSO$_4$, filtered and concentrated under reduced pressure to afford a white solid. The latter was slurried in water (50 mL) for 20 min, and then filtered. The obtained white solid was washed with water (10 mL), and dried under reduced pressure to afford 5-bromo-2-(2-methyl-1,3-dioxolan-2-yl) pyridine IM339 as a white solid: 3.18 g, 89% yield, P=100%, retention time=2.5 min (gradient A), (M+H)+: 244/246.

Stage 2: General Procedure S (replacing Pd(OAc)$_2$ with Pd$_2$(dba)$_3$ and Cs2CO3 with NaOtBu) was used between IM3 and IM339 to afford tert-butyl N-[(3R)-1-[6-(2-methyl-1,3-dioxolan-2-yl)-3-pyridyl]-3-piperidyl]carbamate IM340 as yellowish oil: 146 mg, 7% yield, P=100%, retention time=2.3 min (gradient A), (M+H)+: 364.

Stage 3: A mixture of IM340 (146 mg, 0.38 mmol), iodine (10 mg, 0.04 mmol) and water (35 μL, 1.94 mmol) in acetone (5 mL) was stirred at 60° C. for 48 h. Solvent was removed under reduced pressure, and the brown oil obtained was diluted with dichloromethane (20 mL). The organic phase was washed successively with 5% aqueous Na$_2$S$_2$O$_3$ (10 mL), water (20 mL), and brine (20 mL), dried over MgSO$_4$, filtered and concentrated reduced pressure to dryness to afford crude tert-butyl N-[(3R)-1-(6-acetyl-3-pyridyl)-3-piperidyl]carbamate IM341 as a brown solid: 117 mg, 91% yield, P=95%, retention time=2.3 min (gradient A), (M+H)+: 320.

Stage 4: General Procedure W was used from IM341 to afford crude tert-butyl N-[(3R)-1-[6-(1-aminoethyl)-3-pyridyl]-3-piperidyl]carbamate IM342 as yellow oil: 83 mg, 67% yield, P=90%, retention time=2.1 min (gradient A), (M+H)+: 321.

Stage 5: General Procedure F was used between 4-oxopyrido[1,2-a]pyrimidine-2-carboxylic acid hydrochloride and IM342 to afford tert-butyl N-[(3R)-1-[6-[1-[(4-oxopyrido[1,2-a]pyrimidine-2-carbonyl)amino]ethyl]-3- pyridyl]-3-piperidyl]carbamate IM343 as yellow oil: 88 mg, 69% yield, P=100%, retention time=2.3 min (gradient A), (M+H)⁺: 493.

Stage 6: General Procedure A1 was used from IM343 to afford crude N-[1-[5-[(3R)-3-amino-1-piperidyl]-2-pyridyl] ethyl]-4-oxo-pyrido[1,2-a]pyrimidine-2-carboxamide IM344 as yellow oil: 57 mg, 81% yield, P=100%, retention time=1.9 min (gradient A), (M+H)⁺: 393.

Stage 7: General Procedure H1 was used between cyclopropanecarboxaldehyde and IM344 to afford crude compound 112 as yellow oil: 64 mg, 78% yield, P=79%, retention time=2.0 min (gradient A), (M+H)⁺: 447.

The product was further purified by reverse phase preparative HPLC purification (Waters XBridge C18 5 μm 19×100 mm). Gradient used: increased linearly from 15 to 40% solution "B" over 5.5 min, increased linearly to 85% solution "B" over 0.7 min, held at 85% for 0.3 min and returned to initial conditions over 1.0 min. Flow Rate: 15 mL/min. P=99%.

The mixture of diastereomers was further purified by chiral preparative HPLC purification using Chiralpak IA column (5 μm, 20×250 mm). Eluent used: TBME/MeOH/DEA: 70/30/0.1% at flow rate of 20 mL/min. First eluted diastereomer: P=100%, retention time=7.4 min, chiral HPLC: P=100%, ¹H NMR (300 MHz, CDCl₃) δ 9.07 (d, J=7.2 Hz, 1H), 8.88 (d, J=8.2 Hz, 1H), 8.30 (s, 1H), 7.84-7.69 (m, 2H), 7.29 (s, 1H), 7.23-7.12 (m, 3H), 5.33-5.18 (m, 1H), 3.63 (dd, J=11.5, 3.4 Hz, 1H), 3.49-3.39 (m, 1H), 2.93-2.73 (m, 2H), 2.67 (dd, J=11.6, 8.8 Hz, 1H), 2.62-2.45 (m, 2H), 2.02-1.89 (m, 1H), 1.89-1.76 (m, 1H), 1.76-1.63 (m, 1H), 1.59 (d, J=6.8 Hz, 3H), 1.42-1.23 (m, 1H), 1.02-0.86 (m, 1H), 0.56-0.41 (m, 2H), 0.18-0.04 (m, 2H). 1H exchanged with solvent. Second eluted diastereomer: P=100%, retention time=11.1 min, chiral HPLC: P=100%, ¹H NMR (300 MHz, CDCl₃) δ 9.07 (d, J=7.1 Hz, 1H), 8.88 (d, J=8.1 Hz, 1H), 8.30 (s, 1H), 7.84-7.69 (m, 2H), 7.28 (s, 1H), 7.23-7.12 (m, 3H), 5.33-5.18 (m, 1H), 3.67-3.56 (m, 1H), 3.49-3.38 (m, 1H), 2.93-2.74 (m, 2H), 2.67 (dd, J=11.6, 8.8 Hz, 1H), 2.62-2.46 (m, 2H), 1.99-1.89 (m, 1H), 1.88-1.77 (m, 1H), 1.76-1.64 (m, 1H), 1.59 (d, J=6.8 Hz, 3H), 1.42-1.22 (m, 1H), 1.03-0.85 (m, 1H), 0.55-0.43 (m, 2H), 0.16-0.08 (m, 2H). 1H exchanged with solvent.

Compound 113: 4-((R)-3-((cyclobutylmethyl) amino)piperidin-1-yl)-1-(1-(4-(5-(dimethyl amino) pyridin-3-yl)-1H-1,2,3-triazol-1-yl)ethyl)pyridin-2 (1H)-one was Obtained Using General Scheme 1 Pathway B Stage 1: General Procedure E1 (in THF instead of DMF) was used from 5-bromo-N,N-dimethylpyridin-3-amine to afford N,N-dimethyl-5-((trimethylsilyl)ethynyl)pyridin-3-amine IM345 as a white solid: 306 mg, 94% yield, P=95%, retention time=1.6 min (gradient C), (M+H)⁺: 219.

Stage 2: General Procedure X was used between IM151 and IM345 to afford 4-chloro-1-(1-(4-(5-(dimethylamino) pyridin-3-yl)-1H-1,2,3-triazol-1-yl)ethyl)pyridin-2 (1H)-one IM346 as a beige solid: 117 mg, 71% yield, P=99%, retention time=1.1 min (gradient C), (M+H)⁺: 345/347.

Stage 3: General Procedure C was used between IM3 and IM346 to afford tert-butyl (cyclobutylmethyl)((3R)-1-(1-(1-(4-(5-(dimethylamino)pyridin-3-yl)-1H-1,2,3-triazol-1-yl) ethyl)-2-oxo-1,2-dihydropyridin-4-yl)piperidin-3-yl)carbamate IM347 as a light brown solid: 172 mg, 87% yield, P=98%, retention time=1.6 min (gradient C), (M+H)⁺: 577.

Stage 4: General Procedure A2 was used from IM348 to afford compound 113 as a white solid: 119 mg, 85% yield, P=100%, retention time=2.0 min (gradient E), (M+H)⁺: 477. ¹H NMR (400 MHZ, CD₃OD) δ 8.60 (d, J=2.9 Hz, 1H), 8.29 (s, 1H), 8.01 (d, J=2.7 Hz, 1H), 7.65 (dd, J=8.1, 2.8 Hz, 1H), 7.58 (d, J=1.6 Hz, 1H), 7.55-7.47 (m, 1H), 6.38-6.28 (m, 1H), 5.68 (s, 1H), 3.97-3.86 (m, 1H), 3.83-3.72 (m, 1H), 3.05 (d, J=2.8 Hz, 6H), 3.02-2.92 (m, 1H), 2.86-2.74 (m, 1H), 2.67 (dd, J=7.1, 1.7 Hz, 2H), 2.57 (m, 1H), 2.51-2.40 (m, 1H), 2.15 (dd, J=6.8, 2.3 Hz, 3H), 2.11-2.00 (m, 3H), 1.96-1.81 (m, 2H), 1.80-1.63 (m, 3H), 1.59-1.46 (m, 1H), 1.44-1.32 (m, 1H), 1H exchanged with CD₃OD.

The mixture of diastereomers was further purified by chiral preparative HPLC purification using Chiralpak IA column (5 μm, 20×250 mm). Eluent used: TBME/MeOH/DEA: 60/40/0.1% at flow rate of 20 mL/min. First eluted diastereomer: P=100%, retention time=6.6 min, chiral HPLC: P=100%, ¹H NMR (300 MHz, CDCl₃) δ 8.32 (d, J=1.7 Hz, 1H), 8.09 (m, 2H), 7.55 (q, J=7.0 Hz, 1H), 7.59-7.41 (m, 2H), 5.98 (dd, J=8.1, 2.9 Hz, 1H), 5.65 (d, J=2.8 Hz, 1H), 3.75 (d, J=13.0 Hz, 1H), 3.60 (d, J=13.0 Hz, 1H), 3.02 (2s, 6H), 2.91 (ddd, J=13.8, 10.9, 3.1 Hz, 1H), 2.74-2.53 (m, 4H), 2.44-2.34 (m, 1H), 2.15 (d, J=7.0 Hz, 3H), 2.10-1.52 (m, 10H), 1.47-1.31 (m, 1H). Second eluted diastereomer: P=100%, retention time=21.5 min, chiral HPLC: P=100%, ¹H NMR (300 MHz, CDCl₃) δ 8.31 (d, J=1.7 Hz, 1H), 8.09 (m, 2H), 7.54 (q, J=7.0 Hz, 1H), 7.56-7.40 (m, 2H), 5.97 (dd, J=8.1, 2.9 Hz, 1H), 5.65 (d, J=2.8 Hz, 1H), 3.74 (d, J=12.8 Hz, 1H), 3.60 (d, J=13.3 Hz, 1H), 3.01 (2s, 6H), 2.92 (ddd, J=13.8, 10.9, 3.1 Hz, 1H), 2.73-2.55 (m, 4H), 2.38 (hept, J=7.5 Hz, 1H), 2.15 (d, J=7.1 Hz, 3H), 2.07-1.49 (m, 10H), 1.48-1.30 (m, 1H).

Compound 114: 4-((R)-3-((cyclobutylmethyl) amino)piperidin-1-yl)-1-(1-(4-(5-methoxy-2-methylpyridin-3-yl)-1H-1,2,3-triazol-1-yl)ethyl)pyridin-2 (1H)-one was Obtained Using General Scheme 1 Pathway B Stage 1: To a stirred solution of 3-bromo-5-hydroxy-2-picoline (282 mg, 1.44 mmol) in MeCN (3 mL) was added cesium carbonate (911 mg, 2.74 mmol). The mixture was stirred at rt for 10 min. Then iodomethane (200 μL, 3.19 mmol) was added. The reaction mixture was stirred at rt for 18.5 h. It was then partitioned between EtOAc (2×100 mL) and water (50 mL). The EtOAc layers were dried with MgSO₄, filtered and evaporated under reduced pressure to afford crude 3-bromo-5-methoxy-2-methylpyridine IM349 as brown oil: 291 mg, 100% yield, P=97%, retention time=1.2 min (gradient C), (M+H)⁺: 204.

Stage 2: General Procedure E1 (in THF instead of DMF) was used from IM349 to afford crude 5-methoxy-2-methyl-3-((trimethylsilyl)ethynyl)pyridine IM350 as brown oil: 316 mg, 100% yield, P=95%, retention time=1.7 min (gradient C), (M+H)⁺: 220.

Stage 3: General Procedure X was used between IM151 and IM350 to afford 4-chloro-1-(1-(4-(5-methoxy-2-methylpyridin-3-yl)-1H-1,2,3-triazol-1-yl)ethyl)pyridin-2 (1H)-one IM351 as a white solid: 105 mg, 35% yield, P=98%, retention time=1.0 min (gradient C), (M+H)⁺: 346/348.

Stage 4: General Procedure C was used between IM3 and IM351 to afford tert-butyl (cyclobutylmethyl)((3R)-1-(1-(1-(4-(5-methoxy-2-methylpyridin-3-yl)-1H-1,2,3-triazol-1-yl) ethyl)-2-oxo-1,2-dihydropyridin-4-yl)piperidin-3-yl)carbamate IM352 as a beige solid: 130 mg, 74% yield, P=96%, retention time=1.6 min (gradient C), (M+H)⁺: 578.

Stage 5: General Procedure A2 was used from IM352 to afford compound 114 as an off-white solid: 83 mg, 57% yield, P=98%, retention time=2.0 min (gradient E), (M+H)⁺:

478. $^1$H NMR (400 MHZ, CD$_3$OD) δ 8.45 (s, 1H), 8.13 (d, J=2.9 Hz, 1H), 7.76-7.67 (m, 2H), 7.53 (q, J=7.0 Hz, 1H), 6.34 (dd, J=8.2, 2.9 Hz, 1H), 5.68 (d, J=2.8 Hz, 1H), 3.95-3.90 (m, 1H), 3.90 (s, 3H), 3.82-3.72 (m, 1H), 3.05-2.92 (m, 1H), 2.86-2.76 (m, 1H), 2.69 (d, J=7.4 Hz, 2H), 2.65-2.59 (m, 1H), 2.58 (s, 3H), 2.52-2.40 (m, 1H), 2.16 (d, J=7.0 Hz, 3H), 2.13-2.01 (m, 3H), 1.99-1.83 (m, 2H), 1.82-1.64 (m, 3H), 1.61-1.28 (m, 2H), 1H exchanged with CD$_3$OD.

Compound 115: (R)—N-(cyclobutylmethyl)-1-(6-(1-(4-(5-methoxypyridin-3-yl)-1H-1,2,3-triazol-1-yl)cyclopropyl)pyridazin-3-yl)piperidin-3-amine was Obtained Using General Scheme 1 Pathway A Stage 1: General Procedure C was used between IM3 and 6-chloro-3-pyridazinecarbonitrile to afford tert-butyl (R)-(1-(6-cyanopyridazin-3-yl)piperidin-3-yl)(cyclobutylmethyl)carbamate IM353 as a white foam: 238 mg, 91% yield, P=100%, retention time=2.3 min (gradient A), (M+H)$^+$: 372.

Stage 2: To a solution of IM353 (238 mg, 0.64 mmol) in anhydrous THF (2 mL), were added dropwise titanium (IV) isopropoxide (190 μL, 0.64 mmol), followed by ethylmagnesium bromide 3 N (430 μL, 1.29 mmol) at 0° C. The reaction mixture was allowed to warm to rt and stirred for 1.5 h. Extra titanium (IV) isopropoxide (190 μL, 0.62 mmol) was added to the reaction mixture at rt, followed by ethylmagnesium bromide 3 N (430 μL, 1.29 mmol). After 10 min, reaction was quenched by addition of NaOH 1 N (10 mL) and extracted with EtOAc (3×20 mL). Organics layers were merged, dried over MgSO$_4$, filtered and concentrated under reduced pressure to dryness. The crude product was purified by an automated flash chromatography system (liquid loading, n-heptane/EtOAc: 1/1) to afford tert-butyl (R)-(1-(6-(1-aminocyclopropyl)pyridazin-3-yl)piperidin-3-yl)(cyclobutylmethyl)carbamate IM354 as brown oil: 77 mg, 29% yield, P=96%, retention time=2.3 min (gradient A), (M+H)$^+$: 402.

Stage 3: General Procedure V was used from IM354 to afford tert-butyl (R)-(1-(6-(1-azido cyclopropyl)pyridazin-3-yl)piperidin-3-yl)(cyclobutylmethyl)carbamate IM355 as colourless oil: 14 mg, 18% yield, P=100%, retention time=2.7 min (gradient A), (M+H)$^+$: 428.

Stage 4: General Procedure B was used between IM44 and IM355 to afford tert-butyl (R)-(cyclobutylmethyl)(1-(6-(1-(4-(5-methoxypyridin-3-yl)-1H-1,2,3-triazol-1-yl)cyclopropyl) pyridazin-3-yl)piperidin-3-yl)carbamate IM356 as colourless oil: 18 mg, 95% yield, P=97%, retention time=2.4 min (gradient A), (M+H)$^+$: 561.

Stage 5: General Procedure A1 was used from IM356 to afford compound 115 as a white powder: 14 mg, 95% yield, P=98%, retention time=2.5 min (gradient B), (M+H)$^+$: 461. $^1$H NMR (300 MHZ, CDCl$_3$) δ 8.55 (d, J=1.7 Hz, 1H), 8.28 (d, J=2.8 Hz, 1H), 8.04 (s, 1H), 7.78 (dd, J=2.9, 1.7 Hz, 1H), 6.81 (s, 2H), 4.34 (d, J=12.5 Hz, 1H), 4.11-3.97 (m, 1H), 3.92 (s, 3H), 3.14-2.97 (m, 1H), 2.86 (dd, J=12.8, 9.2 Hz, 1H), 2.78-2.53 (m, 3H), 2.41 (hept, J=7.6 Hz, 1H), 2.13-1.71 (m, 9H), 1.71-0.88 (m, 5H), NH exchanged.

Compound 116: 4-((R)-3-((cyclobutylmethyl)amino)piperidin-1-yl)-1-((R)-1-(4-(5-methoxypyridin-3-yl)-1H-1,2,3-triazol-1-yl)ethyl)pyridine-2(1H)-thione Lawesson's reagent (66 mg, 0.16 mmol) was added to a solution of compound 55 (50 mg, 0.11 mmol) in anhydrous toluene (0.6 mL) and the reaction mixture was heated to reflux for 72 h, before being cooled to rt. Reaction mixture was purified over SCX-2 cartridge (equilibrated with MeOH, reaction mixture loaded as a solution in MeOH (10 mL), rinsed with MeOH (25 mL), and the desired product was released with mixture of MeOH/NH$_3$ (7 N in MeOH): 2/1 (30 mL)) to afford compound 116 as yellow oil: 50 mg, 17% yield, P=18%, retention time=2.8 min (gradient B), (M+H)$^+$: 480.

The product was further purified by reverse phase preparative HPLC purification (Waters XBridge C18 5 μm 19×100 mm). Gradient used: increased linearly from 25 to 40% solution "B" over 4.0 min, increased linearly to 85% solution "B" over 2.2 min, held at 85% for 0.3 min and returned to initial conditions over 0.7 min. Flow Rate: 15 mL/min. P=100%. $^1$H NMR (300 MHz, CDCl$_3$) δ 8.99 (q, J=7.0 Hz, 1H), 8.60 (d, J=1.6 Hz, 1H), 8.41 (s, 1H), 8.28 (d, J=2.9 Hz, 1H), 7.77 (d, J=7.9 Hz, 1H), 7.69 (t, J=2.3 Hz, 1H), 7.04 (d, J=3.1 Hz, 1H), 6.29 (dd, J=7.9, 3.1 Hz, 1H), 3.91 (s, 3H), 3.88-3.77 (m, 1H), 3.75-3.65 (m, 1H), 3.08-2.94 (m, 1H), 2.79 (dd, J=13.1, 9.3 Hz, 1H), 2.71-2.50 (m, 3H), 2.38 (p, J=7.7 Hz, 1H), 2.21 (d, J=6.9 Hz, 3H), 2.14-1.15 (m, 10H), NH exchanged.

Compound 117: N-(1-(5-((R)-3-(cyclopentylamino)piperidin-1-yl)pyridin-2-yl)ethyl)-4-oxo-4H-pyrido[1,2-a]pyrimidine-2-carboxamide was Obtained Using General Scheme 2 Pathway B General Procedure H1 was used between cyclopentanone and IM344 to afford crude compound 117 as colourless oil: 61 mg, 64% yield, P=86% (215 nm), retention time=2.0 min (gradient A), (M+H)$^+$: 461.

The product was further purified by reverse phase preparative HPLC purification (Waters XBridge C18 5 μm 19×100 mm). Gradient used: increased linearly from 5 to 40% solution "B" over 4.5 min, increased linearly to 85% solution "B" over 1.7 min, held at 85% for 0.3 min and returned to initial conditions over 0.7 min. Flow Rate: 15 mL/min. P=99%.

The mixture of diastereomers was further purified by chiral preparative HPLC purification using Chiralpak IA column (5 μm, 20×250 mm). Eluent used: TBME/MeOH/DEA: 60/40/0.1% at flow rate of 20 mL/min. First eluted diastereomer: P=100%, retention time=6.0 min, chiral HPLC: P=100%, $^1$H NMR (300 MHz, CDCl$_3$) δ 9.08 (d, J=7.2 Hz, 1H), 8.88 (d, J=8.1 Hz, 1H), 8.31 (s, 1H), 7.85-7.70 (m, 2H), 7.30 (s, 1H), 7.21-7.13 (m, 3H), 5.32-5.19 (m, 1H), 3.64 (d, J=11.6 Hz, 1H), 3.46 (d, J=12.3 Hz, 1H), 3.24 (p, J=7.0 Hz, 1H), 2.90-2.74 (m, 2H), 2.71-2.57 (m, 1H), 2.01-1.21 (m, 15H), NH exchanged. Second eluted diastereomer: P=100%, retention time=9.9 min, chiral HPLC: P=100%, $^1$H NMR (300 MHz, CDCl$_3$) δ 9.08 (d, J=7.1 Hz, 1H), 8.89 (d, J=7.9 Hz, 1H), 8.35-8.28 (m, 1H), 7.84-7.70 (m, 2H), 7.30 (s, 1H), 7.17 (dd, J=7.7, 2.0 Hz, 3H), 5.32-5.21 (m, 1H), 3.69-3.58 (m, 1H), 3.51-3.41 (m, 1H), 3.29-3.19 (m, 1H), 2.91-2.76 (m, 2H), 2.65 (dd, J=11.8, 8.8 Hz, 1H), 2.00-1.19 (m, 15H), NH exchanged.

Compound 118: (R)—N-(cyclobutylmethyl)-1-(6-((4-(5-methoxypyridazin-3-yl)-1H-1,2,3-triazol-1-yl)methyl)pyridin-3-yl)piperidin-3-amine was Obtained Using General Scheme 1 Pathway B Stage 1: General Procedure E1 (in THF instead of DMF) was used from 3-chloro-5-methoxypyridazine to afford 5-methoxy-3-((trimethylsilyl)ethynyl)pyridazine IM357 as yellow oil: 290 mg, 40% yield, P=98%, retention time=2.6 min (gradient A), (M+H)⁺: 207.

Stage 2: General Procedure X was used between IM128 and IM357 to afford tert-butyl (R)-(cyclobutylmethyl)(1-(6-((4-(5-methoxypyridazin-3-yl)-1H-1,2,3-triazol-1-yl)methyl)pyridin-3-yl)piperidin-3-yl)carbamate IM358 as a beige solid: 35 mg, 58% yield, P=96%, retention time=2.6 min (gradient A), (M+H)⁺: 535.

Stage 3: General Procedure A1 was used from IM358 to afford compound 118 as a white solid: 27 mg, 97% yield, P=98%, retention time=2.6 min (gradient B), (M+H)⁺: 435. ¹H NMR (300 MHz, CD₃OD) δ 8.83 (s, 1H), 8.60 (s, 1H), 8.24 (s, 1H), 7.84 (s, 1H), 7.36 (d, J=7.1 Hz, 2H), 5.69 (s, 2H), 4.05 (s, 3H), 3.79-3.71 (m, 1H), 3.60 (s, 2H), 2.95-2.81 (m, 1H), 2.75-2.66 (m, 3H), 2.54-2.43 (m, 1H), 2.15-1.60 (m, 10H), 1H exchanged with CD₃OD.

Compound 119: 4-((R)-3-((cyclobutylmethyl)amino)piperidin-1-yl)-1-(1-(5-(5-methoxy pyridin-3-yl)-1,3,4-thiadiazol-2-yl)ethyl)pyridin-2 (1H)-one was Obtained Using General Scheme 3 Pathway B Stage 1: To a solution of 2,5-dibromo-1,3,4-thiadiazole (1.25 g, 5.01 mmol) in DMF (15 mL) was added tributyl (1-ethoxyvinyl)tin (1.78 mL, 5.01 mmol) and dichloro bis(triphenylphosphine) palladium(II) (359 mg, 501 μmol) and the reaction mixture was degassed for 5 min with N₂, then heated to 60° C. for 22 h. The mixture was directly purified on C18 column (120 g, 0-100% MeCN in Ammonium bicarbonate), the solvent was evaporated and since the product contained some PPh₃O it was repurified by flash chromatography on silica gel (0-10% EtOAc in hexanes) to afford 2-bromo-5-(1-ethoxyvinyl)-1,3,4-thiadiazole IM359 as a white solid: 496 mg, 42% yield, P=100%, retention time=1.2 min (gradient C).

Stage 2: General Procedure U was used from IM359 to afford 2-(1-ethoxyvinyl)-5-(5-methoxypyridin-3-yl)-1,3,4-thiadiazole IM360 as a light yellow solid: 465 mg, 83% yield, P=99%, retention time=1.3 min (gradient C), (M+H)⁺: 264.

Stage 3: To a suspension of IM360 (465 mg, 1.77 mmol) in acetone (8.3 mL) was added hydrochloric acid (6.24 mL, 18.7 mmol) (3M in water) and the reaction was stirred at rt for 1 h. The mixture was concentrated down to remove acetone. The mixture was partitioned between EtOAc (100 mL) and saturated NaHCO₃ aqueous solution (100 mL), and the organic layer was washed with brine (30 mL), dried over NaSO₄, filtered, and the solvent was evaporated to dryness to afford crude 1-(5-(5-methoxypyridin-3-yl)-1,3,4-thiadiazol-2-yl)ethan-1-one IM361 as yellow oil: 380 mg, 89% yield, P=97%, retention time=1.1 min (gradient C), (M+H)⁺: 236.

Stage 4: To a suspension of IM361 (380 mg, 1.57 mmol) in Methanol (5 mL) at 0° C. was added sodium borohydride (185 mg, 4.70 mmol) and the reaction was stirred at 0° C. for 30 min. The reaction was quenched by the addition of the saturated NaHCO₃ solution. The reaction mixture was partitioned between EtOAc (50 mL) and brine (30 mL). The organic layer was separated, dried over NaSO₄, and purified by flash chromatography on silica gel (0-100% EtOAc in hexanes) to afford 1-(5-(5-methoxypyridin-3-yl)-1,3,4-thiadiazol-2-yl)ethan-1-ol IM362 as light yellow oil: 302 mg, 81% yield, P=100%, retention time=0.8 min (gradient C), (M+H)⁺: 238.

Stage 5: General Procedure P was used from IM362 to afford crude 1-(5-(5-methoxypyridin-3-yl)-1,3,4-thiadiazol-2-yl)ethyl methanesulfonate IM363 as yellow oil: 401 mg, 100% yield, P=100%, retention time=1.1 min (gradient A), (M+H)⁺: 316.

Stage 6: To a solution of 4-chloro-2-hydroxypyridine (339 mg, 2.54 mmol) in DMF (6 mL) was added potassium carbonate (394 mg, 2.79 mmol) and the reaction mixture was stirred at rt for 10 min, before IM363 (400 mg, 1.27 mmol) in DMF (6 mL) was added. The reaction mixture was heated at 50° C. for 7 h. The mixture was cooled down to rt and directly purified by C18 column (0-100% MeCN in ammonium bicarbonate) to afford 4-chloro-1-(1-(5-(5-methoxypyridin-3-yl)-1,3,4-thiadiazol-2-yl)ethyl)pyridin-2 (1H)-one IM364 as a beige solid: 177 mg, 40% yield, P=99%, retention time=1.1 min (gradient C), (M+H)⁺: 349/351.

Stage 7: General Procedure C was used between IM3 and IM364 to afford tert-butyl (cyclobutylmethyl)((3R)-1-(1-(1-(5-(5-methoxypyridin-3-yl)-1,3,4-thiadiazol-2-yl)ethyl)-2-oxo-1,2-dihydropyridin-4-yl)piperidin-3-yl)carbamate IM365 as a light brown gummy solid: 296 mg, 88% yield, P=99%, retention time=1.7 min (gradient C), (M+H)⁺: 581.

Stage 8: General Procedure A2 was used from IM365 to afford compound 119 as a beige solid: 190 mg, 78% yield, P=99%, retention time=2.3 min (gradient E), (M+H)⁺: 481. ¹H NMR (400 MHZ, CD₃OD) δ 8.67 (d, J=1.7 Hz, 1H), 8.40 (d, J=2.8 Hz, 1H), 7.93 (dd, J=2.7, 1.8 Hz, 1H), 7.53 (d, J=8.0 Hz, 1H), 6.45 (q, J=7.0 Hz, 1H), 6.34 (dd, J=8.0, 2.9 Hz, 1H), 5.73 (d, J=2.8 Hz, 1H), 3.97 (s, 3H), 3.96-3.89 (m, 1H), 3.84-3.75 (m, 1H), 3.04-2.93 (m, 1H), 2.81 (ddd, J=13.1, 9.8, 3.4 Hz, 1H), 2.69 (d, J=7.3 Hz, 2H), 2.65-2.54 (m, 1H), 2.54-2.40 (m, 1H), 2.14-2.02 (m, 3H), 1.98 (d, J=7.2 Hz, 3H), 1.95-1.67 (m, 5H), 1.61-1.50 (m, 1H), 1.45-1.34 (m, 1H), 1H exchanged with CD₃OD.

The mixture of diastereomers was further purified by chiral preparative HPLC purification using Chiralpak IA column (5 μm, 20×250 mm). Eluent used: TBME/MeOH/DEA: 60/40/0.1% at flow rate of 20 mL/min. First eluted diastereomer: P=100%, retention time=8.8 min, chiral HPLC: P=100%, ¹H NMR (300 MHz, CDCl₃) δ 8.62 (d, J=1.7 Hz, 1H), 8.38 (d, J=2.8 Hz, 1H), 7.77 (dd, J=2.9, 1.8 Hz, 1H), 7.22 (d, J=8.0 Hz, 1H), 6.57 (q, J=7.2 Hz, 1H), 5.97 (dd, J=8.0, 2.8 Hz, 1H), 5.71 (d, J=2.8 Hz, 1H), 3.89 (s, 3H), 3.80-3.69 (m, 1H), 3.66-3.52 (m, 1H), 2.97-2.82 (m, 1H), 2.77-2.50 (m, 4H), 2.49-2.28 (m, 1H), 2.11-1.99 (m, 2H), 1.95 (d, J=7.2 Hz, 3H), 1.91-1.79 (m, 2H), 1.79-1.45 (m, 5H), 1.42-1.24 (m, 1H). 1H exchanged with solvent. Second eluted diastereomer: P=99%, retention time=13.0 min, chiral HPLC: P=100%, ¹H NMR (300 MHz, CDCl₃) δ 8.63 (d, J=1.8 Hz, 1H), 8.39 (d, J=2.9 Hz, 1H), 7.78 (dd, J=2.9, 1.8 Hz, 1H), 7.23 (d, J=8.0 Hz, 1H), 6.58 (q, J=7.1 Hz, 1H), 5.98 (dd, J=8.0, 2.9 Hz, 1H), 5.73 (d, J=2.8 Hz, 1H), 3.91 (s, 3H), 3.81-3.71 (m, 1H), 3.65-3.55 (m, 1H), 2.99-2.84 (m, 1H), 2.78-2.53 (m, 4H), 2.51-2.32 (m, 1H), 2.11-1.99 (m, 2H), 1.96 (d, J=7.3 Hz, 3H), 1.91-1.79 (m, 2H), 1.78-1.44 (m, 5H), 1.44-1.29 (m, 1H). 1H exchanged with solvent.

Compound 120: 4-((R)-3-((cyclobutylmethyl)amino)piperidin-1-yl)-1-(1-(5-methoxy pyridin-3-yl)-1H-pyrazol-4-yl)ethyl)pyridin-2 (1H)-one was Obtained Using General Scheme 5

Stage 1: To a microwave vial under N₂ were placed 1-(1H-pyrazol-4-yl)ethanone (299 mg, 2.64 mmol), 3-bromo-5-methoxypyridine (460 mg, 2.40 mmol), K₂CO₃ (676 mg, 4.80 mmol), CuI (46.6 mg, 240 μmol) and dry DMF (5.99 mL). The mixture was purged with N₂ for 5 min, the vial was sealed and the reaction mixture was stirred at 100° C. for 90 h. The reaction was cooled down to rt, filtered on Büchner and washed with DCM then concentrated under reduced pressure to removed volatiles. Residue was purified by reverse phase chromatography on a 80 g C18 cartridge, eluting with a gradient of MeCN in basic water (10 mM NH$_4$HCO$_3$/NH$_4$OH buffer pH=10) to afford 1-(1-(5-methoxypyridin-3-yl)-1H-pyrazol-4-yl)ethan-1-one IM366 as a light brown solid: 337 mg, 62% yield, P=96%, retention time=0.9 min (gradient C), (M+H)$^+$: 218.

Stage 2: To a solution of IM366 (337 mg, 1.49 mmol) in MeOH (15.2 mL) at 0° C. was added portion-wise NaBH$_4$ (176 mg, 4.47 mmol). The mixture was stirred overnight while slowly returning to rt. The reaction mixture was quenched by the addition of a saturated aqueous solution of NH$_4$Cl (few drops) and concentrated under reduced pressure. Residue was diluted in water (40 mL) and extracted with DCM (3×15 mL), then EtOAc (3×15 mL). The combined organic layers were dried over MgSO$_4$, filtered and concentrated under reduced pressure to afford crude 1-(1-(5-methoxypyridin-3-yl)-1H-pyrazol-4-yl)ethan-1-ol IM367 as yellow oil: 274 mg, 75% yield, P=89%, retention time=0.8 min (gradient C), (M+H)$^+$: 220.

Stage 3: General Procedure T was used between 4-chloropyridin-2-ol and IM367 to afford 4-chloro-1-(1-(1-(5-methoxypyridin-3-yl)-1H-pyrazol-4-yl)ethyl)pyridin-2 (1H)-one IM368 as a beige solid: 80 mg, 14% yield, P=62%, retention time=1.5 min (gradient C), (M+H)$^+$: 331/333.

Stage 4: General Procedure C was used between IM3 and IM368 to afford tert-butyl (cyclobutylmethyl)((3R)-1-(1-(1-(5-methoxypyridin-3-yl)-1H-pyrazol-4-yl)ethyl)-2-oxo-1,2-dihydropyridin-4-yl)piperidin-3-yl)carbamate IM369 as a brown solid: 56 mg, 50% yield, P=75%, retention time=1.7 min (gradient C), (M+H)$^+$: 564.

Stage 5: General Procedure A2 was used from IM369 to afford compound 120 as a beige solid: 25 mg, 72% yield, P=100%, retention time=2.5 min (gradient E), (M+H)$^+$: 464. $^1$H NMR (400 MHZ, CD$_3$OD) δ 8.62 (d, J=1.9 Hz, 1H), 8.45 (s, 1H), 8.20 (d, J=2.4 Hz, 1H), 7.82 (t, J=2.3 Hz, 1H), 7.72 (s, 1H), 7.36 (d, J=8.0 Hz, 1H), 6.28-6.18 (m, 2H), 5.76 (d, J=2.8 Hz, 1H), 3.96 (s, 3H), 3.94-3.87 (m, 1H), 3.80-3.72 (m, 1H), 3.01-2.91 (m, 1H), 2.78 (ddd, J=12.7, 9.7, 2.6 Hz, 1H), 2.68 (d, J=7.3 Hz, 2H), 2.62-2.55 (m, 1H), 2.47 (dt, J=15.3, 7.7 Hz, 1H), 2.13-2.01 (m, 3H), 1.97-1.83 (m, 2H), 1.80-1.66 (m, 6H), 1.61-1.49 (m, 1H), 1.43-1.33 (m, 1H), 1H labile proton exchanges with CD$_3$OD.

The mixture of diastereomers was further purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=100%, retention time=7.2 min, chiral HPLC: P=100%, $^1$H NMR (300 MHz, CDCl$_3$) δ 8.51 (s, 1H), 8.24 (s, 1H), 7.88 (s, 1H), 7.67 (s, 1H), 7.58 (d, J=2.3 Hz, 1H), 7.25 (d, J=3.0 Hz, 1H), 7.02 (dd, J=7.9, 1.6 Hz, 1H), 6.35 (q, J=7.0 Hz, 1H), 5.92 (d, J=8.4 Hz, 1H), 5.75 (s, 1H), 3.92 (d, J=1.6 Hz, 3H), 3.81-3.71 (m, 1H), 3.65-3.54 (m, 1H), 2.97-2.83 (m, 1H), 2.77-2.58 (m, 4H), 2.50-2.33 (m, 1H), 2.10-1.81 (m, 4H), 1.81-1.51 (m, 8H), 1.42-1.29 (m, 1H). 1 NH exchange with solvent. Second eluted diastereomer: P=100%, retention time=13.5 min, chiral HPLC: P=100%, $^1$H NMR (300 MHz, CDCl$_3$) δ 8.51 (d, J=2.1 Hz, 1H), 8.24 (d, J=2.6 Hz, 1H), 7.89 (s, 1H), 7.67 (s, 1H), 7.62-7.55 (m, 1H), 7.02 (d, J=7.9 Hz, 1H), 6.36 (q, J=7.0 Hz, 1H), 5.92 (dd, J=8.0, 2.9 Hz, 1H), 5.76 (d, J=2.8 Hz, 1H), 3.92 (s, 3H), 3.82-3.72 (m, 1H), 3.65-3.54 (m, 1H), 2.98-2.83 (m, 1H), 2.78-2.56 (m, 4H), 2.50-2.34 (m, 1H), 2.15-1.81 (m, 4H), 1.80-1.46 (m, 8H), 1.44-1.23 (m, 1H). 1 NH exchange with solvent.

Compound 121: 4-((R)-3-((cyclobutylmethyl)amino)piperidin-1-yl)-1-(1-(4-(6-(methyl amino)pyrazin-2-yl)-1H-1,2,3-triazol-1-yl)ethyl)pyridin-2 (1H)-one was Obtained Using General Scheme 1 Pathway B Stage 1: General Procedure E1 (in THF instead of DMF) was used from 6-chloro-N-methylpyrazin-2-amine to afford N-methyl-6-((trimethylsilyl)ethynyl)pyrazin-2-amine IM370 as brown oil: 700 mg, 100% yield, P=98%, retention time=1.2 min (gradient C), (M+H)$^+$: 206.

Stage 2: General Procedure X was used between IM151 and IM370 to afford 4-chloro-1-(1-(4-(6-(methylamino)pyrazin-2-yl)-1H-1,2,3-triazol-1-yl)ethyl)pyridin-2 (1H)-one IM371 as yellowish oil: 225 mg, 99% yield, P=99%, retention time=0.8 min (gradient C), (M+H)$^+$: 332/334.

Stage 3: General Procedure C was used between IM3 and IM371 to afford tert-butyl (cyclobutylmethyl)((3R)-1-(1-(1-(4-(6-(methylamino)pyrazin-2-yl)-1H-1,2,3-triazol-1-yl)ethyl)-2-oxo-1,2-dihydropyridin-4-yl)piperidin-3-yl)carbamate IM372 as yellow oil: 310 mg, 81% yield, P=98%, retention time=1.5 min (gradient C), (M+H)$^+$: 565.

Stage 4: General Procedure A2 was used from IM372 to afford compound 121 as a white solid: 114 mg, 45% yield, P=100%, retention time=2.3 min (gradient E), (M+H)$^+$: 465. $^1$H NMR (400 MHZ, CD$_3$OD) δ 8.56 (s, 1H), 8.27 (s, 1H), 7.78 (s, 1H), 7.67 (d, J=8.1 Hz, 1H), 7.52 (q, J=7.0 Hz, 1H), 6.32 (dd, J=8.2, 2.8 Hz, 1H), 5.67 (d, J=2.8 Hz, 1H), 3.90 (d, J=13.1 Hz, 1H), 3.76 (d, J=13.4 Hz, 1H), 3.02-2.92 (m, 4H), 2.85-2.74 (m, 1H), 2.65 (d, J=7.6 Hz, 2H), 2.60-2.51 (m, 1H), 2.50-2.39 (m, 1H), 2.15 (d, J=7.0 Hz, 3H), 2.11-1.98 (m, 3H), 1.96-1.60 (m, 5H), 1.59-1.45 (m, 1H), 1.43-1.31 (m, 1H).

The mixture of diastereomers was further purified by chiral preparative HPLC purification using Chiralpak IA column (5 μm, 20×250 mm). Eluent used: TBME/MeOH/DCM/DEA: 40/40/20/0.1% at flow rate of 20 ml/min. First eluted diastereomer: P=100%, retention time=3.6 min, chiral HPLC: P=100%, $^1$H NMR (300 MHz, CDCl$_3$) δ 8.58 (s, 1H), 8.31 (s, 1H), 7.81 (s, 1H), 7.58 (q, J=7.0 Hz, 1H), 7.42 (d, J=8.1 Hz, 1H), 5.96 (dd, J=8.1, 2.8 Hz, 1H), 5.64 (d, J=2.8 Hz, 1H), 4.75-4.67 (m, 1H), 3.80-3.68 (m, 1H), 3.64-3.54 (m, 1H), 2.99 (d, J=5.1 Hz, 3H), 2.96-2.82 (m, 1H), 2.76-2.67 (m, 1H), 2.64 (d, J=7.1 Hz, 2H), 2.62-2.49 (m, 1H), 2.49-2.28 (m, 1H), 2.14 (d, J=7.0 Hz, 3H), 2.11-1.81 (m, 5H), 1.79-1.45 (m, 4H), 1.41-1.23 (m, 1H). 1 NH exchanged with solvent. Second eluted diastereomer: P=100%, retention time=6.1 min, chiral HPLC: P=100%, $^1$H NMR (300 MHz, CDCl$_3$) δ 8.58 (s, 1H), 8.31 (s, 1H), 7.81 (s, 1H), 7.57 (q, J=7.0 Hz, 1H), 7.42 (d, J=8.1 Hz, 1H), 5.96 (dd, J=8.1, 2.8 Hz, 1H), 5.64 (d, J=2.8 Hz, 1H), 4.74-4.67 (m, 1H), 3.79-3.69 (m, 1H), 3.65-3.54 (m, 1H), 2.99 (d, J=5.1 Hz, 3H), 2.96-2.83 (m, 1H), 2.76-2.67 (m, 1H), 2.64 (d, J=7.2 Hz, 2H), 2.61-2.51 (m, 1H), 2.46-2.28 (m, 1H), 2.14 (d, J=7.0 Hz, 3H), 2.10-1.79 (m, 5H), 1.78-1.43 (m, 4H), 1.41-1.23 (m, 1H). 1NH exchanged with solvent.

Compound 122: 4-((R)-3-((cyclobutylmethyl) amino)piperidin-1-yl)-1-(1-(4-(5-(methyl amino) pyridazin-3-yl)-1H-1,2,3-triazol-1-yl)ethyl)pyridin-2 (1H)-one was Obtained Using General Scheme 1 Pathway B Stage 1: To a solution of 3,5-dichloropyridazine (350 mg, 2.33 mmol) in dioxane (2.5 mL) was added methylamine (580 μL, 6.70 mmol) (40 wt % in water). The mixture was stirred at 50° C. for 1 h. The mixture was then diluted with methanol (2 mL) and concentrated under reduced pressure to afford crude 6-chloro-N-methylpyridazin-4-amine IM373 as beige solid: 334 mg, 100% yield, P=98%, retention time=0.6 min (gradient C), (M+H)⁺: 144.

Stage 2: General Procedure E1 (in 5:1 mixture of iPrOH and THF instead of DMF) was used from IM373 to afford N-methyl-6-((trimethylsilyl)ethynyl)pyridazin-4-amine IM374 as yellow oil: 322 mg, 11% yield, P=11%, retention time=1.1 min (gradient C), (M+H)⁺: 206.

Stage 3: General Procedure X was used between IM151 and IM374 to afford 4-chloro-1-(1-(4-(5-(methylamino)pyridazin-3-yl)-1H-1,2,3-triazol-1-yl)ethyl)pyridin-2 (1H)-one IM375 as a colorless low-melting solid/oil: 90 mg, 99% yield, P=62%, retention time=0.8 min (gradient C), (M+H)⁺: 332.

Stage 4: General Procedure C was used between IM3 and IM375 to afford tert-butyl (cyclobutylmethyl)((3R)-1-(1-(1-(4-(5-(methylamino)pyridazin-3-yl)-1H-1,2,3-triazol-1-yl)ethyl)-2-oxo-1,2-dihydropyridin-4-yl)piperidin-3-yl)carbamate IM376 as a white foam: 36 mg, 36% yield, P=98%, retention time=1.5 min (gradient C), (M+H)⁺: 565.

Stage 5: General Procedure A2 was used from IM376 to afford compound 122 as an off-white solid: 10 mg, 34% yield, P=100%, retention time=2.1 min (gradient E), (M+H)⁺: 464. ¹H NMR (400 MHZ, CD₃OD) δ 8.64 (s, 1H), 8.46 (d, J=2.8 Hz, 1H), 7.68 (d, J=8.1 Hz, 1H), 7.55 (q, J=6.9 Hz, 1H), 7.28 (d, J=2.8 Hz, 1H), 6.34 (dd, J=8.1, 2.8 Hz, 1H), 5.68 (d, J=2.8 Hz, 1H), 3.98-3.89 (m, 1H), 3.85-3.71 (m, 1H), 2.99 (ddt, J=13.8, 11.6, 2.4 Hz, 1H), 2.92 (s, 3H), 2.88-2.80 (m, 1H), 2.74 (d, J=7.3 Hz, 2H), 2.71-2.61 (m, 1H), 2.54-2.42 (m, 1H), 2.16 (d, J=7.0 Hz, 3H), 2.13-2.05 (m, 3H), 2.00-1.65 (m, 5H), 1.64-1.49 (m, 1H), 1.48-1.35 (m, 1H). 2H exchanged with CD₃OD.

The mixture of diastereomers was further purified by chiral preparative HPLC purification using Chiralpak IA column (5 μm, 20×250 mm). Eluent used: TBME/MeOH/DEA: 60/40/0.1% at flow rate of 20 mL/min. First eluted diastereomer: P=99%, retention time=5.4 min, chiral HPLC: P=100%, ¹H NMR (300 MHz, CDCl₃) δ 8.54-8.44 (m, 2H), 7.61 (q, J=7.0 Hz, 1H), 7.36-7.29 (m, 2H), 5.96 (dd, J=8.1, 2.9 Hz, 1H), 5.67 (d, J=2.8 Hz, 1H), 4.36 (s, 1H), 3.83-3.69 (m, 1H), 3.64-3.53 (m, 1H), 2.98 (d, J=5.1 Hz, 3H), 2.94-2.86 (m, 1H), 2.76-2.54 (m, 4H), 2.41 (hept, J=7.5 Hz, 1H), 2.14 (d, J=7.0 Hz, 3H), 2.09-1.42 (m, 10H), 1H exchanged with solvent. Second eluted diastereomer: P=99%, retention time=6.5 min, chiral HPLC: P=100%, ¹H NMR (300 MHz, CDCl₃) δ 8.55-8.47 (m, 2H), 7.62 (q, J=6.9 Hz, 1H), 7.36-7.29 (m, 2H), 5.97 (dd, J=8.1, 2.8 Hz, 1H), 5.68 (d, J=2.8 Hz, 1H), 4.62 (s, 1H), 3.85-3.70 (m, 1H), 3.67-3.53 (m, 1H), 2.98 (d, J=5.0 Hz, 3H), 2.95-2.86 (m, 1H), 2.81-2.60 (m, 4H), 2.43 (p, J=7.5 Hz, 1H), 2.15 (d, J=7.0 Hz, 3H), 2.10-1.43 (m, 10H), 1H exchanged with solvent.

Compound 123: (R)—N-(cyclobutylmethyl)-1-(4-((4-(6-methoxy-1H-indazol-4-yl)-1-1,2,3-triazol-1-yl)methyl)phenyl)piperidin-3-amine was Obtained Using General Scheme 1 Pathway B Stage 1: General Procedure N was used from 1-bromo-4-(bromomethyl)benzene to afford crude 1-(azidomethyl)-4-bromo-benzene IM377 as pale yellow liquid: 655 mg, 99% yield, P=100%, retention time=3.0 min (gradient A).

Stage 2: General Procedure B was used between IM8 and IM377 to afford 4-(1-(4-bromobenzyl)-1H-1,2,3-triazol-4-yl)-6-methoxy-1H-indazole IM378 as a white foam: 424 mg, 92% yield, P=96%, retention time=3.0 min (gradient A), (M+H)⁺: 468/470.

Stage 3: General Procedure S was used between IM3 and IM378 to afford tert-butyl (R)-(cyclobutylmethyl)(1-(4-((4-(6-methoxy-1H-indazol-4-yl)-1H-1,2,3-triazol-1-yl)methyl)phenyl)piperidin-3-yl)carbamate IM379 as a white foam: 101 mg, 71% yield, P=94% (215 nm), retention time=3.0 min (gradient A), (M+H)⁺: 657.

Stage 4: General Procedure A1 was used from IM380 to afford compound 123 as a white solid: 61 mg, 84% yield, P=94%, retention time=3.4 min (gradient B), (M+H)⁺: 472. ¹H NMR (300 MHz, MeOD) δ 8.46-8.34 (m, 2H), 7.35-7.20 (m, 3H), 7.02-6.88 (m, 3H), 5.56 (s, 2H), 3.89 (s, 3H), 3.70-3.62 (m, 1H), 3.53-3.42 (m, 1H), 2.85-2.72 (m, 1H), 2.72-2.58 (m, 4H), 2.55-2.39 (m, 1H), 2.10-2.04 (m, 1H), 2.00-1.79 (m, 4H), 1.79-1.55 (m, 5H), 2H exchanged with CD₃OD.

Compound 124: 4-((R)-3-((cyclobutylmethyl)amino)piperidin-1-yl)-1-(1-(4-(imidazo[1,5-a]pyridin-8-yl)-1H-1,2,3-triazol-1-yl)ethyl)pyridin-2 (1H)-one was Obtained Using General Scheme 1 Pathway B Stage 1: General Procedure X was used between IM151 and IM13 to afford 4-chloro-1-(1-(4-(imidazo[1,5-a]pyridin-8-yl)-1H-1,2,3-triazol-1-yl)ethyl)pyridin-2 (1H)-one IM381 as yellow oil: 47 mg, 36% yield, P=93%, retention time=2.1 min (gradient A), (M+H)⁺: 341.

Stage 2: General Procedure C was used between IM3 and IM381 to afford tert-butyl (cyclobutylmethyl)((3R)-1-(1-(1-(4-(imidazo[1,5-a]pyridin-8-yl)-1H-1,2,3-triazol-1-yl)ethyl)-2-oxo-1,2-dihydropyridin-4-yl)piperidin-3-yl)carbamate IM382 as brown oil: 34 mg, 43% yield, P=90% (215 nm), retention time=2.6 min (gradient A), (M+H)⁺: 573.

Stage 3: General Procedure A1 was used from IM382 to afford compound 124 as brown oil: 26 mg, 89% yield, P=86%, retention time=2.5 min (gradient B), (M+H)⁺: 473.

The product was further purified by reverse phase preparative HPLC purification (Waters XBridge C18 5 μm 19×100 mm). Gradient used: increased linearly from 10 to 40% solution "B" over 4.5 min, increased linearly to 85% solution "B" over 1.7 min, held at 85% for 0.3 min and returned to initial conditions over 0.7 min. Flow Rate: 15 mL/min. P=100%.

The mixture of diastereomers was further purified by chiral preparative HPLC purification using Chiralpak IE column (5 μm, 10×250 mm). Eluent used: EtOAc/MeOH/DCM/DEA: 80/20/5/0.1% at flow rate of 7 mL/min. First eluted diastereomer: P=100%, retention time=8.1 min, chiral HPLC: P=100%, ¹H NMR (300 MHz, CDCl₃) δ 8.28 (s, 1H), 8.17 (s, 1H), 7.93 (d, J=7.4 Hz, 2H), 7.60 (q, J=7.0 Hz, 1H), 7.46 (d, J=8.1 Hz, 1H), 7.28 (s, 1H), 6.64 (t, J=6.8 Hz, 1H), 6.00 (dd, J=8.1, 2.9 Hz, 1H), 5.67 (d, J=2.8 Hz, 1H), 3.85-3.74 (m, 1H), 3.66-3.55 (m, 1H), 2.99-2.85 (m, 1H), 2.83-2.58 (m, 4H), 2.42 (hept, J=7.5 Hz, 1H), 2.19 (d, J=7.1 Hz, 3H), 2.07-1.70 (m, 8H), 1.70-1.48 (m, 2H), NH exchanged. Second eluted diastereomer: P=100%, retention time=9.4 min, chiral HPLC: P=100%, ¹H NMR (300 MHz, CDCl₃) δ 8.28 (s, 1H), 8.18 (s, 1H), 7.97-7.89 (m, 2H), 7.59 (q, J=6.9 Hz, 1H), 7.46 (d, J=8.1 Hz, 1H), 7.29 (s, 1H), 6.64 (t, J=6.9 Hz, 1H), 6.04-5.96 (m, 1H), 5.68 (d, J=2.8 Hz, 1H), 3.87-3.77 (m, 1H), 3.66-3.56 (m, 1H), 2.99-2.86 (m, 1H), 2.85-2.75 (m, 1H), 2.73-2.56 (m, 3H), 2.47 (hept, J=7.4 Hz, 1H), 2.19 (d, J=7.0 Hz, 3H), 2.10-1.43 (m, 10H), NH exchanged Compound 125: 4-((R)-3-((cyclobutylmethyl)amino)piperidin-1-yl)-1-(1-(3-(5-methoxypyridin-3-yl)-1,2,4-oxadiazol-5-yl)ethyl)pyridin-2 (1H)-one was Obtained was Obtained Using the Following Procedures Stage 1: To a solution of 5-methoxynicotinonitrile (190 mg, 1.39 mmol) in MeOH (2 mL) were added triethylamine (389 µL, 2.78 mmol) and hydroxylamine hydrochloride (195 mg, 2.78 mmol). The reaction mixture was stirred at 60° C. overnight, concentrated under reduced pressure and partitioned between ethyl acetate (20 mL) and brine (2×10 mL). The organic layer was dried over sodium sulfate, filtered and concentrated under reduced pressure to afford (E)-N'-hydroxy-5-methoxynicotinimidamide IM383 as a white solid: 169 mg, 73% yield, P=98%, retention time=0.3 min (gradient C), (M+H)$^+$: 168.

Stage 2: To a solution of IM383 (160 mg, 957 µmol) in acetone (4.82 mL) were added potassium carbonate (135 mg, 957 µmol) and 2-chloropropionyl chloride (111 µL, 1.06 mmol). The reaction mixture was stirred at rt overnight, concentrated under reduced pressure and partitioned between ethyl acetate and water. The layers were separated and the organic one was washed, dried over sodium sulfate, filtered and concentrated under reduced pressure to afford crude (Z)—N'-((2-chloropropanoyl)oxy)-5-methoxynicotinimidamide IM384: 247 mg, 100% yield, P=98%, retention time=0.7 min (gradient C), (M+H)$^+$: 258.

Stage 3: A solution of the crude IM384 (247 mg, 959 µmol) in toluene (2.5 mL) was stirred at 110° C. for 1 h. The reaction mixture was concentrated under reduced pressure and partitioned between ethyl acetate and water. The layers were separated and the organic one was washed, dried over sodium sulfate, filtered and concentrated under reduced pressure to afford crude 5-(1-chloroethyl)-3-(5-methoxypyridin-3-yl)-1,2,4-oxadiazole IM385 as a brown gummy solid: 122 mg, 53% yield, P=90%, retention time=1.0 min (gradient C), (M+H)$^+$: 240.

Stage 4: To a solution of the crude IM385 (115 mg, 480 µmol) in DMF (1.5 mL) were added potassium carbonate (135 mg, 960 µmol) and 4-chloro-2-hydroxypyridine (128 mg, 960 µmol). The reaction mixture was stirred at 60° C. for 50 min, then allowed to cool to rt and concentrated under reduced pressure. The crude was purified by reverse phase flash chromatography (C18 column, ammonium formate buffer/ACN) to afford 4-chloro-1-(1-(3-(5-methoxypyridin-3-yl)-1,2,4-oxadiazol-5-yl)ethyl)pyridin-2 (1H)-one IM386 as a white solid: 46 mg, 26% yield, P=100%, retention time=0.9 min (gradient C), (M+H)$^+$: 333.

Stage 5: General Procedure C was used between IM3 and IM386 to afford tert-butyl (cyclobutylmethyl)((3R)-1-(1-(1-(3-(5-methoxypyridin-3-yl)-1,2,4-oxadiazol-5-yl)ethyl)-2-oxo-1,2-dihydropyridin-4-yl)piperidin-3-yl)carbamate IM387 as colourless oil: 37 mg, 61% yield, P=99%, retention time=1.5 min (gradient A), (M+H)$^+$: 566.

Stage 6: General Procedure A2 was used from IM387 to afford compound 125 as a white solid: 15 mg, 48% yield, P=98%, retention time=2.1 min (gradient E), (M+H)$^+$: 466. $^1$H NMR (400 MHZ, DMSO-d6) δ 8.74 (d, J=1.6 Hz, 1H), 8.51 (d, J=2.9 Hz, 1H), 7.79 (dd, J=2.9, 1.7 Hz, 1H), 7.54 (d, J=8.0 Hz, 1H), 6.23 (dd, J=8.0, 2.8 Hz, 1H), 6.00-5.90 (m, 1H), 5.45 (d, J=2.8 Hz, 1H), 3.92 (s, 3H), 3.79 (d, J=12.9 Hz, 1H), 3.68 (d, J=11.4 Hz, 1H), 2.92-2.79 (m, 1H), 2.70-2.52 (m, 3H), 2.48-2.38 (m, 1H), 2.37-2.26 (m, 1H), 2.01-1.84 (m, 3H), 1.82-1.73 (m, 5H), 1.71-1.55 (m, 4H), 1.45-1.35 (m, 1H), 1.29-1.17 (m, 1H).

Compound 126: 4-((R)-3-((cyclobutylmethyl) amino)piperidin-1-yl)-3-fluoro-1-(1-(4-(5-methoxy-pyridin-3-yl)-1H-1,2,3-triazol-1-yl)ethyl)pyridin-2 (1H)-one was Obtained Using General Scheme 1 Pathway B Stage 1: General Procedure O2 was used from 3-fluoro-4-iodo-1H-pyridin-2-one to afford crude 1-(1-chloroethyl)-3-fluoro-4-iodopyridin-2 (1H)-one IM388 as brown oil: 654 mg, 86% yield, P=83% ($^1$H-NMR), retention time=2.6 min (gradient A), (M+H)$^+$: 302/304.

Stage 2: General Procedure N was used from IM388 to afford 1-(1-azidoethyl)-3-fluoro-4-iodopyridin-2 (1H)-one IM389 as a brown solid: 574 mg, 100% yield, P=94%, retention time=3.9 min (gradient B), (M+Na)$^+$: 331.

Stage 3: General Procedure B was used between IM44 and IM389 to afford 3-fluoro-4-iodo-1-(1-(4-(5-methoxy-pyridin-3-yl)-1H-1,2,3-triazol-1-yl)ethyl)pyridin-2 (1H)-one IM390 as a white foam: 139 mg, 93% yield, P=98%, retention time=2.2 min (gradient A), (M+H)$^+$: 442.

Stage 4: General Procedure C was used between IM3 and IM390 to afford tert-butyl (cyclobutylmethyl)((3R)-1-(3-fluoro-1-(1-(4-(5-methoxypyridin-3-yl)-1H-1,2,3-triazol-1-yl)ethyl)-2-oxo-1,2-dihydropyridin-4-yl)piperidin-3-yl)carbamate IM391 as a white gum: 61 mg, 81% yield, P=97%, retention time=2.4 min (gradient A), (M+H)$^+$: 582.

Stage 5: General Procedure A1 was used from IM391 to afford crude compound 126 as a white gum: 48 mg, 99% yield, P=97%, retention time=2.1 min (gradient A), (M+H)$^+$: 482.

The mixture of diastereomers was further purified by chiral preparative HPLC purification using Chiralpak IA column (5 µm, 20×250 mm). Eluent used: TBME/MeOH/DEA: 60/40/0.1% at flow rate of 20 mL/min. First eluted diastereomer: P=100%, retention time=6.2 min, chiral HPLC: P=100%, $^1$H NMR (300 MHZ, CDCl$_3$) δ 8.59 (d, J=1.7 Hz, 1H), 8.28 (d, J=2.8 Hz, 1H), 8.17 (s, 1H), 7.72-7.65 (m, 1H), 7.53 (q, J=7.0 Hz, 1H), 7.33-7.28 (m, 1H), 5.97 (t, J=7.7 Hz, 1H), 3.91 (s, 3H), 3.85-3.75 (m, 1H), 3.70-3.59 (m, 1H), 3.07-2.93 (m, 1H), 2.87-2.74 (m, 1H), 2.70-2.57 (m, 3H), 2.40 (hept, J=7.6 Hz, 1H), 2.20 (d, J=7.0 Hz, 3H), 2.10-1.27 (m, 10H), NH exchanged. $^{19}$F NMR (282 MHZ, CDCl$_3$) δ −149.94 (d, J=8.4 Hz). Second eluted diastereomer: P=100%, retention time=11.7 min, chiral HPLC: P=100%, $^1$H NMR (300 MHz, CDCl$_3$) δ 8.60 (d, J=1.7 Hz, 1H), 8.28 (d, J=2.9 Hz, 1H), 8.18 (s, 1H), 7.73-7.65 (m, 1H), 7.53 (q, J=7.1 Hz, 1H), 7.30 (dd, J=8.2, 1.5 Hz, 1H), 5.96 (t, J=7.7 Hz, 1H), 3.91 (s, 3H), 3.87-3.78 (m, 1H), 3.67-3.57 (m, 1H), 3.07-2.94 (m, 1H), 2.88-2.75 (m, 1H), 2.71-2.63 (m, 3H), 2.41 (hept, J=7.5 Hz, 1H), 2.20 (d, J=7.0 Hz, 3H), 2.11-1.30 (m, 10H), NH exchanged. $^{19}$F NMR (282 MHZ, CDCl$_3$) δ −150.02 (d, J=7.3 Hz).

Compound d 127: (R)-2-(1-((5-(3-((cyclobutylmethyl)amino)piperidin-1-yl)pyridin-2-yl) methyl)-1H-1,2,3-triazol-4-yl)-4H-pyrido[1,2-a]pyrimidin-4-one was Obtained Using General Scheme 1 Pathway A Stage 1: General Procedure X was used between IM57 and IM128 to afford tert-butyl (R)-(cyclobutylmethyl)(1-(6-((4-(4-oxo-4H-pyrido[1,2-a]pyrimidin-2-yl)-1H-1,2,3-triazol-1-yl) methyl)pyridin-3-yl)piperidin-3-yl)carbamate IM392 as yellow sticky oil: 62 mg, 85% yield, P=95%, retention time=2.6 min (gradient A), (M+H)$^+$: 571.

Stage 2: General Procedure A1 was used from IM392 to afford crude compound 127 as a pale yellow solid: 32 mg, 66% yield, P=89%, retention time=2.7 min (gradient B), (M+H)$^+$: 471.

The product was further purified by reverse phase preparative HPLC purification (Waters XBridge C18 5 µm 19×100 mm). Gradient used: increased linearly from 20 to 40% solution "B" over 4.0 min, increased linearly to 85% solution "B" over 2.3 min, and returned to initial conditions over 1.0 min. Flow Rate: 15 mL/min. P=99%. $^1$H NMR (300

MHz, CDCl₃) δ 9.07 (d, J=7.2 Hz, 1H), 8.33-8.25 (m, 2H), 7.77-7.65 (m, 1H), 7.61 (d, J=8.8 Hz, 1H), 7.27 (s, 1H), 7.18-7.05 (m, 3H), 5.62 (s, 2H), 3.71-3.61 (m, 1H), 3.55-3.44 (m, 1H), 2.94-2.79 (m, 1H), 2.75-2.60 (m, 4H), 2.44 (hept, J=7.7 Hz, 1H), 2.15-1.26 (m, 10H), NH exchanged.

Compound 128: (R)-2-(1-(4-(3-((cyclobutylmethyl)amino)piperidin-1-yl)benzyl)-1H-1,2,3-triazol-4-yl)-4H-pyrido[1,2-a]pyrimidin-4-one was Obtained Using General Scheme 1 Pathway B Stage 1: General Procedure X was used between IM57 and IM377 to afford 2-(1-(4-bromobenzyl)-1H-1,2,3-triazol-4-yl)-4H-pyrido[1,2-a]pyrimidin-4-one IM393 as a brown solid: 62 mg, 34% yield, P=86%, retention time=2.6 min (gradient A), (M+H)⁺: 382/384.

Stage 2: General Procedure S was used between IM3 and IM393 to afford tert-butyl (R)-(cyclobutylmethyl)(1-(4-((4-(4-oxo-4H-pyrido[1,2-a]pyrimidin-2-yl)-1H-1,2,3-triazol-1-yl) methyl)phenyl)piperidin-3-yl)carbamate IM394 as yellow film: 32 mg, 17% yield, P=61%, retention time=2.7 min (gradient A), (M+H)+: 571.

Stage 3: General Procedure A1 was used from IM394 to afford crude compound 128 as yellow oil: 30 mg, 99% yield, P=65%, retention time=2.2 min (gradient A), (M+H)⁺: 471. The product was purified by reverse phase preparative HPLC purification (Waters XBridge C18 5 µm 19×100 mm). Gradient used: increased linearly from 30 to 40% solution "B" over 4.0 min, increased linearly to 85% solution "B" over 2.3 min, held at 85% for 0.5 min and returned to initial conditions over 1.0 min. Flow Rate: 15 mL/min. P=100%. ¹H NMR (300 MHz, CDCl₃) δ 9.07 (d, J=7.2 Hz, 1H), 8.05 (s, 1H), 7.76-7.64 (m, 1H), 7.58 (d, J=8.9 Hz, 1H), 7.29-7.27 (m, 1H), 7.25-7.21 (m, 2H), 7.15-7.04 (m, 1H), 6.92 (d, J=8.6 Hz, 2H), 5.49 (s, 2H), 3.71-3.61 (m, 1H), 3.54-3.39 (m, 1H), 2.89-2.57 (m, 5H), 2.45 (hept, J=7.6 Hz, 1H), 2.16-1.23 (m, 10H), NH exchanged.

Compound 129: 4-((R)-3-((cyclobutylmethyl)amino)piperidin-1-yl)-1-(1-(4-(5-morpholino pyridin-3-yl)-1H-1,2,3-triazol-1-yl)ethyl)pyridin-2 (1H)-one was Obtained Using General Scheme 1 Pathway B Stage 1: IM293 (150 mg, 237 µmol) was solubilized in morpholine (1.2 mL, 13.6 mmol) in a microwave vial. Vial was sealed and reaction mixture was let stirred in an oil bath at 130° C. during 4 days. The reaction mixture was cooled down to rt and directly purified by reverse phase chromatography on a C18 cartridge, eluting with a gradient of MeCN in basic water (10 mM NH₄HCO₃/NH₄OH buffer pH=10) to afford tert-butyl (cyclobutylmethyl)((3R)-1-(1-(1-(4-(5-morpholinopyridin-3-yl)-1H-1,2,3-triazol-1-yl)ethyl)-2-oxo-1,2-dihydropyridin-4-yl)piperidin-3-yl)carbamate IM395 as a beige solid: 53 mg, 35% yield, P=96%, retention time=1.4 min (gradient C), (M+H)⁺: 620. Fractions containing deprotected desired product were kept apart to be combined with deprotected compound after next step.

Stage 2: General Procedure A2 was used from IM395 to afford compound 129 (combined together with fractions recovered at previous step) as a white solid: 43 mg, 100% yield, P=99%, retention time=2.3 min (gradient E), (M+H)⁺: 520. ¹H NMR (400 MHz, CD₃OD) δ 8.61 (s, 1H), 8.46 (d, J=1.2 Hz, 1H), 8.22 (d, J=2.7 Hz, 1H), 7.81 (dd, J=2.7, 1.8 Hz, 1H), 7.65 (d, J=8.1 Hz, 1H), 7.51 (q, J=6.9 Hz, 1H), 6.33 (dd, J=8.2, 2.9 Hz, 1H), 5.68 (d, J=2.8 Hz, 1H), 3.94-3.88 (m, 1H), 3.88-3.85 (m, 4H), 3.81-3.74 (m, 1H), 3.30-3.26 (m, 4H), 3.03-2.94 (m, 1H), 2.85-2.77 (m, 1H), 2.67 (d, J=7.5 Hz, 2H), 2.62-2.54 (m, 1H), 2.45 (dtd, J=15.2, 7.5, 2.6 Hz, 1H), 2.15 (d, J=7.0 Hz, 3H), 2.12-2.01 (m, 3H), 1.96-1.82 (m, 2H), 1.80-1.65 (m, 3H), 1.58-1.48 (m, 1H), 1.44-1.33 (m, 1H), 1H labile proton exchanges with CD₃OD.

The mixture of diastereomers was further purified by chiral preparative HPLC purification using Chiralpak IA column (5 µm, 20×250 mm). Eluent used: TBME/MeOH/DCM/DEA: 60/40/20/0.1% at flow rate of 20 mL/min. First eluted diastereomer: P=100%, retention time=10.1 min, chiral HPLC: P=100%, ¹H NMR (300 MHz, CDCl₃) δ 8.46 (d, J=1.7 Hz, 1H), 8.24 (d, J=2.8 Hz, 1H), 8.14 (s, 1H), 7.67 (dd, J=2.9, 1.8 Hz, 1H), 7.54 (q, J=7.0 Hz, 1H), 7.42 (d, J=8.1 Hz, 1H), 5.98 (dd, J=8.1, 2.8 Hz, 1H), 5.65 (d, J=2.8 Hz, 1H), 3.92-3.82 (m, 4H), 3.81-3.70 (m, 1H), 3.65-3.54 (m, 1H), 3.29-3.20 (m, 4H), 2.99-2.84 (m, 1H), 2.73 (dd, J=12.9, 9.3 Hz, 1H), 2.66 (d, J=7.3 Hz, 2H), 2.59 (dq, J=9.5, 4.5 Hz, 1H), 2.42 (h, J=7.5 Hz, 1H), 2.16 (d, J=7.0 Hz, 3H), 2.12-1.52 (m, 11H), 1.44-1.22 (m, 1H), 1 NH exchanged. Second eluted diastereomer: P=99%, retention time=13.8 min, chiral HPLC: P=100%, ¹H NMR (300 MHz, CDCl₃) δ 8.47 (d, J=1.8 Hz, 1H), 8.24 (d, J=2.9 Hz, 1H), 8.15 (s, 1H), 7.71-7.64 (m, 1H), 7.54 (q, J=7.0 Hz, 1H), 7.43 (d, J=8.1 Hz, 1H), 5.99 (dd, J=8.1, 2.8 Hz, 1H), 5.65 (d, J=2.8 Hz, 1H), 3.87 (dd, J=5.8, 3.9 Hz, 4H), 3.84-3.74 (m, 1H), 3.65-3.55 (m, 1H), 3.29-3.20 (m, 4H), 2.99-2.84 (m, 1H), 2.76 (dd, J=12.9, 9.4 Hz, 1H), 2.67 (d, J=7.3 Hz, 2H), 2.65-2.55 (m, 1H), 2.43 (dq, J=15.0, 7.5 Hz, 1H), 2.16 (d, J=7.0 Hz, 3H), 2.10-1.22 (m, 12H), 1 NH exchanged.

Compound 130: 4-((R)-3-((cyclobutylmethyl)amino)piperidin-1-yl)-1-(1-(3-(5-methoxy pyridin-3-yl)isoxazol-5-yl)ethyl)pyridin-2 (1H)-one was Obtained Using the Following Procedures Stage 1: To a solution of 3-formyl-5-methoxypyridine (1.00 g, 7.07 mmol) in EtOH (20.0 mL) was added hydroxylamine hydrochloride (799 mg, 11.4 mmol) and potassium carbonate (2.00 g, 14.1 mmol). The mixture was stirred at rt for 30 min, the white color suspension was formed. The solvent was evaporated, and the residue was partitioned between EtOAc (50 mL) and water. The organic layer was separated, washed with brine (30 mL), dried over Na₂SO₄, filtered, and the solvent was evaporated. After trituration in a minimal amount of MeOH, (E/Z)-5-methoxynicotinaldehyde oxime IM396 was obtained as a white solid: 920 mg, 85% yield, P=100%, retention time=0.7 min (gradient C), (M+H)⁺: 153, 9:1 mixture of E/Z-isomers by ¹H NMR.

Stage 2: To a solution of IM396 (700 mg, 4.60 mmol) in DMF (7.00 mL) at 0° C. was added N-chlorosuccinimide (701 mg, 5.20 mmol) and the reaction was stirred at rt for 16 h. The reaction mixture was partitioned between EtOAc (100 mL) and brine (100 mL), the organic layer was washed with brine (100 mL), separated, dried over Na₂SO₄, filtered and the solvent was evaporated to afford crude (Z)—N-hydroxy-5-methoxynicotinimidoyl chloride IM397 as a light yellow solid: 858 mg, 100% yield, P=90%, retention time=0.8 min (gradient C), (M+H)⁺: no ionization.

Stage 3: To a solution of crude IM397 (858 mg, 4.6 mmol) in MeOH (35 mL) at 0° C. under nitrogen was added 3-butyn-2-ol (1.86 mL, 23.0 mmol) and triethylamine (1.93 mL, 13.8 mmol). The reaction was stirred for 3 h from 0° C. to rt. The mixture was concentrated down, the residue was partitioned between EtOAc (50 mL) and brine, the organic layer was separated, washed with brine (20 mL), dried over Na₂SO₄, filtered and purified by flash chromatography on silica gel (0-50% EtOAc in hexanes) to afford 1-(3-(5- methoxypyridin-3-yl)isoxazol-5-yl)ethan-1-ol IM398 as a light yellow solid: 235 mg, 22% yield, P=96%, retention time=0.9 min (gradient C), (M+H)+: 221.

Stage 4: General Procedure T was used between 4-chloropyridin-2-ol and IM398 to afford 4-chloro-1-(1-(3-(5-methoxypyridin-3-yl)isoxazol-5-yl)ethyl)pyridin-2 (1H)-one IM399 as a light yellow solid: 700 mg, 38% yield, P=20% (1H NMR: 80% PPh3O), retention time=1.2 min (gradient C), (M+H)+: 332/334.

Stage 5: General Procedure C was used between IM3 and IM399 to afford tert-butyl (cyclobutylmethyl)((3R)-1-(1-(1-(3-(5-methoxypyridin-3-yl)isoxazol-5-yl)ethyl)-2-oxo-1,2-dihydropyridin-4-yl)piperidin-3-yl)carbamate IM400 as a light brown solid: 154 mg, 65% yield, P=100%, retention time=1.8 min (gradient C), (M+H)+: 564.

Stage 6: General Procedure A2 was used from IM400 to afford compound 130 as a beige solid: 105 mg, 84% yield, P=100%, retention time=2.4 min (gradient E), (M+H)+: 464. 1H NMR (400 MHZ, CD3OD) δ 8.60 (d, J=1.6 Hz, 1H), 8.34 (d, J=2.8 Hz, 1H), 7.84 (dd, J=2.8, 1.7 Hz, 1H), 7.37 (d, J=8.0 Hz, 1H), 7.00 (d, J=0.8 Hz, 1H), 6.37-6.27 (m, 2H), 5.75 (d, J=2.9 Hz, 1H), 3.95 (s, 3H), 3.94-3.89 (m, 1H), 3.82-3.75 (m, 1H), 3.04-2.93 (m, 1H), 2.80 (ddd, J=13.0, 9.8, 1.9 Hz, 1H), 2.69 (d, J=7.3 Hz, 2H), 2.66-2.55 (m, 1H), 2.54-2.40 (m, 1H), 2.16-2.02 (m, 3H), 2.00-1.83 (m, 2H), 1.80 (d, J=7.2 Hz, 3H), 1.79-1.74 (m, 1H), 1.74-1.64 (m, 2H), 1.62-1.50 (m, 1H), 1.45-1.34 (m, 1H), 1H exchanged with CD3OD.

The mixture of diastereomers was further purified by chiral preparative HPLC purification using Chiralpak IA column (5 μm, 20×250 mm). Eluent used: TBME/MeOH/DCM/DEA: 60/40/20/0.1% at flow rate of 20 mL/min. First eluted diastereomer: P=100%, retention time=8.5 min, chiral HPLC: P=100%, 1H NMR (300 MHz, CDCl3) δ 8.51 (d, J=1.7 Hz, 1H), 8.34 (d, J=2.8 Hz, 1H), 7.58 (dd, J=2.8, 1.7 Hz, 1H), 7.10 (d, J=8.0 Hz, 1H), 6.51 (s, 1H), 6.46 (q, J=7.2 Hz, 1H), 5.96 (dd, J=8.0, 2.8 Hz, 1H), 5.70 (d, J=2.8 Hz, 1H), 3.87 (s, 3H), 3.79-3.68 (m, 1H), 3.65-3.51 (m, 1H), 2.96-2.81 (m, 1H), 2.76-2.50 (m, 3H), 2.38 (hept, J=7.4 Hz, 1H), 2.11-1.78 (m, 5H), 1.74 (d, J=7.2 Hz, 3H), 1.72-1.43 (m, 5H), 1.41-1.22 (m, 1H), 1 NH exchanged. Second eluted diastereomer: P=100%, retention time=10.5 min, chiral HPLC: P=99.2 1H NMR (300 MHz, CDCl3) δ 8.52 (d, J=1.7 Hz, 1H), 8.35 (d, J=2.9 Hz, 1H), 7.60 (dd, J=2.9, 1.7 Hz, 1H), 7.11 (d, J=8.0 Hz, 1H), 6.57-6.42 (m, 2H), 5.97 (dd, J=8.0, 2.9 Hz, 1H), 5.72 (d, J=2.9 Hz, 1H), 3.88 (s, 3H), 3.81-3.70 (m, 1H), 3.67-3.54 (m, 1H), 2.90 (t, J=3.2 Hz, 1H), 2.77-2.52 (m, 4H), 2.39 (dq, J=15.0, 7.5 Hz, 1H), 2.12-1.78 (m, 5H), 1.76 (d, J=7.3 Hz, 3H), 1.73-1.44 (m, 4H), 1.43-1.24 (m, 1H), 1 NH exchanged.

Compound 131: 4-((R)-3-((cyclobutylmethyl) amino)piperidin-1-yl)-1-(1-(4-(5-morpholino pyridin-3-yl)-1H-1,2,3-triazol-1-yl)ethyl)pyridin-2 (1H)-one was Obtained Using General Scheme 1 Pathway B Stage 1: General Procedure E1 was used from 3-bromo-5-(difluoromethoxy)pyridine to afford 3-(difluoromethoxy)-5-((trimethylsilyl)ethynyl)pyridine IM401 as a yellow solid: 346 mg, 68% yield, P=95%, retention time=1.7 min (gradient C), (M+H)+: 242.

Stage 2: General Procedure X was used between IM401 and IM151 to afford 4-chloro-1-(1-(4-(5-(difluoromethoxy)pyridin-3-yl)-1H-1,2,3-triazol-1-yl)ethyl)pyridin-2 (1H)-one IM402 as a white solid: 180 mg, 64% yield, P=99%, retention time=1.2 min (gradient C), (M+H)+: 368/370.

Stage 3: General Procedure C was used between IM3 and IM402 to afford tert-butyl (cyclobutylmethyl)((3R)-1-(1-(1-(4-(5-(difluoromethoxy)pyridin-3-yl)-1H-1,2,3-triazol-1-yl) ethyl)-2-oxo-1,2-dihydropyridin-4-yl)piperidin-3-yl)carbamate IM403 as a white powder: 153 mg, 91% yield, P=97%, retention time=1.7 min (gradient C), (M+H)+: 601.

Stage 4: General Procedure A2 was used from IM402 to afford compound 131 as an off-white solid: 63 mg, 41% yield, P=100%, retention time=2.4 min (gradient E), (M+H)+: 501. 1H NMR (400 MHZ, CD3OD) δ 8.90 (s, 1H), 8.68 (s, 1H), 8.40 (d, J=2.5 Hz, 1H), 8.09 (s, 1H), 7.65 (d, J=8.1 Hz, 1H), 7.51 (q, J=7.0 Hz, 1H), 7.02 (t, J=72.9 Hz, 1H), 6.35-6.27 (m, 1H), 5.67 (d, J=2.7 Hz, 1H), 3.95-3.85 (m, 1H), 3.82-3.71 (m, 1H), 3.03-2.91 (m, 1H), 2.85-2.74 (m, 1H), 2.66 (d, J=7.3 Hz, 2H), 2.61-2.52 (m, 1H), 2.49-2.38 (m, 1H), 2.15 (d, J=7.0 Hz, 3H), 2.13-1.98 (m, 3H), 1.96-1.80 (m, 2H), 1.79-1.61 (m, 3H), 1.57-1.45 (m, 1H), 1.44-1.31 (m, 1H), 1H exchanged with CD3OD. 19F NMR (376 MHZ, CD3OD) δ −84-−84.10 (m, 1F), −84.19-−84.30 (m, 1F).d The mixture of diastereomers was further purified by chiral preparative HPLC purification using Chiralpak IA column (5 μm, 20×250 mm). Eluent used: TBME/MeOH/DCM/DEA: 60/40/20/0.1% at flow rate of 20 mL/min. First eluted diastereomer: P=100%, retention time=5.8 min, chiral HPLC: P=100%, 1H NMR (300 MHz, CDCl3) δ 8.88 (d, J=1.8 Hz, 1H), 8.43 (d, J=2.7 Hz, 1H), 8.27 (s, 1H), 7.98 (s, 1H), 7.54 (q, J=6.9 Hz, 1H), 7.45 (d, J=8.1 Hz, 1H), 6.60 (t, J=72.7 Hz, 1H), 6.01 (dd, J=8.2, 2.9 Hz, 1H), 5.65 (d, J=2.8 Hz, 1H), 3.93-3.82 (m, 1H), 3.65-3.54 (m, 1H), 2.91 (p, J=10.7 Hz, 2H), 2.78-2.64 (m, 3H), 2.48 (hept, J=7.6 Hz, 1H), 2.17 (d, J=7.1 Hz, 3H), 2.10-1.96 (m, 3H), 1.94-1.60 (m, 7H), 1.56-1.46 (m, 2H), 1 NH exchanged. 19F NMR (282 MHZ, CDCl3) δ −78.59 (d, J=72.0 Hz). Second eluted diastereomer: P=100%, retention time=11.3 min, chiral HPLC: P=100%, 1H NMR (300 MHz, CDCl3) δ 8.80 (d, J=1.8 Hz, 1H), 8.36 (d, J=2.7 Hz, 1H), 8.14 (s, 1H), 7.89 (d, J=2.4 Hz, 1H), 7.47 (q, J=7.0 Hz, 1H), 7.36 (d, J=8.1 Hz, 1H), 6.52 (t, J=72.7 Hz, 1H), 5.93 (dd, J=8.1, 2.9 Hz, 1H), 5.59 (d, J=2.8 Hz, 1H), 3.75-3.64 (m, 1H), 3.59-3.48 (m, 1H), 2.92-2.78 (m, 1H), 2.75-2.46 (m, 5H), 2.35 (hept, J=7.5 Hz, 1H), 2.11 (d, J=7.0 Hz, 3H), 2.02-1.23 (m, 9H), 1 NH exchanged. 19F NMR (282 MHZ, CDCl3) δ −78.57 (d, J=72.0 Hz).

Compound 132: 4-((R)-3-((cyclobutylmethyl) amino)piperidin-1-yl)-1-(1-(1-(5-methoxy pyridin-3-yl)-1H-1,2,3-triazol-4-yl)ethyl)pyridin-2 (1H)-one was Obtained Using the Following Procedures Stage 1: In a reaction flask, 3-amino-5-fluoropyridine (212 mg, 1.83 mmol) was dissolved in EtOAc (4.0 mL), cooled to 0° C., and 6 M hydrochloric acid (2.0 mL, 12.0 mmol) was added. Sodium nitrite (225 mg, 3.23 mmol) was dissolved in water (1.0 mL) and added. The reaction mixture was stirred for 30 min at 0° C. Subsequently, sodium azide (203 mg, 3.10 mmol) in water (1.0 mL) was added slowly at 0° C. (white precipitate formed that dissolved). The mixture was then stirred at rt for 2 h. The mixture was poured into a separatory funnel, diluted with saturated NaHCO3 (15 mL), and extracted with ethyl acetate (2×100 mL). The organic layers were dried with MgSO4, filtered and evaporated on a rotary evaporator (temperature below 30° C.) to afford crude 3-azido-5-fluoropyridine IM403 as pale orange oil (which solidifies on standing at rt): 253 mg, 100% yield, P=100%, retention time=0.9 min (gradient C), (M+H)+: no ionization.

Stage 2: General Procedure B was used between IM403 and 1-(but-3-yn-2-yl)-4-chloropyridin-2 (1H)-one to afford 4-chloro-1-(1-(1-(5-fluoropyridin-3-yl)-1H-1,2,3-triazol-4-yl)ethyl)pyridin-2 (1H)-one IM404 as an off-white solid: 379 mg, 74% yield, P=100%, retention time=1.1 min (gradient C), (M+H)$^+$: 320/322.

Stage 3: General Procedure C was used between IM3 and IM404 to afford tert-butyl (cyclobutylmethyl)((3R)-1-(1-(1-(5-fluoropyridin-3-yl)-1H-1,2,3-triazol-4-yl)ethyl)-2-oxo-1,2-dihydropyridin-4-yl)piperidin-3-yl)carbamate IM405 as a white solid: 92 mg, 53% yield, P=100%, retention time=1.7 min (gradient C), (M+H)$^+$: 552.

Stage 4: In a reaction flask were placed IM405 (92.1 mg, 167 μmol) and 4.3 M sodium methoxide (3.05 mL, 13.1 mmol) in methanol (25 wt %). The mixture was stirred under reflux for 2.5 h. The mixture was concentrated under reduced pressure and diluted with minimal water (quenches the NaOMe). It was then purify by flash chromatography on C-18 column (15%-100% MeCN in 10 mM ammonium bicarbonate to afford tert-butyl (cyclobutylmethyl)((3R)-1-(1-(1-(5-methoxypyridin-3-yl)-1H-1,2,3-triazol-4-yl) ethyl)-2-oxo-1,2-dihydropyridin-4-yl)piperidin-3-yl)carbamate IM406 as a white solid: 125 mg, 100% yield, P=96%, retention time=1.7 min (gradient C), (M+H)$^+$: 564.

Stage 5: General Procedure A2 was used from IM406 to afford compound 132 as a glassy white solid: 45 mg, 58% yield, P=100%, retention time=2.2 min (gradient E), (M+H)$^+$: 464. $^1$H NMR (400 MHZ, CD$_3$OD) δ 8.68 (d, J=2.1 Hz, 1H), 8.67 (s, 1H), 8.36 (d, J=2.6 Hz, 1H), 7.90 (t, J=2.3 Hz, 1H), 7.43 (d, J=8.0 Hz, 1H), 6.34 (q, J=7.1 Hz, 1H), 6.25 (dd, J=8.0, 2.9 Hz, 1H), 5.73 (d, J=2.9 Hz, 1H), 3.97 (s, 3H), 3.94-3.83 (m, 1H), 3.80-3.69 (m, 1H), 3.00-2.89 (m, 1H), 2.80-2.72 (m, 1H), 2.68 (d, J=7.3 Hz, 2H), 2.62-2.53 (m, 1H), 2.52-2.39 (m, 1H), 2.14-2.00 (m, 3H), 1.98-1.83 (m, 2H), 1.81 (d, J=7.1 Hz, 3H), 1.78-1.63 (m, 3H), 1.62-1.45 (m, 1H), 1.43-1.30 (m, 1H), 1H exchanged with CD$_3$OD.

The mixture of diastereomers was further purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=100%, retention time=6.2 min, chiral HPLC: P=99.7%, $^1$H NMR (300 MHz, CDCl$_3$) δ 8.55 (d, J=2.1 Hz, 1H), 8.38 (d, J=2.7 Hz, 1H), 8.07 (s, 1H), 7.64 (t, J=2.4 Hz, 1H), 7.42 (d, J=7.9 Hz, 1H), 6.44 (q, J=7.2 Hz, 1H), 5.96 (dd, J=8.0, 2.9 Hz, 1H), 5.72 (d, J=2.9 Hz, 1H), 3.94 (s, 3H), 3.82-3.72 (m, 1H), 3.65-3.54 (m, 1H), 2.96-2.82 (m, 1H), 2.80-2.58 (m, 4H), 2.43 (hept, J=7.4 Hz, 1H), 2.11-1.30 (m, 13H), 1 NH exchanged. Second eluted diastereomer: P=100%, retention time=9.1 min, chiral HPLC: P=99.8%, $^1$H NMR (300 MHz, CDCl$_3$) δ 8.55 (d, J=2.1 Hz, 1H), 8.37 (d, J=2.7 Hz, 1H), 8.09 (s, 1H), 7.63 (t, J=2.4 Hz, 1H), 7.42 (d, J=8.0 Hz, 1H), 6.44 (q, J=7.2 Hz, 1H), 5.96 (dd, J=8.0, 2.9 Hz, 1H), 5.72 (d, J=2.8 Hz, 1H), 3.93 (s, 3H), 3.83-3.73 (m, 1H), 3.65-3.54 (m, 1H), 2.97-2.82 (m, 1H), 2.79-2.55 (m, 4H), 2.43 (hept, J=7.6 Hz, 1H), 2.12-1.28 (m, 13H), 1 NH exchanged.

Compound 133: 5-(1-(1-(6-((R)-3-((cyclobutylmethyl)amino)piperidin-1-yl)pyridazin-3-yl) ethyl)-1H-1,2,3-triazol-4-yl)-N,N-dimethylpyridin-3-amine was Obtained Using General Scheme 1 Pathway A Stage 1: General Procedure X was used between IM280 and IM345 to afford 5-(1-(1-(6-((R)-3-((cyclobutylmethyl) amino)piperidin-1-yl)pyridazin-3-yl)ethyl)-1H-1,2,3-triazol-4-yl)-N,N-dimethylpyridin-3-amine IM407 as yellow oil: 85 mg, 36% yield, P=65%, retention time=1.8 min (gradient C), (M+H)$^+$: 563.

Stage 2: General Procedure A2 was used from IM407 to afford compound 133 as a white solid: 31 mg, 66% yield, P=97%, retention time=2.5 min (gradient E), (M+H)$^+$: 463. $^1$H NMR (400 MHZ, CD$_3$OD) δ 8.61 (s, 1H), 8.28 (s, 1H), 8.01 (d, J=2.4 Hz, 1H), 7.59 (dd, J=2.8, 1.7 Hz, 1H), 7.45 (d, J=9.6 Hz, 1H), 7.29 (d, J=9.6 Hz, 1H), 6.12 (q, J=7.1 Hz, 1H), 4.53-4.41 (m, 1H), 4.09-3.99 (m, 1H), 3.20-3.07 (m, 2H), 3.05 (s, 6H), 2.93-2.81 (m, 3H), 2.60-2.49 (m, 1H), 2.18-2.09 (m, 3H), 2.07 (d, J=7.1 Hz, 3H), 1.98-1.81 (m, 3H), 1.79-1.70 (m, 2H), 1.67-1.52 (m, 2H), 1H exchanged with CD$_3$OD.

The mixture of diastereomers was further purified by chiral preparative HPLC purification using Chiralpak IA column (5 μm, 20×250 mm). Eluent used: TBME/MeOH/DCM/DEA: 60/40/20/0.1% at flow rate of 20 mL/min. First eluted diastereomer: P=100%, retention time=4.3 min, chiral HPLC: P=99.6%, $^1$H NMR (300 MHz, CDCl$_3$) δ 8.28 (s, 1H), 8.08 (d, J=3.0 Hz, 1H), 8.00 (s, 1H), 7.51 (t, J=2.3 Hz, 1H), 7.21 (d, J=9.5 Hz, 1H), 6.88 (d, J=9.5 Hz, 1H), 6.03 (q, J=7.1 Hz, 1H), 4.44-4.33 (m, 1H), 4.13-4.03 (m, 1H), 3.10 (s, 1H), 3.02 (s, 6H), 2.89 (dd, J=12.8, 9.2 Hz, 1H), 2.75-2.59 (m, 3H), 2.42 (hept, J=7.6 Hz, 1H), 2.15-1.97 (m, 6H), 1.94-1.77 (m, 3H), 1.68-1.32 (m, 4H), 1 NH exchanged. Second eluted diastereomer: P=100%, retention time=8.4 min, chiral HPLC: P=100%, $^1$H NMR (300 MHZ, CDCl$_3$) δ 8.28 (d, J=1.7 Hz, 1H), 8.08 (d, J=3.0 Hz, 1H), 7.99 (s, 1H), 7.51 (dd, J=3.0, 1.7 Hz, 1H), 7.21 (d, J=9.5 Hz, 1H), 6.88 (d, J=9.5 Hz, 1H), 6.03 (q, J=7.1 Hz, 1H), 4.44-4.35 (m, 1H), 4.14-4.04 (m, 1H), 3.17-3.04 (m, 1H), 3.02 (s, 6H), 2.91 (dd, J=12.8, 9.3 Hz, 1H), 2.80-2.60 (m, 3H), 2.43 (p, J=7.6 Hz, 1H), 2.14-1.99 (m, 6H), 1.86 (dtt, J=12.7, 8.8, 4.8 Hz, 4H), 1.69-1.38 (m, 3H), 1 NH exchanged.

Compound 134: (R)—N-(cyclobutylmethyl)-1-(4-(3-(4-(5-methoxypyridin-3-yl)-1H-1,2,3-triazol-1-yl) oxetan-3-yl)phenyl)piperidin-3-amine was Obtained Using General Scheme 1 Pathway A Stage 1: To a flame-dried Schlenk tube under Ar atmosphere was added with 4-bromoiodobenzene (1.0 g, 3.53 mmol) followed by anhydrous THF (5 mL) to afford a colorless solution which was stirred at −78° C. n-Butyl lithium in hexane (1.7 mL, 4.08 mmol) was added to provide a yellow solution which evolved to a yellow suspension. The latter was stirred at −78° C. for 1 h, then a solution of 2-methyl-N-(oxetan-3-ylidene)propane-2-sulfinamide (0.5 g, 2.74 mmol) in anhydrous THF (4 mL) was added at −78° C. and the reaction mixture was stirred at −78° C. for 35 min, then allowed to stir at rt for 1 h. Layers were separated and the aqueous layer was extracted with EtOAc (50 mL). Combined organic layers were washed with brine (20 mL) then dried over MgSO$_4$, filtered and the filtrate was concentrated under reduced pressure to dryness to afford 1.094 g as a crude brown oil. 841 mg was purified by an automated flash system (liquid injection in Toluene, 0 to 100% EtOAc in Heptane) to afford N-(3-(4-bromophenyl)oxetan-3-yl)-2-methylpropane-2-sulfinamide IM408 as yellow oil: 603 mg, 53% yield, P=80% ($^1$H NMR), retention time=4.1 min (gradient B), (M+H)$^+$: 332/334.

Stage 2: General Procedure Y was used between IM3 and IM408 to afford tert-butyl ((3R)-1-(4-(3-((tert-butylsulfinyl) amino)oxetan-3-yl)phenyl)piperidin-3-yl)(cyclobutylmethyl) carbamate IM409 as a yellow solid: 604 mg, 80% yield, P=90% ($^1$H NMR), retention time=2.7 min (gradient A), (M+H)$^+$: 520.

Stage 3: To a solution of IM409 (604 mg, 1.05 mmol) in THF (2.6 mL) and water (500 µL) was added iodine (75 mg, 0.30 mmol) at rt and the reaction mixture was stirred at 55° C. for 1.75 h. Then, extra iodine (30 mg, 0.12 mmol) was added and the reaction mixture was stirred at 55° C. for 10 min extra. The reaction mixture was cooled to rt and diluted with EtOAc (20 mL), then washed with a mixture of Na$_2$S$_2$O$_3$ (2 M, 10 mL) and NaHCO$_3$ saturated solution (10 mL). The aqueous layer was extracted with EtOAc (10 mL) and the combined organic phases were dried over MgSO$_4$, filtered and the filtrate was concentrated under reduced pressure to afford tert-butyl (R)-(1-(4-(3-aminooxetan-3-yl) phenyl)piperidin-3-yl)(cyclobutylmethyl)carbamate IM410 as orange oil: 603 mg, 100% yield, P=72% ($^1$H NMR), retention time=2.4 min (gradient A), (M+H)$^+$: 416.

Stage 4: General Procedure V was used from IM410 to afford tert-butyl (R)-(1-(4-(3-azidooxetan-3-yl)phenyl)piperidin-3-yl)(cyclobutylmethyl)carbamate IM411 as yellow oil: 154 mg, 76% yield, P=99%, retention time=3.1 min (gradient A), (M+H)$^+$: 442.

Stage 5: General Procedure B was used between IM411 and IM44 to afford tert-butyl (R)-(cyclobutylmethyl)(1-(4-(3-(4-(5-methoxypyridin-3-yl)-1H-1,2,3-triazol-1-yl) oxetan-3-yl) phenyl)piperidin-3-yl)carbamate IM412 as colourless oil: 73 mg, 100% yield, P=90%, retention time=2.7 min (gradient A), (M+H)$^+$: 575.

Stage 6: General Procedure A1 was used from IM412 to afford crude compound 134 as a white solid: 46 mg, 80% yield, P=98%, retention time=2.1 min (gradient B), (M+H)$^+$: 475. $^1$H NMR (300 MHz, CDCl$_3$) δ 8.47 (s, 1H), 8.27 (s, 1H), 7.82-7.74 (m, 1H), 7.55 (s, 1H), 7.13 (d, J=8.8 Hz, 2H), 6.95 (d, J=8.8 Hz, 2H), 5.61 (d, J=6.7 Hz, 2H), 5.29 (d, J=6.7 Hz, 2H), 3.92 (s, 3H), 3.74-3.65 (m, 1H), 3.57-3.47 (m, 1H), 2.92-2.79 (m, 1H), 2.77-2.62 (m, 4H), 2.54-2.38 (m, 1H), 2.14-2.01 (m, 2H), 2.01-1.75 (m, 5H), 1.65 (p, J=8.2 Hz, 3H), 1H exchanged with solvent.

Compound 135: 4-((R)-3-((cyclobutylmethyl) amino)piperidin-1-yl)-1-(1-(3-(5-methoxy pyridin-3-yl)-1H-1,2,4-triazol-1-yl)ethyl)pyridin-2 (1H)-one was Obtained Using the Following Procedures Stage 1: To a solution of 5-methoxypyridine-3-carboxylic acid (510 mg, 3.27 mmol) in MeOH (150 mL) was added sulfuric acid (2 mL, 3.27 mmol) and the mixture was heated to reflux for 48 h. The mixture was cooled to rt and solid sodium bicarbonate was added until the bubbling stopped. The mixture was filtered and concentrated. The material was dissolved in DCM and washed with water. The organic phase was collected, dried over anhydrous MgSO$_4$, filtered and concentrated. The crude ester was dissolved in ammonia (7 mL, 49.0 mmol) (7 M in MeOH) and placed in a microwave vial, then sodium cyanide (16.5 mg, 327 µmol) was added and the vial was sealed and heated to 45° C. for 2 days. The mixture was concentrated and the residue was suspended in DCM. The resultant was solid collected by filtration to afford crude O-(5-methoxynicotinoyl)hydroxylamine IM413 as a beige: 300 mg, 60% yield, P=99%, retention time=0.3 min (gradient F), (M+H)$^+$: 153.

Stage 2: IM413 (150 mg, 986 µmol) was dissolved in N,N-dimethylformamide dimethyl acetal (1.34 mL, 9.86 mmol) and the reaction mixture was heated in a sealed tube at 120° C. for 3 h. The solvent was removed under reduced pressure to give a solid that was dissolved in acetic acid (2.41 mL). Hydrazine hydrate solution (75.1 µL, 1.18 mmol) was added and the mixture was heated to 90° C. for 1 h. The mixture was then concentrated to dryness to afford 3-methoxy-5-(1H-1,2,4-triazol-3-yl)pyridine IM414 as black oil: 174 mg, 100% yield, P=100%, retention time=0.6 min (gradient F), (M+H)$^+$: 177.

Stage 3: IM414 (340 mg, 1.93 mmol) was dissolved in DMF (10 mL) and IM150 (635 mg, 2.89 mmol) was added along with K$_2$CO$_3$ (816 mg, 5.79 mmol) and the reaction mixture was heated to 90° C. overnight. Additional IM150 (635 mg, 2.89 mmol) and K$_2$CO$_3$ (816 mg, 5.79 mmol) was added and the reaction mixture was heated for a further 24 h. The mixture was cooled to rt and diluted with EtOAc and washed with water and brine. The organic layer was collected, dried over anhydrous MgSO$_4$, filtered and concentrated. Purification by reverse phase (0-100% MeCN in 10 mM ammonium bicarbonate) afforded 4-chloro-1-(1-(3-(5-methoxypyridin-3-yl)-1H-1,2,4-triazol-1-yl)ethyl)pyridin-2 (1H)-one IM415 as brown oil: 200 mg, 25% yield, P=81%, retention time=1.1 min (gradient F), (M+H)$^+$: 332/334.

Stage 4: General Procedure C was used between IM3 and IM415 to afford tert-butyl (cyclobutylmethyl)((3R)-1-(1-(1-(3-(5-methoxypyridin-3-yl)-1H-1,2,4-triazol-1-yl)ethyl)-2-oxo-1,2-dihydropyridin-4-yl)piperidin-3-yl)carbamate IM416 as a beige solid: 165 mg, 48% yield, P=99%, retention time=1.7 min (gradient F), (M+H)$^+$: 565.

Stage 5: General Procedure A2 was used from IM416 to afford compound 135 as a white solid: 93 mg, 59% yield, P=91%, retention time=2.3 min (gradient E), (M+H)$^+$: 465.

The mixture of diastereomers was further purified by chiral preparative HPLC purification using Chiralpak IA column (5 µm, 20×250 mm). Eluent used: TBME/MeOH/DCM/DEA: 40/40/20/0.1% at flow rate of 20 mL/min. First eluted diastereomer: P=100%, retention time=5.7 min, chiral HPLC: P=100%, $^1$H NMR (300 MHz, CDCl$_3$) δ 8.93 (s, 1H), 8.41 (s, 1H), 8.33 (d, J=2.9 Hz, 1H), 7.89-7.77 (m, 1H), 7.51 (d, J=8.2 Hz, 1H), 7.44 (q, J=6.9 Hz, 1H), 5.98 (dd, J=8.2, 2.8 Hz, 1H), 5.65 (d, J=2.8 Hz, 1H), 3.91 (s, 3H), 3.84-3.72 (m, 1H), 3.65-3.53 (m, 1H), 2.98-2.83 (m, 1H), 2.81-2.52 (m, 4H), 2.41 (hept, J=7.6 Hz, 1H), 2.13-1.32 (m, 13H), 1H exchanged with solvent. Second eluted diastereomer: P=100%, retention time=15.1 min, chiral HPLC: P=100%, $^1$H NMR (300 MHz, CDCl$_3$) δ 8.92 (d, J=1.7 Hz, 1H), 8.44 (s, 1H), 8.33 (d, J=2.9 Hz, 1H), 7.89-7.82 (m, 1H), 7.58-7.38 (m, 2H), 6.00 (dd, J=8.2, 2.8 Hz, 1H), 5.66 (d, J=2.8 Hz, 1H), 3.98-3.93 (m, 1H), 3.91 (s, 3H), 3.64-3.54 (m, 1H), 3.06-2.84 (m, 2H), 2.84-2.65 (m, 3H), 2.52 (hept, J=7.3 Hz, 1H), 2.15-1.46 (m, 13H), 1H exchanged with solvent.

Compound 136: (R)—N-(cyclobutylmethyl)-1-(4-((4-(5-methoxypyridazin-3-yl)-1H-1,2,3-triazol-1-yl) methyl)phenyl)piperidin-3-amine was Obtained Using General Scheme 1 Pathway B Stage 1: General Procedure X was used between IM357 and IM377 to afford 3-(1-(4-bromobenzyl)-1H-1,2,3-triazol-4-yl)-5-methoxypyridazine IM417 as a white solid: 120 mg, 92% yield, P=92%, retention time=2.5 min (gradient A), (M+H)$^+$: 346/348.

Stage 2: General Procedure S was used between IM3 and IM417 to afford tert-butyl (R)-(cyclobutylmethyl)(1-(4-((4-(5-methoxypyridazin-3-yl)-1H-1,2,3-triazol-1-yl)methyl) phenyl) piperidin-3-yl)carbamate IM418 as yellow film: 33 mg, 16% yield, P=45% ($^1$H NMR), retention time=2.7 min (gradient A), (M+H)+: 534.

Stage 3: General Procedure A1 was used from IM418 to afford crude compound 136 as a pale yellow solid: 18 mg, 87% yield, P=58%, retention time=2.2 min (gradient A), (M+H)$^+$: 434.

The product was purified by reverse phase preparative HPLC purification (Waters XBridge C18 5 μm 19×100 mm). Gradient used: increased linearly from 20 to 40% solution "B" over 4.0 min, increased linearly to 85% solution "B" over 2.3 min, and returned to initial conditions over 1.0 min. Flow Rate: 15 mL/min. P=100%. $^1$H NMR (300 MHz, CDCl$_3$) δ 8.79 (d, J=3.0 Hz, 1H), 8.22 (s, 1H), 7.76 (d, J=3.0 Hz, 1H), 7.23 (d, J=8.4 Hz, 2H), 6.91 (d, J=8.6 Hz, 2H), 5.49 (s, 2H), 3.98 (s, 3H), 3.70-3.61 (m, 1H), 3.53-3.43 (m, 1H), 2.90-2.57 (m, 5H), 2.45 (hept, J=7.6 Hz, 1H), 2.15-2.02 (m, 2H), 1.99-1.57 (m, 7H), 1.31 (s, 1H). 1H exchanged with solvent.

Compound 137: (3R)—N-(cyclobutylmethyl)-1-(6-(1-(4-(5-methoxypyridazin-3-yl)-1H-1,2,3-triazol-1-yl)ethyl)pyridazin-3-yl)piperidin-3-amine was Obtained Using General Scheme 1 Pathway A Stage 1: General Procedure X was used between IM357 and IM280 to afford tert-butyl (cyclobutylmethyl)((3R)-1-(6-(1-(4-(5-methoxypyridazin-3-yl)-1H-1,2,3-triazol-1-yl) ethyl) pyridazin-3-yl)piperidin-3-yl)carbamate IM419 as yellow oil: 71 mg, 78% yield, P=98%, retention time=2.5 min (gradient A), (M+2H)+: 276.

Stage 2: General Procedure A1 was used from IM419 to afford crude compound 137 as yellow film: 54 mg, 91% yield, P=98%, retention time=2.0 min (gradient A), (M+H)$^+$: 450.

The mixture of diastereomers was further purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=99%, retention time=7.3 min, chiral HPLC: P=100%, $^1$H NMR (300 MHz, CDCl$_3$) δ 8.80 (d, J=3.0 Hz, 1H), 8.46 (s, 1H), 7.75 (d, J=3.0 Hz, 1H), 7.16 (d, J=9.5 Hz, 1H), 6.87 (d, J=9.5 Hz, 1H), 6.08 (q, J=7.1 Hz, 1H), 4.46-4.37 (m, 1H), 4.14-4.04 (m, 1H), 3.98 (s, 3H), 3.18-3.03 (m, 1H), 2.96-2.83 (m, 1H), 2.81-2.61 (m, 3H), 2.43 (hept, J=7.6 Hz, 1H), 2.17-1.31 (m, 13H), 1H exchanged with solvent. Second eluted diastereomer: P=100%, retention time=9.8 min, chiral HPLC: P=100%, $^1$H NMR (300 MHz, CDCl$_3$) δ 8.81 (d, J=3.0 Hz, 1H), 8.45 (s, 1H), 7.75 (d, J=3.0 Hz, 1H), 7.16 (d, J=9.5 Hz, 1H), 6.87 (d, J=9.5 Hz, 1H), 6.09 (q, J=7.1 Hz, 1H), 4.45-4.36 (m, 1H), 4.17-4.06 (m, 1H), 3.98 (s, 3H), 3.18-3.03 (m, 1H), 2.96-2.83 (m, 1H), 2.77-2.61 (m, 3H), 2.43 (hept, J=7.6 Hz, 1H), 2.17-1.38 (m, 13H), 1H exchanged with solvent.

Compound 138: (3R)—N-(cyclobutylmethyl)-1-(6-fluoro-5-(1-(4-(5-methoxypyridin-3-yl)-1H-1,2,3-triazol-1-yl)ethyl)pyridin-2-yl)piperidin-3-amine was Obtained Using General Scheme 1 Pathway A Stage 1: In a solution of 2,6-difluoropyridine-3-carboxaldehyde (106 mg, 0.72 mmol) and IM3 (272 mg, 1.01 mmol) in DMSO (1.3 mL) was added triethylamine (0.3 mL, 2.13 mmol). The reaction mixture was allowed to heat for 5 h. The reaction mixture was cooled to rt, diluted with EtOAc (50 mL) and rinsed with saturated aqueous solution of NH$_4$Cl (2×25 mL) and brine (2×25 mL), then was dried over MgSO$_4$, filtered and concentrated under reduced pressure to dryness. The crude material was purified by an automated flash system (liquid injection in toluene, 0 to 50% EtOAc in Heptane) to afford tert-butyl (R)-(cyclobutylmethyl)(1-(6-fluoro-5-formylpyridin-2-yl)piperidin-3-yl)carbamate IM420: 182 mg, 58% yield, P=89%, retention time=3.4 min (gradient A), (M+H)$^+$: 392.

Stage 2: General Procedure Q was used from IM420 to afford tert-butyl (cyclobutyl methyl)((3R)-1-(6-fluoro-5-(1-hydroxyethyl)pyridin-2-yl)piperidin-3-yl)carbamate IM421 as yellow oil: 142 mg, 84% yield, P=100%, retention time=3.3 min (gradient A), (M+H)$^+$: 408.

Stage 3: General Procedure M was used from IM421 to afford tert-butyl ((3R)-1-(5-(1-azido ethyl)-6-fluoropyridin-2-yl)piperidin-3-yl)(cyclobutylmethyl)carbamate IM422 as a white solid: 24 mg, 29% yield, P=98%, retention time=3.7 min (gradient A), (M+H)$^+$: 433.

Stage 4: General Procedure B was used between IM422 and IM44 to afford tert-butyl (cyclobutylmethyl)((3R)-1-(6-fluoro-5-(1-(4-(5-methoxypyridin-3-yl)-1H-1,2,3-triazol-1-yl) ethyl)pyridin-2-yl)piperidin-3-yl)carbamate IM423 as colourless oil: 49 mg, 42% yield, P=96%, retention time=2.9 min (gradient A), (M+H)$^+$: 566.

Stage 5: General Procedure A1 was used from IM423 to afford crude compound 138 as colourless oil: 49 mg, 82% yield, P=60%, retention time=2.2 min (gradient A), (M+H)$^+$: 466.

The product was purified by reverse phase preparative HPLC purification (Waters XBridge C18 5 μm 19×100 mm). Gradient used: increased linearly from 25 to 40% solution "B" over 5.0 min, increased linearly to 85% solution "B" over 1.5 min, and returned to initial conditions over 0.8 min. Flow Rate: 15 mL/min. P=100%.

The mixture of diastereomers was further purified by chiral preparative HPLC purification using Chiralpak IE column (5 μm, 10×250 mm). Eluent used: TBME/MeOH/DCM/DEA: 40/40/20/0.1% at flow rate of 7 mL/min. First eluted diastereomer: P=100%, retention time=4.4 min, chiral HPLC: P=100%, $^1$H NMR (300 MHz, CDCl$_3$) δ 8.44 (d, J=1.7 Hz, 1H), 8.19 (d, J=2.9 Hz, 1H), 7.74 (s, 1H), 7.69 (dd, J=2.8, 1.7 Hz, 1H), 7.47 (dd, J=10.2, 8.5 Hz, 1H), 6.37 (dd, J=8.5, 1.9 Hz, 1H), 5.84 (q, J=7.1 Hz, 1H), 4.13-4.02 (m, 1H), 3.97-3.87 (m, 1H), 3.84 (s, 3H), 3.00-2.85 (m, 1H), 2.74 (dd, J=12.8, 9.2 Hz, 1H), 2.69-2.45 (m, 3H), 2.35 (hept, J=7.6 Hz, 1H), 2.12-1.97 (m, 2H), 1.94 (d, J=7.1 Hz, 3H), 1.89-1.23 (m, 10H), 1 NH exchanged with solvent. $^{19}$F NMR (282 MHZ, CDCl$_3$) δ −69.56 (d, J=9.8 Hz). Second eluted diastereomer: P=100%, retention time=5.3 min, chiral HPLC: P=100%, $^1$H NMR (300 MHz, CDCl$_3$) δ 8.44 (d, J=1.7 Hz, 1H), 8.19 (d, J=2.9 Hz, 1H), 7.74 (s, 1H), 7.69 (dd, J=2.9, 1.7 Hz, 1H), 7.47 (dd, J=10.2, 8.5 Hz, 1H), 6.37 (dd, J=8.6, 1.9 Hz, 1H), 5.84 (q, J=7.1 Hz, 1H), 4.16-4.04 (m, 1H), 3.96-3.86 (m, 1H), 3.84 (s, 3H), 3.00-2.85 (m, 1H), 2.74 (dd, J=12.8, 9.2 Hz, 1H), 2.69-2.45 (m, 3H), 2.35 (hept, J=7.6 Hz, 1H), 2.07-1.65 (m, 8H), 1.65-1.41 (m, 3H), 1.38-1.23 (m, 2H), 1 NH exchanged with solvent, $^{19}$F NMR (282 MHZ, CDCl$_3$) δ −69.54 (d, J=9.9 Hz).

Compound 139: (R)-5-(1-((5-(3-((cyclobutylmethyl)amino)piperidin-1-yl)pyridin-2-yl) methyl)-1H-1,2,3-triazol-4-yl)-N,N-dimethylpyridin-3-amine was Obtained Using General Scheme 1 Pathway B Stage 1: General Procedure M was used from 5-bromo-2-(hydroxymethyl)pyridine to afford 2-(azidomethyl)-5-bromopyridine IM424 as yellow liquid: 440 mg, 100% yield, P=77%, retention time=2.7 min (gradient A), (M+H)$^+$: 214.

Stage 2: General Procedure X was used between IM424 and IM345 to afford 5-(1-((5-bromopyridin-2-yl)methyl)-1H-1,2,3-triazol-4-yl)-N,N-dimethylpyridin-3-amine IM425 as a pale yellow solid: 115 mg, 52% yield, P=99%, retention time=2.2 min (gradient A), (M+H)⁺: 359/361.

Stage 3: General Procedure Y was used between IM3 and IM425 to afford tert-butyl (R)-(cyclobutylmethyl)(1-(6-((4-(5-(dimethylamino)pyridin-3-yl)-1H-1,2,3-triazol-1-yl)methyl) pyridin-3-yl)piperidin-3-yl)carbamate IM426 as yellow sticky oil: 134 mg, 74% yield, P=97%, retention time=2.5 min (gradient A), (M+H)⁺: 547.

Stage 4: General Procedure A1 was used from IM426 to afford compound 139 as a yellowish sticky solid: 87 mg, 94% yield, P=98%, retention time=2.5 min (gradient B), (M+H)⁺: 447. ¹H NMR (300 MHz, CDCl₃) δ 8.31-8.23 (m, 2H), 8.09 (d, J=3.0 Hz, 1H), 7.93 (s, 1H), 7.57 (d, J=2.6 Hz, 1H), 7.20-7.12 (m, 2H), 5.59 (s, 2H), 3.71-3.63 (m, 1H), 3.53-3.42 (m, 1H), 3.03 (s, 6H), 2.94-2.79 (m, 1H), 2.75-2.62 (m, 4H), 2.45 (hept, J=7.5 Hz, 1H), 2.12-1.29 (m, 10H), 1H exchanged with solvent.

Compound 140: (R)-5-(1-((5-(3-((cyclobutylmethyl)amino)piperidin-1-yl)benzyl)-1H-1,2,3-triazol-4-yl)-N,N-dimethylpyridin-3-amine was Obtained Using General Scheme 1 Pathway B Stage 1: General Procedure X was used between IM377 and IM345 to afford 5-(1-(4-bromobenzyl)-1H-1,2,3-triazol-4-yl)-N,N-dimethylpyridin-3-amine IM427 as a white solid: 143 mg, 62% yield, P=99%, retention time=2.3 min (gradient A), (M+H)⁺: 358/360.

Stage 2: General Procedure Y was used between IM3 and IM427 to afford tert-butyl (R)-(cyclobutylmethyl)(1-(4-((4-(5-(dimethylamino)pyridin-3-yl)-1H-1,2,3-triazol-1-yl)methyl) phenyl)piperidin-3-yl)carbamate IM428 as colourless sticky oil: 180 mg, 73% yield, P=89%, retention time=2.5 min (gradient A), (M+H)+: 546.

Stage 3: General Procedure A1 was used from IM428 to afford compound 140 as a white solid: 113 mg, 80% yield, P=95%, retention time=2.9 min (gradient B), (M+H)⁺: 446. ¹H NMR (300 MHz, CD₃OD) δ 8.34 (d, J=2.6 Hz, 1H), 8.24 (s, 1H), 7.99 (s, 1H), 7.56 (s, 1H), 7.32-7.23 (m, 2H), 7.02-6.93 (m, 2H), 5.56-5.48 (m, 2H), 3.70-3.60 (m, 1H), 3.51-3.43 (m, 1H), 3.03 (s, 7H), 2.88-2.60 (m, 5H), 2.48 (s, 1H), 2.15-1.54 (m, 8H), 1.33 (s, 1H), 1H exchanged with CD₃OD.

Compound 141: 2-(6-((R)-3-((cyclobutylmethyl)amino)piperidin-1-yl)pyridazin-3-yl)-N-(5-methoxypyridin-3-yl)propanamide was Obtained Using General Scheme 6 Pathway A Stage 1: 3-Amino-5-methoxypyridine (25.9 mg, 203 µmol), lithium 2-(6-chloropyridazin-3-yl)propanoate (39.0 mg, 203 µmol), EDC (43.1 mg, 223 µmol) and HOBt (27.4 mg, 203 µmol) were all mixed in DMF (1 mL) at rt overnight. The mixture was purified by reverse phase column (C18, 0% to 100% MeCN in 10 mM ammonium bicarbonate buffer) to afford 2-(6-chloropyridazin-3-yl)-N-(5-methoxypyridin-3-yl)propanamide IM429 as a white solid: 55 mg, 88% yield, P=95%, retention time=1.0 min (gradient C), (M+H)+: 293/295.

Stage 2: General Procedure C was used between IM3 and IM429 to afford tert-butyl (cyclobutylmethyl)((3R)-1-(6-(1-((5-methoxypyridin-3-yl)amino)-1-oxopropan-2-yl)pyridazin-3-yl)piperidin-3-yl)carbamate IM430 as colourless oil: 52 mg, 48% yield, P=92%, retention time=1.7 min (gradient C), (M+H)⁺: 525.

Stage 3: General Procedure A2 was used from IM430 to afford compound 141 as a white solid: 6 mg, 17% yield, P=98%, retention time=2.4 min (gradient E), (M+H)⁺: 425. ¹H NMR (400 MHZ, CD₃OD) δ 8.29 (d, J=1.9 Hz, 1H), 7.96 (d, J=2.6 Hz, 1H), 7.84 (t, J=2.3 Hz, 1H), 7.53 (d, J=9.6 Hz, 1H), 7.28 (d, J=9.6 Hz, 1H), 4.46-4.34 (m, 1H), 4.16-4.02 (m, 2H), 3.86 (s, 3H), 3.12-3.02 (m, 1H), 2.91 (ddd, J=12.8, 9.5, 3.3 Hz, 1H), 2.79-2.62 (m, 3H), 2.56-2.42 (m, 1H), 2.15-2.01 (m, 3H), 1.99-1.77 (m, 3H), 1.77-1.65 (m, 2H), 1.64-1.53 (m, 1H), 1.59 (d, J=7.2 Hz, 3H), 1.50-1.39 (m, 1H), 2H exchanged with CD₃OD.

Compound 142: 4-((R)-3-((cyclopropylmethyl)amino)piperidin-1-yl)-1-(1-(4-(5-(dimethyl amino)pyridin-3-yl)-1H-1,2,3-triazol-1-yl)ethyl)pyridin-2 (1H)-one was Obtained Using General Scheme 1 Pathway A Stage 1: General Procedure X was used between IM151 and IM345 to afford 4-chloro-1-(1-(4-(5-(dimethylamino)pyridin-3-yl)-1H-1,2,3-triazol-1-yl)ethyl)pyridin-2 (1H)-one IM431 as a green solid: 3.2 g, 53% yield, P=94%, retention time=2.9 min (gradient B), (M+H)⁺: 345/347.

Stage 2: General Procedure C was used between IM431 and tert-butyl (R)-piperidin-3-ylcarbamate to afford tert-butyl ((3R)-1-(1-(1-(4-(5-(dimethylamino)pyridin-3-yl)-1H-1,2,3-triazol-1-yl)ethyl)-2-oxo-1,2-dihydropyridin-4-yl)piperidin-3-yl)carbamate IM432 as a yellow foam: 473 mg, 83% yield, P=98%, retention time=2.3 min (gradient A), (M+H)⁺: 509.

Stage 3: General Procedure A1 was used from IM432 to afford crude 4-((R)-3-aminopiperidin-1-yl)-1-(1-(4-(5-(dimethylamino)pyridin-3-yl)-1H-1,2,3-triazol-1-yl)ethyl)pyridin-2 (1H)-one IM 433 as an off-white solid: 336 mg, 87% yield, P=96%, retention time=1.9 min (gradient A), (M+H)⁺: 409.

Stage 4: General Procedure H1 was used between cyclopropane carboxaldehyde and IM433 to afford crude compound 142 as yellow oil: 70 mg, 99% yield, P=92% (215 nm), retention time=2.5 min (gradient B), (M+H)⁺: 463.

The mixture of diastereomers was purified by chiral preparative HPLC purification using Chiralpak IA column (5 µm, 20×250 mm). Eluent used: TBME/MeOH/DCM/DEA: 60/40/20/0.1% at flow rate of 20 mL/min. First eluted diastereomer: P=99%, retention time=5.7 min, chiral HPLC: P=100%, ¹H NMR (300 MHz, CDCl₃) δ 8.31 (d, J=1.7 Hz, 1H), 8.10 (s, 1H), 8.08 (d, J=3.0 Hz, 1H), 7.54 (q, J=7.0 Hz, 1H), 7.49-7.44 (m, 1H), 7.41 (d, J=8.1 Hz, 1H), 5.97 (dd, J=8.1, 2.9 Hz, 1H), 5.65 (d, J=2.8 Hz, 1H), 3.80-3.70 (m, 1H), 3.65-3.54 (m, 1H), 3.01 (s, 6H), 2.96-2.84 (m, 1H), 2.80-2.57 (m, 2H), 2.57-2.40 (m, 2H), 2.15 (d, J=7.0 Hz, 3H), 2.00-1.23 (m, 4H), 0.96-0.85 (m, 1H), 0.53-0.41 (m, 2H), 0.11-0.02 (m, 2H), 1 NH exchanged with solvent. Second eluted diastereomer: P=100%, retention time=10.1 min, chiral HPLC: P=99.5%, ¹H NMR (300 MHz, CDCl₃) δ 8.31 (d, J=1.7 Hz, 1H), 8.11 (s, 1H), 8.08 (d, J=3.0 Hz, 1H), 7.55 (q, J=7.0 Hz, 1H), 7.46 (dd, J=3.0, 1.7 Hz, 1H), 7.42 (d, J=8.1 Hz, 1H), 5.98 (dd, J=8.1, 2.9 Hz, 1H), 5.65 (d, J=2.8 Hz, 1H), 3.82-3.72 (m, 1H), 3.65-3.55 (m, 1H), 3.01 (s, 6H), 2.96-2.84 (m, 1H), 2.82-2.58 (m, 2H), 2.44 (s, 2H), 2.15 (d, J=7.0 Hz, 3H), 2.02-1.24 (m, 4H), 0.94-0.86 (m, 1H), 0.53-0.41 (m, 2H), 0.08 (dd, J=9.1, 4.3 Hz, 2H), 1 NH exchanged with solvent.

Compound 143: 5-(1-(1-(5-((R)-3-((cyclobutylmethyl)amino)piperidin-1-yl)pyridin-2-yl)ethyl)-1H-1,2,3-triazol-4-yl)-N,N-dimethylpyridin-3-amine was Obtained Using General Scheme 1 Pathway A Stage 1: General Procedure X was used between IM181 and IM345 to afford tert-butyl (cyclobutylmethyl)((3R)-1-

(6-(1-(4-(5-(dimethylamino)pyridin-3-yl)-1H-1,2,3-triazol-1-yl) ethyl)pyridin-3-yl)piperidin-3-yl)carbamate IM434 as a white solid: 80 mg, 89% yield, P=98%, retention time=2.5 min (gradient A), (M+H)$^+$: 561.

Stage 2: General Procedure A1 was used from IM434 to afford crude compound 143 as colourless oil: 65 mg, 99% yield, P=98%, retention time=2.6 min (gradient B), (M+H)$^+$: 461.

The mixture of diastereomers was purified by chiral preparative HPLC purification using Chiralpak IA column (5 μm, 20×250 mm). Eluent used: TBME/MeOH/DCM/DEA: 60/40/20/0.1% at flow rate of 20 mL/min. First eluted diastereomer: P=100%, retention time=4.2 min, chiral HPLC: P=100%, $^1$H NMR (300 MHz, CDCl$_3$) δ 8.32-8.23 (m, 2H), 8.07 (d, J=3.0 Hz, 1H), 7.96 (s, 1H), 7.60-7.52 (m, 1H), 7.16-7.10 (m, 2H), 5.90 (q, J=7.0 Hz, 1H), 3.71-3.62 (m, 1H), 3.52-3.41 (m, 1H), 3.02 (s, 6H), 2.92-2.79 (m, 1H), 2.79-2.63 (m, 4H), 2.45 (hept, J=7.5 Hz, 1H), 2.13-1.46 (m, 12H), 1.39-1.30 (m, 1H), 1 NH exchanged with solvent. Second eluted diastereomer: P=100%, retention time=7.7 min, chiral HPLC: P=100%, $^1$H NMR (300 MHz, CDCl$_3$) δ 8.31-8.23 (m, 2H), 8.10-8.01 (m, 1H), 7.97 (s, 1H), 7.59-7.52 (m, 1H), 7.17-7.05 (m, 2H), 5.90 (q, J=7.1 Hz, 1H), 3.73-3.64 (m, 1H), 3.51-3.38 (m, 1H), 3.01 (d, J=1.1 Hz, 6H), 2.90-2.64 (m, 5H), 2.47 (hept, J=7.6 Hz, 1H), 2.16-1.55 (m, 12H), 1.38 (dd, J=12.1, 7.7 Hz, 1H), 1 NH exchanged with solvent.

Compound 144: (R)—N-(cyclobutylmethyl)-1-(4-((4-(5-methoxypyridin-3-yl)-1H-imidazol-1-yl)methyl)phenyl)piperidin-3-amine was Obtained Using General Scheme 4 Pathway B Stage 1: General Procedure U was used from 4-iodo-1H-imidazole to afford 3-(1H-imidazol-4-yl)-5-methoxypyridine IM435 as a yellow gum: 216 mg, 31% yield, P=100%, retention time=0.7 min (gradient C), (M+H)$^+$: 176.

Stage 2: RBF (50 mL) was charged with sodium hydride 60% in dispersion in mineral oil (59.2 mg, 1.48 mmol) under nitrogen. THF (2 mL) was added and followed by addition of the solution of IM435 (216 mg, 1.23 mmol) in THF (8 mL) under nitrogen. The mixture was stirred at rt for 20 min and then 1-bromo-4-(bromomethyl)benzene (409 mg, 1.60 mmol) solution in THF (4 mL) was added. The reaction mixture was stirred at rt for 30 min (formation of 10:1 mixture of the regioisomers was observed by LC-MS). The mixture was quenched by careful addition of MeOH (1 mL), the solvent was evaporated and the crude mixture was purified by flash chromatography on silica gel (50 g, 0-10% MeOH in DCM) to afford 3-(1-(4-bromobenzyl)-1H-imidazol-4-yl)-5-methoxypyridine IM436 as a yellow solid: 220 mg, 47% yield, P=91%, retention time=1.3 min (gradient C), (M+H)+: 344/346.

Stage 3: General Procedure Y was used between IM3 and IM436 to afford tert-butyl (R)-(cyclobutylmethyl)(1-(4-((4-(5-methoxypyridin-3-yl)-1H-imidazol-1-yl)methyl)phenyl)piperidin-3-yl)carbamate IM437 as light brown gummy oil: 294 mg, 82% yield, P=95%, retention time=1.9 min (gradient C), (M+H)+: 532.

Stage 4: General Procedure A2 was used from IM437 to afford compound 144 as a yellow gummy solid: 148 mg, 65% yield, P=99%, retention time=2.6 min (gradient E), (M+H)$^+$: 432. $^1$H NMR (400 MHZ, CD$_3$OD) δ 8.47 (d, J=1.6 Hz, 1H), 8.07 (d, J=2.8 Hz, 1H), 7.82 (d, J=1.1 Hz, 1H), 7.72 (dd, J=2.7, 1.8 Hz, 1H), 7.65 (d, J=1.2 Hz, 1H), 7.24 (d, J=8.7 Hz, 2H), 6.99 (d, J=8.7 Hz, 2H), 5.15 (s, 2H), 3.91 (s, 3H), 3.69-3.62 (m, 1H), 3.52-3.43 (m, 1H), 2.85-2.76 (m, 2H), 2.73 (d, J=7.1 Hz, 2H), 2.66 (dd, J=11.7, 9.1 Hz, 1H), 2.58-2.43 (m, 1H), 2.17-2.05 (m, 2H), 2.03-1.63 (m, 7H), 1.43-1.29 (m, 1H), 1H exchanged with CD$_3$OD.

Compound 145: (R)—N-(cyclobutylmethyl)-1-(4-((5-(5-methoxypyridin-3-yl)-2H-tetrazol-2-yl)methyl)phenyl)piperidin-3-amine was Obtained Using the Following Procedures Stage 1: To IM320 (230 mg, 1.30 mmol) and potassium carbonate (917 mg, 6.50 mmol) in DMF (7 mL) was added 4-bromobenzyl bromide (805 mg, 3.15 mmol). The reaction mixture was stirred at 100° C. for 5.5 h. Water (15 mL) was added and the mixture was extracted with ethyl acetate (2×100 mL). The organic layers were dried with MgSO$_4$, filtered and evaporated under reduced pressure. The residue was purified on a C-18 column, using 8%-80% MeCN in 10 mM ammonium bicarbonate to afford 3-chloro-6-(1-(5-(5-methoxypyridin-3-yl)-2H-tetrazol-2-yl)ethyl)pyridazine IM438 as colourless oil: 61 mg, 14% yield, P=67%, retention time=1.5 min (gradient C), (M+H)+: 347/349.

Stage 2: General Procedure Y was used between IM438 and IM3 to afford tert-butyl (cyclobutylmethyl)((3R)-1-(6-(1-(5-(5-methoxypyridin-3-yl)-2H-tetrazol-2-yl)ethyl)pyridazin-3-yl)piperidin-3-yl)carbamate IM439 as yellow oil: 97 mg, 100% yield, P=97%, retention time=2.1 min (gradient C), (M+H)$^+$: 534.

Stage 3: General Procedure A2 was used from IM439 to afford compound 145 as a pale yellow solid: 114 mg, 60% yield, P=99%, retention time=3.0 min (gradient E), (M+H)$^+$: 434. $^1$H NMR (400 MHZ, CD$_3$OD) δ 8.82 (d, J=1.6 Hz, 1H), 8.34 (d, J=2.8 Hz, 1H), 8.00 (dd, J=2.8, 1.7 Hz, 1H), 7.35 (d, J=8.7 Hz, 2H), 6.97 (d, J=8.8 Hz, 2H), 5.80 (s, 2H), 3.95 (s, 3H), 3.71-3.64 (m, 1H), 3.54-3.46 (m, 1H), 2.82-2.71 (m, 1H), 2.68 (d, J=7.4 Hz, 2H), 2.67-2.58 (m, 1H), 2.48 (hept, J=7.5 Hz, 1H), 2.15-2.04 (m, 2H), 2.03-1.56 (m, 8H), 1.38-1.24 (m, 1H), 1 proton exchanged with CD$_3$OD.

Compound 146: 1-(1-(4-(5-(1H-pyrazol-1-yl)pyridin-3-yl)-1H-1,2,3-triazol-1-yl)ethyl)-4-((R)-3-((cyclobutylmethyl)amino)piperidin-1-yl)pyridin-2 (1H)-one was Obtained Using General Scheme 1 Pathway B Stage 1: A grey suspension of 3,5-dibromopyridine (1.02 g, 4.2 mmol), 1H-pyrazole (314 mg, 4.61 mmol), potassium carbonate (1.48 g, 10.58 mmol), 1,10-phenanthroline (166 mg, 0.91 mmol) in anhydrous DMF (20 mL) under Ar atmosphere was degassed by Ar bubbling, then copper(I) Iodide (86 mg, 0.45 mmol) was added to afford a dark brown solution which was stirred at 160° C. for 5 h. The reaction mixture was cooled to rt and filtered. The solid was rinsed with EtOAc (2×15 mL) and the filtrate was concentrated under reduced pressure to dryness to afford a crude grey solid. The crude material was purified by an automated flash system (dryload in Celite, 0 to 30% EtOAc in Heptane) to afford 3-bromo-5-(1H-pyrazol-1-yl)pyridine IM440 as a white solid: 510 mg, 54% yield, P=100%, retention time=2.6 min (gradient A), (M+H)+: 224/226.

Stage 2: General Procedure E3 was used from IM440 to afford 3-(1H-pyrazol-1-yl)-5-((trimethylsilyl)ethynyl)pyridine IM441 as orange oil: 441 mg, 74% yield, P=92%, retention time=3.1 min (gradient A), (M+H)$^+$: 242.

Stage 3: General Procedure X was used between IM151 and IM441 to afford 1-(1-(4-(5-(1H-pyrazol-1-yl)pyridin-3-yl)-1H-1,2,3-triazol-1-yl)ethyl)-4-chloropyridin-2 (1H)-one IM442 as yellow oil: 301 mg, 80% yield, P=82% ($^1$H NMR), retention time=2.4 min (gradient A), (M+H)$^+$: 368/370.

Stage 4: General Procedure C was used between IM442 and IM3 to afford tert-butyl ((3R)-1-(1-(1-(4-(5-(1H-pyrazol-1-yl)pyridin-3-yl)-1H-1,2,3-triazol-1-yl)ethyl)-2-oxo-1,2-dihydro pyridin-4-yl)piperidin-3-yl)(cyclobutylmethyl)carbamate IM443 as a light brown solid: 190 mg, 89% yield, P=94%, retention time=2.9 min (gradient A), (M+H)$^+$: 600.

Stage 5: General Procedure A1 was used from IM443 to afford crude compound 146 as off-white solid: 137 mg, 85% yield, P=92%, retention time=3.0 min (gradient B), (M+H)$^+$: 500.

The mixture of diastereomers was purified by chiral preparative HPLC purification using Chiralpak IA column (5 μm, 20×250 mm). Eluent used: TBME/MeOH/DEA: 60/40/0.1% at flow rate of 20 mL/min. First eluted diastereomer: P=100%, retention time=7.9 min, chiral HPLC: P=100%, $^1$H NMR (300 MHZ, CDCl$_3$) δ 8.99 (d, J=2.5 Hz, 1H), 8.96 (d, J=1.9 Hz, 1H), 8.48 (t, J=2.3 Hz, 1H), 8.28 (s, 1H), 8.04 (d, J=2.6 Hz, 1H), 7.78 (d, J=1.7 Hz, 1H), 7.56 (q, J=7.0 Hz, 1H), 7.43 (d, J=8.1 Hz, 1H), 6.53 (t, J=2.2 Hz, 1H), 6.00 (dd, J=8.2, 2.9 Hz, 1H), 5.67 (d, J=2.8 Hz, 1H), 3.83-3.73 (m, 1H), 3.66-3.55 (m, 1H), 2.99-2.86 (m, 1H), 2.66 (t, J=11.7 Hz, 4H), 2.45 (hept, 1H), 2.19 (d, J=7.1 Hz, 3H), 2.10-1.49 (m, 10H), 1 NH exchanged with solvent. Second eluted diastereomer: P=100%, retention time=15.7 min, chiral HPLC: P=99.8%, $^1$H NMR (300 MHZ, CDCl$_3$) δ 8.92 (d, J=2.5 Hz, 1H), 8.90 (d, J=1.9 Hz, 1H), 8.41 (t, J=2.3 Hz, 1H), 8.22 (s, 1H), 7.96 (d, J=2.6 Hz, 1H), 7.71 (d, J=1.8 Hz, 1H), 7.49 (q, J=7.1 Hz, 1H), 7.37 (d, J=8.1 Hz, 1H), 6.46 (t, J=2.2 Hz, 1H), 5.94 (dd, J=8.2, 2.9 Hz, 1H), 5.60 (d, J=2.8 Hz, 1H), 3.80-3.70 (m, 1H), 3.59-3.49 (m, 1H), 2.92-2.79 (m, 1H), 2.71 (d, J=11.1 Hz, 1H), 2.62 (d, J=7.1 Hz, 3H), 2.43-2.32 (m, 1H), 2.12 (d, J=7.0 Hz, 3H), 2.03-1.29 (m, 10H), 1 NH exchanged with solvent.

Compound 147: 1-(1-(4-(1H-pyrazolo[3,4-c]pyridin-4-yl)-1H-1,2,3-triazol-1-yl)ethyl)-4-((R)-3-((cyclobutylmethyl)amino)piperidin-1-yl)pyridin-2(1H)-one was Obtained Using General Scheme 1 Pathway B Stage 1: To a stirred solution of 4-bromo-1H-pyrazolo[3,4-c]pyridine (300 mg, 1.5 mmol) in anhydrous THF (15 mL) were added 3,4-dihydro-2H-pyran (530 mg, 6.11 mmol) and 4-methylbenzenesulfonic acid hydrate (29 mg, 0.15 mmol) one shot at rt. The reaction mixture stirred at refluxed under argon for 15 h, and then cooled to rt, and the solvent was removed under reduced pressure. The residue was taken-up in EtOAc (50 mL) and washed with a saturated aqueous solution of NaHCO$_3$ (2×25 mL), followed by brine (15 mL). Resulting organic layer was dried over MgSO$_4$, filtered and concentrated under reduced pressure to dryness to give the crude as a brown oil. The latter was purified by automated flash chromatography (dry load, nHept/EtOAc: 100/0 to 7/3) to afford 4-bromo-2-tetrahydropyran-2-yl-pyrazolo[3,4-c]pyridine IM444 as colourless oil (266 mg, 61% yield, P=97%, retention time=2.6 min (gradient A), (M+H)$^+$: 282/284) and 4-bromo-1-tetrahydropyran-2-yl-pyrazolo[3,4-c]pyridine IM445 as yellow liquid (92 mg, 20% yield, P=91%, retention time=2.2 min (gradient A), (M+H)$^+$: 282/284).

Stage 2: General Procedure E1 was used from IM445 to afford 2-(tetrahydro-2H-pyran-2-yl)-4-((trimethylsilyl)ethynyl)-2H-pyrazolo[3,4-c]pyridine IM446 as light brown oil: 45 mg, 15% yield, P=89%, retention time=2.9 min (gradient A), (M+H)$^+$: 300.

Stage 3: General Procedure X was used between IM151 and IM446 to afford 4-chloro-1-(1-(4-(2-(tetrahydro-2H-pyran-2-yl)-2H-pyrazolo[3,4-c]pyridin-4-yl)-1H-1,2,3-triazol-1-yl)ethyl) pyridin-2 (1H)-one IM447 as yellow oil: 35 mg, 53% yield, P=73%, retention time=2.3 min (gradient A), (M+H)$^+$: 426/428.

Stage 4: General Procedure C was used between IM447 and IM3 to afford tert-butyl (cyclobutylmethyl)((3R)-1-(2-oxo-1-(1-(4-(2-(tetrahydro-2H-pyran-2-yl)-2H-pyrazolo[3,4-c]pyridin-4-yl)-1H-1,2,3-triazol-1-yl)ethyl)-1,2-dihydropyridin-4-yl)piperidin-3-yl)carbamate IM448 as light brown oil: 35 mg, 79% yield, P=97%, retention time=2.7 min (gradient A), (M+H)$^+$: 658.

Stage 5: General Procedure A1 was used from IM448 to afford crude compound 147 as a white solid: 22 mg, 90% yield, P=100%, retention time=2.6 min (gradient B), (M+H)$^+$: 474.

NMR (300 MHz, CDCl$_3$) δ 8.98 (s, 1H), 8.68 (d, J=5.6 Hz, 2H), 8.41 (s, 1H), 7.72-7.64 (m, 1H), 7.52 (d, J=8.1 Hz, 1H), 6.09-5.99 (m, 1H), 5.73 (d, J=2.8 Hz, 1H), 3.82-3.72 (m, 1H), 3.69-3.59 (m, 1H), 3.00-2.86 (m, 1H), 2.84-2.49 (m, 4H), 2.47-2.32 (m, 1H), 2.23 (d, J=7.1 Hz, 3H), 2.14-1.30 (m, 10H). 2 NH exchanged with solvent.

Compound 148: (R)-5-(1-(3-(4-(3-((cyclobutylmethyl)amino)piperidin-1-yl)phenyl)oxetan-3-yl)-1H-1,2,3-triazol-4-yl)-N,N-dimethylpyridin-3-amine was Obtained Using General Scheme 1 Pathway A Stage 1: General Procedure X was used between IM411 and IM345 to afford tert-butyl (R)-(cyclobutylmethyl)(1-(4-(3-(4-(5-(dimethylamino)pyridin-3-yl)-1H-1,2,3-triazol-1-yl)oxetan-3-yl)phenyl)piperidin-3-yl)carbamate IM449 as a white solid: 43 mg, 72% yield, P=100%, retention time=2.2 min (gradient A), (M+H)$^+$: 588.

Stage 2: General Procedure A1 was used from IM449 to afford crude compound 148 as a white solid: 29 mg, 81% yield, P=100%, retention time=2.9 min (gradient B), (M+H)$^+$: 488. $^1$H NMR (300 MHz, CDCl$_3$) δ 8.20 (s, 1H), 8.09 (s, 1H), 7.62-7.56 (m, 1H), 7.54 (s, 1H), 7.12 (d, J=8.7 Hz, 2H), 6.94 (d, J=8.8 Hz, 2H), 5.61 (d, J=6.7 Hz, 2H), 5.28 (d, J=6.7 Hz, 2H), 3.74-3.65 (m, 1H), 3.57-3.45 (m, 1H), 3.04 (s, 6H), 2.85 (d, J=2.9 Hz, 1H), 2.77-2.62 (m, 4H), 2.47 (hept, J=7.5 Hz, 1H), 2.16-1.76 (m, 7H), 1.75-1.57 (m, 3H), 1 NH exchanged with solvent.

Compound 149: (R)-5-(1-(3-(5-(3-((cyclobutylmethyl)amino)piperidin-1-yl)pyridin-2-yl)oxetan-3-yl)-1H-1,2,3-triazol-4-yl)-N,N-dimethylpyridin-3-amine was Obtained Using General Scheme 1 Pathway A Stage 1: To an oven-dried Schlenk tube under Ar atmosphere were added 2,5-dibromopyridine (0.85 g, 3.52 mmol) and anhydrous toluene (8.8 mL) to afford an orange suspension which was stirred at −78° C. n-Butyl lithium in hexane (1.43 mL, 3.43 mmol) was added over 5 min and the mixture was stirred at −78° C. for 10 min. Then a solution of 2-methyl-N-(oxetan-3-ylidene)propane-2-sulfinamide (0.50 g, 2.74 mmol) in anhydrous toluene (1.0 mL) was added at −78° C. and the reaction mixture was stirred at −78° C. for 30 min and 20 min at 0° C. NH$_4$Cl saturated solution (1.5 mL) was added, followed by water (5 mL) and EtOAc (50 mL). Layers were separated and the aqueous layer was extracted with EtOAc (50 mL). Then combined organic layers were washed with brine (20 mL), dried over MgSO$_4$, filtered and the filtrate was concentrated under reduced pressure to dryness to afford 1.1 g as crude brown oil. The crude material was purified by an automated flash system (liquid injection in DCM, 0 to 100% EtOAc in Heptane) to afford N-(3-(5-bromopyridin-2-yl)oxetan-3-yl)-2-methyl-propane-2-sulfinamide IM450 as orange oil: 348 mg, 36% yield, P=95% (215 nm), retention time=2.4 min (gradient A), (M+H)⁺: 333/335.

Stage 2: General Procedure Y was used between IM3 and IM450 to afford tert-butyl ((3R)-1-(6-(3-((tert-butylsulfinyl)amino)oxetan-3-yl)pyridin-3-yl)piperidin-3-yl)(cyclobutylmethyl) carbamate IM451 as a yellow solid: 350 mg, 38% yield, P=95%, retention time=2.6 min (gradient A), (M+H)+: 521.

Stage 3: To a solution of IM451 (350 mg, 0.64 mmol) in THF (1.6 mL) and water (300 µL) was added iodine (64 mg, 0.25 mmol) at rt and the reaction mixture was stirred at 55° C. for 1.5 h. The reaction mixture was cooled to rt and diluted with EtOAc (20 mL), then washed with a mixture of $Na_2S_2O_3$ (2 M, 10 mL) and $NaHCO_3$ saturated solution (10 mL). The aqueous layer was extracted with EtOAc (10 mL) and the combined organic layers were dried over $MgSO_4$, filtered and the filtrate was concentrated under vacuum to afford crude tert-butyl (R)-(1-(6-(3-aminooxetan-3-yl)pyridin-3-yl)piperidin-3-yl)(cyclobutylmethyl)carbamate IM452 as yellow oil: 283 mg, 80% yield, P=75%, retention time=2.4 min (gradient A), (M+H)+: 416.

Stage 4: General Procedure V was used from IM452 to afford tert-butyl (R)-(1-(6-(3-azidooxetan-3-yl)pyridin-3-yl)piperidin-3-yl)(cyclobutylmethyl)carbamate IM453 as colourless oil: 150 mg, 56% yield, P=100%, retention time=3.0 min (gradient A), (M+H)⁺: 442.

Stage 5: General Procedure D1 was used from IM345 to afford 5-ethynyl-N,N-dimethylpyridin-3-amine IM454 as an off-white solid: 163 mg, 70% yield, P=99% (¹H NMR), retention time=1.8 min (gradient A), (M+H)⁺: 147.

Stage 6: General Procedure B was used between IM453 and IM454 to afford tert-butyl (R)-(cyclobutylmethyl)(1-(6-(3-(4-(5-(dimethylamino)pyridin-3-yl)-1H-1,2,3-triazol-1-yl)oxetan-3-yl)pyridin-3-yl)piperidin-3-yl)carbamate IM455 as colourless oil: 48 mg, 72% yield, P=100%, retention time=2.6 min (gradient A), (M+H)⁺: 589.

Stage 7: General Procedure A1 was used from IM455 to afford crude compound 149 as a white solid: 38 mg, 94% yield, P=99%, retention time=2.7 min (gradient B), (M+H)⁺: 489. ¹H NMR (300 MHz, CDCl₃) δ 8.60-7.90 (brs, 1H), 8.34 (d, J=2.9 Hz, 1H), 7.75 (s, 1H), 7.59 (s, 1H), 7.26 (s, 1H), 7.14 (dd, J=8.9, 3.0 Hz, 1H), 6.90 (d, J=8.7 Hz, 1H), 5.55 (d, J=6.7 Hz, 2H), 5.49 (d, J=6.7 Hz, 2H), 3.74-3.65 (m, 1H), 3.58-3.48 (m, 1H), 3.04 (s, 6H), 2.96-2.83 (m, 1H), 2.83-2.52 (m, 4H), 2.45 (hept, J=7.6 Hz, 1H), 2.13-1.32 (m, 10H), 1 NH exchanged with solvent.

Compound 150: (R)—N-(cyclobutylmethyl)-1-(6-(3-(4-(5-methoxypyridin-3-yl)-1H-1,2,3-triazol-1-yl)oxetan-3-yl)pyridin-3-yl)piperidin-3-amine was Obtained Using General Scheme 1 Pathway A Stage 1: General Procedure B was used between IM44 and IM453 to afford tert-butyl (R)-(cyclobutylmethyl)(1-(6-(3-(4-(5-methoxypyridin-3-yl)-1H-1,2,3-triazol-1-yl)oxetan-3-yl) pyridin-3-yl)piperidin-3-yl)carbamate IM456 as colourless oil: 62 mg, 95% yield, P=100%, retention time=2.7 min (gradient A), (M+H)⁺: 576.

Stage 2: General Procedure A1 was used from IM456 to afford crude compound 150 as a white solid: 49 mg, 96% yield, P=100%, retention time=2.7 min (gradient B), (M+H)⁺: 476. ¹H NMR (300 MHZ, CDCl₃) δ 8.51 (s, 1H), 8.34 (d, J=2.9 Hz, 1H), 8.27 (s, 1H), 7.83-7.74 (m, 2H), 7.15 (dd, J=8.7, 2.9 Hz, 1H), 6.95 (d, J=8.6 Hz, 1H), 5.55 (d, J=6.8 Hz, 2H), 5.49 (d, J=6.7 Hz, 2H), 3.92 (d, J=1.2 Hz, 3H), 3.74-3.65 (m, 1H), 3.58-3.47 (m, 1H), 2.96-2.84 (m, 1H), 2.71 (d, J=7.2 Hz, 4H), 2.44 (hept, J=7.6 Hz, 1H), 2.14-1.29 (m, 10H), 1 NH exchanged with solvent.

Compound 151: 4-((R)-3-((cyclobutylmethyl)amino)piperidin-1-yl)-1-(1-(4-(5-(ethyl(methyl)amino)pyridin-3-yl)-1H-1,2,3-triazol-1-yl)ethyl)pyridin-2 (1H)-one was Obtained Using General Scheme 1 Pathway B Stage 1: General Procedure E1 was used from 3,5-dibromopyridine to afford 3-bromo-5-((trimethylsilyl)ethynyl)pyridine IM457 as brown oil: 1.7 g, 45% yield, P=56% (¹H NMR), retention time=3.4 min (gradient A), (M+H)⁺: 254/256.

Stage 2: General Procedure D1 was used from IM457 to afford 3-bromo-5-ethynylpyridine IM458 as an off-white solid: 630 mg, 81% yield, P=88% (¹H NMR), retention time=2.7 min (gradient A), (M+H)⁺: 182/184.

Stage 3: General Procedure B was used between IM151 and IM458 to afford 1-(1-(4-(5-bromopyridin-3-yl)-1H-1,2,3-triazol-1-yl)ethyl)-4-chloropyridin-2 (1H)-one IM459 as an off-white solid: 1.03 g, 86% yield, P=97%, retention time=2.6 min (gradient A), (M+H)⁺: 380/382.

Stage 4: General Procedure C was used between IM459 and IM3 to afford tert-butyl ((3R)-1-(1-(1-(4-(5-bromopyridin-3-yl)-1H-1,2,3-triazol-1-yl)ethyl)-2-oxo-1,2-dihydropyridin-4-yl)piperidin-3-yl)(cyclobutylmethyl)carbamate IM460 as a white solid: 1.4 g, 84% yield, P=96%, retention time=3.1 min (gradient A), (M+H)⁺: 612/614.

Stage 5: General Procedure Y was used between N-ethylmethylamine and IM460 to afford tert-butyl (cyclobutylmethyl)((3R)-1-(1-(1-(4-(5-(ethyl(methyl)amino)pyridin-3-yl)-1H-1,2,3-triazol-1-yl)ethyl)-2-oxo-1,2-dihydropyridin-4-yl)piperidin-3-yl)carbamate IM461 as colourless oil: 33 mg, 63% yield, P=90%, retention time=2.6 min (gradient A), (M+H)+: 591.

Stage 6: General Procedure A1 was used from IM461 to afford crude compound 151 as colourless oil: 26 mg, 95% yield, P=89%, retention time=2.6 min (gradient B), (M+H)⁺: 491.

The mixture of diastereomers was purified by chiral preparative HPLC purification using Chiralpak IA column (5 µm, 20×250 mm). Eluent used: TBME/MeOH/DCM/DEA: 40/40/20/0.1% at flow rate of 20 mL/min. First eluted diastereomer: P=100%, retention time=6.9 min, chiral HPLC: P=100%, ¹H NMR (300 MHz, CDCl₃) δ 8.29 (d, J=1.7 Hz, 1H), 8.11 (d, J=1.2 Hz, 1H), 8.09 (d, J=2.8 Hz, 1H), 7.56 (q, J=7.0 Hz, 1H), 7.47 (d, J=2.2 Hz, 1H), 7.43 (d, J=8.0 Hz, 1H), 6.03-5.94 (m, 1H), 5.68 (d, J=2.7 Hz, 1H), 3.85-3.75 (m, 1H), 3.66-3.56 (m, 1H), 3.46 (q, J=7.0 Hz, 2H), 2.98 (d, J=1.3 Hz, 3H), 2.96-2.86 (m, 1H), 2.83-2.75 (m, 1H), 2.69 (d, J=7.2 Hz, 2H), 2.65-2.59 (m, 1H), 2.50-2.39 (m, 1H), 2.16 (d, J=6.9 Hz, 3H), 2.08-1.48 (m, 10H), 1.22-1.11 (m, 3H), 1 NH exchanged with solvent. Second eluted diastereomer: P=100%, retention time=10.0 min, chiral HPLC: P=100 ¹H NMR (300 MHz, CDCl₃) δ 8.29 (d, J=1.7 Hz, 1H), 8.14 (s, 1H), 8.08 (d, J=3.0 Hz, 1H), 7.56 (q, J=7.0 Hz, 1H), 7.50-7.41 (m, 2H), 5.99 (dd, J=8.1, 2.8 Hz, 1H), 5.67 (d, J=2.8 Hz, 1H), 3.84 (s, 1H), 3.60 (d, J=13.2 Hz, 1H), 3.46 (q, J=7.1 Hz, 2H), 2.98 (s, 3H), 2.90 (d, J=11.5 Hz, 2H), 2.71 (d, J=6.5 Hz, 2H), 2.48 (s, 1H), 2.16 (d, J=7.0 Hz, 3H), 2.11-1.39 (m, 10H), 1.16 (t, J=7.0 Hz, 3H), 1 NH exchanged with solvent.

Compound 152: 1-(1-(4-(5-bromopyridin-3-yl)-1H-1,2,3-triazol-1-yl)ethyl)-4-((R)-3-((cyclobutylmethyl)amino)piperidin-1-yl)pyridin-2 (1H)-one was Obtained Using General Scheme 1 Pathway B Stage 1: General Procedure A1 was used from IM460 to afford crude compound 152 as a white powder: 32 mg, 74% yield, P=93%, retention time=2.6 min (gradient B), (M+H)$^+$: 512/514.

The mixture of diastereomers was purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=100%, retention time=7.6 min, chiral HPLC: P=100%, $^1$H NMR (300 MHz, CDCl$_3$) δ 8.92 (d, J=1.9 Hz, 1H), 8.62 (d, J=2.3 Hz, 1H), 8.32 (d, J=2.2 Hz, 1H), 8.20 (s, 1H), 7.53 (q, J=7.1 Hz, 1H), 7.43 (d, J=8.1 Hz, 1H), 6.00 (dd, J=8.2, 2.9 Hz, 1H), 5.66 (d, J=2.9 Hz, 1H), 3.84-3.74 (m, 1H), 3.67-3.56 (m, 1H), 2.93 (t, J=12.3 Hz, 1H), 2.77 (s, 1H), 2.68 (d, J=7.2 Hz, 2H), 2.61 (s, 1H), 2.49-2.38 (m, 1H), 2.18 (d, J=7.0 Hz, 3H), 2.12-1.40 (m, 10H), 1 NH exchanged with solvent. Second eluted diastereomer: P=100%, retention time=16.2 min, chiral HPLC: P=99.8%, $^1$H NMR (300 MHz, CDCl$_3$) δ 8.93 (s, 1H), 8.62 (d, J=2.2 Hz, 1H), 8.33 (s, 1H), 8.25 (s, 1H), 7.54 (q, J=6.9 Hz, 1H), 7.46 (d, J=8.1 Hz, 1H), 6.01 (dd, J=8.3, 2.7 Hz, 1H), 5.67 (d, J=2.9 Hz, 1H), 3.86 (s, 1H), 3.61 (d, J=13.5 Hz, 1H), 2.93 (t, J=11.6 Hz, 1H), 2.78-2.63 (m, 3H), 2.49 (s, 2H), 2.18 (d, J=7.0 Hz, 3H), 2.11-1.25 (m, 10H), 1 NH exchanged with solvent.

Compound 153: 4-((R)-3-((cyclobutylmethyl)amino)piperidin-1-yl)-1-(1-(4-(5-(3-methyl-2-oxoimidazolidin-1-yl)pyridin-3-yl)-1H-1,2,3-triazol-1-yl)ethyl)pyridin-2 (1H)-one was Obtained Using General Scheme 1 Pathway B Stage 1: General Procedure Y was used between 1-Methyl-2-imidazolidinone and IM460 to afford tert-butyl (cyclobutylmethyl)((3R)-1-(1-(1-(4-(5-(3-methyl-2-oxoimidazolidin-1-yl) pyridin-3-yl)-1H-1,2,3-triazol-1-yl)ethyl)-2-oxo-1,2-dihydropyridin-4-yl)piperidin-3-yl) carbamate IM462 as colourless oil: 74 mg, 93% yield, P=100%, retention time=2.6 min (gradient A), (M+H)+: 632.

Stage 2: General Procedure A1 was used from IM462 to afford crude compound 153 as a white powder: 52 mg, 83% yield, P=99%, retention time=2.6 min (gradient B), (M+H)$^+$: 532.

The mixture of diastereomers was purified by chiral preparative HPLC purification using Chiralpak IA column (5 μm, 20×250 mm). Eluent used: TBME/MeOH/DCM/DEA: 40/40/20/0.1% at flow rate of 20 ml/min. First eluted diastereomer: P=100%, retention time=10.0 min, chiral HPLC: P=100%, $^1$H NMR (300 MHz, CDCl$_3$) δ 8.83 (d, J=2.6 Hz, 1H), 8.70 (d, J=1.9 Hz, 1H), 8.29 (t, J=2.2 Hz, 1H), 8.13 (s, 1H), 7.54 (q, J=7.0 Hz, 1H), 7.38 (d, J=8.1 Hz, 1H), 5.97 (dd, J=8.1, 2.8 Hz, 1H), 5.64 (d, J=2.8 Hz, 1H), 3.85 (dd, J=9.2, 6.6 Hz, 2H), 3.80-3.69 (m, 1H), 3.65-3.56 (m, 1H), 3.56-3.47 (m, 2H), 2.99-2.84 (m, 4H), 2.77-2.50 (m, 4H), 2.39 (hept, J=7.5 Hz, 1H), 2.14 (d, J=7.0 Hz, 3H), 2.12-1.23 (m, 10H), 1 NH exchanged with solvent. Second eluted diastereomer: P=100%, retention time=11.8 min, chiral HPLC: P=99.1%, $^1$H NMR (300 MHz, CDCl$_3$) δ 8.81 (d, J=2.6 Hz, 1H), 8.69 (d, J=1.8 Hz, 1H), 8.28 (t, J=2.2 Hz, 1H), 8.13 (s, 1H), 7.53 (q, J=7.0 Hz, 1H), 7.37 (d, J=8.1 Hz, 1H), 5.96 (dd, J=8.1, 2.8 Hz, 1H), 5.63 (d, J=2.8 Hz, 1H), 3.84 (dd, J=9.4, 6.5 Hz, 2H), 3.79-3.64 (m, 1H), 3.64-3.47 (m, 3H), 2.97-2.82 (m, 4H), 2.77-2.50 (m, 4H), 2.38 (hept, J=7.6 Hz, 1H), 2.15 (s, 3H), 2.10-1.26 (m, 10H), 1 NH exchanged with solvent.

Compound 154: 4-((R)-3-((cyclobutylmethyl)amino)piperidin-1-yl)-1-(1-(4-(5-(methyl(2,2,2-trifluoroethyl)amino)pyridin-3-yl)-1H-1,2,3-triazol-1-yl)ethyl)pyridin-2 (1H)-one was Obtained Using General Scheme 1 Pathway B Stage 1: General Procedure Y was used between 2,2,2-Trifluoro-N-methylethanamine hydrochloride and IM460 to afford tert-butyl (cyclobutylmethyl)((3R)-1-(1-(1-(4-(5-(methyl(2,2,2-trifluoroethyl)amino)pyridin-3-yl)-1H-1,2,3-triazol-1-yl)ethyl)-2-oxo-1,2-dihydropyridin-4-yl)piperidin-3-yl)carbamate IM463 as a white solid: 70 mg, 70% yield, P=81%, retention time=2.6 min (gradient A), (M+H)+: 645.

Stage 2: General Procedure A1 was used from IM463 to afford crude compound 154 as a yellow solid: 37 mg, 55% yield, P=75%, retention time=2.6 min (gradient B), (M+H)$^+$: 545.

The product was purified by reverse phase preparative HPLC purification (Waters XBridge C18 5 μm, 19×100 mm). Gradient used: increased linearly from 25 to 50% solution "B" over 5.5 min, increased linearly to 85% solution "B" over 0.8 min, and returned to initial conditions over 1.0 min. Flow Rate: 15 mL/min. P=100%.

The mixture of diastereomers was further purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=100%, retention time=5.1 min, chiral HPLC: P=99.8%, $^1$H NMR (300 MHz, CDCl$_3$) δ 8.42 (d, J=1.7 Hz, 1H), 8.18 (d, J=3.0 Hz, 1H), 8.13 (s, 1H), 7.64-7.49 (m, 2H), 7.42 (d, J=8.1 Hz, 1H), 5.98 (dd, J=8.1, 2.8 Hz, 1H), 5.65 (d, J=2.8 Hz, 1H), 3.94 (q, J=8.8 Hz, 2H), 3.81-3.69 (m, 1H), 3.65-3.55 (m, 1H), 3.14 (s, 3H), 2.99-2.84 (m, 1H), 2.78-2.50 (m, 4H), 2.40 (hept, J=7.6 Hz, 1H), 2.16 (d, J=7.0 Hz, 3H), 2.13-1.23 (m, 10H), 1 NH exchanged with solvent. $^{19}$F NMR (282 MHZ, CDCl$_3$) δ −67.35 (t, J=8.9 Hz). Second eluted diastereomer: P=100%, retention time=6.0 min, chiral HPLC: P=99.5%, $^1$H NMR (300 MHz, CDCl$_3$) δ 8.42 (d, J=1.7 Hz, 1H), 8.18 (d, J=3.0 Hz, 1H), 8.13 (s, 1H), 7.64-7.49 (m, 2H), 7.42 (d, J=8.1 Hz, 1H), 5.99 (dd, J=8.1, 2.9 Hz, 1H), 5.65 (d, J=2.8 Hz, 1H), 3.94 (q, J=8.7 Hz, 2H), 3.81-3.71 (m, 1H), 3.65-3.55 (m, 1H), 3.14 (s, 3H), 2.99-2.84 (m, 1H), 2.79-2.52 (m, 4H), 2.40 (hept, J=7.5 Hz, 1H), 2.16 (d, J=7.0 Hz, 3H), 2.11-1.26 (m, 10H), 1 NH exchanged with solvent. $^{19}$F NMR (282 MHZ, CDCl$_3$) δ −67.35 (t, J=8.8 Hz).

Compound 155: (R)-5-(1-(1-(4-(3-((cyclobutylmethyl)amino)piperidin-1-yl)phenyl)vinyl)-1H-1,2,3-triazol-4-yl)-N,N-dimethylpyridin-3-amine was Obtained Using General Scheme 1 Pathway A Stage 1: General Procedure A1 was used from compound 148 to afford crude 3-chloro-2-(4-((R)-3-((cyclobutylmethyl)amino)piperidin-1-yl)phenyl)-2-(4-(5-(dimethylamino)pyridin-3-yl)-1H-1,2,3-triazol-1-yl)propan-1-ol IM464 as colourless oil: 20 mg, 87% yield, P=97%, retention time=2.1 min (gradient A), (M+H)$^+$: 525.

Stage 2: To a mixture of IM464 (20 mg, 0.04 mmol) in anhydrous THF (0.5 mL) under Ar atmosphere at 0° C. was added potassium tert-butoxide in THE solution (60 μL, 0.06 mmol) and the resulting yellow solution was stirred at rt for 10 min. The reaction mixture was quenched with water (5 mL), extracted with EtOAc (15 mL) and washed with brine (3 mL). The organic extract was dried over MgSO$_4$, filtered, and concentrated under reduced pressure to dryness to afford crude compound 155 as a white solid: 17 mg, 95% yield, P=98%, retention time=2.1 min (gradient B), (M+H)$^+$: 458. $^1$H NMR (300 MHz, CDCl$_3$) δ 8.27 (s, 1H), 8.11 (s, 1H), 7.86 (s, 1H), 7.62 (d, J=3.0 Hz, 1H), 7.22 (d, J=8.8 Hz, 2H), 6.90 (d, J=8.6 Hz, 2H), 5.67 (s, 1H), 5.44 (s, 1H), 3.89-3.79 (m, 1H), 3.58-3.48 (m, 1H), 3.05 (s, 3H), 2.99-2.78 (m, 5H), 2.65-2.51 (m, 1H), 2.17-1.20 (m, 10H), 1 NH exchanged with solvent Compound 156: 4-((R)-3-((cyclobutylmethyl) amino)piperidin-1-yl)-1-(1-(1-(5-(dimethyl amino) pyridin-3-yl)-1H-pyrazol-4-yl)ethyl)pyridin-2 (1H)- one was Obtained Using General Scheme 3 Scheme 5

Stage 1: To a solution of 5-bromo-N,N-dimethylpyridin-3-amine (421 mg, 1.99 mmol) in DMF (5 mL) was added 1-(1H-pyrazol-4-yl)ethanone (339 mg, 2.98 mmol), potassium carbonate (842 mg, 5.97 mmol), copper(I) iodide (18.9 mg, 99.5 µmol) and trans-n,n'-dimethylcyclohexane-1,2-diamine (64.7 µL, 398 µmol) and the reaction mixture was stirred at 110° C. for 2 days. The mixture was cooled to rt and filtered. Purification by reverse phase using a gradient elution of 0-100% MeCN in 10 mM ammonium formate solution afforded 1-(1-(5-(dimethylamino)pyridin-3-yl)-1H-pyrazol-4-yl)ethan-1-one IM465: 280 mg, 61% yield, P=100% (1H NMR).

Stage 2: To a solution of IM465 (20.0 mg, 86.9 µmol) in MeOH (1 mL) at 0° C. was added sodium borohydride (6.7 mg, 174 µmol) and the reaction mixture was stirred at 0° C. for 30 min. The mixture was quenched by the addition of saturated NH$_4$Cl solution (5 mL). The mixture was concentrated and the residue was dissolved in DCM (5 mL). Anhydrous MgSO$_4$ was added and the mixture was filtered and concentrated to afford crude 1-(1-(5-(dimethylamino) pyridin-3-yl)-1H-pyrazol-4-yl)ethan-1-ol IM466 as colourless oil: 20 mg, 99% yield, P=100%, retention time=0.8 min (gradient F), (M+H)$^+$: 233.

Stage 3: General Procedure T was used between 4-chloropyridin-2-ol and IM466 to afford 4-chloro-1-(1-(1-(5-(dimethylamino)pyridin-3-yl)-1H-pyrazol-4-yl)ethyl)pyridin-2 (1H)-one IM467 as a yellow solid: 30 mg, 44% yield, P=50% (1H NMR), retention time=1.2 min (gradient F), (M+H)$^+$: 344/346.

Stage 4: General Procedure C was used between IM467 and IM3 to afford tert-butyl (cyclobutylmethyl)((3R)-1-(1-(1-(1-(5-(dimethylamino)pyridin-3-yl)-1H-pyrazol-4-yl) ethyl)-2-oxo-1,2-dihydropyridin-4-yl)piperidin-3-yl)carbamate IM468 as brown oil: 12 mg, 5% yield, P=96%, retention time=1.7 min (gradient F), (M+H)$^+$: 576.

Stage 5: General Procedure A2 was used from IM468 to afford compound 156 as a brown solid: 2 mg, 19% yield, P=96%, retention time=2.4 min (gradient E), (M+H)$^+$: 476.

The mixture of diastereomers was purified by chiral preparative HPLC purification using Chiralpak IA column (5 µm, 20×250 mm). Eluent used: TBME/MeOH/DCM/DEA: 40/40/20/0.1% at flow rate of 20 mL/min. First eluted diastereomer: P=100%, retention time=5.4 min, chiral HPLC: P=99.8, $^1$H NMR (300 MHz, CDCl$_3$) δ 8.20 (d, J=2.2 Hz, 1H), 8.04 (d, J=2.8 Hz, 1H), 7.86 (s, 1H), 7.65 (s, 1H), 7.29 (dd, J=2.5, 2.5 Hz, 1H), 7.02 (d, J=7.9 Hz, 1H), 6.35 (q, J=7.0 Hz, 1H), 5.91 (dd, J=8.0, 2.9 Hz, 1H), 5.75 (d, J=2.9 Hz, 1H), 3.75 (d, J=12.1 Hz, 1H), 3.59 (d, J=13.1 Hz, 1H), 3.04 (s, 6H), 2.96-2.81 (m, 1H), 2.75-2.54 (m, 4H), 2.48-2.32 (m, 1H), 2.17-1.42 (m, 12H), 1.42-1.22 (m, 1H), 1H exchanged with solvent. Second eluted diastereomer: P=100%, retention time=6.4 min, chiral HPLC: P=99.6%, $^1$H NMR (300 MHz, CDCl$_3$) δ 8.20 (d, J=2.1 Hz, 1H), 8.04 (d, J=2.7 Hz, 1H), 7.86 (s, 1H), 7.65 (s, 1H), 7.29 (s, 1H), 7.02 (dd, J=8.0, 1.1 Hz, 1H), 6.34 (q, J=7.0 Hz, 1H), 5.91 (dd, J=8.1, 2.9 Hz, 1H), 5.75 (d, J=2.7 Hz, 1H), 3.80-3.70 (m, 1H), 3.66-3.52 (m, 1H), 3.03 (s, 6H), 2.94-2.81 (m, 1H), 2.76-2.54 (m, 4H), 2.51-2.30 (m, 1H), 2.15-1.44 (m, 12H), 1.39-1.23 (m, 1H), 1H exchanged with solvent.

Compound 157: 2-(6-((R)-3-((cyclobutylmethyl) amino)piperidin-1-yl)pyridazin-3-yl)-N-(5-(dimethylamino)pyridin-3-yl)propanamide was Obtained Using General Scheme 6 Pathway A Stage 1: General Procedure AA was used from between 5-bromo-N,N-dimethyl-pyridin-3-amine and benzylamine to afford N$^3$-benzyl-N$^5$,N$^5$-dimethylpyridine-3,5-diamine IM469 as a white solid: 260 mg, 60% yield, P=90%, retention time=2.2 min (gradient A), (M+H)$^+$: 228.

Stage 2: General Procedure I was used from IM469 to afford crude N$^3$,N$^3$-dimethylpyridine-3,5-diamine IM470 as a white solid: 120 mg, 76% yield, P=100% (215 nm), retention time=1.2 min (gradient A).

Stage 3: General Procedure F was used between lithium 2-(6-chloropyridazin-3-yl)propanoate and IM470 to afford 2-(6-chloropyridazin-3-yl)-N-(5-(dimethylamino)pyridin-3-yl) propanamide IM471 as an off-white solid: 120 mg, 67% yield, P=100%, retention time=2.1 min (gradient A), (M+H)$^+$: 306/308.

Stage 4: General Procedure C was used between IM471 and IM3 to afford tert-butyl (cyclobutylmethyl)((3R)-1-(6-(1-(((5-(dimethylamino)pyridin-3-yl)amino)-1-oxopropan-2-yl) pyridazin-3-yl)piperidin-3-yl)carbamate IM472 as orange oil: 185 mg, 75% yield, P=85%, retention time=2.4 min (gradient A), (M+H)$^+$: 538.

Stage 5: General Procedure A1 was used from IM472 to afford compound 157 as a white solid: 80 mg, 63% yield, P=100%, retention time=2.5 min (gradient B), (M+H)$^+$: 438.

The mixture of diastereomers was purified by chiral preparative HPLC purification using Chiralpak IE column (5 µm, 10×250 mm). Eluent used: TBME/MeOH/DEA: 60/40/0.1% at flow rate of 7 mL/min. First eluted diastereomer: P=99%, retention time=5.0 min, chiral HPLC: P=97.9%, $^1$H NMR (300 MHz, CDCl$_3$) δ 8.91 (s, 1H), 7.95 (d, J=2.1 Hz, 1H), 7.83 (d, J=2.7 Hz, 1H), 7.57-7.51 (m, 1H), 7.25 (d, J=9.6 Hz, 1H), 6.93 (d, J=9.4 Hz, 1H), 4.40-4.26 (m, 1H), 4.11-3.96 (m, 2H), 3.13-3.00 (m, 1H), 2.94 (s, 6H), 2.90-2.79 (m, 1H), 2.79-2.58 (m, 3H), 2.50-2.31 (m, 1H), 2.17-1.92 (m, 3H), 1.92-1.70 (m, 5H), 1.65-1.59 (m, 4H), 1.49-1.30 (m, 1H), 1H exchanged with solvent. Second eluted diastereomer: P=100%, retention time=6.3 min, chiral HPLC: P=97.9%, $^1$H NMR (300 MHz, CDCl$_3$) δ 8.99 (s, 1H), 7.95 (d, J=2.1 Hz, 1H), 7.82 (d, J=2.8 Hz, 1H), 7.56-7.53 (m, 1H), 7.27 (d, J=9.4 Hz, 1H), 6.93 (d, J=9.5 Hz, 1H), 4.38-4.27 (m, 1H), 4.10-3.97 (m, 2H), 3.18-2.99 (m, 1H), 2.93 (s, 6H), 2.90-2.80 (m, 1H), 2.77-2.60 (m, 3H), 2.50-2.33 (m, 1H), 2.11-1.74 (m, 8H), 1.71-1.49 (m, 4H), 1.50-1.33 (m, 1H), 1H exchanged with solvent.

Compound 158: 4-((R)-3-((cyclobutylmethyl) amino)piperidin-1-yl)-1-(1-(4-(5-(isopropyl amino) pyridin-3-yl)-1H-1,2,3-triazol-1-yl)ethyl)pyridin-2 (1H)-one was Obtained Using General Scheme 1 Pathway B Stage 1: General Procedure Y was used between isopropylamine and IM460 to afford tert-butyl (cyclobutylmethyl)

((3R)-1-(1-(1-(4-(5-(isopropylamino)pyridin-3-yl)-1H-1,2,3-triazol-1-yl)ethyl)-2-oxo-1,2-dihydropyridin-4-yl)piperidin-3-yl)carbamate IM473 as a white solid: 64 mg, 43% yield, P=94%, retention time=2.6 min (gradient A), (M+H)+: 591.

Stage 2: General Procedure A1 was used from IM473 to afford crude compound 158 as colourless oil: 25 mg, 85% yield, P=97%, retention time=2.8 min (gradient B), (M+H)$^+$: 491.

The mixture of diastereomers was purified by chiral preparative HPLC purification using Chiralpak ID column (5 μm, 10×250 mm). Eluent used: TBME/MeOH/DCM/DEA: 60/40/10/0.1% at flow rate of 7 mL/min. First eluted diastereomer: P=100%, retention time=8.9 min, chiral HPLC: P=100%, $^1$H NMR (300 MHz, CDCl$_3$) δ 8.26 (d, J=1.8 Hz, 1H), 8.08 (s, 1H), 7.93 (d, J=2.8 Hz, 1H), 7.55 (q, J=7.0 Hz, 1H), 7.41 (d, J=8.0 Hz, 1H), 7.35 (t, J=2.3 Hz, 1H), 5.98 (dd, J=8.1, 2.8 Hz, 1H), 5.65 (d, J=2.8 Hz, 1H), 3.68 (dd, J=41.8, 13.3 Hz, 4H), 2.99-2.84 (m, 1H), 2.77-2.51 (m, 4H), 2.39 (hept, J=7.5 Hz, 1H), 2.16 (d, J=7.0 Hz, 3H), 2.10-1.29 (m, 10H), 1.24 (d, J=6.1 Hz, 6H), 1 NH exchanged with solvent. Second eluted diastereomer: P=100%, retention time=12.6 min, chiral HPLC: P=100%, $^1$H NMR (300 MHZ, CDCl$_3$) δ 8.26 (d, J=1.8 Hz, 1H), 8.08 (s, 1H), 7.93 (d, J=2.8 Hz, 1H), 7.55 (q, J=7.0 Hz, 1H), 7.41 (d, J=8.0 Hz, 1H), 7.35 (t, J=2.3 Hz, 1H), 5.98 (dd, J=8.1, 2.8 Hz, 1H), 5.65 (d, J=2.8 Hz, 1H), 3.68 (dd, J=41.8, 13.3 Hz, 4H), 2.99-2.84 (m, 1H), 2.77-2.51 (m, 4H), 2.39 (hept, J=7.5 Hz, 1H), 2.16 (d, J=7.0 Hz, 3H), 2.10-1.27 (m, 10H), 1.24 (d, J=6.1 Hz, 6H), 1 NH exchanged with solvent.

Compound 159: 4-((R)-3-((cyclobutylmethyl)amino)piperidin-1-yl)-1-(1-(4-(5-(2-oxo pyrrolidin-1-yl)pyridin-3-yl)-1H-1,2,3-triazol-1-yl)ethyl)pyridin-2 (1H)-one was Obtained Using General Scheme 1 Pathway B Stage 1: General Procedure Y was used between 2-pyrrolidinone and IM460 to afford tert-butyl (cyclobutylmethyl)((3R)-1-(2-oxo-1-(1-(4-(5-(2-oxopyrrolidin-1-yl)pyridin-3-yl)-1H-1,2,3-triazol-1-yl)ethyl)-1,2-dihydropyridin-4-yl)piperidin-3-yl)carbamate IM474 as a white solid: 67 mg, 67 yield, P=97%, retention time=2.6 min (gradient A), (M+H)+: 617.

Stage 2: General Procedure A2 was used from IM474 to afford crude compound 159 as a white solid: 50 mg, 88% yield, P=96%, retention time=2.0 min (gradient A), (M+H)$^+$: 517.

The mixture of diastereomers was purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=100%, retention time=14.3 min, chiral HPLC: P=100%, $^1$H NMR (300 MHz, CDCl$_3$) δ 8.85 (d, J=2.5 Hz, 1H), 8.80 (d, J=1.7 Hz, 1H), 8.44 (d, J=2.2 Hz, 1H), 8.24 (s, 1H), 7.51 (q, J=6.9 Hz, 1H), 7.41 (d, J=8.0 Hz, 1H), 5.99 (dd, J=8.2, 2.8 Hz, 1H), 5.67 (d, J=2.7 Hz, 1H), 3.97-3.79 (m, 3H), 3.57 (d, J=13.2 Hz, 1H), 2.97-2.85 (m, 2H), 2.82-2.65 (m, 3H), 2.61 (t, J=8.0 Hz, 2H), 2.50 (hept, J=7.5 Hz, 1H), 2.29-2.17 (m, 2H), 2.13 (d, J=7.0 Hz, 3H), 2.09-1.59 (m, 10H), 1 NH exchanged with solvent. Second eluted diastereomer: P=100%, retention time=20.1 min, chiral HPLC: P=100%, $^1$H NMR (300 MHz, CDCl$_3$) δ 8.79 (d, J=2.6 Hz, 1H), 8.74 (d, J=1.9 Hz, 1H), 8.39 (␣J=2.3 Hz, 1H), 8.23 (s, 1H), 7.46 (q, J=7.0 Hz, 1H), 7.39 (d, J=8.1 Hz, 1H), 5.96 (dd, J=8.2, 2.8 Hz, 1H), 5.61 (d, J=2.8 Hz, 1H), 3.87 (q, J=6.9 Hz, 3H), 3.52 (d, J=13.4 Hz, 1H), 2.96-2.81 (m, 2H), 2.76-2.62 (m, 3H), 2.56 (t, J=8.1 Hz, 2H), 2.52-2.43 (m, 1H), 2.17 (q, J=7.5 Hz, 2H), 2.08 (d, J=7.1 Hz, 3H), 2.05-1.37 (m, 10H), 1 NH exchanged with solvent.

Compound 160: 4-((R)-3-((cyclobutylmethyl)amino)piperidin-1-yl)-1-(1-(4-(5-(pyrrolidin-1-yl)pyridin-3-yl)-1H-1,2,3-triazol-1-yl)ethyl)pyridin-2 (1H)-one was Obtained Using General Scheme 1 Pathway B Stage 1: In a microwave vial (20 mL) under nitrogen, to a solution of IM293 (128 mg, 232 μmol) in NMP (2.3 mL) was added pyrrolidine (481 μL, 5.80 mmol). The vial was capped and heated at 130° C. for 40 h. The reaction mixture was concentrated down to remove excess pyrrolidine and directly purified by C18 column (0-100% MeCN in 10 mM ammonium bicarbonate). After solvent evaporation, tert-butyl (cyclobutylmethyl)((3R)-1-(2-oxo-1-(1-(4-(5-(pyrrolidin-1-yl)pyridin-3-yl)-1H-1,2,3-triazol-1-yl)ethyl)-1,2-dihydropyridin-4-yl)piperidin-3-yl)carbamate IM475 was obtained as a beige gum: 141 mg, 100% yield, P=96%, retention time=1.8 min (gradient C), (M+H)$^+$: 603.

Stage 2: General Procedure A2 was used from IM475 to afford compound 160 as a white solid: 84 mg, 72% yield, P=100%, retention time=2.5 min (gradient E), (M+H)$^+$: 503.

The mixture of diastereomers was purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=100%, retention time=9.5 min, chiral HPLC: P=100%, $^1$H NMR (300 MHz, CDCl$_3$) δ 8.27 (d, J=1.7 Hz, 1H), 8.09 (s, 1H), 7.93 (d, J=2.8 Hz, 1H), 7.55 (q, J=7.0 Hz, 1H), 7.42 (d, J=8.1 Hz, 1H), 7.31-7.27 (m, 1H), 5.98 (dd, J=8.1, 2.8 Hz, 1H), 5.65 (d, J=2.8 Hz, 1H), 3.81-3.70 (m, 1H), 3.65-3.55 (m, 1H), 3.39-3.29 (m, 4H), 2.98-2.83 (m, 1H), 2.72 (dd, J=12.9, 9.3 Hz, 1H), 2.66 (d, J=7.2 Hz, 2H), 2.63-2.50 (m, 1H), 2.40 (hept, J=7.6 Hz, 1H), 2.15 (d, J=7.0 Hz, 3H), 2.11-1.26 (m, 14H), 1H exchanged with solvent. Second eluted diastereomer: P=100%, retention time=16.7 min, chiral HPLC: P=100%, $^1$H NMR (300 MHz, CDCl$_3$) δ 8.27 (d, J=1.7 Hz, 1H), 8.09 (s, 1H), 7.93 (d, J=2.8 Hz, 1H), 7.55 (q, J=7.0 Hz, 1H), 7.42 (d, J=8.1 Hz, 1H), 7.31-7.27 (m, 1H), 5.98 (dd, J=8.1, 2.8 Hz, 1H), 5.65 (d, J=2.8 Hz, 1H), 3.81-3.67 (m, 1H), 3.67-3.51 (m, 1H), 3.33 (d, J=6.5 Hz, 4H), 2.96-2.86 (m, 1H), 2.76-2.68 (m, 1H), 2.66 (d, J=7.2 Hz, 2H), 2.63-2.54 (m, 1H), 2.40 (hept, J=7.6 Hz, 1H), 2.15 (d, J=7.0 Hz, 3H), 2.11-1.25 (m, 14H), 1H exchanged with solvent.

Compound 161: 1-(1-(4-(5-(azetidin-1-yl)pyridin-3-yl)-1H-1,2,3-triazol-1-ylethyl)-4-((R)-3-((cyclobutylmethyl)amino)piperidin-1-yl)pyridin-2 (1H)-one was Obtained Using General Scheme 1 Pathway B Stage 1: In a 15 mL pressure flask, to a solution of IM293 (110 mg, 199 μmol) in NMP (1.98 mL) under nitrogen was added azetidine (707 μL, 9.97 mmol) and the mixture was stirred at 130° C. for 20 h (~ 35% conversion was observed by LC-MS). Azetidine (707 μL, 9.97 mmol) was added, and the mixture was re-heated to 130° C. overnight. This step was done each day for 4 days. After 7 days, reaction mixture was brought to rt, then diluted in water and extracted with Et$_2$O (3×). The combined organic layers were washed with brine, dried with Na$_2$SO$_4$, filtered and concentrated. The crude mixture was purified by normal phase column (SiO$_2$, 0% to 5% MeOH in DCM) to afford tert-butyl ((3R)-1-(1-

(1-(4-(5-(azetidin-1-yl)pyridin-3-yl)-1H-1,2,3-triazol-1-yl)ethyl)-2-oxo-1,2-dihydropyridin-4-yl)piperidin-3-yl)(cyclobutyl methyl)carbamate IM476 as a yellow oil: 53 mg, 44% yield, P=99%, retention time=1.6 min (gradient F), (M+H)$^+$: 590.

Stage 2: General Procedure A2 was used from IM476 to afford compound 161 as a white powder: 14 mg, 33% yield, P=100%, retention time=2.3 min (gradient E), (M+H)$^+$: 489.

The mixture of diastereomers was purified by chiral preparative HPLC purification using Chiralpak IA column (5 μm, 20×250 mm). Eluent used: TBME/MeOH/DCM/DEA: 45/45/10/0.1% at flow rate of 20 mL/min. First eluted diastereomer: P=100%, retention time=7.9 min, chiral HPLC: P=100%, $^1$H NMR (300 MHz, CDCl$_3$) δ 8.35 (d, J=1.8 Hz, 1H), 8.10 (s, 1H), 7.79 (d, J=2.7 Hz, 1H), 7.54 (q, J=7.0 Hz, 1H), 7.42 (d, J=8.1 Hz, 1H), 7.18 (t, J=2.3 Hz, 1H), 5.98 (dd, J=8.1, 2.9 Hz, 1H), 5.66 (d, J=2.8 Hz, 1H), 3.97 (t, J=7.2 Hz, 4H), 3.82-3.71 (m, 1H), 3.66-3.55 (m, 1H), 2.99-2.84 (m, 1H), 2.74 (dd, J=12.8, 9.4 Hz, 1H), 2.67 (d, J=7.2 Hz, 2H), 2.64-2.52 (m, 1H), 2.51-2.35 (m, 3H), 2.16 (d, J=7.0 Hz, 3H), 2.13-1.30 (m, 10H), 1H exchanged with solvent. Second eluted diastereomer: P=100%, retention time=15.7 min, chiral HPLC: P=99.8%, $^1$H NMR (300 MHz, CDCl$_3$) δ 8.35 (d, J=1.8 Hz, 1H), 8.12 (s, 1H), 7.79 (d, J=2.8 Hz, 1H), 7.54 (q, J=7.0 Hz, 1H), 7.43 (d, J=8.1 Hz, 1H), 7.19 (t, J=2.3 Hz, 1H), 5.99 (dd, J=8.1, 2.9 Hz, 1H), 5.66 (d, J=2.8 Hz, 1H), 3.97 (t, J=7.2 Hz, 4H), 3.85-3.75 (m, 1H), 3.65-3.55 (m, 1H), 2.98-2.85 (m, 1H), 2.84-2.71 (m, 1H), 2.68 (d, J=7.2 Hz, 3H), 2.43 (p, J=7.2 Hz, 3H), 2.16 (d, J=7.1 Hz, 3H), 2.08-1.36 (m, 10H), 1H exchanged with solvent.

Compound 162: 2-(4-((R)-3-((cyclobutylmethyl)amino)piperidin-1-yl)-2-oxopyridin-1(2H)-yl)-N-(5-(dimethylamino)pyridin-3-yl)propanamide was Obtained Using General Scheme 6 Pathway B Stage 1: To a solution of 4-chloro-2-hydroxypyridine (300 mg, 2.25 mmol) in anhydrous DMF (10 mL), were added potassium carbonate (470 mg, 3.37 mmol), followed by methyl-2-chloropropionate (320 mg, 2.48 mmol). The mixture was stirred at 100° C. for 2.5 h. The crude product was purified over automated flash chromatography system (liquid load in DCM, 0 to 100% EtOAc in heptane to afford methyl 2-(4-chloro-2-oxopyridin-1(2H)-yl)propanoate IM477 as a colorless oil: 225 mg, 46% yield, P=100%, retention time=2.3 min (gradient A), (M+H)$^+$: 216.

Stage 2: General Procedure C was used between IM477 and IM3 to afford methyl 2-(4-((R)-3-((tert-butoxycarbonyl)(cyclobutylmethyl)amino)piperidin-1-yl)-2-oxopyridin-1(2H)-yl) propanoate IM478 as yellow oil: 60 mg, 26% yield, P=91%, retention time=2.6 min (gradient A), (M+H)$^+$: 448.

Stage 3: To a solution of IM 478 (60 mg, 0.12 mmol) in a mixture of THF (1 mL) and water (1 mL) at rt was added lithium hydroxide (7 mg, 0.29 mmol). The resulting solution was stirred at rt for 20 min. The solvents were removed under reduced pressure to give crude lithium 2-(4-((R)-3-((tert-butoxycarbonyl)(cyclobutylmethyl)amino)piperidin-1-yl)-2-oxopyridin-1(2H)-yl)propanoate IM479 as a white solid: 68 mg, 99% yield, P=78%, retention time=2.7 min (gradient A), (M+H)$^+$: 434.

Stage 4: General Procedure F was used between IM479 and IM470 to afford tert-butyl (cyclobutylmethyl)((3R)-1-(1-(1-((5-(dimethylamino)pyridin-3-yl)amino)-1-oxopropan-2-yl)-2-oxo-1,2-dihydropyridin-4-yl)piperidin-3-yl)carbamate IM480 as an off-white foam: 40 mg, 59% yield, P=98%, retention time=2.5 min (gradient A), (M+H)$^+$: 553.

Stage 5: General Procedure A1 was used from IM480 to afford compound 162 as a white powder: 30 mg, 93% yield, P=99%, retention time=2.6 min (gradient B), (M+H)$^+$: 453.

The mixture of diastereomers was purified by chiral preparative HPLC purification using Chiralpak IA column (5 μm, 20×250 mm). Eluent used: TBME/DCM/MeOH/DEA: 40/40/20/0.1% at flow rate of 20 mL/min. First eluted diastereomer: P=96%, retention time=4.5 min, chiral HPLC: P=100, $^1$H NMR (300 MHz, CDCl$_3$) δ 9.70 (s, 1H), 7.99 (d, J=2.1 Hz, 1H), 7.83 (d, J=2.7 Hz, 1H), 7.46 (d, J=2.5 Hz, 1H), 7.26 (d, J=7.9 Hz, 1H), 6.04 (dd, J=8.0, 2.9 Hz, 1H), 5.78 (d, J=2.8 Hz, 1H), 5.69 (q, J=7.2 Hz, 1H), 3.83-3.74 (m, 1H), 3.69-3.59 (m, 1H), 3.00-2.85 (m, 7H), 2.79-2.53 (m, 4H), 2.49-2.33 (m, 1H), 2.16-1.22 (m, 13H). 1H exchanged with solvent. Second eluted diastereomer: P=100%, retention time=5.8 min, chiral HPLC: P=100%, $^1$H NMR (300 MHz, CDCl$_3$) δ 9.69 (s, 1H), 7.99 (d, J=2.0 Hz, 1H), 7.83 (d, J=2.7 Hz, 1H), 7.47 (d, J=2.5 Hz, 1H), 7.26 (d, J=8.1 Hz, 1H), 6.04 (dd, J=8.1, 2.9 Hz, 1H), 5.78 (d, J=2.8 Hz, 1H), 5.69 (q, J=7.2 Hz, 1H), 3.84-3.74 (m, 1H), 3.68-3.58 (m, 1H), 3.01-2.85 (m, 7H), 2.80-2.55 (m, 4H), 2.49-2.33 (m, 1H), 2.15-1.23 (m, 13H), 1H exchanged with solvent.

Compound 163: (R)-4-(3-((cyclopropylmethyl)amino)piperidin-1-yl)-1-((4-(5-(dimethyl amino)pyridin-3-yl)-1H-1,2,3-triazol-1-yl)methyl)-6-methylpyridin-2(1H)-one was Obtained Using General Scheme 1 Pathway B Stage 1: General Procedure O1 was used from 4-bromo-6-methylpyridin-2(1H)-one to afford 4-bromo-1-(chloromethyl)-6-methylpyridin-2(1H)-one IM481 as a white solid: 515 mg, 42% yield, P=100%, retention time=2.3 min (gradient A), (M+H)$^+$: 236/238.

Stage 2: General Procedure N was used from IM481 to afford 1-(azidomethyl)-4-bromo-6-methylpyridin-2(1H)-one IM482 as yellow oil: 480 mg, 87% yield, P=95%, retention time=2.5 min (gradient A), (M+H)$^+$: 243/245.

Stage 3: General Procedure B was used between IM482 and IM454 to afford 4-bromo-1-((4-(5-(dimethylamino)pyridin-3-yl)-1H-1,2,3-triazol-1-yl)methyl)-6-methylpyridin-2(1H)-one IM483 as a white solid: 150 mg, 86% yield, P=92%, retention time=2.2 min (gradient A), (M+H)$^+$: 389/391.

Stage 1': General Procedure H1 was used from cyclobutanecarboxaldehyde and (R)-1-benzylpiperidin-3-amine to afford (R)-1-benzyl-N-(cyclopropylmethyl)piperidin-3-amine IM484: 20.6 g, 85% yield, P=88% (215 nm), retention time=1.9 min (gradient A), (M+H)$^+$: 245.

Stage 2': General Procedure J was used from IM484 to afford tert-butyl (R)-(1-benzylpiperidin-3-yl)(cyclopropylmethyl)carbamate IM485 as colourless oil: 26.0 g, 89% yield, P=100%, retention time=2.5 min (gradient A), (M+H)$^+$: 345.

Stage 3': General Procedure I was used from IM485 to afford crude tert-butyl (R)-(cyclopropylmethyl)(piperidin-3-yl)carbamate IM486 as yellow oil: 19.0 g, 99% yield, P=100% ($^1$H NMR), retention time=2.3 min (gradient A—no absorbance), (M+H)$^+$: 255.

Stage 4: General Procedure C was used between IM486 and IM483 to afford tert-butyl (R)-(cyclopropylmethyl)(1-(1-((4-(5-(dimethylamino)pyridin-3-yl)-1H-1,2,3-triazol-1-yl)methyl)-6-methyl-2-oxo-1,2-dihydropyridin-4-yl)piperidin-3-yl)carbamate IM487 as yellow oil: 85 mg, 90% yield, P=99%, retention time=2.5 min (gradient A), (M+H)$^+$: 563.

Stage 5: General Procedure A1 was used from IM487 to afford compound 163 as a white solid: 57 mg, 85% yield, P=100%, retention time=2.6 min (gradient B), (M+H)+: 463.

Compound 164: 4-((R)-3-((cyclobutylmethyl) amino)piperidin-1-yl)-1-(1-(4-(6-(dimethyl amino) pyrazin-2-yl)-1H-1,2,3-triazol-1-yl)ethyl)pyridin-2 (1H)-one was Obtained Using General Scheme 1 Pathway B Stage 1: Dimethylamine hydrochloride (452 mg, 5.48 mmol) and N,N-Diisopropylethylamine (2.17 mL, 12.4 mmol) were added to a solution of 2,6-dichloropyrazine (1.00 g, 6.58 mmol) in DMSO (5.42 mL) and stirred at rt overnight. The crude mixture was then injected directly on a reverse phase column (C18, 0% to 100% MeCN in 10 mM ammonium bicarbonate buffer) to afford 6-chloro-N,N-dimethylpyrazin-2-amine IM488 as a yellow solid: 200 mg, 21% yield, P=92%, retention time=1.1 min (gradient C), (M+H)+: 158.

Stage 2: General Procedure E1 was used from IM488 to afford N,N-dimethyl-6-((trimethylsilyl)ethynyl)pyrazin-2-amine IM489 as brown oil: 816 mg, 25% yield, P=30%, retention time=1.6 min (gradient C), (M+H)+: 220.

Stage 3: General Procedure X was used between IM489 and IM151 to 4-chloro-1-(1-(4-(6-(dimethylamino)pyrazin-2-yl)-1H-1,2,3-triazol-1-yl)ethyl)pyridin-2(1H)-one IM490 as a white solid: 280 mg, 70% yield, P=99%, retention time=1.2 min (gradient C), (M+H)+: 346.

Stage 4: General Procedure C was used between IM3 and IM490 to afford tert-butyl (cyclobutylmethyl)((3R)-1-(1-(1-(4-(6-(dimethylamino)pyrazin-2-yl)-1H-1,2,3-triazol-1-yl) ethyl)-2-oxo-1,2-dihydropyridin-4-yl)piperidin-3-yl)carbamate IM491 as a white powder: 188 mg, 56% yield, P=99%, retention time=1.7 min (gradient C), (M+H)+: 579.

Stage 5: General Procedure A2 was used from IM491 to afford compound 164 as a white powder: 109 mg, 70% yield, P=99%, retention time=2.3 min (gradient C), (M+H)+: 478.

The mixture of diastereomers was further purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=100%, retention time=3.9 min, chiral HPLC: P=100%, $^1$H NMR (300 MHz, CDCl$_3$) δ 8.60 (s, 1H), 8.31 (s, 1H), 7.97 (s, 1H), 7.60 (q, J=7.0 Hz, 1H), 7.44 (d, J=8.1 Hz, 1H), 5.97 (dd, J=8.1, 2.8 Hz, 1H), 5.65 (d, J=2.8 Hz, 1H), 3.80-3.70 (m, 1H), 3.66-3.55 (m, 1H), 3.14 (s, 6H), 2.97-2.84 (m, 1H), 2.77-2.54 (m, 4H), 2.40 (hept, J=7.6 Hz, 1H), 2.15 (d, J=7.0 Hz, 3H), 2.11-1.26 (m, 10H), 1H exchanged with solvent. Second eluted diastereomer: P=100%, retention time=12.6 min, chiral HPLC: P=100%, $^1$H NMR (300 MHz, CDCl$_3$) δ 8.53 (s, 1H), 8.24 (s, 1H), 7.90 (s, 1H), 7.52 (q, J=7.0 Hz, 1H), 7.37 (d, J=8.1 Hz, 1H), 5.90 (dd, J=8.2, 2.8 Hz, 1H), 5.59 (d, J=2.8 Hz, 1H), 3.75-3.65 (m, 1H), 3.58-3.48 (m, 1H), 3.07 (s, 6H), 2.91-2.77 (m, 1H), 2.64 (dd, J=25.3, 8.5 Hz, 4H), 2.34 (hept, J=7.6 Hz, 1H), 2.08 (d, J=7.0 Hz, 3H), 2.01-1.25 (m, 10H), 1H exchanged with solvent.

Compound 165: 1-(5-((R)-3-((cyclobutylmethyl) amino)piperidin-1-yl)pyridin-2-yl)-1-(2-(5-methoxypyridin-3-yl)thiazol-5-yl)ethan-1-ol was Obtained Using General Scheme 3 Pathway A Stage 1: To a solution of 2-chlorothiazole (40 mg, 0.33 mmol) in dry THF (2 mL) at −78° C. was added n-butyl lithium in hexane (140 μL, 0.35 mmol) dropwise. After 1 h, a solution of IM341 (111 mg, 0.28 mmol) in dry THF (1 mL) was added dropwise at −78° C. The resulting solution was stirred for 5 min and then slowly warmed to rt for 30 min. The reaction mixture was quenched with a saturated aqueous solution of NH$_4$Cl (20 mL) and extracted with EtOAc (3×15 mL). The organic layers were merged, dried over MgSO$_4$, filtered and concentrated under reduced pressure to dryness. The crude material was purified by an automated flash system (liquid injection in toluene, 0 to 40% EtOAc in Heptane) to afford tert-butyl ((3R)-1-(6-(1-(2-chlorothiazol-5-yl)-1-hydroxyethyl)pyridin-3-yl)piperidin-3-yl)(cyclobutylmethyl)carbamate IM492 as colourless oil: 51 mg, 33% yield, P=92%, retention time=2.7 min (gradient A), (M+H)+: 507/509.

Stage 2: General Procedure U was used from IM492 to afford tert-butyl (cyclobutylmethyl)((3R)-1-(6-(1-hydroxy-1-(2-(5-methoxypyridin-3-yl)thiazol-5-yl)ethyl) pyridin-3-yl)piperidin-3-yl)carbamate IM493 as a yellow gum: 30 mg, 58% yield, P=91%, retention time=2.5 min (gradient A), (M+H)+: 580.

Stage 3: General Procedure A1 was used from IM493 to afford crude compound 165 as yellowish oil: 24 mg, 97% yield, P=91%, retention time=2.0 min (gradient A), (M+H)+: 480.

The product was purified by reverse phase preparative HPLC purification (Waters XBridge C18 5 μm, 19×100 mm). Gradient used: increased linearly from 20 to 50% solution "B" over 4.0 min, increased linearly to 85% solution "B" over 2.3 min, and returned to initial conditions over 1.0 min. Flow Rate: 15 mL/min. P=98%.

The mixture of diastereomers was purified by chiral preparative HPLC purification using Chiralpak IA column (5 μm, 10×250 mm). Eluent used: TBME/MeOH/TFA: 60/40/0.1% at flow rate of 7 mL/min. First eluted diastereomer: P=100%, retention time=2.9 min, chiral HPLC: P=100%. The entire obtained product was dissolved in 1 mL of DMSO and injected onto XBridge C18 5 μm, 19×100 mm using as mobile phase a gradient: 0.02 mM ammonium bicarbonate buffer pH=9.2 (adjusted by NH4OH)/MeCN from 20/80 to 90/10 ratio, flow rate 15.0 mL/min, $^1$H NMR (300 MHZ, CDCl$_3$) δ 8.65 (d, J=1.8 Hz, 1H), 8.32 (d, J=2.9 Hz, 1H), 8.20 (s, 1H), 7.74-7.67 (m, 2H), 7.25-7.21 (m, 2H), 6.15 (s, 1H), 3.90 (s, 3H), 3.69-3.60 (m, 1H), 3.53-3.43 (m, 1H), 2.94-2.80 (m, 1H), 2.80-2.61 (m, 4H), 2.45 (hept, J=7.5 Hz, 1H), 2.08 (d, J=8.6 Hz, 2H), 1.97 (s, 3H), 1.95-1.75 (m, 4H), 1.76-1.59 (m, 3H), 1.42-1.23 (m, 1H), 1H exchanged with solvent. Second eluted diastereomer: P=100%, retention time=4.8 min, chiral HPLC: P=100%. The entire obtained product was dissolved in 1 mL of DMSO and injected onto XBridge C18 5 μm, 19×100 mm using as mobile phase a gradient: 0.02 mM ammonium bicarbonate buffer pH=9.2 (adjusted by NH4OH)/MeCN from 20/80 to 90/10 ratio, flow rate 15.0 mL/min, $^1$H NMR (300 MHz, CDCl$_3$) δ 8.65 (d, J=1.7 Hz, 1H), 8.32 (d, J=2.9 Hz, 1H), 8.20 (s, 1H), 7.75-7.67 (m, 2H), 7.25-7.20 (m, 2H), 6.13 (s, 1H), 3.90 (s, 3H), 3.70-3.60 (m, 1H), 3.53-3.43 (m, 1H), 2.94-2.81 (m, 1H), 2.80-2.61 (m, 4H), 2.45 (hept, J=7.6 Hz, 1H), 2.08 (s, 2H), 1.98 (s, 3H), 1.95-1.78 (m, 4H), 1.75-1.59 (m, 3H), 1.41-1.25 (m, 1H), 1H exchanged with solvent.

Compound 166: 4-((R)-3-((cyclobutylmethyl) amino)piperidin-1-yl)-1-(1-(4-(5-(dimethyl amino) pyridin-3-yl)-1H-imidazol-1-yl)ethyl)pyridin-2(1H)-one was Obtained Using General Scheme 4 Pathway A Stage 1: In a microwave vial were combined 5-bromo-N,N-dimethylpyridin-3-amine (250 mg, 1.18 mmol), bis (pinacolato)diboron (402 mg, 1.54 mmol), potassium acetate (305 mg, 2.95 mmol) and 1,1'-bis(diphenylphosphino)ferrocene dichloropalladium (II) (86.4 mg, 118 μmol). The vial was purged with nitrogen. Dioxane (1.92 mL) was added via syringe and then nitrogen was bubbled through the reaction mixture for 10 min before sealing with a cap and heating to 85° C. overnight. After cooling to rt, the mixture was filtered through a pad of Celite and washed with DCM. Filtrate was concentrated under reduced pressure to give crude N,N-dimethyl-5-(4,4,5,5-tetramethyl-1,3,2-dioxaborolan-2-yl) pyridin-3-amine IM494: 293 mg, 100% yield, P=100%, retention time=0.8 min (gradient C), (M+H)$^+$: 249.

Stage 2: General Procedure U was used between IM494 and IM303 to afford tert-butyl (cyclobutylmethyl)((3R)-1-(1-(1-(4-(5-(dimethylamino)pyridin-3-yl)-1H-imidazol-1-yl)ethyl)-2-oxo-1,2-dihydropyridin-4-yl)piperidin-3-yl)carbamate IM495 as a beige solid: 61 mg, 23% yield, P=80% ($^1$H NMR), retention time=1.6 min (gradient C), (M+H)$^+$: 577.

Stage 3: General Procedure A2 was used from IM495 to afford compound 166 as a white powder: 30 mg, 60% yield, P=97%, retention time=2.1 min (gradient E), (M+H)$^+$: 476.

The mixture of diastereomers was further purified by chiral preparative HPLC purification using Chiralpak IA column (5 μm, 20×250 mm). Eluent used: TBME/MeOH/DEA: 60/40/0.1% at flow rate of 20 mL/min. First eluted diastereomer: P=100%, retention time=5.9 min, chiral HPLC: P=99.9%, $^1$H NMR (300 MHz, CDCl$_3$) δ 8.28 (d, J=1.7 Hz, 1H), 8.01 (d, J=3.0 Hz, 1H), 7.81 (d, J=1.4 Hz, 1H), 7.48-7.42 (m, 1H), 7.42-7.37 (m, 1H), 7.28 (q, J=6.9 Hz, 1H), 6.95 (d, J=8.0 Hz, 1H), 5.96 (dd, J=8.0, 2.9 Hz, 1H), 5.69 (d, J=2.8 Hz, 1H), 3.79-3.69 (m, 1H), 3.65-3.54 (m, 1H), 3.01 (s, 6H), 2.98-2.86 (m, 1H), 2.77-2.51 (m, 4H), 2.40 (hept, J=7.6 Hz, 1H), 2.13-1.96 (m, 2H), 1.94 (d, J=6.8 Hz, 3H), 1.91-1.50 (m, 7H), 1.43-1.22 (m, 1H), 1H exchanged with solvent. Second eluted diastereomer: P=100%, retention time=7.3 min, chiral HPLC: P=99.2%, $^1$H NMR (300 MHz, CDCl$_3$) δ 8.28 (d, J=1.7 Hz, 1H), 8.01 (d, J=2.9 Hz, 1H), 7.81 (d, J=1.3 Hz, 1H), 7.47-7.42 (m, 1H), 7.42-7.38 (m, 1H), 7.33-7.20 (m, 1H), 6.97 (d, J=8.0 Hz, 1H), 5.95 (dd, J=8.1, 2.8 Hz, 1H), 5.68 (d, J=2.8 Hz, 1H), 3.77 (d, J=12.7 Hz, 1H), 3.59 (d, J=13.3 Hz, 1H), 3.00 (s, 6H), 2.98-2.83 (m, 1H), 2.81-2.56 (m, 4H), 2.41 (hept, J=8.0 Hz, 1H), 2.13-1.92 (m, 5H), 1.88-1.31 (m, 8H), 1H exchanged with solvent.

Compound 167: (3R)—N-(cyclobutylmethyl)-1-(6-(1-(2-(6-methoxy-1H-indazol-4-yl)thiazol-5-yl) ethyl)pyridin-3-yl)piperidin-3-amine was Obtained Using General Scheme 3 Pathway A Stage 1: Into a sealable tube, were added IM6 (400 mg, 1.21 mmol), bis-(pinacolato)diboron (406 mg, 1.57 mmol), potassium acetate (485 mg, 4.84 mmol) and 1,1'-bis(diphenylphosphino)ferrocene-palladium(ii)dichloride dichloromethane complex (51 mg, 0.06 mmol). The tube was evacuated and backfilled with argon (3×), then 1,4-dioxane (6 mL) (previously degassed) was added. The red suspension was heated at 100 °C for 18 h. The reaction was cooled to rt, EtOAc (10 mL) was added, filtered over Celite and rinsed with EtOAc (60 mL). The filtrate was concentrated under reduced pressure until dryness to provide a black residue. To the latter was added n-heptane (30 mL), the suspension was sonicated (3 min) and the mixture was filtered over Celite and rinsed with n-heptane (60 mL). The filtrate was concentrated under reduced pressure to dryness to afford 6-methoxy-1-(tetrahydro-2H-pyran-2-yl)-4-(4,4,5, 5-tetramethyl-1,3,2-dioxaborolan-2-yl)-1H-indazole IM496 as a limpid yellow oil: 724 mg, 100% yield, P=60%, retention time=3.2 min (gradient A), (M+H)$^+$: 359.

Stage 2: General Procedure U was used between IM496 and IM492 to afford tert-butyl (cyclobutylmethyl)((3R)-1-(6-(1-hydroxy-1-(2-(6-methoxy-1-(tetrahydro-2H-pyran-2-yl)-1H-indazol-4-yl)thiazol-5-yl)ethyl)pyridin-3-yl)piperidin-3-yl)carbamate IM497 as a brownish gum: 370 mg, 99% yield, P=70%, retention time=2.8 min (gradient A), (M+H)$^+$: 703.

Stage 3: General Procedure Z was used from IM497 to afford tert-butyl cyclobutylmethyl)((3R)-1-(6-(1-(2-(6-methoxy-1-(tetrahydro-2H-pyran-2-yl)-1H-indazol-4-yl) thiazol-5-yl)ethyl)pyridin-3-yl)piperidin-3-yl)carbamate IM498 as a white foam: 70 mg, 42% yield, P=93%, retention time=2.9 min (gradient A), (M+H)$^+$: 687.

Stage 4: General Procedure A1 was used from IM498 to afford crude compound 167 as a yellowish gum: 53 mg, 99% yield, P=90%, retention time=2.2 min (gradient A), (M+H)$^+$: 503.

The product was purified by reverse phase preparative HPLC purification (Waters XBridge C18 5 μm, 19×100 mm). Gradient used: increased linearly from 30 to 50% solution "B" over 4.0 min, increased linearly to 85% solution "B" over 2.2 min, held at 85% for 0.1 min and returned to initial conditions over 1.0 min. Flow Rate: 15 mL/min. P=100%.

The mixture of diastereomers was further purified by chiral preparative HPLC purification using Chiralpak IA column (5 μm, 20×250 mm). Eluent used: TBME/MeOH/DEA: 90/10/0.1% at flow rate of 20 mL/min. First eluted diastereomer: P=100%, retention time=5.9 min, chiral HPLC: P=100%, $^1$H NMR (300 MHz, CDCl$_3$) δ 8.65 (s, 1H), 8.29 (d, J=2.8 Hz, 1H), 7.70 (s, 1H), 7.29 (s, 1H), 7.16 (dd, J=8.7, 2.9 Hz, 1H), 7.09 (d, J=8.5 Hz, 1H), 6.85 (d, J=2.0 Hz, 1H), 4.51 (q, J=7.0 Hz, 1H), 3.84 (s, 3H), 3.69-3.56 (m, 1H), 3.49-3.36 (m, 1H), 2.82 (ddd, J=15.5, 8.5, 3.3 Hz, 1H), 2.77-2.60 (m, 4H), 2.45 (hept, J=7.5 Hz, 1H), 2.06 (ddt, J=11.2, 8.3, 5.1 Hz, 2H), 2.00-1.74 (m, 7H), 1.74-1.58 (m, 3H), 1.41-1.21 (m, 1H), 2H exchanged with solvent. Second eluted diastereomer: P=100%, retention time=7.0 min, chiral HPLC: P=100%, $^1$H NMR (300 MHz, CDCl$_3$) δ 8.65 (s, 1H), 8.29 (d, J=2.9 Hz, 1H), 7.70 (s, 1H), 7.28 (d, J=3.0 Hz, 1H), 7.15 (dd, J=8.6, 2.9 Hz, 1H), 7.09 (d, J=8.5 Hz, 1H), 6.88-6.82 (m, 1H), 4.51 (q, J=7.0 Hz, 1H), 3.84 (s, 3H), 3.66-3.56 (m, 1H), 3.49-3.36 (m, 1H), 2.90-2.77 (m, 1H), 2.77-2.60 (m, 4H), 2.44 (hept, J=7.5 Hz, 1H), 2.15-1.99 (m, 2H), 1.99-1.74 (m, 7H), 1.74-1.58 (m, 3H), 1.39-1.25 (m, 1H), 2H exchanged with solvent.

Compound 168: 4-((R)-3-((cyclobutylmethyl) amino)piperidin-1-yl)-1-(1-(4-(5-(4-methyl piperazin-1-yl)pyridin-3-yl)-1H-1,2,3-triazol-1-yl)ethyl) pyridin-2(1H)-one was Obtained Using General Scheme 1 Pathway B Stage 1: To a microwave vial were added IM293 (128 mg, 230 μmol) and 1-methylpiperazine (1.29 mL, 11.5 mmol) and the reaction mixture was heated to 130° C. for 48 h. NMP (2.30 mL) was added to the reaction (to help conversion) and heating was increased to 140° C. for additional 24 h. After cooling to rt, the mixture was directly loaded onto a C-18 cartridge. Purification by reverse phase chromatography using a gradient of MeCN (0-100%) in basic water (10 mM NH$_4$HCO$_3$/NH$_4$OH buffer pH=10) afforded tert-butyl (cyclobutylmethyl)((3R)-1-(1-(1-(4-(5-(4-methylpiperazin-1-yl)pyridin-3-yl)-1H-1,2,3-triazol-1-yl)ethyl)-2-oxo-1,2-di hydropyridin-4-yl)piperidin-3-yl)carbamate IM499 as pale yellow oil: 112 mg, 72% yield, P=94%, retention time=1.6 min (gradient C), (M+H)⁺: 633.

Stage 2: General Procedure A2 was used from IM499 to afford compound 168 as a white powder: 39 mg, 42% yield, P=100%, retention time=2.2 min (gradient E), (M+H)⁺: 533.

The mixture of diastereomers was further purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=100%, retention time=11.1 min, chiral HPLC: P=94.1%, $^1$H NMR (300 MHz, CDCl$_3$) δ 8.43 (d, J=1.7 Hz, 1H), 8.24 (d, J=2.9 Hz, 1H), 8.13 (s, 1H), 7.70-7.62 (m, 1H), 7.53 (q, J=7.0 Hz, 1H), 7.41 (d, J=8.1 Hz, 1H), 5.98 (dd, J=8.2, 2.8 Hz, 1H), 5.65 (d, J=2.8 Hz, 1H), 3.82-3.71 (m, 1H), 3.65-3.54 (m, 1H), 3.34-3.25 (m, 4H), 2.98-2.83 (m, 1H), 2.74 (dd, J=12.9, 9.3 Hz, 1H), 2.68-2.53 (m, 7H), 2.49-2.36 (m, 1H), 2.34 (s, 3H), 2.15 (d, J=7.0 Hz, 3H), 2.11-1.27 (m, 10H), 1H exchanged with solvent. Second eluted diastereomer: P=100%, retention time=12.0 min, chiral HPLC: P=99.4%, $^1$H NMR (300 MHz, CDCl$_3$) δ 8.37 (d, J=1.7 Hz, 1H), 8.18 (d, J=2.9 Hz, 1H), 8.10 (s, 1H), 7.65-7.57 (m, 1H), 7.47 (q, J=7.0 Hz, 1H), 7.37 (d, J=8.1 Hz, 1H), 5.93 (dd, J=8.1, 2.8 Hz, 1H), 5.60 (d, J=2.8 Hz, 1H), 3.84-3.73 (m, 1H), 3.59-3.48 (m, 1H), 3.24 (t, J=5.0 Hz, 4H), 3.00-2.67 (m, 2H), 2.67-2.45 (m, 7H), 2.39 (hept, J=7.6 Hz, 1H), 2.28 (d, J=2.6 Hz, 3H), 2.09 (d, J=7.0 Hz, 3H), 2.03-1.29 (m, 10H), 1H exchanged with solvent.

Compound 169: 5-(5-(1-(5-((R)-3-((cyclobutylmethyl)amino)piperidin-1-yl)pyridin-2-yl) ethyl)thiazol-2-yl)-N,N-dimethylpyridin-3-amine was Obtained Using General Scheme 1 Pathway B Stage 1: General Procedure U was used between (5-(dimethylamino)pyridin-3-yl)boronic acid and IM492 to afford tert-butyl (cyclobutylmethyl)((3R)-1-(6-(1-(2-(5-(dimethylamino)pyridin-3-yl)thiazol-5-yl)-1-hydroxyethyl)pyridin-3-yl)piperidin-3-yl)carbamate IM500 as a yellowish gum: 63 mg, 54% yield, P=97%, retention time=2.4 min (gradient A), (M+H)⁺: 593.

Stage 2: General Procedure Z was used from IM500 to afford crude tert-butyl (cyclobutylmethyl)((3R)-1-(6-(1-(2-(5-(dimethylamino)pyridin-3-yl)thiazol-5-yl)ethyl)pyridin-3-yl)piperidin-3-yl)carbamate IM501 as a yellowish gum: 120 mg, 99% yield, P=49%, retention time=2.4 min (gradient A), (M+H)⁺: 577.

Stage 3: General Procedure A1 was used from IM501 to afford crude compound 169 as a yellowish gum: 72 mg, 94% yield, P=64%, retention time=2.0 min (gradient A), (M+H)⁺: 477.

The product was purified by reverse phase preparative HPLC purification (Waters XBridge C18 5 μm, 19×100 mm). Gradient used: increased linearly from 20 to 50% solution "B" over 4.0 min, increased linearly to 85% solution "B" over 2.3 min, and returned to initial conditions over 1.0 min. Flow Rate: 15 mL/min. P=100%.

The mixture of diastereomers was further purified by chiral preparative HPLC purification using Chiralpak IA column (5 μm, 20×250 mm). Eluent used: TBME/MeOH/DCM/DEA: 45/45/10/0.1% at flow rate of 20 mL/min. First eluted diastereomer: P=100%, retention time=6.2 min, chiral HPLC: P=100%, $^1$H NMR (300 MHz, CDCl$_3$) δ 8.40 (d, J=1.8 Hz, 1H), 8.28 (d, J=2.9 Hz, 1H), 8.13 (d, J=2.9 Hz, 1H), 7.62 (s, 1H), 7.49-7.45 (m, 1H), 7.16 (dd, J=8.6, 2.9 Hz, 1H), 7.07 (d, J=8.6 Hz, 1H), 4.46 (q, J=7.1 Hz, 1H), 3.73-3.63 (m, 1H), 3.54-3.37 (m, 1H), 3.02 (s, 6H), 2.90-2.68 (m, 5H), 2.61-2.45 (m, 1H), 2.18-2.03 (m, 2H), 2.03-1.78 (m, 4H), 1.74 (d, J=7.2 Hz, 3H), 1.72-1.57 (m, 3H), 1.50-1.36 (m, 1H). 1H exchanged with solvent. Second eluted diastereomer: P=99%, retention time=9.1 min, chiral HPLC: P=100%, $^1$H NMR (300 MHz, CDCl$_3$) δ 8.40 (d, J=1.7 Hz, 1H), 8.27 (d, J=2.9 Hz, 1H), 8.13 (d, J=3.0 Hz, 1H), 7.62 (s, 1H), 7.49-7.44 (m, 1H), 7.17 (dd, J=8.5, 2.9 Hz, 1H), 7.06 (d, J=8.5 Hz, 1H), 4.46 (q, J=7.0 Hz, 1H), 3.84-3.74 (m, 1H), 3.45-3.35 (m, 1H), 3.02 (s, 6H), 2.98-2.75 (m, 5H), 2.69-2.53 (m, 1H), 2.18-1.98 (m, 3H), 1.93-1.78 (m, 3H), 1.73 (d, J=7.0 Hz, 3H), 1.70-1.41 (m, 4H), 1H exchanged with solvent.

Compound 170: 2-(1-(1-(4-((R)-3-((cyclobutylmethyl)amino)piperidin-1-yl)-2-oxopyridin-1(2H)-yl) ethyl)-1H-imidazol-4-yl)-4H-pyrido[1,2-a]pyrimidin-4-one was Obtained Using General Scheme 4 Pathway C1

Stage 1: To a microwave vial, under nitrogen, were added 2-chloro-4H-pyrido[1,2-a]pyrimidin-4-one (60 mg, 319 μmol), 4-(tributylstannyl)-1-tritylimidazole (201 mg, 319 μmol), dichlorobis(triphenylphosphine)palladium(II) (11.4 mg, 1.9 μmol) and dioxane (1.06 mL). The reaction mixture was degassed for 5 min before being sealed and heated to 100° C. overnight. After cooling to rt, mixture was directly loaded onto a C-18 cartridge. Purification by reverse phase (Biotage) using a gradient of MeCN (0-100%) in 10 mM ammonium bicarbonate buffer afforded 2-(1-trityl-1H-imidazol-4-yl)-4H-pyrido[1,2-a]pyrimidin-4-one IM502 as a white foam: 145 mg, 91% yield, P=91%, retention time=1.7 min (gradient C), (M+H)⁺: 455.

Stage 2: To a microwave vial, were added IM502 (145 mg, 319 μmol), MeOH (4 mL) and acetic acid (457 μL, 7.98 mmol). The mixture was heated to 75° C. for 5 h. After cooling to rt, MeOH was removed under reduced pressure. Residue was purified by reverse phase chromatography using a gradient of MeCN (0-100%) in 10 mM ammonium formate buffer to give 2-(1H-imidazol-4-yl)-4H-pyrido[1,2-a]pyrimidin-4-one formate salt IM503 as a green solid: 68 mg, 100% yield, P=100%, retention time=0.6 min (gradient F), (M+H)⁺: 213.

Stage 3: To a solution of IM503 (82.4 mg, 319 μmol) (formate salt) in DMF (919 μL), cooled to 0° C., were added sodium hydride (38 mg, 957 μmol) 60% dispersion in mineral oil and IM151 (306 mg, 1.59 mmol). Then the resulting mixture was warmed to rt and stirred at rt for 1.5 h and then stirred at 50° C. for 1.5 h. Reaction mixture was cooled to rt, quenched with drops of water and then was directly loaded onto a C-18 cartridge. Purification by reverse phase chromatography using a gradient MeCN (0-50%) in 10 mM ammonium bicarbonate buffer afforded 2-(1-(1-(4-chloro-2-oxopyridin-1(2H)-yl)ethyl)-1H-imidazol-4-yl)-4H-pyrido[1,2-a] pyrimidin-4-one IM504 as a beige solid: 22 mg, 18% yield, P=95%, retention time=1.0 min (gradient C), (M+H)⁺: 368/370.

Stage 4: General Procedure C was used between IM3 and IM504 to afford tert-butyl (cyclobutylmethyl)((3R)-1-(2-oxo-1-(1-(4-(4-oxo-4H-pyrido[1,2-a]pyrimidin-2-yl)-1H-imidazol-1-yl)ethyl)-1,2-dihydropyridin-4-yl)piperidin-3-yl)carbamate IM505 as pale yellow oil: 16 mg, 37% yield, P=84%, retention time=1.6 min (gradient C), (M+H)⁺: 601.

Stage 5: General Procedure A2 was used from IM505 to afford compound 170 as a white powder: 7 mg, 48% yield, P=99%, retention time=2.2 min (gradient E), (M+H)⁺: 500.

The mixture of diastereomers was further purified by chiral preparative HPLC purification using Chiralpak IA column (5 µm, 20×250 mm). Eluent used: TBME/MeOH/DCM/DEA: 40/40/20/0.1% at flow rate of 20 mL/min. First eluted diastereomer: P=100%, retention time=6.6 min, chiral HPLC: P=100%, $^1$H NMR (300 MHz, CDCl$_3$) δ 9.04 (d, J=7.2 Hz, 1H), 7.95 (s, 1H), 7.85 (s, 1H), 7.73-7.63 (m, 1H), 7.60 (d, J=8.8 Hz, 1H), 7.35-7.27 (m, 1H), 7.11 (s, 1H), 7.10-7.01 (m, 1H), 6.97 (d, J=8.0 Hz, 1H), 5.93 (dd, J=8.1, 2.8 Hz, 1H), 5.70 (d, J=2.8 Hz, 1H), 3.88-3.77 (m, 1H), 3.64-3.54 (m, 1H), 3.01-2.87 (m, 1H), 2.80-2.60 (m, 3H), 2.58-2.36 (m, 2H), 2.17-1.98 (m, 2H), 1.95 (d, J=7.0 Hz, 3H), 1.90-1.37 (m, 8H), 1H exchanged with solvent. Second eluted diastereomer: P=100%, retention time=12.0 min, chiral HPLC: P=100%, $^1$H NMR (300 MHz, CDCl$_3$) δ 9.04 (d, J=7.1 Hz, 1H), 7.93 (d, J=1.4 Hz, 1H), 7.84 (d, J=1.4 Hz, 1H), 7.73-7.63 (m, 1H), 7.59 (d, J=8.8 Hz, 1H), 7.35-7.27 (m, 1H), 7.10 (s, 1H), 7.08-7.01 (m, 2H), 5.98 (dd, J=8.0, 2.8 Hz, 1H), 5.70 (d, J=2.7 Hz, 1H), 3.88-3.78 (m, 1H), 3.62-3.52 (m, 1H), 3.04-2.89 (m, 1H), 2.78-2.64 (m, 3H), 2.63-2.36 (m, 2H), 2.12-2.02 (m, 2H), 1.97 (d, J=6.8 Hz, 3H), 1.93-1.35 (m, 8H), 1H exchanged with solvent.

Compound 171: 4-((R)-3-((cyclobutylmethyl)amino)piperidin-1-yl)-1-(1-(5-(5-(dimethyl amino)pyridin-3-yl)-1,3,4-thiadiazol-2-yl)ethyl)pyridin-2(1H)-one was Obtained Using General Scheme 3 Pathway B Stage 1: General Procedure U was used between IM359 and IM494 to afford 5-(5-(1-ethoxyvinyl)-1,3,4-thiadiazol-2-yl)-N,N-dimethylpyridin-3-amine IM506 as a yellow solid: 56 mg, 41% yield, P=100%, retention time=1.4 min (gradient C), (M+H)$^+$: 277.

Stage 2: In 50 mL RBF to a suspension of IM506 (50 mg, 181 µmol) in Acetone (909 µL) was added hydrochloric acid (905 µL, 2.71 mmol) (3 M in water) and the reaction was stirred at rt for 1 h. The mixture was concentrated down to remove acetone and water (co-evaporated with EtOH) to afford crude 1-(5-(5-(dimethylamino)pyridin-3-yl)-1,3,4-thiadiazol-2-yl)ethan-1-one IM507: 45 mg, 100% yield, P=100%, retention time=1.1 min (gradient C), (M+H)$^+$: 249.

Stage 3: The crude IM507 was dissolved in MeOH (909 µL) and cooled down to 0° C., sodium borohydride (34.9 mg, 905 µmol) was added to the mixture and stirred at 0 °C for 15 min. The mixture was quenched with saturated NH$_4$Cl solution (2 mL) and was directly purified by C18 column (0-100% MeCN in ammonium bicarbonate) to obtain 1-(5-(5-(dimethylamino)pyridin-3-yl)-1,3,4-thiadiazol-2-yl)ethan-1-ol IM508 as a beige solid: 36 mg, 79% yield, P=100%, retention time=0.9 min (gradient C), (M+H)$^+$: 251.

Stage 4: General Procedure P was used from IM508 to afford crude 1-(5-(5-(dimethylamino)pyridin-3-yl)-1,3,4-thiadiazol-2-yl)ethyl methanesulfonate IM509 as yellow oil: 46 mg, 100% yield, P=100%, retention time=1.1 min (gradient A), (M+H)$^+$: 329.

Stage 5: To a solution of 4-chloro-2-hydroxypyridine (97 mg, 729 µmol) in DMF (0.7 mL) was added potassium carbonate (144 mg, 1.02 mmol) and the reaction mixture was stirred at rt for 10 min, before IM509 (48 mg, 146 µmol) in DMF (0.7 mL) was added. The reaction mixture was heated at 50° C. for 2 h. The mixture was cooled down to rt and directly purified by C18 column (0-100% MeCN in 10 mM ammonium bicarbonate) to afford 4-chloro-1-(1-(5-(5-(dimethylamino)pyridin-3-yl)-1,3,4-thiadiazol-2-yl)ethyl)pyridin-2(1H)-one IM510 as a yellow film: 27 mg, 48% yield, P=94%, retention time=1.2 min (gradient C), (M+H)$^+$: 362/364.

Stage 6: General Procedure C was used between IM3 and IM510 to afford tert-butyl (cyclobutylmethyl)((3R)-1-(1-(5-(5-(dimethylamino)pyridin-3-yl)-1,3,4-thiadiazol-2-yl)ethyl)-2-oxo-1,2-dihydropyridin-4-yl)piperidin-3-yl)carbamate IM511 as a yellow gum: 40 mg, 90% yield, P=100%, retention time=1.8 min (gradient C), (M+H)$^+$: 594.

Stage 7: General Procedure A2 was used from IM511 to afford compound 171 as an off-white solid: 17 mg, 50% yield, P=99%, retention time=2.4 min (gradient E), (M+H)$^+$: 494.

The mixture of diastereomers was further purified by chiral preparative HPLC purification using Chiralpak IA column (5 µm, 20×250 mm). Eluent used: TBME/MeOH/DCM/DEA: 40/40/20/0.1% at flow rate of 20 mL/min. First eluted diastereomer: P=100%, retention time=6.6 min, chiral HPLC: P=100%, $^1$H NMR (300 MHz, CDCl$_3$) δ 8.39 (s, 1H), 8.21 (s, 1H), 7.53 (s, 1H), 7.26 (s, 1H), 6.61 (q, J=6.7 Hz, 1H), 6.05-5.95 (m, 1H), 5.74 (d, J=3.2 Hz, 1H), 3.84-3.74 (m, 1H), 3.67-3.57 (m, 1H), 3.04 (s, 6H), 2.99-2.85 (m, 1H), 2.80-2.59 (m, 4H), 2.52-2.35 (m, 1H), 2.11-2.02 (m, 2H), 1.96 (d, J=7.2 Hz, 4H), 1.91-1.81 (m, 1H), 1.81-1.51 (m, 5H), 1.46-1.32 (m, 1H). 1H exchanged with solvent. Second eluted diastereomer: P=100%, retention time=12.0 min, chiral HPLC: P=100%, $^1$H NMR (300 MHz, CDCl$_3$) δ 8.37 (d, J=1.8 Hz, 1H), 8.21 (d, J=3.0 Hz, 1H), 7.56-7.48 (m, 1H), 7.25 (d, J=8.1 Hz, 1H), 6.60 (q, J=7.1 Hz, 1H), 5.99 (dd, J=8.0, 2.8 Hz, 1H), 5.76 (d, J=2.8 Hz, 1H), 3.90-3.80 (m, 1H), 3.68-3.57 (m, 1H), 3.04 (s, 6H), 3.00-2.88 (m, 1H), 2.88-2.76 (m, 1H), 2.76-2.67 (m, 3H), 2.53-2.40 (m, 1H), 2.16-2.00 (m, 2H), 1.96 (d, J=7.2 Hz, 4H), 1.92-1.38 (m, 7H), 1H exchanged with solvent.

Compound 172: 4-((R)-3-((cyclobutylmethyl)amino)piperidin-1-yl)-1-(1-(4-(5-(2-methyl pyrrolidin-1-yl)pyridin-3-yl)-1H-1,2,3-triazol-1-yl)ethyl)pyridin-2(1H)-one was Obtained Using General Scheme 1 Pathway B Stage 1: To a microwave vial were added IM293 (150 mg, 261 µmol) and 2-methylpyrrolidine (555 µL, 5.22 mmol) and NMP (1 mL). Tube was sealed and reaction was heated to 110° C. for 6 days. After cooling to rt, the mixture was directly loaded onto a C-18 cartridge. Purification by reverse phase chromatography using a gradient of MeCN (0-100%) in 10 mM ammonium bicarbonate buffer afforded tert-butyl (cyclobutylmethyl)((3R)-1-(1-(1-(4-(5-(2-methylpyrrolidin-1-yl)pyridin-3-yl)-1H-1,2,3-triazol-1-yl)ethyl)-2-oxo-1,2-dihydropyridin-4-yl)piperidin-3-yl)carbamate IM512 as yellow oil: 136 mg, 80% yield, P=95%, retention time=1.6 min (gradient C), (M+H)$^+$: 618.

Stage 2: General Procedure A2 was used from IM512 to afford compound 172 as an off-white powder: 64 mg, 56% yield, P=99%, retention time=2.7 min (gradient E), (M+H)$^+$: 518.

The mixture of stereomers was further purified by chiral preparative HPLC purification using Chiralpak IA column (5 µm, 20×250 mm). Eluent used: TBME/MeOH/DEA: 60/40/0.1% at flow rate of 20 mL/min. First eluted stereomer: P=100%, retention time=9.3 min, chiral HPLC: P=100%, $^1$H NMR (300 MHZ, CDCl$_3$) δ 8.24 (d, J=1.8 Hz, 1H), 8.07 (s, 1H), 7.95 (d, J=2.9 Hz, 1H), 7.55 (q, J=7.0 Hz, 1H), 7.41 (d, J=8.1 Hz, 1H), 7.35-7.29 (m, 1H), 5.97 (dd, J=8.1, 2.8 Hz, 1H), 5.65 (d, J=2.8 Hz, 1H), 4.01-3.91 (m, 1H), 3.79-3.68 (m, 1H), 3.65-3.54 (m, 1H), 3.54-3.41 (m, 1H), 3.29-3.15 (m, 1H), 2.98-2.82 (m, 1H), 2.75-2.67 (m, 1H), 2.64 (d, J=7.3 Hz, 2H), 2.62-2.50 (m, 1H), 2.49-2.28 (m, 1H), 2.15 (d, J=7.0 Hz, 3H), 2.12-1.47 (m, 12H), 1.41-1.22 (m, 2H), 1.19 (d, J=6.2 Hz, 3H). 1H exchanged with solvent. Second eluted stereomer: P=100%, retention time=13.9 min, chiral HPLC: P=100%, ¹H NMR (300 MHz, CDCl₃) δ 8.24 (d, J=1.7 Hz, 1H), 8.10 (s, 1H), 7.95 (d, J=2.8 Hz, 1H), 7.56 (q, J=7.0 Hz, 1H), 7.42 (d, J=8.1 Hz, 1H), 7.38-7.31 (m, 1H), 5.98 (dd, J=8.2, 2.8 Hz, 1H), 5.67 (d, J=2.8 Hz, 1H), 4.22 (brs, 1H), 4.02-3.91 (m, 1H), 3.82-3.71 (m, 1H), 3.65-3.55 (m, 1H), 3.54-3.42 (m, 1H), 3.31-3.15 (m, 1H), 2.99-2.85 (m, 1H), 2.81-2.55 (m, 3H), 2.49-2.33 (m, 1H), 2.15 (d, J=7.0 Hz, 3H), 2.13-1.33 (m, 12H), 1.31-1.22 (m, 2H), 1.19 (d, J=6.2 Hz, 3H). 1H exchanged with solvent Third eluted stereomer: P=100%, retention time=16.1 min, chiral HPLC: P=100%, ¹H NMR (300 MHz, CDCl₃) δ 8.24 (d, J=1.7 Hz, 1H), 8.08 (s, 1H), 7.95 (d, J=2.9 Hz, 1H), 7.56 (q, J=7.0 Hz, 1H), 7.42 (d, J=8.1 Hz, 1H), 7.35-7.30 (m, 1H), 5.98 (dd, J=8.2, 2.9 Hz, 1H), 5.67 (d, J=2.8 Hz, 1H), 4.01-3.91 (m, 1H), 3.81-3.65 (m, 1H), 3.66-3.55 (m, 1H), 3.54-3.45 (m, 2H), 3.30-3.18 (m, 1H), 2.99-2.84 (m, 1H), 2.79-2.54 (m, 3H), 2.48-2.35 (m, 1H), 2.15 (d, J=7.0 Hz, 3H), 2.12-1.23 (m, 14H), 1.19 (d, J=6.2 Hz, 3H). 1H exchanged with solvent. Forth eluted stereomer: P=100%, retention time=17.5 min, chiral HPLC: P=100%, ¹H NMR (300 MHz, CDCl₃) δ 8.24 (d, J=1.7 Hz, 1H), 8.09 (s, 1H), 7.95 (d, J=2.8 Hz, 1H), 7.55 (q, J=7.0 Hz, 1H), 7.42 (d, J=8.0 Hz, 1H), 7.36-7.26 (m, 1H), 5.98 (dd, J=8.2, 2.8 Hz, 1H), 5.67 (d, J=2.7 Hz, 1H), 4.52 (brs, 1H), 4.01-3.91 (m, 1H), 3.83-3.72 (m, 1H), 3.65-3.55 (m, 1H), 3.54-3.41 (m, 1H), 3.30-3.18 (m, 1H), 2.99-2.83 (m, 1H), 2.82-2.54 (m, 3H), 2.50-2.34 (m, 1H), 2.15 (d, J=7.0 Hz, 3H), 2.12-1.23 (m, 14H), 1.19 (d, J=6.2 Hz, 3H). 1H exchanged with solvent.

Compound 173: 5-(1-(1-(6-((R)-3-((cyclobutylmethyl)amino)piperidin-1-yl)pyridazin-3-yl)ethyl)-1H-imidazol-4-yl)-N,N-dimethylpyridin-3-amine was Obtained Using General Scheme 4 Pathway A Stage 1: General Procedure P was used from IM105 to afford crude 1-(6-chloropyridazin-3-yl)ethyl methanesulfonate IM513 as yellow solid: 1.01 g, 100% yield, P=100%, retention time=0.8 min (gradient C), (M+H)⁺: 237.

Stage 2: To IM513 (1.00 g, 4.23 mmol) in solution in DMF (28.2 mL) were added K₂CO₃ (1.19 g, 8.45 mmol) and 4-iodoimidazole (1.25 g, 6.34 mmol). The reaction was stirred at 50° C. for 15 h. The reaction mixture was cooled down to rt and directly purified by reverse phase chromatography on a C18 cartridge, eluting with a gradient of MeCN in 10 mM NH₄OCHO to afford the formate salt of 3-chloro-6-(1-(4-iodo-1H-imidazol-1-yl)ethyl)pyridazine IM514 as a beige solid: 435 mg, 20% yield, P=74%, retention time=1.0 min (gradient F), (M+H)⁺: 335/337. Formate salt of IM514 was diluted in a saturated aqueous solution of NaHCO₃ (50 mL). Aqueous phase was extracted with DCM (3×15 mL), dried over MgSO₄, filtered and concentrated under reduced pressure to afford IM514 as a colorless oil.

Stage 3: General Procedure C was used between IM3 and IM514 to afford tert-butyl (cyclobutylmethyl)((3R)-1-(6-(1-(4-iodo-1H-imidazol-1-yl)ethyl)pyridazin-3-yl)piperidin-3-yl)carbamate IM515: 341 mg, 72% yield, P=98%, retention time=1.8 min (gradient C), (M+H)⁺: 567.

Stage 4: General Procedure U was used between IM515 and IM494 to afford tert-butyl (cyclobutylmethyl)((3R)-1-(6-(1-(4-(5-(dimethylamino)-1H-imidazol-4-yl)-1H-imidazol-1-yl)ethyl) pyridazin-3-yl)piperidin-3-yl)carbamate IM516 as a brown solid: 44 mg, 9% yield, P=65%, retention time=1.7 min (gradient C), (M+H)⁺: 561.

Stage 5: General Procedure A2 was used from IM516 to afford compound 173 as an off-white powder: 9 mg, 34% yield, P=93%, retention time=2.3 min (gradient E), (M+H)⁺: 461.

The mixture of diastereomers was further purified by chiral preparative HPLC purification using Chiralpak IE column (5 μm, 10×250 mm). Eluent used: TBME/MeOH/DCM/DEA: 40/40/20/0.1% at flow rate of 7 mL/min. First eluted diastereomer: P=100%, retention time=8.7 min, chiral HPLC: P=100%, ¹H NMR (300 MHz, CDCl₃) δ 8.20 (d, J=1.7 Hz, 1H), 7.93 (d, J=3.0 Hz, 1H), 7.63 (d, J=1.3 Hz, 1H), 7.42-7.34 (m, 1H), 7.28 (d, J=1.3 Hz, 1H), 6.88 (d, J=9.5 Hz, 1H), 6.79 (d, J=9.5 Hz, 1H), 5.45 (q, J=7.0 Hz, 1H), 4.37-4.28 (m, 1H), 4.06-3.96 (m, 1H), 3.11-2.96 (m, 1H), 2.94 (s, 6H), 2.89-2.76 (m, 1H), 2.73-2.52 (m, 3H), 2.43-2.27 (m, 1H), 2.07-1.90 (m, 5H), 1.90-1.68 (m, 3H), 1.66-1.47 (m, 4H), 1.44-1.29 (m, 1H). 1H exchanged with solvent. Second eluted diastereomer: P=100%, retention time=13.1 min, chiral HPLC: P=100%, ¹H NMR (300 MHz, CDCl₃) δ 8.27 (d, J=1.7 Hz, 1H), 8.00 (d, J=3.0 Hz, 1H), 7.69 (d, J=1.3 Hz, 1H), 7.44 (dd, J=3.0, 1.7 Hz, 1H), 7.35 (d, J=1.3 Hz, 1H), 6.95 (d, J=9.5 Hz, 1H), 6.86 (d, J=9.5 Hz, 1H), 5.52 (q, J=7.0 Hz, 1H), 4.44-4.34 (m, 1H), 4.12-4.01 (m, 1H), 3.17-3.03 (m, 1H), 3.00 (s, 6H), 2.91 (dd, J=12.8, 9.3 Hz, 1H), 2.78-2.60 (m, 3H), 2.54-2.33 (m, 1H), 2.13-1.96 (m, 5H), 1.95-1.76 (m, 5H), 1.71-1.33 (m, 3H). 1H exchanged with solvent.

Compound 174: (R)-4-(3-((cyclopropylmethyl)amino)piperidin-1-yl)-1-((4-(5-(dimethyl amino)pyridin-3-yl)-1H-1,2,3-triazol-1-yl)methyl)pyridin-2(1H)-one was Obtained Using General Scheme 1 Pathway B Stage 1: General Procedure D1 was used from IM345 to afford 5-ethynyl-N,N-dimethylpyridin-3-amine IM517 as an off-white solid: 4.28 g, 70% yield, P=98%, retention time=1.8 min (gradient A), (M+H)⁺: 147.

Stage 2: General Procedure B was used between IM517 and IM84 to afford 4-chloro-1-((4-(5-(dimethylamino)pyridin-3-yl)-1H-1,2,3-triazol-1-yl)methyl)pyridin-2(1H)-one IM518 as a white solid: 340 mg, 77% yield, P=92%, retention time=2.1 min (gradient A), (M+H)⁺: 331/333.

Stage 3: General Procedure C was used between IM484 and IM518 to afford tert-butyl (R)-(cyclopropylmethyl)(1-(1-((4-(5-(dimethylamino)pyridin-3-yl)-1H-1,2,3-triazol-1-yl)methyl)-2-oxo-1,2-dihydropyridin-4-yl)piperidin-3-yl) carbamate IM519 as a yellow oil: 67 mg, 55% yield, P=100%, retention time=2.5 min (gradient A), (M+H)⁺: 549.

Stage 4: General Procedure A1 was used from IM519 to afford compound 174 as an off-white powder: 42 mg, 77% yield, P=99%, retention time=2.6 min (gradient B), (M+H)⁺: 449. ¹H NMR (300 MHz, CDCl₃) δ 8.35 (d, J=1.8 Hz, 1H), 8.32 (s, 1H), 8.09 (d, J=3.0 Hz, 1H), 7.46 (dd, J=2.9, 1.8 Hz, 1H), 7.39 (d, J=7.9 Hz, 1H), 6.31 (s, 2H), 5.98 (dd, J=8.0, 2.8 Hz, 1H), 5.66 (d, J=2.8 Hz, 1H), 3.82-3.71 (m, 1H), 3.67-3.56 (m, 1H), 3.02 (s, 6H), 2.98-2.87 (m, 1H), 2.75 (dd, J=12.8, 9.4 Hz, 1H), 2.70-2.58 (m, 1H), 2.58-2.41 (m, 2H), 2.07-1.92 (m, 1H), 1.83-1.70 (m, 1H), 1.56-1.44 (m, 1H), 1.44-1.28 (m, 1H), 0.98-0.79 (m, 1H), 0.54-0.42 (m, 2H), 0.15-0.04 (m, 2H), 1H exchanged with solvent.

Compound 175: (R)-3-(5-(3-((cyclopropylmethyl)amino)piperidin-1-yl)pyridin-2-yl)-N-(5-(dimethylamino)pyridin-3-yl)oxetane-3-carboxamide was Obtained Using General Scheme 6 Pathway B Stage 1: To a vial equipped with a stir bar were added 5-bromo-2-fluoropyridine (300 mg, 1.67 mmol), oxetane-3- carbonitrile (165 mg, 1.89 mmol) and toluene (8.3 mL). The reaction mixture was then cooled to 0° C. while stirring under argon and potassium bis(trimethylsilyl)amide in THF solution (2.3 mL, 2.03 mmol) was then added over 5 min and the reaction was stirred at 0° C. for 5 min. The reaction was quenched by the slow addition of MeOH. The crude reaction mixture was concentrated under reduced pressure. The crude product was purified by an automated flash chromatography system (liquid deposit in DCM, eluting with a gradient of 0-65% EtOAc in heptane) to afford 3-(5-bromopyridin-2-yl)oxetane-3-carbonitrile IM520 as a white solid: 165 mg, 41% yield, P=100%, retention time=2.6 min (gradient A), (M+H)$^+$: 239/241.

Stage 2: General Procedure Y was used between IM484 and IM520 to afford tert-butyl (R)-(1-(6-(3-cyanooxetan-3-yl)pyridin-3-yl)piperidin-3-yl)(cyclopropylmethyl)carbamate IM521 as yellow oil: 330 mg, 84% yield, P=97%, retention time=2.6 min (gradient A), (M+H)$^+$: 413.

Stage 3: To a vial equipped with a stir bar were added IM521 (325 mg, 0.76 mmol), sodium hydroxide (125 mg, 3.09 mmol), ethanol (2.7 mL) and water (1.35 mL). The vial was sealed and heated to 80° C. for 1.5 h. The reaction mixture was concentrated under reduced pressure. The residue was dissolved in EtOAc, and 1 N HCl solution was added dropwise to adjust the pH ~2. Phases were separated and aqueous phase was extracted with EtOAc (2×10 mL). The combined organic phases were dried over MgSO$_4$, filtered, and concentrated under reduced pressure to afford crude (R)-3-(5-(3-((tert-butoxycarbonyl)(cyclopropylmethyl)amino) piperidin-1-yl)pyridin-2-yl)oxetane-3-carboxylic acid IM522 as an off-white solid: 280 mg, 81% yield, P=95%, retention time=2.6 min (gradient A), (M+H)+: 432.

Stage 4: General Procedure F was used between IM522 and IM470 to afford tert-butyl (R)-(cyclopropylmethyl)(1-(6-(3-((5-(dimethylamino)pyridin-3-yl)carbamoyl)oxetan-3-yl)pyridin-3-yl)piperidin-3-yl)carbamate IM523 as colourless oil: 34 mg, 47% yield, P=100%, retention time=2.5 min (gradient A), (M+H)$^+$: 551.

Stage 5: General Procedure A2 was used from IM523 to afford compound 175 as a white powder: 20 mg, 72% yield, P=100%, retention time=2.4 min (gradient B), (M+H)$^+$: 451. $^1$H NMR (300 MHz, CDCl$_3$) δ 8.87 (s, 1H), 8.31 (dd, J=2.6, 1.2 Hz, 1H), 7.82 (d, J=2.7 Hz, 1H), 7.74 (d, J=2.1 Hz, 1H), 7.71-7.66 (m, 2H), 7.23-7.18 (m, 2H), 5.36 (d, J=6.0 Hz, 2H), 5.01 (d, J=6.0 Hz, 2H), 3.73-3.62 (m, 1H), 3.56-3.43 (m, 1H), 2.96 (s, 6H), 2.94-2.67 (m, 3H), 2.64-2.49 (m, 2H), 2.01-1.93 (m, 1H), 1.91-1.77 (m, 1H), 1.72-1.61 (m, 1H), 1.45-1.20 (m, 1H), 1.03-0.86 (m, 1H), 0.56-0.41 (m, 2H), 0.13 (q, J=4.9 Hz, 2H), 1H exchanged with solvent.

Compound 176: 4-((R)-3-((cyclopropylmethyl)
amino)piperidin-1-yl)-1-(1-(4-(5-(pyrrolidin-1-yl)
pyridin-3-yl)-1H-1,2,3-triazol-1-yl)ethyl)pyridin-2
(1H)-one was Obtained Using General Scheme 1
Pathway B Stage 1: General Procedure C was used between IM459 and IM3 to afford tert-butyl ((3R)-1-(1-(1-(4-(5-bromopyridin-3-yl)-1H-1,2,3-triazol-1-yl)ethyl)-2-oxo-1,2-dihydropyridin-4-yl) piperidin-3-yl)(cyclopropylmethyl)carbamate IM524 as a beige foam: 2.24 g, 82% yield, P=95%, retention time=2.9 min (gradient A), (M+H)$^+$: 598/600.

Stage 2: General Procedure AA was used between IM524 and pyrrolidine to afford tert-butyl (cyclopropylmethyl) ((3R)-1-(2-oxo-1-(1-(4-(5-(pyrrolidin-1-yl)pyridin-3-yl)-1H-1,2,3-triazol-1-yl)ethyl)-1,2-dihydropyridin-4-yl)piperidin-3-yl)carbamate IM525 as yellow oil: 53 mg, 85% yield, P=91%, retention time=2.5 min (gradient A), (M+H)$^+$: 589.

Stage 3: General Procedure A1 was used from IM525 to afford crude compound 176 as sticky yellowish oil: 40 mg, 92% yield, P=92%, retention time=2.0 min (gradient A), (M+H)$^+$: 489.

The mixture of diastereomers was purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=99%, retention time=8.8 min, chiral HPLC: P=100%, $^1$H NMR (300 MHz, CDCl$_3$) δ 8.27 (d, J=1.8 Hz, 1H), 8.12 (s, 1H), 7.93 (d, J=2.8 Hz, 1H), 7.53 (q, J=7.0 Hz, 1H), 7.42 (d, J=8.1 Hz, 1H), 7.34-7.28 (m, 1H), 5.98 (dd, J=8.1, 2.8 Hz, 1H), 5.67 (d, J=2.8 Hz, 1H), 3.87-3.77 (m, 1H), 3.64-3.52 (m, 1H), 3.39-3.29 (m, 4H), 3.00-2.79 (m, 2H), 2.78-2.65 (m, 1H), 2.55 (d, J=6.9 Hz, 2H), 2.35 (d, J=11.4 Hz, 1H), 2.14 (d, J=7.0 Hz, 3H), 2.10-1.94 (m, 5H), 1.85-1.71 (m, 1H), 1.59-1.40 (m, 2H), 1.02-0.86 (m, 1H), 0.56-0.42 (m, 2H), 0.22-0.10 (m, 2H). Second eluted diastereomer: P=98%, retention time=13.0 min, chiral HPLC: P=94.8%, $^1$H NMR (300 MHz, CDCl$_3$) δ 8.27 (d, J=1.7 Hz, 1H), 8.14 (s, 1H), 7.93 (d, J=2.8 Hz, 1H), 7.55 (q, J=7.0 Hz, 1H), 7.44 (d, J=8.1 Hz, 1H), 7.34-7.27 (m, 1H), 5.99 (dd, J=8.1, 2.9 Hz, 1H), 5.67 (d, J=2.8 Hz, 1H), 3.89-3.79 (m, 1H), 3.64-3.54 (m, 1H), 3.40-3.29 (m, 4H), 3.00-2.80 (m, 2H), 2.76-2.70 (m, 1H), 2.55 (d, J=6.9 Hz, 2H), 2.26 (s, 1H), 2.15 (d, J=7.0 Hz, 3H), 2.11-1.98 (m, 5H), 1.83-1.72 (m, 1H), 1.54-1.42 (m, 2H), 1.01-0.89 (m, 1H), 0.56-0.44 (m, 2H), 0.22-0.10 (m, 2H).

Compound 177: 4-((R)-3-((cyclobutylmethyl)
amino)piperidin-1-yl)-1-(1-(4-(5-(3-methyl azetidin-
1-yl)pyridin-3-yl)-1H-1,2,3-triazol-1-yl)ethyl)pyridin-2(1H)-one was Obtained Using General
Scheme 1 Pathway B Stage 1: In a 15 mL pressure flask, to a solution of IM293 (200 mg, 348 μmol) and 3-methylazetidine hydrochloride (276 mg, 2.44 mmol) in NMP (3.46 mL) was added cesium carbonate (1.15 g, 3.48 mmol). The mixture was stirred at 130° C. for 44 h. The reaction mixture was cooled down to rt and directly purified by the C18 column (0-100% MeCN in 10 mM ammonium bicarbonate) to afford tert-butyl (cyclobutylmethyl)((3R)-1-(1-(1-(4-(5-(3-methylazetidin-1-yl)pyridin-3-yl)-1H-1,2,3-triazol-1-yl)ethyl)-2-oxo-1,2-dihydropyridin-4-yl)piperidin-3-yl)carbamate IM526 as a white solid: 162 mg, 76% yield, P=99%, retention time=1.8 min (gradient C), (M+H)$^+$: 603.

Stage 2: General Procedure A2 was used from IM526 to afford compound 177 as an off-white powder: 105 mg, 78% yield, P=100%, retention time=2.5 min (gradient E), (M+H)$^+$: 503.

The mixture of diastereomers was further purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=99%, retention time=6.7 min, chiral HPLC: P=100%, $^1$H NMR (300 MHz, CDCl$_3$) δ 8.31 (d, J=1.8 Hz, 1H), 8.08 (s, 1H), 7.75 (d, J=2.8 Hz, 1H), 7.52 (q, J=7.0 Hz, 1H), 7.40 (d, J=8.1 Hz, 1H), 7.14 (t, J=2.3 Hz, 1H), 5.96 (dd, J=8.1, 2.9 Hz, 1H), 5.63 (d, J=2.8 Hz, 1H), 4.12-3.99 (m, 2H), 3.79-3.67 (m, 1H), 3.65-3.53 (m, 1H), 3.53-3.45 (m, 2H), 2.96-2.75 (m, 2H), 2.75-2.48 (m, 4H), 2.48-2.27 (m, 1H), 2.13 (d, J=7.0 Hz, 3H), 2.08-1.41 (m, 9H), 1.41-1.22 (m, 4H), 1H exchanged with solvent. Second eluted diastereomer: P=99%, retention time=9.1 min, chiral HPLC: P=100%, ¹H NMR (300 MHz, CDCl₃) δ 8.27 (d, J=1.8 Hz, 1H), 8.03 (s, 1H), 7.71 (d, J=2.7 Hz, 1H), 7.48 (q, J=7.0 Hz, 1H), 7.35 (d, J=8.1 Hz, 1H), 7.13-7.06 (m, 1H), 5.91 (dd, J=8.1, 2.9 Hz, 1H), 5.59 (d, J=2.8 Hz, 1H), 4.08-3.97 (m, 2H), 3.75-3.63 (m, 1H), 3.60-3.49 (m, 1H), 3.49-3.40 (m, 2H), 2.92-2.73 (m, 2H), 2.71-2.44 (m, 4H), 2.43-2.22 (m, 1H), 2.09 (d, J=7.0 Hz, 3H), 2.06-1.36 (m, 9H), 1.36-1.18 (m, 4H), 1H exchanged with solvent.

Compound 178: 4-((R)-3-((cyclobutylmethyl)amino)piperidin-1-yl)-1-(1-(4-(5-(piperidin-1-yl)pyridin-3-yl)-1H-1,2,3-triazol-1-yl)ethyl)pyridin-2(1H)-one was Obtained Using General Scheme 1 Pathway B Stage 1: To a microwave vial were added IM293 (200 mg, 363 µmol) and piperidine (904 µL, 9.06 mmol) and NMP (2.3 mL). Tube was sealed and reaction was heated to 130° C. for 87 h. After cooling to rt, the mixture was concentrated under reduced pressure. Purification on a C-18 cartridge using a gradient of MeCN (5-100%) in 10 mM ammonium bicarbonate buffer afforded tert-butyl (cyclobutylmethyl)((3R)-1-(2-oxo-1-(1-(4-(5-(piperidin-1-yl)pyridin-3-yl)-1H-1,2,3-triazol-1-yl)ethyl)-1,2-dihydropyridin-4-yl)piperidin-3-yl)carbamate IM527: 221 mg, 92% yield, P=93%, retention time=1.8 min (gradient C), (M+H)⁺: 618.

Stage 2: General Procedure A2 was used from IM527 to afford compound 178 as a white solid: 190 mg, 94% yield, P=100%, retention time=2.8 min (gradient E), (M+H)⁺: 518.

The mixture of diastereomers was further purified by chiral preparative HPLC purification using Chiralpak IA column (5 µm, 20×250 mm). Eluent used: TBME/MeOH/DCM/DEA: 45/45/10/0.1% at flow rate of 20 mL/min. First eluted diastereomer: P=100%, retention time=7.5 min, chiral HPLC: P=97.6%, 1H NMR (300 MHz, CDCl₃) δ 8.40 (d, J=1.7 Hz, 1H), 8.25 (d, J=2.9 Hz, 1H), 8.10 (s, 1H), 7.69-7.62 (m, 1H), 7.55 (q, J=7.0 Hz, 1H), 7.42 (d, J=8.1 Hz, 1H), 5.98 (dd, J=8.1, 2.9 Hz, 1H), 5.66 (d, J=2.8 Hz, 1H), 3.75 (d, J=12.8 Hz, 1H), 3.61 (d, J=13.4 Hz, 1H), 3.30-3.21 (m, 4H), 2.98-2.83 (m, 1H), 2.77-2.50 (m, 4H), 2.48-2.32 (m, 1H), 2.16 (d, J=7.0 Hz, 3H), 2.03-1.80 (m, 4H), 1.79-1.44 (m, 11H), 1.42-1.24 (m, 1H), 1H exchanged with solvent. Second eluted diastereomer: P=100%, retention time=8.9 min, chiral HPLC: P=99.7%, 1H NMR (300 MHz, CDCl₃) δ 8.39 (d, J=1.7 Hz, 1H), 8.25 (d, J=2.9 Hz, 1H), 8.10 (s, 1H), 7.69-7.62 (m, 1H), 7.55 (q, J=7.0 Hz, 1H), 7.42 (d, J=8.1 Hz, 1H), 5.98 (dd, J=8.1, 2.9 Hz, 1H), 5.66 (d, J=2.8 Hz, 1H), 3.75 (d, J=12.7 Hz, 1H), 3.61 (d, J=13.3 Hz, 1H), 3.30-3.21 (m, 4H), 2.99-2.84 (m, 1H), 2.77-2.51 (m, 4H), 2.47-2.31 (m, 1H), 2.16 (d, J=7.0 Hz, 3H), 2.07-1.78 (m, 4H), 1.78-1.46 (m, 11H), 1.42-1.23 (m, 1H). 1H exchanged with solvent.

Compound 179: 4-((R)-3-((cyclobutylmethyl)amino)piperidin-1-yl)-1-(1-(5-(5-(dimethyl amino)pyridin-3-yl)-2H-tetrazol-2-yl)ethyl)pyridin-2(1H)-one was Obtained Using the Following Procedures Stage 1: To a solution of 5-bromo-N,N-dimethylpyridin-3-amine (200 mg, 945 µmol) in DMF (2.0 mL) was added zinc cyanide (66.6 mg, 567 µmol) and tetrakis (triphenylphosphine)palladium(0) (33.1 mg, 28.3 µmol) and the reaction mixture was degassed for 5 min with N₂ gas, then heated overnight at 110° C. The mixture was cooled to rt and filtered. Purification using reverse phase using a gradient of 0-100% MeCN in 10 mM ammonium formate afforded 5-(dimethylamino)nicotinonitrile IM528 as a white solid: 120 mg, 86% yield, P=100%, retention time=0.9 min (gradient F), (M+H)+: 148.

Stage 2: To a solution of IM528 (120 mg, 815 µmol) in DMF (2 mL) was added NaN₃ (69.3 mg, 1.06 mmol) and ammonium chloride (56.7 mg, 1.06 mmol) and the reaction mixture was heated to 100° C. overnight. The mixture was cooled to rt, filtered and loaded directly onto a reverse phase column. Purification using a gradient of 0-100% MeCN in 10 mM ammonium formate afforded N,N-dimethyl-5-(2H-tetrazol-5-yl)pyridin-3-amine IM529 as a yellow solid: 155 mg, 90% yield, P=90%, retention time=0.4 min (gradient F), (M+H)⁺: 191.

Stage 3: To a solution of IM529 (155 mg, 815 µmol) in DMF (6.0 mL) was added IM150 (268 mg, 1.22 mmol) and K₂CO₃ (345 mg, 2.44 mmol) and the mixture was heated to 70° C. for 16 h. The mixture was cooled to rt and filtered. The filtrate was loaded directly onto reverse phase and purified using a gradient of 0-100% MeCN in 10 ammonium formate to afford 4-chloro-1-(1-(5-(5-(dimethylamino)pyridin-3-yl)-2H-tetrazol-2-yl)ethyl)pyridin-2(1H)-one IM530 as a brown solid: 200 mg, 71% yield, P=100%, retention time=1.2 min (gradient F), (M+H)⁺: 346/348.

Stage 4: General Procedure C was used between IM3 and IM530 to afford tert-butyl (cyclobutylmethyl)((3R)-1-(1-(1-(5-(5-(dimethylamino)pyridin-3-yl)-2H-tetrazol-2-yl)ethyl)-2-oxo-1,2-dihydropyridin-4-yl)piperidin-3-yl)carbamate IM531 as a white solid: 130 mg, 39% yield, P=100%, retention time=1.7 min (gradient F), (M+H)⁺: 579.

Stage 5: General Procedure A2 was used from IM531 to afford compound 179 as a white solid: 88 mg, 82% yield, P=100%, retention time=2.4 min (gradient E), (M+H)⁺: 478.

The mixture of diastereomers was further purified by chiral preparative HPLC purification using Chiralpak IE column (5 µm, 10×250 mm). Eluent used: TBME/MeOH/DCM/DEA: 40/40/20/0.1% at flow rate of 7 mL/min. First eluted diastereomer: P=100%, retention time=6.2 min, chiral HPLC: P=100%, 1H NMR (300 MHz, CDCl₃) δ 8.71 (d, J=1.7 Hz, 1H), 8.22 (d, J=3.0 Hz, 1H), 8.04 (q, J=6.9 Hz, 1H), 7.72-7.64 (m, 1H), 7.36 (d, J=8.1 Hz, 1H), 6.00 (dd, J=8.2, 2.9 Hz, 1H), 5.69 (d, J=2.8 Hz, 1H), 3.76 (d, J=12.6 Hz, 1H), 3.61 (d, J=13.4 Hz, 1H), 3.05 (s, 6H), 2.99-2.85 (m, 1H), 2.67 (hept, J=9.7 Hz, 4H), 2.40 (p, J=7.6 Hz, 1H), 2.11 (d, J=7.0 Hz, 3H), 2.07-1.45 (m, 9H), 1.43-1.23 (m, 1H), 1H exchanged with solvent. Second eluted diastereomer: P=100%, retention time=8.0 min, chiral HPLC: P=100%, 1H NMR (300 MHz, CDCl₃) δ 8.70 (d, J=1.7 Hz, 1H), 8.21 (d, J=3.0 Hz, 1H), 8.03 (q, J=7.0 Hz, 1H), 7.71-7.64 (m, 1H), 7.35 (d, J=8.1 Hz, 1H), 6.00 (dd, J=8.2, 2.9 Hz, 1H), 5.69 (d, J=2.9 Hz, 1H), 3.82-3.71 (m, 1H), 3.61 (d, J=13.2 Hz, 1H), 3.05 (s, 6H), 2.99-2.84 (m, 1H), 2.79-2.52 (m, 4H), 2.51-2.32 (m, 1H), 2.11 (d, J=7.0 Hz, 3H), 2.06-1.50 (m, 9H), 1.44-1.22 (m, 1H), 1H exchanged with solvent.

Compound 180: 4-((R)-3-((cyclopropylmethyl)amino)piperidin-1-yl)-1-(1-(4-(6-(pyrrolidin-1-yl)pyrazin-2-yl)-1H-1,2,3-triazol-1-yl)ethyl)pyridin-2(1H)-one was Obtained Using General Scheme 1 Pathway B Stage 1: General Procedure C (in DMSO instead of NMP, at rt) was used between 2,6-dichloropyrazine and pyrrolidine to afford 2-chloro-6-(pyrrolidin-1-yl)pyrazine IM532 as yellow oil: 387 mg, 78% yield, P=98%, retention time=2.8 min (gradient A), (M+H)⁺: 184/186.

Stage 2: General Procedure E2 was used from IM532 to afford crude 2-(pyrrolidin-1-yl)-6-((trimethylsilyl)ethynyl)

pyrazine IM533 as light brown solid: 577 mg, 100% yield, P=90%, retention time=3.1 min (gradient A), (M+H)$^+$: 246.

Stage 3: General Procedure D1 was used from IM533 to afford 2-ethynyl-6-(pyrrolidin-1-yl)pyrazine IM534 as a brown solid: 304 mg, 83% yield, P=100%, retention time=2.5 min (gradient A), (M+H)$^+$: 174.

Stage 4: General Procedure B was used between IM534 and IM151 to afford 4-chloro-1-(1-(4-(6-(pyrrolidin-1-yl)pyrazin-2-yl)-1H-1,2,3-triazol-1-yl)ethyl)pyridin-2(1H)-one IM535 as a pale yellow foam: 132 mg, 83% yield, P=94%, retention time=2.5 min (gradient A), (M+H)$^+$: 372/374.

Stage 5: General Procedure C was used between IM486 and IM535 to afford tert-butyl (cyclopropylmethyl)((3R)-1-(2-oxo-1-(1-(4-(6-(pyrrolidin-1-yl)pyrazin-2-yl)-1H-1,2,3-triazol-1-yl)ethyl)-1,2-dihydropyridin-4-yl)piperidin-3-yl) carbamate IM536 as sticky yellow oil: 138 mg, 100% yield, P=76%, retention time=2.8 min (gradient A), (M+H)$^+$: 590.

Stage 6: General Procedure A1 was used from IM536 to afford crude compound 180 as a yellowish foam: 82 mg, 94% yield, P=99%, retention time=2.2 min (gradient A), (M+H)$^+$: 490.

The mixture of diastereomers was purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=100%, retention time=4.5 min, chiral HPLC: P=zz100%, 1H NMR 1H NMR (300 MHz, CDCl$_3$) δ 8.57 (s, 1H), 8.30 (s, 1H), 7.81 (s, 1H), 7.60 (q, J=6.9 Hz, 1H), 7.44 (d, J=8.1 Hz, 1H), 5.97 (dd, J=8.0, 2.9 Hz, 1H), 5.65 (d, J=2.8 Hz, 1H), 3.76 (d, J=12.4 Hz, 1H), 3.60 (d, J=13.3 Hz, 1H), 3.54-3.47 (m, 4H), 2.98-2.85 (m, 1H), 2.79-2.58 (m, 2H), 2.54-2.42 (m, 2H), 2.15 (d, J=7.0 Hz, 3H), 2.08-1.98 (m, 4H), 1.81-1.70 (m, 1H), 1.63-1.32 (m, 3H), 0.97-0.85 (m, 1H), 0.55-0.43 (m, 2H), 0.10 (d, J=4.9 Hz, 2H), 1H exchanged with solvent. Second eluted diastereomer: P=100%, retention time=9.4 min, chiral HPLC: P=99.4%, 1H NMR (300 MHz, CDCl$_3$) δ 8.57 (s, 1H), 8.30 (s, 1H), 7.81 (s, 1H), 7.60 (q, J=7.0 Hz, 1H), 7.44 (d, J=8.1 Hz, 1H), 5.97 (dd, J=8.2, 2.8 Hz, 1H), 5.65 (d, J=2.8 Hz, 1H), 3.76 (d, J=12.4 Hz, 1H), 3.61 (d, J=13.4 Hz, 1H), 3.56-3.46 (m, 4H), 3.00-2.85 (m, 1H), 2.79-2.59 (m, 2H), 2.56-2.44 (m, 2H), 2.15 (d, J=7.0 Hz, 3H), 2.08-1.99 (m, 4H), 1.80-1.71 (m, 1H), 1.58-1.23 (m, 3H), 0.94-0.85 (m, 1H), 0.54-0.42 (m, 2H), 0.11-0.04 (m, 2H), 1H exchanged with solvent.

Compound 181: (3R)—N-(cyclobutylmethyl)-1-(6-(1-(2-(5-methoxypyridin-3-yl)thiazol-5-yl)ethyl)pyridin-3-yl)piperidin-3-amine was Obtained Using General Scheme 3 Pathway A Stage 1: General Procedure Z was used from IM493 to afford tert-butyl (cyclobutylmethyl) ((3R)-1-(6-(1-(2-(5-methoxypyridin-3-yl)thiazol-5-yl)ethyl)pyridin-3-yl)piperidin-3-yl) carbamate IM537 as colourless oil: 20 mg, 18% yield, P=78%, retention time=2.6 min (gradient A), (M+H)$^+$: 564.

Stage 2: General Procedure A1 was used from IM537 to afford crude compound 181 as a yellow oil: 23 mg, 99% yield, P=55%, retention time=2.0 min (gradient A), (M+H)$^+$: 464.

The product was purified by reverse phase preparative HPLC purification (Waters XBridge C18 5 μm, 19×100 mm). Gradient used: increased linearly from 25 to 50% solution "B" over 4.0 min, increased linearly to 85% solution "B" over 2.3 min, and returned to initial conditions over 1.0 min. Flow Rate: 15 mL/min. P=100%.

The mixture of diastereomers was further purified by chiral preparative HPLC purification using Chiralpak IA column (5 μm, 10×250 mm). Eluent used: TBME/MeOH/DEA: 99/1/0.1% at flow rate of 7 mL/min. First eluted diastereomer: P=100%, retention time=2.9 min, chiral HPLC: P=100%, 1H NMR (300 MHZ, CDCl$_3$) δ 8.66 (d, J=1.8 Hz, 1H), 8.34-8.25 (m, 2H), 7.75-7.68 (m, 1H), 7.65 (s, 1H), 7.16 (dd, J=8.6, 2.9 Hz, 1H), 7.08 (d, J=8.5 Hz, 1H), 4.48 (q, J=7.1 Hz, 1H), 3.90 (s, 3H), 3.62 (d, J=11.1 Hz, 1H), 3.49-3.39 (m, 1H), 2.91-2.82 (m, 1H), 2.82-2.59 (m, 4H), 2.53-2.37 (m, 1H), 2.13-2.02 (m, 2H), 1.99-1.58 (m, 10H), 1.41-1.23 (m, 1H), 1H exchanged with solvent. Second eluted diastereomer: P=98%, retention time=5.9 min, chiral HPLC: P=98.7%, 1H NMR (300 MHz, CDCl$_3$) δ 8.66 (d, J=1.7 Hz, 1H), 8.30 (dd, J=7.1, 2.9 Hz, 2H), 7.76-7.68 (m, 1H), 7.65 (s, 1H), 7.17 (dd, J=8.6, 2.9 Hz, 1H), 7.08 (d, J=8.5 Hz, 1H), 4.48 (q, J=7.1 Hz, 1H), 3.91 (s, 3H), 3.67 (d, J=10.7 Hz, 1H), 3.48-3.38 (m, 1H), 2.84 (s, 1H), 2.76 (d, J=7.5 Hz, 4H), 2.57-2.46 (m, 1H), 2.21-1.44 (m, 13H), 1H exchanged with solvent.

Compound 182: (3R)—N-(cyclobutylmethyl)-1-(6-(1-(4-(5-methoxypyridin-3-yl)-1H-imidazol-1-yl)ethyl)pyridazin-3-yl)piperidin-3-amine was Obtained Using General Scheme 4 Pathway A Stage 1: General Procedure U was used from IM516 to afford tert-butyl (cyclobutylmethyl)((3R)-1-(6-(1-(4-(5-methoxypyridin-3-yl)-1H-imidazol-1-yl)ethyl)pyridazin-3-yl)piperidin-3-yl)carbamate IM538 as a formate salt (reverse phase chromatography using 10 mM ammonium formate). Formate salt of IM538 was diluted in a saturated aqueous solution of NaHCO$_3$ (50 mL) and extracted with DCM (3×15 mL). Organic phases were dried over MgSO$_4$, filtered and concentrated under reduced pressure to afford IM538 as an orange solid: 30 mg, 8% yield, P=90%, retention time=1.6 min (gradient C), (M+H)$^+$: 549.

Stage 2: General Procedure A2 was used from IM538 to afford compound 182 as a beige solid: 36 mg, 71% yield, P=98%, retention time=2.2 min (gradient E), (M+H)$^+$: 448.

The mixture of diastereomers was further purified by chiral preparative HPLC purification using Chiralpak IA column (5 μm, 20×250 mm). Eluent used: EtOAc/MeOH/DEA: 90/10/0.1% at flow rate of 20 mL/min. First eluted diastereomer: P=100%, retention time=8.7 min, chiral HPLC: P=99.7%, 1H NMR (300 MHz, CDCl$_3$) δ 8.49 (d, J=1.7 Hz, 1H), 8.14 (d, J=2.9 Hz, 1H), 7.70 (s, 1H), 7.63 (s, 1H), 7.37 (s, 1H), 6.96 (d, J=9.5 Hz, 1H), 6.87 (d, J=9.5 Hz, 1H), 5.51 (q, J=7.1 Hz, 1H), 4.38 (dd, J=12.7, 3.8 Hz, 1H), 4.11-4.01 (m, 1H), 3.87 (s, 3H), 3.17-3.02 (m, 1H), 2.92 (dd, J=12.8, 9.2 Hz, 1H), 2.72-2.62 (m, 3H), 2.53-2.32 (m, 1H), 2.13-1.95 (m, 7H), 1.90-1.77 (m, 3H), 1.71-1.35 (m, 3H), 1H exchanged with solvent. Second eluted diastereomer: P=100%, retention time=11.8 min, chiral HPLC: P=98.7%, 1H NMR (300 MHz, CDCl$_3$) δ 8.50 (s, 1H), 8.14 (d, J=2.8 Hz, 1H), 7.70 (s, 1H), 7.63 (s, 1H), 7.37 (s, 1H), 6.96 (d, J=9.4 Hz, 1H), 6.86 (d, J=9.5 Hz, 1H), 5.51 (q, J=7.1 Hz, 1H), 4.37 (d, J=12.9 Hz, 1H), 4.05 (d, J=13.0 Hz, 1H), 3.87 (s, 3H), 3.17-3.10 (m, OH), 3.10-3.02 (m, OH), 2.92 (dd, J=12.8, 9.1 Hz, 1H), 2.75-2.65 (m, 4H), 2.47-2.34 (m, 1H), 2.12-1.93 (m, 7H), 1.92-1.77 (m, 3H), 1.71-1.36 (m, 3H), 1H exchanged with solvent.

Compound 183: (R)-5-(1-((6-(3-((cyclopropylmethyl)amino)piperidin-1-yl)pyridazin-3-yl)methyl)-1H-1,2,3-triazol-4-yl)-N,N-dimethylpyridin-3-amine was Obtained Using General Scheme 1 Pathway B Stage 1: General Procedure B was used between IM5 and IM517 to afford 5-(1-((6-chloropyridazin-3-yl)methyl)-1H-1,2,3-triazol-4-yl)-N,N-dimethylpyridin-3-amine IM539 as a yellow solid: 90 mg, 87% yield, P=90%, retention time=2.0 min (gradient A), (M+H)$^+$: 316/318.

Stage 2: General Procedure C was used between IM486 and IM539 to afford tert-butyl (R)-(cyclopropylmethyl)(1-(6-((4-(5-(dimethylamino)pyridin-3-yl)-1H-1,2,3-triazol-1-yl)methyl) pyridazin-3-yl)piperidin-3-yl)carbamate IM540 as yellow oil: 105 mg, 66% yield, P=86%, retention time=2.5 min (gradient A), (M+H)$^+$: 534.

Stage 3: General Procedure A1 was used from IM540 to afford crude compound 183 as a beige solid: 65 mg, 76% yield, P=95%, retention time=2.3 min (gradient B), (M+H)+: 434, $^1$H NMR (300 MHz, CDCl$_3$) δ 8.29 (d, J=1.7 Hz, 1H), 8.11 (d, J=3.0 Hz, 1H), 8.00 (s, 1H), 7.57-7.49 (m, 1H), 7.28 (d, J=9.4 Hz, 1H), 6.91 (d, J=9.5 Hz, 1H), 5.75 (s, 2H), 4.40 (d, J=13.1 Hz, 1H), 4.15-4.03 (m, 1H), 3.22-3.08 (m, 1H), 3.04 (s, 6H), 2.82-2.70 (m, 1H), 2.59 (d, J=6.9 Hz, 2H), 2.16-1.99 (m, 1H), 1.90-1.80 (m, 1H), 1.74-1.40 (m, 3H), 1.04-0.89 (m, 1H), 0.50 (dd, J=8.0, 1.5 Hz, 2H), 0.19-0.08 (m, 2H), 1H exchanged with solvent.

Compound 184: (R)-5-(1-(3-(5-(3-((cyclopropylmethyl)amino)piperidin-1-yl)pyridin-2-yl)oxetan-3-yl)-1H-1,2,3-triazol-4-yl)-N,N-dimethylpyridin-3-amine was Obtained Using General Scheme 1 Pathway A Stage 1: General Procedure Y was used between IM486 and IM450 to afford tert-butyl ((3R)-1-(6-(3-((tert-butylsulfinyl)amino)oxetan-3-yl)pyridin-3-yl)piperidin-3-yl)(cyclopropylmethyl) carbamate IM541 as an orange solid: 2.17 g, 67% yield, P=82%, retention time=2.5 min (gradient A), (M+H)+: 507.

Stage 2: To a solution of IM541 (2.17 g, 3.51 mmol) in THF (10 mL) and water (1.8 mL) was added iodine (352 mg, 1.39 mmol) at rt and the reaction mixture was stirred at 55° C. for 1.25 h. The reaction mixture was cooled to rt and diluted with EtOAc (150 mL), then washed with a mixture of Na$_2$S$_2$O$_3$ (2 M, 30 mL) and NaHCO$_3$ saturated solution (2×25 mL). The aqueous layer was extracted with EtOAc (2×50 mL) and the combined organic layers were dried over MgSO$_4$, filtered and the filtrate was concentrated under vacuum to afford crude tert-butyl (R)-(1-(6-(3-aminooxetan-3-yl)pyridin-3-yl)piperidin-3-yl)(cyclopropylmethyl)carbamate IM542 as brown oil: 2 g, 99% yield, P=70%, retention time=2.4 min (gradient A), (M+H)+: 403.

Stage 3: General Procedure V was used from IM542 to afford tert-butyl (R)-(1-(6-(3-azidooxetan-3-yl)pyridin-3-yl)piperidin-3-yl)(cyclopropylmethyl)carbamate IM543 as yellow oil: 1.23 g, 79% yield, P=96%, retention time=2.8 min (gradient A), (M+H)$^+$: 429.

Stage 4: General Procedure B was used between IM517 and IM543 to afford tert-butyl (R)-(cyclopropylmethyl)(1-(6-(3-(4-(5-(dimethylamino)pyridin-3-yl)-1H-1,2,3-triazol-1-yl)oxetan-3-yl)pyridin-3-yl)piperidin-3-yl)carbamate IM544 as a white solid: 55 mg, 70% yield, P=99%, retention time=2.5 min (gradient A), (M+H)$^+$: 575.

Stage 5: General Procedure A2 was used from IM544 to afford crude compound 184 as an off-white solid: 38 mg, 79% yield, P=93%, retention time=2.6 min (gradient B), (M+H)$^+$: 475. $^1$H NMR (300 MHz, CDCl$_3$) δ 8.34 (d, J=2.9 Hz, 1H), 8.24 (s, 1H), 8.09 (d, J=3.0 Hz, 1H), 7.76 (s, 1H), 7.59 (s, 1H), 7.14 (dd, J=8.7, 3.0 Hz, 1H), 6.91 (d, J=8.7 Hz, 1H), 5.55 (d, J=6.8 Hz, 2H), 5.48 (d, J=6.7 Hz, 2H), 3.71 (d, J=10.7 Hz, 1H), 3.51 (d, J=12.4 Hz, 1H), 3.04 (s, 6H), 2.94-2.70 (m, 3H), 2.60-2.51 (m, 2H), 2.05-1.93 (m, 1H), 1.72-1.44 (m, 3H), 0.95 (d, J=6.0 Hz, 1H), 0.56-0.45 (m, 2H), 0.19-0.08 (m, 2H), 1 NH exchanged with solvent.

Compound 185: (R)—N-(cyclopropylmethyl)-1-(6-(3-(4-(6-(pyrrolidin-1-yl)pyrazin-2-yl)-1H-1,2,3-triazol-1-yl)oxetan-3-yl)pyridin-3-yl)piperidin-3-amine was Obtained Using General Scheme 1 Pathway A Stage 1: General Procedure B was used between IM534 and IM543 to afford tert-butyl (R)-(cyclopropylmethyl)(1-(6-(3-(4-(6-(pyrrolidin-1-yl)pyrazin-2-yl)-1H-1,2,3-triazol-1-yl)oxetan-3-yl)pyridin-3-yl)piperidin-3-yl)carbamate IM545 as a white solid: 65 mg, 79% yield, P=98%, retention time=3.0 min (gradient A), (M+H)$^+$: 602.

Stage 2: General Procedure A2 was used from IM545 to afford crude compound 185 as an off-white solid: 44 mg, 79% yield, P=95%, retention time=3.1 min (gradient B), (M+H)$^+$: 502. $^1$H NMR (300 MHZ, CDCl$_3$) δ 8.63 (s, 1H), 8.34 (d, J=3.0 Hz, 1H), 8.05 (s, 1H), 7.83 (s, 1H), 7.11 (dd, J=8.7, 3.0 Hz, 1H), 6.84 (d, J=8.7 Hz, 1H), 5.61-5.44 (m, 4H), 3.68 (d, J=10.8 Hz, 1H), 3.56-3.44 (m, 5H), 2.97-2.83 (m, 1H), 2.83-2.64 (m, 2H), 2.64-2.45 (m, 2H), 2.09-1.99 (m, 4H), 1.83-1.77 (m, 1H), 1.69-1.63 (m, 2H), 1.43-1.29 (m, 1H), 0.99-0.89 (m, 1H), 0.61-0.44 (m, 2H), 0.18-0.06 (m, 2H), 1 NH exchanged with solvent.

Compound 186: 4-((R)-3-((cyclopropylmethyl)amino)piperidin-1-yl)-1-(1-(4-(6-(dimethyl amino)pyrazin-2-yl)-1H-1,2,3-triazol-1-yl)ethyl)pyridin-2(1H)-one was Obtained Using General Scheme 1 Pathway B Stage 1: General Procedure C was used between IM486 and IM490 to afford tert-butyl (cyclopropylmethyl)((3R)-1-(1-(1-(4-(6-(dimethylamino)pyrazin-2-yl)-1H-1,2,3-triazol-1-yl) ethyl)-2-oxo-1,2-dihydropyridin-4-yl)piperidin-3-yl)carbamate IM546 as yellow sticky film: 68 mg, 37% yield, P=94%, retention time=2.7 min (gradient A), (M+H)$^+$: 564.

Stage 2: General Procedure A1 was used from IM546 to afford crude compound 186 as yellowish oil: 58 mg, 100% yield, P=91%, retention time=2.1 min (gradient A), (M+H)$^+$: 464.

The mixture of diastereomers was purified by chiral preparative HPLC purification using Chiralpak IA column (5 μm, 20×250 mm). Eluent used: TBME/MeOH/DCM/DEA: 40/40/20/0.1% at flow rate of 20 ml/min. First eluted diastereomer: P=100%, retention time=4.2 min, chiral HPLC: P=100%, $^1$H NMR (300 MHz, CDCl$_3$) δ 8.59 (s, 1H), 8.30 (s, 1H), 7.96 (s, 1H), 7.59 (q, J=7.0 Hz, 1H), 7.44 (d, J=8.1 Hz, 1H), 5.97 (dd, J=8.1, 2.8 Hz, 1H), 5.65 (d, J=2.8 Hz, 1H), 3.76 (d, J=12.6 Hz, 1H), 3.60 (d, J=13.4 Hz, 1H), 3.13 (s, 6H), 2.99-2.84 (m, 1H), 2.74 (dd, J=12.7, 9.4 Hz, 1H), 2.67-2.60 (m, 1H), 2.56-2.46 (m, 2H), 2.15 (d, J=7.0 Hz, 3H), 2.04-1.92 (m, 1H), 1.81-1.70 (m, 1H), 1.59-1.34 (m, 2H), 0.98-0.86 (m, 1H), 0.54-0.42 (m, 2H), 0.16-0.07 (m, 2H), 1H exchanged with solvent. Second eluted diastereomer: P=100%, retention time=11.7 min, chiral HPLC: P=100%, $^1$H NMR (300 MHZ, CDCl$_3$) δ 8.57 (s, 1H), 8.30 (s, 1H), 7.95 (s, 1H), 7.57 (q, J=7.0 Hz, 1H), 7.44 (d, J=8.1 Hz, 1H), 5.97 (dd, J=8.1, 2.9 Hz, 1H), 5.65 (d, J=2.8 Hz, 1H), 3.82 (d, J=12.5 Hz, 1H), 3.59 (d, J=13.5 Hz, 1H), 3.12 (s, 6H), 2.98-2.87 (m, 1H), 2.82 (dd, J=12.8, 9.5 Hz, 1H), 2.76-2.64 (m, 1H), 2.53 (d, J=6.9 Hz, 2H), 2.13 (d, J=7.0 Hz, 3H), 2.04-1.95 (m, 1H), 1.81-1.70 (m, 1H), 1.56-1.38 (m, 2H), 1.00-0.87 (m, 1H), 0.55-0.42 (m, 2H), 0.16-0.09 (m, 2H), 1H exchanged with solvent.

Compound 187: (3R)—N-(cyclobutylmethyl)-1-(6-(1-(4-(5-ethoxypyridin-3-yl)-1H-1,2,3-triazol-1-yl)ethyl)pyridazin-3-yl)piperidin-3-amine was Obtained Using General Scheme 1 Pathway B Stage 1: In a microwave vial were placed IM293 (90 mg, 168 µmol) and EtONa (21 wt. % in EtOH) (1.25 mL, 3.35 mmol). Vial was sealed and reaction was stirred at 80° C. overnight. After cooling to rt, reaction mixture was concentrated under reduced pressure. The residue was purified by reverse phase chromatography on C18 cartridge, eluting with a gradient of MeCN in basic water (10 mM $NH_4HCO_3$/$NH_4OH$ buffer pH=10) to afford tert-butyl (cyclobutylmethyl)((3R)-1-(6-(1-(4-(5-ethoxypyridin-3-yl)-1H-1,2,3-triazol-1-yl)ethyl) pyridazin-3-yl)piperidin-3-yl)carbamate IM547 as a yellow oil: 89 mg, 91% yield, P=97%, retention time=1.8 min (gradient C), $(M+H)^+$: 564.

Stage 2: General Procedure A2 was used from IM547 to afford compound 187 as a yellow solid: 51 mg, 68% yield, P=98%, retention time=1.3 min (gradient E), $(M+H)^+$: 464.

The mixture of diastereomers was further purified by chiral preparative HPLC purification using Chiralpak IA column (5 µm, 20×250 mm). Eluent used: TBME/MeOH/DCM/DEA: 40/40/20/0.1% at flow rate of 20 mL/min. First eluted diastereomer: P=100%, retention time=5.2 min, chiral HPLC: P=100%, $^1$H NMR (300 MHz, $CDCl_3$) δ 8.51 (s, 1H), 8.22 (d, J=2.8 Hz, 1H), 8.03 (s, 1H), 7.69 (s, 1H), 7.21 (d, J=9.5 Hz, 1H), 6.88 (d, J=9.5 Hz, 1H), 6.02 (q, J=7.1 Hz, 1H), 4.37 (dd, J=12.9, 3.9 Hz, 1H), 4.18-3.99 (m, 3H), 3.17-3.02 (m, 1H), 2.91 (dd, J=12.9, 9.2 Hz, 1H), 2.76-2.58 (m, 3H), 2.52-2.31 (m, 1H), 2.08 (d, J=7.0 Hz, 3H), 2.05-1.98 (m, 2H), 1.90-1.77 (m, 4H), 1.68-1.56 (m, 3H), 1.43 (t, J=6.9 Hz, 4H), 1H exchanged with solvent. Second eluted diastereomer: P=100%, retention time=14.4 min, chiral HPLC: P=100%, $^1$H NMR (300 MHz, $CDCl_3$) δ 8.52 (d, J=1.7 Hz, 1H), 8.22 (d, J=2.9 Hz, 1H), 8.03 (s, 1H), 7.69 (dd, J=2.8, 1.8 Hz, 1H), 7.22 (d, J=9.5 Hz, 1H), 6.89 (d, J=9.5 Hz, 1H), 6.02 (q, J=7.1 Hz, 1H), 4.45-4.35 (m, 1H), 4.19-4.01 (m, 3H), 3.17-2.92 (m, 2H), 2.80-2.63 (m, 3H), 2.57-2.41 (m, 2H), 2.09 (d, J=7.1 Hz, 3H), 2.06-1.98 (m, 2H), 1.98-1.74 (m, 3H), 1.73-1.47 (m, 4H), 1.43 (t, J=7.0 Hz, 3H), 1H exchanged with solvent.

Compound 188: 4-((R)-3-((cyclobutylmethyl)amino)piperidin-1-yl)-1-(1-(4-(6-methoxy-1H-indazol-4-yl)-1H-imidazol-1-yl)ethyl)pyridin-2(1H)-one was Obtained Using General Scheme 4 Pathway A Stage 1: General Procedure U was used between IM496 and IM303 to afford tert-butyl (cyclobutylmethyl)((3R)-1-(1-(1-(4-(6-methoxy-1-(tetrahydro-2H-pyran-2-yl)-1H-indazol-4-yl)-1H-imidazol-1-yl)ethyl)-2-oxo-1,2-dihydropyridin-4-yl)piperidin-3-yl)carbamate IM548 as a white solid: 80 mg, 39% yield, P=69%, retention time=1.6 min (gradient C), $(M+H)^+$: 687.

Stage 2: General Procedure A2 was used from IM548 to afford compound 188 as a white solid: 21 mg, 34% yield, P=97%, retention time=1.9 min (gradient E), $(M+H)^+$: 502.

The mixture of diastereomers was further purified by chiral preparative HPLC purification using Chiralpak IA column (5 µm, 20×250 mm). Eluent used: TBME/MeOH/DEA: 60/40/0.1% at flow rate of 20 mL/min. First eluted diastereomer: P=100%, retention time=4.6 min, chiral HPLC: P=99.4%, $^1$H NMR (300 MHZ, $CDCl_3$) δ 8.45 (d, J=1.1 Hz, 1H), 7.88 (d, J=1.4 Hz, 1H), 7.55 (d, J=1.4 Hz, 1H), 7.33 (q, J=6.8 Hz, 1H), 7.24 (d, J=2.1 Hz, 1H), 6.95 (d, J=8.0 Hz, 1H), 6.79 (t, J=1.5 Hz, 1H), 5.95 (dd, J=8.1, 2.8 Hz, 1H), 3.87 (s, 3H), 5.71 (d, J=2.8 Hz, 1H), 3.75 (d, J=12.7 Hz, 1H), 3.60 (d, J=13.5 Hz, 1H), 2.98-2.83 (m, 1H), 2.79-2.52 (m, 4H), 2.50-2.32 (m, 1H), 2.13-2.00 (m, 2H), 1.97 (d, J=6.9 Hz, 3H), 1.92-1.46 (m, 7H), 1.42-1.23 (m, 1H). 2H exchanged with solvent. Second eluted diastereomer: P=98%, retention time=5.2 min, chiral HPLC: P=99.3%, $^1$H NMR (300 MHz, $CDCl_3$) δ 8.45 (d, J=1.0 Hz, 1H), 7.88 (d, J=1.3 Hz, 1H), 7.54 (d, J=1.4 Hz, 1H), 7.33 (q, J=6.9 Hz, 1H), 7.24 (d, J=2.0 Hz, 1H), 6.95 (d, J=8.1 Hz, 1H), 6.79 (d, J=1.8 Hz, 1H), 5.95 (dd, J=8.1, 2.8 Hz, 1H), 3.88 (s, 3H), 5.71 (d, J=2.8 Hz, 1H), 3.76 (d, J=12.6 Hz, 1H), 3.60 (d, J=13.4 Hz, 1H), 2.99-2.84 (m, 1H), 2.77-2.53 (m, 4H), 2.48-2.32 (m, 1H), 2.13-2.00 (m, 2H), 1.98 (d, J=6.9 Hz, 3H), 1.95-1.53 (m, 7H), 1.43-1.23 (m, 1H), 1H exchanged with solvent.

Compound 189: 5-(1-(1-(4-((R)3-((cyclobutylmethyl)amino)piperidin-1-yl)phenyl)ethyl)-1H-1,2,3-triazol-4-yl)-N,N-dimethylpyridin-3-amine Stage 1: General Procedure L was used from compound 155 to afford crude compound 189 as yellow oil: 16 mg, 98% yield, P=92%, retention time=2.2 min (gradient A), $(M+H)^+$: 460.

The mixture of diastereomers was further purified by chiral preparative HPLC purification using Chiralpak IA column (5 µm, 20×250 mm). Eluent used: EtOAc/MeOH/DEA: 90/10/0.1% at flow rate of 20 mL/min. First eluted diastereomer: P=99%, retention time=6.9 min, chiral HPLC: P=99.9%, $^1$H NMR (300 MHz, $CDCl_3$) δ 8.20 (d, J=1.7 Hz, 1H), 8.07 (d, J=3.0 Hz, 1H), 7.62 (s, 1H), 7.59-7.53 (m, 1H), 7.22 (d, J=8.6 Hz, 2H), 6.92 (d, J=8.7 Hz, 2H), 5.80 (q, J=7.0 Hz, 1H), 3.66 (d, J=11.2 Hz, 1H), 3.46 (d, J=12.1 Hz, 1H), 3.03 (s, 6H), 2.90-2.62 (m, 5H), 2.52-2.40 (m, 1H), 2.13-2.04 (m, 2H), 1.99 (d, J=7.1 Hz, 3H), 1.95-1.58 (m, 7H), 1.35 (d, J=10.9 Hz, 1H), 1H exchanged with solvent. Second eluted diastereomer: P=97%, retention time=7.5 min, chiral HPLC: P=99.6%, $^1$H NMR (300 MHz, $CDCl_3$) δ 8.20 (s, 1H), 8.07 (d, J=2.9 Hz, 1H), 7.62 (s, 1H), 7.57 (s, 1H), 7.22 (d, J=8.2 Hz, 2H), 6.92 (d, J=8.1 Hz, 2H), 5.79 (q, J=7.0 Hz, 1H), 3.71-3.62 (m, 1H), 3.50-3.40 (m, 1H), 3.02 (d, J=1.2 Hz, 6H), 2.90-2.65 (m, 5H), 2.58-2.44 (m, 3H), 2.15-2.07 (m, 1H), 1.99 (d, J=7.0 Hz, 3H), 1.94-1.53 (m, 6H), 1.45-1.33 (m, 1H), 1H exchanged with solvent.

Compound 190: (3R)—N-(cyclobutylmethyl)-1-(6-(1-(5-(5-methoxypyridin-3-yl)-2H-tetrazol-2-yl)ethyl)pyridazin-3-yl)piperidin-3-amine was Obtained Using the Following Procedures Stage 1: To IM320 (160 mg, 903 µmol) and potassium carbonate (382 mg, 2.71 mmol) in DMF (6 mL) was added IM513 (321 mg, 1.35 mmol). The reaction mixture was stirred at 100° C. for 10 h. The mixture was diluted with ethyl acetate and minimal water and then concentrated under reduced pressure before being loaded using water and minimal DMF to a C-18 column and purified using 0% to 30% MeCN in 10 mM ammonium formate. The product was re-purified by normal phase flash chromatography using 0% to 20% MeOH in DCM to afford 3-chloro-6-(1-(5-(5- methoxypyridin-3-yl)-2H-tetrazol-2-yl)ethyl)pyridazine IM549 as colourless oil: 238 mg, 83% yield, P=100%, retention time=1.1 min (gradient F), (M+H)⁺: 318/320.

Stage 2: General Procedure C was used between IM3 and IM549 to afford tert-butyl (cyclobutylmethyl)((3R)-1-(6-(1-(5-(5-methoxypyridin-3-yl)-2H-tetrazol-2-yl)ethyl) pyridazin-3-yl)piperidin-3-yl)carbamate IM550 as yellow oil: 270 mg, 66% yield, P=100%, retention time=1.8 min (gradient F), (M+H)⁺: 551.

Stage 3: General Procedure A2 was used from IM550 to afford compound 190 as a pale yellow gum: 149 mg, 44% yield, P=100%, retention time=1.0 min (gradient F), (M+H)⁺: 451.

The mixture of diastereomers was further purified by chiral preparative HPLC purification using Chiralpak IA column (5 µm, 20×250 mm). Eluent used: TBME/MeOH/DCM/DEA: 40/40/20/0.1% at flow rate of 20 mL/min. First eluted diastereomer: P=99%, retention time=4.7 min, chiral HPLC: P=100%, ¹H NMR (300 MHz, CDCl₃) δ 8.91 (d, J=1.7 Hz, 1H), 8.35 (d, J=2.9 Hz, 1H), 7.86 (dd, J=2.9, 1.7 Hz, 1H), 7.19 (dd, J=9.5, 1.7 Hz, 1H), 6.86 (d, J=9.6 Hz, 1H), 6.33 (q, J=7.1 Hz, 1H), 4.41-4.29 (m, 1H), 4.12-3.99 (m, 1H), 3.89 (s, 3H), 3.14-2.99 (m, 1H), 2.86 (dd, J=12.8, 9.2 Hz, 1H), 2.75-2.53 (m, 3H), 2.45-2.27 (m, 1H), 2.18-2.10 (m, 3H), 2.07-1.71 (m, 6H), 1.67-1.28 (m, 4H), 1H exchanged with solvent. Second eluted diastereomer: P=99%, retention time=7.7 min, chiral HPLC: P=100%, ¹H NMR (300 MHz, CDCl₃) δ 8.94 (d, J=1.7 Hz, 1H), 8.38 (d, J=2.9 Hz, 1H), 7.89 (dd, J=2.9, 1.7 Hz, 1H), 7.21 (dd, J=9.6, 1.7 Hz, 1H), 6.89 (d, J=9.5 Hz, 1H), 6.36 (q, J=7.1 Hz, 1H), 4.45-4.33 (m, 1H), 4.12-4.01 (m, 1H), 3.91 (s, 3H), 3.17-3.02 (m, 1H), 2.89 (dd, J=12.8, 9.2 Hz, 1H), 2.78-2.57 (m, 3H), 2.41 (hept, J=7.4 Hz, 1H), 2.20-2.12 (m, 3H), 2.09-1.74 (m, 6H), 1.67-1.34 (m, 4H), 1H exchanged with solvent.

Compound 191: 1-(1-(4-(5-(2-oxa-6-azaspiro[3.3] heptan-6-yl)pyridin-3-yl)-1H-1,2,3-triazol-1-yl) ethyl)-4-((R)-3-((cyclobutylmethyl)amino)piperidin-1-yl)pyridin-2(1H)-one was Obtained Using General Scheme 1 Pathway B Stage 1: To IM293 (200 mg, 363 µmol) in NMP (1.5 mL) was added 2-Oxa-6-azaspiro[3.3]heptane (733 mg, 7.40 mmol). The mixture was stirred at 130° C. for 65.5 h. Then cesium carbonate (140 mg, 421 µmol) and N,N-diisopropylethylamine (698 µL, 3.99 mmol) were added and the reaction was continued for 24.5 h. The reaction mixture was concentrated under reduced pressure. The residue was purified on a C-18 column using 2% to 80% acetonitrile in 10 mM ammonium formate to afford tert-butyl ((3R)-1-(1-(4-(5-(2-oxa-6-azaspiro[3.3]heptan-6-yl)pyridin-3-yl)-1H-1,2,3-triazol-1-yl)ethyl)-2-oxo-1,2-dihydro pyridin-4-yl)piperidin-3-yl)(cyclobutylmethyl)carbamate IM551: 139 mg, 61% yield, P=94%, retention time=1.6 min (gradient F), (M+H)⁺: 631.

Stage 2: General Procedure A2 was used from IM551 to afford compound 191 as a white solid: 56 mg, 48% yield, P=100%, retention time=2.1 min (gradient E), (M+H)⁺: 531.

The mixture of diastereomers was further purified by chiral preparative HPLC purification using Chiralpak IA column (5 µm, 20×250 mm). Eluent used: TBME/MeOH/DCM/DEA: 40/40/20/0.1% at flow rate of 20 mL/min. First eluted diastereomer: P=100%, retention time=9.2 min, chiral HPLC: P=100%, ¹H NMR (300 MHz, CDCl₃) δ 8.37 (d, J=1.8 Hz, 1H), 8.11 (s, 1H), 7.80 (d, J=2.7 Hz, 1H), 7.53 (q, J=7.0 Hz, 1H), 7.41 (d, J=8.0 Hz, 1H), 7.23-7.17 (m, 1H), 5.98 (dd, J=8.2, 2.8 Hz, 1H), 5.65 (d, J=2.8 Hz, 1H), 4.84 (s, 4H), 4.10 (s, 4H), 3.79-3.69 (m, 1H), 3.64-3.54 (m, 1H), 2.91 (ddd, J=13.5, 10.7, 3.2 Hz, 1H), 2.78-2.50 (m, 4H), 2.39 (hept, J=7.5 Hz, 1H), 2.15 (d, J=7.0 Hz, 3H), 2.12-1.44 (m, 9H), 1.43-1.22 (m, 1H), 1H exchanged with solvent. Second eluted diastereomer: P=100%, retention time=11.9 min, chiral HPLC: P=99.8%, ¹H NMR (300 MHz, CDCl₃) δ 8.31 (d, J=1.8 Hz, 1H), 8.06 (s, 1H), 7.73 (d, J=2.8 Hz, 1H), 7.47 (q, J=7.0 Hz, 1H), 7.36 (d, J=8.1 Hz, 1H), 7.15 (t, J=2.3 Hz, 1H), 5.92 (dd, J=8.1, 2.9 Hz, 1H), 5.59 (d, J=2.8 Hz, 1H), 4.78 (s, 4H), 4.05 (s, 4H), 3.70 (d, J=12.6 Hz, 1H), 3.54 (d, J=13.5 Hz, 1H), 2.85 (ddd, J=13.6, 10.7, 3.1 Hz, 1H), 2.73-2.46 (m, 4H), 2.33 (hept, J=7.5 Hz, 1H), 2.09 (d, J=7.0 Hz, 3H), 2.04-1.41 (m, 9H), 1.38-1.23 (m, 1H), 1H exchanged with solvent.

Compound 192: (R)-6-(1-(3-(5-(3-((cyclopropylmethyl)amino)piperidin-1-yl)pyridin-2-yl)oxetan-3-yl)-1H-1,2,3-triazol-4-yl)-N,N-dimethylpyrazin-2-amine was Obtained Using General Scheme 1 Pathway A Stage 1: General Procedure X was used between IM489 and IM543 to afford tert-butyl (R)-(cyclopropylmethyl)(1-(6-(3-(4-(6-(dimethylamino)pyrazin-2-yl)-1H-1,2,3-triazol-1-yl)oxetan-3-yl)pyridin-3-yl)piperidin-3-yl)carbamate IM552 as yellow oil: 45 mg, 49% yield, P=84%, retention time=2.9 min (gradient A), (M+H)⁺: 576.

Stage 2: General Procedure A2 was used from IM552 to afford crude compound 192 as a yellow solid: 33 mg, 88% yield, P=83%, retention time=2.9 min (gradient B), (M+H)⁺: 476.

The product was purified by reverse phase preparative HPLC purification (Waters XBridge C18 5 µm, 19×100 mm). Gradient used: increased linearly from 20 to 50% solution "B" over 4.0 min, increased linearly to 85% solution "B" over 2.2 min, held at 85% for 0.1 min and returned to initial conditions over 1.0 min. Flow Rate: 15 mL/min. P=84%.

Compound 192 was further purified by chiral preparative HPLC purification using Chiralpak IA column (5 µm, 10×250 mm). Eluent used: EtOAc/DEA: 100/0.05% at flow rate of 7 mL/min. P=98%, retention time=4.0 min, ¹H NMR (300 MHz, CDCl₃) δ 8.55 (s, 1H), 8.23 (d, J=3.0 Hz, 1H), 7.94 (s, 1H), 7.88 (s, 1H), 7.01 (dd, J=8.8, 3.1 Hz, 1H), 6.75 (d, J=8.7 Hz, 1H), 5.41 (q, J=6.8 Hz, 4H), 3.62-3.52 (m, 1H), 3.45-3.35 (m, 1H), 3.03 (s, 6H), 2.85-2.71 (m, 1H), 2.70-2.54 (m, 2H), 2.52-2.34 (m, 2H), 1.96-1.10 (m, 4H), 0.82 (s, 1H), 0.45-0.33 (m, 2H), 0.07--0.02 (m, 2H), 1H exchanged with solvent.

Compound 193: 1-(1-(4-(5-(2-azaspiro[3.3]heptan-2-yl)pyridin-3-yl)-1H-1,2,3-triazol-1-yl)ethyl)-4-((R)-3-((cyclobutylmethyl)amino)piperidin-1-yl) pyridin-2(1H)-one was Obtained Using General Scheme 1 Pathway B Stage 1: mixture of 2-azaspiro[3.3]heptane hydrochloride (186 mg, 1.32 mmol), potassium carbonate (358 mg, 2.54 mmol) and NMP (3.2 mL) in a reaction vial was stirred for 20 min at 130° C. After cooling the reaction vial to rt, IM293 (200 mg, 363 µmol) and NMP (0.3 mL) were added and the mixture was stirred at 130° C. for 67 h. The reaction mixture was concentrated under reduced pressure. The residue was purified on a C-18 column using 8% to 60% acetonitrile in 10 mM ammonium formate to afford tert-butyl ((3R)-1-(1-(1-(4-(5-(2-azaspiro[3.3]heptan-6-yl)pyridin-3-yl)-1H-1,2, 3-triazol-1-yl)ethyl)-2-oxo-1,2-dihydropyridin-4-yl)piperidin-3-yl)(cyclobutylmethyl)carbamate IM553: 195 mg, 95% yield, P=90%, retention time=1.9 min (gradient C), (M+H)+: 630.

Stage 2: General Procedure A2 was used from IM553 to afford compound 193 as a white solid: 68 mg, 34% yield, P=100%, retention time=2.9 min (gradient E), (M+H)+: 530.

The mixture of diastereomers was further purified by chiral preparative HPLC purification using Chiralpak IE column (5 μm, 10×250 mm). Eluent used: DCM/MeOH/DEA: 90/10/0.1% at flow rate of 7 mL/min. First eluted diastereomer: P=99%, retention time=8.4 min, chiral HPLC: P=100%, $^1$H NMR (300 MHZ, CDCl$_3$) δ 8.32 (d, J=1.8 Hz, 1H), 8.10 (s, 1H), 7.77 (d, J=2.8 Hz, 1H), 7.53 (q, J=7.0 Hz, 1H), 7.42 (d, J=8.1 Hz, 1H), 7.17 (t, J=2.3 Hz, 1H), 5.98 (dd, J=8.1, 2.9 Hz, 1H), 5.65 (d, J=2.8 Hz, 1H), 3.90 (s, 4H), 3.82-3.71 (m, 1H), 3.65-3.54 (m, 1H), 2.91 (ddd, J=13.7, 10.7, 3.1 Hz, 1H), 2.80-2.52 (m, 5H), 2.40 (p, J=7.5 Hz, 1H), 2.27-2.18 (m, 4H), 2.15 (d, J=7.0 Hz, 3H), 2.09-1.30 (m, 11H), 1H exchanged with solvent. Second eluted diastereomer: P=100%, retention time=13.0 min, chiral HPLC: P=100%, $^1$H NMR (300 MHz, CDCl$_3$) δ 8.33 (s, 1H), 8.11 (s, 1H), 7.77 (d, J=2.7 Hz, 1H), 7.53 (q, J=7.0 Hz, 1H), 7.42 (d, J=8.1 Hz, 1H), 7.21-7.14 (m, 1H), 5.98 (dd, J=2.8, 8 Hz, 1H), 5.66 (d, J=2.8 Hz, 1H), 3.90 (s, 4H), 3.85-3.74 (m, 1H), 3.65-3.54 (m, 1H), 2.92 (t, J=11.5 Hz, 1H), 2.79 (dd, J=12.9, 9.5 Hz, 1H), 2.69 (d, J=7.3 Hz, 4H), 2.44 (p, J=7.6 Hz, 1H), 2.22 (t, J=7.6 Hz, 4H), 2.15 (d, J=7.0 Hz, 3H), 2.07-1.37 (m, 11H), 1H exchanged with solvent.

Compound 194: (R)—N-(cyclopropylmethyl)-1-(6-(3-(4-(5-(pyrrolidin-1-yl)pyridin-3-yl)-1H-1,2,3-triazol-1-yl)oxetan-3-yl)pyridin-3-yl)piperidin-3-amine was Obtained Using General Scheme 1 Pathway A Stage 1: General Procedure C (in DMSO) was used between 3,5-dibromopyridine and pyrrolidine to afford 3-bromo-5-(pyrrolidin-1-yl)pyridine IM554 as a white solid: 247 mg, 53% yield, P=100%, retention time=2.1 min (gradient A), (M+H)+: 227/229.

Stage 2: General Procedure E1 was used from IM554 to afford 3-(pyrrolidin-1-yl)-5-((trimethylsilyl)ethynyl)pyridine IM555 as a yellow solid: 84 mg, 74% yield, P=94%, retention time=2.4 min (gradient A), (M+H)+: 245.

Stage 3: General Procedure X was used between IM555 and IM543 to afford tert-butyl (R)-(cyclopropylmethyl)(1-(6-(3-(4-(5-(pyrrolidin-1-yl)pyridin-3-yl)-1H-1,2,3-triazol-1-yl)oxetan-3-yl)pyridin-3-yl)piperidin-3-yl)carbamate IM556 as sticky yellow oil: 34 mg, 41% yield, P=98%, retention time=2.6 min (gradient A), (M+H)+: 601.

Stage 4: General Procedure A2 was used from IM556 to afford compound 194 as an off-white solid: 19 mg, 66% yield, P=96%, retention time=2.8 min (gradient B), (M+H)+: 502.

$^1$H NMR (300 MHz, CDCl$_3$) δ 8.34 (d, J=3.0 Hz, 1H), 8.19 (s, 1H), 7.94 (s, 1H), 7.74 (s, 1H), 7.41 (s, 1H), 7.14 (dd, J=8.7, 3.0 Hz, 1H), 6.90 (d, J=8.7 Hz, 1H), 5.55 (d, J=6.7 Hz, 2H), 5.49 (d, J=6.7 Hz, 2H), 3.75-3.62 (m, 1H), 3.57-3.46 (m, 1H), 3.42-3.32 (m, 4H), 2.96-2.83 (m, 1H), 2.83-2.67 (m, 1H), 2.61-2.46 (m, 3H), 2.09-1.99 (m, 4H), 1.87-1.22 (m, 4H), 0.94 (d, J=7.7 Hz, 1H), 0.55-0.42 (m, 2H), 0.15-0.05 (m, 2H), 1H exchanged with solvent.

Compound 195: (R)-3-(5-(3-((cyclopropylmethyl)amino)piperidin-1-yl)pyridin-2-yl)-N-(5-(pyrrolidin-1-yl)pyridin-3-yl)oxetane-3-carboxamide was Obtained Using General Scheme 6 Pathway B Stage 1: General Procedure AA was used between IM554 and benzylamine to afford N-benzyl-5-(pyrrolidin-1-yl)pyridin-3-amine IM557 as a white solid: 68 mg, 44% yield, P=100%, retention time=2.3 min (gradient A), (M+H)+: 228.

Stage 2: General Procedure I was used from IM557 to afford crude 5-(pyrrolidin-1-yl)pyridin-3-amine IM558 as yellow oil: 25 mg, 40% yield, P=70%, retention time=1.9 min (gradient A), (M+H)+: no ionization.

Stage 3: General Procedure F was used between IM522 and IM558 to afford tert-butyl (R)-(cyclopropylmethyl)(1-(6-(3-((5-(pyrrolidin-1-yl)pyridin-3-yl)carbamoyl)oxetan-3-yl)pyridin-3-yl)piperidin-3-yl)carbamate IM559 as yellow oil: 46 mg, 25% yield, P=35%, retention time=2.5 min (gradient A), (M+H)+: 577.

Stage 4: General Procedure A2 was used from IM559 to afford compound 195 as a white solid: 13 mg, 97% yield, P=99%, retention time=2.6 min (gradient B), (M+H)+: 477, $^1$H NMR (300 MHz, CDCl$_3$) δ 8.79 (s, 1H), 8.33 (dd, J=2.6, 1.1 Hz, 1H), 7.72-7.65 (m, 2H), 7.53 (t, J=2.4 Hz, 1H), 7.22 (t, J=2.2 Hz, 1H), 5.38 (d, J=6.0 Hz, 2H), 5.03 (d, J=6.0 Hz, 2H), 3.77-3.65 (m, 1H), 3.57-3.45 (m, 1H), 3.36-3.25 (m, 4H), 2.98-2.66 (m, 3H), 2.60-2.47 (m, 2H), 2.06-1.94 (m, 4H), 1.92-1.18 (m, 4H), 1.00-0.92 (m, 1H), 0.57-0.47 (m, 2H), 0.14 (q, J=4.9 Hz, 2H), 2H exchanged with solvent.

Compound 196: 4-((R)-3-((cyclopropylmethyl)amino)piperidin-1-yl)-1-(1-(1-(5-(dimethylamino)pyridin-3-yl)-1H-pyrazol-4-yl)ethyl)pyridin-2(1H)-one was Obtained Using General Scheme 3 Scheme 5

Stage 2: General Procedure C was used between IM467 and IM486 to afford tert-butyl (cyclopropylmethyl)((3R)-1-(1-(1-(1-(5-(dimethylamino)pyridin-3-yl)-1H-pyrazol-4-yl)ethyl)-2-oxo-1,2-dihydropyridin-4-yl)piperidin-3-yl)carbamate IM560 as an off-white solid: 114 mg, 78% yield, P=100%, retention time=1.6 min (gradient C), (M+H)+: 562.

Stage 2: General Procedure A2 was used from IM560 to afford compound 196 as a white solid: 85 mg, 88% yield, P=97%, retention time=2.1 min (gradient E), (M+H)+: 462.

The mixture of diastereomers was further purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=100%, retention time=6.5 min, chiral HPLC: P=100%, $^1$H NMR (300 MHz, CDCl$_3$) δ 8.16 (d, J=2.1 Hz, 1H), 7.99 (d, J=2.8 Hz, 1H), 7.83 (s, 1H), 7.61 (s, 1H), 7.24 (d, J=4.3 Hz, 1H), 6.98 (d, J=7.9 Hz, 1H), 6.30 (q, J=7.0 Hz, 1H), 5.87 (dd, J=7.9, 2.9 Hz, 1H), 5.71 (d, J=2.8 Hz, 1H), 3.76-3.66 (m, 1H), 3.60-3.49 (m, 1H), 2.99 (s, 6H), 2.93-2.79 (m, 1H), 2.75-2.56 (m, 2H), 2.55-2.38 (m, 2H), 2.04-1.24 (m, 7H), 0.87 (q, J=6.6 Hz, 1H), 0.50-0.38 (m, 2H), 0.11--0.01 (m, 2H), 1H exchanged with solvent. Second eluted diastereomer: P=99%, retention time=8.2 min, chiral HPLC: P=100%, $^1$H NMR (300 MHz, CDCl$_3$) δ 8.19 (d, J=2.1 Hz, 1H), 8.03 (d, J=2.8 Hz, 1H), 7.86 (s, 1H), 7.64 (s, 1H), 7.28 (d, J=2.5 Hz, 1H), 7.01 (d, J=7.9 Hz, 1H), 6.33 (q, J=7.0 Hz, 1H), 5.90 (dd, J=8.0, 2.9 Hz, 1H), 5.74 (d, J=2.8 Hz, 1H), 3.80-3.70 (m, 1H), 3.63-3.53 (m, 1H), 3.03 (s, 6H), 2.96-2.82 (m, 1H), 2.78-2.61 (m, 2H), 2.58-2.41 (m, 2H), 2.03-1.29 (m, 7H), 0.98-0.83 (m, 1H), 0.53-0.41 (m, 2H), 0.13-0.04 (m, 2H), 1H exchanged with solvent.

Compound 197: 4-((R)-3-((cyclopropylmethyl)amino)piperidin-1-yl)-1-(1-(4-(5-(3,3-difluoroazetidin-1-yl)pyridin-3-yl)-1H-1,2,3-triazol-1-yl)ethyl)pyridin-2(1H)-one was Obtained Using General Scheme 1 Pathway B Stage 1: General Procedure AA was used between IM524 and 3,3-difluoroazetidine hydrochloride to afford tert-butyl (cyclopropylmethyl)((3R)-1-(1-(1-(4-(5-(3,3-difluoroazetidin-1-yl)pyridin-3-yl)-1H-1,2,3-triazol-1-yl)ethyl)-2-oxo-1,2-dihydropyridin-4-yl) piperidin-3-yl)carbamate IM561 as colourless oil: 29 mg, 27% yield, P=71%, retention time=2.6 min (gradient A), (M+H)⁺: 611.

Stage 2: General Procedure A1 was used from IM561 to afford crude compound 197 as colourless oil: 24 mg, 96% yield, P=69%, retention time=2.1 min (gradient B), (M+H)⁺: 511.

The product was purified by reverse phase preparative HPLC purification (Waters XBridge C18 5 μm, 19×100 mm). Gradient used: increased linearly from 25 to 50% solution "B" over 4.0 min, increased linearly to 85% solution "B" over 2.3 min, and returned to initial conditions over 1.0 min. Flow Rate: 15 mL/min. P=97%.

The mixture of diastereomers was further purified by chiral preparative HPLC purification using Chiralpak IA column (5 μm, 20×250 mm). Eluent used: TBME/MeOH/DCM/DEA: 45/45/10/0.1% at flow rate of 20 ml/min. First eluted diastereomer: P=97%, retention time=8.8 min, chiral HPLC: P=96.3%, ¹H NMR (300 MHz, CDCl₃) δ 8.47 (d, J=1.8 Hz, 1H), 8.20 (s, 1H), 7.86 (d, J=2.8 Hz, 1H), 7.53 (q, J=7.0 Hz, 1H), 7.43 (d, J=8.1 Hz, 1H), 7.33 (d, J=2.3 Hz, 1H), 5.99 (dd, J=8.1, 2.9 Hz, 1H), 5.67 (d, J=2.8 Hz, 1H), 4.32 (t, J=11.7 Hz, 4H), 3.86-3.76 (m, 1H), 3.64-3.53 (m, 1H), 2.91 (dt, J=18.6, 11.6 Hz, 2H), 2.72 (s, 1H), 2.55 (d, J=6.9 Hz, 2H), 2.16 (d, J=7.0 Hz, 3H), 2.00 (d, J=8.0 Hz, 1H), 1.78 (d, J=13.0 Hz, 1H), 1.54 (q, J=11.7 Hz, 2H), 0.94 (s, 1H), 0.57-0.42 (m, 2H), 0.14 (t, J=5.2 Hz, 2H), 1H exchanged with solvent. ¹⁹F NMR (282 MHZ, CDCl₃) δ −96.29 (q, J=11.5 Hz). Second eluted diastereomer: P=100%, retention time=10.2 min, chiral HPLC: P=99.6%, ¹H NMR (300 MHz, CDCl₃) δ 8.46 (d, J=1.8 Hz, 1H), 8.22 (s, 1H), 7.86 (d, J=2.9 Hz, 1H), 7.53 (q, J=7.0 Hz, 1H), 7.45 (d, J=8.1 Hz, 1H), 7.37-7.30 (m, 1H), 6.01 (dd, J=8.2, 2.9 Hz, 1H), 5.67 (d, J=2.8 Hz, 1H), 4.32 (t, J=11.7 Hz, 4H), 3.88 (d, J=13.1 Hz, 1H), 3.57 (d, J=13.5 Hz, 1H), 3.00-2.86 (m, 2H), 2.76 (s, 1H), 2.63-2.47 (m, 2H), 2.16 (d, J=7.0 Hz, 3H), 2.00 (s, OH), 1.78 (s, 1H), 1.51 (s, 3H), 0.98 (s, 1H), 0.56-0.47 (m, 2H), 0.26-0.12 (m, 2H), 1H exchanged with solvent ¹⁹F NMR (282 MHz, CDCl₃) δ −96.12−−96.39 (m).

Compound 198: 4-((R)-3-((cyclobutylmethyl) amino)piperidin-1-yl)-1-(1-(4-(5-(dimethyl amino)pyridazin-3-yl)-1H-1,2,3-triazol-1-yl)ethyl)pyridin-2 (1H)-one was Obtained Using General Scheme 1 Pathway B Stage 1: General Procedure E1 was used from 6-chloro-N,N-dimethylpyridazin-4-amine to afford N,N-dimethyl-6-((trimethylsilyl)ethynyl)pyridazin-4-amine IM562 as a yellow solid: 108 mg, 31% yield, P=60%, retention time=1.3 min (gradient C), (M+H)⁺: 220.

Stage 2: General Procedure X was used between IM151 and IM562 to afford (4-chloro-1-(1-(4-(5-(dimethylamino)pyridazin-3-yl)-1H-1,2,3-triazol-1-yl)ethyl)pyridin-2(1H)-one IM563 as a beige solid: 60 mg, 63% yield, P=91%, retention time=1.0 min (gradient C), (M+H)⁺: 346.

Stage 3: General Procedure C was used between IM563 and IM3 to afford tert-butyl (cyclobutylmethyl)((3R)-1-(1-(1-(4-(5-(dimethylamino)pyridazin-3-yl)-1H-1,2,3-triazol-1-yl) ethyl)-2-oxo-1,2-dihydropyridin-4-yl)piperidin-3-yl) carbamate IM564 as a yellow solid: 70 mg, 70% yield, P=100%, retention time=1.6 min (gradient C), (M+H)⁺: 578.

Stage 4: General Procedure A2 was used from IM564 to afford compound 198 as a pale yellow solid: 28 mg, 49% yield, P=97%, retention time=2.1 min (gradient E), (M+H)⁺: 478.

The mixture of diastereomers was further purified by chiral preparative HPLC purification using Chiralpak IE column (5 μm, 10×250 mm). Eluent used: DCM/MeOH/DEA: 90/10/0.1% at flow rate of 7 mL/min. First eluted diastereomer: P=100%, retention time=10.0 min, chiral HPLC: P=99.1%, ¹H NMR (300 MHz, CDCl₃) δ 8.64 (d, J=3.2 Hz, 1H), 8.55 (s, 1H), 7.59 (q, J=6.9 Hz, 1H), 7.41-7.30 (m, 2H), 5.97 (dd, J=8.1, 2.9 Hz, 1H), 5.68 (d, J=2.8 Hz, 1H), 3.90-3.80 (m, 1H), 3.66-3.55 (m, 1H), 3.12 (s, 6H), 2.99-2.79 (m, 2H), 2.78-2.64 (m, 3H), 2.57-2.41 (m, 1H), 2.14 (d, J=7.0 Hz, 3H), 2.11-1.96 (m, 3H), 1.96-1.60 (m, 5H), 1.54-1.45 (m, 2H), 1H exchanged with solvent. Second eluted diastereomer: P=100%, retention time=14.7 min, chiral HPLC: P=99.4%, ¹H NMR (300 MHz, CDCl₃) δ 8.64 (d, J=3.2 Hz, 1H), 8.59 (s, 1H), 7.58 (q, J=6.9 Hz, 1H), 7.41-7.32 (m, 2H), 5.96 (dd, J=8.1, 2.8 Hz, 1H), 5.71 (d, J=2.8 Hz, 1H), 3.96-3.85 (m, 1H), 3.60 (d, J=13.3 Hz, 1H), 3.12 (s, 6H), 3.03-2.89 (m, 2H), 2.87-2.68 (m, 3H), 2.55 (p, J=7.5 Hz, 1H), 2.13 (d, J=7.0 Hz, 3H), 2.10-1.99 (m, 3H), 1.95-1.52 (m, 7H), 1H exchanged with solvent.

Compound 199: 4-((R)-3-((cyclobutylmethyl) amino)piperidin-1-yl)-1-(1-(4-(5-(3-methoxy azetidin-1-yl)pyridin-3-yl)-1H-1,2,3-triazol-1-yl)ethyl) pyridin-2(1H)-one was Obtained Using General Scheme 1 Pathway B Stage 1: In a pressure flask to a solution of IM293 (200 mg, 348 μmol) and 3-methoxyazetidine (221 mg, 2.44 mmol) in NMP (3.5 mL) was added cesium carbonate (229 mg, 696 μmol). The mixture was stirred at 130° C. for 44 h. The reaction mixture was cooled down to rt and directly purified by the C18 column (0-100% MeCN in ammonium bicarbonate) to afford tert-butyl (cyclobutylmethyl)((3R)-1-(1-(1-(4-(5-(3-methoxyazetidin-1-yl)pyridin-3-yl)-1H-1,2,3-triazol-1-yl)ethyl)-2-oxo-1,2-dihydropyridin-4-yl)piperidin-3-yl)carbamate IM565 as a beige solid: 96 mg, 38% yield, P=85%, retention time=1.7 min (gradient C), (M+H)⁺: 619.

Stage 2: General Procedure A2 was used from IM565 to afford compound 199 as a white solid: 43 mg, 61% yield, P=95%, retention time=2.2 min (gradient E), (M+H)⁺: 519.

The mixture of diastereomers was further purified by chiral preparative HPLC purification using Chiralpak IE column (5 μm, 10×250 mm). Eluent used: DCM/MeOH/DEA: 90/10/0.1% at flow rate of 7 mL/min. First eluted diastereomer: P=97%, retention time=8.7 min, chiral HPLC: P=99.6%, ¹H NMR (300 MHz, CDCl₃) δ 8.36 (d, J=1.8 Hz, 1H), 8.14 (s, 1H), 7.80 (d, J=2.8 Hz, 1H), 7.53 (q, J=7.0 Hz, 1H), 7.43 (d, J=8.1 Hz, 1H), 7.22 (t, J=2.4 Hz, 1H), 5.99 (dd, J=8.2, 2.8 Hz, 1H), 5.65 (d, J=2.8 Hz, 1H), 4.44-4.30 (m, 1H), 4.23-4.12 (m, 2H), 3.86-3.75 (m, 3H), 3.64-3.54 (m, 1H), 3.33 (s, 3H), 2.97-2.72 (m, 2H), 2.72-2.57 (m, 3H), 2.55-2.36 (m, 1H), 2.15 (d, J=7.0 Hz, 3H), 2.09-1.34 (m, 10H), 1H exchanged with solvent. Second eluted diastereomer: P=99%, retention time=12.0 min, chiral HPLC: P=99.4%, ¹H NMR (300 MHz, CDCl₃) δ 8.31 (d, J=1.8 Hz, 1H), 8.08 (s, 1H), 7.75 (d, J=2.8 Hz, 1H), 7.46 (q, J=6.9 Hz, 1H), 7.36 (d, J=8.1 Hz, 1H), 7.17 (t, J=2.3 Hz, 1H), 5.92 (dd, J=8.2, 2.8 Hz, 1H), 5.61 (d, J=2.8 Hz, 1H), 4.38-4.25 (m, 1H), 4.17-4.07 (m, 2H), 3.83-3.69 (m, 3H), 3.58-3.48 (m, 1H), 3.28 (s, 3H), 2.93-2.73 (m, 2H), 2.70-2.57 (m, 3H), 2.50-2.34 (m, 1H), 2.08 (d, J=7.1 Hz, 3H), 2.03-1.39 (m, 10H), 1H exchanged with solvent.

Compound 200: 4-((R)-3-((cyclobutylmethyl)amino)piperidin-1-yl)-1-(1-(4-(5-(3-methoxy azetidin-1-yl)pyridin-3-yl)-1H-1,2,3-triazol-1-yl)ethyl)pyridin-2(1H)-one was Obtained Using General Scheme 1 Pathway B Stage 1: To a slurry of sodium hydride 60% dispersion in mineral oil (26.0 mg, 651 μmol) in DMF (500 μL) in a sealed flask under nitrogen was added 2,2,2-trifluoroethanol (100 μL, 1.37 mmol) at rt. The mixture was stirred for 15 min and transferred to a septum-sealed flask containing IM293 (126 mg, 228 μmol) in DMF (550 L) under nitrogen. The reaction mixture was heated at 80° C. for 2.5 h. Then, more 2,2,2-trifluoroethanol/NaH was prepared as follows: 2,2,2-trifluoroethanol (2.80 mL, 38.4 mmol) was added to a mixture of sodium hydride 60% dispersion in mineral oil (41.9 mg, 1.05 mmol) in DMF (1 mL) in a sealed flask under nitrogen. The mixture was stirred for 10 min at rt and transferred to the reaction flask. The reaction mixture was heated for additional 16.5 h at 120° C. The mixture was diluted with saturated NH$_4$Cl (15 mL) and extracted with ethyl acetate. The organic phase was dried with MgSO$_4$, filtered and evaporated under reduced pressure. The residue was purified on a C-18 column using 0%-100% MeCN in 10 mM ammonium bicarbonate to afford tert-butyl (cyclobutylmethyl)((3R)-1-(2-oxo-1-(1-(4-(5-(2,2,2-trifluoroethoxy)pyridin-3-yl)-1H-1,2,3-triazol-1-yl)ethyl)-1,2-dihydropyridin-4-yl)piperidin-3-yl)carbamate IM566 as a white solid: 129 mg, 90% yield, P=99%, retention time=1.8 min (gradient C), (M+H)$^+$: 632.

Stage 2: General Procedure A2 was used from IM566 to afford compound 200 as a white solid: 104 mg, 95% yield, P=100%, retention time=2.6 min (gradient E), (M+H)$^+$: 532.

The mixture of diastereomers was further purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=100%, retention time=8.3 min, chiral HPLC: P=99.9%, $^1$H NMR (300 MHz, CDCl$_3$) δ 8.66 (d, J=1.7 Hz, 1H), 8.31 (d, J=2.9 Hz, 1H), 8.21 (s, 1H), 7.77 (t, J=2.2 Hz, 1H), 7.52 (q, J=7.0 Hz, 1H), 7.42 (d, J=8.0 Hz, 1H), 5.99 (dd, J=8.1, 2.8 Hz, 1H), 5.64 (d, J=2.8 Hz, 1H), 4.45 (q, J=8.0 Hz, 2H), 3.80-3.69 (m, 1H), 3.65-3.52 (m, 1H), 2.98-2.83 (m, 1H), 2.72 (dd, J=12.9, 9.3 Hz, 1H), 2.67-2.50 (m, 3H), 2.39 (hept, J=7.7 Hz, 1H), 2.16 (d, J=7.0 Hz, 3H), 2.12-1.23 (m, 10H), 1H exchanged with solvent. $^{19}$F NMR (282 MHZ, CDCl$_3$) δ −71.06 (t, J=8.1 Hz). Second eluted diastereomer: P=100%, retention time=11.2 min, chiral HPLC: P=99.9%, $^1$H NMR (300 MHz, CDCl$_3$) δ 8.67 (d, J=1.7 Hz, 1H), 8.32 (d, J=2.9 Hz, 1H), 8.22 (s, 1H), 7.78 (dd, J=2.9, 1.7 Hz, 1H), 7.53 (q, J=7.0 Hz, 1H), 7.43 (d, J=8.1 Hz, 1H), 5.99 (dd, J=8.2, 2.8 Hz, 1H), 5.64 (d, J=2.8 Hz, 1H), 4.46 (q, J=8.0 Hz, 2H), 3.83-3.72 (m, 1H), 3.64-3.54 (m, 1H), 2.99-2.84 (m, 1H), 2.74 (dd, J=12.9, 9.4 Hz, 1H), 2.69-2.53 (m, 3H), 2.51-2.30 (m, 1H), 2.17 (d, J=7.1 Hz, 3H), 2.12-1.25 (m, 10H), 1H exchanged with solvent $^{19}$F NMR (282 MHZ, CDCl$_3$) δ −71.06 (t, J=8.1 Hz).

Compound 201: (R)-4-(3-((cyclopropylmethyl)amino)piperidin-1-yl)-1-((4-(6-(pyrrolidin-1-yl)pyrazin-2-yl)-1H-1,2,3-triazol-1-yl)methyl)pyridin-2(1H)-one was Obtained Using General Scheme 1 Pathway B Stage 1: General Procedure B was used between IM534 and IM84 to afford 4-chloro-1-((4-(6-(pyrrolidin-1-yl)pyrazin-2-yl)-1H-1,2,3-triazol-1-yl)methyl)pyridin-2(1H)-one IM567 as a yellow solid: 41 mg, 81% yield, P=98%, retention time=2.5 min (gradient A), (M+H)$^+$: 358.

Stage 2: General Procedure C was used between IM567 and IM486 to afford tert-butyl (R)-(cyclopropylmethyl)(1-(2-oxo-1-((4-(6-(pyrrolidin-1-yl)pyrazin-2-yl)-1H-1,2,3-triazol-1-yl)methyl)-1,2-dihydropyridin-4-yl)piperidin-3-yl)carbamate IM568 as colourless oil: 53 mg, 88% yield, P=100%, retention time=2.8 min (gradient A), (M+H)$^+$: 576.

Stage 3: General Procedure A1 was used from IM568 to afford crude compound 201 as a white solid: 42 mg, 91% yield, P=95%, retention time=2.9 min (gradient B), (M+H)$^+$: 476.

$^1$H NMR (300 MHz, CDCl$_3$) δ 8.56 (s, 1H), 8.50 (s, 1H), 7.80 (s, 1H), 7.39 (d, J=8.0 Hz, 1H), 6.33 (s, 2H), 5.96 (d, J=7.8 Hz, 1H), 5.65 (s, 1H), 3.81-3.73 (m, 1H), 3.66-3.56 (m, 1H), 3.51 (s, 4H), 3.00-2.86 (m, 1H), 2.80-2.56 (m, 2H), 2.49 (s, 2H), 2.02 (s, 4H), 1.96-0.96 (m, 4H), 0.90 (s, 1H), 0.48 (d, J=7.9 Hz, 2H), 0.10 (s, 2H), 1H exchanged with solvent.

Compound 202: (R)—N-(cyclopropylmethyl)-1-(6-(3-(4-(5-(pyrrolidin-1-yl)pyridazin-3-yl)-1H-1,2,3-triazol-1-yl)oxetan-3-yl)pyridin-3-yl)piperidin-3-amine was Obtained Using General Scheme 1 Pathway A Stage 1: In a sealed flask, to a solution of 3,5-dichloropyridazine (1 g, 6.58 mmol) and pyrrolidine (636 μL, 7.24 mmol) in anhydrous MeCN (11 mL) was added potassium carbonate (1.4 g, 10.03 mmol). The flask was sealed and the mixture was stirred at 80° C. for 16 h. Reaction mixture was cooled to rt and filtered on Celite pad. The solid was washed with EtOAc (3×20 mL). Celite was added, and suspension was concentrated under reduced pressure. The crude material was purified by an automated flash chromatography system (dryload, 0 to 100% EtOAc in Heptane) to afford 3-chloro-5-(pyrrolidin-1-yl)pyridazine IM569: 1 g, 83% yield, P=100%, retention time=1.8 min (gradient A), (M+H)$^+$: 184/186.

Stage 2: General Procedure E2 was used from IM569 to afford 5-(pyrrolidin-1-yl)-3-((trimethylsilyl)ethynyl)pyridazine IM570 as a brown solid: 334 mg, 35% yield, P=70%, retention time=2.3 min (gradient A), (M+H)$^+$: 246.

Stage 3: General Procedure X was used between IM570 and IM543 to afford tert-butyl (R)-(cyclopropylmethyl)(1-(6-(3-(4-(5-(pyrrolidin-1-yl)pyridazin-3-yl)-1H-1,2,3-triazol-1-yl)oxetan-3-yl)pyridin-3-yl)piperidin-3-yl)carbamate IM571 as a yellow solid: 94 mg, 96% yield, P=96%, retention time=2.6 min (gradient A), (M+H)$^+$: 602.

Stage 4: General Procedure A2 was used from IM571 to afford compound 202 as an off-white solid: 55 mg, 72% yield, P=99%, retention time=2.0 min (gradient B), (M+H)$^+$: 502.

$^1$H NMR (300 MHz, CDCl$_3$) δ 8.51 (d, J=3.0 Hz, 1H), 8.34 (d, J=3.0 Hz, 1H), 8.20 (s, 1H), 7.33 (d, J=3.0 Hz, 1H), 7.12 (dd, J=8.7, 3.0 Hz, 1H), 6.90 (d, J=8.7 Hz, 1H), 5.56 (d, J=6.7 Hz, 2H), 5.48 (d, J=6.7 Hz, 2H), 3.77-3.67 (m, 1H), 3.57-3.40 (m, 5H), 2.99-2.70 (m, 3H), 2.58 (dd, J=6.9, 3.8 Hz, 2H), 2.16-2.04 (m, 4H), 2.05-1.03 (m, 4H), 0.97 (s, 1H), 0.51 (d, J=7.7 Hz, 2H), 0.20-0.04 (m, 2H), 1H exchanged with solvent.

Compound 203: 4-((R)-3-((cyclopropylmethyl)amino)piperidin-1-yl)-1-(1-(4-(5-((ethyl(methyl)amino)pyridin-3-yl)-1H-1,2,3-triazol-1-yl)ethyl)pyridin-2(1H)-one was Obtained Using General Scheme 1 Pathway B Stage 1: General Procedure Y was used between IM524 and N-ethylmethylamine to afford tert-butyl (cyclopropylmethyl)((3R)-1-(1-(1-(4-(5-(ethyl(methyl)amino)pyridin-3-yl)-1H-1,2,3-triazol-1-yl)ethyl)-2-oxo-1,2-dihydropyridin-4-yl)piperidin-3-yl)carbamate IM572 as colourless oil: 18 mg, 28% yield, P=75%, retention time=2.6 min (gradient A), (M+H)⁺: 577.

Stage 2: General Procedure A1 was used from IM572 to afford crude compound 203 as colourless oil: 14 mg, 99% yield, P=79%, retention time=1.9 min (gradient A), (M+H)⁺: 477.

The product was purified by reverse phase preparative HPLC purification (Waters XBridge C18 5 µm, 19×100 mm). Gradient used: increased linearly from 25 to 50% solution "B" over 4.0 min, increased linearly to 85% solution "B" over 2.3 min, and returned to initial conditions over 1.0 min. Flow Rate: 15 mL/min. P=98%.

The mixture of diastereomers was further purified by chiral preparative HPLC purification using Chiralpak IA column (5 µm, 20×250 mm). Eluent used: TBME/MeOH/DCM/DEA: 40/40/20/0.1% at flow rate of 20 mL/min. First eluted diastereomer: P=96%, retention time=7.8 min, chiral HPLC: P=96.6%, $^1$H NMR (300 MHz, CDCl$_3$) δ 8.28 (s, 1H), 8.12 (s, 1H), 8.07 (s, 1H), 7.58-7.49 (m, 1H), 7.49-7.37 (m, 2H), 5.97 (d, J=8.2 Hz, 1H), 5.68 (s, 1H), 3.87-3.77 (m, 1H), 3.64-3.54 (m, 1H), 3.49-3.41 (m, 2H), 2.97 (s, 4H), 2.92-2.65 (m, 2H), 2.59-2.39 (m, 2H), 2.26-2.10 (m, 3H), 2.01 (s, 1H), 1.76 (s, 1H), 1.53-1.44 (m, 2H), 1.16 (d, J=8.0 Hz, 3H), 0.96 (s, 1H), 0.54-0.46 (m, 2H), 0.15 (s, 2H), 1H exchanged with solvent. Second eluted diastereomer: P=100%, retention time=11.1 min, chiral HPLC: P=98.8%, $^1$H NMR (300 MHz, CDCl$_3$) δ 8.29 (s, 1H), 8.18 (s, 1H), 8.08 (s, 1H), 7.60-7.52 (m, 1H), 7.52-7.43 (m, 2H), 6.01 (d, J=8.0 Hz, 1H), 5.69 (s, 1H), 3.97-3.86 (m, 1H), 3.64-3.54 (m, 1H), 3.51-3.42 (m, 2H), 2.98 (s, 4H), 2.81 (s, 1H), 2.61 (s, 2H), 2.20-2.12 (m, 3H), 2.02 (s, 1H), 1.80 (s, 2H), 1.53 (s, 2H), 1.17 (d, J=7.2 Hz, 3H), 1.02 (s, 1H), 0.58-0.50 (m, 2H), 0.21 (s, 2H), 1H exchanged with solvent.

Compound 204: 4-((R)-3-((cyclobutylmethyl) amino)piperidin-1-yl)-1-(1-(3-(5-methoxy pyridin-3-yl)isothiazol-5-yl)ethyl)pyridin-2(1H)-one was Obtained Using the Following Procedures Stage 1: General Procedure U was used from 3-bromoisothiazole to afford 3-(5-methoxypyridin-3-yl)isothiazole IM573 as a brown solid: 1.1 g, 67% yield, P=81%, retention time=1.1 min (gradient C), (M+H)⁺: 193.

Stage 2: To a solution of IM573 (1.10 g, 4.63 mmol) in Et$_2$O (35.7 mL) under N$_2$, cooled at −78° C., was added dropwise solution of LDA (6.95 mL, 6.95 mmol). Reaction was stirred 30 min, then DMF (1.80 mL, 23.2 mmol) was added and stirring at −78° C. was continued for another 30 min. The reaction mixture was quenched with addition of a saturated aqueous solution of NH$_4$Cl and warm up to rt. Phases were separated and aqueous layer was extracted with EtOAc (5×20 mL). Combined organic layers were washed with brine (30 mL), dried over Na$_2$SO$_4$ and concentrated under reduced pressure to afford crude 3-(5-methoxypyridin-3-yl)isothiazole-5-carbaldehyde IM574 as a beige solid: 745 mg, 33% yield, P=45%, retention time=1.1 min (gradient F), (M+H)⁺: 221.

Stage 3: General Procedure Q was used from IM574 to afford 1-(3-(5-methoxypyridin-3-yl)isothiazol-5-yl)ethan-1-ol IM575 as a sticky orange solid: 741 mg, 93% yield, P=45%, retention time=1.0 min (gradient A), (M+H)⁺: 237.

Stage 4: General Procedure T was used between 4-chloropyridin-2-ol and IM575 to afford 4-chloro-1-(1-(3-(5-methoxypyridin-3-yl)isothiazol-5-yl)ethyl)pyridin-2(1H)-one IM576 as a beige solid: 726 mg, 12% yield, P=8% ($^1$H NMR: 80% PPh$_3$O), retention time=1.3 min (gradient C), (M+H)⁺: 348/350.

Stage 5: General Procedure C was used between IM3 and IM576 to afford tert-butyl (cyclobutylmethyl)((3R)-1-(1-(1-(3-(5-methoxypyridin-3-yl)isothiazol-5-yl)ethyl)-2-oxo-1,2-dihydropyridin-4-yl)piperidin-3-yl)carbamate IM577 as pale brown oil: 73 mg, 38% yield, P=82%, retention time=1.8 min (gradient C), (M+H)⁺: 581.

Stage 6: General Procedure A2 was used from IM577 to afford compound 204 as an off-white solid: 38 mg, 76% yield, P=98%, retention time=2.5 min (gradient E), (M+H)⁺: 480.

The mixture of diastereomers was further purified by chiral preparative HPLC purification using Chiralpak IA column (5 µm, 20×250 mm). Eluent used: TBME/MeOH/DCM/DEA: 40/40/20/0.1% at flow rate of 20 ml/min. First eluted diastereomer: P=100%, retention time=7.0 min, chiral HPLC: P=100%, $^1$H NMR (300 MHz, CDCl$_3$) δ 8.65 (d, J=1.7 Hz, 1H), 8.32 (d, J=2.9 Hz, 1H), 7.76 (dd, J=2.8, 1.8 Hz, 1H), 7.44 (d, J=1.1 Hz, 1H), 7.05 (d, J=8.0 Hz, 1H), 6.62 (q, J=7.1 Hz, 1H), 5.98 (dd, J=8.0, 2.9 Hz, 1H), 5.75 (d, J=2.9 Hz, 1H), 3.91 (s, 3H), 3.78 (s, 1H), 3.66-3.55 (m, 1H), 2.92 (ddd, J=13.5, 10.8, 3.2 Hz, 1H), 2.80-2.55 (m, 4H), 2.43 (dq, J=15.1, 7.5 Hz, 1H), 2.14-1.47 (m, 12H), 1.45-1.28 (m, 1H), 1 NH exchanged with solvent. Second eluted diastereomer: P=99%, retention time=11.1 min, chiral HPLC: P=99.8, $^1$H NMR (300 MHz, CDCl$_3$) δ 8.66 (d, J=1.8 Hz, 1H), 8.32 (d, J=2.9 Hz, 1H), 7.81-7.73 (m, 1H), 7.45 (d, J=1.0 Hz, 1H), 7.05 (d, J=7.9 Hz, 1H), 6.62 (q, J=7.1 Hz, 1H), 5.98 (dd, J=8.0, 2.9 Hz, 1H), 5.76 (d, J=2.9 Hz, 1H), 3.91 (s, 3H), 3.85-3.74 (m, 1H), 3.67-3.56 (m, 1H), 3.00-2.85 (m, 1H), 2.81-2.56 (m, 4H), 2.51-2.34 (m, 1H), 2.14-1.51 (m, 12H), 1.46-1.32 (m, 1H), 1 NH exchanged with solvent.

Compound 205: 4-((R)-3-((cyclopropylmethyl) amino)piperidin-1-yl)-1-(1-(4-(5-((2-hydroxy ethyl) amino)pyridin-3-yl)-1H-1,2,3-triazol-1-yl)ethyl) pyridin-2(1H)-one was Obtained Using General Scheme 1 Pathway B Stage 1: General Procedure AA was used between IM524 and 1,3-oxazolidine to afford tert-butyl (cyclopropylmethyl) ((3R)-1-(1-(1-(4-(5-((2-hydroxyethyl)amino)pyridin-3-yl)-1H-1,2,3-triazol-1-yl)ethyl)-2-oxo-1,2-dihydropyridin-4-yl) piperidin-3-yl)carbamate IM578 as colourless oil: 28 mg, 30% yield, P=100%, retention time=2.4 min (gradient A), (M+H)⁺: 579.

Stage 2: General Procedure A1 was used from IM578 to afford crude compound 205 as colourless oil: 21 mg, 85% yield, P=94%, retention time=1.9 min (gradient A), (M+H)⁺: 479.

The mixture of diastereomers was purified by chiral preparative HPLC purification using Chiralpak IA column (5 µm, 20×250 mm). Eluent used: TBME/MeOH/DCM/DEA: 40/40/20/0.1% at flow rate of 20 mL/min. First eluted diastereomer: P=94%, retention time=5.2 min, chiral HPLC: P=99.2%, $^1$H NMR (300 MHz, CDCl$_3$) δ 8.32 (d, J=1.7 Hz, 1H), 8.10 (s, 1H), 8.01 (d, J=2.8 Hz, 1H), 7.54 (q, J=7.1 Hz, 1H), 7.46-7.37 (m, 2H), 5.99 (dd, J=8.1, 2.9 Hz, 1H), 5.65 (d, J=2.8 Hz, 1H), 4.22 (s, 1H), 3.88 (t, J=5.2 Hz, 2H), 3.76 (d, J=12.4 Hz, 1H), 3.61 (d, J=13.3 Hz, 1H), 3.37 (d, J=5.3 Hz, 2H), 3.00-2.87 (m, 1H), 2.80-2.65 (m, 1H), 2.54-2.40 (m, 3H), 2.16 (d, J=7.0 Hz, 3H), 1.98 (d, J=11.9 Hz, 1H), 1.75 (d, J=13.9 Hz, 1H), 1.35 (d, J=11.7 Hz, 2H), 0.89 (d, J=6.6 Hz, 1H), 0.54-0.42 (m, 2H), 0.10 (d, J=5.1 Hz, 2H), 1H exchanged with solvent. Second eluted diastereomer: P=98%, retention time=7.6 min, chiral HPLC: P=100%, $^1$H NMR (300 MHz, CDCl$_3$) δ 8.32 (d, J=1.8 Hz, 1H), 8.11 (s, 1H), 8.00 (d, J=2.8 Hz, 1H), 7.54 (q, J=7.0 Hz, 1H), 7.46-7.36 (m, 2H), 5.98 (dd, J=8.1, 2.8 Hz, 1H), 5.65 (d, J=2.8 Hz, 1H), 4.26 (s, 1H), 3.93-3.83 (m, 2H), 3.81-3.70 (m, 1H), 3.65-3.55 (m, 1H), 3.40-3.32 (m, 2H), 3.00-2.85 (m, 1H), 2.82-2.69 (m, 2H), 2.69-2.44 (m, 3H), 2.16 (d, J=7.0 Hz, 3H), 2.03-1.93 (m, 1H), 1.83-1.46 (m, 3H), 0.97-0.80 (m, 1H), 0.55-0.43 (m, 2H), 0.10 (dt, J=8.6, 4.2 Hz, 2H), 1H exchanged with solvent.

Compound 206: 4-((R)-3-((cyclopropylmethyl) amino)piperidin-1-yl)-1-(1-(4-(5-(pyrrolidin-1-yl) pyridazin-3-yl)-1H-1,2,3-triazol-1-yl)ethyl)pyridin-2 (1H)-one was Obtained Using General Scheme 1 Pathway B Stage 1: General Procedure X was used between IM570 and IM151 to afford 4-chloro-1-(1-(4-(5-(pyrrolidin-1-yl) pyridazin-3-yl)-1H-1,2,3-triazol-1-yl)ethyl)pyridin-2(1H)-one IM579 as a white solid: 120 mg, 84% yield, P=99%, retention time=2.2 min (gradient A), (M+H)$^+$: 372/374.

Stage 2: General Procedure C was used between IM486 and IM579 to afford tert-butyl (cyclopropylmethyl)((3R)-1-(2-oxo-1-(1-(4-(5-(pyrrolidin-1-yl)pyridazin-3-yl)-1H-1,2,3-triazol-1-yl)ethyl)-1,2-dihydropyridin-4-yl)piperidin-3-yl)carbamate IM580 as a yellow solid: 100 mg, 51% yield, P=96%, retention time=2.5 min (gradient A), (M+H)$^+$: 590.

Stage 3: General Procedure A2 was used from IM580 to afford crude compound 206 as a yellow foam: 70 mg, 86% yield, P=96%, retention time=2.5 min (gradient B), (M+H)$^+$: 490.

The mixture of diastereomers was purified by chiral preparative HPLC purification using Chiralpak IA column (5 µm, 20×250 mm). Eluent used: TBME/MeOH/DCM/DEA: 40/40/20/0.1% at flow rate of 20 mL/min. First eluted diastereomer: P=100%, retention time=6.9 min, chiral HPLC: P=100%, $^1$H NMR (300 MHz, CDCl$_3$) δ 8.54-8.46 (m, 2H), 7.60 (q, J=7.0 Hz, 1H), 7.30 (d, J=8.0 Hz, 1H), 7.24 (d, J=3.1 Hz, 1H), 5.95 (dd, J=8.2, 2.8 Hz, 1H), 5.66 (d, J=2.8 Hz, 1H), 3.81-3.71 (m, 1H), 3.66-3.55 (m, 1H), 3.48-3.38 (m, 4H), 2.99-2.84 (m, 1H), 2.79-2.62 (m, 2H), 2.55-2.42 (m, 2H), 2.17-1.88 (m, 7H), 1.78-1.23 (m, 4H), 0.96-0.84 (m, 1H), 0.54-0.42 (m, 2H), 0.16-0.03 (m, 2H), 1 NH exchanged with solvent. Second eluted diastereomer: P=100%, retention time=8.5 min, chiral HPLC: P=99.8, $^1$H NMR (300 MHz, CDCl$_3$) δ 8.54-8.46 (m, 2H), 7.60 (q, J=6.9 Hz, 1H), 7.31 (s, 1H), 7.24 (d, J=3.0 Hz, 1H), 5.95 (dd, J=8.1, 2.9 Hz, 1H), 5.65 (d, J=2.8 Hz, 1H), 3.81-3.71 (m, 1H), 3.65-3.54 (m, 1H), 3.48-3.37 (m, 4H), 2.98-2.83 (m, 1H), 2.80-2.61 (m, 2H), 2.54-2.45 (m, 2H), 2.16-1.93 (m, 7H), 1.78-1.25 (m, 4H), 0.96-0.81 (m, 1H), 0.53-0.41 (m, 2H), 0.13-0.03 (m, 2H), 1 NH exchanged with solvent.

Compound 207: (R)—N-(cyclopropylmethyl)-1-(5-(3-(4-(6-(pyrrolidin-1-yl)pyrazin-2-yl)-1H-1,2,3-triazol-1-yl)oxetan-3-yl)pyridin-2-yl)piperidin-3-amine was Obtained Using General Scheme 1 Pathway A Stage 1: To a oven-dried Schlenk tube under Ar atmosphere was added 2,5-dibromopyridine (1.68 g, 6.95 mmol) followed by anhydrous diethyl ether (17 mL) to afford a beige suspension which was stirred at −78° C. To this mixture at −78° C., n-butyl lithium in hexane (4.50 mL, 6.8 mmol) was added over 5 min. The mixture was stirred at −78° C. for 20 min, then a solution of 2-methyl-N-(oxetan-3-ylidene)propane-2-sulfinamide (1 g, 5.42 mmol) in anhydrous diethyl ether (2 mL) was added (over 5 min) at −78° C. and the reaction mixture was stirred at −78° C. for 40 min and 1 h at 0° C. NH$_4$Cl saturated solution (10 mL) was added, followed by water (20 mL) and EtOAc (100 mL). Layers were separated and the aqueous layer was extracted with EtOAc (2×50 mL), then combined organic layers were washed with brine (80 mL), dried over MgSO$_4$, filtered and the filtrate was concentrated under reduced pressure to dryness to afford 2.1 g of crude orange oil. The crude material was purified by an automated flash system (liquid injection in DCM, 0 to 100% EtOAc in Heptane) to afford N-(3-(6-bromopyridin-3-yl)oxetan-3-yl)-2-methylpropane-2-sulfinamide IM581 as orange oil: 635 mg, 33% yield, P=94%, retention time=2.4 min (gradient A), (M+H)$^+$: 333/335.

Stage 2: General Procedure S was used between IM486 and IM581 to afford tert-butyl ((3R)-1-(5-(3-((tert-butylsulfinyl)amino)oxetan-3-yl)pyridin-2-yl)piperidin-3-yl) (cyclopropylmethyl) carbamate IM582 as an orange solid: 538 mg, 43% yield, P=68%, retention time=2.4 min (gradient A), (M+H)+: 507.

Stage 3: To a solution of IM582 (538 mg, 0.72 mmol) in THF (2.1 mL) and water (0.38 mL) was added iodine (73 mg, 0.29 mmol) at rt and the reaction mixture was stirred at 55° C. After 4 h at 55° C., the reaction was cooled to rt. The reaction mixture was diluted with EtOAc (50 mL), then washed with a mixture of Na$_2$S$_2$O$_3$ (2 M, 10 mL) and NaHCO$_3$ saturated solution (2×25 mL). The aqueous layer was extracted with EtOAc (2×50 mL) and the combined organic layers were dried over MgSO$_4$, filtered and the filtrate was concentrated under vacuum to afford crude tert-butyl (R)-(1-(5-(3-aminooxetan-3-yl)pyridin-2-yl)piperidin-3-yl)(cyclopropylmethyl) carbamate IM583 as brown oil: 580 mg, 100% yield, P=50%, retention time=2.2 min (gradient A), (M+H)$^+$: 403.

Stage 4: General Procedure V was used from IM583 to afford tert-butyl (R)-(1-(5-(3-azidooxetan-3-yl)pyridin-2-yl) piperidin-3-yl)(cyclopropylmethyl)carbamate IM584 as yellow oil: 231 mg, 73% yield, P=97%, retention time=2.5 min (gradient A), (M+H)$^+$: 429.

Stage 5: General Procedure X was used between IM584 and IM533 to afford tert-butyl (R)-(cyclopropylmethyl)(1-(5-(3-(4-(6-(pyrrolidin-1-yl)pyrazin-2-yl)-1H-1,2,3-triazol-1-yl)oxetan-3-yl)pyridin-2-yl)piperidin-3-yl)carbamate IM585 as yellow oil: 86 mg, 84% yield, P=96%, retention time=2.6 min (gradient A), (M+H)$^+$: 602.

Stage 6: General Procedure A2 was used from IM585 to afford crude compound 207 as an off-white solid: 44 mg, 63% yield, P=96%, retention time=2.9 min (gradient B), (M+H)$^+$: 502.

$^1$H NMR (300 MHz, CDCl$_3$) δ 8.54-8.46 (m, 2H), 7.60 (q, J=7.0 Hz, 1H), 7.30 (d, J=8.0 Hz, 1H), 7.24 (d, J=3.1 Hz, 1H), 5.95 (dd, J=8.2, 2.8 Hz, 1H), 5.66 (d, J=2.8 Hz, 1H), 3.81-3.71 (m, 1H), 3.66-3.55 (m, 1H), 3.48-3.38 (m, 4H), 2.99-2.84 (m, 1H), 2.79-2.62 (m, 2H), 2.55-2.42 (m, 2H), 2.17-1.88 (m, 7H), 1.78-1.23 (m, 4H), 0.96-0.84 (m, 1H), 0.54-0.42 (m, 2H), 0.16-0.03 (m, 2H), 1 NH exchanged.

Compound 208: 2-(4-((R)-3-((cyclobutylmethyl) amino)piperidin-1-yl)-2-oxopyridin-1(2H)-yl)-N-(5-(pyrrolidin-1-yl)pyridin-3-yl)propanamide was Obtained Using General Scheme 6 Pathway B Stage 1: General Procedure F was used between IM479 and IM558 to afford tert-butyl (cyclobutylmethyl)((3R)-1-

(2-oxo-1-(1-oxo-1-((5-(pyrrolidin-1-yl)pyridin-3-yl)amino) propan-2-yl)-1,2-dihydropyridin-4-yl)piperidin-3-yl)carbamate IM586 as colourless oil: 18 mg, 25% yield, P=98%, retention time=2.6 min (gradient A), (M+H)$^+$: 579.

Stage 2: General Procedure A1 was used from IM586 to afford crude compound 208 as colourless oil: 15 mg, 97% yield, P=96%, retention time=2.1 min (gradient A), (M+H)$^+$: 479.

The mixture of diastereomers was purified by chiral preparative HPLC purification using Chiralpak IA column (5 μm, 20×250 mm). Eluent used: TBME/MeOH/DCM/DEA: 40/20/40/0.1% at flow rate of 20 mL/min. First eluted diastereomer: P=100%, retention time=6.2 min, chiral HPLC: P=99.0%, $^1$H NMR (300 MHz, CDCl$_3$) δ 9.66 (s, 1H), 7.93 (d, J=2.1 Hz, 1H), 7.68 (d, J=2.6 Hz, 1H), 7.35-7.27 (m, 2H), 6.04 (dd, J=8.0, 2.9 Hz, 1H), 5.80 (d, J=2.8 Hz, 1H), 5.69 (q, J=7.2 Hz, 1H), 3.87-3.76 (m, 1H), 3.70-3.59 (m, 1H), 3.31-3.21 (m, 4H), 3.01-2.86 (m, 1H), 2.77 (t, J=11.1 Hz, 1H), 2.67 (t, J=11.0 Hz, 3H), 2.52-2.35 (m, 1H), 2.13-1.47 (m, 17H), 1H exchanged with solvent. Second eluted diastereomer: P=100%, retention time=10.2 min, chiral HPLC: P=97.7%, $^1$H NMR (300 MHz, CDCl$_3$) δ 9.66 (s, 1H), 7.95 (d, J=2.1 Hz, 1H), 7.69 (d, J=2.6 Hz, 1H), 7.36-7.26 (m, 2H), 6.03 (dd, J=8.0, 2.8 Hz, 1H), 5.79 (d, J=2.9 Hz, 1H), 5.69 (q, J=7.1 Hz, 1H), 3.88-3.78 (m, 1H), 3.69-3.58 (m, 1H), 3.32-3.22 (m, 4H), 3.02-2.87 (m, 1H), 2.86-2.63 (m, 4H), 2.52-2.36 (m, 1H), 2.13-1.32 (m, 17H), 1H exchanged with solvent.

Compound 209: 4-((R)-3-((cyclopropylmethyl) amino)piperidin-1-yl)-1-(1-(4-(5-(3-(difluoro methyl)azetidin-1-yl)pyridin-3-yl)-1H-1,2,3-triazol-1-ylethyl)pyridin-2(1H)-one was Obtained Using General Scheme 1 Pathway B Stage 1: General Procedure AA was used between IM524 and 3-(difluoromethyl)azetidine hydrochloride to afford tert-butyl (cyclopropylmethyl)((3R)-1-(1-(1-(4-(5-(3-(difluoromethyl) azetidin-1-yl)pyridin-3-yl)-1H-1,2,3-triazol-1-yl) ethyl)-2-oxo-1,2-dihydropyridin-4-yl) piperidin-3-yl) carbamate IM587 as a white solid: 52 mg, 48% yield, P=92%, retention time=2.5 min (gradient A), (M+H)$^+$: 625.

Stage 2: General Procedure A1 was used from IM587 to afford crude 1-(1-(4-(5-((2-chloromethyl)-3,3-difluoropropyl)amino)pyridin-3-yl)-1H-1,2,3-triazol-1-yl)ethyl)-4-((R)-3-((cyclopropylmethyl)amino)piperidin-1-yl)pyridin-2 (1H)-one IM588 as colourless oil: 50 mg, 93% yield, P=80%, retention time=2.1 min (gradient A), (M+H)$^+$: 561/ 563.

Stage 3: In a sealed flask, to a solution of IM588 (50 mg, 0.07 mmol) in anhydrous DMF (1 mL) was added potassium carbonate (15 mg, 0.11 mmol). The flask was sealed and the mixture was stirred at 80° C. for 16 h. Reaction mixture was cooled to rt and diluted with water/EtOAc (10 mL/10 mL). Phases were separated and organic phase was washed with water (2×5 mL) and brine (5 mL), dried over MgSO$_4$, filtered and concentrated under reduced pressure to afford crude compound 209 as colourless oil: 42 mg, 98% yield, P=87%, retention time=2.1 min (gradient A), (M+H)$^+$: 525.

The product was purified by reverse phase preparative HPLC purification (Waters XBridge C18 5 μm, 19×100 mm). Gradient used: increased linearly from 25 to 55% solution "B" over 4.0 min, increased linearly to 85% solution "B" over 2.2 min, held at 85% solution "B" over 0.3 min, and returned to initial conditions over 0.8 min. Flow Rate: 15 mL/min. P=100%.

The mixture of diastereomers was further purified by chiral preparative HPLC purification using Chiralpak IE column (5 μm, 10×250 mm). Eluent used: DCM/MeOH/ DEA: 90/10/0.1% at flow rate of 7 mL/min. First eluted diastereomer: P=97%, retention time=7.0 min, chiral HPLC: P=97.2%, $^1$H NMR (300 MHz, CDCl$_3$) δ 8.24 (d, J=1.7 Hz, 1H), 8.01 (s, 1H), 7.89 (d, J=2.8 Hz, 1H), 7.44 (q, J=7.0 Hz, 1H), 7.33 (d, J=7.8 Hz, 1H), 7.30 (t, J=2.5 Hz, 1H), 6.07 (t, J=55.2 Hz, 1H), 5.89 (dd, J=8.2, 2.8 Hz, 1H), 5.55 (d, J=2.8 Hz, 1H), 5.45-5.35 (m, 2H), 4.13-4.03 (m, 1H), 3.96-3.82 (m, 2H), 3.73-3.63 (m, 1H), 3.55-3.45 (m, 1H), 2.90-2.75 (m, 1H), 2.74-2.50 (m, 2H), 2.45-2.33 (m, 2H), 2.05 (d, J=7.1 Hz, 3H), 1.93-1.22 (m, 4H), 0.80 (s, 1H), 0.44-0.32 (m, 2H), 0.03--0.05 (m, 2H), 1H exchanged with solvent. $^{19}$F NMR (282 MHZ, CDCl$_3$) δ −113.64 (d, J=55.3 Hz). Second eluted diastereomer: P=100%, retention time=9.8 min, chiral HPLC: P=97.9%, $^1$H NMR (300 MHz, CDCl$_3$) δ 8.34 (d, J=1.7 Hz, 1H), 8.11 (s, 1H), 7.99 (d, J=2.8 Hz, 1H), 7.53 (q, J=7.0 Hz, 1H), 7.46-7.37 (m, 2H), 6.17 (t, J=54.2 Hz, 1H), 5.99-5.94 (m, 1H), 5.66 (d, J=2.8 Hz, 1H), 5.55-5.45 (m, 2H), 4.19 (t, J=6.1 Hz, 1H), 4.02 (d, J=6.1 Hz, 2H), 3.77 (d, J=12.8 Hz, 1H), 3.58 (d, J=13.3 Hz, 1H), 3.01-2.88 (m, 1H), 2.88-2.75 (m, 1H), 2.74-2.65 (m, 1H), 2.52 (d, J=6.9 Hz, 2H), 2.14 (d, J=7.1 Hz, 3H), 2.08-1.40 (m, 4H), 0.92 (q, J=6.4 Hz, 1H), 0.55-0.43 (m, 2H), 0.16-0.09 (m, 2H), 1H exchanged with solvent $^{19}$F NMR (282 MHz, CDCl$_3$) δ −113.64 (d, J=55.6 Hz).

Compound 210: 4-((R)-3-((cyclobutylmethyl) amino)piperidin-1-yl)-1-(1-(5-(6-methoxy-1H-indazol-4-yl)-2H-tetrazol-2-yl)ethyl)pyridin-2(1H)-one was Obtained Using the Following Procedures Stage 1: A reaction vial was charged with IM6 (200 mg, 643 μmol), zinc cyanide (83 mg, 707 μmol), Pd$_2$(dba)$_3$ (112 mg, 120 μmol), 1,1'-bis(diphenylphosphino)ferrocene (134 mg, 241 μmol) and DMF (1.1 mL) were added and, after purging with nitrogen, the reaction was heated to 120° C. for 4 h. The mixture was filtered over Celite, rinsing with ethyl acetate. The filtrate was concentrated under reduced pressure and the residue was purified on a C-18 column using 14%-60% MeCN in 10 mM ammonium bicarbonate to afford 6-methoxy-1-(tetrahydro-2H-pyran-2-yl)-1H-indazole-4-carbonitrile IM589 as a white solid: 150 mg, 90% yield, P=100%, retention time=1.4 min (gradient C), (M+H)$^+$: 258.

Stage 2: To IM589 (149 mg, 579 μmol) in DMF (3 mL) was added NH$_4$Cl (54.5 mg, 1.02 mmol) and sodium azide (70.4 mg, 1.08 mmol). The resulting mixture was stirred at 100° C. for 18.5 h. After analysis, sodium azide (79.8 mg, 1.22 mmol) was added and the reaction was continued for 5.5 h. The reaction mixture was concentrated under reduced pressure, and directly purified on a C-18 column using 0%-20% MeCN in 10 mM ammonium bicarbonate to afford 6-methoxy-1-(tetrahydro-2H-pyran-2-yl)-4-(2H-tetrazol-5-yl)-1H-indazole IM590 as a white solid: 173 mg, 99% yield, P=100%, retention time=1.0 min (gradient F), (M+H)$^+$: 301.

Stage 3: To IM590 (173 mg, 576 μmol) and K$_2$CO$_3$ (244 mg, 1.73 mmol) in solution in DMF (3.4 mL) was added IM151 (190 mg, 864 μmol). The reaction was stirred at rt for 25 h, then heated to 100° C. for 2.5 h. The reaction mixture was cooled down to rt and diluted in water (50 mL). Aqueous phase was extracted with EtOAc (3×15 mL). Organic layer was dried over Na$_2$SO$_4$, filtered and concentrated under reduced pressure. Residue was purified by reverse phasechromatography (C18, 5% to 100% MeCN in 10 mM ammonium bicarbonate buffer) to give 4-chloro-1-

(1-(5-(6-methoxy-1-(tetrahydro-2H-pyran-2-yl)-1H-indazol-4-yl)-2H-tetrazol-2-yl)ethyl)pyridin-2(1H)-one IM591 as a beige solid: 170 mg, 52% yield, P=81%, retention time=1.6 min (gradient C), (M+H)$^+$: 456/458.

Stage 4: General Procedure C was used between IM591 and IM3 to afford tert-butyl (cyclobutylmethyl)((3R)-1-(1-(1-(5-(6-methoxy-1-(tetrahydro-2H-pyran-2-yl)-1H-indazol-4-yl)-2H-tetrazol-2-yl)ethyl)-2-oxo-1,2-dihydropyridin-4-yl)piperidin-3-yl)carbamate IM592 as a white powder: 104 mg, 69% yield, P=85%, retention time=2.0 min (gradient C), (M+H)$^+$: 689.

Stage 5: General Procedure A2 was used from IM592 to afford crude compound 210 as a white powder: 51 mg, 64% yield, P=96%, retention time=2.5 min (gradient E), (M+H)$^+$: 504.

The mixture of diastereomers was further purified by chiral preparative HPLC purification using Chiralpak IE column (5 μm, 10×250 mm). Eluent used: DCM/MeOH/DEA: 90/10/0.1% at flow rate of 7 mL/min. First eluted diastereomer: P=100%, retention time=6.0 min, chiral HPLC: P=98.7%, $^1$H NMR (300 MHZ, CDCl$_3$) δ 8.63 (s, 1H), 8.10 (q, J=6.9 Hz, 1H), 7.74 (d, J=2.0 Hz, 1H), 7.41 (d, J=8.1 Hz, 1H), 7.00 (s, 1H), 6.02 (dd, J=8.2, 2.8 Hz, 1H), 5.72 (d, J=2.8 Hz, 1H), 3.91 (s, 3H), 3.79 (d, J=12.7 Hz, 1H), 3.67-3.56 (m, 1H), 2.99-2.84 (m, 1H), 2.79-2.54 (m, 4H), 2.48-2.32 (m, 1H), 2.15 (d, J=7.0 Hz, 3H), 2.09-1.91 (m, 3H), 1.90-1.46 (m, 6H), 1.45-1.28 (m, 1H), 2 NH exchanged with solvent. Second eluted diastereomer: P=100%, retention time=9.6 min, chiral HPLC: P=97.7%, $^1$H NMR (300 MHz, CDCl$_3$) δ 8.62 (s, 1H), 8.09 (q, J=7.0 Hz, 1H), 7.71 (s, 1H), 7.40 (d, J=8.1 Hz, 1H), 7.00 (s, 1H), 6.01 (dd, J=8.2, 2.8 Hz, 1H), 5.73 (d, J=2.8 Hz, 1H), 3.89 (s, 3H), 3.78 (d, J=12.2 Hz, 1H), 3.65-3.54 (m, 1H), 2.99-2.84 (m, 1H), 2.82-2.54 (m, 4H), 2.49-2.33 (m, 1H), 2.14 (d, J=7.0 Hz, 3H), 2.09-1.92 (m, 3H), 1.91-1.47 (m, 6H), 1.43-1.32 (m, 1H), 2 NH exchanged with solvent.

Compound 211: 4-((R)-3-((cyclopropylmethyl)amino)piperidin-1-yl)-1-(1-(4-(5-(1,1-difluoro-5-azaspiro[2.3]hexan-5-yl)pyridin-3-yl)-1H-1,2,3-triazol-1-ylethyl)pyridin-2(1H)-one was Obtained Using General Scheme 1 Pathway B Stage 1: General Procedure AA was used between IM524 and 3-(difluoromethyl)azetidine hydrochloride to afford tert-butyl (cyclopropylmethyl)((3R)-1-(1-(1-(4-(5-(1,1-difluoro-5-azaspiro[2.3]hexan-5-yl)pyridin-3-yl)-1H-1,2,3-triazol-1-yl)ethyl)-2-oxo-1,2-dihydropyridin-4-yl)piperidin-3-yl)carbamate IM593 as colourless oil: 62 mg, 56% yield, P=91%, retention time=2.6 min (gradient A), (M+H)$^+$: 637.

Stage 2: General Procedure A2 was used from IM593 to afford crude compound 211 as colourless oil: 47 mg, 84% yield, P=89%, retention time=3.0 min (gradient A), (M+H)$^+$: 537.

The mixture of diastereomers was further purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=100%, retention time=9.2 min, chiral HPLC: P=100%, $^1$H NMR (300 MHz, CDCl$_3$) δ 8.39 (d, J=1.7 Hz, 1H), 8.13 (s, 1H), 7.83 (d, J=2.7 Hz, 1H), 7.52 (q, J=7.0 Hz, 1H), 7.41 (d, J=8.1 Hz, 1H), 7.25 (s, 1H), 5.97 (dd, J=8.1, 2.8 Hz, 1H), 5.65 (d, J=2.8 Hz, 1H), 4.19 (d, J=7.4 Hz, 2H), 4.06-3.96 (m, 2H), 3.83-3.72 (m, 1H), 3.64-3.53 (m, 1H), 3.04-2.87 (m, 1H), 2.79 (dd, J=12.8, 9.3 Hz, 1H), 2.72-2.61 (m, 1H), 2.51 (d, J=6.8 Hz, 2H), 2.14 (d, J=7.0 Hz, 3H), 2.04-1.91 (m, 1H), 1.81-1.68 (m, 1H), 1.59-1.33 (m, 4H), 1.00-0.84 (m, 1H), 0.50-0.43 (m, 2H), 0.15-0.08 (m, 2H), 1 NH exchanged with solvent. $^{19}$F NMR (282 MHZ, CDCl$_3$) δ −136.34 (t, J=8.5 Hz). Second eluted diastereomer: P=98%, retention time=11.6 min, chiral HPLC: P=98.7%, $^1$H NMR (300 MHz, CDCl$_3$) δ 8.40 (d, J=1.7 Hz, 1H), 8.15 (s, 1H), 7.83 (d, J=2.8 Hz, 1H), 7.53 (q, J=7.0 Hz, 1H), 7.42 (d, J=8.0 Hz, 1H), 7.25 (s, 1H), 5.98 (dd, J=8.1, 2.8 Hz, 1H), 5.65 (d, J=2.8 Hz, 1H), 4.19 (d, J=7.4 Hz, 2H), 4.01 (dd, J=7.7, 2.4 Hz, 2H), 3.80 (d, J=12.9 Hz, 1H), 3.59 (d, J=13.9 Hz, 1H), 3.00-2.86 (m, 1H), 2.80 (dd, J=12.7, 9.4 Hz, 1H), 2.72-2.62 (m, 1H), 2.52 (d, J=6.8 Hz, 2H), 2.15 (d, J=7.0 Hz, 3H), 2.04-1.91 (m, 1H), 1.80-1.70 (m, 1H), 1.57-1.33 (m, 4H), 1.00-0.85 (m, 1H), 0.54-0.40 (m, 2H), 0.12 (d, J=5.0 Hz, 2H), 1 NH exchanged with solvent. 19F NMR (282 MHz, CDCl$_3$) δ −136.36 (t, J=8.7 Hz).

Compound 212: (R)—N-(cyclopropylmethyl)-1-(6-(3-(4-(5-(pyrrolidin-1-yl)pyridin-3-yl)-1H-1,2,3-triazol-1-yl)oxetan-3-yl)pyridazin-3-yl)piperidin-3-amine was Obtained Using General Scheme 1 Pathway A Stage 1: General Procedure C was used between 3-chloropyridazine hydrochloride and IM486 to afford tert-butyl (R)-(cyclopropylmethyl)(1-(pyridazin-3-yl)piperidin-3-yl)carbamate IM594 as brown oil: 3.57 g, 74% yield, P=90%, retention time=2.4 min (gradient A), (M+H)$^+$: 332.

Stage 2: To a solution of IM594 (3.57 g, 9.65 mmol) in anhydrous DCM (20 mL) under Ar atmosphere was added 3-chloroperbenzoic acid (2.99 g, 13.34 mmol) (exotherm observed) to afford a brown solution which was stirred at rt for 1.5 h. The reaction mixture was washed with NaHCO$_3$ saturated solution (3×20 mL) and the organic layer was dried over MgSO$_4$, filtered and the filtrate was concentrated under reduced pressure to afford a crude dark yellow oil which was purified by an automated flash chromatography system (0 to 3% MeOH in DCM) to afford (R)-3-(3-((tert-butoxycarbonyl)(cyclopropylmethyl)amino)piperidin-1-yl)pyridazine 1-oxide IM595 as a pale yellow solid: 2.15 g, 63% yield, P=98%, retention time=2.7 min (gradient A), (M+H)$^+$: 349.

Stage 3: To a colorless solution of 2,2,6,6-tetramethylpiperidine (1 mL, 5.87 mmol) in anhydrous THF (14 mL) under Ar atmosphere at −35° C. was added n-butyl lithium in hexane (4.20 mL, 6.34 mmol) to afford a yellow solution which was stirred at −35° C. for 5 min and then 35 min at 0° C. To this yellow solution cooled at −78° C., a solution of IM595 (1.46 g, 4.11 mmol) in anhydrous THF (5 mL) was added over 2 min to afford a brown solution which was stirred at −78° C. for 15 min. Then a solution of 2-methyl-N-(oxetan-3-ylidene)propane-2-sulfinamide (1 g, 5.42 mmol) in anhydrous THF (5 mL) was added and the resulting dark red solution was stirred at −78° C. for 1.75 h. NH$_4$Cl saturated solution (10 mL) was added at −78° C. and the mixture was heated to 0° C. and diluted with water (5 mL) then diluted with EtOAc (30 mL) and allowed to warm to rt. Layers were separated and the organic layer was washed with brine (20 mL), then dried over MgSO$_4$, filtered and the filtrate was concentrated under reduced pressure to afford 3-((R)-3-((tert-butoxycarbonyl)(cyclopropylmethyl)amino) piperidin-1-yl)-6-(3-((tert-butylsulfinyl)amino)oxetan-3-yl)pyridazine 1-oxide IM596 as yellow foamy solid: 2.5 g, 98% yield, P=84%, retention time=2.8 min (gradient A), (M+H)$^+$: 524. The product was purified by reverse phase preparative HPLC purification (Waters XBridge C18 5 μm, 19×100 mm). Gradient used: increased linearly from 35 to 55% solution "B" over 5.0 min, increased linearly to 85% solution "B" over 1.2 min, held to 85% solution "B" over 0.3 min, and returned to initial conditions over 0.8 min. Flow Rate: 15 mL/min. P=98%.

Stage 4: To a solution of IM596 (1.23 g, 2.28 mmol) in anhydrous ethanol (20 mL) under Ar atmosphere was added molybdenumhexacarbonyl (747 mg, 2.83 mmol). The reaction mixture was stirred at 80° C. for 5.25 h, cooled to rt, then diluted with DCM (50 mL) and washed with NaHCO$_3$ saturated solution (20 mL). The aqueous layer was extracted with DCM (2×50 mL) then combined organic layers were dried over MgSO$_4$, filtered and the filtrate was concentrated under reduced pressure to afford a crude brown solid. The crude material was purified by an automated flash chromatography system (0 to 2% MeOH in EtOAc) to afford tert-butyl ((3R)-1-(6-(3-((tert-butylsulfinyl)amino)oxetan-3-yl)pyridazin-3-yl)piperidin-3-yl) (cyclopropylmethyl)carbamate IM597 as a brown oil: 313 mg, 19% yield, P=69%, retention time=2.4 min (gradient A), (M+H)$^+$: 508.

Stage 5: To a solution of IM597 (338 mg, 0.46 mmol) in THF (1.3 mL) and water (250 µL) was added iodine (49 mg, 0.1900 mmol) at rt and the reaction mixture was stirred at 55° C. for 1.75 h. The reaction mixture (dark green solution) was cooled to rt and diluted with EtOAc (20 mL) then washed three times with a mixture of Na$_2$S$_2$O$_3$ (2 M, 5 mL) and NaHCO$_3$ saturated solution (5 mL). The organic layer was dried over MgSO$_4$, filtered and the filtrate was concentrated under reduced pressure to afford tert-butyl (R)-(1-(6-(3-aminooxetan-3-yl)pyridazin-3-yl)piperidin-3-yl)(cyclopropylmethyl)carbamate IM598 as a crude brown solid: 243 mg, 92% yield, P=70%, retention time=2.2 min (gradient A), (M+H)$^+$: 404.

Stage 6: General Procedure V was used from IM598 to afford tert-butyl (R)-(1-(6-(3-azidooxetan-3-yl)pyridazin-3-yl)piperidin-3-yl)(cyclopropylmethyl)carbamate IM599 as yellow oil: 104 mg, 56% yield, P=97%, retention time=4.0 min (gradient B), (M+H)$^+$: 430.

Stage 7: General Procedure X was used between IM599 and IM555 to afford tert-butyl (R)-(cyclopropylmethyl)(1-(6-(3-(4-(5-(pyrrolidin-1-yl)pyridin-3-yl)-1H-1,2,3-triazol-1-yl)oxetan-3-yl)pyridazin-3-yl)piperidin-3-yl)carbamate IM600 as pale yellow oil: 40 mg, 51% yield, P=93%, retention time=2.4 min (gradient A), (M+H)$^+$: 602.

Stage 8: General Procedure A2 was used from IM600 to afford crude compound 212 as a white solid: 31 mg, 98% yield, P=98%, retention time=2.7 min (gradient B), (M+H)$^+$: 502. $^1$H NMR (300 MHz, CDCl$_3$) δ 8.22 (d, J=1.8 Hz, 1H), 7.95 (d, J=2.9 Hz, 1H), 7.85 (s, 1H), 7.36 (dd, J=2.9, 1.8 Hz, 1H), 7.06 (d, J=9.6 Hz, 1H), 6.90 (d, J=9.6 Hz, 1H), 5.61 (dd, J=6.7, 1.3 Hz, 2H), 5.56 (dd, J=7.0, 1.7 Hz, 2H), 4.40 (dd, J=12.4, 3.6 Hz, 1H), 4.15-4.05 (m, 1H), 3.42-3.31 (m, 4H), 3.24-3.09 (m, 1H), 2.99 (dd, J=12.9, 9.1 Hz, 1H), 2.82-2.67 (m, 1H), 2.56 (d, J=6.8 Hz, 2H), 2.10-1.97 (m, 4H), 1.90-1.78 (m, 1H), 1.60-1.39 (m, 3H), 1.03-0.84 (m, 1H), 0.55-0.40 (m, 2H), 0.17-0.04 (m, 2H), 1 NH exchanged with solvent.

Compound 213: (R)—N-(cyclopropylmethyl)-1-(6-(3-(4-(6-(pyrrolidin-1-yl)pyrazin-2-yl)-1H-1,2,3-triazol-1-yl)oxetan-3-yl)pyridazin-3-yl)piperidin-3-amine was Obtained Using General Scheme 1 Pathway A Stage 1: General Procedure B was used between IM534 and IM599 to afford tert-butyl (R)-(cyclopropylmethyl)(1-(6-(3-(4-(6-(pyrrolidin-1-yl)pyrazin-2-yl)-1H-1,2,3-triazol-1-yl)oxetan-3-yl)pyridazin-3-yl)piperidin-3-yl)carbamate IM601 as a yellow solid: 77 mg, 99% yield, P=94%, retention time=2.6 min (gradient A), (M+H)$^+$: 603.

Stage 2: General Procedure A2 was used from IM601 to afford crude compound 213 as a white solid: 60 mg, 98% yield, P=99%, retention time=2.9 min (gradient B), (M+H)$^+$: 503. $^1$H NMR (300 MHz, CDCl$_3$) δ 8.61 (s, 1H), 8.13 (s, 1H), 7.83 (s, 1H), 7.05 (d, J=9.6 Hz, 1H), 6.88 (d, J=9.6 Hz, 1H), 5.63 (dd, J=6.9, 2.3 Hz, 2H), 5.56 (dd, J=6.9, 3.1 Hz, 2H), 4.39 (d, J=13.2 Hz, 1H), 4.14-4.04 (m, 1H), 3.54-3.46 (m, 4H), 3.21-3.09 (m, 1H), 2.97 (dd, J=12.8, 9.2 Hz, 1H), 2.80-2.66 (m, 1H), 2.56 (d, J=6.9 Hz, 2H), 2.10-1.97 (m, 4H), 1.84 (dt, J=12.4, 4.5 Hz, 1H), 1.69-1.36 (m, 3H), 0.99-0.85 (m, 1H), 0.53-0.44 (m, 2H), 0.16-0.06 (m, 2H), 1 NH exchanged with solvent.

Compound 214: (R)—N-(cyclopropylmethyl)-1-(6-(3-(4-(6-(3,3-dimethylpyrrolidin-1-yl) pyrazin-2-yl)-1H-1,2,3-triazol-1-yl)oxetan-3-yl)pyridin-3-yl)piperidin-3-amine was Obtained Using General Scheme 1 Pathway A Stage 1: General Procedure E1 was used from 2,6-dibromopyrazine to afford 2-bromo-6-((trimethylsilyl)ethynyl)pyrazine IM602: 715 mg, 33% yield, P=50%, retention time=3.2 min (gradient A), (M+H)$^+$: 255/257.

Stage 2: General Procedure D1 was used from IM602 to afford 2-bromo-6-ethynylpyrazine IM603 as colourless oil: 201 mg, 72% yield, P=92%, retention time=2.5 min (gradient A), (M+H)$^+$: 183/185.

Stage 3: General Procedure B was used between IM543 and IM603 to afford tert-butyl (R)-(1-(6-(3-(4-(6-bromopyrazin-2-yl)-1H-1,2,3-triazol-1-yl)oxetan-3-yl)pyridin-3-yl)piperidin-3-yl) (cyclopropylmethyl)carbamate IM604 as a pink solid: 46 mg, 64% yield, P=96%, retention time=3.2 min (gradient A), (M+H)$^+$: 611/613.

Stage 4: General Procedure AA was used between IM604 and 3,3-dimethylpyrrolidine hydrochloride to afford tert-butyl (R)-(cyclopropylmethyl)(1-(6-(3-(4-(6-(3,3-dimethyl pyrrolidin-1-yl)pyrazin-2-yl)-1H-1,2,3-triazol-1-yl)oxetan-3-yl)pyridin-3-yl)piperidin-3-yl) carbamate IM605 as colourless oil: 17 mg, 76% yield, P=97%, retention time=3.2 min (gradient A), (M+H)$^+$: 630.

Stage 5: General Procedure A2 was used from IM605 to afford crude compound 214 as a white solid: 12 mg, 83% yield, P=96%, retention time=3.5 min (gradient B), (M+H)$^+$: 530. $^1$H NMR (300 MHz, CDCl$_3$) δ 8.63 (s, 1H), 8.34 (d, J=3.0 Hz, 1H), 8.06 (s, 1H), 7.80 (s, 1H), 7.12 (dd, J=8.7, 2.9 Hz, 1H), 6.84 (d, J=8.7 Hz, 1H), 5.58-5.48 (m, 5H), 3.69 (d, J=10.7 Hz, 1H), 3.64-3.44 (m, 3H), 3.27 (s, 2H), 2.96-2.83 (m, 1H), 2.83-2.69 (m, 2H), 2.58-2.53 (m, 2H), 2.03-1.92 (m, 1H), 1.82 (t, J=7.0 Hz, 4H), 1.16 (s, 6H), 0.99-0.93 (m, 1H), 0.55-0.47 (m, 2H), 0.17-0.10 (m, 2H), 1 NH exchanged with solvent.

Compound 215: (R)—N-(cyclopropylmethyl)-1-(6-(3-(4-(6-(3,3-difluoropyrrolidin-1-yl) pyrazin-2-yl)-1H-1,2,3-triazol-1-yl)oxetan-3-yl)pyridin-3-yl)piperidin-3-amine was Obtained Using General Scheme 1 Pathway A Stage 1: General Procedure C (in DMSO) was used between 2,6-dichloropyrazine and 3,3-difluoropyrrolidine hydrochloride to afford 2-chloro-6-(3,3-difluoropyrrolidin-1-yl)pyrazine IM606 as yellow oil: 334 mg, 85% yield, P=94%, retention time=2.8 min (gradient A), (M+H)$^+$: 220/222.

Stage 2: General Procedure E2 was used from IM606 to afford 2-(3,3-difluoropyrrolidin-1-yl)-6-((trimethylsilyl)

ethynyl)pyrazine IM607 as a brown solid: 366 mg, 87% yield, P=96%, retention time=3.1 min (gradient A), (M+H)$^+$: 282.

Stage 3: General Procedure X was used between IM607 and IM543 to afford tert-butyl ((3R)-1-(6-(3-(4-(6-(3-azabicyclo[3.1.0]hexan-3-yl)pyrazin-2-yl)-1H-1,2,3-triazol-1-yl)oxetan-3-yl)pyridin-3-yl)piperidin-3-yl)(cyclopropylmethyl)carbamate IM608 as an orange solid: 48 mg, 65% yield, P=93%, retention time=3.0 min (gradient A), (M+H)$^+$: 614.

Stage 4: General Procedure A2 was used from IM608 to afford compound 215 as a yellow solid: 23 mg, 58% yield, P=95%, retention time=3.3 min (gradient B), (M+H)$^+$: 514. $^1$H NMR (300 MHz, CDCl$_3$) δ 8.78 (s, 1H), 8.34 (d, J=2.9 Hz, 1H), 8.04 (s, 1H), 7.86 (s, 1H), 7.13 (dd, J=8.8, 3.0 Hz, 1H), 6.89 (d, J=8.7 Hz, 1H), 5.54 (d, J=6.7 Hz, 2H), 5.50 (d, J=6.7 Hz, 2H), 3.90 (t, J=13.0 Hz, 2H), 3.76 (t, J=7.3 Hz, 2H), 3.69 (d, J=10.5 Hz, 1H), 3.56-3.46 (m, 1H), 2.90 (s, 1H), 2.82-2.66 (m, 2H), 2.64-2.42 (m, 4H), 2.08-1.92 (m, 2H), 1.73-1.63 (m, 2H), 1.00-0.88 (m, 1H), 0.56-0.44 (m, 2H), 0.12 (d, J=5.0 Hz, 2H), 1 NH exchanged with solvent.

Compound 216: (3R)-1-(6-(3-(4-(6-(3-azabicyclo[3.1.0]hexan-3-yl)pyrazin-2-yl)-1H-1,2,3-triazol-1-yl)oxetan-3-yl)pyridin-3-yl)-N-(cyclopropylmethyl)piperidin-3-amine was Obtained Using General Scheme 1 Pathway A Stage 1: General Procedure C (in DMSO) was used between 2,6-dichloropyrazine and 3-azabicyclo[3.1.0]hexane hydrochloride to afford 3-(6-chloropyrazin-2-yl)-3-azabicyclo[3.1.0]hexane IM609 as yellow oil: 318 mg, 93% yield, P=96%, retention time=2.8 min (gradient A), (M+H)$^+$: 196/198.

Stage 2: General Procedure E2 was used from IM609 to afford 3-(6-((trimethylsilyl)ethynyl)pyrazin-2-yl)-3-azabicyclo[3.1.0]hexane IM610 as yellow oil: 358 mg, 79% yield, P=89%, retention time=3.2 min (gradient A), (M+H)$^+$: 258.

Stage 3: General Procedure X was used between IM610 and IM543 to afford tert-butyl ((3R)-1-(6-(3-(4-(6-(3-azabicyclo[3.1.0]hexan-3-yl)pyrazin-2-yl)-1H-1,2,3-triazol-1-yl)oxetan-3-yl) pyridin-3-yl)piperidin-3-yl)(cyclopropylmethyl)carbamate IM611 as an orange solid: 48 mg, 65% yield, P=93%, retention time=3.0 min (gradient A), (M+H)$^+$: 614.

Stage 4: General Procedure A2 was used from IM611 to afford compound 216 as a yellow solid: 23 mg, 58% yield, P=95%, retention time=3.3 min (gradient B), (M+H)$^+$: 514. $^1$H NMR (300 MHz, CDCl$_3$) δ 8.65 (s, 1H), 8.34 (d, J=3.0 Hz, 1H), 8.03 (s, 1H), 7.79 (s, 1H), 7.12 (dd, J=8.7, 3.0 Hz, 1H), 6.85 (d, J=8.8 Hz, 1H), 5.56-5.52 (m, 2H), 5.52-5.48 (m, 2H), 3.77 (d, J=10.2 Hz, 2H), 3.68 (d, J=10.7 Hz, 1H), 3.55-3.45 (m, 3H), 2.97-2.65 (m, 3H), 2.63-2.45 (m, 3H), 2.01-1.60 (m, 6H), 0.99-0.88 (m, 1H), 0.82-0.73 (m, 1H), 0.53-0.44 (m, 2H), 0.31-0.21 (m, 1H), 0.17-0.07 (m, 2H).

Compound 217: (R)-3-(5-(3-((cyclopropylmethyl)amino)piperidin-1-yl)pyridin-2-yl)-N-(4-oxo-4H-pyrido[1,2-a]pyrimidin-2-yl)oxetane-3-carboxamide was Obtained Using General Scheme 6 Pathway B Stage 1: General Procedure C was used between 2-Chloro-4H-pyrido[1,2-a]pyrimidin-4-one and 2,4-dimethoxy benzylamine to afford 2-((2,4-dimethoxybenzyl)amino)-4H-pyrido[1,2-a]pyrimidin-4-one IM612 as yellow oil: 1.035 g, 88% yield, P=70%, retention time=2.4 min (gradient A), (M+H)$^+$: 312.

Stage 2: General Procedure A2 was used from IM612 to afford 2-amino-4H-pyrido[1,2-a]pyrimidin-4-one IM613 as a white solid: 170 mg, 45% yield, P=100%, retention time=0.7 min (gradient B), (M+H)$^+$: no ionisation.

Stage 3: General Procedure F was used between IM522 and IM613 to afford tert-butyl (R)-(cyclopropylmethyl)(1-(6-(3-((4-oxo-4H-pyrido[1,2-a]pyrimidin-2-yl)carbamoyl)oxetan-3-yl) pyridin-3-yl)piperidin-3-yl)carbamate IM614 as colourless oil: 19 mg, 38% yield, P=80%, retention time=2.7 min (gradient A), (M+H)$^+$: 575.

Stage 4: General Procedure A2 was used from IM614 to afford compound 217 as colourless oil: 13 mg, 71% yield, P=73%, retention time=2.1 min (gradient A), (M+H)$^+$: 4754.

The product was purified by reverse phase preparative HPLC purification (Waters XBridge C18 5 µm, 19×100 mm). Gradient used: increased linearly from 25 to 40% solution "B" over 4.0 min, increased linearly to 85% solution "B" over 2.3 min, and returned to initial conditions over 1.0 min. Flow Rate: 15 mL/min. P=94%. $^1$H NMR (300 MHz, CDCl$_3$) δ 9.05 (s, 1H), 8.97 (d, J=7.2 Hz, 1H), 8.39 (d, J=2.7 Hz, 1H), 7.72-7.60 (m, 1H), 7.45-7.33 (m, 2H), 7.23-7.13 (m, 2H), 7.07-6.96 (m, 1H), 5.37 (dd, J=6.2, 1.5 Hz, 2H), 5.04 (d, J=6.1 Hz, 2H), 3.74-3.65 (m, 1H), 3.57-3.47 (m, 1H), 2.97-2.86 (m, 1H), 2.83-2.66 (m, 2H), 2.65-2.47 (m, 3H), 2.04-1.56 (m, 4H), 1.01-0.91 (m, 1H), 0.57-0.45 (m, 2H), 0.17-0.07 (m, 2H).

Compound 218: 1-(1-(4-(5-(1H-imidazol-1-yl)pyridin-3-yl)-1H-1,2,3-triazol-1-yl)ethyl)-4-((R)-3-((cyclopropylmethyl)amino)piperidin-1-yl)pyridin-2 (1H)-one was Obtained Using General Scheme 1 Pathway B Stage 1: General Procedure AA was used between IM524 and imidazole to afford tert-butyl ((3R)-1-(1-(1-(4-(5-(1H-imidazol-1-yl)pyridin-3-yl)-1H-1,2,3-triazol-1-yl)ethyl)-2-oxo-1,2-dihydropyridin-4-yl)piperidin-3-yl)(cyclopropylmethyl)carbamate IM615 as a white solid: 90 mg, 75% yield, P=77%, retention time=2.4 min (gradient A), (M+H)$^+$: 586.

Stage 2: General Procedure A2 was used from IM615 to afford crude compound 218 as a white solid: 80 mg, 98% yield, P=72%, retention time=2.1 min (gradient A), (M+H)$^+$: 537.

The mixture of diastereomers was further purified by chiral preparative HPLC purification using Chiralpak IA column (5 µm, 20×250 mm). Eluent used: TBME/MeOH/DCM/DEA: 40/40/20/0.1% at flow rate of 20 mL/min. First eluted diastereomer: P=97%, retention time=10.4 min, chiral HPLC: P=100%, $^1$H NMR (300 MHz, CDCl$_3$) δ 8.95 (d, J=1.9 Hz, 1H), 8.67 (d, J=2.5 Hz, 1H), 8.29 (s, 1H), 8.23 (d, J=2.2 Hz, 1H), 7.93 (s, 1H), 7.53 (q, J=7.1 Hz, 1H), 7.43 (d, J=8.1 Hz, 1H), 7.34 (d, J=1.5 Hz, 1H), 7.25 (s, 1H), 5.99 (dd, J=8.1, 2.8 Hz, 1H), 5.63 (d, J=2.7 Hz, 1H), 3.80-3.68 (m, 1H), 3.64-3.53 (m, 1H), 3.00-2.85 (m, 1H), 2.80-2.39 (m, 4H), 2.18 (d, J=7.0 Hz, 3H), 2.02-1.91 (m, 1H), 1.80-1.67 (m, 1H), 1.57-1.29 (m, 2H), 0.97-0.80 (m, J=4.9, 3.1 Hz, 1H), 0.52-0.40 (m, 2H), 0.12--0.01 (m, 2H), 1H exchanged with solvent. Second eluted diastereomer: P=98%, retention time=25.1 min, chiral HPLC: P=98.7%, $^1$H NMR (300 MHz, CDCl$_3$) δ 8.95 (d, J=1.9 Hz, 1H), 8.67 (d, J=2.5 Hz, 1H), 8.29 (s, 1H), 8.23 (t, J=2.3 Hz, 1H), 7.93 (s, 1H), 7.53 (q, J=7.1 Hz, 1H), 7.43 (d, J=8.1 Hz, 1H), 7.34 (d, J=1.5 Hz, 1H), 7.25 (s, 1H), 5.99 (dd, J=8.2, 2.9 Hz, 1H), 5.63 (d, J=2.9 Hz, 1H), 3.80-3.69 (m, 1H), 3.64-3.54 (m, 1H), 3.00-2.85 (m, 1H), 2.80-2.39 (m, 4H), 2.18 (d, J=7.0 Hz, 3H), 2.02-1.91 (m, 1H), 1.80-1.67 (m, 1H), 1.58-1.26 (m, 2H), 0.96-0.81 (m, 1H), 0.52-0.40 (m, 2H), 0.09-0.01 (m, 2H), 1H exchanged with solvent.

Compound 219: 4-((R)-3-((cyclopropylmethyl)amino)piperidin-1-yl)-1-(1-(1-(5-(pyrrolidin-1-yl)pyridazin-3-yl)-1H-pyrazol-4-yl)ethyl)pyridin-2(1H)-one was Obtained Using General Scheme 3 Scheme 5

Stage 1: In an microwave vial (5 mL), to a mixture of IM569 (500 mg, 2.70 mmol) and 1-(1H-pyrazol-4-yl)ethanone (337 mg, 2.97 mmol) in NMP (4.95 mL) was added cesium carbonate (1.79 g, 5.39 mmol). The vial was capped and the reaction mixture was heated to 130° C. for 24 h. The mixture was cooled down and directly purified by the C18 column (0-100% MeCN in ammonium bicarbonate 10 mM, and then by silica column (0-5% MeOH in DCM) to afford 1-(1-(5-(pyrrolidin-1-yl)pyridazin-3-yl)-1H-pyrazol-4-yl)ethan-1-one IM616 as an off-white solid: 530 mg, 69% yield, P=91%, retention time=1.0 min (gradient C), (M+H)$^+$: 258.

Stage 2: To IM616 (528 mg, 1.87 mmol) in methanol (8.47 mL) at 0° C. was added portion-wise sodium borohydride (216 mg, 5.60 mmol) and the reaction was stirred at 0° C. for 30 min. The reaction mixture was concentrated down, co-evaporated with DCM (2×10 mL), and directly purified by silica column (0-10% MeOH in DCM) to 1-(1-(6-(pyrrolidin-1-yl)pyrazin-2-yl)-1H-pyrazol-4-yl)ethan-1-ol IM617 as an off-white solid: 406 mg, 82% yield, P=98%, retention time=1.0 min (gradient C), (M+H)$^+$: 260.

Stage 3: General Procedure T was used between 4-chloropyridin-2-ol and IM617 to afford 4-chloro-1-(1-(1-(5-(pyrrolidin-1-yl)pyridazin-3-yl)-1H-pyrazol-4-yl)ethyl)pyridin-2(1H)-one IM618 as a white solid: 68 mg, 12% yield, P=97%, retention time=1.2 min (gradient C), (M+H)$^+$: 371/373.

Stage 4: General Procedure C was used between IM486 and IM618 to afford tert-butyl (cyclopropylmethyl)((3R)-1-(2-oxo-1-(1-(1-(5-(pyrrolidin-1-yl)pyridazin-3-yl)-1H-pyrazol-4-yl) ethyl)-1,2-dihydropyridin-4-yl)piperidin-3-yl)carbamate IM619 as an off-white solid: 74 mg, 70% yield, P=99%, retention time=1.7 min (gradient C), (M+H)$^+$: 589.

Stage 5: General Procedure A2 was used from IM619 to afford compound 219 as a white solid: 56 mg, 94% yield, P=100%, retention time=2.2 min (gradient E), (M+H)$^+$: 489.

The mixture of diastereomers was further purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=100%, retention time=7.5 min, chiral HPLC: P=100%, $^1$H NMR (300 MHz, CDCl$_3$) δ 8.68 (s, 1H), 8.46 (d, J=2.7 Hz, 1H), 7.59 (s, 1H), 7.02 (d, J=2.6 Hz, 1H), 6.99 (d, J=7.9 Hz, 1H), 6.33 (q, J=6.9 Hz, 1H), 5.87 (dd, J=7.9, 2.8 Hz, 1H), 5.73 (d, J=2.8 Hz, 1H), 3.80-3.71 (m, 1H), 3.65-3.52 (m, 1H), 3.48-3.39 (m, 4H), 2.96-2.81 (m, 1H), 2.77-2.60 (m, 2H), 2.57-2.47 (m, 2H), 2.15-2.04 (m, 4H), 2.02-1.92 (m, 1H), 1.79-1.46 (m, 5H), 1.44-1.31 (m, 1H), 1.00-0.85 (m, 1H), 0.53-0.39 (m, 2H), 0.17-0.05 (m, 2H), 1 NH exchanged. Second eluted diastereomer: P=100%, retention time=10.3 min, chiral HPLC: P=99.4%, $^1$H NMR (300 MHZ, CDCl$_3$) δ 8.69 (d, J=1.1 Hz, 1H), 8.46 (d, J=2.7 Hz, 1H), 7.59 (s, 1H), 7.02 (d, J=2.7 Hz, 1H), 6.99 (d, J=7.9 Hz, 1H), 6.34 (q, J=7.0 Hz, 1H), 5.87 (dd, J=8.0, 2.9 Hz, 1H), 5.73 (d, J=2.8 Hz, 1H), 3.80-3.71 (m, 1H), 3.63-3.53 (m, 1H), 3.48-3.38 (m, 4H), 2.96-2.81 (m, 1H), 2.77-2.60 (m, 2H), 2.52-2.43 (m, 2H), 2.10-1.95 (m, 5H), 1.76-1.52 (m, 5H), 1.40-1.30 (m, 1H), 1.00-0.84 (m, 1H), 0.53-0.41 (m, 2H), 0.13-0.04 (m, 2H), 1 NH exchanged.

Compound 220: 4-((R)-3-((cyclopropylmethyl)amino)piperidin-1-yl)-1-(1-(1-(6-(pyrrolidin-1-yl)pyrazin-2-yl)-1H-pyrazol-4-yl)ethyl)pyridin-2(1H)-one was Obtained Using General Scheme 3 Scheme 5

Stage 1: In an microwave vial (5 mL), to a mixture of IM532 (500 mg, 2.70 mmol) and 1-(1H-pyrazol-4-yl)ethanone (337 mg, 2.97 mmol) in NMP (4.95 mL) was added cesium carbonate (1.79 g, 5.39 mmol). The vial was capped and the reaction mixture was heated to 130° C. for 18 h. The mixture was cooled down and directly purified by the C18 column (0-100% MeCN in ammonium bicarbonate 10 mM, then 100% MeOH and 100% THF), and then by silica column (0-5% MeOH in DCM) to afford 1-(1-(6-(pyrrolidin-1-yl)pyrazin-2-yl)-1H-pyrazol-4-yl)ethan-1-one IM620 as a yellow solid: 610 mg, 84% yield, P=97%, retention time=1.3 min (gradient C), (M+H)$^+$: 258.

Stage 2: To IM620 (606 mg, 2.28 mmol) in methanol (10.4 mL) at 0° C. was added portion-wise sodium borohydride (265 mg, 6.85 mmol) and the reaction was stirred at 0° C. for 30 min. The reaction mixture was concentrated down, co-evaporated with DCM (2×10 mL), and directly purified by silica column (0-10% MeOH in DCM) to afford 1-(1-(6-(pyrrolidin-1-yl)pyrazin-2-yl)-1H-pyrazol-4-yl)ethan-1-ol IM621 as an off-white solid: 515 mg, 83% yield, P=95%, retention time=1.1 min (gradient C), (M+H)$^+$: 260.

Stage 3: General Procedure T was used between 4-chloropyridin-2-ol and IM621 to afford 4-chloro-1-(1-(1-(6-(pyrrolidin-1-yl)pyrazin-2-yl)-1H-pyrazol-4-yl)ethyl)pyridin-2(1H)-one IM622 as an off-white solid: 328 mg, 9% yield, P=19% ($^1$H-NMR), retention time=1.4 min (gradient C), (M+H)$^+$: 371/373.

Stage 4: General Procedure C was used between IM486 and IM622 to afford tert-butyl (cyclopropylmethyl)((3R)-1-(2-oxo-1-(1-(1-(6-(pyrrolidin-1-yl)pyrazin-2-yl)-1H-pyrazol-4-yl) ethyl)-1,2-dihydropyridin-4-yl)piperidin-3-yl)carbamate IM623 as an off-white solid: 86 mg, 86% yield, P=99%, retention time=1.8 min (gradient C), (M+H)$^+$: 589.

Stage 5: General Procedure A2 was used from IM623 to afford compound 220 as a white solid: 50 mg, 73% yield, P=100%, retention time=2.5 min (gradient E), (M+H)$^+$: 489.

The mixture of diastereomers was further purified by chiral preparative HPLC purification using Chiralpak IE column (5 μm, 10×250 mm). Eluent used: DCM/MeOH/DEA: 90/10/0.1% at flow rate of 7 mL/min. First eluted diastereomer: P=100%, retention time=6.7 min, chiral HPLC: P=98.9%, $^1$H NMR (300 MHz, CDCl$_3$) δ 8.41 (d, J=1.5 Hz, 1H), 8.36 (d, J=3.3 Hz, 1H), 7.76 (s, 1H), 7.59 (d, J=4.4 Hz, 1H), 7.08 (d, J=7.9 Hz, 1H), 6.24 (q, J=7.0 Hz, 1H), 6.02 (dd, J=8.0, 2.8 Hz, 1H), 5.93 (d, J=2.7 Hz, 1H), 4.45-4.35 (m, 1H), 3.75-3.64 (m, 1H), 3.58-3.40 (m, 5H), 3.19 (s, 1H), 3.00-2.93 (m, 2H), 2.82-2.70 (m, 1H), 2.17 (s, 1H), 2.13-2.00 (m, 5H), 1.94-1.83 (m, 1H), 1.66 (d, J=7.0 Hz, 4H), 1.35-1.27 (m, 1H), 0.67 (d, J=7.9 Hz, 2H), 0.55-0.45 (m, 2H), 1 NH exchanged. Second eluted diastereomer: P=100%, retention time=8.2 min, chiral HPLC: P=98.2%, $^1$H NMR (300 MHz, CDCl$_3$) δ 8.40 (d, J=1.6 Hz, 1H), 8.35 (d, J=3.2 Hz, 1H), 7.75 (s, 1H), 7.58 (d, J=3.6 Hz, 1H), 7.07 (d, J=7.9 Hz, 1H), 6.23 (q, J=7.1 Hz, 1H), 6.02 (dd, J=8.0, 2.8 Hz, 1H), 5.92 (d, J=2.8 Hz, 1H), 4.38 (d, J=13.7 Hz, 1H), 3.66 (s, 1H), 3.51 (q, J=6.6 Hz, 5H), 3.18 (s, 1H), 2.99-2.89 (m, 2H), 2.76 (dd, J=12.5, 7.4 Hz, 1H), 2.15 (s, 1H), 2.09-1.96 (m, 5H), 1.87 (d, J=13.8 Hz, 1H), 1.65 (d, J=6.9

Compound 221: (R)-1-(6-(3-(4-(6-(2-oxa-6-azaspiro [3.3]heptan-6-yl)pyrazin-2-yl)-1H-1,2,3-triazol-1-yl) oxetan-3-yl)pyridin-3-yl)-N-(cyclopropylmethyl) piperidin-3-amine was Obtained Using General Scheme 1 Pathway A Stage 1: General Procedure AA was used between IM604 and 2-oxa-6-azaspiro[3.3]heptane hemioxalate to afford tert-butyl (R)-(1-(6-(3-(4-(6-(2-oxa-6-azaspiro[3.3]heptan-6-yl)pyrazin-2-yl)-1H-1,2,3-triazol-1-yl)oxetan-3-yl)pyridin-3-yl)piperidin-3-yl)(cyclopropylmethyl) carbamate IM624 as colourless oil: 15 mg, 48% yield, P=93%, retention time=2.8 min (gradient A), (M+H)$^+$: 630.

Stage 2: General Procedure A2 was used from IM625 to afford compound 221 as colourless oil: 12 mg, 87% yield, P=85%, retention time=3.5 min (gradient B), (M+H)$^+$: 530.

The product was purified by reverse phase preparative HPLC purification (Waters XBridge C18 5 μm, 19×100 mm). Gradient used: increased linearly from 25 to 40% solution "B" over 4.0 min, increased linearly to 85% solution "B" over 2.3 min, and returned to initial conditions over 1.0 min. Flow Rate: 15 mL/min. P=100%. $^1$H NMR (300 MHz, CDCl$_3$) δ 8.74 (s, 1H), 8.34 (d, J=3.0 Hz, 1H), 8.03 (s, 1H), 7.74 (s, 1H), 7.13 (dd, J=8.7, 3.0 Hz, 1H), 6.88 (d, J=8.7 Hz, 1H), 5.54 (d, J=6.7 Hz, 2H), 5.50 (d, J=6.7 Hz, 2H), 4.85 (s, 4H), 4.26 (s, 4H), 3.73-3.64 (m, 1H), 3.56-3.46 (m, 1H), 2.98-2.83 (m, 1H), 2.81-2.65 (m, 2H), 2.64-2.48 (m, 3H), 1.99 (s, 1H), 1.86-1.23 (m, 3H), 1.00-0.90 (m, 1H), 0.56-0.44 (m, 2H), 0.18-0.08 (m, 2H).

Compound 222: (R)-1-(6-(3-(4-(6-(5-azaspiro[2.4] heptan-5-yl)pyrazin-2-yl)-1H-1,2,3-triazol-1-yl) oxetan-3-yl)pyridin-3-yl)-N-(cyclopropylmethyl) piperidin-3-amine was Obtained Using General Scheme 1 Pathway A Stage 1: General Procedure C (in DMSO) was used between 2,6-dichloropyrazine and 5-Azaspiro[2.4]heptane hydrochloride to afford 5-(6-chloropyrazin-2-yl)-5-azaspiro [2.4]heptane IM626 as orange oil: 296 mg, 79% yield, P=94%, retention time=2.9 min (gradient A), (M+H)$^+$: 210/212.

Stage 2: General Procedure E2 was used from IM626 to afford 5-(6-((trimethylsilyl) ethynyl)pyrazin-2-yl)-5-azaspiro[2.4]heptane IM627 as yellow solid: 336 mg, 91% yield, P=98%, retention time=3.3 min (gradient A), (M+H)$^+$: 272.

Stage 3: General Procedure X was used between IM627 and IM543 to afford tert-butyl (R)-(1-(6-(3-(4-(6-(5-azaspiro[2.4]heptan-5-yl)pyrazin-2-yl)-1H-1,2,3-triazol-1-yl)oxetan-3-yl) pyridin-3-yl)piperidin-3-yl)(cyclopropylmethyl)carbamate IM628 as a yellow solid: 48 mg, 66% yield, P=96%, retention time=3.1 min (gradient A), (M+H)$^+$: 628.

Stage 4: General Procedure A2 was used from IM628 to afford compound 222 as a yellow solid: 29 mg, 75% yield, P=100%, retention time=3.4 min (gradient B), (M+H)$^+$: 528. $^1$H NMR (300 MHz, CDCl$_3$) δ 8.64 (s, 1H), 8.34 (d, J=2.9 Hz, 1H), 8.04 (s, 1H), 7.80 (s, 1H), 7.11 (dd, J=8.7, 3.0 Hz, 1H), 6.84 (d, J=8.7 Hz, 1H), 5.54 (d, J=6.9 Hz, 2H), 5.50 (d, J=6.7 Hz, 2H), 3.73-3.63 (m, 3H), 3.50 (d, J=12.3 Hz, 1H), 3.41 (s, 2H), 2.89 (s, 1H), 2.79-2.66 (m, 2H), 2.53 (h, J=6.0 Hz, 3H), 1.97-1.92 (m, 2H), 1.85-0.87 (m, 5H), 0.70-0.62 (m, 4H), 0.50 (q, J=5.4 Hz, 2H), 0.12 (q, J=5.0 Hz, 2H), 1.53 (s, 1H), 1.37-1.22 (m, 1H), 0.66 (d, J=7.9 Hz, 2H), 0.48 (d, J=5.8 Hz, 2H), 1 NH exchanged.

Compound 223: (R)—N-(cyclopropylmethyl)-1-(5-(3-(4-(5-(pyrrolidin-1-yl)pyridin-3-yl)-1H-1,2,3-triazol-1-yl)oxetan-3-yl)pyridin-2-yl)piperidin-3-amine was Obtained Using General Scheme 1 Pathway A Stage 1: General Procedure X was used between IM584 and IM555 to afford tert-butyl (R)-(cyclopropylmethyl)(1-(5-(3-(4-(5-(pyrrolidin-1-yl)pyridin-3-yl)-1H-1,2,3-triazol-1-yl)oxetan-3-yl)pyridin-2-yl)piperidin-3-yl)carbamate IM629 as a white solid: 52 mg, 59% yield, P=94%, retention time=2.4 min (gradient A), (M+H)$^+$: 601.

Stage 2: General Procedure A2 was used from IM629 to afford compound 223 as an off-white solid: 32 mg, 66% yield, P=96%, retention time=2.6 min (gradient B), (M+H)$^+$: 501. $^1$H NMR (300 MHz, CDCl$_3$) δ 8.17 (s, 1H), 8.07 (d, J=2.7 Hz, 1H), 7.94 (d, J=2.8 Hz, 1H), 7.62 (s, 1H), 7.40 (s, 1H), 7.33 (dd, J=9.0, 2.7 Hz, 1H), 6.68 (d, J=9.0 Hz, 1H), 5.60 (d, J=6.8 Hz, 2H), 5.26 (d, J=6.8 Hz, 2H), 4.28 (d, J=12.9 Hz, 1H), 4.03 (d, J=13.2 Hz, 1H), 3.36 (d, J=6.4 Hz, 4H), 3.05 (t, J=11.9 Hz, 1H), 2.89 (dd, J=12.7, 9.1 Hz, 1H), 2.72 (d, J=10.2 Hz, 1H), 2.61-2.42 (m, 3H), 2.04 (t, J=4.7 Hz, 4H), 1.82-1.34 (m, 4H), 0.95 (s, 1H), 0.48 (d, J=8.0 Hz, 2H), 0.12 (s, 2H).

Compound 224: 4-((R)-3-((cyclopropylmethyl) amino)piperidin-1-yl)-1-(1-(1-(5-(dimethyl amino) pyridazin-3-yl)-1H-pyrazol-4-yl)ethyl)pyridin-2 (1H)-one was Obtained Using General Scheme 3 Scheme 5

Stage 1: In a microwave vial (5 mL), to a mixture of 6-chloro-N,N-dimethylpyridazin-4-amine (250 mg, 1.59 mmol) and 1-(1H-pyrazol-4-yl)ethan-1-one (19 mg, 171 μmol) in NMP (2.8 mL) was added cesium carbonate (1.05 g, 3.17 mmol). The vial was capped and the reaction mixture was heated to 130° C. for 18 h. The mixture was cooled down and directly purified by C18 column (0-100% MeCN in ammonium bicarbonate and then 100% MeOH) and then by silica column (0-5% MeOH in DCM) to afford 1-(1-(5-(dimethylamino)pyridazin-3-yl)-1H-pyrazol-4-yl)ethan-1-one IM630 as an off-white solid: 284 mg, 70% yield, P=91%, retention time=0.9 min (gradient C), (M+H)$^+$: 232.

Stage 2: To IM630 (560 mg, 2.20 mmol) in methanol (10 mL) at 0° C. was added portion-wise
Sodium borohydride (255 mg, 6.61 mmol) and the reaction was stirred at 0° C. for 30 min. The reaction mixture was concentrated down, co-evaporated with DCM (2×10 mL), and directly purified by silica column (0-10% MeOH in DCM) to afford 1-(1-(5-(dimethylamino)pyridazin-3-yl)-1H-pyrazol-4-yl)ethan-1-ol IM631 as a light yellow solid: 484 mg, 93% yield, P=99%, retention time=0.8 min (gradient C), (M+H)$^+$: 234.

Stage 3: General Procedure T was used between 4-chloropyridin-2-ol and IM631 to afford 4-chloro-1-(1-(1-(5-(dimethylamino)pyridazin-3-yl)-1H-pyrazol-4-yl)ethyl) pyridin-2(1H)-one IM632 as a white solid: 80 mg, 12% yield, P=12%, retention time=1.8 min (gradient E), (M+H)$^+$: 345/347.

Stage 4: General Procedure C was used between IM486 and IM632 to afford tert-butyl (cyclopropylmethyl)((3R)-1-(1-(1-(1-(5-(dimethylamino)pyridazin-3-yl)-1H-pyrazol-4-yl)ethyl)-2-oxo-1,2-dihydropyridin-4-yl)piperidin-3-yl)carbamate IM633 as an off-white solid: 70 mg, 60% yield, P=100%, retention time=1.6 min (gradient C), (M+H)$^+$: 563.

Stage 5: General Procedure A2 was used from IM633 to afford compound 224 as a white solid: 45 mg, 83% yield, P=100%, retention time=1.9 min (gradient E), (M+H)$^+$: 463.

The mixture of diastereomers was further purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=100%, retention time=8.4 min, chiral HPLC: P=100%, $^1$H NMR (300 MHz, CDCl$_3$) δ 8.69 (s, 1H), 8.61 (d, J=2.8 Hz, 1H), 7.61 (s, 1H), 7.17 (d, J=2.8 Hz, 1H), 7.01 (d, J=7.9 Hz, 1H), 6.33 (q, J=7.0 Hz, 1H), 5.91 (dd, J=8.0, 2.8 Hz, 1H), 5.78 (d, J=2.7 Hz, 1H), 3.90-3.80 (m, 1H), 3.66-3.55 (m, 1H), 3.13 (s, 6H), 2.99-2.73 (m, 3H), 2.57 (d, J=6.9 Hz, 2H), 2.07-1.96 (m, 1H), 1.80-1.72 (m, 1H), 1.66 (d, J=7.0 Hz, 3H), 1.60-1.43 (m, 2H), 1.08-0.90 (m, 1H), 0.57-0.45 (m, 2H), 0.20-0.12 (m, 2H), 1 NH exchanged. Second eluted diastereomer: P=100%, retention time=13.3 min, chiral HPLC: P=100%, $^1$H NMR (300 MHz, CDCl$_3$) δ 8.69 (s, 1H), 8.61 (d, J=2.8 Hz, 1H), 7.61 (s, 1H), 7.17 (d, J=2.8 Hz, 1H), 7.02 (d, J=7.9 Hz, 1H), 6.32 (q, J=6.9 Hz, 1H), 5.91 (dd, J=7.9, 2.9 Hz, 1H), 5.79 (d, J=2.7 Hz, 1H), 3.94-3.84 (m, 1H), 3.66-3.55 (m, 1H), 3.13 (s, 6H), 2.99-2.72 (m, 3H), 2.65-2.52 (m, 2H), 2.06-1.96 (m, 1H), 1.76 (s, 1H), 1.66 (d, J=7.0 Hz, 3H), 1.54 (s, 2H), 1.02 (s, 1H), 0.59-0.46 (m, 2H), 0.25-0.12 (m, 2H), 1 NH exchanged.

Compound 225: 4-((R)-3-((cyclopropylmethyl)amino)piperidin-1-yl)-1-(1-(1-(6-(dimethyl amino)pyrazin-2-yl)-1H-pyrazol-4-yl)ethyl)pyridin-2(1H)-one was Obtained Using General Scheme 3
Scheme 5

Stage 1: In a microwave vial, to a mixture of IM488 (500 mg, 3.17 mmol) and 1-(1H-Pyrazol-4-yl)ethanone (19.2 mg, 171 μmol) in NMP (5.00 mL) was added cesium carbonate (2.11 g, 6.35 mmol). The vial was capped and the reaction mixture was heated to 130° C. for 18 h. The mixture was cooled down to rt and directly purified by C18 Column (0-100% MeCN in ammonium bicarbonate). The isolated orange solid was repurified by silica column (50 g, 0-5% MeOH in DCM) to afford 1-(1-(6-(dimethylamino)pyrazin-2-yl)-1H-pyrazol-4-yl)ethan-1-one IM634 as a light yellow solid: 635 mg, 87% yield, P=100%, retention time=1.1 min (gradient C), (M+H)$^+$: 232.

Stage 2: To IM634 (635 mg, 2.75 mmol) in methanol (12.5 mL) at 0° C. was added portion-wise
sodium borohydride (318 mg, 8.24 mmol) and the reaction was stirred at 0° C. for 30 min. The reaction mixture was concentrated down, co-evaporated with DCM (2×10 mL), and directly purified by silica column (0-10% MeOH in DCM) to afford 1-(1-(6-(dimethylamino)pyrazin-2-yl)-1H-pyrazol-4-yl)ethan-1-ol IM635 as an off-white solid: 525 mg, 81% yield, P=99%, retention time=1.0 min (gradient C), (M+H)$^+$: 234.

Stage 3: General Procedure T was used between 4-chloropyridin-2-ol and IM635 to afford 4-chloro-1-(1-(1-(6-(dimethylamino)pyrazin-2-yl)-1H-pyrazol-4-yl)ethyl)pyridin-2(1H)-one IM636 as an off-white solid: 1.05 g, 16% yield, P=11% ($^1$H-NMR), retention time=1.3 min (gradient C), (M+H)$^+$: 345/347.

Stage 4: General Procedure C was used between IM486 and IM636 to afford tert-butyl (cyclopropylmethyl)((3R)-1-(1-(1-(6-(dimethylamino)pyrazin-2-yl)-1H-pyrazol-4-yl)ethyl)-2-oxo-1,2-dihydropyridin-4-yl)piperidin-3-yl)carbamate IM637 as an off-white solid: 148 mg, 79% yield, P=100%, retention time=1.9 min (gradient C), (M+H)$^+$: 563.

Stage 5: General Procedure A2 was used from IM637 to afford compound 225 as a white solid: 117 mg, 96% yield, P=100%, retention time=2.2 min (gradient E), (M+H)$^+$: 463.

The mixture of diastereomers was further purified by chiral preparative HPLC purification using Chiralpak IE column (5 μm, 10×250 mm). Eluent used: DCM/MeOH/DEA: 90/10/0.1% at flow rate of 7 mL/min. First eluted diastereomer: P=100%, retention time=5.7 min, chiral HPLC: P=98.9%, $^1$H NMR (300 MHZ, CDCl$_3$) δ 8.44 (s, 1H), 8.36 (s, 1H), 7.90 (s, 1H), 7.62 (s, 1H), 7.02 (d, J=7.9 Hz, 1H), 6.31 (q, J=6.9 Hz, 1H), 5.92 (dd, J=8.0, 2.9 Hz, 1H), 5.78 (d, J=2.8 Hz, 1H), 3.93-3.82 (m, 1H), 3.63-3.53 (m, 1H), 3.15 (s, 6H), 2.98-2.71 (m, 3H), 2.63-2.50 (m, 2H), 2.04-1.91 (m, 1H), 1.83-1.70 (m, 1H), 1.66 (d, J=6.9 Hz, 3H), 1.59-1.43 (m, 2H), 0.99 (s, 1H), 0.58-0.45 (m, 2H), 0.24-0.11 (m, 2H), 1 NH exchanged. Second eluted diastereomer: P=100%, retention time=6.8 min, chiral HPLC: P=98.9%, $^1$H NMR (300 MHz, CDCl$_3$) δ 8.44 (s, 1H), 8.35 (s, 1H), 7.90 (s, 1H), 7.62 (s, 1H), 7.02 (d, J=7.9 Hz, 1H), 6.31 (q, J=6.9 Hz, 1H), 5.93 (dd, J=7.9, 2.8 Hz, 1H), 5.80 (d, J=2.8 Hz, 1H), 4.01-3.91 (m, 1H), 3.67-3.56 (m, 1H), 3.15 (s, 6H), 3.05-2.81 (m, 3H), 2.72-2.53 (m, 2H), 2.10-1.95 (m, 1H), 1.83-1.71 (m, 1H), 1.66 (d, J=7.0 Hz, 3H), 1.62-1.49 (m, 2H), 1.11-0.98 (m, 1H), 0.60-0.48 (m, 2H), 0.28-0.17 (m, 2H), 1 NH exchanged.

Compound 226: 4-((R)-3-((cyclopropylmethyl)amino)piperidin-1-yl)-1-(1-(4-(6-(pyrrolidin-1-yl)pyrazin-2-yl)-1H-imidazol-1-yl)ethyl)pyridin-2(1H)-one was Obtained Using General Scheme 4
Pathway C1

Stage 1: To a microwave vial, under nitrogen, were added IM532 (200 mg, 1.09 mmol), 4-(tributylstannyl)-1-trityl-1H-imidazole (687 mg, 1.09 mmol), dichloro(triphenylphosphine) palladium (II) (39.0 mg, 54.5 μmol) and dioxane (3.63 mL). The reaction mixture was degassed for 5 min before being sealed and heated to 100° C. overnight. After cooling to rt, mixture was concentrated under reduced pressure. The crude residue was purified by silica gel chromatography (Biotage, dry load) using a gradient of EtOAc (0-100%) in heptanes to afford 2-(pyrrolidin-1-yl)-6-(1-trityl-1H-imidazol-4-yl)pyrazine IM638 as a white solid: 292 mg, 59% yield, P=100%, retention time=1.9 min (gradient C), (M+H)$^+$: 458.

Stage 2: To a RBF, equipped with a condenser, were added IM638 (292 mg, 638 μmol), MeOH (7.98 mL) and acetic acid (913 μL, 16.0 mmol). The mixture was heated to 75° C. for 4 h. After cooling to rt, MeOH was removed under reduced pressure. Residue was purified by reverse phase chromatography using a gradient of MeCN (0-100%) in 10 mM ammonium formate buffer to afford 2-(1H-imidazol-4-yl)-6-(pyrrolidin-1-yl)pyrazine IM639 as a green solid: 105 mg, 63% yield, P=100%, retention time=1.0 min (gradient F), (M+H)$^+$: 216.

Stage 3: To a solution of IM639 (102 mg, 390 μmol) (formate salt) in DMF (1.1 mL), cooled to 0° C., was added potassium carbonate (165 mg, 1.17 mmol) and the mixture was stirred at 0° C. for 5 min before adding sodium hydride 60% in dispersion in mineral oil (46.8 mg, 1.17 mmol) and a solution of IM150 (375 mg, 1.95 mmol) in DMF (1.12 mL). Ice bath was then removed and the mixture was heated to 50° C. Mixture was cooled again to 0° C. and more sodium hydride 60% in dispersion in mineral oil (46.8 mg, 1.17 mmol) was added (reaction bubbled with second addition of NaH). Ice bath was removed and mixture was heated to 50° C. After cooling to rt, mixture was quenched with water then was directly loaded onto a C-18 cartridge and purified by reverse phase chromatography using a gradient of MeCN (0-100%) in 10 mM ammonium bicarbonate buffer to afford 4-chloro-1-(1-(4-(6-(pyrrolidin-1-yl)pyrazin-2-yl)-1H-imidazol-1-yl)ethyl)pyridin-2(1H)-one IM640 as brown oil: 100 mg, 41% yield, P=60%, retention time=1.2 min (gradient C), (M+H)⁺: 371/373.

Stage 4: General Procedure C was used between IM486 and IM640 to afford ter-butyl (cyclopropylmethyl)((3R)-1-(2-oxo-1-(1-(4-(6-(pyrrolidin-1-yl)pyrazin-2-yl)-1H-imidazol-1-yl) ethyl)-1,2-dihydropyridin-4-yl)piperidin-3-yl)carbamate IM641 as a beige solid: 59 mg, 58% yield, P=93%, retention time=1.6 min (gradient C), (M+H)⁺: 589.

Stage 5: General Procedure A2 was used from IM641 to afford compound 226 as a white solid: 21 mg, 41% yield, P=95%, retention time=2.2 min (gradient E), (M+H)⁺: 489.

The mixture of diastereomers was further purified by chiral preparative HPLC purification using Chiralpak IE column (5 µm, 10×250 mm). Eluent used: TBME/DCM/MeOH/DEA: 40/20/40/0.1% at flow rate of 7 mL/min. First eluted diastereomer: P=100%, retention time=8.1 min, chiral HPLC: P=99.6%, ¹H NMR (300 MHz, CDCl₃) δ 8.43 (s, 1H), 7.80 (d, J=1.5 Hz, 1H), 7.76 (s, 1H), 7.70 (d, J=1.5 Hz, 1H), 7.33-7.27 (m, 1H), 6.96 (d, J=8.0 Hz, 1H), 5.94 (dd, J=8.2, 2.8 Hz, 1H), 5.69 (d, J=2.7 Hz, 1H), 3.82-3.72 (m, 1H), 3.62-3.48 (m, 5H), 3.01-2.87 (m, 1H), 2.87-2.74 (m, 1H), 2.70 (s, 1H), 2.56-2.49 (m, 2H), 2.02 (d, J=4.0 Hz, 4H), 1.94 (d, J=6.9 Hz, 3H), 1.82-1.70 (m, 2H), 1.61-1.44 (m, 4H), 0.94 (s, 1H), 0.56-0.45 (m, 2H), 0.19-0.08 (m, 2H), 1 NH exchanged. Second eluted diastereomer: P=97%, retention time=9.7 min, chiral HPLC: P=97.0%, ¹H NMR (300 MHz, CDCl₃) δ 8.44 (s, 1H), 7.80 (d, J=1.5 Hz, 1H), 7.76 (s, 1H), 7.73 (d, J=1.4 Hz, 1H), 7.33-7.26 (m, 1H), 6.92 (d, J=8.0 Hz, 1H), 5.91 (dd, J=8.1, 2.9 Hz, 1H), 5.69 (d, J=2.8 Hz, 1H), 3.88-3.78 (m, 1H), 3.63-3.48 (m, 5H), 3.02-2.81 (m, 2H), 2.73 (s, 1H), 2.56 (d, J=6.9 Hz, 2H), 2.07-1.95 (m, 4H), 1.92 (d, J=6.8 Hz, 3H), 1.84-1.71 (m, 2H), 1.50 (s, 2H), 0.97 (s, 1H), 0.57-0.45 (m, 2H), 0.20-0.10 (m, 2H), 1 NH exchanged.

Compound 227: 4-((R)-3-((cyclopropylmethyl)amino)piperidin-1-yl)-1-(1-(4-(6-(3,3-difluoro pyrrolidin-1-yl)pyrazin-2-yl)-1H-1,2,3-triazol-1-yl)ethyl)pyridin-2(1H)-one was Obtained Using General Scheme 1 Pathway B Stage 1: General Procedure X was used between IM607 and IM151 to afford 4-chloro-1-(1-(4-(6-(3,3-difluoropyrrolidin-1-yl)pyrazin-2-yl)-1H-1,2,3-triazol-1-yl)ethyl)pyridin-2(1H)-one IM642 as a yellow solid: 172 mg, 59% yield, P=96%, retention time=2.6 min (gradient A), (M+H)⁺: 408/410.

Stage 2: General Procedure C was used between IM486 and IM642 to afford tert-butyl (cyclopropylmethyl)((3R)-1-(1-(1-(4-(6-(3,3-difluoropyrrolidin-1-yl)pyrazin-2-yl)-1H-1,2,3-triazol-1-yl)ethyl)-2-oxo-1,2-dihydropyridin-4-yl)piperidin-3-yl)carbamate IM643 as a brown solid: 85 mg, 79% yield, P=96%, retention time=2.9 min (gradient A), (M+H)⁺: 626.

Stage 3: General Procedure A2 was used from IM643 to afford compound 227 as a brown solid: 65 mg, 93% yield, P=98%, retention time=3.2 min (gradient B), (M+H)⁺: 526.

The mixture of diastereomers was further purified by chiral preparative HPLC purification using Chiralpak IA column (5 µm, 20×250 mm). Eluent used: TBME/MeOH/DCM/DEA: 40/40/20/0.1% at flow rate of 20 mL/min. First eluted diastereomer: P=98%, retention time=4.7 min, chiral HPLC: P=100%, ¹H NMR (300 MHz, CDCl₃) δ 8.70 (s, 1H), 8.32 (s, 1H), 7.82 (s, 1H), 7.58 (q, J=6.9 Hz, 1H), 7.44 (d, J=8.1 Hz, 1H), 5.98 (dd, J=8.1, 2.9 Hz, 1H), 5.65 (d, J=2.8 Hz, 1H), 3.96-3.82 (m, 2H), 3.81-3.71 (m, 3H), 3.65-3.55 (m, 1H), 3.00-2.85 (m, 1H), 2.80-2.39 (m, 7H), 2.15 (d, J=7.0 Hz, 3H), 2.03-1.93 (m, 1H), 1.80-1.68 (m, 1H), 1.52 (s, 1H), 0.90 (s, 1H), 0.55-0.45 (m, 2H), 0.17-0.07 (m, 2H), 1 NH exchanged. ¹⁹F NMR (282 MHZ, CDCl₃) δ −97.51−−98.12 (m). Second eluted diastereomer: P=100%, retention time=7.3 min, chiral HPLC: P=100%, ¹H NMR (300 MHz, CDCl₃) δ 8.71 (s, 1H), 8.32 (d, J=2.4 Hz, 1H), 7.83 (s, 1H), 7.57 (q, J=6.8 Hz, 1H), 7.44 (d, J=8.1 Hz, 1H), 5.98 (dd, J=8.1, 2.9 Hz, 1H), 5.66 (d, J=2.9 Hz, 1H), 3.96-3.67 (m, 6H), 3.65-3.55 (m, 1H), 3.00-2.85 (m, 1H), 2.85-2.61 (m, 2H), 2.56-2.43 (m, 5H), 2.15 (d, J=7.0 Hz, 3H), 2.02-1.91 (m, 1H), 1.81-1.70 (m, 1H), 1.53-1.38 (m, 2H), 0.91 (s, 1H), 0.55-0.43 (m, 2H), 0.13-0.04 (m, 2H), 1 NH exchanged. ¹⁹F NMR (282 MHz, CDCl₃) δ −97.78−−98.02 (m).

Compound 228: 4-((R)-3-((cyclopropylmethyl)amino)piperidin-1-yl)-1-(1-(5-(6-(pyrrolidin-1-yl)pyrazin-2-yl)-1,3,4-thiadiazol-2-yl)ethyl)pyridin-2 (1H)-one was Obtained Using General Scheme 3 Pathway B Stage 1: To a solution of IM532 (1.00 g, 5.45 mmol) in dry THF (21.8 mL), under nitrogen, cooled to −78° C., was added dropwise 1 M LiHMDS in THF (6.53 mL, 6.53 mmol) and the resulting mixture was stirred at −78° C. for 30 min. Then tributyltin hydride (2.27 mL, 8.17 mmol) was added dropwise. After the addition, the mixture was allowed to reach rt and stirred at rt for 20 h. The reaction mixture was quenched with saturated NH₄Cl solution (10 mL) and partially concentrated in vacuo (removing some THF). Then it was poured into a separatory funnel, diluted with water (5 mL), and extracted with ethyl acetate. The organic phase was dried with magnesium sulfate, filtered and evaporated under reduced pressure. The oily residue obtained was purified using flash chromatography on C-18 using 0%-100%
MeCN in 10 mM ammonium bicarbonate buffer, and then proceeded from 0% to 100% MeOH in MeCN to afford 2-(pyrrolidin-1-yl)-6-(tributylstannyl)pyrazine IM644: 2.4 g, 100% yield, P=97%, retention time=2.3 min (gradient F), (M+H)⁺: 258.

Stage 2: To a microwave vial, under nitrogen, were successively added triphenylphosphine (78.1 mg, 295 µmol), IM644 (321 mg, 1.36 mmol), IM359 (1.03 g, 2.35 mmol), and dioxane (4.55 mL). The reaction mixture was degassed for 5 min before being sealed and heated to 100° C. for 17 h. The mixture was filtered over Celite. The filtrate was concentrated in vacuo and purified on a C-18 column using 0%-100% MeCN in 10 mM ammonium bicarbonate to afford 2-(1-ethoxyvinyl)-5-(6-(pyrrolidin-1-yl)pyrazin-2-yl)-1,3,4-thiadiazole IM645: 95 mg, 17% yield, P=72%, retention time=1.7 min (gradient F), (M+H)⁺: 304.

Stage 3: To IM645 (95.3 mg, 314 µmol) in acetone (1.57 mL) was added 3 N Hydrochloric acid (1.05 mL, 3.14 mmol). The mixture was stirred at rt for 10.5 h. The mixture was evaporated in vacuo to dryness to afford crude 1-(5-(6-(pyrrolidin-1-yl)pyrazin-2-yl)-1,3,4-thiadiazol-2-yl)ethan-1-one IM646: 87 mg, 54% yield, P=54%, retention time=1.5 min (gradient F), (M+H)⁺: 276.

Stage 4: To a solution of IM646 (116 mg, 422 µmol) in MeOH (8.00 mL), cooled to 0° C., was added sodium borohydride (42.1 mg, 1.07 mmol). The mixture was stirred at rt for 30 min. The mixture was evaporated in vacuo and purified on a C-18 column using 0%-80% MeCN in 10 mM ammonium bicarbonate to afford 1-(5-(6-(pyrrolidin-1-yl)pyrazin-2-yl)-1,3,4-thiadiazol-2-yl)ethan-1-ol IM647: 80 mg, 68% yield, P=100%, retention time=1.1 min (gradient F), (M+H)⁺: 278.

Stage 5: General Procedure P was used from IM647 to afford crude 1-(5-(6-(pyrrolidin-1-yl)pyrazin-2-yl)-1,3,4-thiadiazol-2-yl)ethyl methanesulfonate IM648: 90 mg, 100% yield, P=100%, retention time=1.3 min (gradient F), (M+H)⁺: 356.

Stage 6: To a solution of 4-chloro-2-hydroxypyridine (169 mg, 1.27 mmol) in DMF (1.22 mL) was added potassium carbonate (250 mg, 1.77 mmol) and the reaction mixture was stirred at rt for 10 min, before adding a solution of IM648 (90 mg, 253 µmol) in DMF (1.22 mL). Then the resulting mixture was heated to 50° C. for 2 h. After cooling to rt, the mixture was directly purified by reverse phase chromatography using a gradient of MeCN (0-100%) in 10 mM ammonium bicarbonate solution to afford 4-chloro-1-(1-(5-(6-(pyrrolidin-1-yl)pyrazin-2-yl)-1,3,4-thiadiazol-2-yl)ethyl)pyridin-2(1H)-one IM649 as a brownish solid: 99 mg, 47% yield, P=92%, retention time=1.4 min (gradient C), (M+H)⁺: 389/391.

Stage 7: General Procedure C was used between IM486 and IM649 to afford tert-butyl (cyclopropylmethyl)((3R)-1-(2-oxo-1-(1-(5-(6-(pyrrolidin-1-yl)pyrazin-2-yl)-1,3,4-thiadiazol-2-yl)ethyl)-1,2-dihydropyridin-4-yl)piperidin-3-yl) carbamate IM650 as a yellow solid: 44 mg, 56% yield, P=100%, retention time=1.8 min (gradient F), (M+H)⁺: 607.

Stage 8: General Procedure A2 was used from IM650 to afford compound 228 as a yellow solid: 37 mg, 98% yield, P=98%, retention time=2.2 min (gradient E), (M+H)⁺: 508.

The mixture of diastereomers was further purified by chiral preparative HPLC purification using Chiralpak IA column (5 µm, 20×250 mm). Eluent used: TBME/MeOH/DCM/DEA: 40/40/20/0.1% at flow rate of 20 mL/min. First eluted diastereomer: P=100%, retention time=5.9 min, chiral HPLC: P=100%, ¹H NMR (300 MHz, CDCl₃) δ 8.57 (s, 1H), 7.79 (s, 1H), 7.12-7.07 (m, 1H), 6.53 (q, J=7.2 Hz, 1H), 5.84 (dd, J=8.0, 2.9 Hz, 1H), 5.61 (d, J=2.8 Hz, 1H), 3.73-3.63 (m, 1H), 3.53-3.42 (m, 1H), 3.42-3.32 (m, 4H), 2.86-2.72 (m, 1H), 2.72-2.51 (m, 2H), 2.41 (d, J=6.9 Hz, 2H), 1.90 (q, J=5.0 Hz, 4H), 1.80 (d, J=7.2 Hz, 3H), 1.63 (d, J=13.1 Hz, 1H), 1.36 (s, 3H), 0.82 (s, 1H), 0.43-0.31 (m, 2H), 0.04--0.05 (m, 2H), 1 NH exchanged. Second eluted diastereomer: P=100%, retention time=9.8 min, chiral HPLC: P=100%, ¹H NMR (300 MHz, CDCl₃) δ 8.70 (s, 1H), 7.93 (s, 1H), 7.25-7.22 (m, 1H), 6.66 (q, J=7.2 Hz, 1H), 5.98 (dd, J=8.0, 2.9 Hz, 1H), 5.77 (d, J=2.8 Hz, 1H), 3.92-3.82 (m, 1H), 3.67-3.57 (m, 1H), 3.56-3.45 (m, 4H), 2.91 (q, J=13.6 Hz, 2H), 2.76 (s, 1H), 2.62-2.53 (m, 2H), 2.09-1.97 (m, 4H), 1.94 (d, J=7.2 Hz, 3H), 1.77 (s, 1H), 1.52 (s, 3H), 0.99 (s, OH), 0.56-0.46 (m, 2H), 0.22-0.09 (m, 2H), 1 NH exchanged.

Compound 229: 4-((R)-3-((cyclopropylmethyl)amino)piperidin-1-yl)-1-(1-(4-(6-(dimethyl amino)pyrazin-2-yl)-1H-imidazol-1-yl)ethyl)pyridin-2(1H)-one was Obtained Using General Scheme 4 Pathway C1

Stage 1: To a microwave vial, under nitrogen, were added 6-chloro-N,N-dimethylpyrazin-2-amine (309 mg, 1.96 mmol), dichlorobis(triphenylphosphine) palladium(II) (140.4 mg, 200 µmol), 4-(tributylstannyl)-1-tritylimidazole (1.2 g, 2.00 mmol) and dioxane (6.5 mL). The reaction mixture was degassed for 5 min before being sealed and stirred at 100° C. overnight. The crude mixture was concentrated and purified by silica gel chromatography (hexane/EtOAc: 100/0 to 0/100 and DCM/MeOH 100/0 to 90/10) to afford N,N-dimethyl-6-(1-trityl-1H-imidazol-4-yl)pyrazin-2-amine IM651 as orange oil: 580 mg, 69% yield, P=100%, retention time=1.5 min (gradient C), (M+H)⁺: 433.

Stage 2: To a solution of IM651 (580 mg, 1.34 mmol) in MeOH (10 mL) was added acetic acid (1.92 mL, 33.6 mmol). The reaction mixture was stirred at 75° C. for 4.5 h. The reaction mixture was cooled down to rt and directly loaded on column for purification by reverse chromatography (C18, ammonium Formate 10 mM buffer/ACN 95/5 to 60/40) to afford 6-(1H-imidazol-4-yl)-N,N-dimethylpyrazin-2-amine IM652 as a formate salt: 137 mg, 54% yield, P=100%, retention time=0.5 min (gradient C), (M+H)⁺: 190.

Stage 3: To a solution of IM652 formate (137 mg, 582 µmol) in DMF (1.68 mL) were added potassium carbonate (329 mg, 2.33 mmol), 2 minutes later at 0° C., sodium hydride 60% in dispersion in mineral oil (69.9 mg, 1.75 mmol) and IM150 (559 mg, 2.91 mmol). The resulting mixture was warmed to rt and stirred at rt for 1 h. The reaction mixture was quenched with drops of water and directly loaded on column for purification by reverse chromatography (C18, ammonium bicarbonate 10 mM buffer/ACN: 95/5 to 60/40) to afford 4-chloro-1-(1-(4-(6-(dimethylamino)pyrazin-2-yl)-1H-imidazol-1-yl)ethyl)pyridin-2 (1H)-one IM653: 149 mg, 53% yield, P=72%, retention time=0.8 min (gradient C), (M+H)⁺: 345.

Stage 4: General Procedure C was used between IM486 and IM653 to afford tert-butyl (cyclopropylmethyl)((3R)-1-(1-(1-(4-(6-(dimethylamino)pyrazin-2-yl)-1H-imidazol-1-yl)ethyl)-2-oxo-1,2-dihydropyridin-4-yl)piperidin-3-yl)carbamate IM654 as a tan solid: 104 mg, 59% yield, P=100%, retention time=1.3 min (gradient C), (M+H)⁺: 564.

Stage 5: General Procedure A2 was used from IM654 to afford compound 229 as a tan solid: 86 mg, 38% yield, P=100%, retention time=1.1 min (gradient C), (M+H)⁺: 463.

The mixture of diastereomers was further purified by chiral preparative HPLC purification using Chiralpak IE column (5 µm, 10×250 mm). Eluent used: DCM/MeOH/DEA: 90/10/0.1% at flow rate of 7 mL/min. First eluted diastereomer: P=97%, retention time=6.7 min, chiral HPLC: P=99.2%, ¹H NMR (300 MHZ, CDCl₃) δ 8.43 (s, 1H), 7.90 (s, 1H), 7.83 (d, J=1.5 Hz, 1H), 7.74 (d, J=1.5 Hz, 1H), 7.21 (q, J=7.0 Hz, 1H), 7.12 (d, J=7.9 Hz, 1H), 5.98 (dd, J=8.0, 2.8 Hz, 1H), 5.70 (d, J=2.7 Hz, 1H), 3.93-3.82 (m, 1H), 3.51-3.40 (m, 1H), 3.21-3.11 (m, 7H), 3.11-2.84 (m, 2H), 2.76-2.54 (m, 2H), 2.06-1.91 (m, 4H), 1.87-1.76 (m, 1H), 1.66-1.42 (m, 2H), 1.06 (s, 1H), 0.58-0.49 (m, 2H), 0.28-0.19 (m, 2H), 1 NH exchanged. Second eluted diastereomer: P=97%, retention time=8.2 min, chiral HPLC: P=97.3%, ¹H NMR (300 MHz, CDCl₃) δ 8.48 (s, 1H), 7.92 (s, 1H), 7.85-7.78 (m, 2H), 7.13 (q, J=7.0 Hz, 1H), 6.93 (d, J=8.0 Hz, 1H), 5.88 (d, J=8.1 Hz, 1H), 5.73 (d, J=2.7 Hz, 1H), 4.06 (d, J=13.2 Hz, 1H), 3.54-3.46 (m, 1H), 3.46-3.33 (m, 1H), 3.14 (s, 6H), 3.08-2.99 (m, 2H), 2.90-2.78 (m, 1H), 2.75-2.60 (m, 1H), 2.07 (s, 1H), 1.85 (d, J=7.1 Hz, 4H), 1.56 (d, J=10.8 Hz, 1H), 1.48-1.37 (m, 1H), 1.15 (s, 1H), 0.59 (d, J=7.8 Hz, 2H), 0.35 (d, J=5.1 Hz, 2H), 1 NH exchanged.

Compound 230: 4-((R)-3-((cyclopropylmethyl)amino)piperidin-1-yl)-1-(1-(4-(6-(3,3-dimethylpyrrolidin-1-yl)pyrazin-2-yl)-1H-1,2,3-triazol-1-yl)ethyl)pyridin-2(1H)-one was Obtained Using General Scheme 1 Pathway B Stage 1: General Procedure C (in DMSO) was used between 2,6-dichloropyrazine and 3,3-dimethylpyrrolidine hydrochloride to afford 2-chloro-6-(3,3-dimethylpyrrolidin-1-yl)pyrazine IM655 as orange oil: 289 mg, 80% yield, P=98%, retention time=3.0 min (gradient A), (M+H)$^+$: 212/214.

Stage 2: General Procedure E2 was used from IM655 to afford 2-(3,3-dimethylpyrrolidin-1-yl)-6-((trimethylsilyl)ethynyl)pyrazine IM656 as yellow oil: 244 mg, 62% yield, P=93%, retention time=3.3 min (gradient A), (M+H)$^+$: 274.

Stage 3: General Procedure X was used between IM656 and IM151 to afford 4-chloro-1-(1-(4-(6-(3,3-dimethylpyrrolidin-1-yl)pyrazin-2-yl)-1H-1,2,3-triazol-1-yl)ethyl)pyridin-2(1H)-one IM657 as a yellow solid: 90 mg, 33% yield, P=95%, retention time=2.7 min (gradient A), (M+H)$^+$: 400/402.

Stage 4: General Procedure C was used between IM486 and IM657 to afford tert-butyl (cyclopropylmethyl)((3R)-1-(1-(1-(4-(6-(3,3-dimethylpyrrolidin-1-yl)pyrazin-2-yl)-1H-1,2,3-triazol-1-yl)ethyl)-2-oxo-1,2-dihydropyridin-4-yl)piperidin-3-yl)carbamate IM658 as a brown solid: 53 mg, 73% yield, P=95%, retention time=3.0 min (gradient A), (M+H)$^+$: 618.

Stage 5: General Procedure A2 was used from IM658 to afford compound 230 as an off-white solid: 26 mg, 57% yield, P=90%, retention time=3.4 min (gradient B), (M+H)$^+$: 518.

The mixture of diastereomers was further purified by chiral preparative HPLC purification using Chiralpak IA column (5 μm, 20×250 mm). Eluent used: TBME/MeOH/DCM/DEA: 40/40/20/0.1% at flow rate of 20 ml/min. First eluted diastereomer: P=99%, retention time=5.4 min, chiral HPLC: P=100%, $^1$H NMR (300 MHz, CDCl$_3$) δ 8.55 (s, 1H), 8.30 (s, 1H), 7.77 (s, 1H), 7.58 (q, J=7.0 Hz, 1H), 7.43 (d, J=8.1 Hz, 1H), 5.96 (dd, J=8.1, 2.8 Hz, 1H), 5.65 (d, J=2.7 Hz, 1H), 3.82-3.72 (m, 1H), 3.65-3.51 (m, 3H), 3.27 (s, 2H), 2.98-2.84 (m, 1H), 2.82-2.58 (m, 2H), 2.53-2.45 (m, 2H), 2.14 (d, J=7.0 Hz, 3H), 2.03-1.93 (m, 1H), 1.84-1.70 (m, 3H), 1.57-1.34 (m, 2H), 1.15 (s, 6H), 0.97-0.87 (m, 1H), 0.54-0.42 (m, 2H), 0.15-0.07 (m, 2H), 1 NH exchanged. Second eluted diastereomer: P=99%, retention time=8.5 min, chiral HPLC: P=100%, $^1$H NMR (300 MHz, CDCl$_3$) δ 8.55 (s, 1H), 8.30 (s, 1H), 7.77 (s, 1H), 7.58 (q, J=6.9 Hz, 1H), 7.43 (d, J=8.1 Hz, 1H), 5.97 (dd, J=8.1, 2.8 Hz, 1H), 5.66 (d, J=2.8 Hz, 1H), 3.88-3.78 (m, 1H), 3.65-3.51 (m, 3H), 3.27 (s, 2H), 2.99-2.62 (m, 3H), 2.54 (d, J=6.9 Hz, 2H), 2.14 (d, J=7.0 Hz, 3H), 2.05-1.92 (m, 1H), 1.87-1.71 (m, 3H), 1.49 (s, 2H), 1.15 (s, 6H), 0.98-0.89 (m, 1H), 0.56-0.43 (m, 2H), 0.16-0.08 (m, 2H), 1 NH exchanged.

Compound 231: 4-((R)-3-((cyclopopylmethyl)amino)piperidin-1-yl)-1-(1-(5-(6-(dimethyl amino)pyrazin-2-yl)-1,3,4-thiadiazol-2-yl)ethyl)pyridin-2(1H)-one was Obtained Using General Scheme 3 Pathway B Stage 1: To a solution of IM488 (500 mg, 3.17 mmol) in dry THF (12.7 mL), under nitrogen, cooled to −78° C., was added dropwise lithium bis(trimethylsilyl)amide solution (3.81 mL, 3.81 mmol) (1M solution in THF) and the resulting mixture was stirred at −78° C. for 30 min. Then tributyltin hydride (132 μL, 476 μmol) was slowly added dropwise. After the addition completed, dry ice bath was replaced by an ice bath. Mixture was allowed to reach slowly rt, then was stirred at rt overnight. Mixture was quenched with 1 mL of water then was concentrated under reduced pressure. Oily crude residue was purified by silica gel chromatography (dry load) using a gradient of MeOH (0-5%) in DCM to afford N,N-dimethyl-6-(tributylstannyl)pyrazin-2-amine IM659 as a pale yellow oil: 860 mg, 53% yield, P=81%, retention time=2.5 min (gradient C), (M+H)$^+$: 410/412/414.

Stage 2: To a microwave vial, under nitrogen, were successively added IM359 (50 mg, 213 μmol), IM659 (131 mg, 319 μmol), dichlorobis(triphenylphosphine) palladium (II) (7.6 mg, 10.6 μmol) and dioxane (709 μL). The reaction mixture was degassed for 5 min before being sealed and heated to 100° C. After cooling to rt, reaction mixture was directly loaded onto a C-18 cartridge and purified by reverse phase chromatography using a gradient of MeCN (0-100%) in 10 mM ammonium bicarbonate buffer to afford 6-(5-(1-ethoxyvinyl)-1,3,4-thiadiazol-2-yl)-N,N-dimethylpyrazin-2-amine IM660 as a yellow solid: 36 mg, 58% yield, P=95%, retention time=1.5 min (gradient C), (M+H)$^+$: 278.

Stage 3: To a suspension of IM660 (114 mg, 411 μmol) in acetone (2.1 mL) was added hydrochloric acid (2.06 mL, 6.17 mmol) (3 N in water) and the reaction was stirred at rt for 1 h. The mixture was concentrated down to remove acetone and water (co-evaporated with EtOH) to afford crude 1-(5-(6-(dimethylamino)pyrazin-2-yl)-1,3,4-thiadiazol-2-yl)ethan-1-one IM661.

Stage 4: IM661 (102 mg, 411 μmol) was dissolved in MeOH (2.07 mL) and cooled down to 0° C., sodium borohydride (79.3 mg, 2.06 mmol) was added to the mixture and stirred at 0° C. for 15 min. The mixture was quenched with saturated NH$_4$Cl solution and was directly purified by C18 column (0-100% MeCN in ammonium bicarbonate) to afford 1-(5-(6-(dimethylamino)pyrazin-2-yl)-1,3,4-thiadiazol-2-yl)ethan-1-ol IM662 as a yellow solid: 73 mg, 71% yield, P=100%, retention time=1.0 min (gradient C), (M+H)$^+$: 252.

Stage 5: General Procedure P was used from IM662 to afford crude 1-(5-(6-(dimethylamino)pyrazin-2-yl)-1,3,4-thiadiazol-2-yl)ethyl methanesulfonate IM663 as yellow oil: 96 mg, 100% yield, P=100%, retention time=1.2 min (gradient C), (M+H)$^+$: 330.

Stage 6: To a solution of 4-chloro-2-hydroxypyridine (195 mg, 1.46 mmol) in DMF (1.40 mL) was added potassium carbonate (288 mg, 2.04 mmol) and the reaction mixture was stirred at rt for 10 min before adding a solution of IM663 (96.0 mg, 291 μmol) in DMF (1.40 mL). Then the resulting mixture was heated to 50° C. for 1.5 h. After cooling to rt, the mixture was directly purified by reverse phase chromatography using a gradient of MeCN (0-100%) in 10 mM ammonium bicarbonate solution to afford 4-chloro-1-(1-(5-(6-(dimethylamino)pyrazin-2-yl)-1,3,4-thiadiazol-2-yl)ethyl)pyridin-2(1H)-one IM664 as a yellow solid: 67 mg, 63% yield, P=100%, retention time=1.3 min (gradient C), (M+H)$^+$: 363/365.

Stage 7: General Procedure C was used between IM486 and IM664 to afford tert-butyl (cyclopropylmethyl)((3R)-1-(1-(1-(5-(6-(dimethylamino)pyrazin-2-yl)-1,3,4-thiadiazol-2-yl) ethyl)-2-oxo-1,2-dihydropyridin-4-yl)piperidin-3-yl) carbamate IM665 as a yellow solid: 55 mg, 49% yield, P=95%, retention time=1.7 min (gradient F), (M+H)$^+$: 581.

Stage 8: General Procedure A2 was used from IM665 to afford compound 231 as a pale yellow solid: 35 mg, 76% yield, P=97%, retention time=2.0 min (gradient E), (M+H)$^+$: 481.

The mixture of diastereomers was further purified by chiral preparative HPLC purification using Chiralpak IA column (5 μm, 20×250 mm). Eluent used: TBME/MeOH/DCM/DEA: 40/40/20/0.1% at flow rate of 20 ml/min. First eluted diastereomer: P=100%, retention time=5.1 min, chiral HPLC: P=100%, $^1$H NMR (300 MHz, CDCl$_3$) δ 8.72 (s, 1H), 8.08 (s, 1H), 7.23 (s, 1H), 6.66 (q, J=7.2 Hz, 1H), 5.96

(dd, J=8.0, 2.9 Hz, 1H), 5.73 (d, J=2.8 Hz, 1H), 3.82-3.72 (m, 1H), 3.65-3.55 (m, 1H), 3.13 (s, 6H), 3.00-2.84 (m, 1H), 2.82-2.59 (m, 2H), 2.59-2.47 (m, 2H), 1.93 (d, J=7.2 Hz, 3H), 1.81-1.72 (m, 2H), 1.60-1.35 (m, 2H), 1.00-0.82 (m, 1H), 0.54-0.42 (m, 2H), 0.16-0.07 (m, 2H), 1 NH exchanged. Second eluted diastereomer: P=100%, retention time=12.1 min, chiral HPLC: P=99.3%, $^1$H NMR (300 MHz, CDCl$_3$) δ 8.71 (s, 1H), 8.08 (s, 1H), 7.24 (s, 1H), 6.64 (q, J=7.1 Hz, 1H), 5.98 (dd, J=8.0, 2.9 Hz, 1H), 5.75 (d, J=2.8 Hz, 1H), 3.90-3.80 (m, 1H), 3.66-3.55 (m, 1H), 3.13 (s, 6H), 3.00-2.66 (m, 3H), 2.56 (d, J=6.9 Hz, 2H), 2.05-1.96 (m, 1H), 1.93 (d, J=7.1 Hz, 3H), 1.83-1.71 (m, 1H), 1.51 (s, 2H), 1.05-0.92 (m, 1H), 0.56-0.44 (m, 2H), 0.20-0.10 (m, 2H), 1 NH exchanged.

Compound 232: 4-((R)-3-((cyclopropylmethyl) amino)piperidin-1-yl)-1-(1-(4-(5-methoxy pyridin-3-yl)-1H-1,2,3-triazol-1-yl)ethyl)pyridin-2(1H)-one was Obtained Using General Scheme 1 Pathway B Stage 1: General Procedure C was used between IM486 and IM169 to afford tert-butyl (cyclopropylmethyl)((3R)-1-(1-(1-(4-(5-methoxypyridin-3-yl)-1H-1,2,3-triazol-1-yl) ethyl)-2-oxo-1,2-dihydropyridin-4-yl)piperidin-3-yl)carbamate IM666 as a white foam: 135 mg, 73% yield, P=100%, retention time=2.3 min (gradient A), (M+H)$^+$: 550.

Stage 2: General Procedure A1 was used from IM666 to afford compound 232 as colourless sticky film: 110 mg, 99% yield, P=99%, retention time=2.0 min (gradient B), (M+H)$^+$: 450.

The mixture of diastereomers was further purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=100%, retention time=6.2 min, chiral HPLC: P=100%, $^1$H NMR (300 MHz, CDCl$_3$) δ 8.57 (d, J=1.7 Hz, 1H), 8.25 (d, J=2.8 Hz, 1H), 8.15 (s, 1H), 7.72-7.65 (m, 1H), 7.53 (q, J=7.0 Hz, 1H), 7.41 (d, J=8.1 Hz, 1H), 5.98 (dd, J=8.1, 2.8 Hz, 1H), 5.64 (d, J=2.8 Hz, 1H), 3.89 (s, 3H), 3.80-3.70 (m, 1H), 3.64-3.54 (m, 1H), 2.99-2.84 (m, 1H), 2.81-2.40 (m, 4H), 2.16 (d, J=7.0 Hz, 3H), 2.03-1.92 (m, 1H), 1.80-1.67 (m, 1H), 1.59-1.44 (m, 1H), 1.40-1.26 (m, 1H), 0.93-0.83 (m, 1H), 0.53-0.41 (m, 2H), 0.15-0.03 (m, 2H), 1 NH exchanged. Second eluted diastereomer: P=100%, retention time=10.9 min, chiral HPLC: P=100%, $^1$H NMR (300 MHz, CDCl$_3$) δ 8.56 (d, J=1.7 Hz, 1H), 8.24 (d, J=2.8 Hz, 1H), 8.16 (s, 1H), 7.68 (d, J=2.3 Hz, 1H), 7.53 (q, J=7.0 Hz, 1H), 7.41 (d, J=8.0 Hz, 1H), 5.98 (dd, J=8.2, 2.8 Hz, 1H), 5.64 (d, J=2.8 Hz, 1H), 3.88 (s, 3H), 3.81-3.71 (m, 1H), 3.64-3.52 (m, 1H), 2.99-2.84 (m, 1H), 2.82-2.57 (m, 2H), 2.51-2.41 (m, 2H), 2.15 (d, J=7.0 Hz, 3H), 2.02-1.91 (m, 1H), 1.80-1.67 (m, 1H), 1.61-1.31 (m, 2H), 0.97-0.80 (m, 1H), 0.52-0.40 (m, 2H), 0.13-0.01 (m, 2H), 1 NH exchanged.

Compound 233: 4-((R)-3-((cyclopropylmethyl) amino)piperidin-1-yl)-1-(1-(2-(6-(pyrrolidin-1-yl) pyrazin-2-yl)thiazol-5-yl)ethyl)pyridin-2(1H)-one was Obtained Using General Scheme 3 Pathway B Stage 1: A 50 mL round bottom flask was charged with bis(pinacolato)diboron (1.6 g, 6.3 mmol), potassium acetate (1.4 g, 14.12 mmol), palladium(II) acetate (142 mg, 0.61 mmol), tricyclohexylphosphine (327 mg, 1.13 mmol), and 2-chloro-6-pyrrolidin-1-yl-pyrazine (1.14 g, 5.71 mmol). Dry 1,4-dioxane (29 mL) was added and the reaction mixture was heated at 110° C. under nitrogen atmosphere for 16 h. The reaction mixture was cooled to rt, diluted with EtOAc (50 mL) and filtered through Celite®, then concentrated under reduced pressure to afford 3.17 g of crude 2-(pyrrolidin-1-yl)-6-(4,4,5,5-tetramethyl-1,3,2-dioxaborolan-2-yl) pyrazine IM667 as black oil: 3.17 g, 99% yield, P=49% ($^1$H-NMR).

Stage 1': To a solution of 2-chlorothiazole (3.6 mL, 41.31 mmol) in dry THF (60 mL) at −78° C. was added n-butyl lithium in hexane (15.6 mL, 39 mmol) dropwise over 1 min. After 30 min acetaldehyde (2 mL, 35.46 mmol) was added dropwise over 0.5 min at −78° C. The resulting solution was stirred for 5 min at −78° C. and then slowly warmed to rt over 25 min (dry ice/acetone bath removed). The reaction mixture was quenched with a saturated aqueous solution of NH$_4$Cl (200 mL) and extracted with EtOAc (3×200 mL). The organic layers were merged, dried over MgSO$_4$, filtered and concentrated under reduced pressure to dryness. The crude material was purified by an automated flash chromatography system (liquid injection with toluene, 0 to 50% EtOAc in Heptane) to afford 1-(2-chlorothiazol-5-yl)ethan-1-ol IM668 as light yellow oil: 5.48 g, 94% yield, P=100%, retention time=2.2 min (gradient A), (M+H)$^+$: 164.

Stage 2: In a round bottom flask were added IM667 (2.94 g, 5.34 mmol), IM668 (547 mg, 3.34 mmol), tetrakis(triphenylphosphine)palladium(0) (395 mg, 0.33 mmol). The vial was evacuated under vacuum and backfilled with argon (3×), then dry and degassed THF (30 mL) was added, followed by potassium carbonate (4.6 mL, 9.2 mmol). The resultant solution was stirred for 16 h at 80° C. The solution was cooled to rt and filtered through a pad of Celite (washing with EtOAc 50 mL) into a flask containing anhydrous magnesium sulfate. The solution was dried for 10 min and filtered through cotton wool and the solvent was removed under reduced pressure to afford the crude product. The crude material was purified by an automated flash chromatography system (dryload in silica, 0 to 10% MeOH in DCM) to afford 1-(2-(6-(pyrrolidin-1-yl)pyrazin-2-yl)thiazol-5-yl)ethan-1-ol IM669 as an orange solid: 300 mg, 30% yield, P=92%, retention time=2.5 min (gradient A), (M+H)$^+$: 277.

Stage 3: General Procedure T was modified: In a solution of IM669 (300 mg, 1 mmol) in dry toluene (10 mL) at 0° C. was added triphenylphosphine (419 mg, 1.6 mmol), 4-chloro-2-hydroxypyridine (213.4 mg, 1.6 mmol) and tetrabutylammonium iodide (376.4 mg, 1 mmol) and stirred for 5 min. Diisopropylazodicarboxylate (269 μL, 1.3 mmol) was added dropwise to the reaction mixture at 0° C. and allowed to warm slowly to rt over 15 h. The reaction mixture was concentrated under reduced pressure to dryness. The crude material was purified by an automated flash chromatography system (dryload in celite, 0 to 10% MeOH in DCM) to afford 4-chloro-1-(1-(2-(6-(pyrrolidin-1-yl)pyrazin-2-yl)thiazol-5-yl)ethyl)pyridin-2(1H)-one IM670: 416 mg, 48% yield, P=45%, retention time=2.8 min (gradient A), (M+H)$^+$: 388/390.

Stage 4: General Procedure C was used between IM486 and IM670 to afford tert-butyl (cyclopropylmethyl)((3R)-1-(2-oxo-1-(1-(2-(6-(pyrrolidin-1-yl)pyrazin-2-yl)thiazol-5-yl)ethyl)-1,2-dihydropyridin-4-yl)piperidin-3-yl)carbamate IM671 as yellow oil: 57 mg, 15% yield, P=78%, retention time=3.0 min (gradient A), (M+H)$^+$: 606.

Stage 5: General Procedure A2 was used from IM671 to afford crude compound 233 as a yellowish glass: 40 mg, 92% yield, P=85%, retention time=2.3 min (gradient A), (M+H)$^+$: 506.

The product was purified by reverse phase preparative HPLC purification (Waters XBridge C18 5 μm, 19×100 mm). Gradient used: increased linearly from 20 to 50% solution "B" over 4.0 min, increased linearly to 85% solution "B" over 2.3 min, and returned to initial conditions over 1.0 min. Flow Rate: 15 mL/min. P=100%. The mixture of diastereomers was further purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=93%, retention time=5.5 min, chiral HPLC: P=100%, $^1$H NMR (300 MHz, CDCl$_3$) δ 8.57 (s, 1H), 7.89 (s, 1H), 7.79 (s, 1H), 7.02 (d, J=7.9 Hz, 1H), 6.60 (q, J=6.9 Hz, 1H), 5.93 (dd, J=8.0, 2.9 Hz, 1H), 5.77 (d, J=2.8 Hz, 1H), 3.87-3.77 (m, 1H), 3.66-3.48 (m, 5H), 2.99-2.85 (m, 1H), 2.72 (s, 2H), 2.59-2.51 (m, 2H), 2.10-2.00 (m, 4H), 1.77 (d, J=7.1 Hz, 3H), 1.51 (s, 4H), 0.96 (s, 1H), 0.55-0.45 (m, 2H), 0.21-0.11 (m, 2H), 1 NH exchanged with solvent. Second eluted diastereomer: P=100%, retention time=6.4 min, chiral HPLC: P=99.4%, $^1$H NMR (300 MHz, CDCl$_3$) δ 8.57 (s, 1H), 7.88 (s, 1H), 7.78 (s, 1H), 7.03 (d, J=7.9 Hz, 1H), 6.58 (q, J=7.1 Hz, 1H), 5.95 (dd, J=8.0, 2.9 Hz, 1H), 5.78 (d, J=2.8 Hz, 1H), 3.93-3.83 (m, 1H), 3.65-3.56 (m, 1H), 3.56-3.47 (m, 4H), 3.00-2.82 (m, 2H), 2.78 (s, 1H), 2.63-2.54 (m, 2H), 2.07-2.01 (m, 4H), 1.81-1.73 (m, 3H), 1.53 (s, 4H), 1.00 (s, 1H), 0.59-0.47 (m, 2H), 0.26-0.14 (m, 2H), 1 NH exchanged with solvent.

Compound 234: 1-(1-(4-(6-(3-azabicyclo[3.1.0]hexan-3-yl)pyrazin-2-yl)-1H-1,2,3-triazol-1-yl)ethyl)-4-((R)-3-((cyclopropylmethyl)amino)piperidin-1-yl)pyridin-2(1H)-one was Obtained Using General Scheme 1 Pathway B Stage 1: General Procedure X was used between IM610 and IM151 to afford 1-(1-(4-(6-(3-azabicyclo[3.1.0]hexan-3-yl)pyrazin-2-yl)-1H-1,2,3-triazol-1-yl)ethyl)-4-chloropyridin-2(1H)-one IM672 as a yellow solid: 150 mg, 72% yield, P=95%, retention time=2.6 min (gradient A), (M+H)$^+$: 384/386.

Stage 2: General Procedure C was used between IM486 and IM672 to afford tert-butyl ((3R)-1-(1-(1-(4-(6-(3-azabicyclo[3.1.0]hexan-3-yl)pyrazin-2-yl)-1H-1,2,3-triazol-1-yl)ethyl)-2-oxo-1,2-dihydropyridin-4-yl)piperidin-3-yl)(cyclopropylmethyl)carbamate IM673 as a brown solid: 68 mg, 75% yield, P=99%, retention time=2.9 min (gradient A), (M+H)$^+$: 602.

Stage 3: General Procedure A2 was used from IM673 to afford crude compound 234 as a brown solid: 48 mg, 85% yield, P=99%, retention time=2.2 min (gradient A), (M+H)$^+$: 502.

The mixture of diastereomers was purified by chiral preparative HPLC purification using Chiralpak IA column (5 μm, 20×250 mm). Eluent used: TBME/MeOH/DCM/DEA: 40/40/20/0.1% at flow rate of 20 ml/min. First eluted diastereomer: P=100%, retention time=4.3 min, chiral HPLC: P=100%, $^1$H NMR (300 MHz, CDCl$_3$) δ 8.58 (s, 1H), 8.29 (s, 1H), 7.76 (s, 1H), 7.58 (q, J=7.0 Hz, 1H), 7.43 (d, J=8.0 Hz, 1H), 5.96 (dd, J=8.2, 2.8 Hz, 1H), 5.65 (d, J=2.8 Hz, 1H), 3.81-3.71 (m, 3H), 3.65-3.55 (m, 1H), 3.52-3.42 (m, 2H), 2.99-2.84 (m, 1H), 2.80-2.68 (m, 1H), 2.68-2.58 (m, 1H), 2.58-2.41 (m, 2H), 2.14 (d, J=7.0 Hz, 3H), 2.04-1.92 (m, 1H), 1.79-1.32 (m, 5H), 0.97-0.84 (m, 1H), 0.84-0.71 (m, 1H), 0.54-0.42 (m, 2H), 0.30-0.19 (m, 1H), 0.14-0.07 (m, 2H), 1 NH exchanged. Second eluted diastereomer: P=100%, retention time=10.0 min, chiral HPLC: P=100%, $^1$H NMR (300 MHz, CDCl$_3$) δ 8.58 (s, 1H), 8.29 (s, 1H), 7.77 (s, 1H), 7.58 (q, J=7.0 Hz, 1H), 7.43 (d, J=8.1 Hz, 1H), 5.97 (dd, J=8.1, 2.8 Hz, 1H), 5.66 (d, J=2.8 Hz, 1H), 3.85-3.71 (m, 3H), 3.66-3.55 (m, 1H), 3.52-3.42 (m, 2H), 3.00-2.86 (m, 1H), 2.85-2.72 (m, 1H), 2.68 (s, 1H), 2.57-2.48 (m, 2H), 2.14 (d, J=7.0 Hz, 3H), 1.99 (d, J=12.3 Hz, 1H), 1.86-1.38 (m, 5H), 0.93 (s, 1H), 0.78 (q, J=7.7 Hz, 1H), 0.55-0.43 (m, 2H), 0.25 (q, J=4.4 Hz, 1H), 0.15-0.08 (m, 2H), 1 NH exchanged.

Compound 235: 1-(1-(4-(6-(5-azaspiro[2.4]heptan-5-yl)pyrazin-2-yl)-1H-1,2,3-triazol-1-yl)ethyl)-4-((R)-3-((cyclopropylmethyl)amino)piperidin-1-yl)pyridin-2(1H)-one was Obtained Using General Scheme 1 Pathway B Stage 1: General Procedure X was used between IM627 and IM151 to afford 1-(1-(4-(6-(5-azaspiro[2.4]heptan-5-yl)pyrazin-2-yl)-1H-1,2,3-triazol-1-yl)ethyl)-4-chloropyridin-2(1H)-one IM674 as a yellow solid: 94 mg, 43% yield, P=99%, retention time=2.7 min (gradient A), (M+H)$^+$: 398/400.

Stage 2: General Procedure C was used between IM486 and IM674 to afford tert-butyl ((3R)-1-(1-(1-(4-(6-(5-azaspiro[2.4]heptan-5-yl)pyrazin-2-yl)-1H-1,2,3-triazol-1-yl)ethyl)-2-oxo-1,2-dihydropyridin-4-yl)piperidin-3-yl)(cyclopropylmethyl)carbamate IM675 as a brown solid: 54 mg, 75% yield, P=96%, retention time=2.9 min (gradient A), (M+H)$^+$: 616.

Stage 3: General Procedure A2 was used from IM675 to afford crude compound 235 as an off-white solid: 29 mg, 65% yield, P=97%, retention time=3.3 min (gradient A), (M+H)$^+$: 516.

The mixture of diastereomers was purified by chiral preparative HPLC purification using Chiralpak IA column (5 μm, 20×250 mm). Eluent used: TBME/MeOH/DCM/DEA: 40/40/20/0.1% at flow $^1$H NMR (300 MHZ, CDCl$_3$) δ 8.58 (s, 1H), 8.29 (s, 1H), 7.78 (s, 1H), 7.59 (q, J=7.0 Hz, 1H), 7.43 (d, J=8.0 Hz, 1H), 5.97 (dd, J=8.1, 2.9 Hz, 1H), 5.65 (d, J=2.8 Hz, 1H), 3.81-3.72 (m, 1H), 3.72-3.55 (m, 3H), 3.41 (s, 2H), 2.98-2.84 (m, 1H), 2.80-2.57 (m, 2H), 2.56-2.46 (m, 2H), 2.14 (d, J=7.0 Hz, 3H), 2.02-1.89 (m, 3H), 1.61-1.32 (m, 3H), 0.95-0.86 (m, 1H), 0.74-0.60 (m, 4H), 0.55-0.43 (m, 2H), 0.15-0.06 (m, 2H), 1 NH exchanged. Second eluted diastereomer: P=99%, retention time=6.7 min, chiral HPLC: P=100%, $^1$H NMR (300 MHz, CDCl$_3$) δ 8.57 (s, 1H), 8.29 (d, J=2.2 Hz, 1H), 7.78 (s, 1H), 7.58 (q, J=7.0 Hz, 1H), 7.43 (d, J=8.2 Hz, 1H), 5.97 (dd, J=8.1, 2.9 Hz, 1H), 5.65 (d, J=2.8 Hz, 1H), 3.82-3.72 (m, 1H), 3.72-3.55 (m, 3H), 3.41 (s, 2H), 3.00-2.85 (m, 1H), 2.82-2.59 (m, 2H), 2.55-2.46 (m, 2H), 2.14 (d, J=7.1 Hz, 3H), 1.95 (t, J=6.8 Hz, 2H), 1.82-1.29 (m, 4H), 0.97-0.82 (m, 1H), 0.74-0.60 (m, 4H), 0.54-0.42 (m, 2H), 0.16-0.03 (m, 2H), 1 NH exchanged.

Compound 236: 4-((R)-3-((cyclopropylmethyl)amino)piperidin-1-yl)-1-(1-(4-(5-(methyl (trifluoromethyl)amino)pyridin-3-yl)-1H-1,2,3-triazol-1-yl)ethyl)pyridin-2(1H)-one was Obtained Using General Scheme 1 Pathway B Stage 1: General Procedure Y was used between IM524 and N,O-dimethylhydroxylamine hydrochloride to afford tert-butyl (cyclopropylmethyl)((3R)-1-(1-(1-(4-(5-(methylamino) pyridin-3-yl)-1H-1,2,3-triazol-1-yl)ethyl)-2-oxo-1,2-dihydropyridin-4-yl)piperidin-3-yl)carbamate IM676 as colourless gum: 141 mg, 67% yield, P=88%, retention time=2.5 min (gradient A), (M+H)$^+$: 549.

Stage 2: Tetramethylammonium (trifluoromethyl)sulfanide (52 mg, 0.30 mmol) was added to a solution of IM676 (141 mg, 0.23 mmol) in dry DCM (2.2 mL). The mixture was stirred at rt for 15 min at which point silver fluoride (100 mg, 0.79 mmol) was added. The mixture was then stirred at 50° C. for 6 h. The reaction mixture was concentrated under reduced pressure. The crude material was purified by an automated flash chromatography system (dryload in Celite, 0 to 10% MeOH in DCM) to afford tert-butyl (cyclopropylmethyl)((3R)-1-(1-(1-(4-(5-(methyl(trifluoromethyl)amino)pyridin-3-yl)-1H-1,2,3-triazol-1-yl)ethyl)-2-oxo-1,2-dihydro pyridin-4-yl)piperidin-3-yl)carbamate IM677 as black oil: 127 mg, 56% yield, P=62%, retention time=2.8 min (gradient A), (M+H)$^+$: 617.

Stage 3: General Procedure A2 was used from IM677 to afford crude compound 236 as light grey oil: 98 mg, 50% yield, P=54%, retention time=2.2 min (gradient B), (M+H)$^+$: 517.

The product was purified by reverse phase preparative HPLC purification (Waters XBridge C18 5 μm, 19×100 mm). Gradient used: increased linearly from 20 to 50% solution "B" over 4.0 min, increased linearly to 85% solution "B" over 2.3 min, and returned to initial conditions over 1.0 min. Flow Rate: 15 mL/min. P=100%.

The mixture of diastereomers was further purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=99%, retention time=6.1 min, chiral HPLC: P=98.3%, $^1$H NMR (300 MHz, CDCl$_3$) δ 8.85 (d, J=1.9 Hz, 1H), 8.49 (d, J=2.5 Hz, 1H), 8.20 (s, 1H), 8.04 (t, J=2.2 Hz, 1H), 7.54 (q, J=7.0 Hz, 1H), 7.43 (d, J=8.1 Hz, 1H), 5.99 (dd, J=8.2, 2.9 Hz, 1H), 5.66 (d, J=2.8 Hz, 1H), 3.83-3.73 (m, 1H), 3.65-3.55 (m, 1H), 3.15-3.08 (m, 3H), 3.01-2.86 (m, 1H), 2.85-2.72 (m, 1H), 2.72-2.60 (m, 1H), 2.56-2.47 (m, 2H), 2.17 (d, J=7.0 Hz, 3H), 2.04-1.93 (m, 1H), 1.81-1.73 (m, 1H), 1.60-1.48 (m, 2H), 0.98-0.88 (m, 1H), 0.55-0.43 (m, 2H), 0.17-0.09 (m, 2H), 1H exchanged with solvent. $^{19}$F NMR (282 MHZ, CDCl$_3$) δ −57.47. Second eluted diastereomer: P=96%, retention time=6.7 min, chiral HPLC: P=99.2%, $^1$H NMR (300 MHz, CDCl$_3$) δ 8.85 (d, J=1.9 Hz, 1H), 8.48 (d, J=2.5 Hz, 1H), 8.22 (s, 1H), 8.04 (d, J=2.4 Hz, 1H), 7.54 (q, J=7.0 Hz, 1H), 7.44 (d, J=8.1 Hz, 1H), 6.00 (dd, J=8.1, 2.9 Hz, 1H), 5.66 (d, J=2.8 Hz, 1H), 3.86-3.75 (m, 1H), 3.65-3.55 (m, 1H), 3.11 (s, 3H), 3.00-2.86 (m, 1H), 2.86-2.74 (m, 1H), 2.68 (s, 1H), 2.57-2.48 (m, 2H), 2.17 (d, J=7.0 Hz, 3H), 2.04-1.94 (m, 1H), 1.82-1.71 (m, 1H), 1.60-1.38 (m, 2H), 0.94-0.88 (m, 1H), 0.55-0.43 (m, 2H), 0.17-0.09 (m, 2H), 1H exchanged with solvent. $^{19}$F NMR (282 MHZ, CDCl$_3$) δ −57.48.

Compound 237: 1-(1-(4-(6-(2-oxa-6-azaspiro[3.3]heptan-6-yl)pyrazin-2-yl)-1H-1,2,3-triazol-1-yl)ethyl)-4-((R)-3-((cyclopropylmethyl)amino)piperidin-1-yl)pyridin-2(1H)-one was Obtained Using General Scheme 1 Pathway B Stage 1: General Procedure C (in DMSO) was used between 2,6-dichloropyrazine and 2-Oxa-6-azaspiro[3.3]heptane to afford 6-(6-chloropyrazin-2-yl)-2-oxa-6-azaspiro[3.3]heptane IM678 as a white solid: 326 mg, 91% yield, P=99%, retention time=2.8 min (gradient A), (M+H)$^+$: 212/214.

Stage 2: General Procedure E2 was used from IM678 to afford 6-(6-(((trimethylsilyl)ethynyl)pyrazin-2-yl)-2-oxa-6-azaspiro[3.3]heptane IM679 as a dark brown solid: 416 mg, 93% yield, P=93%, retention time=2.8 min (gradient A), (M+H)$^+$: 274.

Stage 3: General Procedure X was used between IM679 and IM151 to afford 1-(1-(4-(6-(2-oxa-6-azaspiro[3.3]heptan-6-yl)pyrazin-2-yl)-1H-1,2,3-triazol-1-yl)ethyl)-4-chloropyridin-2(1H)-one IM680 as yellow oil: 140 mg, 62% yield, P=91%, retention time=2.4 min (gradient A), (M+H)$^+$: 400/402.

Stage 4: General Procedure C was used between IM486 and IM680 to afford tert-butyl ((3R)-1-(1-(1-(4-(6-(3-(chloromethyl)-3-(hydroxymethyl)azetidin-1-yl)pyrazin-2-yl)-1H-1,2,3-triazol-1-yl)ethyl)-2-oxo-1,2-dihydropyridin-4-yl)piperidin-3-yl)(cyclopropylmethyl)carbamate IM681 as brown oil: 65 mg, 59% yield, P=94%, retention time=2.8 min (gradient A), (M+H)$^+$: 654/656.

Stage 5: IM681 (55 mg, 0.08 mmol) was dissolved into anhydrous THF (0.3 mL), and mixture was cooled to 0° C. Then, potassium tert-butoxide in THF solution (1 N, 125 μL, 0.125 mmol) was added. Mixture was stirred at 0° C. for 10 min, then stirred at rt. After 1 h at rt, an extra addition of potassium tert-butoxide in THF solution (1 N, 125 μL, 0.125 mmol) was added to the reaction mixture. 45 min after addition of TBuOK in THF, potassium tert-butoxide (9 mg, 0.08 mmol) was added to the reaction mixture. 2.5 h later, a second addition of potassium tert-butoxide (9 mg, 0.08 mmol) was added to the reaction mixture. After 16 h, an extra addition of potassium tert-butoxide (18 mg, 0.16 mmol) was added to the reaction mixture. 5 h later, anhydrous DMF (0.5 mL) was added to the reaction mixture, which was heated to 60° C. for 22 h. The reaction mixture was cooled to rt, diluted with EtOAc (20 mL) and filtered on celite pad. The solid was rinsed-off with EtOAc (2×10 mL), and DCM/MeOH (2×10 mL, 3/1 v/v). Filtrate was concentrated under reduced pressure and crude material was purified by an automated flash chromatography system (dryload in Celite, 0 to 100% MeOH in DCM) to afford tert-butyl ((3R)-1-(1-(1-(4-(6-(2-oxa-6-azaspiro[3.3]heptan-6-yl)pyrazin-2-yl)-1H-1,2,3-triazol-1-yl)ethyl)-2-oxo-1,2-dihydropyridin-4-yl)piperidin-3-yl)(cyclopropylmethyl) carbamate IM682 as a yellow solid: 46 mg, 44% yield, P=47%, retention time=2.7 min (gradient A), (M+H)$^+$: 618.

Stage 6: General Procedure A2 was used from IM682 to afford crude compound 237 as green oil: 22 mg, 45% yield, P=37%, retention time=2.1 min (gradient A), (M+H)$^+$: 518.

The product was purified by reverse phase preparative HPLC purification (Waters XBridge C18 5 μm, 19×100 mm). Gradient used: increased linearly from 20 to 50% solution "B" over 4.0 min, increased linearly to 85% solution "B" over 2.3 min, and returned to initial conditions over 1.0 min. Flow Rate: 15 mL/min. P=100%.

The mixture of diastereomers was further purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=100%, retention time=6.8 min, chiral HPLC: P=100%, $^1$H NMR (300 MHz, CDCl$_3$) δ 8.68 (s, 1H), 8.32 (s, 1H), 7.72 (s, 1H), 7.56 (t, J=7.1 Hz, 1H), 7.44 (d, J=8.1 Hz, 1H), 6.00 (dd, J=8.2, 2.8 Hz, 1H), 5.68 (d, J=2.8 Hz, 1H), 4.86 (s, 4H), 4.26 (s, 4H), 3.93-3.83 (m, 1H), 3.67-3.56 (m, 1H), 3.06-2.88 (m, 2H), 2.76 (s, 1H), 2.62-2.54 (m, 2H), 2.15 (d, J=7.0 Hz, 3H), 2.06-1.43 (m, 4H), 0.99 (s, 1H), 0.59-0.49 (m, 2H), 0.23-0.15 (m, 2H), 1 NH exchanged. Second eluted diastereomer: P=100%, retention time=9.1 min, chiral HPLC: P=100%, $^1$H NMR (300 MHZ, CDCl$_3$) δ 8.67 (s, 1H), 8.32 (s, 1H), 7.72 (s, 1H), 7.55 (q, J=6.9 Hz, 1H), 7.44 (d, J=8.1 Hz, 1H), 6.00 (dd, J=8.1, 2.8 Hz, 1H), 5.69 (d, J=2.7 Hz, 1H), 4.86 (s, 4H), 4.26 (s, 4H), 4.05-3.90 (m, 1H), 3.65-3.55 (m, 1H), 3.15-2.75 (m, 3H), 2.63 (d, J=7.0 Hz, 2H), 2.16 (d, J=7.1 Hz, 3H), 2.07-1.39 (m, 4H), 0.87 (d, J=8.3 Hz, 1H), 0.56 (d, J=7.9 Hz, 2H), 0.24 (s, 2H), 1 NH exchanged.

Compound 238: 4-((R)-3-((cyclopropylmethyl)amino)piperidin-1-yl)-1-(1-(4-(6-((R)-3-methylpyrrolidin-1-yl)pyrazin-2-yl)-1H-1,2,3-triazol-1-ylethyl)pyridin-2(1H)-one was Obtained Using General Scheme 1 Pathway B Stage 1: General Procedure C (in DMSO) was used between 2,6-dichloropyrazine and (3R)-3-methylpyrrolidine hydrochloride to afford (R)-2-chloro-6-(3-methylpyrrolidin-1-yl)pyrazine IM683 as yellow oil: 256 mg, 48% yield, P=62%, retention time=2.9 min (gradient A), (M+H)$^+$: 198/200.

Stage 2: General Procedure E2 was used from IM683 to afford (R)-2-(3-methylpyrrolidin-1-yl)-6-((trimethylsilyl)ethynyl)pyrazine IM684 as yellow oil: 120 mg, 47% yield, P=82%, retention time=3.2 min (gradient A), (M+H)$^+$: 260.

Stage 3: General Procedure X was used between IM684 and IM151 to afford 4-chloro-1-(1-(4-(6-((R)-3-methylpyrrolidin-1-yl)pyrazin-2-yl)-1H-1,2,3-triazol-1-yl)ethyl)pyridin-2(1H)-one IM685 as a yellow solid: 44 mg, 64% yield, P=99%, retention time=2.6 min (gradient A), (M+H)$^+$: 386/388.

Stage 4: General Procedure C was used between IM486 and IM685 to afford tert-butyl (cyclopropylmethyl)((3R)-1-(1-(1-(4-(6-((R)-3-methylpyrrolidin-1-yl)pyrazin-2-yl)-1H-1,2,3-triazol-1-yl)ethyl)-2-oxo-1,2-dihydropyridin-4-yl)piperidin-3-yl)carbamate IM686 as a yellow solid: 47 mg, 70% yield, P=97%, retention time=2.9 min (gradient A), (M+H)$^+$: 604.

Stage 5: General Procedure A2 was used from IM686 to afford crude compound 238 as a yellow solid: 34 mg, 89% yield, P=100%, retention time=3.2 min (gradient B), (M+H)$^+$: 504.

The mixture of diastereomers was purified by chiral preparative HPLC purification using Chiralpak IA column (5 µm, 20×250 mm). Eluent used: TBME/MeOH/DCM/DEA: 40/40/20/0.1% at flow rate of 20 mL/min. First eluted diastereomer: P=100%, retention time=5.1 min, chiral HPLC: P=100%, $^1$H NMR (300 MHz, CDCl$_3$) δ 8.55 (s, 1H), 8.31 (s, 1H), 7.78 (s, 1H), 7.59 (q, J=7.0 Hz, 1H), 7.44 (d, J=8.0 Hz, 1H), 5.97 (dd, J=8.1, 2.8 Hz, 1H), 5.65 (d, J=2.8 Hz, 1H), 3.83-3.56 (m, 4H), 3.52-3.40 (m, 1H), 3.08-2.97 (m, 1H), 2.97-2.84 (m, 1H), 2.81-2.68 (m, 1H), 2.63 (s, 1H), 2.55-2.33 (m, 3H), 2.21-2.08 (m, 4H), 2.03-1.95 (m, 1H), 1.83-1.33 (m, 4H), 1.14 (d, J=6.6 Hz, 3H), 0.92 (s, 1H), 0.55-0.43 (m, 2H), 0.17-0.09 (m, 2H), 1 NH exchanged. Second eluted diastereomer: P=100%, retention time=9.0 min, chiral HPLC: P=100%, $^1$H NMR (300 MHz, CDCl$_3$) δ 8.55 (s, 1H), 8.31 (s, 1H), 7.77 (s, 1H), 7.59 (q, J=7.0 Hz, 1H), 7.44 (d, J=8.0 Hz, 1H), 5.97 (dd, J=8.1, 2.8 Hz, 1H), 5.65 (d, J=2.8 Hz, 1H), 3.86-3.76 (m, 1H), 3.75-3.55 (m, 3H), 3.51-3.36 (m, 1H), 3.08-2.85 (m, 2H), 2.84-2.59 (m, 2H), 2.55-2.47 (m, 2H), 2.47-2.30 (m, 1H), 2.22-2.07 (m, 4H), 1.99 (d, J=11.8 Hz, 1H), 1.81-1.26 (m, 4H), 1.14 (d, J=6.6 Hz, 3H), 0.98-0.87 (m, 1H), 0.54-0.42 (m, 2H), 0.18-0.07 (m, 2H), 1 NH exchanged.

Compound 239: (R)-3-(5-(3-((cyclobutylmethyl)amino)piperidin-1-yl)pyridin-2-yl)-N-(4-oxo-4H-pyrido[1,2-a]pyrimidin-2-yl)oxetane-3-carboxamide was Obtained Using General Scheme 6 Pathway B Stage 1: General Procedure Y was used between IM520 and IM3 to afford tert-butyl (R)-(1-(6-(3-cyanooxetan-3-yl)pyridin-3-yl)piperidin-3-yl)(cyclobutylmethyl)carbamate IM687 as colourless oil: 440 mg, 97% yield, P=92%, retention time=3.2 min (gradient A), (M+H)$^+$: 427.

Stage 2: To a vial equipped with a stir bar was added IM687 (440 mg, 0.97 mmol), sodium hydroxide (158 mg, 3.91 mmol), ethanol (3.3 mL) and water (1.7 mL). The vial was sealed and heated to 80° C. for 1 h. The crude reaction mixture was concentrated under reduced pressure. The residue was dissolved in water (10 mL) and EtOAc (15 mL), and 10 mL of 1 N HCl (aqueous) was added dropwise to adjust the pH ~2. Phases were separated and aqueous phase was extracted with EtOAc (2×10 mL). The combined organic phases were dried over magnesium sulfate, filtered, and concentrated under reduced pressure to afford crude (R)-3-(5-(3-((tert-butoxycarbonyl)(cyclobutylmethyl)amino)piperidin-1-yl)pyridin-2-yl)oxetane-3-carboxylic acid IM688 as a white solid: 400 mg, 91% yield, P=98%, retention time=2.6 min (gradient A), (M+H)$^+$: 446.

Stage 3: General Procedure F was used between IM688 and IM613 to afford tert-butyl (R)-(cyclobutylmethyl)(1-(6-(3-((4-oxo-4H-pyrido[1,2-a]pyrimidin-2-yl)carbamoyl)oxetan-3-yl)pyridin-3-yl)piperidin-3-yl)carbamate IM689 as yellow oil: 23 mg, 27% yield, P=78%, retention time=2.8 min (gradient A), (M+H)$^+$: 589.

Stage 4: General Procedure A2 was used from IM689 to afford crude compound 239 as colourless oil: 9 mg, 50% yield, P=85%, retention time=2.1 min (gradient A), (M+H)$^+$: 489.

The product was purified by reverse phase preparative HPLC purification (Waters XBridge C18 5 µm, 19×100 mm). Gradient used: increased linearly from 20 to 44% solution "B" over 4.2 min, increased linearly to 90% solution "B" over 0.5 min, held to 90% solution "B" over 0.5 min, and returned to initial conditions over 0.5 min. Flow Rate: 20 ml/min. P=100%. $^1$H NMR (300 MHz, CDCl$_3$) δ 8.98 (s, 1H), 8.90 (d, J=7.2 Hz, 1H), 8.32 (d, J=2.6 Hz, 1H), 7.65-7.53 (m, 1H), 7.38-7.28 (m, 2H), 7.17-7.07 (m, 2H), 6.95 (t, J=6.9 Hz, 1H), 5.29 (d, J=6.1 Hz, 2H), 4.97 (d, J=6.0 Hz, 2H), 3.66-3.54 (m, 1H), 3.50-3.40 (m, 1H), 2.90-2.75 (m, 1H), 2.73-2.56 (m, 4H), 2.38 (hept, J=7.5 Hz, 1H), 2.10-1.70 (m, 6H), 1.60 (dt, J=10.7, 8.0 Hz, 3H), 1.26 (q, J=13.7 Hz, 1H), 1 NH exchanged with solvent.

Compound 240: 4-((R)-3-((cyclopropylmethyl)amino)piperidin-1-yl)-1-(1-(4-(6-((S)-3-methylpyrrolidin-1-yl)pyrazin-2-yl)-1H-1,2,3-triazol-1-ylethyl)pyridin-2(1H)-one was Obtained Using General Scheme 1 Pathway B Stage 1: General Procedure C (in DMSO) was used between 2,6-dichloropyrazine and (3S)-3-methylpyrrolidine hydrochloride to afford (S)-2-chloro-6-(3-methylpyrrolidin-1-yl)pyrazine IM690 as yellow oil: 278 mg, 67% yield, P=80%, retention time=2.8 min (gradient A), (M+H)$^+$: 198/200.

Stage 2: General Procedure E2 was used from IM690 to afford (S)-2-(3-methylpyrrolidin-1-yl)-6-((trimethylsilyl)ethynyl)pyrazine IM691 as yellow oil: 242 mg, 80% yield, P=97%, retention time=3.2 min (gradient A), (M+H)$^+$: 260.

Stage 3: General Procedure X was used between IM690 and IM151 to afford 4-chloro-1-(1-(4-(6-((S)-3-methylpyrrolidin-1-yl)pyrazin-2-yl)-1H-1,2,3-triazol-1-yl)ethyl)pyridin-2(1H)-one IM692 as a yellow solid: 103 mg, 71% yield, P=100%, retention time=2.6 min (gradient A), (M+H)$^+$: 386/388.

Stage 4: General Procedure C was used between IM486 and IM692 to afford tert-butyl (cyclopropylmethyl)((3R)-1-(1-(1-(4-(6-((S)-3-methylpyrrolidin-1-yl)pyrazin-2-yl)-1H-1,2,3-triazol-1-yl)ethyl)-2-oxo-1,2-dihydropyridin-4-yl)piperidin-3-yl)carbamate IM693 as a yellow solid: 79 mg, 33% yield, P=33%, retention time=2.9 min (gradient A), (M+H)+: 604. (Main side product was compound 240: 79 mg, 37% yield, P=37%, retention time=2.2 min (gradient A), (M+H)+: 504).

Stage 5: General Procedure A2 was used from mixture IM693/compound 240 to afford compound 240 as yellow oil: 19 mg, 80% yield, P=91%, retention time=2.8 min (gradient B), (M+H)+: 504.

The mixture of diastereomers was further purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=100%, retention time=4.8 min, chiral HPLC: P=100%, $^1$H NMR (300 MHz, CDCl$_3$) δ 8.55 (s, 1H), 8.31 (s, 1H), 7.78 (s, 1H), 7.63-7.52 (m, 1H), 7.44 (d, J=8.0 Hz, 1H), 5.97 (d, J=8.1 Hz, 1H), 5.65 (s, 1H), 3.85-3.75 (m, 1H), 3.70 (s, 1H), 3.66-3.56 (m, 2H), 3.51-3.36 (m, 1H), 3.08-2.97 (m, 1H), 2.97-2.84 (m, 1H), 2.84-2.70 (m, 1H), 2.65 (s, 1H), 2.55-2.47 (m, 2H), 2.44-2.33 (m, 1H), 2.21-2.10 (m, 4H), 2.04-1.91 (m, 1H), 1.81-1.35 (m, 4H), 1.14 (d, J=6.6 Hz, 3H), 0.93 (s, 1H), 0.53-0.43 (m, 2H), 0.19-0.07 (m, 2H), 1 NH exchanged. Second eluted diastereomer: P=96%, retention time=8.0 min, chiral HPLC: P=96.7%, $^1$H NMR (300 MHz, CDCl$_3$) δ 8.55 (s, 1H), 8.31 (s, 1H), 7.78 (s, 1H), 7.59 (q, J=7.1 Hz, 1H), 7.44 (d, J=8.1 Hz, 1H), 5.98 (dd, J=8.2, 2.8 Hz, 1H), 5.66 (d, J=2.8 Hz, 1H), 3.87-3.77 (m, 1H), 3.74-3.55 (m, 3H), 3.51-3.37 (m, 1H), 3.08-2.98 (m, 1H), 2.98-2.85 (m, 1H), 2.85-2.72 (m, 1H), 2.68 (s, 1H), 2.52 (d, J=7.0 Hz, 2H), 2.46-2.33 (m, 1H), 2.14 (d, J=7.2 Hz, 4H), 2.05-1.95 (m, 1H), 1.81-1.36 (m, 4H), 1.14 (d, J=6.6 Hz, 3H), 0.94 (s, 1H), 0.55-0.43 (m, 2H), 0.21-0.09 (m, 2H), 1 NH exchanged.

Compound 241: 4-((R)-3-((cyclopropylmethyl) amino)piperidin-1-yl)-1-(1-(4-(6-((S)-3-fluoro pyrrolidin-1-yl)pyrazin-2-yl)-1H-1,2,3-triazol-1-yl)ethyl) pyridin-2(1H)-one was Obtained Using General Scheme 1 Pathway B Stage 1: General Procedure C (in DMSO) was used between 2,6-dichloropyrazine and (3S)-3-fluoropyrrolidine hydrochloride to afford (S)-2-chloro-6-(3-fluoropyrrolidin-1-yl)pyrazine IM694 as pink oil: 332 mg, 91% yield, P=93%, retention time=2.6 min (gradient A), (M+H)+: 202/204.

Stage 2: General Procedure E2 was used from IM694 to afford (S)-2-(3-fluoropyrrolidin-1-yl)-6-((trimethylsilyl) ethynyl)pyrazine IM695 as yellow oil: 296 mg, 69% yield, P=94%, retention time=3.0 min (gradient A), (M+H)+: 264.

Stage 3: General Procedure X was used between IM695 and IM151 to afford 4-chloro-1-(1-(4-(6-((S)-3-fluoropyrrolidin-1-yl)pyrazin-2-yl)-1H-1,2,3-triazol-1-yl)ethyl)pyridin-2(1H)-one IM696 as a yellow solid: 162 mg, 72% yield, P=93%, retention time=2.2 min (gradient A), (M+H)+: 390/392.

Stage 4: General Procedure C was used between IM486 and IM696 to afford tert-butyl (cyclopropylmethyl)((3R)-1-(1-(1-(4-(6-((S)-3-fluoropyrrolidin-1-yl)pyrazin-2-yl)-1H-1,2,3-triazol-1-yl)ethyl)-2-oxo-1,2-dihydropyridin-4-yl)piperidin-3-yl)carbamate IM697 as brown oil: 97 mg, 50% yield, P=45%, retention time=2.8 min (gradient A), (M+H)+: 608. (Main side product was compound 241: 97 mg, 49% yield, P=37%, retention time=2.1 min (gradient A), (M+H)+: 508).

Stage 5: General Procedure A2 was used from mixture IM697/compound 241 to afford compound 241 as an off-white solid: 36 mg, 76% yield, P=90%, retention time=3.0 min (gradient B), (M+H)+: 508.

The mixture of diastereomers was further purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=100%, retention time=5.1 min, chiral HPLC: P=100%, $^1$H NMR (300 MHz, CDCl$_3$) δ 8.62 (s, 1H), 8.32 (s, 1H), 7.83 (s, 1H), 7.58 (q, J=6.9 Hz, 1H), 7.44 (d, J=8.0 Hz, 1H), 5.98 (dd, J=8.1, 2.8 Hz, 1H), 5.66 (d, J=2.8 Hz, 1H), 5.39 (dt, J=52.6, 3.7 Hz, 1H), 4.00-3.54 (m, 6H), 2.99-2.85 (m, 1H), 2.85-2.73 (m, 1H), 2.72-2.60 (m, 1H), 2.56-2.48 (m, 2H), 2.46-2.33 (m, 1H), 2.27-2.10 (m, 4H), 2.02-1.94 (m, 1H), 1.81-1.69 (m, 1H), 1.58-1.36 (m, 2H), 0.99-0.88 (m, 1H), 0.55-0.43 (m, 2H), 0.19-0.09 (m, 2H), 1 NH exchanged. $^{19}$F NMR (282 MHZ, CDCl$_3$) δ −173.06−−174.23 (m). Second eluted diastereomer: P=99%, retention time=8.0 min, chiral HPLC: P=98.9%, $^1$H NMR (300 MHz, CDCl$_3$) δ 8.63 (s, 1H), 8.33 (s, 1H), 7.84 (s, 1H), 7.59 (q, J=7.0 Hz, 1H), 7.46 (d, J=8.1 Hz, 1H), 5.98 (dd, J=8.0, 2.8 Hz, 1H), 5.66 (d, J=2.7 Hz, 1H), 5.40 (d, J=52.4 Hz, 1H), 4.00-3.78 (m, 2H), 3.78-3.56 (m, 4H), 2.86 (dt, J=35.7, 11.8 Hz, 2H), 2.68 (s, 1H), 2.52 (d, J=7.0 Hz, 2H), 2.43 (s, 1H), 2.15 (d, J=7.0 Hz, 4H), 1.99 (d, J=12.8 Hz, 1H), 1.75 (d, J=11.7 Hz, 1H), 1.56-1.37 (m, 2H), 0.94 (s, 1H), 0.50 (dd, J=8.8, 4.3 Hz, 2H), 0.13 (t, J=4.9 Hz, 2H), 1 NH exchanged. 19F NMR (282 MHz, CDCl$_3$) δ −173.21−−173.99 (m).

Compound 242: 4-((R)-3-((cyclopropylmethyl) amino)piperidin-1-yl)-1-(1-(2-(6-(pyrrolidin-1-yl) pyrazin-2-yl)oxazol-5-yl)ethyl)pyridin-2(1H)-one was Obtained Using the Following Procedures Stage 1: In a microwave vial (20 mL), were placed IM644 (1.28 g, 2.93 mmol), ethyl 2-bromooxazole-5-carboxylate (665 mg, 2.93 mmol), and dioxane (10 mL). The solution was purged with N$_2$ for 5 min, PdCl$_2$(PPh$_3$)$_2$ (210 mg, 293 μmol) was added, nitrogen was bubbled for another 3 min, the vial was sealed and the reaction was stirred at 100° C. for 20 h. The reaction mixture was cooled down to rt and concentrated under reduced pressure. The product was purified by a silica column (100 g, 0-50% EtOAc in hexanes), and then by a C18 column (40 g, 0-100% MeCN in 10 mM ammonium bicarbonate) to afford ethyl 2-(6-(pyrrolidin-1-yl)pyrazin-2-yl)oxazole-5-carboxylate IM698 as a yellow solid: 152 mg, 16% yield, P=87%, retention time=1.4 min (gradient C), (M+H)+: 289.

Stage 2: To a suspension of IM698 (152 mg, 459 μmol) in THF (1 mL)/MeOH (1 mL) was added a solution of lithium hydroxide monohydate (60.8 mg, 1.38 mmol) in H$_2$O (1 mL) and the mixture was stirred at rt for 30 min. The mixture was concentrated down and directly purified by the C18 column (40 g, 0-100% MeCN in 10 mM ammonium bicarbonate) to afford 2-(6-(pyrrolidin-1-yl)pyrazin-2-yl)oxazole-5-carboxylic acid IM699 as a yellow solid: 119 mg, 100% yield, P=100%, retention time=0.7 min (gradient C), (M+H)+: 261.

Stage 3: To a suspension of IM699 (119 mg, 457 μmol) and N,O-dimethylhydroxylamine hydrochloride (112 mg, 1.14 mmol) in DMF (915 μL) was added DIEA (402 μL, 2.29 mmol). HATU (538 mg, 1.37 mmol) was added to the reaction portion-wise and the mixture was stirred at rt for 10 min. The mixture was directly purified by the C18 column (40 g, 0-100% MeCN in 10 mM ammonium bicarbonate) to afford N-methoxy-2-(6-(pyrrolidin-1-yl)pyrazin-2-yl)oxazole-5-carboxamide IM700 as a yellow solid: 133 mg, 96% yield, P=100%, retention time=1.1 min (gradient C), (M+H)+: 304.

Stage 4: General Procedure Q was used from IM700 to afford 1-(2-(6-(pyrrolidin-1-yl)pyrazin-2-yl)oxazol-5-yl) ethan-1-one IM701 directly used for the reduction step: retention time=1.1 min (gradient C), (M+H)+: 259.

Stage 5: To the crude mixture IM701 was added MeOH (4.5 mL). The reaction mixture was cooled down to 0° C. and sodium borohydride (102 mg, 2.63 mmol) was added portion-wise. The mixture was stirred for 5 min, concentrated down, and directly purified by the C18 column (25 g, 0-100% MeCN in 10 mM ammonium bicarbonate) to afford 1-(2-(6-(pyrrolidin-1-yl)pyrazin-2-yl)oxazol-5-yl)ethan-1-ol IM702 as yellow film: 64 mg, 55% yield (over 2 steps), P=97%, retention time=1.0 min (gradient C), (M+H)+: 261.

Stage 6: General Procedure T was used between 4-chloropyridin-2-ol and IM702 to afford 4-chloro-1-(1-(2-(6-(pyrrolidin-1-yl)pyrazin-2-yl)oxazol-5-yl)ethyl)pyridin-2(1H)-one IM703 as a yellow film: 16 mg, 18% yield, P=98%, retention time=1.3 min (gradient C), (M+H)+: 372/374.

Stage 7: General Procedure C was used between IM486 and IM703 to afford tert-butyl (cyclopropylmethyl)((3R)-1-(2-oxo-1-(1-(2-(6-(pyrrolidin-1-yl)pyrazin-2-yl)oxazol-5-yl)ethyl)-1,2-dihydropyridin-4-yl)piperidin-3-yl)carbamate IM704 as yellow film: 14 mg, 55% yield, P=98%, retention time=1.7 min (gradient C), (M+H)+: 590.

Stage 8: General Procedure A2 was used from IM704 to afford compound 242 as a light yellow powder: 11 mg, 90% yield, P=98%, retention time=2.3 min (gradient E), (M+H)+: 490.

The mixture of diastereomers was further purified by chiral preparative HPLC purification using Chiralpak IE column (5 µm, 10×250 mm). Eluent used: TBME/MeOH/DCM/DEA: 45/45/10/0.1% at flow rate of 7 mL/min. First eluted diastereomer: P=100%, retention time=9.1 min, chiral HPLC: P=99.2%, $^1$H NMR (300 MHz, CDCl$_3$) δ 8.42 (s, 1H), 7.92 (s, 1H), 7.23 (d, J=1.1 Hz, 1H), 7.03 (d, J=7.9 Hz, 1H), 6.46 (q, J=6.9 Hz, 1H), 5.94 (dd, J=8.1, 2.8 Hz, 1H), 5.79 (d, J=2.7 Hz, 1H), 3.94-3.84 (m, 1H), 3.68-3.52 (m, 5H), 3.00-2.86 (m, 2H), 2.80-2.74 (m, 1H), 2.62-2.54 (m, 2H), 2.09-1.99 (m, 5H), 1.76 (s, 1H), 1.69 (d, J=7.1 Hz, 3H), 1.63-1.20 (m, 2H), 1.08-0.92 (m, 1H), 0.58-0.48 (m, 2H), 0.22-0.15 (m, 2H). 1 NH exchanged with solvent. Second eluted diastereomer: P=100%, retention time=10.4 min, chiral HPLC: P=97.5%, $^1$H NMR (300 MHz, CDCl$_3$) δ 8.43 (s, 1H), 7.92 (s, 1H), 7.23 (d, J=1.0 Hz, 1H), 7.04 (d, J=7.9 Hz, 1H), 6.44 (q, J=7.0 Hz, 1H), 5.97 (dd, J=8.0, 2.8 Hz, 1H), 5.84 (s, 1H), 4.13-3.95 (m, 1H), 3.72-3.61 (m, 1H), 3.60-3.52 (m, 4H), 3.16-2.78 (m, 2H), 2.79-2.56 (m, 2H), 2.09-1.99 (m, 5H), 1.87-1.76 (m, 1H), 1.70 (d, J=7.1 Hz, 3H), 1.64-1.50 (m, 2H), 1.29 (s, 1H), 1.10 (s, 1H), 0.61-0.53 (m, 2H), 0.33-0.18 (m, 2H), 1 NH exchanged with solvent.

Compound 243: 4-((R)-3-((cyclopropylmethyl)amino)piperidin-1-yl)-1-(1-(4-(5-(dimethyl amino)pyridazin-3-yl)-1H-imidazol-1-yl)ethyl)pyridin-2(1H)-one was Obtained Using General Scheme 4 pathway C1

Stage 1: To a microwave vial, under nitrogen, were added 6-chloro-N,N-dimethylpyridazin-4-amine (208 mg, 1.32 mmol), dichlorobis(triphenylphosphine) palladium(II) (95 mg, 132 µmol), 4-(tributylstannyl)-1-tritylimidazole (792 mg, 1.32 mmol) and dioxane (4.4 mL). The reaction mixture was degassed for 5 min before being sealed and stirred at 100° C. for 22 h. The crude mixture was concentrated and purified by normal phase chromatography (silica gel, DCM/MeOH: 100/0 to 90/10) to afford N,N-dimethyl-6-(1-trityl-1H-imidazol-4-yl)pyridazin-4-amine IM705 as an orange solid: 201 mg, 35% yield, P=100%, retention time=1.3 min (gradient C), (M+H)+: 433.

Stage 2: To a solution of IM705 (201 mg, 424 µmol) in MeOH (7.3 mL) was added acetic acid (607 µL, 10.6 mmol). The reaction mixture was stirred at 75° C. for 16 h. The reaction mixture was cooled down to rt and 25 other equivalents of acetic acid were added. The reaction mixture was stirred at 75° C. for 4 h. The reaction mixture was cooled down to rt and 25 other equivalents of acetic acid were added. The reaction mixture was stirred at 75° C. for 20 h. The reaction mixture was cooled down to rt and 25 other equivalents of acetic acid were added. The reaction mixture was stirred at 75° C. for 4 h. The reaction was cooled down and directly loaded on column for purification by reverse chromatography (C18, 10 mM ammonium formate buffer/CAN: 95/5 to 70/30) to afford 6-(1H-imidazol-4-yl)-N,N-dimethylpyridazin-4-amine IM706 as a formate salt: 56 mg, 70% yield, P=100%, retention time=0.4 min (gradient C), (M+H)+: 190.

Stage 3: To a solution of IM706 formate salt (56 mg, 238 µmol) in DMF (453 µL), cooled to 0° C., were added potassium carbonate (134 mg, 952 µmol), and then 2 min later sodium hydride 60% in dispersion in mineral oil (29 mg, 714 µmol). The reaction mixture was stirred at 0° C. for 5 min before the addition of IM150 (229 mg, 1.2 mmol). The resulting mixture was warmed to rt and stirred at rt for 1.5 h. The reaction mixture was cooled to 0° C. and 3 eq of sodium hydride was added. The resulting mixture was warmed to rt and stirred for 1.5 h. The reaction mixture was cooled to 0° C. and 2 eq of sodium hydride was added. The resulting mixture was warmed to rt and stirred for 30 min. The crude reaction mixture was directly loaded on column for purification by reverse chromatography (C18, ammonium bicarbonate 10 mM buffer/ACN: 100/0 to 60/40) to afford 4-chloro-1-(1-(4-(5-(dimethylamino)pyridazin-3-yl)-1H-imidazol-1-yl)ethyl)pyridin-2(1H)-one IM707: 82 mg, 47% yield, P=73%, retention time=0.7 min (gradient C), (M+H)+: 345.

Stage 4: General Procedure C was used between IM486 and IM707 to afford tert-butyl (cyclopropylmethyl)((3R)-1-(1-(1-(4-(5-(dimethylamino)pyridazin-3-yl)-1H-imidazol-1-yl)ethyl)-2-oxo-1,2-dihydropyridin-4-yl)piperidin-3-yl)carbamate IM708 as a brown gum: 64 mg, 83% yield, P=82%, retention time=1.1 min (gradient C), (M+H)+: 564.

Stage 5: General Procedure A2 was used from IM708 to afford compound 243 as a tan solid: 5 mg, 10% yield, P=100%, retention time=1.4 min (gradient E), (M+H)+: 464.

The mixture of diastereomers was further purified by chiral preparative HPLC purification using Chiralpak IE column (5 µm, 10×250 mm). Eluent used: TBME/MeOH/DCM/DEA: 45/45/10/0.1% at flow rate of 7 mL/min. First eluted diastereomer: P=98%, retention time=13.9 min, chiral HPLC: P=100%, $^1$H NMR (300 MHz, CDCl$_3$) δ 8.60 (s, 1H), 8.09 (s, 1H), 7.85 (s, 1H), 7.39-7.30 (m, 1H), 7.23 (s, 1H), 7.14 (d, J=8.0 Hz, 1H), 5.91 (d, J=8.0 Hz, 1H), 5.67 (s, 1H), 3.86-3.76 (m, 1H), 3.65-3.55 (m, 1H), 3.11 (s, 6H), 3.00-2.86 (m, 1H), 2.72 (s, 1H), 2.60-2.52 (m, 2H), 2.07-1.91 (m, 4H), 1.76 (s, 2H), 1.60-1.22 (m, 2H), 1.05-0.93 (m, 1H), 0.54-0.45 (m, 2H), 0.18-0.11 (m, 2H), 1 NH exchanged. Second eluted diastereomer: P=100%, retention time=18.7 min, chiral HPLC: P=99.5%, $^1$H NMR (300 MHz, CDCl$_3$) δ 8.59 (d, J=3.1 Hz, 1H), 8.10 (s, 1H), 7.86 (s, 1H), 7.41-7.29 (m, 2H), 7.23 (d, J=2.7 Hz, 1H), 5.98 (d, J=8.1 Hz, 1H), 5.68 (d, J=2.7 Hz, 1H), 4.01-3.75 (m, 1H), 3.68-3.53 (m, 1H), 3.11 (s, 6H), 3.01-2.74 (m, 3H), 2.65-2.55 (m, 2H), 2.08-1.94 (m, 4H), 1.81-1.69 (m, 1H), 1.60-1.22 (m, 2H), 1.00 (s, 1H), 0.54-0.44 (m, 2H), 0.25-0.12 (m, 2H), 1 NH exchanged.

Compound 244: (R)—N-(cyclopropylmethyl)-1-(6-(3-(4-(6-((R)-3-methylpyrrolidin-1-yl) pyrazin-2-yl)-1H-1,2,3-triazol-1-yl)oxetan-3-yl)pyridin-3-yl)piperidin-3-amine was Obtained Using General Scheme 1 Pathway A Stage 1: General Procedure X was used between IM684 and IM543 to afford tert-butyl (cyclopropylmethyl)((R)-1-(6-(3-(4-(6-((R)-3-methylpyrrolidin-1-yl)pyrazin-2-yl)-1H-1,2,3-triazol-1-yl)oxetan-3-yl)pyridin-3-yl)piperidin-3-yl) carbamate IM709 as a yellow solid: 81 mg, 72% yield, P=98%, retention time=2.6 min (gradient A), (M+H)$^+$: 616.

Stage 2: General Procedure A2 was used from IM709 to afford compound 244 as a yellow solid: 50 mg, 74% yield, P=98%, retention time=3.3 min (gradient B), (M+H)$^+$: 516.

$^1$H NMR (300 MHz, CDCl$_3$) δ 8.63 (s, 1H), 8.34 (d, J=3.0 Hz, 1H), 8.05 (d, J=0.9 Hz, 1H), 7.81 (s, 1H), 7.11 (dd, J=8.7, 3.0 Hz, 1H), 6.84 (d, J=8.7 Hz, 1H), 5.54 (d, J=6.8 Hz, 2H), 5.50 (d, J=6.8 Hz, 2H), 3.75-3.59 (m, 3H), 3.56-3.41 (m, 2H), 3.03 (dd, J=10.3, 7.7 Hz, 1H), 2.98-2.82 (m, 1H), 2.82-2.64 (m, 2H), 2.59-2.48 (m, 2H), 2.44-2.33 (m, 1H), 2.20-2.08 (m, 1H), 2.01-1.90 (m, 1H), 1.87-1.77 (m, 1H), 1.73-1.59 (m, 2H), 1.35 (d, J=10.6 Hz, 2H), 1.15 (d, J=6.6 Hz, 3H), 1.00-0.89 (m, 1H), 0.54-0.46 (m, 2H), 0.17-0.06 (m, 2H), 1 NH exchanged with solvent.

Compound 245: 4-((R)-3-((cyclopropylmethyl)amino)piperidin-1-yl)-1-(1-(4-(6-((R)-3-fluoro pyrrolidin-1-yl)pyrazin-2-yl)-1H-1,2,3-triazol-1-ylethyl) pyridin-2(1H)-one was Obtained Using General Scheme 1 Pathway B Stage 1: General Procedure C (in DMSO) was used between 2,6-dichloropyrazine and (3R)-3-fluoropyrrolidine hydrochloride to afford (R)-2-chloro-6-(3-fluoropyrrolidin-1-yl)pyrazine IM710 as yellow oil: 400 mg, 86% yield, P=73%, retention time=2.6 min (gradient A), (M+H)$^+$: 202/204.

Stage 2: General Procedure E2 was used from IM710 to afford (R)-2-(3-fluoropyrrolidin-1-yl)-6-((trimethylsilyl) ethynyl)pyrazine IM711 as light brown oil: 300 mg, 76% yield, P=97%, retention time=3.0 min (gradient A), (M+H)$^+$: 264.

Stage 3: General Procedure X was used between IM711 and IM151 to afford 4-chloro-1-(1-(4-(6-((R)-3-fluoropyrrolidin-1-yl)pyrazin-2-yl)-1H-1,2,3-triazol-1-yl)ethyl)pyridin-2(1H)-one IM712 as a white solid: 194 mg, 88% yield, P=98%, retention time=2.5 min (gradient A), (M+H)$^+$: 390/392.

Stage 4: General Procedure C was used between IM486 and IM712 to afford tert-butyl (cyclopropylmethyl)((3R)-1-(1-(1-(4-(6-((R)-3-fluoropyrrolidin-1-yl)pyrazin-2-yl)-1H-1,2,3-triazol-1-yl)ethyl)-2-oxo-1,2-dihydropyridin-4-yl)piperidin-3-yl)carbamate IM713 as brown oil: 100 mg, 79% yield, P=98%, retention time=2.8 min (gradient A), (M+H)$^+$: 608.

Stage 5: General Procedure A2 was used from IM713 to afford compound 245 as a brown solid: 70 mg, 84% yield, P=98%, retention time=3.0 min (gradient B), (M+H)$^+$: 508.

The mixture of diastereomers was further purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=100%, retention time=5.8 min, chiral HPLC: P=100%, $^1$H NMR (300 MHz, CDCl$_3$) δ 8.63 (s, 1H), 8.31 (s, 1H), 7.83 (s, 1H), 7.58 (q, J=7.1 Hz, 1H), 7.43 (d, J=7.9 Hz, 1H), 5.97 (dd, J=8.1, 2.8 Hz, 1H), 5.64 (d, J=2.8 Hz, 1H), 5.51-5.25 (m, 1H), 3.97-3.81 (m, 1H), 3.79-3.53 (m, 5H), 2.99-2.84 (m, 1H), 2.74 (dd, J=12.7, 9.2 Hz, 1H), 2.69-2.58 (m, 1H), 2.55-2.46 (m, 2H), 2.45-2.32 (m, 1H), 2.30-2.18 (m, 1H), 2.14 (d, J=6.9 Hz, 3H), 2.03-1.93 (m, 1H), 1.79-1.68 (m, 1H), 1.58-1.49 (m, 1H), 1.45-1.32 (m, 1H), 0.99-0.82 (m, 1H), 0.54-0.42 (m, 2H), 0.14-0.07 (m, 2H), 1 NH exchanged. $^{19}$F NMR (282 MHZ, CDCl$_3$) δ −173.12-−173.96 (m). Second eluted diastereomer: P=100%, retention time=10.9 min, chiral HPLC: P=100%, $^1$H NMR (300 MHz, CDCl$_3$) δ 8.64 (s, 1H), 8.32 (s, 1H), 7.84 (s, 1H), 7.58 (q, J=7.0 Hz, 1H), 7.43 (d, J=8.1 Hz, 1H), 5.98 (dd, J=8.1, 2.8 Hz, 1H), 5.66 (d, J=2.8 Hz, 1H), 5.51-5.28 (m, 1H), 3.98-3.55 (m, 6H), 3.00-2.85 (m, 1H), 2.85-2.72 (m, 1H), 2.72-2.61 (m, 1H), 2.56-2.47 (m, 2H), 2.43 (s, 1H), 2.29-2.04 (m, 4H), 2.03-1.93 (m, 1H), 1.81-1.70 (m, 1H), 1.62-1.30 (m, 2H), 0.98-0.86 (m, 1H), 0.55-0.43 (m, 2H), 0.16-0.07 (m, 2H), 1 NH exchanged. $^{19}$F NMR (282 MHZ, CDCl$_3$) δ −173.07-−173.85 (m).

Compound 246: 4-((R)-3-((cyclopropylmethyl)amino)piperidin-1-yl)-1-(1-(4-(6-(3-methoxy azetidin-1-yl)pyrazin-2-yl)-1H-1,2,3-triazol-1-yl)ethyl) pyridin-2(1H)-one was Obtained Using General Scheme 1 Pathway B Stage 1: General Procedure C (in DMSO) was used between 2,6-dichloropyrazine and 3-methoxyazetidine to afford 2-chloro-6-(3-methoxyazetidin-1-yl)pyrazine IM714 as colourless oil: 300 mg, 86% yield, P=96%, retention time=2.8 min (gradient A), (M+H)$^+$: 200/202.

Stage 2: General Procedure E2 was used from IM714 to afford 2-(3-methoxyazetidin-1-yl)-6-((trimethylsilyl)ethynyl)pyrazine IM715 as brown solid: 317 mg, 81% yield, P=96%, retention time=3.0 min (gradient A), (M+H)$^+$: 262.

Stage 3: General Procedure X was used between IM715 and IM151 to afford 4-chloro-1-(1-(4-(6-(3-methoxyazetidin-1-yl)pyrazin-2-yl)-1H-1,2,3-triazol-1-yl)ethyl)pyridin-2(1H)-one IM716 as a yellow solid: 160 mg, 65% yield, P=90%, retention time=2.4 min (gradient A), (M+H)$^+$: 388/390.

Stage 4: General Procedure C was used between IM486 and IM716 to afford tert-butyl (cyclopropylmethyl)((3R)-1-(1-(1-(4-(6-(3-methoxyazetidin-1-yl)pyrazin-2-yl)-1H-1,2,3-triazol-1-yl)ethyl)-2-oxo-1,2-dihydropyridin-4-yl)piperidin-3-yl)carbamate IM717 as brown oil: 106 mg, 72% yield, P=85%, retention time=2.8 min (gradient A), (M+H)$^+$: 606.

Stage 5: General Procedure A2 was used from IM717 to afford compound 246 as brown oil: 60 mg, 73% yield, P=91%, retention time=2.9 min (gradient B), (M+H)$^+$: 506.

The mixture of diastereomers was further purified by chiral preparative HPLC purification using Chiralpak ID column (5 μm, 10×250 mm). Eluent used: TBME/MeOH/DCM/DEA: 40/40/20/0.1% at flow rate of 7 mL/min. First eluted diastereomer: P=100%, retention time=6.4 min, chiral HPLC: P=100%, $^1$H NMR (300 MHz, CDCl$_3$) δ 8.64 (s, 1H), 8.30 (s, 1H), 7.71 (s, 1H), 7.57 (q, J=7.1 Hz, 1H), 7.41 (d, J=8.0 Hz, 1H), 6.01-5.91 (m, 1H), 5.68-5.61 (m, 1H), 4.42-4.32 (m, 1H), 4.32-4.22 (m, 2H), 4.02-3.91 (m, 2H), 3.83-3.73 (m, 1H), 3.65-3.54 (m, 1H), 3.40-3.31 (m, 3H), 2.98-2.84 (m, 1H), 2.84-2.62 (m, 2H), 2.55-2.47 (m, 2H), 2.13 (d, J=7.0 Hz, 3H), 1.99 (s, 1H), 1.81-1.69 (m, 1H), 1.58-1.48 (m, 1H), 1.47-1.34 (m, 1H), 1.02-0.84 (m, 1H), 0.53-0.42 (m, 2H), 0.20-0.06 (m, 2H), 1 NH exchanged. Second eluted diastereomer: P=100%, retention time=18.2 min, chiral HPLC: P=100%, $^1$H NMR (300 MHz, CDCl$_3$) δ 8.64 (s, 1H), 8.31 (s, 1H), 7.72 (s, 1H), 7.56 (q, J=7.0 Hz, 1H), 7.43 (d, J=8.1 Hz, 1H), 5.98 (dd, J=8.1, 2.8 Hz, 1H), 5.66 (d, J=2.8 Hz, 1H), 4.45-4.33 (m, 1H), 4.33-4.22 (m, 2H), 4.02-3.92 (m, 2H), 3.90-3.80 (m, 1H), 3.65-3.55 (m, 1H), 3.35 (s, 3H), 3.00-2.79 (m, 2H), 2.73 (s, 1H), 2.55 (d, J=6.9 Hz, 2H), 2.14 (d, J=6.9 Hz, 3H), 2.00 (d, J=10.0 Hz, 1H), 1.82-1.73 (m, 1H), 1.57-1.41 (m, 2H), 1.03-0.89 (m, 1H), 0.56-0.44 (m, 2H), 0.22-0.08 (m, 2H), 1 NH exchanged.

Compound 247: 1-(1-(4-(6-(5-azaspiro[2.3]hexan-5-yl)pyrazin-2-yl)-1H-1,2,3-triazol-1-yl) ethyl)-4-((R)-3-((cyclopropylmethyl)amino)piperidin-1-yl)pyridin-2(1H)-one was Obtained Using General Scheme 1 Pathway B Stage 1: General Procedure C (in DMSO) was used between 2,6-dichloropyrazine and 5-azaspiro[2.3]hexane hydrochloride to afford 5-(6-chloropyrazin-2-yl)-5-azaspiro[2.3]hexane IM718 as a white solid: 286 mg, 85% yield, P=98%, retention time=2.8 min (gradient A), (M+H)$^+$: 196/198.

Stage 2: General Procedure E2 was used from IM718 to afford 5-(6-((trimethylsilyl)ethynyl)pyrazin-2-yl)-5-azaspiro[2.3]hexane IM719 as brown oil: 313 mg, 79% yield, P=95%, retention time=3.0 min (gradient A), (M+H)$^+$: 258.

Stage 3: General Procedure X was used between IM718 and IM151 to afford 1-(1-(4-(6-(5-azaspiro[2.3]hexan-5-yl)pyrazin-2-yl)-1H-1,2,3-triazol-1-yl)ethyl)-4-chloropyridin-2(1H)-one IM719 as a yellow solid: 164 mg, 76% yield, P=99%, retention time=2.6 min (gradient A), (M+H)$^+$: 384/386.

Stage 4: General Procedure C was used between IM486 and IM719 to afford tert-butyl ((3R)-1-(1-(1-(4-(6-(5-azaspiro[2.3]hexan-5-yl)pyrazin-2-yl)-1H-1,2,3-triazol-1-yl)ethyl)-2-oxo-1,2-dihydropyridin-4-yl)piperidin-3-yl)(cyclopropylmethyl)carbamate IM720 as brown solid: 33 mg, 24% yield, P=92%, retention time=2.9 min (gradient A), (M+H)$^+$: 602.

Stage 5: General Procedure A2 was used from IM720 to afford compound 247 as yellow oil: 25 mg, 91% yield, P=92%, retention time=3.2 min (gradient B), (M+H)$^+$: 502.

The mixture of diastereomers was further purified by chiral preparative HPLC purification using Chiralpak ID column (5 μm, 10×250 mm). Eluent used: TBME/MeOH/DCM/DEA: 40/40/20/0.1% at flow rate of 7 mL/min. First eluted diastereomer: P=100%, retention time=6.7 min, chiral HPLC: P=100%, $^1$H NMR (300 MHz, CDCl$_3$) δ 8.64 (s, 1H), 8.30 (s, 1H), 7.72 (s, 1H), 7.57 (q, J=6.9 Hz, 1H), 7.43 (d, J=8.0 Hz, 1H), 5.97 (dd, J=8.1, 2.9 Hz, 1H), 5.66 (d, J=2.8 Hz, 1H), 4.18 (s, 4H), 3.86-3.76 (m, 1H), 3.66-3.55 (m, 1H), 3.00-2.75 (m, 2H), 2.73-2.67 (m, 1H), 2.54 (d, J=6.8 Hz, 2H), 2.14 (d, J=6.9 Hz, 3H), 2.05-1.95 (m, 1H), 1.81-1.70 (m, 1H), 1.59-1.38 (m, 2H), 1.04-0.86 (m, 1H), 0.71 (s, 4H), 0.56-0.44 (m, 2H), 0.23-0.10 (m, 2H), 1 NH exchanged. Second eluted diastereomer: P=100%, retention time=18.0 min, chiral HPLC: P=100%, $^1$H NMR (300 MHz, CDCl$_3$) δ 8.44 (s, 1H), 8.11 (s, 1H), 7.52 (s, 1H), 7.36 (q, J=7.0 Hz, 1H), 7.24 (d, J=8.1 Hz, 1H), 5.79 (dd, J=8.1, 2.8 Hz, 1H), 5.47 (d, J=2.7 Hz, 1H), 3.98 (s, 4H), 3.76-3.65 (m, 1H), 3.45-3.34 (m, 1H), 2.84-2.66 (m, 2H), 2.66-2.52 (m, 1H), 2.44-2.35 (m, 2H), 1.95 (d, J=7.0 Hz, 3H), 1.85-1.77 (m, 1H), 1.68-1.49 (m, 1H), 1.48-1.23 (m, 2H), 0.89-0.72 (m, 1H), 0.52 (s, 4H), 0.39-0.28 (m, 2H), 0.07--0.04 (m, 2H), 1 NH exchanged.

Compound 248: (R)-3-(5-(3-((cyclopropylmethyl)amino)piperidin-1-yl)pyridin-2-yl)-N-(6-(pyrrolidin-1-yl)pyrazin-2-yl)oxetane-3-carboxamide was Obtained Using General Scheme 6 Pathway B Stage 1: 2,4-Dimethoxybenzylamine (1.50 mL, 9.98 mmol) and N,N-diisopropylethylamine (479 μL, 2.72 mmol) were added to a mixture of IM532 (205 mg, 1.12 mmol) and cesium carbonate (352 mg, 1.06 mmol) in a microwave vial and the mixture was stirred in the sealed vial at 160° C. for 48 h. The crude mixture was allowed to cool to rt and injected directly (loaded with minimal DMF and water) to a C-18 column and purified using 4%-80% MeCN in aq. 10 mM ammonium bicarbonate to afford N-(3,4-dimethylbenzyl)-6-(pyrrolidin-1-yl)pyrazin-2-amine IM721: 269 mg, 76% yield, P=99%, retention time=1.5 min (gradient C), (M+H)$^+$: 315.

Stage 2: General Procedure A2 was used from IM721 to afford 6-(pyrrolidin-1-yl)pyrazin-2-amine IM722: 83 mg, 59% yield, P=100%, retention time=0.7 min (gradient D), (M+H)$^+$: 165.

Stage 3: In a microwave tube were placed IM522 (208 mg, 337 μmol) and HATU (196 mg, 506 μmol) in DMF (1.12 mL). IM722 (61 mg, 371 μmol) and DIPEA (177 μL, 1.01 mmol) were added to the mixture, tube was sealed and reaction was stirred at 45° C. during 2 h. More HATU (151 mg, 388 μmol) was added and stirring at 45° C. was continued for 2 h. The reaction mixture was cooled down to rt and concentrated under reduced pressure to dryness. Residue was purified by reverse phase chromatography on a C18 cartridge, eluting with a gradient of MeCN in 10 mM ammonium bicarbonate/ammonia buffer pH=10 to afford tert-butyl (R)-(cyclopropylmethyl)(1-(6-(3-((6-(pyrrolidin-1-yl)pyrazin-2-yl)carbamoyl)oxetan-3-yl)pyridin-3-yl)piperidin-3-yl)carbamate IM723 as a beige solid: 141 mg, 69% yield, P=96%, retention time=1.9 min (gradient C), (M+H)$^+$: 579.

Stage 4: General Procedure A2 was used from IM723 to afford crude compound 248 as a white solid: 77 mg, 74% yield, P=100%, retention time=2.6 min (gradient E), (M+H)$^+$: 479. $^1$H NMR (400 MHZ, CD$_3$OD) δ 8.56 (s, 1H), 8.31 (d, J=2.6 Hz, 1H), 7.56 (s, 1H), 7.40 (dd, J=8.8, 2.9 Hz, 1H), 7.34 (d, J=8.8 Hz, 1H), 5.25 (d, J=6.3 Hz, 2H), 5.05 (d, J=6.3 Hz, 2H), 3.80-3.73 (m, 1H), 3.58 (dt, J=12.2, 3.8 Hz, 1H), 3.46-3.35 (m, 4H), 2.90-2.75 (m, 2H), 2.74-2.66 (m, 1H), 2.57-2.47 (m, 2H), 2.05-1.96 (m, 5H), 1.87-1.78 (m, 1H), 1.72-1.60 (m, 1H), 1.41-1.30 (m, 1H), 1.01-0.90 (m, 1H), 0.54-0.47 (m, 2H), 0.21-0.13 (m, 2H), 2H labile protons exchange with CD$_3$OD.

Compound 249: (R)—N-(cyclopropylmethyl)-1-(6-(3-(4-(5-methoxypyridin-3-yl)-1H-1,2,3-triazol-1-yl)oxetan-3-yl)pyridin-3-yl)piperidin-3-amine was Obtained Using General Scheme 1 Pathway A Stage 1: General Procedure B was used between IM543 and IM44 to afford tert-butyl (R)-(cyclopropylmethyl)(1-(6-(3-(4-(5-methoxypyridin-3-yl)-1H-1,2,3-triazol-1-yl)oxetan-3-yl)pyridin-3-yl)piperidin-3-yl)carbamate IM724 as colourless oil: 48 mg, 82% yield, P=96%, retention time=2.6 min (gradient A), (M+H)$^+$: 562.

Stage 2: General Procedure A2 was used from IM724 to afford compound 249 as a white solid: 32 mg, 84% yield, P=99%, retention time=2.6 min (gradient B), (M+H)⁺: 462. ¹H NMR (300 MHz, CDCl₃) δ 8.50 (d, J=1.7 Hz, 1H), 8.34 (d, J=3.0 Hz, 1H), 8.27 (d, J=2.8 Hz, 1H), 7.79 (d, J=4.8 Hz, 2H), 7.15 (dd, J=8.8, 3.0 Hz, 1H), 6.94 (d, J=8.8 Hz, 1H), 5.56 (d, J=6.7 Hz, 2H), 5.49 (d, J=6.8 Hz, 2H), 3.92 (s, 3H), 3.75-3.66 (m, 1H), 3.58-3.48 (m, 1H), 2.97-2.82 (m, 1H), 2.82-2.68 (m, 2H), 2.62-2.45 (m, 2H), 2.04-1.76 (m, 2H), 1.70-1.63 (m, 1H), 1.42-1.28 (m, 1H), 1.06-0.83 (m, 1H), 0.59-0.42 (m, 2H), 0.18-0.06 (m, 2H), 1 NH exchanged with solvent.

Compound 250: (R)—N-(cyclopropylmethyl)-1-(6-(3-(4-(6-(pyrrolidin-1-yl)pyrazin-2-yl)-1H-imidazol-1-yl)oxetan-3-yl)pyridin-3-yl)piperidin-3-amine was Obtained Using General Scheme 4 Pathway C2

Stage 1: To a solution of 2,5-dibromopyridine (4.43 g, 18.33 mmol) in dry toluene (60 mL) at −78° C. was added n-butyl lithium in hexane (6.7 mL, 16.75 mmol) dropwise over 2 min. After 10 min, 3-oxetanone (1.0 mL, 15.29 mmol) was added dropwise over 30 s at −78° C. The resulting solution was stirred for 5 min at −78° C. and then slowly allowed to warm to rt over 55 min (dry ice/acetone bath removed). The reaction mixture was quenched with a saturated aqueous solution of NH₄Cl (100 mL) and extracted with EtOAc (3×100 mL). The organic layers were merged, dried over MgSO₄, filtered and concentrated under reduced pressure to dryness. The crude material was purified by an automated flash chromatography system (liquid injection in toluene, 0 to 45% EtOAc in Heptane) to afford 3-(5-bromopyridin-2-yl)oxetan-3-ol IM725 as yellow oil: 2.42 g, 69% yield, P=100%, retention time=2.2 min (gradient A), (M+H)⁺: 230/232.

Stage 2: General Procedure Y was used between IM725 and IM486 to afford tert-butyl (R)-(cyclopropylmethyl)(1-(6-(3-hydroxyoxetan-3-yl)pyridin-3-yl)piperidin-3-yl)carbamate IM726 as yellow gum: 175 mg, 20% yield, P=100%, retention time=2.4 min (gradient A), (M+H)⁺: 404.

Stage 3: General Procedure P was used from IM726 to afford crude (R)-3-(5-(3-((tert-butoxycarbonyl)(cyclopropylmethyl)amino)piperidin-1-yl)pyridin-2-yl)oxetan-3-yl methanesulfonate IM727 as yellow oil: 160 mg, 100% yield, P=95% (¹H-NMR).

Stage 4: Sodium hydride (33 mg, 0.83 mmol) was added to a solution of IM639 (82 mg, 0.38 mmol) in DMF (2 mL) at rt. The reaction mixture was stirred for 30 min. A solution of IM727 (153 mg, 0.32 mmol) in dry DMF (1 mL) freshly prepared was added via syringe and the resulting mixture was stirred for 3 h at 60° C. The reaction mixture was quenched by adding a saturated aqueous solution of NH₄Cl (20 mL). The aqueous phase was extracted with EtOAc (3×20 mL) and the combined organic phases were washed with water (2×20 mL) and brine (20 mL). The organic layer was dried over MgSO₄, filtered and concentrated under reduced pressure to afford crude tert-butyl (R)-(cyclopropylmethyl)(1-(6-(3-(4-(6-(pyrrolidin-1-yl)pyrazin-2-yl)-1H-imidazol-1-yl)oxetan-3-yl)pyridin-3-yl)piperidin-3-yl)carbamate IM728 as an orange gum: 225 mg, 33% yield, P=28%, retention time=2.6 min (gradient A), (M+H)⁺: 601.

Stage 5: General Procedure A2 was used from IM728 to afford crude compound 250 as an orange gum: 177 mg, 21% yield, P=22%, retention time=2.2 min (gradient B), (M+H)⁺: 501.

The product was purified by reverse phase preparative HPLC purification (Luna C18 5 μm, 21.2×100 mm). Solution A was water+0.05% TFA. Gradient used: held to 25% solution "B" over 1.0 min, increased linearly to 40% solution "B" over 4.0 min, increased linearly to 45% solution "B" over 1.0 min, increased linearly to 85% solution "B" over 1.0 min, held to 85% solution "B" over 0.5 min, and returned to initial conditions over 0.7 min. Flow Rate: 15 mL/min. P=97%.

The product was further purified by reverse phase preparative HPLC purification (XBridge OBD C18 5 μm, 19×100 mm). Gradient used: held to 25% solution "B" over 1.0 min, increased linearly to 50% solution "B" over 4.0 min, increased linearly to 45% solution "B" over 1.0 min, increased linearly to 85% solution "B" over 1.0 min, and returned to initial conditions over 0.8 min. Flow Rate: 15 mL/min. P=98%. ¹H NMR (300 MHz, CDCl₃) δ 8.46 (s, 1H), 8.37 (d, J=2.9 Hz, 1H), 7.76 (s, 1H), 7.69 (d, J=1.6 Hz, 1H), 7.51 (d, J=1.5 Hz, 1H), 7.10 (dd, J=8.7, 3.0 Hz, 1H), 6.72 (d, J=8.7 Hz, 1H), 5.44 (d, J=6.6 Hz, 2H), 5.25 (d, J=6.6 Hz, 2H), 3.73-3.64 (m, 1H), 3.58-3.46 (m, 5H), 2.97-2.84 (m, 1H), 2.84-2.65 (m, 2H), 2.63-2.45 (m, 2H), 2.07-1.96 (m, 5H), 1.88-1.76 (m, 1H), 1.72-1.56 (m, 1H), 1.45-1.31 (m, 1H), 1.00-0.90 (m, 1H), 0.56-0.44 (m, 2H), 0.17-0.08 (m, 2H), 1 NH exchanged with solvent.

Compound 251: 2-(6-((R)-3-((cyclopropylmethyl)amino)piperidin-1-yl)pyridazin-3-yl)-N-(5-(pyrrolidin-1-yl)pyridin-3-yl)propanamide was Obtained Using General Scheme 6 Pathway A Stage 1: In a round bottom flask were placed EDC (82.7 mg, 427 μmol), lithium 2-(6-chloropyridazin-3-yl)propanoate (115 mg, 388 μmol), HOBt (55.2 mg, 388 μmol), IM557 (68.1 mg, 388 μmol) and DMF (1.92 mL). The reaction was stirred at rt during 5 h. The reaction mixture was directly purified by reverse phase chromatography on a C18 cartridge, eluting with a gradient of MeCN in basic water (10 mM NH₄HCO₃/NH₄OH buffer pH=10) to afford 2-(6-chloropyridazin-3-yl)-N-(5-(pyrrolidin-1-yl)pyridin-3-yl)propanamide IM729 as a white solid: 92 mg, 69% yield, P=97%, retention time=1.2 min (gradient C), (M+H)⁺: 332.

Stage 2: General Procedure C was used between IM486 and IM729 to afford tert-butyl (cyclopropylmethyl)((3R)-1-(6-(1-oxo-1-((5-(pyrrolidin-1-yl)pyridin-3-yl)amino)propan-2-yl)pyridazin-3-yl)piperidin-3-yl)carbamate IM730 as a beige solid: 142 mg, 83% yield, P=99%, retention time=1.7 min (gradient C), (M+H)⁺: 551.

Stage 3: General Procedure A2 was used from IM730 to afford compound 251 as a white solid: 76 mg, 65% yield, P=99%, retention time=2.5 min (gradient E), (M+H)⁺: 451.

The mixture of diastereomers was further purified by chiral preparative HPLC purification using Chiralpak ID column (5 μm, 10×250 mm). Eluent used: TBME/MeOH/DCM/DEA: 40/20/40/0.1% at flow rate of 7 mL/min. First eluted diastereomer: P=98%, retention time=5.5 min, chiral HPLC: P=98.5%, ¹H NMR (300 MHz, CDCl₃) δ 8.78 (s, 1H), 7.88 (d, J=2.1 Hz, 1H), 7.68 (d, J=2.6 Hz, 1H), 7.36 (s, 1H), 7.25 (d, J=9.3 Hz, 1H), 6.93 (d, J=9.5 Hz, 1H), 4.40-4.29 (m, 1H), 4.12-3.94 (m, 2H), 3.32-3.22 (m, 4H), 3.16-3.04 (m, 1H), 2.90 (dd, J=12.7, 9.2 Hz, 1H), 2.78-2.69 (m, 1H), 2.60-2.51 (m, 2H), 2.04-1.91 (m, 4H), 1.89-1.70 (m, 2H), 1.63 (d, J=7.2 Hz, 3H), 1.62-1.54 (m, 1H), 1.52-1.33 (m, 1H), 1.01-0.84 (m, 1H), 0.54-0.41 (m, 2H), 0.11 (d, J=4.5 Hz, 2H), 1H exchanged with solvent. Second eluted diastereomer: P=100%, retention time=6.7 min, chiral HPLC: P=98.6%, ¹H NMR (300 MHz, CDCl₃) δ 8.78 (s, 1H), 7.89 (d, J=2.1 Hz, 1H), 7.68 (d, J=2.6 Hz, 1H), 7.41-7.33 (m, 1H), 7.26 (d, J=9.5 Hz, 1H), 6.93 (d, J=9.5 Hz, 1H), 4.39-4.29 (m, 1H), 4.09-3.96 (m, 2H), 3.33-3.22 (m, 4H), 3.17-3.05 (m, 1H), 2.93 (dd, J=12.7, 9.2 Hz, 1H), 2.79-2.68 (m, 1H), 2.62-2.50 (m, 2H), 2.09-1.94 (m, 4H), 1.89-1.77 (m, 2H), 1.63 (d, J=7.2 Hz, 3H), 1.62-1.52 (m, 1H), 1.51-1.37 (m, 1H), 1.01-0.86 (m, 1H), 0.51-0.44 (m, 2H), 0.15-0.08 (m, 2H), 1H exchanged with solvent.

Compound 252: 4-((R)-3-((cyclopropylmethyl)amino)piperidin-1-yl)-1-(1-(4-(5-(pyrrolidin-1-yl)pyridin-3-yl)-1H-imidazol-1-yl)ethyl)pyridin-2(1H)-one was Obtained Using General Scheme 4 Pathway C1

Stage 1: To a microwave vial, under nitrogen, were added 4-(tributylstannyl)-1-trityl-1H-imidazole (1.5 g, 2.38 mmol), dichloro(triphenylphosphine) palladium (II) (170 mg, 238 µmol), IM554 (540 mg, 2.38 mmol), and dioxane (7.92 mL). The reaction mixture was degassed for 10 min and heated to 100° C. overnight. After cooling to rt, mixture was concentrated under reduced pressure. The crude residue was purified by silica gel chromatgraphy (Biotage, dry load) using a gradient of EtOAc (0-100%) in heptanes to afford 3-(pyrrolidin-1-yl)-5-(1-trityl-1H-imidazol-4-yl)pyridine IM731 as a pale yellow solid: 1.09 g, 51% yield, P=100%, retention time=1.9 min (gradient C), (M+H)$^+$: 457.

Stage 2: To a RBF, equipped with a condenser, were added IM731 (550 mg, 1.2 µmol), MeOH (15.1 mL) and acetic acid (1.72 mL, 30.1 mmol). The mixture was heated to 75° C. for 10 h. After cooling to rt, mixture was concentrated reduced pressure. Residue was diluted in MeOH (3 mL) then was neutralized with a solution of ammonia in MeOH (2 mL) and concentrated down again. Residue was purified by reverse phase chromatography using a gradient of MeCN (0-100%) in 10 mM ammonium bicarbonate buffer to afford 3-(1H-imidazol-4-yl)-5-(pyrrolidin-1-yl) IM732 as a white solid: 157 mg, 60% yield, P=98%, retention time=1.0 min (gradient F), (M+H)$^+$: 215.

Stage 3: To a solution of IM732 (125 mg, 583 µmol) in DMF (1.168 mL), cooled to 0° C., was added potassium carbonate (247 mg, 1.75 mmol). The mixture was stirred at 0° C. for 5 min before adding sodium hydride 60% in dispersion in mineral oil (46.7 mg, 1.17 mmol) and IM150 (560 mg, 2.92 mmol). Ice bath was then removed and the mixture was stirred at rt for 2.5 h. Mixture was quenched with drops of water then directly loaded onto a C-18 cartridge and purified by reverse phase chromatography using a gradient of MeCN (0-100%) in 10 mM ammonium bicarbonate buffer to afford 4-chloro-1-(1-(4-(5-(pyrrolidin-1-yl)pyridin-3-yl)-1H-imidazol-1-yl)ethyl)pyridin-2(1H)-one IM733 as yellow oil: 109 mg, 38% yield, P=75%, retention time=1.2 min (gradient C), (M+H)$^+$: 370/372.

Stage 4: General Procedure C was used between IM486 and IM733 to afford tert-butyl (cyclopropylmethyl)((3R)-1-(2-oxo-1-(1-(4-(5-(pyrrolidin-1-yl)pyridin-3-yl)-1H-imidazol-1-yl)ethyl)-1,2-dihydropyridin-4-yl)piperidin-3-yl)carbamate IM734 as a brownish solid: 61 mg, 45% yield, P=92%, retention time=1.6 min (gradient C), (M+H)$^+$: 589.

Stage 5: General Procedure A2 was used from IM734 to afford compound 252 as a white solid: 18 mg, 36% yield, P=100%, retention time=2.3 min (gradient E), (M+H)$^+$: 489.

The mixture of diastereomers was further purified by chiral preparative HPLC purification using Chiralpak ID column (5 µm, 10×250 mm). Eluent used: TBME/MeOH/DCM/DEA: 45/45/10/0.1% at flow rate of 7 mL/min. First eluted diastereomer: P=98%, retention time=5.7 min, chiral HPLC: P=100%, $^1$H NMR (300 MHz, CDCl$_3$) δ 8.24 (s, 1H), 7.87 (d, J=2.7 Hz, 1H), 7.81 (d, J=1.4 Hz, 1H), 7.41 (d, J=1.4 Hz, 1H), 7.33-7.21 (m, 2H), 6.97 (d, J=8.0 Hz, 1H), 5.96 (dd, J=8.1, 2.8 Hz, 1H), 5.69 (d, J=2.8 Hz, 1H), 3.81-3.71 (m, 1H), 3.64-3.53 (m, 1H), 3.40-3.30 (m, 4H), 3.01-2.86 (m, 1H), 2.83-2.64 (m, 2H), 2.60-2.43 (m, 2H), 2.08-2.00 (m, 4H), 1.94 (d, J=6.9 Hz, 3H), 1.80-1.69 (m, 2H), 1.64-1.50 (m, 1H), 1.46-1.33 (m, 1H), 0.98-0.85 (m, 1H), 0.55-0.43 (m, 2H), 0.18-0.09 (m, 2H), 1H exchanged with solvent. Second eluted diastereomer: P=100%, retention time=9.3 min, chiral HPLC: P=100%, $^1$H NMR (300 MHz, CDCl$_3$) δ 8.24 (s, 1H), 7.87 (s, 1H), 7.81 (d, J=1.5 Hz, 1H), 7.40 (d, J=1.5 Hz, 1H), 7.34-7.22 (m, 2H), 6.95 (d, J=8.1 Hz, 1H), 5.96 (dd, J=8.1, 2.8 Hz, 1H), 5.69 (d, J=2.8 Hz, 1H), 3.82-3.72 (m, 1H), 3.65-3.55 (m, 1H), 3.40-3.30 (m, 4H), 3.00-2.86 (m, 1H), 2.76 (dd, J=12.7, 9.3 Hz, 1H), 2.67 (d, J=8.7 Hz, 1H), 2.57-2.44 (m, 2H), 2.08-2.00 (m, 4H), 1.94 (d, J=6.8 Hz, 3H), 1.84-1.70 (m, 2H), 1.64-1.48 (m, 1H), 1.47-1.31 (m, 1H), 0.92 (t, J=7.0 Hz, 1H), 0.55-0.43 (m, 2H), 0.18-0.07 (m, 2H), 1H exchanged with solvent.

Compound 253: 4-((R)-3-((cyclopropylmethyl)amino)piperidin-1-yl)-1-(1-(1-(5-(pyrrolidin-1-yl)pyridin-3-yl)-1H-pyrazol-4-yl)ethyl)pyridin-2(1H)-one was Obtained Using General Scheme 3 Scheme 5

Stage 1: A sealed flask was charged with IM554 (1.0 g, 4.40 mmol) and 1-(1H-pyrazol-4-yl)ethanone (750 mg, 6.6 mmol), DMF (4.40 mL), potassium carbonate (1.86 g, 13.2 mmol) and trans-n,n'-dimethylcyclohexane-1,2-diamine (143 µL, 881 µmol). Nitrogen was bubbled for 5 min, copper(I)iodide (41.9 mg, 220 µmol) was added to the reaction, N$_2$ was bubbled for an additional 5 min, and the flask was sealed and heated at 100° C. for 18 h. The mixture was cooled down to rt, partitioned between EtOAc (50 mL) and brine (50 mL+1 mL TEA). The layers were separated, the organic layer was washed with brine (2×30 mL), dried over Na$_2$SO$_4$ and purified by silica column (0-100% EtOAc in heptanes to afford 1-(1-(5-(pyrrolidin-1-yl)pyridin-3-yl)-1H-pyrazol-4-yl)ethan-1-one IM735 as an off-white solid: 850 mg, 75% yield, P=100%, retention time=1.2 min (gradient F), (M+H)$^+$: 257.

Stage 2: To IM735 (850 mg, 3.32 mmol) in methanol (33.2 mL) at 0° C. was added portion-wise sodium borohydride (384 mg, 9.95 mmol) and the reaction was stirred at 0° C. for 30 min. The reaction mixture was concentrated down, co-evaporated with DCM (2×10 mL), and directly purified by silica column (0-100% EtOAC in heptanes) to afford 1-(1-(5-(pyrrolidin-1-yl)pyridin-3-yl)-1H-pyrazol-4-yl)ethan-1-ol IM736 as an off-white gummy solid: 705 mg, 82% yield, P=99%, retention time=1.1 min (gradient C), (M+H)$^+$: 259.

Stage 3: General Procedure T was used between 4-chloropyridin-2-ol and IM736 to afford 4-chloro-1-(1-(1-(5-(pyrrolidin-1-yl)pyridin-3-yl)-1H-pyrazol-4-yl)ethyl)pyridin-2(1H)-one IM737 as an off-white solid: 152 mg, 15% yield, P=99%, retention time=1.4 min (gradient C), (M+H)$^+$: 370/372.

Stage 4: General Procedure C was used between IM486 and IM737 to afford tert-butyl (cyclopropylmethyl)((3R)-1-(2-oxo-1-(1-(1-(5-(pyrrolidin-1-yl)pyridin-3-yl)-1H-pyrazol-4-yl)ethyl)-1,2-dihydropyridin-4-yl)piperidin-3-yl)carbamate IM738 as a white solid: 172 mg, 73% yield, P=100%, retention time=1.7 min (gradient C), (M+H)$^+$: 588.

Stage 5: General Procedure A2 was used from IM738 to afford compound 253 as a white solid: 120 mg, 85% yield, P=99%, retention time=2.4 min (gradient E), (M+H)$^+$: 488.

The mixture of diastereomers was further purified by chiral preparative HPLC purification using Chiralpak IA column (5 µm, 20×250 mm). Eluent used: TBME/MeOH/DCM/DEA: 40/40/20/0.1% at flow rate of 20 mL/min. First eluted diastereomer: P=100%, retention time=7.4 min, chiral HPLC: P=100%, $^1$H NMR (300 MHz, CDCl$_3$) δ 8.16 (d, J=2.2 Hz, 1H), 7.89 (d, J=2.6 Hz, 1H), 7.86 (s, 1H), 7.64 (s, 1H), 7.15-7.10 (m, 1H), 7.02 (d, J=8.0 Hz, 1H), 6.34 (q, J=7.0 Hz, 1H), 5.91 (dd, J=8.0, 2.8 Hz, 1H), 5.75 (d, J=2.8 Hz, 1H), 3.80-3.71 (m, 1H), 3.64-3.53 (m, 1H), 3.41-3.30 (m, 4H), 2.98-2.83 (m, 1H), 2.79-2.59 (m, 2H), 2.59-2.42 (m, 2H), 2.09-1.93 (m, 5H), 1.80-1.69 (m, 1H), 1.66 (d, J=7.0 Hz, 3H), 1.60-1.48 (m, 1H), 1.43-1.28 (m, 1H), 0.99-0.85 (m, 1H), 0.53-0.44 (m, 2H), 0.14-0.07 (m, 2H), 1H exchanged with solvent. Second eluted diastereomer: P=100%, retention time=10.1 min, chiral HPLC: P=100%, $^1$H NMR (300 MHz, CDCl$_3$) δ 8.16 (d, J=2.1 Hz, 1H), 7.89 (d, J=2.6 Hz, 1H), 7.86 (s, 1H), 7.64 (s, 1H), 7.14-7.10 (m, 1H), 7.02 (d, J=7.9 Hz, 1H), 6.33 (q, J=7.0 Hz, 1H), 5.91 (dd, J=8.0, 2.8 Hz, 1H), 5.75 (d, J=2.8 Hz, 1H), 3.83-3.73 (m, 1H), 3.64-3.53 (m, 1H), 3.40-3.30 (m, 4H), 2.98-2.83 (m, 1H), 2.82-2.62 (m, 2H), 2.58-2.45 (m, 2H), 2.09-1.94 (m, 5H), 1.82-1.70 (m, 1H), 1.66 (d, J=7.0 Hz, 3H), 1.63-1.48 (m, 1H), 1.47-1.31 (m, 1H), 1.02-0.85 (m, 1H), 0.54-0.44 (m, 2H), 0.15-0.08 (m, 2H), 1H exchanged with solvent.

Compound 254: 4-((R)-3-((cyclopropylmethyl)amino)piperidin-1-yl)-1-(1-(4-(6-(1,1-difluoro-5-azaspiro[2.3]hexan-5-yl)pyrazin-2-yl)-1H-1,2,3-triazol-1-ylethyl)pyridin-2(1H)-one was Obtained Using General Scheme 1 Pathway B Stage 1: General Procedure C (in DMSO) was used between 2,6-dichloropyrazine and 1,1-difluoro-5-azaspirohexane hydrochloride to afford crude 5-(6-chloropyrazin-2-yl)-1,1-difluoro-5-azaspiro[2.3]hexane IM739 as dark yellow oil: 303 mg, 96% yield, P=99%, retention time=2.8 min (gradient A), (M+H)$^+$: 232/234.

Stage 2: General Procedure E2 was used from IM739 to afford 1,1-difluoro-5-(6-((trimethylsilyl)ethynyl)pyrazin-2-yl)-5-azaspiro[2.3]hexane IM740 as a yellow solid: 306 mg, 78% yield, P=98%, retention time=3.1 min (gradient A), (M+H)$^+$: 294.

Stage 3: General Procedure X was used between IM740 and IM151 to afford 4-chloro-1-(1-(4-(6-(1,1-difluoro-5-azaspiro[2.3]hexan-5-yl)pyrazin-2-yl)-1H-1,2,3-triazol-1-yl)ethyl)pyridin-2(1H)-one IM741 as a white solid: 110 mg, 78% yield, P=100%, retention time=2.7 min (gradient A), (M+H)$^+$: 420/422.

Stage 4: General Procedure C was used between IM486 and IM741 to afford tert-butyl (cyclopropylmethyl)((3R)-1-(1-(1-(4-(6-(1,1-difluoro-5-azaspiro[2.3]hexan-5-yl)pyrazin-2-yl)-1H-1,2,3-triazol-1-yl)ethyl)-2-oxo-1,2-dihydropyridin-4-yl)piperidin-3-yl)carbamate IM742 as colourless oil: 55 mg, 71% yield, P=98%, retention time=2.9 min (gradient A), (M+H)$^+$: 638.

Stage 5: General Procedure A2 was used from IM742 to afford compound 254 as colourless oil: 42 mg, 92% yield, P=100%, retention time=3.3 min (gradient B), (M+H)$^+$: 538.

The mixture of diastereomers was further purified by chiral preparative HPLC purification using Chiralpak IA column (5 µm, 20×250 mm). Eluent used: TBME/MeOH/DCM/DEA: 40/40/20/0.1% at flow rate of 20 ml/min. First eluted diastereomer: P=99%, retention time=5.0 min, chiral HPLC: P=99.9%, $^1$H NMR (300 MHz, CDCl$_3$) δ 8.70 (s, 1H), 8.32 (s, 1H), 7.76 (s, 1H), 7.56 (q, J=7.0 Hz, 1H), 7.42 (d, J=8.1 Hz, 1H), 5.97 (dd, J=8.1, 2.8 Hz, 1H), 5.64 (d, J=2.8 Hz, 1H), 4.32 (d, J=8.4 Hz, 2H), 4.21-4.10 (m, 2H), 3.81-3.71 (m, 1H), 3.65-3.54 (m, 1H), 2.99-2.84 (m, 1H), 2.75 (dd, J=12.7, 9.4 Hz, 1H), 2.70-2.58 (m, 1H), 2.58-2.41 (m, 2H), 2.14 (d, J=7.0 Hz, 3H), 2.04-1.92 (m, 1H), 1.79-1.68 (m, 1H), 1.53 (t, J=8.5 Hz, 3H), 1.45-1.29 (m, 1H), 0.99-0.84 (m, 1H), 0.53-0.44 (m, 2H), 0.15-0.07 (m, 2H), 1H exchanged with solvent. $^{19}$F NMR (282 MHZ, CDCl$_3$) δ −136.34 (t, J=8.5 Hz). Second eluted diastereomer: P=99%, retention time=7.9 min, chiral HPLC: P=100%, $^1$H NMR (300 MHz, CDCl$_3$) δ 8.71 (s, 1H), 8.32 (s, 1H), 7.76 (s, 1H), 7.56 (q, J=7.0 Hz, 1H), 7.43 (d, J=8.0 Hz, 1H), 5.98 (dd, J=8.1, 2.8 Hz, 1H), 5.64 (d, J=2.8 Hz, 1H), 4.33 (d, J=8.4 Hz, 2H), 4.21-4.10 (m, 2H), 3.84-3.74 (m, 1H), 3.65-3.54 (m, 1H), 3.00-2.85 (m, 1H), 2.78 (dd, J=12.7, 9.4 Hz, 1H), 2.72-2.61 (m, 1H), 2.59-2.45 (m, 2H), 2.15 (d, J=7.0 Hz, 3H), 2.00 (s, 1H), 1.78-1.70 (m, 1H), 1.60-1.49 (m, 3H), 1.48-1.33 (m, 1H), 0.99-0.85 (m, 1H), 0.53-0.44 (m, 2H), 0.15-0.07 (m, 2H), 1H exchanged with solvent. $^{19}$F NMR (282 MHz, CDCl$_3$) δ −136.34 (t, J=8.7 Hz).

Compound 255: 4-((R)-3-((cyclopropylmethyl)amino)piperidin-1-yl)-1-(1-(4-(6-methylpyrazin-2-yl)-1H-1,2,3-triazol-1-yl)ethyl)pyridin-2(1H)-one was Obtained Using General Scheme 1 Pathway B Stage 1: General Procedure E2 was used from 2-chloro-6-methylpyrazine to afford 2-methyl-6-((trimethylsilyl)ethynyl)pyrazine IM743 as orange oil: 358 mg, 81% yield, P=98%, retention time=3.0 min (gradient A), (M+H)$^+$: 191.

Stage 2: General Procedure X was used between IM743 and IM151 to afford 4-chloro-1-(1-(4-(6-methylpyrazin-2-yl)-1H-1,2,3-triazol-1-yl)ethyl)pyridin-2(1H)-one IM744 as an off-white solid: 97 mg, 57% yield, P=95%, retention time=2.4 min (gradient A), (M+H)$^+$: 317/319.

Stage 3: General Procedure C was used between IM486 and IM744 to afford tert-butyl (cyclopropylmethyl)((3R)-1-(1-(1-(4-(6-methylpyrazin-2-yl)-1H-1,2,3-triazol-1-yl)ethyl)-2-oxo-1,2-dihydropyridin-4-yl)piperidin-3-yl)carbamate IM745 as a white solid: 40 mg, 53% yield, P=95%, retention time=2.8 min (gradient A), (M+H)$^+$: 535.

Stage 4: General Procedure A2 was used from IM745 to afford crude compound 255 as colourless oil: 28 mg, 88% yield, P=97%, retention time=2.7 min (gradient B), (M+H)$^+$: 435.

The mixture of diastereomers was purified by chiral preparative HPLC purification using Chiralpak IA column (5 µm, 20×250 mm). Eluent used: TBME/MeOH/DCM/DEA: 40/40/20/0.1% at flow rate of 20 mL/min. First eluted diastereomer: P=100%, retention time=5.5 min, chiral HPLC: P=100%, $^1$H NMR (300 MHz, CDCl$_3$) δ 9.13 (s, 1H), 8.44 (s, 1H), 8.36 (s, 1H), 7.57 (q, J=7.0 Hz, 1H), 7.40 (d, J=8.1 Hz, 1H), 5.97 (dd, J=8.1, 2.8 Hz, 1H), 5.64 (d, J=2.8 Hz, 1H), 3.81-3.69 (m, 1H), 3.64-3.53 (m, 1H), 2.99-2.84 (m, 1H), 2.73 (dd, J=12.7, 9.4 Hz, 1H), 2.68-2.57 (m, 1H), 2.54 (s, 3H), 2.52-2.42 (m, 2H), 2.16 (d, J=7.0 Hz, 3H), 2.03-1.92 (m, 1H), 1.78-1.72 (m, 1H), 1.63-1.44 (m, 1H), 1.44-1.22 (m, 1H), 0.98-0.83 (m, 1H), 0.52-0.43 (m, 2H), 0.14-0.06 (m, 2H), 1H exchanged with solvent. Second eluted diastereomer: P=100%, retention time=9.6 min, chiral HPLC: P=100%, $^1$H NMR (300 MHz, CDCl$_3$) δ 9.13 (s, 1H), 8.44 (d, J=1.8 Hz, 1H), 8.36 (s, 1H), 7.56 (q, J=7.0 Hz, 1H), 7.40 (d, J=8.1 Hz, 1H), 5.97 (dd, J=8.2, 2.9 Hz, 1H), 5.64 (d, J=2.9 Hz, 1H), 3.82-3.72 (m, 1H), 3.65-3.55 (m, 1H), 3.00-2.85 (m, 1H), 2.75 (dd, J=12.7, 9.4 Hz, 1H), 2.71-2.59 (m, 1H), 2.54 (s, 3H), 2.53-2.46 (m, 2H), 2.16 (d, J=7.0 Hz, 3H), 2.03-1.92 (m, 1H), 1.80-1.67 (m, 1H), 1.60-1.47 (m, 1H), 1.47-1.32 (m, 1H), 0.98-0.84 (m, 1H), 0.53-0.41 (m, 2H), 0.15-0.03 (m, 2H), 1H exchanged with solvent.

Compound 256: (R)—N-(cyclopropylmethyl)-1-(6-(3-(4-(5-cyclopropylpyridin-3-yl)-1H-1,2,3-triazol-1-yl)oxetan-3-yl)pyridin-3-yl)piperidin-3-amine was Obtained Using General Scheme 1 Pathway A Stage 1: Cesium carbonate (825 mg, 2.5 mmol), cyclopropylboronic acid monohydrate (265 mg, 3.09 mmol) and Pd(PPh$_3$)$_4$ (120 mg, 0.10 mmol) were added to an anhydrous 1,4-dioxane (20 mL) (previously degassed with Ar) solution of 3,5-dibromopyridine (500 mg, 2.07 mmol). The mixture was stirred at 100° C. for 18 h. Then, a second add of cyclopropylboronic acid monohydrate (218 mg, 2.49 mmol) and cesium carbonate (825 mg, 2.5 mmol) was carried out and the reaction was stirred at 100° C. for another 4 h. The reaction was cooled to rt and diluted with EtOAc (20 mL) to give a grey suspension which was filtered. The solid was rinsed with EtOAc (2×20 mL). The resulting yellow filtrate was concentrated in vacuo to give the crude product. The latter was purified by automated flash chromatography (nHept/EtOAc: 100/0 to 80/20) to afford 3-bromo-5-cyclopropylpyridine IM746 as white crystals: 209 mg, 51% yield, P=100%, retention time=2.3 min (gradient A), (M+H)$^+$: 198/200.

Stage 2: General Procedure E1 was used from IM746 to afford 3-cyclopropyl-5-((trimethylsilyl)ethynyl)pyridine IM747: 189 mg, 83% yield, P=100%, retention time=2.7 min (gradient A), (M+H)$^+$: 216.

Stage 3: General Procedure X was used between IM747 and IM543 to afford tert-butyl (R)-(cyclopropylmethyl)(1-(6-(3-(4-(5-cyclopropylpyridin-3-yl)-1H-1,2,3-triazol-1-yl)oxetan-3-yl)pyridin-3-yl)piperidin-3-yl)carbamate IM748 as colourless oil: 35 mg, 59% yield, P=97%, retention time=2.6 min (gradient A), (M+H)$^+$: 572.

Stage 4: General Procedure A2 was used from IM748 to afford crude compound 256 as a yellow powder: 19 mg, 66% yield, P=97%, retention time=2.8 min (gradient B), (M+H)$^+$: 472. $^1$H NMR (300 MHz, CDCl$_3$) δ 8.70 (d, J=2.1 Hz, 1H), 8.36 (dd, J=12.4, 2.5 Hz, 2H), 7.83 (s, 1H), 7.76 (s, 1H), 7.15 (dd, J=8.8, 3.0 Hz, 1H), 6.91 (d, J=8.6 Hz, 1H), 5.59-5.44 (m, 4H), 3.75-3.66 (m, 1H), 3.58-3.48 (m, 1H), 2.95-2.86 (m, 1H), 2.85-2.68 (m, 2H), 2.63-2.45 (m, 2H), 2.03-1.76 (m, 3H), 1.45-1.28 (m, 2H), 1.09-1.00 (m, 2H), 1.00-0.91 (m, 1H), 0.82-0.77 (m, 2H), 0.53-0.46 (m, 2H), 0.15-0.07 (m, 2H), 1H exchanged with solvent.

Compound 257: (3R)—N-(cyclobutylmethyl)-1-(6-(1-(4-(5-(pyrrolidin-1-yl)pyridin-3-yl)-1H-1,2,3-triazol-1-yl)ethyl)pyridazin-3-yl)piperidin-3-amine was Obtained Using General Scheme 1 Pathway A Stage 1: General Procedure X was used between IM280 and IM555 to afford tert-butyl (cyclobutylmethyl)((3R)-1-(6-(1-(4-(5-(pyrrolidin-1-yl)pyridin-3-yl)-1H-1,2,3-triazol-1-yl)ethyl)pyridazin-3-yl)piperidin-3-yl)carbamate IM749 as colourless oil: 61 mg, 87% yield, P=99%, retention time=2.4 min (gradient A), (M+H)$^+$: 588.

Stage 2: General Procedure A2 was used from IM749 to afford crude compound 257 as colourless oil: 43 mg, 82% yield, P=97%, retention time=2.8 min (gradient B), (M+H)$^+$: 488.

The mixture of diastereomers was purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=100%, retention time=7.1 min, chiral HPLC: P=99.7%, $^1$H NMR (300 MHz, CDCl$_3$) δ 8.21 (s, 1H), 7.99 (d, J=6.6 Hz, 1H), 7.90 (s, 1H), 7.39-7.14 (m, 2H), 6.86 (d, J=10.2 Hz, 1H), 6.09-5.94 (m, 1H), 4.47-4.34 (m, 1H), 4.17-4.02 (m, 1H), 3.41-3.27 (m, 4H), 3.12-2.99 (m, 1H), 2.91-2.78 (m, 1H), 2.71-2.59 (m, 3H), 2.48-2.33 (m, 1H), 2.12-1.96 (m, 10H), 1.91-1.72 (m, 3H), 1.60 (s, 3H), 1.48-1.32 (m, 1H), 1H exchanged with solvent. Second eluted diastereomer: P=100%, retention time=17.2 min, chiral HPLC: P=100%, $^1$H NMR (300 MHz, CDCl$_3$) δ 8.17 (s, 1H), 7.93 (s, 1H), 7.86 (s, 1H), 7.27 (d, J=2.2 Hz, 1H), 7.16 (d, J=9.5 Hz, 1H), 6.83 (d, J=9.6 Hz, 1H), 5.97 (q, J=7.2 Hz, 1H), 4.41-4.31 (m, 1H), 4.09-3.99 (m, 1H), 3.29 (q, J=5.1 Hz, 4H), 3.09-2.95 (m, 1H), 2.82 (dd, J=12.8, 9.3 Hz, 1H), 2.74-2.53 (m, 3H), 2.44-2.28 (m, 1H), 2.04 (d, J=7.0 Hz, 3H), 1.98 (dq, J=6.7, 4.2 Hz, 7H), 1.87-1.70 (m, 3H), 1.65-1.47 (m, 3H), 1.45-1.31 (m, 1H), 1H exchanged with solvent.

Compound 258: (3R)—N-(cyclobutylmethyl)-1-(6-(1-(4-(6-methoxypyrazin-2-yl)-1H-1,2,3-triazol-1-yl)ethyl)pyridazin-3-yl)piperidin-3-amine was Obtained Using General Scheme 1 Pathway A Stage 1: General Procedure X was used between IM280 and IM318 to afford tert-butyl (cyclobutylmethyl)((3R)-1-(6-(1-(4-(6-methoxypyrazin-2-yl)-1H-1,2,3-triazol-1-yl)ethyl)pyridazin-3-yl)piperidin-3-yl)carbamate IM750 as colourless oil: 39 mg, 60% yield, P=99%, retention time=2.6 min (gradient A), (M+H)$^+$: 550.

Stage 2: General Procedure A2 was used from IM750 to afford crude compound 258 as colourless oil: 30 mg, 94% yield, P=99%, retention time=3.0 min (gradient B), (M+H)$^+$: 450.

The mixture of diastereomers was purified by chiral preparative HPLC purification using Chiralpak IA column (5 μm, 20×250 mm). Eluent used: TBME/MeOH/DEA: 60/40/0.1% at flow rate of 20 mL/min. First eluted diastereomer: P=100%, retention time=6.0 min, chiral HPLC: P=100%, $^1$H NMR (300 MHz, CDCl$_3$) δ 8.92 (s, 1H), 8.28 (s, 1H), 8.14 (s, 1H), 7.24 (d, J=9.4 Hz, 1H), 6.88 (d, J=9.5 Hz, 1H), 6.05 (q, J=7.1 Hz, 1H), 4.42-4.32 (m, 1H), 4.13-4.01 (m, 1H), 3.99 (s, 3H), 3.18-3.03 (m, 1H), 2.88 (dd, J=12.8, 9.2 Hz, 1H), 2.78-2.57 (m, 3H), 2.51-2.32 (m, 1H), 2.12 (d, J=7.1 Hz, 3H), 2.09-1.95 (m, 3H), 1.95-1.74 (m, 3H), 1.71-1.49 (m, 3H), 1.49-1.31 (m, 1H), 1H exchanged with solvent. Second eluted diastereomer: P=100%, retention time=9.0 min, chiral HPLC: P=100%, $^1$H NMR (300 MHz, CDCl$_3$) δ 8.93 (s, 1H), 8.29 (s, 1H), 8.15 (s, 1H), 7.24 (d, J=9.3 Hz, 1H), 6.89 (d, J=9.5 Hz, 1H), 6.06 (q, J=7.2 Hz, 1H), 4.44-4.33 (m, 1H), 4.15-4.06 (m, 1H), 4.00 (s, 3H), 3.19-3.05 (m, 1H), 2.89 (dd, J=12.8, 9.2 Hz, 1H), 2.80-2.58 (m, 3H), 2.50-2.34 (m, 1H), 2.13 (d, J=7.1 Hz, 3H), 2.10-1.96 (m, 3H), 1.95-1.79 (m, 3H), 1.69-1.54 (m, 3H), 1.50-1.36 (m, 1H), 1H exchanged with solvent.

Compound 259: (3R)—N-(cyclopropylmethyl)-1-(6-(1-(4-(6-(pyrrolidin-1-yl)pyrazin-2-yl)-1H-1,2,3-triazol-1-yl)ethyl)pyridin-3-yl)piperidin-3-amine was Obtained Using General Scheme 1 Pathway A Stage 1: General Procedure C (with addition of 2.3 eq of LiBr) was used between 1-(5-chloropyridin-2-yl)ethan-1-one and IM486 to afford tert-butyl (R)-(1-(6-acetylpyridin-3-yl)piperidin-3-yl)(cyclopropylmethyl)carbamate IM751 as orange oil: 427 mg, 33% yield, P=91%, retention time=2.6 min (gradient A), (M+H)⁺: 374.

Stage 2: General Procedure W was used from IM751 to afford crude tert-butyl ((3R)-1-(6-(1-aminoethyl)pyridin-3-yl)piperidin-3-yl)(cyclopropylmethyl)carbamate IM752 as brown oil: 515 mg, 75% yield, P=71%, retention time=2.4 min (gradient A), (M+H)⁺: 375.

Stage 3: General Procedure V was used from IM752 to afford tert-butyl ((3R)-1-(6-(1-azidoethyl)pyridin-3-yl)piperidin-3-yl)(cyclopropylmethyl)carbamate IM753 as yellow oil: 215 mg, 48% yield, P=87%, retention time=2.6 min (gradient A), (M+H)⁺: 401.

Stage 4: General Procedure B was used between IM753 and IM534 to afford tert-butyl (cyclopropylmethyl)((3R)-1-(6-(1-(4-(6-(pyrrolidin-1-yl)pyrazin-2-yl)-1H-1,2,3-triazol-1-yl)ethyl)pyridin-3-yl)piperidin-3-yl)carbamate IM754 as yellow oil: 61 mg, 96% yield, P=98%, retention time=2.7 min (gradient A), (M+H)⁺: 574.

Stage 2: General Procedure A2 was used from IM754 to afford crude compound 259 as yellow oil: 41 mg, 81% yield, P=97%, retention time=3.0 min (gradient B), (M+H)⁺: 474.

The mixture of diastereomers was purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=100%, retention time=5.1 min, chiral HPLC: P=100%, ¹H NMR (300 MHz, CDCl₃) δ 8.57 (s, 1H), 8.29-8.22 (m, 1H), 8.18 (s, 1H), 7.78 (s, 1H), 7.11 (d, J=1.8 Hz, 2H), 5.91 (q, J=7.1 Hz, 1H), 3.70-3.59 (m, 1H), 3.55-3.38 (m, 5H), 2.92-2.63 (m, 3H), 2.62-2.45 (m, 2H), 2.08-1.89 (m, 8H), 1.85-1.74 (m, 1H), 1.74-1.54 (m, 1H), 1.43-1.22 (m, 1H), 1.02-0.86 (m, 1H), 0.55-0.43 (m, 2H), 0.16-0.07 (m, 2H), 1H exchanged with solvent. Second eluted diastereomer: P=100%, retention time=7.8 min, chiral HPLC: P=99.8%, ¹H NMR (300 MHz, CDCl₃) δ 8.57 (s, 1H), 8.29-8.22 (m, 1H), 8.18 (s, 1H), 7.78 (s, 1H), 7.13-7.05 (m, 2H), 5.90 (q, J=7.1 Hz, 1H), 3.74-3.63 (m, 1H), 3.55-3.46 (m, 4H), 3.46-3.34 (m, 1H), 2.91-2.68 (m, 3H), 2.64-2.50 (m, 2H), 2.08-1.90 (m, 8H), 1.88-1.74 (m, 1H), 1.71-1.53 (m, 1H), 1.47-1.31 (m, 1H), 1.05-0.89 (m, 1H), 0.56-0.41 (m, 2H), 0.22-0.11 (m, 2H), 1H exchanged with solvent.

Compound 260: 6-(1-(1-(5-((R)-3-((cyclopropylmethyl)amino)piperidin-1-yl)pyridin-2-yl)ethyl)-1H-1,2,3-triazol-4-yl)-N,N-dimethylpyrazin-2-amine was Obtained Using General Scheme 1 Pathway A Stage 1: General Procedure X was used between IM753 and IM489 to afford tert-butyl (cyclopropylmethyl)((3R)-1-(6-(1-(4-(6-(dimethylamino)pyrazin-2-yl)-1H-1,2,3-triazol-1-yl)ethyl)pyridin-3-yl)piperidin-3-yl)carbamate IM755 as yellow oil: 35 mg, 58% yield, P=98%, retention time=2.6 min (gradient A), (M+H)⁺: 548.

Stage 2: General Procedure A2 was used from IM755 to afford crude compound 260 as yellow oil: 28 mg, 99% yield, P=99%, retention time=2.8 min (gradient B), (M+H)⁺: 448.

The mixture of diastereomers was purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=99%, retention time=4.7 min, chiral HPLC: P=100%, ¹H NMR (300 MHz, CDCl₃) δ 8.61 (s, 1H), 8.30-8.23 (m, 1H), 8.19 (s, 1H), 7.95 (s, 1H), 7.12 (d, J=1.9 Hz, 2H), 5.92 (q, J=7.1 Hz, 1H), 3.71-3.62 (m, 1H), 3.50-3.40 (m, 1H), 3.14 (s, 6H), 2.92-2.65 (m, 3H), 2.64-2.46 (m, 2H), 2.00 (d, J=6.9 Hz, 3H), 1.97-1.91 (m, 1H), 1.88-1.75 (m, 1H), 1.73-1.59 (m, 1H), 1.45-1.27 (m, 1H), 1.05-0.89 (m, 1H), 0.56-0.44 (m, 2H), 0.20-0.09 (m, 2H), 1H exchanged with solvent. Second eluted diastereomer: P=99%, retention time=8.5 min, chiral HPLC: P=99.2%, ¹H NMR (300 MHz, CDCl₃) δ 8.61 (s, 1H), 8.30-8.24 (m, 1H), 8.20 (s, 1H), 7.95 (s, 1H), 7.16-7.03 (m, 2H), 5.91 (q, J=7.1 Hz, 1H), 3.76-3.67 (m, 1H), 3.45-3.33 (m, 1H), 3.14 (s, 6H), 2.94-2.71 (m, 3H), 2.59 (d, J=7.0 Hz, 2H), 2.00 (d, J=7.0 Hz, 3H), 1.98-1.92 (m, 1H), 1.88-1.76 (m, 1H), 1.72-1.55 (m, 1H), 1.51-1.35 (m, 1H), 1.07-0.92 (m, 1H), 0.58-0.46 (m, 2H), 0.23-0.13 (m, 2H), 1H exchanged with solvent.

Compound 261: (3R)—N-(cyclopropylmethyl)-1-(6-(1-(4-(6-methoxypyrazin-2-yl)-1H-1,2,3-triazol-1-yl)ethyl)pyridin-3-yl)piperidin-3-amine was Obtained Using General Scheme 1 Pathway A Stage 1: General Procedure X was used between IM753 and IM318 to afford tert-butyl (cyclopropylmethyl)((3R)-1-(6-(1-(4-(6-methoxypyrazin-2-yl)-1H-1,2,3-triazol-1-yl)ethyl)pyridin-3-yl)piperidin-3-yl)carbamate IM756 as yellow oil: 44 mg, 75% yield, P=99%, retention time=2.7 min (gradient A), (M+H)⁺: 535.

Stage 2: General Procedure A2 was used from IM756 to afford crude compound 261 as yellow oil: 15 mg, 41% yield, P=96%, retention time=2.9 min (gradient B), (M+H)⁺: 435.

The mixture of diastereomers was purified by chiral preparative HPLC purification using Chiralpak ID column (5 μm, 10×250 mm). Eluent used: TBME/MeOH/DCM/DEA: 40/40/20/0.1% at flow rate of 7 mL/min. First eluted diastereomer: P=100%, retention time=5.3 min, chiral HPLC: P=100%, ¹H NMR (300 MHz, CDCl₃) δ 8.92 (s, 1H), 8.32-8.26 (m, 1H), 8.24 (s, 1H), 8.13 (s, 1H), 7.19-7.10 (m, 2H), 5.93 (q, J=7.1 Hz, 1H), 4.00 (s, 3H), 3.70-3.61 (m, 1H), 3.51-3.42 (m, 1H), 2.94-2.63 (m, 3H), 2.63-2.45 (m, 2H), 2.01 (d, J=7.1 Hz, 3H), 1.99-1.92 (m, 1H), 1.88-1.75 (m, 1H), 1.75-1.55 (m, 1H), 1.41-1.22 (m, 1H), 1.02-0.85 (m, 1H), 0.55-0.43 (m, 2H), 0.15-0.08 (m, 2H), 1H exchanged with solvent. Second eluted diastereomer: P=100%, retention time=13.9 min, chiral HPLC: P=100%, ¹H NMR (300 MHz, CDCl₃) § 8.92 (s, 1H), 8.30-8.26 (m, 1H), 8.24 (s, 1H), 8.13 (s, 1H), 7.20-7.07 (m, 2H), 5.93 (q, J=7.1 Hz, 1H), 4.00 (s, 3H), 3.72-3.61 (m, 1H), 3.51-3.41 (m, 1H), 2.93-2.64 (m, 3H), 2.63-2.46 (m, 2H), 2.01 (d, J=7.0 Hz, 3H), 1.99-1.90 (m, 1H), 1.85-1.76 (m, 1H), 1.73-1.56 (m, 1H), 1.44-1.28 (m, 1H), 1.03-0.90 (m, 1H), 0.56-0.46 (m, 2H), 0.18-0.08 (m, 2H), 1H exchanged with solvent.

Compound 262: (R)-3-(5-(3-((cyclobutylmethyl)amino)piperidin-1-yl)pyridin-2-yl)-N-(6-(pyrrolidin-1-yl)pyrazin-2-yl)oxetane-3-carboxamide was Obtained Using General Scheme 6 Pathway B Stage 1: To a solution of IM688 (30 mg, 0.06 mmol) and HATU (36 mg, 0.09 mmol) in anhydrous DMF (0.2 mL) were added IM722 (12 mg, 0.07 mmol) and DIEA (0.04 mL, 0.25 mmol). The reaction mixture was stirred at 45° C. for 2 h. The reaction was then cooled to rt. The reaction mixture was diluted with water (10 mL) and extracted with EtOAc (3×20 mL). The organic layers were merged and washed with brine (2×10 mL). The organic layer was dried over MgSO₄, filtered and concentrated under reduced pressure to dryness. The crude material was purified by an automated flash chromatography system (liquid injection in DCM, 0 to 5% MeOH in DCM) to afford tert-butyl (R)-(cyclobutylmethyl)(1-(6-(3-((6-(pyrrolidin-1-yl)pyrazin-2-yl)carbamoyl)

oxetan-3-yl)pyridin-3-yl)piperidin-3-yl)carbamate IM757: 33 mg, 65% yield, P=73% (¹H NMR), retention time=2.8 min (gradient A), (M+H)⁺: 592.

Stage 2: General Procedure A2 was used from IM757 to afford crude compound 262 as yellow oil: 20 mg, 43% yield, P=52%, retention time=2.9 min (gradient B), (M+H)⁺: 492.

The product was purified by reverse phase preparative HPLC purification (XBridge OBD C18 5 µm, 19×100 mm). Gradient used: increased linearly from 30% to 45% solution "B" over 4.5 min, increased linearly to 88% solution "B" over 2.0 min, held to 88% solution "B" for 0.3 min, and returned to initial conditions over 1.0 min. Flow Rate: 15 mL/min. P=99%. ¹H NMR (300 MHz, CDCl₃) δ 8.69 (s, 1H), 8.55 (s, 1H), 8.34 (d, J=2.7 Hz, 1H), 7.61 (s, 1H), 7.22 (dd, J=8.7, 2.8 Hz, 1H), 7.17 (d, J=8.7 Hz, 1H), 5.37 (dd, J=6.0, 2.1 Hz, 2H), 5.07 (d, J=6.0 Hz, 2H), 3.71-3.62 (m, 1H), 3.55-3.36 (m, 5H), 2.96-2.81 (m, 1H), 2.81-2.62 (m, 4H), 2.53-2.37 (m, 1H), 2.17-1.77 (m, 9H), 1.77-1.59 (m, 3H), 1.38-1.26 (m, 2H), 1H exchanged with solvent.

Compound 263: (R)-3-(5-(3-(((3-fluorobicyclo [1.1.1]pentan-1-yl)methyl)amino)piperidin-1-yl) pyridin-2-yl)-N-(4-oxo-4H-pyrido[1,2-a]pyrimidin-2-yl)oxetane-3-carboxamide was Obtained Using General Scheme 6 Pathway B Stage 1: General Procedure Y was used between IM520 and IM62 to afford tert-butyl (R)-(1-(6-(3-cyanooxetan-3-yl)pyridin-3-yl)piperidin-3-yl)((3-fluorobicyclo[1.1.1]pentan-1-yl)methyl)carbamate IM758 as orange oil: 95 mg, 51% yield, P=82%, retention time=3.0 min (gradient A), (M+H)⁺: 457.

Stage 2: To flask equipped with a stir bar was added IM758 (95 mg, 0.17 mmol), ethanol (0.55 mL) and a solution of sodium hydroxide (28 mg, 0.69 mmol) in water (0.30 mL). The flask was heated to 80° C. for 1.5 h. Extra sodium hydroxide (20 mg, 0.50 mmol) was added and the mixture was stirred for 1 h more. The crude reaction mixture was concentrated under reduced pressure and the residue was dissolved in water (10 mL), and washed with Et₂O (20 mL). Layers were separated and aqueous layer was acidified to pH ~2.4 (check with pH-meter) with 1 N HCl (aqueous). Acidic solution was extracted with DCM (3×15 mL). The organic phases were merged, dried over magnesium sulfate, filtered, and concentrated under reduced pressure to afford (R)-3-(5-(3-((tert-butoxycarbonyl)((3-fluorobicyclo[1.1.1] pentan-1-yl)methyl)amino)piperidin-1-yl)pyridin-2-yl)oxetane-3-carboxylic acid IM759 as orange oil: 80 mg, 83% yield, P=97%, retention time=2.5 min (gradient A), (M+H)⁺: 476.

Stage 3: General Procedure F was used between IM759 and IM613 to afford tert-butyl (R)-((3-fluorobicyclo[1.1.1] pentan-1-yl)methyl)(1-(6-(3-((4-oxo-4H-pyrido[1,2-a]pyrimidin-2-yl)carbamoyl)oxetan-3-yl)pyridin-3-yl)piperidin-3-yl)carbamate IM760 as yellow oil: 7 mg, 7% yield, P=89%, retention time=2.7 min (gradient A), (M+H)⁺: 619.

Stage 4: General Procedure A2 was used from IM760 to afford crude compound 263 as colourless oil: 7 mg, 95% yield, P=72%, retention time=2.1 min (gradient A), (M+H)⁺: 519.

The product was purified by reverse phase preparative HPLC purification (XBridge OBD C18 5 µm, 19×100 mm). Gradient used: increased linearly from 20% to 40% solution "B" over 4.5 min, increased linearly to 85% solution "B" over 1.5 min, and returned to initial conditions over 1.0 min. Flow Rate: 15 ml/min. P=94%. ¹H NMR (300 MHz, CDCl₃) δ 9.07-8.93 (m, 2H), 8.38 (s, 1H), 7.67 (dd, J=9.0, 6.7 Hz, 1H), 7.45-7.34 (m, 2H), 7.25-7.16 (m, 2H), 7.07-6.97 (m, 1H), 5.37 (d, J=6.1 Hz, 2H), 5.04 (d, J=6.1 Hz, 2H), 3.71-3.61 (m, 1H), 3.56-3.46 (m, 1H), 3.01-2.84 (m, 3H), 2.83-2.64 (m, 2H), 1.98 (d, J=2.6 Hz, 6H), 1.93-1.79 (m, 1H), 1.75-1.58 (m, 1H), 1.43-1.23 (m, 2H), 1H exchanged with solvent. ¹⁹F NMR (282 MHZ, CDCl₃) δ −142.43.

Compound 264: 2-(5-((R)-3-((cyclobutylmethyl) amino)piperidin-1-yl)pyridin-2-yl)-N-(5-(pyrrolidin-1-yl)pyridin-3-yl)propanamide was Obtained Using General Scheme 6 Pathway B Stage 1: To a solution of methyl 2-(5-bromopyridin-2-yl) acetate (500 mg, 2.13 mmol) in THF (5 mL) was added at 0° C. lithium bis(trimethylsilyl)amide solution (2.56 mL, 2.56 mmol). The reaction mixture was stirred at that temperature for 30 min before the addition of iodomethane (201 µL, 3.19 mmol). Then the reaction mixture was stirred at rt for 30 min. The reaction mixture was partitioned between ethyl acetate (30 mL) and water (10 mL). The layers were separated and the organic one was washed with water, dried over sodium sulfate, concentrated and purified by normal chromatography (Teledyne ISCO, Nextgen 300+ combiflash; column: silica gel; solvent: Hexane/EtOAc 100/0 to 90/10) to afford methyl 2-(5-bromopyridin-2-yl)propanoate IM761 as a yellow oil: 360 mg, 69% yield, P=100%, retention time=1.0 min (gradient C), (M+H)⁺: 244/246.

Stage 2: General Procedure Y was used between IM761 and IM3 to afford methyl 2-(5-((R)-3-((tert-butoxycarbonyl) (cyclobutylmethyl)amino)piperidin-1-yl)pyridin-2-yl)propanoate IM762: 253 mg, 44% yield, P=68%, retention time=1.9 min (gradient C), (M+H)⁺: 432.

Stage 3: To a solution of IM762 (253 mg, 398 µmol) in THF (1.37 mL) and MeOH (649 µL) was added a solution of lithium hydroxide, monohydrate (31.7 mg, 717 µmol) in water (1.00 mL) and the mixture was stirred at rt for 1 h. After analysis, lithium hydroxide, monohydrate (10.0 mg, 227 µmol) was added and the reaction was continued for another 1.65 h. The reaction mixture was concentrated in vacuo (removing organic solvents) and acidified with 6 N HCl. The mixture was purified on a C-18 column using 3%-100% MeCN in aqueous ammonium bicarbonate to afford 2-(5-((R)-3-((tert-butoxycarbonyl)(cyclobutylmethyl)amino)piperidin-1-yl)pyridin-2-yl)propanoic acid IM763 as a white solid: 170 mg, 98% yield, P=96%, retention time=1.6 min (gradient C), (M+H)⁺: 418.

Stage 4: To a mixture of IM763 (53.6 mg, 128 µmol) and HATU (88.7 mg, 228 µmol) were added N,N-Diisopropylethylamine (110 µL, 625 µmol), DMF (200 µL) and EtOAc (900 µL). Then IM558 (39.4 mg, 241 µmol) and EtOAc (600 µL) were added and the mixture was stirred at rt for 2 h. The mixture was concentrated in vacuo and directly purified on a C-18 column using 5%-100% MeCN in aqueous ammonium bicarbonate to afford tert-butyl (cyclobutylmethyl) ((3R)-1-(6-(1-oxo-1-((5-(pyrrolidin-1-yl)pyridin-3-yl) amino)propan-2-yl)pyridin-3-yl)piperidin-3-yl)carbamate IM764: 55 mg, 66% yield, P=86%, retention time=1.9 min (gradient C), (M+H)⁺: 564.

Stage 5: General Procedure A2 was used from IM764 to afford compound 264 as a white solid: 30 mg, 78% yield, P=100%, retention time=2.8 min (gradient E), (M+H)⁺: 463.

The mixture of diastereomers was further purified by chiral preparative HPLC purification using Chiralpak ID column (5 µm, 10×250 mm). Eluent used: TBME/MeOH/ DCM/DEA: 40/20/40/0.1% at flow rate of 7 mL/min. First eluted diastereomer: P=100%, retention time=4.2 min, chiral HPLC: P=100%, ¹H NMR (300 MHz, CDCl₃) δ 9.50 (s, 1H), 8.30 (d, J=2.9 Hz, 1H), 7.77 (d, J=2.1 Hz, 1H), 7.67 (d, J=2.6 Hz, 1H), 7.53 (d, J=2.4 Hz, 1H), 7.19 (dd, J=8.6, 2.9 Hz, 1H), 7.12 (d, J=8.6 Hz, 1H), 3.78 (q, J=7.1 Hz, 1H), 3.70-3.60 (m, 1H), 3.51-3.41 (m, 1H), 3.35-3.24 (m, 4H), 2.93-2.61 (m, 5H), 2.55-2.36 (m, 1H), 2.17-1.79 (m, 9H), 1.75-1.57 (m, 7H), 1.45-1.24 (m, 1H), 1H exchanged with solvent. Second eluted diastereomer: P=100%, retention time=7.6 min, chiral HPLC: P=99.1, $^1$H NMR (300 MHz, CDCl$_3$) δ 9.43 (s, 1H), 8.23 (d, J=2.9 Hz, 1H), 7.70 (d, J=2.1 Hz, 1H), 7.60 (d, J=2.6 Hz, 1H), 7.50-7.42 (m, 1H), 7.12 (dd, J=8.6, 2.9 Hz, 1H), 7.06 (d, J=8.6 Hz, 1H), 3.71 (q, J=7.2 Hz, 1H), 3.62-3.52 (m, 1H), 3.45-3.35 (m, 1H), 3.28-3.17 (m, 4H), 2.86-2.53 (m, 5H), 2.47-2.31 (m, 1H), 2.10-1.73 (m, 9H), 1.72-1.46 (m, 7H), 1.35-1.17 (m, 1H), 1H exchanged with solvent.

Compound 265: 2-(5-((R)-3-((cyclobutylmethyl) amino)piperidin-1-yl)pyridin-2-yl)-N-(4-oxo-4H-pyrido[1,2-a]pyrimidin-2-yl)propanamide was Obtained Using General Scheme 6 Pathway B Stage 1: General Procedure F was used between IM763 and IM613 to afford tert-butyl (cyclobutylmethyl)((3R)-1-(6-(1-oxo-1-((4-oxo-4H-pyrido[1,2-a]pyrimidin-2-yl) amino)propan-2-yl)pyridin-3-yl)piperidin-3-yl)carbamate IM765: 95 mg, 66% yield, P=99%, retention time=1.8 min (gradient C), (M+H)$^+$: 561.

Stage 2: General Procedure A2 was used from IM765 to afford compound 265 as a white solid: 73 mg, 93% yield, P=100%, retention time=2.5 min (gradient E), (M+H)$^+$: 461.

The mixture of diastereomers was further purified by chiral preparative HPLC purification using Chiralpak IE column (5 μm, 10×250 mm). Eluent used: TBME/MeOH/DCM/DEA: 40/20/40/0.1% at flow rate of 7 mL/min. First eluted diastereomer: P=100%, retention time=7.9 min, chiral HPLC: P=99.1%, $^1$H NMR (300 MHz, CDCl$_3$) δ 9.82 (s, 1H), 8.95 (d, J=6.6 Hz, 1H), 8.35 (d, J=2.9 Hz, 1H), 7.70-7.58 (m, 1H), 7.46-7.39 (m, 1H), 7.36 (s, 1H), 7.17 (dd, J=8.5, 3.0 Hz, 1H), 7.10 (d, J=8.6 Hz, 1H), 7.04-6.93 (m, 1H), 3.80 (q, J=7.2 Hz, 1H), 3.70-3.61 (m, 1H), 3.52-3.41 (m, 1H), 2.92-2.61 (m, 5H), 2.54-2.35 (m, 1H), 2.17-2.01 (m, 2H), 2.01-1.78 (m, 4H), 1.74-1.57 (m, 6H), 1.44-1.23 (m, 1H), 1H exchanged with solvent. Second eluted diastereomer: P=99%, retention time=11.4 min, chiral HPLC: P=98.4%, $^1$H NMR (300 MHz, CDCl$_3$) δ 9.81 (s, 1H), 8.95 (dd, J=7.4, 1.5 Hz, 1H), 8.35 (d, J=2.9 Hz, 1H), 7.64 (ddd, J=8.6, 6.6, 1.6 Hz, 1H), 7.45-7.40 (m, 1H), 7.36 (s, 1H), 7.18 (dd, J=8.6, 2.9 Hz, 1H), 7.11 (d, J=8.6 Hz, 1H), 7.05-6.93 (m, 1H), 3.81 (q, J=7.2 Hz, 1H), 3.71-3.62 (m, 1H), 3.52-3.39 (m, 1H), 2.92-2.80 (m, 1H), 2.72 (dd, J=8.7, 4.9 Hz, 4H), 2.58-2.37 (m, 1H), 2.16-2.02 (m, 2H), 2.02-1.76 (m, 4H), 1.76-1.57 (m, 6H), 1.44-1.22 (m, 1H), 1H exchanged with solvent.

Compound 266: 4-((R)-3-((cyclopropylmethyl) amino)piperidin-1-yl)-1-(1-(4-(5-(dimethyl amino) pyridin-3-yl)-1H-imidazol-1-yl)ethyl)pyridin-2(1H)-one was Obtained Using General Scheme 4 Pathway A Stage 1: General Procedure C was used between IM302 and IM486 to afford tert-butyl ((3R)-1-(1-(1-(4-bromo-1H-imidazol-1-yl)ethyl)-2-oxo-1,2-dihydropyridin-4-yl)piperidin-3-yl)(cyclopropylmethyl)carbamate IM766 as a yellow solid: 427 mg, 61% yield, P=98%, retention time=1.6 min (gradient C), (M+H)$^+$: 520/522.

Stage 2: General Procedure U was used between IM494 and IM766 to afford tert-butyl (cyclopropylmethyl)((3R)-1-(1-(1-(4-(5-(dimethylamino)pyridin-3-yl)-1H-imidazol-1-yl)ethyl)-2-oxo-1,2-dihydropyridin-4-yl)piperidin-3-yl)carbamate IM767 as a brown foam: 67 mg, 15% yield, P=97%, retention time=1.5 min (gradient C), (M+H)$^+$: 562.

Stage 3: General Procedure A2 was used from IM767 to afford compound 266 as a white solid: 33 mg, 62% yield, P=100%, retention time=2.1 min (gradient E), (M+H)$^+$: 462.

The mixture of diastereomers was further purified by chiral preparative HPLC purification using Chiralpak ID column (5 μm, 10×250 mm). Eluent used: TBME/MeOH/DCM/DEA: 40/40/20/0.1% at flow rate of 7 mL/min. First eluted diastereomer: P=98%, retention time=5.3 min, chiral HPLC: P=100%, $^1$H NMR (300 MHz, CDCl$_3$) δ 8.27 (s, 1H), 7.99 (d, J=3.0 Hz, 1H), 7.79 (s, 1H), 7.45-7.37 (m, 2H), 7.30-7.20 (m, 1H), 6.96 (d, J=8.1 Hz, 1H), 5.94 (dd, J=8.0, 2.8 Hz, 1H), 5.66 (d, J=2.9 Hz, 1H), 3.80-3.70 (m, 1H), 3.61-3.51 (m, 1H), 2.98 (s, 6H), 2.97-2.83 (m, 1H), 2.82-2.59 (m, 2H), 2.59-2.43 (m, 2H), 2.03-1.95 (m, 1H), 1.92 (d, J=6.9 Hz, 3H), 1.79-1.68 (m, 1H), 1.60-1.46 (m, 1H), 1.38 (t, J=11.4 Hz, 1H), 0.98-0.83 (m, 1H), 0.52-0.40 (m, 2H), 0.14-0.04 (m, 2H), 1H exchanged with solvent. Second eluted diastereomer: P=99%, retention time=7.2 min, chiral HPLC: P=100%, $^1$H NMR (300 MHz, CDCl$_3$) δ 8.13 (d, J=1.8 Hz, 1H), 7.86 (d, J=3.1 Hz, 1H), 7.65 (d, J=1.4 Hz, 1H), 7.31-7.24 (m, 2H), 7.12 (q, J=4.8 Hz, 1H), 6.81 (d, J=8.0 Hz, 1H), 5.80 (dd, J=8.1, 2.9 Hz, 1H), 5.53 (d, J=2.9 Hz, 1H), 3.68-3.58 (m, 1H), 3.49-3.39 (m, 1H), 2.85 (s, 6H), 2.83-2.71 (m, 1H), 2.69-2.47 (m, 2H), 2.40-2.31 (m, 2H), 1.91-1.82 (m, 1H), 1.79 (d, J=7.0 Hz, 3H), 1.67-1.53 (m, 1H), 1.48-1.33 (m, 1H), 1.32-1.19 (m, 1H), 0.82-0.72 (m, 1H), 0.39-0.27 (m, 2H), 0.02--0.07 (m, 2H), 1H exchanged with solvent.

Compound 267: (R)—N-(cyclo)-1-(6-(3-(4-(5-methoxypyridin-3-yl)-1H-imidazol-1-yl)oxetan-3-yl) pyridin-3-yl)piperidin-3-amine was Obtained Using General Scheme 4 Pathway D Stage 1: (R)-3-Boc-aminopiperidine hydrochloride (2 g, 8.11 mmol), 2-bromo-5-iodopyridine (2.20 g, 7.52 mmol), XantPhos (673 mg, 1.13 mmol), Pd$_2$(dba)$_3$ (344 mg, 0.380 mmol) and potassium tert-butoxide (2.53 g, 22.55 mmol) were added in a round bottom flask. The reaction mixture was evacuated and backfilled with argon (3×) before dry toluene (50 mL) was added and the solution heated at 90° C. for 17 h. The reaction was cooled to rt, diluted with AcOEt (30 mL) and filtered through celite. The celite was rinsed with AcOEt (50 mL) and the filtrate was concentrated under reduced pressure. The crude material was purified by an automated flash chromatography system (dryload in silica, 0 to 50% EtOAc in Heptane) to afford tert-butyl (R)-(1-(6-bromopyridin-3-yl)piperidin-3-yl)carbamate IM768 as a yellow solid: 1.32 g, 49% yield, P=99%, retention time=2.9 min (gradient A), (M+H)$^+$: 356/358.

Stage 2: Sodium hydride (655 mg, 16.38 mmol) was poured in a solution of IM768 (1.47 g, 4.09 mmol) in dry DMF (27 mL) at 0° C. The reaction mixture was stirred for 30 min before (bromomethyl)cyclobutane (1.40 mL, 12.21 mmol) was added dropwise and allowed to warm to rt and stirred for 16 h. The reaction mixture was quenched with NH$_4$Cl (100 mL) and extracted with EtOAc (3×100 mL). The organic layers were merged and washed with water (3×100 mL), followed by brine (100 mL). The organic layer was dried over MgSO$_4$, filtered and concentrated under reduced pressure to dryness. The crude material was purified by an automated flash chromatography system (dryload in silica, 0 to 80% EtOAc in Heptane) to afford tert-butyl (R)-(1-(6-bromopyridin-3-yl)piperidin-3-yl)(cyclobutylmethyl)carbamate IM769 as light yellow gum: 761 mg, 43% yield, P=99%, retention time=3.5 min (gradient A), (M+H)$^+$: 424/426.

Stage 3: To a solution of IM769 (761 mg, 1.78 mmol) in dry THF (12 mL) under argon at −78° C. was added n-butyl lithium in hexane (1.30 mL, 2.08 mmol) dropwise over 5 s (which turned the reaction red). After 5 min, 3-oxetanone (165 µL, 2.52 mmol) was added dropwise over 5 s at −78° C. The resulting solution was stirred for 5 min at −78° C. and then slowly allowed to warm to rt over 55 min (dry ice/acetone bath removed). The reaction mixture was quenched with a saturated aqueous solution of NH$_4$Cl (50 mL) and extracted with EtOAc (3×50 mL). The organic layers were merged, dried over MgSO$_4$, filtered and concentrated under reduced pressure to dryness. The crude material was purified by an automated flash chromatography system (dryload in silica, 0 to 100% EtOAc in Heptane) to afford tert-butyl (R)-(cyclobutylmethyl)(1-(6-(3-hydroxyoxetan-3-yl)pyridin-3-yl)piperidin-3-yl)carbamate IM770 as light yellow gum: 497 mg, 54% yield, P=81%, retention time=2.5 min (gradient A), (M+H)$^+$: 418.

Stage 4: General Procedure P was used from IM770 to afford crude (R)-3-(5-(3-((tert-butoxycarbonyl)(cyclobutylmethyl)amino)piperidin-1-yl)pyridin-2-yl)oxetan-3-yl methanesulfonate IM771 as a yellow foam: 260 mg, 99% yield, P=82% ($^1$H-NMR).

Stage 5: 4-Iodoimidazole (172 mg, 0.87 mmol) and potassium carbonate (199 mg, 1.43 mmol) were added to a solution of IM771 (214.61 mg, 0.43 mmol) in dry DMF (3 mL) at rt under argon. The reaction mixture was stirred for 1 h at 60° C. The reaction mixture was quenched with saturated aqueous solution of NH$_4$Cl (30 mL) and extracted with EtOAc (3×30 mL). The organic layers were merged and washed with water (3×30 mL), followed by brine (30 mL). The organic layer was dried over MgSO$_4$, filtered and concentrated under reduced pressure to dryness. The crude material was purified by an automated flash chromatography system (liquid injection in DCM, 0 to 3% MeOH in DCM) to afford crude tert-butyl (R)-(cyclobutylmethyl)(1-(6-(3-(4-iodo-1H-imidazol-1-yl)oxetan-3-yl)pyridin-3-yl)piperidin-3-yl)carbamate IM772 as a light yellow gum: 53 mg, 19% yield, P=91%, retention time=2.8 min (gradient A), (M+H)$^+$: 594.

Stage 6: General Procedure U was used from IM772 to afford tert-butyl (R)-(cyclobutylmethyl)(1-(6-(3-(4-(5-methoxypyridin-3-yl)-1H-imidazol-1-yl)oxetan-3-yl)pyridin-3-yl)piperidin-3-yl)carbamate IM773 as a white solid: 22 mg, 41% yield, P=86%, retention time=2.6 min (gradient A), (M+H)$^+$: 575.

Stage 7: General Procedure A2 was used from IM773 to afford crude compound 267 as an off-white solid: 16 mg, 97% yield, P=95%, retention time=2.0 min (gradient B), (M+H)$^+$: 475. $^1$H NMR (300 MHz, CDCl$_3$) δ 8.53 (d, J=1.8 Hz, 1H), 8.36 (d, J=3.0 Hz, 1H), 8.18 (d, J=2.8 Hz, 1H), 7.67 (dd, J=2.8, 1.7 Hz, 1H), 7.59 (d, J=1.4 Hz, 1H), 7.36 (d, J=1.4 Hz, 1H), 7.13 (dd, J=8.7, 3.0 Hz, 1H), 6.78 (d, J=8.7 Hz, 1H), 5.45 (d, J=6.7 Hz, 2H), 5.21 (d, J=6.7 Hz, 2H), 3.89 (s, 3H), 3.75-3.58 (m, 1H), 3.58-3.47 (m, 1H), 2.96-2.83 (m, 1H), 2.78-2.63 (m, 4H), 2.52-2.35 (m, 1H), 2.15-1.77 (m, 7H), 1.75-1.60 (m, 3H), 1H exchanged with solvent.

Compound 268: (R)-3-(5-(3-((cyclobutylmethyl)amino)piperidin-1-yl)pyridin-2-yl)-N-(6-cyclopentylpyrazin-2-yl)oxetane-3-carboxamide was Obtained Using General Scheme 6 Pathway B Stage 1: n-Butyl lithium in hexane (6.80 mL, 17 mmol) was added dropwise (over 5 min) to a mixture of 2,6-dibromopyrazine (2 g, 8.41 mmol) in anhydrous DCM (20 mL) at −78° C., then cyclopentanone (2.30 mL, 25.74 mmol) was added dropwise (over 5 min) to the suspension at −78° C. The reaction mixture was stirred at −78° C. for 30 min under argon. Saturated aqueous ammonium chloride solution (30 mL) was added and reaction mixture was allowed to stir a rt. Then, reaction mixture was extracted with EtOAc (60 mL×3), and the organic layers were merged, washed with brine (30 mL). The organic layer was dried over MgSO$_4$, filtered, and concentrated under reduced pressure to give a orange oil. The crude material was purified by an automated flash chromatography system (liquid injection in n-heptane, 0 to 50% EtOAc in Heptane to afford 2-(6-bromopyrazin-2-yl)cyclopentan-1-ol IM774 as yellow oil: 1.94 g, 89% yield, P=94%, retention time=2.6 min (gradient A), (M+H)$^+$: 243/245.

Stage 2: Into a sealed tube, 2,4-dimethoxybenzylamine (684 µL, 4.46 mmol), IM774 (0.94 g, 3.63 mmol) and triethylamine (684 µL, 4.91 mmol) were mixed in anhydrous NMP (3.6 mL).

Tube was sealed and mixture was stirred at 120° C. for 16 h. The reaction mixture was cooled to rt, diluted with EtOAc (200 mL) and washed with water (2×100 mL) and then brine (50 mL). Organic layer was dried over MgSO$_4$, filtered and concentrated under reduced pressure to dryness to afford 2-(6-((3,4-dimethylbenzyl)amino)pyrazin-2-yl)cyclopentan-1-ol IM775 as orange oil: 713 mg, 50% yield, P=84%, retention time=2.4 min (gradient A), (M+H)$^+$: 330.

Stage 3: To a mixture of M775 (0.60 g, 1.53 mmol) in anhydrous pyridine (15.3 mL) under Ar atmosphere at 0° C. was added thionyl chloride (1.20 mL, 16.29 mmol) and resulting brown solution was stirred at 0° C. for 50 min and at rt for 20 min. Reaction mixture was cooled to 0° C., quenched with NaHCO$_3$ saturated solution (50 mL) and extracted with EtOAc (4×100 mL). Organics layers were merged, washed with brine (2×50 mL), dried over MgSO$_4$, filtered and concentrated under reduced pressure to afford brown solid. The crude material was purified by an automated flash chromatography system (dryload, 0 to 55% EtOAc in Heptane) to afford 6-(cyclopent-1-en-1-yl)-N-(3,4-dimethylbenzyl)pyrazin-2-amine IM776 as yellow solid: 223 mg, 46% yield, P=99%, retention time=2.7 min (gradient A), (M+H)$^+$: 312.

Stage 4: To a solution of IM776 (194 mg, 0.62 mmol) in anhydrous methanol (6.2 mL) was added palladium on activated carbon (65 mg, 0.06 mmol). Suspension was flushed with argon (3×) and then with hydrogen. Reaction was stirred at rt for 1.5 h. Reaction was filtered on celite pad, rinsed-off with MeOH (3×20 mL). Filtrate was concentrated under reduced pressure to afford a yellow oil. The crude material was purified by an automated flash chromatography system (liquid injection in DCM, 0 to 1% MeOH in DCM) to afford 6-cyclopentyl-N-(3,4-dimethylbenzyl)pyrazin-2-amine IM777 as colourless oil: 188 mg, 90% yield, P=93%, retention time=2.6 min (gradient A), (M+H)$^+$: 314.

Stage 5: General Procedure A2 was used from IM777 to afford 6-cyclopentylpyrazin-2-amine IM778 as a white solid: 95 mg, 97% yield, P=93%, retention time=2.0 min (gradient A), (M+H)$^+$: 164.

Stage 6: Into a vial, to a solution of IM688 (40 mg, 0.08 mmol) and HATU (38 mg, 0.10 mmol) in anhydrous DMF (0.30 mL) were added DIEA (100 µL, 0.57 mmol) and IM778 (20 mg, 0.11 mmol). Tube was sealed and reaction was stirred at 45° C. for 1.3 h. Extra HATU (38 mg, 0.10 mmol) and DIEA (100 µL, 0.57 mmol) were added to the reaction mixture and a 3$^{rd}$ addition of HATU (31 mg, 0.08 mmol) after 1.7 h more. After 4.2 h more, the reaction mixture was cooled to rt, diluted with water (10 mL) and extracted with EtOAc (3×20 mL). The organic layers were merged and washed with brine (2×10 mL), dried over MgSO$_4$, filtered and concentrated under reduced pressure to dryness to afford brown oil. The crude material was purified by an automated flash chromatography system (liquid injection in toluene, 0 to 40% EtOAc in heptane) to afford tert-butyl (R)-(cyclobutylmethyl)(1-(6-(3-((6-cyclopentylpyrazin-2-yl)carbamoyl)oxetan-3-yl)pyridin-3-yl)piperidin-3-yl)carbamate IM779 as colourless oil: 16 mg, 20% yield, P=62%, retention time=3.2 min (gradient A), (M+H)$^+$: 591.

Stage 7: General Procedure A2 was used from IM779 to afford crude compound 268 as colourless oil: 12 mg, 70% yield, P=57%, retention time=3.5 min (gradient B), (M+H)$^+$: 491.

The product was purified by reverse phase preparative HPLC purification (XBridge OBD C18 5 μm, 19×100 mm). Gradient used: increased linearly from 30% to 45% solution "B" over 4.5 min, increased linearly to 88% solution "B" over 2.0 min, held to 88% for 0.3 min, and returned to initial conditions over 1.0 min. Flow Rate: 15 mL/min. P=100%. $^1$H NMR (300 MHz, CDCl$_3$) δ 9.31 (s, 1H), 8.98 (s, 1H), 8.37 (d, J=2.6 Hz, 1H), 8.19 (s, 1H), 7.25-7.15 (m, 2H), 5.38 (dd, J=6.0, 1.1 Hz, 2H), 5.07 (d, J=6.0 Hz, 2H), 3.73-3.64 (m, 1H), 3.57-3.47 (m, 1H), 3.15-3.01 (m, 1H), 2.97-2.82 (m, 1H), 2.81-2.58 (m, 4H), 2.53-2.38 (m, 1H), 2.19-1.94 (m, 5H), 1.92-1.61 (m, 11H), 1.42-1.23 (m, 2H), 1H exchanged with solvent.

Compound 269: (R)-3-(5-(3-(((3-fluorobicyclo [1.1.1]pentan-1-yl)methyl)amino)piperidin-1-yl) pyridin-2-yl)-N-(6-(pyrrolidin-1-yl)pyrazin-2-yl) oxetane-3-carboxamide was Obtained Using General Scheme 6 Pathway B Stage 1: General Procedure F was used between IM759 and IM722 to afford tert-butyl (R)-((3-fluorobicyclo[1.1.1] pentan-1-yl)methyl)(1-(6-(3-((6-(pyrrolidin-1-yl)pyrazin-2-yl)carbamoyl)oxetan-3-yl)pyridin-3-yl)piperidin-3-yl)carbamate IM780 as yellow oil: 38 mg, 58% yield, P=89%, retention time=2.7 min (gradient A), (M+H)$^+$: 619.

Stage 2: General Procedure A2 was used from IM780 to afford crude compound 269 as colourless oil: 30 mg, 94% yield, P=72%, retention time=2.1 min (gradient A), (M+H)$^+$: 519.

The product was purified by reverse phase preparative HPLC purification (XBridge OBD C18 5 μm, 19×100 mm). Gradient used: increased linearly from 30% to 45% solution "B" over 5.0 min, increased linearly to 88% solution "B" over 1.2 min, held to 88% for 0.6 min, and returned to initial conditions over 1.0 min. Flow Rate: 15 mL/min. P=100%. $^1$H NMR (300 MHz, CDCl$_3$) δ 8.69 (s, 1H), 8.53 (s, 1H), 8.33 (d, J=2.7 Hz, 1H), 7.61 (s, 1H), 7.24-7.12 (m, 2H), 5.37 (dd, J=6.0, 2.7 Hz, 2H), 5.06 (d, J=6.0 Hz, 2H), 3.69-3.59 (m, 1H), 3.55-3.36 (m, 5H), 2.96 (s, 2H), 2.94-2.83 (m, 1H), 2.82-2.63 (m, 2H), 2.04-1.91 (m, 11H), 1.89-1.77 (m, 1H), 1.76-1.62 (m, 1H), 1.43-1.24 (m, 1H), 1H exchanged with solvent. $^{19}$F NMR (282 MHZ, CDCl$_3$) δ −142.43.

Compound 270: N-(6-(3-azabicyclo[3.1.0]hexan-3-yl)pyrazin-2-yl)-3-(5-((R)-3-((cyclobutyl methyl) amino)piperidin-1-yl)pyridin-2-yl)oxetane-3-carboxamide was Obtained Using General Scheme 6 Pathway B Stage 1: To a solution of 3-azabicyclo[3.1.0]hexane hydrochloride (200 mg, 1.59 mmol) in dry methanol (3 mL) was added 2,6-dibromopyrazine (0.30 g, 1.24 mmol). The mixture was stirred at rt for 16 h. The mixture was quenched with water (50 mL) and extracted with DCM (50 mL×3). The organic layer was dried over MgSO$_4$, filtered and concentrated under reduced pressure. The crude material was purified by an automated flash chromatography system (dryload in silica, 0 to 30% EtOAc in Heptane) to afford 3-(6-bromopyrazin-2-yl)-3-azabicyclo[3.1.0]hexane IM781: 242 mg, 55% yield, P=67%, retention time=2.8 min (gradient A), (M+H)$^+$: 228/230.

Stage 2: In a tube, were added IM781 (242 mg, 0.68 mmol), cesium carbonate (600 mg, 1.81 mmol), tert-butylcarbamate (250 mg, 2.09 mmol), XantPhos (60 mg, 0.10 mmol), Pd$_2$(dba)$_3$ (65 mg, 0.07 mmol). The tube was flushed with argon, anhydrous and previously degassed 1,4-dioxane (3 mL) was added and the reaction was allowed to heat at 100° C. and stirred for 16 h. The reaction mixture was cooled to rt, cesium carbonate (600 mg, 1.81 mmol), XantPhos (60 mg, 0.10 mmol), tert-butylcarbamate (250 mg, 2.09 mmol), Pd$_2$(dba)$_3$ (65 mg, 0.07 mmol) were added to the reaction mixture which was heated to 100° C. for 16 additional hours. The reaction mixture was filtered through celite, rinsed with AcOEt (20 mL), and concentrated under reduced pressure. The crude material was purified by an automated flash system (dry load, 0 to 20% of EtOAc in n-heptane) to afford tert-butyl (6-(3-azabicyclo[3.1.0]hexan-3-yl)pyrazin-2-yl)carbamate IM782 as yellow solid: 400 mg, 92% yield, P=43%, retention time=2.5 min (gradient A), (M+H)$^+$: 277.

Stage 3: General Procedure A2 was used from IM782 to afford 6-(3-azabicyclo[3.1.0]hexan-3-yl)pyrazin-2-amine IM783 as a yellow solid: 58 mg, 49% yield, P=93%, retention time=2.0 min (gradient A), (M+H)$^+$: 177.

Stage 4: Into a vial, under argon atmosphere, IM688 (40 mg, 0.08 mmol) and HATU (47 mg, 0.12 mmol) were mixed in anhydrous DMF (280 μL). IM783 (20 mg, 0.09 mmol) and DIEA (47.7 μL, 0.27 mmol) were added to the mixture, the tube was sealed and reaction was stirred at 45° C. for 16 h and then cooled to rt. The reaction mixture was diluted with EtOAc (30 mL) and washed with an aqueous saturated solution of NaHCO$_3$ (3×10 mL), followed by water (10 mL) and brine (10 mL). Organic layer was dried over MgSO$_4$, filtered and concentrated under reduced pressure to afford brown oil. The crude material was purified by an automated flash chromatography system (liquid injection in DCM, 0 to 60% EtOAc in n-heptane) to afford tert-butyl ((3R)-1-(6-(3-((6-(3-azabicyclo[3.1.0]hexan-3-yl)pyrazin-2-yl)carbamoyl)oxetan-3-yl)pyridin-3-yl)piperidin-3-yl)(cyclobutylmethyl)carbamate IM784 as a white solid: 40 mg, 66% yield, P=82%, retention time=2.9 min (gradient A), (M+H)$^+$: 604.

Stage 5: General Procedure A2 was used from IM784 to afford crude compound 270 as colourless oil: 17 mg, 43% yield, P=69%, retention time=3.0 min (gradient B), (M+H)$^+$: 504.

The product was purified by reverse phase preparative HPLC purification (XBridge OBD C18 5 μm, 19×100 mm). Gradient used: increased linearly from 30% to 45% solution "B" over 5.0 min, increased linearly to 88% solution "B" over 1.2 min, held to 88% for 0.6 min, and returned to initial conditions over 1.0 min. Flow Rate: 15 mL/min. P=100%. $^1$H NMR (300 MHz, CDCl$_3$) δ 8.70 (s, 1H), 8.59 (s, 1H), 8.34 (d, J=2.8 Hz, 1H), 7.56 (s, 1H), 7.21 (dd, J=8.7, 2.9 Hz, 1H), 7.16 (d, J=8.7 Hz, 1H), 5.36 (dd, J=6.0, 1.7 Hz, 2H), 5.05 (d, J=6.0 Hz, 2H), 3.77-3.61 (m, 3H), 3.55-3.45 (m, 1H), 3.44-3.34 (m, 2H), 2.96-2.81 (m, 1H), 2.79-2.63 (m, 4H), 2.53-2.35 (m, 1H), 2.16-2.01 (m, 2H), 2.01-1.78 (m, 4H), 1.76-1.55 (m, 5H), 1.43-1.26 (m, 1H), 0.85-0.65 (m, 1H), 0.28-0.15 (m, 1H), 1 NH exchanged with solvent.

Compound 271: (R)-2-(5-(3-((cyclobutylmethyl)
amino)piperidin-1-yl)pyridin-2-yl)-N-(5-(pyrrolidin-
1-yl)pyridin-3-yl)acetamide was Obtained Using
General Scheme 6 Pathway B Stage 1: General Procedure Y was used between ethyl 2-(5-bromopyridin-2-yl)acetate and IM3 to afford ethyl (R)-2-(5-(3-((tert-butoxycarbonyl)(cyclobutylmethyl)amino)piperidin-1-yl)pyridin-2-yl)acetate IM785 as orange oil: 192 mg, 30% yield, P=93%, retention time=1.6 min (gradient C), (M+H)$^+$: 432.

Stage 2: To a solution of lithium hydroxide monohydrate (29.3 mg, 664 µmol) in a 1:1 mixture of THF (3.32 mL) and H$_2$O (3.32 mL), IM785 (191 mg, 443 µmol) was added and the reaction was stirred at rt for 18 h. THF was removed under reduced pressure. Residue was diluted with water then a solution of HCl 1N was added dropwise until pH 3-4 was reached (precipitation of desired product observed). The aqueous layer was extracted with EtOAc (×4). Combined organic extracts were washed with brine, dried (MgSO$_4$), filtered and concentrated under reduced pressure to afford crude (R)-2-(5-(3-((tert-butoxycarbonyl)(cyclobutylmethyl)amino)piperidin-1-yl)pyridin-2-yl)acetic acid IM786 as yellow oil: 152 mg, 85% yield, P=100%, retention time=1.2 min (gradient C), (M+H)$^+$: 404.

Stage 3: In a 50 mL round bottom flask under nitrogen, a solution of IM786 (120 mg, 297 µmol), IM558 (72.8 mg, 446 µmol) and HATU (173 mg, 446 µmol) in DMF (2.40 mL) was added. Then, N,N-diisopropylethylamine (255 µL, 1.45 mmol) was added. The mixture was stirred at rt for 1 h. The mixture was directly loaded, using minimal water and DMF, to a C-18 column and purified using 0%-100% MeCN in 10 mM ammonium bicarbonate to afford tert-butyl (R)-(cyclobutylmethyl)(1-(6-(2-oxo-2-((5-(pyrrolidin-1-yl)pyridin-3-yl)amino)ethyl)pyridin-3-yl)piperidin-3-yl)carbamate IM787 as yellow oil: 120 mg, 63% yield, P=85%, retention time=1.5 min (gradient C), (M+H)$^+$: 550.

Stage 4: General Procedure A2 was used from IM787 to afford compound 271 as a white solid: 28 mg, 29% yield, P=100%, retention time=2.6 min (gradient E), (M+H)$^+$: 450. $^1$H NMR (400 MHZ, CD$_3$OD) δ 8.16 (d, J=2.8 Hz, 1H), 7.93 (d, J=1.9 Hz, 1H), 7.59 (d, J=2.5 Hz, 1H), 7.40-7.35 (m, 2H), 7.27 (d, J=8.6 Hz, 1H), 3.78 (s, J=7.8 Hz, 2H), 3.69 (d, J=11.7 Hz, 1H), 3.51 (dt, J=7.5, 3.5 Hz, 1H), 3.28-3.23 (m, 4H), 2.88-2.79 (m, 1H), 2.79-2.63 (m, 4H), 2.56-2.42 (m, 1H), 2.17-2.05 (m, 2H), 2.05-2.00 (m, 4H), 1.99-1.77 (m, 4H), 1.76-1.60 (m, 3H), 1.42-1.28 (m, 1H). 1H labile proton exchanges with CD$_3$OD.

Compound 272: (R)-3-(5-(3-((cyclobutylmethyl)
(methyl)amino)piperidin-1-yl)pyridin-2-yl)-N-(4-
oxo-4H-pyrido[1,2-a]pyrimidin-2-yl)oxetane-3-car-
boxamide was Obtained Using General Scheme 6
Pathway B Stage 1: A colorless solution of compound 239 (44 mg, 0.09 mmol), acetic acid (5 µL, 0.09 mmol) and formaldehyde solution 37% in water (10 µL, 0.13 mmol) in MeCN (820 µL) was stirred at rt for 35 min, then sodium cyanoborohydride (6 mg, 0.10 mmol) was added at rt to afford a pale yellow suspension which was stirred at rt for 2.5 h. The reaction mixture was diluted with EtOAc (20 mL) and washed with NaHCO$_3$ saturated solution (15 mL). The aqueous layer was extracted with EtOAc (20 mL) and the combined organic layers were dried over MgSO$_4$, filtered and the filtrate was concentrated under reduced pressure to dryness to afford 73 mg of a crude yellow solid. The crude material was purified by an automated flash chromatography system (0 to 5.5% MeOH in DCM) to afford compound 272 as a white solid: 22 mg, 49% yield, P=96%, retention time=2.9 min (gradient A), (M+H)$^+$: 503. $^1$H NMR (300 MHz, CDCl$_3$) δ 9.07 (s, 1H), 8.96 (dt, J=7.1, 1.4 Hz, 1H), 8.38 (dd, J=2.6, 1.1 Hz, 1H), 7.66 (ddd, J=8.6, 6.7, 1.6 Hz, 1H), 7.40 (dt, J=8.7, 1.1 Hz, 1H), 7.38 (s, 1H), 7.25-7.15 (m, 2H), 7.02 (td, J=6.9, 1.4 Hz, 1H), 5.36 (d, J=6.1 Hz, 2H), 5.04 (d, J=6.1 Hz, 2H), 3.81-3.73 (m, 1H), 3.72-3.60 (m, 1H), 2.79-2.61 (m, 3H), 2.59-2.43 (m, 3H), 2.31 (s, 3H), 2.14-2.02 (m, 3H), 2.02-1.75 (m, 4H), 1.75-1.56 (m, 2H), 1.53-1.34 (m, 1H).

Compound 273: (R)-3-(5-(3-((cyclobutylmethyl)
amino)piperidin-1-yl)pyridin-2-yl)-N-(6-methoxy-
1H-indazol-4-yl)oxetane-3-carboxamide was
Obtained Using General Scheme 6 Pathway C Stage 1: To a solution of IM688 (1.30 g, 2.7 mmol) in anhydrous DMF (5.4 mL) were added NH$_4$Cl (63.3 mg, 1.18 mmol), HATU (1.12 g, 2.95 mmol) and DIEA (945 µL, 5.4 mmol). The reaction was stirred at rt under argon for 20 min. The reaction mixture was diluted with EtOAc (15 mL) and then washed with an aqueous saturated solution of NaHCO$_3$ (2×50 mL), water (50 mL), brine (50 mL), dried over MgSO$_4$, filtered and concentrated under reduced pressure to dryness. The crude material was purified by an automated flash chromatography system (liquid injection in DCM, 0 to 3% MeOH in DCM) to afford tert-butyl (R)-(1-(6-(3-carbamoyloxetan-3-yl)pyridin-3-yl)piperidin-3-yl)(cyclobutylmethyl)carbamate IM788 as a white foam: 1.12 g, 88% yield, P=94%, retention time=2.5 min (gradient A), (M+H)$^+$: 445.

Stage 2: General Procedure AB was used between IM788 and IM6 to afford tert-butyl (cyclobutylmethyl)((3R)-1-(6-(3-((6-methoxy-1-(tetrahydro-2H-pyran-2-yl)-1H-indazol-4-yl)carbamoyl)oxetan-3-yl)pyridin-3-yl)piperidin-3-yl)carbamate IM789 as colourless sticky oil: 78 mg, 84% yield, P=98%, retention time=3.0 min (gradient A), (M+H)$^+$: 675.

Stage 3: General Procedure A2 was used from IM789 to afford compound 273 as a white solid: 32 mg, 59% yield, P=96%, retention time=2.9 min (gradient B), (M+H)$^+$: 491. $^1$H NMR (300 MHz, CDCl$_3$) δ 9.84 (s, 1H), 8.42 (s, 1H), 7.93 (s, 1H), 7.70 (s, 1H), 7.35-7.27 (m, 2H), 6.60 (s, 1H), 5.47-5.41 (m, 2H), 5.08-5.00 (m, 2H), 3.86 (s, 3H), 3.75-3.66 (m, 1H), 3.58-3.48 (m, 1H), 2.97-2.84 (m, 1H), 2.83-2.68 (m, 4H), 2.53-2.42 (m, 1H), 2.22-1.31 (m, 10H), 2 NH exchanged with solvent.

Compound 274: 2-(5-((R)-3-((cyclobutylmethyl)
amino)piperidin-1-yl)pyridin-2-yl)-N-(6-(pyrrolidin-
1-yl)pyrazin-2-yl)propanamide was Obtained Using
General Scheme 6 Pathway B Stage 1: General Procedure F was used between IM763 and IM721 to afford tert-butyl (cyclobutylmethyl)((3R)-1-(6-(1-oxo-1-((6-(pyrrolidin-1-yl)pyrazin-2-yl)amino)propan-2-yl)pyridin-3-yl)piperidin-3-yl)carbamate IM790 as a beige solid: 77 mg, 82% yield, P=97%, retention time=2.0 min (gradient C), (M+H)$^+$: 564.

Stage 2: General Procedure A2 was used from IM790 to afford compound 274 as a white solid: 59 mg, 83% yield, P=99%, retention time=2.9 min (gradient E), (M+H)$^+$: 464.

The mixture of diastereomers was further purified by chiral preparative HPLC purification using Chiralpak ID column (5 μm, 10×250 mm). Eluent used: TBME/MeOH/DCM/DEA: 40/40/20/0.1% at flow rate of 7 mL/min. First eluted diastereomer: P=100%, retention time=4.8 min, chiral HPLC: P=99.5%, $^1$H NMR (300 MHz, CDCl$_3$) δ 9.12 (s, 1H), 8.67 (s, 1H), 8.30 (s, 1H), 7.67-7.55 (m, 1H), 7.22-7.13 (m, 2H), 3.91-3.79 (m, 1H), 3.72-3.58 (m, 1H), 3.43 (d, J=9.0 Hz, 5H), 2.86 (s, 1H), 2.72 (q, J=9.5 Hz, 4H), 2.47 (s, 1H), 2.09 (s, 2H), 1.92 (d, J=41.1 Hz, 8H), 1.74-1.56 (m, 6H), 1.35 (s, 1H), 1 NH exchanged with solvent. Second eluted diastereomer: P=100%, retention time=12.7 min, chiral HPLC: P=99.4%, $^1$H NMR (300 MHZ, CDCl$_3$) δ 9.13 (s, 1H), 8.68 (s, 1H), 8.30 (s, 1H), 7.59 (s, 1H), 7.23-7.08 (m, 2H), 3.86-3.77 (m, 1H), 3.71-3.61 (m, 1H), 3.46-3.38 (m, 5H), 2.89-2.70 (m, 5H), 2.58-2.38 (m, 1H), 2.21-2.06 (m, 2H), 2.04-1.90 (m, 6H), 1.90-1.76 (m, 2H), 1.72-1.57 (m, 6H), 1.49-1.25 (m, 1H), 1 NH exchanged with solvent.

Compound 275: 2-(6-((R)-3-((cyclobutylmethyl)amino)piperidin-1-yl)pyridazin-3-yl)-N-(4-oxo-4H-pyrido[1,2-a]pyrimidin-2-yl)propanamide was Obtained Using General Scheme 6 Pathway C Stage 1: In a flame dried flask under N$_2$ were placed NaH (2.10 g, 52.6 mmol) and dry dioxane (128 mL). Solution was cooled down to 0° C. and diethyl methylmalonate (6.80 mL, 39.5 mmol) was added dropwise. The reaction was stirred at 0° C. during 1 h, then allowed to reach rt. 3,6-Dichloropyridazine (4.00 g, 26.3 mmol) was added portion wise at this temperature, then flask was equipped with a condenser and the reaction was stirred at reflux during 1 h. The reaction was cooled down to rt and concentrated under reduced pressure. Residue was diluted with EtOAc, washed with a saturated aqueous solution of NaHCO$_3$. The organic phase was washed with brine, dried (MgSO$_4$), filtered and concentrated under reduced pressure to give crude product as a brown oil. The latter was purified by silica gel chromatography, eluting with a gradient of EtOAc in hexanes (0 to 25%) to afford diethyl 2-(6-chloropyridazin-3-yl)-2-methylmalonate IM791 as a light yellow oil: 3.38 g, 34% yield, P=75%, retention time=1.3 min (gradient C), (M+H)$^+$: 287.

Stage 2: In a microwave tube were placed IM791 (1.65 g, 4.32 mmol), NaCl (303 mg, 5.18 mmol), DMSO (10.2 mL) and H$_2$O (154 μL). Tube was sealed and solution was heated in a microwave at 175° C. for 1.5 h on high absorbance. The reaction was cooled down to rt and poured into water (80 mL). The aqueous phase was extracted with EtOAc (3×30 mL) and the organic phase was then washed with brine (2×25 mL). The organic phase was dried over MgSO$_4$, filtered and concentrated under reduced pressure. Residue was purified by silica gel chromatography, eluting with a gradient of EtOAc in heptanes (0 to 40%) to afford ethyl 2-(6-chloropyridazin-3-yl)propanoate IM792 as yellow oil: 419 mg, 42% yield, P=92%, retention time=1.0 min (gradient C), (M+H)$^+$: 215.

Stage 3: General Procedure C was used between IM792 and IM3 to afford ethyl 2-(6-((R)-3-((tert-butoxycarbonyl)(cyclobutylmethyl)amino)piperidin-1-yl)pyridazin-3-yl)propanoate IM793 as brown oil: 533 mg, 62% yield, P=90%, retention time=1.9 min (gradient C), (M+H)$^+$: 447.

Stage 4: LiOH (81.7 mg, 3.34 mmol) was added to IM793 (553 mg, 1.11 mmol) in solution in THF (4.22 mL) and H$_2$O (4.22 mL). The reaction was stirred at rt for 2 h then concentrated under reduced pressure. The residue was dissolved in a minimum of water and directly purified by reverse phase chromatography on C18 cartridge, eluting with a gradient of MeCN in acidic water (10 mM ammonium formate) (5% to 80%) to afford 2-(6-((R)-3-((tert-butoxycarbonyl)(cyclobutylmethyl)amino)piperidin-1-yl)pyridazin-3-yl)propanoic acid IM794 as a white solid: 363 mg, 77% yield, P=99%, retention time=1.2 min (gradient C), (M+H)$^+$: 419.

Stage 5: To a solution of IM794 (100 mg, 237 μmol) in DMF (473 μL) were added NH$_4$Cl (63.3 mg, 1.18 mmol), HATU (91.8 mg, 237 μmol) and DIEA (41.6 μL, 237 μmol). The reaction was stirred at rt during 3 h. The reaction mixture was directly purified by reverse phase chromatography on a C18 cartridge, eluting with a gradient of MeCN in basic water (10 mM NH$_4$HCO$_3$/NH$_4$OH buffer pH=10) (5% to 100%) to afford tert-butyl ((3R)-1-(6-(1-amino-1-oxopropan-2-yl)pyridazin-3-yl)piperidin-3-yl)(cyclobutylmethyl)carbamate IM795 as a white solid: 88 mg, 89% yield, P=100%, retention time=1.5 min (gradient C), (M+H)$^+$: 418.

Stage 6: General Procedure AB was used between IM795 and 2-chloro-4H-pyrido[1,2-a]pyrimidin-4-one to afford tert-butyl (cyclobutylmethyl)((3R)-1-(6-(1-oxo-1-((4-oxo-4H-pyrido[1,2-a]pyrimidin-2-yl)amino)propan-2-yl)pyridazin-3-yl)piperidin-3-yl)carbamate IM796 as a yellow solid: 82 mg, 69% yield, P=100%, retention time=1.7 min (gradient C), (M+H)$^+$: 563.

Stage 7: General Procedure A2 was used from IM796 to afford compound 275 as a white solid: 46 mg, 66% yield, P=96%, retention time=2.4 min (gradient E), (M+H)$^+$: 463.

The mixture of diastereomers was further purified by chiral preparative HPLC purification using Chiralpak ID column (5 μm, 10×250 mm). Eluent used: DCM/MeOH/DEA: 90/10/0.1% at flow rate of 7 mL/min. First eluted diastereomer: P=100%, retention time=3.9 min, chiral HPLC: P=98.1%, $^1$H NMR (300 MHz, CDCl$_3$) δ 9.02 (s, 1H), 8.93 (d, J=7.2 Hz, 1H), 7.63 (t, J=8.1 Hz, 1H), 7.37 (d, J=9.2 Hz, 1H), 7.31 (s, 1H), 7.23 (d, J=10.6 Hz, 1H), 7.05-6.96 (m, 1H), 6.93 (d, J=9.5 Hz, 1H), 4.38 (d, J=12.6 Hz, 1H), 4.11-3.99 (m, 2H), 3.16-3.02 (m, 1H), 2.97-2.84 (m, 1H), 2.83-2.61 (m, 3H), 2.50-2.36 (m, 1H), 2.15-1.96 (m, 4H), 1.94-1.73 (m, 3H), 1.67-1.59 (m, 5H), 1.52-1.39 (m, 1H), 1 NH exchanged with solvent. Second eluted diastereomer: P=100%, retention time=7.4 min, chiral HPLC: P=97.9%, $^1$H NMR (300 MHz, CDCl$_3$) δ 9.00 (s, 1H), 8.88 (d, J=7.1 Hz, 1H), 7.58 (t, J=7.9 Hz, 1H), 7.31 (d, J=9.1 Hz, 1H), 7.26 (s, 1H), 7.19 (d, J=8.0 Hz, 1H), 6.95 (d, J=6.6 Hz, 1H), 6.92-6.84 (m, 1H), 4.43-4.30 (m, 1H), 4.05-3.94 (m, 2H), 3.04 (t, J=11.7 Hz, 1H), 2.92 (t, J=11.2 Hz, 1H), 2.70 (d, J=7.4 Hz, 3H), 2.50-2.33 (m, 1H), 1.99 (d, J=10.2 Hz, 3H), 1.90-1.72 (m, 3H), 1.58 (d, J=7.3 Hz, 6H), 1.53-1.39 (m, 1H), 1 NH exchanged with solvent.

Compound 276: (3R)—N-(cyclobutylmethyl)-1-(6-(1-(4-(5-methoxypyridin-3-yl)-1H-imidazol-1-yl)ethyl)pyridin-3-yl)piperidin-3-amine was Obtained Using General Scheme 4 Pathway C1

Stage 1: To a solution of 1-(5-chloropyridin-2-yl)ethanone (310 mg, 1.95 mmol) in methanol (8.68 mL), cooled to 0° C., was added portion-wise sodium borohydride (124 mg, 3.20 mmol), then the mixture was stirred at 0° C. for 30 min. Reaction mixture was quenched by adding drops of saturated NH$_4$Cl solution then was concentrated under reduced pressure. The crude residue was purified by silica gelchromatography (dry load, using a gradient of MeOH (0-10%) in DCM) to afford 1-(5-chloropyridin-2-yl)ethan-1-ol IM797 as a colorless oil: 200 mg, 65% yield, P=100%, retention time=0.9 min (gradient C), (M+H)$^+$: 158/160.

Stage 2: General Procedure P was used from IM797 to afford crude 1-(5-chloropyridin-2-yl)ethyl methanesulfonate IM798 as a white solid: 395 mg, 100% yield, P=100%, retention time=1.1 min (gradient C), (M+H)$^+$: 236/238.

Stage 3: To a solution of IM435 (214 mg, 1.22 mmol) in DMF (3.70 mL), cooled to 0° C., was added potassium carbonate (172 mg, 1.22 mmol). Reaction mixture was stirred at 0° C. for 5 min before adding sodium hydride 60% in dispersion in mineral oil (147 mg, 3.66 mmol). Then a solution of IM798 (288 mg, 1.22 mmol) in DMF (1.80 mL) was added dropwise still at 0° C. and the resulting mixture was warmed to rt and stirred for 4 h. Reaction was quenched by adding drops of saturated NH$_4$Cl solution. Mixture was then directly purified by reverse phase chromatography (Sfar C-18 60 g cartridge, using a gradient of MeCN (0-100%) in 10 mM ammonium bicarbonate solution) to afford 5-chloro-2-(1-(4-(5-methoxypyridin-3-yl)-1H-imidazol-1-yl)ethyl)pyridine IM799 as brown oil: 159 mg, 38% yield, P=93%, retention time=1.2 min (gradient C), (M+H)$^+$: 315/317.

Stage 4: General Procedure Y was used between IM799 and IM3 to afford tert-butyl (cyclobutylmethyl)((3R)-1-(6-(1-(4-(5-methoxypyridin-3-yl)-1H-imidazol-1-yl)ethyl)pyridin-3-yl)piperidin-3-yl)carbamate IM800 as pale yellow oil: 252 mg, 94% yield, P=98%, retention time=1.8 min (gradient C), (M+H)$^+$: 548.

Stage 5: General Procedure A2 was used from IM800 to afford compound 276 as an off-white solid: 149 mg, 72% yield, P=99%, retention time=2.5 min (gradient E), (M+H)$^+$: 447.

The mixture of diastereomers was further purified by chiral preparative HPLC purification using Chiralpak IE column (5 μm, 10×250 mm). Eluent used: DCM/MeOH/DEA: 90/10/0.1% at flow rate of 7 mL/min. First eluted diastereomer: P=100%, retention time=6.0 min, chiral HPLC: P=100%, $^1$H NMR (300 MHz, CDCl$_3$) δ 8.50 (s, 1H), 8.25 (s, 1H), 8.13 (s, 1H), 7.67 (s, 1H), 7.63 (d, J=2.9 Hz, 1H), 7.36 (s, 1H), 7.11 (d, J=8.3 Hz, 1H), 6.93 (d, J=8.5 Hz, 1H), 5.33 (q, J=7.1 Hz, 1H), 3.89-3.82 (m, 3H), 3.70-3.60 (m, 1H), 3.49-3.37 (m, 1H), 2.89-2.75 (m, 1H), 2.74-2.62 (m, 4H), 2.53-2.36 (m, 1H), 2.14-1.97 (m, 2H), 1.98-1.72 (m, 7H), 1.72-1.54 (m, 3H), 1.42-1.28 (m, 1H), 1 NH exchanged with solvent. Second eluted diastereomer: P=100%, retention time=7.5 min, chiral HPLC: P=100%, $^1$H NMR (300 MHZ, CDCl$_3$) δ 8.50 (s, 1H), 8.25 (d, J=2.9 Hz, 1H), 8.13 (d, J=2.9 Hz, 1H), 7.67 (s, 1H), 7.65-7.62 (m, 1H), 7.37 (s, 1H), 7.10 (dd, J=8.6, 3.1 Hz, 1H), 6.93 (d, J=8.5 Hz, 1H), 5.33 (q, J=7.0 Hz, 1H), 3.86 (s, 3H), 3.74-3.64 (m, 1H), 3.48-3.36 (m, 1H), 2.90-2.66 (m, 5H), 2.58-2.40 (m, 1H), 2.14-2.00 (m, 2H), 1.99-1.73 (m, 7H), 1.73-1.54 (m, 3H), 1.43-1.32 (m, 1H), 1 NH exchanged with solvent.

Compound 277: (R)-2-(5-(3-((cyclobutylmethyl)amino)piperidin-1-yl)pyridin-2-yl)-N-(6-(pyrrolidin-1-yl)pyrazin-2-yl)acetamide was Obtained Using General Scheme 6 Pathway B Stage 1: In a 50 mL RBF under nitrogen, a solution of IM786 (210 mg, 520 μmol), IM721 (128 mg, 780 μmol), and HATU (303 mg, 780 μmol) in DMF (4.20 mL) were added. Then, DIPEA (457 μL, 2.60 mmol) was added. The mixture was stirred at rt for 1 h. Additional HATU (303 mg, 780 μmol) and DIPEA (457 μL, 2.60 mmol) were added and the reaction was stirred over 3 days. Additional HATU (303 mg, 780 μmol) and DIPEA (457 μL, 2.60 mmol) were added and reaction mixture was stirred for 1 h. Mixture was diluted with DCM and washed with brine (3×). The organic layer was collected and dried with Na$_2$SO$_4$. Reaction mixture was directly loaded, using minimal DMF and EtOAc, to a SiO$_2$ column and purified using 0%-100% EtOAc in heptane, to afford tert-butyl (R)-(cyclobutylmethyl)(1-(6-(2-oxo-2-((6-(pyrrolidin-1-yl)pyrazin-2-yl)amino)ethyl)pyridin-3-yl)piperidin-3-yl)carbamate IM801 as orange oil: 23 mg, 8% yield, P=100%, retention time=1.6 min (gradient F), (M+H)$^+$: 551.

Stage 2: General Procedure A2 was used from IM801 to afford compound 277 as a white solid: 14 mg, 68% yield, P=94%, retention time=2.7 min (gradient E), (M+H)$^+$: 451. $^1$H NMR (400 MHZ, CD$_3$OD) δ 8.49 (s, 1H), 8.19 (d, J=2.8 Hz, 1H), 7.57 (s, 1H), 7.39 (dd, J=8.6, 2.9 Hz, 1H), 7.28 (d, J=8.6 Hz, 1H), 3.84 (s, J=7.7 Hz, 2H), 3.76-3.68 (m, 1H), 3.60-3.51 (m, 1H), 3.51-3.42 (m, 4H), 2.91-2.80 (m, 1H), 2.79-2.63 (m, 4H), 2.56-2.44 (m, 1H), 2.17-2.06 (m, 2H), 2.06-1.79 (m, 8H), 1.79-1.60 (m, 3H), 1.43-1.30 (m, 1H). Two labile protons exchange with CD$_3$OD.

Compound 278: (R)-3-(4-(3-((cyclobutylmethyl)amino)piperidin-1-yl)phenyl)-N-(4-oxo-4H-pyrido[1,2-a]pyrimidin-2-yl)oxetane-3-carboxamide was Obtained Using General Scheme 6 Pathway C Stage 1: Potassium acetate (1.80 g, 18.34 mmol) and paraformaldehyde (13 g, 137.1 mmol) were added to a solution of methyl 2-(4-bromophenyl)acetate (10.23 g, 44.66 mmol) in dry DMSO (80 mL) at rt under argon and stirred for 21 h. HCl IN (500 mL) and EtOAc (500 mL) were added and the milky mixture was filtered through celite. The layers were separated and the aqueous layer was further extracted with EtOAc (2×500 mL). The combined organic layers were washed with water (3×500 mL), followed by brine (500 mL). The organic layer was dried over MgSO$_4$, filtered and concentrated under reduced pressure to dryness. The crude material was purified by an automated flash chromatography system (liquid injection in toluene, 0 to 100% EtOAc in Heptane) to afford methyl 2-(4-bromophenyl)-3-hydroxy-2-(hydroxymethyl)propanoate IM802 as colourless oil: 11.26 g, 65% yield, P=75%, retention time=2.4 min (gradient A), (M+H)+: 289/291.

Stage 2: To a solution of IM802 (9.82 g, 33.97 mmol) in dry 1,4-dioxane (100 mL) under argon was added triphenylphosphine (18 g, 68.63 mmol). The resulting mixture was stirred for 5 min until the entire solid dissolved. Zinc dimethyldithiocarbamate (16 g, 50.75 mmol) was added at rt. Diethyl azodicarboxylate (11 mL, 67.76 mmol) was added dropwise over 10 min at 25° C. The reaction was heated to 30° C. and stirred for 14 h. Heptane (100 mL) was added to the reaction. The reaction mixture was filtered through celite and washed with heptane/EtOAc (200 mL, 1/1) and EtOAc (200 mL). The filtrate was concentrated to dryness to afford a white oil with solid. A mixture of heptane/EtOAc (200 mL, 1/1) was added to the crude mixture and filtered through a pad of silica (10×2.5 cm) and rinsed with a mixture of heptane/EtOAc (600 mL, 1/1). The filtrate was concentrated to dryness to afford a white oil with solid. The crude material was purified by an automated flash chromatography system (dryload in silica, 0 to 40% EtOAc in Heptane) to afford methyl 3-(4-bromophenyl)oxetane-3-carboxylate IM803 as a white solid: 1.91 g, 19% yield, P=92%, retention time=2.8 min (gradient A), (M+H)+: 253/255.

Stage 3: General Procedure AB was used between IM803 and IM3 to afford methyl (R)-3-(4-(3-((tert-butoxycarbonyl)(cyclobutylmethyl)amino)piperidin-1-yl)phenyl)oxetane-3-carboxylate IM804 as colourless gum: 53 mg, 30% yield, P=90%, retention time=4.8 min (gradient B), (M+H)+: 458.

Stage 4: To a solution of IM804 (500 mg, 0.8300 mmol) in THF (2.5 mL) and water (2.5 mL) was added lithium hydroxide (40 mg, 1.57 mmol) at rt. The resulting solution was kept stirring for 1.5 h. The resulting mixture was adjusted to pH 2 with 1 N HCl (1.6 mL). The resulting solution was extracted with EtOAc (3×25 mL), the organic layers were combined and washed with brine (25 mL), dried over MgSO$_4$, and concentrated to afford 3-[4-[(3R)-3-[tert-butoxycarbonyl(cyclobutylmethyl)amino]-1-piperidyl]phenyl]oxetane-3-carboxylic acid hydrochloride salt IM805 as a light orange foam: 468 mg, 100% yield, P=85%, retention time=2.6 min (gradient A), (M+H)$^+$: 445.

Stage 5: To a solution of IM805 (454 mg, 0.80 mmol) in anhydrous DMF (2 mL) were added ammonium chloride (176 mg, 3.22 mmol), HATU (254 mg, 0.67 mmol) and DIEA (190 µL, 1.09 mmol). The reaction was stirred at rt under argon for 1.5 h. Extra DIEA (190 µL, 1.09 mmol) (2nd addition) was added and the reaction mixture was stirred for 1.3 h. Extra HATU (137 mg, 0.36 mmol) (3rd addition) was added and the reaction mixture was stirred for 1 h. The reaction mixture was diluted with EtOAc (30 mL) and then washed with an aqueous saturated solution of NaHCO$_3$ (30 mL), water (30 mL), brine (30 mL), dried over MgSO$_4$, filtered and concentrated under reduced pressure to dryness. The crude material was purified by an automated flash chromatography system (dryload in silica, 0 to 5% MeOH in DCM) to afford tert-butyl (R)-(1-(4-(3-carbamoyloxetan-3-yl)phenyl)piperidin-3-yl)(cyclobutylmethyl)carbamate IM806 as a light yellow foam: 345 mg, 95% yield, P=98%, retention time=2.5 min (gradient A), (M+H)+: 444.

Stage 6: General Procedure AB was used between IM806 and 2-chloro-4H-pyrido[1,2-a]pyrimidin-4-one to afford tert-butyl (R)-(cyclobutylmethyl)(1-(4-(3-((4-oxo-4H-pyrido[1,2-a]pyrimidin-2-yl)carbamoyl)oxetan-3-yl)phenyl)piperidin-3-yl)carbamate IM807 as light green gum: 75 mg, 89% yield, P=92%, retention time=2.7 min (gradient A), (M+H)$^+$: 588.

Stage 7: General Procedure A2 was used from IM807 to afford crude compound 278 as a yellow glass: 65 mg, 68% yield, P=60%, retention time=3.1 min (gradient B), (M+H)$^+$: 488.

The product was purified by reverse phase preparative HPLC purification (XBridge OBD C18 5 µm, 19×100 mm). Gradient used: increased linearly from 20% to 40% solution "B" over 4.5 min, increased linearly to 85% solution "B" over 1.5 min, and returned to initial conditions over 1.0 min. Flow Rate: 15 mL/min. P=100%. $^1$H NMR (300 MHz, CDCl$_3$) δ 8.97 (d, J=7.3 Hz, 1H), 7.65 (ddd, J=8.7, 6.6, 1.7 Hz, 1H), 7.44 (s, 1H), 7.42 (s, 1H), 7.35-7.27 (m, 1H), 7.22-7.12 (m, 2H), 7.07-6.94 (m, 3H), 5.32 (d, J=5.8 Hz, 2H), 4.99 (d, J=5.8 Hz, 2H), 3.74-3.64 (m, 1H), 3.57-3.46 (m, 1H), 2.85 (td, J=11.3, 3.2 Hz, 1H), 2.77-2.70 (m, 3H), 2.66 (dd, J=11.2, 8.9 Hz, 1H), 2.57-2.38 (m, 1H), 2.17-2.03 (m, 2H), 2.02-1.60 (m, 7H), 1.41-1.23 (m, 1H), 1 NH exchanged with solvent.

Compound 279: 2-(6-((R)-3-((cyclobutylmethyl)amino)piperidin-1-yl)pyridazin-3-yl)-N-(6-(pyrrolidin-1-yl)pyrazin-2-yl)propanamide was Obtained Using General Scheme 6 Pathway C Stage 1: To a solution of IM794 (235 mg, 556 µmol) in DMF (1.11 mL) were added NH$_4$Cl (149 mg, 2.78 mmol), HATU (216 mg, 556 µmol) and DIPEA (97.8 µL, 556 µmol). The reaction was stirred at rt during 2.25 h. The reaction mixture was directly purified by reverse phase chromatography on a C18 cartridge, eluting with a gradient of MeCN in basic water (10 mM NH$_4$HCO$_3$/NH$_4$OH buffer pH=10) to afford tert-butyl ((3R)-1-(6-(1-amino-1-oxopropan-2-yl)pyridazin-3-yl)piperidin-3-yl)(cyclobutylmethyl)carbamate IM808 as an off-white solid: 216 mg, 93% yield, P=100%, retention time=1.5 min (gradient C), (M+H)+: 418.

Stage 2: General Procedure AB was used between IM808 and M532 to afford tert-butyl (cyclobutylmethyl)((3R)-1-(6-(1-oxo-1-((6-(pyrrolidin-1-yl)pyrazin-2-yl)amino)propan-2-yl)pyridazin-3-yl)piperidin-3-yl)carbamate IM809 as a yellow solid: 99 mg, 80% yield, P=98%, retention time=1.9 min (gradient C), (M+H)$^+$: 566.

Stage 3: General Procedure A2 was used from IM809 to afford compound 279 as a white solid: 53 mg, 65% yield, P=98%, retention time=2.8 min (gradient E), (M+H)$^+$: 465.

The mixture of diastereomers was further purified by chiral preparative HPLC purification using Chiralpak IE column (5 µm, 10×250 mm). Eluent used: TBME/DCM/MeOH/DEA: 40/20/40/0.1% at flow rate of 7 mL/min. First eluted diastereomer: P=100%, retention time=5.1 min, chiral HPLC: P=98.6%, $^1$H NMR (300 MHz, CDCl$_3$) δ 8.63 (s, 1H), 8.34 (s, 1H), 7.59 (s, 1H), 7.28 (d, J=10.2 Hz, 1H), 6.92 (d, J=9.5 Hz, 1H), 4.43-4.33 (m, 1H), 4.12-3.99 (m, 2H), 3.45-3.35 (m, 4H), 3.08 (ddd, J=13.5, 10.7, 3.1 Hz, 1H), 2.91 (dd, J=12.8, 9.2 Hz, 1H), 2.81-2.61 (m, 3H), 2.45 (hept, J=7.5 Hz, 1H), 2.14-1.74 (m, 11H), 1.73-1.39 (m, 6H), 1 NH exchanged. Second eluted diastereomer: P=100%, retention time=8.7 min, chiral HPLC: P=97.6%, $^1$H NMR (300 MHz, CDCl$_3$) δ 8.63 (s, 1H), 8.42 (s, 1H), 7.59 (s, 1H), 7.29 (d, J=9.5 Hz, 1H), 6.94 (d, J=9.5 Hz, 1H), 4.54-4.41 (m, 1H), 4.16-3.98 (m, 2H), 3.44-3.34 (m, 4H), 3.09 (ddd, J=13.4, 10.5, 3.0 Hz, 1H), 2.95 (dd, J=12.7, 9.4 Hz, 1H), 2.81-2.68 (m, 3H), 2.48 (hept, J=7.5 Hz, 1H), 2.13-1.75 (m, 11H), 1.75-1.44 (m, 6H), 1 NH exchanged.

Compound 280: (3R)—N-(cyclobutylmethyl)-1-(6-(1-(4-(6-(pyrrolidin-1-yl)pyrazin-2-yl)-1H-1,2,3-triazol-1-yl)ethyl)pyridin-3-yl)piperidin-3-amine was Obtained Using General Scheme 1 Pathway A Stage 1: A solution of 1-(5-chloropyridin-2-yl)ethanone (496 mg, 3.12 mmol), IM3 (1 g, 3.73 mmol), DIEA (0.85 mL, 4.86 mmol) and lithium bromide (335 mg, 3.78 mmol) in NMP (2.1 mL) was heated at 120° C. for 26 h. The reaction mixture was cooled to rt and quenched with water (20 mL) and extracted with EtOAc (3×20 mL). The organic layers were merged and washed with water (3×20 mL), followed by brine (2×10 mL). The organic layer was dried over MgSO$_4$, filtered and concentrated under reduced pressure to dryness. The crude material was purified by an automated flash chromatography system (liquid load in DCM, 0 to 40% EtOAc in Heptane) to afford tert-butyl (R)-(1-(6-acetylpyridin-3-yl)piperidin-3-yl)(cyclobutylmethyl)carbamate IM810 as yellow oil: 700 mg, 54% yield, P=93%, retention time=2.8 min (gradient A), (M+H)+: 388.

Stage 2: General Procedure W was used from IM810 to afford crude tert-butyl ((3R)-1-(6-(1-aminoethyl)pyridin-3-yl)piperidin-3-yl)(cyclobutylmethyl)carbamate IM811 as yellow oil: 520 mg, 64% yield, P=80%, retention time=2.4 min (gradient A), (M+H)+: 389.

Stage 3: General Procedure V was used from IM811 to afford tert-butyl ((3R)-1-(6-(1-azidoethyl)pyridin-3-yl)piperidin-3-yl)(cyclobutylmethyl)carbamate IM812 as yellow oil: 273 mg, 59% yield, P=96%, retention time=2.6 min (gradient A), (M+H)$^+$: 415.

Stage 4: General Procedure B was used between IM812 and IM534 to afford tert-butyl (cyclobutylmethyl)((3R)-1-(6-(1-(4-(6-(pyrrolidin-1-yl)pyrazin-2-yl)-1H-1,2,3-triazol- 1-yl)ethyl)pyridin-3-yl)piperidin-3-yl)carbamate IM813 as yellow gum: 121 mg, 76% yield, P=85%, retention time=2.8 min (gradient A), (M+H)$^+$: 588.

Stage 5: General Procedure A2 was used from IM813 to afford crude compound 280 as dark yellow oil: 77 mg, 88% yield, P=98%, retention time=2.2 min (gradient A), (M+H)$^+$: 488.

The mixture of diastereomers was purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=99%, retention time=5.1 min, chiral HPLC: P=98.4%, $^1$H NMR (300 MHz, CDCl$_3$) δ 8.58 (s, 1H), 8.27-8.22 (m, 1H), 8.21 (s, 1H), 7.79 (s, 1H), 7.08 (d, J=8.5 Hz, 1H), 7.05-6.96 (m, 1H), 5.90 (q, J=7.1 Hz, 1H), 3.92-3.77 (m, 1H), 3.57-3.46 (m, 4H), 3.39-3.29 (m, 1H), 2.82 (dq, J=19.5, 9.7 Hz, 4H), 2.73-2.51 (m, 2H), 2.10 (t, J=7.1 Hz, 2H), 2.06-1.94 (m, 8H), 1.96-1.67 (m, 5H), 1.63-1.46 (m, 2H), 1 NH exchanged. Second eluted diastereomer: P=100%, retention time=8.0 min, chiral HPLC: P=99.8%, $^1$H NMR (300 MHz, CDCl$_3$) δ 8.58 (s, 1H), 8.24 (s, 1H), 8.21 (s, 1H), 7.79 (s, 1H), 7.08 (d, J=8.5 Hz, 1H), 7.01 (d, J=8.6 Hz, 1H), 5.90 (q, J=7.2 Hz, 1H), 3.88-3.79 (m, 1H), 3.57-3.46 (m, 4H), 3.39-3.29 (m, 1H), 2.94-2.52 (m, 6H), 2.15-1.94 (m, 10H), 1.93-1.65 (m, 5H), 1.64-1.40 (m, 2H), 1 NH exchanged.

Compound 281: (R)-3-(4-(3-((cyclobutylmethyl)amino)piperidin-1-yl)phenyl)-N-(6-(pyrrolidin-1-yl)pyrazin-2-yl)oxetane-3-carboxamide was Obtained Using General Scheme 6 Pathway C Stage 1: General Procedure AB was used between IM806 and M532 to afford tert-butyl (R)-(cyclobutylmethyl)(1-(4-(3-((6-(pyrrolidin-1-yl)pyrazin-2-yl)carbamoyl)oxetan-3-yl)phenyl)piperidin-3-yl)carbamate IM814 as light yellow gum: 74 mg, 89% yield, P=94%, retention time=2.7 min (gradient A), (M+H)$^+$: 591.

Stage 2: General Procedure A2 was used from IM814 to afford compound 281 as a white solid: 56 mg, 93% yield, P=96%, retention time=3.2 min (gradient B), (M+H)$^+$: 491. $^1$H NMR (300 MHz, CDCl$_3$) δ 8.72 (s, 1H), 7.57 (s, 1H), 7.37 (s, 1H), 7.21-7.11 (m, 2H), 7.00-6.89 (m, 2H), 5.29 (dd, J=5.8, 1.4 Hz, 2H), 4.94 (dd, J=5.8, 1.4 Hz, 2H), 3.72-3.57 (m, 1H), 3.52-3.41 (m, 1H), 3.38-3.26 (m, 4H), 2.81 (ddd, J=11.8, 10.2, 3.2 Hz, 1H), 2.76-2.69 (m, 3H), 2.65 (dd, J=11.4, 8.9 Hz, 1H), 2.45 (hept, J=7.5 Hz, 1H), 2.14-1.73 (m, 10H), 1.72-1.57 (m, 3H), 1.40-1.23 (m, 1H), 1 NH exchanged.

Compound 282: (R)—N-(cyclobutylmethyl)-1-(6-((4-(6-(pyrrolidin-1-yl)pyrazin-2-yl)-1H-1,2,3-triazol-1-yl)methyl)pyridin-3-yl)piperidin-3-amine was Obtained Using General Scheme 1 Pathway B Stage 1: General Procedure B was used between IM424 and IM534 to afford 2-(1-((5-bromopyridin-2-yl)methyl)-1H-1,2,3-triazol-4-yl)-6-(pyrrolidin-1-yl)pyrazine IM815 as yellow oil: 110 mg, 96% yield, P=82%, retention time=2.6 min (gradient A), (M+H)$^+$: 386/388.

Stage 2: General Procedure Y was used between IM815 and IM3 to afford tert-butyl (R)-(cyclobutylmethyl)(1-(6-((4-(6-(pyrrolidin-1-yl)pyrazin-2-yl)-1H-1,2,3-triazol-1-yl)methyl)pyridin-3-yl)piperidin-3-yl)carbamate IM816 as yellow oil: 63 mg, 44% yield, P=93%, retention time=2.7 min (gradient A), (M+H)$^+$: 574.

Stage 3: General Procedure A2 was used from IM816 to afford crude compound 282 as a white solid: 35 mg, 70% yield, P=97%, retention time=3.0 min (gradient B), (M+H)$^+$: 474. $^1$H NMR (300 MHz, CDCl$_3$) δ 8.59 (s, 1H), 8.30-8.23 (m, 1H), 8.16 (s, 1H), 7.80 (s, 1H), 7.21-7.08 (m, 2H), 5.60 (s, 2H), 3.64 (d, J=9.5 Hz, 1H), 3.59-3.43 (m, 5H), 2.93-2.78 (m, 1H), 2.77-2.59 (m, 4H), 2.52-2.36 (m, 1H), 2.16-1.74 (m, 9H), 1.74-1.55 (m, 3H), 1.47-1.12 (m, 2H), 1 NH exchanged with solvent.

Compound 283: (R)—N-(cyclobutylmethyl)-1-(6-(3-(4-(6-cyclopropylpyrazin-2-yl)-1H-1,2,3-triazol-1-yl)oxetan-3-yl)pyridin-3-yl)piperidin-3-amine was Obtained Using General Scheme 1 Pathway A Stage 1: General Procedure B was used between IM453 and IM603 to afford tert-butyl (R)-(1-(6-(3-(4-(6-bromopyrazin-2-yl)-1H-1,2,3-triazol-1-yl)oxetan-3-yl)pyridin-3-yl)piperidin-3-yl)(cyclobutylmethyl)carbamate IM817 as a white solid: 137 mg, 82% yield, P=97%, retention time=3.4 min (gradient A), (M+H)$^+$: 625/627.

Stage 2: Into a vial, IM817 (137 mg, 0.21 mmol), potassium phosphate tribasic (160 mg, 0.74 mmol), tricyclohexylphosphine (7 mg, 0.02 mmol), cyclopropylboronic acid (36 mg, 0.42 mmol), palladium(II) acetate (2.6 mg, 0.01 mmol), were merged, flushed by vaccuo/argon cycles (3 times). Then toluene (0.6 mL) and water (0.13 mL) were added (both previously degassed by argon bubbling for 20 min). Mixture was heated to 100° C. for 1 h. Reaction mixture was cooled to rt, diluted with EtOAc (30 mL), and washed with water (10 mL), followed by brine (10 mL). Organic layer was dried over MgSO$_4$, filtered and concentrated under reduced pressure to dryness to afford a brown oil. The crude material was purified by an automated flash chromatography system (liquid injection in DCM, 0 to 1.5% MeOH in DCM) to afford tert-butyl (R)-(cyclobutylmethyl)(1-(6-(3-(4-(6-cyclopropylpyrazin-2-yl)-1H-1,2,3-triazol-1-yl)oxetan-3-yl)pyridin-3-yl)piperidin-3-yl)carbamate IM818 as a white solid: 97 mg, 76% yield, P=98%, retention time=3.3 min (gradient A), (M+H)$^+$: 587.

Stage 3: General Procedure A2 was used from IM818 to afford crude compound 283 as a white solid: 58 mg, 71% yield, P=96%, retention time=3.4 min (gradient B), (M+H)$^+$: 487. $^1$H NMR (300 MHz, CDCl$_3$) δ 9.17 (s, 1H), 8.40 (s, 1H), 8.34 (d, J=2.9 Hz, 1H), 8.08 (s, 1H), 7.13 (dd, J=8.8, 3.0 Hz, 1H), 6.89 (d, J=8.7 Hz, 1H), 5.54 (d, J=6.8 Hz, 2H), 5.50 (d, J=6.7 Hz, 2H), 3.69 (d, J=8.5 Hz, 1H), 3.60-3.47 (m, 1H), 2.97-2.83 (m, 1H), 2.80-2.64 (m, 4H), 2.54-2.35 (m, 1H), 2.11-2.03 (m, 2H), 2.03-1.77 (m, 4H), 1.75-1.58 (m, 3H), 1.49-1.30 (m, 2H), 1.13-1.03 (m, 4H), 1 NH exchanged with solvent.

Compound 284: (3R)-1-(6-(1-(4-(6-(3-azabicyclo[3.1.0]hexan-3-yl)pyrazin-2-yl)-1H-1,2,3-triazol-1-yl)ethyl)pyridazin-3-yl)-N-(cyclobutylmethyl)piperidin-3-amine was Obtained Using General Scheme 1 Pathway A Stage 1: General Procedure X was used between IM610 and IM280 to afford tert-butyl ((3R)-1-(6-(1-(4-(6-(3-azabicyclo[3.1.0]hexan-3-yl)pyrazin-2-yl)-1H-1,2,3-triazol-1-yl)ethyl)pyridazin-3-yl)piperidin-3-yl)(cyclobutylmethyl)carbamate IM819 as yellow solid: 66 mg, 95% yield, P=98%, retention time=2.7 min (gradient A), (M+H)$^+$: 601.

Stage 2: General Procedure A2 was used from IM819 to afford crude compound 284 as an off-white solid: 28 mg, 51% yield, P=98%, retention time=2.1 min (gradient B), (M+H)$^+$: 502.

The mixture of diastereomers was purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=96%, retention time=4.7 min, chiral HPLC: P=98.2%, $^1$H NMR (300 MHz, CDCl$_3$ before lyoph) δ 8.59 (s, 1H), 8.19 (s, 1H), 7.75 (s, 1H), 7.20 (d, J=9.5 Hz, 1H), 6.86 (d, J=9.5 Hz, 1H), 6.03 (q, J=7.2 Hz, 1H), 4.43-4.31 (m, 1H), 4.13-4.01 (m, 1H), 3.76 (d, J=10.2 Hz, 2H), 3.54-3.38 (m, 2H), 3.09 (ddd, J=13.5, 10.8, 3.1 Hz, 1H), 2.87 (dd, J=12.8, 9.3 Hz, 1H), 2.75-2.57 (m, 3H), 2.41 (hept, J=7.5 Hz, 1H), 2.10 (d, J=7.1 Hz, 3H), 2.08-1.74 (m, 6H), 1.72-1.48 (m, 5H), 1.48-1.30 (m, 1H), 0.84-0.72 (m, 1H), 0.28-0.21 (m, 1H), 1 NH exchanged with solvent. Second eluted diastereomer: P=100%, retention time=9.5 min, chiral HPLC: P=100%, $^1$H NMR (300 MHz, CDCl$_3$) δ 8.58 (s, 1H), 8.19 (s, 1H), 7.76 (s, 1H), 7.24 (d, J=9.2 Hz, 1H), 6.97 (d, J=9.5 Hz, 1H), 6.04 (q, J=7.2 Hz, 1H), 4.73-4.63 (m, 1H), 4.14-4.04 (m, 1H), 3.75 (d, J=10.2 Hz, 2H), 3.51-3.42 (m, 2H), 3.34-3.21 (m, 1H), 3.14-2.96 (m, 2H), 2.93 (d, J=7.3 Hz, 2H), 2.78-2.62 (m, 1H), 2.25-2.05 (m, 5H), 1.96-1.52 (m, 8H), 1.49-1.38 (m, 2H), 0.83-0.70 (m, 1H), 0.30-0.17 (m, 1H), 1 NH exchanged with solvent.

Compound 285: (3R)—N-(cyclobutylmethyl)-1-(6-(1-(4-(6-(pyrrolidin-1-yl)pyrazin-2-yl)-1H-1,2,3-triazol-1-yl)ethyl)pyridazin-3-yl)piperidin-3-amine was Obtained Using General Scheme 1 Pathway A Stage 1: General Procedure X was used between IM533 and IM280 to afford tert-butyl (cyclobutylmethyl)((3R)-1-(6-(1-(4-(6-(pyrrolidin-1-yl)pyrazin-2-yl)-1H-1,2,3-triazol-1-yl)ethyl)pyridazin-3-yl)piperidin-3-yl)carbamate IM820 as yellow oil: 100 mg, 100% yield, P=93%, retention time=2.6 min (gradient A), (M+H)$^+$: 589.

Stage 2: General Procedure A2 was used from IM820 to afford crude compound 284 as yellow oil: 48 mg, 60% yield, P=96%, retention time=3.1 min (gradient B), (M+H)$^+$: 589.

The mixture of diastereomers was purified by chiral preparative HPLC purification using Chiralpak ID column (5 μm, 10×250 mm). Eluent used: TBME/MeOH/DCM/DEA: 40/40/20/0.1% at flow rate of 7 mL/min. First eluted diastereomer: P=100%, retention time=6.6 min, chiral HPLC: P=100%, $^1$H NMR (300 MHz, CDCl$_3$) δ 8.51 (s, 1H), 8.14 (s, 1H), 7.73 (s, 1H), 7.15 (d, J=9.4 Hz, 1H), 6.81 (d, J=9.5 Hz, 1H), 5.97 (q, J=7.1 Hz, 1H), 4.41-4.30 (m, 1H), 4.05-3.95 (m, 1H), 3.51-3.38 (m, 4H), 3.10-2.95 (m, 1H), 2.88 (dd, J=12.8, 9.2 Hz, 1H), 2.76-2.56 (m, 3H), 2.47-2.31 (m, 1H), 2.04 (d, J=7.0 Hz, 3H), 2.02-1.91 (m, 7H), 1.91-1.69 (m, 3H), 1.67-1.36 (m, 4H), 1 NH exchanged with solvent. Second eluted diastereomer: P=99%, retention time=13.6 min, chiral HPLC: P=100%, $^1$H NMR (300 MHz, CDCl$_3$) δ 8.56 (s, 1H), 8.20 (s, 1H), 7.79 (s, 1H), 7.21 (d, J=9.5 Hz, 1H), 6.89 (d, J=9.5 Hz, 1H), 6.03 (q, J=7.1 Hz, 1H), 4.52-4.42 (m, 1H), 4.12-4.00 (m, 1H), 3.54-3.44 (m, 4H), 3.15-2.93 (m, 2H), 2.81-2.67 (m, 3H), 2.58-2.39 (m, 1H), 2.14-1.75 (m, 13H), 1.75-1.48 (m, 4H), 1 NH exchanged with solvent.

Compound 286: (3R)-1-(6-(1-(4-(6-(3-azabicyclo[3.1.0]hexan-3-yl)pyrazin-2-yl)-1H-1,2,3-triazol-1-yl)ethyl)pyridin-3-yl)-N-(cyclobutylmethyl)piperidin-3-amine was Obtained Using General Scheme 1 Pathway A Stage 1: General Procedure X was used between IM610 and IM812 to afford tert-butyl ((3R)-1-(6-(1-(4-(6-(3-azabicyclo[3.1.0]hexan-3-yl)pyrazin-2-yl)-1H-1,2,3-triazol-1-yl)ethyl)pyridin-3-yl)piperidin-3-yl)(cyclobutylmethyl)carbamate IM821 as colourless oil: 58 mg, 81% yield, P=97%, retention time=2.9 min (gradient A), (M+H)$^+$: 600.

Stage 2: General Procedure A2 was used from IM821 to afford crude compound 286 as yellow oil: 48 mg, 99% yield, P=98%, retention time=2.2 min (gradient A), (M+H)$^+$: 500.

The mixture of diastereomers was purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=100%, retention time=4.7 min, chiral HPLC: P=100%, $^1$H NMR (300 MHz, CDCl$_3$) δ 8.60 (s, 1H), 8.27 (t, J=1.8 Hz, 1H), 8.17 (s, 1H), 7.75 (s, 1H), 7.11 (d, J=1.8 Hz, 2H), 5.91 (q, J=7.0 Hz, 1H), 3.77 (d, J=10.1 Hz, 2H), 3.71-3.61 (m, 1H), 3.52-3.39 (m, 3H), 2.91-2.78 (m, 1H), 2.77-2.62 (m, 4H), 2.53-2.36 (m, 1H), 2.15-2.03 (m, 2H), 2.04-1.97 (m, 3H), 1.97-1.75 (m, 4H), 1.73-1.57 (m, 5H), 1.44-1.22 (m, 1H), 0.83-0.71 (m, 1H), 0.30-0.22 (m, 1H), 1H exchanged with solvent. Second eluted diastereomer: P=100%, retention time=9.4 min, chiral HPLC: P=100%, $^1$H NMR (300 MHz, CDCl$_3$) δ 8.59 (s, 1H), 8.26 (s, 1H), 8.17 (s, 1H), 7.74 (s, 1H), 7.14-7.04 (m, 2H), 5.90 (q, J=7.1 Hz, 1H), 3.77 (dd, J=10.2, 1.9 Hz, 2H), 3.74-3.67 (m, 1H), 3.52-3.35 (m, 3H), 2.86-2.66 (m, 5H), 2.57-2.39 (m, 1H), 2.16-2.03 (m, 2H), 1.98 (d, J=7.1 Hz, 3H), 1.96-1.74 (m, 4H), 1.73-1.55 (m, 5H), 1.46-1.31 (m, 1H), 0.82-0.71 (m, 1H), 0.29-0.21 (m, 1H), 1H exchanged with solvent.

Compound 287: (R)—N-(cyclobutylmethyl)-1-(4-((4-(6-(pyrrolidin-1-yl)pyrazin-2-yl)-1H-1,2,3-triazol-1-yl)methyl)phenyl)piperidin-3-amine was Obtained Using General Scheme 1 Pathway A Stage 1: General Procedure S was used between IM3 and 4-bromobenzaldehyde to afford tert-butyl (R)-(cyclobutylmethyl)(1-(4-formylphenyl)piperidin-3-yl)carbamate IM822 as light yellow glass: 178 mg, 28% yield, P=95%, retention time=3.3 min (gradient A), (M+H)+: 373.

Stage 2: To a solution of IM822 (268 mg, 0.68 mmol) in dry Ethanol (3.4 mL) at 0° C. was added sodium borohydride (40 mg, 1.06 mmol) at once. The reaction was stirred at 0° C. for 20 min and then at rt for 15 min. The reaction was quenched with water (20 mL) and the resulting mixture was extracted with EtOAc (3×25 mL). The combined organic layers were washed with brine (25 mL), dried over MgSO$_4$, filtered and concentrated to give tert-butyl (R)-(cyclobutylmethyl)(1-(4-(hydroxymethyl)phenyl)piperidin-3-yl)carbamate IM823 as light yellow oil: 270 mg, 96% yield, P=91%, retention time=2.5 min (gradient A), (M+H)+: 375.

Stage 3: General Procedure M was used from IM823 to afford tert-butyl (R)-(1-(4-(azidomethyl)phenyl)piperidin-3-yl)(cyclobutylmethyl)carbamate IM824 as colourless oil: 309 mg, 74% yield, P=92%, retention time=3.0 min (gradient A), (M+H)+: 400.

Stage 4: General Procedure X was used between IM824 and IM533 to afford tert-butyl (R)-(cyclobutylmethyl)(1-(4-((4-(6-(pyrrolidin-1-yl)pyrazin-2-yl)-1H-1,2,3-triazol-1-yl)methyl)phenyl)piperidin-3-yl)carbamate IM825 as yellow glass: 48 mg, 46% yield, P=74%, retention time=2.9 min (gradient A), (M+H)$^+$: 574.

Stage 5: General Procedure A2 was used from IM825 to afford crude compound 287 as yellow glass: 54 mg, 99% yield, P=54%, retention time=2.3 min (gradient A), (M+2H)$^+$: 237.

The product was purified by reverse phase preparative HPLC purification (XBridge OBD C18 5 μm, 19×100 mm). Gradient used: increased linearly from 40% to 60% solution "B" over 4.0 min, increased linearly to 88% solution "B" over 2.2 min, held for 0.6 min, and returned to initial conditions over 1.0 min. Flow Rate: 15 mL/min. P=96%. $^1$H NMR (300 MHz, CDCl$_3$) δ 8.58 (s, 1H), 7.90 (s, 1H), 7.78 (s, 1H), 7.20 (d, J=8.4 Hz, 2H), 6.90 (d, J=8.8 Hz, 2H), 5.46 (s, 2H), 3.69-3.58 (m, 1H), 3.56-3.40 (m, 5H), 2.89-2.75 (m, 1H), 2.75-2.65 (m, 3H), 2.61 (dd, J=11.4, 8.9 Hz, 1H), 2.54-2.33 (m, 1H), 2.15-1.73 (m, 10H), 1.74-1.57 (m, 3H), 1.38-1.21 (m, 1H), 1H exchanged with solvent.

Compound 288: (3R)-1-(4-((4-(6-(3-azabicyclo [3.1.0]hexan-3-yl)pyrazin-2-yl)-1H-1,2,3-triazol-1-yl)methyl)phenyl)-N-(cyclobutylmethyl)piperidin-3-amine was Obtained Using General Scheme 1 Pathway A Stage 1: General Procedure X was used between IM824 and IM610 to afford tert-butyl ((3R)-1-(4-((4-(6-(3-azabicyclo[3.1.0]hexan-3-yl)pyrazin-2-yl)-1H-1,2,3-triazol-1-yl)methyl)phenyl)piperidin-3-yl)(cyclobutylmethyl)carbamate IM826 as a yellow glass: 62 mg, 55% yield, P=72%, retention time=2.9 min (gradient A), (M+H)$^+$: 585.

Stage 2: General Procedure A2 was used from IM826 to afford crude compound 288 as a yellow glass: 57 mg, 99% yield, P=64%, retention time=2.4 min (gradient A), (M+H)$^+$: 485.

The product was purified by reverse phase preparative HPLC purification (XBridge OBD C18 5 μm, 19×100 mm). Gradient used: increased linearly from 40% to 60% solution "B" over 4.0 min, increased linearly to 88% solution "B" over 2.2 min, held for 0.6 min, and returned to initial conditions over 1.0 min. Flow Rate: 15 mL/min. P=99%. $^1$H NMR (300 MHz, CDCl$_3$) δ 8.54 (s, 1H), 7.82 (s, 1H), 7.69 (s, 1H), 7.14 (d, J=8.7 Hz, 2H), 6.84 (d, J=8.4 Hz, 2H), 5.40 (s, 2H), 3.68 (d, J=10.1 Hz, 2H), 3.63-3.53 (m, 1H), 3.46-3.35 (m, 3H), 2.83-2.69 (m, 1H), 2.69-2.60 (m, 3H), 2.55 (dd, J=11.3, 8.9 Hz, 1H), 2.38 (p, J=7.6 Hz, 1H), 2.09-1.95 (m, 2H), 1.92-1.69 (m, 4H), 1.65-1.50 (m, 4H), 1.32-1.15 (m, 2H), 0.70 (q, J=7.6 Hz, 1H), 0.18 (q, J=4.3 Hz, 1H), 1H exchanged with solvent.

Compound 289: (R)-1-(6-(3-(4-(6-(1H-pyrazol-1-yl) pyrazin-2-yl)-1H-1,2,3-triazol-1-yl)oxetan-3-yl)pyridin-3-yl)-N-(cyclobutylmethyl)piperidin-3-amine was Obtained Using General Scheme 1 Pathway A Stage 1: To a RBF was added 2,6-dichloropyrazine (2 g, 13.16 mmol), 1H-pyrazole (0.90 g, 13.22 mmol), potassium carbonate (3.70 g, 26.5 mmol), and anhydrous DMA (5 mL). The reaction was stirred at 50° C. under argon for 4.3 h. The reaction was cooled to rt and diluted with EtOAc (60 mL). The organic was then washed with water (60 mL), brine (30 mL) and concentrated under reduced pressure. The crude product was purified by automatic flash chromatography (liquid injection with toluene, nHept/EtOAc: 1/0 to 0/1) to give 2-chloro-6-pyrazol-1-yl-pyrazine IM827 as a white solid: 1.58 g, 67% yield, P=100%, retention time=2.7 min (gradient A), (M+H)$^+$: 181/183.

Stage 2: General Procedure E2 was used from IM827 to afford 2-(1H-pyrazol-1-yl)-6-((trimethylsilyl)ethynyl)pyrazine IM828 as light brown oil: 355 mg, 88% yield, P=100%, retention time=3.2 min (gradient A), (M+H)$^+$: 243.

Stage 3: General Procedure X was used between IM453 and IM828 to afford tert-butyl (R)-(1-(6-(3-(4-(6-(1H-pyrazol-1-yl)pyrazin-2-yl)-1H-1,2,3-triazol-1-yl)oxetan-3-yl) pyridin-3-yl)piperidin-3-yl)(cyclobutylmethyl)carbamate IM829 as yellow oil: 50 mg, 65% yield, P=86%, retention time=3.3 min (gradient A), (M+H)$^+$: 613.

Stage 4: General Procedure A2 was used from IM829 to afford compound 289 as a white solid: 19 mg, 51% yield, P=97%, retention time=3.4 min (gradient B), (M+H)$^+$: 513. $^1$H NMR (300 MHz, CDCl$_3$) δ 9.33 (s, 1H), 9.26 (s, 1H), 8.51 (d, J=2.7 Hz, 1H), 8.35 (d, J=2.9 Hz, 1H), 8.17 (s, 1H), 7.80 (d, J=1.6 Hz, 1H), 7.16 (dd, J=8.8, 2.9 Hz, 1H), 6.98 (d, J=8.7 Hz, 1H), 6.55-6.48 (m, 1H), 5.57 (d, J=6.8 Hz, 2H), 5.52 (d, J=6.9 Hz, 2H), 3.74-3.65 (m, 1H), 3.58-3.48 (m, 1H), 2.97-2.83 (m, 1H), 2.74-2.66 (m, 4H), 2.52-2.36 (m, 1H), 2.20-1.77 (m, 6H), 1.75-1.58 (m, 3H), 1.43-1.26 (m, 1H), 1H exchanged with solvent.

Compound 290: (R)—N-(cyclobutylmethyl)-1-(6-(3-(4-(6-(pyrrolidin-1-yl)pyrazin-2-yl)-1H-1,2,3-triazol-1-yl)oxetan-3-yl)pyridin-3-yl)piperidin-3-amine was Obtained Using General Scheme 1 Pathway A Stage 1: General Procedure X was used between IM453 and IM533 to afford tert-butyl (R)-(cyclobutylmethyl)(1-(6-(3-(4-(6-(pyrrolidin-1-yl)pyrazin-2-yl)-1H-1,2,3-triazol-1-yl)oxetan-3-yl)pyridin-3-yl)piperidin-3-yl)carbamate IM830 as a yellow solid: 43 mg, 49% yield, P=83%, retention time=3.1 min (gradient A), (M+H)$^+$: 616.

Stage 2: General Procedure A2 was used from IM830 to afford compound 290 as a white solid: 25 mg, 81% yield, P=97%, retention time=3.3 min (gradient B), (M+H)$^+$: 517. $^1$H NMR (300 MHz, CDCl$_3$) δ 8.63 (s, 1H), 8.34 (d, J=2.9 Hz, 1H), 8.04 (s, 1H), 7.82 (s, 1H), 7.11 (dd, J=8.8, 3.0 Hz, 1H), 6.84 (d, J=8.7 Hz, 1H), 5.53 (dd, J=6.7, 1.3 Hz, 2H), 5.50 (d, J=6.8 Hz, 2H), 3.71-3.60 (m, 1H), 3.56-3.44 (m, 5H), 2.95-2.80 (m, 1H), 2.78-2.61 (m, 4H), 2.51-2.35 (m, 1H), 2.15-1.76 (m, 10H), 1.73-1.55 (m, 3H), 1.42-1.28 (m, 1H), 1H exchanged with solvent.

Compound 291: (3R)-1-(6-(3-(4-(6-(3-azabicyclo [3.1.0]hexan-3-yl)pyrazin-2-yl)-1H-1,2,3-triazol-1-yl)oxetan-3-yl)pyridin-3-yl)-N-(cyclobutylmethyl) piperidin-3-amine was Obtained Using General Scheme 1 Pathway A Stage 1: General Procedure X was used between IM453 and IM610 to afford tert-butyl ((3R)-1-(6-(3-(4-(6-(3-azabicyclo[3.1.0]hexan-3-yl)pyrazin-2-yl)-1H-1,2,3-triazol-1-yl) oxetan-3-yl)pyridin-3-yl)piperidin-3-yl)(cyclobutylmethyl) carbamate IM831 as a dark yellow solid: 52 mg, 70% yield, P=92%, retention time=3.2 min (gradient A), (M+H)$^+$: 628.

Stage 2: General Procedure A2 was used from IM831 to afford compound 291 as a yellow solid: 25 mg, 55% yield, P=88%, retention time=3.4 min (gradient B), (M+H)$^+$: 528.

The product was further purified by chiral preparative HPLC purification using Chiralpak ID column (5 μm, 10×250 mm). Eluent used: TBME/MeOH/DCM/DEA: 40/40/20/0.1% at flow rate of 7 mL/min. P=100%, retention time=7.3 min, $^1$H NMR (300 MHz, CDCl$_3$) δ 8.64 (s, 1H), 8.33 (d, J=2.9 Hz, 1H), 8.03 (s, 1H), 7.78 (s, 1H), 7.11 (dd, J=8.8, 3.0 Hz, 1H), 6.84 (d, J=8.7 Hz, 1H), 5.52 (d, J=6.7 Hz, 2H), 5.49 (d, J=6.7 Hz, 2H), 3.80-3.66 (m, 3H), 3.54-3.41 (m, 3H), 2.94-2.80 (m, 1H), 2.80-2.66 (m, 4H), 2.54-2.38 (m, 1H), 2.16-2.00 (m, 2H), 2.00-1.75 (m, 4H), 1.74-1.56 (m, 5H), 1.44-1.29 (m, 1H), 0.83-0.71 (m, 1H), 0.31-0.21 (m, 1H), 1H exchanged with solvent.

Compound 292: (3R)—N-(cyclobutylmethyl)-1-(6-(1-(4-(6-cyclopropylpyrazin-2-yl)-1H-1,2,3-triazol-1-yl)ethyl)pyridin-3-yl)piperidin-3-amine was Obtained Using General Scheme 1 Pathway A Stage 1: General Procedure B was used between IM812 and IM603 to afford tert-butyl ((3R)-1-(6-(1-(4-(6-bromopyrazin-2-yl)-1H-1,2,3-triazol-1-yl)ethyl)pyridin-3-yl)piperidin-3-yl)(cyclobutylmethyl)carbamate IM832 as an off-white solid: 77 mg, 98% yield, P=99%, retention time=3.0 min (gradient A), (M+H)$^+$: 597/599.

Stage 2: Into a vial, IM832 (77 mg, 0.13 mmol), potassium phosphate tribasic (96 mg, 0.44 mmol), tricyclohexylphosphine (4 mg, 0.01 mmol), cyclopropylboronic acid (22 mg, 0.26 mmol), palladium(II) acetate (1.5 mg, 0.01 mmol), were merged, flushed by vaccuo/argon cycles (3 times). Then toluene (0.36 mL) and water (0.08 mL) were added (both previously degassed by argon bubbling for 20 min). Mixture was heated to 100° C. for 1.6 h. Reaction mixture was cooled to rt, diluted with EtOAc (30 mL), and washed with water (10 mL), followed by brine (10 mL). Organic layer was dried over MgSO$_4$, filtered and concentrated under reduced pressure to dryness to afford a brown oil. The crude material was purified by an automated flash chromatography system (liquid injection in DCM, 0 to 1% MeOH in DCM) to afford tert-butyl (cyclobutylmethyl) ((3R)-1-(6-(1-(4-(6-cyclopropylpyrazin-2-yl)-1H-1,2,3-triazol-1-yl)ethyl)pyridin-3-yl)piperidin-3-yl)carbamate IM833 as colourless oil: 41 mg, 57% yield, P=99%, retention time=2.9 min (gradient A), (M+2H)$^+$: 280.

Stage 3: General Procedure A2 was used from IM833 to afford crude compound 292 as a colourless oil: 30 mg, 89% yield, P=99%, retention time=3.2 min (gradient B), (M+H)$^+$: 459.

The mixture of diastereomers was purified by chiral preparative HPLC purification using Chiralpak ID column (5 µm, 10×250 mm). Eluent used: TBME/MeOH/DCM/DEA: 40/40/20/0.1% at flow rate of 7 mL/min. First eluted diastereomer: P=100%, retention time=3.9 min, chiral HPLC: P=100%, $^1$H NMR (300 MHz, CDCl$_3$) δ 9.11 (s, 1H), 8.36 (s, 1H), 8.28 (t, J=1.8 Hz, 1H), 8.22 (s, 1H), 7.13 (d, J=1.8 Hz, 2H), 5.92 (q, J=7.1 Hz, 1H), 3.66 (d, J=9.3 Hz, 1H), 3.52-3.40 (m, 1H), 2.85 (ddd, J=12.2, 10.4, 3.2 Hz, 1H), 2.79-2.62 (m, 4H), 2.45 (hept, J=7.6 Hz, 1H), 2.16-2.03 (m, 3H), 2.00 (d, J=7.1 Hz, 3H), 1.98-1.74 (m, 4H), 1.75-1.56 (m, 4H), 1.43-1.23 (m, 1H), 1.15-0.97 (m, 4H) Second eluted diastereomer: P=100%, retention time=8.6 min, chiral HPLC: P=100%, $^1$H NMR (300 MHz, CDCl$_3$) δ 9.11 (s, 1H), 8.36 (s, 1H), 8.31-8.25 (m, 1H), 8.23 (s, 1H), 7.12 (d, J=1.4 Hz, 2H), 5.92 (q, J=7.1 Hz, 1H), 3.70 (d, J=9.2 Hz, 1H), 3.50-3.40 (m, 1H), 2.90-2.77 (m, 1H), 2.77-2.65 (m, 4H), 2.48 (hept, J=7.6 Hz, 1H), 2.16-2.02 (m, 4H), 2.00 (d, J=7.1 Hz, 3H), 1.97-1.74 (m, 4H), 1.74-1.55 (m, 3H), 1.45-1.32 (m, 1H), 1.15-0.98 (m, 4H).

Compound 293: (3R)-1-(6-(1-(4-(6-(1H-pyrazol-1-yl)pyrazin-2-yl)-1H-1,2,3-triazol-1-yl)ethyl)pyridin-3-yl)-N-(cyclobutylmethyl)piperidin-3-amine was Obtained Using General Scheme 1 Pathway B Stage 1: General Procedure X was used between IM828 and IM231 to afford 2-(1-(1-(5-bromopyridin-2-yl)ethyl)-1H-1,2,3-triazol-4-yl)-6-(1H-pyrazol-1-yl)pyrazine IM834 as an off-white solid: 135 mg, 69% yield, P=96%, retention time=2.8 min (gradient A), (M+H)$^+$: 397/399.

Stage 2: General Procedure Y was used between IM834 and IM3 to afford tert-butyl ((3R)-1-(6-(1-(4-(6-(1H-pyrazol-1-yl)pyrazin-2-yl)-1H-1,2,3-triazol-1-yl)ethyl)pyridin-3-yl)piperidin-3-yl)(cyclobutylmethyl)carbamate IM835 as yellow oil: 120 mg, 59% yield, P=93%, retention time=2.9 min (gradient A), (M+Na)$^+$: 607.

Stage 3: General Procedure A1 was used from IM835 to afford crude compound 293 as yellow oil: 87 mg, 83% yield, P=88%, retention time=3.2 min (gradient B), (M+H)$^+$: 485.

The mixture of diastereomers was purified by chiral preparative HPLC purification using Chiralpak ID column (5 µm, 10×250 mm). Eluent used: TBME/MeOH/DCM/DEA: 40/40/20/0.1% at flow rate of 7 mL/min. First eluted diastereomer: P=100%, retention time=5.4 min, chiral HPLC: P=100%, $^1$H NMR (300 MHz, CDCl$_3$) δ 9.28 (s, 1H), 9.23 (s, 1H), 8.56 (dd, J=2.7, 0.7 Hz, 1H), 8.36 (s, 1H), 8.30 (dd, J=2.6, 1.0 Hz, 1H), 7.80 (dd, J=1.7, 0.7 Hz, 1H), 7.23-7.10 (m, 2H), 6.52 (dd, J=2.6, 1.6 Hz, 1H), 5.97 (q, J=7.1 Hz, 1H), 3.67 (d, J=9.0 Hz, 1H), 3.53-3.43 (m, 1H), 2.94-2.79 (m, 1H), 2.77-2.62 (m, 4H), 2.45 (p, J=7.6 Hz, 1H), 2.18-1.76 (m, 9H), 1.73-1.61 (m, 3H), 1.37-1.29 (m, 1H), 1H exchanged with solvent. Second eluted diastereomer: P=100%, retention time=14.6 min, chiral HPLC: P=100%, $^1$H NMR (300 MHz, CDCl$_3$) δ 9.28 (s, 1H), 9.23 (s, 1H), 8.56 (d, J=2.7 Hz, 1H), 8.36 (s, 1H), 8.30 (d, J=2.7 Hz, 1H), 7.80 (d, J=1.7 Hz, 1H), 7.17 (d, J=8.5 Hz, 1H), 7.12 (dd, J=8.6, 2.8 Hz, 1H), 6.52 (dd, J=2.7, 1.7 Hz, 1H), 5.96 (q, J=7.1 Hz, 1H), 3.72 (d, J=8.9 Hz, 1H), 3.50-3.40 (m, 1H), 2.90-2.67 (m, 5H), 2.49 (p, J=7.6 Hz, 1H), 2.14-1.57 (m, 12H), 1.46-1.32 (m, 1H), 1 NH exchanged with solvent.

Compound 294: 2-(4-((R)-3-((cyclobutylmethyl)amino)piperidin-1-yl)phenyl)-N-(6-(pyrrolidin-1-yl)pyrazin-2-yl)propanamide was Obtained Using General Scheme 6 Pathway A Stage 1: General Procedure AC was used from 4-chloromethylphenylacetic acid to afford 2-(4-chlorophenyl)propanamide IM836 as colourless oil: 238 mg, 36% yield, P=80%, retention time=2.4 min (gradient A), (M+H)$^+$: 184.

Stage 2: General Procedure AB was used between IM836 and M532 to afford 2-(4-chlorophenyl)-N-(6-(pyrrolidin-1-yl)pyrazin-2-yl)propanamide IM837 as orange gum: 110 mg, 72% yield, P=93%, retention time=2.6 min (gradient A), (M+H)$^+$: 331.

Stage 3: An argon filled sealable tube was charged with chloro(1-t-butylindenyl)palladium(II) dimer (20 mg, 0.03 mmol) and RuPhos (30 mg, 0.06 mmol). THF (2 mL) was added to the vial via syringe; the mixture was stirred for 10 minutes. In a sealable vial, sodium tert-butoxide (70 mg, 0.71 mmol) was added with a magnetic stir bar. IM837 (110 mg, 0.31 mmol) and IM3 (100 mg, 0.37 mmol) were added and the vial was evacuated and backfilled with argon. The precatalyst solution was added via syringe. The vial was sealed and heated at 85° C. for 2 h. The vial was cooled to rt and the reaction mixture was quenched with saturated aqueous NH$_4$Cl (5 mL) and extracted with EtOAc (2×10 mL). The organic layers were merged and dried over MgSO$_4$, filtered and concentrated under reduced pressure to dryness. The crude material was purified by an automated flash chromatography system (liquid load in DCM, 0 to 3% of MeOH in DCM) to afford tert-butyl (cyclobutylmethyl)((3R)-1-(4-(1-oxo-1-((6-(pyrrolidin-1-yl)pyrazin-2-yl)amino)propan-2-yl)phenyl)piperidin-3-yl)carbamate IM838 as yellow oil: 61 mg, 20% yield, P=58%, retention time=2.6 min (gradient A), (M+H)$^+$: 563.

Stage 4: General Procedure A1 was used from IM838 to afford crude compound 294 as yellow oil: 36 mg, 66% yield, P=53%, retention time=3.2 min (gradient B), (M+H)$^+$: 463.

The mixture of diastereomers was purified by chiral preparative HPLC purification using Chiralpak ID column (5 μm, 10×250 mm). Eluent used: TBME/MeOH/DEA: 80/20/0.1% at flow rate of 7 mL/min. First eluted diastereomer: P=94%, retention time=3.9 min, chiral HPLC: P=95.2%, $^1$H NMR (300 MHZ, CDCl$_3$) δ 8.70 (s, 1H), 7.60 (s, 1H), 7.40 (s, 1H), 7.20 (d, J=8.6 Hz, 2H), 6.98-6.87 (m, 2H), 3.69-3.56 (m, 2H), 3.48-3.41 (m, 1H), 3.41-3.32 (m, 4H), 2.87-2.70 (m, 4H), 2.65 (dd, J=11.4, 8.9 Hz, 1H), 2.49 (p, J=7.6 Hz, 1H), 2.17-1.58 (m, 13H), 1.54 (d, J=7.1 Hz, 3H), 1.43-1.23 (m, 1H), 1H exchanged with solvent. Second eluted diastereomer: P=100%, retention time=5.6 min, chiral HPLC: P=100%, $^1$H NMR (300 MHz, CDCl$_3$) δ 8.70 (s, 1H), 7.59 (s, 1H), 7.35 (s, 1H), 7.24-7.17 (m, 2H), 6.98-6.88 (m, 2H), 3.71-3.57 (m, 2H), 3.49-3.32 (m, 5H), 2.87-2.67 (m, 4H), 2.62 (dd, J=11.5, 8.8 Hz, 1H), 2.46 (p, J=7.5 Hz, 1H), 2.16-2.01 (m, 2H), 2.01-1.76 (m, 8H), 1.71-1.58 (m, 3H), 1.55 (d, J=7.1 Hz, 3H), 1.36-1.23 (m, 1H), 1H exchanged with solvent.

Compound 295: (R)-1-(6-(3-(4-(6-(1H-pyrrol-1-yl)pyrazin-2-yl)-1H-1,2,3-triazol-1-yl)oxetan-3-yl)pyridin-3-yl)-N-(cyclobutylmethyl)piperidin-3-amine was Obtained Using General Scheme 1 Pathway A Stage 1: Sodium hydride (68 mg, 1.7 mmol) was added to a solution of pyrrole (0.11 mL, 1.54 mmol) in DMF (2 mL) at rt under Ar. The reaction mixture was stirred for 30 min and was added via a syringe over 5 min to a solution of 2,6-dichloropyrazine (200 mg, 1.32 mmol) in anhydrous DMF (1 mL) at rt under Ar. The resulting mixture was stirred for 20 min at rt. The reaction mixture was quenched by adding a saturated aqueous solution of NH$_4$Cl (15 mL). The aqueous phase was extracted with EtOAc (3×10 mL) and the combined organic phases were washed with water (2×10 mL) and brine (10 mL). The organic layer was dried over MgSO$_4$ and concentrated under reduced pressure to afford brown oil. The crude material was purified by an automated flash chromatography system (liquid load in DCM, 0 to 10% of EtOAc in Heptane) to afford 2-chloro-6-(1H-pyrrol-1-yl)pyrazine IM839 as white crystals: 172 mg, 72% yield, P=99%, retention time=2.9 min (gradient A), (M+2H)+: 180.

Stage 2: General Procedure E2 was used from IM839 to afford 2-(1H-pyrrol-1-yl)-6-((trimethylsilyl)ethynyl)pyrazine IM840 as a white solid: 205 mg, 92% yield, P=98%, retention time=3.2 min (gradient A), (M+H)$^+$: 242.

Stage 3: General Procedure X was used between IM453 and IM840 to afford tert-butyl (R)-(1-(6-(3-(4-(6-(1H-pyrrol-1-yl)pyrazin-2-yl)-1H-1,2,3-triazol-1-yl)oxetan-3-yl)pyridin-3-yl)piperidin-3-yl)(cyclobutylmethyl)carbamate IM841 as yellow oil: 44 mg, 52% yield, P=83%, retention time=3.3 min (gradient A), (M+H)$^+$: 612.

Stage 4: General Procedure A2 was used from IM841 to afford crude compound 295 as a colourless oil: 16 mg, 45% yield, P=85%, retention time=2.4 min (gradient B), (M+H)$^+$: 512.

The compound was purified by chiral preparative HPLC purification using Chiralpak ID column (5 μm, 10×250 mm). Eluent used: TBME/MeOH/DCM/DEA: 40/40/20/0.1% at flow rate of 7 mL/min. P=100%, retention time=12.1 min, $^1$H NMR (300 MHz, CDCl$_3$) δ 9.23 (s, 1H), 8.65 (s, 1H), 8.33 (d, J=2.9 Hz, 1H), 8.17 (s, 1H), 7.56-7.48 (m, 2H), 7.15 (dd, J=8.8, 3.0 Hz, 1H), 6.95 (d, J=8.7 Hz, 1H), 6.43-6.36 (m, 2H), 5.55 (d, J=6.8 Hz, 2H), 5.50 (d, J=6.8 Hz, 2H), 3.80-3.68 (m, 1H), 3.58-3.45 (m, 1H), 2.88 (ddd, J=12.2, 10.6, 3.3 Hz, 1H), 2.76 (dd, J=13.0, 5.0 Hz, 4H), 2.47 (dq, J=15.1, 7.6 Hz, 1H), 2.17-1.56 (m, 10H), 1H exchanged with solvent.

Compound 296: (3R)—N-(cyclobutylmethyl)-1-(4-(1-(4-(5-methoxypyridin-3-yl)-1H-imidazol-1-yl)ethyl)phenyl)piperidin-3-amine was Obtained Using General Scheme 4 Pathway C1

Stage 1: To IM435 (212 mg, 726 μmol) was added potassium carbonate (335 mg, 2.37 mmol) and DMF (4.60 mL). The mixture was stirred at rt for 10 min. Then, 1-bromo-4-(1-bromoethyl)benzene (601 mg, 2.16 mmol) was added and the resulting mixture was stirred at 40° C. overnight (21.5 h). The reaction mixture was purified on a C-18 column using 0%-80% MeCN in aqueous ammonium bicarbonate to afford 3-(1-(1-(4-bromophenyl)ethyl)-1H-imidazol-4-yl)-5-methoxypyridine IM842 as a viscous oil: 75 mg, 28% yield, P=96%, retention time=1.4 min (gradient F), (M+H)$^+$: 360.

Stage 2: General Procedure Y was used between IM842 and IM3 to afford tert-butyl (cyclobutylmethyl)((3R)-1-(4-(1-(4-(5-methoxypyridin-3-yl)-1H-imidazol-1-yl)ethyl)phenyl)piperidin-3-yl)carbamate IM843 as pale yellow oil: 106 mg, 68% yield, P=70%, retention time=2.0 min (gradient F), (M+H)$^+$: 547.

Stage 3: General Procedure A2 was used from IM843 to afford compound 296 as viscous pale yellow oil: 27 mg, 43% yield, P=99%, retention time=2.9 min (gradient E), (M+H)$^+$: 446.

The mixture of diastereomers was further purified by chiral preparative HPLC purification using Chiralpak ID column (5 μm, 10×250 mm). Eluent used: TBME/MeOH/DCM/DEA: 40/40/20/0.1% at flow rate of 7 mL/min. First eluted diastereomer: P=99%, retention time=4.5 min, chiral HPLC: P=99.4%, $^1$H NMR (300 MHz, CDCl$_3$) δ 8.50 (d, J=1.7 Hz, 1H), 8.15 (d, J=2.9 Hz, 1H), 7.65 (dd, J=2.8, 1.7 Hz, 1H), 7.61 (d, J=1.4 Hz, 1H), 7.24 (d, J=1.3 Hz, 1H), 7.15-7.04 (m, 2H), 6.96-6.85 (m, 2H), 5.28 (q, J=7.0 Hz, 1H), 3.88 (s, 3H), 3.72-3.62 (m, 1H), 3.50-3.40 (m, 1H), 2.88-2.61 (m, 5H), 2.49 (hept, J=7.6 Hz, 1H), 2.17-1.55 (m, 12H), 1.44-1.23 (m, 1H), 1 NH exchanged with solvent. Second eluted diastereomer: P=100%, retention time=6.2 min, chiral HPLC: P=100%, $^1$H NMR (300 MHz, CDCl$_3$) δ 8.48 (d, J=1.8 Hz, 1H), 8.13 (d, J=2.9 Hz, 1H), 7.66-7.61 (m, 1H), 7.58 (d, J=1.4 Hz, 1H), 7.22 (d, J=1.3 Hz, 1H), 7.12-7.02 (m, 2H), 6.93-6.82 (m, 2H), 5.26 (q, J=7.0 Hz, 1H), 3.86 (s, 3H), 3.72-3.61 (m, 1H), 3.47-3.37 (m, 1H), 2.85-2.61 (m, 5H), 2.48 (p, J=7.7 Hz, 1H), 2.14-1.59 (m, 12H), 1.44-1.30 (m, 1H), 1 NH exchanged with solvent.

Compound 297: (R)-3-(5-(3-((cyclobutylmethyl)amino)piperidin-1-yl)pyridin-2-yl)-N-(quinoxalin-2-yl)oxetane-3-carboxamide was Obtained Using General Scheme 6 Pathway C Stage 1: General Procedure AB was used between IM788 and 2-bromoquinoxaline to afford tert-butyl (R)-(cyclobutylmethyl)(1-(6-(3-(quinoxalin-2-ylcarbamoyl)oxetan-3-yl)pyridin-3-yl)piperidin-3-yl)carbamate IM844 as yellow oil: 70 mg, 94% yield, P=81%, retention time=2.5 min (gradient A), (M+H)$^+$: 573.

Stage 2: General Procedure A2 was used from IM844 to afford compound 297 as a white solid: 25 mg, 52% yield, P=98%, retention time=3.2 min (gradient B), (M+H)$^+$: 473. $^1$H NMR (300 MHz, CDCl$_3$) δ 9.85 (s, 1H), 9.54 (s, 1H), 8.42 (t, J=1.8 Hz, 1H), 8.06 (dd, J=8.0, 1.7 Hz, 1H), 7.88-7.79 (m, 1H), 7.75-7.57 (m, 2H), 7.24 (d, J=1.8 Hz, 2H), 5.42 (d, J=6.1 Hz, 2H), 5.09 (d, J=6.1 Hz, 2H), 3.75-3.63 (m, 1H), 3.59-3.49 (m, 1H), 2.98-2.83 (m, 1H), 2.81-2.64 (m, 4H), 2.44 (dq, J=15.2, 7.6 Hz, 1H), 2.19-1.79 (m, 5H), 1.68 (q, J=9.1 Hz, 3H), 1.41-1.21 (m, 2H), 1 NH exchanged with solvent.

Compound 298: (R)-3-(5-(3-((cyclobutylmethyl)amino)piperidin-1-yl)-3-fluoropyridin-2-yl)-N-(4-oxo-4H-pyrido[1,2-a]pyrimidin-2-yl)oxetane-3-carboxamide was Obtained Using General Scheme 6 Pathway C Stage 1: To a mixture (colorless solution) of 5-bromo-2,3-difluoropyridine (803 mg, 4.06 mmol) and oxetane-3-carbonitrile (412 mg, 4.71 mmol) in anhydrous THF (8 mL) under Ar atmosphere at 0° C. was added KHMDS in toluene solution (6.35 mL, 4.44 mmol) dropwise over 2 min to afford a brown solution which was stirred at 0° C. for 50 min then at rt for 1.75 h. The reaction was quenched by the addition of MeOH (2 mL) then the reaction mixture was concentrated under reduced pressure to dryness. The crude material was purified by an automated flash chromatography system (dryload in silica, 0 to 10% EtOAc in Heptane) to afford 3-(5-bromo-3-fluoropyridin-2-yl)oxetane-3-carbonitrile IM845 as a white solid: 190 mg, 18% yield, P=98%, retention time=2.7 min (gradient A), (M+H)$^+$: 257/259.

Stage 2: General Procedure Y was used between IM845 and IM3 to afford tert-butyl (R)-(1-(6-(3-cyanooxetan-3-yl)-5-fluoropyridin-3-yl)piperidin-3-yl)(cyclobutylmethyl)carbamate IM846 as yellow oil: 210 mg, 53% yield, P=94%, retention time=3.4 min (gradient A), (M+H)+: 445.

Stage 3: General Procedure AD was used from IM846 to afford crude (R)-3-(5-(3-((tert-butoxycarbonyl)(cyclobutylmethyl)amino)piperidin-1-yl)-3-fluoropyridin-2-yl)oxetane-3-carboxylic acid IM847 as yellow oil: 227 mg, 84% yield, P=82%, retention time=3.0 min (gradient A), (M+H)+: 464.

Stage 4: General Procedure AC was used from IM847 to afford tert-butyl (R)-(1-(6-(3-carbamoyloxetan-3-yl)-5-fluoropyridin-3-yl)piperidin-3-yl)(cyclobutylmethyl)carbamate IM848 as a white solid: 185 mg, 100% yield, P=93%, retention time=3.0 min (gradient A), (M+H)+: 463.

Stage 5: General Procedure AB was used between IM848 and 2-chloro-4H-pyrido[1,2-a]pyrimidin-4-one to afford tert-butyl (R)-(cyclobutylmethyl)(1-(5-fluoro-6-(3-((4-oxo-4H-pyrido[1,2-a]pyrimidin-2-yl)carbamoyl)oxetan-3-yl)pyridin-3-yl)piperidin-3-yl)carbamate IM849 as yellow oil: 95 mg, 92% yield, P=94%, retention time=3.2 min (gradient A), (M+H)$^+$: 607.

Stage 6: General Procedure A2 was used from IM849 to afford compound 298 as a white solid: 52 mg, 68% yield, P=98%, retention time=2.2 min (gradient B), (M+H)$^+$: 507. $^1$H NMR (300 MHz, CDCl$_3$) δ 8.97 (dt, J=6.9, 1.3 Hz, 1H), 8.18 (dd, J=2.5, 1.6 Hz, 1H), 8.09 (s, 1H), 7.66 (ddd, J=8.6, 6.7, 1.6 Hz, 1H), 7.40 (s, 1H), 7.37 (dt, J=8.9, 1.1 Hz, 1H), 7.02 (td, J=6.9, 1.4 Hz, 1H), 6.87 (dd, J=13.2, 2.5 Hz, 1H), 5.28 (dd, J=6.4, 1.3 Hz, 2H), 5.18 (dt, J=6.4, 1.1 Hz, 2H), 3.77-3.63 (m, 1H), 3.59-3.49 (m, 1H), 3.01-2.86 (m, 1H), 2.80-2.67 (m, 4H), 2.44 (p, J=7.5 Hz, 1H), 2.17-1.79 (m, 6H), 1.77-1.58 (m, 3H), 1.43-1.20 (m, 1H), 1 NH exchanged with solvent. $^{19}$F NMR (282 MHz, CDCl$_3$) δ −120.48 (d, J=13.5 Hz).

Compound 299: (R)-3-(5-(3-((cyclobutylmethyl)amino)piperidin-1-yl)pyridin-2-yl)-N-(1H-pyrrolo[2,3-b]pyridin-5-yl)oxetane-3-carboxamide was Obtained Using General Scheme 6 Pathway B Stage 1: To a solution of IM688 (80 mg, 0.16 mmol), 5-amino-7-azaindole (25 mg, 0.18 mmol) and HATU (77 mg, 0.20 mmol) in anhydrous DMF (500 µL) under Ar atmosphere at rt was added DIEA (70 µL, 0.40 mmol) and the resulting dark brown solution was stirred at rt for 4.5 h. The reaction mixture was diluted with EtOAc (15 mL) and washed NaHCO$_3$ saturated solution (2×20 mL), then brine (3×20 mL), then dried over MgSO$_4$, filtered and the filtrate was concentrated under reduced pressure to dryness to afford a crude yellow oil. The latter was purified by an automated flash chromatography system (0 to 5% MeOH in DCM) to afford tert-butyl (R)-(1-(6-(3-((1H-pyrrolo[2,3-b]pyridin-5-yl)carbamoyl)oxetan-3-yl)pyridin-3-yl)piperidin-3-yl)(cyclobutylmethyl)carbamate IM850 as pale yellow oil: 84 mg, 88% yield, P=95%, retention time=2.6 min (gradient A), (M+H)+: 562.

Stage 2: General Procedure A2 was used from IM850 to afford compound 299 as a white solid: 54 mg, 82% yield, P=99%, retention time=2.6 min (gradient A), (M+H)$^+$: 461. $^1$H NMR (300 MHZ, CDCl$_3$) δ 9.83 (s, 1H), 8.90 (s, 1H), 8.35 (t, J=1.8 Hz, 1H), 8.29 (d, J=2.3 Hz, 1H), 8.22 (d, J=2.4 Hz, 1H), 7.31 (d, J=3.1 Hz, 1H), 7.25 (d, J=1.8 Hz, 2H), 6.45 (d, J=3.3 Hz, 1H), 5.43 (d, J=5.9 Hz, 2H), 5.06 (d, J=6.0 Hz, 2H), 3.74-3.65 (m, 1H), 3.57-3.47 (m, 1H), 2.97-2.83 (m, 1H), 2.83-2.66 (m, 4H), 2.46 (p, J=7.5 Hz, 1H), 2.17-1.78 (m, 6H), 1.74-1.58 (m, 3H), 1.42-1.24 (m, 1H), 1 NH exchanged with solvent.

Compound 300: 4-((R)-3-((cyclopropylmethyl)amino)piperidin-1-yl)-1-(1-(1-(5-(pyrrolidin-1-yl)pyridin-3-yl)-1H-pyrazol-4-yl)ethyl)pyridin-2(1H)-one was Obtained Using General Scheme 5 Pathway B Stage 1: A solution of 1-(5-chloropyridin-2-yl)ethanone (2.00 g, 12.6 mmol) and 2,6-di-tert-butyl-4-methylpyridine (3.04 g, 14.5 mmol) in DCM (39 mL) was cooled to 0 °C and trifluoromethanesulfonic anhydride (2.72 mL, 15.5 mmol) was added. The reaction mixture was warmed to rt and stirred overnight (there was heavy precipitation to a brown suspension about 5 minutes after adding Tf$_2$O; hence vigorous stirring was required). The mixture was filtered. The white precipitate (pyridinium salt) collected was washed with DCM. The filtrate was transferred to a separatory funnel and partitioned with saturated NH$_4$Cl (80 mL). The organic layer was removed. The aqueous layer was extracted further with DCM. The combined organic extracts were dried with MgSO$_4$ and evaporated to afford crude 1-(5-chloropyridin-2-yl)vinyl trifluoromethanesulfonate IM851: 4.89 g, 90% yield, P=67%, retention time=1.7 min (gradient F), (M+H)$^+$: no ionisation.

Stage 2: To a 100 mL RBF, under nitrogen, crude IM851 (1.00 g, 3.48 mmol), 1-(tetrahydro-2H-pyran-2-yl)-4-(4,4,5,5-tetramethyl-1,3,2-dioxaborolan-2-yl)-1H-pyrazole (997 mg, 3.48 mmol), K$_2$CO$_3$ (1.23 g, 8.69 mmol), tetrakis(triphenylphosphine)palladium(0) (243 mg, 209 µmol), dioxane (22.3 mL) and H$_2$O (4.47 mL) were successively added. The reaction mixture was degassed with nitrogen for 5 min and stirred at 100° C. for 1 h. After cooling to rt, mixture was concentrated under reduced pressure. The crude residue was purified by normal phase chromatography (dry load, 0-100% EtOAc in Heptanes) to afford 5-chloro-2-(1-(1-(tetrahydro-2H-pyran-2-yl)-1H-pyrazol-4-yl)vinyl)pyridine IM852 as a colorless oil (turning dark pink over time): 815 mg, 81% yield, P=100%, retention time=1.5 min (gradient C), (M+H)$^+$: 290/292.

Stage 3: In a 10 mL RBF, a mixture of Palladium on carbon 10% loading (8.45 mg, 7.94 µmol) and IM852 (230 mg, 794 µmol) was degassed three times with nitrogen. Then MeOH (1.98 mL) was added. The solution was backfilled under hydrogen atmosphere and allowed to stir at rt. After 30 min, mixture was filtered through a Pad of celite and washed several times with MeOH. Solvent was removed under reduced pressure and crude residue was purified by reverse phase chromatography using a gradient of MeCN (0-100%) in 10 mM ammonium bicarbonate buffer to afford 5-chloro-2-(1-(1-(tetrahydro-2H-pyran-2-yl)-1H-pyrazol-4-yl)ethyl)pyridine IM853 as a white solid: 77 mg, 31% yield, P=94%, retention time=1.4 min (gradient C), (M+H)$^+$: 292/294.

Stage 4: General Procedure A1 was used from IM853 to afford 2-(1-(1H-pyrazol-4-yl)ethyl)-5-chloropyridine IM854 as a white solid oil: 56 mg, 100% yield, P=100%, retention time=1.1 min (gradient C), (M+H)$^+$: 208/210.

Stage 5: In a microwave vial, under nitrogen, were successively added IM854 (56 mg, 270 µmol), 3-bromo-5-methoxypyridine (362 mg, 1.89 mmol), copper(I) iodide (78.6 mg, 405 µmol), cesium carbonate (224 mg, 674 µmol), N,N-dimethylglycine (41.7 mg, 405 µmol) and DMF (1.35 mL). Nitrogen was bubbled through the reaction mixture for 5 min, then vial was capped and the reaction mixture was heated at 100° C. for 2 h. After cooling to rt, reaction mixture was directly loaded onto a C-18 cartridge and purified by reverse phase chromatography using a gradient of MeCN (0-100%) in 10 mM ammonium bicarbonate buffer to afford 5-chloro-2-(1-(1-(5-methoxypyridin-3-yl)-1H-pyrazol-4-yl)ethyl)pyridine IM855 as a beige solid: 85 mg, 98% yield, P=98%, retention time=1.4 min (gradient C), (M+H)$^+$: 315/317.

Stage 6: General Procedure Y was used between IM855 and IM3 to afford tert-butyl (cyclobutylmethyl)((3R)-1-(6-(1-(1-(5-methoxypyridin-3-yl)-1H-pyrazol-4-yl)ethyl)pyridin-3-yl)piperidin-3-yl)carbamate IM856 as pale yellow oil: 83 mg, 55% yield, P=98%, retention time=2.0 min (gradient C), (M+H)+: 548.

Stage 7: General Procedure A2 was used from IM856 to afford compound 300 as a white solid: 26 mg, 38% yield, P=100%, retention time=2.8 min (gradient E), (M+H)$^+$: 447.

The compound was further purified by chiral preparative HPLC purification using Chiralpak ID column (5 µm, 10×250 mm). Eluent used: TBME/MeOH/DCM/DEA: 40/40/20/0.1% at flow rate of 7 mL/min. First eluted diastereomer: P=99%, retention time=15.2 min, chiral HPLC: P=100%, $^1$H NMR (300 MHz, CDCl$_3$) δ 8.48 (d, J=2.1 Hz, 1H), 8.26 (d, J=2.9 Hz, 1H), 8.20 (d, J=2.6 Hz, 1H), 7.77 (s, 1H), 7.63-7.55 (m, 2H), 7.20 (dd, J=8.6, 2.9 Hz, 1H), 7.04 (d, J=8.5 Hz, 1H), 4.17 (q, J=7.1 Hz, 1H), 3.90 (s, 4H), 3.44-3.34 (m, 1H), 3.00 (d, J=10.2 Hz, 2H), 2.90 (t, J=6.5 Hz, 3H), 2.70 (p, J=7.5 Hz, 1H), 2.21-2.06 (m, 3H), 1.95-1.58 (m, 10H), 1 NH exchanged with solvent. Second eluted diastereomer: P=99%, retention time=27.6 min, chiral HPLC: P=100%, $^1$H NMR (300 MHz, CDCl$_3$) δ 8.48 (d, J=2.1 Hz, 1H), 8.26 (d, J=2.9 Hz, 1H), 8.20 (d, J=2.6 Hz, 1H), 7.77 (s, 1H), 7.63-7.55 (m, 2H), 7.20 (dd, J=8.6, 3.0 Hz, 1H), 7.05 (d, J=8.5 Hz, 1H), 4.17 (q, J=7.1 Hz, 1H), 3.90 (s, 3H), 3.84 (d, J=9.6 Hz, 1H), 3.45-3.35 (m, 1H), 3.07-2.76 (m, 5H), 2.68 (p, J=7.5 Hz, 1H), 2.21-2.01 (m, 2H), 1.96-1.58 (m, 10H), 1.42 (dd, J=9.2, 6.7 Hz, 1H), 1 NH exchanged with solvent.

Compound 301: (R)—N-(cyclobutylmethyl)-1-(4-(3-(4-(6-(pyrrolidin-1-yl)pyrazin-2-yl)-1H-1,2,3-triazol-1-yl)oxetan-3-yl)phenyl)piperidin-3-amine was Obtained Using General Scheme 1 Pathway A Stage 1: General Procedure X was used between IM533 and IM411 to afford tert-butyl (R)-(cyclobutylmethyl)(1-(4-(3-(4-(6-(pyrrolidin-1-yl)pyrazin-2-yl)-1H-1,2,3-triazol-1-yl)oxetan-3-yl)phenyl)piperidin-3-yl)carbamate IM857 as a yellow glass: 53 mg, 59% yield, P=94%, retention time=3.0 min (gradient A), (M+H)$^+$: 615.

Stage 2: General Procedure A2 was used from IM857 to afford crude compound 301 as a yellow gum: 50 mg, 89% yield, P=75%, retention time=2.3 min (gradient A), (M+2H)$^+$: 258.

The product was purified by reverse phase preparative HPLC purification (XBridge OBD C18 5 µm, 19×100 mm). Gradient used: increased linearly from 35% to 50% solution "B" over 4.0 min, increased linearly to 88% solution "B" over 2.5 min, held for 0.3 min, and returned to initial conditions over 1.0 min. Flow Rate: 15 mL/min. P=100%. $^1$H NMR (300 MHz, CDCl$_3$) δ 8.63 (s, 1H), 7.85 (s, 1H), 7.82 (s, 1H), 7.17-7.06 (m, 2H), 6.98-6.87 (m, 2H), 5.60 (dd, J=6.8, 1.3 Hz, 2H), 5.27 (d, J=6.7 Hz, 2H), 3.71-3.61 (m, 1H), 3.54-3.44 (m, 5H), 2.83 (ddd, J=12.2, 10.4, 3.3 Hz, 1H), 2.77-2.58 (m, 4H), 2.44 (hept, J=7.6 Hz, 1H), 2.16-1.56 (m, 12H), 1.40-1.23 (m, 2H), 1H exchanged with solvent.

Compound 302: (R)-3-(5-(3-((cyclobutylmethyl)amino)piperidin-1-yl)pyridin-2-yl)-N-(1-oxo-1,2-dihydroisoquinolin-3-yl)oxetane-3-carboxamide was Obtained Using General Scheme 6 Pathway B Stage 1: To a solution of IM688 (72 mg, 0.14 mmol) in anhydrous DMF (0.60 mL) were added under argon, HATU (67 mg, 0.18 mmol), DIEA (50 µL, 0.29 mmol) and 3-amino-1,2-dihydroisoquinolin-1-one (32 mg, 0.19 mmol). The reaction was stirred at rt under argon for 16 h. The reaction mixture was diluted with EtOAc (30 mL) and then washed with an aqueous saturated solution of NaHCO$_3$ (20 mL), water (20 mL), and brine (20 mL), dried over MgSO$_4$, filtered and concentrated under reduced pressure to dryness. The crude material was purified by an automated flash chromatography system (dryload in silica, 0 to 4% MeOH in DCM) to afford tert-butyl (R)-(cyclobutylmethyl)(1-(6-(3-((1-oxo-1,2-dihydroisoquinolin-3-yl)carbamoyl)oxetan-3-yl)pyridin-3-yl)piperidin-3-yl)carbamate IM858 as colourless glass: 44 mg, 46% yield, P=89%, retention time=2.9 min (gradient A), (M+H)+: 588.

Stage 2: General Procedure A2 was used from IM858 to afford crude compound 302 as a light yellow gum: 39 mg, 100% yield, P=83%, retention time=2.2 min (gradient A), (M+H)$^+$: 488.

The product was purified by reverse phase preparative HPLC purification (XBridge OBD C18 5 µm, 19×100 mm). Gradient used: increased linearly from 35% to 50% solution "B" over 4.0 min, increased linearly to 88% solution "B" over 2.5 min, held for 0.3 min, and returned to initial conditions over 1.0 min. Flow Rate: 15 mL/min. P=99%. $^1$H NMR (300 MHz, CDCl$_3$) δ 10.11 (s, 1H), 8.34-8.26 (m, 2H), 7.55 (ddd, J=8.2, 7.0, 1.4 Hz, 1H), 7.42-7.20 (m, 4H), 6.08 (s, 1H), 5.37 (d, J=6.1 Hz, 2H), 4.96 (d, J=6.1 Hz, 2H), 3.72-3.60 (m, 1H), 3.56-3.46 (m, 1H), 2.89 (ddd, J=12.0, 10.4, 3.3 Hz, 1H), 2.80-2.63 (m, 4H), 2.44 (p, J=7.5 Hz, 1H), 2.17-1.77 (m, 6H), 1.77-1.57 (m, 3H), 1.35 (s, 1H), 2H exchanged with solvent.

Compound 303: (3R)—N-(cyclobutylmethyl)-1-(5-fluoro-6-(1-(4-(6-(pyrrolidin-1-yl)pyrazin-2-yl)-1H-1,2,3-triazol-1-yl)ethyl)pyridin-3-yl)piperidin-3-amine was Obtained Using General Scheme 1 Pathway B Stage 1: 1-(5-bromo-3-fluoro-2-pyridyl)ethanone (600 mg, 2.75 mmol) was dissolved in methanol (27 mL) at 0° C.

Then sodium borohydride (105 mg, 2.78 mmol) was added over 30 sec. The reaction was stirred at 0° C. for 1 h. Acetone (6 mL) was added at 0° C. The reaction was stirred 2 min at 0° C. and then 2 min a rt. The mixture was concentrated in vacuo to dryness. EtOAc (40 mL) was added to the residue, and was washed with brine (3×20 mL). Organic layer was dried over MgSO$_4$, filtered and concentrated under reduced pressure to afford 1-(5-bromo-3-fluoropyridin-2-yl)ethan-1-ol IM859 as yellow liquid: 505 mg, 83% yield, P=100%, retention time=2.4 min (gradient A), (M+H)$^+$: 220/222.

Stage 2: General Procedure P was used from IM859 to afford 1-(5-bromo-3-fluoropyridin-2-yl)ethyl methanesulfonate IM860 as yellow oil: 534 mg, 69% yield, P=88%, retention time=2.6 min (gradient A), (M+H)$^+$: 298/300.

Stage 3: General Procedure N was used from IM860 to afford 2-(1-azidoethyl)-5-bromo-3-fluoropyridine IM861 as dark yellow oil: 412 mg, 99% yield, P=93%, retention time=3.0 min (gradient A), (M+H)$^+$: 245/247.

Stage 4: General Procedure X was used between IM861 and IM533 to afford 2-(1-(1-(5-bromo-3-fluoropyridin-2-yl)ethyl)-1H-1,2,3-triazol-4-yl)-6-(pyrrolidin-1-yl)pyrazine IM862 as a yellow foam: 240 mg, 65% yield, P=86%, retention time=2.7 min (gradient A), (M+H)$^+$: 418/420.

Stage 5: General Procedure Y was used between IM862 and IM3 to afford tert-butyl (cyclobutylmethyl)((3R)-1-(5-fluoro-6-(1-(4-(6-(pyrrolidin-1-yl)pyrazin-2-yl)-1H-1,2,3-triazol-1-yl)ethyl)pyridin-3-yl)piperidin-3-yl)carbamate IM863 as orange sticky oil: 136 mg, 65% yield, P=71%, retention time=3.3 min (gradient A), (M+H)$^+$: 606.

Stage 6: General Procedure A2 was used from IM863 to afford crude compound 303 as orange oil: 106 mg, 68% yield, P=52%, retention time=3.5 min (gradient B), (M+H)$^+$: 506.

The mixture of diastereomers was purified by chiral preparative HPLC purification using Chiralpak ID column (5 µm, 10×250 mm). Eluent used: TBME/MeOH/DEA: 80/20/0.1% at flow rate of 7 mL/min. First eluted diastereomer: P=100%, retention time=5.3 min, chiral HPLC: P=100%, $^1$H NMR (300 MHz, CDCl$_3$) δ 8.51 (s, 1H), 8.16 (s, 1H), 8.04 (dd, J=2.5, 1.2 Hz, 1H), 7.72 (s, 1H), 6.75 (dd, J=12.7, 2.5 Hz, 1H), 6.28-6.15 (m, 1H), 3.67-3.52 (m, 1H), 3.51-3.36 (m, 5H), 2.82 (ddd, J=12.5, 10.6, 3.3 Hz, 1H), 2.69-2.54 (m, 4H), 2.36 (hept, J=7.5 Hz, 1H), 2.08-1.68 (m, 13H), 1.66-1.46 (m, 3H), 1.30-1.17 (m, 1H), 1H exchanged with solvent. $^{19}$F NMR (282 MHZ, CDCl$_3$) δ -122.91 (d, J=12.5 Hz). Second eluted diastereomer: P=100%, retention time=6.3 min, chiral HPLC: P=98.6. $^1$H NMR (300 MHz, CDCl$_3$) δ 8.58 (s, 1H), 8.23 (s, 1H), 8.11 (dd, J=2.5, 1.2 Hz, 1H), 7.79 (s, 1H), 6.82 (dd, J=12.7, 2.5 Hz, 1H), 6.35-6.22 (m, 1H), 3.74-3.59 (m, 1H), 3.58-3.43 (m, 5H), 2.89 (ddd, J=12.4, 10.6, 3.3 Hz, 1H), 2.76-2.62 (m, 4H), 2.43 (hept, J=7.5 Hz, 1H), 2.15-1.73 (m, 13H), 1.73-1.53 (m, 3H), 1.45-1.23 (m, 1H), 1 NH exchanged with solvent. 19F NMR (282 MHz, CDCl$_3$) δ -122.92 (d, J=12.4 Hz).

Compound 304: (3R)—N-((3-fluorobicyclo[1.1.1]
pentan-1-yl)methyl)-1-(6-(1-(4-(6-(pyrrolidin-1-yl)
pyrazin-2-yl)-1H-1,2,3-triazol-1-yl)ethyl)pyridin-3-
yl)piperidin-3-amine was Obtained Using General
Scheme 1 Pathway B Stage 1: General Procedure X was used between IM231 and IM533 to afford 2-(1-(1-(5-bromopyridin-2-yl)ethyl)-1H-1,2,3-triazol-4-yl)-6-(pyrrolidin-1-yl)pyrazine IM864 as light brown solid: 280 mg, 81% yield, P=94%, retention time=2.7 min (gradient A), (M+H)$^+$: 400/402.

Stage 2: General Procedure Y was used between IM864 and IM62 to afford tert-butyl ((3-fluorobicyclo[1.1.1]pentan-1-yl)methyl)((3R)-1-(6-(1-(4-(6-(pyrrolidin-1-yl)pyrazin-2-yl)-1H-1,2,3-triazol-1-yl)ethyl)pyridin-3-yl)piperidin-3-yl)carbamate IM865 as yellow oil: 130 mg, 88% yield, P=88%, retention time=2.8 min (gradient A), (M+H)$^+$: 618.

Stage 3: General Procedure A2 was used from IM865 to afford crude compound 304 as a yellow solid: 66 mg, 55% yield, P=80%, retention time=3.5 min (gradient B), (M+H)$^+$: 518.

The mixture of diastereomers was purified by chiral preparative HPLC purification using Chiralpak ID column (5 µm, 10×250 mm). Eluent used: TBME/MeOH/DCM/DEA: 40/40/20/0.1% at flow rate of 7 mL/min. First eluted diastereomer: P=95%, retention time=4.4 min, chiral HPLC: P=94.0%, $^1$H NMR (300 MHz, CDCl$_3$) δ 8.59 (s, 1H), 8.30-8.21 (m, 1H), 8.18 (s, 1H), 7.79 (s, 1H), 7.12 (d, J=1.8 Hz, 2H), 5.92 (q, J=7.1 Hz, 1H), 3.66-3.56 (m, 1H), 3.56-3.38 (m, 5H), 2.95 (s, 2H), 2.93-2.61 (m, 3H), 2.10-1.90 (m, 14H), 1.87-1.74 (m, 1H), 1.74-1.59 (m, 1H), 1.42-1.23 (m, 1H), 1H exchanged with solvent. $^{19}$F NMR (282 MHZ, CDCl$_3$) δ -142.47. Second eluted diastereomer: P=98%, retention time=12.8 min, chiral HPLC: P=99.5%, $^1$H NMR (300 MHz, CDCl$_3$) δ 8.58 (s, 1H), 8.29-8.22 (m, 1H), 8.18 (s, 1H), 7.79 (s, 1H), 7.16-7.04 (m, 2H), 5.91 (q, J=7.1 Hz, 1H), 3.64 (d, J=11.0 Hz, 1H), 3.56-3.37 (m, 5H), 2.97 (s, 2H), 2.95-2.64 (m, 3H), 2.09-1.88 (m, 14H), 1.87-1.73 (m, 1H), 1.73-1.53 (m, 1H), 1.45-1.31 (m, 1H), 1 NH exchanged with solvent. $^{19}$F NMR (282 MHz, CDCl$_3$) δ -142.54.

Compound 305: (3R)—N-((3-fluorobicyclo[1.1.1]
pentan-1-yl)methyl)-1-(6-(1-(4-(6-(pyrrolidin-1-yl)
pyrazin-2-yl)-1H-1,2,3-triazol-1-yl)ethyl)pyridazin-
3-yl)piperidin-3-amine was Obtained Using General
Scheme 1 Pathway B Stage 1: General Procedure X was used between IM106 and IM533 to afford 3-chloro-6-(1-(4-(6-(pyrrolidin-1-yl)pyrazin-2-yl)-1H-1,2,3-triazol-1-yl)ethyl)pyridazine IM866 as a yellow solid: 88 mg, 41% yield, P=84%, retention time=2.4 min (gradient A), (M+H)$^+$: 357/359.

Stage 2: General Procedure C was used between IM866 and IM62 to afford tert-butyl ((3-fluorobicyclo[1.1.1]pentan-1-yl)methyl)((3R)-1-(6-(1-(4-(6-(pyrrolidin-1-yl)pyrazin-2-yl)-1H-1,2,3-triazol-1-yl)ethyl)pyridazin-3-yl)piperidin-3-yl)carbamate IM867 as yellow oil: 98 mg, 63% yield, P=82%, retention time=2.6 min (gradient A), (M+H)$^+$: 619.

Stage 3: General Procedure A2 was used from IM867 to afford crude compound 305 as yellow oil: 70 mg, 84% yield, P=81%, retention time=3.1 min (gradient B), (M+H)$^+$: 519.

The mixture of diastereomers was purified by chiral preparative HPLC purification using Chiralpak ID column (5 µm, 10×250 mm). Eluent used: TBME/MeOH/DCM/DEA: 40/40/20/0.1% at flow rate of 7 mL/min. First eluted diastereomer: P=100%, retention time=6.1 min, chiral HPLC: P=100%, $^1$H NMR (300 MHz, CDCl$_3$) δ 8.57 (s, 1H), 8.20 (s, 1H), 7.79 (s, 1H), 7.21 (d, J=9.5 Hz, 1H), 6.86 (d, J=9.5 Hz, 1H), 6.03 (q, J=7.2 Hz, 1H), 4.46-4.34 (m, 1H), 4.05-3.93 (m, 1H), 3.55-3.44 (m, 4H), 3.10 (ddd, J=13.5, 10.6, 3.1 Hz, 1H), 3.03-2.85 (m, 3H), 2.76-2.61 (m, 1H), 2.10 (d, J=7.1 Hz, 3H), 2.08-1.91 (m, 11H), 1.88-1.74 (m, 1H), 1.67-1.32 (m, 2H), 1H exchanged with solvent. $^{19}$F NMR (282 MHZ, CDCl$_3$) δ -142.40. Second eluted diastereomer: P=100%, retention time=11.1 min, chiral HPLC: P=100%, $^1$H NMR (300 MHz, CDCl$_3$) δ 8.57 (s, 1H), 8.20

(s, 1H), 7.79 (s, 1H), 7.21 (d, J=9.4 Hz, 1H), 6.86 (d, J=9.5 Hz, 1H), 6.04 (q, J=7.2 Hz, 1H), 4.49-4.37 (m, 1H), 4.06-3.94 (m, 1H), 3.55-3.44 (m, 4H), 3.17-2.99 (m, 1H), 2.97 (s, 2H), 2.96-2.87 (m, 1H), 2.78-2.64 (m, 1H), 2.10 (d, J=7.1 Hz, 3H), 2.08-1.92 (m, 11H), 1.88-1.75 (m, 1H), 1.66-1.48 (m, 1H), 1.48-1.37 (m, 1H), 1 NH exchanged with solvent. $^{19}$F NMR (282 MHZ, CDCl$_3$) δ −142.46.

Compound 306: (R)—N-(cyclobutylmethyl)-1-(6-(3-(4-(5-cyclopropylpyridin-3-yl)-1H-1,2,3-triazol-1-yl)oxetan-3-yl)pyridin-3-yl)piperidin-3-amine was Obtained Using General Scheme 1 Pathway A Stage 1: General Procedure X was used between IM747 and IM453 to afford tert-butyl (R)-(cyclobutylmethyl)(1-(6-(3-(4-(5-cyclopropylpyridin-3-yl)-1H-1,2,3-triazol-1-yl)oxetan-3-yl)pyridin-3-yl)piperidin-3-yl)carbamate IM868 as yellow oil: 17 mg, 17% yield, P=95%, retention time=2.6 min (gradient A), (M+H)$^+$: 586.

Stage 2: General Procedure A2 was used from IM868 to afford crude compound 306 as yellow oil: 18 mg, 99% yield, P=74%, retention time=2.1 min (gradient A), (M+H)$^+$: 486.

The product was purified by reverse phase preparative HPLC purification (XBridge OBD C18 5 µm, 19×100 mm). Gradient used: increased linearly from 35% to 50% solution "B" over 4.0 min, increased linearly to 88% solution "B" over 2.5 min, held for 0.3 min, and returned to initial conditions over 1.0 min. Flow Rate: 15 mL/min. P=98%. $^1$H NMR (300 MHz, CDCl$_3$) δ 8.70 (d, J=2.0 Hz, 1H), 8.37 (d, J=2.2 Hz, 1H), 8.33 (d, J=2.9 Hz, 1H), 7.83 (t, J=2.2 Hz, 1H), 7.76 (s, 1H), 7.14 (dd, J=8.7, 3.0 Hz, 1H), 6.92 (d, J=8.7 Hz, 1H), 5.58-5.44 (m, 4H), 3.76-3.61 (m, 1H), 3.59-3.46 (m, 1H), 2.89 (ddd, J=12.5, 10.5, 3.3 Hz, 1H), 2.75-2.62 (m, 4H), 2.43 (hept, J=7.5 Hz, 1H), 2.15-1.75 (m, 7H), 1.75-1.55 (m, 3H), 1.32 (s, 1H), 1.11-0.96 (m, 2H), 0.85-0.73 (m, 2H), 1H exchanged with solvent.

Compound 307: (R)-1-(6-(3-(4-(5-cyclobutoxypyridin-3-yl)-1H-1,2,3-triazol-1-yl)oxetan-3-yl)pyridin-3-yl)-N-(cyclobutylmethyl)piperidin-3-amine was Obtained Using General Scheme 1 Pathway B Stage 1: To a mixture of 3-bromo-5-hydroxypyridine (500 mg, 2.82 mmol), anhydrous toluene (17 mL), triphenylphosphine (1.10 g, 4.19 mmol) and cyclobutanol (340 µL, 4.21 mmol) under argon was slowly added diethyl azodicarboxylate (1.65 mL, 4.19 mmol) over 2 minutes. The mixture was heated at 90° C. for 3.5 h. The reaction was cooled to 0° C. (let stir for 5 min) and filtered over fritted (to remove reduced DIAD). The resulting solid was washed with cold toluene (5 mL) and the filtrate was concentrated in vacuo to dryness. The crude material was purified by an automated flash chromatography system (dryload in Celite, 0 to 10% EtOAc in n-heptane) to afford 3-bromo-5-cyclobutoxypyridine IM869 as limpid colorless: 488 mg, 71% yield, P=93%, retention time=2.8 min (gradient A), (M+H)$^+$: 228/230.

Stage 2: General Procedure E3 was used from IM869 to afford 3-cyclobutoxy-5-((trimethylsilyl)ethynyl)pyridine IM870 as yellow oil: 298 mg, 93% yield, P=94%, retention time=3.0 min (gradient A), (M+H)$^+$: 246.

Stage 1': General Procedure P was used from IM725 to afford 3-(5-bromopyridin-2-yl)oxetan-3-yl methanesulfonate IM871 as light brown solid: 646 mg, 93% yield, P=96%, retention time=2.5 min (gradient A), (M+H)$^+$: 308/310.

Stage 2': General Procedure N was used from IM871 to afford 2-(3-azidooxetan-3-yl)-5-bromopyridine IM872 as colourless oil: 243 mg, 56% yield, P=100%, retention time=2.8 min (gradient A), (M+H)$^+$: 255/257.

Stage 3: General Procedure X was used between IM870 and IM872 to afford 5-bromo-2-(3-(4-(5-cyclobutoxypyridin-3-yl)-1H-1,2,3-triazol-1-yl)oxetan-3-yl)pyridine IM873 as dark yellow sticky oil: 143 mg, 60% yield, P=84%, retention time=2.5 min (gradient A), (M+H)$^+$: 428/430.

Stage 4: General Procedure Y was used between IM873 and IM3 to afford tert-butyl (R)-(1-(6-(3-(4-(5-cyclobutoxypyridin-3-yl)-1H-1,2,3-triazol-1-yl)oxetan-3-yl)pyridin-3-yl)piperidin-3-yl)(cyclobutylmethyl)carbamate IM874 as orange sticky oil: 66 mg, 59% yield, P=81%, retention time=2.9 min (gradient A), (M+H)$^+$: 616.

Stage 5: General Procedure A2 was used from IM874 to afford compound 307 as a white foam: 43 mg, 93% yield, P=97%, retention time=3.1 min (gradient B), (M+H)$^+$: 516. $^1$H NMR (300 MHZ, CDCl$_3$) δ 8.49 (d, J=1.7 Hz, 1H), 8.34 (d, J=3.0 Hz, 1H), 8.19 (d, J=2.8 Hz, 1H), 7.75 (s, 1H), 7.67 (dd, J=2.8, 1.7 Hz, 1H), 7.15 (dd, J=8.7, 3.0 Hz, 1H), 6.94 (d, J=8.8 Hz, 1H), 5.55 (d, J=6.8 Hz, 2H), 5.49 (d, J=6.7 Hz, 2H), 4.75 (p, J=7.2 Hz, 1H), 3.74-3.65 (m, 1H), 3.58-3.48 (m, 1H), 2.98-2.83 (m, 1H), 2.71 (d, J=7.3 Hz, 4H), 2.58-2.36 (m, 3H), 2.30-1.56 (m, 11H), 1.48-1.22 (m, 3H), 1H exchanged with solvent.

Compound 308: (R)—N-((3-fluorobicyclo[1.1.1]pentan-1-yl)methyl)-1-(6-(3-(4-(6-(pyrrolidin-1-yl)pyrazin-2-yl)-1H-1,2,3-triazol-1-yl)oxetan-3-yl)pyridin-3-yl)piperidin-3-amine was Obtained Using General Scheme 1 Pathway B Stage 1: General Procedure X was used between IM533 and IM872 to afford 2-(1-(3-(5-bromopyridin-2-yl)oxetan-3-yl)-1H-1,2,3-triazol-4-yl)-6-(pyrrolidin-1-yl)pyrazine IM875 as a yellow foam: 92 mg, 67% yield, P=86%, retention time=2.6 min (gradient A), (M+H)$^+$: 428/430.

Stage 2: General Procedure Y was used between IM875 and IM62 to afford tert-butyl (R)-((3-fluorobicyclo[1.1.1]pentan-1-yl)methyl)(1-(6-(3-(4-(6-(pyrrolidin-1-yl)pyrazin-2-yl)-1H-1,2,3-triazol-1-yl)oxetan-3-yl)pyridin-3-yl)piperidin-3-yl)carbamate IM876 as orange oil: 85 mg, 97% yield, P=68%, retention time=3.0 min (gradient A), (M+H)$^+$: 646.

Stage 3: General Procedure A2 was used from IM876 to afford crude compound 308 as yellow oil: 52 mg, 93% yield, P=87%, retention time=2.3 min (gradient A), (M+H)$^+$: 546.

The product was purified by reverse phase preparative HPLC purification (XBridge OBD C18 5 µm, 19×100 mm). Gradient used: increased linearly from 35% to 50% solution "B" over 4.0 min, increased linearly to 88% solution "B" over 2.5 min, held for 0.3 min, and returned to initial conditions over 1.0 min. Flow Rate: 15 mL/min. P=100%. $^1$H NMR (300 MHz, CDCl$_3$) δ 8.63 (s, 1H), 8.33 (d, J=2.9 Hz, 1H), 8.06 (s, 1H), 7.83 (s, 1H), 7.11 (dd, J=8.8, 3.0 Hz, 1H), 6.85 (d, J=8.7 Hz, 1H), 5.58-5.46 (m, 4H), 3.70-3.60 (m, 1H), 3.56-3.44 (m, 5H), 2.95 (s, 2H), 2.94-2.81 (m, 1H), 2.79-2.63 (m, 2H), 2.08-1.91 (m, 11H), 1.89-1.75 (m, 1H), 1.74-1.60 (m, 1H), 1.40-1.26 (m, 1H), 1H exchanged with solvent. $^{19}$F NMR (282 MHZ, CDCl$_3$) δ −142.49.

Compound 309: (3R)—N-(cyclopropylmethyl)-1-(6-(1-(4-(6-(pyrrolidin-1-yl)pyrazin-2-yl)-1H-1,2,3-triazol-1-yl)ethyl)pyridazin-3-yl)piperidin-3-amine was Obtained Using General Scheme 1 Pathway B Stage 1: General Procedure X was used between IM533 and IM106 to afford 3-chloro-6-(1-(4-(6-(pyrrolidin-1-yl)pyrazin-2-yl)-1H-1,2,3-triazol-1-yl)ethyl)pyridazine IM877 as orange oil: 120 mg, 75% yield, P=79%, retention time=2.6 min (gradient A), (M+H)⁺: 575.

Stage 2: General Procedure C was used between IM877 and IM486 to afford tert-butyl (cyclopropylmethyl)((3R)-1-(6-(1-(4-(6-(pyrrolidin-1-yl)pyrazin-2-yl)-1H-1,2,3-triazol-1-yl)ethyl)pyridazin-3-yl)piperidin-3-yl)carbamate IM878 as orange oil: 120 mg, 75% yield, P=79%, retention time=2.6 min (gradient A), (M+H)⁺: 575.

Stage 3: General Procedure A2 was used from IM878 to afford crude compound 309 as orange oil: 95 mg, 100% yield, P=82%, retention time=2.1 min (gradient A), (M+H)⁺: 475.

The mixture of diastereomers was purified by chiral preparative HPLC purification using Chiralpak ID column (5 μm, 10×250 mm). Eluent used: TBME/MeOH/DCM/DEA: 40/40/20/0.1% at flow rate of 7 mL/min. First eluted diastereomer: P=99%, retention time=6.7 min, chiral HPLC: P=98.0%, ¹H NMR (300 MHz, CDCl₃) δ 8.58 (s, 1H), 8.21 (s, 1H), 7.80 (s, 1H), 7.21 (d, J=9.4 Hz, 2H), 6.87 (d, J=9.5 Hz, 1H), 6.04 (q, J=7.2 Hz, 1H), 4.44-4.33 (m, 1H), 4.13-4.02 (m, 1H), 3.56-3.46 (m, 4H), 3.19-3.04 (m, 1H), 2.92 (dd, J=12.8, 9.2 Hz, 1H), 2.79-2.65 (m, 1H), 2.55 (d, J=6.8 Hz, 2H), 2.11 (d, J=7.1 Hz, 3H), 2.08-1.98 (m, 5H), 1.89-1.76 (m, 1H), 1.65-1.37 (m, 3H), 1.03-0.86 (m, 1H), 0.54-0.43 (m, 2H), 0.18-0.08 (m, 2H), 1H exchanged with solvent. Second eluted diastereomer: P=98%, retention time=15.0 min, chiral HPLC: P=100%, ¹H NMR (300 MHz, CDCl₃) δ 8.58 (s, 1H), 8.20 (s, 1H), 7.80 (s, 1H), 7.21 (d, J=9.5 Hz, 2H), 6.88 (d, J=9.5 Hz, 1H), 6.04 (q, J=7.1 Hz, 1H), 4.46-4.36 (m, 1H), 4.12-4.02 (m, 1H), 3.56-3.45 (m, 4H), 3.19-3.04 (m, 1H), 2.97 (dd, J=12.8, 9.2 Hz, 1H), 2.81-2.69 (m, 1H), 2.58 (d, J=6.8 Hz, 2H), 2.15-1.97 (m, 8H), 1.88-1.77 (m, 1H), 1.64-1.40 (m, 2H), 1.01-0.92 (m, 1H), 0.53-0.42 (m, 2H), 0.19-0.10 (m, 2H), 1 NH exchanged with solvent.

Compound 310: (R)-3-(5-(3-((cyclobutylmethyl)amino)piperidin-1-yl)pyridin-2-yl)-N-(1-methyl-2-oxo-6-(pyrrolidin-1-yl)-1,2-dihydropyridin-4-yl)oxetane-3-carboxamide was Obtained Using General Scheme 6 Pathway C Stage 1: To a solution of 4-bromo-6-chloro-pyridin-2-ol (468 mg, 2.04 mmol) in anhydrous DMF (10 mL) was added sodium carbonate (455 mg, 4.09 mmol) and iodomethane (160 μL, 2.54 mmol) (dropwise over 15 seconds) at rt. The solution was stirred for 2 hours at rt. The reaction was diluted with water (100 mL) and extracted with ethyl acetate (3×50 mL). The combined organic layers were washed with water (4×50 mL), brine (20 mL), dried with MgSO₄, filtered and concentrated in vacuo. The crude material was purified by an automated flash chromatography system (dryload in Celite, 0 to 25% EtOAc in n-heptane to afford 4-bromo-6-chloro-1-methylpyridin-2(1H)-one IM879 as a white solid: 200 mg, 44% yield, P=100%, retention time=2.4 min (gradient A), (M+H)⁺: 222/224/226.

Stage 2: General Procedure C was used between IM879 and pyrrolidine to afford 4-bromo-1-methyl-6-(pyrrolidin-1-yl)pyridin-2(1H)-one IM880 as a light beige solid: 189 mg, 82% yield, P=100%, retention time=2.5 min (gradient A), (M+H)⁺: 257/259.

Stage 3: General Procedure AB was used between IM880 and IM788 to afford tert-butyl (R)-(cyclobutylmethyl)(1-(6-(3-((1-methyl-2-oxo-6-(pyrrolidin-1-yl)-1,2-dihydropyridin-4-yl)carbamoyl)oxetan-3-yl)pyridin-3-yl)piperidin-3-yl)carbamate IM881 as pale yellow foam: 93 mg, 86% yield, P=98%, retention time=2.7 min (gradient A), (M+H)⁺: 622.

Stage 4: General Procedure A2 was used from IM881 to afford compound 310 as a white solid: 66 mg, 89% yield, P=100%, retention time=3.0 min (gradient B), (M+H)⁺: 521. ¹H NMR (300 MHz, CDCl₃) δ 8.93 (s, 1H), 8.22 (d, J=2.7 Hz, 1H), 7.12 (s, 2H), 6.59 (d, J=2.2 Hz, 1H), 5.76 (d, J=2.2 Hz, 1H), 5.25 (d, J=6.0 Hz, 2H), 4.92 (d, J=6.0 Hz, 2H), 3.66-3.57 (m, 1H), 3.49-3.40 (m, 1H), 3.38 (s, 3H), 3.18-3.08 (m, 4H), 2.82 (s, 1H), 2.73-2.59 (m, 4H), 2.40 (p, J=7.5 Hz, 1H), 2.10-1.50 (m, 13H), 1.36-1.18 (m, 1H), 1 NH exchanged.

Compound 311: (R)-3-(5-(3-((cyclobutylmethyl)amino)piperidin-1-yl)pyridin-2-yl)-N-(5-oxo-5H-thiazolo[3,2-a]pyrimidin-7-yl)oxetane-3-carboxamide was Obtained Using General Scheme 6 Pathway C Stage 1: To a yellow suspension of 2-aminothiazole (1 g, 9.69 mmol) and monoethyl malonic acid (1.30 mL, 10.46 mmol) in anhydrous MeCN (25 mL) under Ar atmosphere was added chloro-n,n,n',n'-tetramethylformamidinium hexafluorophosphate (3.30 g, 11.53 mmol) at once, followed by 1-methylimidazole (2.50 mL, 31.05 mmol) at rt. The reaction mixture was stirred at rt for 30 min. Reaction mixture was diluted with NaHCO₃ saturated solution (20 mL), and extracted with EtOAc (4×30 mL). Organics layer were merged, washed with brine (20 mL) and dried over MgSO₄, filtered and concentrated under reduced pressure to afford a light brown solid. The crude material was purified by an automated flash chromatography system (dryload in celite, 0 to 100% EtOAc in n-heptane) to provide a white solid. The latter was triturated in Et₂O (50 mL), and resulting powder was filtered, rinsed with Et₂O (2×20 mL). Solid was dry under reduced pressure for 1 h to afford ethyl 3-oxo-3-(thiazol-2-ylamino)propanoate IM882 as a white solid: 820 mg, 37% yield, P=93%, retention time=2.2 min (gradient A), (M+H)⁺: 215.

Stage 2: IM882 (100 mg, 0.43 mmol) was added to a mixture polyphosphoric acid (40 mg, 0.17 mmol) and phosphorus(V) oxychloride (125 μL, 1.33 mmol). Reaction mixture was heated to 130° C. for 1.5 h. Extra add of phosphorus (V) oxychloride (400 μL, 4.25 mmol) was added to the reaction mixture, which was then stirred at 130° C. for 16 h. Then, polyphosphoric acid (120 mg, 0.50 mmol) was added to the reaction, which was stirred for 1 additional h at 130° C. Reaction was cooled to 0° C., and water was added (5 mL), then poured on NaHCO₃ solid (10 g, huge bubbling) and diluted with water (20 mL). When no more bubbling was observed, aqueous layer was extracted with EtOAc (3×50 mL). Organics layer were merged, washed with brine (20 mL), dried over MgSO₄, filtered and concentrated under reduced pressure to afford 7-chloro-5H-thiazolo[3,2-a]pyrimidin-5-one IM883 as a yellow solid: 51 mg, 60% yield, P=95%, retention time=2.2 min (gradient A), (M+H)⁺: 187/189.

Stage 3: General Procedure AB was used between IM883 and IM788 to afford tert-butyl (R)-(cyclobutylmethyl)(1-(6-(3-((5-oxo-5H-thiazolo[3,2-a]pyrimidin-7-yl)carbamoyl)oxetan-3-yl)pyridin-3-yl)piperidin-3-yl)carbamate IM884 as a yellow solid: 67 mg, 61% yield, P=85%, retention time=2.8 min (gradient A), (M+H)⁺: 595.

Stage 4: General Procedure A2 was used from IM884 to afford crude compound 311 as yellow oil: 34 mg, 47% yield, P=65%, retention time=2.8 min (gradient B), (M+H)⁺: 495.

The product was purified by reverse phase preparative HPLC purification (XBridge OBD C18 5 μm, 19×100 mm). Gradient used: increased linearly from 20% to 40% solution "B" over 4.0 min, increased linearly to 88% solution "B" over 2.5 min, held for 0.3 min, and returned to initial conditions over 1.0 min. Flow Rate: 15 mL/min. P=100%. $^1$H NMR (300 MHz, CDCl$_3$) δ 9.15 (s, 1H), 8.41-8.34 (m, 1H), 7.91 (d, J=4.9 Hz, 1H), 7.25-7.16 (m, 3H), 6.85 (d, J=4.9 Hz, 1H), 5.34 (d, J=6.1 Hz, 2H), 5.02 (d, J=6.1 Hz, 2H), 3.74-3.65 (m, 1H), 3.58-3.48 (m, 1H), 2.97-2.82 (m, 1H), 2.76-2.63 (m, 4H), 2.46 (p, J=7.5 Hz, 1H), 2.17-1.79 (m, 6H), 1.75-1.60 (m, 3H), 1.39-1.23 (m, 1H), 1H exchanged with solvent.

Compound 312: (R)-1-(6-(3-(4-(5-cyclobutylpyridin-3-yl)-1H-1,2,3-triazol-1-yl)oxetan-3-yl)pyridin-3-yl)-N-(cyclopropylmethyl)piperidin-3-amine was Obtained Using General Scheme 1 Pathway A Stage 1: A solution of 3,5-dibromopyridine (4 g, 16.55 mmol) and Pd(PPh$_3$)$_4$ (980 mg, 0.83 mmol) in anhydrous THF (33 mL) was added to bromo(cyclobutyl)zinc (83.5 mL, 20.88 mmol) under argon atmosphere. Reaction mixture was heated to 60° C. for 2 h. Reaction mixture was cooled to rt, diluted with NaHCO$_3$ saturated solution (100 mL) and extracted with EtOAc (3×150 mL). Organics layers were merged and washed with brine (2×50 mL), dried over MgSO$_4$, filtered and concentrated under reduced pressure to afford a yellow solid. The crude material was purified by an automated flash chromatography system (dryload in silica, 0 to 15% EtOAc in Heptane) to afford 3-bromo-5-cyclobutylpyridine IM885 as orange oil: 676 mg, 15% yield, P=80%, retention time=2.5 min (gradient A), (M+H)$^+$: 212/214.

Stage 2: General Procedure E3 was used from IM885 to afford 3-cyclobutyl-5-((trimethylsilyl)ethynyl)pyridine IM886 as yellow oil: 247 mg, 89% yield, P=94%, retention time=2.8 min (gradient A), (M+H)$^+$: 230.

Stage 3: General Procedure X was used between IM886 and IM543 to afford tert-butyl (R)-(1-(6-(3-(4-(5-cyclobutylpyridin-3-yl)-1H-1,2,3-triazol-1-yl)oxetan-3-yl)pyridin-3-yl)piperidin-3-yl)(cyclopropylmethyl)carbamate IM887 as dark orange oil: 75 mg, 44% yield, P=77%, retention time=3.2 min (gradient A), (M+H)$^+$: 586.

Stage 4: General Procedure A2 was used from IM887 to afford compound 312 as an off-white solid: 30 mg, 61% yield, P=97%, retention time=2.8 min (gradient B), (M+H)$^+$: 486. $^1$H NMR (300 MHZ, CDCl$_3$) δ 8.76 (s, 1H), 8.42 (s, 1H), 8.34 (d, J=2.8 Hz, 1H), 8.09 (s, 1H), 7.78 (s, 1H), 7.16 (dd, J=8.7, 2.9 Hz, 1H), 6.94 (d, J=8.7 Hz, 1H), 5.60-5.43 (m, 4H), 3.78-3.67 (m, 1H), 3.67-3.57 (m, 1H), 3.57-3.43 (m, 1H), 2.97-2.69 (m, 3H), 2.63-2.50 (m, 2H), 2.50-2.35 (m, 2H), 2.28-1.76 (m, 5H), 1.72-1.54 (m, 2H), 1.45-1.33 (m, 1H), 0.97 (s, 1H), 0.59-0.49 (m, 2H), 0.19-0.10 (m, 2H), 1H exchanged with solvent.

Compound 313: (R)-1-(6-(3-(4-(5-cyclopentylpyridin-3-yl)-1H-1,2,3-triazol-1-yl)oxetan-3-yl)pyridin-3-yl)-N-(cyclopropylmethyl)piperidin-3-amine was Obtained Using General Scheme 1 Pathway A Stage 1: A solution of 3,5-dibromopyridine (5 g, 20.68 mmol) and Pd(PPh$_3$)$_4$ (1.23 g, 1.04 mmol) in anhydrous THF (41 mL) was added to bromo(cyclopentyl)zinc (39 mL, 24.96 mmol) under argon atmosphere. Reaction mixture was heated to 60° C. for 1.5 h. Reaction mixture was cooled to rt, diluted with NaHCO$_3$ saturated solution (100 mL) and extracted with EtOAc (3×150 mL). Organics layers were merged and washed with brine (2×50 mL), dried over MgSO$_4$, filtered and concentrated under reduced pressure to afford a yellow solid. The crude material was purified by an automated flash chromatography system (dryload in silica, 0 to 20% EtOAc in Heptane) to afford 3-bromo-5-cyclopentylpyridine IM888 as yellow oil: 2.43 g, 49% yield, P=95%, retention time=2.6 min (gradient A), (M+H)$^+$: 226/228.

Stage 2: General Procedure E3 was used from IM888 to afford 3-cyclopentyl-5-((trimethylsilyl)ethynyl)pyridine IM889 as yellow oil: 937 mg, 89% yield, P=97%, retention time=2.8 min (gradient A), (M+H)$^+$: 244.

Stage 3: General Procedure X was used between IM889 and IM543 to afford tert-butyl (R)-(1-(6-(3-(4-(5-cyclopentylpyridin-3-yl)-1H-1,2,3-triazol-1-yl)oxetan-3-yl)pyridin-3-yl)piperidin-3-yl)(cyclopropylmethyl)carbamate IM890 as brown oil: 95 mg, 58% yield, P=82%, retention time=2.7 min (gradient A), (M+H)$^+$: 600.

Stage 4: General Procedure A2 was used from IM890 to afford compound 313 as an off-white solid: 38 mg, 57% yield, P=97%, retention time=3.0 min (gradient B), (M+H)$^+$: 500. $^1$H NMR (300 MHz, CDCl$_3$) δ 8.63 (s, 1H), 8.33 (s, 1H), 8.21 (s, 1H), 7.95 (s, 1H), 7.63 (s, 1H), 7.01 (d, J=8.7 Hz, 1H), 6.79 (d, J=8.7 Hz, 1H), 5.42 (d, J=6.8 Hz, 2H), 5.35 (d, J=6.7 Hz, 2H), 3.57 (d, J=10.9 Hz, 1H), 3.39 (d, J=12.3 Hz, 1H), 2.93 (t, J=8.3 Hz, 1H), 2.77 (t, J=11.3 Hz, 1H), 2.62 (d, J=10.4 Hz, 2H), 2.42 (s, 2H), 1.99 (d, J=10.7 Hz, 2H), 1.83 (s, 1H), 1.77-1.07 (m, 9H), 0.82 (s, 1H), 0.37 (d, J=7.7 Hz, 2H), 0.09--0.08 (m, 2H), 1H exchanged with solvent.

Compound 314: (R)-4-(1-(3-(5-(3-((cyclopropylmethyl)amino)piperidin-1-yl)pyridin-2-yl)oxetan-3-yl)-1H-1,2,3-triazol-4-yl)-1-methyl-6-(pyrrolidin-1-yl)pyridin-2(1H)-one was Obtained Using General Scheme 1 Pathway A Stage 1: General Procedure E1 was used from IM880 to afford 1-methyl-6-(pyrrolidin-1-yl)-4-((trimethylsilyl)ethynyl)pyridin-2(1H)-one IM891 as brown oil: 83 mg, 73% yield, P=94%, retention time=2.9 min (gradient A), (M+H)$^+$: 275.

Stage 2: General Procedure X was used between IM891 and IM543 to afford tert-butyl (R)-(cyclopropylmethyl)(1-(6-(3-(4-(1-methyl-2-oxo-6-(pyrrolidin-1-yl)-1,2-dihydropyridin-4-yl)-1H-1,2,3-triazol-1-yl)oxetan-3-yl)pyridin-3-yl)piperidin-3-yl)carbamate IM892 as brown solid: 150 mg, 80% yield, P=96%, retention time=2.8 min (gradient A), (M+H)$^+$: 631.

Stage 3: General Procedure A2 was used from IM892 to afford compound 314 as an off-white solid: 84 mg, 68% yield, P=98%, retention time=3.1 min (gradient B), (M+H)$^+$: 531. $^1$H NMR (300 MHz, CDCl$_3$) δ 8.33 (d, J=3.0 Hz, 1H), 7.68 (s, 1H), 7.14 (dd, J=8.7, 3.0 Hz, 1H), 6.92 (d, J=8.7 Hz, 1H), 6.48 (d, J=1.7 Hz, 1H), 6.37 (d, J=1.7 Hz, 1H), 5.53 (d, J=6.8 Hz, 2H), 5.46 (d, J=6.8 Hz, 2H), 3.76-3.67 (m, 1H), 3.53 (s, 4H), 3.32-3.22 (m, 4H), 2.99-2.67 (m, 3H), 2.65-2.46 (m, 2H), 2.04-1.93 (m, 5H), 1.87-1.26 (m, 3H), 0.95 (d, J=5.6 Hz, 1H), 0.56-0.44 (m, 2H), 0.18-0.04 (m, 2H), 1H exchanged with solvent.

Compound 315: (R)—N-(cyclopropylmethyl)-1-(6-(1-(4-(5-cyclopropylpyridin-3-yl)-1H-1,2,3-triazol-1-yl)-3,3-difluorocyclobutyl)pyridin-3-yl)piperidin-3-amine was Obtained Using General Scheme 1 Pathway B Stage 1: A solution of 5-bromo-2-iodopyridine (1.20 g, 4.1 mmol) in anhydrous diethyl ether (55 mL) under Ar atmosphere was cooled to −78° C. to afford a white suspension. n-Butyl lithium in hexane (2.60 mL, 4.16 mmol) was added over 5 min to this white suspension to afford an orange solution which was stirred at −78° C. for 1 h. Then, a solution of 3,3-difluorocyclobutanone (500 mg, 4.57 mmol) in anhydrous THF (1 mL) was added at −78° C. and the reaction mixture was stirred at this temperature for 45 min. NH₄Cl saturated solution (15 mL) was added at −78° C. to afford a black suspension which was allowed to reach rt, then water (20 mL) and EtOAc (100 mL) were added and the layers were separated. The aqueous layer was extracted with EtOAc (2×20 mL). The combined organic layers were washed with brine (2×20 mL), dried over MgSO₄, filtered and the filtrate was concentrated under reduced pressure to afford a crude dark brown oil. The crude material was purified by an automated flash chromatography system (0 to 15% EtOAc in n-heptane) to afford 1-(5-bromopyridin-2-yl)-3,3-difluorocyclobutan-1-ol IM893 as brown oil: 277 mg, 25% yield, P=97%, retention time=2.7 min (gradient A), (M+H)⁺: 264/266.

Stage 2: General Procedure P was used from IM893 to afford 1-(5-bromopyridin-2-yl)-3,3-difluorocyclobutyl methanesulfonate IM894 as a reddish oil: 386 mg, 100% yield, P=90%, retention time=2.8 min (gradient A), (M+H)⁺: 342/344.

Stage 3: General Procedure N was used from IM894 to afford 2-(1-azido-3,3-difluorocyclobutyl)-5-bromopyridine IM895 as colourless oil: 242 mg, 77% yield, P=96%, retention time=3.1 min (gradient A), (M+H)⁺: 289/291.

Stage 1': General Procedure D1 was used from IM747 to afford 3-cyclopropyl-5-ethynylpyridine IM896 as dark brown liquid: 120 mg, 85% yield, P=94%, retention time=2.0 min (gradient A), (M+H)⁺: 144.

Stage 4: General Procedure B was used between IM896 and IM895 to afford 5-bromo-2-(1-(4-(5-cyclopropylpyridin-3-yl)-1H-1,2,3-triazol-1-yl)-3,3-difluorocyclobutyl)pyridine IM897 as colourless oil: 139 mg, 84% yield, P=94%, retention time=2.5 min (gradient A), (M+H)⁺: 432/434.

Stage 5: General Procedure Y was used between IM897 and IM486 to afford tert-butyl (R)-(cyclopropylmethyl)(1-(6-(1-(4-(5-cyclopropylpyridin-3-yl)-1H-1,2,3-triazol-1-yl)-3,3-difluorocyclobutyl)pyridin-3-yl)piperidin-3-yl)carbamate IM898 as an off-white foam: 146 mg, 66% yield, P=83%, retention time=2.7 min (gradient A), (M+H)⁺: 607.

Stage 6: General Procedure A2 was used from IM898 to afford crude compound 315 as orange gum: 127 mg, 90% yield, P=72%, retention time=2.2 min (gradient A), (M+H)⁺: 507.

The product was purified by reverse phase preparative HPLC purification (XBridge OBD C18 5 μm, 19×100 mm). Gradient used: increased linearly from 35% to 50% solution "B" over 4.0 min, increased linearly to 88% solution "B" over 2.5 min, and returned to initial conditions over 0.7 min. Flow Rate: 15 mL/min. P=100%. ¹H NMR (300 MHz, CDCl₃) δ 8.67 (d, J=2.0 Hz, 1H), 8.34 (d, J=2.2 Hz, 1H), 8.27 (d, J=2.9 Hz, 1H), 7.78 (t, J=2.2 Hz, 1H), 7.76 (s, 1H), 7.10 (dd, J=8.8, 2.9 Hz, 1H), 6.93 (d, J=8.7 Hz, 1H), 3.80 (t, J=11.4 Hz, 4H), 3.71-3.62 (m, 1H), 3.55-3.42 (m, 1H), 2.95-2.81 (m, 1H), 2.81-2.63 (m, 2H), 2.61-2.42 (m, 2H), 2.01-1.73 (m, 3H), 1.73-1.53 (m, 1H), 1.42-1.21 (m, 1H), 1.08-0.98 (m, 2H), 0.98-0.83 (m, 1H), 0.82-0.71 (m, 2H), 0.53-0.39 (m, 2H), 0.15-0.04 (m, 2H), 1H exchanged with solvent. ¹⁹F NMR (282 MHz, CDCl₃) δ −87.40 (dp, J=198.6, 12.1 Hz), −88.84 (dp, J=198.5, 10.7 Hz).

Compound 316: (R)-2-(1-(3-(5-(3-((cyclopropylmethyl)amino)piperidin-1-yl)pyridin-2-yl)oxetan-3-yl)-1H-1,2,3-triazol-4-yl)-4H-pyrido[1,2-a]pyrimidin-4-one was Obtained Using General Scheme 1 Pathway A Stage 1: General Procedure X was used between IM543 and IM57 to afford tert-butyl (R)-(cyclopropylmethyl)(1-(6-(3-(4-(4-oxo-4H-pyrido[1,2-a]pyrimidin-2-yl)-1H-1,2,3-triazol-1-yl)oxetan-3-yl)pyridin-3-yl)piperidin-3-yl)carbamate IM899 as a yellow solid: 104 mg, 87% yield, P=93%, retention time=2.9 min (gradient A), (M+H)⁺: 599.

Stage 2: General Procedure A2 was used from IM899 to afford compound 316 as grey oil: 80 mg, 90% yield, P=91%, retention time=2.9 min (gradient B), (M+H)⁺: 499.

The product was further purified by reverse phase preparative HPLC purification (XBridge OBD C18 5 μm, 19×100 mm). Gradient used: increased linearly from 20% to 40% solution "B" over 4.0 min, increased linearly to 88% solution "B" over 2.5 min, held for 0.3 min, and returned to initial conditions over 1.0 min. Flow Rate: 15 mL/min. P=100%. ¹H NMR (300 MHz, CDCl₃) δ 9.08 (d, J=7.1 Hz, 1H), 8.34 (d, J=2.9 Hz, 1H), 8.18 (s, 1H), 7.72 (ddd, J=8.4, 6.6, 1.6 Hz, 1H), 7.64-7.55 (m, 1H), 7.32 (s, 1H), 7.19-7.05 (m, 2H), 6.92 (d, J=8.7 Hz, 1H), 5.55 (d, J=6.8 Hz, 2H), 5.50 (d, J=6.8 Hz, 2H), 3.74-3.65 (m, 1H), 3.57-3.47 (m, 1H), 2.98-2.84 (m, 1H), 2.84-2.65 (m, 2H), 2.63-2.45 (m, 2H), 2.03-1.92 (m, 1H), 1.90-1.76 (m, 1H), 1.75-1.61 (m, 1H), 1.44-1.30 (m, 1H), 1.02-0.85 (m, 1H), 0.56-0.44 (m, 2H), 0.17-0.10 (m, 2H, 1H exchanged with solvent.

Compound 317: (3R)—N-(cyclopropylmethyl)-1-(6-(1-(4-(5-cyclopropylpyridin-3-yl)-1H-1,2,3-triazol-1-yl)ethyl)pyridazin-3-yl)piperidin-3-amine was Obtained Using General Scheme 1 Pathway B Stage 1: General Procedure B was used between IM106 and IM896 to afford 3-chloro-6-(1-(4-(5-cyclopropylpyridin-3-yl)-1H-1,2,3-triazol-1-yl)ethyl)pyridazine IM900 as a yellow solid: 102 mg, 91% yield, P=96%, retention time=2.5 min (gradient A), (M+H)⁺: 327/329.

Stage 2: General Procedure C was used between IM900 and IM486 to afford tert-butyl (cyclopropylmethyl)((3R)-1-(6-(1-(4-(5-cyclopropylpyridin-3-yl)-1H-1,2,3-triazol-1-yl)ethyl)pyridazin-3-yl)piperidin-3-yl)carbamate IM901 as an off-white solid: 150 mg, 85% yield, P=96%, retention time=2.3 min (gradient A), (M+H)⁺: 546.

Stage 3: General Procedure A2 was used from IM901 to afford crude compound 317 as colourless oil: 110 mg, 90% yield, P=96%, retention time=2.0 min (gradient A), (M+H)⁺: 446.

The mixture of diastereomers was purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=100%, retention time=4.9 min, chiral HPLC: P=100%, ¹H NMR (300 MHz, CDCl₃) δ 8.73 (d, J=2.0 Hz, 1H), 8.36 (d, J=2.2 Hz, 1H), 8.02 (s, 1H), 7.77 (t, J=2.2 Hz, 1H), 7.22 (d, J=9.5 Hz, 1H), 6.88 (d, J=9.5 Hz, 1H), 6.02 (q, J=7.1 Hz, 1H), 4.43-4.31 (m, 1H), 4.13-4.02 (m, 1H), 3.12 (ddd, J=13.5, 10.6, 3.2 Hz, 1H), 2.94 (dd, J=12.8, 9.2 Hz, 1H), 2.79-2.64 (m, 1H), 2.54 (d, J=6.9 Hz, 2H), 2.09 (d, J=7.1 Hz, 3H), 2.06-1.76 (m, 3H), 1.68-1.35 (m, 4H), 1.10-0.99 (m, 2H), 0.99-0.82 (m, 1H), 0.82-0.72 (m, 2H), 0.55-0.39 (m, 2H), 0.17-0.07 (m, 2H), 1H exchanged with solvent. Second eluted diastereomer: P=100%, retention time=18.9 min, chiral HPLC: P=100%, ¹H NMR (300 MHz, CDCl₃) δ 8.74 (d, J=2.1 Hz, 1H), 8.36 (d, J=2.2 Hz, 1H), 8.03 (s, 1H), 7.78 (t, J=2.1 Hz, 1H), 7.23 (d, J=9.4 Hz, 1H), 6.92 (d, J=9.5 Hz, 1H), 6.03 (q, J=7.1 Hz, 1H), 4.49-4.39 (m, 1H), 4.10-3.99 (m, 1H), 3.21-3.08 (m, 2H), 2.88 (s, 1H), 2.65 (d, J=7.0 Hz, 2H), 2.09 (d, J=7.1 Hz, 4H), 2.01-1.81 (m, 2H), 1.61 (s, 1H), 1.10-0.98 (m, 3H), 0.84-0.73 (m, 2H), 0.58-0.46 (m, 2H), 0.25-0.15 (m, 2H), 1H exchanged with solvent.

Compound 318: (3R)—N-(cyclopropylmethyl)-1-(6-(1-(4-(5-cyclopropylpyridin-3-yl)-1H-1,2,3-triazol-1-yl)ethyl)-5-methylpyridin-3-yl)piperidin-3-amine was Obtained Using General Scheme 1 Pathway B Stage 1: General Procedure F was used between 5-bromo-3-methylpicolinic acid and N,O-dimethylhydroxylamine hydrochloride to afford 5-bromo-N-methoxy-N,3-dimethylpicolinamide IM902 as orange oil: 2.9 g, 94% yield, P=95%, retention time=2.4 min (gradient A), (M+H)⁺: 259/261.

Stage 2: General Procedure Q was used from IM902 to 1-(5-bromo-3-methylpyridin-2-yl)ethan-1-one IM903 as a yellow liquid: 1.95 g, 82% yield, P=96%, retention time=2.8 min (gradient A), (M+H)⁺: 214/216.

Stage 3: IM903 (1.95 g, 8.75 mmol) was dissolved in methanol (80 mL) at 0° C. Then sodium borohydride (340 mg, 8.99 mmol) was added over 30 sec (note: initial pale orange solution becomes a pale yellow solution upon addition of NaBH₄). The reaction was stirred at 0° C. for 1 h. Acetone (8 mL) was added at 0° C., the reaction was stirred 2 min at 0° C. and then 2 min at rt. The mixture was concentrated in vacuo to dryness. EtOAc (80 mL) was added to the residue, and washed with brine (3×40 mL). Organic layer was dried over MgSO₄, filtered and concentrated under reduced pressure to give crude 1-(5-bromo-3-methylpyridin-2-yl)ethan-1-ol IM904 as yellow liquid: 1.85 g, 94% yield, P=96%, retention time=1.8 min (gradient A), (M+H)⁺: 216/218.

Stage 4: General Procedure P was used from IM904 to afford 1-(5-bromo-3-methylpyridin-2-yl)ethyl methanesulfonate IM905 as yellow oil: 2.4 g, 90% yield, P=91%, retention time=2.6 min (gradient A), (M+H)⁺: 294/296.

Stage 5: General Procedure N was used from IM905 to afford 2-(1-azidoethyl)-5-bromo-3-methylpyridine IM906 as pink oil: 2.12 g, 99% yield, P=84%, retention time=3.0 min (gradient A), (M+H)⁺: 241/243.

Stage 6: General Procedure B was used between IM906 and IM896 to afford 5-bromo-2-(1-(4-(5-cyclopropylpyridin-3-yl)-1H-1,2,3-triazol-1-yl)ethyl)-3-methylpyridine IM907 as a white solid: 140 mg, 61% yield, P=87%, retention time=2.4 min (gradient A), (M+H)⁺: 384/386.

Stage 7: General Procedure Y was used between IM907 and IM486 to afford tert-butyl (cyclopropylmethyl)((3R)-1-(6-(1-(4-(5-cyclopropylpyridin-3-yl)-1H-1,2,3-triazol-1-yl)ethyl)-5-methylpyridin-3-yl)piperidin-3-yl)carbamate IM908 as colourless oil: 73 mg, 79% yield, P=96%, retention time=2.5 min (gradient A), (M+H)⁺: 558.

Stage 8: General Procedure A2 was used from IM908 to afford crude compound 318 as colourless oil: 60 mg, 96% yield, P=84%, retention time=2.0 min (gradient A), (M+H)⁺: 458.

The mixture of diastereomers was purified by chiral preparative HPLC purification using Chiralpak ID column (5 μm, 10×250 mm). Eluent used: MeOH/DCM/DEA: 2/98/0.1% at flow rate of 7 mL/min. First eluted diastereomer: P=100%, retention time=4.2 min, chiral HPLC: P=95.9%, ¹H NMR (300 MHZ, CDCl₃) δ 8.70 (d, J=2.0 Hz, 1H), 8.33 (d, J=2.2 Hz, 1H), 8.16 (d, J=2.8 Hz, 1H), 7.95 (s, 1H), 7.78 (t, J=2.2 Hz, 1H), 6.93 (d, J=2.8 Hz, 1H), 6.21 (q, J=7.0 Hz, 1H), 3.72-3.62 (m, 1H), 3.53-3.40 (m, 1H), 2.92-2.63 (m, 3H), 2.63-2.45 (m, 2H), 2.33 (s, 3H), 2.05-1.73 (m, 7H), 1.73-1.58 (m, 1H), 1.44-1.21 (m, 1H), 1.07-0.85 (m, 3H), 0.82-0.71 (m, 2H), 0.55-0.42 (m, 2H), 0.17-0.08 (m, 2H), 1H exchanged with solvent. Second eluted diastereomer: P=99%, retention time=5.0 min, chiral HPLC: P=99.0%, ¹H NMR (300 MHz, CDCl₃) δ 8.70 (d, J=2.0 Hz, 1H), 8.33 (d, J=2.2 Hz, 1H), 8.16 (d, J=2.8 Hz, 1H), 7.95 (s, 1H), 7.78 (t, J=2.2 Hz, 1H), 6.95 (d, J=2.8 Hz, 1H), 6.21 (q, J=7.0 Hz, 1H), 3.73-3.62 (m, 1H), 3.53-3.40 (m, 1H), 2.92-2.46 (m, 5H), 2.33 (s, 3H), 2.00-1.74 (m, 6H), 1.73-1.54 (m, 1H), 1.44-1.22 (m, 1H), 1.10-0.86 (m, 3H), 0.84-0.69 (m, 2H), 0.55-0.41 (m, 2H), 0.18-0.09 (m, 2H), 1 NH exchanged with solvent.

Compound 319: (R)-3-(6-(3-((cyclobutylmethyl)amino)piperidin-1-yl)pyridin-3-yl)-N-(6-(pyrrolidin-1-yl)pyrazin-2-yl)oxetane-3-carboxamide was Obtained Using General Scheme 6 Pathway C Stage 1: To a colourless solution of methyl 2-(6-chloro-3-pyridyl)acetate (3.61 g, 19.45 mmol) in anhydrous DMF (20 mL) under Ar atmosphere was added potassium acetate (688.24 mg, 6.87 mmol) at rt to afford a light orange solution. Paraformaldehyde (5.15 g, 54.31 mmol) was added to afford an orange suspension which was stirred at rt for 5.5 h. The reaction mixture was filtered and the white solid was rinsed with MeOH (4×20 mL), then the filtrate was concentrated under reduced pressure to dryness to afford a crude yellow oil. The crude material was purified by an automated flash chromatography system (0 to 4% MeOH in DCM) to afford methyl 2-(6-chloropyridin-3-yl)-3-hydroxy-2-(hydroxymethyl)propanoate IM909 as colourless oil: 3.42 g, 63% yield, P=88%, retention time=2.1 min (gradient A), (M+H)⁺: 246/248.

Stage 2: To a solution of methyl 2-(6-chloro-3-pyridyl)-3-hydroxy-2-(hydroxymethyl)propanoate (3.42 g, 12.25 mmol) in anhydrous THF (60 mL) at 0° C. was added lithium borohydride in THF solution (20 mL, 40 mmol) over 5 min to afford a yellow solution which was stirred at 0° C. for 5 h. MeOH (20 mL) was added at 0° C. to afford a white suspension, which was stirred at 0° C. for 15 min, then allowed to stir at rt for 19 h. Celite was added to the suspension and the solvent was removed under reduced pressure to dryness. The crude material was purified by an automated flash chromatography system (dryload in Celite, 0 to 20% of AcOH/MeOH (1/9) in DCM) to afford a product contaminated by AcOH. The material obtained (2.641 g-1 g kept aside) was re-purified by an automated flash chromatography system (dryload in Celite, 0 to 50% of NH₄OH (28-30% w/w)/MeOH (5/95) in DCM) to afford 2-(6-chloropyridin-3-yl)-2-(hydroxymethyl)propane-1,3-diol IM910 as white sticky oil: 2.26 g (+1 g), 63% yield (+24%), P=75% (63%), retention time=1.3 min (gradient A), (M+H)⁺: 218/220.

Stage 3: To a solution of IM910 (475 mg, 2.07 mmol) in pyridine (3.5 mL) under Ar atmosphere at 0° C. was added p-toluenesulfonylchloride (410 mg, 2.15 mmol) to afford a yellow solution which was stirred at 0° C. for 3.25 h. The reaction mixture was diluted with DCM (50 mL) and n-heptane (50 mL) and the solvent was removed under reduced pressure. This operation was repeated a total of 3 times in order to afford a crude yellow oil. The crude material was purified by an automated flash chromatography system (0 to 3% MeOH in DCM, then 5% to 50% of NH₄OH (28-30% w/w)/MeOH (5/95) in DCM) to afford 2-(6-chloropyridin-3-yl)-3-hydroxy-2-(hydroxymethyl)propyl 4-methylbenzenesulfonate IM911 as colourless oil: 432 mg, 55% yield, P=98%, retention time=2.5 min (gradient A), (M+H)+: 372/374.

Stage 4: To a solution of IM911 (432 mg, 1.14 mmol) in anhydrous ethanol (6 mL) at rt was added sodium ethoxide 20% (w/w) in EtOH (1.10 mL, 2.84 mmol) to afford a white suspension which was stirred at rt for 4.75 h. Celite was added to the reaction mixture and the solvent was evaporated under reduced pressure. The crude material was purified by an automated flash chromatography system (dryload in Celite, 0 to 4.5% MeOH in DCM) to afford (3-(6-chloropyridin-3-yl)oxetan-3-yl)methanol IM912 as pale yellow solid: 171 mg, 75% yield, P=100%, retention time=2.0 min (gradient A), (M+H)+: 200/202.

Stage 5: To a solution of IM912 (180 mg, 0.90 mmol) in MeCN (2.8 mL) and water (300 μL) under Ar atmosphere at rt was added TEMPO (9 mg, 0.06 mmol), followed by diacetoxyiodosobenzene (657 mg, 2 mmol) and acetic acid ammonium salt (300 mg, 3.89 mmol) to afford a pale yellow solution which was stirred at rt for 17.5 h. Celite was added to the reaction mixture and the solvent was removed under reduced pressure to dryness. The crude material was purified by an automated flash chromatography system (dryload in Celite, 0 to 30% EtOAc in n-heptane) to afford 3-(6-chloropyridin-3-yl)oxetane-3-carbonitrile IM913 as colourless oil: 126 mg, 70% yield, P=97%, retention time=2.4 min (gradient A), (M+H)+: 195/197.

Stage 6: General Procedure Y was used between IM3 and IM913 to afford tert-butyl (R)-(1-(5-(3-cyanooxetan-3-yl)pyridin-2-yl)piperidin-3-yl)(cyclobutylmethyl)carbamate IM914 as colourless oil: 95 mg, 71 yield, P=100%, retention time=2.6 min (gradient A), (M+H)+: 427.

Stage 7: General Procedure AD was used from IM914 to afford crude (R)-3-(6-(3-((tert-butoxycarbonyl)(cyclobutylmethyl)amino)piperidin-1-yl)pyridin-3-yl)oxetane-3-carboxylic acid hydrochloride IM915 as yellow oil: 147 mg, 100% yield, P=73%, retention time=2.5 min (gradient A), (M+H)+: 446.

General Procedure AC was used from IM915 to afford tert-butyl (R)-(1-(5-(3-carbamoyloxetan-3-yl)pyridin-2-yl)piperidin-3-yl)(cyclobutylmethyl)carbamate IM916 as a colourless oil: 79 mg, 76% yield, P=95%, retention time=2.4 min (gradient A), (M+H)+: 445.

Stage 1': To a solution of 2,6-dibromopyrazine (2.05 g, 8.45 mmol) in dry methanol (20 mL) was added pyrrolidine (2.20 mL, 25.04 mmol). The mixture was stirred at 15° C. for 4 h. The mixture was quenched with water (50 mL) and extracted with DCM (50 mL×3). The organic layer was dried over MgSO₄, filtered and concentrated under reduced pressure. The crude material was purified by an automated flash chromatography system (dryload in silica, 0 to 30% EtOAc in Heptane) to afford 2-bromo-6-(pyrrolidin-1-yl)pyrazine IM917 as colourless oil: 1.94 g, 99% yield, P=98%, retention time=2.8 min (gradient A), (M+H)+: 228/230.

Stage 9: General Procedure AB was used between IM916 and IM917 to afford tert-butyl (R)-(cyclobutylmethyl)(1-(5-(3-((6-(pyrrolidin-1-yl)pyrazin-2-yl)carbamoyl)oxetan-3-yl)pyridin-2-yl)piperidin-3-yl)carbamate IM918 as yellow solid: 55 mg, 88% yield, P=81%, retention time=2.5 min (gradient A), (M+H)+: 593.

Stage 10: General Procedure A2 was used from IM918 to afford crude compound 319 as a yellow oil: 35 mg, 77% yield, P=81%, retention time=2.7 min (gradient B), (M+H)+: 492.

The product was purified by reverse phase preparative HPLC purification (XBridge OBD C18 5 μm, 19×100 mm). Gradient used: increased linearly from 30% to 40% solution "B" over 4.0 min, increased linearly to 88% solution "B" over 2.5 min, and returned to initial conditions over 0.7 min. Flow Rate: 15 mL/min. P=99%. ¹H NMR (300 MHz, CDCl₃) δ 8.73 (s, 1H), 8.18 (d, J=2.7 Hz, 1H), 7.64 (s, 1H), 7.40 (dd, J=8.9, 2.7 Hz, 1H), 7.26 (s, 1H), 6.72 (d, J=9.0 Hz, 1H), 5.33 (d, J=5.9 Hz, 2H), 4.96 (d, J=5.9 Hz, 2H), 4.33-4.22 (m, 1H), 4.10-3.99 (m, 1H), 3.43-3.33 (m, 4H), 3.08-2.93 (m, 1H), 2.87-2.57 (m, 4H), 2.44 (p, J=7.6 Hz, 1H), 2.14-1.94 (m, 7H), 1.90-1.77 (m, 2H), 1.72-1.53 (m, 3H), 1.46-1.34 (m, 2H), 1H exchanged with solvent.

Compound 320: 4-((R)-3-((cyclopropylmethyl)amino)piperidin-1-yl)-1-(1-(4-(5-cyclopropylpyridin-3-yl)-1H-1,2,3-triazol-1-yl)ethyl)pyridin-2(1H)-one was Obtained Using General Scheme 1 Pathway B Stage 1: General Procedure X was used between IM747 and IM151 to afford 4-chloro-1-(1-(4-(5-cyclopropylpyridin-3-yl)-1H-1,2,3-triazol-1-yl)ethyl)pyridin-2(1H)-one IM919 as colourless oil: 107 mg, 74% yield, P=92%, retention time=2.2 min (gradient A), (M+H)+: 342.

Stage 2: General Procedure C was used between IM919 and IM486 to afford tert-butyl (cyclopropylmethyl)((3R)-1-(1-(1-(4-(5-cyclopropylpyridin-3-yl)-1H-1,2,3-triazol-1-yl)ethyl)-2-oxo-1,2-dihydropyridin-4-yl)piperidin-3-yl)carbamate IM920 as orange oil: 165 mg, 54% yield, P=53%, retention time=2.5 min (gradient A), (M+H)+: 561.

Stage 3: General Procedure A2 was used from IM920 to afford crude compound 320 as orange oil: 103 mg, 85% yield, P=58%, retention time=2.1 min (gradient A), (M+H)+: 461.

The product was purified by reverse phase preparative HPLC purification (XBridge OBD C18 5 μm, 19×100 mm). Gradient used: increased linearly from 35% to 40% solution "B" over 4.0 min, increased linearly to 88% solution "B" over 1.5 min, held for 0.3 min, and returned to initial conditions over 1.0 min. Flow Rate: 15 mL/min. P=100%. The mixture of diastereomers was further purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=100%, retention time=6.6 min, chiral HPLC: P=100%, ¹H NMR (300 MHz, CDCl₃) δ 8.76 (d, J=2.0 Hz, 1H), 8.36 (d, J=2.2 Hz, 1H), 8.13 (s, 1H), 7.74 (t, J=2.1 Hz, 1H), 7.53 (q, J=7.0 Hz, 1H), 7.41 (d, J=8.1 Hz, 1H), 5.97 (dd, J=8.1, 2.8 Hz, 1H), 5.64 (d, J=2.8 Hz, 1H), 3.82-3.70 (m, 1H), 3.64-3.54 (m, 1H), 2.92 (ddd, J=13.6, 10.8, 3.1 Hz, 1H), 2.75 (dd, J=12.8, 9.3 Hz, 1H), 2.70-2.57 (m, 1H), 2.57-2.41 (m, 2H), 2.15 (d, J=7.0 Hz, 3H), 2.03-1.84 (m, 2H), 1.81-1.67 (m, 1H), 1.63-1.27 (m, 2H), 1.09-0.98 (m, 2H), 0.98-0.81 (m, 1H), 0.81-0.71 (m, 2H), 0.53-0.39 (m, 2H), 0.18-0.07 (m, 2H), 1H exchanged with solvent. Second eluted diastereomer: P=100%, retention time=12.7 min, chiral HPLC: P=100%, ¹H NMR (300 MHZ, CDCl₃) δ 8.76 (d, J=2.0 Hz, 1H), 8.36 (d, J=2.2 Hz, 1H), 8.15 (s, 1H), 7.74 (t, J=2.2 Hz, 1H), 7.53 (q, J=7.0 Hz, 1H), 7.42 (d, J=8.1 Hz, 1H), 5.98 (dd, J=8.1, 2.8 Hz, 1H), 5.65 (d, J=2.8 Hz, 1H), 3.85-3.74 (m, 1H), 3.64-3.52 (m, 1H), 2.92 (ddd, J=13.4, 10.7, 3.1 Hz, 1H), 2.80 (dd, J=12.8, 9.4 Hz, 1H), 2.74-2.60 (m, 1H), 2.51 (d, J=6.9 Hz, 2H), 2.15 (d, J=7.0 Hz, 3H), 2.03-1.84 (m, 2H), 1.81-1.68 (m, 1H), 1.60-1.32 (m, 2H), 1.09-0.98 (m, 2H), 0.98-0.82 (m, 1H), 0.82-0.71 (m, 2H), 0.53-0.39 (m, 2H), 0.16-0.08 (m, 2H), 1H exchanged with solvent.

Compound 321: (R)-3-(6-(3-((cyclopropylmethyl) amino)piperidin-1-yl)pyridin-3-yl)-N-(4-oxo-4H-pyrido[1,2-a]pyrimidin-2-yl)oxetane-3-carboxamide was Obtained Using General Scheme 6 Pathway C Stage 1: General Procedure Y was used between IM486 and IM913 to afford tert-butyl (R)-(1-(5-(3-cyanooxetan-3-yl)pyridin-2-yl)piperidin-3-yl)(cyclopropylmethyl)carbamate IM921 as colourless gum: 97 mg, 74% yield, P=98%, retention time=2.5 min (gradient A), (M+H)$^+$: 413.

Stage 2: General Procedure AD was used from IM921 to afford crude (R)-3-(6-(3-((tert-butoxycarbonyl)(cyclopropylmethyl)amino)piperidin-1-yl)pyridin-3-yl)oxetane-3-carboxylic acid hydrochloride IM922 as light yellow oil: 125 mg, 99% yield, P=83%, retention time=2.4 min (gradient A), (M+H)+: 432.

Stage 3: General Procedure AC was used from IM922 to afford tert-butyl (R)-(1-(5-(3-carbamoyloxetan-3-yl)pyridin-2-yl)piperidin-3-yl)(cyclopropylmethyl)carbamate IM923 as a white foam: 92 mg, 98% yield, P=98%, retention time=2.3 min (gradient A), (M+H)$^+$: 431.

Stage 4: General Procedure AB was used between IM923 and 2-chloro-4H-pyrido[1,2-a]pyrimidin-4-one to afford tert-butyl (R)-(cyclopropylmethyl)(1-(5-(3-((4-oxo-4H-pyrido[1,2-a]pyrimidin-2-yl)carbamoyl)oxetan-3-yl)pyridin-2-yl)piperidin-3-yl)carbamate IM924 as a light yellow gum: 60 mg, 81% yield, P=92%, retention time=2.4 min (gradient A), (M+H)+: 575.

Stage 5: General Procedure A2 was used from IM924 to afford crude compound 321 as a light yellow gum: 46 mg, 89% yield, P=88%, retention time=2.4 min (gradient B), (M+H)$^+$: 475.

The product was purified by reverse phase preparative HPLC purification (XBridge OBD C18 5 μm, 19×100 mm). Gradient used: increased linearly from 30% to 40% solution "B" over 4.0 min, increased linearly to 88% solution "B" over 2.5 min, and returned to initial conditions over 0.7 min. Flow Rate: 15 mL/min. P=100%. $^1$H NMR (300 MHz, CDCl$_3$) δ 8.97 (d, J=7.2 Hz, 1H), 8.16 (d, J=2.7 Hz, 1H), 7.66 (ddd, J=8.6, 6.7, 1.6 Hz, 1H), 7.42 (s, 1H), 7.37 (dd, J=8.9, 2.7 Hz, 1H), 7.31 (d, J=9.0 Hz, 1H), 7.03 (td, J=6.9, 1.3 Hz, 1H), 6.72 (d, J=8.9 Hz, 1H), 5.31 (d, J=5.9 Hz, 2H), 4.96 (d, J=6.0 Hz, 2H), 4.34-4.24 (m, 1H), 4.09-3.98 (m, 1H), 3.03 (ddd, J=13.4, 10.8, 3.2 Hz, 1H), 2.84 (dd, J=12.5, 9.1 Hz, 1H), 2.76-2.64 (m, 1H), 2.64-2.47 (m, 2H), 2.05-1.95 (m, 1H), 1.87-1.75 (m, 1H), 1.68-1.52 (m, 1H), 1.49-1.30 (m, 1H), 1.24 (d, J=7.0 Hz, OH), 1.00-0.87 (m, 1H), 0.54-0.42 (m, 2H), 0.16-0.08 (m, 2H), 2H exchanged with solvent.

Compound 322: (R)-3-(6-(3-((cyclobutylmethyl) amino)piperidin-1-yl)pyridin-3-yl)-N-(4-oxo-4H-pyrido[1,2-a]pyrimidin-2-yl)oxetane-3-carboxamide was Obtained Using General Scheme 6 Pathway C Stage 1: General Procedure AB was used between IM916 and 2-chloro-4H-pyrido[1,2-a]pyrimidin-4-one to afford tert-butyl (R)-(cyclobutylmethyl)(1-(5-(3-((4-oxo-4H-pyrido[1,2-a]pyrimidin-2-yl)carbamoyl)oxetan-3-yl)pyridin-2-yl)piperidin-3-yl)carbamate IM925 as a yellow solid: 38 mg, 71% yield, P=93%, retention time=2.5 min (gradient A), (M+H)$^+$: 589.

Stage 2: General Procedure A2 was used from IM925 to afford crude compound 322 as a white solid: 19 mg, 65% yield, P=100%, retention time=2.6 min (gradient B), (M+H)$^+$: 489. $^1$H NMR (300 MHz, CDCl$_3$) δ 9.03-8.93 (m, 1H), 8.17 (dd, J=2.7, 0.8 Hz, 1H), 7.67 (ddd, J=8.5, 6.7, 1.6 Hz, 1H), 7.48 (s, 1H), 7.42 (s, 1H), 7.38 (dd, J=8.9, 2.7 Hz, 1H), 7.33 (dt, J=8.9, 1.1 Hz, 1H), 7.04 (td, J=6.9, 1.4 Hz, 1H), 6.73 (dd, J=9.0, 0.8 Hz, 1H), 5.32 (d, J=6.0 Hz, 2H), 4.97 (d, J=6.0 Hz, 2H), 4.34-4.24 (m, 1H), 4.11-4.00 (m, 1H), 3.02 (ddd, J=13.4, 10.7, 3.2 Hz, 1H), 2.82 (dd, J=12.5, 9.2 Hz, 1H), 2.77-2.70 (m, 2H), 2.70-2.58 (m, 1H), 2.53-2.37 (m, 1H), 2.16-1.74 (m, 6H), 1.73-1.53 (m, 3H), 1.45-1.32 (m, 1H), 1H exchanged with solvent.

Compound 323: (R)—N-(cyclopropylmethyl)-1-(6-(3-(4-(6-cyclopropylpyrazin-2-yl)-1H-1,2,3-triazol-1-yl)oxetan-3-yl)pyridin-3-yl)piperidin-3-amine was Obtained Using General Scheme 1 Pathway B Stage 1: 2,6-Dibromopyrazine (3 g, 12.36 mmol), potassium phosphate tribasic (3.40 g, 15.7 mmol), palladium(II) acetate (131 mg, 0.58 mmol), tricyclohexylphosphine (376 mg, 1.27 mmol), were merged, flushed by vacuum/argon cycles (3 times). Then toluene (33 mL) and water (8 mL) were added (both previously degassed by argon bubbling for 20 min). Mixture stirred at 50° C. for 28 h. The reaction mixture was cooled to rt, and diluted with EtOAc (20 mL). The layers were separated, and organic layer was washed with brine (15 mL). The organic layer was dried over MgSO$_4$, filtered and concentrated under reduced pressure to dryness to afford brown oil. The crude material was purified by an automated flash chromatography system (liquid injection in n-heptane, 0 to 10% EtOAc in Heptane) to afford 2-bromo-6-cyclopropylpyrazine IM926 as yellow oil: 864 mg, 22% yield, P=63%, retention time=2.8 min (gradient A), (M+H)$^+$: 199/201.

Stage 2: General Procedure E1 was used from IM926 to afford 2-cyclopropyl-6-((trimethylsilyl)ethynyl)pyrazine IM927 as brown oil: 500 mg, 82% yield, P=97%, retention time=3.2 min (gradient A), (M+H)$^+$: 217.

Stage 3: General Procedure X was used between IM927 and IM872 to afford 2-(1-(3-(5-bromopyridin-2-yl)oxetan-3-yl)-1H-1,2,3-triazol-4-yl)-6-cyclopropylpyrazine IM928 as orange oil: 179 mg, 79% yield, P=83%, retention time=2.8 min (gradient A), (M+H)$^+$: 399/401.

Stage 4: General Procedure Y was used between IM928 and IM486 to afford tert-butyl (R)-(cyclopropylmethyl)(1-(6-(3-(4-(6-cyclopropylpyrazin-2-yl)-1H-1,2,3-triazol-1-yl)oxetan-3-yl)pyridin-3-yl)piperidin-3-yl)carbamate IM929 as a white solid: 88 mg, 74% yield, P=80%, retention time=3.1 min (gradient A), (M+H)$^+$: 573.

Stage 5: General Procedure A2 was used from IM929 to afford compound 323 as a white powder: 38 mg, 63% yield, P=96%, retention time=3.2 min (gradient B), (M+H)$^+$: 473. $^1$H NMR (300 MHz, CDCl$_3$) δ 9.16 (s, 1H), 8.39 (s, 1H), 8.33 (d, J=2.9 Hz, 1H), 8.07 (s, 1H), 7.12 (dd, J=8.8, 3.0 Hz, 1H), 6.88 (d, J=8.7 Hz, 1H), 5.57-5.45 (m, 4H), 3.73-3.64 (m, 1H), 3.56-3.45 (m, 1H), 2.90 (ddd, J=12.3, 10.4, 3.3 Hz, 1H), 2.83-2.64 (m, 2H), 2.63-2.44 (m, 2H), 2.14-1.92 (m, 1H), 1.89-1.76 (m, 1H), 1.76-1.56 (m, 1H), 1.45-1.28 (m, 2H), 1.10-1.01 (m, 4H), 1.01-0.82 (m, 1H), 0.55-0.43 (m, 2H), 0.17-0.04 (m, 2H), 1H exchanged with solvent.

Compound 324: (R)-3-(6-(3-((cyclopropylmethyl) amino)piperidin-1-yl)pyridin-3-yl)-N-(6-(pyrrolidin-1-yl)pyrazin-2-yl)oxetane-3-carboxamide was Obtained Using General Scheme 6 Pathway C Stage 1: General Procedure AB was used between IM923 and IM917 to afford tert-butyl (R)-(cyclopropylmethyl)(1-

(5-(3-((6-(pyrrolidin-1-yl)pyrazin-2-yl)carbamoyl)oxetan-3-yl)pyridin-2-yl)piperidin-3-yl)carbamate IM930 as a light yellow gum: 53 mg, 73% yield, P=93%, retention time=2.4 min (gradient A), (M+H)$^+$: 578.

Stage 2: General Procedure A2 was used from IM930 to afford crude compound 324 as a white powder: 42 mg, 99% yield, P=96%, retention time=2.6 min (gradient B), (M+H)$^+$: 478. $^1$H NMR (300 MHz, CDCl$_3$) δ 8.70 (s, 1H), 8.15 (d, J=2.6 Hz, 1H), 7.59 (s, 1H), 7.38 (dd, J=9.0, 2.7 Hz, 2H), 6.69 (d, J=8.9 Hz, 1H), 5.29 (d, J=6.2 Hz, 2H), 4.92 (d, J=6.0 Hz, 2H), 4.34-4.20 (m, 1H), 4.06-3.94 (m, 1H), 3.42-3.25 (m, 4H), 3.00 (ddd, J=13.4, 10.7, 3.2 Hz, 1H), 2.81 (dd, J=12.5, 9.1 Hz, 1H), 2.74-2.64 (m, 1H), 2.62-2.44 (m, 2H), 2.05-1.88 (m, 5H), 1.85-1.72 (m, 1H), 1.65-1.28 (m, 3H), 0.98-0.84 (m, 1H), 0.54-0.38 (m, 2H), 0.17-0.00 (m, 2H).

Compound 325: (R)-3-(5-(3-((cyclopentylmethyl)amino)piperidin-1-yl)pyridin-2-yl)-N-(4-oxo-4H-pyrido[1,2-a]pyrimidin-2-yl)oxetane-3-carboxamide was Obtained Using General Scheme 6 Pathway C Stage 1: General Procedure Y was used between IM520 and tert-butyl (R)-piperidin-3-ylcarbamate to afford tert-butyl (R)-(1-(6-(3-cyanooxetan-3-yl)pyridin-3-yl)piperidin-3-yl)carbamate IM931 as a crystalline light yellow solid: 701 mg, 45% yield, P=93%, retention time=2.7 min (gradient A), (M+H)$^+$: 359.

Stage 2: General Procedure AD was used from IM931 to afford crude (R)-3-(5-(3-((tert-butoxycarbonyl)amino)piperidin-1-yl)pyridin-2-yl)oxetane-3-carboxylic acid IM932 as light yellow foam: 591 mg, 71% yield, P=95%, retention time=2.2 min (gradient A), (M+H)+: 378.

Stage 3: General Procedure AC was used from IM932 to afford tert-butyl (R)-(1-(6-(3-carbamoyloxetan-3-yl)pyridin-3-yl)piperidin-3-yl)carbamate IM933 as a light yellow foam: 512 mg, 86% yield, P=97%, retention time=2.2 min (gradient A), (M+H)$^+$: 377.

Stage 4: General Procedure AB was used between IM933 and 2-chloro-4H-pyrido[1,2-a]pyrimidin-4-one to afford tert-butyl (R)-(1-(6-(3-((4-oxo-4H-pyrido[1,2-a]pyrimidin-2-yl)carbamoyl)oxetan-3-yl)pyridin-3-yl)piperidin-3-yl)carbamate IM934 as a yellow foam: 99 mg, 63% yield, P=86%, retention time=2.4 min (gradient A), (M+H)$^+$: 521.

Stage 5: General Procedure A2 was used from IM934 to afford (R)-3-(5-(3-aminopiperidin-1-yl)pyridin-2-yl)-N-(4-oxo-4H-pyrido[1,2-a]pyrimidin-2-yl)oxetane-3-carboxamide IM935 as a yellow solid: 194 mg, 99% yield, P=82%, retention time=1.9 min (gradient A), (M+H)$^+$: 421.

Stage 6: General Procedure AE was used between IM935 and cyclopentanecarboxaldehyde to afford crude compound 325 as a yellowish gum: 62 mg, 73% yield, P=51%, retention time=2.1 min (gradient A), (M+H)$^+$: 503.

The product was purified by reverse phase preparative HPLC purification (XBridge OBD C18 5 μm, 19×100 mm). Gradient used: increased linearly from 30% to 40% solution "B" over 4.0 min, increased linearly to 88% solution "B" over 2.5 min, and returned to initial conditions over 0.7 min. Flow Rate: 15 mL/min. P=100%. $^1$H NMR (300 MHz, CDCl$_3$) δ 8.97 (s, 1H), 8.89 (d, J=7.0 Hz, 1H), 8.30 (d, J=2.8 Hz, 1H), 7.59 (ddd, J=8.7, 6.7, 1.6 Hz, 1H), 7.33 (d, J=9.3 Hz, 1H), 7.19 (s, 1H), 7.16 (dd, J=8.6, 2.7 Hz, 1H), 7.10 (d, J=8.6 Hz, 1H), 6.94 (td, J=6.9, 1.4 Hz, 1H), 5.29 (dd, J=6.0, 1.3 Hz, 2H), 4.96 (d, J=6.1 Hz, 2H), 3.76-3.62 (m, 1H), 3.49-3.39 (m, 1H), 2.89-2.66 (m, 3H), 2.60 (d, J=7.1 Hz, 2H), 2.07-1.89 (m, 2H), 1.86-1.28 (m, 9H), 1.11 (s, 2H), 1H exchanged with solvent.

Compound 326: (R)-3-(5-(3-(cyclopentylamino)piperidin-1-yl)pyridin-2-yl)-N-(4-oxo-4H-pyrido[1,2-a]pyrimidin-2-yl)oxetane-3-carboxamide was Obtained Using General Scheme 6 Pathway C Stage 1: General Procedure AE was used between IM935 and cyclopentanone to afford crude compound 326 as a yellow gum: 44 mg, 81% yield, P=79%, retention time=2.1 min (gradient A), (M+H)$^+$: 489.

The product was purified by reverse phase preparative HPLC purification (XBridge OBD C18 5 μm, 19×100 mm). Gradient used: increased linearly from 30% to 40% solution "B" over 4.0 min, increased linearly to 88% solution "B" over 2.5 min, and returned to initial conditions over 0.7 min. Flow Rate: 15 mL/min. P=97%. $^1$H NMR (300 MHz, CDCl$_3$) δ 9.05 (s, 1H), 9.01-8.93 (m, 1H), 8.43-8.36 (m, 1H), 7.66 (ddd, J=8.7, 6.7, 1.6 Hz, 1H), 7.40 (d, J=10.1 Hz, 2H), 7.22 (dd, J=8.7, 2.6 Hz, 1H), 7.20-7.14 (m, 1H), 7.02 (td, J=6.9, 1.4 Hz, 1H), 5.36 (dd, J=6.1, 1.5 Hz, 2H), 5.04 (dd, J=6.1, 1.2 Hz, 2H), 3.71 (d, J=10.5 Hz, 1H), 3.58-3.48 (m, 1H), 3.25 (p, J=6.8 Hz, 1H), 2.96-2.75 (m, 2H), 2.69 (dd, J=11.8, 9.0 Hz, 1H), 2.05-1.67 (m, 6H), 1.56 (dd, J=7.5, 4.7 Hz, 2H), 1.47-1.25 (m, 4H), 1H exchanged with solvent.

Compound 327: (R)-3-(5-(3-(cyclobutylamino)piperidin-1-yl)pyridin-2-yl)-N-(4-oxo-4H-pyrido[1,2-a]pyrimidin-2-yl)oxetane-3-carboxamide was Obtained Using General Scheme 6 Pathway C Stage 1: General Procedure AE was used between IM935 and cyclobutanone to afford crude compound 327 as a yellow gum: 53 mg, 75% yield, P=59%, retention time=2.0 min (gradient A), (M+H)$^+$: 475.

The product was purified by reverse phase preparative HPLC purification (XBridge OBD C18 5 μm, 19×100 mm). Gradient used: increased linearly from 30% to 40% solution "B" over 4.0 min, increased linearly to 88% solution "B" over 2.5 min, and returned to initial conditions over 0.7 min. Flow Rate: 15 ml/min. P=100%. $^1$H NMR (300 MHz, CDCl$_3$) δ 9.04 (s, 1H), 8.97 (d, J=7.1 Hz, 1H), 8.38 (s, 1H), 7.72-7.60 (m, 1H), 7.40 (d, J=10.1 Hz, 2H), 7.20 (d, J=2.7 Hz, 2H), 7.02 (t, J=6.9 Hz, 1H), 5.37 (d, J=6.1 Hz, 2H), 5.04 (d, J=6.1 Hz, 2H), 3.70-3.60 (m, 1H), 3.57-3.47 (m, 1H), 3.45-3.31 (m, 1H), 2.95-2.73 (m, 2H), 2.66 (dd, J=11.7, 9.0 Hz, 1H), 2.31-2.23 (m, 2H), 1.99-1.79 (m, 2H), 1.75-1.60 (m, 5H), 1.41-1.23 (m, 1H), 1H exchanged with solvent.

Compound 328: (R)—N-(4-oxo-4H-pyrido[1,2-a]pyrimidin-2-yl)-3-(5-(3-(((1-(trifluoromethyl)cyclopropyl)methyl)amino)piperidin-1-yl)pyridin-2-yl)oxetane-3-carboxamide was Obtained Using General Scheme 6 Pathway C Stage 1: General Procedure AE was used between IM935 and 1-(trifluoromethyl)cyclopropanecarbaldehyde to afford crude compound 328 as an orange gum: 69 mg, 58% yield, P=51%, retention time=2.1 min (gradient A), (M+H)$^+$: 503.

The product was purified by reverse phase preparative HPLC purification (XBridge OBD C18 5 μm, 19×100 mm). Gradient used: increased linearly from 30% to 40% solution "B" over 4.0 min, increased linearly to 88% solution "B" over 2.5 min, and returned to initial conditions over 0.7 min. Flow Rate: 15 mL/min. P=100%. $^1$H NMR (300 MHz, CDCl$_3$) δ 9.04 (s, 1H), 8.97 (d, J=7.2 Hz, 1H), 8.38 (d, J=2.4 Hz, 1H), 7.66 (t, J=7.7 Hz, 1H), 7.40 (d, J=10.4 Hz, 2H), 7.20 (d, J=2.7 Hz, 2H), 7.02 (t, J=6.9 Hz, 1H), 5.37 (d, J=6.1 Hz, 2H), 5.04 (d, J=6.1 Hz, 2H), 3.68-3.59 (m, 1H), 3.54-

3.44 (m, 1H), 3.01-2.81 (m, 3H), 2.80-2.64 (m, 2H), 2.01-1.91 (m, 1H), 1.90-1.79 (m, 1H), 1.76-1.62 (m, 1H), 1.37-1.23 (m, 1H), 1.03-0.93 (m, 2H), 0.72 (s, 2H), 1H exchanged with solvent. $^{19}$F NMR (282 MHZ, CDCl$_3$) δ −66.43.

Compound 329: (R)-1-(6-(3-(4-(5-cyclopropylpyridin-3-yl)-1H-1,2,3-triazol-1-yl)oxetan-3-yl)pyridin-3-yl)-N-isobutylpiperidin-3-amine was Obtained Using General Scheme 1 Pathway B Stage 1: General Procedure B was used between IM872 and IM896 to afford 5-bromo-2-(3-(4-(5-cyclopropylpyridin-3-yl)-1H-1,2,3-triazol-1-yl)oxetan-3-yl)pyridine IM936 as a white foam: 1.31 g, 83% yield, P=99%, retention time=2.5 min (gradient A), (M+H)$^+$: 398/400.

Stage 1': To a yellow suspension of (R)-1-benzylpiperidin-3-amine (1.5 g, 7.73 mmol) and 1-fluorocyclopropanecarboxylic acid (890 mg, 8.12 mmol) in anhydrous MeCN (77 mL) under Ar atmosphere was added chloro-N,N,N',N'-tetramethylformamidinium hexafluorophosphate (3 g, 10.48 mmol) at once, followed by 1-methylimidazole (2.1 mL, 26.08 mmol). The reaction mixture was stirred at rt for 1.15 h. Reaction mixture was concentrated under reduced pressure to afford orange oil. The latter was dissolved with EtOAc (100 mL), washed with NaHCO$_3$ saturated solution (30 mL), water (30 mL) and brine (20 mL). Organic layer was dried over MgSO$_4$, filtered and concentrated under reduced pressure to afford a pale pink solid (3.05 g). Product was slurried in water (45 mL) under stirring for 1 h, and resulting powder was filtered, rinsed with water (2×15 mL). Solid was dry under reduced pressure for 1 h to afford (R)—N-(1-benzylpiperidin-3-yl)-1-fluorocyclopropane-1-carboxamide IM937 as an off-white solid: 2.01 g, 94% yield, P=100%, retention time=2.1 min (gradient A), (M+H)$^+$: 277.

Stage 2': To a suspension of IM937 (50 mg, 0.18 mmol) in anhydrous THF (6.8 mL) at 0° C. under argon atmosphere, was added borane THF complex 1 M in THF (1.3 mL, 1.3 mmol) dropwise (over 50 min) and the resulting mixture was stirred at 50° C. for 9 h. Reaction was cooled to 0° C., and anhydrous methanol (41 mL) was added dropwise (bubbling, issue with stirring) over 10 min. After addition, reaction was heated to 50° C. for 16 h. Reaction mixture was cooled to rt and concentrated under reduced pressure to afford an orange syrup, which was taken up with EtOAc (100 mL) and washed with an aqueous saturated solution of NaHCO$_3$ (3×50 mL). Layers were separated, organic layer was washed with brine (10 mL) and dried over MgSO$_4$, filtered and concentrated under reduced pressure to dryness to afford crude (R)-1-benzyl-N-((1-fluorocyclopropyl)methyl)piperidin-3-amine IM938 as colorless oil: 1.8 g, 93% yield, P=93%, retention time=1.8 min (gradient A), (M+H)$^+$: 263.

Stage 3': To an colorless solution of crude IM938 (1.8 g, 6.38 mmol) in anhydrous DCM (45 mL) under Ar atmosphere at 0° C. was added triethylamine (1.7 mL, 12.14 mmol), followed by a solution of di-tert-butyldicarbonate (1.7 g, 7.79 mmol) in anhydrous DCM (4.8 mL) over 15 min to afford a colorless solution, which was stirred at rt for 72 h. Reaction mixture was diluted with DCM (100 mL), washed with an aqueous saturated NaHCO$_3$ solution (2×50 mL) and Brine (50 mL). Organic layer was dried over MgSO$_4$, filtered and concentrated in vaccuo to dryness to afford an orange oil with solid. The crude material was purified by an automated flash system (liquid injection in DCM, 0 to 25% EtOAc in n-Heptane to afford tert-butyl (R)-(1-benzylpiperidin-3-yl)((1-fluorocyclopropyl)methyl) carbamate IM939 as a colorless oil: 1.8 g, 75% yield, P=97%, retention time=2.4 min (gradient A), (M+H)$^+$: 363.

Stage 4': General Procedure I was used from IM939 to afford crude tert-butyl (R)-isobutyl(piperidin-3-yl)carbamate IM940 (minor by-product of intended reaction) as mixture with isobutene analog and desired 1-fluorocyclopropyl analog as colourless oil: 1.27 g, 35% yield, P=35%, retention time=2.3 min (gradient A), (M+H)$^+$: 273.

Stage 5: General Procedure Y was used between IM940 (as mixture) and IM936 to afford tert-butyl (R)-(1-(6-(3-(4-(5-cyclopropylpyridin-3-yl)-1H-1,2,3-triazol-1-yl)oxetan-3-yl)pyridin-3-yl)piperidin-3-yl)(isobutyl)carbamate IM941 as a white solid: 44 mg, 17% yield, P=45%, retention time=2.6 min (gradient A), (M+H)$^+$: 574.

Stage 6: General Procedure A2 was used from IM941 to afford crude compound 329 as a yellow oil: 29 mg, 99% yield, P=56%, retention time=3.0 min (gradient B), (M+H)$^+$: 474.

The product was purified by reverse phase preparative HPLC purification (XBridge OBD C18 5 μm, 19×100 mm). Gradient used: increased linearly from 30% to 40% solution "B" over 4.0 min, increased linearly to 88% solution "B" over 2.5 min, and returned to initial conditions over 0.7 min. Flow Rate: 15 mL/min. P=100%. $^1$H NMR (300 MHz, CDCl$_3$) δ 8.70 (d, J=2.0 Hz, 1H), 8.38 (d, J=2.2 Hz, 1H), 8.34 (d, J=2.9 Hz, 1H), 7.84 (t, J=2.2 Hz, 1H), 7.76 (s, 1H), 7.14 (dd, J=8.8, 3.0 Hz, 1H), 6.93 (d, J=8.7 Hz, 1H), 5.55 (d, J=6.7 Hz, 2H), 5.48 (d, J=6.8 Hz, 2H), 3.77-3.62 (m, 1H), 3.58-3.47 (m, 1H), 2.98-2.83 (m, 1H), 2.78-2.64 (m, 2H), 2.48 (d, J=6.8 Hz, 2H), 2.02-1.88 (m, 2H), 1.88-1.61 (m, 3H), 1.40-1.31 (m, 1H), 1.11-0.97 (m, 2H), 0.91 (d, J=6.6 Hz, 6H), 0.87-0.74 (m, 2H), 1H exchanged with solvent.

Compound 330: (R)-3-(5-(3-(((1-fluorocyclopropyl)methyl)amino)piperidin-1-yl)pyridin-2-yl)-N-(4-oxo-4H-pyrido[1,2-a]pyrimidin-2-yl)oxetane-3-carboxamide was Obtained Using General Scheme 6 Pathway C Stage 1: General Procedure AE was used between IM935 and 1-fluorocyclopropanecarbaldehyde to afford compound 330 as a white solid: 43 mg, 85% yield, P=96%, retention time=2.7 min (gradient B), (M+H)$^+$: 493. $^1$H NMR (300 MHZ, CDCl$_3$) δ 9.05 (s, 1H), 8.96 (d, J=7.1 Hz, 1H), 8.38 (d, J=2.7 Hz, 1H), 7.66 (ddd, J=8.6, 6.6, 1.7 Hz, 1H), 7.40 (d, J=8.8 Hz, 1H), 7.37 (s, 1H), 7.22 (dd, J=8.7, 2.8 Hz, 1H), 7.18 (d, J=8.6 Hz, 1H), 7.01 (td, J=7.0, 1.4 Hz, 1H), 5.35 (d, J=6.1 Hz, 2H), 5.03 (d, J=6.1 Hz, 2H), 3.76-3.63 (m, 1H), 3.57-3.42 (m, 1H), 3.07 (d, J=8.8 Hz, 1H), 3.00 (d, J=9.3 Hz, 1H), 2.96-2.90 (m, 1H), 2.90-2.83 (m, 1H), 2.75 (dd, J=11.8, 8.9 Hz, 1H), 2.07-1.94 (m, 1H), 1.92-1.82 (m, 1H), 1.79 (s, 1H), 1.75-1.61 (m, 1H), 1.45-1.29 (m, 1H), 1.16-0.96 (m, 2H), 0.69-0.56 (m, 2H). $^{19}$F NMR (282 MHZ, CDCl$_3$) δ −183.62 (dt, J=19.9, 10.4 Hz).

Compound 331: (R)-3-(5-(3-(((1-methylcyclopropyl)methyl)amino)piperidin-1-yl)pyridin-2-yl)-N-(4-oxo-4H-pyrido[1,2-a]pyrimidin-2-yl)oxetane-3-carboxamide was Obtained Using General Scheme 6 Pathway C Stage 1: General Procedure AE was used between IM935 and 1-methylcyclopropanecarbaldehyde to afford compound 331 as a white solid: 44 mg, 88% yield, P=96%, retention time=2.8 min (gradient B), (M+H)$^+$: 489. $^1$H NMR (300 MHZ, CDCl$_3$) δ 9.08 (s, 1H), 8.95 (d, J=7.1 Hz, 1H), 8.36 (d, J=2.7 Hz, 1H), 7.66 (t, J=7.9 Hz, 1H), 7.39 (d, J=8.9 Hz, 1H), 7.37 (s, 1H), 7.24-7.19 (m, 1H), 7.17 (d, J=8.8 Hz, 1H), 7.02 (t, J=6.9 Hz, 1H), 5.35 (d, J=6.1 Hz, 2H), 5.03 (d, J=6.1 Hz, 2H), 3.83-3.58 (m, 1H), 3.60-3.42 (m, 1H), 3.00-2.85 (m, 1H), 2.84-2.66 (m, 2H), 2.55 (s, 2H), 2.40 (s, 1H), 2.06-1.91 (m, 1H), 1.90-1.76 (m, 1H), 1.76-1.54 (m, 1H), 1.48-1.27 (m, 1H), 1.12 (s, 3H), 0.43-0.23 (m, 4H).

Compound 332: (R)-1-(6-(3-(4-(5-cyclopropylpyridin-3-yl)-1H-1,2,3-triazol-1-yl)oxetan-3-yl)pyridin-3-yl)-N-((1-fluorocyclopropyl)methyl)piperidin-3-amine was Obtained Using General Scheme 1 Pathway B Stage 1: General Procedure Y was used between tert-butyl (R)-piperidin-3-ylcarbamate and IM936 to afford tert-butyl (R)-(1-(6-(3-(4-(5-cyclopropylpyridin-3-yl)-1H-1,2,3-triazol-1-yl)oxetan-3-yl)pyridin-3-yl)piperidin-3-yl)carbamate IM942 as a yellow solid: 720 mg, 83% yield, P=99%, retention time=2.4 min (gradient A), (M+H)$^+$: 518.

Stage 2: General Procedure A2 was used from IM942 to afford (R)-1-(6-(3-(4-(5-cyclopropylpyridin-3-yl)-1H-1,2,3-triazol-1-yl)oxetan-3-yl)pyridin-3-yl)piperidin-3-amine IM943 as a yellow solid: 510 mg, 87% yield, P=99%, retention time=2.0 min (gradient A), (M+H)$^+$: 418.

Stage 3: General Procedure AE was used between IM943 and 1-fluorocyclopropanecarbaldehyde to afford compound 332 as a white solid: 41 mg, 71% yield, P=100%, retention time=2.7 min (gradient B), (M+H)$^+$: 490. $^1$H NMR (300 MHZ, CDCl$_3$) δ 8.70 (d, J=2.1 Hz, 1H), 8.38 (d, J=2.1 Hz, 1H), 8.34 (d, J=3.0 Hz, 1H), 7.84 (s, 1H), 7.76 (s, 1H), 7.15 (dd, J=8.8, 2.9 Hz, 1H), 6.93 (d, J=8.7 Hz, 1H), 5.54 (d, J=6.7 Hz, 2H), 5.48 (d, J=6.8 Hz, 2H), 3.81-3.62 (m, 1H), 3.62-3.46 (m, 1H), 3.06 (d, J=9.2 Hz, 1H), 2.98 (d, J=10.0 Hz, 1H), 2.96-2.80 (m, 2H), 2.75 (dd, J=11.7, 8.9 Hz, 1H), 2.08-1.76 (m, 3H), 1.73-1.61 (m, 1H), 1.46-1.33 (m, 1H), 1.12-1.00 (m, 4H), 0.84-0.74 (m, 2H), 0.66-0.57 (m, 2H), 1H exchanged with solvent. $^{19}$F NMR (282 MHz, CDCl$_3$) δ −183.66 (ddp, J=27.6, 18.4, 9.2 Hz).

Compound 333: (R)-1-(6-(3-(4-(5-cyclopropylpyridin-3-yl)-1H-1,2,3-triazol-1-yl)oxetan-3-yl)pyridin-3-yl)-N-((1-methylcyclopropyl)methyl)piperidin-3-amine was Obtained Using General Scheme 1 Pathway B Stage 1: General Procedure AE was used between IM943 and 1-methylcyclopropanecarbaldehyde to afford compound 333 as a white solid: 44 mg, 76% yield, P=100%, retention time=2.8 min (gradient B), (M+H)$^+$: 486. $^1$H NMR (300 MHZ, CDCl$_3$) δ 8.71 (d, J=2.0 Hz, 1H), 8.38 (d, J=2.2 Hz, 1H), 8.34 (d, J=3.0 Hz, 1H), 7.84 (t, J=2.2 Hz, 1H), 7.76 (s, 1H), 7.14 (dd, J=8.8, 3.0 Hz, 1H), 6.93 (d, J=8.8 Hz, 1H), 5.55 (d, J=6.7 Hz, 2H), 5.49 (d, J=6.7 Hz, 2H), 3.74-3.65 (m, 1H), 3.59-3.48 (m, 1H), 2.97-2.83 (m, 1H), 2.76-2.58 (m, 2H), 2.58-2.43 (m, 2H), 2.04-1.76 (m, 3H), 1.76-1.57 (m, 1H), 1.42-1.29 (m, 1H), 1.11 (s, 3H), 1.09-0.99 (m, 2H), 0.80 (dt, J=6.7, 4.8 Hz, 2H), 0.37-0.21 (m, 4H), 1H exchanged with solvent.

Compound 334: (R)—N-cyclobutyl-1-(6-(3-(4-(5-cyclopropylpyridin-3-yl)-1H-1,2,3-triazol-1-yl)oxetan-3-yl)pyridin-3-yl)piperidin-3-amine was Obtained Using General Scheme 1 Pathway B Stage 1: General Procedure AE was used between IM943 and cyclobutanone to afford compound 334 as a white solid: 35 mg, 62% yield, P=99%, retention time=2.7 min (gradient B), (M+H)$^+$: 472. $^1$H NMR (300 MHZ, CDCl$_3$) δ 8.71 (d, J=2.0 Hz, 1H), 8.38 (d, J=2.2 Hz, 1H), 8.33 (d, J=2.9 Hz, 1H), 7.84 (dd, J=2.2, 2.2 Hz, 1H), 7.77 (s, 1H), 7.14 (dd, J=8.8, 3.0 Hz, 1H), 6.93 (d, J=8.7 Hz, 1H), 5.55 (d, J=6.8 Hz, 2H), 5.48 (d, J=6.7 Hz, 2H), 3.68-3.60 (m, 1H), 3.55-3.46 (m, 1H), 3.40 (m, 1H), 2.99-2.66 (m, 3H), 2.34-2.21 (m, 2H), 2.00-1.88 (m, 2H), 1.86-1.60 (m, 7H), 1.45-1.29 (m, 1H), 1.12-0.99 (m, 2H), 0.80 (m, 2H).

Compound 335: (R)-1-(6-(3-(4-(5-cyclopropylpyridin-3-yl)-1H-1,2,3-triazol-1-yl)oxetan-3-yl)pyridin-3-yl)-N-((1-(trifluoromethyl)cyclopropyl)methyl)piperidin-3-amine was Obtained Using General Scheme 1 Pathway B Stage 1: General Procedure AE was used between IM943 and 1-(trifluoromethyl)cyclopropanecarbaldehyde to afford compound 335 as a white solid: 37 mg, 57% yield, P=99%, retention time=2.1 min (gradient B), (M+H)$^+$: 540. $^1$H NMR (300 MHz, CDCl$_3$) δ 8.71 (d, J=2.0 Hz, 1H), 8.39 (d, J=2.2 Hz, 1H), 8.33 (d, J=2.9 Hz, 1H), 7.84 (s, 1H), 7.76 (s, 1H), 7.14 (dd, J=8.8, 3.0 Hz, 1H), 6.93 (d, J=8.7 Hz, 1H), 5.55 (d, J=6.8 Hz, 2H), 5.49 (d, J=6.7 Hz, 2H), 3.70-3.56 (m, 1H), 3.55-3.44 (m, 1H), 2.97-2.78 (m, 3H), 2.78-2.64 (m, 2H), 2.05-1.90 (m, 2H), 1.89-1.76 (m, 1H), 1.74-1.60 (m, 1H), 1.42-1.25 (m, 1H), 1.10-1.01 (m, 2H), 1.01-0.94 (m, 2H), 0.84-0.77 (m, 2H), 0.73-0.67 (m, 2H), 1H exchanged with solvent. $^{19}$F NMR (282 MHz, CDCl$_3$) δ −66.43.

Compound 336: 3-(5-((3R)-3-((1-cyclobutylethyl)amino)piperidin-1-yl)pyridin-2-yl)-N-(4-oxo-4H-pyrido[1,2-a]pyrimidin-2-yl)oxetane-3-carboxamide was Obtained Using General Scheme 6 Pathway C Stage 1: General Procedure AE was used between IM935 and cyclobutyl methyl ketone to afford compound 336 as a light yellow foam: 89 mg, 76% yield, P=85%, retention time=2.1 min (gradient A), (M+H)$^+$: 503.

The mixture of diastereomers was further purified by chiral preparative HPLC purification using Chiralpak IA column (5 µm, 20×250 mm). Eluent used: EtOAc/EtOH/DEA: 90/10/0.1% at flow rate of 20 mL/min. First eluted diastereomer: P=100%, retention time=6.2 min, chiral HPLC: P=100%, $^1$H NMR (300 MHz, CDCl$_3$) δ 9.05 (s, 1H), 8.96 (d, J=7.1 Hz, 1H), 8.38 (d, J=2.6 Hz, 1H), 7.71-7.59 (m, 1H), 7.43-7.36 (m, 2H), 7.24-7.14 (m, 2H), 7.01 (dd, J=6.9, 6.9 Hz, 1H), 5.35 (d, J=6.0 Hz, 2H), 5.04 (d, J=6.1 Hz, 2H), 3.71-3.60 (m, 1H), 3.53-3.43 (m, 1H), 2.96-2.85 (m, 1H), 2.83-2.74 (m, 1H), 2.73-2.59 (m, 2H), 2.26-2.09 (m, 1H), 2.04-1.58 (m, 8H), 1.44-1.22 (m, 2H), 0.95 (d, J=6.1 Hz, 3H), 1H exchanged with solvent. Second eluted diastereomer: P=100%, retention time=12.6 min, chiral HPLC: P=100%, $^1$H NMR (300 MHz, CDCl$_3$) δ 9.09 (s, 1H), 8.96 (d, J=7.2 Hz, 1H), 8.38 (d, J=2.7 Hz, 1H), 7.72-7.61 (m, 1H), 7.45-7.35 (m, 2H), 7.25-7.13 (m, 2H), 7.01 (dd, J=6.9, 6.9 Hz, 1H), 5.36 (d, J=6.1 Hz, 2H), 5.04 (d, J=6.1 Hz, 2H), 3.67-3.57 (m, 1H), 3.47 (d, J=11.2 Hz, 1H), 2.98-2.86 (m, 1H), 2.85-2.63 (m, 3H), 2.25-2.11 (m, 1H), 2.10-1.93 (m, 3H), 1.91-1.63 (m, 5H), 1.53 (s, 2H), 1.36-1.21 (m, 1H), 0.94 (d, J=6.1 Hz, 3H).

Compound 337: (R)—N-(4-oxo-4H-pyrido[1,2-a]pyrimidin-2-yl)-3-(5-(3-(((1-(trifluoromethyl)cyclobutyl)methyl)amino)piperidin-1-yl)pyridin-2-yl)oxetane-3-carboxamide was Obtained Using General Scheme 6 Pathway C Stage 1: General Procedure AE was used between IM935 and 1-(trifluoromethyl)cyclobutanecarbaldehyde to afford crude compound 337 as a light orange gum: 90 mg, 75% yield, P=48%, retention time=2.1 min (gradient A), (M+H)⁺: 557.

The product was purified by reverse phase preparative HPLC purification (XBridge OBD C18 5 μm, 19×100 mm). Gradient used: increased linearly from 50% to 60% solution "B" over 4.0 min, increased linearly to 88% solution "B" over 2.5 min, and returned to initial conditions over 0.7 min. Flow Rate: 15 mL/min. P=99%. ¹H NMR (300 MHz, CDCl₃) δ 9.05 (s, 1H), 8.96 (d, J=7.0 Hz, 1H), 8.39 (d, J=2.7 Hz, 1H), 7.66 (ddd, J=8.6, 6.6, 1.6 Hz, 1H), 7.40 (d, J=8.3 Hz, 1H), 7.38 (s, 1H), 7.25-7.16 (m, 2H), 7.01 (dd, J=6.9, 1.4 Hz, 1H), 5.36 (d, J=6.1 Hz, 2H), 5.04 (d, J=6.1 Hz, 2H), 3.75-3.61 (m, 1H), 3.57-3.45 (m, 1H), 3.00-2.82 (m, 3H), 2.81-2.67 (m, 2H), 2.34-2.20 (m, 2H), 2.05-1.94 (m, 5H), 1.90-1.78 (m, 1H), 1.78-1.58 (m, 1H), 1.47-1.28 (m, 1H). ¹⁹F NMR (282 MHZ, CDCl₃) δ −73.46.

Compound 338: (R)-3-(5-(3-(((3,3-difluorocyclobutyl)methyl)amino)piperidin-1-yl)pyridin-2-yl)-N-(4-oxo-4H-pyrido[1,2-a]pyrimidin-2-yl)oxetane-3-carboxamide was Obtained Using General Scheme 6 Pathway C Stage 1: General Procedure AE was used between IM935 and 3,3-difluorocyclobutanecarbaldehyde to afford crude compound 338 as an orange gum: 90 mg, 52% yield, P=30%, retention time=2.1 min (gradient A), (M+H)⁺: 525.

The product was purified by reverse phase preparative HPLC purification (XBridge OBD C18 5 μm, 19×100 mm). Gradient used: increased linearly from 30% to 50% solution "B" over 4.0 min, increased linearly to 88% solution "B" over 2.5 min, and returned to initial conditions over 0.7 min. Flow Rate: 15 mL/min. P=99%. ¹H NMR (300 MHz, CDCl₃) δ 9.04 (s, 1H), 8.96 (d, J=7.2 Hz, 1H), 8.38 (d, J=2.6 Hz, 1H), 7.66 (ddd, J=8.6, 6.6, 1.6 Hz, 1H), 7.43-7.36 (m, 2H), 7.25-7.15 (m, 2H), 7.02 (dd, J=6.9, 1.4 Hz, 1H), 5.36 (dd, J=6.1, 1.4 Hz, 2H), 5.04 (d, J=6.1 Hz, 2H), 3.70-3.59 (m, 1H), 3.55-3.42 (m, 1H), 2.99-2.86 (m, 1H), 2.86-2.57 (m, 6H), 2.35-2.12 (m, 3H), 2.02-1.91 (m, 1H), 1.91-1.78 (m, 1H), 1.78-1.58 (m, 1H), 1.44-1.24 (m, 1H). ¹⁹F NMR (282 MHZ, CDCl₃) δ −80.17 (dq, J=195.4, 9.9 Hz), −90.14 (ddt, J=193.6, 31.2, 12.9 Hz).

Compound 339: (R)-1-(6-(3-(4-(5-cyclopropylpyridin-3-yl)-1H-1,2,3-triazol-1-yl)oxetan-3-yl)pyridin-3-yl)-N-((1-(trifluoromethyl)cyclobutyl)methyl)piperidin-3-amine was Obtained Using General Scheme 1 Pathway B Stage 1: General Procedure AE was used between IM943 and 1-(trifluoromethyl)cyclopropanecarbaldehyde to afford compound 339 as colourless oil: 40 mg, 57% yield, P=94%, retention time=2.1 min (gradient B), (M+H)⁺: 554.

The product was purified by reverse phase preparative HPLC purification (XBridge OBD C18 5 μm, 19×100 mm). Gradient used: increased linearly from 50% to 60% solution "B" over 4.0 min, increased linearly to 88% solution "B" over 2.5 min, and returned to initial conditions over 0.7 min. Flow Rate: 15 mL/min. P=99%. ¹H NMR (300 MHz, CDCl₃) δ 8.70 (d, J=2.0 Hz, 1H), 8.38 (d, J=2.2 Hz, 1H), 8.35 (d, J=2.9 Hz, 1H), 7.84 (dd, J=2.2, 2.2 Hz, 1H), 7.76 (s, 1H), 7.15 (dd, J=8.7, 3.0 Hz, 1H), 6.93 (d, J=8.6 Hz, 1H), 5.55 (d, J=6.7 Hz, 2H), 5.48 (d, J=6.8 Hz, 2H), 3.76-3.62 (m, 1H), 3.51 (m, 1H), 3.00-2.81 (m, 3H), 2.80-2.66 (m, 2H), 2.33-2.18 (m, 2H), 2.05-1.90 (m, J=5.0 Hz, 6H), 1.89-1.77 (m, 1H), 1.75-1.61 (m, 2H), 1.46-1.28 (m, 1H), 1.10-1.01 (m, 2H), 0.85-0.74 (m, 2H). ¹⁹F NMR (282 MHz, CDCl₃) δ −73.46.

Compound 340: (3R)—N-(cyclopropylmethyl)-1-(6-(1-(4-(6-(pyrrolidin-1-yl)pyrazin-2-yl)-1H-imidazol-1-yl)ethyl)pyridazin-3-yl)piperidin-3-amine was Obtained Using General Scheme 4 Pathway A Stage 1: General Procedure C was used between IM514 and IM486 to afford tert-butyl (cyclopropylmethyl)((3R)-1-(6-(1-(4-iodo-1H-imidazol-1-yl)ethyl)pyridazin-3-yl)piperidin-3-yl)carbamate IM944 as an off-white solid: 1.56 g, 81% yield, P=93%, retention time=2.4 min (gradient A), (M+H)⁺: 553.

Stage 2: To a mixture of IM944 (204 mg, 0.34 mmol), tributyl-(6-pyrrolidin-1-ylpyrazin-2-yl)stannane (170 mg, 0.39 mmol), cesium fluoride (11 mg, 0.07 mmol), copper(I) iodide (5 mg, 0.03 mmol) under Ar atmosphere was added degassed and anhydrous DMF (850 μL), followed by palladium(II) chloride (2 mg, 0.01 mmol) and a solution of tri-tert-butylphosphine (6 mg, 0.03 mmol) in anhydrous and degassed DMF (100 μL). The rxn mixture was stirred at 45° C. for 30 h. The solution was cooled to rt and diluted with EtOAc (20 mL) then washed with brine (5×30 mL). The organic layer was dried over MgSO₄, filtered and concentrated under reduced pressure to afford the crude product. The latter was purified by an automated flash chromatography system (liquid injection in DCM, 0 to 6.5% MeOH in DCM) to afford tert-butyl (cyclopropylmethyl)((3R)-1-(6-(1-(4-(6-(pyrrolidin-1-yl)pyrazin-2-yl)-1H-imidazol-1-yl)ethyl)pyridazin-3-yl)piperidin-3-yl)carbamate IM945 as an off-white foamy solid: 52 mg, 24% yield, P=90%, retention time=3.8 min (gradient B), (M+H)⁺: 574.

Stage 3: General Procedure A2 was used from IM945 to afford crude compound 340 as a pale yellow solid: 34 mg, 78% yield, P=89%, retention time=2.0 min (gradient A), (M+H)⁺: 474.

The mixture of diastereomers was purified by chiral preparative HPLC purification using Chiralpak IA column (5 μm, 20×250 mm). Eluent used: TBME/MeOH/DCM/DEA: 60/30/10/0.1% at flow rate of 20 mL/min. First eluted diastereomer: P=100%, retention time=5.2 min, chiral HPLC: P=100%, ¹H NMR (300 MHz, CDCl₃) δ 8.40 (s, 1H), 7.71 (s, 1H), 7.67 (d, J=1.4 Hz, 1H), 7.62 (d, J=1.4 Hz, 1H), 6.95 (d, J=9.4 Hz, 1H), 6.87 (d, J=9.5 Hz, 1H), 5.52 (q, J=7.1 Hz, 1H), 4.50-4.40 (m, 1H), 4.08-3.97 (m, 1H), 3.54-3.44 (m, 4H), 3.17-2.99 (m, 3H), 2.90-2.77 (m, 1H), 2.62 (d, J=7.0 Hz, 2H), 2.12-1.94 (m, 7H), 1.89-1.76 (m, 1H), 1.82 (s, 1H), 1.67-1.47 (m, 2H), 1.07-0.90 (m, 1H), 0.56-0.43 (m, 2H), 0.22-0.10 (m, 2H). Second eluted diastereomer: P=100%, retention time=7.7 min, chiral HPLC: P=100%, ¹H NMR (300 MHZ, CDCl₃) δ 8.39 (s, 1H), 7.71 (s, 1H), 7.66 (d, J=1.4 Hz, 1H), 7.62 (d, J=1.4 Hz, 1H), 7.01 (d, J=9.5 Hz, 1H), 6.94 (d, J=9.6 Hz, 1H), 5.52 (q, J=7.1 Hz, 1H), 4.69-4.58 (m, 1H), 4.05-3.95 (m, 1H), 3.54-3.43 (m, 4H), 3.33 (dd, J=12.9, 9.5 Hz, 1H), 3.05 (m, 3H), 2.88-2.67 (m, 2H), 2.21-2.11 (m, 1H), 2.06-1.95 (m, 7H), 1.91-1.82 (m, 1H), 1.63-1.51 (m, 1H), 1.41 (t, J=7.3 Hz, 1H), 1.29-1.07 (m, 1H), 0.64-0.53 (m, 2H), 0.39-0.26 (m, 2H).

Compound 341: (R)-1-(6-(3-(4-(5-cyclopropylpyridin-3-yl)-1H-1,2,3-triazol-1-yl)oxetan-3-yl)pyridin-3-yl)-N-((3,3-difluorocyclobutyl)methyl)piperidin-3-amine was Obtained Using General Scheme 1 Pathway B Stage 1: General Procedure AE was used between IM943 and 3,3-difluorocyclobutanecarbaldehyde to afford crude compound 341 as colourless oil: 57 mg, 53% yield, P=58%, retention time=2.9 min (gradient B), (M+H)+: 522.

The product was purified by reverse phase preparative HPLC purification (XBridge OBD C18 5 µm, 19×100 mm). Gradient used: increased linearly from 50% to 60% solution "B" over 4.0 min, increased linearly to 88% solution "B" over 2.5 min, and returned to initial conditions over 0.7 min. Flow Rate: 15 mL/min. P=100%. $^1$H NMR (300 MHz, CDCl$_3$) δ 8.69 (d, J=2.0 Hz, 1H), 8.36 (d, J=2.2 Hz, 1H), 8.32 (d, J=2.9 Hz, 1H), 7.82 (dd, J=2.1, 2.1 Hz, 1H), 7.77 (s, 1H), 7.13 (dd, J=8.8, 3.0 Hz, 1H), 6.92 (d, J=8.7 Hz, 1H), 5.53 (d, J=6.8 Hz, 2H), 5.47 (d, J=6.8 Hz, 2H), 3.74-3.57 (m, 1H), 3.56-3.40 (m, 1H), 3.06-2.84 (m, 1H), 2.84-2.52 (m, 6H), 2.32-2.10 (m, 3H), 2.05-1.90 (m, 2H), 1.91-1.56 (m, 3H), 1.45-1.21 (m, 1H), 1.10-0.99 (m, 2H), 0.84-0.72 (m, 2H). $^{19}$F NMR (282 MHz, CDCl$_3$) δ −80.17 (dq, J=193.5, 9.8 Hz), −88.78−−91.36 (m).

Compound 342: (3R)—N-(cyclopropylmethyl)-1-(6-(1-(4-(5-cyclopropylpyridin-3-yl)-1H-imidazol-1-yl)ethyl)pyridazin-3-yl)piperidin-3-amine was Obtained Using General Scheme 4 Pathway A Stage 1: To a solution of IM944 (400 mg, 0.67 mmol) and isopropoxyboronic acid, pinacol ester (200 µL, 0.94 mmol) in anhydrous THF (1.7 mL) under Ar atmosphere at 0° C. was added isopropylmagnesium chloride-lithium chloride in THF (1.3 M) (580 µL, 0.75 mmol). The reaction mixture was stirred at 0° C. for 1.25 h, then extra isopropylmagnesium chloride-lithium chloride in THF (1.3M) (650 µL, 0.85 mmol) was added at 0° C. and the reaction mixture was stirred at this temperature for an extra 15 min. It was then concentrated under reduced pressure to afford a pale yellow solid. Et$_2$O (10 mL) was added to the solid and the suspension was filtered. The solid was rinsed with Et$_2$O (3×5 mL), then pentane (2×5 mL). The solid was collected and dried under vacuum to afford (1-(1-(6-((R)-3-((tert-butoxycarbonyl)(cyclopropylmethyl)amino)piperidin-1-yl)pyridazin-3-yl)ethyl)-1H-imidazol-4-yl)boronic acid IM946 as an off-white solid: 668 mg, 99% yield, P=47%, retention time=2.3 min (gradient A), (M+H)+: 471/472.

Stage 2: To a mixture of IM946 (200 mg, 0.2 mmol), 3-bromo-5-cyclopropyl-pyridine (60 mg, 0.3 mmol), potassium carbonate (85 mg, 0.61 mmol) and Pd(PPh$_3$)$_4$ (35 mg, 0.03 mmol) under Ar atmosphere was added degassed 1,4-dioxane (900 µL) and degassed water (200 µL). The rxn mixture was stirred at 100° C. for 45 min. The solution was cooled to rt, diluted with EtOAc (30 mL) and washed with brine (15 mL). The aqueous layer was extracted with EtOAc (20 mL) and the combined organic layers were washed with brine (15 mL) then dried over MgSO$_4$, filtered and concentrated under reduced pressure to afford tert-butyl (cyclopropylmethyl)((3R)-1-(6-(1-(4-(5-cyclopropylpyridin-3-yl)-1H-imidazol-1-yl)ethyl)pyridazin-3-yl)piperidin-3-yl)carbamate IM947 as a yellow oil: 183 mg, 37% yield, P=22%, retention time=3.5 min (gradient B), (M+H)+: 545.

Stage 3: General Procedure A2 was used from IM947 to afford crude compound 342 as yellow oil: 155 mg, 99% yield, P=21%, retention time=2.0 min (gradient A), (M+H)+: 444.

The product was purified by reverse phase preparative HPLC purification (XBridge OBD C18 5 µm, 19×100 mm). Gradient used: increased linearly from 15% to 40% solution "B" over 4.0 min, increased linearly to 88% solution "B" over 2.5 min, and returned to initial conditions over 0.7 min. Flow Rate: 15 mL/min. P=99%.

The mixture of diastereomers was purified by chiral preparative HPLC purification using Chiralpak Id column (5 µm, 10×250 mm). Eluent used: TBME/MeOH/DCM/DEA: 60/30/10/0.1% at flow rate of 7 mL/min. First eluted diastereomer: P=100%, retention time=8.8 min, chiral HPLC: P=100%, $^1$H NMR (300 MHz, CDCl$_3$) δ 8.60 (d, J=2.0 Hz, 1H), 8.19 (d, J=2.2 Hz, 1H), 7.64-7.56 (m, 2H), 7.26 (s, 1H), 6.87 (d, J=9.5 Hz, 1H), 6.79 (d, J=9.5 Hz, 1H), 5.43 (q, J=7.1 Hz, 1H), 4.36-4.26 (m, 1H), 4.02-3.92 (m, 1H), 3.11-2.98 (m, 1H), 2.91 (dd, J=12.9, 9.2 Hz, 1H), 2.75-2.62 (m, 1H), 2.49 (d, J=6.8 Hz, 2H), 2.00-1.88 (m, 5H), 1.87-1.68 (m, 2H), 1.58-1.37 (m, 1H), 0.98-0.80 (m, 3H), 0.74-0.63 (m, 2H), 0.46-0.34 (m, 2H), 0.11-0.02 (m, 2H), 1H exchanged with solvent. Second eluted diastereomer: P=100%, retention time=11.2 min, chiral HPLC: P=97.7%, $^1$H NMR (300 MHz, CDCl$_3$) δ 8.69 (d, J=2.0 Hz, 1H), 8.27 (d, J=2.2 Hz, 1H), 7.72-7.65 (m, 2H), 7.35 (d, J=1.4 Hz, 1H), 6.97 (d, J=9.5 Hz, 1H), 6.89 (d, J=9.5 Hz, 1H), 5.51 (q, J=7.1 Hz, 1H), 4.47-4.37 (m, 1H), 4.09-3.99 (m, 1H), 3.20-3.00 (m, 2H), 2.90-2.76 (m, 1H), 2.61 (d, J=7.0 Hz, 2H), 2.12-2.01 (m, 1H), 1.99 (d, J=7.0 Hz, 3H), 1.94-1.75 (m, 2H), 1.66-1.50 (m, 2H), 1.08-0.89 (m, 3H), 0.82-0.71 (m, 2H), 0.55-0.47 (m, 2H), 0.22-0.11 (m, 2H), 1H exchanged with solvent.

Compound 343: (R)—N-(cyclopropylmethyl)-1-(6-(3-(4-(5-cyclopropylpyridazin-3-yl)-1H-1,2,3-triazol-1-yl)oxetan-3-yl)pyridin-3-yl)piperidin-3-amine was Obtained Using General Scheme 1 Pathway B Stage 1: In a seal tube under argon was added 3,5-dichloropyridazine (500 mg, 3.29 mmol), cyclopropylboronic acid (340 mg, 3.96 mmol), Q-Phos (45 mg, 0.06 mmol), bis(dibenzylideneacetone)palladium(0) (20 mg, 0.03 mmol), potassium phosphate tribasic (1425 mg, 6.58 mmol) and anhydrous toluene (6.5 mL) (previously degassed). The mixture was stirred at 100° C. (pre-heated bath) for 2 h45. The reaction was cooled to rt and diluted with EtOAc (5 mL). The mixture was filtered over Celite and the Celite was rinsed with EtOAc (2×5 mL). The filtrate was concentrated in vacuo to give the crude product. The latter was purified by an automated flash chromatography system (liquid injection in toluene, 0 to 30% EtOAc in n-heptane) to afford 3-chloro-5-cyclopropylpyridazine IM948 as yellowish liquid: 390 mg, 77% yield, P=100%, retention time=2.3 min (gradient A), (M+H)+: 155/157.

Stage 2: General Procedure E3 was used from IM948 to afford 5-cyclopropyl-3-((trimethylsilyl)ethynyl)pyridazine IM949 as brown oil: 402 mg, 51% yield, P=80%, retention time=2.9 min (gradient A), (M+H)+: 217.

Stage 3: General Procedure D1 was used from IM949 to afford 5-cyclopropyl-3-ethynylpyridazine IM950 as a brown liquid: 285 mg, 100% yield, P=76%, retention time=2.1 min (gradient A), (M+H)+: 145.

Stage 4: General Procedure B was used between IM950 and IM872 to afford 3-(1-(3-(5-bromopyridin-2-yl)oxetan-3-yl)-1H-1,2,3-triazol-4-yl)-5-cyclopropylpyridazine IM951 as sticky yellow oil: 134 mg, 66% yield, P=93%, retention time=2.4 min (gradient A), (M+H)+: 399/401.

Stage 5: General Procedure Y was used between IM486 and IM951 to afford tert-butyl (R)-(cyclopropylmethyl)(1-(6-(3-(4-(5-cyclopropylpyridazin-3-yl)-1H-1,2,3-triazol-1-yl)oxetan-3-yl)pyridin-3-yl)piperidin-3-yl)carbamate IM952 as sticky yellow oil: 120 mg, 56% yield, P=83%, retention time=2.8 min (gradient A), (M+H)+: 573.

Stage 6: General Procedure A2 was used from IM952 to afford compound 343 as a white solid: 65 mg, 78% yield, P=99%, retention time=2.9 min (gradient B), (M+H)⁺: 473. ¹H NMR (300 MHz, CDCl₃) δ 8.88 (s, 1H), 8.34 (s, 1H), 8.22 (d, J=2.3 Hz, 1H), 7.92 (s, 1H), 7.14 (d, J=8.6 Hz, 1H), 6.94 (d, J=8.4 Hz, 1H), 5.57 (d, J=6.6 Hz, 2H), 5.49 (d, J=6.8 Hz, 2H), 3.77-3.65 (m, 1H), 3.58-3.48 (m, 1H), 3.02-2.70 (m, 3H), 2.66-2.48 (m, 2H), 2.07-1.62 (m, 4H), 1.47-1.31 (m, 1H), 1.27-1.19 (m, 2H), 1.06-0.89 (m, 3H), 0.51 (d, J=7.7 Hz, 2H), 0.17-0.11 (m, 2H), 1H exchanged with solvent.

Compound 344: (R)—N-(cyclopropylmethyl)-1-(6-(3-(5-(5-cyclopropylpyridin-3-yl)-1,3,4-oxadiazol-2-yl)oxetan-3-yl)pyridin-3-yl)piperidin-3-amine was Obtained was Obtained Using the Following Procedures Stage 1: A Schlenk tube of 100 mL, was charged with methyl 5-bromopyridine-3-carboxylate (1.64 g, 7.14 mmol), toluene (36 mL) and water (4 mL), followed by cyclopropylboronic acid (955 mg, 11.12 mmol) and potassium phosphate tribasic (4.83 g, 22.3 mmol) at rt. The reaction was bubbled with argon for 10 min. Palladium(II) acetate (95 mg, 0.41 mmol) and tricyclohexylphosphine (240 mg, 0.81 mmol) were added and again bubbled with argon for 10 min. The reaction mixture was heated at 100° C. for 1 h. The reaction mixture was cooled to rt and diluted with water (100 mL) and extracted with EtOAc (3×100 mL). The organic layer was washed with H₂O (150 mL) and brine (150 mL), then dried over MgSO₄ and concentrated under reduced pressure. The crude material was purified by an automated flash chromatography system (dryload in silica, 0 to 50% EtOAc in Heptane) to afford methyl 5-cyclopropylnicotinate IM953 as light yellow oil: 1.14 g, 88% yield, P=98%, retention time=2.0 min (gradient A), (M+H)⁺: 178.

Stage 2: To a stirred solution methyl IM953 (500 mg, 2.77 mmol) in ethanol (5.5 mL) was added hydrazine monohydrate (1.40 mL, 28.28 mmol). The reaction was stirred at 70° C. for 30 min. The solvent was coevaporated with toluene and DCM and evaporated under reduced pressure to afford 5-cyclopropylnicotinohydrazide IM954 as a white solid: 492 mg, 100% yield, P=100%, retention time=0.6 min (gradient A), (M+H)⁺: 178.

Stage 3: DIEA (400 μL, 2.25 mmol) was added to a suspension of IM932 (400 mg, 0.84 mmol), IM954 (165 mg, 0.93 mmol) and HATU (409 mg, 1.08 mmol) in anhydrous DMF (2.1 mL) under Ar. The reaction mixture was stirred at rt for 10 min. The reaction mixture was diluted with EtOAc (50 mL) and then washed with an aqueous saturated solution of NaHCO₃ (2×25 mL), and brine (2×25 mL), dried over MgSO₄, filtered and concentrated under reduced pressure to dryness. The crude material was purified by an automated flash chromatography system (liquid injection in DCM, 0 to 8% of MeOH in DCM) to afford tert-butyl (R)-(1-(6-(3-(2-(5-cyclopropylnicotinoyl)hydrazine-1-carbonyl)oxetan-3-yl)pyridin-3-yl)piperidin-3-yl)carbamate IM955 as an off-white solid: 420 mg, 89% yield, P=96%, retention time=2.2 min (gradient A), (M+H)⁺: 573.

Stage 4: A mixture of IM955 (420 mg, 0.75 mmol) in anhydrous THF (4.2 mL) under Ar was added to (methoxycarbonylsulfamoyl)triethylammoniumhydroxide salt (400 mg, 1.56 mmol). Reaction was stirred at rt for 20 h. The rxn mixt was diluted with EtOAc (15 mL) and washed with water (10 mL), NaHCO₃ saturated aqueous solution (10 mL) and brine (5 mL). The organic layer was dried over MgSO₄, filtered and concentrated under reduced pressure to dryness to afford crude tert-butyl (R)-(1-(6-(3-(5-(5-cyclopropylpyridin-3-yl)-1,3,4-oxadiazol-2-yl)oxetan-3-yl)pyridin-3-yl)piperidin-3-yl)carbamate IM956 as yellow oil: 237 mg, 60% yield, P=98%, retention time=2.4 min (gradient A), (M+H)⁺: 520.

Stage 5: General Procedure A2 was used from IM956 to afford crude (R)-1-(6-(3-(5-(5-cyclopropylpyridin-3-yl)-1,3,4-oxadiazol-2-yl)oxetan-3-yl)pyridin-3-yl)piperidin-3-amine IM957 as an off-white solid: 150 mg, 78% yield, P=94%, retention time=2.0 min (gradient A), (M+H)⁺: 419.

Stage 6: General Procedure AE was used between IM957 and cyclopropanecarboxaldehyde to afford crude compound 344 as colourless oil: 69 mg, 83% yield, P=74%, retention time=2.1 min (gradient A), (M+H)⁺: 573.

The product was purified by chiral preparative HPLC purification using Chiralpak IA column (5 μm, 20×250 mm). Eluent used: EtOAc/EtOH/DEA: 90/10/0.1% at flow rate of 20 mL/min. P=100%, retention time=7.8 min, ¹H NMR (300 MHZ, CDCl₃) δ 8.94 (d, J=2.0 Hz, 1H), 8.52 (d, J=2.2 Hz, 1H), 8.28 (d, J=2.8 Hz, 1H), 7.90 (dd, J=2.1, 2.1 Hz, 1H), 7.19 (dd, J=8.7, 2.9 Hz, 1H), 7.12 (d, J=8.7 Hz, 1H), 5.41-5.30 (m, 4H), 3.71-3.60 (m, 1H), 3.53-3.40 (m, 1H), 2.95-2.66 (m, 3H), 2.63-2.45 (m, 2H), 2.32 (brs, 1H), 2.02-1.88 (m, 2H), 1.87-1.76 (m, 1H), 1.74-1.56 (m, 1H), 1.45-1.20 (m, 1H), 1.16-1.01 (m, 2H), 1.01-0.86 (m, 1H), 0.84-0.73 (m, 2H), 0.54-0.40 (m, 2H), 0.21-0.09 (m, 2H).

Compound 345: (R)—N-(cyclopropylmethyl)-1-(6-(3-(4-(5-(prop-1-yn-1-yl)pyridin-3-yl)-1H-1,2,3-triazol-1-yl)oxetan-3-yl)pyridin-3-yl)piperidin-3-amine was Obtained Using General Scheme 1 Pathway B Stage 1: General Procedure E3 was used between 3,5-dibromopyridine and 1-(Trimethylsilyl)-1-propyne to afford 3-bromo-5-(prop-1-yn-1-yl)pyridine IM958 as a white powder: 605 mg, 74% yield, P=99%, retention time=2.8 min (gradient A), (M+H)⁺: 196/198.

Stage 2: General Procedure E1 was used from IM958 to afford 3-(prop-1-yn-1-yl)-5-((trimethylsilyl)ethynyl)pyridine IM959 as brown oil: 568 mg, 83% yield, P=95%, retention time=3.2 min (gradient A), (M+H)⁺: 214.

Stage 3: General Procedure D1 was used from IM959 to afford 3-ethynyl-5-(prop-1-yn-1-yl)pyridine IM960 as a brown oil: 69 mg, 100% yield, P=91%, retention time=2.6 min (gradient A), (M+H)⁺: 142.

Stage 4: General Procedure B was used between IM960 and IM872 to afford 5-bromo-2-(3-(4-(5-(prop-1-yn-1-yl)pyridin-3-yl)-1H-1,2,3-triazol-1-yl)oxetan-3-yl)pyridine IM961 as an off-white solid: 126 mg, 67% yield, P=94%, retention time=2.6 min (gradient A), (M+H)⁺: 396/398.

Stage 5: General Procedure Y was used between IM486 and IM961 to afford tert-butyl (R)-(cyclopropylmethyl)(1-(6-(3-(4-(5-(prop-1-yn-1-yl)pyridin-3-yl)-1H-1,2,3-triazol-1-yl)oxetan-3-yl)pyridin-3-yl)piperidin-3-yl)carbamate IM962 as a white solid: 65 mg, 60% yield, P=81%, retention time=2.9 min (gradient A), (M+H)⁺: 570.

Stage 6: General Procedure A2 was used from IM962 to afford crude compound 345 as colourless oil: 36 mg, 66% yield, P=80%, retention time=2.0 min (gradient B), (M+H)⁺: 470.

The product was purified by reverse phase preparative HPLC purification (XBridge OBD C18 5 μm, 19×100 mm). Gradient used: increased linearly from 30% to 40% solution "B" over 4.0 min, increased linearly to 88% solution "B" over 2.5 min, and returned to initial conditions over 0.7 min. Flow Rate: 15 mL/min. P=100%. ¹H NMR (300 MHz, CDCl₃) δ 8.85 (d, J=2.1 Hz, 1H), 8.53 (d, J=2.0 Hz, 1H), 8.31 (d, J=2.9 Hz, 1H), 8.11 (dd, J=2.1, 2.1 Hz, 1H), 7.75 (s, 1H), 7.13 (dd, J=8.8, 3.0 Hz, 1H), 6.94 (d, J=8.7 Hz, 1H), 5.52 (d, J=6.7 Hz, 2H), 5.46 (d, J=6.7 Hz, 2H), 3.73-3.64 (m, 1H), 3.58-3.45 (m, 1H), 2.97-2.83 (m, 1H), 2.83-2.64 (m, 2H), 2.62-2.43 (m, 2H), 2.06 (s, 3H), 2.02-1.91 (m, 1H), 1.81 (m, 1H), 1.73-1.59 (m, 1H), 1.43-1.24 (m, 1H), 1.02-0.83 (m, 1H), 0.54-0.40 (m, 2H), 0.15-0.07 (m, 2H), 1H exchanged with solvent.

Compound 346: (R)—N-(cyclopropylmethyl)-1-(6-(3-(4-(5-(cyclopropylmethyl)pyridin-3-yl)-1H-1,2,3-triazol-1-yl)oxetan-3-yl)pyridin-3-yl)piperidin-3-amine was Obtained Using General Scheme 1 Pathway B Stage 1: 5-bromonicotinaldehyde (1 g, 5.21 mmol) and 4-methylbenzene-sulfonhydrazide (972 mg, 5.22 mmol) were merged and backfilled with Argon followed by addition of anhydrous 1,4-dioxane (21 mL). The reaction mixture was stirred for 16 h at rt. Then, cyclopropylboronic acid (672 mg, 7.82 mmol) and cesium carbonate (2.60 g, 7.85 mmol) were added to the reaction mixture, which was heated to 110° C. and stirred for 7 h30. The reaction mixture was cooled to rt, quenched with water (30 mL) and diluted with EtOAc (30 mL). The layers were separated and the aqueous phase extracted with EtOAc (3×20 mL). The combined organic layers were dried over MgSO$_4$, filtered and concentrated under reduced pressure. The crude material was purified by an automated flash chromatography system (dryload in silica, 0 to 30% EtOAc in Heptane) to afford 3-bromo-5-(cyclopropylmethyl)pyridine IM963 as colourless oil: 440 mg, 39% yield, P=97%, retention time=2.5 min (gradient A), (M+H)$^+$: 212/214.

Stage 2: General Procedure E1 was used from IM963 to afford 3-(cyclopropylmethyl)-5-((trimethylsilyl)ethynyl)pyridine IM964 as brown oil: 373 mg, 73% yield, P=88%, retention time=2.8 min (gradient A), (M+H)$^+$: 230.

Stage 3: General Procedure D1 was used from IM964 to afford 3-(cyclopropylmethyl)-5-ethynylpyridine IM965 as a brown oil: 206 mg, 90% yield, P=98%, retention time=2.2 min (gradient A), (M+H)$^+$: 158.

Stage 4: General Procedure B was used between IM965 and IM872 to afford 5-bromo-2-(3-(4-(5-(cyclopropylmethyl)pyridin-3-yl)-1H-1,2,3-triazol-1-yl)oxetan-3-yl)pyridine IM966 as colourless oil: 155 mg, 88% yield, P=96%, retention time=2.3 min (gradient A), (M+H)$^+$: 412/414.

Stage 5: General Procedure Y was used between IM486 and IM966 to afford tert-butyl (R)-(cyclopropylmethyl)(1-(6-(3-(4-(5-(cyclopropylmethyl)pyridin-3-yl)-1H-1,2,3-triazol-1-yl)oxetan-3-yl)pyridin-3-yl)piperidin-3-yl)carbamate IM967 as colourless oil: 117 mg, 90% yield, P=84%, retention time=2.6 min (gradient A), (M+H)$^+$: 586.

Stage 6: General Procedure A2 was used from IM967 to afford crude compound 346 as colourless oil: 70 mg, 80% yield, P=93%, retention time=2.8 min (gradient B), (M+H)$^+$: 486.

The product was purified by reverse phase preparative HPLC purification (XBridge OBD C18 5 μm, 19×100 mm). Gradient used: increased linearly from 30% to 40% solution "B" over 4.0 min, increased linearly to 88% solution "B" over 2.5 min, and returned to initial conditions over 0.7 min. Flow Rate: 15 mL/min. P=100%. $^1$H NMR (300 MHz, CDCl$_3$) δ 8.77 (s, 1H), 8.44 (s, 1H), 8.33 (s, 1H), 8.11 (s, 1H), 7.78 (s, 1H), 7.13 (d, J=8.5 Hz, 1H), 6.92 (d, J=8.8 Hz, 1H), 5.54 (d, J=6.7 Hz, 2H), 5.47 (d, J=6.9 Hz, 2H), 3.73-3.64 (m, 1H), 3.56-3.46 (m, 1H), 2.96-2.83 (m, 1H), 2.80-2.64 (m, 2H), 2.62-2.47 (m, 4H), 2.01-1.91 (m, 1H), 1.88-1.77 (m, 1H), 1.74-1.60 (m, 1H), 1.39-1.29 (m, 1H), 1.07-0.88 (m, 2H), 0.60-0.52 (m, 2H), 0.52-0.44 (m, 2H), 0.28-0.19 (m, 2H), 0.10 (m, 2H), 1H exchanged with solvent.

Compound 347: (3R)—N-(cyclopropylmethyl)-1-(6-(1-(5-(6-(pyrrolidin-1-yl)pyrazin-2-yl)-1,3,4-oxadiazol-2-yl)ethyl)pyridazin-3-yl)piperidin-3-amine was Obtained Using the Following Procedures Stage 1: To a solution of 6-(pyrrolidin-1-yl)pyrazine-2-carbaldehyde (500 mg, 2.82 mmol) in anhydrous methanol (15 mL) at 0° C. was added a solution of potassium hydroxide (571 mg, 10 mmol) in anhydrous methanol (5 mL), followed by a solution of iodine (1.24 g, 4.89 mmol) in methanol (10 mL). The reaction mixture was stirred at 0° C. for 1.25 h, quenched at 0° C. by adding an aqueous solution of sodium sulfite 30% until the reaction turned to a yellow suspension. The mixture was diluted with DCM (40 mL) and water (10 mL), then layers were separated and the aqueous layer was extracted with DCM (2×20 mL). The combined organic layers were washed with brine (10 mL), dried over MgSO$_4$, filtered and the filtrate was concentrated under reduced pressure to dryness to afford methyl 6-(pyrrolidin-1-yl)pyrazine-2-carboxylate IM968 as crude brown oil: 597 mg, 97% yield, P=95%, retention time=2.4 min (gradient A), (M+H)$^+$: 208.

Stage 2: To a stirred solution of IM968 (607 mg, 2.72 mmol) in ethanol (6 mL) was added hydrazine monohydrate (0.7 mL, 14.14 mmol). The reaction was stirred at 70° C. for 1.5 h. The reaction mixture was cooled to rt and the solvent was evaporated under reduced pressure to dryness to afford crude 6-(pyrrolidin-1-yl)pyrazine-2-carbohydrazide IM969 as an orange solid: 607 mg, 100% yield, P=93%, retention time=1.9 min (gradient A), (M+H)$^+$: 208.

Stage 3: To a mixture of IM969 (293 mg, 1.31 mmol), lithium 2-(6-chloropyridazin-3-yl)propanoate lithium (350 mg, 1.36 mmol) and HATU (670 mg, 1.76 mmol) in anhydrous DMF (6.7 mL) under Ar atmosphere was added triethylamine (380 μL, 2.71 mmol) and the reaction mixture was stirred at rt for 45 min. The reaction mixture was diluted with EtOAc (20 mL) and washed with brine (5×50 mL), then dried over MgSO$_4$, filtered and the filtrate was concentrated under reduced pressure to dryness to afford a crude yellow oil. The crude material was purified by an automated flash chromatography system (liquid injection in DCM, 0 to 4% MeOH in DCM) to afford N'-(2-(6-chloropyridazin-3-yl)propanoyl)-6-(pyrrolidin-1-yl)pyrazine-2-carbohydrazide IM970 as yellow oil: 288 mg, 36% yield, P=62%, retention time=2.3 min (gradient A), (M+H)$^+$: 376/378.

Stage 4: General Procedure C was used between IM970 and (R)-3-Boc-aminopiperidine to afford tert-butyl ((3R)-1-(6-(1-oxo-1-(2-(6-(pyrrolidin-1-yl)pyrazine-2-carbonyl)hydrazineyl)propan-2-yl)pyridazin-3-yl)piperidin-3-yl)carbamate IM971 as a yellow solid: 284 mg, 85% yield, P=77%, retention time=2.3 min (gradient A), (M+H)$^+$: 540.

Stage 5: A mixture of IM971 (205 mg, 0.33 mmol) in anhydrous THF (1.8 mL) was added (methoxycarbonylsulfamoyl)triethylammoniumhydroxide salt (174 mg, 0.68 mmol). Reaction was stirred at rt for 16 h. An extra add of (methoxycarbonylsulfamoyl)triethylammoniumhydroxide salt (5 mg, 0.02 mmol) was added to the reaction mixture. The reaction mixture was diluted with EtOAc (20 mL) and washed with NaHCO$_3$ saturated aqueous solution (10 mL) and brine (5 mL). The organic layer was dried over MgSO$_4$, filtered and concentrated under reduced pressure to dryness to afford yellow oil. The crude material was purified by an automated flash chromatography system (liquid injection in DCM, 0 to 3% MeOH in DCM) to afford tert-butyl ((3R)-1-(6-(1-(5-(6-(pyrrolidin-1-yl)pyrazin-2-yl)-1,3,4-oxadiazol-2-yl)ethyl)pyridazin-3-yl)piperidin-3-yl)carbamate IM972 as yellow solid: 117 mg, 60% yield, P=87%, retention time=2.2 min (gradient A), (M+H)+: 522.

Stage 6: General Procedure A2 was used from IM972 to afford crude (3R)-1-(6-(1-(5-(6-(pyrrolidin-1-yl)pyrazin-2-yl)-1,3,4-oxadiazol-2-yl)ethyl)pyridazin-3-yl)piperidin-3-amine IM973 as yellow oil: 71 mg, 74% yield, P=86%, retention time=2.0 min (gradient A), (M+H)+: 422.

Stage 7: General Procedure AE was used between IM973 and cyclopropanecarboxaldehyde to afford crude compound 347 as yellow oil: 62 mg, 56% yield, P=62%, retention time=2.1 min (gradient A), (M+H)+: 476.

The product was purified by reverse phase preparative HPLC purification (XBridge OBD C18 5 µm, 19×100 mm). Gradient used: increased linearly from 25% to 45% solution "B" over 4.5 min, increased linearly to 88% solution "B" over 1.5 min, held to 88% solution "B" for 1.5 min, and returned to initial conditions over 0.7 min. Flow Rate: 15 mL/min. P=100%. The mixture of diastereomers was purified by chiral preparative HPLC purification using Chiralpak IA column (5 µm, 20×250 mm). Eluent used: TBME/MeOH/DCM/DEA: 60/30/10/0.1% at flow rate of 20 mL/min. First eluted diastereomer: P=100%, retention time=5.7 min, chiral HPLC: P=94.3%, $^1$H NMR (300 MHz, CDCl$_3$) δ 8.50 (s, 1H), 7.97 (s, 1H), 7.28 (d, J=10.1 Hz, 1H), 6.94 (d, J=9.6 Hz, 1H), 4.78 (q, J=7.4 Hz, 1H), 4.52-4.42 (m, 1H), 4.09-3.99 (m, 1H), 3.61-3.51 (m, 4H), 3.19-3.01 (m, 2H), 2.96-2.81 (m, 1H), 2.64 (d, J=7.1 Hz, 2H), 2.10-2.00 (m, 5H), 1.92-1.77 (m, 4H), 1.69-1.54 (m, 2H), 1.08-0.97 (m, 1H), 0.56-0.47 (m, 2H), 0.23-0.15 (m, 2H), 1H exchanged with solvent. Second eluted diastereomer: P=98%, retention time=6.9 min, chiral HPLC: P=98.6%, $^1$H NMR (300 MHZ, CDCl$_3$) δ 8.50 (s, 1H), 7.96 (s, 1H), 7.26 (d, J=9.8 Hz, 1H), 6.91 (d, J=9.4 Hz, 1H), 4.77 (q, J=7.3 Hz, 1H), 4.45-4.35 (m, 1H), 4.11-4.00 (m, 1H), 3.61-3.50 (m, 4H), 3.16-3.01 (m, 1H), 2.93 (dd, J=12.8, 9.1 Hz, 1H), 2.81-2.67 (m, 1H), 2.57 (d, J=6.9 Hz, 2H), 2.09-1.98 (m, 5H), 1.91-1.76 (m, 4H), 1.64-1.39 (m, 2H), 1.04-0.86 (m, 1H), 0.52-0.43 (m, 2H), 0.18-0.07 (m, 2H), 1H exchanged with solvent.

Compound 348: (3R)—N-((1-methylcyclopropyl)methyl)-1-(6-(1-(4-(6-(pyrrolidin-1-yl)pyrazin-2-yl)-1H-imidazol-1-yl)ethyl)pyridazin-3-yl)piperidin-3-amine was Obtained Using General Scheme 4 Pathway A Stage 1: General Procedure C was used between IM514 and (R)-3-Boc-aminopiperidine to afford tert-butyl ((3R)-1-(6-(1-(4-iodo-1H-imidazol-1-yl)ethyl)pyridazin-3-yl)piperidin-3-yl)carbamate IM974 as a pasty off-white solid: 1.22 g, 99% yield, P=85%, retention time=2.1 min (gradient A), (M+H)+: 499.

Stage 2: To a solution of IM974 (876 mg, 1.37 mmol) and isopropoxyboronic acid, pinacol ester (550 µL, 2.59 mmol) in anhydrous THF (4 mL) under Ar atmosphere at 0° C. was added isopropylmagnesium chloride-lithium chloride in THF (1.3M) (3.40 mL, 4.42 mmol) over 1 min. The reaction mixture was stirred at 0° C. for 50 min, concentrated under reduced pressure to afford an orange solid. Et$_2$O (10 mL) was added to the solid and the suspension was filtered. The solid was rinsed with Et$_2$O (2×10 mL), then pentane (10 mL). The solid was collected and dried under vacuum to afford crude (1-(1-(6-(((R)-3-((tert-butoxycarbonyl)amino)piperidin-1-yl)pyridazin-3-yl)ethyl)-1H-imidazol-4-yl)boronic acid IM975 as a yellow solid: 1.99 g, 98% yield, P=28%, retention time=2.0 min (gradient A), (M+H)+: 417.

Stage 3: General Procedure U was used between crude IM975 and IM917 to afford crude tert-butyl ((3R)-1-(6-(1-(4-(6-(pyrrolidin-1-yl)pyrazin-2-yl)-1H-imidazol-1-yl)ethyl)pyridazin-3-yl)piperidin-3-yl)carbamate IM976 as an orange solid: 2.01 g, 64% yield, P=22%, retention time=2.2 min (gradient A), (M+H)+: 520.

The product was purified by reverse phase preparative HPLC purification (XBridge OBD C18 5 µm, 19×100 mm). Gradient used: increased linearly from 45% to 50% solution "B" over 4.5 min, increased linearly to 88% solution "B" over 1.5 min, held to 88% solution "B" for 1.5 min, and returned to initial conditions over 0.7 min. Flow Rate: 15 mL/min. P=99%.

Stage 4: General Procedure A2 was used from IM976 to afford crude (3R)-1-(6-(1-(4-(6-(pyrrolidin-1-yl)pyrazin-2-yl)-1H-imidazol-1-yl)ethyl)pyridazin-3-yl)piperidin-3-amine IM977 as a white solid: 164 mg, 82% yield, P=100%, retention time=1.9 min (gradient A), (M+H)+: 420.

Stage 5: General Procedure AE was used between IM977 and 1-methylcyclopropanecarbaldehyde to afford crude compound 348 as yellow oil: 75 mg, 92% yield, P=91%, retention time=2.0 min (gradient A), (M+H)+: 488.

The mixture of diastereomers was purified by chiral preparative HPLC purification using Chiralpak IA column (5 µm, 20×250 mm). Eluent used: EtOAc/MeOH/DEA: 95/5/0.1% at flow rate of 20 mL/min. First eluted diastereomer: P=95%, retention time=4.9 min, chiral HPLC: P=100%, $^1$H NMR (300 MHZ, CDCl$_3$) δ 8.43 (s, 1H), 7.74 (s, 1H), 7.68 (s, 1H), 7.64 (s, 1H), 6.92 (d, J=9.4 Hz, 1H), 6.84 (d, J=9.5 Hz, 1H), 5.54 (q, J=7.1 Hz, 1H), 4.41-4.31 (m, 1H), 4.13-4.02 (m, 1H), 3.57-3.47 (m, 4H), 3.18-3.05 (m, 1H), 2.90 (dd, J=12.8, 9.2 Hz, 1H), 2.73-2.61 (m, 1H), 2.56 (d, J=11.6 Hz, 1H), 2.49 (d, J=11.7 Hz, 1H), 2.08-1.94 (m, 8H), 1.93-1.72 (m, 1H), 1.67-1.60 (m, 1H), 1.47-1.32 (m, 1H), 1.09 (s, 3H), 0.29 (d, J=11.2 Hz, 4H), 1H exchanged with solvent. Second eluted diastereomer: P=99%, retention time=8.6 min, chiral HPLC: P=98.4%, $^1$H NMR (300 MHz, CDCl$_3$) δ 8.42 (s, 1H), 7.73 (s, 1H), 7.67 (d, J=1.6 Hz, 1H), 7.63 (d, J=1.5 Hz, 1H), 6.92 (d, J=9.5 Hz, 1H), 6.84 (d, J=9.5 Hz, 1H), 5.53 (q, J=7.1 Hz, 1H), 4.41-4.29 (m, 1H), 4.11-4.01 (m, 1H), 3.56-3.46 (m, 4H), 3.17-3.03 (m, 1H), 2.90 (dd, J=12.8, 9.2 Hz, 1H), 2.72-2.60 (m, 1H), 2.55 (d, J=11.6 Hz, 1H), 2.48 (d, J=11.7 Hz, 1H), 2.00 (m, 8H), 1.87-1.76 (m, 1H), 1.61-1.50 (m, 1H), 1.47-1.34 (m, 1H), 1.08 (s, 3H), 0.36-0.21 (m, 4H), 1H exchanged with solvent.

Compound 349: (R)—N-(cyclopropylmethyl)-1-(6-(3-(4-(5-cyclopropylpyridin-3-yl)-1H-1,2,3-triazol-1-yl)azetidin-3-yl)pyridin-3-yl)piperidin-3-amine was Obtained Using General Scheme 1 Pathway B Stage 1: To a solution of 2,5-dibromopyridine (4.62 g, 19.11 mmol) in dry toluene (50 mL) at −78° C. was added n-butyl lithium in hexane (7.60 mL, 19 mmol) dropwise over 2 min. After 10 min, tert-butyl 3-oxoazetidine-1-carboxylate (2.99 g, 17.12 mmol) in anhydrous toluene (10 mL) was added dropwise over 1 min at −78° C. The resulting solution was stirred for 15 min at −78° C. and then slowly allowed to warm to rt over 1 h (dry ice/acetone bath removed). The reaction mixture was quenched with a saturated aqueous solution of NH$_4$Cl (100 mL) and extracted with EtOAc (3×100 mL). The organic layers were merged, dried over MgSO$_4$, filtered and concentrated under reduced pressure to dryness. The crude material was purified by an automated flash chromatography system (dryload in Celite, 0 to 40% EtOAc in Heptane) to afford tert-butyl 3-(5-bromopyridin-2-yl)-3-hydroxyazetidine-1-carboxylate IM978 as light yellow oil: 2.75 g, 47% yield, P=96%, retention time=2.8 min (gradient A), (M-tBu)$^+$: 273/275.

Stage 2: General Procedure P was used from IM978 to afford tert-butyl 3-(5-bromopyridin-2-yl)-3-((methylsulfonyl)oxy)azetidine-1-carboxylate IM979 as a light yellow gum: 633 mg, 96% yield, P=90%, retention time=2.9 min (gradient A), (M-tBu)$^+$: 351/353.

Stage 3: General Procedure N (in DMSO) was used from IM979 to afford tert-butyl 3-azido-3-(5-bromopyridin-2-yl)azetidine-1-carboxylate IM980 as colourless oil: 426 mg, 86% yield, P=100%, retention time=3.0 min (gradient A), (M-tBu)$^+$: 298/300.

Stage 4: General Procedure B was used between IM980 and IM896 to afford tert-butyl 3-(5-bromopyridin-2-yl)-3-(4-(5-cyclopropylpyridin-3-yl)-1H-1,2,3-triazol-1-yl)azetidine-1-carboxylate IM981 as a light yellow foam: 490 mg, 80% yield, P=98%, retention time=2.5 min (gradient A), (M+H)$^+$: 497/499.

Stage 5: General Procedure Y was used between IM981 and IM486 to afford tert-butyl (R)-3-(5-(3-((tert-butoxycarbonyl)(cyclopropylmethyl)amino)piperidin-1-yl)pyridin-2-yl)-3-(4-(5-cyclopropylpyridin-3-yl)-1H-1,2,3-triazol-1-yl)azetidine-1-carboxylate IM982 as a white foam: 144 mg, 92% yield, P=86%, retention time=2.7 min (gradient A), (M+H)$^+$: 671.

Stage 6: General Procedure A2 was used from IM982 to afford crude compound 349 as an orange gum: 97 mg, 100% yield, P=88%, retention time=1.9 min (gradient A), (M+H)$^+$: 471.

The product was purified by reverse phase preparative HPLC purification (XBridge OBD C18 5 µm, 19×100 mm). Gradient used: increased linearly from 25% to 40% solution "B" over 4.0 min, increased linearly to 88% solution "B" over 2.5 min, and returned to initial conditions over 0.7 min. Flow Rate: 15 mL/min. P=100%. $^1$H NMR (300 MHz, CDCl$_3$) δ 8.70 (d, J=2.0 Hz, 1H), 8.37 (d, J=2.2 Hz, 1H), 8.33 (d, J=2.9 Hz, 1H), 7.83 (dd, J=2.2, 2.2 Hz, 1H), 7.75 (s, 1H), 7.13 (dd, J=8.7, 3.0 Hz, 1H), 6.95 (d, J=8.7 Hz, 1H), 4.60 (d, J=8.9 Hz, 2H), 4.54 (d, J=8.8 Hz, 2H), 3.73-3.63 (m, 1H), 3.56-3.46 (m, 1H), 2.97-2.82 (m, 1H), 2.81-2.64 (m, 2H), 2.63-2.45 (m, 2H), 2.02-1.90 (m, 2H), 1.90-1.76 (m, 2H), 1.76-1.61 (m, 1H), 1.44-1.23 (m, 1H), 1.11-0.91 (m, 3H), 0.85-0.74 (m, 2H), 0.56-0.44 (m, 2H), 0.13 (d, J=4.9 Hz, 2H), 1H exchanged with solvent.

Compound 350: (R)—N-(cyclopropylmethyl)-1-(6-(3-(4-(5-cyclopropylpyridin-3-yl)-1H-1,2,3-triazol-1-yl)-1-methylazetidin-3-yl)pyridin-3-yl)piperidin-3-amine was Obtained Using General Scheme 1 Pathway B Stage 1: General Procedure A2 was used from IM981 to afford crude 5-bromo-2-(3-(4-(5-cyclopropylpyridin-3-yl)-1H-1,2,3-triazol-1-yl)azetidin-3-yl)pyridine IM983 as a light yellow foam: 196 mg, 93% yield, P=93%, retention time=1.9 min (gradient A), (M+H)$^+$: 397/399.

Stage 2: General Procedure AE was used between IM983 and to afford crude 5-bromo-2-(3-(4-(5-cyclopropylpyridin-3-yl)-1H-1,2,3-triazol-1-yl)-1-methylazetidin-3-yl)pyridine IM984 as a colourless gum: 91 mg, 88% yield, P=94%, retention time=2.0 min (gradient A), (M+H)$^+$: 411/413.

Stage 3: General Procedure Y was used between IM984 and IM486 to afford tert-butyl (R)-(cyclopropylmethyl)(1-(6-(3-(4-(5-cyclopropylpyridin-3-yl)-1H-1,2,3-triazol-1-yl)-1-methylazetidin-3-yl)pyridin-3-yl)piperidin-3-yl)carbamate IM985 as an orange gum: 125 mg, 84% yield, P=82%, retention time=2.3 min (gradient A), (M+H)$^+$: 585.

Stage 4: General Procedure A2 was used from IM985 to afford crude compound 350 as an orange gum: 83 mg, 96% yield, P=98%, retention time=1.9 min (gradient A), (M+H)$^+$: 485.

The product was purified by reverse phase preparative HPLC purification (XBridge OBD C18 5 µm, 19×100 mm). Gradient used: increased linearly from 30% to 40% solution "B" over 4.0 min, increased linearly to 88% solution "B" over 2.5 min, and returned to initial conditions over 0.7 min. Flow Rate: 15 mL/min. P=100%. $^1$H NMR (300 MHz, CDCl$_3$) δ 8.71 (d, J=2.0 Hz, 1H), 8.37 (d, J=2.2 Hz, 1H), 8.30 (d, J=2.8 Hz, 1H), 7.86-7.78 (m, 2H), 7.14 (dd, J=8.7, 2.9 Hz, 1H), 7.06 (d, J=8.7 Hz, 1H), 4.25-4.13 (m, 4H), 3.72-3.62 (m, 1H), 3.54-3.44 (m, 1H), 2.95-2.64 (m, 3H), 2.61-2.45 (m, 5H), 2.03-1.87 (m, 2H), 1.87-1.75 (m, 1H), 1.75-1.57 (m, 1H), 1.43-1.25 (m, 1H), 1.11-0.99 (m, 2H), 0.99-0.88 (m, 1H), 0.85-0.74 (m, 2H), 0.56-0.44 (m, 2H), 0.17-0.08 (m, 2H), 1H exchanged with solvent.

Compound 351: (S)—N-(cyclopropylmethyl)-1-(6-(3-(4-(5-cyclopropylpyridin-3-yl)-1H-1,2,3-triazol-1-yl)oxetan-3-yl)pyridin-3-yl)piperidin-3-amine was Obtained Using General Scheme 1 Pathway B Stage 1: General Procedure Y was used between IM936 and tert-butyl (S)-piperidin-3-ylcarbamate to afford tert-butyl (S)-(1-(6-(3-(4-(5-cyclopropylpyridin-3-yl)-1H-1,2,3-triazol-1-yl)oxetan-3-yl)pyridin-3-yl)piperidin-3-yl)carbamate IM986 as a white solid: 590 mg, 71% yield, P=93%, retention time=2.4 min (gradient A), (M+H)$^+$: 518.

Stage 2: General Procedure A2 was used from IM986 to afford crude (S)-1-(6-(3-(4-(5-cyclopropylpyridin-3-yl)-1H-1,2,3-triazol-1-yl)oxetan-3-yl)pyridin-3-yl)piperidin-3-amine IM987 as colourless oil: 460 mg, 95% yield, P=91%, retention time=2.0 min (gradient A), (M+H)$^+$: 418.

Stage 3: General AE used between Procedure was IM987 and cyclopropanecarboxaldehyde to afford compound 351 as a white solid: 303 mg, 65% yield, P=100%, retention time=2.7 min (gradient B), (M+H)$^+$: 472. $^1$H NMR (300 MHZ, CDCl$_3$) δ 8.71 (d, J=1.9 Hz, 1H), 8.38 (d, J=2.1 Hz, 1H), 8.33 (d, J=2.9 Hz, 1H), 7.83 (d, J=2.1 Hz, 1H), 7.76 (s, 1H), 7.14 (dd, J=8.7, 2.9 Hz, 1H), 6.93 (d, J=8.7 Hz, 1H), 5.54 (d, J=6.7 Hz, 2H), 5.48 (d, J=6.8 Hz, 2H), 3.76-3.67 (m, 1H), 3.56-3.45 (m, 1H), 2.98-2.84 (m, 1H), 2.83-2.74 (m, 2H), 2.65-2.47 (m, 2H), 2.04-1.79 (m, 3H), 1.75-1.58 (m, 1H), 1.49-1.32 (m, 1H), 1.11-1.01 (m, 2H), 1.01-0.93 (m, 1H), 0.84-0.76 (m, 2H), 0.57-0.45 (m, 2H), 0.19-0.10 (m, 2H), 1H exchanged with solvent.

Compound 352: (R)—N-(cyclopropylmethyl)-1-(6-(3-(5-(5-cyclopropylpyridin-3-yl)-1,3,4-thiadiazol-2-yl)oxetan-3-yl)pyridin-3-yl)piperidin-3-amine was Obtained Using General Scheme 3 Pathway C Stage 1: Into a sealed tube, Lawesson's reagent (3.50 g, 8.48 mmol) and 5-cyclopropylpyridine-3-carbohydrazide (570 mg, 3.15 mmol) were mixed, flushed with argon, and anhydrous 1,4-dioxane (6 mL) was added. Tube was sealed and heated to 110 °C for 5 h. Reaction mixture was cooled to rt, and 1,4-dioxane (20 mL) was added and filtered. Solid was rinsed-off with 1,4-dioxane (2×20 mL). Filtrate was concentrated under reduced pressure to afford yellow oil. The crude material was purified by an automated flash chromatography system (dryload silica, 0 to 10% MeOH in DCM) to afford 5-cyclopropylpyridine-3-carbothiohydrazide IM988 as yellow solid: 388 mg, 50% yield, P=78%, retention time=1.7 min (gradient A), (M+H)$^+$: 194.

Stage 2: General Procedure F was used between IM988 and IM932 to afford tert-butyl (R)-(1-(6-(3-(5-(5-cyclopropylpyridin-3-yl)-1,3,4-thiadiazol-2-yl)oxetan-3-yl)pyridin-3-yl)piperidin-3-yl)carbamate IM989 as colourless oil: 74 mg, 30% yield, P=74%, retention time=2.4 min (gradient A), (M+H)$^+$: 535.

Stage 3: General Procedure A2 was used from IM989 to afford crude (R)-1-(6-(3-(5-(5-cyclopropylpyridin-3-yl)-1,3,4-thiadiazol-2-yl)oxetan-3-yl)pyridin-3-yl)piperidin-3-amine IM990 as colourless oil: 42 mg, 80% yield, P=85%, retention time=2.0 min (gradient A), (M+H)$^+$: 435.

The product was purified by reverse phase preparative HPLC purification (XBridge OBD C18 5 µm, 19×100 mm). Gradient used: increased linearly from 25% to 45% solution "B" over 4.5 min, increased linearly to 88% solution "B" over 1.5 min, held to 88% for 1.5 min, and returned to initial conditions over 0.7 min. Flow Rate: 15 mL/min. P=100%.

Stage 4: General Procedure AE was used between IM990 and cyclopropanecarboxaldehyde to afford crude compound 352 as colourless oil: 38 mg, 79% yield, P=83%, retention time=2.8 min (gradient B), (M+H)$^+$: 489.

The product was purified by reverse phase preparative HPLC purification (XBridge OBD C18 5 µm, 19×100 mm). Gradient used: increased linearly from 40% to 45% solution "B" over 6.0 min, increased linearly to 50% solution "B" over 1.0 min, increased linearly to 88% solution "B" over 2.5 min, held to 88% for 1.5 min, and returned to initial conditions over 1.5 min. Flow Rate: 18 mL/min. P=100%. $^1$H NMR (300 MHz, CDCl$_3$) δ 8.80 (d, J=2.2 Hz, 1H), 8.49 (d, J=2.2 Hz, 1H), 8.32 (d, J=2.2 Hz, 1H), 7.88 (dd, J=2.2, 2.2 Hz, 1H), 7.23-7.17 (m, 2H), 5.46 (d, J=6.0 Hz, 2H), 5.35 (d, J=5.9 Hz, 2H), 3.72-3.62 (m, 1H), 3.55-3.43 (m, 1H), 2.96-2.84 (m, 1H), 2.83-2.65 (m, 2H), 2.63-2.44 (m, 2H), 2.03-1.88 (m, 2H), 1.89-1.76 (m, 1H), 1.75-1.58 (m, 1H), 1.40-1.26 (m, 1H), 1.14-1.02 (m, 2H), 1.02-0.87 (m, 1H), 0.85-0.73 (m, 2H), 0.55-0.43 (m, 2H), 0.17-0.07 (m, 2H), 1H exchanged with solvent.

Compound 353: (3R)—N-(cyclopropylmethyl)-1-(6-(1-(5-(6-(pyrrolidin-1-yl)pyrazin-2-yl)-1,3,4-thiadiazol-2-yl)ethyl)pyridazin-3-yl)piperidin-3-amine was Obtained Using General Scheme 3 Pathway C Stage 1: Into a sealed tube, IM969 (700 mg, 3.38 mmol) and Lawesson's reagent (3.75 g, 9.09 mmol) were mixed, flushed with argon, and anhydrous 1,4-dioxane (6.4 mL) was added. Tube was sealed and heated to 110° C. for 2.5 h. Then, reaction was cooled to rt diluted with 1,4 dioxane (40 mL), and concentrated under reduced pressure. Residue was dissolved in methanol (30 mL) and water (30 mL), and NaOH (10 mL, 20 mmol) was added. Suspension was heated to 90° C. for 16 h, and at 110° C. for 6 h. Reaction mixture was cooled to rt, concentrated under reduced pressure to afford orange oil. The crude material was purified by an automated flash chromatography system (dryload silica, 0 to 10% MeOH in DCM) to afford desired product as brown residue. The latter (715 mg) was slurried in Et$_2$O (30 mL) for 1 h, and resulting suspension was filtered, rinsed with Et$_2$O (2×20 mL). Solid was dried under reduced pressure to afford 6-(pyrrolidin-1-yl)pyrazine-2-carbothiohydrazide IM991 as brown precipitate: 270 mg, 26% yield, P=74%, retention time=2.3 min (gradient A), (M+H)$^+$: 224.

Stage 2: General Procedure F was used between IM991 and lithium 2-(6-chloropyridazin-3-yl)propanoate lithium to afford 2-(1-(6-chloropyridazin-3-yl)ethyl)-5-(6-(pyrrolidin-1-yl)pyrazin-2-yl)-1,3,4-thiadiazole IM992 as orange oil: 130 mg, 48% yield, P=69%, retention time=2.7 min (gradient A), (M+H)$^+$: 374/376.

Stage 3: General Procedure C was used between IM992 and IM486 to afford tert-butyl (cyclopropylmethyl)((3R)-1-(6-(1-(5-(6-(pyrrolidin-1-yl)pyrazin-2-yl)-1,3,4-thiadiazol-2-yl)ethyl)pyridazin-3-yl)piperidin-3-yl)carbamate IM993 as orange oil: 122 mg, 62% yield, P=71%, retention time=2.6 min (gradient A), (M+H)$^+$: 592.

Stage 4: General Procedure A2 was used from IM993 to afford crude compound 353 as orange oil: 85 mg, 74% yield, P=63%, retention time=3.2 min (gradient B), (M+H)$^+$: 492.

The product was purified by reverse phase preparative HPLC purification (XBridge OBD C18 5 µm, 19×100 mm). Gradient used: increased linearly from 40% to 45% solution "B" over 6.0 min, increased linearly to 50% solution "B" over 1.0 min, increased linearly to 88% solution "B" over 2.5 min, held to 88% for 1.0 min, and returned to initial conditions over 1.5 min. Flow Rate: 18 mL/min. P=100%.

The mixture of diastereomers was further purified by chiral preparative HPLC purification using Chiralpak IA column (5 µm, 20×250 mm). Eluent used: TBME/MeOH/DCM/DEA: 60/30/10/0.1% at flow rate of 20 mL/min. First eluted diastereomer: P=100%, retention time=5.8 min, chiral HPLC: P=98.8%, $^1$H NMR (300 MHz, CDCl$_3$) δ 8.69 (s, 1H), 7.91 (s, 1H), 7.30 (d, J=9.4 Hz, 1H), 6.97 (d, J=9.5 Hz, 1H), 4.89 (q, J=7.2 Hz, 1H), 4.66-4.56 (m, 1H), 4.02 (m, 1H), 3.55-3.45 (m, 4H), 3.35-3.21 (m, 1H), 3.19-2.98 (m, 2H), 2.87-2.68 (m, 2H), 2.23-2.13 (m, 1H), 2.09-1.96 (m, 4H), 1.95-1.73 (m, 4H), 1.69-1.55 (m, 1H), 1.21-1.08 (m, 1H), 0.93-0.82 (m, 1H), 0.62-0.53 (m, 2H), 0.34-0.27 (m, 2H), 1H exchanged with solvent. Second eluted diastereomer: P=99%, retention time=7.2 min, chiral HPLC: P=98.1%, 1H NMR (300 MHz, CDCl$_3$) δ 8.68 (s, 1H), 7.91 (s, 1H), 7.32 (d, J=9.4 Hz, 1H), 7.00 (d, J=9.4 Hz, 1H), 4.89 (q, J=7.2 Hz, 1H), 4.75-4.65 (m, 1H), 4.06-3.95 (m, 1H), 3.55-3.45 (m, 4H), 3.45-3.35 (m, 1H), 3.21-3.06 (m, 2H), 2.97-2.75 (m, 2H), 2.32-2.20 (m, 1H), 2.09-2.00 (m, 4H), 2.00-1.86 (m, 4H), 1.69-1.54 (m, 1H), 1.25-1.18 (m, 1H), 0.93-0.82 (m, 1H), 0.66-0.57 (m, 2H), 0.42-0.34 (m, 2H), 1H exchanged with solvent.

Compound 354: (3R)—N-(cyclopropylmethyl)-1-(6-(1-(1-(6-(pyrrolidin-1-yl)pyrazin-2-yl)-1H-pyrazol-4-yl)ethyl)pyridin-3-yl)piperidin-3-amine was Obtained Using General Scheme 5 Pathway B Stage 1: In a microwave vial, under argon, were successively added IM854 (120 mg, 0.36 mmol), IM917 (254 mg, 1.09 mmol), copper(I) iodide (106 mg, 0.56 mmol), cesium carbonate (366 mg, 1.11 mmol), N,N-dimethylglycine hydrochloride (79 mg, 0.55 mmol) and anhydrous DMF (1.8 mL). Argon was bubbled through the reaction mixture for 5 min, then the vial was capped and the reaction mixture was heated at 100° C. for 4 h. Water (15 mL) and EtOAc (15 mL) were added and filtered through a pad of celite. The layers were separated and the organic layer was further extracted with EtOAc (2×25 mL). The combined organic layers were washed with brine (2×25 mL), dried over MgSO$_4$, filtered and concentrated under reduced pressure. The crude material was purified by an automated flash chromatography system (dryload in Celite, 0 to 40% EtOAc in Heptane) to afford 2-(4-(1-(5-chloropyridin-2-yl)ethyl)-1H-pyrazol-1-yl)-6-(pyrrolidin-1-yl)pyrazine IM994 as colourless gum: 51 mg, 38% yield, P=95%, retention time=2.9 min (gradient A), (M+H)$^+$: 355/357.

Stage 2: General Procedure Y was used between IM994 and IM486 to afford tert-butyl (cyclopropylmethyl)((3R)-1-(6-(1-(1-(6-(pyrrolidin-1-yl)pyrazin-2-yl)-1H-pyrazol-4-yl)ethyl)pyridin-3-yl)piperidin-3-yl)carbamate IM995 as a light yellow gum: 58 mg, 61% yield, P=85%, retention time=2.6 min (gradient A), (M+H)$^+$: 573.

Stage 3: General Procedure A2 was used from IM995 to afford crude (3R)—N-(cyclopropylmethyl)-1-(6-(1-(1-(6-(pyrrolidin-1-yl)pyrazin-2-yl)-1H-pyrazol-4-yl)ethyl)pyridin-3-yl)piperidin-3-amine IM996 as light orange gum: 53 mg, 92% yield, P=71%, retention time=2.2 min (gradient A), (M+H)$^+$: 473.

The product was purified by reverse phase preparative HPLC purification (XBridge OBD C18 5 μm, 19×100 mm). Gradient used: increased linearly from 40% to 45% solution "B" over 6.0 min, increased linearly to 50% solution "B" over 1.0 min, increased linearly to 88% solution "B" over 2.5 min, held to 88% for 1.0 min, and returned to initial conditions over 1.5 min. Flow Rate: 18 mL/min. P=100%.

The mixture of diastereomers was further purified by chiral preparative HPLC purification using Chiralpak ID column (5 μm, 10×250 mm). Eluent used: TBME/MeOH/DCM/DEA: 60/30/10/0.1% at flow rate of 7 mL/min. First eluted diastereomer: P=100%, retention time=6.0 min, chiral HPLC: P=98.6%, $^1$H NMR (300 MHz, CDCl$_3$) δ 8.43 (s, 1H), 8.27 (s, 1H), 8.25 (d, J=2.9 Hz, 1H), 7.72 (s, 1H), 7.58 (s, 1H), 7.15 (dd, J=8.6, 2.9 Hz, 1H), 7.03 (d, J=8.6 Hz, 1H), 4.19 (q, J=7.2 Hz, 1H), 3.69-3.59 (m, 1H), 3.58-3.48 (m, 4H), 3.44-3.34 (m, 1H), 2.94-2.70 (m, 3H), 2.60 (d, J=6.9 Hz, 2H), 2.10-1.92 (m, 5H), 1.90-1.78 (m, 1H), 1.76-1.59 (m, 4H), 1.51-1.37 (m, 1H), 1.08-0.93 (m, 1H), 0.93-0.83 (m, OH), 0.58-0.46 (m, 2H), 0.22-0.12 (m, 2H), 1H exchanged with solvent. Second eluted diastereomer: P=100%, retention time=6.5 min, chiral HPLC: P=98.3%, $^1$H NMR (300 MHz, CDCl$_3$) δ 8.42 (s, 1H), 8.27 (s, 1H), 8.24 (d, J=2.9 Hz, 1H), 7.71 (s, 1H), 7.57 (s, 1H), 7.17 (dd, J=8.6, 2.9 Hz, 1H), 7.03 (d, J=8.6 Hz, 1H), 4.18 (q, J=7.2 Hz, 1H), 3.81-3.71 (m, 1H), 3.58-3.47 (m, 4H), 3.40-3.30 (m, 1H), 3.13-3.07 (m, 1H), 3.02-2.89 (m, 1H), 2.88-2.76 (m, 1H), 2.74-2.67 (m, 2H), 2.11-1.99 (m, 5H), 1.91-1.80 (m, 1H), 1.69-1.58 (m, 4H), 1.15-1.05 (m, 1H), 0.93-0.83 (m, 1H), 0.62-0.50 (m, 2H), 0.31-0.21 (m, 2H), 1H exchanged with solvent Compound 355: (3R)—N-(cyclopropylmethyl)-1-(6-(1-(4-(6-(pyrrolidin-1-yl)pyrazin-2-yl)-1H-imidazol-1-yl)ethyl)pyridin-3-yl)piperidin-3-amine was Obtained Using General Scheme 4 Pathway E Stage 1: To a solution IM798 (1.53 g, 6.49 mmol) in anhydrous DMF (43 mL) under Ar atmosphere was added potassium carbonate (1.85 g, 13.25 mmol), followed by 4-iodoimidazole (1.80 g, 9.09 mmol) and the reaction mixture was stirred at 55° C., to afford a thick gel which was barely stirreable, 16 h to afford a yellow suspension. The reaction mixture was cooled to rt then diluted with EtOAc (10 mL) and filtered. The solid was rinsed with EtOAc (2×10 mL) and the filtrate was concentrated under vacuum to afford a crude brown oily solid. The crude material was purified by an automated flash chromatography system (liquid injection in DCM 0 to 4% MeOH in DCM) to afford 5-chloro-2-(1-(4-iodo-1H-imidazol-1-yl)ethyl)pyridine IM997 as a white solid: 1.45 g, 62% yield, P=92%, retention time=2.2 min (gradient A), (M+H)$^+$: 334/336.

Stage 2: To a mixture of IM997 (730 mg, 2.19 mmol), cesium fluoride (660 mg, 4.3 mmol), copper(I) iodide (80 mg, 0.41 mmol) and Pd(PPh$_3$)$_4$ (128 mg, 0.11 mmol) under Ar atmosphere was added degassed anhydrous DMF (2.9 mL), followed by IM644 (1.11 g, 2.53 mmol). The reaction mixture was stirred at 90° C. for 0.5 h. The solution was cooled to rt and diluted with EtOAc (80 mL), then washed with brine (5×25 mL). The organic layer was dried over MgSO$_4$, filtered and concentrated under reduced pressure to afford the crude product. The crude material was purified by an automated flash chromatography system (liquid injection in DCM, 0 to 10% MeOH in DCM) to afford 2-(1-(1-(5-chloropyridin-2-yl)ethyl)-1H-imidazol-4-yl)-6-(pyrrolidin-1-yl)pyrazine IM998 as an off-white foamy solid: 0.6 g, 73% yield, P=95%, retention time=3.4 min (gradient A), (M+H)$^+$: 355.

Stage 3: General Procedure Y was used between IM998 and IM486 to afford tert-butyl (cyclopropylmethyl)((3R)-1-(6-(1-(4-(6-(pyrrolidin-1-yl)pyrazin-2-yl)-1H-imidazol-1-yl)ethyl)pyridin-3-yl)piperidin-3-yl)carbamate IM999 as an off-white solid: 0.9 g, 87% yield, P=91%, retention time=2.6 min (gradient A), (M+H)$^+$: 573.

Stage 4: General Procedure A2 was used from IM999 to afford crude compound 355 as a yellow foam: 0.7 g, 95% yield, P=92%, retention time=2.6 min (gradient A), (M+H)$^+$: 472.

The mixture of diastereomers was purified by chiral preparative HPLC purification using Chiralpak IA column (5 μm, 20×250 mm). Eluent used: TBME/MeOH/DCM/DEA: 55/30/15/0.1% at flow rate of 20 mL/min. First eluted diastereomer: P=100%, retention time=6.2 min, chiral HPLC: P=99.3%, $^1$H NMR (300 MHz, CDCl$_3$) δ 8.42 (s, 1H), 8.24 (d, J=2.9 Hz, 1H), 7.71 (s, 1H), 7.65 (d, J=1.4 Hz, 1H), 7.63 (d, J=1.4 Hz, 1H), 7.09 (dd, J=8.6, 2.9 Hz, 1H), 6.90 (d, J=8.6 Hz, 1H), 5.35 (q, J=7.0 Hz, 1H), 3.71-3.60 (m, 1H), 3.59-3.46 (m, 4H), 3.44-3.35 (m, 1H), 2.90-2.80 (m, 2H), 2.72 (dd, J=11.6, 8.9 Hz, 1H), 2.62-2.50 (m, 2H), 2.06-1.93 (m, 5H), 1.89 (d, J=7.1 Hz, 3H), 1.83-1.73 (m, 1H), 1.73-1.53 (m, 1H), 1.46-1.28 (m, 1H), 1.06-0.90 (m, 1H), 0.54-0.45 (m, 2H), 0.17-0.09 (m, 2H), 1H exchanged with solvent. Second eluted diastereomer: P=99%, retention time=8.8 min, chiral HPLC: P=98.9%, $^1$H NMR (300 MHz, CDCl$_3$) δ 8.42 (s, 1H), 8.24 (d, J=2.9 Hz, 1H), 7.71 (s, 1H), 7.65 (d, J=1.4 Hz, 1H), 7.63 (d, J=1.4 Hz, 1H), 7.09 (dd, J=8.6, 2.9 Hz, 1H), 6.90 (d, J=8.6 Hz, 1H), 5.35 (q, J=7.0 Hz, 1H), 3.71-3.60 (m, 1H), 3.55-3.46 (m, 4H), 3.46-3.36 (m, 1H), 2.89-2.78 (m, 2H), 2.72 (dd, J=11.6, 8.9 Hz, 1H), 2.64-2.47 (m, 2H), 2.06-1.93 (m, 5H), 1.89 (d, J=7.1 Hz, 3H), 1.86-1.73 (m, 1H), 1.73-1.53 (m, 1H), 1.46-1.28 (m, 1H), 1.06-0.80 (m, 1H), 0.55-0.45 (m, 2H), 0.17-0.09 (m, 2H), 1H exchanged with solvent.

Compound 356: (3R)—N-(cyclopropylmethyl)-1-(6-(1-(1-(5-cyclopropylpyridin-3-yl)-1H-pyrazol-4-yl)ethyl)pyridin-3-yl)piperidin-3-amine was Obtained Using General Scheme 5 Pathway B Stage 1: In a microwave vial, under argon, were successively added IM854 (170 mg, 0.72 mmol), IM746 (567 mg, 2.78 mmol), copper(I) iodide (211 mg, 1.11 mmol), cesium carbonate (748 mg, 2.24 mmol), N,N-dimethylglycine hydrochloride (170 mg, 1.19 mmol) and anhydrous DMF (3 mL). Argon was bubbled through the reaction mixture for 5 min then the vial was capped and the reaction mixture was heated at 100° C. for 18 h. Water (25 mL) and EtOAc (25 mL) were added and filtered through a pad of celite. The layers were separated and the organic layer was further extracted with EtOAc (2×25 mL). The combined organic layers were washed with brine (2×25 mL), dried over MgSO$_4$, filtered and concentrated under reduced pressure.

The crude material was purified by an automated flash chromatography system (dryload in Celite, 0 to 80% EtOAc in Heptane) to afford 5-chloro-2-(1-(1-(5-cyclopropylpyridin-3-yl)-1H-pyrazol-4-yl)ethyl)pyridine IM1000 as light yellow gum: 195 mg, 79% yield, P=95%, retention time=2.4 min (gradient A), (M+H)$^+$: 325.

Stage 2: General Procedure Y was used between IM1000 and IM486 to afford tert-butyl (cyclopropylmethyl)((3R)-1-(6-(1-(1-(5-cyclopropylpyridin-3-yl)-1H-pyrazol-4-yl)ethyl)pyridin-3-yl)piperidin-3-yl)carbamate IM1001 as a orange gum: 181 mg, 40% yield, P=69% ($^1$H-NMR), retention time=2.4 min (gradient A), (M+H)$^+$: 543.

Stage 3: General Procedure A2 was used from IM1001 to afford crude compound 356 as a light yellow gum: 109 mg, 78% yield, P=73%, retention time=2.0 min (gradient A), (M+H)$^+$: 443.

The product was purified by reverse phase preparative HPLC purification (XBridge OBD C18 5 µm, 19×100 mm). Gradient used: increased linearly from 45% to 50% solution "B" over 5.0 min, increased linearly to 88% solution "B" over 4.5 min, held to 88% for 1.0 min, and returned to initial conditions over 1.5 min. Flow Rate: 18 mL/min. P=100%.

The mixture of diastereomers was further purified by chiral preparative HPLC purification using Chiralpak ID column (5 µm, 10×250 mm). Eluent used: TBME/MeOH/DCM/DEA: 60/30/10/0.1% at flow rate of 7 mL/min. First eluted diastereomer: P=100%, retention time=6.9 min, chiral HPLC: P=100%, $^1$H NMR (300 MHz, CDCl$_3$) δ 8.66 (d, J=2.3 Hz, 1H), 8.31 (d, J=2.0 Hz, 1H), 8.27 (d, J=2.7 Hz, 1H), 7.74 (s, 1H), 7.66-7.62 (m, 1H), 7.61 (s, 1H), 7.16 (dd, J=8.7, 2.7 Hz, 1H), 7.05 (d, J=8.6 Hz, 1H), 4.18 (q, J=7.2 Hz, 1H), 3.65-3.55 (m, 1H), 3.47-3.37 (m, 1H), 2.91-2.75 (m, 2H), 2.67 (dd, J=11.5, 8.9 Hz, 1H), 2.62-2.46 (m, 2H), 2.02-1.90 (m, 2H), 1.89-1.79 (m, 1H), 1.77-1.62 (m, 4H), 1.42-1.24 (m, 1H), 1.13-1.02 (m, 2H), 1.02-0.86 (m, 1H), 0.85-0.77 (m, 2H), 0.56-0.44 (m, 2H), 0.17-0.09 (m, 2H), 1H exchanged with solvent. Second eluted diastereomer: P=100%, retention time=9.1 min, chiral HPLC: P=99.8%, $^1$H NMR (300 MHz, CDCl$_3$) δ 8.65 (d, J=2.4 Hz, 1H), 8.29 (d, J=2.0 Hz, 1H), 8.25 (d, J=2.9 Hz, 1H), 7.73 (s, 1H), 7.64-7.60 (m, 1H), 7.59 (s, 1H), 7.14 (dd, J=8.6, 2.8 Hz, 1H), 7.03 (d, J=8.6 Hz, 1H), 4.17 (q, J=7.2 Hz, 1H), 3.64-3.54 (m, 1H), 3.47-3.34 (m, 1H), 2.90-2.72 (m, 2H), 2.65 (dd, J=11.6, 8.8 Hz, 1H), 2.61-2.44 (m, 2H), 2.01-1.86 (m, 2H), 1.84-1.75 (m, 1H), 1.73-1.62 (m, 4H), 1.41-1.23 (m, 1H), 1.11-1.00 (m, 2H), 0.99-0.83 (m, 1H), 0.84-0.72 (m, 2H), 0.54-0.42 (m, 2H), 0.16-0.08 (m, 2H), 1H exchanged with solvent.

Compound 357: (3R)—N-(cyclopropylmethyl)-1-(6-(1-(4-(5-cyclopropylpyridin-3-yl)-1H-1,2,3-triazol-1-yl)ethyl)pyridin-3-yl)piperidin-3-amine was Obtained Using General Scheme 1 Pathway B Stage 1: General Procedure B was used between IM231 and IM896 to afford 5-bromo-2-(1-(4-(5-cyclopropylpyridin-3-yl)-1H-1,2,3-triazol-1-yl)ethyl)pyridine IM1002 as a yellow sticky gum: 151 mg, 88% yield, P=97%, retention time=2.3 min (gradient A), (M+H)$^+$: 370/372.

Stage 2: General Procedure Y was used between IM1002 and IM486 to afford tert-butyl (cyclopropylmethyl)((3R)-1-(6-(1-(4-(5-cyclopropylpyridin-3-yl)-1H-1,2,3-triazol-1-yl)ethyl)pyridin-3-yl)piperidin-3-yl)carbamate IM1003 as yellow sticky oil: 204 mg, 82% yield, P=88%, retention time=2.1 min (gradient A), (M+H)$^+$: 544.

Stage 3: General Procedure A2 was used from IM1003 to afford crude compound 357 as a light yellow foam: 133 mg, 84% yield, P=93%, retention time=2.6 min (gradient B), (M+H)$^+$: 444.

The mixture of diastereomers was purified by chiral preparative HPLC purification using Chiralpak IA column (5 µm, 20×250 mm). Eluent used: TBME/MeOH/DCM/DEA: 40/40/20/0.1% at flow rate of 20 mL/min. First eluted diastereomer: P=100%, retention time=9.4 min, chiral HPLC: P=100%, $^1$H NMR (300 MHz, CDCl$_3$) δ 8.70 (s, 1H), 8.34 (s, 1H), 8.27 (s, 1H), 7.97 (s, 1H), 7.79 (s, 1H), 7.17-7.07 (m, 2H), 5.89 (q, J=7.0 Hz, 1H), 3.69-3.59 (m, 1H), 3.51-3.39 (m, 1H), 2.92-2.80 (m, 1H), 2.79-2.61 (m, 2H), 2.60-2.42 (m, 2H), 2.02-1.85 (m, 5H), 1.85-1.73 (m, 1H), 1.70-1.57 (m, 1H), 1.37-1.22 (m, 1H), 1.07-0.97 (m, 2H), 0.97-0.85 (m, 1H), 0.82-0.71 (m, 2H), 0.53-0.41 (m, 2H), 0.13-0.02 (m, 2H), 1H exchanged with solvent. Second eluted diastereomer: P=100%, retention time=15.3 min, chiral HPLC: P=100%, $^1$H NMR (300 MHz, CDCl$_3$) δ 8.72 (s, 1H), 8.35 (s, 1H), 8.27 (s, 1H), 7.98 (s, 1H), 7.80 (s, 1H), 7.19-7.09 (m, 2H), 5.90 (q, J=7.1 Hz, 1H), 3.71-3.61 (m, 1H), 3.46 (m, 1H), 2.94-2.64 (m, 3H), 2.62-2.43 (m, 2H), 1.98 (d, J=7.0 Hz, 3H), 1.97-1.86 (m, 2H), 1.85-1.75 (m, 1H), 1.71-1.57 (m, 1H), 1.44-1.29 (m, 1H), 1.09-0.99 (m, 2H), 0.99-0.89 (m, 1H), 0.83-0.72 (m, 2H), 0.54-0.42 (m, 2H), 0.16-0.08 (m, 2H), 1H exchanged with solvent.

Compound 358: (3R)—N-(cyclopropylmethyl)-1-(6-(1-(5-(5-cyclopropylpyridin-3-yl)-1,3,4-thiadiazol-2-yl)ethyl)pyridazin-3-yl)piperidin-3-amine was Obtained Using General Scheme 3 Pathway D Stage 1: General Procedure F was used between IM988 and lithium 2-(6-chloropyridazin-3-yl)propanoate lithium to afford 2-(1-(6-chloropyridazin-3-yl)ethyl)-5-(5-cyclopropylpyridin-3-yl)-1,3,4-thiadiazole IM1004 as orange oil: 80 mg, 30% yield, P=93%, retention time=2.3 min (gradient A), (M+H)$^+$: 344/346.

Stage 2: General Procedure C was used between IM1004 and IM486 to afford tert-butyl (cyclopropylmethyl)((3R)-1-(6-(1-(5-(5-cyclopropylpyridin-3-yl)-1,3,4-thiadiazol-2-yl)ethyl)pyridazin-3-yl)piperidin-3-yl)carbamate IM1005 as orange oil: 84 mg, 57% yield, P=82%, retention time=2.4 min (gradient A), (M+H)$^+$: 562.

Stage 3: General Procedure A2 was used from IM1005 to afford crude compound 358 as orange oil: 55 mg, 83% yield, P=85%, retention time=2.7 min (gradient B), (M+H)$^+$: 462.

The mixture of diastereomers was purified by chiral preparative HPLC purification using Chiralpak IA column (5 µm, 20×250 mm). Eluent used: TBME/MeOH/DCM/DEA: 40/40/20/0.1% at flow rate of 20 mL/min. First eluted diastereomer: P=96%, retention time=6.8 min, chiral HPLC: P=67.4%, $^1$H NMR (300 MHz, CDCl$_3$) δ 8.87 (s, 1H), 8.52 (s, 1H), 7.88 (dd, J=2.2 Hz, 1H), 7.30 (d, J=2.5 Hz, 1H), 6.93 (d, J=9.5 Hz, 1H), 4.90 (q, J=7.2 Hz, 1H), 4.44-4.34 (m, 1H), 4.16-4.04 (m, 1H), 3.21-3.07 (m, 1H), 3.02-2.88 (m, 1H), 2.81-2.69 (m, 1H), 2.58 (d, J=6.9 Hz, 2H), 2.09-1.97 (m, 2H), 1.93 (d, J=7.2 Hz, 3H), 1.91-1.78 (m, 1H), 1.69-1.57 (m, 1H), 1.55-1.38 (m, 1H), 1.17-1.02 (m, 2H), 1.01-0.89 (m, 1H), 0.88-0.76 (m, 2H), 0.56-0.44 (m, 2H), 0.18-0.09 (m, 2H), 1H exchanged with solvent. Second eluted diastereomer: P=91%, retention time=13.9 min, chiral HPLC: P=68%, $^1$H NMR (300 MHz, CDCl$_3$) δ 8.83 (s, 1H), 8.48 (s, 1H), 7.84 (dd, J=2.2 Hz, 1H), 7.24 (d, J=9.5 Hz, 1H), 6.89 (d, J=9.4 Hz, 1H), 4.86 (q, J=7.2 Hz, 1H), 4.41-4.30 (m, 1H), 4.12-4.00 (m, 1H), 3.16-3.05 (m, 1H), 3.00-2.87 (m, 1H), 2.80-2.68 (m, 1H), 2.61-2.48 (m, 2H), 2.00-1.92 (m, 2H), 1.89 (d, J=7.2 Hz, 3H), 1.86-1.75 (m, 1H), 1.61 (m, 1H), 1.50-1.37 (m, 1H), 1.12-1.02 (m, 2H), 0.97-0.89 (m, 1H), 0.83-0.76 (m, 2H), 0.52-0.43 (m, 2H), 0.15-0.07 (m, 2H), 1H exchanged with solvent.

Compound 359: (3R)—N-(cyclopropylmethyl)-1-(6-(1-(5-(5-cyclopropylpyridin-3-yl)-1,3,4-thiadiazol-2-yl)ethyl)pyridin-3-yl)piperidin-3-amine was Obtained Using General Scheme 3 Pathway C Stage 1: General Procedure Y was used between IM761 and IM486 to afford methyl 2-(5-((R)-3-((tert-butoxycarbonyl)(cyclopropylmethyl)amino)piperidin-1-yl)pyridin-2-yl)propanoate IM1006 as yellow oil: 564 mg, 21% yield, P=66%, retention time=2.5 min (gradient A), (M+H)+: 418.

Stage 2: Lithium hydroxide (45 mg, 1.77 mmol) was added to a solution of IM1006 (564 mg, 0.89 mmol) in THF (6 mL) and water (3 mL). Reaction mixture was stirred at rt for 2 h before an extra addition of lithium hydroxide (11 mg, 0.43 mmol) was added to the reaction mixture. After 16 h stirring at rt, reaction mixture was concentrated under reduced pressure and co-evaporated with DCM/MeOH (2×10 mL, ½) to afford crude lithium 2-(5-((R)-3-((tert-butoxycarbonyl)(cyclopropylmethyl)amino)piperidin-1-yl)pyridin-2-yl)propanoate IM1007 as yellow solid: 502 mg, 100% yield, P=73%, retention time=2.4 min (gradient A), (M+H)+: 404.

Stage 3: General Procedure F was used between IM1007 and IM988 to afford tert-butyl (cyclopropylmethyl)((3R)-1-(6-(1-(5-(5-cyclopropylpyridin-3-yl)-1,3,4-thiadiazol-2-yl)ethyl)pyridin-3-yl)piperidin-3-yl)carbamate IM1008 as colourless oil: 37 mg, 29% yield, P=76%, retention time=2.3 min (gradient A), (M+H)+: 561.

Stage 4: General Procedure A2 was used from IM1008 to afford crude compound 359 as yellow oil: 21 mg, 71% yield, P=78%, retention time=2.0 min (gradient A), (M+H)+: 461.

The mixture of diastereomers was purified by chiral preparative HPLC purification using Chiralpak IA column (5 μm, 20×250 mm). Eluent used: TBME/MeOH/DCM/DEA: 60/30/10/0.1% at flow rate of 20 mL/min. First eluted diastereomer: P=98%, retention time=11.4 min, chiral HPLC: P=88.9%, $^1$H NMR (300 MHz, CDCl$_3$) δ 8.83 (d, J=2.1 Hz, 1H), 8.48 (d, J=2.2 Hz, 1H), 8.31 (d, J=2.5 Hz, 1H), 7.88 (dd, J=2.2, 2.2 Hz, 1H), 7.23-7.10 (m, 2H), 4.76 (q, J=7.1 Hz, 1H), 3.69-3.59 (m, 1H), 3.50-3.40 (m, 1H), 2.93-2.74 (m, 2H), 2.67 (dd, J=11.6, 8.8 Hz, 1H), 2.61-2.46 (m, 2H), 2.02-1.90 (m, 2H), 1.88-1.77 (m, 4H), 1.74-1.60 (m, 1H), 1.38-1.23 (m, 1H), 1.12-1.04 (m, 2H), 1.02-0.89 (m, 1H), 0.84-0.76 (m, 2H), 0.55-0.43 (m, 2H), 0.17-0.08 (m, 2H), 1H exchanged with solvent. Second eluted diastereomer: P=97%, retention time=13.8 min, chiral HPLC: P=85.1%, $^1$H NMR (300 MHz, CDCl$_3$) δ 8.83 (s, 1H), 8.48 (s, 1H), 8.30 (d, J=2.5 Hz, 1H), 7.88 (dd, J=2.1, 2.1 Hz, 1H), 7.23-7.10 (m, 2H), 4.76 (q, J=7.1 Hz, 1H), 3.68-3.59 (m, 1H), 3.50-3.39 (m, 1H), 2.93-2.74 (m, 2H), 2.68 (dd, J=11.6, 8.8 Hz, 1H), 2.63-2.45 (m, 2H), 2.02-1.91 (m, 2H), 1.87-1.77 (m, 4H), 1.74-1.65 (m, 1H), 1.37-1.24 (m, 1H), 1.13-1.03 (m, 2H), 1.01-0.89 (m, 1H), 0.83-0.74 (m, 2H), 0.55-0.43 (m, 2H), 0.16-0.09 (m, 2H), 1H exchanged with solvent.

Compound 360: (3R)—N-(cyclopropylmethyl)-1-(6-(1-(5-(6-(pyrrolidin-1-yl)pyrazin-2-yl)-1,3,4-thiadiazol-2-yl)ethyl)pyridin-3-yl)piperidin-3-amine was Obtained Using General Scheme 3 Pathway C Stage 1: General Procedure F was used between IM991 and IM1007 to afford tert-butyl (cyclopropylmethyl)((3R)-1-(6-(1-(5-(6-(pyrrolidin-1-yl)pyrazin-2-yl)-1,3,4-thiadiazol-2-yl)ethyl)pyridin-3-yl)piperidin-3-yl)carbamate IM1009 as yellow oil: 71 mg, 45% yield, P=75%, retention time=2.3 min (gradient A), (M+H)+: 591.

Stage 2: General Procedure A2 was used from IM1009 to afford crude compound 360 as yellow oil: 100 mg, 99% yield, P=44%, retention time=2.2 min (gradient A), (M+H)+: 491.

The mixture of diastereomers was purified by chiral preparative HPLC purification using Chiralpak IA column (5 μm, 20×250 mm). Eluent used: TBME/MeOH/DCM/DEA: 70/25/5/0.1% at flow rate of 20 mL/min. First eluted diastereomer: P=95%, retention time=7.0 min, chiral HPLC: P=96.2%, $^1$H NMR (300 MHz, CDCl$_3$) δ 8.71 (s, 1H), 8.30 (s, 1H), 7.90 (s, 1H), 7.23-7.09 (m, 2H), 4.76 (q, J=7.2 Hz, 1H), 3.63 (m, 1H), 3.57-3.50 (m, 4H), 3.49-3.39 (m, 1H), 2.92-2.75 (m, 2H), 2.74-2.59 (m, 1H), 2.59-2.48 (m, 2H), 2.11-2.00 (m, 4H), 2.00-1.90 (m, 1H), 1.88-1.76 (m, 4H), 1.67 (d, J=11.3 Hz, 1H), 1.41-1.24 (m, 1H), 1.02-0.89 (m, 1H), 0.54-0.45 (m, 2H), 0.16-0.10 (m, 2H), 1H exchanged with solvent. Second eluted diastereomer: P=100%, retention time=8.2 min, chiral HPLC: P=97.5%, $^1$H NMR (300 MHz, CDCl$_3$) δ 8.71 (s, 1H), 8.30 (s, 1H), 7.90 (s, 1H), 7.22-7.10 (m, 2H), 4.76 (q, J=7.1 Hz, 1H), 3.69-3.59 (m, 1H), 3.57-3.48 (m, 4H), 3.48-3.39 (m, 1H), 2.92-2.76 (m, 2H), 2.74-2.64 (m, 1H), 2.62-2.46 (m, 2H), 2.11-2.02 (m, 4H), 2.01-1.93 (m, 1H), 1.88-1.80 (m, 4H), 1.75-1.65 (m, 1H), 1.45-1.23 (m, 1H), 1.03-0.88 (m, 1H), 0.56-0.46 (m, 2H), 0.18-0.10 (m, 2H), 1H exchanged with solvent.

Compound 361: (R)—N-(cyclopropylmethyl)-1-(6-((5-(6-(pyrrolidin-1-yl)pyrazin-2-yl)-1,3,4-thiadiazol-2-yl)methyl)pyridin-3-yl)piperidin-3-amine was Obtained Using General Scheme 3 Pathway C Stage 1: General Procedure Y was used between ethyl 2-(5-bromopyridin-2-yl)acetate and IM486 to afford ethyl (R)-2-(5-(3-((tert-butoxycarbonyl)(cyclopropylmethyl)amino)piperidin-1-yl)pyridin-2-yl)acetate IM1010 as light yellow gum: 88 mg, 51% yield, P=97%, retention time=2.5 min (gradient A), (M+H)+: 418.

Stage 2: A solution of lithium hydroxide (60 mg, 2.36 mmol) in water (1.2 mL) was added to a solution of IM1010 (447 mg, 0.95 mmol) in THF (8.5 mL). Reaction mixture was stirred at rt for 17 h. Reaction mixture was concentrated under reduced pressure and residue was taken-up in water (10 mL) and was acidified with HCl 1N (1.4 mL) until pH ~ 5 and extracted with EtOAc (4×10 mL). Organics layers were merged, dried over MgSO$_4$ and filtered. Filtrate was concentrated under reduced pressure to dryness to afford crude (R)-2-(5-(3-((tert-butoxycarbonyl)(cyclopropylmethyl)amino)piperidin-1-yl)pyridin-2-yl)acetic acid IM1011 as a light yellow foam: 387 mg, 95% yield, P=91%, retention time=2.4 min (gradient A), (M+H)+: 390.

Stage 3: General Procedure F was used between IM1011 and IM991 to afford tert-butyl (R)-(cyclopropylmethyl)(1-(6-((5-(6-(pyrrolidin-1-yl)pyrazin-2-yl)-1,3,4-thiadiazol-2-yl)methyl)pyridin-3-yl)piperidin-3-yl)carbamate IM1012 as light yellow foam: 76 mg, 74% yield, P=98%, retention time=2.6 min (gradient A), (M+H)+: 577.

Stage 4: General Procedure A2 was used from IM1012 to afford crude compound 361 as orange foam: 62 mg, 96% yield, P=95%, retention time=2.1 min (gradient A), (M+H)+: 477.

The product was purified by reverse phase preparative HPLC purification (XBridge OBD C18 5 μm, 19×100 mm). Gradient used: increased linearly from 40% to 50% solution "B" over 4.0 min, increased linearly to 88% solution "B" over 2.5 min, and returned to initial conditions over 0.7 min. Flow Rate: 15 mL/min. P=99%, $^1$H NMR (300 MHz, CDCl$_3$) δ 8.70 (s, 1H), 8.27 (d, J=2.6 Hz, 1H), 7.89 (s, 1H), 7.23-7.09 (m, 2H), 4.53 (s, 2H), 3.68-3.56 (m, 1H), 3.55-3.38 (m, 5H), 2.91-2.73 (m, 2H), 2.66 (dd, J=11.6, 8.9 Hz, 1H), 2.61-2.44 (m, 2H), 2.08-2.00 (m, 4H), 2.00-1.90 (m, 1H), 1.87-1.76 (m, 1H), 1.71-1.60 (m, 1H), 1.41-1.23 (m, 1H), 1.00-0.87 (m, 1H), 0.55-0.43 (m, 2H), 0.16-0.08 (m, 2H), 1H exchanged with solvent.

Compound 362: (R)—N-(cyclopropylmethyl)-1-(6-((5-(5-cyclopropylpyridin-3-yl)-1,3,4-thiadiazol-2-yl)methyl)pyridin-3-yl)piperidin-3-amine was Obtained Using General Scheme 3 Pathway C Stage 1: General Procedure F was used between IM1011 and IM988 to afford tert-butyl (R)-(cyclopropylmethyl)(1-(6-((5-(5-cyclopropylpyridin-3-yl)-1,3,4-thiadiazol-2-yl)methyl)pyridin-3-yl)piperidin-3-yl)carbamate IM1013 as light yellow foam: 57 mg, 58% yield, P=97%, retention time=2.5 min (gradient A), (M+H)$^+$: 547.

Stage 2: General Procedure A2 was used from IM1013 to afford crude compound 362 as orange gum: 47 mg, 99% yield, P=95%, retention time=2.0 min (gradient A), (M+H)$^+$: 447.

The product was purified by reverse phase preparative HPLC purification (XBridge OBD C18 5 μm, 19×100 mm). Gradient used: increased linearly from 35% to 40% solution "B" over 4.0 min, increased linearly to 88% solution "B" over 2.5 min, and returned to initial conditions over 0.7 min. Flow Rate: 15 ml/min. P=98%, $^1$H NMR (300 MHz, CDCl$_3$) δ 8.80 (d, J=2.1 Hz, 1H), 8.47 (d, J=2.2 Hz, 1H), 8.27 (d, J=2.5 Hz, 1H), 7.88 (d, J=2.3 Hz, 1H), 7.22-7.11 (m, 2H), 4.53 (s, 2H), 3.67-3.57 (m, 1H), 3.50-3.37 (m, 1H), 2.93-2.72 (m, 2H), 2.66 (dd, J=11.5, 8.9 Hz, 1H), 2.60-2.43 (m, 2H), 2.01-1.87 (m, 2H), 1.87-1.75 (m, 1H), 1.75-1.59 (m, 1H), 1.41-1.22 (m, 1H), 1.12-1.01 (m, 2H), 1.00-0.88 (m, 1H), 0.84-0.73 (m, 2H), 0.54-0.42 (m, 2H), 0.14-0.07 (m, 2H), 1H exchanged with solvent.

Compound 363: (R)—N-(cyclopropylmethyl)-1-(6-(2-(5-(5-cyclopropylpyridin-3-yl)-1,3,4-thiadiazol-2-yl)propan-2-yl)pyridin-3-yl)piperidin-3-amine was Obtained Using General Scheme 3 Pathway C Stage 1: To a solution of ethyl 2-(5-bromopyridin-2-yl)acetate (518 mg, 2.06 mmol) in anhydrous DMF (5 mL) under argon at 0° C. was added sodium hydride (89 mg, 2.23 mmol) and the reaction mixture was stirred for 10 min at 0° C. before addition of iodomethane (130 μL, 2.07 mmol). The reaction was stirred at the same temperature for 10 min before sodium hydride (125 mg, 3.13 mmol) was added and stirred for 10 min. Iodomethane (260 μL, 4.13 mmol) was finally added. The reaction mixture was stirred at rt for 1.5 h. The reaction mixture was quenched with NH$_4$Cl saturated solution (25 mL) and extracted with EtOAc (3×25 mL). The organic layers were merged and washed with water (2×25 mL), followed by brine (2×25 mL). The organic layer was dried over MgSO$_4$, filtered and concentrated under reduced pressure to dryness to afford a yellow oil. The crude material was purified by an automated flash chromatography system (dryload in silica, 0 to 10% EtOAc in Heptane) to ethyl 2-(5-bromopyridin-2-yl)-2-methylpropanoate IM1014 as a colorless oil: 539 mg, 94% yield, P=98%, retention time=3.0 min (gradient A), (M+H)$^+$: 272/274.

Stage 2: General Procedure Y was used between IM1014 and IM486 to afford ethyl (R)-2-(5-(3-((tert-butoxycarbonyl)(cyclopropylmethyl)amino)piperidin-1-yl)pyridin-2-yl)-2-methylpropanoate IM1015 as light yellow gum: 330 mg, 78% yield, P=96%, retention time=2.6 min (gradient A), (M+H)$^+$: 446.

Stage 3: A solution of lithium hydroxide (46 mg, 1.81 mmol) in water (1 mL) was added to a solution of IM1015 (330 mg, 0.7100 mmol) in THF (6.5 mL). Reaction mixture was stirred at rt for 2.25 h. Then sodium hydroxide (70 mg, 1.73 mmol) was added to the reaction mixture and stirred for 16 h. The reaction mixture was heated at 70 °C for 2.5 h before an extra sodium hydroxide (230 mg, 5.69 mmol) in water (1 mL) was added and stirred at 70° C. for 3.5 h. Methanol (1 mL) was added and reaction was stirred at 70° C. for 17 h. Reaction mixture was concentrated under reduced pressure and residue was taken-up in water (15 mL) and was acidified with HCl 1N (7 mL) until pH ~5 and extracted with EtOAc (4×15 mL). Organics layers were merged, dried over MgSO$_4$ and filtered. Filtrate was concentrated under reduced pressure to dryness to afford (R)-2-(5-(3-((tert-butoxycarbonyl)(cyclopropylmethyl)amino)piperidin-1-yl)pyridin-2-yl)-2-methylpropanoic acid IM1016 as a light yellow gum: 283 mg, 81% yield, P=85%, retention time=2.5 min (gradient A), (M+H)$^+$: 418.

Stage 4: General Procedure F was used between IM1016 and IM988 to afford tert-butyl (R)-(cyclopropylmethyl)(1-(6-(2-(5-(5-cyclopropylpyridin-3-yl)-1,3,4-thiadiazol-2-yl)propan-2-yl)pyridin-3-yl)piperidin-3-yl)carbamate IM1017 as colourless gum: 53 mg, 56% yield, P=92%, retention time=2.6 min (gradient A), (M+H)$^+$: 575.

Stage 5: General Procedure A2 was used from IM1017 to afford crude compound 363 as light yellow gum: 45 mg, 99% yield, P=89%, retention time=2.1 min (gradient A), (M+H)$^+$: 475.

The product was purified by reverse phase preparative HPLC purification (XBridge OBD C18 5 μm, 19×100 mm). Gradient used: increased linearly from 35% to 40% solution "B" over 4.0 min, increased linearly to 88% solution "B" over 2.5 min, and returned to initial conditions over 0.7 min. Flow Rate: 15 ml/min. P=95%, $^1$H NMR (300 MHz, CDCl$_3$) δ 8.80 (d, J=2.1 Hz, 1H), 8.46 (d, J=2.2 Hz, 1H), 8.28 (d, J=2.9 Hz, 1H), 7.85 (dd, J=2.1, 2.1 Hz, 1H), 7.24 (d, J=8.5 Hz, 1H), 7.13 (dd, J=8.8, 2.9 Hz, 1H), 3.68-3.57 (m, 1H), 3.44 (m, 1H), 2.91-2.72 (m, 2H), 2.66 (dd, J=11.5, 8.9 Hz, 1H), 2.60-2.43 (m, 2H), 2.00-1.87 (m, 8H), 1.86-1.75 (m, 1H), 1.73-1.58 (m, 1H), 1.41-1.22 (m, 1H), 1.14-1.01 (m, 2H), 1.00-0.89 (m, 1H), 0.82-0.74 (m, 2H), 0.53-0.41 (m, 2H), 0.10 (m, 2H), 1H exchanged with solvent.

Compound 364: (R)—N-(cyclopropylmethyl)-1-(6-(2-(5-(6-(pyrrolidin-1-yl)pyrazin-2-yl)-1,3,4-thiadiazol-2-yl)propan-2-yl)pyridin-3-yl)piperidin-3-amine was Obtained Using General Scheme 3 Pathway C Stage 1: General Procedure F was used between IM1016 and IM991 to afford tert-butyl (R)-(cyclopropylmethyl)(1-(6-(2-(5-(6-(pyrrolidin-1-yl)pyrazin-2-yl)-1,3,4-thiadiazol-2-yl)propan-2-yl)pyridin-3-yl)piperidin-3-yl)carbamate IM1018 as a yellow foam: 98 mg, 54% yield, P=82%, retention time=2.8 min (gradient A), (M+H)$^+$: 605.

Stage 2: General Procedure A2 was used from IM1018 to afford crude compound 364 as yellow gum: 78 mg, 99% yield, P=85%, retention time=2.2 min (gradient A), (M+H)$^+$: 505.

The product was purified by reverse phase preparative HPLC purification (XBridge OBD C18 5 μm, 19×100 mm). Gradient used: increased linearly from 40% to 50% solution "B" over 4.0 min, increased linearly to 88% solution "B" over 2.5 min, and returned to initial conditions over 0.7 min. Flow Rate: 15 ml/min. P=98%, $^1$H NMR (300 MHz, CDCl$_3$) δ 8.69 (d, J=3.4 Hz, 1H), 8.26 (s, 1H), 7.87 (d, J=3.9 Hz, 1H), 7.21 (dd, J=8.8, 2.8 Hz, 1H), 7.11 (dd, J=8.8, 3.0 Hz, 1H), 3.67-3.56 (m, 1H), 3.54-3.36 (m, 5H), 2.90-2.72 (m, 2H), 2.71-2.61 (m, 1H), 2.51 (dt, J=7.8, 3.7 Hz, 2H), 2.07-1.96 (m, 4H), 1.95-1.88 (m, 7H), 1.86-1.74 (m, 1H), 1.72-1.56 (m, 1H), 1.40-1.26 (m, 1H), 1.01-0.85 (m, 1H), 0.53-0.40 (m, 2H), 0.17-0.04 (m, 2H), 1H exchanged with solvent.

Compound 365: (3R)—N-((1-methylcyclopropyl)methyl)-1-(6-(1-(4-(6-(pyrrolidin-1-yl)pyrazin-2-yl)-1H-imidazol-1-yl)ethyl)pyridin-3-yl)piperidin-3-amine was Obtained Using General Scheme 4 Pathway E Stage 1: To a yellow suspension of 1-methylcyclopropane-1-carboxylic acid (4.30 g, 42.09 mmol) and (R)-1-benzylpiperidin-3-amine (7.50 g, 38.63 mmol) in anhydrous MeCN (385 mL) under argon atmosphere was added TCFH (15 g, 52.39 mmol) at once followed by 1-methylimidazole (10.50 mL, 130.41 mmol, 3.38 eq.) at rt. Reaction mixture was stirred at rt for 10 min. Reaction mixture was concentrated under reduced pressure to afford orange oil. This oil was dissolved with EtOAc (100 mL), washed with NaHCO$_3$ saturated solution (3×50 mL), water (50 mL) and brine (20 mL). Organic layer was dried over MgSO$_4$, filtered and concentrated under reduced pressure. The crude material was purified by an automated flash chromatography system (liquid injection in DCM, 0 to 4% MeOH in DCM) to afford (R)—N-(1-benzylpiperidin-3-yl)-1-methylcyclopropane-1-carboxamide IM1019 as orange oil: 12.25 g, 81% yield, P=70%, retention time=2.1 min (gradient A), (M+H)$^+$: 273.

Stage 2: To a solution of IM1019 (5.50 g, 14.13 mmol) in anhydrous THF (15 mL) at 0° C. under argon atmosphere, was added borane THF complex 1 N in THF (97 mL, 97 mmol) dropwise (over 10 min) and the resulting mixture was stirred at 50° C. for 1 h. Then, reaction was cooled to 0° C., and methanol (93 mL) was added dropwise (huge bubbling) over 5 min. After addition, reaction was heated to 50° C. for 40 h. Reaction mixture was cooled to rt and concentrated under reduced pressure to afford a colorless syrup. Crude product was taken up with EtOAc (250 mL), washed with an aqueous saturated solution of NaHCO$_3$ (3×80 mL), brine (80 mL) and dried over MgSO$_4$, filtered and concentrated under reduced pressure to dryness to afford (R)-1-benzyl-N-((1-methylcyclopropyl)methyl)piperidin-3-amine IM1020 as a colorless oil: 3.4 g, 81% yield, P=87%, retention time=1.9 min (gradient A), (M+H)$^+$: 259.

Stage 3: General Procedure J was used from IM1020 to afford tert-butyl (R)-(1-benzylpiperidin-3-yl)((1-methylcyclopropyl)methyl)carbamate IM1021 as colourless oil: 4.0 g, 94% yield, P=96%, retention time=2.5 min (gradient A), (M+H)$^+$: 359.

Stage 4: General Procedure I was used from IM1021 to afford crude tert-butyl (R)-((1-methylcyclopropyl)methyl)(piperidin-3-yl)carbamate IM1022 as colourless oil: 2.7 g, 89% yield, P=100% ($^1$H NMR), retention time=2.3 min (gradient A—no absorbance), (M+H)$^+$: 269.

Stage 5: General Procedure Y was used between IM1022 and IM998 to afford tert-butyl ((1-methylcyclopropyl)methyl)((3R)-1-(6-(1-(4-(6-(pyrrolidin-1-yl)pyrazin-2-yl)-1H-imidazol-1-yl)ethyl)pyridin-3-yl)piperidin-3-yl)carbamate IM1023 as an orange foamy solid: 2.4 g, 72% yield, P=86%, retention time=2.6 min (gradient A), (M+H)$^+$: 587.

Stage 6: General Procedure A2 was used from IM1023 to afford crude compound 365 as yellow foam: 3.96 g, 59% yield, P=92%, retention time=2.1 min (gradient A), (M+H)$^+$: 487.

The product was purified by reverse phase preparative HPLC purification (XBridge OBD C18 5 μm, 19×100 mm). Gradient used: increased linearly from 45% to 50% solution "B" over 4.5 min, increased linearly to 88% solution "B" over 1.7 min, held to 88% solution "B" for 0.3 min, and returned to initial conditions over 0.9 min. Flow Rate: 15 mL/min. P=100%.

The mixture of diastereomers was further purified by chiral preparative HPLC purification using Chiralpak IA column (5 μm, 20×250 mm). Eluent used: TBME/MeOH/DCM/DEA: 40/40/20/0.1% at flow rate of 20 mL/min. First eluted diastereomer: P=100%, retention time=7.9 min, chiral HPLC: P=99.0%, $^1$H NMR (300 MHz, CDCl$_3$) δ 8.39 (s, 1H), 8.21 (d, J=2.9 Hz, 1H), 7.66 (s, 1H), 7.63-7.58 (m, 2H), 7.05 (dd, J=8.7, 2.9 Hz, 1H), 6.88 (d, J=8.6 Hz, 1H), 5.31 (q, J=7.1 Hz, 1H), 3.63-3.54 (m, 1H), 3.51-3.34 (m, 5H), 2.78 (m, 1H), 2.71-2.57 (m, 2H), 2.46 (m, 2H), 2.01-1.89 (m, 5H), 1.86 (d, J=7.0 Hz, 3H), 1.79-1.68 (m, 1H), 1.67-1.52 (m, 1H), 1.36-1.18 (m, 1H), 1.05 (s, 3H), 0.34-0.18 (m, 4H), 1H exchanged with solvent. Second eluted diastereomer: P=100%, retention time=10.4 min, chiral HPLC: P=99.1%, $^1$H NMR (300 MHz, CDCl$_3$) δ 8.34 (s, 1H), 8.16 (d, J=2.8 Hz, 1H), 7.64-7.54 (m, 3H), 7.00 (dd, J=8.6, 2.9 Hz, 1H), 6.84 (d, J=8.6 Hz, 1H), 5.26 (q, J=7.0 Hz, 1H), 3.59-3.50 (m, 1H), 3.45-3.28 (m, 5H), 2.80-2.51 (m, 3H), 2.47-2.37 (m, 2H), 1.96-1.83 (m, 5H), 1.82-1.76 (m, 3H), 1.76-1.62 (m, 1H), 1.62-1.45 (m, 1H), 1.32-1.14 (m, 1H), 1.01 (s, 3H), 0.29-0.12 (m, 4H), 1H exchanged with solvent.

Compound 366: (3R)—N-((1-methylcyclopropyl)methyl)-1-(6-(1-(5-(6-(pyrrolidin-1-yl)pyrazin-2-yl)-1,3,4-thiadiazol-2-ylethyl)pyridin-3-yl)piperidin-3-amine was Obtained Using General Scheme 3 Pathway C Stage 1: To a solution of ethyl 2-(5-bromopyridin-2-yl)acetate (7.40 g, 29.41 mmol) in anhydrous DMF (140 mL) under argon at 0° C. was added sodium hydride (1.12 g, 28 mmol) and the reaction mixture was stirred for 30 min at 0° C. before addition of iodomethane (1.90 mL, 30.21 mmol). The reaction was stirred at rt for 1.5 h. The reaction mixture was quenched with NH$_4$Cl saturated solution (200 mL) and extracted with EtOAc (4×250 mL). The organic layers were merged and washed with water (5×200 mL), followed by brine (250 mL). The organic layer was dried over MgSO$_4$, filtered and concentrated under reduced pressure to dryness to afford yellow oil. The crude material was purified by an automated flash chromatography system (liquid injection in toluene, 0 to 20% EtOAc in Heptane) to afford ethyl 2-(5-bromo-2-pyridyl)propanoate IM1024 as yellow oil: 6.4 g, 82% yield, P=97%, retention time=2.8 min (gradient A), (M+H)$^+$: 258/260.

Stage 2: General Procedure Y was used between IM1024 and IM1022 to afford ethyl 2-(5-((R)-3-((tert-butoxycarbonyl)((1-methylcyclopropyl)methyl)amino)piperidin-1-yl)pyridin-2-yl)propanoate IM1025 as yellow oil: 1.1 g, 42% yield, P=81%, retention time=2.5 min (gradient A), (M+H)$^+$: 446.

Stage 3: Lithium hydroxide (101 mg, 3.97 mmol) was added to a solution of IM1025 (1.10 g, 2 mmol) in THF (14 mL) and water (7 mL). Reaction mixture was stirred at rt for 22 h. Reaction mixture was concentrated under reduced pressure and co-evaporated with DCM/MeOH (2×10 mL, ½) to afford crude lithium 2-(5-((R)-3-((tert-butoxycarbonyl)((1-methylcyclopropyl)methyl)amino)piperidin-1-yl)pyridin-2-yl)propanoate IM1026 as orange solid: 1.1 g, 100% yield, P=80%, retention time=2.5 min (gradient A), (M+H)$^+$: 418.

Stage 4: General Procedure F was used between IM1026 and IM991 to afford tert-butyl ((1-methylcyclopropyl)methyl)((3R)-1-(6-(1-(5-(6-(pyrrolidin-1-yl)pyrazin-2-yl)-1,3,4-thiadiazol-2-yl)ethyl)pyridin-3-yl)piperidin-3-yl)carbamate IM1027 as an orange solid: 500 mg, 42% yield, P=95%, retention time=2.3 min (gradient A), (M+H)$^+$: 605.

Stage 5: General Procedure A2 was used from IM1027 to afford crude compound 366 as yellow foam: 394 mg, 57% yield, P=56%, retention time=2.6 min (gradient A), (M+H)$^+$: 505.

The product was purified by reverse phase preparative HPLC purification (XBridge OBD C18 5 μm, 19×100 mm). Gradient used: increased linearly from 50% to 55% solution "B" over 4.5 min, increased linearly to 88% solution "B" over 1.7 min, held to 88% solution "B" for 0.3 min, and returned to initial conditions over 0.9 min. Flow Rate: 15 mL/min. P=100%.

The mixture of diastereomers was further purified by chiral preparative HPLC purification using Chiralpak ID column (5 μm, 10×250 mm). Eluent used: EtOAc/DEA: 100/0.1% at flow rate of 7 ml/min. First eluted diastereomer: P=100%, retention time=6.9 min, chiral HPLC: P=99.1%, $^1$H NMR (300 MHz, CDCl$_3$) δ 8.67 (s, 1H), 8.27 (d, J=2.7 Hz, 1H), 7.85 (s, 1H), 7.20-7.06 (m, 2H), 4.73 (q, J=7.1 Hz, 1H), 3.65-3.54 (m, 1H), 3.52-3.35 (m, 5H), 2.88-2.66 (m, 2H), 2.62 (dd, J=11.4, 8.8 Hz, 1H), 2.55-2.41 (m, 2H), 2.07-1.96 (m, 4H), 1.95-1.85 (m, 1H), 1.81 (d, J=7.1 Hz, 3H), 1.78-1.72 (m, 1H), 1.68-1.56 (m, 1H), 1.38-1.21 (m, 1H), 1.08 (s, 3H), 0.36-0.19 (m, 4H), 1H exchanged with solvent. Second eluted diastereomer: P=100%, retention time=8.2 min, chiral HPLC: P=97.4%, $^1$H NMR (300 MHz, CDCl$_3$) δ 8.65 (s, 1H), 8.25 (d, J=2.6 Hz, 1H), 7.83 (s, 1H), 7.18-7.04 (m, 2H), 4.70 (q, J=7.1 Hz, 1H), 3.63-3.52 (m, 1H), 3.50-3.31 (m, 5H), 2.86-2.65 (m, 2H), 2.61 (dd, J=11.4, 8.8 Hz, 1H), 2.53-2.39 (m, 2H), 2.13 (s, 1H), 2.05-1.93 (m, 4H), 1.93-1.83 (m, 1H), 1.83-1.69 (m, 4H), 1.69-1.53 (m, 1H), 1.37-1.14 (m, 1H), 1.06 (s, 3H), 0.34-0.17 (m, 4H).

Compound 367: (R)—N-((1-methylcyclopropyl)methyl)-1-(6-(3-(5-(6-(pyrrolidin-1-yl)pyrazin-2-yl)-1,3,4-thiadiazol-2-yl)oxetan-3-yl)pyridin-3-yl)piperidin-3-amine was Obtained Using General Scheme 3 Pathway C Stage 1: General Procedure Y was used between IM1022 and IM520 to afford tert-butyl (R)-(1-(6-(3-cyanooxetan-3-yl)pyridin-3-yl)piperidin-3-yl)((1-methylcyclopropyl)methyl)carbamate IM1028 as orange oil: 1.2 g, 65% yield, P=85%, retention time=3.1 min (gradient A), (M+H)$^+$: 427.

Stage 2: General Procedure AD was used from IM1028 to afford crude (R)-3-(5-(3-((tert-butoxycarbonyl)((1-methylcyclopropyl)methyl)amino)piperidin-1-yl)pyridin-2-yl)oxetane-3-carboxylic acid HCl salt IM1029 as light brown solid: 1.0 g, 81% yield, P=89%, retention time=2.5 min (gradient A), (M+H)+: 446.

Stage 3: General Procedure F was used between IM1029 and IM991 to afford tert-butyl (R)-((1-methylcyclopropyl)methyl)(1-(6-(3-(5-(6-(pyrrolidin-1-yl)pyrazin-2-yl)-1,3,4-thiadiazol-2-yl)oxetan-3-yl)pyridin-3-yl)piperidin-3-yl)carbamate IM1030 as a yellow solid: 420 mg, 60% yield, P=84%, retention time=3.1 min (gradient A), (M+H)$^+$: 633.

Stage 4: General Procedure A2 was used from IM1030 to afford compound 367 as yellow solid: 236 mg, 81% yield, P=100%, retention time=3.4 min (gradient B), (M+H)$^+$: 533. $^1$H NMR (300 MHz, CDCl$_3$) δ 8.60 (s, 1H), 8.19 (s, 1H), 7.79 (s, 1H), 7.10-6.99 (m, 2H), 5.38-5.31 (m, 2H), 5.26 (d, J=5.9 Hz, 2H), 3.54 (d, J=10.6 Hz, 1H), 3.44-3.30 (m, 5H), 2.80-2.67 (m, 1H), 2.69-2.48 (m, 2H), 2.45-2.31 (m, 2H), 2.00-1.78 (m, 5H), 1.78-1.63 (m, 1H), 1.63-1.45 (m, 1H), 1.26-1.10 (m, 1H), 0.98 (s, 3H), 0.18 (d, J=8.0 Hz, 4H), 1H exchanged with solvent.

Compound 368: (R)-1-(6-(3-(5-(5-cyclopropylpyridin-3-yl)-1,3,4-thiadiazol-2-yl)oxetan-3-yl)pyridin-3-yl)-N-((1-methylcyclopropyl)methyl)piperidin-3-amine was Obtained Using General Scheme 3 Pathway C Stage 1: General Procedure F was used between IM1029 and IM988 to afford tert-butyl (R)-(1-(6-(3-(5-(5-cyclopropylpyridin-3-yl)-1,3,4-thiadiazol-2-yl)oxetan-3-yl)pyridin-3-yl)piperidin-3-yl)((1-methylcyclopropyl)methyl)carbamate IM1031 as an off-white solid: 380 mg, 64% yield, P=94%, retention time=2.8 min (gradient A), (M+H)$^+$: 603.

Stage 2: General Procedure A2 was used from IM1031 to afford compound 368 as orange oil: 258 mg, 89% yield, P=100%, retention time=2.9 min (gradient B), (M+H)$^+$: 503. $^1$H NMR (300 MHz, CDCl$_3$) δ 8.81 (d, J=2.2 Hz, 1H), 8.50 (d, J=2.3 Hz, 1H), 8.33 (s, 1H), 7.89 (d, J=2.3 Hz, 1H), 7.23-7.19 (m, 2H), 5.48 (d, J=6.0 Hz, 2H), 5.36 (d, J=5.9 Hz, 2H), 3.72-3.64 (m, 1H), 3.57-3.46 (m, 1H), 2.94-2.82 (m, 1H), 2.79-2.63 (m, 2H), 2.57-2.46 (m, 2H), 2.02-1.90 (m, 2H), 1.89-1.77 (m, 1H), 1.75-1.60 (m, 1H), 1.39-1.24 (m, 1H), 1.16-1.06 (m, 5H), 0.85-0.76 (m, 2H), 0.36-0.26 (m, 4H), 1H exchanged with solvent.

Compound 369: (R)—N-(cyclopropylmethyl)-1-(6-(3-(5-(6-(pyrrolidin-1-yl)pyrazin-2-yl)-1,3,4-thiadiazol-2-yl)oxetan-3-yl)pyridin-3-yl)piperidin-3-amine was Obtained Using General Scheme 3 Pathway C Stage 1: General Procedure AD was used from IM521 to afford crude (R)-3-(5-(3-((tert-butoxycarbonyl)(cyclopropylmethyl)amino)piperidin-1-yl)pyridin-2-yl)oxetane-3-carboxylic acid HCl salt IM1032 as an orange solid: 2.2 g, 76% yield, P=91%, retention time=2.5 min (gradient A), (M+H)+: 432.

Stage 2: General Procedure F was used between IM1032 and IM991 to afford tert-butyl (R)-(cyclopropylmethyl)(1-(6-(3-(5-(6-(pyrrolidin-1-yl)pyrazin-2-yl)-1,3,4-thiadiazol-2-yl)oxetan-3-yl)pyridin-3-yl)piperidin-3-yl)carbamate IM1033 as a yellow foamy solid: 587 mg, 42% yield, P=75%, retention time=5.2 min (gradient B), (M+H)$^+$: 619.

Stage 3: General Procedure A2 was used from IM1033 to afford compound 369 as yellow solid: 333 mg, 89% yield, P=99%, retention time=3.3 min (gradient B), (M+H)$^+$: 519. $^1$H NMR (300 MHz, CDCl$_3$) δ 8.73 (s, 1H), 8.32 (dd, J=2.5, 1.2 Hz, 1H), 7.92 (s, 1H), 7.25-7.12 (m, 2H), 5.47 (dd, J=5.9, 2.2 Hz, 2H), 5.38 (d, J=5.9 Hz, 2H), 3.73-3.61 (m, 1H), 3.56-3.42 (m, 5H), 2.96-2.84 (m, 1H), 2.84-2.74 (m, 1H), 2.70 (dd, J=11.4, 8.8 Hz, 1H), 2.63-2.45 (m, 2H), 2.11-2.01 (m, 4H), 2.00-1.91 (m, 1H), 1.89-1.77 (m, 1H), 1.76-1.60 (m, 1H), 1.44-1.22 (m, 1H), 1.05-0.86 (m, 1H), 0.56-0.45 (m, 2H), 0.17-0.09 (m, 2H), 1H exchanged with solvent.

BIOLOGY EXAMPLES

Example 1: METTL3/14 Methyltransferase Assay

Biochemical Assay: METTL3/14 Scintillation Proximity Assay (SPA)

Method: An enzymatic assay was established to determine IC50 values for inhibition of RNA methyltransferase activity. The enzyme used was recombinant METTL3/METTL14 complex from Active Motif (311970). The recombinant METTL3/METTL14 complex is composed of the full length human METTL3 (accession number NP_062826.2) without tag and full length METTL14 protein (accession number NP_066012.1) with an N-terminal FLAG-Tag; this complex is expressed in Sf9 cells. The molecular weights of METTL3 and METTL14 are 64.5 kDa and 53.3 kDa, respectively. Enzymatic reactions were performed at room temperature in 384-well plates using a final reaction volume of 10 µl containing Tris 20 mM pH 7.5, Triton 0.01%. The METTL3/14 complex, used at a final concentration of 5.31 nM, was pre-incubated with test compounds at predetermined concentrations for 10 minutes, followed by addition of 250 nM (final concentration) of synthetic RNA substrate 5'biotinylated-UACACUCGAUCUGGACUAAAGGUGCUC-3' (SEQ ID NO:1) and 1 µM final concentration of tritiated S-adenosyl-methionine (3HSAM). The reaction was incubated for a further 90 minutes at room temperature. Then the reaction was stopped by addition of trifluoroacetic acid (TFA) and yttrium silicate (YSI) beads (PerkinElmer, RPNQ0013) at 0.05% and 1 mg/ml respectively in the final assay. The assay plates were incubated at room temperature for 30 min. Buffer (45 µl, Tris 20 mM pH 7.5, Triton 0.01%.) was added to each well before centrifugation of plates (2000 rpm, 10 min: Allergra 6R centrifuge: GH3.8). The incorporated radioactivity was measured with a Topcount reader. The raw data are generated in CPM. The results were expressed in % of inhibition and normalized to control wells without METTL3/14 complex (=100% inhibition) and without inhibition (DMSO only, =0% inhibition).

Results: IC50 values were calculated based on testing of a concentration response for individual compounds and summarized in Table 2, with +++: IC50≤50 nM, ++: 50 nM<IC50≤500 nM, +: 500 nM<IC50≤3500 nM.

Conclusion: These data demonstrate that compounds of the invention are inhibitors of the enzymatic activity of METTL3 subunit and so inhibitors of the enzymatic activity of the METTL3/METTL14 complex.

TABLE 2

| Cpd | SPA IC50 |
| --- | --- |
| 001 | +++ |
| 002 | +++ |
| 003 | +++ |
| 004 | + |
| 005 | ++ |
| 006* | +++ |
| 007* | +++ |
| 008* | +++ |
| 009 | +++ |
| 010 | ++ |
| 011* | ++ |
| 012 | +++ |
| 013 | +++ |
| 014* | ++ |
| 015 | +++ |
| 016 | ++ |
| 017 | +++ |
| 018 | +++ |
| 019 | +++ |
| 020* | +++ |
| 021 | ++ |
| 022 | +++ |
| 023 | +++ |
| 024 | +++ |
| 025* | +++ |
| 026* | +++ |
| 027* | +++ |
| 028* | +++ |
| 029 | ++ |
| 030 | +++ |
| 031 | +++ |
| 032 | +++ |
| 033* | +++ |
| 034 | +++ |
| 035* | +++ |
| 036* | +++ |
| 037* | +++ |
| 038 | ++ |
| 039 | +++ |
| 040 | +++ |
| 041 | ++ |
| 042 | +++ |
| 043* | +++ |
| 044* | +++ |
| 045* | +++ |
| 046* | ++ |
| 047* | +++ |
| 048 | +++ |
| 049* | +++ |
| 050* | +++ |
| 051* | +++ |
| 052* | ++ |
| 053* | ++ |
| 054* | + |
| 055* | +++ |
| 056 | +++ |
| 057 | +++ |
| 058* | +++ |
| 059* | ++ |
| 060 | +++ |
| 061 | +++ |
| 062 | +++ |
| 063 | +++ |
| 064* | +++ |
| 065* | +++ |
| 066* | +++ |
| 067* | +++ |
| 068 | +++ |
| 069 | +++ |
| 070 | +++ |
| 071* | +++ |
| 072 | ++ |
| 073* | +++ |
| 074 | +++ |
| 075 | +++ |
| 076* | +++ |
| 077 | +++ |
| 078 | +++ |
| 079 | +++ |
| 080 | +++ |
| 081 | +++ |
| 082 | +++ |
| 083* | +++ |
| 084* | +++ |
| 085* | +++ |
| 086 | +++ |
| 087 | +++ |
| 088* | +++ |
| 089* | +++ |
| 090 | +++ |
| 091 | +++ |
| 092 | +++ |
| 093 | +++ |
| 094 | +++ |
| 095 | +++ |
| 096 | +++ |

TABLE 2-continued

| Cpd | SPA IC50 |
|---|---|
| 097 | +++ |
| 098 | +++ |
| 099 | +++ |
| 100 | ++ |
| 101 | ++ |
| 102 | +++ |
| 103 | +++ |
| 104 | ++ |
| 105 | +++ |
| 106 | +++ |
| 107 | +++ |
| 108 | +++ |
| 109 | +++ |
| 110* | +++ |
| 111 | ++ |
| 112 | +++ |
| 113 | +++ |
| 114 | +++ |
| 115 | +++ |
| 116 | +++ |
| 117 | ++ |
| 118 | +++ |
| 119 | +++ |
| 120 | +++ |
| 121 | +++ |
| 122 | +++ |
| 123 | +++ |
| 124* | +++ |
| 125* | ++ |
| 126* | +++ |
| 127 | +++ |
| 128 | +++ |
| 129 | +++ |
| 130 | +++ |
| 131 | +++ |
| 132 | +++ |
| 133 | +++ |
| 134 | +++ |
| 135* | +++ |
| 136 | +++ |
| 137* | ++ |
| 138* | +++ |
| 139 | +++ |
| 140 | +++ |
| 141 | ++ |
| 142* | +++ |
| 143* | +++ |
| 144 | +++ |
| 145 | ++ |
| 146 | +++ |
| 147 | +++ |
| 148 | +++ |
| 149 | +++ |
| 150 | +++ |
| 151* | +++ |
| 152* | +++ |
| 153* | +++ |
| 154* | +++ |
| 155 | +++ |
| 156 | +++ |
| 157 | ++ |
| 158* | +++ |
| 159* | +++ |
| 160* | +++ |
| 161* | +++ |
| 162 | ++ |
| 163 | +++ |
| 164* | +++ |
| 165* | +++ |
| 166* | +++ |
| 167* | +++ |
| 168* | +++ |
| 169* | +++ |
| 170* | +++ |
| 171* | +++ |
| 172* | ++ |
| 173* | +++ |
| 174 | +++ |
| 175 | +++ |
| 176* | +++ |
| 177* | +++ |
| 178* | +++ |
| 179* | +++ |
| 180* | +++ |
| 181* | +++ |
| 182* | +++ |
| 183 | +++ |
| 184 | +++ |
| 185 | +++ |
| 186* | +++ |
| 187* | +++ |
| 188* | +++ |
| 189* | +++ |
| 190* | +++ |
| 191* | +++ |
| 192 | +++ |
| 193* | +++ |
| 194 | +++ |
| 195 | +++ |
| 196* | +++ |
| 197* | +++ |
| 198* | +++ |
| 199* | +++ |
| 200* | +++ |
| 201 | +++ |
| 202 | +++ |
| 203* | +++ |
| 204 | +++ |
| 205* | +++ |
| 206* | +++ |
| 207 | +++ |
| 208* | +++ |
| 209* | +++ |
| 210* | +++ |
| 211* | +++ |
| 212 | +++ |
| 213 | +++ |
| 214 | +++ |
| 215 | +++ |
| 216 | +++ |
| 217 | +++ |
| 218* | +++ |
| 219* | +++ |
| 220* | +++ |
| 221 | +++ |
| 222 | +++ |
| 223 | +++ |
| 224 | +++ |
| 225* | +++ |
| 226* | +++ |
| 227* | +++ |
| 228* | +++ |
| 229* | +++ |
| 230* | +++ |
| 231* | +++ |
| 232* | +++ |
| 233* | +++ |
| 234* | +++ |
| 235* | +++ |
| 236* | +++ |
| 237* | +++ |
| 238* | +++ |
| 239 | +++ |
| 240* | +++ |
| 241* | +++ |
| 242* | +++ |
| 243* | +++ |
| 244 | +++ |
| 245* | +++ |
| 246* | +++ |
| 247* | +++ |
| 248 | +++ |
| 249 | +++ |
| 250 | +++ |
| 251 | +++ |
| 252* | +++ |

TABLE 2-continued

| Cpd | SPA IC50 |
|---|---|
| 253* | +++ |
| 254* | +++ |
| 255* | ++ |
| 256 | +++ |
| 257* | +++ |
| 258* | +++ |
| 259* | +++ |
| 260* | +++ |
| 261* | +++ |
| 262 | +++ |
| 263 | +++ |
| 264* | +++ |
| 265* | +++ |
| 266* | +++ |
| 267 | +++ |
| 268 | +++ |
| 269 | +++ |
| 270 | +++ |
| 271 | +++ |
| 272 | +++ |
| 273 | +++ |
| 274* | +++ |
| 275* | ++ |
| 276* | +++ |
| 277 | +++ |
| 278 | +++ |
| 279* | +++ |
| 280* | +++ |
| 281 | +++ |
| 282 | +++ |
| 283 | +++ |
| 284* | +++ |
| 285* | +++ |
| 286* | +++ |
| 287 | +++ |
| 288 | +++ |
| 289 | +++ |
| 290 | +++ |
| 291 | +++ |
| 292* | +++ |
| 293* | +++ |
| 294* | +++ |
| 295 | +++ |
| 296* | +++ |
| 297 | +++ |
| 298 | +++ |
| 299 | ++ |
| 300* | +++ |
| 301 | +++ |
| 302 | +++ |
| 303* | +++ |
| 304* | +++ |
| 305* | +++ |
| 306 | +++ |
| 307 | +++ |
| 308 | +++ |
| 309* | +++ |
| 310 | +++ |
| 311 | +++ |
| 312 | +++ |
| 313 | +++ |
| 314 | +++ |
| 315 | +++ |
| 316 | +++ |
| 317* | +++ |
| 318* | +++ |
| 319 | +++ |
| 320* | +++ |
| 321 | +++ |
| 322 | +++ |
| 323 | +++ |
| 324 | +++ |
| 325 | +++ |
| 326 | +++ |
| 327 | +++ |
| 328 | +++ |
| 329 | +++ |
| 330 | +++ |
| 331 | +++ |
| 332 | +++ |
| 333 | +++ |
| 334 | +++ |
| 335 | +++ |
| 336 | +++ |
| 337 | +++ |
| 338 | +++ |
| 339 | +++ |
| 340* | +++ |
| 341 | +++ |
| 342* | +++ |
| 343 | +++ |
| 344 | ++ |
| 345 | +++ |
| 346 | +++ |
| 347* | +++ |
| 348* | +++ |
| 349 | +++ |
| 350 | +++ |
| 351 | ++ |
| 352 | +++ |
| 353 | +++ |
| 354* | +++ |
| 355* | +++ |
| 356* | +++ |
| 357* | +++ |
| 358 | +++ |
| 359 | +++ |
| 360* | +++ |
| 361 | +++ |
| 362 | +++ |
| 363 | +++ |
| 364 | +++ |
| 365* | +++ |
| 366* | +++ |
| 367 | +++ |
| 368 | +++ |
| 369 | +++ |

Example 2: Cell Viability Assay

Kasumi-1 Cell Culture

Kasumi-1 cell line was purchased from ATCC (ATCC® CRL2724™). Cells were isolated from the peripheral blood of a 7-year-old boy with acute myeloid leukemia (AML FAB M2) (in 2nd relapse after bone marrow transplantation) in 1989. Most cells are round. Kasumi-1 cells are observed to grow individually or in small clumps in suspension.

Kasumi-1 cells are cultured in RPMI-1640 (Gibco A10491-01) containing 10% heat-inactivated and 0.22 μm filtered FBS (Gibco 10270-106) at a density of 3E+5 and 3E+6 viable cell/mL following the certificate of analysis.

Cellular viability assay: Kasumi-1 cells were plated (50 μL) in 96-well cell culture microplates (PS, F-Bottom black, Cellstar, Greiner 655086) at final concentration of 15000 cells/well. The compounds of the invention were dissolved in DMSO, and a titration curve was generated at 1000× final concentration. Compounds were then diluted 500× in tissue culture medium (RPMI-1640, 10% FBS). Then 50 μl of test compound were added to Kasumi-1 cells in a final DMSO concentration of 0.1%, final volume 100 μl. A gas permeable sealing membrane was applied to the plate to prevent evaporation (Breathe-Easy sealing membrane, Sigma Z380059-1PK) and cells were incubated for 72 h at 37° C., 5% $CO_2$, 80% RH. After 72 h of treatment, the plates were taken out of the incubator and left for a few minutes at room temperature. 100 μl of the reconstituted reagent ATP-Lite One Step (Perkin Elmer, 6016739) was added to each well. The plates were shaken for 2 min at 700 rpm and placed in the dark for 10 minutes at room temperature before measurement of luminescence intensity with Envision instrument. The raw data were expressed in RLU. Results were expressed in % of viability relative to DMSO control and an IC50 was calculated based on the concentration-response profile of individual compounds. IC50 is the concentration of compound of the invention (METTL3/14 inhibitors) that induces 50% inhibition of cellular viability.

Results are summarized in Table 3, with +++: IC50≤0.5 M, ++: 0.5 μM<IC50≤5 μM, +: IC50>5 M.

Caov-3 Cell Culture

Caov-3 cell line was purchased from ATCC (ATCC® HTB-75™). Cells were isolated from the ovary of a 54-year-old, White, female ovarian cancer patient.

Caov-3 cells are cultured in DMEM (ATCC 30-2002) containing 10% heat-inactivated and 0.22 μm filtered FBS (Gibco 10270-106). The cells are seeded at 2.5E+4 cell/cm² within the recommended subcultivation ratio of 1:3 to 1:6, as stated on the certificate of analysis issues by the provider of the cells.

Cellular viability assay: Caov-3 cells were plated (50 μL) in 96-well cell culture microplates (PS, F-Bottom black, Cellstar, Greiner 655086) at final concentration of 10000 cells/well. The compounds of the invention were dissolved in DMSO, and a titration curve was generated at 1000× final concentration. Compounds were then diluted 500× in tissue culture medium (RPMI-1640, 10% FBS). Then 50 μl of test compound were added to Caov-3 cells in a final DMSO concentration of 0.1%, final volume 100 μl. A gas permeable sealing membrane was applied to the plate to prevent evaporation (Breathe-Easy sealing membrane, Sigma Z380059-1PK) and cells were incubated for 72 h at 37° C., 5% CO₂, 80% RH. After 72 h of treatment, the plates were taken out of the incubator and left for a few minutes at room temperature. 100 μl of the reconstituted reagent ATP-Lite One Step (Perkin Elmer, 6016739) were added to each well. The plates were shaken for 2 min at 700 rpm and placed in the dark for 10 minutes at room temperature before measurement of luminescence intensity with Envision instrument. The raw data were expressed in RLU. Results were expressed in % of viability relative to DMSO control and an IC50 was calculated based on the concentration-response profile of individual compounds. IC50 is the concentration of compound of the invention (METTL3/14 inhibitors) that induces 50% inhibition of cellular viability.

Results are summarized in Table 3, with +++: IC50≤0.5 μM, ++: 0.5 μM<IC50≤5 μM, +: IC50>5 μM.

Conclusion: Collectively, these data from the cellular viability assays demonstrate that the compounds of the invention, previously identified as inhibitors of the enzymatic activity of the METTL3/METTL14 complex, additionally inhibit the cellular viability of cancer cells of liquid (hematological) tumors (Kasumi-1) and solid tumors (Caov-3).

TABLE 3

The results are provided for the compounds for which the results are provided in Table 2.

| Cpd | CAOV-3 IC50 | KASUMI-1 IC50 |
| --- | --- | --- |
| 001 | +++ | ++ |
| 002 | + | + |
| 003 | + | ++ |
| 006 | ++ | ++ |
| 007 | ++ | ++ |
| 008 | ++ | + |
| 009 | ++ | ++ |
| 010 | + | + |
| 011 | + | + |
| 012 | ++ | ++ |
| 013 | +++ | ++ |
| 015 | +++ | ++ |
| 017 | + | + |
| 018 | +++ | ++ |
| 019 | + | + |
| 020 | ++ | ++ |
| 022 | + | ++ |
| 023 | ++ | ++ |
| 024 | + | + |
| 025 | +++ | ++ |
| 026 | + | ++ |
| 027 | +++ | +++ |
| 028 | ++ | ++ |
| 030 | ++ | ++ |
| 031 | ++ | ++ |
| 032 | +++ | ++ |
| 036 | + | + |
| 037 | +++ | +++ |
| 039 | NA | + |
| 040 | +++ | +++ |
| 041 | NA | + |
| 042 | +++ | +++ |
| 043 | NA | + |
| 046 | NA | + |
| 047 | + | ++ |
| 050 | +++ | +++ |
| 051 | ++ | + |
| 052 | NA | + |
| 055 | +++ | +++ |
| 056 | + | + |
| 057 | ++ | ++ |
| 058 | ++ | ++ |
| 060 | + | + |
| 063 | ++ | ++ |
| 065 | ++ | + |
| 066 | ++ | ++ |
| 067 | ++ | ++ |
| 068 | ++ | ++ |
| 071 | ++ | ++ |
| 073 | ++ | ++ |
| 075 | ++ | + |
| 076 | ++ | ++ |
| 077 | ++ | ++ |
| 081 | +++ | ++ |
| 082 | ++ | ++ |
| 083 | ++ | + |
| 085 | ++ | + |
| 086 | ++ | ++ |
| 087 | ++ | ++ |
| 088 | ++ | ++ |
| 093 | ++ | ++ |
| 095 | +++ | ++ |
| 097 | +++ | +++ |
| 107 | +++ | +++ |
| 116 | +++ | +++ |
| 123 | +++ | +++ |
| 124 | ++ | + |
| 126 | ++ | + |
| 134 | +++ | +++ |
| 135 | ++ | ++ |
| 138 | ++ | ++ |
| 139 | +++ | +++ |
| 140 | +++ | +++ |
| 142 | +++ | +++ |
| 143 | +++ | +++ |
| 144 | ++ | ++ |
| 148 | +++ | +++ |
| 149 | +++ | +++ |
| 150 | +++ | +++ |
| 151 | +++ | +++ |
| 153 | + | + |

TABLE 3-continued

The results are provided for the compounds for which the results are provided in Table 2.

| Cpd | CAOV-3 IC50 | KASUMI-1 IC50 |
|---|---|---|
| 154 | +++ | +++ |
| 156 | +++ | +++ |
| 158 | +++ | +++ |
| 159 | ++ | ++ |
| 160 | +++ | +++ |
| 161 | +++ | +++ |
| 164 | +++ | +++ |
| 166 | +++ | +++ |
| 168 | +++ | ++ |
| 169 | +++ | +++ |
| 171 | +++ | +++ |
| 173 | +++ | +++ |
| 174 | +++ | +++ |
| 175 | ++ | ++ |
| 176 | +++ | +++ |
| 177 | +++ | +++ |
| 178 | +++ | +++ |
| 179 | +++ | +++ |
| 180 | +++ | +++ |
| 181 | ++ | ++ |
| 182 | +++ | ++ |
| 183 | +++ | ++ |
| 184 | +++ | +++ |
| 185 | +++ | +++ |
| 186 | +++ | +++ |
| 187 | +++ | ++ |
| 188 | ++ | ++ |
| 189 | +++ | +++ |
| 191 | +++ | ++ |
| 192 | +++ | +++ |
| 193 | +++ | +++ |
| 194 | +++ | +++ |
| 195 | ++ | ++ |
| 196 | +++ | +++ |
| 197 | ++ | ++ |
| 198 | ++ | ++ |
| 199 | +++ | +++ |
| 200 | ++ | ++ |
| 201 | +++ | +++ |
| 202 | +++ | +++ |
| 203 | +++ | +++ |
| 205 | ++ | + |
| 206 | +++ | ++ |
| 207 | +++ | +++ |
| 208 | ++ | ++ |
| 209 | ++ | ++ |
| 210 | +++ | ++ |
| 211 | +++ | +++ |
| 212 | +++ | +++ |
| 213 | +++ | +++ |
| 214 | +++ | +++ |
| 215 | +++ | +++ |
| 216 | +++ | +++ |
| 217 | +++ | +++ |
| 218 | ++ | + |
| 219 | +++ | ++ |
| 220 | +++ | +++ |
| 221 | ++ | ++ |
| 222 | +++ | +++ |
| 223 | +++ | +++ |
| 225 | +++ | +++ |
| 226 | +++ | +++ |
| 227 | +++ | +++ |
| 228 | +++ | +++ |
| 229 | +++ | +++ |
| 230 | +++ | +++ |
| 231 | +++ | +++ |
| 232 | +++ | +++ |
| 233 | +++ | +++ |
| 234 | +++ | +++ |
| 235 | +++ | +++ |
| 237 | ++ | ++ |
| 238 | +++ | +++ |
| 239 | +++ | +++ |
| 240 | +++ | +++ |
| 241 | +++ | +++ |
| 242 | +++ | +++ |
| 243 | ++ | ++ |
| 244 | +++ | +++ |
| 245 | +++ | +++ |
| 246 | +++ | +++ |
| 247 | +++ | +++ |
| 248 | +++ | +++ |
| 249 | +++ | +++ |
| 250 | +++ | +++ |
| 252 | +++ | +++ |
| 253 | +++ | +++ |
| 254 | +++ | +++ |
| 256 | +++ | +++ |
| 257 | +++ | +++ |
| 258 | ++ | ++ |
| 259 | +++ | +++ |
| 260 | +++ | +++ |
| 262 | +++ | +++ |
| 263 | +++ | +++ |
| 267 | ++ | ++ |
| 268 | ++ | ++ |
| 269 | +++ | +++ |
| 270 | +++ | +++ |
| 272 | ++ | ++ |
| 276 | +++ | ++ |
| 278 | +++ | +++ |
| 279 | ++ | ++ |
| 280 | +++ | +++ |
| 281 | +++ | +++ |
| 282 | +++ | +++ |
| 283 | +++ | +++ |
| 284 | +++ | +++ |
| 285 | +++ | +++ |
| 286 | +++ | +++ |
| 287 | +++ | +++ |
| 288 | +++ | +++ |
| 289 | +++ | +++ |
| 290 | +++ | +++ |
| 291 | +++ | +++ |
| 292 | ++ | ++ |
| 293 | ++ | ++ |
| 295 | ++ | +++ |
| 296 | ++ | ++ |
| 297 | ++ | + |
| 298 | ++ | ++ |
| 301 | +++ | +++ |
| 303 | +++ | +++ |
| 304 | +++ | +++ |
| 305 | +++ | +++ |
| 306 | +++ | +++ |
| 307 | +++ | +++ |
| 308 | +++ | +++ |
| 309 | +++ | +++ |
| 310 | +++ | ++ |
| 311 | +++ | +++ |
| 312 | +++ | +++ |
| 313 | +++ | +++ |
| 315 | ++ | ++ |
| 316 | ++ | ++ |
| 317 | +++ | +++ |
| 319 | +++ | +++ |
| 320 | +++ | +++ |
| 321 | ++ | ++ |
| 322 | ++ | ++ |
| 323 | +++ | +++ |
| 324 | +++ | +++ |
| 325 | +++ | ++ |
| 326 | +++ | ++ |
| 327 | ++ | ++ |
| 328 | +++ | ++ |
| 329 | +++ | +++ |
| 330 | ++ | ++ |
| 331 | +++ | +++ |
| 332 | +++ | +++ |

TABLE 3-continued

The results are provided for the compounds for which the results are provided in Table 2.

| Cpd | CAOV-3 IC50 | KASUMI-1 IC50 |
|---|---|---|
| 333 | +++ | +++ |
| 334 | +++ | +++ |
| 335 | +++ | ++ |
| 336 | +++ | +++ |
| 337 | +++ | ++ |
| 338 | +++ | +++ |
| 339 | +++ | ++ |
| 340 | +++ | +++ |
| 341 | +++ | +++ |
| 342 | +++ | +++ |
| 343 | +++ | ++ |
| 344 | + | ++ |
| 345 | +++ | +++ |
| 346 | +++ | +++ |
| 347 | ++ | ++ |
| 348 | +++ | +++ |
| 349 | ++ | + |
| 350 | ++ | ++ |
| 351 | NA | ++ |
| 352 | +++ | +++ |
| 353 | +++ | NA |
| 354 | +++ | +++ |
| 355 | +++ | +++ |
| 356 | +++ | +++ |
| 357 | +++ | +++ |
| 358 | +++ | ++ |
| 359 | +++ | +++ |
| 360 | +++ | +++ |
| 361 | ++ | +++ |
| 362 | +++ | +++ |
| 363 | ++ | ++ |
| 364 | +++ | +++ |
| 365 | + | + |
| 366 | + | +++ |
| 367 | ++ + | +++ |
| 368 | +++ | +++ |
| 369 | +++ | +++ |

NA: not available

The invention claimed is:

1. A compound of Formula (I):

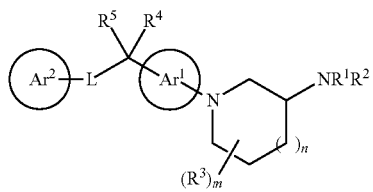

or a pharmaceutically acceptable salt and/or solvate thereof, wherein:

$R^1$ is $C_{2-12}$-alkyl, $C_{2-12}$-haloalkyl, $C_{3-8}$-cycloalkyl-$C_{1-3}$-alkyl, heterocyclyl-$C_{1-3}$-alkyl, $C_{3-8}$-cycloalkyl, or heterocyclyl;
  in which the cycloalkyl and heterocyclyl moieties are optionally substituted by one of more substituents selected from $C_{1-4}$-alkyl, $C_{3-6}$-cycloalkyl, $C_{1-4}$-haloalkyl, halo, cyano, hydroxy, $C_{1-4}$-alkoxy, and $C_{1-4}$-haloalkoxy;
  and/or the cycloalkyl and heterocyclyl moieties are optionally spiro-fused to a $C_{3-6}$-cycloalkyl or heterocyclyl ring, which spiro-ring can optionally be substituted by one or more substituent selected from $C_{1-4}$-alkyl, $C_{3-6}$-cycloalkyl, $C_{1-4}$-haloalkyl, halo, cyano, hydroxy, $C_{1-4}$-alkoxy, and $C_{1-4}$-haloalkoxy;
  and/or the cycloalkyl and heterocyclyl moieties are optionally bridged ring systems;

$R^2$ is H, a $C_{1-4}$-alkyl optionally substituted by one or more substituent selected from halo, cyano, hydroxy, $C_{1-4}$-alkoxy, and $C_{1-4}$-haloalkoxy; or a $C_{3-6}$-cycloalkyl;

or $R^1$ and $R^2$ form together with the nitrogen atom to which they are attached a heterocyclic ring,
  wherein the heterocyclic ring is optionally substituted by one or more substituent selected from $C_{1-4}$-alkyl, $C_{3-6}$-cycloalkyl, $C_{1-4}$-haloalkyl, halo, cyano, hydroxy, $C_{1-4}$-alkoxy, and $C_{1-4}$-haloalkoxy;
  and/or the heterocyclic ring is optionally spiro-fused to a $C_{3-6}$-cycloalkyl or heterocyclyl ring, which spiro-ring can optionally be substituted by one or more substituent selected from $C_{1-4}$-alkyl, $C_{3-6}$-cycloalkyl, $C_{1-4}$-haloalkyl, halo, cyano, hydroxy, $C_{1-4}$-alkoxy, and $C_{1-4}$-haloalkoxy;
  and/or the heterocyclyl ring is optionally a bridged ring system;

each $R^3$ is independently $C_{1-4}$-alkyl, $C_{3-6}$-cycloalkyl, $C_{1-4}$-haloalkyl, halo, cyano, hydroxy, $C_{1-4}$-alkoxy, $C_{1-4}$-haloalkoxy, oxo, or thioxo; or two $R^3$ groups present on the same carbon atom form together with the carbon atom to which they are attached a spiro-fused $C_{3-6}$-cycloalkyl; or two $R^3$ groups present on two adjacent carbon atoms form together with the carbon atoms to which they are attached a fused $C_{3-6}$-cycloalkyl; or two $R^3$ groups present on two non-adjacent carbon atoms are linked and form a $C_{1-4}$-alkyl bridge;

m is 0, 1, 2, 3 or 4;

n is 1 or 2;

$R^4$ and $R^5$ are each independently H, $C_{1-4}$-alkyl, $C_{1-4}$-haloalkyl, $C_{3-6}$-cycloalkyl, halo, cyano or hydroxy; or $R^4$ and $R^5$ form together with the carbon atom to which they are attached a heterocyclyl ring or a $C_{3-4}$-cycloalkyl ring, in which the heterocyclyl and cycloalkyl moieties are optionally substituted by one or more substituent selected from $C_{1-4}$-alkyl, $C_{3-6}$-cycloalkyl, $C_{1-4}$-haloalkyl, halo, or cyano; or $R^4$ and $R^5$ form together with the carbon atom to which they are attached an ethylenyl;

Ar¹ is an aryl or heteroaryl group selected from (Ar¹ᵃ), (Ar¹ᵇ) and (Ar¹ᶜ):

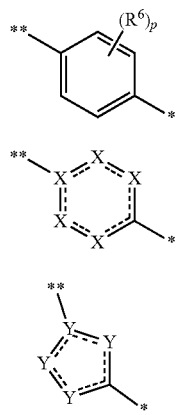

wherein:
p is 0, 1, 2, 3 or 4;
R⁶ is $C_{1-4}$-alkyl, $C_{3-6}$-cycloalkyl, $C_{1-4}$-haloalkyl, halo, or cyano;
each X is independently selected from N, NR⁷, C, CR⁸, C(O), and C(S), wherein at least one of X is N or NR⁷;
R⁷ is H, $C_{1-4}$-alkyl, $C_{3-6}$-cycloalkyl, or $C_{1-4}$-haloalkyl;
R⁸ is H, $C_{1-4}$-alkyl, $C_{3-6}$-cycloalkyl, $C_{1-4}$-haloalkyl, halo, cyano, hydroxy, $C_{1-4}$-alkoxy, or $C_{1-4}$-haloalkoxy;
each Y is independently selected from N, NR⁹, S, O, C, CR¹⁰, C(O), and C(S), wherein at least one of Y is N, NR⁹, S, or O;
R⁹ is H, $C_{1-4}$-alkyl, $C_{3-6}$-cycloalkyl, or $C_{1-4}$-haloalkyl;
R¹⁰ is H, $C_{1-4}$-alkyl, $C_{3-6}$-cycloalkyl, $C_{1-4}$-haloalkyl, halo, cyano, hydroxy, $C_{1-4}$-alkoxy, or $C_{1-4}$-haloalkoxy;
--- represents a single or double bond, depending on X or Y;
* represents the point of attachment to the piperidine ring; and
** represents the point of attachment to the —CR⁴R⁵— moiety;
L is selected from (L¹), (L²) and 5-membered heteroaryl (L³):

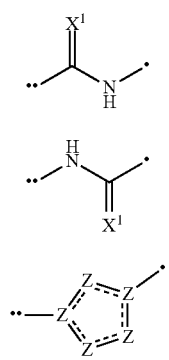

wherein:
X¹ is O or S;
each Z is independently selected from N, NR¹¹, S, O, C, CR¹², C(O), and C(S), wherein at least one of Z is N, NR¹¹, S, or O;
R¹¹ is H, $C_{1-4}$-alkyl, $C_{3-6}$-cycloalkyl, or $C_{1-4}$-haloalkyl;
R¹² is H, $C_{1-4}$-alkyl, $C_{3-6}$-cycloalkyl, $C_{1-4}$-haloalkyl, halo, cyano, hydroxy, $C_{1-4}$-alkoxy, or $C_{1-4}$-haloalkoxy;
--- represents a single or double bond, depending on Z;
• represents the point of attachment to the —CR⁴R⁵— moiety; and
•• represents the point of attachment to Ar²;
Ar² is a 5- to 10-membered, mono- or bicyclo-, aryl or heteroaryl group, optionally substituted by one or more substituent selected from halo, cyano, oxo, hydroxy, amino, $C_{1-4}$-alkylamino, $C_{1-4}$-haloalkylamino, di($C_{1-4}$-alkyl)amino, di($C_{1-4}$-haloalkyl)amino, N—($C_{1-4}$-alkyl)-N—($C_{1-4}$-haloalkyl)amino, $C_{1-4}$-alkoxy, $C_{1-4}$-haloalkoxy, $C_{3-6}$-cycloalkyloxy, ($C_{1-4}$-alkyl)aminocarbonyl, ($C_{1-4}$-haloalkyl)aminocarbonyl, di($C_{1-4}$-alkyl)aminocarbonyl, di($C_{1-4}$-haloalkyl)aminocarbonyl, N—($C_{1-4}$-alkyl)-N—($C_{1-4}$-haloalkyl)aminocarbonyl, $C_{1-4}$-alkyl, $C_{1-4}$-haloalkyl, $C_{3-6}$-cycloalkyl, $C_{2-4}$-alkynyl, $C_{6-10}$-aryl, heteroaryl, and heterocyclyl; wherein the substituents are optionally substituted by one or more group selected from halo, cyano, Oxo, hydroxy, $C_{1-4}$-alkyl, $C_{1-4}$-haloalkyl, $C_{3-6}$-cycloalkyl, $C_{1-4}$-alkoxy, $C_{1-4}$-haloalkoxy, amino, $C_{1-4}$-alkylamino, $C_{1-4}$-haloalkylamino, di($C_{1-4}$-alkyl)amino, di($C_{1-4}$-haloalkyl)amino, and N—($C_{1-4}$-alkyl)-N—($C_{1-4}$-haloalkyl)amino; or fused to the heterocyclyl substituent may be one or more $C_{3-6}$-cycloalkyl or heterocyclyl group; or spiro-fused to the heterocyclyl substituent may be one or more $C_{3-6}$-cycloalkyl or heterocyclyl group optionally substituted by one or more halo.

2. The compound according to claim 1, wherein X¹ is O.
3. The compound according to claim 1, wherein —NR¹R² is selected from:

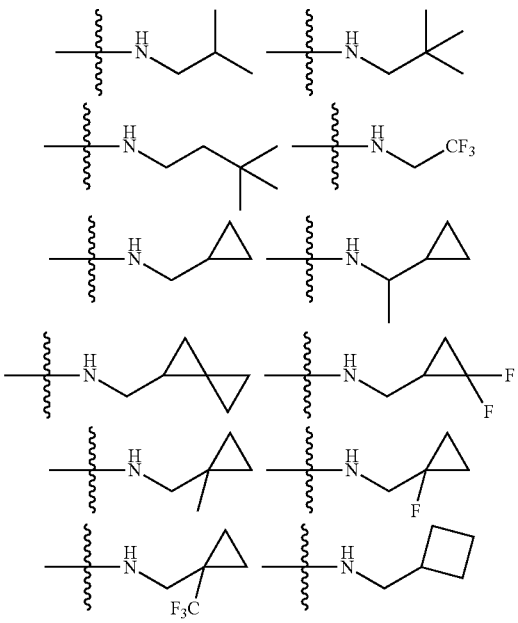

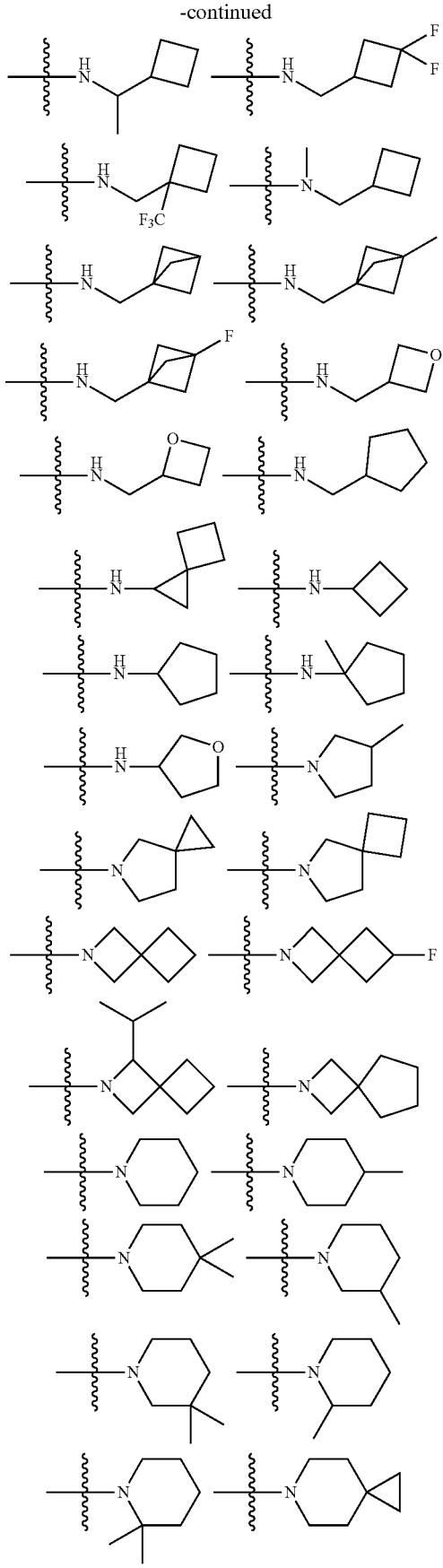
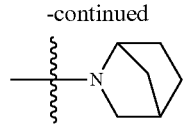
wherein -⅏- represents the point of attachment to the rest of the compound.
4. The compound according to claim 1, wherein $Ar^1$ is selected from:
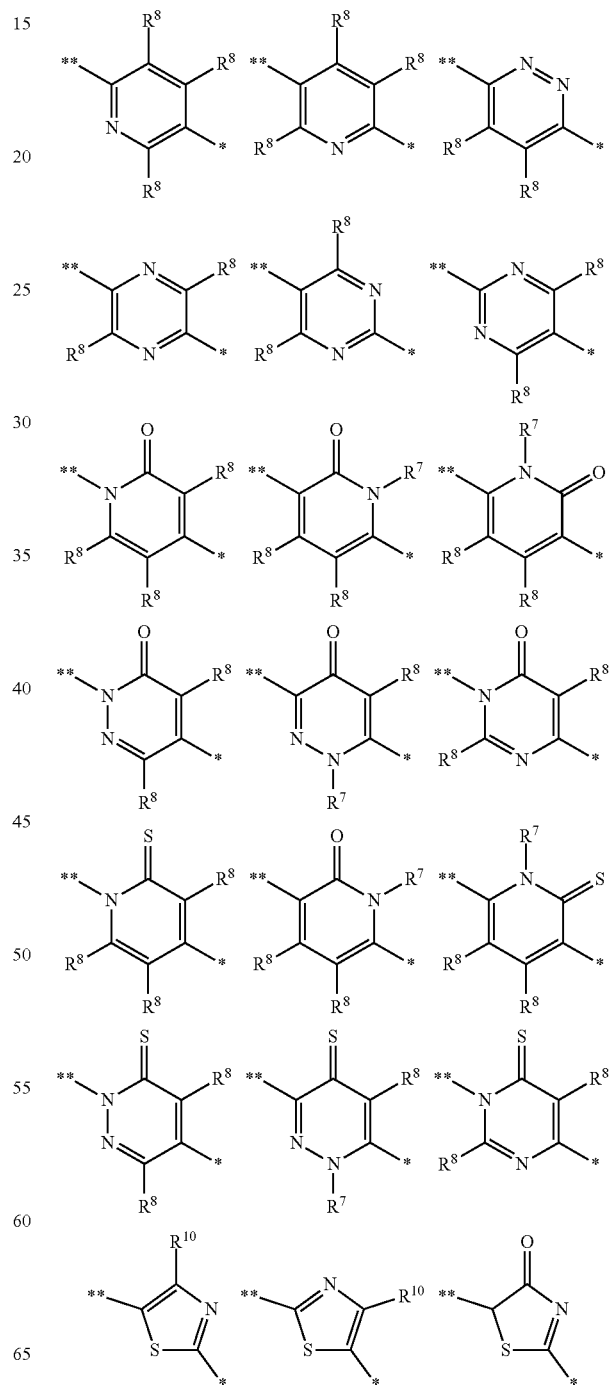

493

-continued

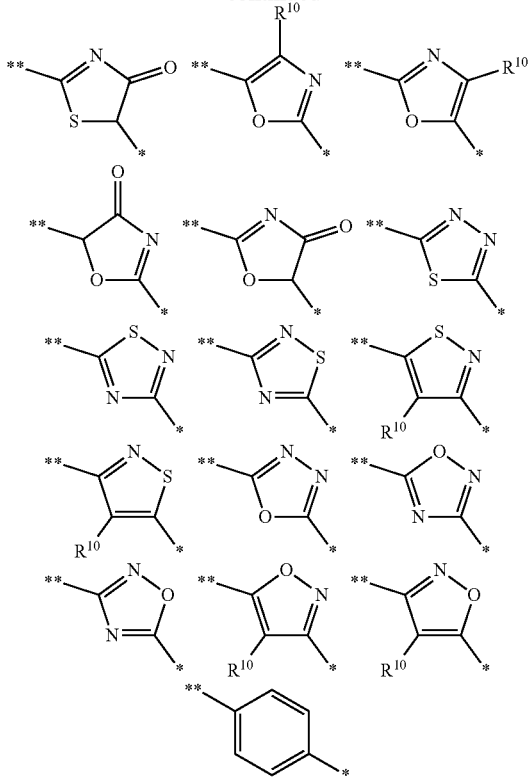

wherein:
R[7] is H, $C_{1-4}$-alkyl, $C_{3-6}$-cycloalkyl, or $C_{1-4}$-haloalkyl;
R[8] is H, $C_{1-4}$-alkyl, $C_{3-6}$-cycloalkyl, $C_{1-4}$-haloalkyl, halo, cyano, hydroxy, $C_{1-4}$-alkoxy, or $C_{1-4}$-haloalkoxy;
R[10] is H, $C_{1-4}$-alkyl, $C_{3-6}$-cycloalkyl, $C_{1-4}$-haloalkyl, halo, cyano, hydroxy, $C_{1-4}$-alkoxy, or $C_{1-4}$-haloalkoxy;
\* represents the point of attachment to the piperidine ring; and
\*\* represents the point of attachment to the —CR[4]R[5]— moiety.

5. The compound according to claim 4, wherein R[7] is H; R[8] is H, methyl, or halo; and R[10] is H.

6. The compound according to claim 4, wherein R[7] is H; R[8] is H; and R[10] is H.

7. The compound according to claim 1, wherein L is selected from:

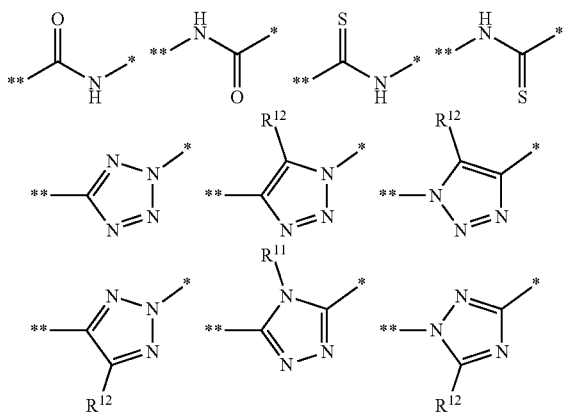

494

-continued

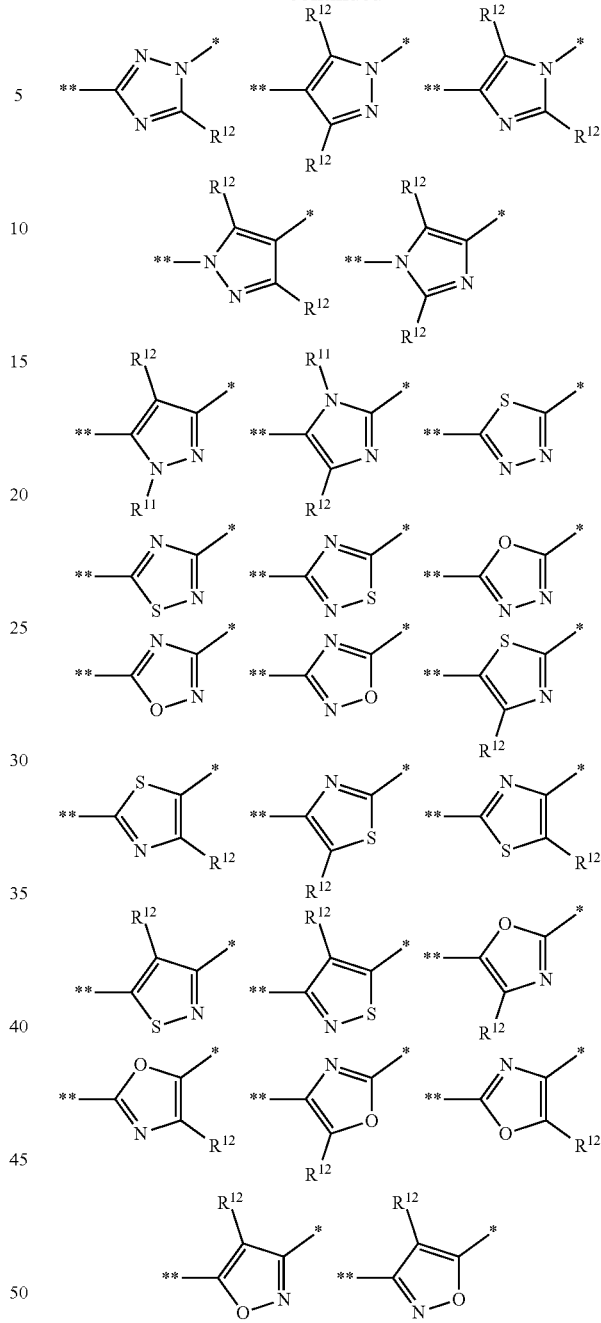

wherein:
each R[11] is independently H, $C_{1-4}$-alkyl, $C_{3-6}$-cycloalkyl, or $C_{1-4}$-haloalkyl;
each R[12] is independently H, $C_{1-4}$-alkyl, $C_{3-6}$-cycloalkyl, $C_{1-4}$-haloalkyl, halo, cyano, hydroxy, $C_{1-4}$-alkoxy, or $C_{1-4}$-haloalkoxy;
• represents the point of attachment to the —CR[4]R[5]— moiety; and
•• represents the point of attachment to Ar[2].

8. The compound according to claim 7, wherein R[11] is H or methyl; and R[12] is H, methyl, halo, cyano, or methoxy.

9. The compound according to claim 7, wherein R[11] is H; and R[12] is H.

10. The compound according to claim 1, wherein Ar[2] is selected from:

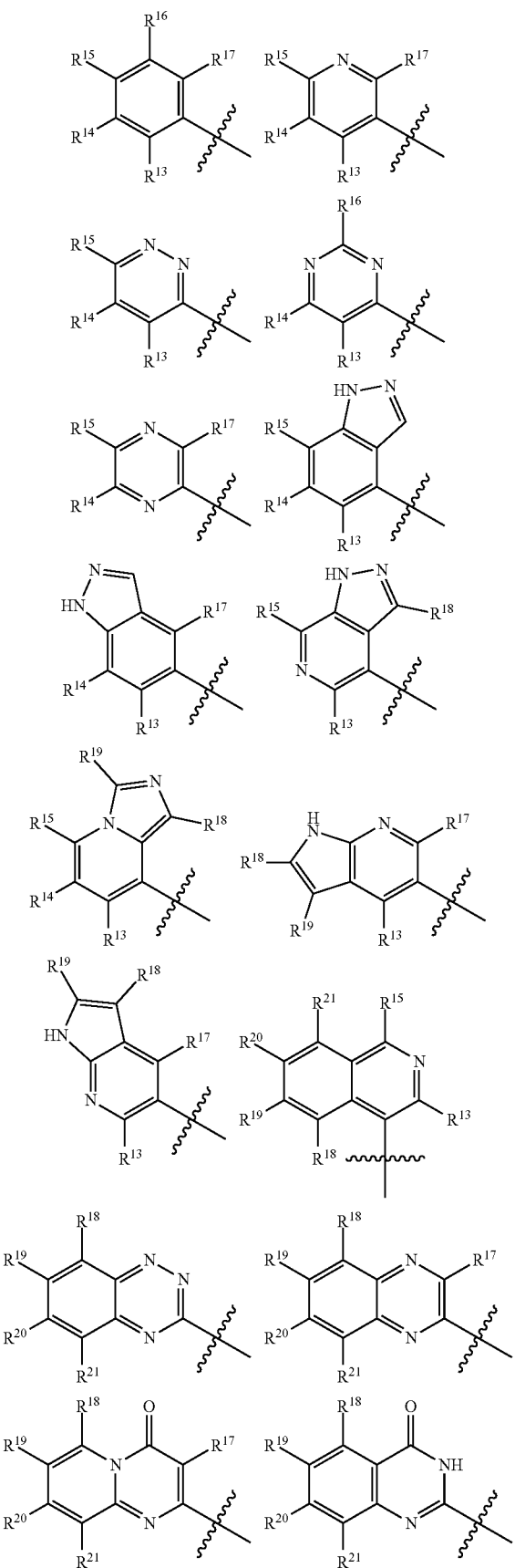
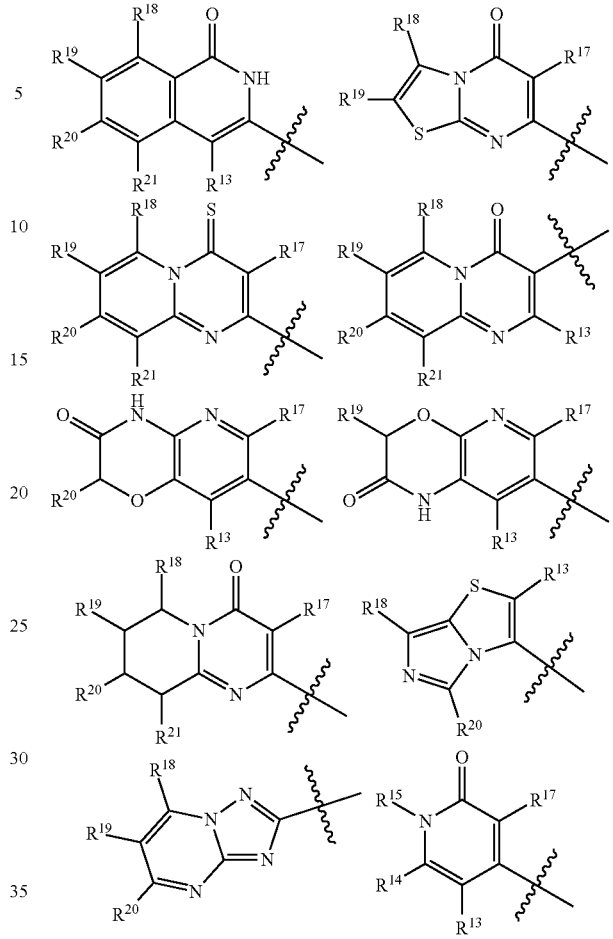

wherein $R^{13}$, $R^{14}$, $R^{15}$, $R^{16}$, $R^{17}$, $R^{18}$, $R^{19}$, $R^{20}$, and $R^{21}$, are each independently selected from H, halo, cyano, oxo, hydroxy, amino, $C_{1-4}$-alkylamino, $C_{1-4}$-haloalkylamino, di($C_{1-4}$-alkyl)amino, di($C_{1-4}$-haloalkyl)amino, N—($C_{1-4}$-alkyl)-N—($C_{1-4}$-haloalkyl)amino, $C_{1-4}$-alkoxy, $C_{1-4}$-haloalkoxy, $C_{3-6}$-cycloalkyloxy, ($C_{1-4}$-alkyl)aminocarbonyl, ($C_{1-4}$-haloalkyl)aminocarbonyl, di($C_{1-4}$-haloalkyl)aminocarbonyl, di($C_{1-4}$-alkyl)aminocarbonyl, N—($C_{1-4}$-alkyl)-N—($C_{1-4}$-haloalkyl)aminocarbonyl, $C_{1-4}$-alkyl, $C_{1-4}$-haloalkyl, $C_{3-6}$-cycloalkyl, $C_{2-4}$-alkynyl, $C_{6-10}$-aryl, heteroaryl, and heterocyclyl; wherein these substituents are optionally substituted by one or more group selected from halo, cyano, oxo, hydroxy, $C_{1-4}$-alkyl, $C_{1-4}$-haloalkyl, $C_{3-6}$-cycloalkyl, $C_{1-4}$-alkoxy, $C_{1-4}$-haloalkoxy, amino, $C_{1-4}$-alkylamino, $C_{1-4}$-haloalkylamino, di($C_{1-4}$-alkyl)amino, di($C_{1-4}$-haloalkyl)amino, and N—($C_{1-4}$-alkyl)-N—($C_{1-4}$-haloalkyl)amino; or fused to the heterocyclyl substituent may be one or more $C_{3-6}$-cycloalkyl or heterocyclyl group; or spiro-fused to the heterocyclyl substituent may be one or more $C_{3-6}$-cycloalkyl or heterocyclyl group optionally substituted by one or more halo; and ⁓ represents the point of attachment to the rest of the compound.

11. The compound according to claim 1, wherein n is 1.
12. The compound according to claim 1, of Formula (I-2)

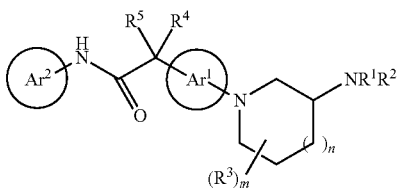

(I-2)

or a pharmaceutically acceptable salt and/or solvate thereof, wherein $R^1$, $R^2$, $R^3$, $R^4$, $R^5$, m, n, $Ar^1$ and $Ar^2$ are as defined above.

13. The compound according to claim 1, of Formula (I-3)

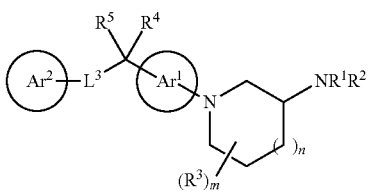

(I-3)

or a pharmaceutically acceptable salt and/or solvate thereof, wherein $R^1$, $R^2$, $R^3$, $R^4$, $R^5$, m, n, $L^3$, $Ar^1$ and $Ar^2$ are as defined above; and $L^3$ is selected from:

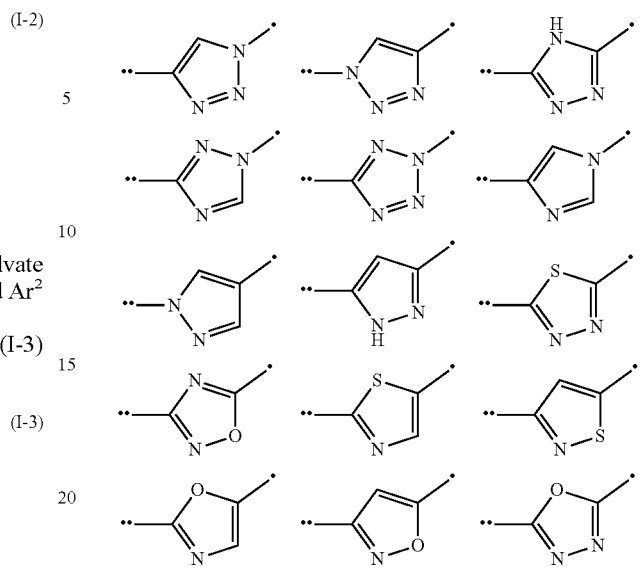

wherein • represents the point of attachment to the —$CR^4R^5$— moiety; and •• represents the point of attachment to $Ar^2$.

14. The compound according to claim 1, selected from:

| | |
|---|---|
| 001 | (R)-N-(cyclobutylmethyl)-1-(6-((4-(6-methoxy-1H-indazol-4-yl)-1H-1,2,3-triazol-1-yl)methyl)pyridazin-3-yl)piperidin-3-amine |
| 002 | (R)-N-((6-(3-((cyclobutylmethyl)amino)piperidin-1-yl)pyridazin-3-yl)methyl)-4-oxo-4H-pyrido[1,2-a]pyrimidine-2-carboxamide |
| 003 | (R)-N-(cyclobutylmethyl)-1-(6-((4-(imidazo[1,5-a]pyridin-8-yl)-1H-1,2,3-triazol-1-yl)methyl)pyridazin-3-yl)piperidin-3-amine |
| 004 | (R)-N-((6-(3-((cyclobutylmethyl)amino)piperidin-1-yl)pyridazin-3-yl)methyl)-5-methoxynicotinamide |
| 005 | (R)-N-((6-(3-((cyclobutylmethyl)amino)piperidin-1-yl)pyridazin-3-yl)methyl)-6-methoxy-1H-indazole-4-carboxamide |
| 006 | 4-(1-((6-(4,4-dimethyl-[1,3'-bipiperidin]-1'-yl)pyridazin-3-yl)methyl)-1H-1,2,3-triazol-4-yl)-6-methoxy-1H-indazole |
| 007 | 6-methoxy-4-(1-((6-(4-methyl-[1,3'-bipiperidin]-1'-yl)pyridazin-3-yl)methyl)-1H-1,2,3-triazol-4-yl)-1H-indazole |
| 008 | 4-(1-((6-(3-(6-azaspiro[3.4]octan-6-yl)piperidin-1-yl)pyridazin-3-yl)methyl)-1H-1,2,3-triazol-4-yl)-6-methoxy-1H-indazole |
| 009 | (R)-1-(6-((4-(1H-pyrrolo[2,3-b]pyridin-5-yl)-1H-1,2,3-triazol-1-yl)methyl)pyridazin-3-yl)-N-(cyclobutylmethyl)piperidin-3-amine |
| 010 | (R)-N-((6-(3-((cyclobutylmethyl)amino)piperidin-1-yl)pyridazin-3-yl)methyl)-5-oxo-5H-thiazolo[3,2-a]pyrimidine-7-carboxamide |
| 011 | N-((6-(3-(((3-fluorobicyclo[1.1.1]pentan-1-yl)methyl)amino)piperidin-1-yl)pyridazin-3-yl)methyl)-4-oxo-4H-pyrido[1,2-a]pyrimidine-2-carboxamide |
| 012 | (R)-N-(cyclobutylmethyl)-1-(6-((4-(5-methoxypyridin-3-yl)-1H-1,2,3-triazol-1-yl)methyl)pyridazin-3-yl)piperidin-3-amine |
| 013 | (R)-N-(cyclobutylmethyl)-1-(6-((4-(6-methoxyimidazo[1,5-a]pyridin-8-yl)-1H-1,2,3-triazol-1-yl)methyl)pyridazin-3-yl)piperidin-3-amine |
| 014 | N-((6-(3-(6-azaspiro[2.5]octan-6-yl)piperidin-1-yl)pyridazin-3-yl)methyl)-4-oxo-4H-pyrido[1,2-a]pyrimidine-2-carboxamide |
| 015 | (R)-N-(cyclopropylmethyl)-1-(6-((4-(6-methoxy-1H-indazol-4-yl)-1H-1,2,3-triazol-1-yl)methyl)pyridazin-3-yl)piperidin-3-amine |
| 016 | (R)-N-((6-(3-((cyclopropylmethyl)amino)piperidin-1-yl)pyridazin-3-yl)methyl)-4-oxo-4H-pyrido[1,2-a]pyrimidine-2-carboxamide |
| 017 | (R)-2-(1-((6-(3-((cyclobutylmethyl)amino)piperidin-1-yl)pyridazin-3-yl)methyl)-1H-1,2,3-triazol-4-yl)-4H-pyrido[1,2-a]pyrimidin-4-one |
| 018 | (R)-N-((3-fluorobicyclo[1.1.1]pentan-1-yl)methyl)-1-(6-((4-(6-methoxy-1H-indazol-4-yl)-1H-1,2,3-triazol-1-yl)methyl)pyridazin-3-yl)piperidin-3-amine |
| 019 | (R)-3-(1-((6-(3-((cyclobutylmethyl)amino)piperidin-1-yl)pyridazin-3-yl)methyl)-1H-1,2,3-triazol-4-yl)-5-methoxypicolinonitrile |
| 020 | 1-(6-((4-(6-methoxy-1H-indazol-4-yl)-1H-1,2,3-triazol-1-yl)methyl)pyridazin-3-yl)-N-((3-methylbicyclo[1.1.1]pentan-1-yl)methyl)piperidin-3-amine |
| 021 | (R)-5-(1-((6-(3-((cyclobutylmethyl)amino)piperidin-1-yl)pyridazin-3-yl)methyl)-1H-1,2,3-triazol-4-yl)nicotinonitrile |

-continued 022 (R)-N-(cyclobutylmethyl)-1-(6-((4-(6-methoxy-1H-indazol-4-yl)-1H-1,2,3-triazol-1-yl)methyl)pyridazin-3-yl)-N-methylpiperidin-3-amine
023 (R)-N-cyclopentyl-1-(6-((4-(6-methoxy-1H-indazol-4-yl)-1H-1,2,3-triazol-1-yl)methyl)pyridazin-3-yl)piperidin-3-amine
024 (R)-N-(3,3-dimethylbutyl)-1-(6-((4-(6-methoxy-1H-indazol-4-yl)-1H-1,2,3-triazol-1-yl)methyl)pyridazin-3-yl)piperidin-3-amine
025 1-(6-((4-(6-methoxy-1H-indazol-4-yl)-1H-1,2,3-triazol-1-yl)methyl)pyridazin-3-yl)-N-(spiro[2.3]hexan-1-yl)piperidin-3-amine
026 N-(cyclobutylmethyl)-1-(5-((4-(6-methoxy-1H-indazol-4-yl)-1H-1,2,3-triazol-1-yl)methyl)thiazol-2-yl)piperidin-3-amine
027 4-(3-((cyclobutylmethyl)amino)piperidin-1-yl)-1-((4-(6-methoxy-1H-indazol-4-yl)-1H-1,2,3-triazol-1-yl)methyl)pyridin-2(1H)-one
028 5-(3-((cyclobutylmethyl)amino)piperidin-1-yl)-2-((4-(6-methoxy-1H-indazol-4-yl)-1H-1,2,3-triazol-1-yl)methyl)pyridazin-3(2H)-one
029 (R)-2-(1-((6-(3-((cyclobutylmethyl)amino)piperidin-1-yl)pyridazin-3-yl)methyl)-1H-1,2,3-triazol-4-yl)quinazolin-4(3H)-one
030 (R)-N-cyclobutyl-1-(6-((4-(6-methoxy-1H-indazol-4-yl)-1H-1,2,3-triazol-1-yl)methyl)pyridazin-3-yl)piperidin-3-amine
031 (R)-N-isobutyl-1-(6-((4-(6-methoxy-1H-indazol-4-yl)-1H-1,2,3-triazol-1-yl)methyl)pyridazin-3-yl)piperidin-3-amine
032 (R)-1-(6-((4-(6-methoxy-1H-indazol-4-yl)-1H-1,2,3-triazol-1-yl)methyl)pyridazin-3-yl)-N-neopentylpiperidin-3-amine
033 (3R)-1-(6-((4-(6-methoxy-1H-indazol-4-yl)-1H-1,2,3-triazol-1-yl)methyl)pyridazin-3-yl)-N-(tetrahydrofuran-3-yl)piperidin-3-amine
034 (R)-N-(cyclobutylmethyl)-1-(6-((4-(imidazo[5,1-b]thiazol-3-yl)-1H-1,2,3-triazol-1-yl)methyl)pyridazin-3-yl)piperidin-3-amine
035 4-(1-((6-(3-(2-azaspiro[3.3]heptan-2-yl)piperidin-1-yl)pyridazin-3-yl)methyl)-1H-1,2,3-triazol-4-yl)-6-methoxy-1H-indazole
036 N-(cyclobutylmethyl)-1-(5-((4-(6-methoxy-1H-indazol-4-yl)-1H-1,2,3-triazol-1-yl)methyl)-1,3,4-thiadiazol-2-yl)piperidin-3-amine
037 (3R)-N-(cyclobutylmethyl)-1-(6-(1-(4-(6-methoxy-1H-indazol-4-yl)-1H-1,2,3-triazol-1-yl)ethyl)pyridazin-3-yl)piperidin-3-amine
038 (3R,6S)-N-(cyclobutylmethyl)-1-(6-((4-(5-methoxypyridin-3-yl)-1H-1,2,3-triazol-1-yl)methyl)pyridazin-3-yl)-6-methylpiperidin-3-amine
039 (R)-6-(3-((cyclobutylmethyl)amino)piperidin-1-yl)-3-((4-(6-methoxy-1H-indazol-4-yl)-1H-1,2,3-triazol-1-yl)methyl)pyridazin-4(1H)-one
040 (R)-N-(cyclobutylmethyl)-1-(5-((4-(6-methoxy-1H-indazol-4-yl)-1H-1,2,3-triazol-1-yl)methyl)pyridin-2-yl)piperidin-3-amine
041 (R)-6-(3-((cyclobutylmethyl)amino)piperidin-1-yl)-3-((4-(6-methoxy-1H-indazol-4-yl)-1H-1,2,3-triazol-1-yl)methyl)pyrimidin-4(3H)-one
042 (R)-N-(cyclobutylmethyl)-1-(6-((4-(6-methoxy-1H-indazol-4-yl)-1H-1,2,3-triazol-1-yl)methyl)pyridazin-3-yl)piperidin-3-amine
043 N-(cyclobutylmethyl)-1-(2-((4-(6-methoxy-1H-indazol-4-yl)-1H-1,2,3-triazol-1-yl)methyl)pyrimidin-5-yl)piperidin-3-amine
044 (3R)-N-(1-cyclobutylethyl)-1-(6-((4-(6-methoxy-1H-indazol-4-yl)-1H-1,2,3-triazol-1-yl)methyl)pyridazin-3-yl)piperidin-3-amine
045 (3R)-N-(1-cyclopropylethyl)-1-(6-((4-(6-methoxy-1H-indazol-4-yl)-1H-1,2,3-triazol-1-yl)methyl)pyridazin-3-yl)piperidin-3-amine
046 N-(cyclobutylmethyl)-1-(5-((4-(6-methoxy-1H-indazol-4-yl)-1H-1,2,3-triazol-1-yl)methyl)pyrimidin-2-yl)piperidin-3-amine
047 N-(cyclobutylmethyl)-1-(5-((4-(6-methoxy-1H-indazol-4-yl)-1H-1,2,3-triazol-1-yl)methyl)pyrazin-2-yl)piperidin-3-amine
048 (R)-3-(1-((6-(3-((cyclobutylmethyl)amino)piperidin-1-yl)pyridazin-3-yl)methyl)-1H-1,2,3-triazol-4-yl)isoquinolin-1(2H)-one
049 N-(cyclobutylmethyl)-1-(2-((4-(6-methoxy-1H-indazol-4-yl)-1H-1,2,3-triazol-1-yl)methyl)thiazol-5-yl)piperidin-3-amine
050 4-((R)-3-((cyclobutylmethyl)amino)piperidin-1-yl)-1-(1-(4-(6-methoxy-1H-indazol-4-yl)-1H-1,2,3-triazol-1-yl)ethyl)pyridin-2(1H)-one
051 N-(1-(6-((R)-3-((cyclobutylmethyl)amino)piperidin-1-yl)pyridazin-3-yl)ethyl)-4-oxo-4H-pyrido[1,2-a]pyrimidine-2-carboxamide
052 3-(3-((cyclobutylmethyl)amino)piperidin-1-yl)-6-((4-(6-methoxy-1H-indazol-4-yl)-1H-1,2,3-triazol-1-yl)methyl)pyridin-2(1H)-one
053 N-(cyclobutylmethyl)-1-(6-((4-(5-methoxypyridin-3-yl)-1H-1,2,3-triazol-1-yl)methyl)pyridazin-3-yl)-3-methylpiperidin-3-amine
054 4-(3-((cyclobutylmethyl)amino)piperidin-1-yl)-5-fluoro-1-((4-(6-methoxy-1H-indazol-4-yl)-1H-1,2,3-triazol-1-yl)methyl)pyridin-2(1H)-one
055 4-((R)-3-((cyclobutylmethyl)amino)piperidin-1-yl)-1-(1-(4-(5-methoxypyridin-3-yl)-1H-1,2,3-triazol-1-yl)ethyl)pyridin-2(1H)-one
056 (3R,5S)-N-(cyclobutylmethyl)-5-fluoro-1-(6-((4-(5-methoxypyridin-3-yl)-1H-1,2,3-triazol-1-yl)methyl)pyridazin-3-yl)piperidin-3-amine
057 (R)-1-(6-((4-(6-chloro-1H-indazol-4-yl)-1H-1,2,3-triazol-1-yl)methyl)pyridazin-3-yl)-N-(cyclobutylmethyl)piperidin-3-amine
058 N-(1-(5-((R)-3-((cyclobutylmethyl)amino)piperidin-1-yl)pyridin-2-yl)ethyl)-4-oxo-4H-pyrido[1,2-a]pyrimidine-2-carboxamide
059 N-(cyclobutylmethyl)-4,4-difluoro-1-(6-((4-(5-methoxypyridin-3-yl)-1H-1,2,3-triazol-1-yl)methyl)pyridazin-3-yl)piperidin-3-amine -continued 060 (R)-N-((5-(3-((cyclobutylmethyl)amino)piperidin-1-yl)pyridin-2-yl)methyl)-4-oxo-4H-pyrido[1,2-a]pyrimidine-2-carboxamide
061 (R)-N-((6-(3-((cyclobutylmethyl)amino)piperidin-1-yl)pyridin-3-yl)methyl)-4-oxo-4H-pyrido[1,2-a]pyrimidine-2-carboxamide
062 (R)-5-(3-((cyclobutylmethyl)amino)piperidin-1-yl)-2-((4-(5-methoxypyridin-3-yl)-1H-1,2,3-triazol-1-yl)methyl)pyridazin-3(2H)-one
063 (R)-4-(3-((cyclobutylmethyl)amino)piperidin-1-yl)-1-((4-(5-methoxypyridin-3-yl)-1H-1,2,3-triazol-1-yl)methyl)pyridin-2(1H)-one
064 (3R)-N-(cyclobutylmethyl)-1-(6-(2,2,2-trifluoro-1-(4-(5-methoxypyridin-3-yl)-1H-1,2,3-triazol-1-yl)ethyl)pyridazin-3-yl)piperidin-3-amine
065 N-(1-(6-((R)-3-((cyclobutylmethyl)amino)piperidin-1-yl)pyridazin-3-yl)-2,2,2-trifluoroethyl)-4-oxo-4H-pyrido[1,2-a]pyrimidine-2-carboxamide
066 (3R)-N-(cyclobutylmethyl)-1-(6-(1-(4-(5-methoxypyridin-3-yl)-1H-1,2,3-triazol-1-yl)ethyl)pyridazin-3-yl)piperidin-3-amine
067 5-((R)-3-((cyclobutylmethyl)amino)piperidin-1-yl)-2-(1-(4-(5-methoxypyridin-3-yl)-1H-1,2,3-triazol-1-yl)ethyl)pyridazin-3(2H)-one
068 (R)-N-(cyclobutylmethyl)-1-(4-((4-(5-methoxypyridin-3-yl)-1H-1,2,3-triazol-1-yl)methyl)phenyl) piperidin-3-amine
069 (R)-N-(cyclobutylmethyl)-1-(6-((5-(5-methoxypyridin-3-yl)-4H-1,2,4-triazol-3-yl)methyl)pyridazin-3-yl)piperidin-3-amine
070 (R)-N-(4-(3-((cyclobutylmethyl)amino)piperidin-1-yl)benzyl)-4-oxo-4H-pyrido[1,2-a]pyrimidine-2-carboxamide
071 (3R)-N-(cyclobutylmethyl)-1-(5-(1-(4-(5-methoxypyridin-3-yl)-1H-1,2,3-triazol-1-yl)ethyl)pyridin-2-yl)piperidin-3-amine
072 N-(1-(6-((R)-3-((cyclobutylmethyl)amino)piperidin-1-yl)pyridin-3-yl)ethyl)-4-oxo-4H-pyrido[1,2-a]pyrimidine-2-carboxamide
073 (3R)-N-(cyclobutylmethyl)-1-(6-(1-(4-(5-methoxypyridin-3-yl)-1H-1,2,3-triazol-1-yl)ethyl)pyridin-3-yl)piperidin-3-amine
074 N-((S)-1-(4-((R)-3-((cyclobutylmethyl)amino)piperidin-1-yl)phenyl)ethyl)-4-oxo-4H-pyrido[1,2-a]pyrimidine-2-carboxamide
075 (R)-4-(3-((cyclobutylmethyl)amino)piperidin-1-yl)-1-((1-(5-methoxypyridin-3-yl)-1H-1,2,3-triazol-4-yl)methyl)pyridin-2(1H)-one
076 (3R)-N-(cyclobutylmethyl)-1-(4-(1-(4-(5-methoxypyridin-3-yl)-1H-1,2,3-triazol-1-yl)ethyl)phenyl)piperidin-3-amine
077 (R)-4-(3-((cyclobutylmethyl)amino)piperidin-1-yl)-1-((5-(5-methoxypyridin-3-yl)-1,3,4-thiadiazol-2-yl)methyl)pyridin-2(1H)-one
078 1-(1-(4-(5-chloropyridin-3-yl)-1H-1,2,3-triazol-1-yl)ethyl)-4-((R)-3-((cyclobutylmethyl)amino)piperidin-1-yl)pyridin-2(1H)-one
079 4-((R)-3-((cyclobutylmethyl)amino)piperidin-1-yl)-1-(1-(4-(pyridin-3-yl)-1H-1,2,3-triazol-1-yl)ethyl)pyridin-2(1H)-one
080 4-((R)-3-((cyclobutylmethyl)amino)piperidin-1-yl)-1-(1-(4-(5-methylpyridin-3-yl)-1H-1,2,3-triazol-1-yl)ethyl)pyridin-2(1H)-one
081 (R)-N-(cyclobutylmethyl)-1-(6-((4-(5-methoxypyridin-3-yl)-1H-imidazol-1-yl)methyl)pyridazin-3-yl)piperidin-3-amine
082 (R)-N-(cyclobutylmethyl)-1-(6-(2-(4-(5-methoxypyridin-3-yl)-1H-1,2,3-triazol-1-yl)propan-2-yl)pyridazin-3-yl)piperidin-3-amine
083 N-(1-(6-((R)-3-((cyclobutylmethyl)amino)piperidin-1-yl)pyridazin-3-yl)propyl)-4-oxo-4H-pyrido[1,2-a]pyrimidine-2-carboxamide
084 (3R)-N-(cyclobutylmethyl)-1-(6-(cyclopropyl(4-(5-methoxypyridin-3-yl)-1H-1,2,3-triazol-1-yl)methyl)pyridazin-3-yl)piperidin-3-amine
085 (3R)-N-(cyclobutylmethyl)-1-(6-(1-(4-(5-methoxypyridin-3-yl)-1H-1,2,3-triazol-1-yl)propyl)pyridazin-3-yl)piperidin-3-amine
086 (R)-N-(cyclobutylmethyl)-1-(5-((4-(5-methoxypyridin-3-yl)-1H-1,2,3-triazol-1-yl)methyl)pyridin-2-yl)piperidin-3-amine
087 (R)-N-(cyclobutylmethyl)-1-(6-((4-(5-methoxypyridin-3-yl)-1H-1,2,3-triazol-1-yl)methyl)pyridin-3-yl)piperidin-3-amine
088 2-(1-(1-(4-((R)-3-((cyclobutylmethyl)amino)piperidin-1-yl)-2-oxopyridin-1(2H)-yl)ethyl)-1H-1,2,3-triazol-4-yl)-4H-pyrido[1,2-a]pyrimidin-4-one
089 2-(1-(1-(6-((R)-3-((cyclobutylmethyl)amino)piperidin-1-yl)pyridazin-3-yl)ethyl)-1H-1,2,3-triazol-4-yl)-4H-pyrido[1,2-a]pyrimidin-4-one
090 7-chloro-2-(1-(1-(6-((R)-3-((cyclobutylmethyl)amino)piperidin-1-yl)pyridazin-3-yl)ethyl)-1H-1,2,3-triazol-4-yl)-4H-pyrido[1,2-a]pyrimidin-4-one
091 N-(1-(6-((R)-3-((cyclobutylmethyl)amino)piperidin-1-yl)pyridazin-3-yl)ethyl)-8-(methylamino)-4-oxo-4H-pyrido[1,2-a]pyrimidine-2-carboxamide
092 N-(1-(6-((R)-3-((cyclobutylmethyl)amino)piperidin-1-yl)pyridazin-3-yl)ethyl)-7-methoxy-1H-indazole-4-carboxamide
093 4-((R)-3-((cyclobutylmethyl)amino)piperidin-1-yl)-1-(1-(4-(5-methoxypyridazin-3-yl)-1H-1,2,3-triazol-1-yl)ethyl)pyridin-2(1H)-one
094 4-((R)-3-((cyclobutylmethyl)amino)piperidin-1-yl)-1-(1-(4-(5-fluoropyridin-3-yl)-1H-1,2,3-triazol-1-yl)ethyl)pyridin-2(1H)-one
095 (R)-4-(3-((cyclobutylmethyl)amino)piperidin-1-yl)-1-((5-(5-methoxypyridin-3-yl)-1H-pyrazol-3-yl)methyl)pyridin-2(1H)-one
096 4-((R)-3-((cyclobutylmethyl)amino)piperidin-1-yl)-1-(1-(4-(5-(methylamino)pyridin-3-yl)-1H-1,2,3-triazol-1-yl)ethyl)pyridin-2(1H)-one

| | |
|---|---|
| 097 | (R)-4-(3-((cyclobutylmethyl)amino)piperidin-1-yl)-1-((2-(5-methoxypyridin-3-yl)thiazol-5-yl)methyl)pyridin-2(1H)-one |
| 098 | 4-((R)-3-((cyclobutylmethyl)amino)piperidin-1-yl)-1-(1-(4-(5-methoxypyridin-3-yl)-1H-imidazol-1-yl)ethyl)pyridin-2(1H)-one |
| 099 | 2-(1-(1-(5-((R)-3-((cyclobutylmethyl)amino)piperidin-1-yl)pyridin-2-yl)ethyl)-1H-1,2,3-triazol-4-yl)-4H-pyrido[1,2-a]pyrimidin-4-one |
| 100 | N-(1-(4-((R)-3-((cyclobutylmethyl)amino)piperidin-1-yl)phenyl)ethyl)-4-oxo-4H-pyrido[1,2-a]pyrimidine-2-carboxamide |
| 101 | N-(cyclobutylmethyl)-1-(6-((4-(5-methoxypyridin-3-yl)-1H-1,2,3-triazol-1-yl)methyl)pyridazin-3-yl)azepan-3-amine |
| 102 | 2-(1-(1-(4-((R)-3-((cyclobutylmethyl)amino)piperidin-1-yl)phenyl)ethyl)-1H-1,2,3-triazol-4-yl)-4H-pyrido[1,2-a]pyrimidin-4-one |
| 103 | 4-((R)-3-((cyclobutylmethyl)amino)piperidin-1-yl)-1-(1-(4-(5-ethoxypyridin-3-yl)-1H-1,2,3-triazol-1-yl)ethyl)pyridin-2(1H)-one |
| 104 | 4-((R)-3-((cyclobutylmethyl)amino)piperidin-1-yl)-1-(1-(4-(5-methoxy-6-methylpyridin-3-yl)-1H-1,2,3-triazol-1-yl)ethyl)pyridin-2(1H)-one |
| 105 | 4-((R)-3-((cyclobutylmethyl)amino)piperidin-1-yl)-1-(1-(4-(6-methoxypyrazin-2-yl)-1H-1,2,3-triazol-1-yl)ethyl)pyridin-2(1H)-one |
| 106 | 4-((R)-3-((cyclobutylmethyl)amino)piperidin-1-yl)-1-(1-(5-(5-methoxypyridin-3-yl)-2H-tetrazol-2-yl)ethyl)pyridin-2(1H)-one |
| 107 | (R)-4-(3-((cyclobutylmethyl)amino)piperidin-1-yl)-1-((1-(5-methoxypyridin-3-yl)-1H-pyrazol-4-yl)methyl)pyridin-2(1H)-one |
| 108 | 4-((R)-3-((cyclobutylmethyl)amino)piperidin-1-yl)-1-(1-(4-(5-methoxy-4-methylpyridin-3-yl)-1H-1,2,3-triazol-1-yl)ethyl)pyridin-2(1H)-one |
| 109 | 3-(1-(1-(4-((R)-3-((cyclobutylmethyl)amino)piperidin-1-yl)-2-oxopyridin-1(2H)-yl)ethyl)-1H-1,2,3-triazol-4-yl)-5-methoxypicolinonitrile |
| 110 | N-(1-(6-((R)-3-((cyclobutylmethyl)amino)piperidin-1-yl)pyridazin-3-yl)ethyl)-4-thioxo-4H-pyrido[1,2-a]pyrimidine-2-carboxamide |
| 111 | N-(1-(6-((R)-3-((cyclobutylmethyl)amino)piperidin-1-yl)pyridazin-3-yl)ethyl)-4-oxo-4H-pyrido[1,2-a]pyrimidine-2-carbothioamide |
| 112 | N-(1-(5-((R)-3-((cyclopropylmethyl)amino)piperidin-1-yl)pyridin-2-yl)ethyl)-4-oxo-4H-pyrido[1,2-a]pyrimidine-2-carboxamide |
| 113 | 4-((R)-3-((cyclobutylmethyl)amino)piperidin-1-yl)-1-(1-(4-(5-(dimethylamino)pyridin-3-yl)-1H-1,2,3-triazol-1-yl)ethyl)pyridin-2(1H)-one |
| 114 | 4-((R)-3-((cyclobutylmethyl)amino)piperidin-1-yl)-1-(1-(4-(5-methoxy-2-methylpyridin-3-yl)-1H-1,2,3-triazol-1-yl)ethyl)pyridin-2(1H)-one |
| 115 | (R)-N-(cyclobutylmethyl)-1-(6-(1-(4-(5-methoxypyridin-3-yl)-1H-1,2,3-triazol-1-yl)cyclopropyl)pyridazin-3-yl)piperidin-3-amine |
| 116 | 4-((R)-3-((cyclobutylmethyl)amino)piperidin-1-yl)-1-((R)-1-(4-(5-methoxypyridin-3-yl)-1H-1,2,3-triazol-1-yl)ethyl)pyridine-2(1H)-thione |
| 117 | N-(1-(5-((R)-3-(cyclopentylamino)piperidin-1-yl)pyridin-2-yl)ethyl)-4-oxo-4H-pyrido[1,2-a]pyrimidine-2-carboxamide |
| 118 | (R)-N-(cyclobutylmethyl)-1-(6-((4-(5-methoxypyridazin-3-yl)-1H-1,2,3-triazol-1-yl)methyl)pyridin-3-yl)piperidin-3-amine |
| 119 | 4-((R)-3-((cyclobutylmethyl)amino)piperidin-1-yl)-1-(1-(5-(5-methoxy pyridin-3-yl)-1,3,4-thiadiazol-2-yl)ethyl)pyridin-2(1H)-one |
| 120 | 4-((R)-3-((cyclobutylmethyl)amino)piperidin-1-yl)-1-(1-(1-(5-methoxy pyridin-3-yl)-1H-pyrazol-4-yl)ethyl)pyridin-2(1H)-one |
| 121 | 4-((R)-3-((cyclobutylmethyl)amino)piperidin-1-yl)-1-(1-(4-(6-(methyl amino)pyrazin-2-yl)-1H-1,2,3-triazol-1-yl)ethyl)pyridin-2(1H)-one |
| 122 | 4-((R)-3-((cyclobutylmethyl)amino)piperidin-1-yl)-1-(1-(4-(5-(methyl amino)pyridazin-3-yl)-1H-1,2,3-triazol-1-yl)ethyl)pyridin-2(1H)-one |
| 123 | (R)-N-(cyclobutylmethyl)-1-(4-((4-(6-methoxy-1H-indazol-4-yl)-1-1,2,3-triazol-1-yl)methyl)phenyl)piperidin-3-amine |
| 124 | 4-((R)-3-((cyclobutylmethyl)amino)piperidin-1-yl)-1-(1-(4-(imidazo[1,5-a]pyridin-8-yl)-1H-1,2,3-triazol-1-yl)ethyl)pyridin-2(1H)-one |
| 125 | 4-((R)-3-((cyclobutylmethyl)amino)piperidin-1-yl)-1-(1-(3-(5-methoxypyridin-3-yl)-1,2,4-oxadiazol-5-yl)ethyl)pyridin-2(1H)-one |
| 126 | 4-((R)-3-((cyclobutylmethyl)amino)piperidin-1-yl)-3-fluoro-1-(1-(4-(5-methoxypyridin-3-yl)-1H-1,2,3-triazol-1-yl)ethyl)pyridin-2(1H)-one |
| 127 | (R)-2-(1-((5-(3-((cyclobutylmethyl)amino)piperidin-1-yl)pyridin-2-yl)methyl)-1H-1,2,3-triazol-4-yl)-4H-pyrido[1,2-a]pyrimidin-4-one |
| 128 | (R)-2-(1-(4-(3-((cyclobutylmethyl)amino)piperidin-1-yl)benzyl)-1H-1,2,3-triazol-4-yl)-4H-pyrido[1,2-a]pyrimidin-4-one |
| 129 | 4-((R)-3-((cyclobutylmethyl)amino)piperidin-1-yl)-1-(1-(4-(5-morpholinopyridin-3-yl)-1H-1,2,3-triazol-1-yl)ethyl)pyridin-2(1H)-one |
| 130 | 4-((R)-3-((cyclobutylmethyl)amino)piperidin-1-yl)-1-(1-(3-(5-methoxypyridin-3-yl)isoxazol-5-yl)ethyl)pyridin-2(1H)-one |
| 131 | 4-((R)-3-((cyclobutylmethyl)amino)piperidin-1-yl)-1-(1-(4-(5-(difluoromethoxy)pyridin-3-yl)-1H-1,2,3-triazol-1-yl)ethyl)pyridin-2(1H)-one |
| 132 | 4-((R)-3-((cyclobutylmethyl)amino)piperidin-1-yl)-1-(1-(1-(5-methoxypyridin-3-yl)-1H-1,2,3-triazol-4-yl)ethyl)pyridin-2(1H)-one |
| 133 | 5-(1-(1-(6-((R)-3-((cyclobutylmethyl)amino)piperidin-1-yl)pyridazin-3-yl)ethyl)-1H-1,2,3-triazol-4-yl)-N,N-dimethylpyridin-3-amine |
| 134 | (R)-N-(cyclobutylmethyl)-1-(4-(3-(4-(5-methoxypyridin-3-yl)-1H-1,2,3-triazol-1-yl)oxetan-3-yl)phenyl)piperidin-3-amine |
| 135 | 4-((R)-3-((cyclobutylmethyl)amino)piperidin-1-yl)-1-(1-(3-(5-methoxypyridin-3-yl)-1H-1,2,4-triazol-1-yl)ethyl)pyridin-2(1H)-one |

| | |
|---|---|
| 136 | (R)-N-(cyclobutylmethyl)-1-(4-((4-(5-methoxypyridazin-3-yl)-1H-1,2,3-triazol-1-yl)methyl)phenyl)piperidin-3-amine |
| 137 | (3R)-N-(cyclobutylmethyl)-1-(6-(1-(4-(5-methoxypyridazin-3-yl)-1H-1,2,3-triazol-1-yl)ethyl)pyridazin-3-yl)piperidin-3-amine |
| 138 | (3R)-N-(cyclobutylmethyl)-1-(6-fluoro-5-(1-(4-(5-methoxypyridin-3-yl)-1H-1,2,3-triazol-1-yl)ethyl)pyridin-2-yl)piperidin-3-amine |
| 139 | (R)-5-(1-((5-(3-(((cyclobutylmethyl)amino)piperidin-1-yl)pyridin-2-yl)methyl)-1H-1,2,3-triazol-4-yl)-N,N-dimethylpyridin-3-amine |
| 140 | (R)-5-(1-(4-(3-((cyclobutylmethyl)amino)piperidin-1-yl)benzyl)-1H-1,2,3-triazol-4-yl)-N,N-dimethylpyridin-3-amine |
| 141 | 2-(6-((R)-3-((cyclobutylmethyl)amino)piperidin-1-yl)pyridazin-3-yl)-N-(5-methoxypyridin-3-yl)propanamide |
| 142 | 4-((R)-3-((cyclopropylmethyl)amino)piperidin-1-yl)-1-(1-(4-(5-(dimethylamino)pyridin-3-yl)-1H-1,2,3-triazol-1-yl)ethyl)pyridin-2(1H)-one |
| 143 | 5-(1-(1-(5-((R)-3-((cyclobutylmethyl)amino)piperidin-1-yl)pyridin-2-yl)ethyl)-1H-1,2,3-triazol-4-yl)-N,N-dimethylpyridin-3-amine |
| 144 | (R)-N-(cyclobutylmethyl)-1-(4-((4-(5-methoxypyridin-3-yl)-1H-imidazol-1-yl)methyl)phenyl)piperidin-3-amine |
| 145 | (R)-N-(cyclobutylmethyl)-1-(4-((5-(5-methoxypyridin-3-yl)-2H-tetrazol-2-yl)methyl)phenyl)piperidin-3-amine |
| 146 | 1-(1-(4-(5-(1H-pyrazol-1-yl)pyridin-3-yl)-1H-1,2,3-triazol-1-yl)ethyl)-4-((R)-3-((cyclobutylmethyl)amino)piperidin-1-yl)pyridin-2(1H)-one |
| 147 | 1-(1-(4-(1H-pyrazolo[3,4-c]pyridin-4-yl)-1H-1,2,3-triazol-1-yl)ethyl)-4-((R)-3-((cyclobutylmethyl)amino)piperidin-1-yl)pyridin-2(1H)-one |
| 148 | (R)-5-(1-(3-(4-(3-((cyclobutylmethyl)amino)piperidin-1-yl)phenyl)oxetan-3-yl)-1H-1,2,3-triazol-4-yl)-N,N-dimethylpyridin-3-amine |
| 149 | (R)-5-(1-(3-(5-(3-((cyclobutylmethyl)amino)piperidin-1-yl)pyridin-2-yl)oxetan-3-yl)-1H-1,2,3-triazol-4-yl)-N,N-dimethylpyridin-3-amine |
| 150 | (R)-N-(cyclobutylmethyl)-1-(6-(3-(4-(5-methoxypyridin-3-yl)-1H-1,2,3-triazol-1-yl)oxetan-3-yl)pyridin-3-yl)piperidin-3-amine |
| 151 | 4-((R)-3-((cyclobutylmethyl)amino)piperidin-1-yl)-1-(1-(4-(5-(ethyl(methyl)amino)pyridin-3-yl)-1H-1,2,3-triazol-1-yl)ethyl)pyridin-2(1H)-one |
| 152 | 1-(1-(4-(5-bromopyridin-3-yl)-1H-1,2,3-triazol-1-yl)ethyl)-4-((R)-3-((cyclobutylmethyl)amino)piperidin-1-yl)pyridin-2(1H)-one |
| 153 | 4-((R)-3-((cyclobutylmethyl)amino)piperidin-1-yl)-1-(1-(4-(5-(3-methyl-2-oxoimidazolidin-1-yl)pyridin-3-yl)-1H-1,2,3-triazol-1-yl)ethyl)pyridin-2(1H)-one |
| 154 | 4-((R)-3-((cyclobutylmethyl)amino)piperidin-1-yl)-1-(1-(4-(5-(methyl(2,2,2-trifluoroethyl)amino)pyridin-3-yl)-1H-1,2,3-triazol-1-yl)ethyl)pyridin-2(1H)-one |
| 155 | (R)-5-(1-(1-(4-(3-((cyclobutylmethyl)amino)piperidin-1-yl)phenyl)vinyl)-1H-1,2,3-triazol-4-yl)-N,N-dimethylpyridin-3-amine |
| 156 | 4-((R)-3-((cyclobutylmethyl)amino)piperidin-1-yl)-1-(1-(5-(dimethylamino)pyridin-3-yl)-1H-pyrazol-4-yl)ethyl)pyridin-2(1H)-one |
| 157 | 2-(6-((R)-3-((cyclobutylmethyl)amino)piperidin-1-yl)pyridazin-3-yl)-N-(5-(dimethylamino)pyridin-3-yl)propanamide |
| 158 | 4-((R)-3-((cyclobutylmethyl)amino)piperidin-1-yl)-1-(1-(4-(5-(isopropylamino)pyridin-3-yl)-1H-1,2,3-triazol-1-yl)ethyl)pyridin-2(1H)-one |
| 159 | 4-((R)-3-((cyclobutylmethyl)amino)piperidin-1-yl)-1-(1-(4-(5-(2-oxopyrrolidin-1-yl)pyridin-3-yl)-1H-1,2,3-triazol-1-yl)ethyl)pyridin-2(1H)-one |
| 160 | 4-((R)-3-((cyclobutylmethyl)amino)piperidin-1-yl)-1-(1-(4-(5-(pyrrolidin-1-yl)pyridin-3-yl)-1H-1,2,3-triazol-1-yl)ethyl)pyridin-2(1H)-one |
| 161 | 1-(1-(4-(5-(azetidin-1-yl)pyridin-3-yl)-1H-1,2,3-triazol-1-yl)ethyl)-4-((R)-3-((cyclobutylmethyl)amino)piperidin-1-yl)pyridin-2(1H)-one |
| 162 | 2-(4-((R)-3-((cyclobutylmethyl)amino)piperidin-1-yl)-2-oxopyridin-1(2H)-yl)-N-(5-(dimethylamino)pyridin-3-yl)propanamide |
| 163 | (R)-4-(3-((cyclopropylmethyl)amino)piperidin-1-yl)-1-((4-(5-(dimethylamino)pyridin-3-yl)-1H-1,2,3-triazol-1-yl)methyl)-6-methylpyridin-2(1H)-one |
| 164 | 4-((R)-3-((cyclobutylmethyl)amino)piperidin-1-yl)-1-(1-(4-(6-(dimethylamino)pyrazin-2-yl)-1H-1,2,3-triazol-1-yl)ethyl)pyridin-2(1H)-one |
| 165 | 1-(5-((R)-3-((cyclobutylmethyl)amino)piperidin-1-yl)pyridin-2-yl)-1-(2-(5-methoxypyridin-3-yl)thiazol-5-yl)ethan-1-ol |
| 166 | 4-((R)-3-((cyclobutylmethyl)amino)piperidin-1-yl)-1-(1-(4-(5-(dimethylamino)pyridin-3-yl)-1H-imidazol-1-yl)ethyl)pyridin-2(1H)-one |
| 167 | (3R)-N-(cyclobutylmethyl)-1-(6-(1-(2-(6-methoxy-1H-indazol-4-yl)thiazol-5-yl)ethyl)pyridin-3-yl)piperidin-3-amine |
| 168 | 4-((R)-3-((cyclobutylmethyl)amino)piperidin-1-yl)-1-(1-(4-(5-(4-methylpiperazin-1-yl)pyridin-3-yl)-1H-1,2,3-triazol-1-yl)ethyl)pyridin-2(1H)-one |
| 169 | 5-(5-(1-(5-((R)-3-((cyclobutylmethyl)amino)piperidin-1-yl)pyridin-2-yl)ethyl)thiazol-2-yl)-N,N-dimethylpyridin-3-amine |
| 170 | 2-(1-(1-(4-((R)-3-((cyclobutylmethyl)amino)piperidin-1-yl)-2-oxopyridin-1(2H)-yl)ethyl)-1H-imidazol-4-yl)-4H-pyrido[1,2-a]pyrimidin-4-one |

| | |
|---|---|
| 171 | 4-((R)-3-((cyclobutylmethyl)amino)piperidin-1-yl)-1-(1-(5-(5-(dimethylamino)pyridin-3-yl)-1,3,4-thiadiazol-2-yl)ethyl)pyridin-2(1H)-one |
| 172 | 4-((R)-3-((cyclobutylmethyl)amino)piperidin-1-yl)-1-(1-(4-(5-(2-methylpyrrolidin-1-yl)pyridin-3-yl)-1H-1,2,3-triazol-1-yl)ethyl)pyridin-2(1H)-one |
| 173 | 5-(1-(1-(6-((R)-3-((cyclobutylmethyl)amino)piperidin-1-yl)pyridazin-3-yl)ethyl)-1H-imidazol-4-yl)-N,N-dimethylpyridin-3-amine |
| 174 | (R)-4-(3-((cyclopropylmethyl)amino)piperidin-1-yl)-1-((4-(5-(dimethylamino)pyridin-3-yl)-1H-1,2,3-triazol-1-yl)methyl)pyridin-2(1H)-one |
| 175 | (R)-3-(5-(3-((cyclopropylmethyl)amino)piperidin-1-yl)pyridin-2-yl)-N-(5-(dimethylamino)pyridin-3-yl)oxetane-3-carboxamide |
| 176 | 4-((R)-3-((cyclopropylmethyl)amino)piperidin-1-yl)-1-(1-(4-(5-(pyrrolidin-1-yl)pyridin-3-yl)-1H-1,2,3-triazol-1-yl)ethyl)pyridin-2(1H)-one |
| 177 | 4-((R)-3-((cyclobutylmethyl)amino)piperidin-1-yl)-1-(1-(4-(5-(3-methylazetidin-1-yl)pyridin-3-yl)-1H-1,2,3-triazol-1-yl)ethyl)pyridin-2(1H)-one |
| 178 | 4-((R)-3-((cyclobutylmethyl)amino)piperidin-1-yl)-1-(1-(4-(5-(piperidin-1-yl)pyridin-3-yl)-1H-1,2,3-triazol-1-yl)ethyl)pyridin-2(1H)-one |
| 179 | 4-((R)-3-((cyclobutylmethyl)amino)piperidin-1-yl)-1-(1-(5-(5-(dimethylamino)pyridin-3-yl)-2H-tetrazol-2-yl)ethyl)pyridin-2(1H)-one |
| 180 | 4-((R)-3-((cyclopropylmethyl)amino)piperidin-1-yl)-1-(1-(4-(6-(pyrrolidin-1-yl)pyrazin-2-yl)-1H-1,2,3-triazol-1-yl)ethyl)pyridin-2(1H)-one |
| 181 | (3R)-N-(cyclobutylmethyl)-1-(6-(1-(2-(5-methoxypyridin-3-yl)thiazol-5-yl)ethyl)pyridin-3-yl)piperidin-3-amine |
| 182 | (3R)-N-(cyclobutylmethyl)-1-(6-(1-(4-(5-methoxypyridin-3-yl)-1H-imidazol-1-yl)ethyl)pyridazin-3-yl)piperidin-3-amine |
| 183 | (R)-5-(1-((6-(3-((cyclopropylmethyl)amino)piperidin-1-yl)pyridazin-3-yl)methyl)-1H-1,2,3-triazol-4-yl)-N,N-dimethylpyridin-3-amine |
| 184 | (R)-5-(1-(3-(5-(3-((cyclopropylmethyl)amino)piperidin-1-yl)pyridin-2-yl)oxetan-3-yl)-1H-1,2,3-triazol-4-yl)-N,N-dimethylpyridin-3-amine |
| 185 | (R)-N-(cyclopropylmethyl)-1-(6-(3-(4-(6-(pyrrolidin-1-yl)pyrazin-2-yl)-1H-1,2,3-triazol-1-yl)oxetan-3-yl)pyridin-3-yl)piperidin-3-amine |
| 186 | 4-((R)-3-((cyclopropylmethyl)amino)piperidin-1-yl)-1-(1-(4-(6-(dimethylamino)pyrazin-2-yl)-1H-1,2,3-triazol-1-yl)ethyl)pyridin-2(1H)-one |
| 187 | (3R)-N-(cyclobutylmethyl)-1-(6-(1-(4-(5-ethoxypyridin-3-yl)-1H-1,2,3-triazol-1-yl)ethyl)pyridazin-3-yl)piperidin-3-amine |
| 188 | 4-((R)-3-((cyclobutylmethyl)amino)piperidin-1-yl)-1-(1-(4-(6-methoxy-1H-indazol-4-yl)-1H-imidazol-1-yl)ethyl)pyridin-2(1H)-one |
| 189 | 5-(1-(1-(4-((R)-3-((cyclobutylmethyl)amino)piperidin-1-yl)phenyl)ethyl)-1H-1,2,3-triazol-4-yl)-N,N-dimethylpyridin-3-amine |
| 190 | (3R)-N-(cyclobutylmethyl)-1-(6-(1-(5-(5-methoxypyridin-3-yl)-2H-tetrazol-2-yl)ethyl)pyridazin-3-yl)piperidin-3-amine |
| 191 | 1-(1-(4-(5-(2-oxa-6-azaspiro[3.3]heptan-6-yl)pyridin-3-yl)-1H-1,2,3-triazol-1-yl)ethyl)-4-((R)-3-((cyclobutylmethyl)amino)piperidin-1-yl)pyridin-2(1H)-one |
| 192 | (R)-6-(1-(3-(5-(3-((cyclopropylmethyl)amino)piperidin-1-yl)pyridin-2-yl)oxetan-3-yl)-1H-1,2,3-triazol-4-yl)-N,N-dimethylpyrazin-2-amine |
| 193 | 1-(1-(4-(5-(2-azaspiro[3.3]heptan-2-yl)pyridin-3-yl)-1H-1,2,3-triazol-1-yl)ethyl)-4-((R)-3-((cyclobutylmethyl)amino)piperidin-1-yl)pyridin-2(1H)-one |
| 194 | (R)-N-cyclopropylmethyl)-1-(6-(3-(4-(5-(pyrrolidin-1-yl)pyridin-3-yl)-1H-1,2,3-triazol-1-yl)oxetan-3-yl)pyridin-3-yl)piperidin-3-amine |
| 195 | (R)-3-(5-(3-((cyclopropylmethyl)amino)piperidin-1-yl)pyridin-2-yl)-N-(5-(pyrrolidin-1-yl)pyridin-3-yl)oxetane-3-carboxamide |
| 196 | 4-((R)-3-((cyclopropylmethyl)amino)piperidin-1-yl)-1-(1-(1-(5-(dimethylamino)pyridin-3-yl)-1H-pyrazol-4-yl)ethyl)pyridin-2(1H)-one |
| 197 | 4-((R)-3-((cyclopropylmethyl)amino)piperidin-1-yl)-1-(1-(4-(5-(3,3-difluoroazetidin-1-yl)pyridin-3-yl)-1H-1,2,3-triazol-1-yl)ethyl)pyridin-2(1H)-one |
| 198 | 4-((R)-3-((cyclobutylmethyl)amino)piperidin-1-yl)-1-(1-(4-(5-(dimethylamino)pyridazin-3-yl)-1H-1,2,3-triazol-1-yl)ethyl)pyridin-2(1H)-one |
| 199 | 4-((R)-3-((cyclobutylmethyl)amino)piperidin-1-yl)-1-(1-(4-(5-(3-methoxyazetidin-1-yl)pyridin-3-yl)-1H-1,2,3-triazol-1-yl)ethyl)pyridin-2(1H)-one |
| 200 | 4-((R)-3-((cyclobutylmethyl)amino)piperidin-1-yl)-1-(1-(4-(5-(2,2,2-trifluoroethoxy)pyridin-3-yl)-1H-1,2,3-triazol-1-yl)ethyl)pyridin-2(1H)-one |
| 201 | (R)-4-(3-((cyclopropylmethyl)amino)piperidin-1-yl)-1-((4-(6-(pyrrolidin-1-yl)pyrazin-2-yl)-1H-1,2,3-triazol-1-yl)methyl)pyridin-2(1H)-one |
| 202 | (R)-N-(cyclopropylmethyl)-1-(6-(3-(4-(5-(pyrrolidin-1-yl)pyridazin-3-yl)-1H-1,2,3-triazol-1-yl)oxetan-3-yl)pyridin-3-yl)piperidin-3-amine |
| 203 | 4-((R)-3-((cyclopropylmethyl)amino)piperidin-1-yl)-1-(1-(4-(5-(ethyl(methyl)amino)pyridin-3-yl)-1H-1,2,3-triazol-1-yl)ethyl)pyridin-2(1H)-one |

| | |
|---|---|
| 204 | 4-((R)-3-((cyclobutylmethyl)amino)piperidin-1-yl)-1-(1-(3-(5-methoxypyridin-3-yl)isothiazol-5-yl)ethyl)pyridin-2(1H)-one |
| 205 | 4-((R)-3-((cyclopropylmethyl)amino)piperidin-1-yl)-1-(1-(4-(5-((2-hydroxyethyl)amino)pyridin-3-yl)-1H-1,2,3-triazol-1-yl)ethyl)pyridin-2(1H)-one |
| 206 | 4-((R)-3-((cyclopropylmethyl)amino)piperidin-1-yl)-1-(1-(4-(5-(pyrrolidin-1-yl)pyridazin-3-yl)-1H-1,2,3-triazol-1-yl)ethyl)pyridin-2(1H)-one |
| 207 | (R)-N-(cyclopropylmethyl)-1-(5-(3-(4-(6-(pyrrolidin-1-yl)pyrazin-2-yl)-1H-1,2,3-triazol-1-yl)oxetan-3-yl)pyridin-2-yl)piperidin-3-amine |
| 208 | 2-(4-((R)-3-((cyclobutylmethyl)amino)piperidin-1-yl)-2-oxopyridin-1(2H)-yl)-N-(5-(pyrrolidin-1-yl)pyridin-3-yl)propanamide |
| 209 | 4-((R)-3-((cyclopropylmethyl)amino)piperidin-1-yl)-1-(1-(4-(5-(3-(difluoromethyl)azetidin-1-yl)pyridin-3-yl)-1H-1,2,3-triazol-1-yl)ethyl)pyridin-2(1H)-one |
| 210 | 4-((R)-3-((cyclobutylmethyl)amino)piperidin-1-yl)-1-(1-(5-(6-methoxy-1H-indazol-4-yl)-2H-tetrazol-2-yl)ethyl)pyridin-2(1H)-one |
| 211 | 4-((R)-3-((cyclopropylmethyl)amino)piperidin-1-yl)-1-(1-(4-(5-(1,1-difluoro-5-azaspiro[2.3]hexan-5-yl)pyridin-3-yl)-1H-1,2,3-triazol-1-yl)ethyl)pyridin-2(1H)-one |
| 212 | (R)-N-(cyclopropylmethyl)-1-(6-(3-(4-(5-(pyrrolidin-1-yl)pyridin-3-yl)-1H-1,2,3-triazol-1-yl)oxetan-3-yl)pyridazin-3-yl)piperidin-3-amine |
| 213 | (R)-N-(cyclopropylmethyl)-1-(6-(3-(4-(6-(pyrrolidin-1-yl)pyrazin-2-yl)-1H-1,2,3-triazol-1-yl)oxetan-3-yl)pyridazin-3-yl)piperidin-3-amine |
| 214 | (R)-N-(cyclopropylmethyl)-1-(6-(3-(4-(6-(3,3-dimethylpyrrolidin-1-yl)pyrazin-2-yl)-1H-1,2,3-triazol-1-yl)oxetan-3-yl)pyridin-3-yl)piperidin-3-amine |
| 215 | (R)-N-(cyclopropylmethyl)-1-(6-(3-(4-(6-(3,3-difluoropyrrolidin-1-yl)pyrazin-2-yl)-1H-1,2,3-triazol-1-yl)oxetan-3-yl)pyridin-3-yl)piperidin-3-amine |
| 216 | (3R)-1-(6-(3-(4-(6-(3-azabicyclo[3.1.0]hexan-3-yl)pyrazin-2-yl)-1H-1,2,3-triazol-1-yl)oxetan-3-yl)pyridin-3-yl)-N-(cyclopropylmethyl)piperidin-3-amine |
| 217 | (R)-3-(5-(3-((cyclopropylmethyl)amino)piperidin-1-yl)pyridin-2-yl)-N-(4-oxo-4H-pyrido[1,2-a]pyrimidin-2-yl)oxetane-3-carboxamide |
| 218 | 1-(1-(4-(5-(1H-imidazol-1-yl)pyridin-3-yl)-1H-1,2,3-triazol-1-yl)ethyl)-4-((R)-3-((cyclopropylmethyl)amino)piperidin-1-yl)pyridin-2(1H)-one |
| 219 | 4-((R)-3-((cyclopropylmethyl)amino)piperidin-1-yl)-1-(1-(1-(5-(pyrrolidin-1-yl)pyridazin-3-yl)-1H-pyrazol-4-yl)ethyl)pyridin-2(1H)-one |
| 220 | 4-((R)-3-((cyclopropylmethyl)amino)piperidin-1-yl)-1-(1-(1-(6-(pyrrolidin-1-yl)pyrazin-2-yl)-1H-pyrazol-4-yl)ethyl)pyridin-2(1H)-one |
| 221 | (R)-1-(6-(3-(4-(6-(2-oxa-6-azaspiro[3.3]heptan-6-yl)pyrazin-2-yl)-1H-1,2,3-triazol-1-yl)oxetan-3-yl)pyridin-3-yl)-N-(cyclopropylmethyl)piperidin-3-amine |
| 222 | (R)-1-(6-(3-(4-(6-(5-azaspiro[2.4]heptan-5-yl)pyrazin-2-yl)-1H-1,2,3-triazol-1-yl)oxetan-3-yl)pyridin-3-yl)-N-(cyclopropylmethyl)piperidin-3-amine |
| 223 | (R)-N-(cyclopropylmethyl)-1-(5-(3-(4-(5-(pyrrolidin-1-yl)pyridin-3-yl)-1H-1,2,3-triazol-1-yl)oxetan-3-yl)pyridin-2-yl)piperidin-3-amine |
| 224 | 4-((R)-3-((cyclopropylmethyl)amino)piperidin-1-yl)-1-(1-(1-(5-(dimethylamino)pyridazin-3-yl)-1H-pyrazol-4-yl)ethyl)pyridin-2(1H)-one |
| 225 | 4-((R)-3-((cyclopropylmethyl)amino)piperidin-1-yl)-1-(1-(1-(6-(dimethylamino)pyrazin-2-yl)-1H-pyrazol-4-yl)ethyl)pyridin-2(1H)-one |
| 226 | 4-((R)-3-((cyclopropylmethyl)amino)piperidin-1-yl)-1-(1-(4-(6-(pyrrolidin-1-yl)pyrazin-2-yl)-1H-imidazol-1-yl)ethyl)pyridin-2(1H)-one |
| 227 | 4-((R)-3-((cyclopropylmethyl)amino)piperidin-1-yl)-1-(1-(4-(6-(3,3-difluoropyrrolidin-1-yl)pyrazin-2-yl)-1H-1,2,3-triazol-1-yl)ethyl)pyridin-2(1H)-one |
| 228 | 4-((R)-3-((cyclopropylmethyl)amino)piperidin-1-yl)-1-(1-(5-(6-(pyrrolidin-1-yl)pyrazin-2-yl)-1,3,4-thiadiazol-2-yl)ethyl)pyridin-2(1H)-one |
| 229 | 4-((R)-3-((cyclopropylmethyl)amino)piperidin-1-yl)-1-(1-(4-(6-(dimethylamino)pyrazin-2-yl)-1H-imidazol-1-yl)ethyl)pyridin-2(1H)-one |
| 230 | 4-((R)-3-((cyclopropylmethyl)amino)piperidin-1-yl)-1-(1-(4-(6-(3,3-dimethylpyrrolidin-1-yl)pyrazin-2-yl)-1H-1,2,3-triazol-1-yl)ethyl)pyridin-2(1H)-one |
| 231 | 4-((R)-3-((cyclopropylmethyl)amino)piperidin-1-yl)-1-(1-(5-(6-(dimethylamino)pyrazin-2-yl)-1,3,4-thiadiazol-2-yl)ethyl)pyridin-2(1H)-one |
| 232 | 4-((R)-3-((cyclopropylmethyl)amino)piperidin-1-yl)-1-(1-(4-(5-methoxypyridin-3-yl)-1H-1,2,3-triazol-1-yl)ethyl)pyridin-2(1H)-one |
| 233 | 4-((R)-3-((cyclopropylmethyl)amino)piperidin-1-yl)-1-(1-(2-(6-(pyrrolidin-1-yl)pyrazin-2-yl)thiazol-5-yl)ethyl)pyridin-2(1H)-one |
| 234 | 1-(1-(4-(6-(3-azabicyclo[3.1.0]hexan-3-yl)pyrazin-2-yl)-1H-1,2,3-triazol-1-yl)ethyl)-4-((R)-3-((cyclopropylmethyl)amino)piperidin-1-yl)pyridin-2(1H)-one |
| 235 | 1-(1-(4-(6-(5-azaspiro[2.4]heptan-5-yl)pyrazin-2-yl)-1H-1,2,3-triazol-1-yl)ethyl)-4-((R)-3-((cyclopropylmethyl)amino)piperidin-1-yl)pyridin-2(1H)-one |
| 236 | 4-((R)-3-((cyclopropylmethyl)amino)piperidin-1-yl)-1-(1-(4-(5-(methyl(trifluoromethyl)amino)pyridin-3-yl)-1H-1,2,3-triazol-1-yl)ethyl)pyridin-2(1H)-one |

-continued 237 1-(1-(4-(6-(2-oxa-6-azaspiro[3.3]heptan-6-yl)pyrazin-2-yl)-1H-1,2,3-triazol-1-yl)ethyl)-4-((R)-3-((cyclopropylmethyl)amino)piperidin-1-yl)pyridin-2(1H)-one
238 4-((R)-3-((cyclopropylmethyl)amino)piperidin-1-yl)-1-(1-(4-(6-((R)-3-methylpyrrolidin-1-yl)pyrazin-2-yl)-1H-1,2,3-triazol-1-yl)ethyl)pyridin-2(1H)-one
239 (R)-3-(5-(3-((cyclobutylmethyl)amino)piperidin-1-yl)pyridin-2-yl)-N-(4-oxo-4H-pyrido[1,2-a]pyrimidin-2-yl)oxetane-3-carboxamide
240 4-((R)-3-((cyclopropylmethyl)amino)piperidin-1-yl)-1-(1-(4-(6-((S)-3-methylpyrrolidin-1-yl)pyrazin-2-yl)-1H-1,2,3-triazol-1-yl)ethyl)pyridin-2(1H)-one
241 4-((R)-3-((cyclopropylmethyl)amino)piperidin-1-yl)-1-(1-(4-(6-((S)-3-fluoropyrrolidin-1-yl)pyrazin-2-yl)-1H-1,2,3-triazol-1-yl)ethyl)pyridin-2(1H)-one
242 4-((R)-3-((cyclopropylmethyl)amino)piperidin-1-yl)-1-(1-(2-(6-(pyrrolidin-1-yl)pyrazin-2-yl)oxazol-5-yl)ethyl)pyridin-2(1H)-one
243 4-((R)-3-((cyclopropylmethyl)amino)piperidin-1-yl)-1-(1-(4-(5-(dimethylamino)pyridazin-3-yl)-1H-imidazol-1-yl)ethyl)pyridin-2(1H)-one
244 (R)-N-(cyclopropylmethyl)-1-(6-(3-(4-(6-((R)-3-methylpyrrolidin-1-yl)pyrazin-2-yl)-1H-1,2,3-triazol-1-yl)oxetan-3-yl)pyridin-3-yl)piperidin-3-amine
245 4-((R)-3-((cyclopropylmethyl)amino)piperidin-1-yl)-1-(1-(4-(6-((R)-3-fluoropyrrolidin-1-yl)pyrazin-2-yl)-1H-1,2,3-triazol-1-yl)ethyl)pyridin-2(1H)-one
246 4-((R)-3-((cyclopropylmethyl)amino)piperidin-1-yl)-1-(1-(4-(6-(3-methoxyazetidin-1-yl)pyrazin-2-yl)-1H-1,2,3-triazol-1-yl)ethyl)pyridin-2(1H)-one
247 1-(1-(4-(6-(5-azaspiro[2.3]hexan-5-yl)pyrazin-2-yl)-1H-1,2,3-triazol-1-yl)ethyl)-4-((R)-3-((cyclopropylmethyl)amino)piperidin-1-yl)pyridin-2(1H)-one
248 (R)-3-(5-(3-((cyclopropylmethyl)amino)piperidin-1-yl)pyridin-2-yl)-N-(6-(pyrrolidin-1-yl)pyrazin-2-yl)oxetane-3-carboxamide
249 (R)-N-(cyclopropylmethyl)-1-(6-(3-(4-(5-methoxypyridin-3-yl)-1H-1,2,3-triazol-1-yl)oxetan-3-yl)pyridin-3-yl)piperidin-3-amine
250 (R)-N-(cyclopropylmethyl)-1-(6-(3-(4-(6-(pyrrolidin-1-yl)pyrazin-2-yl)-1H-imidazol-1-yl)oxetan-3-yl)pyridin-3-yl)piperidin-3-amine
251 2-(6-((R)-3-((cyclopropylmethyl)amino)piperidin-1-yl)pyridazin-3-yl)-N-(5-(pyrrolidin-1-yl)pyridin-3-yl)propanamide
252 4-((R)-3-((cyclopropylmethyl)amino)piperidin-1-yl)-1-(1-(4-(5-(pyrrolidin-1-yl)pyridin-3-yl)-1H-imidazol-1-yl)ethyl)pyridin-2(1H)-one
253 4-((R)-3-((cyclopropylmethyl)amino)piperidin-1-yl)-1-(1-(1-(5-(pyrrolidin-1-yl)pyridin-3-yl)-1H-pyrazol-4-yl)ethyl)pyridin-2(1H)-one
254 4-((R)-3-((cyclopropylmethyl)amino)piperidin-1-yl)-1-(1-(4-(6-(1,1-difluoro-5-azaspiro[2.3]hexan-5-yl)pyrazin-2-yl)-1H-1,2,3-triazol-1-yl)ethyl)pyridin-2(1H)-one
255 4-((R)-3-((cyclopropylmethyl)amino)piperidin-1-yl)-1-(1-(4-(6-methylpyrazin-2-yl)-1H-1,2,3-triazol-1-yl)ethyl)pyridin-2(1H)-one
256 (R)-N-(cyclopropylmethyl)-1-(6-(3-(4-(5-cyclopropylpyridin-3-yl)-1H-1,2,3-triazol-1-yl)oxetan-3-yl)pyridin-3-yl)piperidin-3-amine
257 (3R)-N-(cyclobutylmethyl)-1-(6-(1-(4-(5-(pyrrolidin-1-yl)pyridin-3-yl)-1H-1,2,3-triazol-1-yl)ethyl)pyridazin-3-yl)piperidin-3-amine
258 (3R)-N-(cyclobutylmethyl)-1-(6-(1-(4-(6-methoxypyrazin-2-yl)-1H-1,2,3-triazol-1-yl)ethyl)pyridazin-3-yl)piperidin-3-amine
259 (3R)-N-(cyclopropylmethyl)-1-(6-(1-(4-(6-(pyrrolidin-1-yl)pyrazin-2-yl)-1H-1,2,3-triazol-1-yl)ethyl)pyridin-3-yl)piperidin-3-amine
260 6-(1-(1-(5-((R)-3-((cyclopropylmethyl)amino)piperidin-1-yl)pyridin-2-yl)ethyl)-1H-1,2,3-triazol-4-yl)-N,N-dimethylpyrazin-2-amine
261 (3R)-N-(cyclopropylmethyl)-1-(6-(1-(4-(6-methoxypyrazin-2-yl)-1H-1,2,3-triazol-1-yl)ethyl)pyridin-3-yl)piperidin-3-amine
262 (R)-3-(5-(3-((cyclobutylmethyl)amino)piperidin-1-yl)pyridin-2-yl)-N-(6-(pyrrolidin-1-yl)pyrazin-2-yl)oxetane-3-carboxamide
263 (R)-3-(5-(3-(((3-fluorobicyclo[1.1.1]pentan-1-yl)methyl)amino)piperidin-1-yl)pyridin-2-yl)-N-(4-oxo-4H-pyrido[1,2-a]pyrimidin-2-yl)oxetane-3-carboxamide
264 2-(5-((R)-3-((cyclobutylmethyl)amino)piperidin-1-yl)pyridin-2-yl)-N-(5-(pyrrolidin-1-yl)pyridin-3-yl)propanamide
265 2-(5-((R)-3-((cyclobutylmethyl)amino)piperidin-1-yl)pyridin-2-yl)-N-(4-oxo-4H-pyrido[1,2-a]pyrimidin-2-yl)propanamide
266 4-((R)-3-((cyclopropylmethyl)amino)piperidin-1-yl)-1-(1-(4-(5-(dimethylamino)pyridin-3-yl)-1H-imidazol-1-yl)ethyl)pyridin-2(1H)-one
267 (R)-N-(cyclobutylmethyl)-1-(6-(3-(4-(5-methoxypyridin-3-yl)-1H-imidazol-1-yl)oxetan-3-yl)pyridin-3-yl)piperidin-3-amine
268 (R)-3-(5-(3-((cyclobutylmethyl)amino)piperidin-1-yl)pyridin-2-yl)-N-(6-cyclopentylpyrazin-2-yl)oxetane-3-carboxamide
269 (R)-3-(5-(3-(((3-fluorobicyclo[1.1.1]pentan-1-yl)methyl)amino)piperidin-1-yl)pyridin-2-yl)-N-(6-(pyrrolidin-1-yl)pyrazin-2-yl)oxetane-3-carboxamide
270 N-(6-(3-azabicyclo[3.1.0]hexan-3-yl)pyrazin-2-yl)-3-(5-((R)-3-((cyclobutylmethyl)amino)piperidin-1-yl)pyridin-2-yl)oxetane-3-carboxamide -continued 271 (R)-2-(5-(3-((cyclobutylmethyl)amino)piperidin-1-yl)pyridin-2-yl)-N-(5-(pyrrolidin-1-yl)pyridin-3-yl)acetamide
272 (R)-3-(5-(3-((cyclobutylmethyl)(methyl)amino)piperidin-1-yl)pyridin-2-yl)-N-(4-oxo-4H-pyrido[1,2-a]pyrimidin-2-yl)oxetane-3-carboxamide
273 (R)-3-(5-(3-((cyclobutylmethyl)amino)piperidin-1-yl)pyridin-2-yl)-N-(6-methoxy-1H-indazol-4-yl)oxetane-3-carboxamide
274 2-(5-((R)-3-((cyclobutylmethyl)amino)piperidin-1-yl)pyridin-2-yl)-N-(6-(pyrrolidin-1-yl)pyrazin-2-yl)propanamide
275 2-(6-((R)-3-((cyclobutylmethyl)amino)piperidin-1-yl)pyridazin-3-yl)-N-(4-oxo-4H-pyrido[1,2-a]pyrimidin-2-yl)propanamide
276 (3R)-N-(cyclobutylmethyl)-1-(6-(1-(4-(5-methoxypyridin-3-yl)-1H-imidazol-1-yl)ethyl)pyridin-3-yl)piperidin-3-amine
277 (R)-2-(5-(3-((cyclobutylmethyl)amino)piperidin-1-yl)pyridin-2-yl)-N-(6-(pyrrolidin-1-yl)pyrazin-2-yl)acetamide
278 (R)-3-(4-(3-((cyclobutylmethyl)amino)piperidin-1-yl)phenyl)-N-(4-oxo-4H-pyrido[1,2-a]pyrimidin-2-yl)oxetane-3-carboxamide
279 2-(6-((R)-3-((cyclobutylmethyl)amino)piperidin-1-yl)pyridazin-3-yl)-N-(6-(pyrrolidin-1-yl)pyrazin-2-yl)propanamide
280 (3R)-N-(cyclobutylmethyl)-1-(6-(1-(4-(6-(pyrrolidin-1-yl)pyrazin-2-yl)-1H-1,2,3-triazol-1-yl)ethyl)pyridin-3-yl)piperidin-3-amine
281 (R)-3-(4-(3-((cyclobutylmethyl)amino)piperidin-1-yl)phenyl)-N-(6-(pyrrolidin-1-yl)pyrazin-2-yl)oxetane-3-carboxamide
282 (R)-N-(cyclobutylmethyl)-1-(6-((4-(6-(pyrrolidin-1-yl)pyrazin-2-yl)-1H-1,2,3-triazol-1-yl)methyl)pyridin-3-yl)piperidin-3-amine
283 (R)-N-(cyclobutylmethyl)-1-(6-(3-(4-(6-cyclopropylpyrazin-2-yl)-1H-1,2,3-triazol-1-yl)oxetan-3-yl)pyridin-3-yl)piperidin-3-amine
284 (3R)-1-(6-(1-(4-(6-(3-azabicyclo[3.1.0]hexan-3-yl)pyrazin-2-yl)-1H-1,2,3-triazol-1-yl)ethyl)pyridazin-3-yl)-N-(cyclobutylmethyl)piperidin-3-amine
285 (3R)-N-(cyclobutylmethyl)-1-(6-(1-(4-(6-(pyrrolidin-1-yl)pyrazin-2-yl)-1H-1,2,3-triazol-1-yl)ethyl)pyridazin-3-yl)piperidin-3-amine
286 (3R)-1-(6-(1-(4-(6-(3-azabicyclo[3.1.0]hexan-3-yl)pyrazin-2-yl)-1H-1,2,3-triazol-1-yl)ethyl)pyridin-3-yl)-N-(cyclobutylmethyl)piperidin-3-amine
287 (R)-N-(cyclobutylmethyl)-1-(4-((4-(6-(pyrrolidin-1-yl)pyrazin-2-yl)-1H-1,2,3-triazol-1-yl)methyl)phenyl)piperidin-3-amine
288 (3R)-1-(4-((4-(6-(3-azabicyclo[3.1.0]hexan-3-yl)pyrazin-2-yl)-1H-1,2,3-triazol-1-yl)methyl)phenyl)-N-(cyclobutylmethyl)piperidin-3-amine
289 (R)-1-(6-(3-(4-(6-(1H-pyrazol-1-yl)pyrazin-2-yl)-1H-1,2,3-triazol-1-yl)oxetan-3-yl)pyridin-3-yl)-N-(cyclobutylmethyl)piperidin-3-amine
290 (R)-N-(cyclobutylmethyl)-1-(6-(3-(4-(6-(pyrrolidin-1-yl)pyrazin-2-yl)-1H-1,2,3-triazol-1-yl)oxetan-3-yl)pyridin-3-yl)piperidin-3-amine
291 (3R)-1-(6-(3-(4-(6-(3-azabicyclo[3.1.0]hexan-3-yl)pyrazin-2-yl)-1H-1,2,3-triazol-1-yl)oxetan-3-yl)pyridin-3-yl)-N-(cyclobutylmethyl)piperidin-3-amine
292 (3R)-N-(cyclobutylmethyl)-1-(6-(1-(4-(6-cyclopropylpyrazin-2-yl)-1H-1,2,3-triazol-1-yl)ethyl)pyridin-3-yl)piperidin-3-amine
293 (3R)-1-(6-(1-(4-(6-(1H-pyrazol-1-yl)pyrazin-2-yl)-1H-1,2,3-triazol-1-yl)ethyl)pyridin-3-yl)-N-(cyclobutylmethyl)piperidin-3-amine
294 2-(4-((R)-3-((cyclobutylmethyl)amino)piperidin-1-yl)phenyl)-N-(6-(pyrrolidin-1-yl)pyrazin-2-yl)propanamide
295 (R)-1-(6-(3-(4-(6-(1H-pyrrol-1-yl)pyrazin-2-yl)-1H-1,2,3-triazol-1-yl)oxetan-3-yl)pyridin-3-yl)-N-(cyclobutylmethyl)piperidin-3-amine
296 (3R)-N-(cyclobutylmethyl)-1-(4-(1-(4-(5-methoxypyridin-3-yl)-1H-imidazol-1-yl)ethyl)phenyl)piperidin-3-amine
297 (R)-3-(5-(3-((cyclobutylmethyl)amino)piperidin-1-yl)pyridin-2-yl)-N-(quinoxalin-2-yl)oxetane-3-carboxamide
298 (R)-3-(5-(3-((cyclobutylmethyl)amino)piperidin-1-yl)-3-fluoropyridin-2-yl)-N-(4-oxo-4H-pyrido[1,2-a]pyrimidin-2-yl)oxetane-3-carboxamide
299 (R)-3-(5-(3-((cyclobutylmethyl)amino)piperidin-1-yl)pyridin-2-yl)-N-(1H-pyrrolo[2,3-b]pyridin-5-yl)oxetane-3-carboxamide
300 (3R)-N-(cyclobutylmethyl)-1-(6-(1-(1-(5-methoxypyridin-3-yl)-1H-pyrazol-4-yl)ethyl)pyridin-3-yl)piperidin-3-amine
301 (R)-N-(cyclobutylmethyl)-1-(4-(3-(4-(6-(pyrrolidin-1-yl)pyrazin-2-yl)-1H-1,2,3-triazol-1-yl)oxetan-3-yl)phenyl)piperidin-3-amine
302 (R)-3-(5-(3-((cyclobutylmethyl)amino)piperidin-1-yl)pyridin-2-yl)-N-(1-oxo-1,2-dihydroisoquinolin-3-yl)oxetane-3-carboxamide
303 (3R)-N-(cyclobutylmethyl)-1-(5-fluoro-6-(1-(4-(6-(pyrrolidin-1-yl)pyrazin-2-yl)-1H-1,2,3-triazol-1-yl)ethyl)pyridin-3-yl)piperidin-3-amine
304 (3R)-N-((3-fluorobicyclo[1.1.1]pentan-1-yl)methyl)-1-(6-(1-(4-(6-(pyrrolidin-1-yl)pyrazin-2-yl)-1H-1,2,3-triazol-1-yl)ethyl)pyridin-3-yl)piperidin-3-amine
305 (3R)-N-((3-fluorobicyclo[1.1.1]pentan-1-yl)methyl)-1-(6-(1-(4-(6-(pyrrolidin-1-yl)pyrazin-2-yl)-1H-1,2,3-triazol-1-yl)ethyl)pyridazin-3-yl)piperidin-3-amine
306 (R)-N-(cyclobutylmethyl)-1-(6-(3-(4-(5-cyclopropylpyridin-3-yl)-1H-1,2,3-triazol-1-yl)oxetan-3-yl)pyridin-3-yl)piperidin-3-amine
307 (R)-1-(6-(3-(4-(5-cyclobutoxypyridin-3-yl)-1H-1,2,3-triazol-1-yl)oxetan-3-yl)pyridin-3-yl)-N-(cyclobutylmethyl)piperidin-3-amine

| | |
|---|---|
| 308 | (R)-N-((3-fluorobicyclo[1.1.1]pentan-1-yl)methyl)-1-(6-(3-(4-(6-(pyrrolidin-1-yl)pyrazin-2-yl)-1H-1,2,3-triazol-1-yl)oxetan-3-yl)pyridin-3-yl)piperidin-3-amine |
| 309 | (3R)-N-(cyclopropylmethyl)-1-(6-(1-(4-(6-(pyrrolidin-1-yl)pyrazin-2-yl)-1H-1,2,3-triazol-1-yl)ethyl)pyridazin-3-yl)piperidin-3-amine |
| 310 | (R)-3-(5-(3-((cyclobutylmethyl)amino)piperidin-1-yl)pyridin-2-yl)-N-(1-methyl-2-oxo-6-(pyrrolidin-1-yl)-1,2-dihydropyridin-4-yl)oxetane-3-carboxamide |
| 311 | (R)-3-(5-(3-((cyclobutylmethyl)amino)piperidin-1-yl)pyridin-2-yl)-N-(5-oxo-5H-thiazolo[3,2-a]pyrimidin-7-yl)oxetane-3-carboxamide |
| 312 | (R)-1-(6-(3-(4-(5-cyclobutylpyridin-3-yl)-1H-1,2,3-triazol-1-yl)oxetan-3-yl)pyridin-3-yl)-N-(cyclopropylmethyl)piperidin-3-amine |
| 313 | (R)-1-(6-(3-(4-(5-cyclopentylpyridin-3-yl)-1H-1,2,3-triazol-1-yl)oxetan-3-yl)pyridin-3-yl)-N-(cyclopropylmethyl)piperidin-3-amine |
| 314 | (R)-4-(1-(3-(5-(3-((cyclopropylmethyl)amino)piperidin-1-yl)pyridin-2-yl)oxetan-3-yl)-1H-1,2,3-triazol-4-yl)-1-methyl-6-(pyrrolidin-1-yl)pyridin-2(1H)-one |
| 315 | (R)-N-(cyclopropylmethyl)-1-(6-(1-(4-(5-cyclopropylpyridin-3-yl)-1H-1,2,3-triazol-1-yl)-3,3-difluorocyclobutyl)pyridin-3-yl)piperidin-3-amine |
| 316 | (R)-2-(1-(3-(5-(3-((cyclopropylmethyl)amino)piperidin-1-yl)pyridin-2-yl)oxetan-3-yl)-1H-1,2,3-triazol-4-yl)-4H-pyrido[1,2-a]pyrimidin-4-one |
| 317 | (3R)-N-(cyclopropylmethyl)-1-(6-(1-(4-(5-cyclopropylpyridin-3-yl)-1H-1,2,3-triazol-1-yl)ethyl)pyridazin-3-yl)piperidin-3-amine |
| 318 | (3R)-N-(cyclopropylmethyl)-1-(6-(1-(4-(5-cyclopropylpyridin-3-yl)-1H-1,2,3-triazol-1-yl)ethyl)-5-methylpyridin-3-yl)piperidin-3-amine |
| 319 | (R)-3-(6-(3-((cyclobutylmethyl)amino)piperidin-1-yl)pyridin-3-yl)-N-(6-(pyrrolidin-1-yl)pyrazin-2-yl)oxetane-3-carboxamide |
| 320 | 4-((R)-3-((cyclopropylmethyl)amino)piperidin-1-yl)-1-(1-(4-(5-cyclopropylpyridin-3-yl)-1H-1,2,3-triazol-1-yl)ethyl)pyridin-2(1H)-one |
| 321 | (R)-3-(6-(3-((cyclopropylmethyl)amino)piperidin-1-yl)pyridin-3-yl)-N-(4-oxo-4H-pyrido[1,2-a]pyrimidin-2-yl)oxetane-3-carboxamide |
| 322 | (R)-3-(6-(3-((cyclobutylmethyl)amino)piperidin-1-yl)pyridin-3-yl)-N-(4-oxo-4H-pyrido[1,2-a]pyrimidin-2-yl)oxetane-3-carboxamide |
| 323 | (R)-N-(cyclopropylmethyl)-1-(6-(3-(4-(6-cyclopropylpyrazin-2-yl)-1H-1,2,3-triazol-1-yl)oxetan-3-yl)pyridin-3-yl)piperidin-3-amine |
| 324 | (R)-3-(6-(3-((cyclopropylmethyl)amino)piperidin-1-yl)pyridin-3-yl)-N-(6-(pyrrolidin-1-yl)pyrazin-2-yl)oxetane-3-carboxamide |
| 325 | (R)-3-(5-(3-((cyclopentylmethyl)amino)piperidin-1-yl)pyridin-2-yl)-N-(4-oxo-4H-pyrido[1,2-a]pyrimidin-2-yl)oxetane-3-carboxamide |
| 326 | (R)-3-(5-(3-(cyclopentylamino)piperidin-1-yl)pyridin-2-yl)-N-(4-oxo-4H-pyrido[1,2-a]pyrimidin-2-yl)oxetane-3-carboxamide |
| 327 | (R)-3-(5-(3-(cyclobutylamino)piperidin-1-yl)pyridin-2-yl)-N-(4-oxo-4H-pyrido[1,2-a]pyrimidin-2-yl)oxetane-3-carboxamide |
| 328 | (R)-N-(4-oxo-4H-pyrido[1,2-a]pyrimidin-2-yl)-3-(5-(3-(((1-(trifluoromethyl)cyclopropyl)methyl)amino)piperidin-1-yl)pyridin-2-yl)oxetane-3-carboxamide |
| 329 | (R)-1-(6-(3-(4-(5-cyclopropylpyridin-3-yl)-1H-1,2,3-triazol-1-yl)oxetan-3-yl)pyridin-3-yl)-N-isobutylpiperidin-3-amine |
| 330 | (R)-3-(5-(3-(((1-fluorocyclopropyl)methyl)amino)piperidin-1-yl)pyridin-2-yl)-N-(4-oxo-4H-pyrido[1,2-a]pyrimidin-2-yl)oxetane-3-carboxamide |
| 331 | (R)-3-(5-(3-(((1-methylcyclopropyl)methyl)amino)piperidin-1-yl)pyridin-2-yl)-N-(4-oxo-4H-pyrido[1,2-a]pyrimidin-2-yl)oxetane-3-carboxamide |
| 332 | (R)-1-(6-(3-(4-(5-cyclopropylpyridin-3-yl)-1H-1,2,3-triazol-1-yl)oxetan-3-yl)pyridin-3-yl)-N-((1-fluorocyclopropyl)methyl)piperidin-3-amine |
| 333 | (R)-1-(6-(3-(4-(5-cyclopropylpyridin-3-yl)-1H-1,2,3-triazol-1-yl)oxetan-3-yl)pyridin-3-yl)-N-((1-methylcyclopropyl)methyl)piperidin-3-amine |
| 334 | (R)-N-cyclobutyl-1-(6-(3-(4-(5-cyclopropylpyridin-3-yl)-1H-1,2,3-triazol-1-yl)oxetan-3-yl)pyridin-3-yl)piperidin-3-amine |
| 335 | (R)-1-(6-(3-(4-(5-cyclopropylpyridin-3-yl)-1H-1,2,3-triazol-1-yl)oxetan-3-yl)pyridin-3-yl)-N-((1-(trifluoromethyl)cyclopropyl)methyl)piperidin-3-amine |
| 336 | 3-(5-((3R)-3-((1-cyclobutylethyl)amino)piperidin-1-yl)pyridin-2-yl)-N-(4-oxo-4H-pyrido[1,2-a]pyrimidin-2-yl)oxetane-3-carboxamide |
| 337 | (R)-N-(4-oxo-4H-pyrido[1,2-a]pyrimidin-2-yl)-3-(5-(3-(((1-(trifluoromethyl)cyclobutyl)methyl)amino)piperidin-1-yl)pyridin-2-yl)oxetane-3-carboxamide |
| 338 | (R)-3-(5-(3-(((3,3-difluorocyclobutyl)methyl)amino)piperidin-1-yl)pyridin-2-yl)-N-(4-oxo-4H-pyrido[1,2-a]pyrimidin-2-yl)oxetane-3-carboxamide |
| 339 | (R)-1-(6-(3-(4-(5-cyclopropylpyridin-3-yl)-1H-1,2,3-triazol-1-yl)oxetan-3-yl)pyridin-3-yl)-N-((1-(trifluoromethyl)cyclobutyl)methyl)piperidin-3-amine |
| 340 | (3R)-N-(cyclopropylmethyl)-1-(6-(1-(4-(6-(pyrrolidin-1-yl)pyrazin-2-yl)-1H-imidazol-1-yl)ethyl)pyridazin-3-yl)piperidin-3-amine |
| 341 | (R)-1-(6-(3-(4-(5-cyclopropylpyridin-3-yl)-1H-1,2,3-triazol-1-yl)oxetan-3-yl)pyridin-3-yl)-N-((3,3-difluorocyclobutyl)methyl)piperidin-3-amine |
| 342 | (3R)-N-(cyclopropylmethyl)-1-(6-(1-(4-(5-cyclopropylpyridin-3-yl)-1H-imidazol-1-yl)ethyl)pyridazin-3-yl)piperidin-3-amine |
| 343 | (R)-N-(cyclopropylmethyl)-1-(6-(3-(4-(5-cyclopropylpyridazin-3-yl)-1H-1,2,3-triazol-1-yl)oxetan-3-yl)pyridin-3-yl)piperidin-3-amine |

344 (R)-N-(cyclopropylmethyl)-1-(6-(3-(5-(5-cyclopropylpyridin-3-yl)-1,3,4-oxadiazol-2-yl)oxetan-3-yl)pyridin-3-yl)piperidin-3-amine
345 (R)-N-(cyclopropylmethyl)-1-(6-(3-(4-(5-(prop-1-yn-1-yl)pyridin-3-yl)-1H-1,2,3-triazol-1-yl)oxetan-3-yl)pyridin-3-yl)piperidin-3-amine
346 (R)-N-(cyclopropylmethyl)-1-(6-(3-(4-(5-(cyclopropylpyridin-3-yl)-1H-1,2,3-triazol-1-yl)oxetan-3-yl)pyridin-3-yl)piperidin-3-amine
347 (3R)-N-(cyclopropylmethyl)-1-(6-(1-(5-(6-(pyrrolidin-1-yl)pyrazin-2-yl)-1,3,4-oxadiazol-2-yl)ethyl)pyridazin-3-yl)piperidin-3-amine
348 (3R)-N-((1-methylcyclopropyl)methyl)-1-(6-(1-(4-(6-(pyrrolidin-1-yl)pyrazin-2-yl)-1H-imidazol-1-yl)ethyl)pyridazin-3-yl)piperidin-3-amine
349 (R)-N-(cyclopropylmethyl)-1-(6-(3-(4-(5-cyclopropylpyridin-3-yl)-1H-1,2,3-triazol-1-yl)azetidin-3-yl)pyridin-3-yl)piperidin-3-amine
350 (R)-N-(cyclopropylmethyl)-1-(6-(3-(4-(5-cyclopropylpyridin-3-yl)-1H-1,2,3-triazol-1-yl)-1-methylazetidin-3-yl)pyridin-3-yl)piperidin-3-amine
351 (S)-N-(cyclopropylmethyl)-1-(6-(3-(4-(5-cyclopropylpyridin-3-yl)-1H-1,2,3-triazol-1-yl)oxetan-3-yl)pyridin-3-yl)piperidin-3-amine
352 (R)-N-(cyclopropylmethyl)-1-(6-(3-(5-(5-cyclopropylpyridin-3-yl)-1,3,4-thiadiazol-2-yl)oxetan-3-yl)pyridin-3-yl)piperidin-3-amine
353 (3R)-N-(cyclopropylmethyl)-1-(6-(1-(5-(6-(pyrrolidin-1-yl)pyrazin-2-yl)-1,3,4-thiadiazol-2-yl)ethyl)pyridazin-3-yl)piperidin-3-amine
354 (3R)-N-(cyclopropylmethyl)-1-(6-(1-(1-(6-(pyrrolidin-1-yl)pyrazin-2-yl)-1H-pyrazol-4-yl)ethyl)pyridin-3-yl)piperidin-3-amine
355 (3R)-N-(cyclopropylmethyl)-1-(6-(1-(4-(6-(pyrrolidin-1-yl)pyrazin-2-yl)-1H-imidazol-1-yl)ethyl)pyridin-3-yl)piperidin-3-amine
356 (3R)-N-(cyclopropylmethyl)-1-(6-(1-(1-(5-cyclopropylpyridin-3-yl)-1H-pyrazol-4-yl)ethyl)pyridin-3-yl)piperidin-3-amine
357 (3R)-N-(cyclopropylmethyl)-1-(6-(1-(4-(5-cyclopropylpyridin-3-yl)-1H-1,2,3-triazol-1-yl)ethyl)pyridin-3-yl)piperidin-3-amine
358 (3R)-N-(cyclopropylmethyl)-1-(6-(1-(5-(5-cyclopropylpyridin-3-yl)-1,3,4-thiadiazol-2-yl)ethyl)pyridazin-3-yl)piperidin-3-amine
359 (3R)-N-(cyclopropylmethyl)-1-(6-(1-(5-(5-cyclopropylpyridin-3-yl)-1,3,4-thiadiazol-2-yl)ethyl)pyridin-3-yl)piperidin-3-amine
360 (3R)-N-(cyclopropylmethyl)-1-(6-(1-(5-(6-(pyrrolidin-1-yl)pyrazin-2-yl)-1,3,4-thiadiazol-2-yl)ethyl)pyridin-3-yl)piperidin-3-amine
361 (R)-N-(cyclopropylmethyl)-1-(6-((5-(6-(pyrrolidin-1-yl)pyrazin-2-yl)-1,3,4-thiadiazol-2-yl)methyl)pyridin-3-yl)piperidin-3-amine
362 (R)-N-(cyclopropylmethyl)-1-(6-((5-(5-cyclopropylpyridin-3-yl)-1,3,4-thiadiazol-2-yl)methyl)pyridin-3-yl)piperidin-3-amine
363 (R)-N-(cyclopropylmethyl)-1-(6-(2-(5-(5-cyclopropylpyridin-3-yl)-1,3,4-thiadiazol-2-yl)propan-2-yl)pyridin-3-yl)piperidin-3-amine
364 (R)-N-(cyclopropylmethyl)-1-(6-(2-(5-(6-(pyrrolidin-1-yl)pyrazin-2-yl)-1,3,4-thiadiazol-2-yl)propan-2-yl)pyridin-3-yl)piperidin-3-amine
365 (3R)-N-((1-methylcyclopropyl)methyl)-1-(6-(1-(4-(6-(pyrrolidin-1-yl)pyrazin-2-yl)-1H-imidazol-1-yl)ethyl)pyridin-3-yl)piperidin-3-amine
366 (3R)-N-((1-methylcyclopropyl)methyl)-1-(6-(1-(5-(6-(pyrrolidin-1-yl)pyrazin-2-yl)-1,3,4-thiadiazol-2-yl)ethyl)pyridin-3-yl)piperidin-3-amine
367 (R)-N-((1-methylcyclopropyl)methyl)-1-(6-(3-(5-(6-(pyrrolidin-1-yl)pyrazin-2-yl)-1,3,4-thiadiazol-2-yl)oxetan-3-yl)pyridin-3-yl)piperidin-3-amine
368 (R)-1-(6-(3-(5-(5-cyclopropylpyridin-3-yl)-1,3,4-thiadiazol-2-yl)oxetan-3-yl)pyridin-3-yl)-N-((1-methylcyclopropyl)methyl)piperidin-3-amine, and
369 (R)-N-(cyclopropylmethyl)-1-(6-(3-(5-(6-(pyrrolidin-1-yl)pyrazin-2-yl)-1,3,4-thiadiazol-2-yl)oxetan-3-yl)pyridin-3-yl)piperidin-3-amine and pharmaceutically acceptable salts and solvates thereof.

15. A pharmaceutical composition comprising a compound according to claim 1, or a pharmaceutically acceptable salt and/or solvate thereof, and at least one pharmaceutically acceptable carrier.

16. A method for treating a proliferative condition in a patient in need thereof, comprising administering to said patient a therapeutically effective amount of a compound according to claim 1, or a pharmaceutically acceptable salt and/or solvate thereof, wherein the proliferative condition is a cancer selected from acute lymphocytic leukaemia, acute myeloid leukaemia (AML), chronic myeloid leukaemia, leukaemia, lymphoma, multiple myeloma, non-Hodgkin's lymphoma (NHL), bladder cancer, bone cancer, breast cancer, cervical cancer, colorectal cancer, endometrial cancer, esophageal/upper aerodigestive cancer, glioblastoma, hepatocellular carcinoma, kidney cancer, liver cancer, lung cancer, non small cell lung cancer (NSCLC), head and neck cancer, oral squamous cell carcinoma, melanoma, mesothelioma, ovarian cancer, pancreatic cancer, prostate cancer, sarcoma, skin cancer, stomach cancer, and thyroid cancer.

17. A method for inhibiting METTL3 activity in a patient in need thereof, comprising administering to said patient a therapeutically effective amount of a compound according to claim 1, or a pharmaceutically acceptable salt and/or solvate thereof.

* * * * *

UNITED STATES PATENT AND TRADEMARK OFFICE
CERTIFICATE OF CORRECTION

| | |
|---|---|
| PATENT NO. | : 12,091,400 B2 |
| APPLICATION NO. | : 18/417159 |
| DATED | : September 17, 2024 |
| INVENTOR(S) | : Guillaume Dutheuil et al. |

It is certified that error appears in the above-identified patent and that said Letters Patent is hereby corrected as shown below:

In the Specification

Under Column 482 at Line 37, please insert directly under the line which ends table 2, --* denotes that the compound exists as two diastereomeric or enantiomeric forms (non-chiral synthesis) which were separated as reported in the experimental section, that both forms were tested and are both at least in the "+" range, and the provided result is the best of the two tested forms.--

Signed and Sealed this
Nineteenth Day of November, 2024

Katherine Kelly Vidal
*Director of the United States Patent and Trademark Office*